(12) United States Patent
Hamaoka et al.

(10) Patent No.: US 8,399,520 B2
(45) Date of Patent: *Mar. 19, 2013

(54) SELECTIVE ESTROGEN RECEPTOR MODULATOR

(75) Inventors: Shinichi Hamaoka, Tsukuba (JP); Noritaka Kitazawa, Tsukuba (JP); Kazumasa Nara, Tsukuba (JP); Atsushi Sasaki, Tsukuba (JP); Atsushi Kamada, Tsukuba (JP); Tadashi Okabe, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/048,391

(22) Filed: Mar. 15, 2011

(65) Prior Publication Data

US 2012/0004315 A1    Jan. 5, 2012

Related U.S. Application Data

(60) Division of application No. 12/544,965, filed on Aug. 20, 2009, now Pat. No. 7,960,412, which is a division of application No. 11/158,245, filed on Jun. 22, 2005, now Pat. No. 7,612,114, which is a continuation-in-part of application No. PCT/JP03/16808, filed on Dec. 25, 2003.

(30) Foreign Application Priority Data

Dec. 26, 2002 (JP) ................... 2002-378729

(51) Int. Cl.
  A61K 31/137   (2006.01)
  C07C 217/84   (2006.01)
(52) U.S. Cl. ........................ 514/647; 564/308
(58) Field of Classification Search .............. 514/647; 564/308
  See application file for complete search history.

(56) References Cited

U.S. PATENT DOCUMENTS

| | | | |
|---|---|---|---|
| 3,274,213 | A | 9/1966 | Lednicer |
| 4,133,814 | A | 1/1979 | Jones et al. |
| 4,418,068 | A | 11/1983 | Jones |
| 6,204,286 | B1 | 3/2001 | Cameron et al. |
| 6,410,516 | B1 | 6/2002 | Baltimore et al. |
| 7,612,114 | B2 * | 11/2009 | Hamaoka et al. ............ 514/647 |

FOREIGN PATENT DOCUMENTS

| | | |
|---|---|---|
| DE | 29 09 754 A1 | 9/1980 |
| EP | 0 226 508 A1 | 6/1987 |
| EP | 0 406 734 A2 | 1/1991 |
| EP | 0 802 183 A1 | 10/1997 |
| EP | 1 199 069 A2 | 4/2002 |
| JP | 3-24069 A | 2/1991 |
| WO | WO 01/32631 A2 | 5/2001 |
| WO | WO 02/16316 A1 | 2/2002 |

OTHER PUBLICATIONS

Berge et al. "Pharmaceutical salts" J. Pharm. Sci. v, 66(1) p. 1-19 (1977).*
ACOG practice bulletin, "Selective Estrogen Receptor Modulators", International Journal of Gynecology & Obstetrics 79, 2002, pp. 289-298.
Barragja et al., Bioorganic & Medicinal Chemistry, vol. 7, pp. 1591-1596 (1999).
Bencze et al., J. Medicinal Chemistry, vol. 10, No. 2, pp. 138-144 (1967).
Boyer et al.: Synthesis, vol. 3, 1978, p. 205, XP002464895.
Compston, Physiological Reviews, vol. 81, No. 1, pp. 419-447 (2001).
Cummings et al., "The Effect of Raloxifene on Risk of Breast Cancer in Postmenopausal Women: Results from the More Randomized Trial", JAMA, Jun. 16, 1999, vol. 281, No. 23, pp. 2189-2197.
Database Beilstein [online], "Beilstein Institute for Organic Chemistry", Frankfurt-Main, DE; Database accession No. 173027 (Feb. 2010).

(Continued)

*Primary Examiner* — Celia Chang
(74) *Attorney, Agent, or Firm* — Birch, Stewart, Kolasch & Birch, LLP

(57) ABSTRACT

The present invention provides a compound represented by the following formula (I);

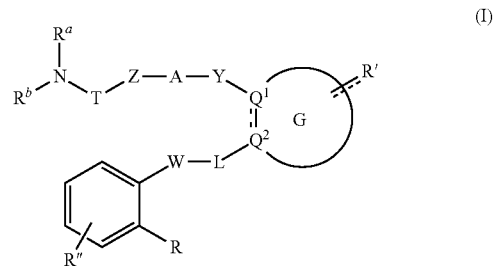

[wherein T represents a single bond, a C1-C4 alkylene group which may have a substituent and the like;

(I-1)

formula (I-1) represents a single bond or a double bond; A represents a single bond, a bivalent 5- to 14-membered heterocyclic group which may have a substituent and the like; Y represents a single bond and the like; Z represents a methylene group and the like; ring G represents a phenylene group and the like which may condense with a 5- to 6-membered ring and may have a heteroatom; $R^a$ and $R^b$ are the same as or different from each other and represent a hydrogen atom and the like; W represents a single bond and the like; R' represents 1 to 4 independent hydrogen atoms and the like; and R" represents 1 to 4 independent hydrogen atoms and the like] or a salt thereof, or a hydrate thereof.

3 Claims, No Drawings

OTHER PUBLICATIONS

Database Beilstein [online], "Beilstein Institute for Organic Chemistry", Frankfurt-Main, DE; Database accession No. 2109126 (Feb. 2010).
Database Beilstein [online], "Beilstein Institute for Organic Chemistry", Frankfurt-Main, DE; Database accession No. 8619569 (Feb. 2010).
Duka et al., Psychopharmacology, vol. 149, pp. 129-139 (2000).
Ettinger et al., "Reduction of Vertebral Fracture Risk in Postmenopausal Women with Osteoporosis Treated with Raloxifene", JAMA, Aug. 18, 1999, vol. 282, No. 7, pp. 637-645.
Evans et al., JAMA, vol. 262, No. 18 (1989).
Fu et al.: Tetrahedron Letters, vol. 31, No. 12, 1990, pp. 1665-1668, XP002327011.
Gopinath et al: Journal of the Chemical Society, No. 1958, 1958, pp. 504-509. XP002099088.
Gottardis et al., "Effect of Steroidal and Nonsteroidal Antiestrogens on the Growth of a Tamoxifen-stimulated Human Endometiral Carcinoma (EnCa101) in Athymic Mice", Cancer Research 50, Jun. 1, 1990, pp. 3189-3192.
Hamaoka et al., Drugs Fut, vol. 29 (Suppl A), International Symposium on Medicinal Chemistry, pp. 177-183 (2004).
Hamel et al., J. Chem. Soc., Chem. Commun, (16) pp. 1072-1074 (1990).
Henderson, CNS Drugs, vol. 5, No. 8, pp. 343-351 (Nov. 1997).
Henderson, Neurology, vol. 48, (5 Suppl 7), pp. S27-S35 (May 1997).
Jones et al., J. Med. Chem., vol. 27, pp. 1057-1066 (1984).
Jordon et al., Breast Cancer Research and Treatment, vol. 10, pp. 31-35 (1987).
Labrie et al., "EM-652 (SCH57068), a pure SERM having Complete Antiestrogenic Activity in the Mammary Gland and Endometrium", Journal of Steroid Biochemistry & Molecular Biology 79, 2000, pp. 213-225.
Lednicer et al., J. Medicinal Chemistry, vol. 10, No. 1, pp. 78-84 (1967).
Lednicer et al., J. Medicinal Chemistry, vol. 12, No. 5, pp. 881-885 (1969).
Littleton-Kearney et al., "Selective Estrogen Receptor Modulators: Tissue Actions and Potential for CNS Protection", CNS Drug Reviews, vol. 8, No. 3, pp. 309-330.
Lombardi et al., Molecular and Cellular Endocrinology, vol. 178, pp. 51-55 (2001).
Loose-Mitchell et al., Goodman and Gilman's, The Pharmaceutical Basis of Therapeutics, 10th Edition, Chapter 58—Estrogens and Progestins, pp. 1597-1634 (2001).
Mendelsohn et al., The New England Journal of Medicine, vol. 340, No. 23, pp. 1801-1811 (1999).
Neven et al., "The Effect of Raloxifene on the Incidence of Ovarian Cancer in Postmenopausal Women", Gynecologic Oncology 85, 2002, pp. 388-390.
Nicolaus, "Symbiotic Approach to Drug Design", Decision Making in Drug Research, Jan. 1, 1983, pp. 173-186, XP001111439.
Notice of Allowance dated Dec. 17, 2010 for U.S. Appl. No. 12/544,965.
Office Action dated Aug. 11, 2010 for U.S. Appl. No. 12/544,965.
Office Action dated Dec. 10, 2009 for Japanese Application No. 2004-562947.
Office Action dated Jan. 9, 2007 for Australian Application No. 2003292625.
Office Action dated Jul. 21, 2010 for European Application No. 03782904.1.
Office Action dated Nov. 18, 2008 for Canadian Application No. 2512000.
Ohkura et al., Endocrine Journal, vol. 41, No. 4, pp. 361-371 (1994).
Pearce et al., "Psychological and Sexual Aspects of the Menopause and HRT", Bailliere's Clinical Obstetrics and Gynaecology, vol. 10, No. 3, Sep. 1996, pp. 385-399.
Phillips et al., "Muscle Weakness in Women Occurs at an Earlier Age than in Men, but Strength is Preserved by Hormone Replacement Therapy", Clinical Science, 1993, 84, pp. 95-98.
Prince et al., The New England Journal of Medicine, vol. 325, No. 17, pp. 1189-1195 (1991).
Reddy et al., Indian Journal of Chemistry, vol. 27B, (16), pp. 563-564 (Jun. 1988).
SCRIP, No. 1812/13, (Apr. 16-20), p. 31 (1993).
Sharp et al., "Synthetic Connections to the Aromatic Directed Metalation Reaction, Functionalized Aryl Boronic Acids by IPSO Borodesilylation, General Synthesis of Unsymmetrical Biphenyls and m-Terphenyls," Tetrahedron Letters, vol. 28, No. 43, 1987, pp. 5093-5096.
Sherwin, Psychoneuroedocrinology, vol. 13, No. 4, pp. 345-357 (1988).
Walsh et al., "Effects of Raloxifene on Serum Lipids and Coagulation Factors in Healthy Postmenopausal Women", JAMA, May 13, 1998, vol. 279, No. 18, pp. 1445-1451.
Walsh et al., "The Effects of Hormone Replacement Therapy and Raloxifene on C-Reactive Protein and Homocysteine in Healthy Postmenopausal Women: A Randomized, Controlled Trial*", The Journal of Clinical Endocrinology & Metabolism, vol. 85, No. 1,. pp. 214-218.
Wittig et al.: vol. 91, 1958, pp. 2358-2365. XP002464896.
Yakugaku Zasshi, Journal of the Pharmaceutical Society of Japan, vol. 124, Suppl. 3, p. 183 (2004).
European Office Action dated Apr. 3, 2012 for European Application No. 03782904.1.
Australian Notice of Acceptance, dated Jul. 24, 2008, for Australian Application No. 2003292625.
Canadian Notice of Allowance, dated Dec. 8, 2010, for Canadian Application No. 2,512,000.
Canadian Office Action, dated May 3, 2010, for Canadian Application No. 2,512,000.
Canadian Office Action, dated Sep. 30, 2009, for Canadian Application No. 2,512,000.
Japanese Decision to Grant a Patent, dated Mar. 19, 2010, for Japanese Application No. 2004-562947, including an English translation.
Response to Australian Examiner's First Report, filed on Jul. 8, 2008, for Australian Application No. 2003292625.
Response to Canadian Office Action, filed on Apr. 9, 2009, for Canadian Application No. 2,512,000.
Response to Canadian Office Action, filed on Jan. 13, 2010, for Canadian Application No. 2,512,000.
Response to Canadian Office Action, filed on Oct. 22, 2010, for Canadian Application No. 2,512,000.
Response to European Examination Report, filed on Jan. 31, 2011, for European Application No. 03782904.1.
Response to Japanese Notice of Reasons for Rejection, filed on Feb. 8, 2010, for Japanese Application No. 2004-562947, including an English translation.

* cited by examiner

SELECTIVE ESTROGEN RECEPTOR MODULATOR

CROSS-REFERENCE TO RELATED APPLICATIONS

The present application is a 37 C.F.R. §1.53(b) divisional of U.S. application Ser. No. 12/544,965, filed Aug. 20, 2009 now U.S. Pat. No. 7,960,412. Application Ser. No. 12/544,965 is a divisional of U.S. application Ser. No. 11/158,245, filed on Jun. 22, 2005, now U.S. Pat. No. 7,612,114, which in turn is a Continuation-In-Part of PCT International Application No. PCT/JP03/16808, filed on Dec. 25, 2003. Priority is claimed to Japanese Application No. 2002-378729, filed Dec. 26, 2002. The entire contents of each of these applications is hereby incorporated by reference.

TECHNICAL FIELD

The present invention relates to a novel compound, which is a selective estrogen receptor modulator.

BACKGROUND ART

Estrogen is a "female hormone" whose various physiological activities have been described in a number of references (for instance, D. S. Loose-Mitchell and G. M. Stancel, *Goodman and Gilman's, The Pharmacological Basis of Therapeutics*, 10$^{th}$ Ed., J. G. Hardman and L. E. Limbird Eds, 2001, p. 1597-1634). In addition, estrogen regulates the development and function of the reproduction system, and affects a variety of physiological function (including maintenance of vaginal inner layer, retention of bone density and temperature regulation). In recent years, investigations showed that estrogen has a number of function other than physiological functions associated with female reproduction and genital tissue functions. On the other hand, in males, it is also known that estrogen is present in the body, and that the estrogen receptor is present in a variety of tissues (for instance, G. Lombardi et al., *Mol Cell Endocrinol*, 2001, Vol. 178 (1-2), p. 51-55). In addition, estrogen decreases low density lipoproteins (LDLs) and regulates the production of cholesterol in liver. Furthermore, estrogen is thought to be involved in decreasing the risk of manifestation of Alzheimer's disease, and to alleviate the manifestation thereof (for instance, V. W. Henderson, *Neurology*, 1997, Vol. 48, (5 Suppl 7), S27-35).

Thus, estrogen is involved in a variety of functions in vivo, and when estrogen can no longer be produced, physiologically important alterations arise. Among others, estrogen production in healthy females is known to decrease sharply at menopause. Examples of effects of decrease in estrogen production include, in addition to the problems of urinary incontinence, vaginal dryness and decrease in skin tone, the problems of neurological symptoms, emotional instability and modulation of temperature regulation, as well as increase in blood lipid (leading to a large increase of the occurrence of cardiac diseases) and decrease in bone density (osteoporosis) and the like.

For example, in addition to urinary incontinence, vaginal dryness, increase in the rate of incidence of autoimmune diseases and loss of skin tone, problems related to the increase in the occurrence of autoimmune diseases, vasomotor complications (hot flashes), and neurological symptoms and the like, are symptoms which are associated with menopause, and are known to be alleviated or improved by estrogen replacement therapy.

However, estrogen administration leads to the increase of serious dangers such as breast cancer and endometrial cancer as well as thrombus formation.

A estrogen-dependent breast cancer is an example of pathological state associated with abnormal cell response to endogenous tissue estrogen. Estrogen-dependent tumor cells proliferate in the presence of estrogen. Current chemotherapies against these cancers largely rely on the use of anti-estrogen compounds, for instance, tamoxifen. Although such estrogen agonists-antagonists have beneficial effects in the treatment of these cancers and are acceptable in situations where adverse events of estrogen is life-threatening, they are not ideal. For instance, these agents, due to the estrogen (agonist) characteristics that they have, sometimes exhibit estrogenic stimulation of a group of cancer cells present in the uterus. A better therapy to treat these cancers is an agent, which is an anti-estrogen compound whose estrogen agonist characteristics may be ignored against the proliferating tissue or is completely inexistent.

Another estrogen-dependent symptom is uterine fibrosis (uterine fibroid tumor disease). This uterine fibrosis is fundamentally a state where a deposition of fibroid tissue is present on the uterine wall. This state is responsible for dysmenorrhea and infecundity in females. Except for the suggested evidence of an inadequate response of the fibroid tissue to estrogen, the exact cause of this state is not well known. The most general treatment of uterine fibrosis include surgical operations, which is expensive and sometimes cause complications such as abdominal adhesion and infection and the like.

In addition, another estrogen-dependent disease is endometritis, a serious dysmenorrhea state accompanied by sharp pain and hemorrhage into the endometrial mass or peritonea, often leading to infecundity. The cause for the occurrence of this state is thought to be the growth of a heterotropic endometrium present in an inadequate tissue, which respond inadequately to a normally hormonal regulation.

For a long time, estrogen replacement therapy has been practised for a number of important health problems caused by the inability to produce estrogen; however, due to an increase in the adverse effects and risks thereof, the use thereof became limited.

In addition, in case of problems related to osteoporosis caused by estrogen being no longer produced, one of the most general types of osteoporosis is associated with menopause. Here, osteoporosis means a group of diseases resulting from various causes of disease, and is characterized by the net loss of bone mass. This loss of bone mass and the resulting fracture lead to weakening of the skeleton that sufficiently maintains the body in structural terms. The majority of females lose approximately 20% to approximately 60% of bone mass in the trabecular constituent portion of the bone within 3 to 6 years after missed menstruation. Osteoporosis is a general and serious illness for postmenopausal females. Osteoporosis induces psychological damages to patients and family members; in addition, due to the chronical nature of this disease, large economical losses are sustained, and wide-range and lengthy care (hospitalization and home care nursing) is required due to the aftereffects of this illness. An excellent method for treating osteoporosis is estrogen replacement therapy (for instance, R. L. Prince et al., *N. Engl. J. Med.*, 1991, Vol. 325, p. 1189-1195 and J. E. Compston, *Physiol Rev*, 2001, Vol. 81, p. 419-447). As mentioned above, estrogen therapy often provokes undesirable adverse effects, in particular in uterine and mammary tissues, the use of estrogen is limited, although this therapy has a therapeutic effect.

Further, in case of cardiovascular related problems, it has been long known that during the premenopausal period, the rate of incidence of cardiovascular illness for a majority of females is lower than males of the same age. However, at postmenopause, the rate of incidence of cardiovascular illness in females increases slowly in comparison to the proportion seen in males. This increase in rate of incidence is associated with a loss of estrogen, and particularly to a loss of estrogen that adjusts the serum lipid level. Postmenopausal females receiving estrogen replacement therapy have been reported to make their cardiovascular protection improve to a level that is equivalent to premenopausal state. Therefore, estrogen is thought to be a rational treatment for this state (for instance, M. E. Mendelsohn et al., *N. Engl. J. Med.*, 1999, Vol. 340, p. 1801-1811). However, the adverse effects of estrogen replacement therapy cannot be accepted by a number of females, such that the use of this therapy is limited.

Meanwhile, Alzheimer's disease (hereinafter referred to as "AD") is clinically a regressive neurodegenerative disease characterized by the gradual loss of memory, recognition, deduction, judgement and emotional stability, provoking gradually remarkable psychological depression and ultimately leading to death. AD is a general cause of progressive psychological impairment (dementia) in the elderly, and in the U.S. it is believed to be the 4$^{th}$ general medical cause of death. AD is observed in a variety of populations and ethnic groups in the world and represents a present and future major public health problem. The frequency of occurrence of this disease increases with age, and approximately 10% of the elderly population of 65 years and older is estimated to be affected (for instance, Evans et al., *J. Amer. Med. Assoc.*, 1989, Vol. 262, p. 2551-2556). Thus far, AD has been shown to be incurable, and AD is expected to multiply in the world as human life span becomes longer.

Several studies in human have shown that the use of estrogen prevented the decline of the recognition function, then led to recovery (for instance, B. B. Sherwin, *Psychoneuroendocrinology*, 1988, Vol. 13, No. 4, p. 345-357 and T. Duka et al., *Psychopharmacology*, 2000, Vol. 149, No. 2, p. 129-139). Several epidemiological studies reported that the use of estrogen also decreases the risk of AD episode (for instance, V. W. Henderson, *Neurology*, 1997, Vol. 48, (5 Suppl 7), S27-35). In addition, estrogen appears to improve recognition function in AD patients (for instance, Ohkura et al., *Endocrine J.*, 1994, Vol. 41, p. 361-371 and V. W. Henderson, *CNS Drugs*, 1997, Vol. 8, No. 5, p. 343-351). Further, estrogen is known to possess an action of protecting nerve cells, which are beneficial to the treatment of neurodegenerative diseases such as AD, and an action of activating neurotrophic factors. However, the use of estrogen is also associated with a number of disadvantageous adverse effects including the increase in the risk of breast cancer and uterine cancer. It is possible that estrogen agonists or antagonists, while maintaining a large number of estrogen actions, lack adverse effects on tissues such as mammary gland and uterus.

Thus far, the discovery that a number of agents worked as estrogen agonists on some tissues (for instance, bone) and as antagonists on other tissues (for instance, mammary gland) provided effective treatments for symptoms provoked by a decrease in estrogen or estrogen-dependent diseases. Best known among these so-called selective estrogen receptor modulators (hereinafter referred to as "SERM"), tamoxifen, that is 1-(4-β-dimethylaminoethoxyphenyl)-1,2-diphenyl-but-1-ene, has been demonstrated to be therapeutically useful in the treatment and the prophylaxis of breast cancers, as well as in the decrease in LDL concentration. However, as tamoxifen simultaneously has an estrogenic stimulatory action on the uterus, it turned out to increase the risk of endometrial cancer.

In recent years, newer SERMs, for instance, raloxifene, that is 6-hydroxy-2-(4-hydroxyphenyl)-3-[4-(2-piperidinoethoxy)benzoyl]benz[b]thiophene, were reported to be, in regard to bone and lipid, similar to the desired action of estrogen, but in contrast to estrogen, uterine stimulation was minimal (for instance, *Scrip*, 1993, April 16/20, No. 1812/13, p. 31 and *Breast Cancer Research and Treatment*, 1987, Vol. 10, No. 1, p. 31-36).

Raloxifene and related compounds are described as anti-estrogen substances and anti-androgen substances that are effective for the treatment of breast cancers and prostate cancers (for instance, U.S. Pat. No. 4,418,068 and *Journal of Medicinal Chemistry*, 1984, Vol. 27, No. 8, p. 1057-1066).

Other compounds such as those mentioned below are known as SERMs.

Derivatives of 2-phenyl-3-aroylbenzothiophene and 2-phenyl-3-aroylbenzothiophene-1-oxide, which are useful as contraceptive drugs and useful in inhibiting the growth of breast cancers, have been disclosed (for instance, U.S. Pat. No. 4,133,814).

An estrogen antagonist represented by the following formula;

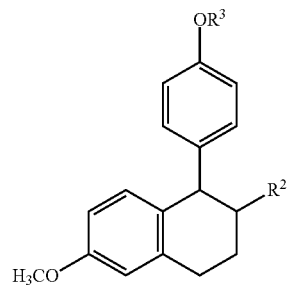

(wherein $R^2$ represents phenyl or cyclopentyl and $R^3$ represents H,

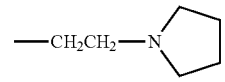

or —CH$_2$CHOHCH$_2$OH) has been described (for instance, *Journal of Medicinal Chemistry*, 1969, Vol. 12, No. 5, p. 881-885).

Preparation of a series of tetrahydronaphthalenes intended to achieve the separation of estrogen activity, contraception activity, and hypocholesterolemia activity has been described. These structures are represented by the formula;

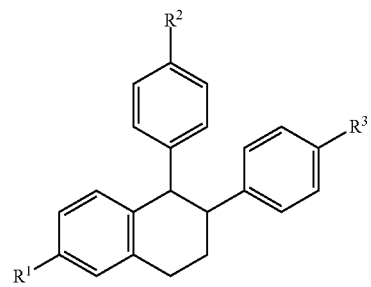

(wherein $R^1$ represents H or OCH$_3$; $R^2$ represents H, OH, OCH$_3$, OPO(OC$_2$H$_5$)$_2$, OCH$_2$CH$_2$N(C$_2$H$_5$)$_2$, OCH$_2$COOH or OCH(CH₃)COOH) (for instance, *Journal of Medicinal Chemistry*, 1967, Vol. 10, No. 2, p. 138-144).

An estrogen agonist and antagonist represented by the following formula;

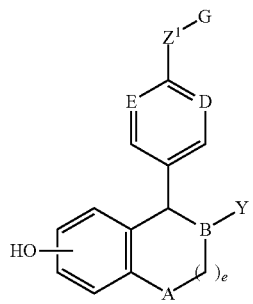

have been disclosed (for instance, U.S. Pat. No. 6,204,286).

A compound represented by the following formula;

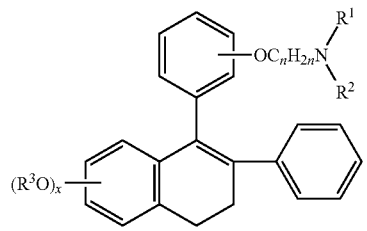

(wherein R³ represents a lower alkyl, R¹ and R² are selected from the group consisting of lower alkyls and 5 to 7 membered saturated heterocyclic ring formed by bonding lower alkyls to each other) has been disclosed (for instance, U.S. Pat. No. 3,274,213 and *Journal of Medicinal Chemistry*, 1967, Vol. 10, No. 1, p. 78-84).

An estrogenic compound represented by the following formula;

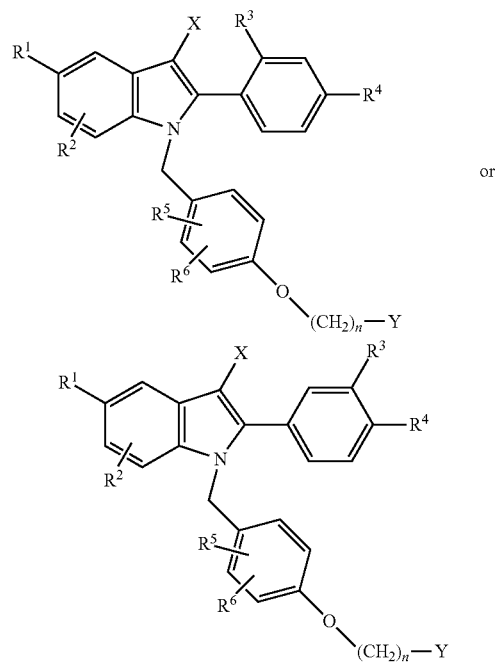

is disclosed (for instance, European patent application No. 802,183).

However, so far, there may be the current situation that no therapeutic agent exists, which is effective against symptoms caused by a decrease in estrogen and a variety of estrogen-dependent diseases and symptoms, furthermore, against central nervous system diseases including Alzheimer's disease. Therefore, there is a need for development of a compound that selectively has the activity which is an estrogen receptor modulator, and the property which is satisfactory as a desired medicine.

DISCLOSURE OF INVENTION

Thus, as a result of the earnest studies undertaken in view of the situation described above, the present inventors discovered a novel compound having the activity of a selective estrogen receptor modulator with a higher safety, and completed the present invention.

That is to say, the present invention provides a compound represented by the following formula (I);

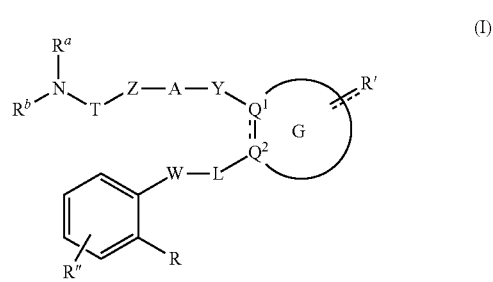

[wherein T represents a single bond, a C1-C4 alkylene group which may have a substituent, a C2-C4 alkenylene group which may have a substituent, or a C2-C4 alkynylene group which may have a substituent;

$$\text{-----------} \quad (I-1)$$

formula (I-1) represents a single bond or a double bond;

A represents a single bond, a bivalent 5- to 14-membered heterocyclic group which may have a substituent, a 5- to 14-membered heteroarylene group which may have a substituent, a bivalent C3-C14 carbocyclic group which may have a substituent or a C6-C14 arylene group which may have a substituent;

Y represents a single bond, or —(CH₂)ⱼ—V—(CH₂)ₖ— {wherein V represents a single bond, —(CR^f R^g)_g—, —O—, —S—, —S(═O)—, —SO₂—, —SO₂N^c—, —NR^c SO₂—, —C(═O)—, —C(═O)O—, —OC(═O)—, —NR^c—, —NR^c—C(═O)—, —C(═O)—NR^c—, —NR^c—C(═O) O—, —OC(═O)—NR^c— (wherein R^c represents a hydrogen atom, a C1-C6 alkyl group which may have a substituent, a C2-C6 alkenyl group which may have a substituent, a C2-C7 acyl group which may have a substituent, a C6-C14 aryl group which may have a substituent, a 5- to 14-membered heteroaryl group which may have a substituent, a C3-C8 cycloalkyl group which may have a substituent, or 5- to 14-membered heterocyclic group which may have a substituent, or, when A is other than an single bond, may form, together with A, a 5- to 8-membered ring containing 1 to 2 heteroatoms, R^f and R^g independently represent a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent or a 5- to 14-membered heteroaryl group which may have a substituent, and g stands for an integer from 0 to 2), and l and k independently stand for an integer from 0 to 6, the sum of l and k being an integer from 0 to 6};

Z represents —(CH$_2$)$_l$—V'—(CH$_2$)$_k$— {wherein V' represents a single bond, —(CR$^f$R$^{g'}$)$_{g'}$—, —(CR$^f$R$^{g'}$)$_{g'}$—CH$_2$—O—, —O—, —S—, —S(=O)—, —SO$_2$—, —SO$_2$NR$^{c'}$—, —NR$^{c'}$SO$_2$—, —C(=O)—, —C(=O)—CH$_2$—O—, —C(=O)O—, —OC(=O)—, —NR$^{c'}$—, —NR$^{c'}$—C(=O)—, —C(=O)—NR$^{c'}$—, —NR$^{c'}$—C(=O)O— or —OC(=O)—NR$^{c'}$— (wherein R$^{c'}$ represents a hydrogen atom, a C1-C6 alkyl group which may have a substituent, a C2-C6 alkenyl group which may have a substituent, a C2-C7 acyl group which may have a substituent, a C6-C14 aryl group which may have a substituent, a 5- to 14-membered heteroaryl group which may have a substituent, a C3-C8 cycloalkyl group which may have a substituent, or a 5- to 14-membered heterocyclic group which may have a substituent, R$^{f'}$ and R$^{g'}$ independently represent a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent or a 5- to 14-membered heteroaryl group which may have a substituent, or, R$^{f'}$ and R$^{g'}$ may form, with the carbon atoms to which R$^{f'}$ and R$^{g'}$ are bonded, a 5- to 6-membered spiro ring, and g' stands for an integer from 0 to 2), and l' and k' independently stand for an integer from 0 to 6, the sum of l' and k' being an integer from 0 to 6};

ring G represents, together with Q$^1$ and Q$^2$, a phenylene group, a bivalent C5-C6 carbocyclic group, a 5- to 6-membered heteroarylene group or a bivalent 5- to 6-membered heterocyclic group, which may condense with a 5- to 6-membered ring which may have a heteroatom, Q$^1$ and Q$^2$ independently representing a carbon atom or a nitrogen atom;

R$^a$ and R$^b$ are the same as or different from each other and each represents a hydrogen atom, a C1-C6 alkyl group which may have a substituent, a C2-C6 alkenyl group which may have a substituent, a C2-C6 alkynyl group which may have a substituent, a C3-C8 cycloalkyl group which may have a substituent, a C6-C14 aryl group which may have a substituent, a 5- to 14-membered heterocyclic group which may have a substituent, a 5- to 14-membered heteroaryl group which may have a substituent, a C6-C14 arylalkyl group which may have a substituent, a 5- to 14-membered heteroarylalkyl group which may have a substituent, a C1-C6 alkoxy group which may have a substituent or a C2-C7 acyl group which may have a substituent, or when R$^a$ and R$^b$ are bonded together, they may form, together with the nitrogen atom that is adjacent to R$^a$ and R$^b$, a 4- to 10-membered single ring, a double ring, or a Spiro ring which may have a substituent, when R$^a$ and/or R$^b$ is bonded to T, they may form, together with the nitrogen atom which R$^a$ and R$^b$ are bonded to, a 5- to 10-membered single ring or double ring which may have a substituent, or, when T, Z, A and Y all represent a single bond, R$^a$ or R$^b$ may be bonded to an atom that constitutes ring G to form a condensed ring;

W represents a single bond, —(CR$^d$R$^e$)$_f$—CHX—, —CHX—(CR$^d$R$^e$)$_f$—, —CR$^d$X—(CH$_2$)$_q$—, —CR$^d$=CX—, —CX=CR$^d$—, —C≡C—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O— or any group from the group represented by the groups having the following formula;

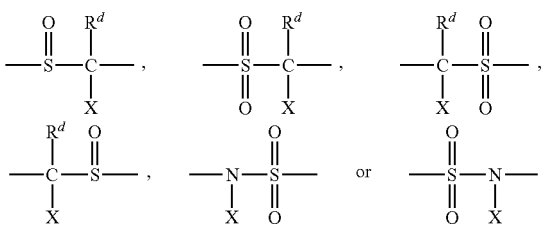

(R$^d$ and R$^e$ have the same meaning as defined by R$^f$ and R$^g$, respectively, X represents a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent, or a 5- to 14-membered heteroaryl group which may have a substituent, f has the same meaning as defined by g, and q stands for an integer from 0 to 4), or a group having the following formula;

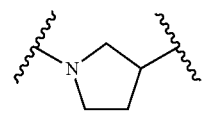 [SMILES: *C1CCN(*)C1]

R' represents 1 to 4 independent hydrogen atoms, oxygen atoms, sulphur atoms, hydroxyl groups (that may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C2-C7 acyl groups which may have a substituent, C3-C8 cycloalkylthio groups which may have a substituent, C6-C14 aryl groups which may have a substituent or 5- to 14-membered heteroaryl groups which may have a substituent, or when R' is in the number of 2 to 4, R' may be bonded to one another to form a 5- to 8-membered ring which may have a substituent, or when W represents any one selected from the group consisting of —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O— or —CR$^d$X—, R' may form, together with X, a 5- to 8-membered ring, that may contain 1 to 2 heteroatoms, which may have a substituent;

R" represents 1 to 4 independent hydrogen atoms, hydroxyl groups (that may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C2-C7 acyl groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C3-C8 cycloalkylthio groups which may have a substituent, C6-C14 aryl groups which may have a substituent or a 5- to 14-membered heteroaryl groups which may have a substituent, or when R" is in the number of 2 to 4, R" may be bonded to one another to form a 5- to 8-membered ring which may have a substituent;

R represents a hydrogen atom, a hydroxyl group, a halogen atom, a formyl group, a cyano group, a carboxyl group, a carbamoyl group, a C1-C6 alkyl group which may have a substituent, a C2-C6 alkenyl group which may have a substituent, a C1-C6 alkoxy group which may have a substituent, an amino group which may have a substituent, a C2-C7 acyl group which may have a substituent, a C1-C6 alkylthio group which may have a substituent, a C3-C8 cycloalkyl group which may have a substituent, a C3-C8 cycloalkyloxy group which may have a substituent, a C2-C7 alkylcarbonyloxy group which may have a substituent, a C3-C8 cycloalkylthio group which may have a substituent, a C6-C14 aryl group which may have a substituent or a 5- to 14-membered heteroaryl group which may have a substituent, or when W represents —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O— or —CR$^d$X—, R may form, together with X, a 5- to 7-membered ring, that may contain 1 to 2 heteroatoms, which may have a substituent;

L represents a single bond, a C1-C4 alkylene group that may have a substituent, a C2-C4 alkenylene group which may have a substituent, or a C2-C4 alkynylene group which may have a substituent] or a salt thereof, or a hydrate thereof.

The present invention also provides the compound represented by the above-mentioned formula (I) or a salt thereof, or a hydrate thereof, to be used as a drug.

In addition, the present invention provides a medicament, a pharmaceutical composition, a selective estrogen receptor modulator, a preventive and/or therapeutic agent for neurologic manifestation, central nervous disease, osteoporosis, hypercholesterolaemia, hyperlipidaemia, arteriosclerosis, breast cancer, endometrial cancer, uterine cancer, ovarian cancer, colpoxerosis or muscle amount decrease which are estrogen-dependent, a preventive and/or therapeutic agent for estrogen-dependent central nervous diseases indicating dementia symptom including Alzheimer's disease or cerebrovascular dementia, and an estrogen receptor modulator indicating estrogenic action in the central nervous system, bone tissue and lipid metabolism, and/or an anti-estrogenic action in reproductive organs and mammary glands, containing the compound represented by the above-mentioned formula (I) or a salt thereof, or a hydrate thereof.

Further, the present invention provides a use of the compound represented by the above-mentioned formula (I) or a salt thereof, or a hydrate thereof, for the manufacture of a preventive and/or therapeutic agent for neurologic manifestation, central nervous disease, osteoporosis, hypercholesterolaemia, hyperlipidaemia, arteriosclerosis, breast cancer, endometrial cancer, uterine cancer, ovarian cancer, colpoxerosis or muscle amount decrease which are estrogen-dependent.

Furthermore, the present invention provides a method for preventing and/or treating neurologic manifestation, central nervous diseases, osteoporosis, hypercholesterolaemia, hyperlipidaemia, arteriosclerosis, breast cancer, endometrial cancer, uterine cancer, ovarian cancer, colpoxerosis or muscle mass decrease which are estrogen-dependent, comprising administering to a mammalian animal an effective amount of the compound represented by the above-mentioned formula (I) or a salt thereof, or a hydrate thereof.

BEST MODE FOR CARRYING OUT THE INVENTION

The definition and usage of the terms and the like used in the present specification and claims are as follows:

Although the structural formula of the compound is sometimes described as representing a given isomer for the sake of convenience, the present invention includes all the isomers that may be generated in terms of compound structures, including geometric isomers, optical isomers, stereoisomers, tautomers and the like, and it is not limited to the formula given for the sake of convenience regardless of whether it is a single isomer (for instance, enantiomer) or a mixture of isomers (for instance, racemic mixture).

The term "and/or" is used with the meaning that includes both the "and" case and the "or" case.

The term "halogen atom" used herein means a fluorine atom, a chlorine atom, a bromine atom, an iodine atom and the like, preferably a fluorine atom or a chlorine atom, and more preferably a fluorine atom.

The term "C1-C6 alkyl group" or a C1-C6 alkyl group portion in a substituent containing a C1-C6 alkyl group portion (for instance, C6-C14 arylalkyl group) which are used herein means a linear or a branched alkyl group having 1 to 6 carbons, specifically, examples include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like, and preferably methyl group, ethyl group, n-propyl group, iso-propyl group, n-butyl group, iso-butyl group, sec-butyl group, tert-butyl group, n-pentyl group and the like.

The term "C2-C6 alkenyl group" used herein means a linear or a branched alkenyl group with 2 to 6 carbons, specifically, examples include vinyl group, allyl group, 1-propenyl group, isopropenyl group, 2-methyl-1-propenyl group, 2-methyl-2-propenyl group, 1-butenyl group, 2-butenyl group, 3-butenyl group, 1-pentenyl group, 1-hexenyl group, 1,3-hexadienyl group, 1,5-hexadienyl group and the like.

The term "C2-C6 alkynyl group" used herein means a linear or a branched alkynyl group with 2 to 6 carbons, specifically, examples include ethynyl group, 1-propynyl group, 2-propynyl group, 1-butynyl group, 2-butynyl group, 3-butynyl group, 1-ethynyl-2-propynyl group, 1-methyl-2-propynyl group, 1-pentynyl group, 1-hexynyl group, 1,3-hexadiynyl group, 1,5-hexadiynyl group and the like.

The term "alkylene group" used herein means a bivalent group derived by further removing one hydrogen atom at any position from the "alkyl group" defined above, specifically, examples of "C1-C4 alkylene group" include methylene group, ethylene group, methylethylene group, ethylethylene group, 1,1-dimethylethylene group, 1,2-dimethylethylene group, trimethylene group, 1-methyltrimethylene group, 2-methyltrimethylene group, tetramethylene group and the like, and preferably, methylene group, ethylene group, methylethylene group, 1,1-dimethylethylene group, trimethylene group and the like.

The term "alkenylene group" used herein means a bivalent group derived by further removing one hydrogen atom at any position from the "alkenyl group" defined above, specifically, examples of "C2-C4 alkenylene group" include vinylene group, propenylene group, butenylene group and the like, and preferably, vinylene group, propenylene group and butenylene group.

The term "alkynylene group" used herein means a bivalent group derived by further removing one hydrogen atom at any position from the "alkynyl group" defined above, specifically, examples of "C2-C4 alkynylene group" include ethynylene group, propynylene group, butynylene group and the like, and preferably, ethynylene group, propynylene group and butynylene group.

The term "C3-C8 cycloalkyl group" used herein means an aliphatic hydrocarbon cyclic group with 3 to 8 carbon atoms, specifically, examples include cyclopropyl group, cyclobutyl group, cyclopentyl group, cyclohexyl group, cycloheptyl group, cyclooctyl group and the like, and preferably, cyclopropyl group, cyclobutyl group, cyclopentyl group and cyclohexyl group.

The term "C1-C6 alkoxy group" used herein means an oxy group to which the "C1-C6 alkyl group" defined above is bonded, specifically, examples include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like, preferably methoxy group, ethoxy group, n-propoxy group and iso-propoxy group, and more preferably, methoxy group and ethoxy group.

The term "C3-C8 cycloalkyloxy group" used herein means an oxy group to which the "C3-C8 cycloalkyl group" defined above is bonded, specifically, examples include cyclopropoxy group, cyclobutoxy group, cyclopentyloxy group, cyclohexyloxy group, cycloheptyloxy group, cyclooctyloxy group and the like, and preferably, cyclopropyloxy group, cyclobutyloxy group and cyclopentyloxy group.

The term "C2-C7 acyl group" used herein means a carbonyl group to which the "C1-C6 alkyl group" defined above is bonded, specifically, examples include acetyl group, propionyl group, butyryl group, isobutyryl group, valeryl group, isovaleryl group, pivaloyl group and the like, and preferably, acetyl group, propionyl group, butyryl group, isobutyryl group, valeryl group, isovaleryl group and pivaloyl group.

The term "C1-C6 alkylthio group" used herein means a thio group to which the "C1-C6 alkyl group" defined above is bonded, specifically, examples include methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, n-hexylthio group, 1-ethyl-2-methylpropylthio group, 1,1,2-trimethylpropylthio group, 1-ethylbutylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, 3-methylpentylthio group and the like.

The term "C3-C8 cycloalkylthio group" used herein means a thio group to which the "C3-C8 cycloalkyl group" defined above is bonded, specifically, examples include cyclopropylthio group, cyclobutylthio group, cyclopentylthio group, cyclohexylthio group, cycloheptylthio group, or cyclooctylthio group and the like, and preferably, cyclopropylthio group, cyclobutylthio group and cyclopentylthio group.

The term "C3-C14 carbocyclic group" used herein means a monovalent or a bivalent cyclic group which is a saturated, partially saturated or unsaturated and which is formed by 3 to 14 carbon atoms, containing the a C3-C8 cycloalkyl group described above and a C5-C6 carbocyclic group described below. Specific examples of this group include C3-C8 cycloalkenyl groups such as cyclopropenyl, cyclobutenyl, 1,3-cyclobutadienyl, cyclopentenyl, 1,3-cyclopentadienyl, cyclohexenyl, 1,3-cyclohexadienyl and 1,4-cyclohexadienyl, a bicyclic or tricyclic C9-C14 ring group which is saturated, partially saturated or unsaturated, such as decahydronaphthyl group, octahydroindenyl group, tetradecahydroanthracenyl group, tetrahydrophenanthrenyl group, octahydronaphthyl group and hexahydroindenyl group and the like, as well as bivalent groups corresponding thereto, preferably, C3-C8 cycloalkyl group.

The term "C6-C14 aryl group" used herein means an aryl group formed by 6 to 14 carbon atoms containing a monocyclic ring group, or a condensed ring group such as a bicyclic or a tricyclic ring group. Specific examples of this group include phenyl group, indenyl group, naphthyl group, azulenyl group, heptalenyl group, biphenyl group, indacenyl group, acenaphthylenyl group, fluorenyl group, phenalenyl group, phenanthrenyl group, anthracenyl group, cyclopentacyclooctenyl group or benzocyclooctenyl group and the like. The preferred "C6-C14 aryl group" is C6-C10 aryl group, that is to say, phenyl group, naphthyl group or indenyl group.

The term "C6-C14 arylene group" used herein means a bivalent group derived by further removing one hydrogen atom from the C6-C14 aryl group described above.

The term "5- to 14-membered heteroaryl group" used herein means a monocyclic, bicyclic or tricyclic heteroaryl group, whose number of atoms forming the ring is 5 to 14, and containing not less than one heteroatom from not less than one species selected from the group consisting of a nitrogen atom, a sulfur atom, and an oxygen atom, and containing 5- to 6-membered heteroaryl groups described below. Specific examples of this group include, 1) for instance, pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthylidinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, perimidinyl group, phenanthrolinyl group, phenazinyl group, imidazopyridinyl group, imidazopyrimidinyl group, pyrazolopyridinyl group and the like as a nitrogen-containing heteroaryl group; 2) thienyl group, benzothienyl group and the like as a sulfur-containing heteroaryl group; 3) furyl group, pyranyl group, benzofuryl group, isobenzofuryl group and the like as an oxygen-containing heteroaryl group; 4) thiazolyl group, isothiazolyl group, benzothiazolyl group, benzothiaziazolyl group, phenothiazinyl group, isoxazolyl group, furazanyl group, phenoxazinyl group, oxazolyl group, benzooxazolyl group, oxadiazolyl group, pyrazolooxazolyl group, imidazothiazolyl group, thienofuranyl group, furopyrrolyl group, pyridooxazinyl group and the like as a heteroaryl group whose structure contains not less than two different species of heteroatoms. A 5- to 10-membered heteroaryl group is preferable, that is to say, a monocyclic or a bicyclic heteroaryl group whose number of atoms forming the ring of the cyclic group is 5 to 10, containing not less than one heteroatom among the atoms forming the ring of the cyclic group. Specific examples of this group include 1) for instance, pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthylidinyl group, quinoxalinyl group, quinazolinyl group, cinnolinyl group, pteridinyl group, imidazotriazinyl group, pyrazinopyridazinyl group, imidazopyridinyl group, imidazopyrimidinyl group, pyrazolopyridinyl group and the like as a nitrogen-containing heteroaryl group; 2) thienyl group, benzothienyl group and the like as a sulfur-containing heteroaryl group; 3) furyl group, pyranyl group, benzofuryl group, isobenzofuryl group and the like as an oxygen-containing heteroaryl group; 4) thiazolyl group, isothiazolyl group, benzothiazolyl group, benzothiaziazolyl group, isoxazolyl group, furazanyl group, oxazolyl group, benzooxazolyl group, oxadiazolyl group, pyrazolooxazolyl group, imidazothiazolyl group, thienofuranyl group, furopyrrolyl group, pyridooxazinyl group and the like as a heteroaryl group whose structure contains not less than two different species of heteroatoms.

Pyrrolyl group, furyl group, thienyl group, pyridyl group, benzothienyl group, benzofuryl group, indolyl group, benzlyl group and indazolyl group are more preferred.

The term "5- to 14-membered heteroarylene group" used herein means a bivalent group which is derived by further removing one hydrogen atom from the 5- to 14-membered heteroaryl group described above, and which contains 5- to 6-membered heteroarylene group described below.

The term "5- to 14-membered heterocyclic group" used herein means a group:

1) whose number of atoms forming the ring of the cyclic group is 5 to 14;

2) containing not less than one heteroatom from not less than one species selected from the group consisting of a nitrogen atom, a sulfur atom and an oxygen atom among the atoms forming the ring of the cyclic group;

3) that may contain 1 to 3 carbonyl groups in the ring;

4) that is monovalent or bivalent;

5) that may be non-aromatic monocyclic, bicyclic or tricyclic heterocyclic, and containing a 5- to 6-membered heterocyclic group described below. Specific examples of this group include pyrrolidinyl group, pyrrolyl group, piperidyl group, piperidino group, piperazinyl group, imidazolyl group, pirazolidinyl group, imidazolidinyl group, morpholinyl group, morpholino group, tetrahydrofuryl group, tetrahydropyranyl group and the like, as well as the bivalent groups corresponding thereto, as well as groups derived from pyridone ring and non-aromatic condensed ring groups (groups derived from, for instance, phthalimide ring, succinimide ring and the like). Pyrrolidinyl group, pyrrolinyl group, piperidyl group, piperazinyl group, imidazolinyl group, pirazolidinyl group, imidazolidinyl group, morpholinyl group, tetrahydrofuryl group, tetrahydropyranyl group, aziridinyl group and the like are preferred.

The term "5- to 6-membered heteroaryl group" used herein means a monocyclic heteroaryl group, whose number of atoms forming the ring is 5 to 6, and containing 1 to 3 heteroatoms of not less than one species selected from the group consisting of a nitrogen atom, a sulfur atom and an oxygen atom, among the atoms forming the ring. Examples include pyrrolyl group, imidazolyl group, pyrazolyl group, triazolyl group, pyridyl group, pyridazinyl group, pyrimidinyl group, pyrazinyl group, triazinyl group, furyl group, thienyl group, thiazolyl group, oxazolyl group, isoxazolyl group and the like, the term "heteroaryl group" herein also includes pyridonyl group that may have a substituent on the nitrogen atom. Pyrrolyl group, pyridyl group, pyridonyl group, pyridazinyl group, pyrimidinyl group, pyrazinyl group, furyl group or thienyl group is preferred.

The term "5- to 6-membered heteroarylene group" used herein means a bivalent group derived by further removing one hydrogen atom from the 5- to 6-membered heteroaryl group described above.

The term "5- to 6-membered heterocyclic group" used herein means a monovalent or a bivalent heterocyclic group, whose number of atoms forming the ring is 5 to 6, and containing not less than one heteroatom selected from the group consisting of a nitrogen atom, a sulfur atom and an oxygen atom. Specifically, examples include piperidyl group, piperazinyl group, morpholinyl group, thiomorpholinyl group, tetrahydro-2-pyronyl group, tetrahydropyranyl group, tetrahydrothiopyranyl group, piperidin-2-onyl group, tetrahydrofuranyl group, tetrahydrothyenyl group, pyrrolidinyl group, tetrahydrofuran-2-onyl group, pyrrolidin-2-onyl group, group represented by the following formula:

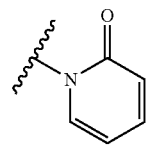

and the like, as well as bivalent groups corresponding thereto. Preferred examples of this "5- to 6-membered heterocyclic group" include piperidyl group, piperazinyl group, morpholinyl group, thiomorpholinyl group, tetrahydro-2-pyronyl group, tetrahydropyranyl group, tetrahydrothiopyranyl group, piperidine-2-onyl group, group represented by the following formula:

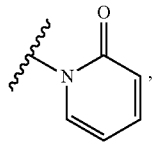

or bivalent groups corresponding thereto.

The term "C5-C6 carbocyclic group" used herein means a monovalent or a bivalent cyclic group formed by 5 to 6 carbon atoms, which may be saturated, partially saturated or unsaturated.

The term "C6-C14 aryl C1-C6 alkoxy group" used herein means a group resulting from the substitution of any hydrogen atom in the C1-C6 alkoxy group by the C6-C14 aryl group, and examples include benzyloxy group and the like.

Representative examples of the substituent as in "may have a substituent" include, in case no other particular expression is given, the group of substituent including:

(1) halogen atoms
(for instance, a fluorine atom, a chlorine atom, a bromine atom, an iodine atom and the like);
(2) hydroxyl groups;
(3) cyano groups;
(4) nitro groups;
(5) carboxyl groups;
(6) oxo groups;
(7) amino groups;
(8) C1-C6 alkyl groups
(for instance, methyl group, ethyl group, n-propyl group, iso-propyl group, n-butyl group, tert-butyl group, n-pentyl group, 1,1-dimethylpropyl group, 1,2-dimethylpropyl group, 2,2-dimethylpropyl group, 1-ethylpropyl group, 2-methylbutyl group, n-hexyl group and the like);
(9) C2-C6 alkenyl groups
(for instance, vinyl group, allyl group, 1-propenyl group, isopropenyl group, 2-methyl-1-propenyl group, 1-butenyl group and the like);
(10) C2-C6 alkynyl groups
(for instance, ethinyl group, 1-propynyl group, 2-propynyl group, 1-butynyl group, 2-butynyl group, 3-butynyl group, 1-ethynyl-2-propynyl group, 1-methyl-2-propynyl group and the like);
(11) C3-C8 cycloalkyl groups
(for instance, cyclopropyl group, cyclobutyl group, cyclopentyl group, cyclohexyl group, cycloheptyl group, cyclooctyl group and the like);
(12) C3-C8 cycloalkenyl groups
(for instance, cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl and the like);
(13) C1-C6 alkoxy groups
(for instance, methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group and the like);
(14) C1-C6 alkenyloxy groups
(for instance, vinyloxy group, aryloxy group, 1-propenyloxy group, isopropenyloxy group, 2-methyl-1-propenyloxy group, 1-butenyloxy group, 2-butenyloxy group, 3-butenyloxy group, 1-pentenyloxy group, 1-hexenyloxy group, 1,3-hexanedienyloxy group and the like);
(15) C1-C6 alkylthio groups
(for instance, methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-methylbutylthio group, n-hexylthio group, 1,3-dimethylbutylthio group and the like);
(16) C1-C6 alkenylthio groups
(for instance, vinylthio group, allylthio group, 1-propenylthio group, isopropenylthio group, 2-methyl-1-propenylthio group, 2-methyl-2-propenylthio group, 1-butenylthio group, 2-butenylthio group, 3-butenylthio group, 1-pentenylthio group, 1-hexenylthio group, 1,3-hexadienylthio group and the like);
(17) C1-C14 aryloxy groups
(for instance, phenoxy group and the like);
(18) C2-C7 acyl groups
(for instance, acetyl group, propionyl group, butyryl group and the like);
(19) C6-C14 aryl groups
(for instance, phenyl group, 1-naphthyl group, 2-naphthyl group and the like);
(20) 5- to 14-membered heterocyclic groups
(for instance, 1) pyrrolidinyl group, pyrrolinyl group, piperidyl group, piperazinyl group, imidazolinyl group, pirazolidinyl group, imidazolidinyl group, morpholinyl group, tetrahydrofuryl group, tetrahydropyranyl group, aziridinyl group, oxiranyl group and oxathiolanyl group; 2) groups derived from pyridone ring; 3) groups derived from condensed ring such as phthalimide ring and succinimide ring, and the like);
(21) 5- to 14-membered heteroaryl groups
(for instance, pyrrolyl group, pyridyl group, pyridazinyl group, pyrimidinyl group, pyrazinyl group, imidazolyl group, benzimidazolyl group, indolyl group, indazolyl group, quinolyl group, isoquinolyl group, thienyl group, benzothienyl group, furyl group, pyranyl group, benzofuryl group, thiazolyl group, benzothiazolyl group and the like);
(22) carbamoyl groups;
(23) sulfonyl groups having a C1-C6 alkyl group as substituent;
(24) sulfonamide groups;
(25) C1-C6 alkyl carbamoyl groups;
(26) C1-C6 alkoxycarbonyl groups;
(27) C1-C6 alkyl carbonyloxy groups;
(28) C1-C6 alkyl sulfonyl groups;
(29) C1-C6 alkylsulfinyl groups;
(30) formyl groups;
and the like, and "may have a substituent" indicates that 1 to 5 groups of not less than 1 species selected from the substituent group mentioned above may be present as a substituent.

In addition, the amino groups, the C1-C6 alkyl groups, the C2-C6 alkenyl groups, the C2-C6 alkynyl groups, the C3-C8 cycloalkyl groups, the C3-C8 cycloalkenyl groups, the C1-C6 alkoxy groups, the C1-C6 alkenyloxy groups, the C1-C6 alkylthio groups, the C1-C6 alkenylthio groups, the C1-C14 aryloxy groups, the C2-C7 acyl groups, the C6-C14 aryl groups, the 5- to 14-membered heterocyclic groups or the 5- to 14-membered heteroaryl groups, the carbamoyl groups, the sulfonyl groups having a C1-C6 alkyl group as substituent, or the sulfonamide groups of (7) to (24) mentioned above, which are enumerated as the substituent as in "may have a substituent", may be further substituted by 1 to 5 groups selected from the group consisting of:

(a) halogen atoms;
(b) hydroxyl groups;
(c) cyano groups;
(d) nitro groups;
(e) carboxyl groups;
(f) an oxo group;
(g) amino groups;
(h) C1-C6 alkyl groups;
(i) C2-C6 alkenyl groups;
(j) C2-C6 alkynyl groups;
(k) C3-C8 cycloalkyl groups;
(l) C3-C8 cycloalkenyl groups;
(m) C1-C6 alkoxy groups;
(n) C1-C6 alkenyloxy groups;
(o) C1-C6 alkylthio groups;
(p) C1-C6 alkenylthio groups;
(q) C1-C14 aryloxy groups;
(r) C2-C7 acyl groups;
(s) C6-C14 aryl groups;
(t) C5-C14 heterocyclic groups;
(u) 5- to 14-membered heteroaryl groups;
(v) carbamoyl groups;
(w) sulfonyl groups having C1-C6 alkyl group as a substituent; and
(x) sulfonamide groups described in (1) to (24) mentioned above.

The substituents or partial structures in the compound according to the present invention represented by formula (I) will be described in the following.

T represents a single bond, a C1-C4 alkylene group which may have a substituent, a C2-C4 alkenylene group which may have a substituent, or a C2-C4 alkynylene group which may have a substituent.

Among these, the single bond or the C1-C4 alkylene group which may have the substituent is preferred as T, and among the C1-C4 alkylene groups which may have the substituent, methylene group, ethylene group, trimethylene group, 1,1-dimethylethylene group, 2-methylethylene group and the like are preferred.

A represents a single bond, a bivalent 5- to 14-membered heterocyclic group which may have a substituent, a 5- to 14-membered heteroarylene group which may have a substituent, a bivalent C3-C14 carbocyclic group which may have a substituent, or a C6-C14 arylene group which may have a substituent.

Among these, the single bond, a bivalent 5- to 6-membered heterocyclic group which may have a substituent, a 5- to 6-membered heteroarylene group which may have a substituent, a 5- to 6-membered carbocyclic group which may have a substituent bivalent, or a phenylene group that may have a substituent is preferred as A. Here, for the 5- to 6-membered heteroarylene group which may have the substituent or the phenylene group which may have a substituent, a ring forming the heteroarylene group or phenylene group having a structure represented by the following formula (IV):

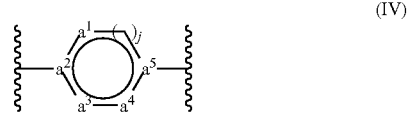

(wherein j stands for 0 or 1, $a^1$, $a^3$, and $a^4$ independently represent —CH═, —N═, —NH—, —S—, or —O—, and $a^2$ and $a^5$ represent >C═) is preferred, specifically, a structure represented by the following formulae:

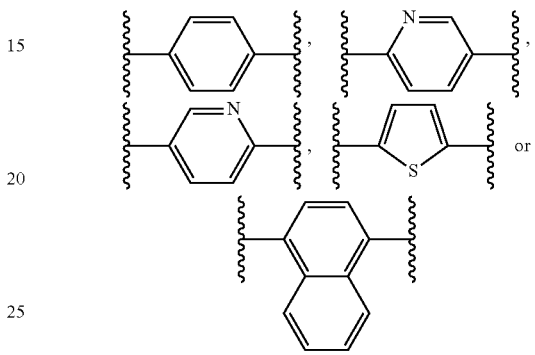

is more preferred, in particular, a phenylene group which may have a substituent is preferred.

Here, when A is a cyclic group and "may have a substituent", as the "substituent", a halogen atom, a C1-C6 alkyl group, a C3-C8 cycloalkyl group, a C1-C6 alkoxy group, or a trifluoromethyl group is preferred, a halogen atom is more preferred, in particular, a fluorine atom is preferred.

Y represents —(CH$_2$)$_l$—V—(CH$_2$)$_k$— {wherein V represents a single bond, —(CR$^f$R$^g$)$_g$—, —(CR$^f$R$^g$)$_g$—O—, —O—, —S—, —S(═O)—, —SO$_2$—, —SO$_2$NR$^c$, —NR$^c$SO$_2$—, —C(═O)—, —C(═O)—CH$_2$—O—, —C(═O)O—, —OC(═O)—, —NR$^c$—, —NR$^c$—C(═O)—, —C(═O)—NR$^c$—, —NR$^c$—C(═O)O—, or —OC(═O)—NR$^c$— (R$^c$ represents a hydrogen atom, a C1-C6 alkyl group which may have a substituent, a C2-C6 alkenyl group which may have a substituent, a C2-C7 acyl group which may have a substituent, a C6-C14 aryl group which may have a substituent, a 5- to 14-membered heteroaryl group which may have a substituent, a C3-C8 cycloalkyl group which may have a substituent, or a 5- to 14-membered heterocyclic group which may have a substituent, or, when A is a group other than the single bond, R$^c$ may form, together with A, a 5- to 8-membered ring containing 1 to 2 heteroatoms, while R$^f$ and R$^g$ independently represent a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent, or a 5- to 14-membered heteroaryl group which may have a substituent, and g stands for an integer from 0 to 2), l and k independently stand for an integer from 0 to 6, the sum of l and k being an integer from 0 to 6}.

Among these, —(CH$_2$)$_l$—V—(CH$_2$)$_k$— {wherein l and k stand for an integer from 0 to 2, the sum of l and k being an integer from 0 to 2, V represents a single bond, —(CR$^f$R$^g$)$_g$—, —O—, —C(=O)—, —NR$^c$, or —C(=O)—NR$^c$— (wherein g, R$^f$, R$^g$, and R$^c$ are the same meaning as the definition described above)} is preferred as Y, in particular, a single bond, —CH$_2$—, —(CH$_2$)$_2$—, —O—, —C(=O)—, —CH$_2$—NR$^c$—, —(CH$_2$)$_2$—NR$^c$—, —NR$^c$—, or —C(=O)—NR$^c$— (R$^c$ is the same meaning as the definition described above) is more preferable. Here, for R$^C$, a hydrogen atom, a C1-C6 alkyl group which may have a substituent selected from the Substituent Group a mentioned below, a C2-C7 acyl group which may have a substituent selected from the Substituent Group a mentioned below, or a C3-C8 cycloalkyl group which may have a substituent selected from the Substituent Group a mentioned below is preferred, a hydrogen atom, methyl group, ethyl group, 2-fluoroethyl group, 2-benzyloxyethyl group, 2-hydroxyethyl group, 2,2,2-trifluoroethyl group, cyclopropylmethyl group, 2-methoxyethyl group, n-propyl group, or iso-propyl group is more preferred, and in particular ethyl group or 2-hydroxyethyl group is preferred.

Substituent Group a: a group consisting of hydroxyl group, a halogen atom, a C1-C6 alkyl group, a C3-C8 cycloalkyl group, a C1-C6 alkoxy group and a C6-C14 aryl C1-C6 alkoxy group.

As mentioned above, "when A is a group other than the single bond, R$^c$ may form, together with A, a 5- to 8-membered ring containing 1 to 2 heteroatoms", which means that when A is a cyclic group, R$^c$ can be bonded to an atom which is on the A ring to form a 5- to 8-membered ring containing 1 to 2 heteroatoms (the 5- to 8-membered ring may have a substituent and may be saturated, partially saturated or unsaturated), examples include the cases where a partial structure -A-Y— is the partial structure represented by the following formulae:

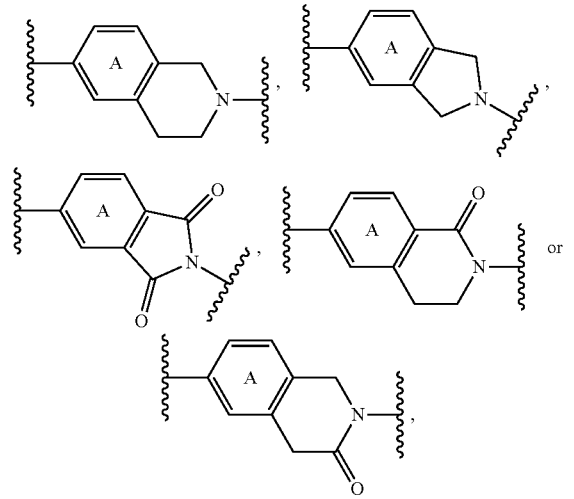

and among these, the case where the partial structure -A-Y— is the partial structure represented by the following formulae is preferred.

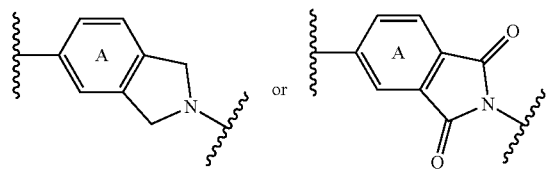

Z represents —(CH$_2$)$_{l'}$—V'—(CH$_2$)$_{k'}$— {wherein V' represents a single bond, —(CR$^f$R$^g$)$_g$—, —(CR$^f$R$^g$)$_g$—CH$_2$— O—, —O—, —S—, —S(=O)—, —SO$_2$—, —SO$_2$NR$^c$—, —NR$^c$SO$_2$—, —C(=O)—, —C(=O)—CH$_2$—O—, —C(=O)O—, —OC(=O)—, —NR$^{c'}$—, —NR$^{c'}$—C (=O)—, —C(=O)—NR$^{c'}$—, —NR$^{c'}$—C(=O)O—, or —OC(=O)—NR$^{c'}$— (wherein R$^{c'}$ represents a hydrogen atom, a C1-C6 alkyl group which may have a substituent, a C2-C6 alkenyl group which may have a substituent, a C2-C7 acyl group which may have a substituent, a C6-C14 aryl group which may have a substituent, a 5- to 14-membered heteroaryl group which may have a substituent, a C3-C8 cycloalkyl group which may have a substituent, or a 5- to 14-membered heterocyclic group which may have a substituent, while R$^{f'}$ and R$^{g'}$ independently represent a hydrogen atom, hydroxyl group, a halogen atom, formyl group, cyano group, carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent, or a 5- to 14-membered heteroaryl group which may have a substituent, or, R$^{f'}$ and R$^{g'}$ may form, together with the carbon atom which R$^{f'}$ and R$^{g'}$ are bonded to, a 5- to 6-membered Spiro ring, g' stands for an integer from 0 to 2), l' and k' independently stand for an integer from 0 to 6, the sum of l' and k' being an integer from 0 to 6}.

Among these, for Z, the single bond or —(CH$_2$)$_{l'}$—V'—(CH$_2$)$_{k'}$— {wherein l' and k' stand for an integer from 0 to 3, the sum of l' and k' being an integer from 0 to 3, V' represents the single bond, —(CR$^{f'}$R$^{g'}$)$_g$—CH$_2$—O—, —O—, —C(=O)—CH$_2$—O—, or —NR$^{c'}$— (wherein g', R$^{c'}$, R$^{f'}$ and R$^{g'}$ are the same meaning as the definition described above)} is preferred.

Z and T may also form a partial structure -T-Z— together with each other; for the partial structure, a single bond or -T-V'— {wherein T represents a single bond or a C1-C4 alkylene group, V' represents a single bond, —(CR$^{f'}$R$^{f'}$)$_g$— CH$_2$—O—, —O—, —C(=O)—CH$_2$—O—, or —N$^{c'}$— (wherein g', R$^{c'}$, R$^{f'}$ and R$^{g'}$ are the same meaning as the definition described above)} is preferred, and the single bond, methylene group, ethylene group, trimethylene group, and a partial structure represented by the following formulae:

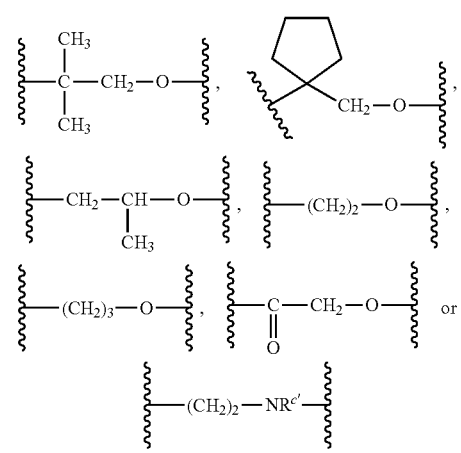

are more preferred.

Ring G represents, together with Q¹ and Q², a phenylene group, a bivalent C5-C6 carbocyclic group, a 5- to 6-membered heteroarylene group or a bivalent 5- to 6-membered heterocyclic group, which may condense with a 5- to 6-membered ring which may have a heteroatom, Q¹ and Q² independently representing a carbon atom or a nitrogen atom; specifically, examples include 5- to 6-membered saturated or unsaturated carbocyclic groups such as cyclopentane, cyclohexane, cyclopentene, cyclohexene and the like, 5- to 6-membered saturated or unsaturated heterocyclic groups such as pyrrolidine, imidazolidine, pyrroline, pyrazolidine, piperidine and piperazine and the like, benzene, or bivalent 5- to 6-membered heteroaryl groups such as pyridine, pyrazine, pyrimidine, pyridazine, thiophene, furan, pyrrole, imidazole, pyrazole, thiazole, oxazole and the like. Examples also include the 5- to 6-membered rings which may form by condensation, for instance, a 8- to 14-membered bicyclic or tricyclic condensed ring that may contain a heteroatom such as benzodioxole and the like.

Among these, the cases where ring G, together with Q¹ and Q², represent a phenylene group, a pyridylene group, a piperidylene group, a thienylene group, a cyclohexylene group, or a group represented by the following formula:

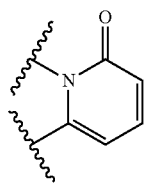 [SMILES: *c1cccc(=O)n1*]

are preferred, the cases where ring G represents a group represented by the following formulae:

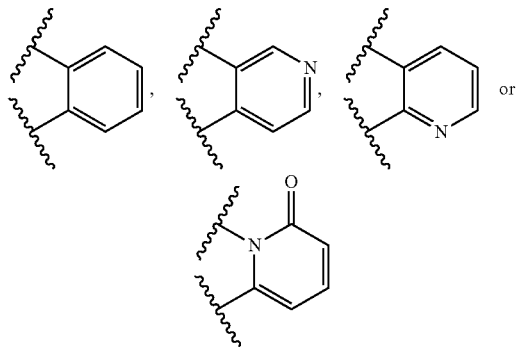

are more preferred, and the case where ring G represents a group represented by the following formula:

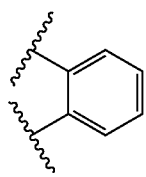 [SMILES: *c1ccccc1*]

is even more preferred.

$R^a$ and $R^b$ independently represents a hydrogen atom, a C1-C6 alkyl group which may have a substituent, a C2-C6 alkenyl group which may have a substituent, a C2-C6 alkynyl group which may have a substituent, a C3-C8 cycloalkyl group which may have a substituent, a C6-C14 aryl group which may have a substituent, a 5- to 14-membered heterocyclic group which may have a substituent, a 5- to 14-membered heteroaryl group that which have a substituent, a C6-C14 arylalkyl group which may have a substituent, a 5- to 14-membered heteroarylalkyl group which may have a substituent, or C1-C6 alkoxy group which may have a substituent, or, when $R^a$ and $R^b$ are bonded to one another, they may form, together with the nitrogen atom that is adjacent to $R^a$ and $R^b$, a 4- to 10-membered single ring, double ring, or Spiro ring which may have a substituent, or, when $R^a$ and/or $R^b$ are/is bonded to T, they may form, together with the nitrogen atom $R^a$ and $R^b$ are bonded to, a 5- to 10-membered single ring or double ring which may have a substituent, or, when T, Z, A and Y are all single bonds, $R^a$ or $R^b$ may be bonded to atoms forming ring G to form a condensed ring.

Here, when "$R^a$ and $R^b$ independently represent a hydrogen atom, a C1-C6 alkyl group which may have a substituent, a C2-C6 alkenyl group that which may have a substituent, a C2-C6 alkynyl group which may have a substituent, a C3-C8 cycloalkyl group which may have a substituent, a C6-C14 aryl group which may have a substituent, a 5- to 14-membered heterocyclic group which may have a substituent, a 5- to 14-membered heteroaryl group which may have a substituent, a C6-C14 arylalkyl group which may have a substituent, a 5- to 14-membered heteroarylalkyl group which may have a substituent, a C1-C6 alkoxy group which may have a substituent, or a C2-C7 acyl group which may have a substituent", it is preferred that $R^a$ and $R^b$ specifically and independently represent a hydrogen atom, methyl group, ethyl group, n-propyl group, iso-propyl group, n-butyl group, iso-butyl group, tert-butyl group, benzyl group, phenethyl group, cyclopropylmethyl group, 2-fluoroethyl group, 2-methoxyethyl group, 3-methoxypropyl group, 2-methylthioethyl group, 2-ethoxyethyl group, 2-pyridylmethyl group, 3-pyridylmethyl group, 4-pyridylmethyl group, cyclopropyl group, cyclobutyl group, cyclohexyl group, allyl group, phenyl group, tert-butoxycarbonyl group, a group represented by the following formulae:

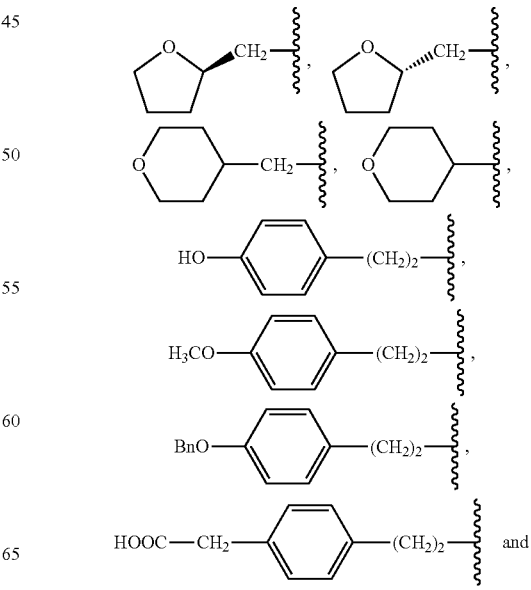

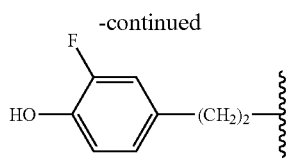

and the like. It is more preferred that $R^a$ and $R^b$ independently represent a hydrogen atom, methyl group, ethyl group, n-propyl group, iso-propyl group, n-butyl group, iso-butyl group, tert-butyl group, benzyl group, phenethyl group, cyclopropylmethyl group, 2-fluoroethyl group, 2-methoxyethyl group, 3-methoxypropyl group, 2-methylthioethyl group, 2-ethoxyethyl group, 2-pyridylmethyl group, 3-pyridylmethyl group, 4-pyridylmethyl group, cyclopropyl group, cyclobutyl group, cyclohexyl group, allyl group, phenyl group, or a group represented by the following formula:

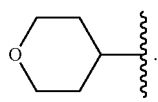

In the case "when $R^a$ and $R^b$ are bonded to each other, they may form, together with the nitrogen atom that is adjacent to $R^a$ and $R^b$, a 4- to 10-membered single ring, double ring, or Spiro ring that may have a substituent", as the ring that may be formed by the partial structure mentioned below in formula (I):

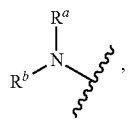

examples include 4- to 8-membered single rings (which may have a substituent, a portion of the ring may be unsaturated, and may further contain 1 to 2 heteroatoms) represented by the following formulae:

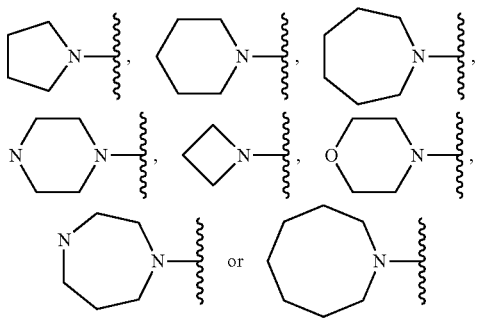

or, for instance, 6- to 10-membered double rings (which may have a substituent, a portion of the ring may be unsaturated, and may further contain 1 to 2 heteroatoms) represented by the following formulae:

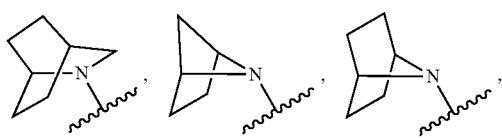

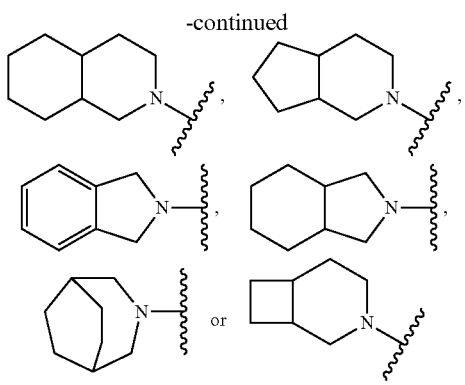

or, for instance, 7- to 10-membered Spiro rings (which may have a substituent, a portion of the ring may be unsaturated, and may further contain 1 to 2 heteroatoms) represented by the following formulae:

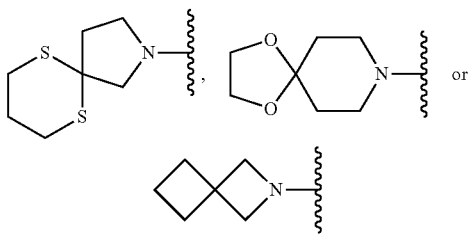

Among these, the partial structure represented by the following formulae:

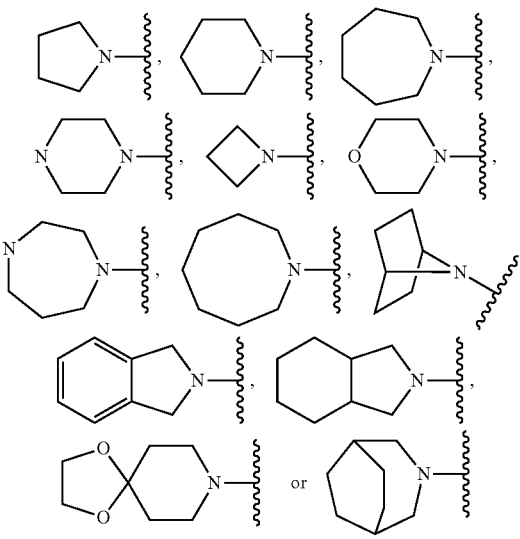

is preferred. Note that, 1 to 5 substituents may be present on the atoms of the ring to be formed, and examples of preferred substituents include a C1-C6 alkyl group, a hydroxyl group and the like.

In the case "when $R^a$ and/or $R^b$ are/is bonded to T, they may form, together with the nitrogen atom $R^a$ and $R^b$ are bonded to, a 5- to 10-membered single ring or double ring that may have a substituent", examples of ring in formula (I) that may be formed by the partial structure mentioned below:

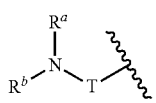

include 5- to 10-membered single ring or double ring (either may have a substituent, a portion of the ring may be unsaturated, and may further contain 1 to 2 heteroatoms) represented by the following formulae:

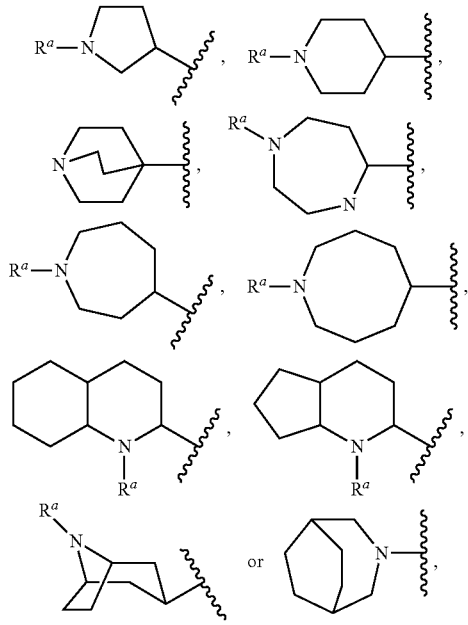

and preferably the partial structure represented by

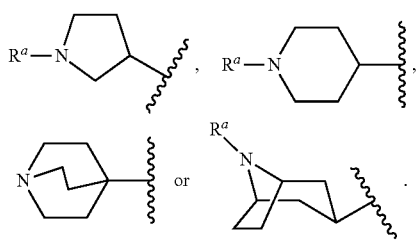

In the case "when T, Z, A and Y are all single bonds, $R^a$ or $R^b$ may be bonded to atoms forming ring G to form a condensed ring", examples of ring in formula (I) that may be formed by the partial structure mentioned below

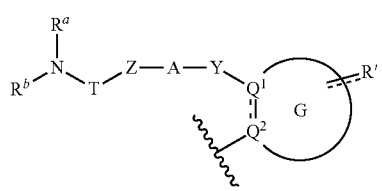

include 5- to 8-membered ring which may have a substituent, a portions of whose ring may be saturated or unsaturated, and may have 1 to 2 heteroatoms, and specifically includes the partial structure represented by the following formulae:

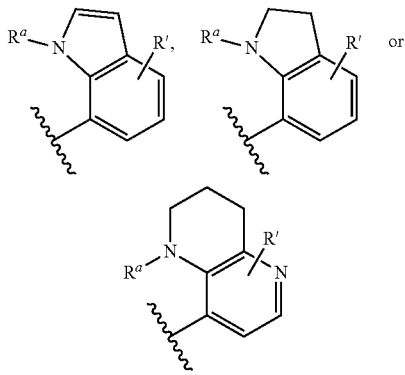

Among these, it is preferred that $R^a$ is a C1-C6 alkyl group which may have 1 to 3 substituents selected from Substituent Group b mentioned below or a C3-C8 cycloalkyl group which may have 1 to 3 substituents selected from Substituent Group b mentioned below.

Substituent Group b: a group consisting of a halogen atom, a C1-C6 alkyl group, a 5- to 14-membered heteroaryl group, a C6-C14 aryl group, hydroxyl group, a C1-C6 alkoxy group and a 5- to 14-membered heterocyclic group.

W represents a single bond, $-(CR^dR^e)_f-CHX-$, $-CHX-(CR^dR^e)_f-$, $-CR^d=CX-$, $-CX=CR^d-$, $-C\equiv C-$, $-(CR^dR^e)_f-NX-$, $-NX-(CR^dR^e)_f-$, $-NR^d-CHX-$, $-CHX-NR^d-$, $-N=CX-$, $-CX=N-$, $-C(=O)-CR^dX-$, $-CR^dX-C(=O)-$, $-C(=O)-NX-$, $-NX-C(=O)-$, $-S-CR^dX-$, $-CR^dX-S-$, $-S-NX-$, $-NX-S-$, $-O-NX-$, $-NX-O-$, $-O-CR^dX-$, $-CR^dX-O-$, $-CR^dX-$, or a group selected from the group consisting of the following formulae:

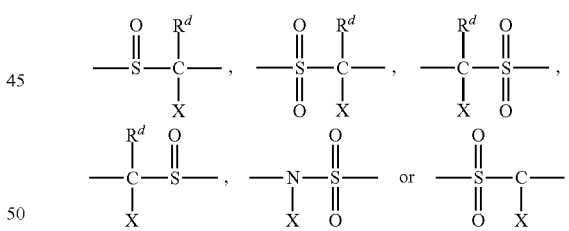

(wherein $R^d$ and $R^e$ respectively have the same meaning as the definition of $R^f$ and $R^g$ described above, X represents a hydrogen atom, hydroxyl group, a halogen atom, formyl group, cyano group, carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent, or a 5- to 14-membered heteroaryl group which may have a substituent, f has the same meaning as the definition of g described above), or a group represented by the following formula:

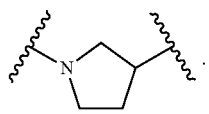 [SMILES: *C1CCN(*)C1]

Among these, for W, a single bond, —(CR$^d$R$^e$)$_f$—CHX—, —CHX—(CR$^d$R$^e$)$_f$—, —CR$^d$=CX—, —C≡C—, —N=CX— (wherein R$^d$, R$^e$, X and f are the same meaning as the definition described above), or a group represented by the following formula:

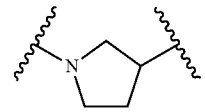

is preferred.

R' represents 1 to 4 independent hydrogen atoms, oxygen atoms, sulfur atoms, hydroxyl groups (which may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C2-C7 acyl groups which may have a substituent, C3-C8 cycloalkylthio groups which may have a substituent, C6-C14 aryl groups which may have a substituent, or 5- to 14-membered heteroaryl groups which may have a substituent, or, when R' is in the number of 2 to 4, R' may be bonded to one another to form a 5- to 8-membered ring which may have a substituent, or, when W represents any of —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O—, or —CR$^d$X—, R' may form, together with X, a 5- to 8-membered ring which may have a substituent and which may contain 1 to 2 heteroatoms.

Here, when R' "represents 1 to 4 independent hydrogen atoms, oxygen atoms, sulfur atoms, hydroxyl groups (which may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C2-C7 acyl groups which may have a substituent, C3-C8 cycloalkylthio groups which may have a substituent, C6-C14 aryl groups which may have a substituent, or 5- to 14-membered heteroaryl groups which may have a substituent", a hydrogen atom, hydroxyl group (which may be further protected by a protecting group), halogen atoms, C1-C6 alkyl groups which may have a substituent, C1-C6 alkoxy groups which may have a substituent (2 alkoxy groups which be bonded to form a 5- to 6-membered ring), or C2-C7 alkylcarbonyloxy groups which may have a substituent are preferred, hydrogen atoms, hydroxyl groups, fluorine atoms, trifluoromethyl groups, or methoxy groups are more preferred.

"When R' is in the number of 2 to 4, R' may be bonded to one another to form a 5- to 8-membered ring that may have a substituent" also means a ring may be formed, which may have a substituent, and which may have aromaticity, a portion of whose ring may be unsaturated and which may have 1 to 2 heteroatoms on the ring. Examples include a partial structure represented by the following formulae:

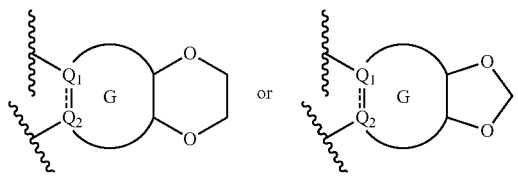

and the partial structure represented by the following formula:

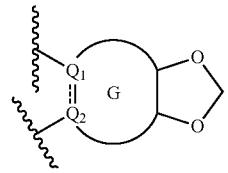

is preferred.

"When W represents any of —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O—, or —CR$^d$X—, R' may form, together with X, a 5- to 8-membered ring which may have a substituent, and which may contain 1 to 2 heteroatoms" also means that R' on ring G and X may form, together with ring G, a condensed ring. That is to say, examples of the partial structure in formula (I) represented by the following formula:

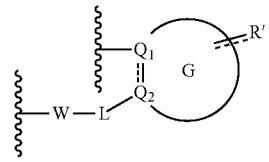

include the partial structure represented by the following formulae:

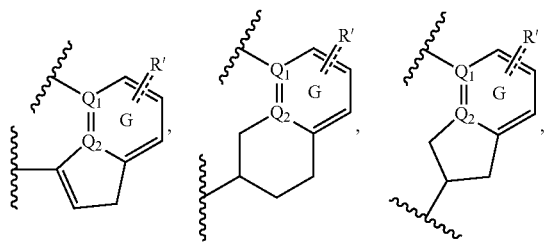

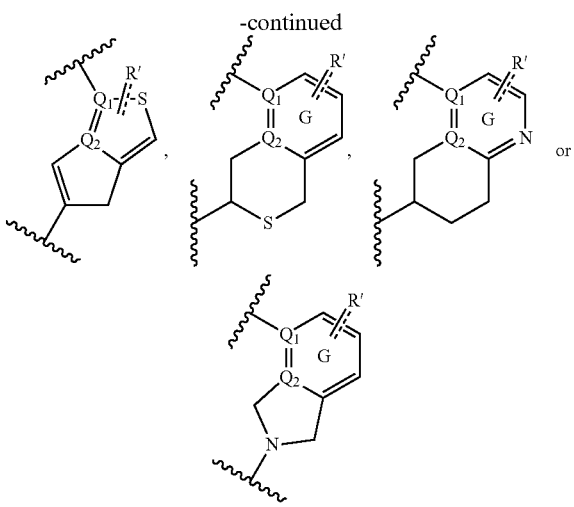

(the above partial structure may have a substituent, may have 1 to 2 heteroatoms as atoms forming the ring, and a portion of the ring may be unsaturated).

Among these, the structure represented by the following formulae:

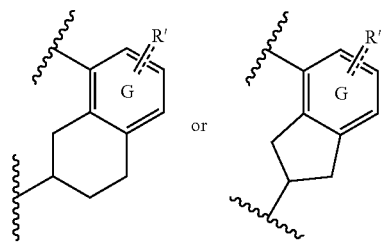

is preferred, and hydroxyl group or methoxy group is preferred as substituent that these structures may have.

R" represents 1 to 4 independent hydrogen atoms, hydroxyl groups (which may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C2-C7 acyl groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C3-C8 cycloalkylthio groups which may have a substituent, C6-C14 aryl groups which may have a substituent, or 5- to 14-membered heteroaryl groups which may have a substituent, or, when R" is in the number of 2 to 4, R" may be bonded to one another to form a 5- to 8-membered ring which may have a substituent.

Here, when R" "represents 1 to 4 independent hydrogen atoms, hydroxyl groups (which may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C2-C7 acyl groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C3-C8 cycloalkylthio groups which may have a substituent, C6-C14 aryl groups which may have a substituent, or 5- to 14-membered heteroaryl groups which may have a substituent" hydrogen atoms, hydroxyl groups (which may be further protected by a protecting group), halogen atoms, C1-C6 alkyl groups which may have a substituent, or C1-C6 alkoxy groups which may have a substituent are preferred, and hydroxyl groups are more preferred.

"When R" is in the number of 2 to 4, R" may be bonded to one another to form a 5- to 8-membered ring which may have a substituent" also means that a ring may be formed, which may have a substituent, and which may have aromaticity, a portion of whose ring may be unsaturated and which may have 1 to 2 heteroatoms on the ring. Examples include the partial structure represented by the following formulae:

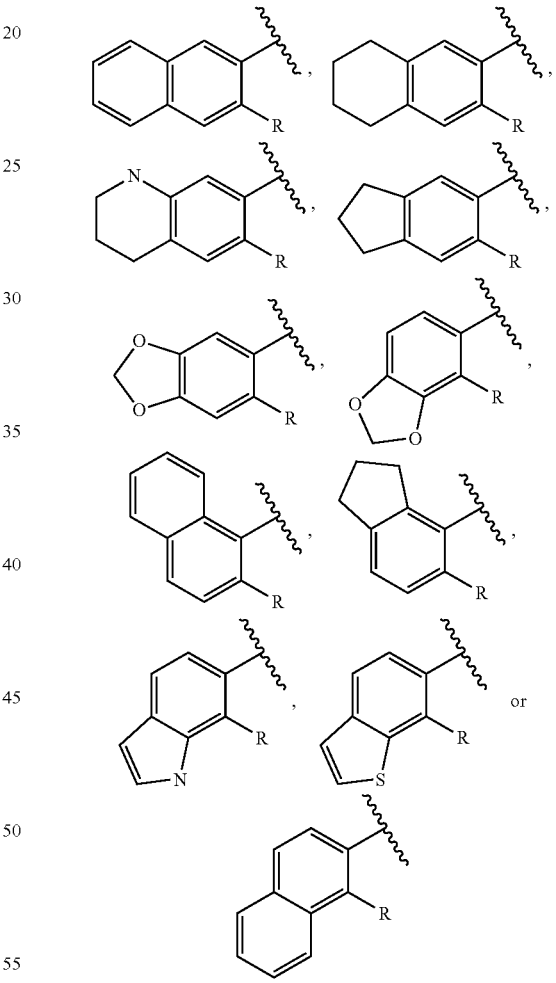

which may have a substituent, and the like, and the partial structure represented by the following formulae:

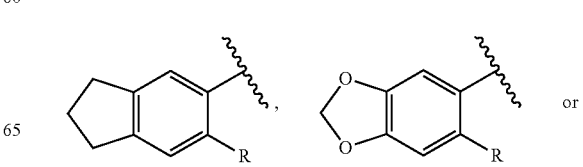

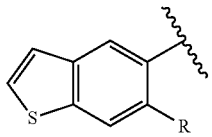

which may have a substituent such as hydroxyl group (which may be further protected by a protecting group), oxo group and hydroxyimino group are preferred.

R represents a hydrogen atom, hydroxyl group, a halogen atom, formyl group, cyano group, carboxyl group, carbamoyl group, a C1-C6 alkyl group which may have a substituent, a C2-C6 alkenyl group which may have a substituent, a C1-C6 alkoxy group which may have a substituent, an amino group which may have a substituent, a C2-C7 acyl group which may have a substituent, a C1-C6 alkylthio group which may have a substituent, a C3-C8 cycloalkyl group which may have a substituent, a C3-C8 cycloalkyloxy group which may have a substituent, a C2-C7 alkylcarbonyloxy group which may have a substituent, a C3-C8 cycloalkylthio group which may have a substituent, a C6-C14 aryl group which may have a substituent, or 5- to 14-membered heteroaryl group which may have a substituent, or, when W represents —(CR$^d$R$^e$)$_f$— CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, or —CR$^d$X—O—, R may form, with X, form a 5- to 7-membered ring, which may contain 1 to 2 heteroatoms, and which may have a substituent.

Here, when R represents "1 to 4 independent hydrogen atoms, hydroxyl groups, halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C2-C7 acyl groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C3-C8 cycloalkylthio groups which may have a substituent, C6-C14 aryl groups which may have a substituent, or 5- to 14-membered heteroaryl groups which may have a substituent", hydrogen atoms, hydroxyl groups, halogen atoms, C1-C6 alkyl groups which may have a substituent, or C1-C6 alkoxy groups which may have a substituent are preferred, and hydrogen atoms are more preferred.

"When W represents —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, or —CR$^d$X—O—, R may form, with X, a 5- to 7-membered ring, which may contain 1 to 2 heteroatoms, and which may have a substituent" also means that R may form, with X, a condensed ring together with a benzene ring to which R is bonded. Specifically, this means that the partial structure in formula (I) represented by the following formula:

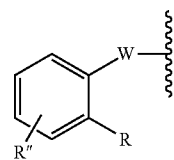

takes the from of the partial structure represented by the following formula:

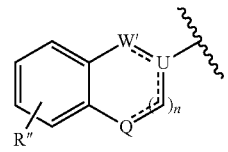

{wherein W' represents —(CR$^d$R$^e$)$_{f'}$—, —CR$^d$=, —C(=O)—, —NR$^d$—, —N=, —S—, or —O— (wherein R$^d$ and R$^e$ has the same meaning as the definition described above, and f represents 1 or 2), U represents >CR$^{d'}$—, >C=, or >N— (wherein R$^{d'}$ has the same meaning as the definition of R$^d$ described above), Q represents —(CR$^{d''}$R$^{e''}$)$_{f''}$—, —CR$^{d''}$=, —C(=O)—, —NR$^{d''}$—, —N=, —S—, or —O— (wherein R$^{d''}$ and R$^{e''}$ have the same meaning as the definitions of R$^d$ and R$^e$ described above, and f'' has the same meaning as of the definition of f described above), and n stands for an integer from 0 to 2}, and preferred examples include the partial structure group A mentioned below.

Partial Structure Group A: a group consisting of:

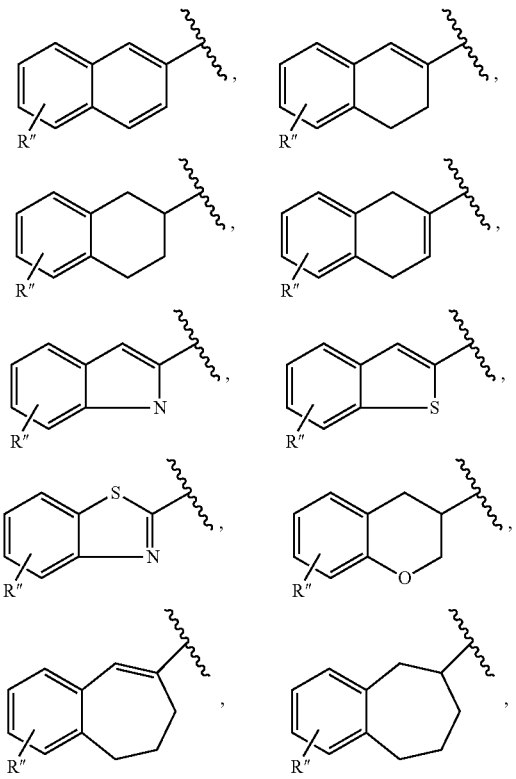

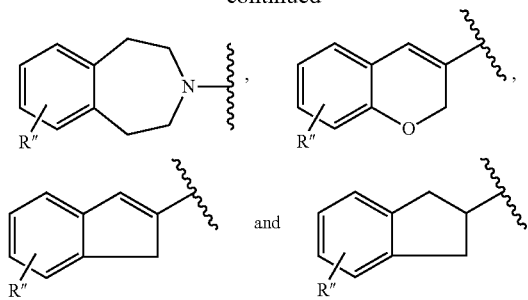

Among these, partial structure group B and partial structure group C mentioned below are more preferred.

Partial Structure Group B: a group consisting of:

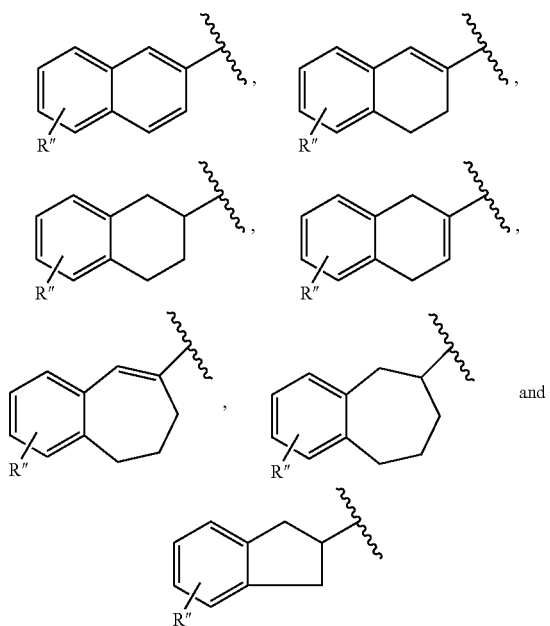

Partial Structure Group C: a group consisting of:

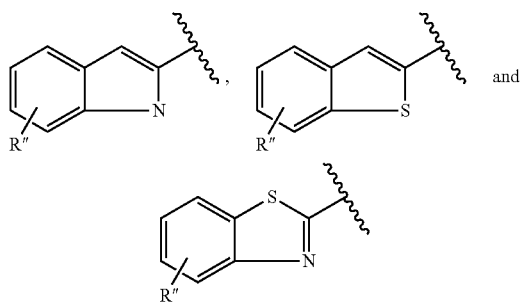

The substituents of the ring structure adjacent to the benzene ring substituted with R″ in each partial structure from partial structure group A, group B and group C are $R^d$, $R^{d'}$, $R^{d''}$, $R^e$, $R^{e'}$ and $R^{e''}$, each independently represents a hydrogen atom, hydroxyl group, a halogen atom, formyl group, cyano group, carboxyl group, C1-C6 alkyl group which may have a substituent, a C2-C6 alkenyl group which may have a substituent, a C1-C6 alkoxy group which may have a substituent, an amino group which may have a substituent, a C1-C6 alkylthio group that may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent, or a 5- to 14-membered heteroaryl group which may have a substituent. Among these, a hydrogen atom, hydroxyl group, a halogen atom, a C1-C6 alkyl group which may have a substituent, or a C1-C6 alkoxy group which may have a substituent is preferred, a hydrogen atom, hydroxyl group, a fluorine atom, a chlorine atom, methyl group, or methoxy group is more preferred.

L represents a single bond, a C1-C4 alkylene group which may have a substituent, a C2-C4 alkenylene group which may have a substituent, or a C2-C4 alkynylene group which may have a substituent, among these, the single bond or the C1-C4 alkylene group is preferred, the single bond or a C1-C2 alkylene group is more preferred.

Here, for partial structure W-L, a single bond, —$CR^dX$— $(CH_2)_q$— (wherein $R^d$ and X have the same meaning as the definition described above, and q stands for an integer from 0 to 4), —C≡C—, or —CH=CH— is preferred, among these, the single bond, a C1-C4 alkylene group, —C≡C—, or —CH=CH— is more preferred, and the single bond, methylene group, ethylene group, —C≡C—, —CH=CH—, or a group represented by the following formula:

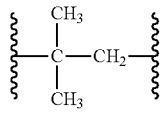

is particularly preferred.

The compound according to the present invention represented by the formula (I):

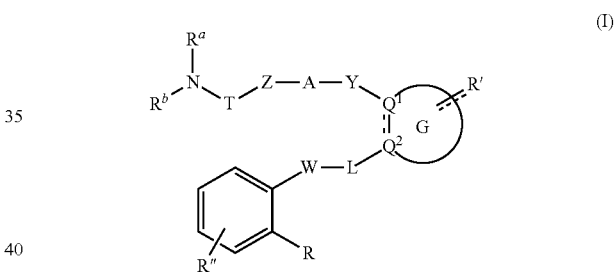

(wherein each substituent and each partial structure have the same meaning as the definitions described above) can be prepared by, for instance, such methods as mentioned below; however the methods are not limited to these.

[General Preparation Method 1]

A representative method for preparing the compound represented by formula (I) according to the present invention is shown below:

General Preparation Method 1

COUPLING REACTION

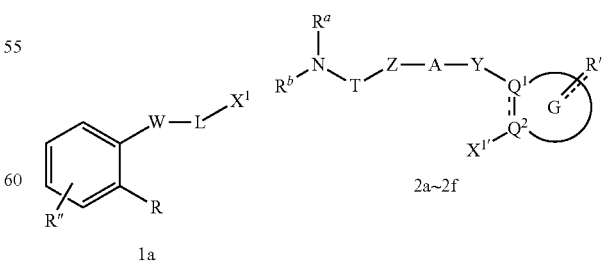

↓

35
-continued
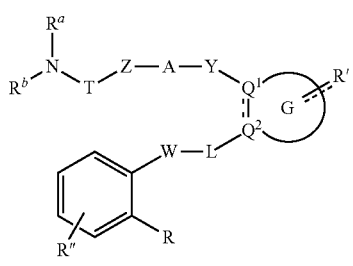
3
| MODIFICATION OF R' AND/OR R''
36
-continued
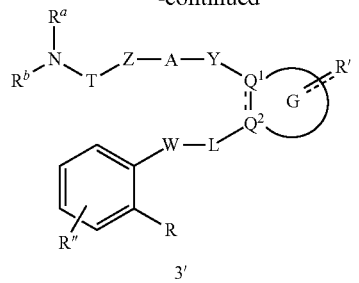
3'
$X^1, X^{1'}$ = H, Cl, Br, I, OTf, $N_2^+X''$ ($X''$ = Cl, Br, $BF_4$), $B(OR^1)_2$, $Sn(R^1)_3$
$R^1$ = H, Me, Et, n-Pr, i-Pr, n-Bu
General Preparation Method 1-1
(Synthesis of 2)
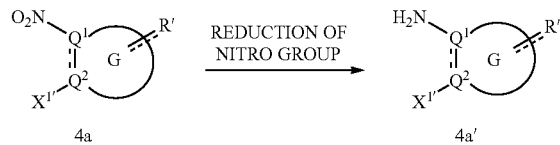
4a → 4a'
REDUCTION OF NITRO GROUP
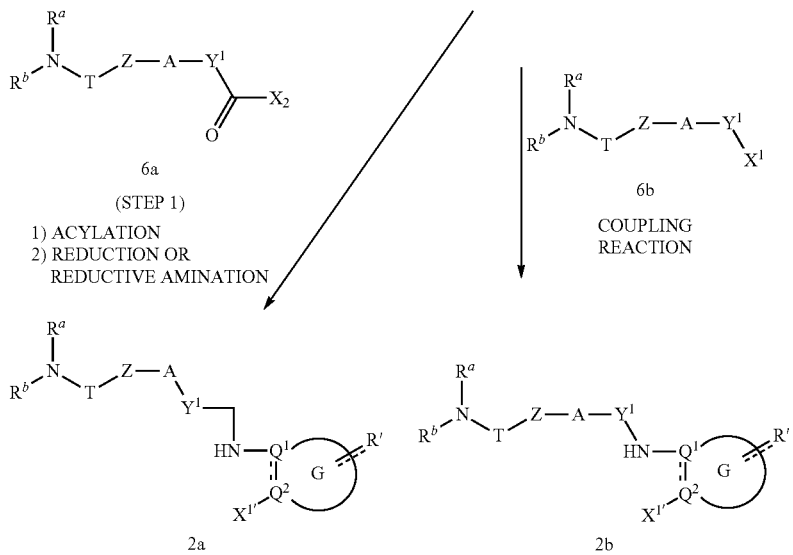
2a  2b
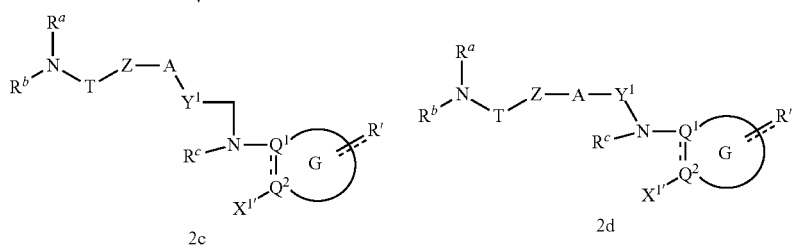
2c  2d
$X^2$ = H, Cl, OH
$Y^1$ = Y General Preparation Method 1-2
(Synthesis of 2)

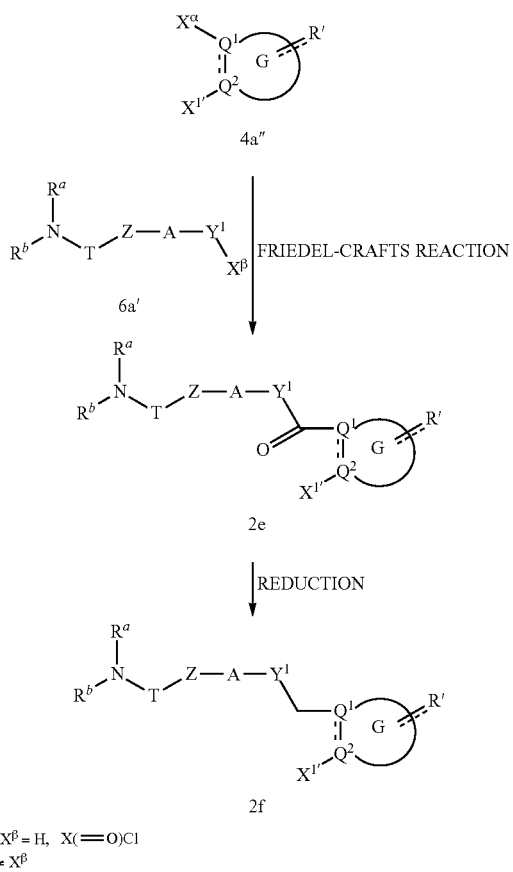

$X^\alpha, X^\beta = H$, $X(=O)Cl$
$X^\alpha \ne X^\beta$ (wherein T, Z, A, Y, ring G, $Q^1$, $Q^2$, $R^a$, $R^b$, $R^c$, R, R', R", W, and L have the same meanings as the definition of formula (I), $X^1$ and $X^{1'}$ represent a hydrogen atom, a halogen atom such as a chlorine atom, a bromine atom or an iodine atom, sulfonate such as triflate, a diazonium salt ($N_2^+X^{"-}$; wherein X" represents chloride, bromide or tetrafluoroborate), boronic acid or boronic acid esters ($B(OR^1)_2$; wherein $R^1$ represents a hydrogen atom, a lower alkyl group such as methyl group, ethyl group, n-propyl group, iso-propyl group or n-butyl group) or trialkyltins ($Sn(R^1)_3$; wherein $R^1$ has the same meaning as the definition described above), $X^2$ represents a hydrogen atom, a halogen atom such as a chlorine atom, or hydroxyl group, $Y^1$ has the same meaning as the definition of Y, and $X^\alpha$ and $X^\beta$, which are different from each other, represent a hydrogen atom or —C(=O)Cl.)

The Preparation Method 1 is a method wherein the compound (1a) and the compounds (2a to 2f) obtained by the General Preparation Method 1-1 or 1-2 are subjected to the coupling reaction using a transition metal catalyst to bond $Q^2$ and L into the compound (3), followed by modifying R' and/or R", thus preparing the compound (3') according to the present invention. The General Preparation Method 1-1 and 1-2 are methods for preparing the compounds (2a to 2f) that are used in General Preparation Method 1.

The compound (2a) or the compound (2b) can be obtained by carrying out our Step 1 including reduction of the nitro group of the compound (4a) and transformation of it into an amine compound (4a'). That is to say, examples of the method for preparing the compound (2a) in Step 1 include the two-step method wherein the compound (4a') is N-acylated by carboxylic acid compounds (6a; wherein $X^2$ represents hydroxyl group or a chlorine atom), then carboxamide is reduced, or reductive amination of the compound (4a') by an aldehyde compound (6a; wherein $X^2$ represents a hydrogen atom). Examples of method for preparing the compound (2b) include the coupling reaction between the compound (4a') and the compound (6b; wherein $X^1$ preferably represents a halogen atom or triflate) using a transition metal catalyst. The compound (2c) or the compound (2d) can be prepared from the compound (2a) or the compound (2b) by substituent modification of the nitrogen adjacent to $Q^1$ shown in Step 2. That is to say, examples of the preparation method in Step 2 include the two-step method wherein N-acylation and reduction are carried out sequentially, reductive amination by aldehydes, or N-alkylation by an alkyl halide or alkylsulfonates and the like. Note that, as a separate method, by first applying the preparation method shown in Step 2 to the compound (4a'), then applying the preparation method shown in Step 1, the compound (2c) or the compound (2d) that are identical to the above can also be prepared.

The compound (2f) can be prepared by obtaining the ketone compound (2e) with Friedel-Crafts acylation between the compound (4a") and the compound (6a'), and then carrying out reduction of the ketone.

(General Preparation Method 1-1)
[Preparation of Compound (4a) and Compound (4a')]

The nitro compound (4a), which is the starting material used in the reaction for preparing the compound (4a'), is either commercially available or prepared by the method well known to those skilled in the art. For instance, the nitro compound (4a) can be prepared by a number of well known nitrations, and examples include the method using nitric acid, fuming nitric acid or potassium nitrate and the like in an acidic solvent, the method using nitronium tetrafluoroborate and the like, and the representative method is, for instance, the conventional method which will be described in the following Preparation Example 108. The following step, which prepares the compound (4a') from the compound (4a), is a step wherein nitro group is reduced to convert it into the corresponding amino group. A variety of methods well known to those skilled in the art can be used to carry out this conversion. Examples include the method using metal hydrides such as lithium aluminum hydride in an inert solvent such as tetrahydrofuran, or the method using a nitro reducing agent such as sodium dithionite and the like. A catalytic hydrogenation that uses noble metal catalysts such as Raney nickel, palladium, ruthenium, rhodium or platinum can also be used, in this case, examples of preferred method include those using palladium-activated charcoal or palladium hydroxide-activated charcoal, which will be described in the following Example 22 or the following Example 102 and the like. Examples also include the method using iron, tin or zinc under an acidic condition, and the other representative methods include the reduction by iron under a neutral condition, which will be described in the following Example 57 and the like.

[Preparation of Compound (6a)]

The compound (6a) used in the reaction for preparing the compound (2a) can be obtained by a number of well known methods, and examples thereof include a variety of reactions depending on the nature of Z.

(1) When Z represents an oxygen atom, the compound (6a) is either commercially available or can be synthesized by the methods well known to those skilled in the art. For instance, either hydroxyarenecarboxylic acid esters which may have a substituent can be O-alkylated under a basic condition onto the aromatic ring with aminoalkyl halide, which is commercially available or can be synthesized by the methods well known to those skilled in the art, or the same ether compound can be synthesized by Mitsunobu reaction with an aminoalkyl alcohol, then the ester group subjected to alkaline hydrolysis to easily prepare the corresponding carboxylic acid compound (6a; wherein $X^2$ represents hydroxyl group). Alternatively, for O-alkylation, haloalkylcarboxamide, which is commercially available or synthesized by the methods well known to those skilled in the art (for instance, it can be prepared by the conventional method described in the following Preparation Example 119) can be used as an alkylation agent. From the point of view of operativity and stirrability, it is preferred that the O-alkylation under the basic condition is carried out in the presence of a solvent; the solvent used varies depending on the starting material and the reagents used, and the solvent is not limited in particular as long as it does not inhibit the reaction, dissolves the starting materials to some extent and is always inert during the reaction, and the solvents are preferably tetrahydrofuran, acetone, methylethyl ketone or N,N-dimethylformamide and the like. The base to be used is preferably an alkaline metal carbonate (most preferably, sodium carbonate, potassium carbonate or cesium carbonate) or an alkaline metal hydride, of which sodium hydride is a representative. These bases are used for allowing the hydroxyl group of the compound to exist as a phenoxide ion, and for allowing it to accelerate the substitution of one of the leaving groups of the alkylation agent. The reaction temperature should be a temperature that is sufficient to complete the alkylation without accelerating the formation of the undesirable by-products, and is preferably from room temperature to 100° C. Under the preferred reaction conditions, this reaction is completed in 1 to 24 hours, and the progress of the reaction can be monitored by the well known chromatographic techniques. The hydrolysis of ester groups can be carried out by a number of the well known methods, examples include the method of heating in acidic aqueous solution or the method of carrying out hydrolysis by lithium hydroxide in a tetrahydrofuran-water mixed solvent and the like, examples of the representative method include the method using an alkaline aqueous solution, preferably an aqueous solution of sodium hydroxide or potassium hydroxide, which will be described in the following Preparation Example 1. The aldehyde compound (6a; wherein $X^2$ represents a hydrogen atom) can easily be obtained by subjecting the alcohol derivative, which is obtained by reduction in an inert solvent such as tetrahydrofuran using a metal hydride such as lithium aluminum hydride without hydrolyzing an ester group, to the well known oxidation. Examples of the oxidation used in this case include the method well known to those skilled in the art such as Swern oxidation, Dess-Martin oxidation or oxidation using sulfur trioxide-pyridine complex, and examples of the representative method include the method which will be described in the following Preparation Example 13. Using a more potent oxidizing agent, the aldehyde compound can be converted into the corresponding carboxylic acid (6a; wherein $X^2$ represents hydroxyl group), specifically as will be described in the following Preparation Example 53.

The aldehyde compound (6a; wherein $X^2$ represents a hydrogen atom) can also be obtained as described in M. M. Joullie et al., *Tetrahedron*, 1998, Vol. 54, No. 44, p. 13371-13390, by the nucleophilic substitution under a basic condition of p-fluoroarenenitrile which may be substituted and aminoalkyl alcohol to obtain the compound whose cyano group is converted into formyl group by the reduction to obtain the aldehyde compound (6a; wherein $X^2$ represents a hydrogen atom). In the nucleophilic substitution, the most preferred solvent used is dimethylsulfoxide and the most preferred base used is sodium hydride, and while the reaction temperature is not a critical issue, satisfactory results (shortening of reaction time, increase in the yield and the like) can be obtained at room temperature and the above thereof, specifically as will be described in the following Preparation Example 15. As for the reduction to convert the cyano group into the formyl group, the reduction using metal hydride such as diisobutylaluminum hydride in an inert solvent such as tetrahydrofuran and the like, are well known to those skilled in the art, and in the case of the present reaction, the reduction using Raney nickel described in T. Sohda et al., *Chem. Pharm. Bull.*, 1991, Vol. 39, No. 6, p. 1440-1445 or O. G. Backeberg et al., *J. Chem. Soc.*, 1962, p. 3961-3963 is more preferred, and the method of heating in a formic acid-water mixed solvent or the method using sodium hypophosphite in pyridine-acetic acid-water mixed solvent and carrying out the reaction at room temperature to 40° C. is most preferred, specifically as will be described in the following Preparation Example 16 or the following Preparation Example 20.

Alternatively, if hydroxyaryl halide, preferably hydroxyaryl bromides or iodides, which may have a substituent on the aromatic ring, is subjected to O-alkylation by aminoalkyl halide under a basic condition described above so as to obtain the ether compound (6b; wherein $Y^1$ represents a single bond and $X^1$ represents a halogen atom, preferably a bromine atom or an iodine atom), which undergoes the carbon monoxide insertion well known to those skilled in the art in the presence of alcohols, preferably methanol, ethanol or tert-butanol, using a transition metal catalyst, preferably a commercially available palladium complex such as palladium(II) acetate, the halogen atom can be converted into the desired carboxylic acid ester group; therefore, subsequently carrying out the alkaline hydrolysis such as described above provides the corresponding carboxylic acid compound (6a; wherein $X^2$ represents hydroxyl group). The desired carboxylic acid compound (6a; wherein $X^2$ represents hydroxyl group) may also be obtained by carrying out the halogen-metal exchange on the above ether compound (6b) using a commercially available organic metallic reagent, preferably an alkyllithium reagent such as n-, sec- or tert-butyllithium, a Grignard reagent such as isopropyl magnesium bromide or metallic magnesium to prepare the corresponding aryllithium reagent or the arylmagnesium reagent, then bubbling carbon dioxide into the reaction solution. The solvent used in the present step varies depending on the starting material and the reagent used; and the solvent is not limited in particular as long as it dissolves the starting materials to some extent without inhibiting the reaction and is always inert during the reaction, and diethyl ether, tetrahydrofuran, benzene or toluene and the like are preferred. The reaction temperature varies depending on the starting material and the reagent used, it is preferably maintained low (−78° C.) to keep by-product formation to a minimum, specifically as will be described in the following Preparation Example 51. The prepared aryllithium reagent or arylmagnesium reagent can be converted into the corresponding aldehyde compound (6a; wherein $X^2$ represents a hydrogen atom) by reacting with a commercially available formylation agent, preferably a reagent such as N,N-dimethylformamide or N-formylmorpholine and the like. This formylation is well known to those skilled in the art. The conditions of the nucleophilic substitution of the above aminoalkyl alcohol under the basic conditions, when a heteroarene, preferably pyridine, quinoline or isoquinoline derivative and the like, which has not less than 2 halogen atoms, preferably chlorine atoms or bromine atoms, is used as the starting material, reactivity is promoted by the presence of heteroatoms, and the desired nucleophilic substitution proceeds, which converts one of the halogen atoms into an aminoalkoxy group, the corresponding halogenated heterocyclic compound (6b; wherein $Y^1$ represents a single bond and $X^1$ represents a halogen atom, preferably a chlorine atom or bromine atom) is obtained and via the two-step method comprising the same halogen-metal exchange as described above and then the reaction with carbon dioxide, the corresponding carboxylic acid compound (6a; wherein $X^2$ represents hydroxyl group) can be obtained. The corresponding aldehyde compound (6a; wherein $X^2$ represents a hydrogen atom) can also be prepared by carrying out the same formylation as described above, with the organolithium reagent or the organomagnesium reagent prepared by the halogen-metal exchange.

(2) When Z represents a nitrogen atom, the compound (6a) is either commercially available or can be synthesized by the methods well known to those skilled in the art. For instance, obtained via the coupling reaction using a transition metal catalyst between diamine, preferably N,N-dialkylaminoalkylamine and the like, and arenenitrile halides (preferably chloride, bromide or iodide), which may be substituted, or cyanoallenylsulfonates (preferably triflate), which may be substituted, a nitrile compound can be subjected to the above-mentioned reduction conditions to be converted into the corresponding aldehyde compound (6a; wherein $X^2$ represents a hydrogen atom). The coupling reaction using the transition metal catalyst of this case, for instance, S. L. Buchwald et al., *J. Am. Chem. Soc.*, 1996, Vol. 118, No. 30, p. 7215-'7216, as a method using palladium catalyst, and S. L. Buchwald et al., *Org. Lett.*, 2002, Vol. 4, No. 4, p. 581-584, as the method using a copper catalyst and the like are described.

(3) When Z is a carbon atom, the compound (6a) is either commercially available or can be synthesized by the methods well known to those skilled in the art. For instance, by carrying out the reductive amination with a primary or a secondary amine, which is commercially available or can be synthesized by the methods well known to those skilled in the art, and subjecting the resulting N-alkyl or N,N-dialkylaminoalkyl arylcarboxylic acid ester to the above-mentioned alkyl hydrolysis conditions, formylarenecarboxylic acid esters which may have a substituent on the aromatic ring can be converted into the corresponding carboxylic acid compound (6a; wherein $X^2$ represents hydroxyl group). Alternatively, when formylarene halide (preferably bromide or iodide) which may have a substituent on the aromatic ring is used as the starting material, after reductive amination by a primary or a secondary amine, the corresponding carboxylic acid compound (6a; wherein $X^2$ represents hydroxyl group) can be obtained via the above-mentioned halogen-metal exchange followed by reacting with carbon dioxide, or the corresponding aldehyde compound (6a; wherein $X^2$ represents a hydrogen atom) can be obtained via the halogen-metal exchange followed by reacting with a formylation agent. The reductive amination on the formyl group can be carried out by a number of the methods well known to those skilled in the art, and examples include the method wherein, obtained from an aldehyde compound and a primary amine via the dehydration by refluxing in the presence of an acid catalyst (preferably a typical inorganic acid such as hydrochloric acid or sulfuric acid, an organic acid such as methanesulfonic acid, p-toluenesulfonic acid or camphorsulfonic acid, or an organic salt such as pyridinium p-toluenesulfonate), an imine derivative is reduced by a typical reducing agent such as sodium borohydride and the like, or the method wherein the reaction in the presence of a Lewis acid catalyst, preferably titanium(IV) isopropoxide and the like, in an inert solvent such as tetrahydrofuran, is carried out followed by reducing with sodium borohydride and the like, a representative method being the conventional method as will be described in the following Example 212. From the point of view of operativity and stirrability, it is preferred that the present reaction is carried out in the presence of a solvent; the solvent used varies depending on the starting material and the reagent used, and the solvent is not limited in particular as long as it does not inhibit the reaction, dissolves the starting materials to some extent and is always inert during the reaction, alcohol such as methanol, ethanol or isopropyl alcohol, ether such as tetrahydrofuran or halogenated solvent such as dichloromethane or 1,2-dichloroethane are preferred. Furthermore, for the present reaction, it is preferred that the reaction is carried out under a weakly acidic condition, preferably the condition including addition of not less than catalytic amounts of acetic acid. The preferred reducing agent used in the present reaction is boron hydride, and the most preferred examples include the well known reducing agents such as sodium triacetoxy borohydride, sodium cyanoborohydride or borane-methyl sulfide complex and the like. The reaction temperature is not limited in particular, in general from room temperature to below heat reflux, and preferably from room temperature to 100° C. Under the preferred reaction conditions, this reaction is completed in 1 to 24 hours, the progress of the reaction can be monitored by the well known chromatographic thechniques, and the undesirable by-products can be removed by the well known chromatographic thechniques. In order to achieve the present reaction with a satisfactory reaction speed, in general, using a small excess of amine with respect to the aldehyde raw materials, or using a small excess of aldehyde with respect to the amine source is the general rule; however, depending on the reactivity of the reagent used, using 1 to 10 molar equivalents is more preferred. Since the aldehyde compound serving as the starting materials can also be converted into homoaldehyde by the method of the following Preparation Example 56 using a commercially available Wittig reagent such as methoxymethyltriphenylphosphonium chloride, by using a homoaldehyde as the starting materials, subjecting it to the well known reductive amination conditions, followed by ester hydrolysis or halogen-metal exchange, and reaction with carbon dioxide or a formylation agent, a homolog of the above compound (6a) can be prepared.

In addition, via Sonogashira reaction between halogenated-(preferably chloro-, bromo- or iodo-)arenecarboxylic acid esters which may have a substituent on the aromatic ring or arenes having not less than 2 halogen atoms or halogenated allenylsulfonates (preferably triflate), which are commercially available or can be synthesized by the methods well known to those skilled in the art, and alkyl amines having a terminal acetylene functional group (a representative preparation method is the conventional method of the following Preparation Example 44), which are commercially available or can be synthesized by the methods well known to those skilled in the art, a carbon-carbon bond formation is achieved, and thereafter, the corresponding compound (6a; wherein $X^2$ represents a hydrogen atom or hydroxyl group) can be prepared by the similar technique as described above, a representative method will be described in the following Preparation Example 46. The reaction conditions for Sonogashira reaction varies depending on the starting material, the solvent and the transition metal catalyst, and the reaction conditions are not limited in particular as long as they are conditions similar to the present reaction, and the methods well known to those skilled in the art can be used. Examples of preferred solvent include acetonitrile, tetrahydrofuran, 1,4-dioxane, 1,2-dimethoxyethane, benzene, toluene, xylene, 1-methyl-2- pyrrolidone, N,N-dimethylformamide or dimethylsulfoxide, and more preferably tetrahydrofuran, 1,4-dioxane, 1-methyl-2-pyrrolidone or N,N-dimethylformamide. The reaction temperature should be a temperature that is sufficient to complete the coupling reaction, and is preferably from room temperature to 100° C. The present reaction is preferably carried out under an inert gas atmosphere, more preferably under a nitrogen or an argon gas atmosphere. Under the preferred reaction conditions, this reaction is completed in 1 to 24 hours, and the progress of the reaction can be monitored by the well known chromatographic techniques. The transition metal catalyst is preferably the well known palladium complex, and more preferable examples include the well known palladium complexes such as palladium(II) acetate, dichlorobis(triphenylphosphine)palladium(II), tetrakis(triphenylphosphine)palladium(0) or tris(dibenzylideneacetone)dipalladium(0). Furthermore, in the present reaction, a phosphorous chelating agent (preferably triphenylphosphine, tri-o-tolylphosphine or tri-tert-butylphosphine and the like) may be added in order to obtain satisfactory results (lowering of the reaction temperature required, shortening of the reaction time or increase in the yield and the like). In the present reaction, metal halide or a quaternary ammonium salt and the like, preferably copper (I) iodide, lithium chloride, tetrabutylammonium fluoride or silver(I) oxide and the like may also be added in order to obtain satisfactory results. Preferred results can also be provided in the presence of a base; the base used is not limited in particular as long as it is used in the coupling reaction similar to the present reaction, and preferably examples include basic solvent such as diethylamine, triethylamine, N,N-diisopropylethylamine, piperidine or pyridine.

Also, the carboxylic acid compound (6a; wherein $X^2$ represents hydroxyl group) can easily be converted into the corresponding carboxylic acid chloride (6a; wherein $X^2$ represents a chlorine atom) with the well known halogenation agent such as thionyl chloride or oxalyl chloride, and a representative conventional method will be described in the following Example 114 or the following Example 378.

[Preparation of Compound (6b)]

The compound (6b) used in the reaction for preparing the compound (2b), when $X^1$ represents a halogen atom such as a chlorine atom, a bromine atom or an iodine atom, can be prepared basically under the conditions that have been described in (1) to (3) of the method for preparing the compound (6a). In the case of the compound (6b) wherein $X^1$ represents triflate, it can be prepared using a number of the well known methods with the compound wherein the portion corresponding to $X^1$ is hydroxyl group as the raw materials, examples include the method wherein the reaction with suitable sulfonic anhydride or mixed sulfonic anhydride, preferably commercially available trifluoromethanesulfonic anhydride, is carried out in the presence of a base (preferably a basic substance such as pyridine, lutidine or 2,6-di-tert-butyl-4-methylpyridine and the like), and the method wherein the reaction using a suitable sulfonic acid derivative, preferably N-phenyltrifluoromethanesulfoneimide, is carried out under a basic condition, preferably in the presence of an alkaline metal hydride such as sodium hydride, a base such as potassium tert-butoxide or lithium hexamethyldisilazide, in an inert solvent such as tetrahydrofuran, specifically, as will be described in the following Preparation Example 80 or the following Preparation Example 82. The above compound whose portion corresponding to $X^1$ is hydroxyl group can be prepared by the method well known to those skilled in the art; for instance, when $X^1$ represents a protected hydroxy group, it suffices to deprotect the group by the well known procedure, and various reactions related to this formation and elimination of such protecting groups are abundantly described in a number of the well known references, for instance, in T. Greene et al., *Protective Groups in Organic Synthesis* (John Wiley & Sons. Inc., New York, 1981 year) (hereinafter referred to as "Synthesis Reference 1") and the like. Regarding the elimination of the preferred hydroxy-protecting group, in particular methyl group, it can be carried out by a number of the well known methods, and examples include the method of using hydrogen bromide in water or acetic acid and heating at 60° C. to 150° C. (specifically refer to the following Example 785), the method of using a large excess of pyridine hydrochloride with respect to the starting materials and heating/melting at 160° C. to 220° C. (specifically refer to the following Example 779), the method of adding methionine in methanesulfonic acid solvent and heating at 60° C. to 150° C. (specifically refer to the following Example 326) and the like, and representatively, the elimination can be conveniently achieved by the method of using a commercially available acid catalyst such as boron tribromide or boron trichloride, and reacting in a reaction solvent such as halogenated solvent, preferably dichloromethane or 1,2-dichloroethane, at −78° C. to 60° C., most preferably at not less than room temperature (specifically refer to the following Example 364), method as taught in E. Fujita et al., *J. Org. Chem.,* 1980, Vol. 45, No. 22, p. 4275-4277, wherein the reaction is carried out by adding thiols, preferably ethanethiol, in the presence of a Lewis acid, preferably aluminum chloride or aluminum bromide, in a reaction solvent such as halogenated solvent, preferably dichloromethane or 1,2-dichloroethane, at −78° C. to 60° C., most preferably at not less than room temperature. For the present reaction, it is preferred that not less than 3 molar equivalents of each of Lewis acid and thiol are used with respect to 1 molar equivalent of methoxy group in order to obtain satisfactory results (lowering of the reaction temperature required, shortening of the reaction time or increase in the yield and the like), specifically as will be described in the following Example 111.

When $X^1$ represents boronic acid ($B(OR^1)_2$; wherein $R^1$ represents a hydrogen atom), the compound (6b) can be obtained with commercially available trialkyl borate, preferably trimethyl borate or triisopropyl borate and the above-mentioned halogen-metal exchange, and can be prepared by mixing the corresponding aryllithium derivative or arylmagnesium derivative at −50° C. to −100° C. and purifying with an acidic aqueous solution.

[(Step 1) from Compound (4a') to Compound (2a)]

Examples of Step 1 for preparing the compound (2a) from the compound (4a') include the reductive amination using the above-mentioned the compound (6a; wherein $X^2$ represents a hydrogen atom), or the two-step method wherein after N-acylation by the compound (6a; wherein $X^2$ represents hydroxyl group or a chlorine atom), the carboxamide functional group is reduced, and the like. Examples of the N-acylation, which is the first step of the two-step method, include a number of the methods well known to those skilled in the art, for instance, when $X^2$ represents hydroxyl group, the method wherein N-acylation of the amine compound (4a') is achieved by forming mixed acid anhydride or activated ester of suitable carboxylic acid (for instance, acid anhydride or ester and the like formed by a known reagent such as ethyl chloroformate, dicyclohexylcarbodiimide, acyl imidazole, nitrophenol, pentachlorophenol, N-hydroxysuccinimide or 1-hydroxybenzotriazole). When $X^2$ represents a chlorine atom, examples include the method wherein the reaction is carried out in a basic solvent such as pyridine, lutidine, quinoline or isoquinoline at a temperature that is not less than the room temperature, the Schotten-Baumann method (refer to the following Preparation Example 87), wherein the reaction is carried out in a two-phase partitioning system consisting of a an alkaline aqueous solution, preferably an aqueous solution such as sodium hydroxide or potassium hydroxide, and a halogenated solvent, preferably dichloromethane or 1,2-dichloroethane and the like. Examples of the other preferred reaction conditions also include the method as will be described in the following Preparation Example 86, wherein a tertiary amine is used as the base. The present reaction is carried out in an inert solvent, preferably tetrahydrofuran or 1,4-dioxane, to which at least 1 equivalent of the tertiary amine, preferably triethylamine or N,N-diisopropylethylamine was added as an acid scavenger; if desired, an acylation catalyst such as 4-dimethylaminopyridine or 4-pyrrolidinopyridine may be used. The reaction temperature varies depending on the starting material and the reagent used, the temperature is not limited in particular as long as it a temperature that is sufficient to complete the acylation, and is preferably from room temperature to 100° C.

For the reduction of the carboxamide functional group, which is the second step of the present reaction, examples include a number of the methods well known to those skilled in the art, for instance, the reduction wherein heating is carried out in an inert solvent such as diethyl ether or tetrahydrofuran, using commercially available borane or lithium aluminum hydride, specifically the method as will be described in the following Example 337. The solvent used in the present reaction varies depending on the starting material, the reagent used and the like, and the solvent is not limited in particular as long as it is an inert solvent that dissolves the starting materials to some extent without inhibiting the reaction, most preferably ether such as diethyl ether or tetrahydrofuran; the reaction temperature should be a temperature that is sufficient to complete the reduction without promoting the formation of the undesirable by-products, preferably from 0° C. to room temperature. Under the preferred reaction conditions, the present reaction is completed in 0.1 to 12 hours, the progress of the reaction can be monitored by the well known chromatographic techniques. Furthermore, for the present reaction, the procedure wherein not less than 3 equivalents of lithium aluminum hydride with respect to 1 molar equivalent of the amide functional group of the starting material is suspended in an inert solvent, preferably diethyl ether or tetrahydrofuran, then aluminum chloride in the same amounts to lithium aluminum hydride is added at 0° C., and after stirring preferably for 0.1 to 1 hour, the starting materials are added, is more preferred.

[(Step 1) from Compound (4a') to Compound (2b)]

Examples of Step 1 for preparing the compound (2b) from the compound (4a') include the N-arylation by a transition metal catalyst using the above-mentioned the compound (6b; wherein $X^1$ represents a halogen atom such as a chlorine atom, a bromine atom or an iodine atom, or triflate), specifically as will be described in the following Example 116. The reaction conditions of the present reaction vary depending on the starting material, the solvent and the transition metal catalyst, and the conditions are not limited in particular as long as they are conditions similar to the present reaction, and the methods well known to those skilled in the art can be used. Examples of the preferred solvent include acetonitrile, tetrahydrofuran, 1,4-dioxane, 1,2-dimethoxyethane, benzene, toluene, xylene, 1-methyl-2-pyrrolidone, N,N-dimethylformamide or dimethylsulfoxide, more preferably tetrahydrofuran, 1,4-dioxane, benzene or toluene. The reaction temperature should be a temperature that is sufficient to complete the coupling reaction, preferably from 60° C. to 120° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. The transition metal catalyst is preferably the well known palladium complex, and more preferable examples include the well known palladium complexes such as palladium(II) acetate, dichlorobis(triphenylphosphine)palladium(II), tetrakis(triphenylphosphine) palladium(0) or tris(dibenzylideneacetone)dipalladium(0). Furthermore, a phoshorous chelating agent (preferably triphenylphosphine, tri-o-tolylphosphine, tri-tert-butylphosphine, 2,2'-bis(diphenylphosphino)-1,1'-binaphthyl, 1,1'-bis(diphenylphosphino)ferrocene or Xantphos (refer to P. W. N. M. van Leeuwen et al., *Tetrahedron Lett.*, 1999, Vol. 40, No. 19, p. 3789-3790) and the like) or an imidazolium-type carbene chelator such as described in S. P. Nolan et al., *Org. Lett.*, 1999, Vol. 1, No. 8, p. 1307-1309, may be added in the present reaction in order to obtain satisfactory results (lowering of the reaction temperature required, shortening of the reaction time or increase in the yield and the like). The present reaction provides preferred results in the presence of a base, and the base that is used in this case is not limited in particular as long as it is used in the coupling reaction that is similar to the present reaction, preferably, sodium carbonate, potassium carbonate, cesium carbonate, potassium phosphate, sodium tert-butoxide, potassium tert-butoxide or lithium hexamethyldisilazide and the like.

When, as described in S. L. Buchwald et al., *Org. Lett.*, 2002, Vol. 4, No. 4, p. 581-584, a copper complex, preferably copper(I) iodide, is used as the transition metal catalyst, alcohol, preferably isopropyl alcohol, is used as the reaction solvent, and diols (preferably ethylene glycol and the like) or phenol (preferably 2,6-dimethylphenol and the like) may be added into the reaction system in order to obtain satisfactory results (lowering of the reaction temperature required, shortening of the reaction time or increase in the yield and the like).

Examples of Step 1 for preparing the compound (2b) from the compound (4a') include the coupling reaction by a copper catalyst using the above-mentioned boronic acid compound (6b; wherein $X^1$ represents $B(OR^1)_2$ and $R^1$ represents a hydrogen atom), and the method thereof is described in, for instance, D. M. T. Chan et al., *Tetrahedron Lett.*, 1998, Vol. 39, No. 19, p. 2933-2936.

[(Step 2) from Compound (2a) or (2b) to Compound (2c) or (2d)]

Step 2 wherein the compound (2c) or the compound (2d) is prepared from the compound (2a) or the compound (2b), is a step wherein a substituent of the nitrogen adjacent to $Q^1$ is modified. Various methods well known to those skilled in the art can be used to carry out this conversion. Examples include the method wherein N-acylation is carried out by reacting with activated ester of suitable carboxylic acid and the like or suitable carboxylic anhydride or mixed anhydride formed by an acylation agent such as acyl chloride or acyl bromide that is commercially available or that can be synthesized by the methods well known to those skilled in the art, or a known reagent such as dicyclohexylcarbodiimide, acyl imidazole or 1-hydroxybenzotriazole as mentioned above, the method wherein, after N-carbamation with ethyl chloroformate and the like (refer to the following Example 135) or the above-mentioned N-acylation, the carboxamide functional group is further reduced under the conditions such as described above, or the reductive amination under the conditions as described above by aldehydes that are commercially available or that can be synthesized by the methods well known to those skilled in the art, and the like. Example also includes N-alkylation using an alkylation agent such as alkyl halide, preferably alkyl chloride, bromide or iodide, or triflate, methanesulfonate or p-toluenesulfonate, which are commercially available or can be synthesized by the methods well known to those skilled in the art, specifically the method as will be described in the following Example 119.
(General Preparation Method 1-2)

The compound (2e) can be prepared from the compound (4a'') and the compound (6a') according to the synthesis route shown in General Preparation Method 1-2 by Friedel-Crafts acylation, which is well known to those skilled in the art, by subjecting r of the compound (4a'') and $X^\beta$ of the compound (6a') to the desired conversion to bond $Q^1$ and $Y^1$ via carbonyl group. In the present reaction, $X^\alpha$ and $X^\beta$, which are different from each other, represent a hydrogen atom or —C(=O)Cl, and in the case of the hydrogen atom, as they become an acyl acceptor, it is most preferred that they have an electron donor group, preferably amino group, hydroxyl group or an alkoxy group and the like, at the o- or p-position with respect to the hydrogen atom. When the compound (4a'') is commercially available or can be synthesized by the method well known to those skilled in the art, and, as described above, the carboxylic acid derivative can easily be converted into carboxylic acid chloride (r represents —C(=O)Cl) with a halogenation agent such as thionyl chloride or oxalyl chloride. The compound (6a') is commercially available or can be prepared by the similar method to the above-mentioned the compound (6a). From the point of view of operativity and stirrability, it is preferred that the Friedel-Crafts acylation is carried out in the presence of a solvent; the solvent used varies depending on the starting material and the reagent used, and the solvent is not limited in particular as long as it does not inhibit the reaction, dissolves the starting materials to some extent and is always inert during the reaction, and the solvent is preferably a halogenated solvent such as dichloromethane or 1,2-dichloroethane. Examples of preferred Lewis acid used in the present reaction include tin(IV) chloride, iron(III) chloride, titanium(IV) chloride, trifluoroboron-diethyl ether complex, aluminum chloride, dimethylaluminum chloride or trimethylaluminum and the like, and most preferably aluminum chloride. The reaction temperature is not limited in particular, and should be a temperature that is sufficient to complete the acylation, which it suffices to carry out preferably from 0° C. to below heat reflux. Under the preferred reaction conditions, this reaction is completed in 1 to 24 hours, the progress of the reaction can be monitored by the well known chromatographic techniques, and the undesirable by-products can be removed by the well known chromatographic techniques, specifically as will be described in the following Preparation Example 66.

The step wherein the compound (2f) is prepared from the compound (2e), is a step wherein carbonyl group is reduced to convert into methylene group. Examples of the method that are preferred for the present step include a number of the methods well known to those skilled in the art, for instance, catalytic hydrogenation using a noble metal catalyst well known to those skilled in the art such as nickel, palladium or platinum, reduction by hydrosilane, Wolff-Kishner reduction (specifically refer to the following Preparation Example 204), Clemmensen reduction, or the reaction wherein carbonyl group is dithio-modified then desulfurized by Raney nickel, as described in *The Chemical Society of Japan Ed., 4th Edition, Experimental Chemistry Course (Vol. 26) Organic Synthesis VIII—Asymmetric Synthesis/Reduction/Sugar/Labeled Compound*, Maruzen Co., April 1992, p. 176-178, p. 197-203 and p. 259-263 and the like. Examples also include the method wherein a representative commercially available reducing agent such as sodium borohydride is used to reduce the carbonyl group and convert it into the corresponding alcohol derivative, then catalytic hydrogenation by the noble metal catalyst or reduction by hydrosilane is carried out, and the Barton-McCombie method, well known to those skilled in the art, wherein the above-mentioned alcohol derivative is converted into xanthogenate, then reduced via radicals using tributyl tin hydride and the like, specifically, it was discovered that the desired methylene compound (2f) can be prepared in one step by the method of the following Example 337 used for the above-mentioned reduction of the carboxamide.

When $Q^1$ represents a nitrogen atom in the compound (20, the corresponding N-alkyl compound (2f) can be obtained by using N-alkylation under the above-mentioned conditions wherein the above-mentioned compound (6b; wherein $X^1$ most preferably represents a halogen atom such as chlorine atom, bromine atom or iodine atom, or sulfonate such as triflate, methanesulfonate or p-toluenesulfonate, $Y^1$ most preferably represents —CH$_2$— or —(CH$_2$)$_2$—) is used, specifically as will be described in the following Preparation Example 68.

When $X^{1'}$ represents diazonium salts ($N_2^+X''^-$; wherein $X''$ represents chloride, bromide or tetrafluoroborate) in the compounds (2a to 2f), diazonium derivatives (2a to 2f) can be prepared by subjecting the corresponding amine compound to the diazotization. Diazotization conditions remarkably vary depending on the properties of the corresponding amine, and the conditions are not limited as long as the conditions do not inhibit the reaction, and the desired diazonium salts (2a) can be prepared using the method well known to those skilled in the art described in *The Chemical Society of Japan Eds. New Experimental Chemistry Course (Vol. 14) Synthesis of Organic Compound and Reaction I*, Maruzen Co., November 1977, p. 383-388 and the like.

When $X^{1'}$ represents boronic acid or boronic acid esters $(B(OR^1)_2$; wherein $R^1$ represents a lower alkyl group such as a hydrogen atom, methyl group, ethyl group, n-propyl group, iso-propyl group or n-butyl group), the corresponding boronic acid derivatives (2a to 2f) can be prepared by subjecting the compound wherein $X^{1'}$ represents a halogen atom, preferably a bromine atom or an iodine atom stepwise to halogen-metal exchange, to the reaction with trialkyl borate and to purification by an acidic aqueous solution under the above conditions, specifically as will be described in the following Preparation Example 78. Boronic acid esters (2a to 2f) can also be prepared by the well known cross-coupling reaction with a commercially available diboron compound, preferably bis(pinacolato)diboron and the like using a transition metal catalyst, preferably a palladium complex, without carrying out a halogen-metal exchange.

When $X^{1'}$ represents trialkyltins ($Sn(R^1)_3$; wherein $R^1$ has the same meaning as the definition described above), aryltin derivatives (2a to 2f) can be prepared by mixing at −50° C. to −100° C. halotrialkyltin, preferably commercially available trimethyltin chloride or tributyltin chloride, and an aryllithium derivative prepared by halogen-metal exchange, specifically as will be described in the following Preparation Example 74. Examples of another route for preparing similar aryltin derivatives (2a to 2f) also includes the coupling reaction using bis(trialkyl)tin, preferably commercially available bis(tributyl)tin or bis(trimethyl)tin and the corresponding halide (preferably chloride, bromide or iodide, and most preferably bromide) or a transition metal catalyst of sulfonates (most preferably triflate), specifically as will be described in the following Preparation Example 76. The transition metal catalyst is preferably the well known palladium complex, more preferably well known palladium complex such as tetrakis(triphenylphosphine)palladium(0). In the present reaction, when the starting material is triflate, a salt such as lithium chloride or tetrabutylammonium chloride may be added in order to obtain satisfactory results (lowering of the reaction temperature required, shortening of the reaction time or increase in the yield and the like), specifically as will be described in the following Preparation Example 69.
(General Preparation Method 1)
[Preparation of Compound (1a)]

The compound (1a) in General Preparation Method 1 may be commercially available, or when not commercially available, may be prepared by the methods well known to those skilled in the art. Preferably the desired derivative can be prepared using the similar method as for preparing the compounds (2a to 2f). For instance, by using the similar technique as the substituent conversion of $X^{1'}$ described above, the compound (1a) having a halogen atom, diazonium salts, boronic acid esters or trialkyltins at 2 or 3 position, such as indole, benzothiazole, benzoxazole, benzimidazole, imidazopyridine, benzothiophene or benzofuran can easily be obtained, or commercially available 1- or 2-bromonaphthalene can be converted into the corresponding boronic acid ester or trialkyltin functional group, and the compound (1a) having the desired halide, diazonium salts, boronic acid esters or trialkyltins can also be obtained from the corresponding quinoline, isoquinoline, quinazoline or quinoxaline and the like.

A styrene derivative (1a; wherein W represents —CH=CH—, L represents a single bond and $X^1$ represents a hydrogen atom) can be prepared from the corresponding aryl halide derivative and commercially available tributyl (vinyl)tin and the like via the Stille coupling reaction well known to those skilled in the art, or an acetylene derivative (1a; wherein W represents —C≡C—, L represents a single bond and $X^1$ represents a hydrogen atom) can be prepared by carrying out Sonogashira reaction with commercially available trimethylsilylacetylene and then the desilylation under the alkaline conditions. For instance, these reaction are described in R. P. HSUNG et al, *Tetrahedron Lett.*, 1995, Vol. 36, No. 26, p. 4525-4528, and specifically as will be described in the following Preparation Example 117.

The compound (1a; wherein W represents —CH=CX—, R represents a C2 alkyl group that may be substituted and forms a 6-membered ring together with X, L represents a single bond and $X^1$ represents a bromine atom), which is the preferred one of the compound (1a), can also be prepared via the 3 steps method. That is to say, the dihydronaphthalene derivative (1a) having a bromine atom at 2 position can be prepared by brominating the a position of the corresponding 1-tetralone derivative with a commercially available bromination agent such as bromine or copper(II) bromide, reducing the carbonyl group into an alcohol with a commercially available reducing agent such as sodium borohydride, and then subjecting the resulting product to the dehydration using an acid catalyst (for instance, as described in M. Adamczyk et al., *J. Org. Chem.*, 1984, Vol. 49, No. 22, p. 4226-4237).

From the point of view of operativity and stirrability, it is preferred that the bromination of the first step is carried out in the presence of a solvent; the solvent used varies depending on the starting material and the reagent used, and the solvent is not limited in particular as long as it does not inhibit the reaction, dissolves the starting materials to some extent and is always inert during the reaction, and in cases where bromine is used, ethers are preferred, and diethyl ether being most preferred. In order to obtain satisfactory results (decrease in by-products and increase in yields and the like), it is adequate to add dropwise 1.1 to 1.5 equivalents of bromine gradually at room temperature. In the present reaction, although the compound wherein the α position of ketone is dibrominated is obtained as a by-product, this can be removed by the well known chromatographic techniques; even if a contamination by the above by-product exists, since one among the two bromine atoms of the by-product can be debrominated in the reduction of the second step, no stringent purification is required, which characterizes this step. The above by-product is not generated when 2 equivalents of copper(II) bromide is used as the bromination agent (refer to the following Preparation Example 95). For the reaction temperature, the reaction is completed at room temperature in cases where bromine is used, and heating is required, preferably at 60° C. to 100° C., in cases where copper(II) bromide is used.

In the reduction by sodium borohydride of the second step, alcohol, preferably methanol or ethanol solution, is used as a reaction solvent. The reaction temperature is not limited in particular as long as it is a temperature that is sufficient to complete the reduction, and is preferably room temperature. Under the preferred reaction conditions, this reaction is completed in 1 to 24 hours, and the progress of the reaction can be monitored by the well known chromatographic techniques. In cases where the desired alcohol derivative is a crystal, it can be purified by subjecting the suspension to filtration followed by washing with water, and in cases where no crystal is precipitated, purification is carried out by extraction with an organic solvent, preferably such as diethyl ether, ethyl acetate or chloroform.

From the point of view of operativity and stirrability, it is preferred that the dehydration of the third step is carried out in the presence of a solvent; the solvent used varies depending on the starting material and the reagent used, and the solvent is not limited in particular as long as it does not inhibit the reaction, dissolves the starting materials to some extent and is always inert during the reaction, and the solvent is preferably a hydrocarbon solvent such as benzene, toluene or xylene. The present reaction provides satisfactory results when an acid catalyst, preferably an organic acid such as p-toluene sulfonic acid is used. For the purpose of eliminating by azeotropy the water generated in the system, the reaction temperature is not less than the boiling point of the solvent used, preferably 80 to 140° C. Under the preferred reaction conditions, this reaction is completed in 0.5 to 5 hours, the progress of the reaction can be monitored by the well known chromatographic techniques, and undesired by-products can be removed by the usual chromatographic techniques; however, it is preferred that the reaction is terminated at the point of time when the starting material has disappeared, specifically as will be described in the following Preparation Example 106.

For instance, taking a 1-tetralone compound which may be substituted as the starting material, which can be synthesized according to the description in D. Lednicer et al., *J. Org. Chem.*, 1971, Vol. 36, No. 22, p. 3260-3266, the corresponding 2-bromodihydronaphthalene derivative (1a) can be prepared using the methods similar to the above 3 steps. In addition, taking a chromanone derivative which may be substituted as the starting material, which can be synthesized according to the description in T. Ohta et al., *Chem. Pharm. Bull.*, 1977, Vol. 25, No. 9, p. 2788-2789, the corresponding 3-bromochromene derivative (1a) can also be prepared.

The compound (1a; wherein W represents —CH=CX—, R represents a C2 alkyl group that may be substituted and forms a 6-membered ring together with X, L represents a single bond and $X^1$ represents triflate), which is the preferred one of the compound (1a), can be obtained by enolizing the corresponding 2-tetralone derivative under the basic conditions, then reacting with a suitable trifluoromethanesulfonic acid derivative. The solvent used in the present reaction varies depending on the starting material and the reagent used; and it is not limited in particular as long as it does not inhibit the reaction, dissolves the starting materials to some extent and is always inert during the reaction, and ethers are preferred, most preferably tetrahydrofuran. In the present reaction, enolization of ketone requires a base, a preferably commercially available basic substance such as pyridine, lutidine or 2,6-ditert-butyl-4-methylpyridine, an alkaline metal hydride such as sodium hydride, butyllithium, lithium diisopropylamide (LDA), lithium hexamethyldisilazide or potassium tert-butoxide and the like, more preferably lithium hexamethyldisilazide. The triflation agent used is, for instance, suitable sulfonic anhydride or mixed sulfonic anhydride, preferably commercially available trifluoromethanesulfonic anhydride or a suitable sulfonic acid derivative, most preferably N-phenyltrifluoromethanesulfonimide. In the present reaction, a positional isomer of enol triflate is obtained as an undesired by-product; however, the formation of the by-product can be inhibited by maintaining a low reaction temperature (−78° C.). At least 1 equivalent of each of base and triflation agent is required, and under the preferred reaction conditions, the reaction is completed in 0.5 to 5 hours, specifically as will be described in the following Preparation Example 82.

Taking a 2-benzocycloheptanone derivative as the starting material, which can be synthesized according to the description in E. C. Taylor et al., *Tetrahedron Lett.*, 1977, Vol. 18, No. 21, p. 1827-1830, the corresponding benzocycloheptenyl triflate derivative (1a) and the like can be obtained by using the similar method as the above triflation. Triflates can be converted into the corresponding trialkyltin derivative (1a) by using the well known coupling reaction using bis(trialkyl)tin described above as the transition metal catalyst, specifically as will be described in the following Preparation Example 69.

The compound (1a; wherein W represents —(CH$_2$)$_2$—NX—, R represents a C2 alkyl group that may be substituted and forms a 7-membered ring together with X, L represents a single bond, and X$^1$ represents a hydrogen atom), which is the preferred one of the compound (1a), can be prepared according to W. E. Bondinell et al., EP285287.

[Preparation of Compound (3)]

The compound (3) can be prepared by the coupling reaction between the compound (1a) and the compound (2a to 2f) using a transition metal catalyst, according to the synthesis route of General Preparation Method 1. When X$^1$ represents a hydrogen atom and X$^{1'}$ represents a halogen atom or triflate, N-arylation of primary or secondary amines (1a) using the transition metal catalyst under the conditions as described above, Sonogashira reaction of acetylene compounds (1a), Mizoroki-Heck reaction of styrenes (1a) and the like can be used.

The reaction conditions for Mizoroki-Heck reaction vary according to the starting material, the solvent and the transition metal catalyst, and the reaction conditions are not limited in particular as long as they are conditions similar to the present reaction, and the methods well known to those skilled in the art can be used. Examples of the solvent include, preferably, acetonitrile, tetrahydrofuran, 1,4-dioxane, 1,2-dimethoxyethane, benzene, toluene, 1-methyl-2-pyrrolidone or N,N-dimethylformamide, and more preferably, acetonitrile, tetrahydrofuran, 1,4-dioxane or N,N-dimethylformamide. The reaction temperature should be a temperature that is sufficient to complete the coupling reaction, and is preferably from room temperature to 100° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. Examples of the transition metal catalyst include, preferably, palladium complex, and more preferably the well known palladium complexes such as palladium(II) acetate, dichlorobis(triphenylphosphine)palladium(II), tetrakis(triphenylphosphine)palladium(0) or tris(dibenzylideneacetone)dipalladium(0). Furthermore, a phoshorous chelating agent (preferably triphenylphosphine, tri-o-tolylphosphine, tri-tert-butylphosphine or 2-(di-tert-butylphosphino)biphenyl and the like) may be added in the present reaction in order to obtain satisfactory results (lowering of the reaction temperature required, shortening of the reaction time or increase in the yield and the like). The present reaction can also provide preferred results in the presence of a base, and the base used is not limited in particular as long as it is similar to that used in the coupling reaction of the present reaction, preferably, triethylamine, N,N-diisopropylethylamine or N,N-dicyclohexylmethylamine and the like, specifically as will be described in the following Example 107.

Alternatively, when X$^{1'}$ represents boronic acid or boronic acid ester, conversion of styrene compound (1a) similar to the above-mentioned Mizoroki-Heck reaction can be carried out, and the corresponding stilbene compound (3) can be prepared. Reaction is carried out as described in A. Mori et al., *Org. Lett.*, 2001, Vol. 3, No. 21, p. 3313-3316, using a transition metal catalyst, preferably the well known palladium complex, more preferably palladium(II) acetate or dichlorobenzonitrilepalladium(II), tetrahydrofuran or N,N-dimethylformamide as the solvent, at 50 to 100° C., and more preferably, it is adequate to add copper(II) acetate as a reoxidizing agent of zero valent palladium.

Alternatively, when X$^{1'}$ represents a diazonium salt (N$_2^+$ X''$^-$; wherein X'' represents chloride, bromide or tetrafluoroborate, and most preferably tetrafluoroborate), as described in M. B. Andrus et al., *Org. Lett.*, 2002, Vol. 4, No. 12, p. 2079-2082, using a transition metal catalyst, preferably palladium(II) acetate and an imidazolium-type carbene chelator, a conversion similar to Mizoroki-Heck reaction is carried out, and from the styrene compound (1a), the corresponding stilbene compound (3) can be prepared.

When X$^1$ and X$^{1'}$ are different from each other, and each represents a trialkyltin, a halogen atom or triflate, the compound (3) is obtained by the Stille coupling reaction, which is the well known reaction to those skilled in the art, and which uses a transition metal catalyst. The reaction conditions of the present reaction vary depending on the starting material, the solvent and the transition metal catalyst, are not limited in particular as long as they are conditions similar to the present reaction, and the methods well known to those skilled in the art can be used. Examples of solvent include, preferably, acetonitrile, tetrahydrofuran, 1,4-dioxane, 1,2-dimethoxyethane, benzene, toluene, xylene, 1-methyl-2-pyrrolidone, N,N-dimethylformamide or dimethylsulfoxide, and more preferably, tetrahydrofuran, 1,4-dioxane, N,N-dimethylformamide or dimethylsulfoxide. The reaction temperature should be a temperature that is sufficient to complete the coupling reaction, and is preferably from room temperature to 100° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. The transition metal catalyst is preferably the well known palladium complex, and more preferably the well known palladium complex such as palladium(II) acetate, dichlorobis(triphenylphosphine)palladium(II), tetrakis(triphenylphosphine)palladium(0) or tris(dibenzylideneacetone)dipalladium(0). Furthermore, a phosphorous chelating agent (preferably triphenylphosphine, tri-o-tolylphosphine or tri-tert-butylphosphine and the like) may be added in the present reaction in order to obtain satisfactory results (lowering of the reaction temperature required, shortening of the reaction time or increase in the yield and the like). Metal halide or a quarternary ammonium salt and the like, preferably copper chloride(I), copper(I) iodide, lithium chloride or tetrabutylammonium chloride and the like may also be added in the present reaction, specifically as will be described in the following Example 1.

When $X^1$ and $X^{1'}$ are different from each other and each represents a boronic acid, a boronic acid ester, a halogen atom or triflate, the compound (3) is obtained by Suzuki-Miyaura coupling reaction, which is the well known reaction to those skilled in the art, and which uses a transition metal catalyst. The reaction conditions of the present reaction vary depending on the starting material, the solvent and the transition metal catalyst, are not limited in particular as long as they are conditions similar to the present reaction, and the methods well known to those skilled in the art can be used. Examples of solvent include, preferably, acetonitrile, tetrahydrofuran, 1,4-dioxane, 1,2-dimethoxyethane, 2-methoxyethylether, benzene, toluene, xylene, 1-methyl-2-pyrrolidone or N,N-dimethylformamide, and more preferably, tetrahydrofuran, 1,4-dioxane, 1,2-dimethoxyethane, toluene, 1-methyl-2-pyrrolidone or N,N-dimethylformamide. The reaction temperature should be a temperature that is sufficient to complete the coupling reaction, and is preferably from room temperature to 100° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. The transition metal catalyst is preferably the well known palladium complex, and more preferably the well known palladium complex such as palladium(II) acetate, dichlorobis(triphenylphosphine)palladium(II), tetrakis(triphenylphosphine)palladium(0) or tris(dibenzylideneacetone)dipalladium(0). Furthermore, a phosphorous chelating agent (preferably triphenylphosphine, tri-o-tolylphosphine or tri-tert-butylphosphine and the like) may be added in the present reaction in order to obtain satisfactory results (lowering of the reaction temperature required, shortening of the reaction time or increase in the yield and the like). A quarternary ammonium salt, preferably tetrabutylammonium chloride or bromide and the like may also be added in the present reaction in order to obtain satisfactory results. The present reaction can also provide preferred results in the presence of a base, the base used varies depending on the starting material, the solvent used is not limited in particular, and the solvent is, preferably, sodium hydroxide, barium hydroxide, potassium fluoride, cesium fluoride, sodium carbonate, potassium carbonate, cesium carbonate or potassium phosphate and the like, specifically as will be described in the following Preparation Example 79 or the following Example 24.

Alternatively, when $X^1$ and $X^{1'}$ are different from each other and each represents boronic acid, boronic acid ester or a diazonium salt ($N_2^+X''^-$; wherein X'' represents chloride, bromide or tetrafluoroborate, and most preferably tetrafluoroborate), the compound (3) can be prepared by using the method described in J-P. Genet et al., *Tetrahedron Lett.*, 1996, Vol. 37, No. 22, p. 3857-3860, under the similar conditions to Suzuki-Miyaura coupling reaction, which uses a transition metal catalyst, specifically as will be described in the following Preparation Example 114.

[From Compound (3) to Compound (3')]

The step for preparing the compound (3') from the compound (3) is a step for converting R' and/or R" into a functional group. The substituent R' and/or R" in the compound (3') according to the present invention can be converted by a variety of reactions which are well known to those skilled in the art.

That is to say, (1) when R' and/or R" is an alkoxy group, examples of conversion into the functional group from the alkoxy group include the method of converting into alcohol or a phenol derivative by deprotection, and the elimination of the hydroxy-protecting group described above is abundantly described in a number of well known references, for instance, Synthesis Reference 1 and the like. The alcohol or the phenol derivative generated by the present method, can be further converted into the corresponding ester compound by dehydration-condensation with a carbon derivative or by reaction with carboxylic acid or sulfonic acid chloride as described above, and an ether compound and the like can easily be obtained via Mitsunobu reaction or condensation with a halogen compound.

(2) When R' and/or R" represents nitro group, a variety of reactions are known for the conversion from the nitro group into a functional group, the product resulting from the method and conversion is not limited in particular, and examples include the method of conversion into an amine derivative by the reduction. The reduction conditions are generally not limited in particular, and examples of preferred conditions include the method wherein iron, zinc or tin acts under the acidic conditions, the catalytic hydrogenation method having nickel, palladium, rhodium, ruthenium, platinum or a complex thereof as a catalyst, and the like. If an amine derivative generated by the present reduction is used, it can easily be converted further into an amide compound, a carbamate compound, a sulfonamide compound, a halide compound or a substituted amine compound and the like.

(3) When R' and/or R" represents formyl group, a variety of reactions are known for the conversion from the formyl group into a functional group, the product resulting from the method and conversion is not limited in particular, and examples include the method of conversion into a carboxylic acid derivative by the oxidation. In addition, the carboxylic acid derivative generated by the present method can easily be converted into an ester compound, a ketone compound and the like by the well known method and the like. From the carboxylic acid derivative, the corresponding alcohol derivative by the reduction, or the corresponding amine derivative by the reductive amination, then the secondary alcohol derivative by the addition of an organometallic reagent, furthermore, various alkyl derivatives and the like by the Wittig reaction, can easily be prepared.

(4) When R' and/or R" represents a halogen atom, examples of the method of conversion of the halogen atom as a substituent into a functional group include the method of conversion into a nitrile derivative by the substitution using a transition metal catalyst. An easy conversion into diverse compounds can also be carried out via, for instance, organolithium, organomagnesium, organotin, organozinc, organicboronic acid derivative and the like.

[General Preparation Method 2]

A representative method for preparing the compound according to the present invention represented by the above formula (I) is shown below:

General Preparation Method 2
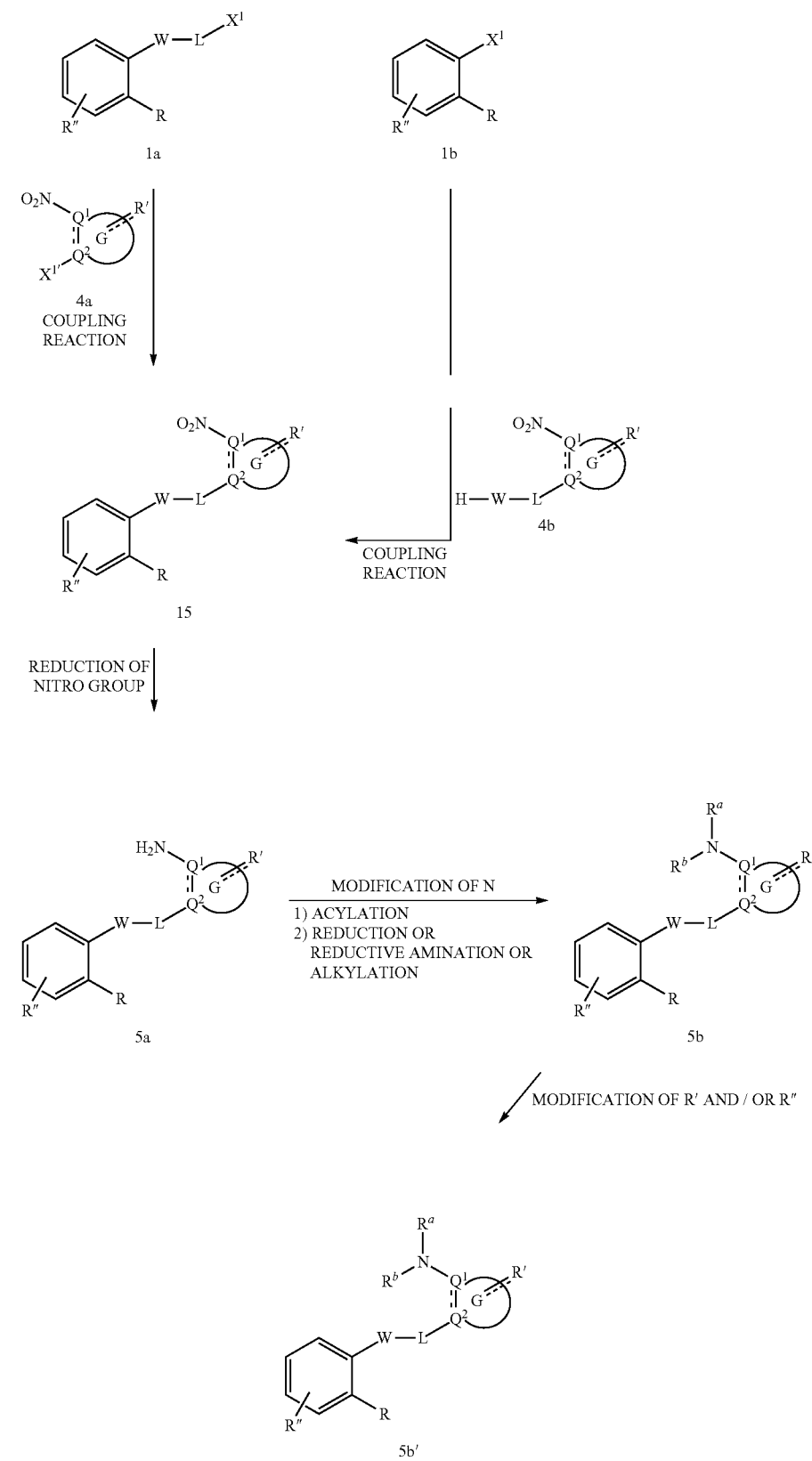

(wherein ring G, Q¹, Q², R^a, R^b, R, R', R", W, L, X¹ and X¹' have the same meaning as the definition described above.)

The Preparation Method 2 is a method wherein Q² and L are bonded via the coupling reaction between the compound (1a) obtained in General Preparation Method 1 and a nitro compound (4a) using a transition metal catalyst, or a benzene ring, which is substituted with R and R", and W are bonded by the coupling reaction between the compound (1b) and a nitro compound (4b) to prepare the nitro compound (15), which is transformed into an amine compound (5a) by reducing the nitro group, then, substituents on the nitrogen atom adjacent to Q¹ are converted according to such step as indicated in General Preparation Method 1 to go through the compound (5b), and further according to the steps indicated in General Preparation Method 1 followed by modifying R' and/or R", the compound (5b') according to the present invention is prepared.

[Preparation of Compound (1b)]

The compound (1b) is either commercially available or can be obtained as the desired halide, sulfonate derivative (preferably triflate), diazonium salts, boronic acid or boronic acid esters or trialkyltin derivative by the same method as for preparing the compound (1a) indicated in General Preparation Method 1. For instance, when two or more R" are present on the compound (1b) and R"s are bonded to each other so as to form a 5- to 8-membered ring, the compound (1b) can be prepared by the method which will be described in the following Example 78, preferably with a commercially available bromoindanone derivative and the like as the starting material.

Alternatively, the preferred (3-halostyrene compound (1a; wherein W represents —CH=CH—, L represents a single bond and X¹ represents a halogen atom) can be prepared by the halodecarboxylation of α,β-unsaturated carboxylic acid (preferably cinnamic acids) with N-halosuccinimide using lithium acetate as a catalyst, such as described in S. Roy et al., *J. Org. Chem.*, 1997, Vol. 62, No. 1, p. 199-200, and specifically as will be described in the following Preparation Example 111.

[Preparation of Compound (4a)]

The compound (4a) is either commercially available or can be obtained as the desired halide, sulfonate derivative (preferably triflate), diazonium salts, boronic acid or boronic acid esters or trialkyltin derivatives and the like by the same method as for preparing the compound (2a) indicated in General Preparation Method 1. For instance, the compound (4a; wherein X¹' represents a halogen atom, preferably a chlorine atom, a bromine atom or an iodine atom), which is the preferred example of the compound (4a), is either commercially available or can be obtained by subjecting the corresponding amine compound to Sandmeyer reaction which is well known to those skilled in the art. The corresponding amine compound can also be obtained as the desired diazonium salt (4a; wherein X¹' represents N₂⁺X"⁻; X" represents chloride, bromide or tetrafluoroborate) by the diazotization which is well known to those skilled in the art. The compound (4a; wherein X¹' represents sulfonate, preferably triflate) can easily be obtained by such method as described in General Synthesis Method 1 on the corresponding phenol derivative, which is the preferred one of the compound (4a). The above halide or triflate can also be converted into boronic acid, boronic acid esters or a trialkyltin derivative by the method such as described in General Synthesis Method 1 (refer to the following Preparation Example 76).

[Preparation of Compound (4b)]

The compound (4b) is either commercially available or can be prepared by the method well known to those skilled in the art, wherein the compound (4b; wherein W represents —CH=CH— and L represents a single bond), which is the preferred of the compound (4b), can be synthesized from the corresponding compound (4a; wherein X¹' represents a halogen atom or triflate) and commercially available tributyl(vinyl)tin and the like by using Stille coupling reaction well known to those skilled in the art, and another preferred one of the compound (4b; wherein W represents —C≡C— and L represents a single bond) can be synthesized by Sonogashira reaction, well known to those skilled in the art, representatively as will be described in the following Preparation Example 117. Another preferred one of the compound (4b; wherein W represents a formula:

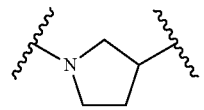 [SMILES: *C1CCN(*)C1]

and L represents a single bond) can be prepared by taking the above compound (4a; wherein X¹' represents a halogen atom, preferably a bromine atom or an iodine atom) as the starting material, converting it into a vinyl derivative (4a; wherein X¹' represents CH₂=CH—) by Stille coupling reaction well known to those skilled in the art, carrying out a 1,3-dipolar addition according to the description in K. Achiwa et al., *Chem. Pharm. Bull.* (1985, Vol. 33, No. 7, p. 2762-2766) to form a N-benzylpyrrolidine ring, and then carrying out the N-benzyl group elimination. The above 1,3-dipolar addition is well known to those skilled in the art, wherein the reaction is carried out in an inert solvent such as dichloromethane, at room temperature, using at least 1 equivalent of commercially available N-benzylic-N-(methoxymethyl)-N-trimethylsilylmethylamine with respect to the starting material vinyl derivative (4a), with the addition of an acid catalyst, most preferably trifluoroacetic acid, and 1,3-dipolar cycloaddition occurs between azothinylide generated in the reaction system under the acidic conditions and vinyl group of the compound (4a), to form the corresponding pyrrolidine ring. As having an electron-attracting functional group on the aromatic ring that is to be bonded to the vinyl group is advantageous for cyclization due to frontier orbital energy reasons necessary for cyclization, as taught in E. Laborde, *Tetrahedron Lett.*, 1992, Vol. 33, No. 44, p. 6607-6610, it is convenient for the present reaction to accomplish the desired reaction when the compound (4a) has nitro group at the o-position of the vinyl group, specifically as will be described in the following Preparation Example 103. The N-benzyl group elimination can be carried out by the reaction well known to those skilled in the art, and examples include catalytic hydrogenation and the like using a noble metal catalyst such as nickel, palladium or platinum; however, to prevent the nitro group from being reduced, it is preferable to use a effective dealkylation agent (preferably 1-chloroethyl chloroformate (ACE-Cl)) that is a tertiary amine, as described in R. A. Olofson et al., *J. Org. Chem.*, 1984, Vol. 49, No. 11, p. 2081-2082. The reaction temperature should be a temperature that is sufficient to complete the 1-chloroethoxycarbonylation that occurs concomitantly with dealkylation, and preferably from 60° C. to 150° C. The solvent used in the present reaction varies depending on the starting material, the reagent and the like, and examples of the preferred solvent include a halogen solvent such as dichloromethane, chloroform or 1,2-dichloroethane, a hydrocarbon solvent such as benzene or toluene, and more preferably 1,2-dichloroethane or toluene. Since 1-chloroethoxycarbonyl group decomposes to produce acetaldehyde dimethylacetal and carbon dioxide by adding methanol and heating (preferably 60° C. to 150° C.), the desired debenzylation can be achieved. When water solubility of the pyrrolidine compound (4b) is high and purification/isolation by extraction operation is difficult, the desired pyrrolidine compound (4b) with high purity is obtained by N-tert-butoxycarbonyl (Boc)-derivatization (refer to the following Preparation Example 19) of the crude product by the method well known to those skilled in the art and purification by the well known column chromatography, and then carrying out the Boc-removal which is well known to those skilled in the art, with an acidic solvent, preferably trifluoroacetic acid (refer to the following Example 215), specifically as will be described in the following Preparation Example 104.

[Preparation of Compound (15)]

The conditions of the coupling reaction for preparing the compound (15) from the compound (1a) and the compound (4a) vary depending on the starting material, the solvent and the transition metal catalyst, the conditions are not limited in particular as long as they are conditions similar to the present reaction, and the method well known to those skilled in the art may be used, and examples of the method include Suzuki-Miyaura coupling reaction, Sonogashira reaction, Mizoroki-Heck reaction or N-arylation and the like, preferably under the conditions such as described in General Preparation Method 1.

When a dihydronaphthalene derivative (1a; wherein W represents —CH=CX—, R represents a C2 alkyl group that may be substituted and forms a 6-membered ring together with X, L represents a single bond and $X^1$ represents a bromine atom) having a bromo group at 2 position as described in General Preparation Method 1 is used as the preferred starting material, the corresponding 3-aryl-1,2-dihydronaphthalene derivative (15; wherein ring G, $Q^1$, $Q^2$, R, R' and R" have the same meanings as the definition described above, W represents —CH=CX—, R represents a C2 alkyl group that may be substituted and forms a 6-membered ring together with X, and L represents a single bond) can be prepared by the cross-coupling reaction with the halogenated nitrate compound (4a; wherein $X^1$ preferably represents a bromine atom) using a palladium catalyst and a copper complex and the like to achieve the carbon-carbon bond formation similar to well known Ullmann reaction. The present reaction is preferably carried out in the presence of 1 equivalent of the compound (1a) and not less than 2 equivalents of the compound (4a), and at least not less than 4 equivalents of copper and a suitable solvent, as described in N. Shimizu et al., *Tetrahedron Lett.*, 1993, Vol. 34, No. 21, p. 3421-3424. The preferred solvent used in the reaction is dimethylsulfoxide, and the reaction temperature should be a temperature that is sufficient to complete the coupling reaction, preferably from 100° C. to 150° C. The present reaction is preferably carried out under an inert gas atmosphere, and more preferably carried out under a nitrogen or an argon atmosphere. Under the preferred reaction conditions this reaction is completed in 0.5 to 24 hours, the progress of the reaction can be monitored by the well known chromatographic techniques. Examples of the preferred transition metal catalyst include the well known palladium complexes such as palladium complex, and more preferably, palladium(II) chloride, dichlorobis(triphenylphosphine)palladium(II) or tetrakis(triphenylphosphine)palladium(0). Using the conditions that are similar to the present reaction, the corresponding desired compound (15) can be prepared from a bromoolefin derivative (preferably, chromene or a benzocycloheptene derivative) having a similar structure to the above 3-bromo-1,2-dihydronaphthalene (1a). Since the reaction also proceeds satisfactorily when the starting material such as a 2,2-dimethyl-3-bromo-1,2-dihydronaphthalene derivative (1a) is used, a bulky compound (15) can also be prepared. In the compound (4a) used in the present reaction, the bromo group is preferably at the o-position with respect to the nitro group. The undesired by-products can be removed by the well known chromatographic techniques, specifically as will be described in the following Preparation Example 107.

The methods well known to those skilled in the art can be used for Stille coupling reaction using a trialkyltin derivative (4a; wherein $X^{1'}$ represents $Sn(R^1)_3$; $R^1$ represents a lower alkyl group and most preferably methyl group or n-butyl group) having the nitro group at 2 position, when preparing the preferred compound (15). Examples of the preferred compound (1a) used as the raw material include commercially available 2-bromonaphthalene, 2-chlorobenzothiazole or 3,4-dihydronaphthalene-2-yl triflate described in General Preparation Method 1 and the like. The present reaction is generally carried out by using 1 equivalent of the compound (1a) and not less than 1.1 equivalents of the compound (4a) and not less than at least 3 equivalents of copper(I) chloride and lithium chloride, in the presence of a suitable solvent. The preferred solvent used in the reaction is N,N-dimethylformamide, N,N-dimethylacetamide, 1-methyl-2-pyrrolidone or dimethylsulfoxide, and more preferably, dimethylsulfoxide. The reaction temperature should be a temperature that is sufficient to complete the coupling reaction, and is preferably from room temperature to 100° C. The preferred transition metal catalyst is palladium complex, and examples include, preferably, the well known palladium complexes such as palladium(II) acetate, dichlorobis(triphenylphosphine)palladium(II), tetrakis(triphenylphosphine)palladium(0) or tris(dibenzylideneacetone)dipalladium(0), and most preferably tetrakis(triphenylphosphine)palladium(0) or tris(dibenzylideneacetone)dipalladium(0). The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. Using the similar reaction conditions as the present reaction, the corresponding compound (15) can be prepared from the compound (1a; wherein $X^1$ represents $Sn(R^1)_3$; $R^1$ represents a lower alkyl group, and preferably methyl group) and the compound (4a; wherein $X^{1'}$ represents a halogen atom (preferably a bromine atom) or triflate exist), specifically as will be described in the following Preparation Example 77.

Alternatively, the desired stilbene derivative (15) can be obtained from the β-halo styrene compound (1a; wherein W represents —CH=CH—, L represents a single bond, $X^1$ represents a halogen atom, and most preferably an iodine atom), which is the preferred one of the compound (1a), and a trialkyltin derivative (4a; wherein $X^{1'}$ represents $Sn(R^1)_3$; $R^1$ represents a lower alkyl group and most preferably methyl group or n-butyl group), which is the preferred one of the compound (4a), according to the description in S. Liebeskind et al., *J. Am. Chem. Soc.* (1996, Vol. 118, No. 11, p. 2748-2749). The present reaction is generally carried out by using 1 equivalent of the compound (1a) and at least not less than 1 equivalent of the compound (4a) and at least not less than 1 equivalent of copper(I) carboxylates (most preferably copper (I) thiophene-2-carboxylate) that are commercially available or can be prepared by the method well known to those skilled in the art, in the presence of a suitable solvent (most preferably 1-methyl-2-pyrrolidone). The reaction temperature should be a temperature that is sufficient to complete the coupling reaction, preferably from 0° C. to room temperature. The present reaction is preferably carried out under an inert gas atmosphere, and more preferably carried out under a nitrogen or an argon atmosphere. Under the preferred reaction conditions, completion is in general between 0.1 to 1 hour, and the progress of the reaction can be monitored by the well known chromatographic techniques, specifically as will be described in the following Preparation Example 111.

The conditions of the coupling reaction for preparing the compound (15) from the compound (1b) and the compound (4b) vary depending on the starting material, the solvent and the transition metal catalyst, the conditions are not limited in particular as long as they are conditions similar to the present reaction, and the methods well known to those skilled in the art may be used, examples of the method include Sonogashira reaction, Mizoroki-Heck reaction or N-arylation reaction and the like, preferably under the conditions described in General Preparation Method 1.

[Preparation of Compound (5a)]

The compound (5a) can be prepared by reducing the nitro group of the compound (15). The present step is the same as the step for preparing the compound (4a') from the compound (4a) in General Preparation Method 1, and is carried out under the conditions as described above; preferably, for instance, when only the nitro group is to be reduced without reducing olefin, the method of the following Example 57 and the like is used, and when olefin is also to be reduced simultaneously with the reduction of the nitro group, catalytic hydrogenation (refer to the following Example 22) is carried out by using a noble metal catalyst such as nickel, palladium or platinum.

[Preparation of Compound (5b)]

The compound (5b) can be prepared by the method well known to those skilled in the art by modifying the nitrogen substituent that is adjacent to $Q^1$, preferably, according to the method indicated in Step 2 of General Preparation Method 1-1. That is to say, the two-step method consisting of N-acylation and reduction of carboxamide after N-acylation, reductive amination or N-alkylation is preferred, and the compound (5b) wherein $R^a$ and $R^b$ are not hydrogen atoms can be prepared when these transformations are carried out twice consecutively, and the compound (5b) wherein $R^a$ or $R^b$ is not a hydrogen atom can be prepared if they are carried out once.

During N-acylation, the chloro or bromoacetyl compound (5b), which are obtained by using a commercially available halogenated acyl halide reagent (preferably chloroacetyl chloride or chloroacetyl bromide) (refer to the following Preparation Example 88), can be converted into the corresponding aminoacetyl derivative (5b) by reacting with an amine, preferably a secondary amine (refer to the following Preparation Example 89); furthermore, by reducing the carboxamide, the corresponding aminoalkyl derivative (5b) can also be obtained.

[Preparation of Compound (5b')]

The compound (5b') can be prepared by modifying R' and/or R'' of the compound (5b) according to the steps indicated in General Preparation Method 1.

[General Preparation Method 3]

A representative method for preparing the compound according to the present invention represented by the above formula (I) is shown below:

General Preparation Method 3

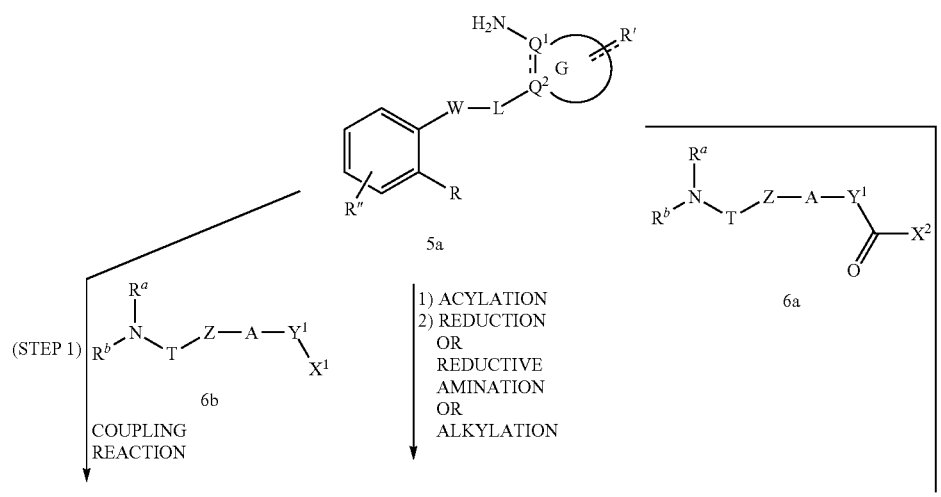

-continued

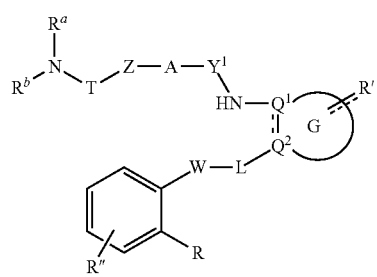

5e

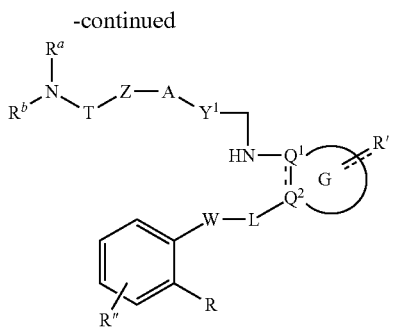

5c (STEP 2)
1) ACYLATION
2) REDUCTION OR REDUCTIVE AMINATION OR ALKYLATION

MODIFICATION OF N

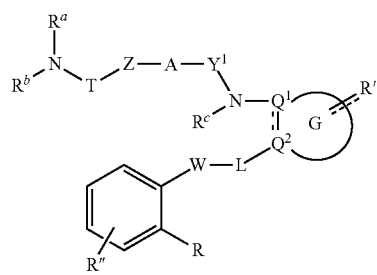

5f

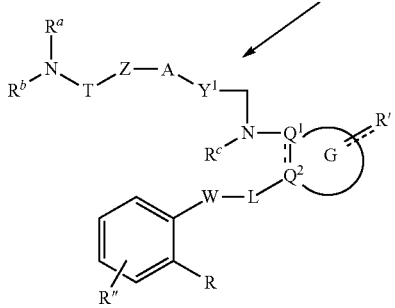

5d

MODIFICATION OF R' AND / OR R''

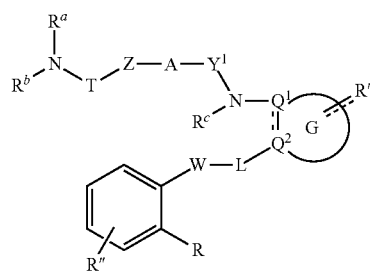

5f'

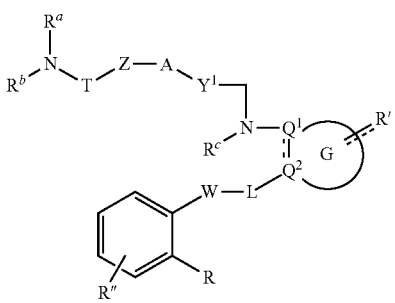

5d'

(wherein T, Z, A, Y$^1$, ring G; Q$^1$, Q$^2$, R$^a$, R$^b$, R$^c$, R, R', R'', W, L, X$^1$ and X$^2$ have the same meanings as the definition described above.)

The Preparation Method 3 is a method wherein the compound (5c) or the compound (5e) is prepared from the compound (5a) obtained in the General Preparation Method 2 according to Step 1 indicated in General Preparation Method 1-1, and then is transformed into the compound (5d) or the compound (5f) by modification of a nitrogen substituent adjacent to Q$^1$ according to Step 2 indicated in General Preparation Method 1-1, and followed by modifying R' and/or R'' according to the step indicated in General Preparation Method 1 to provide the compound (5d') or the compound (5f') according to the present invention. The Preparation Method 3 is also a method wherein the compound (5d) or the compound (5f) is prepared from the compound (5a) as the starting material, without going through the compound (5c) or the compound (5e).

[Preparation of Compound (6a) or (6b)]

The compound (6a) or the compound (6b) used in preparation of the compound (5c) or the compound (5e) can be prepared by the same method as described in General Preparation Method 1-1.

[Preparation of Compound (5c)]

Examples of the method for preparing the compound (5c) from the compound (5a) according to Step 1 include the reductive amination using the compound (6a; wherein $X^2$ represents a hydrogen atom), the two-step method consisting of N-acylation by the compound (6a; wherein $X^2$ represents hydroxyl group or a chlorine atom) followed by the reduction of a carboxamide functional group and the like, and the same method as described in General Preparation Method 1-1 can be used.

[Preparation of Compound (5e)]

Examples of the method for preparing the compound (5e) from the compound (5a) according to Step 1 include the coupling reaction by a transition metal catalyst using the compound (6b; wherein $X^1$ represents a halogen atom such as a chlorine atom, a bromine atom or an iodine atom, or triflate) and the like, and the same method as described in General Preparation Method 1-1 can be used.

[Preparation of Compound (5d) or (5f)]

Step 2 for preparing the compound (5d) or the compound (5f) from the compound (5c) or the compound (5e), is a step wherein a nitrogen substituent adjacent to $Q^1$ is modified, wherein the conditions well known to those skilled in the art may be used, and for which preferably the same method as indicated in General Preparation Method 1-1 can be used. More preferably, the two-step method wherein N-acylation and reduction are sequentially carried out, and the method such as reductive amination by aldehydes, N-alkylation by alkyl halide or alkylsulfonates can be used. The compound (5d) or the compound (5f) can also be prepared from the compound (5a) as the starting material, by first applying the Preparation Method indicated in Step 2 and subsequently applying the Preparation Method indicated in Step 1. The compound (5d) can be prepared from the compound (5a) as the starting material and N-phthaloylation well known to those skilled in the art using the preferred phthalic acid derivative (6a; wherein A represents a 6-membered aromatic cyclic group substituted with a carboxyl group, an alkoxycarbonyl group or chlorocarbonyl group, $Y^1$ represents a single bond, and $X^2$ represents hydroxyl group or a chlorine atom) via a cyclic imide wherein A and $R^c$ form a ring, which is subsequently subjected to the reduction. The methods described in a number of well known references, for instance, Synthesis Reference 1 or T. Tom et al., *J. Org. Chem.* (1997, Vol. 62, No. 8, p. 2652-2654) and the like can be used for N-phthaloylation. It is more preferable to use the method wherein the compound (5a) and phthalic acid derivative (6a) are heated in acetic acid to carry out dehydration condensation, specifically as will be described in the following Preparation Example 112. The phthalimide derivative wherein A and $R^c$ form a ring, can be subjected to the reduction which is well known to those skilled in the art and converted into a preferred isoindoline derivative (5d; wherein A represents a 6-membered aromatic group ring that may be substituted, $R^c$ represents a C1 alkyl group that may be substituted bound to A to form a ring, and $Y^1$ represents a single bond).

[Preparation of Compound (5d') or (5f')]

According to the steps indicated in General Preparation Method 1, the compound (5d') or the compound (5f') can be prepared by modifying R' and/or R" of the compound (5d) or the compound (5f).

[General Preparation Method 4]

A representative method for preparing the compound according to the present invention represented by the above formula (I) is shown below:

General Preparation Method 4

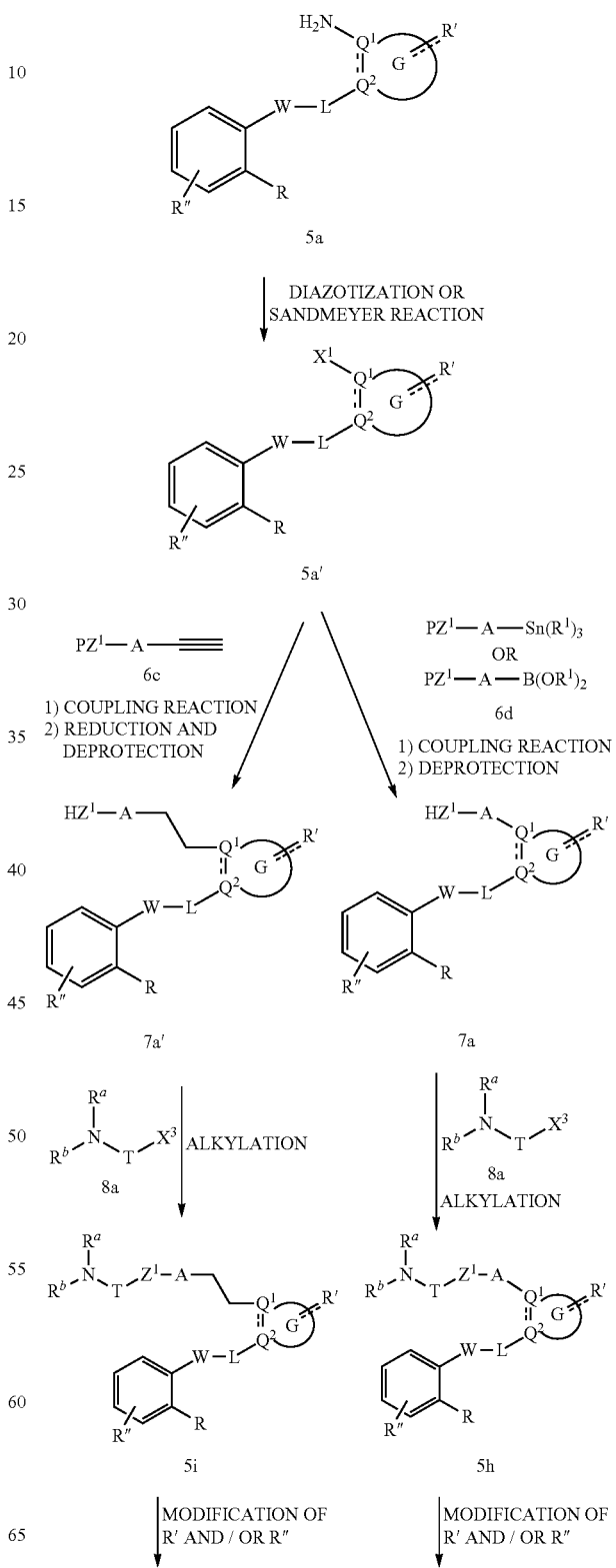

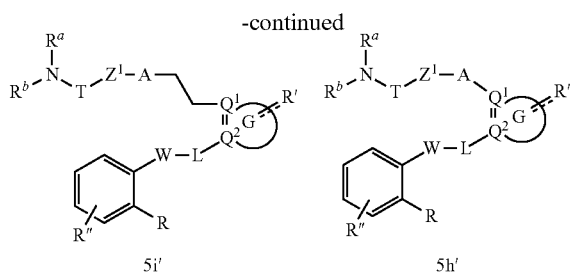

(wherein T, A, ring G, $Q^1$, $Q^2$, $R^a$, $R^b$, R', R", W, R, $R^1$, L, $X^1$, $X^2$ and $X^3$ have the same meanings as the definition described above, $Z^1$ has the same meaning as the definition of V' (1=0), P represents a protecting group for an oxygen atom, a sulfur atom or a nitrogen atom, and in the present Preparation Method, the most preferred groups for V' are an oxygen atom and a nitrogen atom, and the most preferred group for P is (1) benzyl group or an alkylsilyl group when V' represents the oxygen atom, or (2) benzyl group or an alkyl carbamoyl group when V' represents the nitrogen atom.)

The Preparation Method 4 is either a method wherein the compound (5a) obtained in General Preparation Method 2 is transformed into (5a') through diazotization or Sandmeyer reaction, then $Q^1$ and A are bonded by the coupling reaction using arylboronic acid derivative or aryltin derivative (6d) and a transition metal catalyst, suitable deprotection gives the compound (7a) through which, via alkylation by the compound (8a), the compound (5h) is obtained, and further, according to the steps indicated in General Preparation Method 1 followed by modifying R' and/or R", the compound (5h') is prepared, or, a method wherein $Q^1$ and A are bonded by the coupling reaction of the compound (5a') and alkynyl compound (6c) to give the compound (7a'), through which, via the same alkylation as above, the compound (5i) is obtained, and through which, further, according to the steps indicated in General Preparation Method followed by modifying R' and/or R", the compound (5i') is prepared.

[Preparation of Compound (5a')]

The conditions for diazotization or Sandmeyer reaction for preparing the compound (5a') notably vary depending on the properties of the amine, and the conditions are not limited as long as they are not inhibitory for the above reaction, and the well known method (for instance *The Chemical Society of Japan Eds. New Experimental Chemistry Course (Vol. 14) Synthesis and Reaction Of Organic Compounds I*, Maruzen Co., November 1977, p. 383-388 and the like) can be used.

[Preparation of Compound (6d)]

The preferred arylboronic acid derivative or aryltin derivative (6d) used in the reaction for preparing the compound (7a) may be commercially available, and when not commercially available, may be prepared by the methods well known to those skilled in the art. The arylboronic acid derivative is prepared by mixing trialkyl borate, preferably trimethyl borate or triisopropyl borate and the corresponding aryllithium derivative or arylmagnesium derivative at −50° C. to −100° C., and purifying with an acidic aqueous solution. The aryltin derivative is prepared by mixing trialkyltin halide, preferably trimethyltin chloride or tributyltin chloride, and the corresponding aryllithium derivative at −50° C. to −100° C. The aryllithium derivative that is not commercially available is prepared by the halogen-metal exchange between n-butyllithium or tert-butyllithium and the corresponding halide, preferably bromide. The arylmagnesium derivative that is not commercially available is prepared by the halogen-metal exchange between metallic magnesium or a Grignard reagent and the corresponding halide, preferably bromide. The aryltin derivative can also be prepared by subjecting bis(trialkyl)tin, preferably bis(tributyl)tin or bis(trimethyl)tin and the corresponding halide, preferably bromide, to the coupling reaction in the presence of a transition metal catalyst. Examples of the preferred transition metal catalyst include palladium or nickel catalyst, and more preferably, well known palladium complexes such as tetrakis(triphenylphosphine) palladium(0).

[Preparation of Compound (7a)]

The conditions of the coupling reaction, which is the first step for preparing the compound (7a) vary depending on the starting material, the solvent and the transition metal catalyst, and the conditions are not limited in particular as long as they are conditions similar to the present reaction, and the methods well known to those skilled in the art can be used. Examples of the solvents include, preferably, acetonitrile, tetrahydrofuran, 1,4-dioxane, 1,2-dimethoxyethane, benzene, toluene, xylene, N,N-dimethylformamide or dimethylsulfoxide, and more preferably, 1,4-dioxane, xylene, N,N-dimethylformamide or dimethylsulfoxide. The reaction temperature should be a temperature that is sufficient to complete the coupling reaction, and is preferably from room temperature to 100° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. Examples of the preferred transition metal catalyst include palladium or nickel catalyst, and more preferably, well known palladium complexes such as palladium(II) acetate, dichlorobis(triphenylphosphine)palladium(II), tetrakis(triphenylphosphine) palladium(0) or tris(dibenzylideneacetone)dipalladium(0). A phoshorous chelating agent, preferably triphenylphosphine, tri-o-tolylphosphine or tri-tert-butylphosphine, may be added to the present reaction in order to obtain satisfactory results. When an aryltin derivative is used as the starting material, metal halide or a quarternary ammonium salt, preferably copper(I) iodide, lithium chloride or tetrabutylammonium fluoride may be added to the present reaction in order to obtain satisfactory results. Preferred results can be obtained from the present reaction when the arylboronic acid derivative is used as the starting material in the presence of a base; the base used varies depending on the starting material, the solvent used and the like, the base is not limited in particular, and is, preferably, sodium hydroxide, barium hydroxide, potassium fluoride, cesium fluoride, sodium carbonate, potassium carbonate, cesium carbonate or potassium phosphate and the like.

The deprotection, which is the second step of the present reaction step, can be carried out by the well known methods (for instance Synthesis Reference 1 and the like). Deprotection of benzyl group or benzylcarbamoyl group in the presence of a noble metal catalyst in a reaction-inert solvent under a hydrogen atmosphere, or, deprotection of tert-butylcarbamoyl group or an alkylsilyl group in the acidic conditions, is preferred.

[Preparation of Compound (5h)]

The compound (5h) can be prepared by reacting the compound (7a) and an alkylation agent (8a) under the basic condition. The alkylation agent (8a) used in the present reaction may be commercially available or may be synthesized by the methods well known to those skilled in the art; in a case it is to be synthesized, a method wherein the alkylation agent (8a) can be obtained in the presence of a halogenation agent, preferably phosphorus tribromide, thionyl chloride, thionyl bromide or triphenylphosphine, by halogenation of the hydroxyl group of the corresponding alcohol derivative by a bromination agent such as N-bromosuccinimide or carbon tetrachloride or the like, or, a method wherein the alkylation agent (8a) can be obtained as sulfonic acid ester by the hydroxyl group of the corresponding alcohol derivative is converted with a sulfonyl halide, preferably methanesulfonyl chloride or p-toluenesulfonyl chloride, and the like.

The present reaction is generally carried out in the presence of 1 equivalent of the compound (7a) and not less than 1.5 equivalents of alkylation agent (8a) and at least not less than 2 equivalents of alkaline metal carbonate, preferably sodium carbonate, potassium carbonate or cesium carbonate, and a suitable solvent. This reaction solvent is a solvent that always remains inert during the reaction, or a mixture thereof, and is preferably tetrahydrofuran, methyl ethyl ketone, acetone or N,N-dimethylformamide. The reaction temperature should be a temperature that is sufficient to complete alkylation without promoting the formation of the undesirable by-products, and preferably from room temperature to 100° C.; under the preferred reaction conditions, this reaction is completed in 1 to 24 hours, and the progress of the reaction can be monitored by the well known chromatographic techniques.

[Preparation of Compound (7a')]

The compound (7a') is obtained by a first step of subjecting the compound (5a') and alkynyl compound (6c) to the coupling reaction in the presence of a transition metal catalyst, and a second step of subjecting the products to catalytic hydrogenation that uses a noble metal catalyst. The alkynyl compound (6c) used in the present reaction is obtained by the well known method (for instance R. P. Hsung et al., "Tetrahedron Lett.", 1995, Vol. 36, No. 26, p. 4525-4528), and specifically can be prepared by Sonogashira reaction of the corresponding aryl halide derivative and trimethylsilylacetylene.

The conditions for the coupling reaction, that is, for the first step in preparing the compound (7a') vary depending on the starting material, the solvent and the transition metal catalyst, and the conditions are not limited in particular as long as they are conditions similar to the present reaction, and the methods well known to those skilled in the art can be used. Examples of the solvents include, preferably, acetonitrile, tetrahydrofuran, 1,4-dioxane, 1,2-dimethoxyethane, benzene, toluene, xylene, N,N-dimethylformamide or dimethylsulfoxide, and more preferably, tetrahydrofuran, 1,4-dioxane or N,N-dimethylformamide. The reaction temperature should be a temperature that is sufficient to complete the coupling reaction, and is preferably from room temperature to 100° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. Examples of the preferred transition metal catalyst include palladium catalysts, and more preferably well known palladium complexes such as palladium(II) acetate, dichlorobis(triphenylphosphine)palladium (II), tetrakis(triphenylphosphine)palladium(0) or tris(dibenzylideneacetone)dipalladium(0) and the like. Metal halide or a quarternary ammonium salt and the like, preferably copper (I) iodide, lithium chloride, tetrabutylammonium fluoride or silver(I) oxide may be added in the present reaction in order to obtain satisfactory results. The preferred results can also be provided in the presence of a base, and the base used varies depending on the starting material, the solvent used and the like, and the base is not limited in particular, and is, preferably, triethylamine, N,N-diisopropylethylamine or pyridine and the like.

For the reduction and deprotection, that is the second step in preparing the compound (7a'), the methods well known to those skilled in the art may be used, and they can conveniently be carried out by catalytic hydrogenation using a catalyst such as palladium, platinum or nickel, preferably with the benzyl group as the protecting group.

[Preparation of Compound (5i)]

The compound (5i) can be prepared according to the similar method as that of the above-mentioned compound (5h), and can be obtained by reacting the compound (7a') and an alkylation agent (8a) under the basic conditions.

[Preparation of Compound (5i') and Compound (5h')]

The compound (5i') and the compound (5h') can be prepared according to the steps indicated in General Preparation Method 1 followed by modifying R' and/or R".

[General Preparation Method 5]

A representative method for preparing the compound according to the present invention represented by the above formula (I) is shown below:

General Preparation Method 5

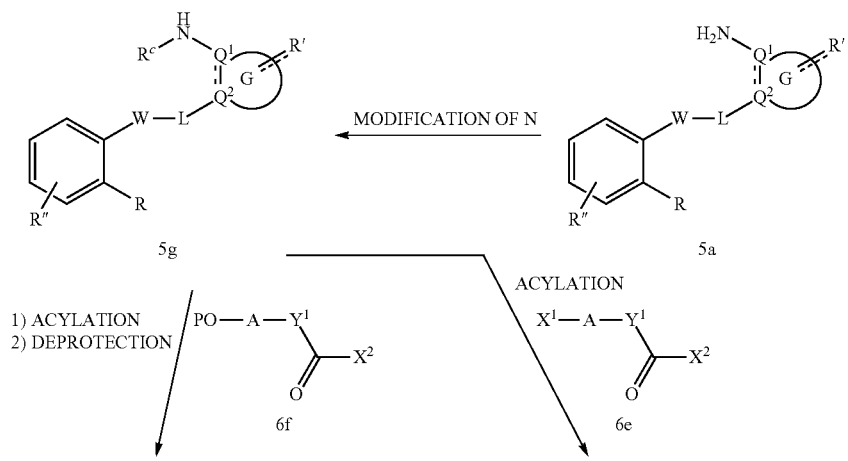

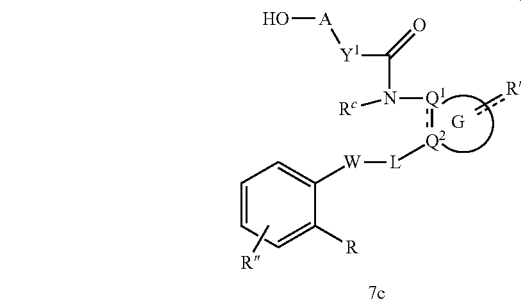

7c

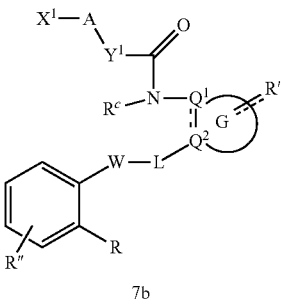

7b

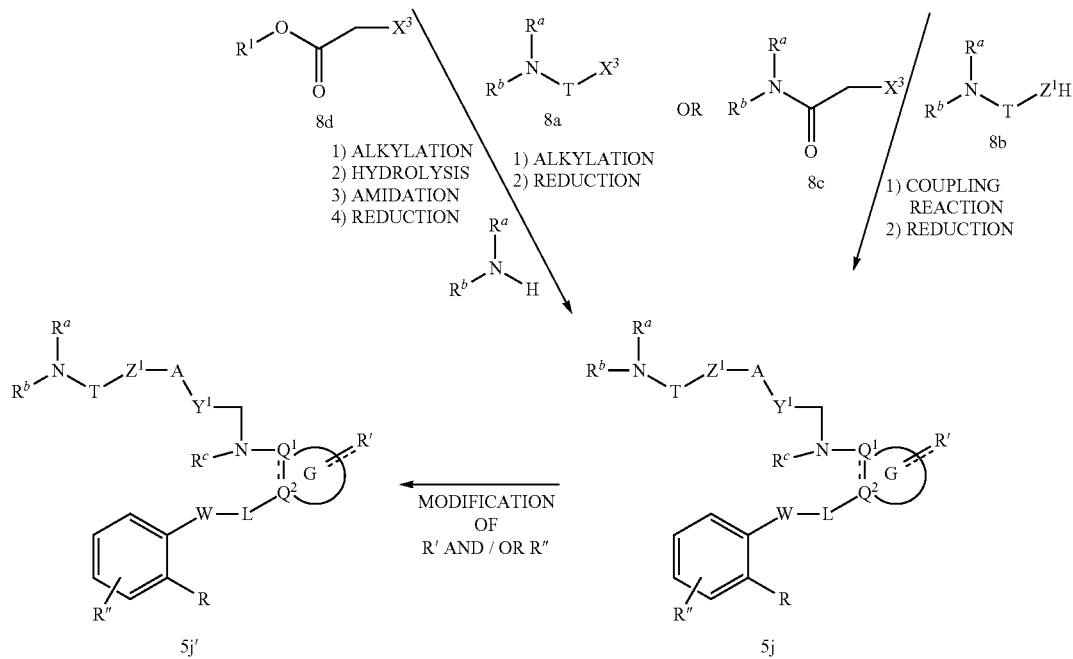

(wherein T, A, ring G, $Q^1$, $Q^2$, $R^a$, $R^b$, R', R'', W, R, $R^c$, $R^1$, L, $X^1$, $X^2$ and $X^3$ have the same meanings as the definition described above, $Y^1$ has the same meaning as the definition of Y, $Z^1$ has the same meaning as the definition of V' (k=0), P represents a protecting group for an oxygen atom; in present Preparation Method, the most preferred groups for V' are an oxygen atom and a nitrogen atom, and the most preferred group for P is benzyl group, an alkylsilyl group or acyl group.)

The Preparation Method 5 is either a method wherein the amine substituent of the compound (5a) obtained in General Preparation Method 2 is modified to give the compound (5g), then acylation with compound (6e) gives the compound (7b) through which, by bonding A and $Z^1$ by the coupling reaction with compound (8b) using a transition metal catalyst and conversion into the compound (5j), further, according to the steps indicated in General Preparation Method 1 followed by modifying R' and/or R'', the compound (5j') is prepared, or, a method wherein the compound (5g), which undergoes the acylation with the compound (6f) having a suitable protecting group and a deprotection, to give the compound (7c) through which, after reaction with an alkylation agent (8a), (8c) or (8d), the product is subjected to a suitable conversion to be converted into the compound (5j), further, according to the steps indicated in General Preparation Method 1 followed by modifying R' and/or R'', the compound (5j') is prepared. Alternatively, the compound (7b) can be prepared by converting the hydroxyl group of the compound (7c) into $X^1$.

[Preparation of Compound (5g)]

The compound (5g) can be prepared by modifying the amine substituent of the compound (5a) according to the same method as indicated in General Preparation Method 1.

[Preparation of Compound (6e)]

The preferred compound (6e) used in the reaction for preparing compound (7b) may be commercially available, and when not commercially available, may be prepared by the methods well known to those skilled in the art. For instance, the compound (6e) wherein $X^2$ represents a chlorine atom can be prepared by reacting a halogenation agent, preferably thionyl chloride or oxalyl chloride with the corresponding carboxylic acid derivative (wherein $X^2$ represents hydroxyl group), using the well known method. The corresponding carboxylic acid derivative (wherein $X^2$ represents hydroxyl group) may be commercially available, and when not commercially available, may be prepared by the methods well known to those skilled in the art, and can be prepared by (1) a method wherein the corresponding halogen derivative is converted into the carboxylic acid derivative, (2) a method wherein the corresponding alcohol derivative is oxidized into the carboxylic acid derivative, (3) a method wherein the corresponding aldehyde derivative is oxidized into the carboxylic acid derivative, and the like.

[Preparation of Compound (7b) from Compound (5g)]

For the reaction conditions for preparing the compound (7b) from the compound (5g), the methods well known to those skilled in the art can be used. Preferably, in a case of the compound (6e; wherein $X^2$ represents a chlorine atom), the compound (7b) can be conveniently prepared by mixing with the compound (5g) under the basic condition, in this case, the base, the solvent and the reaction temperature used vary depending on the starting material, and are not limited in particular, and (1) a method using pyridine, lutidine, quinoline or isoquinoline and the like as the solvent, (2) a method using pyridine, triethylamine or N,N-diisopropylethylamine and the like as the base, a solvent that always remains inert during the reaction, or a mixture thereof, preferably tetrahydrofuran or 1,4-dioxane and the like, and (3) a method using alkaline aqueous solution, preferably aqueous solution of sodium hydroxide or potassium hydroxide and the like as the base, two-phase partitioning system of halogenated solvent, preferably dichloromethane or 1,2-dichloroethane and the like, are preferred. The reaction temperature should be a temperature that is sufficient to complete acylation without promoting the formation of the undesirable by-products, and is preferably from room temperature to 100° C. Under the preferred reaction conditions, this reaction is completed in 1 to 24 hours, and the progress of the reaction can be monitored by the well known chromatographic techniques.

In a case of the preferred compound (6e; wherein $X^2$ represents hydroxyl group) for preparing the compound (7b) from the compound (5g), the methods well known to those skilled in the art can be used. Preferably, the compound (7b) can be conveniently prepared by activating the compound (6e) with a mixed anhydride or activated ester of a suitable carboxylic acid, and mixing with the compound (5g); in this case, the reagent, solvent and reaction temperature used vary depending on the starting material, and are not limited in particular, and the well known reagents such as ethyl chloroformate, dicyclohexylcarbodiimide, acyl imidazole, nitrophenol, pentachlorophenol, N-hydroxysuccinimide or 1-hydroxybenzotriazole and the like are used as the preferred activators. Examples of the solvents include, preferably, dichloromethane, tetrahydrofuran or N,N-dimethylformamide, and the reaction temperature should be a temperature that is sufficient to complete acylation without promoting the formation of the undesirable by-products, and is preferably from room temperature to 100° C. Under the preferred reaction conditions, this reaction is completed in 1 to 24 hours, and the progress of the reaction can be monitored by the well known chromatographic techniques.

[Preparation of Compound (8b)]

The preferred compound (8b) used in the reaction for preparing the compound (5j) from the compound (7b) may be commercially available, and when not commercially available, may be prepared by the methods well known to those skilled in the art. For instance, for the alcohol compound (8b) wherein $Z^1$ represents an oxygen atom, the alcohol can be prepared by subjecting the corresponding carboxylic acid derivative or aldehyde derivative to the reduction well known to those skilled in the art. The amine compound (8b) wherein $Z^1$ represents a nitrogen atom can be prepared by the methods such as (1) a method wherein the corresponding nitrile derivative and the like are subjected to the reduction well known to those skilled in the art to convert into an amine, (2) a method wherein the corresponding alcohol is converted into an amine by the method well known to those skilled in the art, and (3) a method wherein the corresponding halogenated derivative is converted into an amine by the method well known to those skilled in the art, which are described in a number of standard documents (for instance *The Chemical Society of Japan* Eds. *New Experimental Chemistry Course* (*Vol.* 14) *Synthesis and Reaction of Organic Compounds III*, Maruzen Co., November 1977, p. 1332-1399 and *Organic Chemistry Experiment Handbook* (*Vol.* 3) *Synthesis Reaction I*, Kagakudojin, August 1990, p. 128-134 and the like).

[Preparation of Compound (5j) from Compound (7b)]

For the reaction conditions for preparing the compound (5j) from the compound (7b), the methods well known to those skilled in the art may be used; The compound (5j) can be prepared by bonding A and $Z^1$ as a first step, and subjecting the product to the reduction to convert the carboxamide functional group into an amine functional group as a second step. The reaction conditions for the first step for bonding A and $Z^1$ vary depending on the starting material, and the conditions are not limited in particular, and when $Z^1$ in the compound (8b) represents an oxygen atom, substitution under the basic conditions with $X^1$ in the compound (7b) as a leaving group is preferred. The base, the solvent and the reaction temperature used vary depending on the starting material, and are not limited in particular, and a solvent that always remains inert during the reaction, or a mixture thereof, preferably tetrahydrofuran or N,N-dimethylformamide can be used, with preferably potassium hydride, sodium hydride or n-butyllithium as the base. The reaction temperature should be a temperature that is sufficient to complete the reaction without promoting the formation of the undesirable by-products, preferably from room temperature to 200° C., and more preferably from 50° C. to 150° C. Under the preferred reaction conditions, this reaction is completed in 1 to 24 hours, and the progress of the reaction can be monitored by the well known chromatographic techniques.

For the preferred reaction conditions for the first step for bonding A and $Z^1$, when $Z^1$ in the compound (8b) is an oxygen atom or a nitrogen atom, the coupling reaction using a transition metal catalyst is satisfactory. The reaction conditions of the present reaction vary depending on the starting material, the solvent and the transition metal catalyst, and the conditions are not limited in particular as long as they are conditions similar to the present reaction, and the methods well known to those skilled in the art can be used. Examples of the solvents include, preferably, acetonitrile, tetrahydrofuran, 1,4-dioxane, 1,2-dimethoxyethane, benzene, toluene, xylene, N,N-dimethylformamide or dimethylsulfoxide, and more preferably, tetrahydrofuran, 1,4-dioxane, benzene or toluene. The reaction temperature should be a temperature that is sufficient to complete the coupling reaction, preferably 60° C. to 120° C. The present reaction is preferably carried out under an inert gas atmosphere, and more preferably carried out under a nitrogen or an argon atmosphere. Under the preferred reaction conditions, this reaction is completed in 1 to 24 hours, and the progress of the reaction can be monitored by the well known chromatographic techniques. Examples of the preferred transition metal catalysts include well known palladium complexes, and more preferably, well known palladium complexes such as palladium(II) acetate, dichlorobis (triphenylphosphine)palladium(II), tetrakis(triphenylphosphine)palladium(0) or tris(dibenzylideneacetone) dipalladium(0). Furthermore, a phosphorous chelating agent (preferably triphenylphosphine, tri-o-tolylphosphine, tri-tert-butylphosphine, 2,2'-bis(diphenylphosphino)-1,1'-binaphthyl, 2-(di-tert-butylphosphino)-1,1'-binaphthyl, 2-(di-tert-butylphosphino)-2'-(dimethylamino)-1,1'-binaphthyl, 1,1'-bis(diphenylphosphino)ferrocene or Xantphos (refer to P. W. N. M. van Leeuwen et al., *Tetrahedron Lett.*, 1999, Vol. 40, No. 19, p. 3789-3790) and the like) or an imidazolium-type carbene chelator (described in, for instance, S. P. Nolan et al., *Org. Lett.*, 1999, Vol. 1, No. 8, p. 1307-1309) may be added in the present reaction in order to obtain satisfactory results (lowering of the reaction temperature required, shortening of the reaction time or increase in the yield). The present reaction can also provide the preferred results in the presence of a base, and the base used is not limited in particular as long as the base is used in the coupling reaction similar to the present reaction, preferably, sodium carbonate, potassium carbonate, cesium carbonate, potassium phosphate, sodium tert-butoxide, potassium tert-butoxide or lithium hexamethyldisilazide and the like (for instance, S. L. Buchwald et al., *J. Am. Chem. Soc.*, 2001, Vol. 123, p. 10770-10771).

For the reduction, which is the second step in the step for preparing the compound (5j), the methods well known to those skilled in the art can be used. The reaction solvent varies depending on the starting material, the reagent used and the like, the solvent is not limited in particular as long as it is an inert solvent that dissolves the starting materials to some extent without inhibiting the reaction, and the solvent is preferably, diethyl ether or tetrahydrofuran. The preferred reducing agent is the well known borane or lithium aluminum hydride. The reaction temperature used in the present reaction should be a temperature that is sufficient to complete the reduction without promoting the formation of the undesirable by-products, and is preferably from 0° C. to room temperature. Under the preferred reaction conditions, the present reaction is completed in 0.1 to 12 hours, and the progress of the reaction can be monitored by the well known chromatographic techniques. For the present reduction, a procedure is more preferred, wherein not less than 3 equivalents of lithium aluminum hydride with respect to 1 molar equivalent of amide functional group of the starting material is suspended in an inert solvent, preferably diethyl ether or tetrahydrofuran, then the same equivalent of aluminum chloride as lithium aluminum hydride is added at 0° C., then stirred preferably for 0.1 to 1 hour, then the starting materials are added, and satisfactory results (shortening of the reaction time or increase in the yield and the like) can be obtained.

[Preparation of Compound (6f)]

The preferred compound (6f) used in the reaction for preparing the compound (7c) may be commercially available, and when not commercially available, may be prepared by the methods well known to those skilled in the art. For instance, the compound (6f) wherein $X^2$ represents a chlorine atom can be prepared by reacting a halogenation agent, preferably thionyl chloride or oxalyl chloride, with the corresponding carboxylic acid derivative (wherein $X^2$ represents hydroxyl group) using the well known method. The corresponding carboxylic acid derivative (wherein $X^2$ represents hydroxyl group) may be commercially available, and when not commercially available, may be prepared by the methods well known to those skilled in the art, and can be prepared by (1) a method wherein the corresponding halogen derivative is converted into the carboxylic acid derivative, (2) a method wherein the corresponding alcohol derivative is oxidized into the carboxylic acid derivative, (3) a method wherein the corresponding aldehyde derivative is oxidized into the carboxylic acid derivative, or the like. The hydroxy-protecting group P of the compound (6f) is not limited in particular as long as it is acceptable under the present reaction conditions, and substituents described in Chapter 3 of Synthesis Reference 1 or the like may be used, preferably an alkyl group, benzyl group, an alkylsilyl group, acyl group or the like, and more preferably, benzyl group, tert-butyldimethylsilyl group or acetyl group.

[Preparation of Compound (7c)]

For the acylation, which is the first step in preparing the compound (7c) from the compound (5g), the methods well known to those skilled in the art can be used. Preferably, the compound (7c) can be conveniently prepared according to the same method having the same reaction conditions as for preparing the compound (7b).

For the deprotection, which is the second step in preparing the compound (7c) from the compound (5g), the methods well known to those skilled in the art may be used, which vary depending on the starting material and the methods are not limited in particular; for instance the method described in Chapter 3 of Synthesis Reference 1 can be used. Preferably, it is convenient to use the deprotection by a noble metal catalyst under a hydrogen atmosphere when the protecting group P represents benzyl ether group, the deprotection under the acidic conditions or using tetrabutylammonium fluoride when the protecting group P represents tert-butyldimethylsilyl group, the deprotection using potassium carbonate, sodium carbonate, potassium hydroxide or sodium hydroxide and the like when protecting group P represents acetyl group.

[Preparation of Compound (8a), (8c) or (8d)]

The preferred alkylation agent (8a), (8c) or (8d) used in the reaction for preparing the compound (5j) from the compound (7c) may be commercially available, and when not commercially available, may be prepared by the methods well known to those skilled in the art. For instance, the alkylation agent (8a) can be prepared by the same method as described in General Preparation Method 4. The alkylation agent (8c) can be prepared by the well known method wherein the corresponding amine is acylated with α-halogenoacetyl halide, or by the method wherein after acylation with α-hydroxyacetyl halide, the hydroxyl group is converted into sulfonic acid ester. The preferred alkylation agent (8d) is ethyl bromoacetate or tert-butyl bromoacetate.

[Preparation of Compound (5j) from Compound (7c)]

For the conditions for the alkylation, which is the first step in preparing the compound (5j) from the compound (7c), the methods well known to those skilled in the art may be used, and preferably, the same method as described in General Preparation Method 4 can be used.

When the alkylation agent (8a) or (8c) is used, the reduction is preferred as the reaction in the second step for preparing the compound (5j). In this case, the reagent, solvent and reaction temperature used vary depending on the starting material, and are not limited in particular, and preferably, the same conditions as for the above-mentioned reduction that is the second step in preparing the compound (5j) from the compound (7b) can be used.

When the alkylation agent (8d) is used, the compound (5j) can also be prepared by carrying out the above-mentioned alkylation, at the second step, subjecting the product to alkaline hydrolysis by the well known method as the reaction, as the third step, forming an amide bond with a commercially available or well known amine compound prepared by the well known method, and at the fourth step, subjecting the product to the same reduction as described above.

[Preparation of Compound (7b) from Compound (7c)]

The step for preparing the compound (7b) from the compound (7c) varies depending on the starting material, and is not limited in particular, and for instance, the same method as the method for synthesizing the compound (6b) in General Preparation Method 1 can be used.

[Preparation of Compound (5j')]

The compound (5j') can be prepared from the compound (5j) according to the steps indicated in General Preparation Method 1 followed by modifying R' and/or R".

[General Preparation Method 6]

A representative method for preparing the compound according to the present invention represented by the above formula (I) is shown below:

General Preparation Method 6

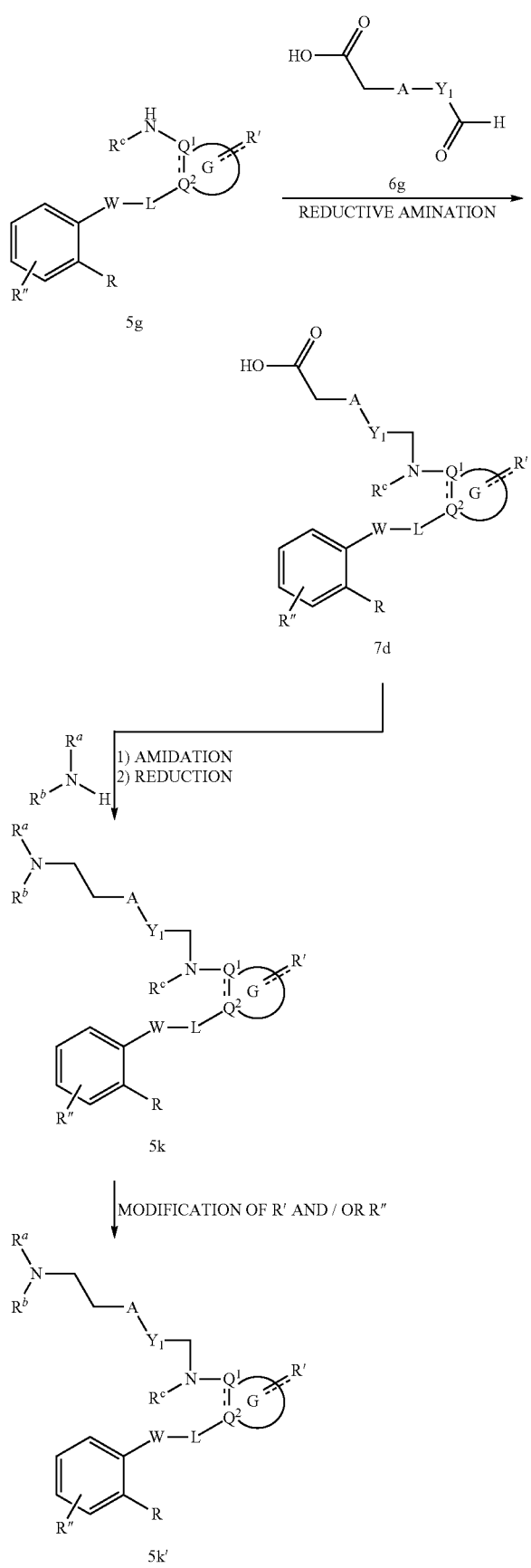

(wherein A, ring G, $Q^1$, $Q^2$, $R^a$, $R^b$, R', R", W, R, $R^c$ and L have the same meanings as the definition described above, and $Y^1$ has the same meaning as the definition of Y.)

The Preparation Method 6 is a method wherein the compound (5g) obtained in General Preparation Method 5, by the reductive amination with formyl carboxylic acid derivative (6g), is converted into the compound (7d), an amide bond with an amine compound is formed, then the product is subjected to the reduction to give the compound (5k), through which, further, according to the steps indicated in General Preparation Method 1 followed by modifying R' and/or R", the compound (5k') can be prepared.

[Preparation of Compound (6g)]

The preferred compound (6g) used in the reaction for preparing the compound (7d) may be commercially available, and when not commercially available, may be prepared by the methods well known to those skilled in the art. For instance, the compound (6g) can be prepared by the method wherein after the oxidation of the corresponding hydroxymethyl carboxylic acid ester, the resulting product is hydrolyzed by the methods well known to those skilled in the art to convert into formyl carboxylic acid. For the oxidation, the oxidation using manganese(IV) oxide as an oxidizing agent, or dimethylsulfoxide oxidation having oxalyl chloride, trifluoroacetic anhydride or sulfur trioxide-pyridine complex or the like as an electrophilic agent is preferred. The preferred compound (6g) can also be prepared by subjecting a halomethylcarboxylic acid derivative to the well known oxidation (for instance, "Org. Synth.", 1963, Vol. 4, p. 690-693), specifically as will be described in the following Preparation Example 170.

[Preparation of Compound (7d)]

For the reductive amination for preparing the compound (7d) from the compound (5g), the methods well known to those skilled in the art can be used. Preferably, the same method as the reductive amination described in General Preparation Method 1 can be used.

The preferred amine derivative used in the reaction for preparing the compound (5k) may be commercially available, and when not commercially available, may be prepared by the methods well known to those skilled in the art. For instance, the secondary amine derivative can be prepared by converting a commercially available primary amine derivative by the method well known to those skilled in the art, preferably by the 2-step reaction consisting of acylation and reduction, or by reductive amination, into secondary amine. The amine derivative can also be prepared from a halogen derivative or a alcohol derivative, alternatively the amine can be prepared by the methods that are described in a number of standard documents (for instance *The Chemical Society of Japan Eds. New Experimental Chemistry Course* (Vol. 14) *Synthesis and Reaction of Organic Compounds III*, Maruzen Co., November 1977, p. 1332-1399 and *Organic Chemistry Experiment Handbook* (Vol. 3) *Synthesis Reaction I*, Kagakudojin, August 1990, p. 128-134 and the like).

[Preparation of Compound (5k)]

For the amidation and reduction for preparing the compound (5k) from the compound (7d), the methods well known to those skilled in the art may be used, preferably, the same method as the method for preparing the compound (2a) described in General Preparation Method 1 can be used. That is to say, it is preferred to use the method wherein the carboxylic acid functional group of the compound (7d) is converted into acid halide by a halogenation agent, then an amide bond with an amine derivative is formed under the basic conditions, and the resulting product is subjected to the reduction, specifically as will be described in the following Example 715.

For the method for preparing the compound (5k), it is also preferred to use the method wherein the carboxylic acid functional group of the compound (7d) is activated with a mixed anhydride or activated ester, an amide bond is formed with an amine derivative, then the resulting product is subjected to the reduction. The amidation, which is the first step, varies depending on the reagent, solvent, reaction temperature and the starting material used, and the reaction are not limited in particular, and the well known reagent such as ethyl chloroformate, dicyclohexylcarbodiimide, acyl imidazole, nitrophenol, pentachlorophenol, N-hydroxysuccinimide or 1-hydroxybenzotriazole is used as the preferred activator. Examples of the solvents include, preferably, dichloromethane, tetrahydrofuran or N,N-dimethylformamide, and the reaction temperature should be a temperature that is sufficient to complete acylation without promoting the formation of the undesirable by-products, and is preferably from room temperature to 100° C. Under the preferred reaction conditions, this reaction is completed in 1 to 24 hours, and the progress of the reaction can be monitored by the well known chromatographic techniques. For the reduction, which is the second step, the method well known to those skilled in the art may be used, and the same method as described above is preferred.

[Preparation of Compound (5k')]

The compound (5k') can be prepared from the compound (5k) according to the steps indicated in General Preparation Method 1 followed by modifying R' and/or R".

[General Preparation Method 7]

A representative method for preparing the compound according to the present invention represented by the above formula (I) is shown below:

General Preparation Method 7

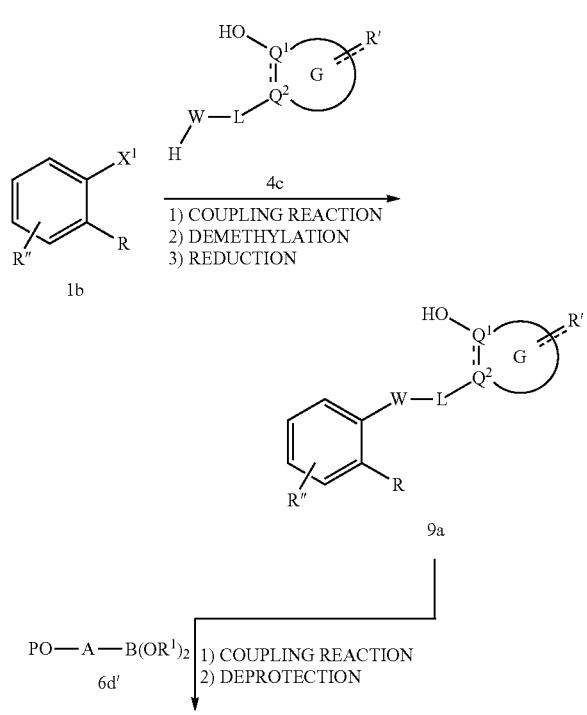

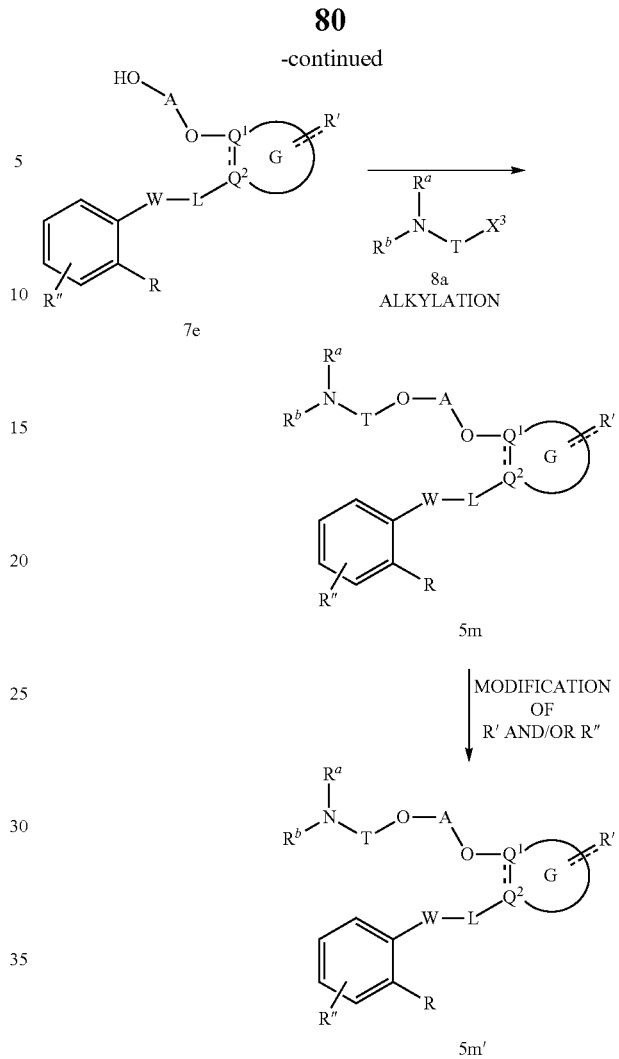

(wherein L, W, T, A, ring G, $Q^1$, $Q^2$, $R^a$, $R^b$, R', R", R, $R^1$, X, $X^1$ and $X^3$ have the same meanings as the definition described above, X may be bonded to ring G to form a ring; P represents a protecting group for an oxygen atom; in the present Preparation Method, the Preferred Substituent of L is a Single Bond, the Preferred substituent of W is —CHX—$CH_2$— or —CHX—C(=O)—, and the preferred substituent of P is benzyl group or an alkylsilyl group.)

The Preparation Method 7 is a method wherein the compound (1b) obtained in General Preparation Method 2 and the compound (4c) are subjected to the coupling reaction using a transition metal catalyst followed by demethylation, if necessary, the resulting product is converted into the compound (9a), through suitable substituent conversion to give the compound (7e) via the 2-step reaction consisting of the coupling reaction with arylboronic acid derivative (6d') and the deprotection of the protecting group P, the compound (5m) is obtained by alkylation by the compound (8a), further, according to the steps indicated in General Preparation Method 1 followed by modifying R' and/or R", the compound (5 m') can be prepared.

[Preparation of Compound (4c)]

The preferred compound (4c) used in the preparation of the compound (9a) may be commercially available, and when not commercially available, may be prepared by the methods well known to those skilled in the art. For instance, a 1-tetralone derivative (4c) can be synthesized with a 4-phenylbutyric acid derivative as the starting material, by intramolecular cyclization whose key reaction is the Friedel-Crafts acylation well known to those skilled in the art. If a 3-phenylpropionic acid derivative is the starting material, a 1-indanone derivative (4c) can be synthesized (for instance, R. J. Heffner et al., *Synth. Commun.*, 1991, Vol. 21, No. 21, p. 2231-2256), specifically as will be described in the following Preparation Example 175.

[Preparation of Compound (9a)]

The compound (9a) can be prepared by using the method well known to those skilled in the art, for instance, can be prepared through the 3-step method consisting of the coupling reaction between the compound (1b) and the compound (4c) using a transition metal catalyst, followed by the demethylation and then the reduction. The conditions for the coupling reaction between the compound (1b) and the compound (4c) vary depending on the starting material, the solvent and the transition metal catalyst, and the conditions are not limited in particular as long as they are conditions similar to the present reaction, and the methods well known to those skilled in the art may be used; preferably, conditions such as described in General Preparation Method 1 can be used. More preferably, the reaction conditions such as described in S. L. Buchwald et al., *J. Am. Chem. Soc.*, 2000, Vol. 122, p. 1360-1370 or, J. F. Hartwig et al., *J. Am. Chem. Soc.*, 1999, Vol. 121, p. 1473-1478 can be used. The conditions for the demethylation, which is the second step in preparing the compound (9a), vary depending on the starting material and solvent and the like, and the conditions are not limited in particular as long as they are conditions similar to the present reaction, and conditions well known to those skilled in the art may be used; preferably, the same conditions as described in Preparation of Compound (6b) of General Preparation Method 1-1 can be used. The conditions described in J. S. Yadav et al., *Chem. Lett.*, 2000, p. 738-739 are more preferred, and the demethylation proceeds conveniently when refluxing in an acetonitrile solvent in the presence of cerium(III) chloride and sodium iodide, specifically as will be described in the following Preparation Example 192. The conditions for the reduction, which is the third step in preparing compound (9a), vary depending on the starting material and solvent and the like, and the condition are not limited in particular as long as they are conditions similar to the present reaction, and the conditions well known to those skilled in the art may be used; preferably, the same conditions as described in Preparation of Compound (2f) of General Preparation Method 1-2 can be used. The conditions where carbonyl group is reduced with a metallic reducing reagent, then the resulting product is subjected to catalytic hydrogenation using a noble metal catalyst are more preferred, specifically as will be described in the following Preparation Example 178.

[Preparation of Compound (6d')]

The preferred arylboronic acid derivative (6d') used in the preparation of the compound (7e) may be commercially available, and when not commercially available, may be prepared by the methods well known to those skilled in the art. The non-commercially available arylboronic acid derivative (6d') can be synthesized by the same method as described in Preparation of Compound (6d) of General Preparation Method 4.

[Preparation of Compound (7e)]

The compound (7e) can be prepared by using the method well known to those skilled in the art, and can be prepared by the two-step reaction consisting of the coupling reaction with an arylboronic acid derivative (6d') using a transition metal and the deprotection of the protecting group P. The conditions for the coupling reaction between the compound (9a) and the compound (6d') vary depending on the starting material, the solvent and the transition metal catalyst, and the conditions are not limited in particular as long as they are conditions similar to the present reaction, and the methods well known to those skilled in the art may be used; preferably, the conditions such as described in General Preparation Method 1 can be used. More preferably, the reaction conditions such as described in D. M. T. Chan et al., *Tetrahedron Lett.*, 1998, Vol. 39, p. 2933-2936, or, D. A. Evans et al., *Tetrahedron Lett.*, 1998, Vol. 39, p. 2937-2940 can be used. The conditions for the deprotection, which is the second step in preparing the compound (7e), vary depending on the starting material and solvent and the like, and the conditions are not limited in particular as long as they are conditions similar to the present reaction, and the conditions well known to those skilled in the art may be used; preferably, the same conditions as described in Preparation of Compound (7a) of General Preparation Method 4 can be used.

[Preparation of Compound (5m)]

The compound (5m) can be prepared by using the method well known to those skilled in the art, and can be prepared by subjecting the compound (7e) and the compound (8a) described in General Preparation Method 4 to the well known alkylation. Preferably, the compound (5m) can be prepared by the same method as described in the preparation method for the compound (5h) in General Preparation Method 4.

[Preparation of Compound (5 m')]

The compound (5 m') can be prepared according to the steps indicated in General Preparation Method 1 followed by modifying R' and/or R" of the compound (5m).

[General Preparation Method 8]

A representative method for preparing the compound according to the present invention represented by the above formula (I) is shown below:

General Preparation Method 8-1

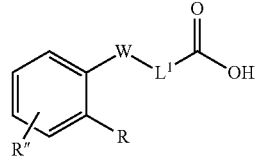

10

FRIEDEL-CRAFTS REACTION 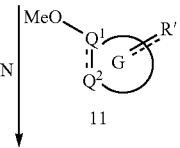

11

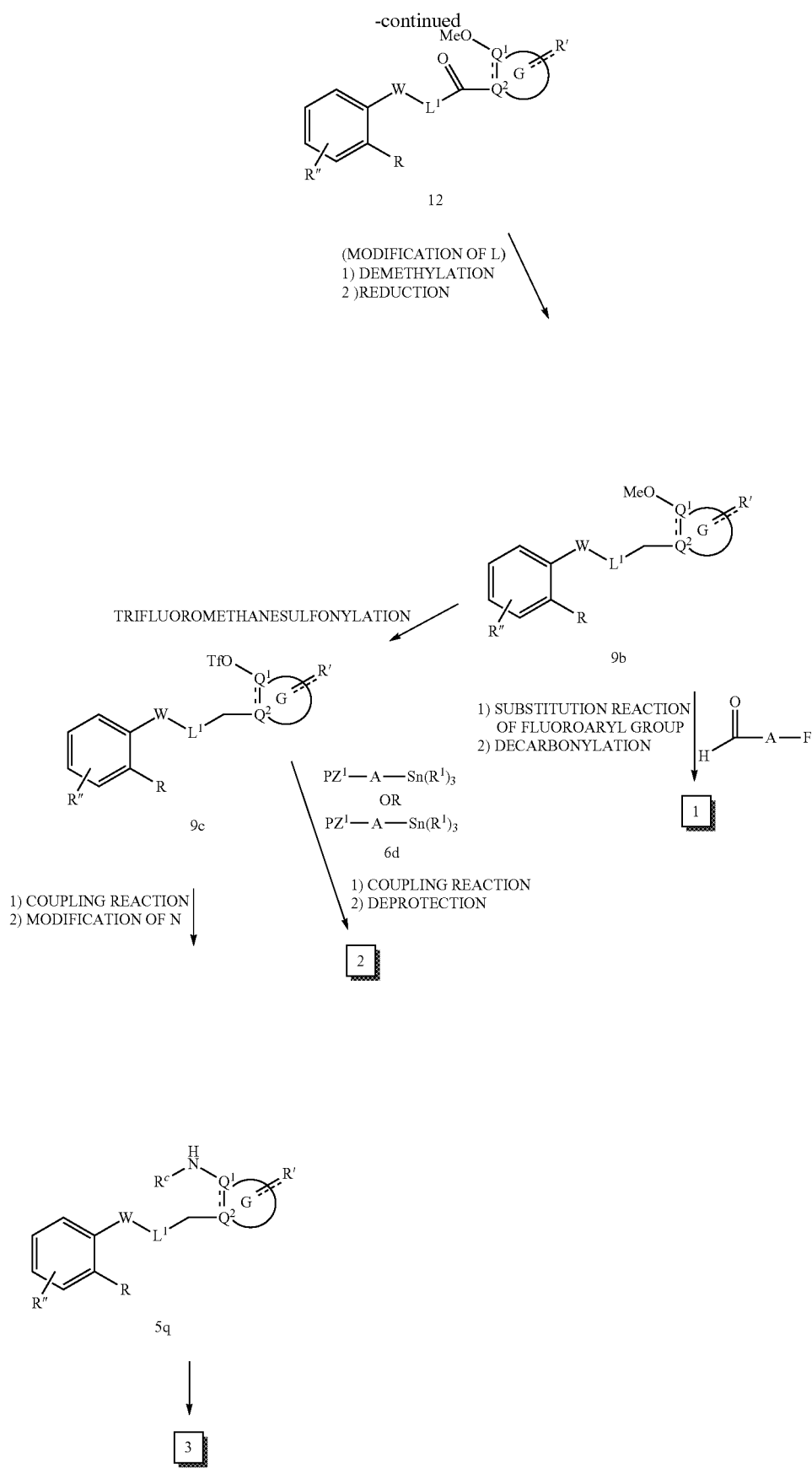

General Preparation Method 8-2

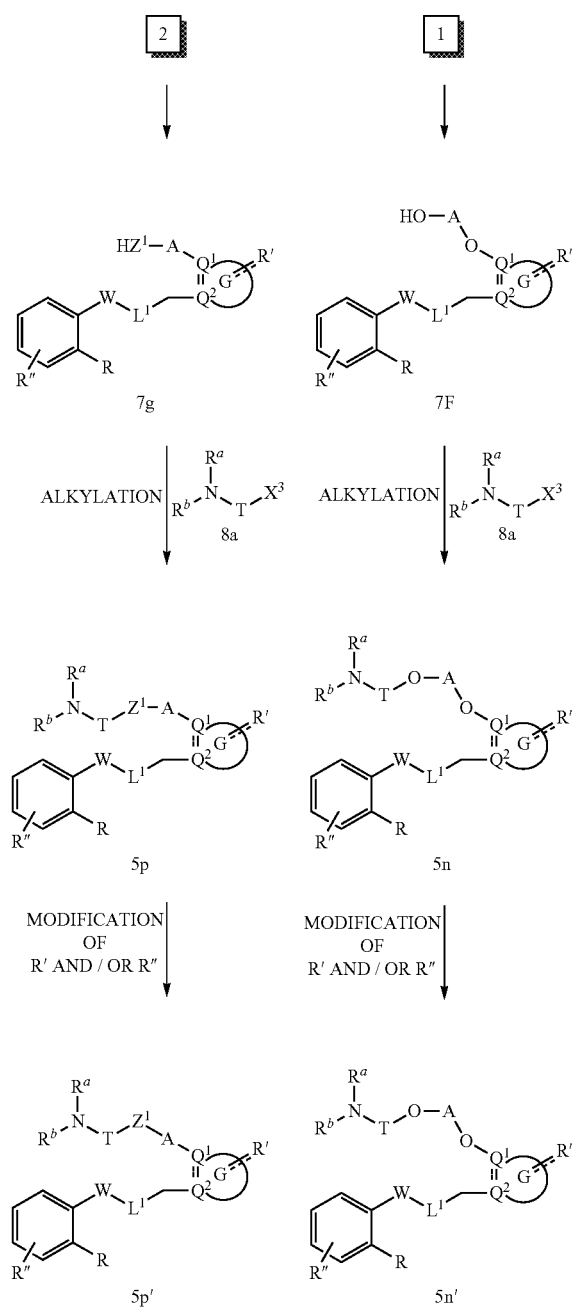

General Preparation Method 8-3

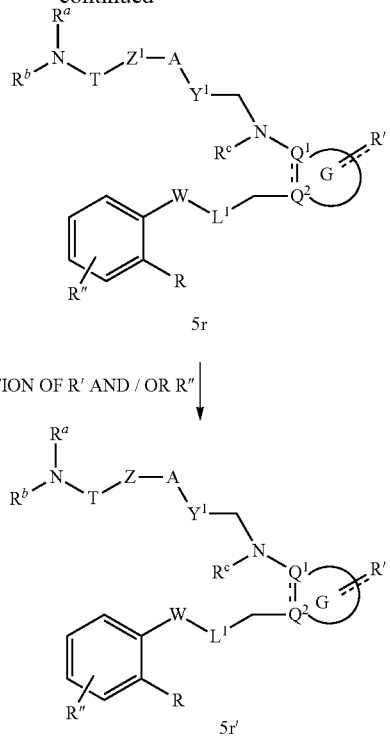

(wherein T, A, ring G, $Q^1$, $Q^2$, $R^a$, $R^b$, $R^c$, R', R", R, $R^1$, $X^2$, $X^3$, Z and $Y^1$ have the same meanings as the definition described above, $L^1$ has the same meaning as the definition of L, $Z^1$ has the same meaning as the definition of V' (l=0), P represents a protecting group for an oxygen atom, a sulfur atom or a nitrogen atom; in the present Preparation Method, the most preferred groups for V' are an oxygen atom and a nitrogen atom, the most preferred group for P is (1) acyl group, benzyl group or an alkylsilyl group when V' represents an oxygen atom, or (2) benzyl group or an alkyl carbamoyl group when V' represents a nitrogen atom.)

The Preparation Method 8 is a method wherein Friedel-Crafts acylation between a carboxylic acid derivative (10) and a methoxyaryl derivative (11) gives the compound (12) wherein $Q^2$ is acylated, then the demethylation of methoxy group and the reduction of carbonyl group gives the compound (9b), through which arylation by a fluoroaryl aldehyde derivative and decarbonylation by oxidation give the compound (70 wherein $Q^1$ and A are ether-bonded, then by alkylation by the compound (8a), the compound (5n) is obtained, further, according to the steps indicated in General Preparation Method 1 followed by modifying R' and/or R", the compound (5n') is prepared, a method wherein the coupling reaction between the compound (9c) obtained by trifluoromethanesulfonylation of the compound (9b) and an arylboronic acid derivative or an aryltin derivative (6d) gives the compound (7g) wherein $Q^1$ and A are bonded, through which via the same alkylation as described above, the compound (5p) is obtained, according to the steps indicated in General Preparation Method 1 followed by modifying R' and/or R", the compound (5p') is prepared, or a method wherein the coupling reaction between the compound (9c) and an amine gives the compound (5q), then either by N-acylation by a carboxylic acid derivative (6a; wherein $X^2$ represents hydroxyl group or a chlorine atom) and further reduction of carboxamide, or by the reductive amination by an aldehyde derivative (6a; wherein $X^2$ represents a hydrogen atom), the compound (5r) is obtained, according to the steps indicated in General Preparation Method 1 followed by modifying R' and/or R", the compound (5r') is prepared.

[Preparation of Compound (10)]

The compound (12) used in the reaction for preparing the carboxylic acid derivative (10) is either commercially available or is prepared by the methods well known to those skilled in the art. Preferably, examples include the method wherein the corresponding alcohol derivative or aldehyde derivative is oxidized by an oxidizing agent such as potassium permanganate, silver(I) oxide, activated manganese(IV) dioxide or pyridinium dichromate, the method wherein the corresponding ester is hydrolyzed by an acid or alkali, and the like. Specifically, preparation can be carried out by the method described in "*Fourth Edition Experimental Chemistry Course Vol. 22 Organic Synthesis IV Acids/Amino Acids/Peptides*", The Chemical Society of Japan Eds., Maruzen Co., November 1992, p. 1-14, or the like.

[Preparation of Compound (11)]

The methoxyaryl derivative (11) is either commercially available or is prepared by the methods well known to those skilled in the art. Examples of the methods include substitution between the corresponding aryl halide and methanol under the basic conditions, the coupling reaction between aryl halide and methanol in the presence of a transition metal catalyst, and the like. The preferred methoxyaryl derivative (11) is anisole or 1,3-dimethoxybenzene.

[Preparation of Compound (12)]

The compound (12) can be prepared by the well known Friedel-Crafts acylation. Preferably, the same method as Preparation of Compound (2e) described in General Preparation Method 1-2 can be used.

[Preparation of Compound (9b)]

The compound (9b) can be prepared by subjecting the compound (12) to the demethylation as a first step, and by reducing carbonyl group into methylene group as a second step. The conditions well known to those skilled in the art may be used as the conditions for the demethylation that is the first step in preparing the compound (9b), and the conditions abundantly described in a number of well known references, for instance, in T. Greene et al., *Protective Groups in Organic Synthesis 2nd edition*, John Wiley & Sons. Inc., New York, 1991, p. 15-17 and the like can be used. Methods wherein the reaction is carried out by refluxing in acetonitrile using cerium(III) chloride and sodium iodide, as described in J. S. Yadav et al., *Chem. Lett.*, 2000, No. 7, p. 738-739 and the like are preferred, specifically as will be described in Preparation Example 192. The second step in preparing the compound (9b) is the reduction of the carbonyl group into the methylene group, and the method well known to those skilled in the art can be used. Preferably, the method described in General Preparation Method 1 can be used. In the present step, the method described in D. Mitchell et al., *Tetrahedron Lett.*, 1995, Vol. 36, No. 30, p. 5335-5338, is preferred, specifically as will be described in Preparation Example 185. In the present step, prior to subjecting to the demethylation of the first step, if necessary, suitable modification of $L^1$ can be carried out by the method well known to those skilled in the art, specifically as will be described in Preparation Example 181.

[Preparation of Compound (7f)]

The compound (7f) can be prepared by arylating the compound (9b) with a fluoroaryl aldehyde derivative as a first step, then coverting formyl group by oxidation into hydroxyl group as a second step. The fluoroaryl aldehyde derivative used in the first step in preparing the compound (7f) is either commercially available or prepared by the methods well known to those skilled in the art. Examples include the method wherein the corresponding alcohol derivative is oxidized by an oxidizing agent such as pyridinium chlorochromate, activated manganese(IV) dioxide or dimethylsulfoxide-oxalyl chloride (Swern oxidation), the method wherein the corresponding aryl halide is lithiated by an alkyllithium derivative such as butyllithium, then formylation agent such as N,N-dimethylformamide is made to act, or, the method wherein the corresponding aryl halide and carbon monoxide are coupled in the presence of a transition metal catalyst and the like. Specifically, preparation can be carried out by the methods described in *Fourth Edition Experimental Chemistry Course Vol. 21 Organic Synthesis III Aldehydes/Ketones/Quinones*, The Chemical Society of Japan Eds., Maruzen Co., February 1991, p. 1-148, and the like. The first step in preparing the compound (7f) is the O-arylation of the compound (9b) using a fluoroaryl aldehyde derivative. For the present step, the method well known to those skilled in the art may be used, for instance, the method of heating while using an alkaline metal carbonate as a base is preferred. The second step in preparing the compound (7f) is a reaction wherein formyl group is converted into hydroxyl group. The present step can be carried out by the method well known to those skilled in the art, preferably, by the method wherein, obtained by reacting hydrogen peroxide with aldehyde derivative under the basic conditions, arylformate is hydrolyzed, or by the method wherein, obtained by oxidizing an aldehyde derivative by a peracid such as peracetic acid, trifluoroperacetic acid or m-chloroperbenzoic acid into phenol ester (Baeyer-Villiger oxidation), an ester is hydrolyzed, and the like. Preferably, the methods described in G. W. Yeager et al., "*Synthesis*", 1991, No. 1, p. 63-68, and the like may be used, specifically, as will be described in Preparation Example 190.

[Preparation of Compound (5n)]

The compound (5n) can be prepared by reacting the compound (7f) and the alkylation agent (8a) described in General Preparation Method 4 under the basic conditions. For the conditions for the reaction between the compound (70 and alkylation agent (8a), the methods well known to those skilled in the art may be used; preferably, the conditions described in General Preparation Method 1 can be used. More preferably, the method using alkaline metal hydride as the base may be cited, specifically, as will be described in Preparation Example 40.

[Preparation of Compound (5n')]

The compound (5n') can be prepared by modifying R' and/or R" according to the steps indicated in General Preparation Method 1.

[Preparation of Compound (9c)]

The step wherein the compound (9b) is trifluoromethanesulfonylated to obtain the compound (9c), is achieved by the methods well known to those skilled in the art. Preferably, the method described in General Preparation Method 1 may be used, more preferably, the method wherein commercially available trifluoromethanesulfonic anhydride is reacted in the presence of a base such as pyridine or lutidine, the method wherein a sulfonic acid derivative such as N-phenyltrifluoromethanesulfonimide is reacted under the basic conditions, and the like can be used.

[Preparation of Compound (7g)]

The compound (7g) can be prepared by subjecting the compound (9c) to the coupling reaction with an arylboronic acid derivative or an aryltin derivative (6d) prepared using the method indicated in General Preparation Method 4 as a first step, and carrying out the suitable deprotection as a second step. For the first step in preparing the compound (7g), the method well known to those skilled in the art may be used, preferably, the method described in General Preparation Method 4 can be used. For instance, the coupling reaction using a palladium complex such as palladium(II) acetate, tetrakis(triphenylphosphine)palladium(0), or tris(dibenzylideneacetone)dipalladium(0) as a catalyst and the like are preferred. For the deprotection that is the second step in preparing the compound (7g), the method well known to those skilled in the art may be used, and the reaction can be carried out by the well known methods abundantly described in a number of the well known references, for instance, T. Greene et al., *Protective Groups in Organic Synthesis 2nd edition*, John Wiley & Sons Inc., New York, 1991 and the like. Preferably, the deprotection of benzyl group or benzylcarbamoyl group by catalytic hydrogenation in the presence of a noble metal catalyst, or, the deprotection of tert-butylcarbamoyl group or an alkylsilyl group under the acidic conditions can be used.

[Preparation of Compound (5p)]

The compound (5p) can be prepared by reacting the compound (7g) with the alkylation agent (8a) under the basic conditions, similarly to the above-mentioned Preparation of Compound (5n).

[Preparation of Compound (5p')]

The compound (5p') can be prepared by modifying R' and/or R'' according to the steps indicated in General Preparation Method 1 similarly to the above-mentioned Preparation of Compound (5n').

[Preparation of Compound (5q)]

The compound (5q) can be prepared by subjecting the compound (9c) to the coupling reaction with an amine derivative as a first step, and subjecting the substituent on the nitrogen atom adjacent to $Q^1$ to the suitable modification as a second step. The amine derivative used in the first step in preparing the compound (5q) is either commercially available or is prepared by the methods well known to those skilled in the art. For instance, preparation can be carried out by the methods described in *Fourth Edition Experimental Chemistry Course Vol. 20 Organic Synthesis II Alcohols/Amines*, The Chemical Society of Japan Eds., Maruzen Co., July 1992, p. 279-318, and the like. The first step in preparing the compound (5q) is the coupling reaction between the compound (9c) and the amine derivative. For the present step, the method well known to those skilled in the art may be used, and preferably, the method described in General Preparation Method 1 can be used. The method described in J. P. Wolfe et al., *Tetrahedron Lett.*, 1997, Vol. 38, No. 36, p. 6367-6370 is more preferred. The second step in preparing the compound (5q) modifies the substituent on the nitrogen atom adjacent to $Q^1$. When the modification in the present step is the deprotection, it can be carried out by the well known methods that are abundantly described in a number of the well known references, for instance, T. Greene et al., *Protective Groups in Organic Synthesis 2nd edition*, John Wiley & Sons. Inc., New York, 1991, and the like. In addition, as described in General Preparation Method 1, the nitrogen atom may be modified by the method such as N-acylation and the subsequent reduction of the carboxamide functional group, reductive amination, or N-alkylation.

[Preparation of Compound (5r)]

The compound (5r) is obtained by the reaction between the compound (5q) and the compound (6a). The compound (6a) used in the present step is either commercially available or is prepared by the methods well known to those skilled in the art, and preferably can be prepared by the method indicated in General Preparation Method 1. For the step for preparing the compound (5r) from the compound (5q), the method well known to those skilled in the art may be used, and preferably the method indicated in General Preparation Method 1 can be used. That is to say, reductive amination using the compound (6a; wherein $X^2$ represents a hydrogen atom), two-step method consisting of N-acylation by the compound (6a; wherein $X^2$ represents hydroxyl group or a chlorine atom), then reduction of the carboxamide functional group and the like may be used.

[Preparation of Compound (5r')]

The compound (5r') can be prepared by modifying R' and/or R'' according to the steps indicated in General Preparation Method 1, in the same way as the above-mentioned Preparation of Compound (5n').

[General Preparation Method 9]

A representative method for preparing the compound according to the present invention represented by the above formula (I) is shown below:

General Preparation Method 9

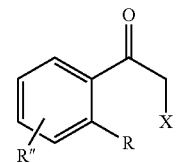

13

1) DEHYDRATION CONDENSATION
2) REDUCTION
3) TRIFLUOROMETHANESULFONYLATION

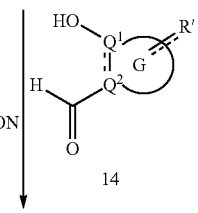

14

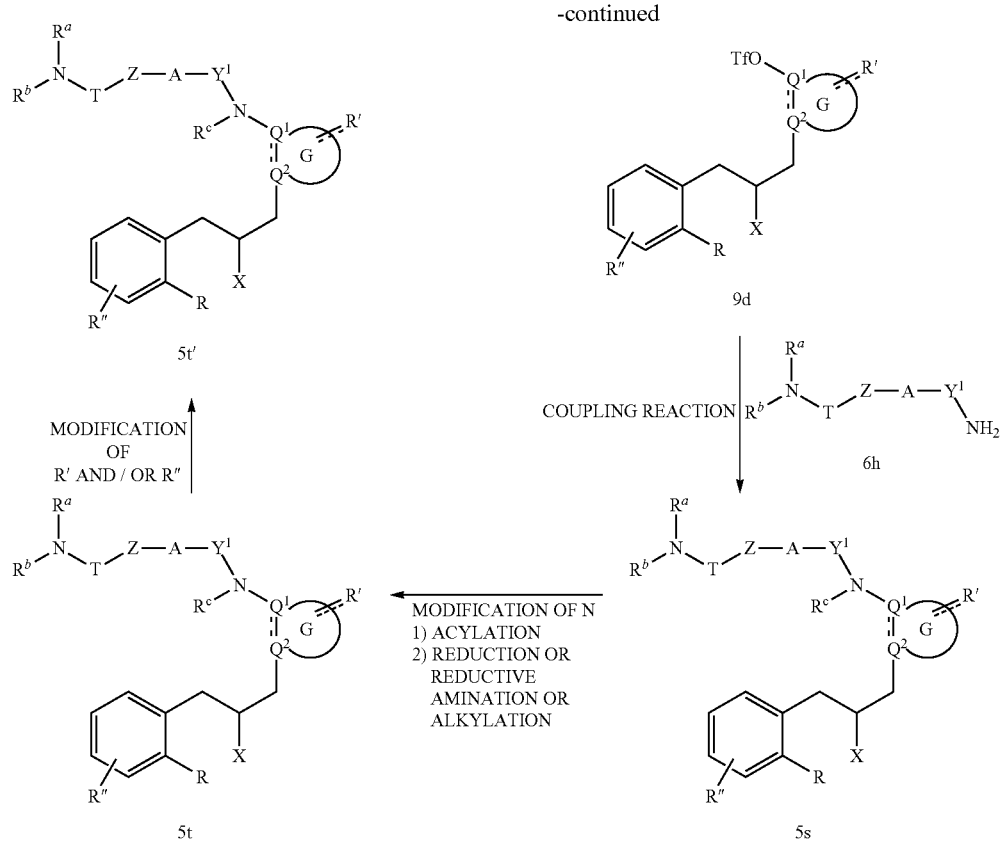

(wherein T, A, ring G, $Q^1$, $Q^2$, R, $R^a$, $R^b$, $R^c$, R', R'', X and Z have the same meanings as the definition described above, $Y^1$ has the same meaning as the definition of Y.)

The Preparation Method 9 is a method wherein the compound (13) and a 2-formyl-1-hydroxycyclic compound (14) are subjected to dehydration condensation, then to reduction, the compound (9d) is prepared by trifluoromethane sulfonylation, converted into the compound (5s) by the coupling reaction with an amine derivative (6h) using a transition metal catalyst, then nitrogen atom is suitably modified to give the compound (5t), through which by modifying R' and/or R'', the compound (5t') is prepared.

[Preparation of Compound (13)]

The preferred compound (13) used in the preparation of the compound (9d) may be commercially available, and when not commercially available, may be prepared by the methods well known to those skilled in the art. The preferred compound (13; wherein R forms a ring together with X) can be prepared by the same method as described in Preparation of Compound (4c) of General Preparation Method 7. That is to say, the compound (13) can be synthesized, taking a 4-phenylbutyric acid derivative or a 3-phenylpropionic acid derivative as the starting material, by intramolecular cyclization having Friedel-Crafts acylation well known to those skilled in the art as the key reaction. (for instance, E. L. Martin et al., *J. Am. Chem. Soc.,* 1952, Vol. 74, p. 4721 or, G. J. Quallich et al., *J. Org. Chem.,* 1990, Vol. 55, p. 4971-4973). Accordingly, although obvious to those skilled in the art, the groups of compounds that can be prepared by the present reaction is highly useful in the preparation of the foregoing formula (I) according to the present invention, and they can be used not only as starting materials but also as structures forming ring G

[Preparation of Compound (14)]

The preferred 2-formyl-1-hydroxycyclic compound (14) used in the preparation of Compound (9d) may be commercially available, and when not commercially available, may be prepared by the methods well known to those skilled in the art. When not commercially available, preparation can be carried out by reducing a 2-hydroxy-1-carboxylic acid derivative into a 2-hydroxy-1-hydroxymethyl derivative by the well known method, followed by the well known oxidation (for instance, M. Mirza-Aghayan et al., *Synth. Commun.,* 1999, Vol. 29. p. 785-789).

[Preparation of Compound (9d)]

The compound (9d) can be prepared by using the method well known to those skilled in the art, and can be prepared by the well known dehydration condensation between the compound (13) and the 2-formyl-1-hydroxycyclic compound (14), then subjecting the resulting product to the reduction, and through trifluoromethanesulfonylation. For the dehydration condensation of the first step, the well known method may be used; preferably, the dehydration condensation is completed by refluxing in a suitable solvent under the acidic conditions or under the basic conditions. More preferably, the reaction conditions such as described in A. K. Sinha et al., *Indian. J. Chem. Sect B,* 1991, Vol. 30, p. 684-692 or, A. Riahi et al., *Synth. Commun.,* 1998, Vol. 28, p. 4339-4344, can be used. The reduction, which is the second step in the preparation of the compound (9d), varies depending on the starting material and the solvent and the like, and the reaction conditions are not limited in particular as long as they are conditions similar to the present reaction, and the conditions well known to those skilled in the art can be used, and preferably, the same conditions as described in Preparation of Compound (2f) of General Preparation Method 1-2 can be used. The conditions for subjecting to catalytic hydrogenation using a noble metal catalyst are more preferred. For the trifluoromethanesulfonylation, which is the third step, the methods well known to those skilled in the art may be used, and preferably, the same conditions as described in Preparation of Compound (6b) of General Preparation Method 1-1 can be used.

[Preparation of Compound (6h)]

The preferred amine derivative (6h) used in the preparation of the compound (5s) may be commercially available, and when not commercially available, may be prepared by the methods well known to those skilled in the art. Preferably, the amine derivative (6h) can be prepared under the same conditions as described in Preparation of Compound (8b) of General Preparation Method 5.

[Preparation of Compound (5s)]

The compound (5s) can be prepared by using the method well known to those skilled in the art, and can be prepared by the coupling reaction between the compound (9d) and the compound (6h) using a transition metal catalyst. The coupling reaction conditions vary depending on the starting material, the solvent and the transition metal catalyst, and the conditions are not limited in particular as long as they are conditions similar to the present reaction, and the methods well known to those skilled in the art may be used; preferably, the same conditions as described in General Preparation Method 1 can be used.

[Preparation of Compound (5t)]

The compound (5t) can be prepared by using the method well known to those skilled in the art, and preferably can be prepared according to the method of Step 2 described in General Preparation Method 1-1 for the compound (5s).

[Preparation of Compound (5t')]

The compound (5t') can be prepared according to the steps indicated in General Preparation Method 1 followed by modifying R' and/or R" of the compound (5t).

The above are representative examples of the methods for preparing the compounds according to the present invention; the starting compounds and various reagents in these Preparation Methods may form a salt, a hydrate, or a solvate, and can be suitably selected depending on the starting material and the solvent used.

Further, when the compounds according to the present invention are obtained in a free form, they can be converted into a salt or a hydrate thereof by the conventional methods.

The term "salt" used herein is not limited as long as the salt is formed with the compound according to the present invention, and is pharmacologically acceptable; the preferred examples of the salt include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, an alkaline metal salt (for instance, sodium salt, potassium salt and the like), an alkaline earth metal salt (magnesium salt, calcium salt and the like) and the like. In addition, hydrochloride salt, sulfate salt, methanesulfonate salt, acetate salt and the like are preferred as "pharmacologically acceptable salt" of the compounds according to the present invention.

Furthermore, when the compound according to the present invention may take various isomers (for instance, a geometric isomers, an optical isomer, a rotamer, a tautomer and the like), it can be purified by using the general separation means, for instance, recrystallization, optical resolution such as diastereomeric salt method, enzyme fractionation method, various chromatographies (for instance, thin layer chromatography, column chromatography, glass chromatography and the like) into a single isomer. The term "a single isomer" herein includes not only an isomer having a purity of 100%, but also an isomer containing an isomer other than the target, which exists even through the conventional purification operation. When using the compound according to the present invention as a raw material for a medicinal drug, the above-mentioned single isomer may be used, in addition, a mixture of isomers in any proportions may also be used.

A crystal polymorph sometimes exists for the compound according to the present invention, a salt thereof, or a hydrate thereof, and all crystal polymorphs thereof are included in the present invention. The crystal polymorph is sometimes single or sometimes a mixture, and both are included in the present invention.

Moreover, the present invention also includes the compounds still exhibiting the desired pharmacological activity even after the compound according to the present invention is metabolized in vivo such as by oxidation or hydrolysis.

In addition, the present invention also includes compounds that are metabolized in vivo such as by oxidation, reduction or hydrolysis to generate the compound according to the present invention, i.e., so-called prodrugs.

The compound according to the present invention or a salt thereof, or a hydrate thereof, can be formulated according to the conventional method. Examples of the preferred dosage forms include a tablet, a powder, a subtle granule, a granule, a coated tablet, a capsule, a syrup, a troche, an inhalant, a suppository, an injectable, an ointment, an ophthalmic ointment, an eye drop, a nasal drop, an ear drop, a cataplasm, a lotion and the like. In the formulation, generally used additives such as a diluent, a binder, an disintegrant, a lubricant, a colorant, a flavoring agent, and if necessary, a stabilizer, an emulsifyer, an absorption enhancer, a surfactant, a pH adjuster, an antiseptic, an antioxidant and the like can be used. In addition, the formulation is also carried out by combining compositions that are generally used as a raw material for pharmaceutical formulation, according to the conventional methods. Examples of these compositions (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate and aluminum silicate; (13) purified water, and the like.

Among the above-mentioned additives, 1) for instance, lactose, corn starch, sucrose, glucose, mannitol, sorbitol, crystalline cellulose and silicon dioxide as the diluent; 2) for instance, polyvinyl alcohol, polyvinyl ether, methyl cellulose, ethyl cellulose, gum arabic, tragacanth, gelatine, shellac, hydroxypropyl cellulose, hydroxypropylmethyl cellulose, polyvinylpyrrolidone, polypropylene glycol-poly oxyethylene-block co-polymer, meglumine, calcium citrate, dextrin, pectin and the like as the binder; 3) for instance, starch, agar, gelatine powder, crystalline cellulose, calcium carbonate, sodium bicarbonate, calcium citrate, dextrin, pectic, carboxymethylcellulose/calcium and the like as the disintegrant; 4) for instance, magnesium stearate, talc, polyethyleneglycol, silica, condensed plant oil and the like as the lubricant; 5) any colorants whose addition is pharmaceutically acceptable is adequate as the colorant; 6) for instance, cocoa powder, menthol, aromatizer, peppermint oil, cinnamon powder as the flavoring agent; 7) for instance, antioxidants whose addition is pharmaceutically accepted such as ascorbic acid and α-tophenol as the antioxidants, are used, respectively.

The dosage of the medicinal drug according to the present invention varies depending on the extent of the symptom, age, sex, body weight, administration mode and a salt type, variation in susceptibility to the drug, the specific type of the disease, and the like, in general, for an adult, it is adequate to administer per day approximately 30 μg to 1000 mg, preferably 100 μg to 500 mg, more preferably 100 μg to 100 mg via an oral administration, and approximately 1 to 3000 μg/kg, preferably 3 to 1000 μg/kg via injection, respectively, at once or divided into several times.

In the following, examples are given for detailed and specific description of the present invention; it is needless to say that the present invention is not limited to these examples.

Preparation Example 1

4-(2-Piperidin-1-ylethoxy)benzoic acid hydrochloride

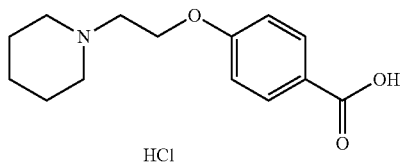 [SMILES: O=C(O)c1ccc(OCCN2CCCCC2)cc1 ; Cl]

To a solution of 4-hydroxybenzoic acid ethyl ester (5.0 g) in N,N-dimethylformamide (50 ml) were sequentially added potassium carbonate (6.2 g) and 1-(2-chloroethyl)piperidine (8.3 g), and the solution was stirred for 1.5 hours at 60° C. The solution was filtered through celite pad, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to obtain 4-(2-piperidin-1-ylethoxy)benzoic acid ethyl ester (8.3 g). To a solution of 4-(2-piperidin-1-ylethoxy)benzoic acid ethyl ester (34 g) dissolved in ethanol (200 ml) was added an aqueous solution of 2N sodium hydroxide (100 ml), and the solution was refluxed for 1 hour. Ethanol was evaporated in vacuo, water was added and stirred, the solid that was precipitated by adding 2N hydrochloric acid (180 ml) was filtered to provide the title compound (28.2 g).

$^1$H-NMR (400 MHz, DMSO-$d_6$); δ (ppm): 1.31-1.48 (m, 1H), 1.60-1.83 (m, 5H), 2.85-3.60 (m, 6H), 4.46 (t, 2H), 7.07 (d, 2H), 7.91 (d, 2H), 10.29 (brs, 1H), 12.68 (brs, 1H).

Preparation Example 2

4-(2-Azepan-1-ylethoxy)benzoic acid hydrochloride

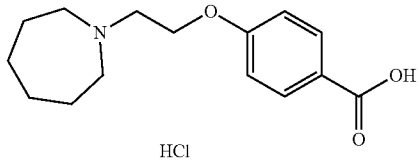 [SMILES: O=C(O)c1ccc(OCCN2CCCCCC2)cc1 ; Cl]

The title compound (17.4 g) was obtained according to an analogous synthetic method to Preparation Example 1 using 4-hydroxybenzoic acid ethyl ester (19 g) and 1-(2-chloroethyl)azepane (25 g).

$^1$H-NMR (400 MHz, DMSO-$d_6$); δ (ppm): 1.52-1.68 (m, 4H), 1.77-1.86 (m, 4H), 3.13-3.26 (m, 2H), 3.36-3.46 (m, 2H), 3.49-3.56 (m, 2H), 4.45 (t, 2H), 7.07 (d, 2H), 7.91 (d, 2H), 10.46 (brs, 1H), 12.70 (brs, 1H).

Preparation Example 3

4-(2-Diisopropylaminoethoxy)benzoic acid hydrochloride

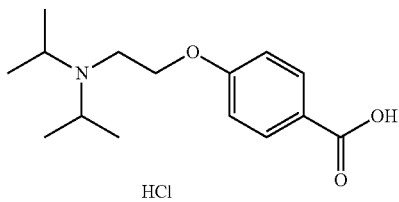 [SMILES: CC(C)N(CCOc1ccc(C(=O)O)cc1)C(C)C ; Cl]

The title compound (11.2 g) was obtained according to an analogous synthetic method to Preparation Example 1 using 4-hydroxybenzoic acid ethyl ester (7.5 g) and (2-chloroethyl)diisopropylamine (10.2 g).

$^1$H-NMR (400 MHz, DMSO-$d_6$); δ (ppm): 1.30 (d, 6H), 1.35 (d, 6H), 3.49-3.55 (m, 2H), 3.61-3.72 (m, 2H), 4.43 (t, 2H), 7.02 (d, 2H), 7.90 (d, 2H), 9.98 (s, 1H), 12.71 (s, 1H).

Preparation Example 4

3-Fluoro-4-hydroxybenzoic acid ethyl ester

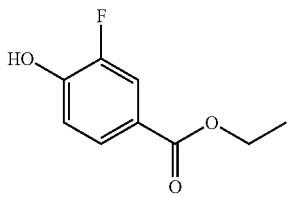

A mixture of 3-fluoro-4-hydroxybenzoic acid (5.0 g), ethanol (100 ml) and concentrated sulfuric acid (1 ml) was refluxed for 1 day. The reaction mixture was poured into ice water, the crystal that was precipitated was filtered, then dried to provide the title compound (24.3 g).

$^1$H-NMR (400 MHz, CDCl$_3$); δ (ppm): 1.38 (m, 3H), 4.34 (q, 2H), 5.75 (brs, 1H), 7.01 (t, 1H), 7.75-7.80 (m, 2H).

Preparation Example 5

3-Fluoro-4-(2-piperidin-1-ylethoxy)benzoic acid hydrochloride

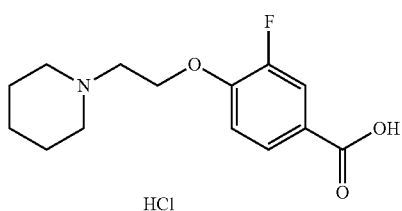 [SMILES: O=C(O)c1ccc(OCCN2CCCCC2)c(F)c1 ; Cl]

The title compound (17.3 g) was obtained according to an analogous synthetic method to Preparation Example 1 using 3-fluoro-4-hydroxybenzoic acid ethyl ester (8.2 g) and 1-(2-chloroethyl)piperidine (12.2 g).

$^1$H-NMR (400 MHz, DMSO-$d_6$); δ (ppm): 1.30-1.41 (m, 1H), 1.61-1.82 (m, 5H), 2.95-3.08 (m, 2H), 3.40-3.52 (m, 4H), 4.55-4.61 (m, 2H), 7.30 (t, 1H), 7.69 (d, 1H), 7.78 (d, 1H).

Preparation Example 6

4-(2-Azepan-1-ylethoxy)-3-fluorobenzoic acid hydrochloride

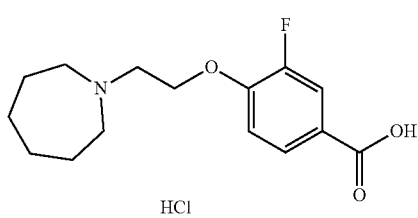 [SMILES: O=C(O)c1ccc(OCCN2CCCCCC2)c(F)c1 ; Cl]

The title compound (11.1 g) was obtained according to an analogous synthetic method to Preparation Example 1 using 3-fluoro-4-hydroxybenzoic acid ethyl ester (7.0 g) and 1-(2-chloroethyl)azepane (11.3 g).

$^1$H-NMR (400 MHz, DMSO-$d_6$); δ (ppm): 1.55-1.66 (m, 4H), 1.78-1.86 (m, 4H), 3.25-3.38 (m, 4H), 3.51-3.58 (m, 2H), 4.55 (t, 2H), 7.32 (t, 1H), 7.68 (d, 1H), 7.77 (d, 1H).

Preparation Example 7

4-(2-Diisopropylaminoethoxy)-3-fluorobenzoic acid hydrochloride

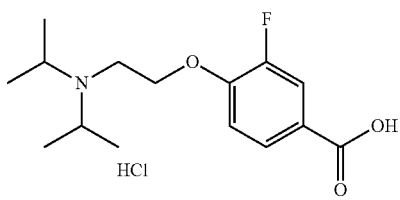 [SMILES: CC(C)N(CCOc1ccc(C(=O)O)cc1F)C(C)C ; Cl]

The title compound (9.7 g) was obtained according to an analogous synthetic method to Preparation Example 1 using 3-fluoro-4-hydroxybenzoic acid ethyl ester (7.0 g) and (2-chloroethyl)diisopropylamine (11.4 g).

$^1$H-NMR (400 MHz, DMSO-$d_6$); δ (ppm): 1.29 (d, 6H), 1.33 (d, 6H), 3.56-3.61 (m, 2H), 3.62-3.71 (m, 2H), 4.42 (t, 2H), 7.28 (t, 1H), 7.71 (d, 1H), 7.77 (d, 1H), 9.27 (brs, 1H), 13.03 (brs, 1H).

Preparation Example 8

3-(2-Piperidin-1-ylethoxy)benzoic acid hydrochloride

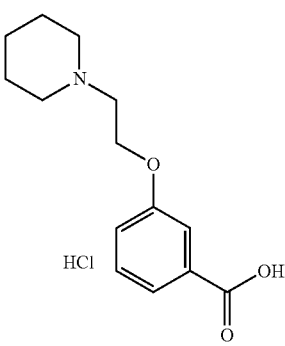 [SMILES: O=C(O)c1cccc(OCCN2CCCCC2)c1 ; Cl]

The title compound (28.6 g) was obtained according to an analogous synthetic method to Preparation Example 1 using 3-hydroxybenzoic acid ethyl ester (16.6 g) and 1-(2-chloroethyl)piperidine (25 g).

$^1$H-NMR (400 MHz, DMSO-$d_6$); δ (ppm): 1.32-1.41 (m, 1H), 1.51-1.83 (m, 5H), 2.91-3.05 (m, 2H), 3.43-3.53 (m, 4H), 4.44 (t, 2H), 7.24 (d, 1H), 7.44 (t, 1H), 7.49 (s, 1H), 7.56 (d, 1H).

Preparation Example 9

[3-Fluoro-4-(2-piperidin-1-ylethoxy)phenyl]acetic acid hydrochloride

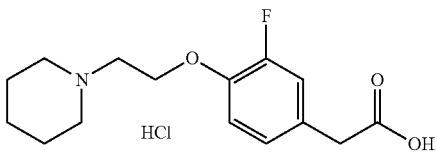 [SMILES: O=C(O)Cc1ccc(OCCN2CCCCC2)c(F)c1 ; Cl]

The title compound (3.7 g) was obtained according to an analogous synthetic method to Preparation Example 1 using (3-fluoro-4-hydroxyphenyl)acetic acid ethyl ester (2.9 g) and 1-(2-chloroethyl)piperidine (4.1 g).

$^1$H-NMR (400 MHz, DMSO-$d_6$); δ (ppm): 1.30-1.42 (m, 1H), 1.63-1.84 (m, 5H), 2.94-3.05 (m, 2H), 3.45-3.55 (m, 6H), 4.44 (t, 2H), 7.00-7.04 (m, 1H), 7.12-7.18 (m, 2H), 10.24 (brs, 1H), 12.37 (brs, 1H).

Preparation Example 10

[4-(2-Piperidin-1-ylethoxy)phenyl]acetic acid hydrochloride

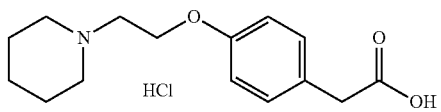 [SMILES: O=C(O)Cc1ccc(OCCN2CCCCC2)cc1 ; Cl]

The title compound (8.8 g) was obtained according to an analogous synthetic method to Preparation Example 1 using (4-hydroxyphenyl)acetic acid methyl ester (5.0 g) and 1-(2-chloroethyl)piperidine (8.3 g).

$^1$H-NMR (400 MHz, DMSO-d$_6$); δ (ppm): 1.30-1.42 (m, 1H), 1.62-1.82 (m, 5H), 2.90-3.02 (m, 2H), 3.40-3.51 (m, 6H), 4.33 (t, 2H), 6.92 (d, 2H), 7.18 (d, 2H), 9.90 (brs, 1H), 12.25 (brs, 1H).

Preparation Example 11

[4-(2-Azepan-1-ylethoxy)phenyl]acetic acid hydrochloride

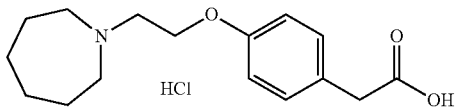 [SMILES: O=C(O)Cc1ccc(OCCN2CCCCCC2)cc1 ; Cl]

The title compound (6.4 g) was obtained according to an analogous synthetic method to Preparation Example 1 using (4-hydroxyphenyl)acetic acid methyl ester (5.0 g) and 1-(2-chloroethyl)azepane (8.9 g).

$^1$H-NMR (400 MHz, DMSO-d$_6$); δ (ppm): 1.50-1.70 (m, 4H), 1.74-1.90 (m, 4H), 3.15-3.45 (m, 2H), 3.36-3.45 (m, 2H), 3.48-3.55 (m, 4H), 4.34 (t, 2H), 6.92 (d, 2H), 7.18 (d, 2H), 10.19 (brs, 1H), 12.25 (brs, 1H).

Preparation Example 12

[4-(2-Diisopropylaminoethoxy)phenyl]acetic acid hydrochloride

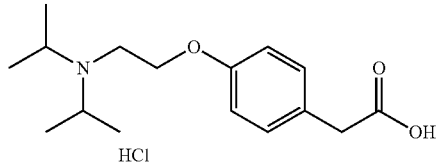 [SMILES: CC(C)N(CCOc1ccc(CC(=O)O)cc1)C(C)C ; Cl]

The title compound (9.1 g) was obtained according to an analogous synthetic method to Preparation Example 1 using (4-hydroxyphenyl)acetic acid methyl ester (5.0 g) and (2-chloroethyl)diisopropylamine (9.0 g).

$^1$H-NMR (400 MHz, DMSO-d$_6$); δ (ppm): 1.29 (d, 6H), 1.32 (d, 6H), 3.33-3.52 (m, 4H), 3.60-3.72 (m, 2H), 4.27 (t, 2H), 6.88 (d, 2H), 7.19 (d, 2H), 9.33 (brs, 1H), 12.25 (brs, 1H).

Preparation Example 13

4-(2-Piperidin-1-ylethoxy)benzaldehyde

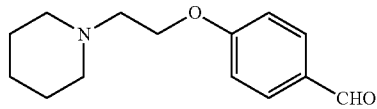 [SMILES: O=Cc1ccc(OCCN2CCCCC2)cc1]

To a suspension of lithium aluminum hydride (1.5 g) in tetrahydrofuran (50 ml) under a nitrogen atmosphere was added 4-(2-piperidin-1-ylethoxy)benzoic acid ethyl ester (5.0 g) on an ice bath, and the solution was refluxed for 1 hour. Ammonia solution was added thereto on an ice bath, the solution was filtered through celite pad, then the solvent was evaporated in vacuo, and [4-(2-piperidin-1-ylethoxy)phenyl]methanol (3.5 g) was obtained. To a solution of this compound (1.7 g) in chloroform (30 ml) was added manganese (IV) oxide (7.5 g), the solution was stirred overnight at room temperature, then filtered, and the solvent was evaporated in vacuo to provide the title compound (1.7 g).

$^1$H-NMR (400 MHz, CDCl$_3$); δ (ppm): 1.42-1.54 (m, 2H), 1.59-1.72 (m, 4H), 2.47-2.62 (m, 4H), 2.85 (t, 2H), 4.24 (t, 2H), 7.06 (d, 2H), 7.88 (d, 2H), 9.93 (s, 1H).

Preparation Example 14

4-(2-Azepan-1-ylethoxy)benzaldehyde

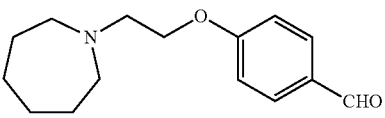 [SMILES: O=Cc1ccc(OCCN2CCCCCC2)cc1]

To a solution of 4-(2-azepan-1-ylethoxy)benzoic acid ethyl ester (6.0 g) in tetrahydrofuran (60 ml) was added lithium aluminum hydride (1.5 g) under a nitrogen atmosphere, the solution was stirred overnight at room temperature, tetrahydrofuran and aqueous ammonia were then sequentially added thereto on an ice bath, the solution was filtered through celite pad, the solvent was evaporated in vacuo to provide [4-(2-azepan-1-ylethoxy)phenyl]methanol (3.6 g). The title compound (194 mg) was obtained according to an analogous synthetic method to Preparation Example 13 using the above compound (200 mg).

$^1$H-NMR (400 MHz, CDCl$_3$); δ (ppm): 1.58-1.67 (m, 8H), 2.75-2.79 (m, 4H), 2.98 (t, 2H), 4.14 (t, 2H), 7.00 (d, 2H), 7.81 (d, 2H), 9.86 (s, 1H).

Preparation Example 15

4-(8-Methyl-8-azabicyclo[3.2.1]oct-3-yloxy)benzonitrile

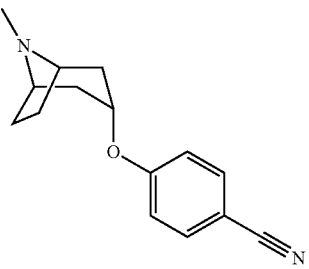 [SMILES: CN1C2CCC1CC(Oc1ccc(C#N)cc1)C2]

The title compound was synthesized by referring to *Tetrahedron*, 1998, 54, 13371. Tropine hydrate (1.0 g) was dissolved in ethanol, the solvent was evaporated in vacuo, toluene was added thereto and the solvent was evaporated in vacuo to provide anhydrous tropine (980 mg), which was dissolved in dimethylsulfoxide (10 ml) under a nitrogen atmosphere, 4-fluorobenzonitrile (1.3 g) and 60% sodium hydride (560 mg) were sequentially added thereto followed by stirring at room temperature for 1 hour. A saturated aqueous solution of ammonium chloride was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (ethyl acetate-methanol system) to provide the title compound (1.4 g).
$^1$H-NMR (400 MHz, CDCl$_3$); δ (ppm): 1.89-2.04 (m, 6H), 2.13-2.20 (m, 2H), 2.30 (s, 3H), 3.11-3.17 (m, 2H), 4.57 (t, 1H), 6.85 (d, 2H), 7.56 (d, 2H).

Preparation Example 16

4-(8-Methyl-8-azabicyclo[3.2.1]oct-3-yloxy)benzaldehyde

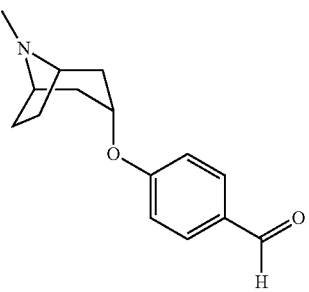 [SMILES: CN1C2CCC1CC(Oc1ccc(C=O)cc1)C2]

The title compound was synthesized by referring to *Chem. Pharm. Bull.*, 1991, 39, 1440. To a solution of 4-(8-methyl-8-azabicyclo[3.2.1]oct-3-yloxy)benzonitrile (300 mg) in formic acid (5 ml) was added Raney nickel (50% suspension in water) (1 ml), and the solution was stirred for 2 hours at 100° C. After filtration through celite pad and several wash with tetrahydrofuran and methanol, the solvent was evaporated in vacuo, and the resulting residue was neutralized by adding a saturated aqueous solution of sodium bicarbonate. After extraction with chloroform and washing with brine, the solution was dried over anhydrous magnesium sulfate, then the solvent was evaporated in vacuo to provide the title compound (266 mg).
$^1$H-NMR (400 MHz, CDCl$_3$); δ (ppm): 1.95-2.09 (m, 6H), 2.22-2.32 (m, 2H), 2.34 (s, 3H), 3.17-3.25 (m, 2H), 4.65 (t, 1H), 6.92 (d, 2H), 7.83 (d, 2H), 9.88 (s, 1H).

Preparation Example 17

4-(2-Amino-2-methylpropoxy)benzonitrile

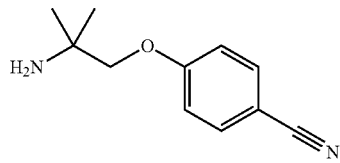

The title compound (3.2 g) was obtained according to an analogous synthetic method to Preparation Example 15 using 2-amino-2-methylpropan-1-ol (2.0 g) and 4-fluorobenzonitrile (3.8 g).
$^1$H-NMR (400 MHz, CDCl$_3$); δ (ppm): 1.24 (s, 6H), 3.73 (s, 2H), 6.95 (d, 2H), 7.57 (d, 2H).

Preparation Example 18

4-(2-Dimethylamino-2-methylpropoxy)benzonitrile

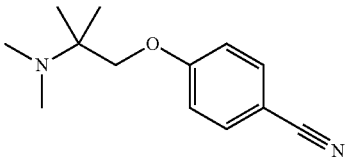 [SMILES: CN(C)C(C)(C)COc1ccc(C#N)cc1]

To a solution of 4-(2-amino-2-methylpropoxy)benzonitrile (1.1 g) in tetrahydrofuran (50 ml) were sequentially added 35% formaldehyde solution (2.5 ml), acetic acid (3.3 ml) and sodium triacetoxyborohydride (6.0 g), and the solution was stirred for 3 days at room temperature. The solution was neutralized with ammonia solution, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (1.0 g).
$^1$H-NMR (400 MHz, CDCl$_3$); δ (ppm): 1.17 (s, 6H), 2.34 (s, 6H), 3.85 (s, 2H), 6.98 (d, 2H), 7.57 (d, 2H).

Preparation Example 19 tert-Butyl[2-(4-cyanophenoxy)-1,1-dimethylethyl]carbamate

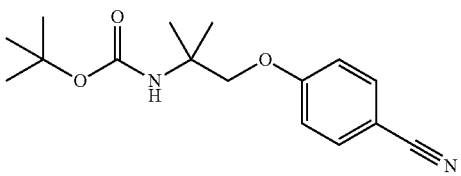 [SMILES: CC(C)(COc1ccc(C#N)cc1)NC(=O)OC(C)(C)C]

To a solution of 4-(2-amino-2-methylpropoxy)benzonitrile (3.2 g) in dichloromethane (50 ml) and triethylamine (6 ml) was added di-tert-butyl dicarbonate (4.5 g) on an ice bath, and the solution was stirred overnight followed by warming up to room temperature. Water was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (4.2 g).

$^1$H-NMR (400 MHz, CDCl$_3$); δ (ppm): 1.40 (s, 15H), 4.07 (s, 2H), 4.62 (s, 1H), 6.96 (d, 2H), 7.56 (d, 2H).

Preparation Example 20 tert-Butyl[2-(4-formylphenoxy)-1,1-dimethylethyl]carbamate

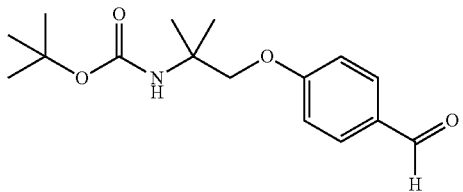 [SMILES: CC(C)(COc1ccc(C=O)cc1)NC(=O)OC(C)(C)C]

The title compound was synthesized by referring to *J. Chem. Soc.*, 1962, 3961. To a solution of sodium hypophosphite monohydrate (1.5 g) in water (3 ml) were sequentially added tert-butyl[2-(4-cyanophenoxy)-1,1-dimethylethyl]carbamate (500 mg), pyridine (10 ml) and acetic acid (5 ml). While stirring at room temperature, Raney nickel (50% suspension in water) (2 ml) was added dropwise to the reaction mixture and the solution was stirred for 15 minutes at room temperature and for 1 hour at 40° C. After filtration through celite pad and several wash with tetrahydrofuran and methanol, the solvent was evaporated in vacuo, and the residue was neutralized by adding a saturated aqueous solution of sodium bicarbonate. After extraction with ethyl acetate, the solution was washed with brine, dried over anhydrous magnesium sulfate, and then the solvent was evaporated in vacuo. The residue was purified by silica gel column chromatography (hexane-ethyl acetate system) to provide the title compound (443 mg).

$^1$H-NMR (400 MHz, CDCl$_3$); δ (ppm): 1.41 (s, 15H), 4.09 (s, 2H), 4.66 (s, 1H), 7.02 (d, 2H), 7.81 (d, 2H), 9.87 (s, 1H).

Preparation Example 21

4-(2-Dimethylamino-2-methylpropoxy)benzaldehyde

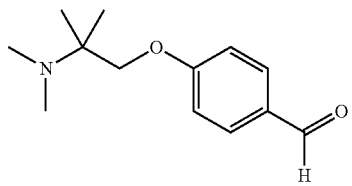 [SMILES: CN(C)C(C)(C)COc1ccc(C=O)cc1]

The title compound (327 mg) was obtained according to an analogous synthetic method to Preparation Example 16 using 4-(2-dimethylamino-2-methylpropoxy)benzonitrile (500 mg).

$^1$H-NMR (400 MHz, CDCl$_3$); δ (ppm): 1.20 (s, 6H), 2.36 (s, 6H), 3.90 (s, 2H), 7.04 (d, 2H), 7.82 (d, 2H), 9.87 (s, 1H).

Preparation Example 22

4-(4-Cyanophenoxy)piperidine-1-carboxylic acid tert-butyl ester

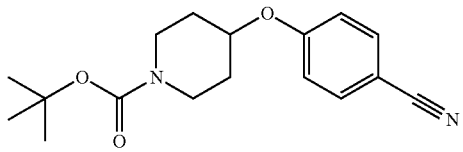 [SMILES: CC(C)(C)OC(=O)N1CCC(Oc2ccc(C#N)cc2)CC1]

The title compound (4.3 g) was obtained according to an analogous synthetic method to Preparation Example 15 using 4-hydroxypiperidine-1-carboxylic acid tert-butyl ester (4.0 g) and 4-fluorobenzonitrile (3.4 g).

$^1$H-NMR (400 MHz, CDCl$_3$); δ (ppm): 1.47 (s, 9H), 1.72-1.81 (m, 2H), 1.89-1.98 (m, 2H), 3.36 (ddd, 2H), 3.68 (ddd, 2H), 4.54 (tt, 1H), 6.94 (d, 2H), 7.57 (d, 2H).

Preparation Example 23

4-(4-Formylphenoxy)piperidine-1-carboxylic acid tert-butyl ester

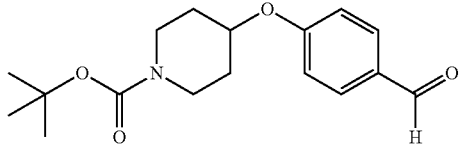 [SMILES: CC(C)(C)OC(=O)N1CCC(Oc2ccc(C=O)cc2)CC1]

The title compound (898 mg) was obtained according to an analogous synthetic method to Preparation Example 20 using 4-(4-cyanophenoxy)piperidine-1-carboxylic acid tert-butyl ester (1.0 g).

$^1$H-NMR (400 MHz, CDCl$_3$); δ (ppm): 1.47 (s, 9H), 1.74-1.83 (m, 2H), 1.91-1.99 (m, 2H), 3.38 (ddd, 2H), 3.69 (ddd, 2H), 4.60 (tt, 1H), 6.99 (d, 2H), 7.82 (d, 2H), 9.86 (s, 1H).

Preparation Example 24

4-(1-Acetylpiperidin-4-yloxy)benzonitrile

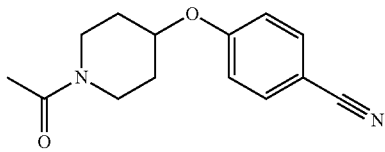 [SMILES: CC(=O)N1CCC(Oc2ccc(C#N)cc2)CC1]

Synthesized from 4-(4-cyanophenoxy)piperidine-1-carboxylic acid tert-butyl ester (1.5 g) according to an analogous synthetic method to Example 215 described below, the total amount of 4-(piperidin-4-yloxy)benzonitrile crude product was dissolved in acetic anhydride (20 ml) and pyridine (20 ml), and the solution was stirred overnight at room temperature. The reaction mixture was concentrated in vacuo, extracted with ethyl acetate, then sequentially washed with a saturated aqueous solution of sodium bicarbonate, water and brine, dried over anhydrous magnesium sulfate, and then the solvent was evaporated in vacuo. The residue was purified by NH silica gel column chromatography (hexane-ethyl acetate system) to provide the title compound (1.1 g).

$^1$H-NMR (400 MHz, CDCl$_3$); δ (ppm): 1.76-2.02 (m, 4H), 2.12 (s, 3H), 3.40-3.47 (m, 1H), 3.63-3.78 (m, 3H), 4.62 (tt, 1H), 6.95 (d, 2H), 7.58 (d, 2H).

Preparation Example 25

4-(1-Acetylpiperidin-4-yloxy)benzaldehyde

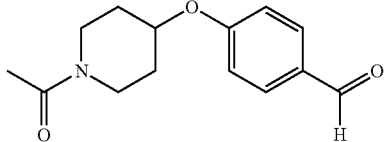 [SMILES: CC(=O)N1CCC(Oc2ccc(C=O)cc2)CC1]

The title compound (805 mg) was obtained according to an analogous synthetic method to Preparation Example 20 using 4-(1-acetylpiperidin-4-yloxy)benzonitrile (1.0 g).

$^1$H-NMR (400 MHz, CDCl$_3$); δ (ppm): 1.79-2.03 (m, 4H), 2.13 (s, 3H), 3.41-3.49 (m, 1H), 3.65-3.80 (m, 3H), 4.68 (tt, 1H), 7.00 (d, 2H), 7.83 (d, 2H), 9.87 (s, 1H).

Preparation Example 26

4-(1-Methylpiperidin-4-yloxy)benzaldehyde

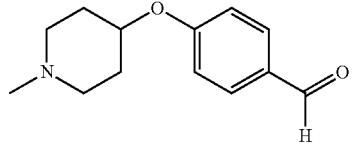 [SMILES: CN1CCC(Oc2ccc(C=O)cc2)CC1]

Synthesized from 4-hydroxy-1-methylpiperidine and 4-fluorobenzonitrile according to an analogous synthetic method to Preparation Example 15, 4-(1-methylpiperidin-4-yloxy)benzonitrile (500 mg) was used according to an analogous synthetic method to Preparation Example 16 to provide the title compound (350 mg).

$^1$H-NMR (400 MHz, CDCl$_3$); δ (ppm): 1.83-1.93 (m, 2H), 2.00-2.08 (m, 2H), 2.29-2.36 (m, 5H), 2.65-2.74 (m, 2H), 4.41-4.49 (m, 1H), 6.98 (d, 2H), 7.81 (d, 2H), 9.86 (s, 1H).

Preparation Example 27

4-(1-Azabicyclo[2.2.2]oct-4-ylmethoxy)benzaldehyde

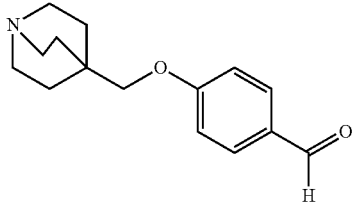 [SMILES: O=Cc1ccc(OCC23CCN(CC2)CC3)cc1]

Synthesized from (1-azabicyclo[2.2.2]oct-4-yl)methanol and 4-fluorobenzonitrile according to an analogous synthetic method to Preparation Example 15, 4-(1-azabicyclo[2.2.2]oct-4-ylmethoxy)benzonitrile (200 mg) was used according to an analogous synthetic method to Preparation Example 16 to provide the title compound (120 mg).

$^1$H-NMR (400 MHz, CDCl$_3$); δ (ppm): 1.60 (t, 6H), 3.01 (t, 6H), 3.70 (s, 2H), 6.98 (d, 2H), 7.82 (d, 2H), 9.87 (s, 1H).

Preparation Example 28

4-(1-Aminocyclopentylmethoxy)benzonitrile

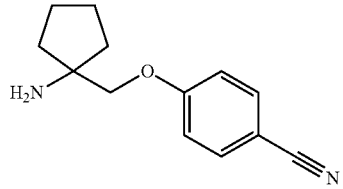 [SMILES: N#Cc1ccc(OCC2(N)CCCC2)cc1]

The title compound (2.3 g) was obtained according to an analogous synthetic method to Preparation Example 15 using (1-aminocyclopentyl)methanol (1.4 g) and 4-fluorobenzonitrile (2.1 g).

$^1$H-NMR (400 MHz, CDCl$_3$); δ (ppm): 1.50-1.90 (m, 8H), 3.84 (s, 2H), 6.96 (d, 2H), 7.57 (d, 2H).

Preparation Example 29

4-(1-Dimethylaminocyclopentylmethoxy)benzaldehyde

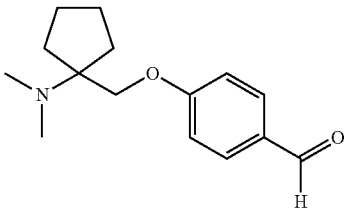 [SMILES: CN(C)C1(COc2ccc(C=O)cc2)CCCC1]

Synthesized from 4-(1-aminocyclopentylmethoxy)benzonitrile according to an analogous synthetic method to Preparation Example 18, 4-(1-dimethylaminocyclopentylmethoxy)benzonitrile (1.2 g) was used according to an analogous synthetic method to Preparation Example 16 to provide the title compound (1.2 g).

$^1$H-NMR (400 MHz, CDCl$_3$); δ (ppm): 1.60-1.88 (m, 8H), 2.47 (s, 6H), 4.00 (s, 2H), 7.03 (d, 2H), 7.83 (d, 2H), 9.88 (s, 1H).

Preparation Example 30 tert-Butyl[1-(4-formylphenoxymethyl)cyclopentyl]carbamate

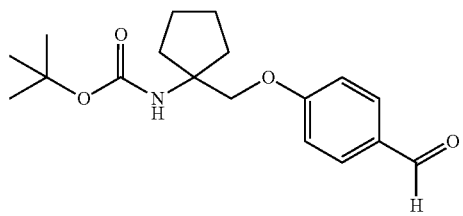 [SMILES: CC(C)(C)OC(=O)NC1(COc2ccc(C=O)cc2)CCCC1]

Synthesized from 4-(1-aminocyclopentylmethoxy)benzonitrile according to an analogous synthetic method to Preparation Example 19, tert-butyl[1-(4-cyanophenoxymethyl)cyclopentyl]carbamate (1.0 g) was used according to an analogous synthetic method to Preparation Example 20 to provide the title compound (688 mg).

$^1$H-NMR (400 MHz, CDCl$_3$); δ (ppm): 1.39 (s, 9H), 1.64-1.98 (m, 8H), 4.17 (s, 2H), 4.69 (s, 1H), 7.01 (d, 2H), 7.81 (d, 2H), 9.86 (s, 1H).

Preparation Example 31

4-(2-Amino-2-methylpropoxy)-3-fluorobenzonitrile

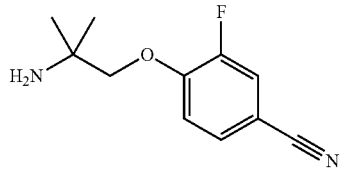

The title compound (4.5 g) was obtained according to an analogous synthetic method to Preparation Example 15 using 2-amino-2-methylpropan-1-ol (2.0 g) and 3,4-difluorobenzonitrile (4.4 g).

$^1$H-NMR (400 MHz, CDCl$_3$); δ (ppm): 1.26 (s, 6H), 3.80 (s, 2H), 7.00 (t, 1H), 7.37 (dd, 1H), 7.41 (ddd, 1H).

Preparation Example 32

4-(2-Dimethylamino-2-methylpropoxy)-3-fluorobenzaldehyde

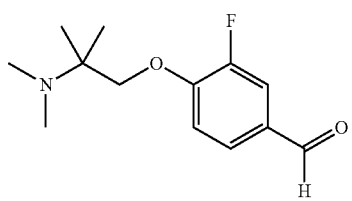 [SMILES: CN(C)C(C)(C)COc1ccc(C=O)cc1F]

Synthezised from 4-(2-amino-2-methylpropoxy)-3-fluorobenzonitrile according to an analogous synthetic method to Preparation Example 18, 4-(2-dimethylamino-2-methylpropoxy)-3-fluorobenzonitrile (1.4 g) was used according to an analogous synthetic method to Preparation Example 16 to provide the title compound (965 mg).

$^1$H-NMR (400 MHz, CDCl$_3$); δ (ppm): 1.29 (s, 6H), 2.45 (s, 6H), 4.04 (s, 2H), 7.08 (t, 1H), 7.57-7.64 (m, 2H), 9.85 (s, 1H).

Preparation Example 33 tert-Butyl[2-(2-fluoro-4-formylphenoxy)-1,1-dimethylethyl]carbamate

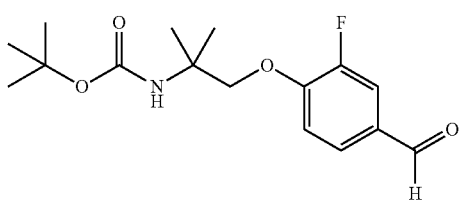 [SMILES: CC(C)(COc1ccc(C=O)cc1F)NC(=O)OC(C)(C)C]

Synthesized from 4-(2-amino-2-methylpropoxy)-3-fluorobenzonitrile according to an analogous synthetic method to Preparation Example 19, tert-butyl[2-(4-cyano-2-fluorophenoxy)-1,1-dimethylethyl]carbamate (1.0 g) was used according to an analogous synthetic method to Preparation Example 20 to provide the title compound (715 mg).

$^1$H-NMR (400 MHz, CDCl$_3$); δ (ppm): 1.39 (s, 9H), 1.42 (s, 6H), 4.19 (s, 2H), 4.66 (s, 1H), 7.10 (t, 1H), 7.56-7.62 (m, 2H), 9.84 (s, 1H).

Preparation Example 34

4-(4-Cyano-2-fluorophenoxy)piperidine-1-carboxylic acid tert-butyl ester

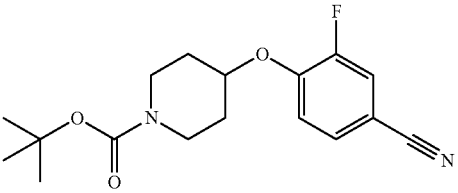 [SMILES: CC(C)(C)OC(=O)N1CCC(Oc2ccc(C#N)cc2F)CC1]

The title compound (6.1 g) was obtained according to an analogous synthetic method to Preparation Example 15 using 4-hydroxypiperidine-1-carboxylic acid tert-butyl ester (4.0 g) and 3,4-difluorobenzonitrile (3.9 g).

$^1$H-NMR (400 MHz, CDCl$_3$); δ (ppm): 1.47 (s, 9H), 1.76-1.85 (m, 2H), 1.89-1.98 (m, 2H), 3.38 (ddd, 2H), 3.69 (ddd, 2H), 4.59 (tt, 1H), 7.02 (t, 1H), 7.34-7.41 (m, 2H).

Preparation Example 35

4-(2-Fluoro-4-formylphenoxy)piperidine-1-carboxylic acid tert-butyl ester

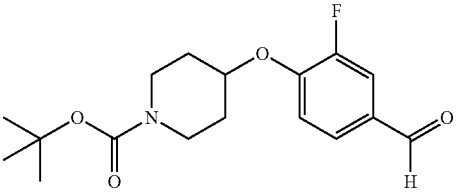 [SMILES: CC(C)(C)OC(=O)N1CCC(Oc2ccc(C=O)cc2F)CC1]

The title compound (750 mg) was obtained according to an analogous synthetic method to Preparation Example 20 using 4-(4-cyano-2-fluorophenoxy)piperidine-1-carboxylic acid tert-butyl (1.0 g).

$^1$H-NMR (400 MHz, CDCl$_3$); δ (ppm): 1.47 (s, 9H), 1.78-1.88 (m, 2H), 1.91-2.01 (m, 2H), 3.39 (ddd, 2H), 3.70 (ddd, 2H), 4.64 (tt, 1H), 7.08 (t, 1H), 7.58-7.63 (m, 2H), 9.85 (s, 1H).

Preparation Example 36

4-(1-Acetylpiperidin-4-yloxy)-3-fluorobenzonitrile

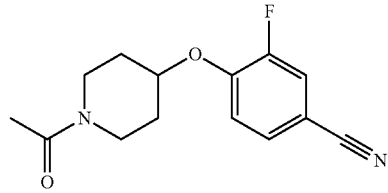 [SMILES: CC(=O)N1CCC(Oc2ccc(C#N)cc2F)CC1]

Synthesized from 4-(4-cyano-2-fluorophenoxy)piperidine-1-carboxylic acid tert-butyl ester (2.8 g) according to an analogous synthetic method to Example 215 described below, the total amount of 3-fluoro-4-(piperidin-4-yloxy)benzonitrile crude product was dissolved in acetic anhydride (30 ml) and pyridine (30 ml), and the solution was stirred overnight at room temperature. The solvent was evaporated in vacuo, the solution was extracted with ethyl acetate, then sequentially washed with a saturated aqueous solution of sodium bicarbonate, water and brine, dried over anhydrous magnesium sulfate, and then the solvent was evaporated in vacuo. The residue was purified by NH silica gel column chromatography (hexane-ethyl acetate system) to provide the title compound (2.2 g).

$^1$H-NMR (400 MHz, CDCl$_3$); δ (ppm): 1.80-2.02 (m, 4H), 2.12 (s, 3H), 3.41-3.48 (m, 1H), 3.67-3.74 (m, 3H), 4.67 (tt, 1H), 7.03 (t, 1H), 7.36-7.42 (m, 2H).

Preparation Example 37

4-(1-Acetylpiperidin-4-yloxy)-3-fluorobenzaldehyde

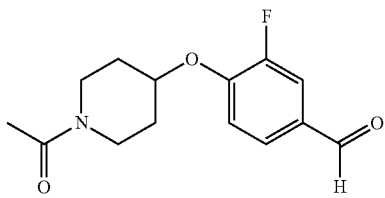 [SMILES: CC(=O)N1CCC(Oc2ccc(C=O)cc2F)CC1]

The title compound (809 mg) was obtained according to an analogous synthetic method to Preparation Example 20 using 4-(1-acetylpiperidin-4-yloxy)-3-fluorobenzonitrile (1.0 g).

$^1$H-NMR (400 MHz, CDCl$_3$); δ (ppm): 1.82-2.03 (m, 4H), 2.13 (s, 3H), 3.42-3.50 (m, 1H), 3.68-3.76 (m, 3H), 4.71 (tt, 1H), 7.09 (t, 1H), 7.60-7.65 (m, 2H), 9.85 (s, 1H).

Preparation Example 38

3-Fluoro-4-(1-methylpiperidin-4-yloxy)benzaldehyde

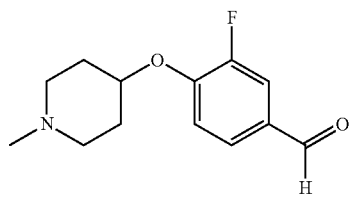 [SMILES: CN1CCC(Oc2ccc(C=O)cc2F)CC1]

Synthesized from 4-hydroxy-1-methylpiperidine and 3,4-difluorobenzonitrile according to an analogous synthetic method to Preparation Example 15, 3-fluoro-4-(1-methylpiperidin-4-yloxy)benzonitrile (1.1 g) was used according to an analogous synthetic method to Preparation Example 16 to provide the title compound (1.1 g).

$^1$H-NMR (400 MHz, CDCl$_3$); δ (ppm): 1.85-2.10 (m, 4H), 2.28-2.40 (m, 5H), 2.65-2.77 (m, 4H), 4.46-4.53 (m, 1H), 7.06 (t, 1H), 7.58-7.62 (m, 2H), 9.84 (s, 1H).

Preparation Example 39

4-(4-Methylpiperazin-1-yl)benzaldehyde

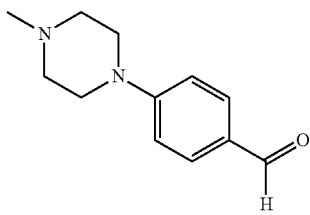

To a solution of 4-fluorobenzonitrile (2.0 g) and 1-methylpiperazine (2.5 g) in dimethylsulfoxide (30 ml) was added potassium carbonate (4.6 g), and the solution was stirred for 1 hour at 120° C. Water was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide 4-(4-methylpiperazin-1-yl)benzonitrile (2.34 g). This compound (1.1 g) was used according to an analogous synthetic method to Preparation Example 16 to provide the title compound (1.1 g).

$^1$H-NMR (400 MHz, CDCl$_3$); δ (ppm): 2.35 (s, 3H), 2.55 (t, 4H), 3.41 (t, 4H), 6.91 (d, 2H), 7.74 (d, 2H), 9.77 (s, 1H).

Preparation Example 40

1-[2-(4-Bromophenoxy)ethyl]azepane

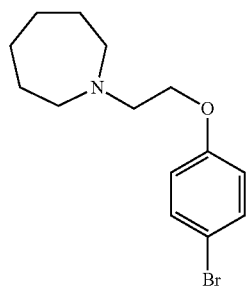 [SMILES: Brc1ccc(OCCN2CCCCCC2)cc1]

To a suspension of 60% sodium hydride (1.6 g) in N,N-dimethylformamide (50 ml) was added 4-bromophenol (3.0 g) under a nitrogen atmosphere, the solution was stirred for 10 minutes at room temperature, then 1-(2-chloroethyl)azepane hydrochloride (4.0 g) and sodium iodide (in catalytic amounts) were sequentially added thereto followed by stirring overnight at 80° C. Water was added thereto followed by stirring, the solution was extracted with ethyl acetate, then sequentially washed with water and brine, and the solvent was evaporated in vacuo. The residue was purified by NH silica gel column chromatography (hexane-ethyl acetate system) to provide the title compound (5.0 g).

$^1$H-NMR (400 MHz, CDCl$_3$); δ (ppm): 1.58-1.67 (m, 8H), 2.73-2.79 (m, 4H), 2.93 (t, 2H), 4.02 (t, 2H), 6.79 (d, 2H), 7.36 (d, 2H).

Preparation Example 41

1-[2-(4-Bromo-2-fluorophenoxy)ethyl]piperidine

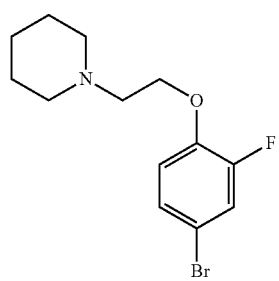 [SMILES: Fc1cc(Br)ccc1OCCN1CCCCC1]

The title compound (5.1 g) was obtained according to an analogous synthetic method to Preparation Example 40 using 4-bromo-2-fluorophenol (3.4 g) and 1-(2-chloroethyl)piperidine hydrochloride (4.0 g).

$^1$H-NMR (400 MHz, CDCl$_3$); δ (ppm): 1.41-1.48 (m, 2H), 1.56-1.64 (m, 4H), 2.44-2.55 (m, 4H), 2.79 (t, 2H), 4.14 (t, 2H), 6.86 (t, 1H), 7.17 (ddd, 1H), 7.23 (dd, 1H).

Preparation Example 42

1-[2-(4-Bromo-2-fluorophenoxy)ethyl]azepane

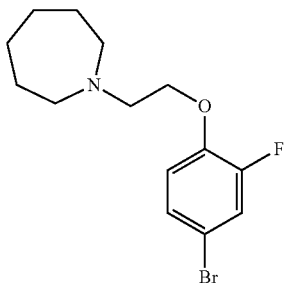 [SMILES: Fc1cc(Br)ccc1OCCN1CCCCCC1]

The title compound (5.4 g) was obtained according to an analogous synthetic method to Preparation Example 40 using 4-bromo-2-fluorophenol (3.4 g) and 1-(2-chloroethyl)azepane hydrochloride (4.0 g).
$^1$H-NMR (400 MHz, CDCl$_3$); δ (ppm): 1.54-1.69 (m, 8H), 2.74-2.78 (m, 4H), 2.96 (t, 2H), 4.10 (t, 2H), 6.86 (t, 1H), 7.17 (ddd, 1H), 7.22 (dd, 1H).

Preparation Example 43

[2-(4-Bromo-2-fluorophenoxy)ethyl]diisopropylamine

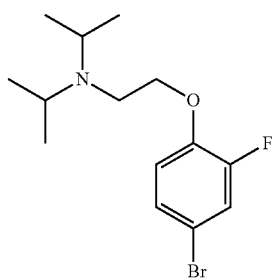 [SMILES: CC(C)N(CCOc1ccc(Br)cc1F)C(C)C]

The title compound (5.6 g) was obtained according to an analogous synthetic method to Preparation Example 40 using 4-bromo-2-fluorophenol (3.4 g) and (2-chloroethyl)diisopropylamine hydrochloride (4.0 g).
$^1$H-NMR (400 MHz, CDCl$_3$); δ (ppm): 1.03 (d, 12H), 2.85 (t, 2H), 3.04 (hept, 2H), 3.91 (t, 2H), 6.85 (t, 1H), 7.17 (ddd, 1H), 7.22 (dd, 1H).

Preparation Example 44

1-Prop-2-ynylpiperidine

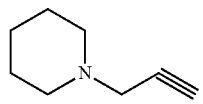

To a solution of piperidine (8.5 ml) in diethyl ether (100 ml) was added propargyl bromide (3 ml) on an ice bath, the solution was stirred overnight at room temperature, then diethyl ether was added thereto followed by filtering, and the solvent was evaporated in vacuo to provide the title compound (6.0 g).
$^1$H-NMR (400 MHz, CDCl$_3$); δ (ppm): 1.39-1.47 (m, 2H), 1.58-1.66 (m, 4H), 2.23 (t, 1H), 2.45-2.56 (m, 4H), 3.28 (d, 2H).

Preparation Example 45

1-[3-(4-Bromo-2-fluorophenyl)prop-2-ynyl]piperidine

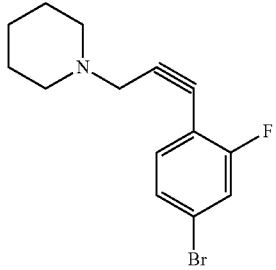 [SMILES: Fc1cc(Br)ccc1C#CCN1CCCCC1]

To a solution of 1-bromo-3-fluoro-4-iodobenzene (2.5 g), 1-prop-2-ynylpiperidine (1.5 g), dichlorobis(triphenylphosphine)palladium(II) (300 mg) and copper(I) iodide (40 mg) in N,N-dimethylformamide (20 ml) was added triethylamine (10 ml) under a nitrogen atmosphere, and the solution was stirred for 1.5 hours at room temperature. A saturated aqueous solution of ammonium chloride was added thereto followed by stirring, the solution was extracted with ethyl acetate, then sequentially washed with water and brine, and dried over anhydrous magnesium sulfate, and then the solvent was evaporated in vacuo. The residue was purified by NH silica gel column chromatography (hexane-ethyl acetate system) to provide the title compound (1.1 g).
$^1$H-NMR (400 MHz, CDCl$_3$); δ (ppm): 1.41-1.49 (m, 2H), 1.58-1.68 (m, 4H), 2.48-2.62 (m, 4H), 3.51 (s, 2H), 7.21-7.31 (m, 3H).

Preparation Example 46

3-Fluoro-4-(3-piperidin-1-ylpropyl)benzoic acid hydrochloride

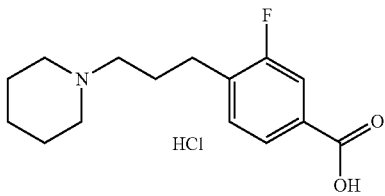 [SMILES: O=C(O)c1ccc(CCCN2CCCCC2)c(F)c1 ; Cl]

To a solution of 3-fluoro-4-hydroxybenzoic acid ethyl ester (1.5 g) in dichloromethane (50 ml) was added pyridine (1 ml) on an ice bath, trifluoromethanesulfonic anhydride (1.5 ml) was added dropwise thereto followed by stirring overnight at room temperature. Water was added thereto followed by stirring, and the solution was extracted with ethyl acetate, then sequentially washed with water and brine, and dried over anhydrous magnesium sulfate, then the solvent was evaporated in vacuo to provide 3-fluoro-4-trifluoromethanesulfonyloxybenzoic acid ethyl ester. Synthesized from this compound (2.6 g) and 1-prop-2-ynylpiperidine (2.0 g) according to an analogous synthetic method to Preparation Example 45, 3-fluoro-4-(3-piperidin-1-ylprop-1-ynyl)benzoic acid ethyl ester (2.3 g) was stirred in methanol (40 ml), to which was added 10% palladium-activated charcoal (500 mg), and the solution was stirred overnight at room temperature under a hydrogen atmosphere at ambient pressure. Obtained after filtration through celite pad and after the solvent was evaporated in vacuo, 3-fluoro-4-(3-piperidin-1-ylpropyl)benzoic acid ethyl ester (1.8 g) was stirred in ethanol (20 ml), to which was added an aqueous solution of 2N sodium hydroxide (10 ml), and the solution was refluxed for 1 hour. Ethanol was evaporated in vacuo, water was added thereto followed by stirring, and the solid that was precipitated by adding 2N hydrochloric acid (12 ml) was filtered and collected to provide the title compound (2.0 g).

$^1$H-NMR (400 MHz, DMSO-$d_6$); δ (ppm): 1.26-1.42 (m, 1H), 1.60-1.80 (m, 5H), 1.95-2.06 (m, 2H), 2.71 (t, 2H), 2.72-2.90 (m, 2H), 3.00 (t, 2H), 3.22-3.46 (m, 2H), 7.47 (t, 1H), 7.61 (dd, 1H), 7.72 (dd, 1H).

Preparation Example 47

4-Azepan-1-ylmethylbenzoic acid hydrochloride

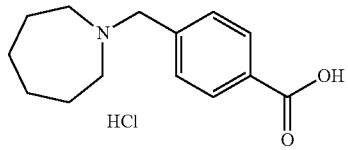 [SMILES: O=C(O)c1ccc(CN2CCCCCC2)cc1 ; Cl]

Synthesized from 4-formylbenzoic acid methyl ester and hexamethyleneimine according to an analogous synthetic method to Example 38 described below, 4-azepan-1-ylmethylbenzoic acid methyl ester (3.2 g) was stirred in methanol (40 ml), to which was added an aqueous solution of 2N sodium hydroxide (20 ml), and the solution was stirred for 1.5 hours at 80° C. Methanol was evaporated in vacuo, then the solid that was precipitated by sequential addition of water and 2N hydrochloric acid was filtered to provide the title compound (2.3 g).

$^1$H-NMR (400 MHz, DMSO-$d_6$); δ (ppm): 1.50-1.70 (m, 4H), 1.75-1.86 (m, 4H), 2.95-3.08 (m, 2H), 3.18-3.30 (m, 2H), 4.37 (s, 2H), 7.74 (d, 2H), 7.97 (d, 2H), 10.72 (brs, 1H), 13.12 (brs, 1H).

Preparation Example 48

4-(2-Azepan-1-ylethyl)benzoic acid hydrochloride

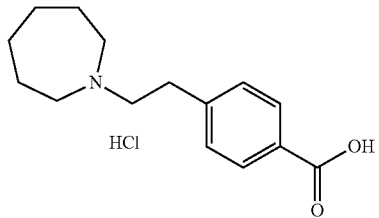 [SMILES: O=C(O)c1ccc(CCN2CCCCCC2)cc1 ; Cl]

To a suspension of (methoxymethyl)triphenylphosphonium chloride (12.5 g) in tetrahydrofuran (50 ml) was added dropwise potassium tert-butoxide (1.0 M solution in tetrahydrofuran) (40 ml) on an ice bath under a nitrogen atmosphere, and the solution was stirred for 20 minutes, then a solution of 4-formylbenzoic acid methyl ester (5.0 g) in tetrahydrofuran (16 ml) was added dropwise thereto followed by stirring overnight at room temperature. A saturated aqueous solution of ammonium chloride was added thereto followed by stirring. The solution was extracted with ethyl acetate, then sequentially washed with water and brine, dried over anhydrous magnesium sulfate, and then the solvent was evaporated in vacuo. Obtained by purifying the residue by NH silica gel column chromatography (hexane-ethyl acetate system), 4-(2-methoxyvinyl)benzoic acid methyl ester (5.2 g) was stirred in dichloromethane (30 ml), to which was added formic acid (20 ml), and the solution was stirred overnight at room temperature. Water was added thereto followed by stirring, the solution was extracted with ethyl acetate, then sequentially washed with a saturated aqueous solution of sodium bicarbonate and brine, and dried over anhydrous magnesium sulfate, then the solvent was evaporated in vacuo, and 4-(2-oxoethyl)benzoic acid methyl ester (4.6 g). Synthesized from this compound and hexamethyleneimine according to an analogous synthetic method to Example 38 described below, 4-(2-azepan-1-ylethyl)benzoic acid methyl ester (3.7 g) was stirred in methanol (40 ml), to which was added an aqueous solution of 2N sodium hydroxide (20 ml), and the solution was stirred for 1 hour at 80° C. Methanol was evaporated in vacuo, then the solid that was precipitated by the several addition of water and 2N hydrochloric acid was filtered to provide the title compound (3.4 g).

$^1$H-NMR (400 MHz, DMSO-$d_6$); δ (ppm): 1.55-1.64 (m, 4H), 1.78-1.88 (m, 4H), 3.13-3.18 (m, 2H), 3.20-3.35 (m, 6H), 7.40 (d, 2H), 7.88 (d, 2H).

Preparation Example 49

4-(3-Azepan-1-ylpropyl)benzoic acid hydrochloride

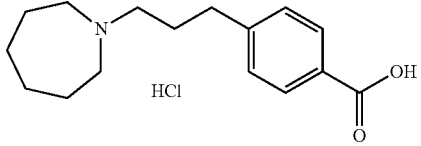 [SMILES: O=C(O)c1ccc(CCCN2CCCCCC2)cc1 ; Cl]

Synthesized from hexamethyleneimine according to an analogous synthetic method to Preparation Example 44, 1-prop-2-ynylazepane (6.0 g) and 4-iodobenzoic acid ethyl ester (7.0 g) were used according to an analogous synthetic method to Preparation Example 46 to provide the title compound (3.3 g).

$^1$H-NMR (400 MHz, DMSO-$d_6$); δ (ppm): 1.50-1.65 (m, 4H), 1.72-1.84 (m, 4H), 1.98-2.07 (m, 2H), 2.68 (t, 2H), 2.99-3.10 (m, 4H), 3.24-3.36 (m, 2H), 7.35 (d, 2H), 7.86 (d, 2H), 10.42 (brs, 1H), 12.81 (brs, 1H).

Preparation Example 50

1-[2-(5-Bromopyridin-2-yloxy)ethyl]azepane

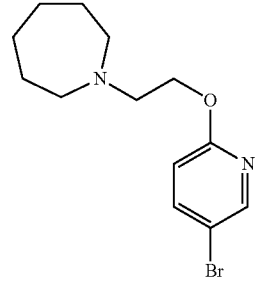 [SMILES: Brc1ccc(OCCN2CCCCCC2)nc1]

To a solution of 2-azepan-1-ylethanol (5.0 g) in N,N-dimethylformamide (100 ml) was added 60% sodium hydride (1.5 g) under a nitrogen atmosphere, the solution was stirred for 1 hour at room temperature, 2,5-dibromopyridine (7.5 g) was then added thereto followed by stirring for 4.5 hours at room temperature. Water was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (9.1 g).

$^1$H-NMR (400 MHz, CDCl$_3$); δ (ppm): 1.56-1.66 (m, 8H), 2.77 (t, 4H), 2.92 (t, 2H), 4.36 (t, 2H), 6.67 (d, 1H), 8.17 (d, 1H).

Preparation Example 51

6-(2-Azepan-1-ylethoxy)nicotinic acid hydrochloride

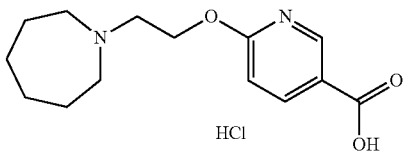 [SMILES: O=C(O)c1ccc(OCCN2CCCCCC2)nc1 ; Cl]

To a solution of 1-[2-(5-bromopyridin-2-yloxy)ethyl] azepane (4.0 g) in tetrahydrofuran (40 ml) cooled to −78° C., was added dropwise n-butyllithium (2.46 M solution in hexane) (6 ml) under a nitrogen atmosphere. After stirring for 20 minutes, carbon dioxide was bubbled therein, and stirred overnight while warming from −78° C. to room temperature. Water was added thereto followed by stirring, tetrahydrofuran was evaporated in vacuo, 5N hydrochloric acid (5 ml) was then added thereto, and the resulting solid was filtered to provide the title compound (2.3 g).

$^1$H-NMR (400 MHz, DMSO-$d_6$); δ (ppm): 1.49-1.70 (m, 4H), 1.73-1.92 (m, 4H), 3.10-3.58 (m, 6H), 4.72 (t, 2H), 6.96 (d, 1H), 8.17 (dd, 1H), 8.71 (d, 1H), 10.87 (s, 1H), 13.13 (brs, 1H).

Preparation Example 52

5-Benzyloxypyridine-2-carbaldehyde

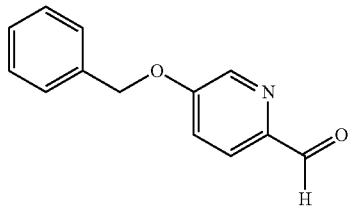 [SMILES: O=Cc1ccc(OCc2ccccc2)cn1]

The title compound was synthesized by referring to *Tetrahedron*, 2001, 57, 3479. To a solution of 3-hydroxy-6-methylpyridine (5.0 g) in methanol (100 ml) was added an aqueous solution of 5N sodium hydroxide (9.2 ml), and the solution was stirred for 15 minutes at room temperature. The solvent was evaporated in vacuo, toluene was added thereto, and to the residue obtained by evaporating the solvent in vacuo, were sequentially added N,N-dimethylformamide (100 ml) and benzyl bromide (5.5 ml) under a nitrogen atmosphere, and the solution was stirred for 30 minutes at 60° C. Water was added thereto followed by stirring, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to obtain 5-benzyloxy-2-methylpyridine (7.4 g). To a solution of 65% 3-chloroperbenzoic acid (13 g) in dichloromethane (200 ml) was added dropwise a solution of 5-benzyloxy-2-methylpyridine (9.7 g) in dichloromethane (16 ml) on an ice bath, and the solution was stirred for 5.5 hours at room temperature, which was then neutralized with a saturated aqueous solution of sodium bicarbonate. The solution was extracted with dichloromethane, then sequentially washed with water and brine, dried over anhydrous magnesium sulfate, then the solvent was evaporated in vacuo to obtain 5-benzyloxy-2-methylpyridine 1-oxide. This compound (10.4 g) was dissolved in acetic anhydride (120 ml), and the solution was stirred for 1.5 hours at 120° C. To the residue obtained by evaporating the solvent in vacuo were sequentially added an aqueous solution of 5N sodium hydroxide (50 ml) and ethanol (150 ml), and the solution was stirred for 30 minutes at 90° C. The insoluble material was filtered through celite pad, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to obtain (5-benzyloxypyridin-2-yl)methanol (7.2 g). To a solution of this compound (5.0 g) in chloroform (100 ml) were sequentially added triethylamine (13 ml) and dimethylsulfoxide (26 ml), the solution was stirred, sulfur trioxide pyridine complex (11 g) was added thereto on an ice bath, and the solution was stirred for 10 hours while warming to room temperature. Water and a saturated aqueous solution of sodium bicarbonate were sequentially added thereto followed by stirring, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (3.8 g).

$^1$H-NMR (400 MHz, CDCl$_3$); δ (ppm): 5.20 (s, 2H), 7.32-7.44 (m, 6H), 7.94 (d, 1H), 8.49 (d, 1H), 9.97 (s, 1H).

Preparation Example 53

5-Benzyloxypyridine-2-carboxylic acid

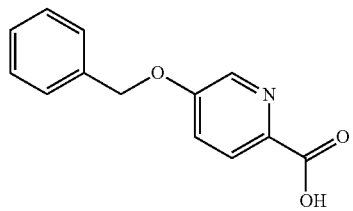 [SMILES: O=C(O)c1ccc(OCc2ccccc2)cn1]

To a solution of 5-benzyloxypyridine-2-carbaldehyde (3.8 g) in acetone (50 ml) was added water (50 ml), sulfamic acid (2.4 g) and sodium chlorite (2.2 g) were sequentially added thereto on an ice bath, and the solution was stirred for 6 hours at room temperature. The solid that was precipitated was filtered and rinsed with water to provide the title compound (3.0 g).

$^1$H-NMR (400 MHz, DMSO-$d_6$); δ (ppm): 5.26 (s, 2H), 7.32-7.48 (m, 5H), 7.57 (dd, 1H), 8.01 (d, 1H), 8.41 (d, 1H), 12.85 (brs, 1H).

Preparation Example 54

Sodium 5-(2-azepan-1-ylethoxy)pyridine-2-carboxylate

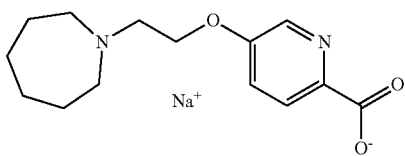 [SMILES: O=C([O-])c1ccc(OCCN2CCCCCC2)cn1 ; [Na+]]

To a residue obtained by stirring a solution of 5-benzyloxypyridine-2-carboxylic acid (680 mg) in thionyl chloride (10 ml) at 80° C. for 50 minutes and then evaporating the solvent was in vacuo, was added ethanol (10 ml), the solution was stirred overnight at room temperature, then was neutralized by adding a saturated aqueous solution of sodium bicarbonate. The solution was extracted with ethyl acetate, then sequentially washed with water and brine, dried over anhydrous magnesium sulfate, and then the solvent was evaporated in vacuo. Obtained by purifying the residue by NH silica gel column chromatography (hexane-ethyl acetate system), 5-benzyloxypyridine-2-carboxylic acid ethyl ester (691 mg) was stirred in methanol (10 ml), 10% palladium-activated charcoal (150 mg) was added thereto followed by stirring for 1.5 hours at room temperature under a hydrogen atmosphere at ambient pressure. Obtained by filtrating through celite pad and then evaporating the solvent in vacuo, 5-hydroxypyridine-2-carboxylic acid ethyl ester (415 mg) was stirred in N,N-dimethylformamide (10 ml), potassium carbonate (510 mg) and 1-(2-chloroethyl)azepane (640 mg) were sequentially added thereto followed by stirring for 30 minutes at 60° C. Water was added thereto followed by stirring, the solution was extracted with ethyl acetate, then sequentially washed with water and brine, dried over anhydrous magnesium sulfate, and then the solvent was evaporated in vacuo. Obtained by purifying the residue by NH silica gel column chromatography (hexane-ethyl acetate system), 5-(2-azepan-1-ylethoxy)pyridine-2-carboxylic acid ethyl ester (526 mg) was stirred in ethanol (6 ml), an aqueous solution of 2N sodium hydroxide (3 ml) was added thereto, and the solution was refluxed for 45 minutes. Ethanol was evaporated in vacuo, water was added thereto and the solution was cooled on an ice bath, and the solid that was precipitated was filtered to provide the title compound (270 mg).

$^1$H-NMR (400 MHz, DMSO-d$_6$); δ (ppm): 1.48-1.61 (m, 8H), 2.64-2.70 (m, 4H), 2.84 (t, 2H), 4.08 (t, 2H), 7.31 (dd, 1H), 7.86 (d, 1H), 8.06 (d, 1H).

Preparation Example 55

6-Bromopyridine-3-carbaldehyde

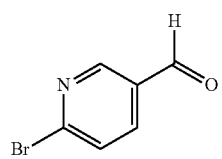

2,5-Dibromopyridine (5.4 g) was stirred in diethyl ether (100 ml) under a nitrogen atmosphere, the solution was cooled at −78° C., then n-butyllithium (2.66M solution in hexane) (8.5 ml) was added dropwise thereto followed by stirring for 20 minutes, then N,N-dimethylformamide (4.0 ml) was added dropwise thereto followed by stirring for 10 minutes. A saturated aqueous solution of ammonium chloride and water were sequentially added thereto followed by stirring, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (2.2 g).

$^1$H-NMR (400 MHz, CDCl$_3$); δ (ppm): 7.68 (d, 1H), 8.01 (dd, 1H), 8.82 (d, 1H), 10.08 (s, 1H).

Preparation Example 56

(6-Bromopyridin-3-yl)acetaldehyde

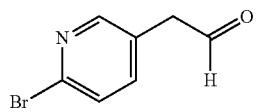

To a suspension of (methoxymethyl)triphenylphosphonium chloride (4.65 g) in tetrahydrofuran (20 ml) was added dropwise potassium tert-butoxide (1.0 M solution in tetrahydrofuran) (14.6 ml) on an ice bath under a nitrogen atmosphere, the solution was stirred for 20 minutes, then a solution of 6-bromopyridine-3-carbaldehyde (2.1 g) in tetrahydrofuran (16 ml) was added dropwise thereto followed by stirring overnight at room temperature. A saturated aqueous solution of ammonium chloride was added thereto followed by stirring, the solution was extracted with ethyl acetate, then sequentially washed with water and brine, dried over anhydrous magnesium sulfate, and then the solvent was evaporated in vacuo. Obtained by purifying the residue by NH silica gel column chromatography (hexane-ethyl acetate system), 2-bromo-5-(2-methoxyvinyl)pyridine (2.2 g) was stirred in acetone (20 ml), water (10 m) and concentrated sulfuric acid (1 ml) were sequentially added thereto, the solution was stirred for 1.5 hours at 80° C., and then neutralized with a saturated aqueous solution of sodium bicarbonate. The solution was extracted with ethyl acetate, then sequentially washed with water and brine, dried over anhydrous magnesium sulfate, and then the solvent was evaporated in vacuo to provide the title compound (1.5 g).

$^1$H-NMR (400 MHz, CDCl$_3$); δ (ppm): 3.73 (s, 2H), 7.41 (dd, 1H), 7.49 (d, 1H), 8.22 (d, 1H), 9.79 (s, 1H).

Preparation Example 57

1-[2-(6-Bromopyridin-3-yl)ethyl]azepane

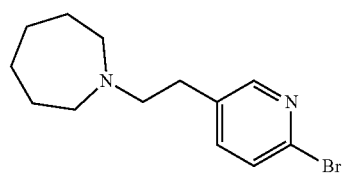 [SMILES: Brc1ccc(CCN2CCCCCC2)cn1]

The title compound (1.5 g) was obtained according to an analogous synthetic method to the Preparation Example 38 described below using (6-bromopyridin-3-yl)acetaldehyde (1.5 g) and hexamethyleneimine (1 ml).

$^1$H-NMR (400 MHz, CDCl$_3$); δ (ppm): 1.56-1.66 (m, 8H), 2.67 (t, 4H), 2.69-2.72 (m, 4H), 7.37 (dd, 1H), 7.40 (dd, 1H), 8.21 (d, 1H).

Preparation Example 58

1-[2-(5-Bromothiophen-2-yl)ethyl]azepane

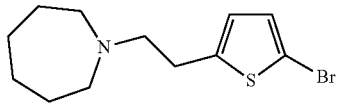 [SMILES: Brc1ccc(CCN2CCCCCC2)s1]

Synthesized from 5-bromo-2-thiophenecarboxaldehyde according to an analogous synthetic method to Preparation Example 56, (5-bromothiophen-2-yl) acetaldehyde (2.2 g) and hexamethyleneimine (1.5 ml) were used according to an analogous synthetic method to Example 38 described below to provide the title compound (568 mg).

$^1$H-NMR (400 MHz, CDCl$_3$); δ (ppm): 1.58-1.70 (m, 8H), 2.65-2.72 (m, 6H), 2.88 (t, 2H), 6.55 (dt, 1H), 6.82 (d, 1H).
ESI-Mass; 288 [M$^+$+H], 290 [M$^+$+H+2]

Preparation Example 59

Lithium 5-(2-azepan-1-ylethyl)thiophene-2-carboxylate

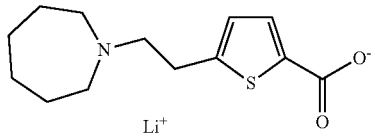 [SMILES: O=C([O-])c1ccc(CCN2CCCCCC2)s1 ; [Li+]]

The title compound (410 mg) was obtained according to an analogous synthetic method to the Preparation Example 51 using 1-[2-(5-bromothiophen-2-yl)ethyl]azepane (565 mg).

$^1$H-NMR (400 MHz, DMSO-d$_6$); δ (ppm): 1.51-1.62 (m, 8H), 2.61-2.66 (m, 4H), 2.68 (t, 2H), 2.84 (t, 2H), 6.71 (s, 1H), 7.14 (s, 1H).
ESI-Mass; 254 [M$^+$+H]

Preparation Example 60

4-(2-Piperidin-1-ylethoxy)naphthalene-1-carboxylic acid hydrochloride

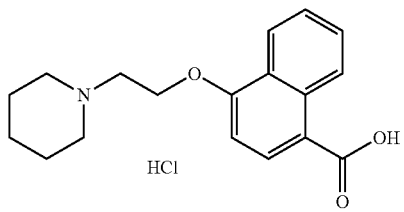 [SMILES: O=C(O)c1ccc(OCCN2CCCCC2)c2ccccc12 ; Cl]

To a solution of 4-bromonaphthalen-1-ol (1.1 g) in N,N-dimethylformamide (30 ml) were sequentially added potassium carbonate (1.0 g) and 1-(2-chloroethyl)piperidine (1.1 g), and the solution was stirred for 1 hour at 60° C. Water was added thereto followed by stirring, the solution was extracted with ethyl acetate, then sequentially washed with water and brine, dried over anhydrous magnesium sulfate, and the solvent was then evaporated in vacuo. The residue was purified by NH silica gel column chromatography (hexane-ethyl acetate system) to obtain 1-[2-(4-bromonaphthalen-1-yloxy)ethyl]piperidine (1.59 g). This compound (800 mg) was used according to an analogous synthetic method to Preparation Example 51 to provide the title compound (518 mg).

$^1$H-NMR (400 MHz, DMSO-d$_6$); δ (ppm): 1.35-1.50 (m, 1H), 1.64-1.89 (m, 5H), 3.00-3.16 (m, 2H), 3.47-3.70 (m, 4H), 4.66 (t, 2H), 7.09 (d, 1H), 7.59 (t, 1H), 7.67 (t, 1H), 8.22 (d, 1H), 8.35 (d, 1H), 9.01 (d, 1H), 10.49 (brs, 1H), 12.81 (brs, 1H).

Preparation Example 61

N-(2-Bromo-5-methoxyphenyl)-3-fluoro-4-(2-piperidin-1-ylethoxy)benzamide

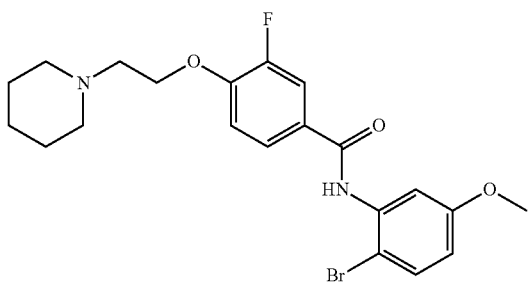 [SMILES: COc1ccc(Br)c(NC(=O)c2ccc(OCCN3CCCCC3)c(F)c2)c1]

A mixture of 3-fluoro-4-(2-piperidin-1-ylethoxy)benzoic acid hydrochloride (4.0 g), thionyl chloride (8 ml) and toluene (10 ml) was refluxed for 30 minutes. To the residue obtained by concentrating the reaction mixture in vacuo, were added 2-bromo-5-methoxyaniline (2.0 g) and pyridine (10 ml) on an ice bath, and the solution was stirred overnight at room temperature. The reaction mixture was diluted with water, extracted with ethyl acetate, then washed with brine, dried over anhydrous magnesium sulfate, and then the solvent was evaporated in vacuo. The residue was purified by NH silica gel column chromatography (hexane-ethyl acetate system) to provide the title compound (2.9 g).

$^1$H-NMR (400 MHz, CDCl$_3$); δ (ppm): 1.40-1.49 (m, 2H), 1.60-1.63 (m, 4H), 2.50-2.58 (m, 4H), 2.82 (t, 2H), 3.82 (s, 3H), 4.25 (t, 2H), 6.60 (d, 1H), 7.08 (t, 1H), 7.42 (d, 1H), 7.61-7.70 (m, 2H) 8.21 (d, 1H), 8.39 (brs, 1H).

Preparation Example 62

(2-Bromo-5-methoxyphenyl)[3-fluoro-4-(2-piperidin-1-ylethoxy)benzyl]amine

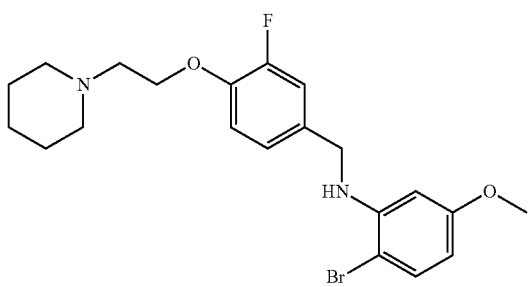 [SMILES: COc1ccc(Br)c(NCc2ccc(OCCN3CCCCC3)c(F)c2)c1]

Synthesized from N-(2-bromo-5-methoxyphenyl)-3-fluoro-4-(2-piperidin-1-ylethoxy)benzamide (1.0 g) according to an analogous synthetic method to Example 337 described below, the title compound (740 mg) was obtained.

¹H-NMR (400 MHz, CDCl₃); δ (ppm): 1.40-1.49 (m, 2H), 1.55-1.69 (m, 4H), 2.46-2.58 (m, 4H), 2.80 (t, 2H), 3.70 (s, 3H), 4.16 (t, 2H), 4.29 (d, 2H), 4.69 (brs, 1H), 6.12 (s, 1H), 6.16 (d, 1H), 6.94 (t, 1H), 7.01-7.10 (m, 2H) 7.30 (d, 1H).

Preparation Example 63

N-(2-Bromo-5-methoxyphenyl)-N-[3-fluoro-4-(2-piperidin-1-ylethoxy)benzyl]acetamide

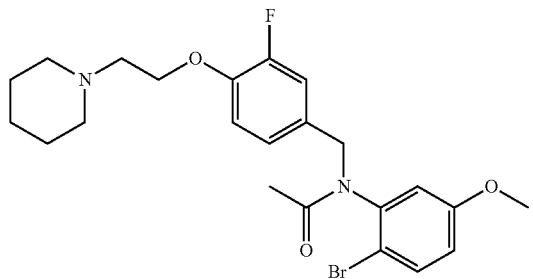 [SMILES: COc1ccc(Br)c(N(Cc2ccc(OCCN3CCCCC3)c(F)c2)C(C)=O)c1]

A mixture of (2-bromo-5-methoxyphenyl)[3-fluoro-4-(2-piperidin-1-ylethoxy)benzyl]amine (690 mg), pyridine (2 ml) and acetic anhydride (2 ml) was stirred for 4 hours at 80° C. The reaction mixture was diluted with an aqueous solution of 1N sodium hydroxide, extracted with ethyl acetate, then washed with brine, dried over anhydrous magnesium sulfate, and then the solvent was evaporated in vacuo. The residue was purified by NH silica gel column chromatography (hexane-ethyl acetate system) to provide the title compound (530 mg).

¹H-NMR (400 MHz, CDCl₃); δ (ppm): 1.42-1.50 (m, 2H), 1.60-1.69 (m, 4H), 1.83 (s, 3H), 2.52-2.62 (m, 4H), 2.89 (t, 2H), 3.62 (s, 3H), 3.95 (d, 1H), 4.19 (t, 2H), 5.42 (d, 1H), 6.33 (s, 1H), 6.76 (d, 1H), 6.80-6.90 (m, 2H), 7.00 (d, 1H), 7.54 (d, 1H).

Preparation Example 64

Acetic acid 3-{acetyl-[3-fluoro-4-(2-piperidin-1-ylethoxy)benzyl]amino}-4-bromophenyl ester

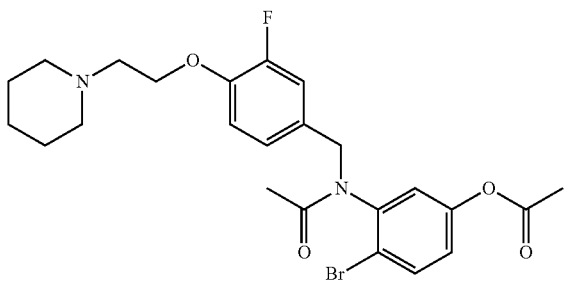 [SMILES: CC(=O)Oc1ccc(Br)c(N(Cc2ccc(OCCN3CCCCC3)c(F)c2)C(C)=O)c1]

To the total amount of N-(2-bromo-5-hydroxyphenyl)-N-[3-fluoro-4-(2-piperidin-1-ylethoxy)benzyl]acetamide crude product, which was synthesized from N-(2-bromo-5-methoxyphenyl)-N-[3-fluoro-4-(2-piperidin-1-ylethoxy)benzyl]acetamide (380 mg) synthesized according to an analogous synthetic method to Example 364 described below, were added pyridine (2 ml) and acetic anhydride (2 ml), and the solution was stirred for 1 hour at room temperature. To the reaction mixture was added a saturated aqueous solution of sodium bicarbonate, the solution was extracted with ethyl acetate, then washed with brine, dried over anhydrous magnesium sulfate, and then the solvent was evaporated in vacuo. The residue was purified by silica gel column chromatography (chloroform-methanol system) to provide the title compound (350 mg).

¹H-NMR (400 MHz, CDCl₃); δ (ppm): 1.42-1.50. (m, 2H), 1.58-1.66 (m, 4H), 1.85 (s, 3H), 2.26 (s, 3H), 2.50-2.62 (m, 4H), 2.83 (t, 2H), 4.02 (d, 1H), 4.16 (t, 2H), 5.41 (d, 1H), 6.61 (s, 1H), 6.83-6.86 (m, 2H), 6.97-7.03 (m, 2H), 7.66 (d, 1H).

Preparation Example 65

Acetic Acid 4-bromo-3-{ethyl[3-fluoro-4-(2-piperidin-1-ylethoxy)benzyl]amino}phenyl ester

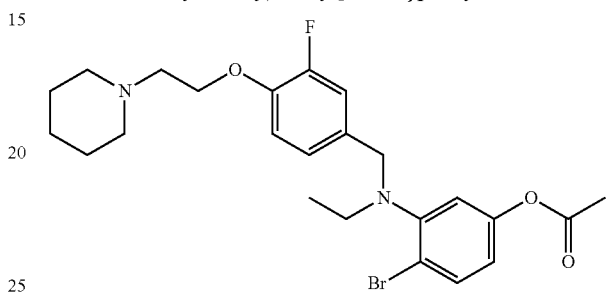

To the total amount of 4-bromo-3-{ethyl[3-fluoro-4-(2-piperidin-1-ylethoxy)benzyl]amino}phenol crude product, which was synthesized from acetic acid 3-{acetyl-[3-fluoro-4-(2-piperidin-1-ylethoxy)benzyl]amino}-4-bromophenyl ester (300 mg) synthesized according to an analogous synthetic method to Example 337 described below, were added pyridine (3 ml) and acetic anhydride (3 ml), and the solution was stirred overnight at room temperature. To reaction mixture was added a saturated aqueous solution of sodium bicarbonate, the solution was extracted with ethyl acetate, then washed with brine, dried over anhydrous magnesium sulfate, and then the solvent was evaporated in vacuo. The residue was purified by silica gel column chromatography (chloroform-methanol system) to provide the title compound (200 mg).

¹H-NMR (400 MHz, CDCl₃); δ (ppm): 1.00 (t, 3H), 1.40-1.49 (m, 2H), 1.55-1.65 (m, 4H), 2.29 (s, 3H), 2.50-2.58 (m, 4H), 2.80 (t, 2H), 3.00 (q, 2H), 4.10 (s, 2H), 4.15 (t, 2H), 6.68-6.71 (m, 1H), 6.78 (s, 1H), 6.89 (t, 1H), 7.01 (d, 1H), 7.18 (d, 1H), 7.58 (d, 1H).

Preparation Example 66

(2-Bromo-4-methoxyphenyl) [4-(2-piperidin-1-ylethoxy)phenyl]methanone

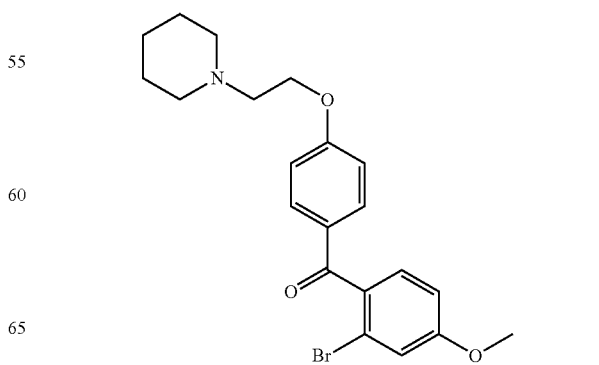

To a solution of 4-(2-piperidin-1-ylethoxy)benzoic acid hydrochloride (7.0 g) in thionyl chloride (70 ml) was added toluene (70 ml), the solution was stirred for 1.5 hours at 110° C., then the solvent was evaporated in vacuo. To a suspension of the resulting 4-(2-piperidin-1-ylethoxy)benzoyl chloride hydrochloride (4.5 g) in dichloromethane (100 ml) were sequentially added 3-bromoanisole (1.7 ml) and aluminum chloride (4.1 g) on an ice bath under a nitrogen atmosphere, and the solution was stirred overnight at room temperature. Tetrahydrofuran and aqueous ammonia were sequentially added thereto on the ice bath, the solution was filtered through celite pad, anhydrous magnesium sulfate was added thereto followed by stirring. The residue obtained by filtration, and then evaporation of the solvent in vacuo, was purified by NH silica gel column chromatography (hexane-ethyl acetate system) to provide the title compound (2.8 g).

$^1$H-NMR (400 MHz, CDCl$_3$); δ (ppm): 1.41-1.50 (m, 2H), 1.57-1.64 (m, 4H), 2.46-2.54 (m, 4H), 2.79 (t, 2H), 3.86 (s, 3H), 4.17 (t, 2H), 6.92 (dd, 1H), 6.93 (d, 2H), 7.17 (d, 1H), 7.29 (d, 1H), 7.77 (d, 2H).

Preparation Example 67

(2-Bromo-4-methoxyphenyl)[3-fluoro-4-(2-piperidin-1-ylethoxy)phenyl]methanone

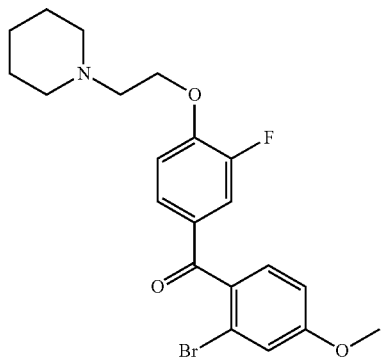 [SMILES: COc1ccc(C(=O)c2ccc(OCCN3CCCCC3)c(F)c2)c(Br)c1]

Synthesized from 3-bromoanisole (1.1 ml) and 3-fluoro-4-(2-piperidin-1-ylethoxy)benzoic acid hydrochloride (3.3 g) according to an analogous synthetic method to Preparation Example 66, the title compound (1.6 g) was obtained.

$^1$H-NMR (400 MHz, CDCl$_3$); δ (ppm): 1.41-1.49 (m, 2H), 1.56-1.64 (m, 4H), 2.48-2.56 (m, 4H), 2.84 (t, 2H), 3.87 (s, 3H), 4.24 (t, 2H), 6.93 (dd, 1H), 6.98 (t, 1H), 7.18 (d, 1H), 7.29 (d, 1H), 7.52 (ddd, 1H), 7.58 (dd, 1H).

Preparation Example 68

1-(4-Benzyloxybenzyl)-6-bromo-1H-pyridin-2-one

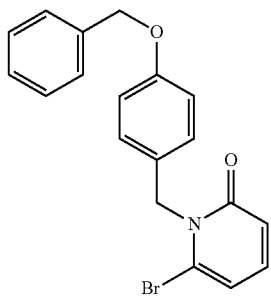 [SMILES: O=c1cccc(Br)n1Cc1ccc(OCc2ccccc2)cc1]

By referring to the synthetic method of *Synthesis*, 1974, 707, to a solution of 2,6-dibromopyridine (5.0 g) in tert-butanol (100 ml) was added potassium tert-butoxide (25 g), the solution was stirred overnight at 100° C., then ice was added to the reaction mixture, which was brought to pH 1 with 5N hydrochloric acid, then the solution was stirred overnight at room temperature. The solution was extracted with chloroform, then sequentially washed with water and brine, dried over anhydrous magnesium sulfate, then the solvent was evaporated in vacuo to provide 6-bromo-1H-pyridin-2-one (2.5 g). By referring to the synthetic method of *Tetrahedron Lett.*, 1995, 36, 8917, to a solution of 6-bromo-1H-pyridin-2-one (1.9 g) in 1,2-dimethoxyethane (27 ml) and N,N-dimethylformamide (3 ml) was added 60% sodium hydride (470 mg) on an ice bath under a nitrogen atmosphere, the solution was stirred for 15 minutes, then lithium bromide (3.85 g) was added thereto followed by stirring for 25 minutes at room temperature, 4-benzyloxybenzyl chloride (5.4 g) was added thereto followed by stirring overnight at 70° C. Water was added thereto followed by stirring, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (2.3 g).

$^1$H-NMR (400 MHz, CDCl$_3$); δ (ppm): 5.04 (s, 2H), 5.46 (s, 2H), 6.48 (dd, 1H), 6.56 (dd, 1H), 6.92 (d, 2H), 7.15 (dd, 1H), 7.29 (d, 2H), 7.30-7.43 (m, 5H).

Preparation Example 69

(6-Methoxy-3,4-dihydronaphthalen-2-yl)trimethyltin

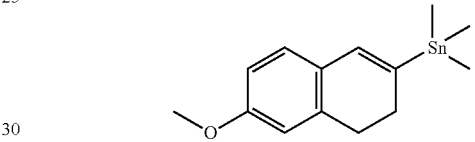

The title compound was synthesized by referring to *J. Org. Chem.*, 1986, 51, 277. 6-Methoxy-3,4-dihydronaphthalen-2-yl trifluoromethanesulfonate (1.5 g), bis(trimethyl)tin (1.7 g), tetrakis(triphenylphosphine)palladium(0) (170 mg) and lithium chloride (1.0 g) were dissolved in tetrahydrofuran (20 ml) under a nitrogen atmosphere and stirred for 1.5 hours at 60° C. A saturated aqueous solution of sodium bicarbonate was added thereto followed by stirring, the solution was extracted with ethyl acetate, then sequentially washed with water and brine, and the solvent was evaporated in vacuo to provide the title compound (1.6 g).

$^1$H-NMR (400 MHz, CDCl$_3$); δ (ppm): 0.18 (s, 9H), 2.30 (t, 2H), 2.72 (t, 2H), 3.79 (s, 3H), 6.58 (s, 1H), 6.66 (s, 1H), 6.69 (dd, 1H), 6.93 (d, 1H).

Example 1

[4-Methoxy-2-(6-methoxy-3,4-dihydronaphthalen-2-yl)phenyl][4-(2-piperidin-1-ylethoxy)phenyl]methanone

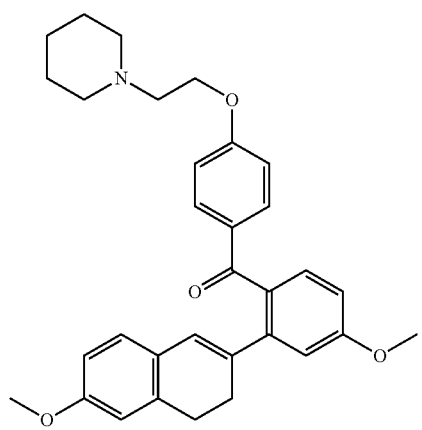

A suspension of (2-bromo-4-methoxyphenyl)[4-(2-piperidin-1-ylethoxy)phenyl]methanone (570 mg), (6-methoxy-3,4-dihydronaphthalen-2-yl)trimethyltin (542 mg), tetrakis(triphenylphosphine)palladium(0) (80 mg) and copper(I) iodide (25 mg) in toluene (10 ml) was stirred for 5 hours at 100° C. under a nitrogen atmosphere. Ethyl acetate was added thereto, the insoluble material was removed by filtration, the solvent was evaporated in vacuo, and the resulting residue was purified by NH silica gel column chromatography (hexane-ethyl acetate system) to provide the title compound (263 mg).

$^1$H-NMR (400 MHz, CDCl$_3$); δ (ppm): 1.41-1.49 (m, 2H), 1.55-1.64 (m, 4H), 2.39-2.55 (m, 8H), 2.74 (t, 2H), 3.76 (s, 3H), 3.89 (s, 3H), 4.10 (t, 2H), 6.37 (s, 1H), 6.58 (d, 1H), 6.63 (dd, 1H), 6.82 (d, 2H), 6.86-6.93 (m, 3H), 7.43 (d, 1H), 7.68 (d, 2H).

Example 2

6-{5-Hydroxy-2-[4-(2-piperidin-1-ylethoxy)benzyl]phenyl}-5,6,7,8-tetrahydronaphthalen-2-ol

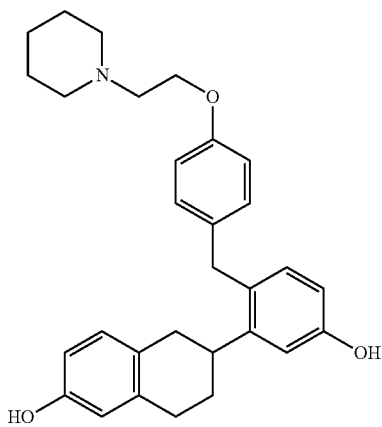 [SMILES: Oc1ccc2c(c1)CCC(c1cc(O)ccc1Cc1ccc(OCCN3CCCCC3)cc1)C2]

Synthesized from [4-methoxy-2-(6-methoxy-3,4-dihydronaphthalen-2-yl)phenyl][4-(2-piperidin-1-ylethoxy)phenyl]methanone according to an analogous synthetic method to Example 337 described below, 1-{2-{4-[4-methoxy-2-(6-methoxy-3,4-dihydronaphthalen-2-yl)benzyl]phenoxy}ethyl}piperidine (228 mg) was used according to an analogous synthetic method to Example 30 described below to provide 1-{2-{4-[4-methoxy-2-(6-methoxy-1,2,3,4-tetrahydronaphthalen-2-yl)benzyl]phenoxy}ethyl}piperidine (190 mg). This compound (188 mg) was used according to an analogous synthetic method to Example 364 described below to provide the title compound (104 mg).

$^1$H-NMR (400 MHz, DMSO-d$_6$); δ (ppm): 1.31-1.39 (m, 2H), 1.42-1.50 (m, 4H), 1.55-1.76 (m, 2H), 2.33-2.42 (m, 4H), 2.51-2.75 (m, 6H), 2.91-2.99 (m, 1H), 3.82 (dd, 2H), 3.96 (t, 2H), 6.42-6.48 (m, 2H), 6.54 (dd, 1H), 6.65 (d, 1H), 6.74 (d, 1H), 6.77 (d, 2H), 6.92-6.96 (m, 3H), 9.00 (s, 1H), 9.12 (s, 1H).

ESI-Mass; 458 [M$^+$+H]

Example 3

[4-Methoxy-2-(7-methoxy-3,4-dihydronaphthalen-2-yl)phenyl][4-(2-piperidin-1-ylethoxy)phenyl]methanone

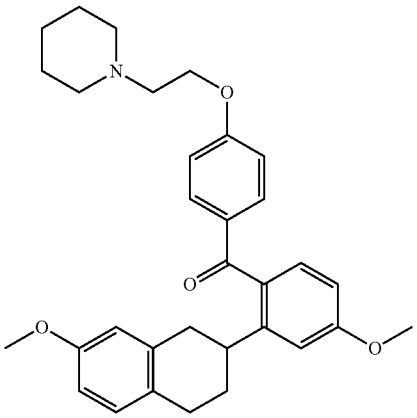

Synthesized from 7-methoxy-2-tetralone according to an analogous synthetic method to Preparation Example 82 described below, 7-methoxy-3,4-dihydronaphthalen-2-yl trifluoromethanesulfonate (400 mg) was used according to an analogous synthetic method to Preparation Example 69 to provide (7-methoxy-3,4-dihydronaphthalen-2-yl)trimethyltin (416 mg). Synthesized from the total amount of this compound and (2-bromo-4-methoxyphenyl)[4-(2-piperidin-1-ylethoxy)phenyl]methanone (420 mg) according to an analogous synthetic method to Example 1, the title compound (320 mg) was obtained.

$^1$H-NMR (400 MHz, CDCl$_3$); δ (ppm): 1.40-1.48 (m, 2H), 1.56-1.63 (m, 4H), 2.41-2.52 (m, 8H), 2.74 (t, 2H), 3.76 (s, 3H), 3.89 (s, 3H), 4.11 (t, 2H), 6.38 (s, 1H), 6.55 (d, 1H), 6.62 (dd, 1H), 6.83 (d, 2H), 6.88-6.93 (m, 3H), 7.43 (d, 1H), 7.69 (d, 2H).

Example 4

7-{5-Hydroxy-2-[4-(2-piperidin-1-ylethoxy)benzyl]phenyl}-5,6,7,8-tetrahydronaphthalen-2-ol

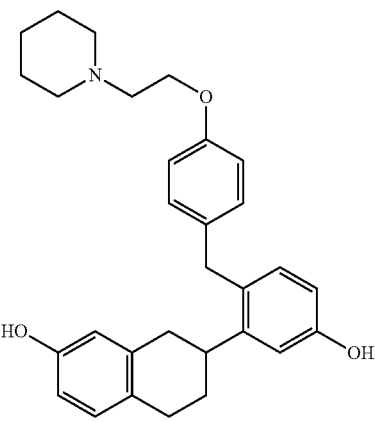 [SMILES: Oc1ccc2c(c1)CC(c1cc(O)ccc1Cc1ccc(OCCN3CCCCC3)cc1)CC2]

Synthesized from [4-methoxy-2-(7-methoxy-3,4-dihydronaphthalen-2-yl)phenyl][4-(2-piperidin-1-ylethoxy)phenyl]methanone according to an analogous synthetic method to Example 337 described below, the total amount of 1-{2-{4-[4-methoxy-2-(7-methoxy-3,4-dihydronaphthalen-2-yl)

benzyl]phenoxy}ethyl}piperidine (274 mg) was used according to an analogous synthetic method to Example 30 described below to provide 1-{2-{4-[4-methoxy-2-(7-methoxy-1,2,3,4-tetrahydronaphthalen-2-yl)benzyl]phenoxy}ethyl}piperidine (238 mg). This compound (236 mg) was used according to an analogous synthetic method to Example 111 described below to provide the title compound (75 mg).

$^1$H-NMR (400 MHz, DMSO-$d_6$); δ (ppm): 1.30-1.37 (m, 2H), 1.42-1.49 (m, 4H), 1.56-1.63 (m, 2H), 2.36-2.43 (m, 4H), 2.50-2.80 (m, 6H), 2.92-3.02 (m, 1H), 3.82 (dd, 2H), 3.96 (t, 2H), 6.44-6.95 (m, 10H), 8.99 (s, 1H), 9.12 (s, 1H).

ESI-Mass; 458 [M$^+$+H]

Example 5

[3-Fluoro-4-(2-piperidin-1-ylethoxy)phenyl][4-methoxy-2-(6-methoxy-3,4-dihydronaphthalen-2-yl)phenyl]methanone

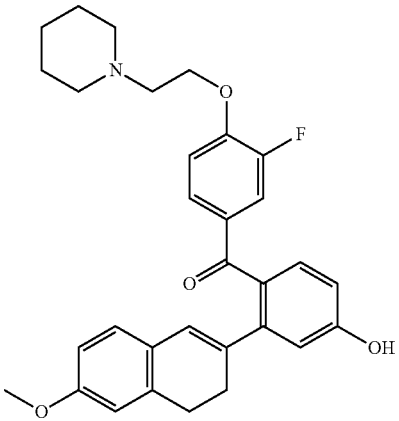 [SMILES: COc1ccc2c(c1)CCC(c1cc(O)ccc1C(=O)c1ccc(OCCN3CCCCC3)c(F)c1)=C2]

Synthesized from (2-bromo-4-methoxyphenyl)[3-fluoro-4-(2-piperidin-1-ylethoxy)phenyl]methanone (420 mg) and (6-methoxy-3,4-dihydronaphthalen-2-yl)trimethyltin (352 mg) according to an analogous synthetic method to Example 1, the title compound (295 mg) was obtained.

$^1$H-NMR (400 MHz, CDCl$_3$); δ (ppm): 1.40-1.48 (m, 2H), 1.55-1.64 (m, 4H), 2.41-2.58 (m, 8H), 2.77 (t, 2H), 3.77 (s, 3H), 3.89 (s, 3H), 4.16 (t, 2H), 6.34 (s, 1H), 6.59 (d, 1H), 6.63 (dd, 1H), 6.84-6.92 (m, 4H), 7.42-7.47 (m, 3H).

Example 6

6-{2-[3-Fluoro-4-(2-piperidin-1-ylethoxy)benzyl]-5-hydroxyphenyl}-5,6,7,8-tetrahydronaphthalen-2-ol

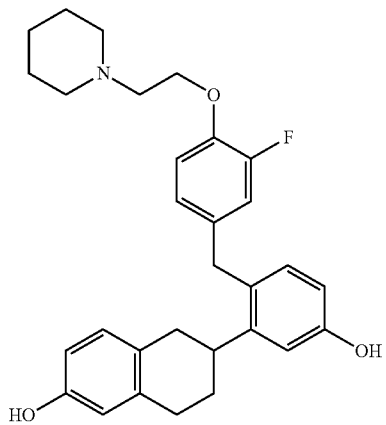 [SMILES: Oc1ccc2c(c1)CCC(c1cc(O)ccc1Cc1ccc(OCCN3CCCCC3)c(F)c1)C2]

Synthesized from [3-fluoro-4-(2-piperidin-1-ylethoxy)phenyl][4-methoxy-2-(6-methoxy-3,4-dihydronaphthalen-2-yl)phenyl]methanone according to an analogous synthetic method to Example 337 described below, 1-{2-{2-fluoro-4-[4-methoxy-2-(6-methoxy-3,4-dihydronaphthalen-2-yl)benzyl]phenoxy}ethyl}piperidine (228 mg) was used according to an analogous synthetic method to Example 30 described below to provide 1-{2-{2-fluoro-4-[4-methoxy-2-(6-methoxy-1,2,3,4-tetrahydronaphthalen-2-yl)benzyl]phenoxy}ethyl}piperidine (200 mg). This compound (197 mg) was used according to an analogous synthetic method to Example 111 described below to provide the title compound (180 mg).

$^1$H-NMR (400 MHz, DMSO-$d_6$); δ (ppm): 1.30-1.38 (m, 2H), 1.42-1.49 (m, 4H), 1.52-1.68 (m, 2H), 2.34-2.43 (m, 4H), 2.50-2.70 (m, 6H), 2.87-2.97 (m, 1H), 3.83 (dd, 2H), 4.05 (t, 2H), 6.42-6.48 (m, 2H), 6.55 (dd, 1H), 6.66 (d, 1H), 6.74 (d, 1H), 6.78 (d, 1H), 6.84 (dd, 1H), 6.95 (d, 1H), 7.02 (t, 1H), 9.00 (s, 1H), 9.16 (s, 1H).

ESI-Mass; 476 [M$^+$+H]

Preparation Example 70

(4-Nitrobenzyl) phenyl ether

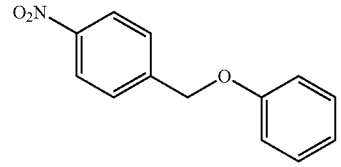 [SMILES: O=[N+]([O-])c1ccc(COc2ccccc2)cc1]

A mixture of phenol (11.3 g), 4-nitrobenzyl bromide (25.9 g), potassium carbonate (16.6 g) and methyl ethyl ketone (100 ml) was stirred for 15.5 hours at 80° C. Ethyl acetate was added thereto, the insoluble material was removed by filtration, the solvent was evaporated in vacuo, and the resulting residue was recrystallized from hexane-ethyl acetate to provide the title compound (pale yellow powder) (24.9 g).

$^1$H-NMR (400 MHz, CDCl$_3$); δ (ppm): 5.18 (s, 2H), 6.95-7.02 (m, 3H), 7.26-7.33 (m, 2H), 7.61 (d, 2H), 8.25 (d, 2H).

Preparation Example 71

(2-Bromo-5-methoxyphenyl)[4-(4-nitrobenzyloxy)phenyl]methanone

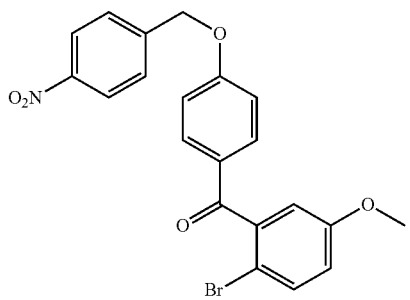 [SMILES: COc1ccc(Br)c(C(=O)c2ccc(OCc3ccc([N+](=O)[O-])cc3)cc2)c1]

A mixture of 2-bromo-5-methoxybenzoic acid (8.0 g) and thionyl chloride (20 ml) was refluxed for 2.5 hours, the reaction mixture was concentrated in vacuo. To a solution of the resulting 2-bromo-5-methoxybenzoyl chloride crude product in dichloromethane (50 ml) were sequentially added (4-nitrobenzyl) phenyl ether (8.0 g) and aluminum chloride (4.6 g), the solution was stirred for 13 hours at room temperature. To the reaction mixture was added ice, the solution was extracted with dichloromethane, then sequentially washed with water and brine, dried over anhydrous magnesium sulfate, then the solvent was evaporated in vacuo, the resulting crude crystal was washed with hexane-ethyl acetate to provide the title compound (light gray powder) (13.1 g).

$^1$H-NMR (400 MHz, CDCl$_3$); δ (ppm): 3.80 (s, 3H), 5.25 (s, 2H), 6.85 (d, 1H), 6.89 (dd, 1H), 7.01 (d, 2H), 7.50 (d, 1H), 7.61 (d, 2H), 7.82 (2H, d), 8.26 (2H, d)

Preparation Example 72

(4-Hydroxyphenyl)[5-methoxy-2-(6-methoxynaphthalen-2-yl)phenyl]methanone

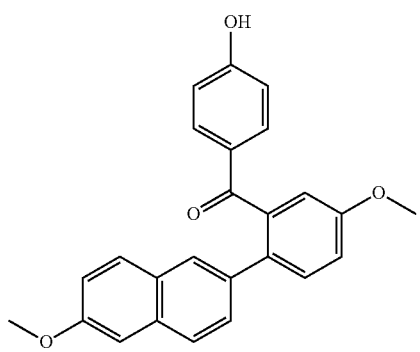

To a solution of (6-methoxynaphthalen-2-yl)boronic acid in diethyl ether (60 ml) was added 1,3-propanediol (2.3 ml), the solution was stirred for 15 minutes at room temperature, then ethyl acetate (70 ml) was added thereto followed by stirring for 10 minutes at room temperature. To the reaction mixture was added anhydrous magnesium sulfate, the solution was stirred, then insoluble material was removed by filtration, the solvent was evaporated in vacuo. To the total amount of the resulting 2-(6-methoxynaphthalen-2-yl)[1.3.2]dioxaborinane crude product were sequentially added (2-bromo-5-methoxyphenyl)[4-(4-nitrobenzyloxy)phenyl]methanone (6.9 g), cesium carbonate (10.2 g), N,N-dimethylformamide (80 ml) and tetrakis(triphenylphosphine)palladium(0) (900 mg), and the solution was stirred for 10.5 hours at 80° C. Ethyl acetate and water were added thereto, insoluble material was removed by filtration, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (brown foam) (4.1 g).

$^1$H-NMR (400 MHz, CDCl$_3$); δ (ppm): 3.87 (s, 6H), 5.69 (brs, 1H), 6.60 (d, 2H), 7.00-7.02 (m, 2H), 7.05-7.08 (m, 1H), 7.10-7.13 (m, 1H), 7.32 (d, 1H), 7.46-7.49 (m, 1H), 7.53 (d, 1H), 7.58-7.60 (m, 4H).

ESI-Mass; 385 [M$^+$+H]

Example 7

[5-Methoxy-2-(6-methoxynaphthalen-2-yl)phenyl][4-(2-piperidin-1-yl-ethoxy)phenyl]methanone

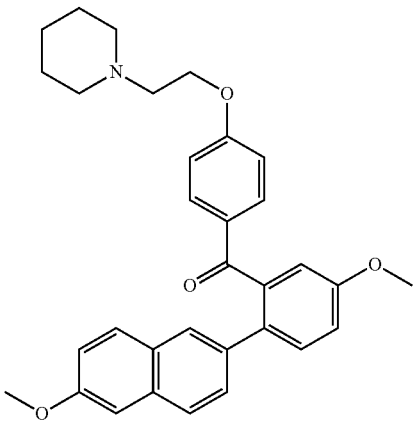

Synthesized from (4-hydroxyphenyl)[5-methoxy-2-(6-methoxynaphthalen-2-yl)phenyl]methanone (1.3 g) and 1-(2-chloroethyl)piperidine hydrochloride (970 mg) according to an analogous synthetic method to Example 383 described below, the title compound (yellow viscous oil) (1.4 g) was obtained.

$^1$H-NMR (400 MHz, CDCl$_3$); δ (ppm): 1.39-1.46 (m, 2H), 1.53-1.60 (m, 4H), 2.44 (brs, 4H), 2.68 (t, 2H), 3.88 (s, 6H), 4.02 (t, 2H), 6.69 (2H, d), 7.01-7.02 (m, 2H), 7.07 (dd, 1H), 7.12 (dd, 1H), 7.34 (dd, 1H), 7.48 (d, 1H), 7.54 (d, 1H), 7.60-7.65 (m, 4H).

Example 8

[5-Hydroxy-2-(6-hydroxynaphthalen-2-yl)phenyl][4-(2-piperidin-1-yl-ethoxy)phenyl]methanone

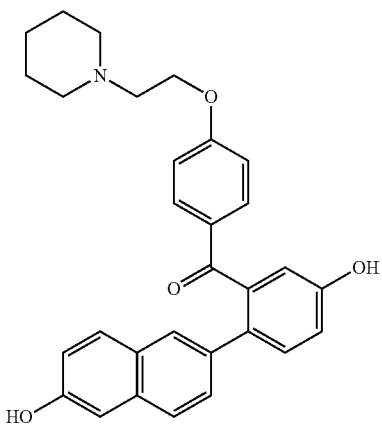 [SMILES: O=C(c1ccc(OCCN2CCCCC2)cc1)c1cc(O)ccc1-c1ccc2cc(O)ccc2c1]

Synthesized from [5-methoxy-2-(6-methoxynaphthalen-2-yl)phenyl][4-(2-piperidin-1-yl-ethoxy)phenyl]methanone (220 mg) according to an analogous synthetic method to Example 364 described below, the title compound (pale yellow foam) (80 mg) was obtained.

$^1$H-NMR (400 MHz, DMSO-d$_6$); δ (ppm): 1.34-1.38 (m, 2H), 1.42-1.48 (m, 4H), 2.37 (brs, 4H), 2.57 (t, 2H), 3.94 (t, 2H), 6.57 (d, 1H), 6.72-6.77 (m, 4H), 6.94 (dd, 1H), 7.07 (d, 2H), 7.17 (d, 1H), 7.57 (d, 1H), 7.62 (d, 1H), 7.76-7.84 (m, 2H), 9.48 (s, 1H), 9.67 (s, 1H)

Example 9

1-{2-{4-[5-Methoxy-2-(6-methoxynaphthalen-2-yl)benzyl]phenoxy}ethyl}piperidine

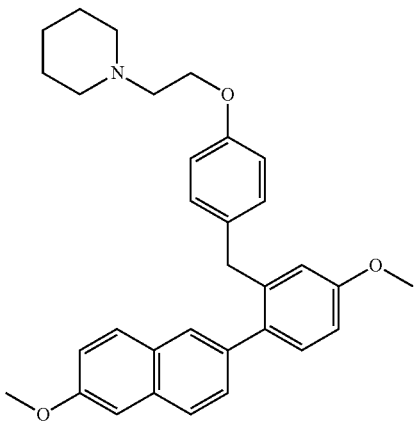

Synthesized from [5-methoxy-2-(6-methoxynaphthalen-2-yl)phenyl][4-(2-piperidin-1-yl-ethoxy)phenyl]methanone (530 mg) according to an analogous synthetic method to Example 337 described below, the title compound (colorless viscous oil) (230 mg) was obtained.

$^1$H-NMR (400 MHz, CDCl$_3$); δ (ppm): 1.40-1.46 (m, 2H), 1.57-1.62 (m, 4H), 2.48 (brs, 4H), 2.73 (t, 2H), 3.79 (s, 3H), 3.89 (s, 2H), 3.92 (s, 3H), 4.04 (t, 2H), 6.74 (d, 2H), 6.77 (d, 1H), 6.83 (dd, 1H), 6.89 (d, 2H), 7.13-7.16 (m, 2H), 7.25 (d, 1H), 7.33 (dd, 1H), 7.58 (d, 1H), 7.66 (d, 1H), 7.70 (d, 1H).

Example 10

6-{4-Hydroxy-2-{4-[2-(piperidin-1-yl)ethoxy]benzyl}phenyl}naphthalen-2-ol

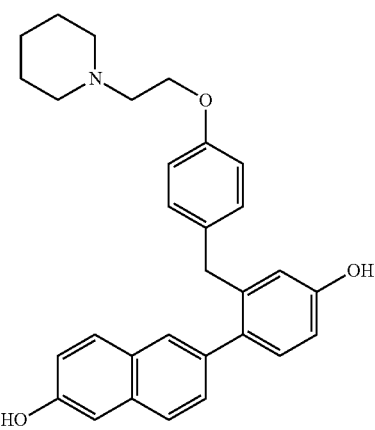 [SMILES: Oc1ccc(-c2ccc3cc(O)ccc3c2)c(Cc2ccc(OCCN3CCCCC3)cc2)c1]

Synthesized from 1-{2-{4-[5-methoxy-2-(6-methoxynaphthalen-2-yl)benzyl]phenoxy}ethyl}piperidine (220 mg) according to an analogous synthetic method to Example 364 described below, the title compound (pale yellow foam) (70 mg) was obtained.

$^1$H-NMR (400 MHz, DMSO-d$_6$); δ (ppm): 1.32-1.38 (m, 2H), 1.45-1.50 (m, 4H), 2.39 (m, 4H), 2.60 (t, 2H), 3.81 (s, 2H), 3.97 (t, 2H), 6.58 (d, 1H), 6.68 (dd, 1H), 6.78 (d, 2H), 6.88 (d, 2H), 7.08-7.14 (m, 3H), 7.29 (dd, 1H), 7.61 (brs, 1H), 7.67 (d, 1H), 7.71 (d, 1H), 9.36 (brs, 1H), 9.73 (brs, 1H).

Example 11

[4-(2-Diisopropylaminoethoxy)phenyl][5-methoxy-2-(6-methoxynaphthalen-2-yl)phenyl]methanone

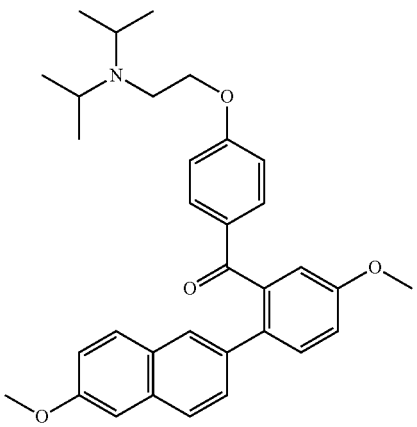

Synthesized from (4-hydroxyphenyl)[5-methoxy-2-(6-methoxynaphthalen-2-yl)phenyl]methanone (1.3 g) and (2-chloroethyl)diisopropylamine hydrochloride (787 mg) according to an analogous synthetic method to Preparation Example 40, the title compound (1.6 g) was obtained.

$^1$H-NMR (400 MHz, CDCl$_3$); δ (ppm): 0.98 (s, 6H), 0.99 (s, 6H), 2.73 (t, 2H), 2.95-3.03 (m, 2H), 3.82 (t, 2H), 3.88 (s, 3H), 6.65-6.70 (m, 2H), 7.01 (d, 1H), 7.07 (dd, 1H), 7.11 (dd, 1H), 7.34 (dd, 1H), 7.48 (d, 1H), 7.54 (d, 1H), 7.61 (d, 1H), 7.62-7.676 (m, 6H).

Example 12

6-{2-[4-(2-Diisopropylaminoethoxy)benzyl]-4-hydroxyphenyl}naphthalen-2-ol

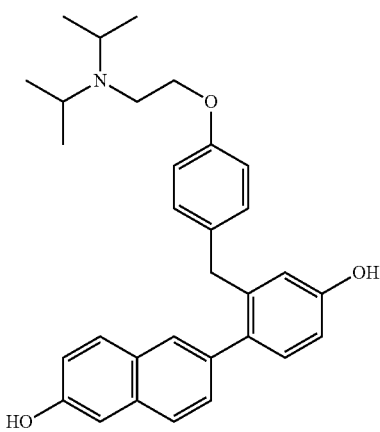 [SMILES: CC(C)N(CCOc1ccc(Cc2cc(O)ccc2-c2ccc3cc(O)ccc3c2)cc1)C(C)C]

Synthesized from [4-(2-diisopropylaminoethoxy)phenyl][5-methoxy-2-(6-methoxynaphthalen-2-yl)phenyl]methanone according to an analogous synthetic method to Example 337 described below, diisopropyl{2-{4-[5-methoxy-2-(6-methoxynaphthalen-2-yl)benzyl]phenoxy}ethyl}amine (398 mg) was used according to an analogous synthetic method to Example 111 described below to provide the title compound (80 mg).

¹H-NMR (400 MHz, CDCl₃); δ (ppm): 1.03 (s, 6H), 1.04 (s, 6H), 2.80 (t, 2H), 2.98-3.08 (m, 2H), 3.80 (s, 3H), 3.84 (s, 2H), 3.86 (t, 2H), 6.65 (d, 1H), 6.70-6.78 (m, 3H), 6.87-6.93 (m, 2H), 7.10 (dd, 1H), 7.16 (d, 1H), 7.19 (d, 1H), 7.33 (dd, 1H), 7.59 (s, 1H), 7.66 (dd, 1H).

ESI-Mass; 470 [M⁺+H]

Example 13

6-{2-[4-(2-Azepan-1-ylethoxy)benzyl]-4-hydroxyphenyl}naphthalen-2-ol

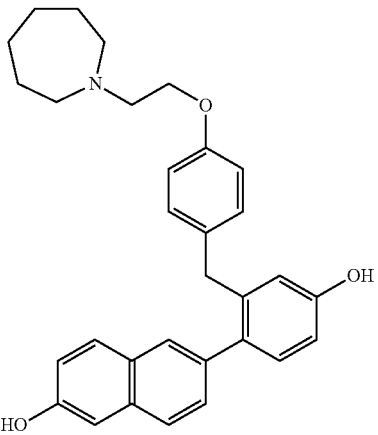 [SMILES: Oc1ccc(-c2ccc3cc(O)ccc3c2)c(Cc2ccc(OCCN3CCCCCC3)cc2)c1]

Synthesized from (4-hydroxyphenyl)[5-methoxy-2-(6-methoxynaphthalen-2-yl)phenyl]methanone and 1-(2-chloroethyl)azepane hydrochloride according to an analogous synthetic method to Preparation Example 40, [4-(2-azepan-1-ylethoxy)phenyl][5-methoxy-2-(6-methoxynaphthalen-2-yl)phenyl]methanone (1.0 g) was used according to an analogous synthetic method to Example 337 described below to provide 1-{2-{4-[5-methoxy-2-(6-methoxynaphthalen-2-yl)benzyl]phenoxy}ethyl}azepane (700 mg). This compound (421 mg) was used according to an analogous synthetic method to Example 111 described below to provide the title compound (105 mg).

¹H-NMR (400 MHz, CDCl₃); δ (ppm): 1.57-1.63 (s, 8H), 2.79 (t, 4H), 2.91 (t, 2H), 3.82 (s, 2H), 3.98 (t, 2H), 6.60 (d, 1H), 6.63-6.69 (m, 2H), 6.74 (dd, 1H), 6.83-6.89 (m, 2H), 7.08 (dd, 1H), 7.12-7.19 (m, 2H), 7.29 (dd, 1H), 7.57 (s, 2H), 7.62 (dd, 2H).

ESI-Mass; 468 [M⁺+H]

Example 14

[4-(2-Diisopropylaminoethoxy)phenyl][5-hydroxy-2-(6-hydroxynaphthalen-2-yl)phenyl]methanone

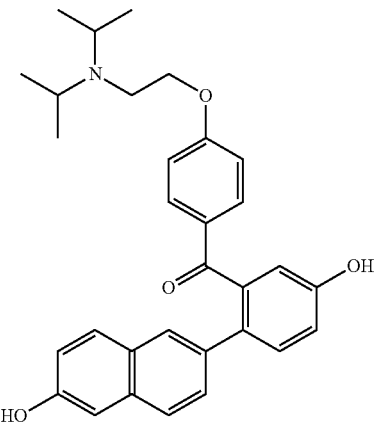 [SMILES: CC(C)N(CCOc1ccc(C(=O)c2cc(O)ccc2-c2ccc3cc(O)ccc3c2)cc1)C(C)C]

Synthesized from [4-(2-diisopropylaminoethoxy)phenyl][5-methoxy-2-(6-methoxynaphthalen-2-yl)phenyl]methanone (615 mg) according to an analogous synthetic method to Example 111 described below, the title compound (213 mg) was obtained.

¹H-NMR (400 MHz, CD₃OD); δ (ppm): 0.98 (s, 6H), 0.99 (s, 6H), 2.75 (t, 2H), 2.96-3.05 (m, 2H), 3.85 (t, 2H), 6.69-6.74 (m, 2H), 6.87 (d, 1H), 6.94-7.00 (m, 2H), 7.04 (dd, 1H), 7.22 (dd, 1H), 7.41 (dd, 1H), 7.49-7.60 (m, 4H).

ESI-Mass; 484 [M⁺+H]

Preparation Example 73

1-(4-Hydroxybenzyl)-6-(2-methoxy-8,9-dihydro-7H-benzocyclohepten-6-yl)-1H-pyridin-2-one

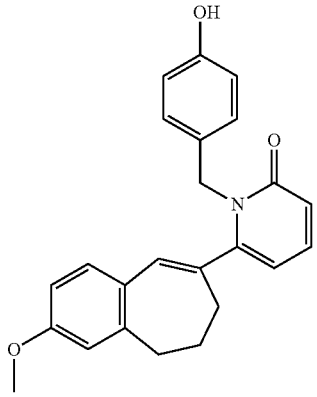 [SMILES: COc1ccc2c(c1)CCCC(c1cccc(=O)n1Cc1ccc(O)cc1)=C2]

Synthesized from 2-methoxy-8,9-dihydro-7H-benzocyclohepten-6-yl trifluoromethanesulfonate according to an analogous synthetic method to Preparation Example 69, (2-methoxy-8,9-dihydro-7H-benzocyclohepten-6-yl)trimethyltin (3.25 g) and 1-(4-benzyloxybenzyl)-6-bromo-1H-pyridin-2-one (2.2 g) were used according to an analogous synthetic method to Example 1 to provide 1-(4-benzyloxybenzyl)-6-(2-methoxy-8,9-dihydro-7H-benzocyclohepten-6-yl)-1H-pyridin-2-one (646 mg). The total amount of this compound was used according to an analogous synthetic method to Example 22 described below to provide the title compound (404 mg).

¹H-NMR (400 MHz, DMSO-d₆); δ (ppm): 1.80-1.88 (m, 2H), 2.20-2.27 (m, 2H), 2.72-2.78 (m, 2H), 3.73 (s, 3H), 5.08 (s, 2H), 6.14 (dd, 1H), 6.31 (s, 1H), 6.38 (dd, 1H), 6.58-6.74 (m, 4H), 6.85 (d, 2H), 6.96 (d, 1H), 7.40 (d, 1H), 9.28 (s, 1H).

Example 15

1-[4-(2-Azepan-1-ylethoxy)benzyl]-6-(2-hydroxy-8,9-dihydro-7H-benzocyclohepten-6-yl)-1H-pyridin-2-one

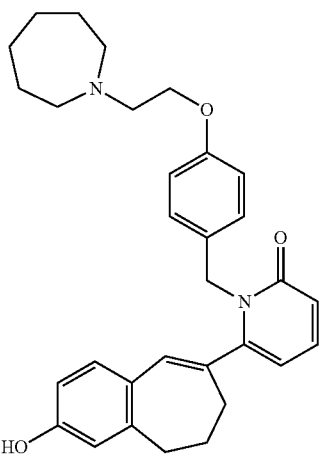 [SMILES: O=c1cccc(C2=Cc3ccc(O)cc3CCC2)n1Cc1ccc(OCCN2CCCCCC2)cc1]

Synthesized from 1-(4-hydroxybenzyl)-6-(2-methoxy-8,9-dihydro-7H-benzocyclohepten-6-yl)-1H-pyridin-2-one and 1-(2-chloroethyl)azepane according to an analogous synthetic method to Example 383 described below, 1-[4-(2-azepan-1-ylethoxy)benzyl]-6-(2-methoxy-8,9-dihydro-7H-benzocyclohepten-6-yl)-1H-pyridin-2-one (317 mg) was used according to an analogous synthetic method to Example 111 described below to provide the title compound (222 mg).

$^1$H-NMR (400 MHz, DMSO-$d_6$); δ (ppm): 1.47-1.58 (m, 8H), 1.79-1.88 (m, 2H), 2.20-2.27 (m, 2H), 2.61-2.64 (m, 4H), 2.65-2.70 (m, 2H), 2.78 (t, 2H), 3.95 (t, 2H), 5.11 (s, 2H), 6.13 (dd, 1H), 6.23 (s, 1H), 6.38 (dd, 1H), 6.52 (dd, 1H), 6.54 (d, 1H), 6.80 (d, 2H), 6.81 (d, 1H), 6.95 (d, 2H), 7.41 (d, 1H), 9.51 (s, 1H).

ESI-Mass; 485 [M$^+$+H]

Preparation Example 74

2-Tributylstannylbenzothiazole

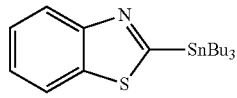

To a solution of benzothiazole (30.7 g) in tetrahydrofuran (700 ml), which was cooled at −78° C., was added dropwise n-butyllithium (2.5M solution in hexane) (100 ml) under a nitrogen atmosphere, the solution was stirred for 10 minutes at −78° C. Tributyltin chloride (77.9 g) was added dropwise thereto, the solution was stirred for 1.5 hours at −78° C., and then stirred for 2 hours while warming from −78° C. to room temperature. The reaction mixture was concentrated in vacuo, diethyl ether (400 ml) was added thereto, insoluble material was removed by filtration, and then the solvent was evaporated in vacuo. The residue was purified by distillation in vacuo (0.5 mmHg, 170 to 184° C.) to provide the title compound (73.0 g).

$^1$H-NMR (400 MHz, CDCl$_3$); δ (ppm): 0.90 (t, 9H), 1.27-1.41 (m, 12H), 1.58-1.67 (m, 6H), 7.37 (brt, 1H), 7.46 (brt, 1H), 7.96 (brd, 1H), 8.17 (brd, 1H).

Example 16

N-(2-Benzothiazol-2-yl-5-methoxyphenyl)-3-fluoro-4-(2-piperidin-1-ylethoxy)benzamide

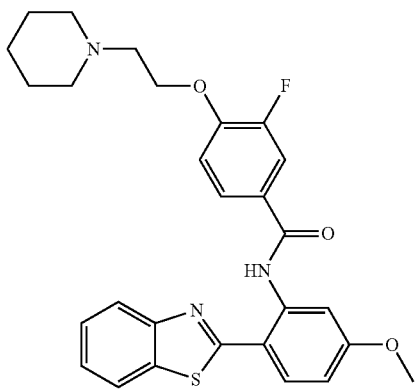 [SMILES: COc1ccc(-c2nc3ccccc3s2)c(NC(=O)c2ccc(OCCN3CCCCC3)c(F)c2)c1]

A mixture of N-(2-bromo-5-methoxyphenyl)-3-fluoro-4-(2-piperidin-1-ylethoxy)benzamide (1.0 g), dichlorobis(triphenylphosphine)palladium(II) (150 mg), xylene (30 ml) and 2-tributylstannylbenzothiazole (1.9 g) was refluxed for 2 hours. The reaction mixture was concentrated in vacuo and the resulting residue was purified by NH silica gel column chromatography (hexane-ethyl acetate system) to provide the title compound (810 mg).

$^1$H-NMR (400 MHz, CDCl$_3$); δ (ppm): 1.42-1.53 (m, 2H), 1.60-1.71 (m, 4H), 2.51-2.68 (m, 4H), 2.91 (t, 2H), 3.96 (s, 3H), 4.32 (t, 2H), 6.72 (d, 1H), 7.11 (t, 1H), 7.40 (t, 1H), 7.51 (t, 1H), 7.75 (d, 1H), 7.86 (d, 1H), 7.99 (d, 2H), 8.02 (d, 1H), 8.64 (s, 1H), 13.46 (s, 1H).

Example 17

(2-Benzothiazol-2-yl-5-methoxyphenyl)[3-fluoro-4-(2-piperidin-1-ylethoxy)benzyl]amine

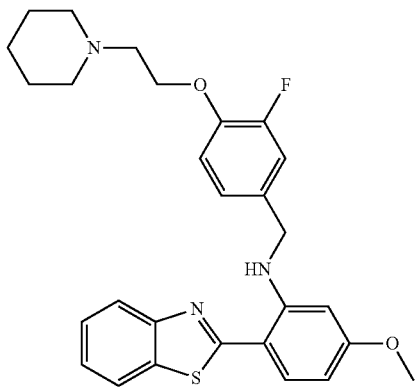 [SMILES: COc1ccc(-c2nc3ccccc3s2)c(NCc2ccc(OCCN3CCCCC3)c(F)c2)c1]

To a suspension of lithium aluminum hydride (90 mg) in tetrahydrofuran (5 ml) was added dropwise a solution of N-(2-benzothiazol-2-yl-5-methoxyphenyl)-3-fluoro-4-(2-piperidin-1-ylethoxy)benzamide (300 mg) in tetrahydrofuran (1 ml) on an ice bath, and the solution was stirred for 4 hours at room temperature. To the reaction mixture were sequentially added tetrahydrofuran (10 ml), water (0.14 ml), an aqueous solution of 5N sodium hydroxide (0.14 ml) and water (0.42 ml) on an ice bath, the resulting suspension was filtered, and the filtrate was concentrated in vacuo. The residue was purified by NH silica gel column chromatography (hexane-chloroform system) to provide the title compound (120 mg).

$^1$H-NMR (400 MHz, CDCl$_3$); δ (ppm): 1.41-1.50 (m, 2H), 1.59-1.66 (m, 4H), 2.50-2.60 (m, 4H), 2.81 (t, 2H), 3.88 (s, 3H), 4.18 (t, 2H), 4.49 (d, 2H), 6.17 (s, 1H), 6.30 (d, 1H), 6.97 (t, 1H), 7.10 (d, 1H), 7.19 (d, 1H), 7.30 (t, 1H), 7.41 (t, 1H), 7.62 (d, 1H), 7.81 (d, 2H), 9.53 (t, 1H).

Example 18

4-Benzothiazol-2-yl-3-[3-fluoro-4-(2-piperidin-1-ylethoxy)benzylamino]phenol

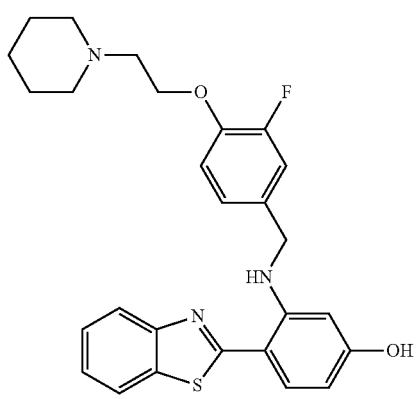 [SMILES: Oc1ccc(-c2nc3ccccc3s2)c(NCc2ccc(OCCN3CCCCC3)c(F)c2)c1]

Synthesized from (2-benzothiazol-2-yl-5-methoxyphenyl)[3-fluoro-4-(2-piperidin-1-ylethoxy)benzyl]amine (120 mg) according to an analogous synthetic method to Example 364 described below, the title compound (23 mg) was obtained.

¹H-NMR (400 MHz, DMSO-d₆); δ (ppm): 1.30-1.50 (m, 2H), 1.52-1.75 (m, 4H), 2.45-2.59 (m, 4H), 3.16-3.35 (m, 2H), 4.30-4.39 (m, 2H), 4.47 (d, 2H), 6.07 (s, 1H), 6.18 (d, 1H), 7.11-7.28 (m, 3H), 7.36 (t, 1H), 7.45 (t, 1H), 7.54 (d, 1H), 7.84 (d, 1H), 8.02 (d, 1H), 9.40 (t, 1H), 9.93 (s, 1H).
ESI-Mass; 478 [M⁺+H]

Example 19

N-(2-Benzothiazol-2-yl-5-hydroxyphenyl)-N-[3-fluoro-4-(2-piperidin-1-ylethoxy)benzyl]acetamide

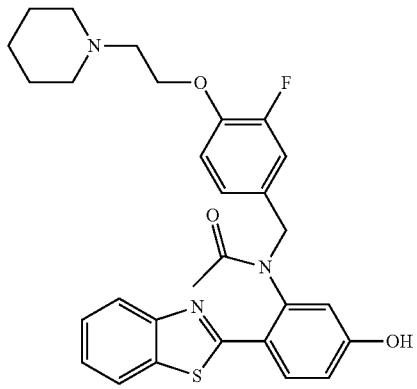 [SMILES: CC(=O)N(Cc1ccc(OCCN2CCCCC2)c(F)c1)c1cc(O)ccc1-c1nc2ccccc2s1]

A mixture of acetic acid 3-{acetyl-[3-fluoro-4-(2-piperidin-1-ylethoxy)benzyl]amino}-4-bromophenyl ester (50 mg) and dichlorobis(triphenylphosphine)palladium (II) (7 mg), xylene (1 ml) and 2-tributylstannylbenzothiazole (84 mg) was refluxed for 1.5 hours. The reaction mixture was cooled at room temperature, methanol (2 ml), water (1 ml) and potassium carbonate (50 mg) was added thereto, and the solution was vigourously stirred for 15 minutes at room temperature. The reaction mixture was diluted with water, extracted with ethyl acetate, then dried over anhydrous magnesium sulfate, and the solvent was evaporated in vacuo. The residue was purified by NH silica gel column chromatography (ethyl acetate-methanol system) to provide the title compound (20 mg).
¹H-NMR (400 MHz, CDCl₃); δ (ppm): 1.45-1.53 (m, 2H), 1.60-1.70 (m, 4H), 1.87 (s, 3H), 2.55-2.70 (m, 4H), 2.80-2.88 (m, 2H), 3.67 (d, 1H), 4.17 (t, 2H), 5.73 (d, 1H), 6.11 (s, 1H), 6.76 (t, 1H), 6.85 (d, 1H), 6.95 (d, 1H), 7.01 (d, 1H), 7.38 (t, 1H), 7.49 (t, 1H), 7.89 (d, 1H), 8.05 (d, 1H), 8.28 (d, 1H).
ESI-Mass; 520 [M⁺+H]

Example 20

4-Benzothiazol-2-yl-3-{ethyl[3-fluoro-4-(2-piperidin-1-ylethoxy)benzyl]amino}phenol

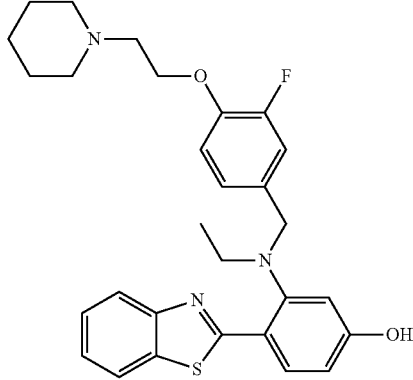 [SMILES: CCN(Cc1ccc(OCCN2CCCCC2)c(F)c1)c1cc(O)ccc1-c1nc2ccccc2s1]

Synthesized from acetic acid 4-bromo-3-{ethyl[3-fluoro-4-(2-piperidin-1-ylethoxy)benzyl]amino}phenyl ester (50 mg) and 2-tributylstannylbenzothiazole (100 mg) according to an analogous synthetic method to Example 19, the title compound (3 mg) was obtained.
¹H-NMR (400 MHz, CDCl₃); δ (ppm): 1.04 (t, 3H), 1.45-1.57 (m, 2H), 1.71-1.80 (m, 4H), 2.75-2.80 (m, 4H), 2.95-3.05 (m, 4H), 4.00 (s, 2H), 4.20 (t, 2H), 6.40 (s, 1H), 6.60-6.72 (m, 3H), 6.91 (d, 1H), 7.33 (t, 1H), 7.43 (t, 1H), 7.88 (d, 1H), 7.98 (d, 1H), 8.17 (d, 1H).
ESI-Mass; 506 [M⁺+H]

Preparation Example 75

7-Methoxy-2,3,4,5-tetrahydro-1H-benzo[d]azepine

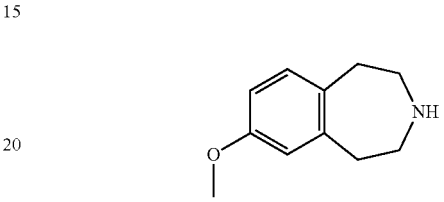

The title compound was synthesized by referring to the synthetic method of EP285287. To a solution of (3-methoxyphenyl)acetic acid (16 g) in tetrahydrofuran (150 ml) were sequentially added N,N-dimethylformamide (0.1 ml) and oxalyl chloride (10 ml) under a nitrogen atmosphere, the solution was stirred for 5 hours at room temperature, and then the reaction mixture was concentrated in vacuo to provide (3-methoxyphenyl)acetyl chloride (18.8 g). To a solution of aminoacetaldehyde dimethylacetal (11 g) and triethylamine (11 g) in chloroform (150 ml) was added (3-methoxyphenyl)acetyl chloride (18.8 g) on an ice bath, and the solution was stirred for 9.5 hours at room temperature. Water was added thereto, the solution was stirred, extracted with ethyl acetate, then sequentially washed with water and brine, and the solvent was evaporated in vacuo. Obtained by purifying the residue by NH silica gel column chromatography (hexane-ethyl acetate system), a solution of N-(2,2-dimethoxyethyl)-2-(3-methoxyphenyl)acetamide (24.9 g) in acetic acid (75 ml) was added dropwise to concentrated hydrochloric acid (50 ml), and the solution was stirred overnight at room temperature. The reaction mixture was poured into an ice water, ethyl acetate and tetrahydrofuran were sequentially added thereto, insoluble material was removed by filtration, then the filtrate was concentrated in vacuo. To the residue was added water, the resulting solid was filtered and collected. To a solution of the resulting 8-methoxy-1,3-dihydrobenz[d]azepin-2-one (6.3 g) in acetic acid (100 ml) was added 10% palladium-activated charcoal (1.5 g), and the solution was stirred for 23 hours at room temperature under a hydrogen atmosphere at 4 atmospheric pressures. After filtration through celite pad, the solvent was evaporated in vacuo, was neutralized by sequentially adding water and aqueous ammonia. The resulting solid was filtered to provide 8-methoxy-1,3,4,5-tetrahydrobenz[d]azepin-2-one (5.6 g). To a suspension of this compound (1.5 g) in tetrahydrofuran (15 ml) was added dropwise borane-tetrahydrofuran complex (1.0 M solution in tetrahydrofuran) (15 ml), and the solution was refluxed for 2 hours. 5N hydrochloric acid (5 ml) was added thereto on an ice bath, the solution was refluxed for 45 minutes, and then neutralized with aqueous ammonia. The solution was extracted with ethyl acetate, then sequentially washed with water and brine, and the solvent was evaporated in vacuo. The residue was purified by NH silica gel column chromatography (hexane-ethyl acetate system) to provide the title compound (752 mg).
¹H-NMR (400 MHz, CDCl₃); δ (ppm): 2.84-2.98 (m, 8H), 3.78 (s, 3H), 6.64 (dd, 1H), 6.67 (d, 1H), 7.01 (d, 1H).

Example 21

3-{5-Hydroxy-2-[4-(2-piperidin-1-ylethoxy)benzyl]phenyl}-2,3,4,5-tetrahydro-1H-benz[d]azepin-7-ol

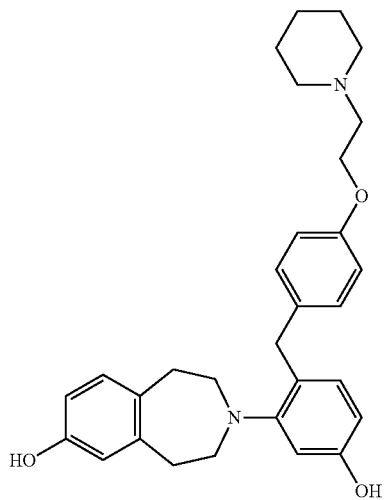 [SMILES: Oc1ccc2c(c1)CCN(c1cc(O)ccc1Cc1ccc(OCCN3CCCCC3)cc1)CC2]

Synthesized from 7-methoxy-2,3,4,5-tetrahydro-1H-benz[d]azepine and (2-bromo-4-methoxyphenyl)[4-(2-piperidin-1-ylethoxy)phenyl]methanone according to an analogous synthetic method to Example 116 described below, [4-methoxy-2-(7-methoxy-1,2,4,5-tetrahydrobenz[d]azepin-3-yl)phenyl][4-(2-piperidin-1-ylethoxy)phenyl]methanone (632 mg) was used according to an analogous synthetic method to Example 337 described below to provide 7-methoxy-3-{5-methoxy-2-[4-(2-piperidin-1-ylethoxy)benzyl]phenyl}-2,3,4,5-tetrahydro-1H-benz[d]azepine (514 mg). The total amount of this compound was used according to an analogous synthetic method to Example 111 described below to provide the title compound (355 mg).

$^1$H-NMR (400 MHz, DMSO-$d_6$); δ (ppm): 1.30-1.38 (m, 2H), 1.41-1.50 (m, 4H), 2.33-2.43 (m, 4H), 2.59 (t, 2H), 2.72-2.83 (m, 8H), 3.87 (s, 2H), 3.98 (t, 2H), 6.39 (dd, 1H), 6.41 (d, 1H), 6.47 (dd, 1H), 6.53 (d, 1H), 6.81 (d, 2H), 6.85 (d, 1H), 6.88 (d, 1H), 7.08 (d, 2H), 9.09 (s, 2H).

ESI-Mass; 473 [M$^+$+H]

Preparation Example 76

Tributyl(4-methoxy-2-nitrophenyl)tin

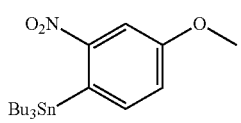

A suspension of 4-bromo-3-nitroanisole (11.6 g), hexabutylditin (32 g) and tetrakis(triphenylphosphine)palladium(0) (1.2 g) in xylene (100 ml) was stirred for 1 hour at 140° C. The solvent was evaporated in vacuo, and the residue was purified by silica gel column chromatography (hexane-ethyl acetate system) to provide the title compound (12.7 g).

$^1$H-NMR (400 MHz, CDCl$_3$); δ (ppm): 0.87 (t, 9H), 1.07-1.12 (m, 6H), 1.26-1.35 (m, 6H), 1.44-1.50 (m, 6H), 3.89 (s, 3H), 7.19 (dd, 1H), 7.54 (d, 1H), 7.84 (d, 1H).

Preparation Example 77

2-Methoxy-6-(4-methoxy-2-nitrophenyl)naphthalene

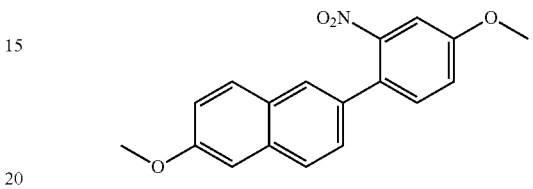

The title compound was synthesized by referring to *J. Am. Chem. Soc.*, 1999, 121, 760. A suspension of 6-methoxy-2-bromonaphthalene (500 mg), tributyl(4-methoxy-2-nitrophenyl)tin (1.1 g), tetrakis(triphenylphosphine)palladium(0) (250 mg), copper(I) chloride (1.0 g) and lithium chloride (540 mg) in dimethylsulfoxide (15 ml) was stirred at 60° C. for 5 hours under a nitrogen atmosphere. Ethyl acetate and aqueous ammonia were sequentially added thereto, the solution was filtered through celite pad, extracted with ethyl acetate, then sequentially washed with water and brine, dried over anhydrous magnesium sulfate, and then the solvent was evaporated in vacuo. The residue was washed with a hexane-diethyl ether system to provide the title compound (412 mg).

$^1$H-NMR (400 MHz, CDCl$_3$); δ (ppm): 3.92 (s, 3H), 3.94 (s, 3H), 7.16-7.20 (m, 3H), 7.33 (dd, 1H), 7.41 (d, 1H), 7.44 (d, 1H), 7.70 (s, 1H), 7.74 (d, 1H), 7.76 (d, 1H).

Example 22

5-Methoxy-2-(6-methoxynaphthalen-2-yl)phenylamine

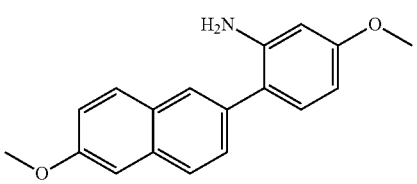

To a solution of 2-methoxy-6-(4-methoxy-2-nitrophenyl)naphthalene (390 mg) in tetrahydrofuran (6 ml) and methanol (6 ml) was added 10% palladium-activated charcoal (100 mg), and the solution was stirred overnight at room temperature under a hydrogen atmosphere at ambient pressure. After filtration through celite pad, the solvent was evaporated in vacuo, and the resulting solid was washed with a hexane-diethyl ether system to provide the title compound (285 mg).

$^1$H-NMR (400 MHz, CDCl$_3$); δ (ppm): 3.83 (s, 5H), 3.95 (s, 3H), 6.38 (dd, 1H), 6.46 (dd, 1H), 7.14-7.20 (m, 3H), 7.54 (dd, 1H), 7.75-7.82 (m, 3H).

Preparation Example 78

(6-Methoxynaphthalen-2-yl)boronic acid

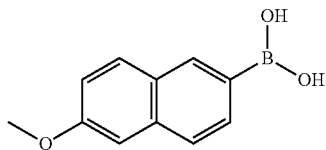

A solution of 6-methoxy-2-bromonaphthalene (25 g) in tetrahydrofuran (300 ml) was cooled at −78° C. under a nitrogen atmosphere. n-Butyllithium (2.66 M solution in hexane) (42 ml) was added dropwise thereto over 1.5 hours, and the solution was stirred for 30 minutes. Triisopropyl borate (26.5 ml) was added dropwise thereto for 30 minutes, then the solution was stirred for 40 minutes while warming from −78° C. to 0° C. 1N hydrochloric acid (200 ml) and ethyl acetate (200 ml) were sequentially added thereto, the solution was stirred, extracted with ethyl acetate, then washed with brine, dried over anhydrous magnesium sulfate, then the solvent was evaporated in vacuo, the resulting solid was washed with a hexane-diethyl ether system to provide the title compound (18 g).

$^1$H-NMR (400 MHz, DMSO-$d_6$); δ (ppm): 3.86 (s, 3H), 7.12 (d, 1H), 7.26 (s, 1H), 7.72 (d, 1H), 7.76-7.84 (m, 2H), 8.07 (brs, 2H), 8.27 (s, 1H).

Preparation Example 79

2-Methoxy-6-(2-nitrophenyl)naphthalene

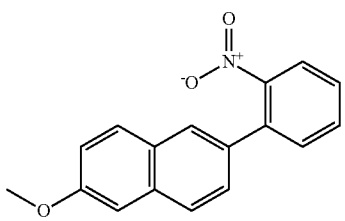

To a suspension of 2-iodo-1-nitrobenzene (2.5 g), (6-methoxynaphthalen-2-yl)boronic acid (2.9 g) and tetrakis(triphenylphosphine)palladium(0) (600 mg) in toluene (50 ml) was added an aqueous solution of 2N sodium carbonate (15 ml) under a nitrogen atmosphere, and the solution was stirred for 7 hours at 110° C. Ethyl acetate was added thereto, the solution was filtered through celite pad, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (1.2 g).

$^1$H-NMR (400 MHz, CDCl$_3$); δ (ppm): 3.95 (s, 3H), 7.16-7.21 (m, 2H), 7.37 (dd, 1H), 7.50 (ddd, 1H), 7.54 (dd, 1H), 7.64 (dt, 1H), 7.74-7.79 (m, 3H), 7.89 (dd, 1H).

Example 23

2-(6-Methoxynaphthalen-2-yl)phenylamine

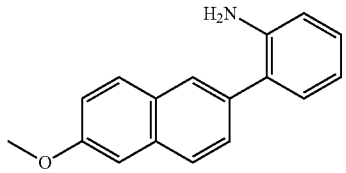 [SMILES: COc1ccc2cc(-c3ccccc3N)ccc2c1]

Synthesized from 2-methoxy-6-(2-nitrophenyl)naphthalene (1.6 g) according to an analogous synthetic method to Example 63 described below, the title compound (1.1 g) was obtained.

$^1$H-NMR (400 MHz, CDCl$_3$); δ (ppm): 3.80 (brs, 2H), 3.95 (s, 3H), 6.81 (d, 1H), 6.86 (dt, 1H), 7.16-7.23 (m, 4H), 7.55 (dd, 1H), 7.76 (d, 1H), 7.81 (d, 1H), 7.85 (s, 1H).

Example 24

5-Fluoro-2-(6-methoxynaphthalen-2-yl)phenylamine

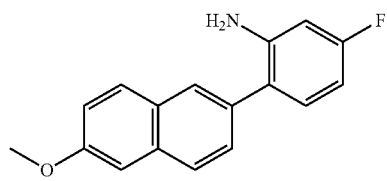 [SMILES: COc1ccc2cc(-c3ccc(F)cc3N)ccc2c1]

Synthesized from 4-fluoro-2-nitrophenol (3.0 g) according to an analogous synthetic method to Preparation Example 80 described below, 4-fluoro-2-nitrophenyl trifluoromethanesulfonate (5.5 g) was obtained. To a suspension of (6-methoxynaphthalen-2-yl)boronic acid (2.5 g) in diethyl ether (60 ml) was added 1,3-propanediol (0.9 ml), and the solution was stirred for 2 hours at room temperature. Tetrahydrofuran and anhydrous magnesium sulfate were sequentially added thereto, the solution was stirred, then filtered, and the filtrate was concentrated in vacuo. To a solution of the resulting 2-(6-methoxynaphthalen-2-yl)-[1,3,2]dioxaborinane (3.1 and 4-fluoro-2-nitrophenyl trifluoromethanesulfonate (2.8 g) in N,N-dimethylformamide (50 ml) were added tetrakis(triphenylphosphine)palladium(0) (350 mg) and cesium carbonate (6.0 g), and the solution was stirred for 2 hours at 100° C. under a nitrogen atmosphere. Ethyl acetate and tetrahydrofuran were sequentially added thereto, the solution was stirred, then insoluble material was removed by filtration, the solution was extracted with ethyl acetate, then sequentially washed with water and brine, dried over anhydrous magnesium sulfate, then the solvent was evaporated in vacuo, the resulting solid was washed with a hexane-diethyl ether system to provide 2-(4-fluoro-2-nitrophenyl)-6-methoxy-1,2,3,4-tetrahydronaphthalene (2.4 g). The total amount of this compound was used according to an analogous synthetic method to Example 22 to provide the title compound (1.6 g).

$^1$H-NMR (400 MHz, CDCl$_3$); δ (ppm): 3.90 (brs, 2H), 3.95 (s, 3H), 6.50 (dd, 1H), 6.54 (dt, 1H), 7.14 (dd, 1H), 7.16-7.20 (m, 2H), 7.49 (dd, 1H), 7.75 (d, 1H), 7.78-7.82 (m, 2H).

143

Preparation Example 80

5-Fluoro-2-nitrophenyl trifluoromethanesulfonate

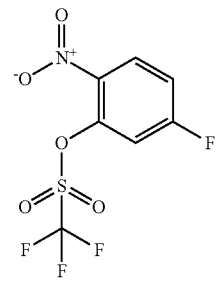

To a solution of 5-fluoro-2-nitrophenol (3.0 g) in dichloromethane (50 ml) was added pyridine (5 ml), and trifluoromethanesulfonic anhydride (3.5 ml) was then added dropwise thereto on an ice bath. The solution was stirred overnight at room temperature, then water was added thereto, the solution was stirred, extracted with ethyl acetate, then sequentially washed with water and brine, dried over anhydrous magnesium sulfate, and then the solvent was evaporated in vacuo to provide the title compound (5.4 g).

$^1$H-NMR (400 MHz, CDCl$_3$); δ (ppm): 7.21 (dd, 1H), 7.30 (ddd, 1H), 8.28 (dd, 1H).

Example 25

4-Fluoro-2-(6-methoxynaphthalen-2-yl)phenylamine

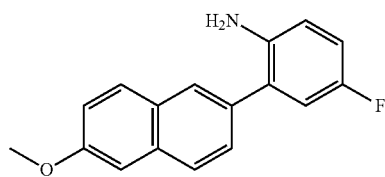 [SMILES: COc1ccc2cc(-c3cc(F)ccc3N)ccc2c1]

Synthesized from (6-methoxynaphthalen-2-yl)boronic acid and 5-fluoro-2-nitrophenyl trifluoromethanesulfonate according to an analogous synthetic method to Example 24, 2-(5-fluoro-2-nitrophenyl)-6-methoxy-1,2,3,4-tetrahydronaphthalene (1.3 g) was used according to an analogous synthetic method to Example 22 to provide the title compound (1.1 g).

$^1$H-NMR (400 MHz, CDCl$_3$); δ (ppm): 3.95 (s, 5H), 6.73 (dd, 1H), 6.89 (dt, 1H), 6.96 (dd, 1H), 7.17-7.21 (m, 2H), 7.52 (dd, 1H), 7.76 (d, 1H), 7.81-7.84 (m, 2H).

Example 26

5-Methoxy-(2-naphthalen-2-yl)phenylamine

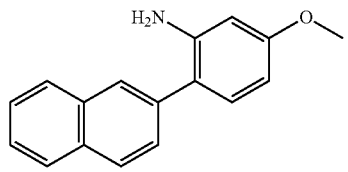 [SMILES: COc1ccc(-c2ccc3ccccc3c2)c(N)c1]

144

Synthesized from 2-naphthylboronic acid and 4-bromo-3-nitroanisole according to an analogous synthetic method to Preparation Example 79, 2-(4-methoxy-2-nitrophenyl)naphthalene (2.3 g) was used according to an analogous synthetic method to Example 22 to provide the title compound (1.4 g).

$^1$H-NMR (400 MHz, CDCl$_3$); δ (ppm): 3.82 (s, 5H), 6.37 (d, 1H), 6.45 (dd, 1H), 7.15 (d, 1H), 7.46-7.53 (m, 2H), 7.57 (dd, 1H), 7.82-7.92 (m, 4H).

Preparation Example 81

4-Bromo-3-nitropyridine

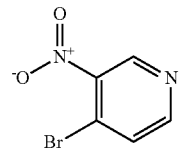

To 4-methoxy-3-nitropyridine (3.5 g) was added 48% hydrobromic acid (30 ml), and the solution was stirred overnight at 80° C. Toluene was added thereto followed by stirring. The solvent was evaporated in vacuo. To the total amount of the resulting 3-nitropyridin-4-ol (crude product) were added phosphorous oxybromide (20 g) and chloroform (30 ml), and the solution was stirred for 2 hours at 110° C. To the reaction mixture was added an ice, the solution was neutralized with aqueous ammonia, extracted with ethyl acetate, then sequentially washed with water and brine, dried over anhydrous magnesium sulfate, then filtered through silica gel, and the solvent was evaporated in vacuo to provide the title compound (2.6 g).

$^1$H-NMR (400 MHz, CDCl$_3$); δ (ppm): 7.74 (d, 1H), 8.58 (d, 1H), 9.08 (s, 1H).

Example 27

4-(6-Methoxynaphthalen-2-yl)pyridin-3-ylamine

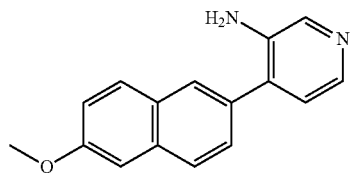 [SMILES: COc1ccc2cc(-c3ccncc3N)ccc2c1]

Synthesized from (6-methoxynaphthalen-2-yl)boronic acid and 4-bromo-3-nitropyridine according to an analogous synthetic method to Preparation Example 79, 4-(6-methoxynaphthalen-2-yl)-3-nitropyridine (2.1 g) was used according to an analogous synthetic method to Example 22 to provide the title compound (1.7 g).

$^1$H-NMR (400 MHz, CDCl$_3$); δ (ppm): 3.85 (brs, 2H), 3.96 (s, 3H), 7.12 (d, 1H), 7.19 (d, 1H), 7.22 (dd, 1H), 7.54 (dd, 1H), 7.78 (d, 1H), 7.85 (d, 1H), 7.87 (s, 1H), 8.10 (d, 1H), 8.19 (s, 1H).

Preparation Example 82

6-Methoxy-3,4-dihydronaphthalen-2-yl trifluoromethanesulfonate

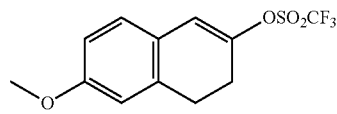

To a solution of 6-methoxy-2-tetralone (2.0 g) in tetrahydrofuran (30 ml), which was cooled at −78° C., was added dropwise lithium hexamethyldisilazide (1.0 M solution in tetrahydrofuran) (12.5 ml) under a nitrogen atmosphere, the solution was stirred for 30 minutes, then N-phenyltrifluoromethanesulfonimide (4.3 g) was added thereto, and the solution was stirred for 30 minutes while warming from −78° C. to room temperature. A saturated aqueous solution of ammonium chloride was added thereto, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (2.7 g).

$^1$H-NMR (400 MHz, CDCl$_3$); δ (ppm): 2.67 (t, 2H), 3.04 (t, 2H), 3.81 (s, 3H), 6.44 (s, 1H), 6.70-6.74 (m, 2H), 7.01 (d, 1H).

Preparation Example 83

7-Methoxy-3-(4-methoxy-2-nitrophenyl)-1,2-dihydronaphthalene

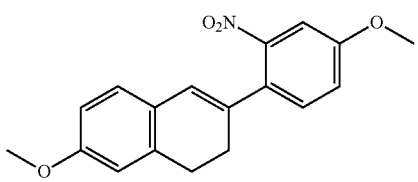

Synthesized from 6-methoxy-3,4-dihydronaphthalen-2-yl trifluoromethanesulfonate (2.3 g) and tributyl(4-methoxy-2-nitrophenyl)tin (3.9 g) according to an analogous synthetic method to Preparation Example 77, the title compound (1.7 g) was obtained.

$^1$H-NMR (400 MHz, CDCl$_3$); δ (ppm): 2.45 (t, 2H), 2.94 (t, 2H), 3.82 (s, 3H), 3.88 (s, 3H), 6.43 (s, 1H), 6.69-6.74 (m, 2H), 7.02 (d, 1H), 7.12 (dd, 1H), 7.32 (d, 1H), 7.43 (d, 1H).

Example 28

5-Methoxy-2-(6-methoxy-1,2,3,4-tetrahydronaphthalen-2-yl)phenylamine

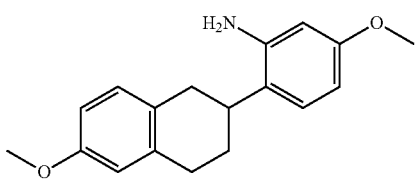

Synthesized from 7-methoxy-3-(4-methoxy-2-nitrophenyl)-1,2-dihydronaphthalene (600 mg) according to an analogous synthetic method to Example 22, the title compound (333 mg) was obtained.

$^1$H-NMR (400 MHz, CDCl$_3$); δ (ppm): 1.88-1.98 (m, 1H), 2.06-2.13 (m, 1H), 2.72-2.78 (m, 1H), 2.83-3.03 (m, 4H), 3.70 (brs, 2H), 3.77 (s, 3H), 3.79 (s, 3H), 6.29 (d, 1H), 6.37 (dd, 1H), 6.68 (s, 1H), 6.71 (dd, 1H), 7.01 (d, 1H), 7.04 (d, 1H).

Preparation Example 84

6-Methoxy-3-(4-methoxy-2-nitrophenyl)-1,2-dihydronaphthalene

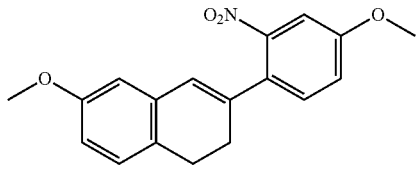

Synthesized from 7-methoxy-2-tetralone according to an analogous synthetic method to Preparation Example 82 described above, 7-methoxy-3,4-dihydronaphthalen-2-yl trifluoromethanesulfonate (3.5 g) and tributyl(4-methoxy-2-nitrophenyl)tin (18 g) were used according to an analogous synthetic method to Preparation Example 77 to provide the title compound (1.9 g).

$^1$H-NMR (400 MHz, CDCl$_3$); δ (ppm): 2.47 (t, 2H), 2.90 (t, 2H), 3.80 (s, 3H), 3.89 (s, 3H), 6.43 (s, 1H), 6.66 (s, 1H), 6.71 (d, 1H), 7.07 (d, 1H), 7.12 (d, 1H), 7.32 (d, 1H), 7.46 (s, 1H).

Example 29

5-Methoxy-2-(7-methoxy-1,2,3,4-tetrahydronaphthalen-2-yl)phenylamine

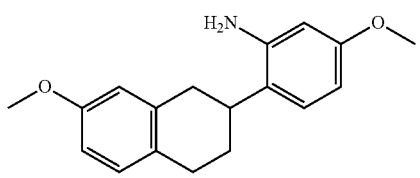

Synthesized from 6-methoxy-3-(4-methoxy-2-nitrophenyl)-1,2-dihydronaphthalene (1.9 g) according to an analogous synthetic method to Example 22, the title compound (1.1 g) was obtained.

$^1$H-NMR (400 MHz, CDCl$_3$); δ (ppm): 1.88-2.00 (m, 1H), 2.08-2.15 (m, 1H), 2.74-2.94 (m, 4H), 3.00-3.08 (m, 1H), 3.71 (brs, 2H), 3.77 (s, 3H), 3.79 (s, 3H), 6.30 (s, 1H), 6.35-6.39 (m, 1H), 6.64 (s, 1H), 6.73 (d, 1H), 7.02-7.08 (m, 2H).

Preparation Example 85

7-Methoxy-3-(2-nitrophenyl)-1,2-dihydronaphthalene

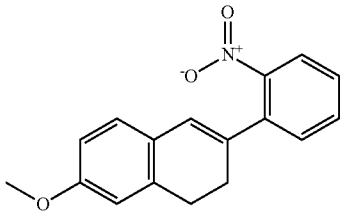

Synthesized from 1-bromo-2-nitrobenzene according to an analogous synthetic method to Preparation Example 76, tributyl(2-nitrophenyl)tin (7.3 g) and 6-methoxy-3,4-dihydronaphthalen-2-yl trifluoromethanesulfonate (2.2 g) were used according to an analogous synthetic method to Preparation Example 77 to provide the title compound (1.5 g).

¹H-NMR (400 MHz, CDCl₃); δ (ppm): 2.50 (t, 2H), 2.95 (t, 2H), 3.82 (s, 3H), 6.49 (s, 1H), 6.70-6.74 (m, 2H), 7.03 (d, 1H), 7.39-7.45 (m, 2H), 7.57 (dt, 1H), 7.90 (dd, 1H).

Example 30

2-(6-Methoxy-1,2,3,4-tetrahydronaphthalen-2-yl)phenylamine

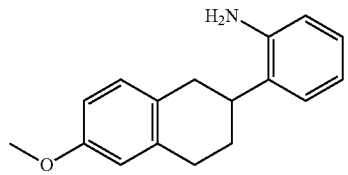 [SMILES: COc1ccc2c(c1)CCC(c1ccccc1N)C2]

To a solution of 7-methoxy-3-(2-nitrophenyl)-1,2-dihydronaphthalene (1.5 g) in tetrahydrofuran (10 ml) and methanol (10 ml) were sequentially added 10% palladium-activated charcoal (300 mg) and concentrated hydrochloric acid (0.8 ml), and the solution was stirred for 25 hours at room temperature under a hydrogen atmosphere at 4 atmospheric pressures. After filtration through celite pad, the solution was neutralized with ammonia solution, extracted with ethyl acetate, then sequentially washed with water and brine, dried over anhydrous magnesium sulfate, then the solvent was evaporated in vacuo, the resulting solid was washed with a hexane-diethyl ether system to provide the title compound (949 mg).

¹H-NMR (400 MHz, CDCl₃); δ (ppm): 1.91-2.02 (m, 1H), 2.09-2.16 (m, 1H), 2.78 (dd, 1H), 2.88-3.06 (m, 4H), 3.68 (brs, 2H), 3.79 (s, 3H), 6.68 (d, 1H), 6.71 (d, 1H), 6.72 (d, 1H), 6.80 (dt, 1H), 7.01 (d, 1H), 7.06 (dt, 1H), 7.14 (dd, 1H).

Example 31

5-Fluoro-2-(6-methoxy-1,2,3,4-tetrahydronaphthalen-2-yl)phenylamine

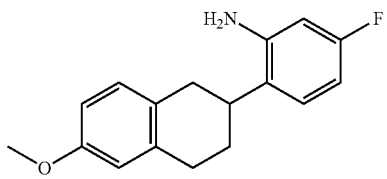 [SMILES: COc1ccc2c(c1)CCC(c1ccc(F)cc1N)C2]

Synthesized from 1-bromo-4-fluoro-2-nitrobenzene according to an analogous synthetic method to Preparation Example 76, tributyl(4-fluoro-2-nitrophenyl)tin (7.1 g) and 6-methoxy-3,4-dihydronaphthalen-2-yl trifluoromethanesulfonate (2.2 g) were used according to an analogous synthetic method to Preparation Example 77 to provide 3-(4-fluoro-2-nitrophenyl)-7-methoxy-1,2-dihydronaphthalene (1.4 g). The total amount of this compound was used according to an analogous synthetic method to Example 30 to provide the title compound (1.1 g).

¹H-NMR (400 MHz, CDCl₃); δ (ppm): 1.88-1.98 (m, 1H), 2.06-2.13 (m, 1H), 2.73 (dd, 1H), 2.82-2.90 (m, 1H), 2.92-3.04 (m, 3H), 3.78 (brs, 2H), 3.79 (s, 3H), 6.41 (dd, 1H), 6.47 (ddd, 1H), 6.68 (d, 1H), 6.72 (dd, 1H), 7.01 (d, 1H), 7.05 (dd, 1H).

Example 32

6-Methoxy-2-(6-methoxy-1,2,3,4-tetrahydronaphthalen-2-yl)pyridin-3-ylamine

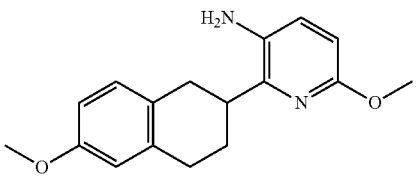

Synthesized from 2-chloro-6-methoxy-3-nitropyridine according to an analogous synthetic method to Preparation Example 76, 6-methoxy-3-nitro-2-tributylstannylpyridine (5.5 and 6-methoxy-3,4-dihydronaphthalen-2-yl trifluoromethanesulfonate (1.5 g) were used according to an analogous synthetic method to Preparation Example 77 to provide 6-methoxy-2-(6-methoxy-3,4-dihydronaphthalen-2-yl)-3-nitropyridine (933 mg). This compound (930 mg) was used according to an analogous synthetic method to Example 30 to provide the title compound (340 mg).

¹H-NMR (400 MHz, CDCl₃); δ (ppm): 2.03-2.18 (m, 2H), 2.84-2.97 (m, 3H), 2.99-3.07 (m, 1H), 3.16 (dd, 1H), 3.33 (brs, 2H), 3.80 (s, 3H), 3.82 (s, 3H), 6.46 (d, 1H), 6.68 (d, 1H), 6.71 (dd, 1H), 7.00 (d, 1H), 7.04 (d, 1H).

Example 33

2-(6-Methoxy-1,2,3,4-tetrahydronaphthalen-2-yl)-5-trifluoromethylphenylamine

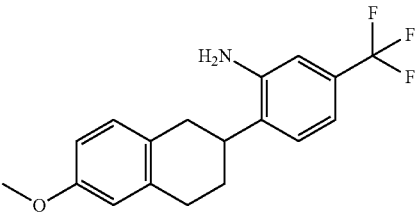 [SMILES: COc1ccc2c(c1)CCC(c1ccc(C(F)(F)F)cc1N)C2]

Synthesized from 1-bromo-2-nitro-4-trifluoromethylbenzene according to an analogous synthetic method to Preparation Example 76, tributyl(2-nitro-4-trifluoromethylphenyl)tin (7.4 and 6-methoxy-3,4-dihydronaphthalen-2-yl trifluoromethanesulfonate (2.2 g) were used according to an analogous synthetic method to Preparation Example 77 to provide 7-methoxy-3-(2-nitro-4-trifluoromethylphenyl)-1,2-dihydronaphthalene (1.5 g). The total amount of this compound was used according to an analogous synthetic method to Example 30 to provide the title compound (1.0 g).

¹H-NMR (400 MHz, CDCl₃); δ (ppm): 1.92-2.05 (m, 1H), 2.08-2.16 (m, 1H), 2.77 (dd, 1H), 2.90-3.07 (m, 4H), 3.80 (s, 3H), 3.86 (brs, 2H), 6.69 (d, 1H), 6.73 (dd, 1H), 6.93 (s, 1H), 7.02 (d, 2H), 7.22 (d, 1H).

Example 34

4-Fluoro-2-(6-methoxy-1,2,3,4-tetrahydronaphthalen-2-yl)phenylamine

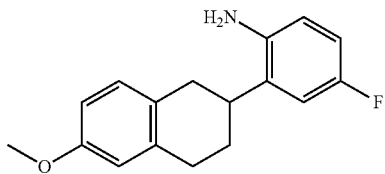 [SMILES: COc1ccc2c(c1)CCC(c1cc(F)ccc1N)C2]

Synthesized from 5-fluoro-2-nitrophenyl trifluoromethanesulfonate and (6-methoxy-3,4-dihydronaphthalen-2-yl)trimethyltin according to an analogous synthetic method to Preparation Example 77, 3-(5-fluoro-2-nitrophenyl)-7-methoxy-1,2-dihydronaphthalene (396 mg) was used according to an analogous synthetic method to Example 30 to provide the title compound (286 mg).

$^1$H-NMR (400 MHz, CDCl$_3$); δ (ppm): 1.86-1.97 (m, 1H), 2.08-2.15 (m, 1H), 2.73 (dd, 1H), 2.88-3.05 (m, 4H), 3.55 (brs, 2H), 3.80 (s, 3H), 6.65 (dd, 1H), 6.68 (d, 1H), 6.72 (dd, 1H), 6.76 (ddd, 1H), 6.86 (dd, 1H), 7.02 (d, 1H).

Example 35

[5-Methoxy-2-(6-methoxy-1,2,3,4-tetrahydronaphthalen-2-yl)phenyl]methylamine

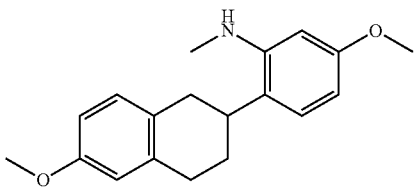

Synthesized from 5-methoxy-2-(6-methoxy-1,2,3,4-tetrahydronaphthalen-2-yl)phenylamine (231 mg) according to an analogous synthetic method to Example 119 described below, the title compound (105 mg) was obtained.

$^1$H-NMR (400 MHz, CDCl$_3$); δ (ppm): 1.93-2.18 (m, 2H), 2.70-3.07 (m, 5H), 2.93 (s, 3H), 3.81 (brs, 1H), 3.86 (s, 3H), 3.87 (s, 3H), 6.31 (d, 1H), 6.36 (dd, 1H), 6.74 (s, 1H), 6.77 (d, 1H), 7.08 (d, 1H), 7.10 (d, 1H).

Example 36

Ethyl[5-methoxy-2-(6-methoxy-1,2,3,4-tetrahydronaphthalen-2-yl)phenyl]amine

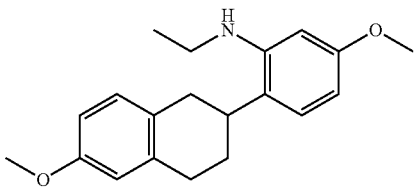

To a solution of 5-methoxy-2-(6-methoxy-1,2,3,4-tetrahydronaphthalen-2-yl)phenylamine (1.0 g) in pyridine (5 ml) was added acetic anhydride (5 ml), and the solution was stirred for 10 minutes at room temperature. An ice water was added thereto, the solution was stirred, was neutralized with a saturated aqueous solution of sodium bicarbonate, and the resulting solid was filtered and purified by silica gel column chromatography (hexane-ethyl acetate system) to provide N-[5-methoxy-2-(6-methoxy-1,2,3,4-tetrahydronaphthalen-2-yl)phenyl]acetamide (1.1 g). To a suspension of lithium aluminum hydride (400 mg) in tetrahydrofuran (20 ml) was added aluminum chloride (1.4 g) on an ice bath under a nitrogen atmosphere, the solution was stirred for 15 minutes at room temperature, then N-[5-methoxy-2-(6-methoxy-1,2,3,4-tetrahydronaphthalen-2-yl)phenyl]acetamide (1.1 g) was added thereto followed by stirring for 1 hour at room temperature. Tetrahydrofuran and aqueous ammonia were sequentially added thereto, the resulting suspension was filtered through celite pad, and the filtrate was concentrated in vacuo. The residue was purified by silica gel column chromatography (hexane-ethyl acetate system) to provide the title compound (604 mg).

$^1$H-NMR (400 MHz, CDCl$_3$); δ (ppm): 1.27 (t, 3H), 1.89-2.00 (m, 1H), 2.05-2.12 (m, 1H), 2.68-2.76 (m, 1H), 2.77-2.86 (m, 1H), 2.92-3.03 (m, 3H), 3.17 (q, 2H), 3.62 (brs, 1H), 3.80 (s, 6H), 6.25 (d, 1H), 6.29 (dd, 1H), 6.69 (d, 1H), 6.72 (dd, 1H), 7.02 (d, 1H), 7.03 (d, 1H).

Example 37

Ethyl[5-methoxy-2-(6-methoxy-1,2,3,4-tetrahydronaphthalen-2-yl)phenyl]methylamine

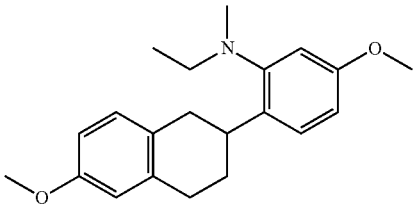

Synthesized from ethyl[5-methoxy-2-(6-methoxy-1,2,3,4-tetrahydronaphthalen-2-yl)phenyl]amine (300 mg) according to an analogous synthetic method to Preparation Example 18, the title compound (259 mg) was obtained.

$^1$H-NMR (400 MHz, CDCl$_3$); δ (ppm): 1.04 (t, 3H), 1.80-1.97 (m, 2H), 2.62 (s, 3H), 2.73-3.02 (m, 6H), 3.45-3.55 (m, 1H), 3.80 (s, 6H), 6.64-6.72 (m, 4H), 6.99 (d, 1H), 7.17 (d, 1H).

Example 38

Isopropyl[5-methoxy-2-(6-methoxy-1,2,3,4-tetrahydronaphthalen-2-yl)phenyl]amine

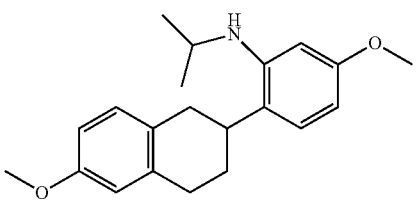

To a solution of 5-methoxy-2-(6-methoxy-1,2,3,4-tetrahydronaphthalen-2-yl)phenylamine (300 mg) in tetrahydrofuran (8 ml) were sequentially added acetone (0.4 ml), acetic acid (0.1 ml) and sodium triacetoxyborohydride (780 mg), and the solution was stirred for 2 days at room temperature. The solution was neutralized with ammonia solution, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (309 mg).

$^1$H-NMR (400 MHz, CDCl$_3$); δ (ppm): 1.22 (d, 3H), 1.23 (d, 3H), 1.88-1.96 (m, 1H), 2.05-2.12 (m, 1H), 2.68-2.83 (m, 2H), 2.92-3.02 (m, 3H), 3.55 (brs, 1H), 3.60-3.71 (m, 1H), 3.79 (s, 3H), 3.80 (s, 3H), 6.24-6.28 (m, 2H), 6.69 (d, 1H), 6.72 (dd, 1H), 7.01 (s, 1H), 7.03 (d, 1H).

Example 39

6-(2-Amino-4-hydroxyphenyl)-5,6,7,8-tetrahydronaphthalen-2-ol

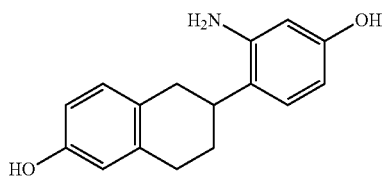 [SMILES: Nc1cc(O)ccc1C1CCc2cc(O)ccc2C1]

Synthesized from 5-methoxy-2-(6-methoxy-1,2,3,4-tetrahydronaphthalen-2-yl)phenylamine (200 mg) according to an analogous synthetic method to Example 364 described below, the title compound (145 mg) was obtained.

$^1$H-NMR (400 MHz, DMSO-d$_6$); δ (ppm): 1.59-1.71 (m, 1H), 1.80-1.88 (m, 1H), 2.45-2.53 (m, 1H), 2.65-2.89 (m, 4H), 4.74 (s, 2H), 5.94 (dd, 1H), 6.06 (d, 1H), 6.45-6.50 (m, 2H), 6.73 (d, 1H), 6.83 (d, 1H), 8.65 (s, 1H), 8.95 (s, 1H).

ESI-Mass; 256 [M$^+$+H]

Example 40

6-(4-Hydroxy-2-methylaminophenyl)-5,6,7,8-tetrahydronaphthalen-2-ol

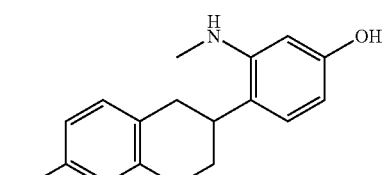

Synthesized from [5-methoxy-2-(6-methoxy-1,2,3,4-tetrahydronaphthalen-2-yl)phenyl]methylamine (195 mg) according to an analogous synthetic method to Example 364 described below, the title compound (177 mg) was obtained.

$^1$H-NMR (400 MHz, DMSO-d$_6$); δ (ppm): 1.63-1.75 (m, 1H), 1.78-1.86 (m, 1H), 2.42-2.51 (m, 1H), 2.62 (d, 3H), 2.66-2.88 (m, 4H), 5.14 (q, 1H), 5.91 (d, 1H), 5.96 (dd, 1H), 6.45-6.50 (m, 2H), 6.77 (d, 1H), 6.82 (d, 1H), 8.75 (s, 1H), 8.96 (s, 1H).

ESI-Mass; 270 [M$^+$+H]

Example 41

6-(2-Ethylamino-4-hydroxyphenyl)-5,6,7,8-tetrahydronaphthalen-2-ol

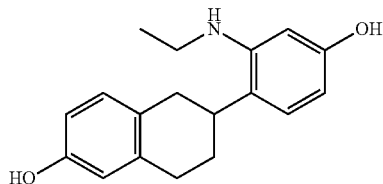 [SMILES: CCNc1cc(O)ccc1C1CCc2cc(O)ccc2C1]

Synthesized from ethyl[5-methoxy-2-(6-methoxy-1,2,3,4-tetrahydronaphthalen-2-yl)phenyl]amine (250 mg) according to an analogous synthetic method to Example 111 described below, the title compound (227 mg) was obtained.

$^1$H-NMR (400 MHz, DMSO-d$_6$); δ (ppm): 1.13 (t, 3H), 1.64-1.86 (m, 2H), 2.66-2.92 (m, 4H), 2.97-3.03 (m, 2H), 3.34-3.37 (m, 1H), 4.84 (t, 1H), 5.95-5.98 (m, 2H), 6.46-6.50 (m, 2H), 6.77 (d, 1H), 6.83 (d, 1H), 8.75 (brs, 1H), 8.98 (brs, 1H).

ESI-Mass; 284 [M$^+$+H]

Example 42

6-(2-Dimethylamino-4-hydroxyphenyl)-5,6,7,8-tetrahydronaphthalen-2-ol

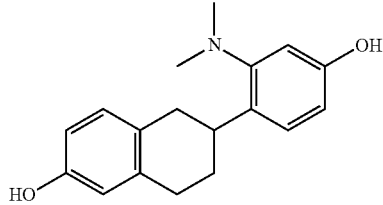 [SMILES: CN(C)c1cc(O)ccc1C1CCc2cc(O)ccc2C1]

Synthesized from 5-methoxy-2-(6-methoxy-1,2,3,4-tetrahydronaphthalen-2-yl)phenylamine according to an analogous synthetic method to Preparation Example 18, [5-methoxy-2-(6-methoxy-1,2,3,4-tetrahydronaphthalen-2-yl)phenyl]dimethylamine (120 mg) was used according to an analogous synthetic method to Example 364 described below to provide the title compound (96 mg).

$^1$H-NMR (400 MHz, DMSO-d$_6$); δ (ppm): 1.71-1.79 (m, 2H), 2.53 (s, 6H), 2.56-2.67 (m, 2H), 2.70-2.83 (m, 2H), 3.19-3.27 (m, 1H), 6.43 (dd, 1H), 6.45-6.50 (m, 2H), 6.51 (d, 1H), 6.81 (d, 1H), 7.01 (d, 1H), 8.98 (s, 1H), 9.08 (s, 1H).

ESI-Mass; 284 [M$^+$+H]

Example 43

6-[2-(Ethylmethylamino)-4-hydroxyphenyl]-5,6,7,8-tetrahydronaphthalen-2-ol

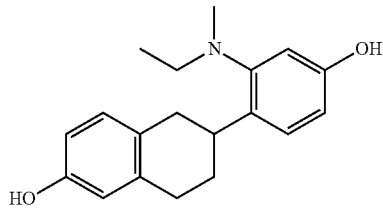 [SMILES: CCN(C)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine (239 mg) according to an analogous synthetic method to Example 111 described below, the title compound (219 mg) was obtained.

$^1$H-NMR (400 MHz, DMSO-d$_6$); δ (ppm): 0.94 (t, 3H), 1.70-1.78 (m, 2H), 2.51 (s, 3H), 2.59-2.63 (m, 2H), 2.71-2.80 (m, 4H), 3.22-3.29 (m, 1H), 6.44-6.49 (m, 3H), 6.52 (s, 1H), 6.81 (d, 1H), 7.02 (d, 1H), 8.99 (brs, 1H), 9.08 (brs, 1H).
ESI-Mass; 298 [M$^+$+H]

Example 44

6-(2-Diethylamino-4-hydroxyphenyl)-5,6,7,8-tetrahydronaphthalen-2-ol

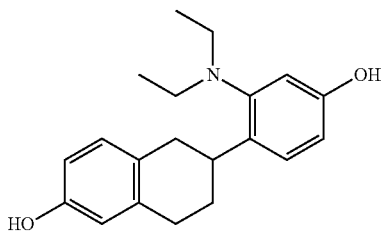 [SMILES: CCN(CC)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine according to an analogous synthetic method to Example 36, diethyl[5-methoxy-2-(6-methoxy-1,2,3,4-tetrahydronaphthalen-2-yl)phenyl]amine (288 mg) was used according to an analogous synthetic method to Example 111 described below to provide the title compound (210 mg).
$^1$H-NMR (400 MHz, DMSO-d$_6$); δ (ppm): 0.85 (t, 6H), 1.67-1.76 (m, 2H), 2.55-2.62 (m, 2H), 2.70-2.78 (m, 2H), 2.82 (q, 4H), 3.40-3.48 (m, 1H), 6.45-6.53 (m, 3H), 6.55 (s, 1H), 6.80 (d, 1H), 7.04 (d, 1H), 8.99 (brs, 1H), 9.07 (brs, 1H).
ESI-Mass; 312 [M$^+$+H]

Preparation Example 86

N-Ethyl-N-[5-methoxy-2-(6-methoxy-1,2,3,4-tetrahydronaphthalen-2-yl)phenyl]benzamide

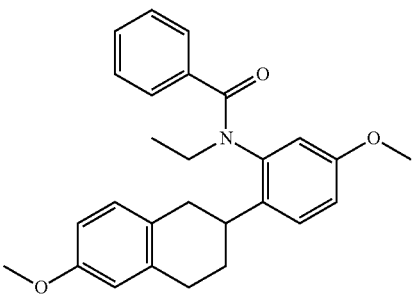

To a solution of ethyl[5-methoxy-2-(6-methoxy-1,2,3,4-tetrahydronaphthalen-2-yl)phenyl]amine (100 mg) in 1,4-dioxane (3 ml) were sequentially added N,N-diisopropylethylamine (0.34 ml) and benzoyl chloride (0.05 ml), and the solution was stirred for 1 hour at 100° C. The solution was let to cool down, then a saturated aqueous solution of sodium bicarbonate was added thereto, the solution was extracted with ethyl acetate, then sequentially washed with an aqueous solution of 10% citric acid and brine, dried over anhydrous magnesium sulfate, and then the solvent was evaporated in vacuo. The residue was purified by silica gel column chromatography (hexane-ethyl acetate-tetrahydrofuran system) to provide the title compound (133 mg).

$^1$H-NMR (400 MHz, CDCl$_3$); δ (ppm): 0.52-0.61 (m, 0.5H), 1.21-1.29 (m, 3H), 1.44-1.90 (m, 2.5H), 2.37-2.46 (m, 0.5H), 2.61-2.91 (m, 4H), 3.77-3.82 (m, 6H), 3.88-3.98 (m, 1.5H), 6.60-7.34 (m, 11H).

Example 45

6-[2-(Benzylethylamino)-4-hydroxyphenyl]-5,6,7,8-tetrahydronaphthalen-2-ol

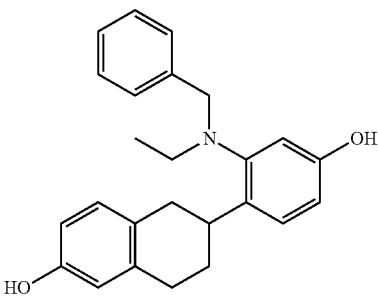

Synthesized from N-ethyl-N-[5-methoxy-2-(6-methoxy-1,2,3,4-tetrahydronaphthalen-2-yl)phenyl]benzamide according to an analogous synthetic method to Example 337 described below, benzylethyl[5-methoxy-2-(6-methoxy-1,2,3,4-tetrahydronaphthalen-2-yl)phenyl]amine (151 mg) was used according to an analogous synthetic method to Example 111 described below to provide the title compound (90 mg).
$^1$H-NMR (400 MHz, DMSO-d$_6$); δ (ppm): 0.86 (t, 3H), 1.52-1.70 (m, 2H), 2.51-2.58 (m, 2H), 2.69-2.75 (m, 2H), 2.82 (q, 2H), 3.43-3.53 (m, 1H), 3.95 (s, 2H), 6.45-6.50 (m, 3H), 6.63 (s, 1H), 6.79 (d, 1H), 7.01 (d, 1H), 7.12-7.24 (m, 5H), 9.00 (brs, 1H), 9.10 (brs, 1H).
ESI-Mass; 374 [M$^+$+H]

Preparation Example 87

N-Ethyl-N-[5-methoxy-2-(6-methoxy-1,2,3,4-tetrahydronaphthalen-2-yl)phenyl]-2-phenylacetamide

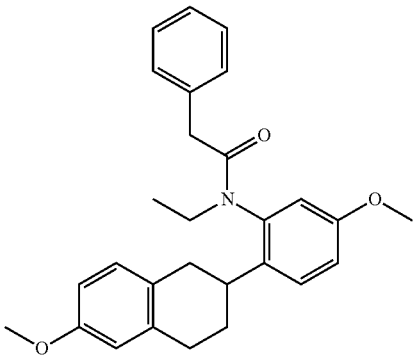

To a solution of ethyl[5-methoxy-2-(6-methoxy-1,2,3,4-tetrahydronaphthalen-2-yl)phenyl]amine (100 mg) in dichloromethane (3 ml) were sequentially added an aqueous solution of 1N sodium hydroxide (1 ml) and phenylacetyl chloride (0.06 ml) on an ice bath, and the solution was stirred overnight while warming to room temperature. To the reaction solution was added water, the solution was extracted with ethyl acetate, then washed with brine, dried over anhydrous magnesium sulfate, and then the solvent was evaporated in vacuo to provide the title compound (140 mg).

¹H-NMR (400 MHz, CDCl₃); δ (ppm): 1.16 (t, 3H), 1.66-1.73 (m, 0.5H), 1.79-1.92 (m, 1.5H), 2.58-2.66 (m, 0.5H), 2.75-3.20 (m, 5.5H), 3.33-3.47 (m, 2H), 3.68-3.73 (m, 3H), 3.80 (s, 3H), 4.14-4.29 (m, 1H), 6.47 (dd, 1H), 6.64-6.72 (m, 2H), 6.89-7.09 (m, 4H), 7.19-7.32 (m, 4H).

Example 46

6-[2-(Ethylphenethylamino)-4-hydroxyphenyl]-5,6,7,8-tetrahydronaphthalen-2-ol

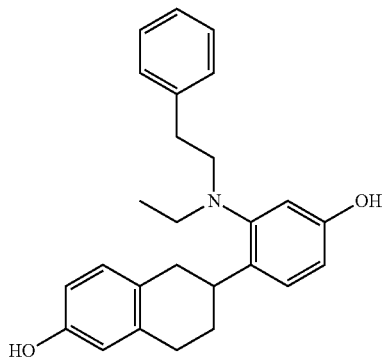 [SMILES: CCN(CCc1ccccc1)c1cc(O)ccc1C1CCc2cc(O)ccc2C1]

Synthesized from N-ethyl-N-[5-methoxy-2-(6-methoxy-1,2,3,4-tetrahydronaphthalen-2-yl)phenyl]-2-phenylacetamide according to an analogous synthetic method to Example 337 described below, ethyl[5-methoxy-2-(6-methoxy-1,2,3,4-tetrahydronaphthalen-2-yl)phenyl]phenethylamine (137 mg) was used according to an analogous synthetic method to Example 111 described below to provide the title compound (77 mg).

¹H-NMR (400 MHz, DMSO-d₆); δ (ppm): 0.87 (t, 3H), 1.58-1.76 (m, 2H), 2.54-2.70 (m, 6H), 2.84-2.94 (m, 2H), 3.04 (t, 2H), 3.25-3.30 (m, 1H), 6.43-6.53 (m, 3H), 6.63 (s, 1H), 6.79 (d, 1H), 7.01-7.19 (m, 6H), 8.98 (brs, 1H), 9.11 (brs, 1H).

ESI-Mass; 388 [M⁺+H]

Example 47

[5-Methoxy-2-(6-methoxy-1,2,3,4-tetrahydronaphthalen-2-yl)phenyl][2-(4-methoxyphenyl) ethyl]amine

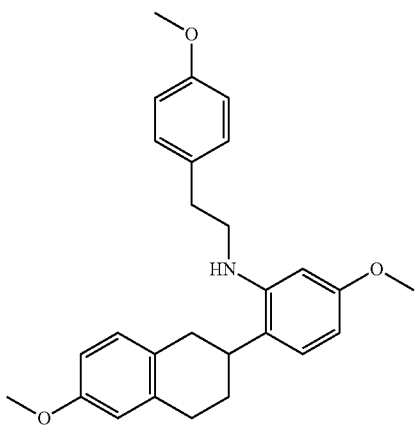

A mixture of 5-methoxy-2-(6-methoxy-1,2,3,4-tetrahydronaphthalen-2-yl)phenylamine (700 mg), 4-methoxyphenylacetyl chloride (680 mg) and pyridine (10 ml) was stirred for 2 hours at room temperature. The reaction mixture was diluted with a saturated aqueous solution of sodium bicarbonate, the crystal that was precipitated was filtered, rinsed with water, then dried at 50° C. overnight. The total amount of the resulting N-[5-methoxy-2-(6-methoxy-1,2,3,4-tetrahydronaphthalen-2-yl)phenyl]-2-(4-methoxyphenyl)acetamide (crude product) was used according to an analogous synthetic method to Example 337 described below to provide the title compound (690 mg).

¹H-NMR (400 MHz, CDCl₃); δ (ppm): 1.78-1.89 (m, 1H), 1.91-1.99 (m, 1H), 2.55-2.68 (m, 2H), 2.76-2.92 (m, 5H), 3.37 (t, 2H), 3.76 (s, 3H), 3.80 (s, 6H), 6.26-6.30 (m, 2H), 6.65 (s, 1H), 6.70 (d, 1H), 6.79 (d, 1H), 6.94 (d, 1H), 7.01 (d, 1H), 7.11 (d, 1H).

Example 48

6-{4-Hydroxy-2-{[2-(4-hydroxyphenyl)ethyl]methylamino}phenyl}-5,6,7,8-tetrahydronaphthalen-2-ol

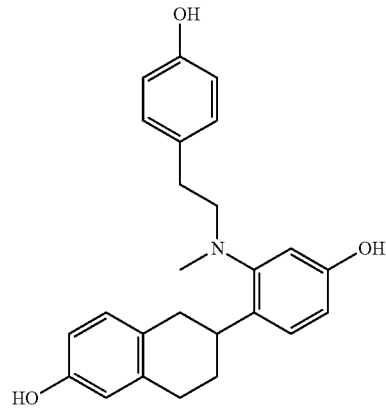 [SMILES: CN(CCc1ccc(O)cc1)c1cc(O)ccc1C1CCc2cc(O)ccc2C1]

Synthesized from [5-methoxy-2-(6-methoxy-1,2,3,4-tetrahydronaphthalen-2-yl)phenyl][2-(4-methoxyphenyl)ethyl]amine (250 mg) according to an analogous synthetic method to Preparation Example 18, [5-methoxy-2-(6-methoxy-1,2,3,4-tetrahydronaphthalen-2-yl)phenyl][2-(4-methoxyphenyl)ethyl]methylamine (crude product) was obtained. Synthesized from the total amount of this compound according to an analogous synthetic method to Example 364 described below, the title compound (50 mg) was obtained.

¹H-NMR (400 MHz, DMSO-d₆); δ (ppm): 1.64-1.78 (m, 2H), 2.52-2.64 (m, 4H), 2.57 (s, 3H), 2.68-2.75 (m, 2H), 2.86-2.95 (m, 2H), 3.20-3.32 (m, 1H), 6.44-6.51 (m, 3H), 6.54-6.60 (m, 3H), 6.80 (d, 1H), 6.88 (d, 2H), 7.02 (d, 1H), 8.98 (brs, 1H), 9.09 (brs, 2H).

Example 49

6-{2-{Ethyl[2-(4-hydroxyphenyl)ethyl]amino}-4-hydroxyphenyl}-5,6,7,8-tetrahydronaphthalen-2-ol

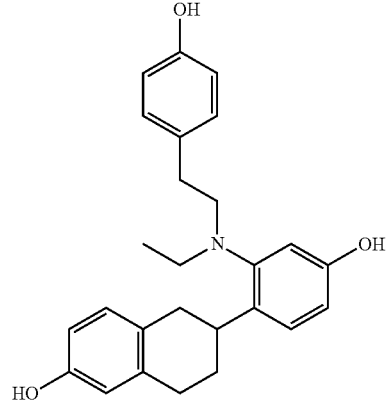 [SMILES: CCN(CCc1ccc(O)cc1)c1cc(O)ccc1C1CCc2cc(O)ccc2C1]

Synthesized from [5-methoxy-2-(6-methoxy-1,2,3,4-tetrahydronaphthalen-2-yl)phenyl][2-(4-methoxyphenyl)ethyl]amine (250 mg) according to an analogous synthetic method to Example 36, ethyl[5-methoxy-2-(6-methoxy-1,2,3,4-tetrahydronaphthalen-2-yl)phenyl][2-(4-methoxyphenyl)ethyl]amine (crude product) was obtained. Synthesized from the total amount of this compound according to an analogous synthetic method to Example 364 described below, the title compound (120 mg) was obtained.

$^1$H-NMR (400 MHz, DMSO-d$_6$); δ (ppm): 0.87 (t, 3H), 1.62-1.76 (m, 2H), 2.42-2.50 (m, 2H), 2.55-2.62 (m, 2H), 2.68-2.74 (m, 2H), 2.87 (q, 2H), 2.96 (t, 2H), 3.33-3.44 (m, 1H), 6.45-6.53 (m, 3H), 6.56-6.64 (m, 3H), 6.80 (d, 1H), 6.87 (d, 2H), 7.05 (d, 1H), 8.98 (brs, 1H), 9.09 (brs, 2H).

Preparation Example 88

2-Chloro-N-ethyl-N-[5-methoxy-2-(6-methoxy-1,2,3,4-tetrahydronaphthalen-2-yl)phenyl]acetamide

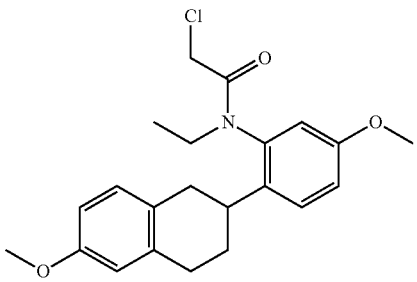

Synthesized from ethyl[5-methoxy-2-(6-methoxy-1,2,3,4-tetrahydronaphthalen-2-yl)phenyl]amine (100 mg) and chloroacetyl chloride (0.04 ml) according to an analogous synthetic method to Preparation Example 87, the title compound (133 mg) was obtained.

$^1$H-NMR (400 MHz, CDCl$_3$); δ (ppm): 1.19 (t, 3H), 1.86-1.93 (m, 2H), 2.73-3.02 (m, 5H), 3.10-3.23 (m, 1H), 3.74-3.81 (m, 5H), 3.83 (s, 3H), 4.15-4.27 (m, 1H), 6.64-6.67 (m, 2H), 6.70 (d, 1H), 6.95 (d, 1H), 6.99 (dd, 1H), 7.32 (d, 1H).

Preparation Example 89

N-Ethyl-N-[5-methoxy-2-(6-methoxy-1,2,3,4-tetrahydronaphthalen-2-yl)phenyl]-2-piperidin-1-ylacetamide

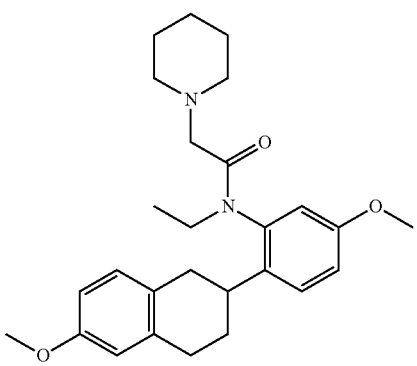

To a solution of 2-chloro-N-ethyl-N-[5-methoxy-2-(6-methoxy-1,2,3,4-tetrahydronaphthalen-2-yl)phenyl]acetamide (129 mg) in N,N-dimethylformamide (5 ml) were sequentially added piperidine (0.07 ml) and potassium carbonate (184 mg), and the solution was stirred overnight at 60° C. The solution was let to cool, then a saturated aqueous solution of sodium bicarbonate was added thereto, the solution was extracted with ethyl acetate, then washed with brine, dried over anhydrous potassium carbonate, and then the solvent was evaporated in vacuo. The residue was purified by silica gel column chromatography (hexane-ethyl acetate system) to provide the title compound (139 mg).

$^1$H-NMR (400 MHz, CDCl$_3$); δ (ppm): 1.16 (t, 3H), 1.33-1.42 (m, 2H), 1.50-1.58 (m, 4H), 1.84-1.94 (m, 2H), 2.29-2.38 (m, 2H), 2.40-2.48 (m, 2H), 2.65-3.10 (m, 8H), 3.79 (s, 3H), 3.82 (s, 3H), 4.10-4.26 (m, 1H), 6.60-6.72 (m, 3H), 6.91-6.98 (m, 2H), 7.29 (s, 1H).

Example 50

6-{2-[Ethyl(2-piperidin-1-ylethyl)amino]-4-hydroxyphenyl}-5,6,7,8-tetrahydronaphthalen-2-ol

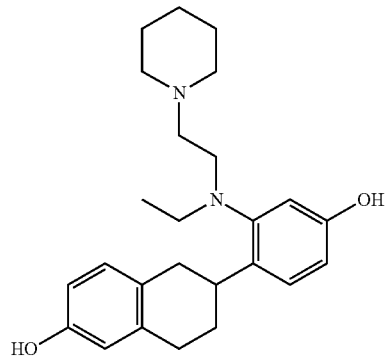 [SMILES: CCN(CCN1CCCCC1)c1cc(O)ccc1C1CCc2cc(O)ccc2C1]

Synthesized from N-ethyl-N-[5-methoxy-2-(6-methoxy-1,2,3,4-tetrahydronaphthalen-2-yl)phenyl]-2-piperidin-1-ylacetamide according to an analogous synthetic method to Example 337 described below, the total amount of ethyl[5-methoxy-2-(6-methoxy-1,2,3,4-tetrahydronaphthalen-2-yl)phenyl](2-piperidin-1-ylethyl)amine (108 mg) was used according to an analogous synthetic method to Example 111 described below to provide the title compound (84 mg).

$^1$H-NMR (400 MHz, DMSO-d$_6$); δ (ppm): 0.85 (t, 3H), 1.24-1.32 (m, 2H), 1.35-1.42 (m, 4H), 1.65-1.76 (m, 2H), 2.15-2.27 (m, 6H), 2.59 (d, 2H), 2.70-2.78 (m, 2H), 2.84 (q, 2H), 2.90 (t, 2H), 3.35-3.45 (m, 1H), 6.44-6.51 (m, 3H), 6.58 (d, 1H), 6.80 (d, 1H), 7.03 (d, 1H), 8.99 (brs, 1H), 9.07 (brs, 1H).

ESI-Mass; 395 [M$^+$+H]

Example 51

6-{2-[Ethyl(2-pyrrolidin-1-ylethyl)amino]-4-hydroxyphenyl}-5,6,7,8-tetrahydronaphthalen-2-ol

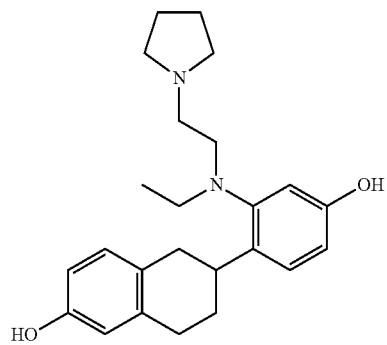 [SMILES: CCN(CCN1CCCC1)c1cc(O)ccc1C1CCc2cc(O)ccc2C1]

Synthesized from 2-chloro-N-ethyl-N-[5-methoxy-2-(6-methoxy-1,2,3,4-tetrahydronaphthalen-2-yl)phenyl]acetamide and pyrrolidine according to an analogous synthetic method to Preparation Example 89, N-ethyl-N-[5-methoxy-2-(6-methoxy-1,2,3,4-tetrahydronaphthalen-2-yl)phenyl]-2-pyrrolidin-1-ylacetamide (119 mg) was used according to an analogous synthetic method to Example 337 described below to provide ethyl[5-methoxy-2-(6-methoxy-1,2,3,4-tetrahydronaphthalen-2-yl)phenyl](2-pyrrolidin-1-ylethyl)amine (96 mg). This compound (95 mg) was used according to an analogous synthetic method to Example 111 described below to provide the title compound (92 mg).

$^1$H-NMR (400 MHz, DMSO-d$_6$); δ (ppm): 0.85 (t, 3H), 1.52-1.60 (m, 4H), 1.65-1.78 (m, 2H), 2.28-2.37 (m, 6H), 2.58 (d, 2H), 2.70-2.78 (m, 2H), 2.84 (q, 2H), 2.91 (t, 2H), 3.37-3.47 (m, 1H), 6.44-6.51 (m, 3H), 6.58 (d, 1H), 6.80 (d, 1H), 7.04 (d, 1H), 8.99 (brs, 1H), 9.08 (brs, 1H).

ESI-Mass; 381 [M$^+$+H]

Example 52

6-{2-[Ethyl(pyridin-2-ylmethyl)amino]-4-hydroxyphenyl}-5,6,7,8-tetrahydronaphthalen-2-ol

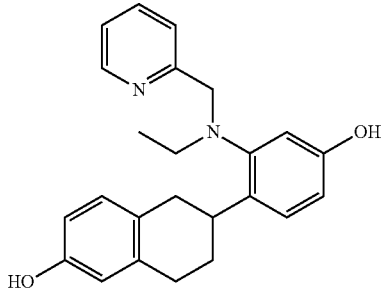 [SMILES: CCN(Cc1ccccn1)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine and picolinoyl chloride hydrochloride according to an analogous synthetic method to Preparation Example 87, pyridine-2-carboxylic acid ethyl[5-methoxy-2-(6-methoxy-1,2,3,4-tetrahydronaphthalen-2-yl)phenyl]amide (129 mg) was used according to an analogous synthetic method to Example 337 described below to provide ethyl[5-methoxy-2-(6-methoxy-1,2,3,4-tetrahydronaphthalen-2-yl)phenyl]pyridin-2-ylmethylamine (100 mg). This compound (93 mg) was used according to an analogous synthetic method to Example 111 described below to provide the title compound (108 mg).

$^1$H-NMR (400 MHz, DMSO-d$_6$); δ (ppm): 0.90 (t, 3H), 1.57-1.71 (m, 2H), 2.55-2.62 (m, 2H), 2.68-2.75 (m, 2H), 2.88 (q, 2H), 3.41-3.52 (m, 1H), 4.09 (s, 2H), 6.45-6.50 (m, 3H), 6.62 (d, 1H), 6.80 (d, 1H), 6.85 (s, 1H), 7.03 (d, 1H), 7.15-7.19 (m, 1H), 7.26 (d, 1H), 7.61-7.66 (m, 1H), 8.39-8.43 (m, 1H), 8.99 (brs, 1H), 9.10 (brs, 1H).

ESI-Mass; 375 [M$^+$+H]

Example 53

6-{2-[Ethyl(pyridin-3-ylmethyl)amino]-4-hydroxyphenyl}-5,6,7,8-tetrahydronaphthalen-2-ol

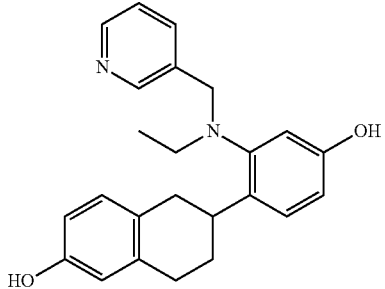 [SMILES: CCN(Cc1cccnc1)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine and nicotinoyl chloride hydrochloride according to an analogous synthetic method to Preparation Example 86, pyridine-3-carboxylic acid ethyl[5-methoxy-2-(6-methoxy-1,2,3,4-tetrahydronaphthalen-2-yl)phenyl]amide (162 mg) was used according to an analogous synthetic method to Example 337 described below to provide ethyl[5-methoxy-2-(6-methoxy-1,2,3,4-tetrahydronaphthalen-2-yl)phenyl]pyridin-3-ylmethylamine (30 mg). The total amount of this compound was used according to an analogous synthetic method to Example 111 described below to provide the title compound (23 mg).

$^1$H-NMR (400 MHz, DMSO-d$_6$); δ (ppm): 0.89 (t, 3H), 1.40-1.50 (m, 1H), 1.58-1.70 (m, 1H), 2.50-2.58 (m, 2H), 2.67-2.74 (m, 2H), 2.85 (q, 2H), 3.35-3.45 (m, 1H), 4.00 (q, 2H), 6.44-6.51 (m, 3H), 6.64 (d, 1H), 6.78 (d, 1H), 7.00 (d, 1H), 7.24 (dd, 1H), 7.54 (dd, 1H), 8.33-8.38 (m, 2H), 9.00 (brs, 1H), 9.13 (brs, 1H).

ESI-Mass; 375 [M$^+$+H]

Example 54

6-{2-[Ethyl(pyridin-4-ylmethyl)amino]-4-hydroxyphenyl}-5,6,7,8-tetrahydronaphthalen-2-ol

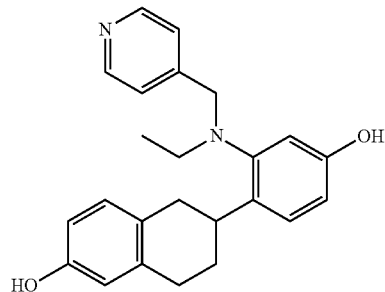 [SMILES: CCN(Cc1ccncc1)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine and isonicotinoyl chloride hydrochloride according to an analogous synthetic method to Preparation Example 86, pyridine-4-carboxylic acid ethyl[5-methoxy-2-(6-methoxy-1,2,3,4-tetrahydronaphthalen-2-yl)phenyl]amide (163 mg) was used according to an analogous synthetic method to Example 337 described below to provide ethyl[5-methoxy-2-(6-methoxy-1,2,3,4-tetrahydronaphthalen-2-yl)phenyl]pyridin-4-ylmethylamine (43 mg). The total amount of this compound was used according to an analogous synthetic method to Example 111 described below to provide the title compound (42 mg).

$^1$H-NMR (400 MHz, DMSO-d$_6$); δ (ppm): 0.90 (t, 3H), 1.53-1.71 (m, 2H), 2.50-2.60 (m, 2H), 2.70-2.77 (m, 2H), 2.85 (q, 2H), 3.37-3.48 (m, 1H), 4.01 (s, 2H), 6.45-6.51 (m, 3H), 6.62 (d, 1H), 6.80 (d, 1H), 7.03 (d, 1H), 7.21 (d, 2H), 8.40 (dd, 2H), 9.00 (brs, 1H), 9.13 (brs, 1H).

ESI-Mass; 375 [M$^+$+H]

Preparation Example 90

1-Ethyl-4-methoxy-7-(6-methoxy-1,2,3,4-tetrahydronaphthalen-2-yl)-1H-indole-2,3-dione

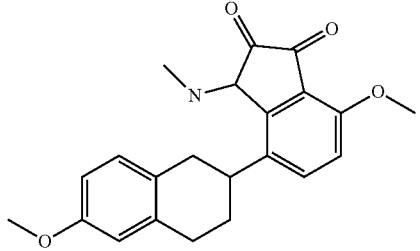

To a solution of ethyl[5-methoxy-2-(6-methoxy-1,2,3,4-tetrahydronaphthalen-2-yl)phenyl]amine (260 mg) in diethyl ether (30 ml) was added dropwise oxalyl chloride (0.21 ml) on an ice bath, and the solution was stirred for 30 minutes at room temperature. The reaction solution was concentrated in vacuo, the total amount of the resulting {ethyl[5-methoxy-2-(6-methoxy-1,2,3,4-tetrahydronaphthalen-2-yl)phenyl]amino}oxoacetyl chloride (crude product) was stirred in dichloromethane (5 ml), a solution of aluminum chloride (220 mg) in dichloromethane (20 ml) was added dropwise thereto on an ice bath, and the solution was stirred overnight at room temperature. The reaction mixture was diluted with ice water, extracted with chloroform, then washed with brine, dried over anhydrous magnesium sulfate, and then the solvent was evaporated in vacuo. The residue was purified by silica gel column chromatography (hexane-ethyl acetate system) to provide the title compound (160 mg).

$^1$H-NMR (400 MHz, CDCl$_3$); δ (ppm): 1.29 (t, 3H), 1.89-2.12 (m, 2H), 2.82-3.00 (m, 4H), 3.21-3.30 (m, 1H), 3.79 (s, 3H), 3.72-3.90 (m, 1H), 3.99 (s, 3H), 4.00-4.16 (m, 1H), 6.61-6.78 (m, 3H), 7.03 (d, 1H), 7.49 (d, 1H).

Example 55

1-Ethyl-7-(6-hydroxy-1,2,3,4-tetrahydronaphthalen-2-yl)-1H-indol-4-ol

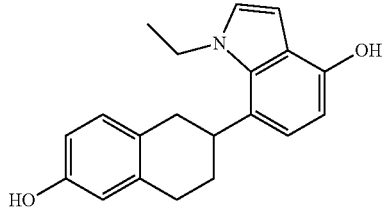 [SMILES: CCn1ccc2c(O)ccc(C3CCc4cc(O)ccc4C3)c21]

A mixture of 1-ethyl-4-methoxy-7-(6-methoxy-1,2,3,4-tetrahydronaphthalen-2-yl)-1H-indole-2,3-dione (160 mg), borane-tetrahydrofuran complex (1.0 M solution in tetrahydrofuran) (1.8 ml) and tetrahydrofuran (10 ml) was refluxed for 1 hour. After dilution with ice water, ammonia solution was added thereto, the solution was extracted with ethyl acetate, then washed with brine, dried over magnesium sulfate, and then the solvent was evaporated in vacuo. The residue was purified by silica gel column chromatography (hexane-ethyl acetate system), the resulting 1-ethyl-4-methoxy-7-(6-methoxy-1,2,3,4-tetrahydronaphthalen-2-yl)-1H-indole (58 mg) was used according to an analogous synthetic method to Example 364 described below to provide the title compound (7 mg).

$^1$H-NMR (400 MHz, DMSO-d$_6$); δ (ppm): 1.28 (t, 3H), 1.81-1.95 (m, 1H), 2.00-2.10 (m, 1H), 2.75-2.96 (m, 5H), 4.25 (q, 2H), 6.36 (d, 1H), 6.46-6.57 (m, 3H), 6.84 (d, 1H), 6.90 (d, 1H), 7.14 (s, 1H), 9.06 (brs, 1H), 9.16 (brs, 1H).

Preparation Example 91

2-Methoxy-5,7,8,9-tetrahydrobenzocyclohepten-6-one

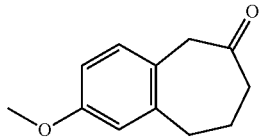

The title compound was synthesized by referring to *Tetrahedron Lett.*, 1977, 21, 1827. To a suspension of methyltriphenylphosphonium bromide (11.5 g) in tetrahydrofuran (50 ml) was added dropwise potassium tert-butoxide (1.0 M solution in tetrahydrofuran) (40 ml) on an ice bath under a nitrogen atmosphere, the solution was stirred for 1 hour, then a solution of 6-methoxy-1-tetralone (4.74 g) in tetrahydrofuran (26 ml) was added dropwise thereto followed by stirring for 2.5 hours at room temperature. Water was added thereto, the solution was stirred, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide 6-methoxy-1-methylene-1,2,3,4-tetrahydronaphthalene (4.4 g). To a solution of thallium(III) nitrate trihydrate (4.5 g) in methanol (40 ml) was added dropwise a solution of 6-methoxy-1-methylene-1,2,3,4-tetrahydronaphthalene (1.7 g) in methanol (13 ml) on an ice bath, and the solution was stirred for 10 minutes at room temperature. Chloroform was added thereto, the solution was stirred, then filtered through celite pad, extracted with diethyl ether, then sequentially washed with water and brine, dried over anhydrous magnesium sulfate, and then the solvent was evaporated in vacuo. The residue was purified by silica gel column chromatography (hexane-ethyl acetate system) to provide the title compound (1.7 g).

$^1$H-NMR (400 MHz, CDCl$_3$); δ (ppm): 1.99 (pent, 2H), 2.55 (t, 2H), 2.91 (t, 2H), 3.66 (s, 2H), 3.80 (s, 3H), 6.70-6.74 (m, 2H), 7.06 (d, 1H).

Preparation Example 92

3-Methoxy-8-(4-methoxy-2-nitrophenyl)-6,7-dihydro-5H-benzocycloheptene

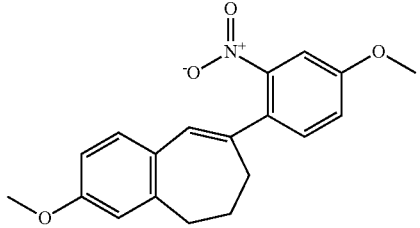

Synthesized from 2-methoxy-5,7,8,9-tetrahydrobenzocyclohepten-6-one according to an analogous synthetic method to Preparation Example 82, 2-methoxy-8,9-dihydro-7H-benzocyclohepten-6-yl trifluoromethanesulfonate (3.0 g) and tributyl(4-methoxy-2-nitrophenyl)tin (10.8 g) were used according to an analogous synthetic method to Preparation Example 77 to provide the title compound (2.8 g).

$^1$H-NMR (400 MHz, CDCl$_3$); δ (ppm): 2.09-2.16 (m, 2H), 2.53 (t, 2H), 2.87-2.91 (m, 2H), 3.81 (s, 3H), 3.88 (s, 3H), 6.31 (s, 1H), 6.68-6.72 (m, 2H), 7.03 (d, 1H), 7.10 (dd, 1H), 7.31 (d, 1H), 7.40 (d, 1H).

Example 56

5-Methoxy-2-(2-methoxy-6,7,8,9-tetrahydro-5H-benzocyclohepten-6-yl)phenylamine

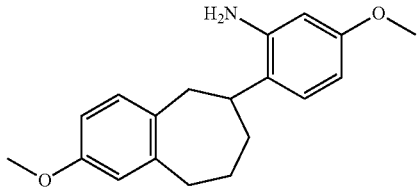

Synthesized from 3-methoxy-8-(4-methoxy-2-nitrophenyl)-6,7-dihydro-5H-benzocycloheptene (1.4 g) according to an analogous synthetic method to Example 30, the title compound (520 mg) was obtained.

$^1$H-NMR (400 MHz, CDCl$_3$); δ (ppm): 1.46-1.59 (m, 1H), 1.82-1.92 (m, 1H), 2.07-2.18 (m, 2H), 2.45 (t, 1H), 2.73-2.82 (m, 2H), 2.92 (t, 1H), 3.09 (dd, 1H), 3.63 (brs, 2H), 3.77 (s, 3H), 3.80 (s, 3H), 6.28 (d, 1H), 6.38 (dd, 1H), 6.65 (dd, 1H), 6.73 (d, 1H), 7.05 (d, 1H), 7.10 (d, 1H).

Example 57

5-Methoxy-2-(6-methoxy-3,4-dihydronaphthalen-2-yl)phenylamine

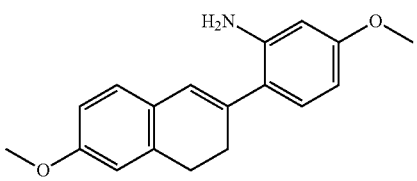

To a suspension of 7-methoxy-3-(4-methoxy-2-nitrophenyl)-1,2-dihydronaphthalene (600 mg), iron (430 mg) and ammonium chloride (830 mg) in methanol (15 ml) was added water (6 ml), and the solution was stirred for 6 hours at 80° C. The solution was filtered through celite pad, extracted with ethyl acetate, then sequentially washed with water and brine, and the solvent was evaporated in vacuo. The residue was purified by NH silica gel column chromatography (hexane-ethyl acetate system) to provide the title compound (356 mg).

$^1$H-NMR (400 MHz, CDCl$_3$); δ (ppm): 2.59 (t, 2H), 2.93 (t, 2H), 3.79 (s, 3H), 3.82 (s, 3H), 6.31 (d, 1H), 6.36 (dd, 1H), 6.58 (s, 1H), 6.69-6.76 (m, 2H), 7.00 (d, 1H), 7.04 (d, 1H).

Example 58

5-Methoxy-2-(2-methoxy-8,9-dihydro-7H-benzocyclohepten-6-yl)phenylamine

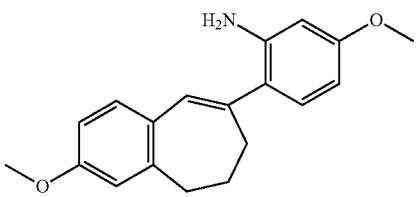

Synthesized from 3-methoxy-8-(4-methoxy-2-nitrophenyl)-6,7-dihydro-5H-benzocycloheptene (1.4 g) according to an analogous synthetic method to Example 57, the title compound (757 mg) was obtained.

$^1$H-NMR (400 MHz, CDCl$_3$); δ (ppm): 2.08-2.16 (m, 2H), 2.55 (t, 2H), 2.85-2.89 (m, 2H), 3.78 (s, 3H), 3.81 (s, 3H), 3.85 (brs, 2H), 6.30 (d, 1H), 6.34 (dd, 1H), 6.45 (s, 1H), 6.70-6.73 (m, 2H), 7.01 (d, 1H), 7.07 (d, 1H).

Example 59

2-(2-Methoxy-6,7,8,9-tetrahydro-5H-benzocyclohepten-6-yl)phenylamine

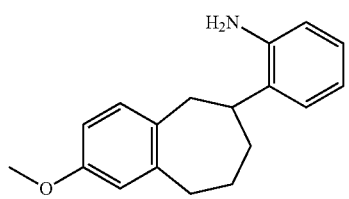 [SMILES: COc1ccc2c(c1)CCCC(c1ccccc1N)C2]

Synthesized from 2-methoxy-8,9-dihydro-7H-benzocyclohepten-6-yl trifluoromethanesulfonate and tributyl(2-nitrophenyl)tin according to an analogous synthetic method to Preparation Example 77, 3-methoxy-8-(2-nitrophenyl)-6,7-dihydro-5H-benzocycloheptene (850 mg) was used according to an analogous synthetic method to Example 30 to provide the title compound (500 mg).

$^1$H-NMR (400 MHz, CDCl$_3$); δ (ppm): 1.46-1.60 (m, 1H), 1.84-1.95 (m, 1H), 2.09-2.22 (m, 2H), 2.52 (t, 1H), 2.74-2.84 (m, 2H), 2.94 (t, 1H), 3.12 (dd, 1H), 3.61 (brs, 2H), 3.80 (s, 3H), 6.66 (dd, 1H), 6.71 (dd, 1H), 6.74 (d, 1H), 6.81 (dt, 1H), 7.02-7.07 (m, 2H), 7.20 (dd, 1H).

Example 60

2-(2-Methoxy-8,9-dihydro-7H-benzocyclohepten-6-yl)phenylamine

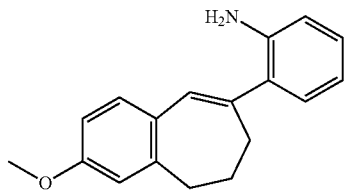 [SMILES: COc1ccc2c(c1)CCCC(c1ccccc1N)=C2]

Synthesized from 2-methoxy-8,9-dihydro-7H-benzocyclohepten-6-yl trifluoromethanesulfonate and tributyl(2-nitrophenyl)tin according to an analogous synthetic method to Preparation Example 77, 3-methoxy-8-(2-nitrophenyl)-6,7-dihydro-5H-benzocycloheptene (830 mg) was used according to an analogous synthetic method to Example 57 to provide the title compound (442 mg).

$^1$H-NMR (400 MHz, CDCl$_3$); δ (ppm): 2.10-2.16 (m, 2H), 2.58 (t, 2H), 2.87-2.91 (m, 2H), 3.82 (s, 5H), 6.47 (s, 1H), 6.70-6.79 (m, 4H), 7.06-7.11 (m, 3H).

Example 61

6-(2-Amino-4-methoxyphenyl)-6,7,8,9-tetrahydro-5H-benzocyclohepten-2-ol

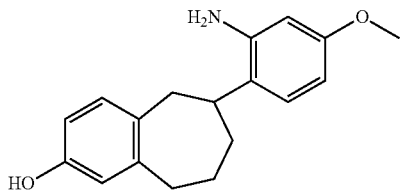 [SMILES: COc1ccc(C2CCCc3cc(O)ccc3C2)c(N)c1]

Synthesized from 6-benzyloxy-3,4-dihydro-2H-naphthalen-1-one according to an analogous synthetic method to Preparation Example 91, 2-benzyloxy-5,7,8,9-tetrahydrobenzocyclohepten-6-one (7.2 g) was used according to an analogous synthetic method to Preparation Example 82 to provide 2-benzyloxy-8,9-dihydro-7H-benzocyclohepten-6-yl trifluoromethanesulfonate (6.7 g). Synthesized from this compound and tributyl(4-methoxy-2-nitrophenyl)tin according to an analogous synthetic method to Preparation Example 77, 3-benzyloxy-8-(4-methoxy-2-nitrophenyl)-6,7-dihydro-5H-benzocycloheptene (4.7 g) was used according to an analogous synthetic method to Example 30 to provide the title compound (2.4 g).

¹H-NMR (400 MHz, DMSO-d₆); δ (ppm): 1.38-1.48 (m, 1H), 1.52-1.63 (m, 1H), 1.88-1.99 (m, 2H), 2.42-2.48 (m, 1H), 2.54-2.62 (m, 2H), 2.78 (t, 1H), 3.03 (dd, 1H), 3.62 (s, 3H), 4.72 (brs, 2H), 6.12 (dd, 1H), 6.20 (d, 1H), 6.44 (d, 1H), 6.53 (d, 1H), 6.86 (d, 1H), 6.91 (d, 1H), 9.00 (s, 1H).

Example 62

{2-[2-(tert-Butyldimethylsilyloxy)-6,7,8,9-tetrahydro-5H-benzocyclohepten-6-yl]-5-methoxyphenyl}ethylamine

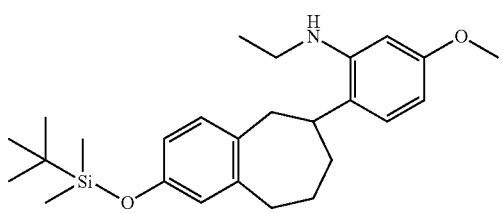 [SMILES: CCNc1cc(OC)ccc1C1CCCc2cc(O[Si](C)(C)C(C)(C)C)ccc2C1]

Synthesized from 6-(2-amino-4-methoxyphenyl)-6,7,8,9-tetrahydro-5H-benzocyclohepten-2-ol according to an analogous synthetic method to Example 201 described below, 2-[2-(tert-butyldimethylsilyloxy)-6,7,8,9-tetrahydro-5H-benzocyclohepten-6-yl]-5-methoxyphenylamine (1.3 g) was used according to an analogous synthetic method to Example 36 to provide the title compound (1.1 g).

¹H-NMR (400 MHz, CDCl₃); δ (ppm): 0.20 (s, 6H), 0.98 (s, 9H), 1.43-1.53 (m, 1H), 1.80-1.91 (m, 1H), 2.04-2.17 (m, 2H), 2.41-2.47 (m, 1H), 2.70 (dd, 1H), 2.76 (d, 1H), 2.88 (t, 1H), 3.06 (dd, 1H), 3.63 (brs, 2H), 3.76 (s, 3H), 6.27 (d, 1H), 6.36 (dd, 1H), 6.56 (dd, 1H), 6.63 (d, 1H), 6.95 (d, 1H), 7.08 (d, 1H).

Preparation Example 93

6-Methoxy-2-(4-methoxy-2-nitrophenyl)-1,1-dimethyl-1,4-dihydronaphthalene

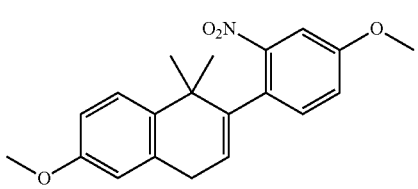

To a suspension of 60% sodium hydride (680 mg) in tetrahydrofuran (25 ml) was added dropwise a solution of 6-methoxy-2-tetralone (700 mg) in tetrahydrofuran (5 ml) on an ice bath under a nitrogen atmosphere, the solution was stirred for 10 minutes at room temperature, then methyl iodide (2.5 ml) was added dropwise thereto followed by refluxing for 5 hours. 1N Hydrochloric acid was added thereto followed by stirring, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide 6-methoxy-1,1-dimethyl-3,4-dihydro-1H-naphthalen-2-one (1.2 g). This compound (696 mg) was used according to an analogous synthetic method to Preparation Example 82 to provide 6-methoxy-1,1-dimethyl-1,4-dihydronaphthalen-2-yl trifluoromethanesulfonate (930 mg). Synthesized from this compound (926 mg) and tributyl(4-methoxy-2-nitrophenyl)tin (1.5 g) according to an analogous synthetic method to Preparation Example 77, the title compound (559 mg) was obtained.

¹H-NMR (400 MHz, CDCl₃); δ (ppm): 3.48 (d, 2H), 3.81 (s, 3H), 3.88 (s, 3H), 5.80 (t, 1H), 6.68 (d, 1H), 6.80 (dd, 1H), 7.08 (dd, 1H), 7.25 (d, 1H), 7.31 (d, 1H), 7.36 (d, 1H).

Example 63

5-Methoxy-2-(6-methoxy-1,1-dimethyl-1,2,3,4-tetrahydronaphthalen-2-yl)phenylamine

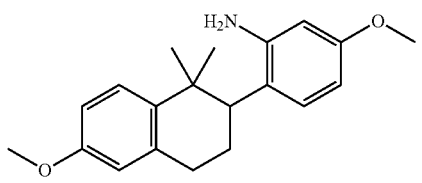

To a solution of 6-methoxy-2-(4-methoxy-2-nitrophenyl)-1,1-dimethyl-1,4-dihydronaphthalene (433 mg) in tetrahydrofuran (6 ml) and methanol (6 ml) was added 10% palladium-activated charcoal (200 mg), and the solution was stirred for 3.5 hours at room temperature under a hydrogen atmosphere at 4 atmospheric pressures. After filtration through celite pad, the solvent was evaporated in vacuo, and the resulting solid was washed with hexane-diethyl ether system to provide the title compound (314 mg).

¹H-NMR (400 MHz, CDCl₃); δ (ppm): 1.16 (s, 3H), 1.31 (s, 3H), 1.82-1.90 (m, 1H), 2.17-2.28 (m, 1H), 2.80-3.01 (m, 3H), 3.69 (brs, 2H), 3.77 (s, 3H), 3.79 (s, 3H), 6.27 (d, 1H), 6.34 (dd, 1H), 6.62 (d, 1H), 6.76 (dd, 1H), 6.97 (d, 1H), 7.30 (d, 1H).

Example 64

5-Methoxy-2-(6-methoxy-1,1-dimethyl-1,4-dihydronaphthalen-2-yl)phenylamine

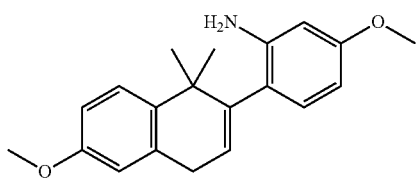

Synthesized from 6-methoxy-2-(4-methoxy-2-nitrophenyl)-1,1-dimethyl-1,4-dihydronaphthalene (2.6 g) according to an analogous synthetic method to Example 57, the title compound (1.1 g) was obtained.

¹H-NMR (400 MHz, CDCl₃); δ (ppm): 1.34 (s, 3H), 1.38 (s, 3H), 3.51 (dd, 2H), 3.68 (brs, 2H), 3.78 (s, 3H), 3.82 (s, 3H), 5.82 (t, 1H), 6.28 (d, 1H), 6.32 (dd, 1H), 6.69 (d, 1H), 6.82 (dd, 1H), 6.92 (d, 1H), 7.36 (d, 1H).

Preparation Example 94

6-Methoxy-3,3-dimethyl-3,4-dihydro-2H-naphthalen-1-one

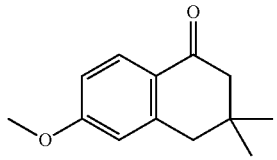

The title compound was synthesized by referring to *J. Org. Chem.*, 1971, 36, 3260. To a suspension of magnesium (2.7 g) in diethyl ether (5 ml) was added a solution of 3-methoxybenzyl chloride (15 ml) in diethyl ether (90 ml) dropwise on an ice bath under a nitrogen atmosphere, the solution was stirred for 20 minutes at room temperature. To a resulting solution of 3-methoxybenzyl magnesium chloride in diethyl ether, which was cooled on an ice, was added dropwise solution of diethyl 2-isopropylidenemalonate (14.8 g) in diethyl ether (9 ml) thereto, then diethyl ether (30 ml) was added thereto followed by stirring overnight at room temperature. The solution was brought to pH 2 by adding 5N hydrochloric acid on an ice bath, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide 2-[2-(3-methoxyphenyl)-1,1-dimethylethyl]malonic acid diethyl ester (19.7 g). To a solution of the total amount of this compound in ethanol (200 ml) was added an aqueous solution of 5N sodium hydroxide (40 ml), and the solution was refluxed overnight. Water was added thereto followed by stirring, then ethanol was evaporated in vacuo, then the solution was washed with diethyl ether, and the resulting aqueous solution was brought to pH 1 with concentrated hydrochloric acid. The solution was extracted with ethyl acetate, then sequentially washed with water and brine, dried over anhydrous magnesium sulfate, and then the solvent was evaporated in vacuo. The residue was washed with a hexane-diethyl ether system, and the resulting 2-[2-(3-methoxyphenyl)-1,1-dimethylethyl]malonic acid (13.4 g) was heated for 30 minutes at 180° C. to provide 4-(3-methoxyphenyl)-3,3-dimethylbutyric acid (11.2 g). To a solution of the total amount of this compound in toluene (70 ml) was added thionyl chloride (15 ml), the solution was stirred for 1 hour at 100° C., then the solvent was evaporated in vacuo, and the resulting 4-(3-methoxyphenyl)-3,3-dimethylbutyryl chloride (12.5 g) was used according to an analogous synthetic method to Preparation Example 66 to provide the title compound (8.0 g).

$^1$H-NMR (400 MHz, CDCl$_3$); δ (ppm): 1.07 (s, 6H), 2.45 (s, 2H), 2.80 (s, 2H), 3.86 (s, 3H), 6.68 (d, 1H), 6.82 (dd, 1H), 8.00 (d, 1H).

Preparation Example 95

3-Bromo-7-methoxy-2,2-dimethyl-1,2-dihydronaphthalene

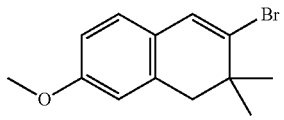

By referring to the synthetic method of *J. Chem. Soc. Perkin Trans. I*, 1995, 197, to a suspension of copper(II) bromide (26.5 g) in ethyl acetate (120 ml) and chloroform (120 ml) was added a solution of 6-methoxy-3,3-dimethyl-3,4-dihydro-2H-naphthalen-1-one (12 g) in ethyl acetate (14 ml), and the solution was stirred for 1.5 hours at 80° C. Diethyl ether was added thereto followed by stirring. The solution was filtered through celite pad, extracted with diethyl ether, then sequentially washed with a saturated aqueous solution of sodium bicarbonate, water and brine, dried over anhydrous magnesium sulfate, then filtered through silica gel, the solvent was evaporated in vacuo. To the resulting 2-bromo-6-methoxy-3,3-dimethyl-3,4-dihydro-2H-naphthalen-1-one (16.9 g) was added ethanol (200 ml) followed by stirring, sodium borohydride (2.3 g) was added thereto, and the solution was stirred overnight at room temperature. An ice water was added thereto followed by stirring, the solution was extracted with ethyl acetate, then sequentially washed with water and brine, dried over anhydrous magnesium sulfate, then the solvent was evaporated in vacuo to provide 2-bromo-6-methoxy-3,3-dimethyl-1,2,3,4-tetrahydronaphthalen-1-ol (15.8 g). To a suspension of the total amount of this compound in toluene (200 ml) was added p-toluenesulfonic acid monohydrate (1.1 g), and the solution was refluxed for 1 hour. A saturated aqueous solution of sodium bicarbonate was added thereto followed by stirring. The solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (12.8 g).

$^1$H-NMR (400 MHz, CDCl$_3$); δ (ppm): 1.13 (s, 6H), 2.82 (s, 2H), 3.78 (s, 3H), 6.64 (d, 1H), 6.67 (dd, 1H), 6.69 (s, 1H), 6.90 (d, 1H).

Example 65

5-Methoxy-2-(6-methoxy-3,3-dimethyl-1,2,3,4-tetrahydronaphthalen-2-yl)phenylamine

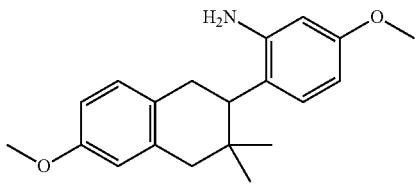

Synthesized from 3-bromo-7-methoxy-2,2-dimethyl-1,2-dihydronaphthalene and 4-bromo-3-nitroanisole according to an analogous synthetic method to Preparation Example 107 described below, 7-methoxy-3-(4-methoxy-2-nitrophenyl)-2,2-dimethyl-1,2-dihydronaphthalene (1.9 g) was used according to an analogous synthetic method to Example 30 to provide the title compound (1.5 g).

$^1$H-NMR (400 MHz, CDCl$_3$); δ (ppm): 0.94 (s, 3H), 0.98 (s, 3H), 2.62 (d, 1H), 2.74 (d, 1H), 2.83-2.92 (m, 2H), 3.06 (dd, 1H), 3.68 (brs, 2H), 3.75 (s, 3H), 3.79 (s, 3H), 6.26 (d, 1H), 6.31 (dd, 1H), 6.62 (d, 1H), 6.70 (dd, 1H), 7.00 (d, 2H).

Example 66

5-Methoxy-2-(6-methoxy-3,3-dimethyl-3,4-dihydronaphthalen-2-yl)phenylamine

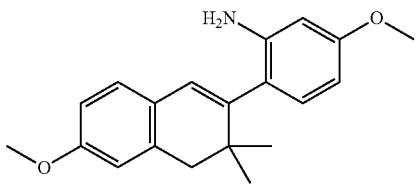

Synthesized from 3-bromo-7-methoxy-2,2-dimethyl-1,2-dihydronaphthalene and 4-bromo-3-nitroanisole according to an analogous synthetic method to Preparation Example 107 described below, 7-methoxy-3-(4-methoxy-2-nitrophenyl)-2,2-dimethyl-1,2-dihydronaphthalene (1.9 g) was used according to an analogous synthetic method to Example 57 to provide the title compound (1.3 g).

$^1$H-NMR (400 MHz, CDCl$_3$); δ (ppm): 1.02 (s, 3H), 1.09 (s, 3H), 2.69 (d, 1H), 2.91 (d, 1H), 3.78 (s, 3H), 3.79 (brs, 2H), 3.82 (s, 3H), 6.28 (s, 1H), 6.29-6.33 (m, 2H), 6.71 (dd, 1H), 6.73 (s, 1H), 6.90 (d, 1H), 6.98 (d, 1H).

Example 67

2-(6-Methoxy-3,3-dimethyl-1,2,3,4-tetrahydronaphthalen-2-yl)phenylamine

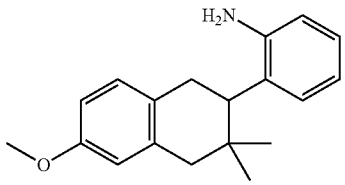 [SMILES: COc1ccc2c(c1)CC(C)(C)C(c1ccccc1N)C2]

Synthesized from 3-bromo-7-methoxy-2,2-dimethyl-1,2-dihydronaphthalene and 1-bromo-2-nitrobenzene according to an analogous synthetic method to Preparation Example 107 described below, 7-methoxy-2,2-dimethyl-3-(2-nitrophenyl)-1,2-dihydronaphthalene (1.4 g) was used according to an analogous synthetic method to Example 30 to provide the title compound (948 mg).

$^1$H-NMR (400 MHz, CDCl$_3$); δ (ppm): 0.96 (s, 3H), 0.99 (s, 3H), 2.64 (d, 1H), 2.76 (d, 1H), 2.86-2.98 (m, 2H), 3.10 (dd, 1H), 3.67 (brs, 2H), 3.79 (s, 3H), 6.63 (d, 1H), 6.68-6.76 (m, 3H), 7.00-7.05 (m, 2H), 7.11 (dd, 1H).

Example 68

2-(6-Methoxy-3,3-dimethyl-3,4-dihydronaphthalen-2-yl)phenylamine

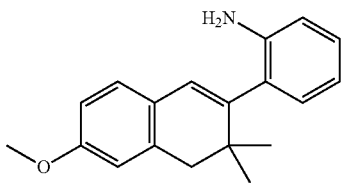 [SMILES: COc1ccc2c(c1)CC(C)(C)C(c1ccccc1N)=C2]

Synthesized from 3-bromo-7-methoxy-2,2-dimethyl-1,2-dihydronaphthalene and 1-bromo-2-nitrobenzene according to an analogous synthetic method to Preparation Example 107 described below, 7-methoxy-2,2-dimethyl-3-(2-nitrophenyl)-1,2-dihydronaphthalene (1.4 g) was used according to an analogous synthetic method to Example 57 to provide the title compound (676 mg).

$^1$H-NMR (400 MHz, CDCl$_3$); δ (ppm): 1.03 (s, 3H), 1.10 (s, 3H), 2.69 (d, 1H), 2.93 (d, 1H), 3.78 (brs, 2H), 3.82 (s, 3H), 6.29 (s, 1H), 6.68-6.75 (m, 3H), 6.98 (d, 2H), 7.08 (ddd, 1H).

Preparation Example 96

7-Methoxy-2,2-dimethylchroman-4-one

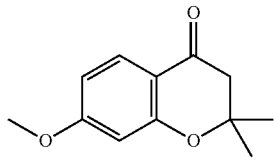

The title compound was synthesized by referring to *Chem. Pharm. Bull.*, 1977, 25, 2788. To 3-methoxyphenol (8.5 g) and 3,3-dimethylacrylic acid (7.5 g) was added polyphosphoric acid (80 ml), and the solution was stirred for 2 hours at 100° C. The reaction mixture was poured into an ice water, the solution was stirred, and then extracted with diethyl ether, then sequentially washed with an aqueous solution of 2N sodium hydroxide, water and brine, dried over anhydrous magnesium sulfate, then filtered through NH silica gel, and the solvent was evaporated in vacuo. The residue was washed with a hexane-diethyl ether system to provide the title compound (10.6 g).

$^1$H-NMR (400 MHz, CDCl$_3$); δ (ppm): 1.45 (s, 6H), 2.67 (s, 2H), 3.82 (s, 3H), 6.37 (d, 1H), 6.53 (dd, 2H), 7.79 (d, 1H).

Preparation Example 97

3-Bromo-7-methoxy-2,2-dimethyl-2H-chromene

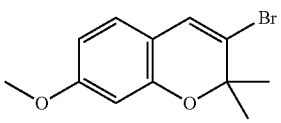

Synthesized from 7-methoxy-2,2-dimethylchroman-4-one (14.5 g) according to an analogous synthetic method to Preparation Example 95, the title compound (7.0 g) was obtained.

$^1$H-NMR (400 MHz, CDCl$_3$); δ (ppm): 1.54 (s, 6H), 3.76 (s, 3H), 6.37 (d, 1H), 6.42 (dd, 1H), 6.63 (s, 1H), 6.83 (d, 1H).

Example 69

5-Methoxy-2-(7-methoxy-2,2-dimethylchroman-3-yl)phenylamine

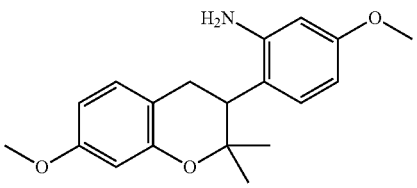

Synthesized from 3-bromo-7-methoxy-2,2-dimethyl-2H-chromene and 4-bromo-3-nitroanisole according to an analogous synthetic method to Preparation Example 107 described below, 7-methoxy-3-(4-methoxy-2-nitrophenyl)-2,2-dimethyl-2H-chromene (1.2 g) was used according to an analogous synthetic method to Example 30 to provide the title compound (988 mg).

$^1$H-NMR (400 MHz, CDCl$_3$); δ (ppm): 1.27 (s, 3H), 1.36 (s, 3H), 2.78 (dd, 1H), 3.00-3.10 (m, 2H), 3.73 (brs, 2H), 3.75 (s, 3H), 3.77 (s, 3H), 6.26 (d, 1H), 6.33 (dd, 1H), 6.41 (d, 1H), 6.46 (dd, 1H), 6.95 (d, 1H), 7.04 (d, 1H).

Example 70

2-(7-Methoxy-2,2-dimethylchroman-3-yl)phenylamine

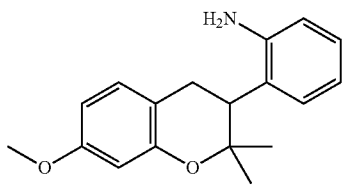 [SMILES: COc1ccc2c(c1)OC(C)(C)C(c1ccccc1N)C2]

Synthesized from 3-bromo-7-methoxy-2,2-dimethyl-2H-chromene and 1-bromo-2-nitrobenzene according to an analogous synthetic method to Preparation Example 107 described below, 7-methoxy-2,2-dimethyl-3-(2-nitrophenyl)-2H-chromene (790 mg) was used according to an analogous synthetic method to Example 30 to provide the title compound (580 mg).

$^1$H-NMR (400 MHz, CDCl$_3$); δ (ppm): 1.29 (s, 3H), 1.37 (s, 3H), 2.82 (dd, 1H), 3.05-3.15 (m, 2H), 3.72 (brs, 2H), 3.77 (s, 3H), 6.42 (d, 1H), 6.46 (dd, 1H), 6.71 (dd, 1H), 6.75 (dt, 1H), 6.95 (d, 1H), 7.05 (ddd, 1H), 7.15 (dd, 1H).

Preparation Example 98

1-Benzenesulfonyl-6-methoxy-2-(4-methoxy-2-nitrophenyl)-1H-indole

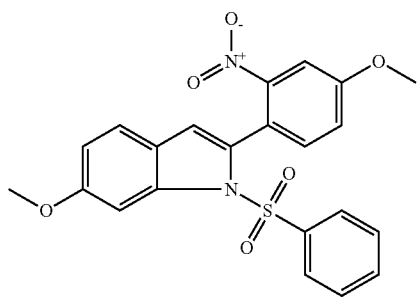

The title compound was synthesized by referring to *Tetrahedron*, 1994, 50 (6), 1899. A mixture of 1-benzenesulfonyl-6-methoxy-2-tributylstannyl-1H-indole (12.1 g), 4-bromo-3-nitroanisole (4.6 g), tetrakis(triphenylphosphine)palladium (0) (1.1 g), copper(I) iodide (760 mg) and toluene (90 ml) was stirred for 1 hour at 100° C. The reaction mixture was cooled to room temperature, NH silica gel (20 g) was added thereto, the solution was concentrated in vacuo, and the resulting residue was purified by NH silica gel column chromatography (hexane-ethyl acetate system) to provide the title compound (4.9 g).

$^1$H-NMR (400 MHz, CDCl$_3$); δ (ppm): 3.91 (s, 3H), 3.95 (s, 3H), 6.49 (s, 1H), 6.91 (d, 1H), 7.09 (d, 1H), 7.18 (d, 1H), 7.30-7.51 (m, 6H), 7.68 (s, 1H), 7.80 (s, 1H).

Preparation Example 99

6-Methoxy-2-(4-methoxy-2-nitrophenyl)-1H-indole

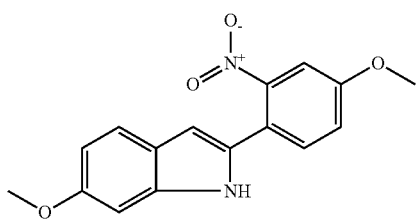

A mixture of 1-benzenesulfonyl-6-methoxy-2-(4-methoxy-2-nitrophenyl)-1H-indole (2.0 g), tetrabutylammonium fluoride (1.0 M solution in tetrahydrofuran) (11.4 ml) and tetrahydrofuran (40 ml) was stirred for 5 hours at 80° C. The reaction mixture was diluted with water, extracted with ethyl acetate, then washed with brine, dried over anhydrous magnesium sulfate, and the solvent was evaporated in vacuo. The residue was purified by NH silica gel column chromatography (hexane-ethyl acetate system) to provide the title compound (1.0 g).

$^1$H-NMR (400 MHz, CDCl$_3$); δ (ppm): 3.86 (s, 3H), 3.91 (s, 3H), 6.53 (s, 1H), 6.80 (d, 1H), 6.89 (s, 1H), 7.15 (d, 1H), 7.30 (s, 1H), 7.48 (d, 1H), 7.59 (d, 1H), 8.46 (brs, 1H).

Example 71

5-Methoxy-2-(6-methoxy-1-methyl-1H-indol-2-yl)phenylamine

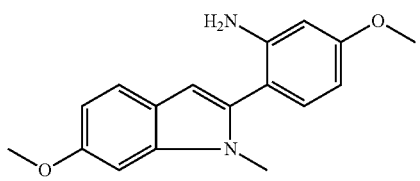

To a solution of 6-methoxy-2-(4-methoxy-2-nitrophenyl)-1H-indole (1.0 g) in N,N-dimethylformamide (10 ml) was added 60% sodium hydride (160 mg) on an ice bath. The solution was stirred for 20 minutes at room temperature, then methyl iodide (570 mg) was added dropwise thereto on an ice bath, and the solution was stirred for 2 hours at room temperature. The reaction mixture was diluted with water, extracted with ethyl acetate, then washed with brine, dried over anhydrous magnesium sulfate, and then the solvent was evaporated in vacuo. Obtained by purifying the residue by NH silica gel column chromatography (hexane-ethyl acetate system), the total amount of 6-methoxy-2-(4-methoxy-2-nitrophenyl)-1-methyl-1H-indole was used according to an analogous synthetic method to Example 22 to provide the title compound (720 mg).

¹H-NMR (400 MHz, CDCl₃); δ (ppm): 3.53 (s, 3H), 3.82 (s, 3H), 3.90 (s, 3H), 6.34 (s, 1H), 6.38-6.42 (m, 2H), 6.80-6.82 (m, 2H), 7.07 (d, 1H), 7.49 (d, 1H).

Example 72

Diethyl[5-methoxy-2-(6-methoxy-1-methyl-1H-indol-2-yl)phenyl]amine

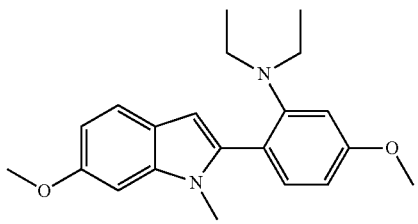

Synthesized from 5-methoxy-2-(6-methoxy-1-methyl-1H-indol-2-yl)phenylamine (200 mg) according to an analogous synthetic method to Example 786 described below, the title compound (110 mg) was obtained.

¹H-NMR (400 MHz, CDCl₃); δ (ppm): 0.88 (t, 6H), 2.93 (q, 4H), 3.49 (s, 3H), 3.85 (s, 3H), 3.90 (s, 3H), 6.34 (s, 1H), 6.54 (d, 1H), 6.60 (s, 1H), 6.77-6.80 (m, 2H), 7.22 (d, 1H), 7.48 (d, 1H).

Example 73

[2-(3-Chloro-6-methoxy-1-methyl-1H-indol-2-yl)-5-methoxyphenyl]diethylamine

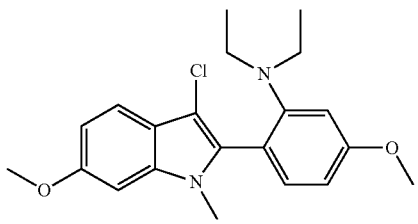

To a solution of diethyl[5-methoxy-2-(6-methoxy-1-methyl-1H-indol-2-yl)phenyl]amine (110 mg) in tetrahydrofuran (5 ml) was added N-chlorosuccinimide (50 mg), and the solution was stirred for 1 hour at room temperature. To the reaction solution was added a saturated aqueous solution of sodium bicarbonate, the solution was extracted with ethyl acetate, then washed with brine, dried over anhydrous magnesium sulfate, and then the solvent was evaporated in vacuo. The residue was purified by silica gel column chromatography (ethyl acetate-methanol system) to provide the title compound (96 mg).

¹H-NMR (400 MHz, CDCl₃); δ (ppm): 0.86 (t, 6H), 2.82-2.98 (m, 4H), 3.46 (s, 3H), 3.86 (s, 3H), 3.90 (s, 3H), 6.59 (d, 1H), 6.63 (s, 1H), 6.78 (s, 1H), 6.85 (d, 1H), 7.22 (d, 1H), 7.50 (d, 1H).

Example 74

3-Chloro-2-(2-diethylamino-4-hydroxyphenyl)-1-methyl-1H-indol-6-ol and 3-Chloro-2-(2-diethylamino-4-methoxyphenyl)-1-methyl-1H-indol-6-ol

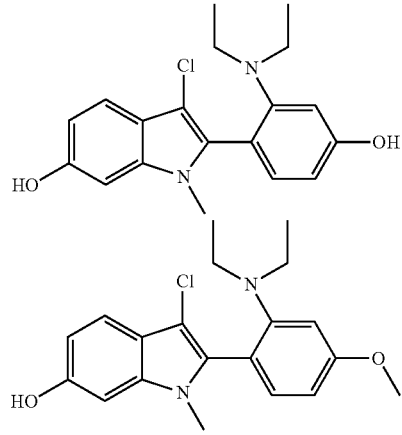

Synthesized from [2-(3-chloro-6-methoxy-1-methyl-1H-indol-2-yl)-5-methoxyphenyl]diethylamine (96 mg) according to an analogous synthetic method to Example 364 described below, 3-chloro-2-(2-diethylamino-4-hydroxyphenyl)-1-methyl-1H-indol-6-ol (37 mg) and 3-chloro-2-(2-diethylamino-4-methoxyphenyl)-1-methyl-1H-indol-6-ol (35 mg) were obtained. 3-Chloro-2-(2-diethylamino-4-hydroxyphenyl)-1-methyl-1H-indol-6-ol:

¹H-NMR (400 MHz, DMSO-d₆); δ (ppm): 0.77 (t, 6H), 2.71-2.86 (m, 4H), 3.33 (s, 3H), 6.43 (d, 1H), 6.51 (s, 1H), 6.64 (d, 1H), 6.74 (s, 1H), 6.96 (d, 1H), 7.23 (d, 1H), 9.21 (brs, 1H), 9.55 (brs, 1H).

ESI-Mass; 345 [M⁺+H]

3-Chloro-2-(2-diethylamino-4-methoxyphenyl)-1-methyl-1H-indol-6-ol

¹H-NMR (400 MHz, DMSO-d₆); δ (ppm): 0.77 (t, 6H), 2.74-2.90 (m, 4H), 3.33 (s, 3H), 3.78 (s, 3H), 6.59-6.67 (m, 3H), 6.75 (s, 1H), 7.01 (d, 1H), 7.25 (d, 1H), 9.24 (brs, 1H).

ESI-Mass; 359 [M⁺+H]

Example 75

5-Methoxy-2-(6-methoxybenzothiazol-2-yl)phenylamine

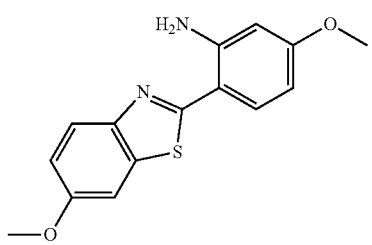

Synthesized from 2-chloro-6-methoxybenzothiazole and tributyl(4-methoxy-2-nitrophenyl)tin according to an analogous synthetic method to Preparation Example 77, to a suspension of the resulting 6-methoxy-2-(4-methoxy-2-nitrophenyl)benzothiazole (695 mg) in ethanol (10 ml) and concentrated hydrochloric acid (2 ml) was added tin(II) chloride dihydrate (1.3 g), and the solution was stirred for 7 hours at room temperature. The solution was neutralized with ammonia solution on an ice bath, then filtered through celite pad, extracted with ethyl acetate, then sequentially washed with water and brine, the solvent was evaporated in vacuo, the resulting solid was washed with a hexane-diethyl ether system to provide the title compound (475 mg).

$^1$H-NMR (400 MHz, CDCl$_3$); δ (ppm): 3.83 (s, 3H), 3.89 (s, 3H), 6.26 (s, 1H) 6.34 (dd, 1H), 6.40 (brs, 2H), 7.02 (dd, 1H), 7.32 (s, 1H), 7.56 (d, 1H), 7.80 (d, 1H).

Preparation Example 100

6-Methoxybenzo[b]thiophene

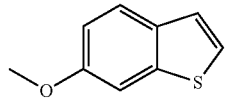

The title compound was synthesized by referring to *J. Med. Chem.*, 1989, 32, 2548. To a solution of 3-methoxybenzenethiol (26.9 g) in acetone (100 ml) was added potassium carbonate (27 g), then 2-bromo-1,1-diethoxyethane (29 ml) was added dropwise thereto followed by stirring overnight at room temperature. To the reaction solution was added acetone, the solution was filtered, the solvent was evaporated in vacuo, the resulting residue was purified by silica gel column chromatography (hexane-ethyl acetate system) to provide 1-(2,2-diethoxyethylsulfanyl)-3-methoxybenzene (39.1 g). To dichloromethane (2 l) was added boron trifluoride diethyl ether complex (12.7 ml) under a nitrogen atmosphere, then a solution of 1-(2,2-diethoxyethylsulfanyl)-3-methoxybenzene (25.6 g) in dichloromethane (200 ml) was added dropwise over 1.5 hours, the solution was stirred for 40 minutes at room temperature, then a saturated aqueous solution of sodium carbonate (1 l) was added thereto followed by stirring for 1 hour at room temperature. The solution was extracted with dichloromethane, then dried over anhydrous magnesium sulfate, the solvent was evaporated in vacuo, and the resulting residue was purified by silica gel column chromatography (hexane-ethyl acetate system) to provide the title compound (10.8 g).

$^1$H-NMR (400 MHz, CDCl$_3$); δ (ppm): 3.88 (s, 3H), 7.00 (dd, 1H), 7.23-7.27 (m, 2H), 7.35 (d, 1H), 7.69 (d, 1H).

Example 76

5-Methoxy-2-(6-methoxybenzo[b]thiophen-2-yl)phenylamine

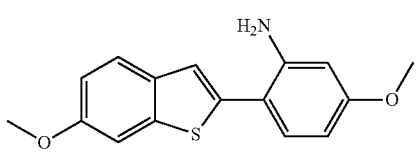

Synthesized from 6-methoxybenzo[b]thiophene according to an analogous synthetic method to Preparation Example 78, (6-methoxybenzo[b]thiophen-2-yl)boronic acid (3.2 g) and 4-bromo-3-nitroanisole (3.4 g) were used according to an analogous synthetic method to Preparation Example 79 to provide 6-methoxy-2-(4-methoxy-2-nitrophenyl)benzo[b]thiophene (1.7 g). Synthesized from this compound (1.9 g) according to an analogous synthetic method to Example 22, the title compound (1.6 g) was obtained.

$^1$H-NMR (400 MHz, CDCl$_3$); δ (ppm): 3.80 (s, 3H), 3.88 (s, 3H), 3.90-4.10 (brs, 2H), 6.33 (d, 1H), 6.40 (dd, 1H), 6.99 (dd, 1H), 7.24 (s, 1H), 7.25 (d, 1H), 7.31 (d, 1H), 7.63 (d, 1H).

Preparation Example 101

5-Methoxybenzo[b]thiophene

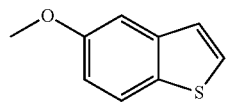

To a solution of 4-bromobenzenethiol (24.7 g) in acetone (100 ml) was added potassium carbonate (18.5 g), then 2-bromo-1,1-diethoxyethane (19.5 ml) was added dropwise thereto, the solution was stirred overnight at room temperature, then acetone was added thereto. The solution was filtered, and the solvent was evaporated in vacuo. The residue was purified by silica gel column chromatography (hexane-ethyl acetate system). To a solution of the resulting 1-bromo-4-(2,2-diethoxyethylsulfanyl)benzene (32.5 g) in chlorobenzene (350 ml) was added polyphosphoric acid (60 ml), and then the solution was stirred for 2 hours at 140° C. The reaction mixture was poured into an ice, extracted with ethyl acetate, then sequentially washed with aqueous ammonia, water and brine, dried over anhydrous magnesium sulfate, the solvent was evaporated in vacuo, the resulting residue was purified by silica gel column chromatography (hexane) to provide 5-bromobenzo[b]thiophene (13.7 g). By referring to the synthetic method of *Tetrahedron Lett.*, 1993, 34, 1007, to 5-bromobenzo[b]thiophene (13.7 g) was added sodium methoxide (28% solution in methanol) (200 ml). Copper(I) bromide (13.5 g) and ethyl acetate (40 ml) were sequentially added thereto followed by stirring for 4.5 hours at 80° C. Ethyl acetate and water were sequentially added thereto, the solution was stirred, then filtered through celite pad, extracted with ethyl acetate, then sequentially washed with water and brine, dried over anhydrous magnesium sulfate, the solvent was evaporated in vacuo, and the resulting residue was purified by silica gel column chromatography (hexane-ethyl acetate system) to provide the title compound (9.2 g).

$^1$H-NMR (400 MHz, CDCl$_3$); δ (ppm): 3.87 (s, 3H), 7.00 (dd, 1H), 7.26 (d, 1H), 7.28 (d, 1H), 7.44 (d, 1H), 7.73 (d, 1H).

Example 77

5-Methoxy-2-(5-methoxybenzo[b]thiophen-2-yl)phenylamine

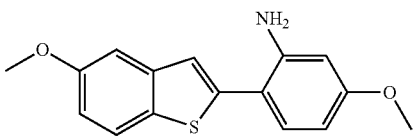

Synthesized from 5-methoxybenzo[b]thiophene according to an analogous synthetic method to Preparation Example 78, (5-methoxybenzo[b]thiophen-2-yl)boronic acid (6.2 g) and 4-bromo-3-nitroanisole (5.5 g) were used according to an analogous synthetic method to Preparation Example 79 to provide 5-methoxy-2-(4-methoxy-2-nitrophenyl)benzo[b]thiophene (2.7 g). The total amount of this compound was used according to an analogous synthetic method to Example 22 to provide the title compound (2.3 g).

$^1$H-NMR (400 MHz, CDCl$_3$); δ (ppm): 3.81 (s, 3H), 3.88 (s, 3H), 4.14 (brs, 2H), 6.33 (d, 1H), 6.40 (dd, 1H), 6.97 (dd, 1H), 7.22 (d, 1H), 7.25-7.28 (m, 2H), 7.68 (d, 1H).

Preparation Example 102

5-(tert-Butyldimethylsilyloxy)-2-[1-(tert-butyldimethylsilyloxy)indan-5-yl]phenylamine

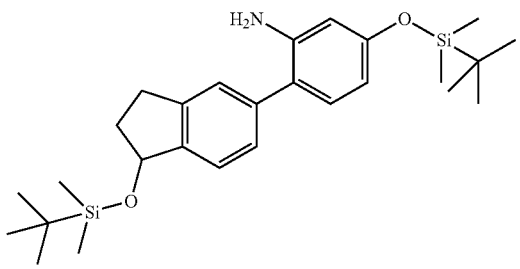 [SMILES: CC(C)(C)[Si](C)(C)Oc1ccc(-c2ccc3c(c2)CCC3O[Si](C)(C)C(C)(C)C)c(N)c1]

Synthesized from 4-bromo-3-nitroanisole according to an analogous synthetic method to Example 364 described below, 4-bromo-3-nitrophenol (2.0 g) was used according to an analogous synthetic method to Example 201 described below to provide (4-bromo-3-nitrophenoxy)tert-butyldimethylsilane (2.1 g). To a solution of 5-bromo-1-indanone (1.3 g) in methanol (25 ml) was added sodium borohydride (350 mg) on an ice bath, and the solution was stirred for 40 minutes. A saturated aqueous solution of ammonium chloride was added thereto followed by stirring. The solution was extracted with ethyl acetate, then sequentially washed with water and brine, dried over anhydrous magnesium sulfate, and then the solvent was evaporated in vacuo to provide 5-bromoindan-1-ol (1.4 g). Synthesized from 5-bromoindane-1-ol according to an analogous synthetic method to Example 201 described below, a solution of (5-bromoindan-1-yloxy)tert-butyldimethylsilane (1.9 g) in tetrahydrofuran (30 ml) was cooled at −78° C., then n-butyllithium (2.46 M solution in hexane) (2.5 ml) was added dropwise thereto over 20 minutes under a nitrogen atmosphere, and the solution was stirred for 40 minutes. Trimethyl borate (10.75 ml) was added thereto followed by stirring for 2 hours while warming from −78° C. to room temperature, then water (0.5 ml) was added thereto followed by stirring for 2 hours at room temperature. The solution was neutralized with an aqueous solution of 10% citric acid, extracted with ethyl acetate, then sequentially washed with water and brine, dried over anhydrous magnesium sulfate, then the solvent was evaporated in vacuo. To the resulting residue was added diethyl ether (25 ml), 1,3-propanediol (0.43 ml) was added dropwise thereto, and the reaction mixture was stirred for 25 minutes at room temperature. Anhydrous magnesium sulfate was added thereto, the solution was stirred at room temperature for 40 minutes, then filtered through silica gel, and the solvent was evaporated in vacuo to provide 2-[1-(tert-butyldimethylsilyloxy)indan-5-yl][1,3,2]dioxaborinane (1.8 g). To a solution of (4-bromo-3-nitrophenoxy)tert-butyldimethylsilane (1.2 g) and 2-[1-(tert-butyldimethylsilyloxy)indan-5-yl][1,3,2]dioxaborinane (1.8 g) in N,N-dimethylformamide (30 ml) were sequentially added cesium carbonate (2.4 g) and tetrakis(triphenylphosphine)palladium(0) (210 mg) under a nitrogen atmosphere, and the solution stirred overnight at 80° C. Ethyl acetate was added thereto followed by stirring. The solution was filtered through celite pad, extracted with ethyl acetate, then sequentially washed with water and brine, dried over anhydrous magnesium sulfate, then the solvent was evaporated in vacuo, the resulting residue was purified by silica gel column chromatography (hexane-ethyl acetate system) to provide 4-[1-(tert-butyldimethylsilyloxy)indan-5-yl]-3-nitrophenol (1.4 g). This compound was used according to an analogous synthetic method to Example 201 described below to provide 1-(tert-butyldimethylsilyloxy)-5-[4-(tert-butyldimethyl silyloxy)-2-nitrophenyl]indan (1.6 g), then according to an analogous synthetic method to Example 57 described above, the title compound (1.2 g) was obtained.

$^1$H-NMR (400 MHz, CDCl$_3$); δ (ppm): 0.19 (s, 3H), 0.22 (s, 3H), 0.24 (s, 6H), 0.99 (s, 9H), 1.01 (s, 9H), 1.92-2.02 (m, 1H), 2.44-2.53 (m, 1H), 2.76-2.86 (m, 1H), 2.97-3.06 (m, 1H), 3.72 (brs, 2H), 5.32 (t, 1H), 6.28 (d, 1H), 6.32 (dd, 1H), 6.96 (d, 1H), 7.23-7.28 (m, 3H).

Example 78

2-[1-(tert-Butyldimethylsilyloxy)indan-5-yl]-5-methoxyphenylamine

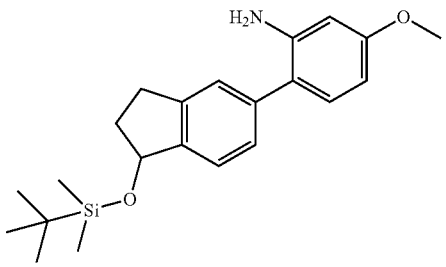 [SMILES: COc1ccc(-c2ccc3c(c2)CCC3O[Si](C)(C)C(C)(C)C)c(N)c1]

Synthesized from 5-bromo-1-indanone and tributyl(4-methoxy-2-nitrophenyl)tin according to an analogous synthetic method to Preparation Example 77, to a suspension of the resulting 5-(4-methoxy-2-nitrophenyl)indan-1-one (1.3 g) in methanol (40 ml) was added sodium borohydride (350 mg) on an ice bath, and the solution was stirred for 2.5 hours. A saturated aqueous solution of ammonium chloride was added thereto followed by stirring. The solution was extracted with ethyl acetate, then sequentially washed with water and brine, dried over anhydrous magnesium sulfate, and then the solvent was evaporated in vacuo. Obtained by purifying the residue by silica gel column chromatography (hexane-ethyl acetate system), 5-(4-methoxy-2-nitrophenyl)indan-1-ol (1.1 g) was used according to an analogous synthetic method to Example 201 described below to provide tert-butyl[5-(4-methoxy-2-nitrophenyl)indan-1-yloxy]dimethylsilane (910 mg). The total amount of this compound was used according to an analogous synthetic method to Example 57 to provide the title compound (729 mg).

$^1$H-NMR (400 MHz, CDCl$_3$); δ (ppm): 0.18 (s, 3H), 0.20 (s, 3H), 0.97 (s, 9H), 1.91-2.05 (m, 1H), 2.44-2.51 (m, 1H), 2.80 (dt, 1H), 3.01 (ddd, 1H), 3.77 (brs, 2H), 3.80 (s, 3H), 5.30 (t, 1H), 6.32 (d, 1H), 6.39 (dd, 1H), 7.02 (d, 1H), 7.23-7.29 (m, 2H), 7.36 (d, 1H).

Preparation Example 103

1-Benzyl-3-(4-methoxy-2-nitrophenyl)pyrrolidine

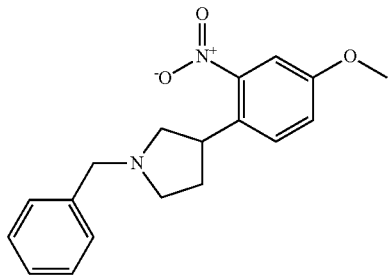

The title compound was synthesized by referring to *Chem. Pharm. Bull.*, 1985, 33, 2762. A suspension of 4-bromo-3-nitroanisole (1.7 g), tributyl(vinyl)tin (2.5 g) and tetrakis(triphenylphosphine)palladium(0) (270 mg) in toluene (30 ml) was stirred under a nitrogen atmosphere for 4 hours at 120° C. The solvent was evaporated in vacuo, the resulting residue was purified by silica gel column chromatography (hexane-ethyl acetate system). To a solution of the resulting 4-methoxy-2-nitro-1-vinylbenzene (1.3 g) in dichloromethane (15 ml) was added trifluoroacetic acid (0.2 ml), a solution of N-benzyl-N-(methoxymethyl)-N-trimethylsilylmethylamine (2.1 g) in dichloromethane (2.5 ml) was added dropwise thereto followed by stirring at room temperature for 1 week. The solution was then neutralized with a saturated aqueous solution of sodium bicarbonate. The solution was extracted with ethyl acetate, then sequentially washed with water and brine, dried over anhydrous magnesium sulfate, and then the solvent was evaporated in vacuo. The residue was purified by silica gel column chromatography (chloroform-methanol system) to provide the title compound (650 mg).

$^1$H-NMR (400 MHz, CDCl$_3$); δ (ppm): 1.81 (ddd, 1H), 2.37-2.46 (m, 1H), 2.54 (m, 1H), 2.70 (dd, 1H), 2.81 (dd, 1H), 2.90 (ddd, 1H), 3.66 (dd, 2H), 3.66-3.72 (m, 1H), 3.82 (s, 3H), 7.09 (dd, 1H), 7.18 (d, 1H), 7.21-7.36 (m, 5H), 7.63 (d, 1H).

Preparation Example 104

3-(4-Methoxy-2-nitrophenyl)pyrrolidine

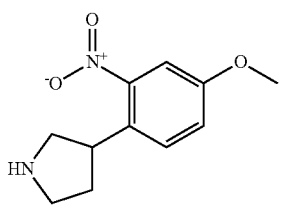

By referring to the synthetic method of *J. Org. Chem.*, 1984, 49, 2081, to a solution of 1-benzyl-3-(4-methoxy-2-nitrophenyl)pyrrolidine (647 mg) in 1,2-dichloroethane (15 ml) was added chloroformic acid 1-chloroethyl ester (0.33 ml) on an ice bath, the solution was stirred for 2 hours at 80° C., and then stirred for 2.5 hours at 100° C. Methanol (5 ml) was added thereto, the solution was stirred for 3 hours at 80° C., then triethylamine (1 ml) and di-tert-butyl dicarbonate (0.7 ml) were sequentially added thereto on an ice bath, and the solution was stirred for 40 minutes at room temperature. Water was added thereto followed by stirring. The solution was extracted with ethyl acetate, then sequentially washed with water and brine, dried over anhydrous magnesium sulfate, and then the solvent was evaporated in vacuo. Obtained by purifying the residue by silica gel column chromatography (hexane-ethyl acetate system), 3-(4-methoxy-2-nitrophenyl)pyrrolidine-1-carboxylic acid tert-butyl ester (436 mg) was dissolved in trifluoroacetic acid (2 ml), the solution was stirred for 1 hour at room temperature, and neutralized with ammonia solution. The solution was extracted with ethyl acetate, then sequentially washed with water and brine, dried over anhydrous magnesium sulfate, and then the solvent was evaporated in vacuo to provide the title compound (207 mg).

$^1$H-NMR (400 MHz, CDCl$_3$); δ (ppm): 1.80-1.87 (m, 1H), 2.22-2.32 (m, 1H), 2.85 (dd, 1H), 3.06-3.20 (m, 2H), 3.40 (dd, 1H), 3.56 (ddd, 1H), 3.84 (s, 3H), 7.09 (dd, 1H), 7.24 (d, 1H), 7.39 (d, 1H).

Example 79

5-Methoxy-2-[1-(3-methoxyphenyl)pyrrolidin-3-yl]phenylamine

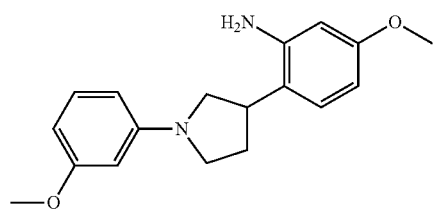

Synthesized from 3-(4-methoxy-2-nitrophenyl)pyrrolidine and 3-bromoanisole according to an analogous synthetic method to Example 116 described below, 3-(4-methoxy-2-nitrophenyl)-1-(3-methoxyphenyl)pyrrolidine (156 mg) was used according to an analogous synthetic method to Example 22 to provide the title compound (145 mg).

$^1$H-NMR (400 MHz, CDCl$_3$); δ (ppm): 2.09-2.18 (m, 1H), 2.27-2.37 (m, 1H), 3.33-3.43 (m, 3H), 3.45-3.51 (m, 1H), 3.61-3.69 (m, 1H), 3.75 (s, 3H), 3.77 (brs, 2H), 3.80 (s, 3H), 6.15 (t, 1H), 6.23 (dd, 1H), 6.26-6.32 (m, 3H), 6.98 (d, 1H), 7.14 (t, 1H).

Example 80

2-[1-(3-Methoxyphenyl)pyrrolidin-3-yl]phenylamine

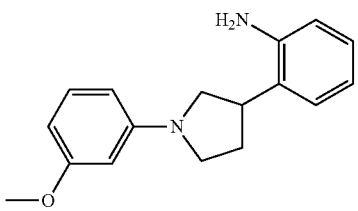 [SMILES: COc1cccc(N2CCC(c3ccccc3N)C2)c1]

Synthesized from 1-bromo-2-nitrobenzene according to an analogous synthetic method to Preparation Example 103, 1-benzyl-3-(2-nitrophenyl)pyrrolidine (1.0 g) was used according to an analogous synthetic method to Preparation Example 104 to provide 3-(2-nitrophenyl)pyrrolidine (184 mg). Synthesized from 3-(2-nitrophenyl)pyrrolidine and 3-bromoanisole according to an analogous synthetic method to Example 116 described below, 1-(3-methoxyphenyl)-3-(2-nitrophenyl)pyrrolidine (141 mg) was used according to an analogous synthetic method to Example 22 to provide the title compound (126 mg).

¹H-NMR (400 MHz, CDCl₃); δ (ppm): 2.12-2.21 (m, 1H), 2.32-2.40 (m, 1H), 3.35-3.53 (m, 4H), 3.68 (dd, 1H), 3.75 (brs, 2H), 3.80 (s, 3H), 6.16 (t, 1H), 6.24 (dd, 1H), 6.28 (dd, 1H), 6.71 (dd, 1H), 6.74 (dt, 1H), 7.05 (dt, 1H), 7.08 (d, 1H), 7.15 (t, 1H).

Preparation Example 105

6-Benzyloxy-3,4-dihydro-2H-naphthalen-1-one

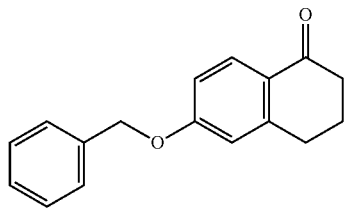 [SMILES: O=C1CCCc2cc(OCc3ccccc3)ccc21]

A suspension of 6-methoxy-1-tetralone (99 g) in 48% hydrobromic acid (800 ml) was stirred overnight at 120° C. The reaction mixture was poured into ice water, the resulting solid was sequentially washed with water and hexane-diethyl ether system. To a solution of the resulting 6-hydroxy-3,4-dihydro-2H-naphthalen-1-one (76 g) in N,N-dimethylformamide (400 ml) were sequentially added potassium carbonate (76 g) and benzyl bromide (59 ml), and the solution was stirred for 4 hours at room temperature. The reaction mixture was poured into water, the resulting solid was sequentially washed with water and hexane-diethyl ether system to provide the title compound (110 g).

¹H-NMR (400 MHz, CDCl₃); δ (ppm): 2.12 (pent, 2H), 2.61 (t, 2H), 2.92 (t, 2H), 5.12 (s, 2H), 6.79 (d, 1H), 6.90 (dd, 1H), 7.32-7.45 (m, 5H), 8.01 (d, 1H).

Preparation Example 106

7-Benzyloxy-3-bromo-1,2-dihydronaphthalene

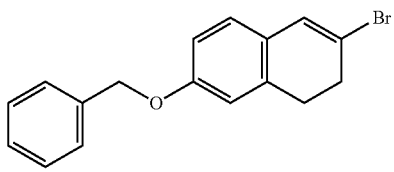 [SMILES: BrC1=Cc2ccc(OCc3ccccc3)cc2CC1]

The title compound was synthesized by referring to *J. Org. Chem.*, 1984, 49 (22), 4226. To a suspension of 6-benzyloxy-3,4-dihydro-2H-naphthalen-1-one (200 g) in diethyl ether (2 l) was added dropwise bromine (60 ml) on an ice bath, and the solution was stirred overnight at room temperature. The reaction mixture was poured into ice water, extracted with diethyl ether, then sequentially washed with a saturated aqueous solution of sodium bicarbonate, water and brine, dried over anhydrous magnesium sulfate, then filtered through NH silica gel, the solvent was evaporated in vacuo. To the resulting 6-benzyloxy-2-bromo-3,4-dihydro-2H-naphthalen-1-one (250 g) was added ethanol (2.5 l), the solution was stirred, sodium borohydride (25 g) was added thereto on an ice bath followed by stirring overnight at room temperature. The reaction mixture was poured into ice water, and the resulting solid was washed with water to provide 6-benzyloxy-2-bromo-1,2,3,4-tetrahydronaphthalen-1-ol (290 g). To a suspension of this compound (260 g) in toluene (800 ml) was added p-toluenesulfonic acid monohydrate (6.0 g), and the solution was refluxed for 2 hours. The reaction mixture was poured into ice water, extracted with ethyl acetate, then sequentially washed with water and brine, dried over anhydrous magnesium sulfate, then filtered through NH silica gel, and the solvent was evaporated in vacuo. The residue was purified by NH silica gel column chromatography (hexane-ethyl acetate system) to provide the title compound (34 g).

¹H-NMR (400 MHz, CDCl₃); δ (ppm): 2.73 (t, 2H), 2.92 (t, 2H), 5.04 (s, 2H), 6.72-6.76 (m, 3H), 6.90 (d, 1H), 7.30-7.44 (m, 5H).

Preparation Example 107

7-Benzyloxy-3-(4-methoxy-2-nitrophenyl)-1,2-dihydronaphthalene

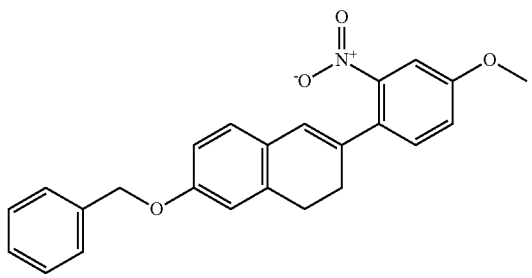

The title compound was synthesized by referring to *Tetrahedron Lett.*, 1993, 34 (21), 3421. A suspension of 7-benzyloxy-3-bromo-1,2-dihydronaphthalene (38 g), 4-bromo-3-nitroanisole (59 g), dichlorobis(triphenylphosphine)palladium (II) (4.5 g) and copper (32 g) in dimethyl sulfoxide (400 ml) was stirred under a nitrogen atmosphere at 120° C. for 1 hour. Ethyl acetate and water was added thereto, the solution was filtered through celite pad, extracted with ethyl acetate, then sequentially washed with aqueous ammonia, water and brine, dried over anhydrous magnesium sulfate, and then the solvent was evaporated in vacuo. The residue was purified by silica gel column chromatography (hexane-ethyl acetate system) to provide the title compound (19 g).

¹H-NMR (400 MHz, CDCl₃); δ (ppm): 2.45 (t, 2H), 2.93 (t, 2H), 3.88 (s, 3H), 5.08 (s, 2H), 6.43 (s, 1H), 6.78 (dd, 1H), 6.81 (s, 1H), 7.01 (d, 1H), 7.11 (dd, 1H), 7.30-7.46 (m, 7H).

Example 81

6-(2-Amino-4-methoxyphenyl)-5,6,7,8-tetrahydronaphthalen-2-ol

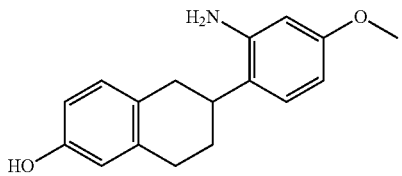 [SMILES: COc1ccc(C2CCc3cc(O)ccc3C2)c(N)c1]

Synthesized from 7-benzyloxy-3-(4-methoxy-2-nitrophenyl)-1,2-dihydronaphthalene (19 g) according to an analogous synthetic method to Example 30, the title compound (8.0 g) was obtained.

$^1$H-NMR (400 MHz, DMSO-d$_6$); δ (ppm): 1.68 (ddd, 1H), 1.81-1.89 (m, 1H), 2.52 (dd, 1H), 2.65-2.90 (m, 4H), 3.61 (s, 3H), 4.89 (s, 2H), 6.09 (dd, 1H), 6.20 (d, 1H), 6.45-6.52 (m, 2H), 6.83 (d, 1H), 6.85 (d, 1H), 8.97 (s, 1H).

Example 82

6-(4-Methoxy-2-methylaminophenyl)-5,6,7,8-tetrahydronaphthalen-2-ol

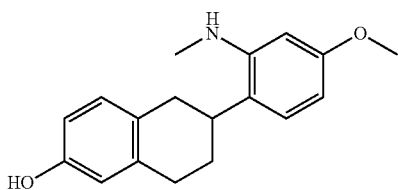 [SMILES: CNc1cc(OC)ccc1C1CCc2cc(O)ccc2C1]

A mixture of 6-(2-amino-4-methoxyphenyl)-5,6,7,8-tetrahydronaphthalen-2-ol (800 mg) and formic acid (8 ml) was refluxed overnight. The reaction mixture was diluted with a saturated aqueous solution of sodium bicarbonate, extracted with ethyl acetate, then washed with brine, dried over anhydrous magnesium sulfate, then the solvent was evaporated in vacuo. Synthesized from the resulting residue according to an analogous synthetic method to Example 337 described below, the title compound (730 mg) was obtained.

$^1$H-NMR (400 MHz, CDCl$_3$); δ (ppm): 1.85-1.99 (m, 1H), 2.01-2.10 (m, 1H), 2.65-3.00 (m, 5H), 2.86 (s, 3H), 3.80 (s, 3H), 4.70 (brs, 1H), 6.23 (s, 1H), 6.28 (d, 1H), 6.58-6.63 (m, 2H), 6.94 (d, 1H), 7.01 (d, 1H).

Example 83

Pivalic acid 6-(4-methoxy-2-methylaminophenyl)-5,6,7,8-tetrahydronaphthalen-2-yl ester

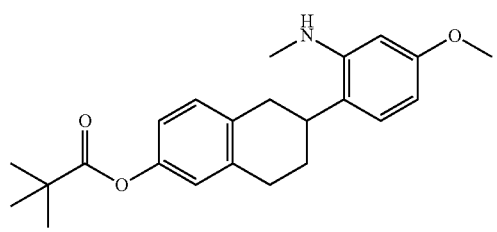 [SMILES: CNc1cc(OC)ccc1C1CCc2cc(OC(=O)C(C)(C)C)ccc2C1]

Synthesized from 6-(4-methoxy-2-methylaminophenyl)-5,6,7,8-tetrahydronaphthalen-2-ol (730 mg) according to an analogous synthetic method to Example 85 described below, the title compound (810 mg) was obtained.

$^1$H-NMR (400 MHz, CDCl$_3$); δ (ppm): 1.36 (s, 9H), 1.89-2.00 (m, 1H), 2.04-2.14 (m, 1H), 2.72-2.84 (m, 2H), 2.87 (s, 3H), 2.91-3.06 (m, 3H), 3.81 (s, 3H), 6.25 (s, 1H), 6.29 (d, 1H), 6.78-6.82 (m, 2H), 7.02 (d, 1H), 7.07 (d, 1H).

Example 84

6-(2-Ethylamino-4-methoxyphenyl)-5,6,7,8-tetrahydronaphthalen-2-ol

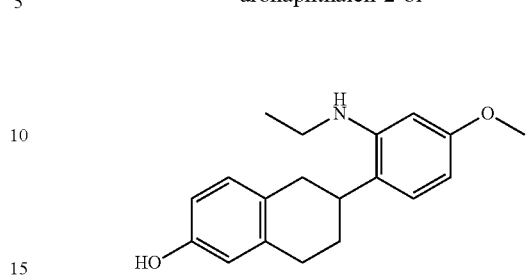

Synthesized from 6-(2-amino-4-methoxyphenyl)-5,6,7,8-tetrahydronaphthalen-2-ol (1.5 g) according to an analogous synthetic method to Example 36, the title compound (1.0 g) was obtained.

$^1$H-NMR (400 MHz, CDCl$_3$); δ (ppm): 1.27 (t, 3H), 1.88-1.98 (m, 1H), 2.04-2.11 (m, 1H), 2.70 (dd, 1H), 2.76-2.84 (m, 1H), 2.87-3.01 (m, 3H), 3.17 (q, 2H), 3.61 (brs, 1H), 3.79 (s, 3H), 4.53 (s, 1H), 6.24 (d, 1H), 6.27 (dd, 1H), 6.60-6.64 (m, 2H), 6.96 (d, 1H), 7.01 (d, 1H).

ESI-Mass; 298 [M$^+$+H]

Example 85

Pivalic Acid 6-(2-ethylamino-4-methoxyphenyl)-5,6,7,8-tetrahydronaphthalen-2-yl Ester

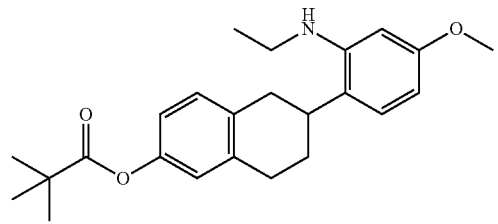 [SMILES: CCNc1cc(OC)ccc1C1CCc2cc(OC(=O)C(C)(C)C)ccc2C1]

To a solution of 6-(2-ethylamino-4-methoxyphenyl)-5,6,7,8-tetrahydronaphthalen-2-ol (500 mg) in tetrahydrofuran (15 ml) was added 60% sodium hydride (75 mg) under a nitrogen atmosphere, the solution was stirred for 30 minutes at room temperature, then 2,2-dimethyl-1-(2-thioxothiazolidin-3-yl)propan-1-one (380 mg) was added thereto on an ice bath followed by stirring for 25 minutes. A saturated aqueous solution of ammonium chloride was added thereto, the solution was stirred, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (640 mg).

$^1$H-NMR (400 MHz, CDCl$_3$); δ (ppm): 1.28 (t, 3H), 1.35 (s, 9H), 1.89-2.00 (m, 1H), 2.04-2.12 (m, 1H), 2.72-2.86 (m, 2H), 2.93-3.05 (m, 3H), 3.17 (q, 2H), 3.60 (brs, 1H), 3.79 (s, 3H), 6.24 (d, 1H), 6.27 (dd, 1H), 6.79 (dd, 1H), 6.81 (s, 1H), 7.01 (d, 1H), 7.07 (d, 1H).

Example 86

Pivalic Acid (S)- and (R)-6-(2-ethylamino-4-methoxyphenyl)-5,6,7,8-tetrahydronaphthalen-2-yl Ester

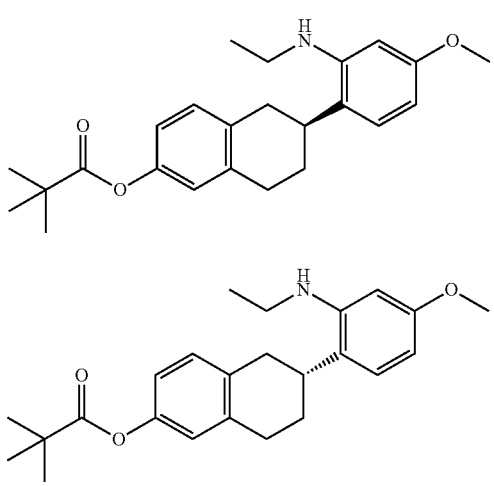

Optical resolution was carried out according to Example 188 described below to provide pivalic acid (S)-6-(2-ethylamino-4-methoxyphenyl)-5,6,7,8-tetrahydronaphthalen-2-yl ester exhibiting a short retention time and pivalic acid (R)-6-(2-ethylamino-4-methoxyphenyl)-5,6,7,8-tetrahydronaphthalen-2-yl ester exhibiting a long retention time.

Pivalic acid (S)-6-(2-ethylamino-4-methoxyphenyl)-5,6,7,8-tetrahydronaphthalen-2-yl ester:

retention time: 11.8 minutes

Pivalic acid (R)-6-(2-ethylamino-4-methoxyphenyl)-5,6,7,8-tetrahydronaphthalen-2-yl ester:

retention time: 13.9 minutes

Example 87

6-(4-Methoxy-2-propylaminophenyl)-5,6,7,8-tetrahydronaphthalen-2-ol

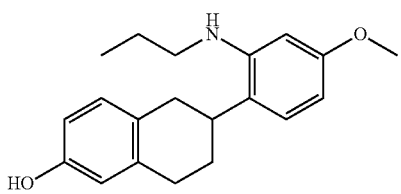 [SMILES: CCCNc1cc(OC)ccc1C1CCc2cc(O)ccc2C1]

Synthesized from 6-(2-amino-4-methoxyphenyl)-5,6,7,8-tetrahydronaphthalen-2-ol (500 mg) and propionic anhydride (1 ml) according to an analogous synthetic method to Example 36, the title compound (270 mg) was obtained.

$^1$H-NMR (400 MHz, CDCl$_3$); δ (ppm): 1.00 (t, 3H), 1.62-1.69 (m, 2H), 1.88-1.99 (m, 1H), 2.05-2.11 (m, 1H), 2.67-3.15 (m, 7H), 3.71 (brs, 1H), 3.79 (s, 3H), 4.60 (s, 1H), 6.22-6.29 (m, 2H), 6.60-6.68 (m, 2H), 6.92-7.40 (m, 2H).

Example 88

Pivalic Acid 6-(4-methoxy-2-propylaminophenyl)-5,6,7,8-tetrahydronaphthalen-2-yl Ester

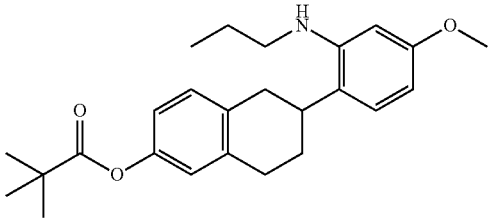 [SMILES: CCCNc1cc(OC)ccc1C1CCc2cc(OC(=O)C(C)(C)C)ccc2C1]

Synthesized from 6-(4-methoxy-2-propylaminophenyl)-5,6,7,8-tetrahydronaphthalen-2-ol (110 mg) according to an analogous synthetic method to Example 85, the title compound (120 mg) was obtained.

$^1$H-NMR (400 MHz, CDCl$_3$); δ (ppm): 1.01 (t, 3H), 1.36 (s, 9H), 1.63-1.70 (m, 2H), 1.90-1.99 (m, 1H), 2.07-2.13 (m, 1H), 2.74-3.14 (m, 7H), 3.70 (brs, 1H), 3.80 (s, 3H), 6.24-6.30 (m, 2H), 6.78-6.84 (m, 2H), 7.02 (d, 1H), 7.08 (d, 1H).

Example 89

6-(2-Isopropylamino-4-methoxyphenyl)-5,6,7,8-tetrahydronaphthalen-2-ol

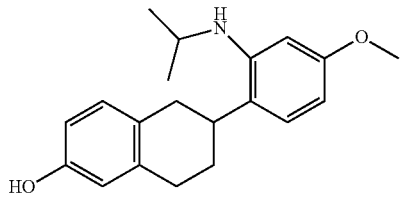 [SMILES: COc1ccc(C2CCc3cc(O)ccc3C2)c(NC(C)C)c1]

Synthesized from 6-(2-amino-4-methoxyphenyl)-5,6,7,8-tetrahydronaphthalen-2-ol (1.4 g) and acetone (1.5 ml) according to an analogous synthetic method to Example 38, the title compound (1.2 g) was obtained.

$^1$H-NMR (400 MHz, CDCl$_3$); δ (ppm): 1.18-1.25 (m, 6H), 1.85-1.96 (m, 1H), 2.04-2.10 (m, 1H), 2.66-2.81 (m, 2H), 2.85-2.98 (m, 3H), 3.53 (brs, 1H), 3.59-3.68 (m, 1H), 3.78 (s, 3H), 4.61 (brs, 1H), 6.22-6.27 (m, 2H), 6.58-6.65 (m, 2H), 6.96 (d, 1H), 7.01 (d, 1H).

Example 90

Pivalic Acid 6-(2-isopropylamino-4-methoxyphenyl)-5,6,7,8-tetrahydronaphthalen-2-yl Ester

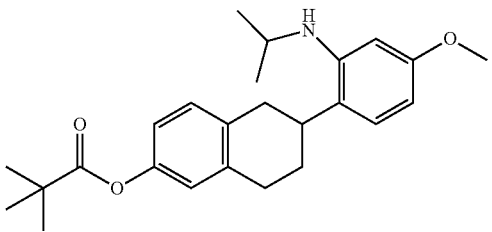 [SMILES: COc1ccc(C2CCc3cc(OC(=O)C(C)(C)C)ccc3C2)c(NC(C)C)c1]

Synthesized from 6-(2-isopropylamino-4-methoxyphenyl)-5,6,7,8-tetrahydronaphthalen-2-ol (1.2 g) according to an analogous synthetic method to Example 85, the title compound (1.4 g) was obtained.

¹H-NMR (400 MHz, CDCl₃); δ (ppm): 1.20-1.25 (m, 6H), 1.35 (s, 9H), 1.87-1.98 (m, 1H), 2.06-2.12 (m, 1H), 2.71-2.84 (m, 2H), 2.90-3.04 (m, 3H), 3.52 (brs, 1H), 3.59-3.69 (m, 1H), 3.78 (s, 3H), 6.23-6.28 (m, 2H), 6.78-6.83 (m, 2H), 7.00 (d, 1H), 7.07 (d, 1H).

Example 91

Pivalic acid (S)- and (R)-6-(2-isopropylamino-4-methoxyphenyl)-5,6,7,8-tetrahydronaphthalen-2-yl Ester

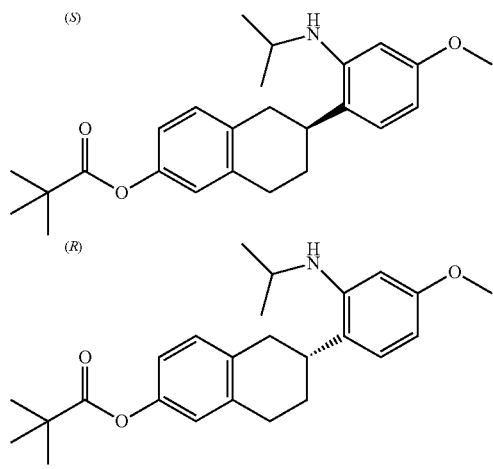

Optical resolution was carried out according to Example 188 described below to provide pivalic acid (S)-6-(2-isopropylamino-4-methoxyphenyl)-5,6,7,8-tetrahydronaphthalen-2-yl ester exhibiting a short retention time and pivalic acid (R)-6-(2-isopropylamino-4-methoxyphenyl)-5,6,7,8-tetrahydronaphthalen-2-yl ester exhibiting a long retention time.
Pivalic acid (S)-6-(2-isopropylamino-4-methoxyphenyl)-5,6,7,8-tetrahydronaphthalen-2-yl ester:
  retention time: 9.9 minutes
Pivalic acid (R)-6-(2-isopropylamino-4-methoxyphenyl)-5,6,7,8-tetrahydronaphthalen-2-yl ester:
  retention time: 11.5 minutes

Example 92

6-(2-Ethylaminophenyl)-5,6,7,8-tetrahydronaphthalen-2-ol

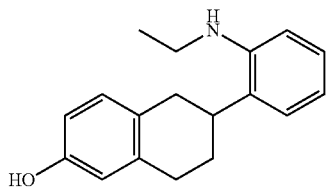 [SMILES: CCNc1ccccc1C1CCc2cc(O)ccc2C1]

A mixture of 2-(6-methoxy-1,2,3,4-tetrahydronaphthalen-2-yl)phenylamine (3.7 g), acetic anhydride (19 ml) and pyridine (19 ml) was stirred for 1 hour at room temperature. The reaction solution was concentrated in vacuo, then ethyl acetate (20 ml) and chloroform (5 ml) were added thereto, the crystal that was precipitated was filtered and dried. Synthesized from the total amount of the resulting N-[2-(6-methoxy-1,2,3,4-tetrahydronaphthalen-2-yl)phenyl]acetamide according to an analogous synthetic method to Example 364 described below, the total amount of N-[2-(6-hydroxy-1,2,3,4-tetrahydronaphthalen-2-yl)phenyl]acetamide was used according to an analogous synthetic method to Example 337 described below to provide the title compound (2.3 g).
¹H-NMR (400 MHz, CDCl₃); δ (ppm): 1.28 (t, 3H), 1.90-2.04 (m, 1H), 2.06-2.14 (m, 1H), 2.68-2.78 (m, 1H), 2.84-2.94 (m, 3H), 2.96-3.04 (m, 1H), 3.19 (q, 2H), 6.59-6.64 (m, 2H), 6.67 (d, 1H), 6.73 (t, 1H), 6.96 (d, 1H), 7.10-7.16 (m, 2H).

Example 93

Pivalic acid 6-(2-ethylaminophenyl)-5,6,7,8-tetrahydronaphthalen-2-yl ester

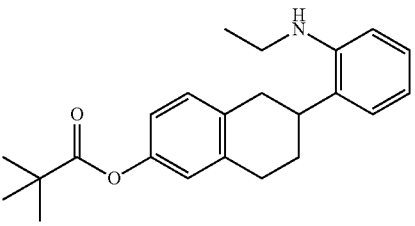 [SMILES: CCNc1ccccc1C1CCc2cc(OC(=O)C(C)(C)C)ccc2C1]

Synthesized from 6-(2-ethylaminophenyl)-5,6,7,8-tetrahydronaphthalen-2-ol (2.3 g) according to an analogous synthetic method to Example 85, the title compound (2.5 g) was obtained.
¹H-NMR (400 MHz, CDCl₃); δ (ppm): 0.89 (t, 3H), 1.29 (s, 9H), 1.92-2.05 (m, 1H), 2.06-2.15 (m, 1H), 2.74-2.85 (m, 3H), 3.02-3.10 (m, 1H), 3.19 (q, 2H), 6.69 (d, 1H), 6.75 (t, 1H), 6.79-6.84 (m, 2H), 7.07-7.18 (m, 3H).

Example 94

Pivalic acid (S)- and (R)-6-(2-ethylaminophenyl)-5,6,7,8-tetrahydronaphthalen-2-yl ester

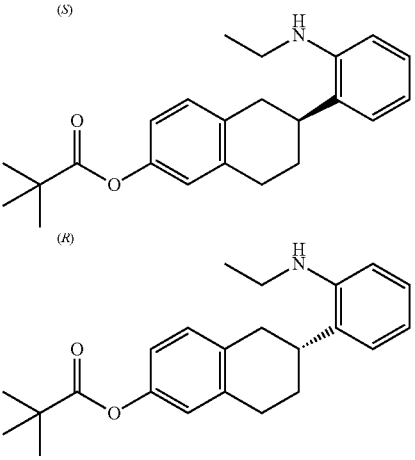

Optical resolution was carried out according to Example 188 described below to provide pivalic acid (S)-6-(2-ethylaminophenyl)-5,6,7,8-tetrahydronaphthalen-2-yl ester exhibiting a short retention time and pivalic acid (R)-6-(2-ethylaminophenyl)-5,6,7,8-tetrahydronaphthalen-2-yl ester exhibiting a long retention time.

Pivalic acid (S)-6-(2-ethylaminophenyl)-5,6,7,8-tetrahydronaphthalen-2-yl ester:
retention time: 9.6 minutes Pivalic acid (R)-6-(2-ethylaminophenyl)-5,6,7,8-tetrahydronaphthalen-2-yl ester:
retention time: 11.5 minutes Preparation Example 108

3-Bromo-4-nitrophenol

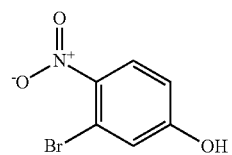

To a solution of 3-bromophenol (10 g) in chloroform (50 ml) and acetic acid (50 ml) was added 70% nitric acid (60 ml) dropwise on an ice bath, and the solution was stirred for 1 hour. The reaction mixture was poured into ice water, extracted with ethyl acetate, then sequentially washed with a saturated aqueous solution of sodium bicarbonate, water and brine, dried over anhydrous magnesium sulfate, and then the solvent was evaporated in vacuo. The residue was purified by silica gel column chromatography (hexane-ethyl acetate system) to provide the title compound (4.1 g) and 5-bromo-2-nitrophenol (1.8 g).

$^1$H-NMR (400 MHz, DMSO-$d_6$); δ (ppm): 6.91 (d, 1H), 7.18 (s, 1H), 7.99 (d, 1H), 11.19 (s, 1H).

Example 95

6-(2-Amino-5-methoxyphenyl)-5,6,7,8-tetrahydronaphthalen-2-ol

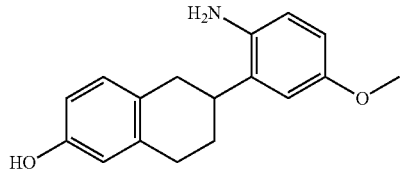 [SMILES: COc1ccc(N)c(C2CCc3cc(O)ccc3C2)c1]

To a solution of 3-bromo-4-nitrophenol (4.1 g) in N,N-dimethylformamide (40 ml) were sequentially added cesium carbonate (9.2 g) and methyl iodide (1.5 ml), and the solution was stirred overnight at room temperature. Water was added thereto, the solution was stirred, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide 2-bromo-4-methoxy-1-nitrobenzene (4.1 g). Synthesized from 7-benzyloxy-3-bromo-1,2-dihydronaphthalene and 2-bromo-4-methoxy-1-nitrobenzene according to an analogous synthetic method to Preparation Example 107, 7-benzyloxy-3-(5-methoxy-2-nitrophenyl)-1,2-dihydronaphthalene (3.4 g) was used according to an analogous synthetic method to Example 30 to provide the title compound (1.6 g).

$^1$H-NMR (400 MHz, DMSO-$d_6$); δ (ppm): 1.74 (ddd, 1H), 1.85-1.92 (m, 1H), 2.56 (dd, 1H), 2.68-2.75 (m, 1H), 2.78-2.98 (m, 3H), 3.60 (s, 3H), 4.44 (brs, 2H), 6.48-6.59 (m, 5H), 6.84 (d, 1H), 8.97 (s, 1H).

Example 96

6-(2-Ethylamino-5-methoxyphenyl)-5,6,7,8-tetrahydronaphthalen-2-ol

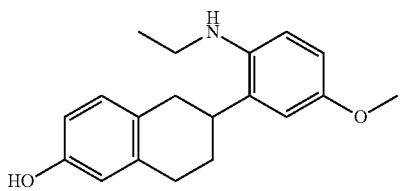 [SMILES: CCNc1ccc(OC)cc1C1CCc2cc(O)ccc2C1]

Synthesized from 6-(2-amino-5-methoxyphenyl)-5,6,7,8-tetrahydronaphthalen-2-ol (540 mg) according to an analogous synthetic method to Example 36, the title compound (463 mg) was obtained.

$^1$H-NMR (400 MHz, DMSO-$d_6$); δ (ppm): 1.14 (t, 3H), 1.72-1.90 (m, 2H), 2.52 (dd, 1H), 2.68-2.89 (m, 3H), 2.95-3.07 (m, 3H), 3.61 (s, 3H), 4.48 (brs, 1H), 6.46-6.50 (m, 3H), 6.60-6.65 (m, 2H), 6.84 (d, 1H), 8.97 (s, 1H).

Example 97

Pivalic Acid 6-(2-ethylamino-5-methoxyphenyl)-5,6,7,8-tetrahydronaphthalen-2-yl Ester

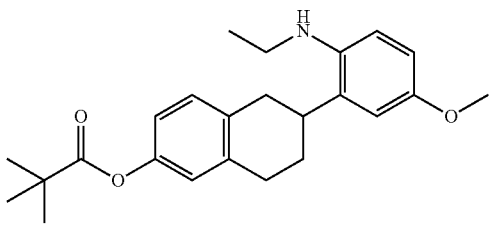 [SMILES: CCNc1ccc(OC)cc1C1CCc2cc(OC(=O)C(C)(C)C)ccc2C1]

Synthesized from 6-(2-ethylamino-5-methoxyphenyl)-5,6,7,8-tetrahydronaphthalen-2-ol (400 mg) according to an analogous synthetic method to Example 85, the title compound (380 mg) was obtained.

$^1$H-NMR (400 MHz, CDCl$_3$); δ (ppm): 1.27 (t, 3H), 1.35 (s, 9H), 1.90-2.01 (m, 1H), 2.07-2.14 (m, 1H), 2.77 (dd, 1H), 2.89-2.99 (m, 3H), 3.00-3.08 (m, 1H), 3.14 (dq, 2H), 3.25 (brs, 1H), 3.75 (s, 3H), 6.63 (d, 1H), 6.72 (dd, 1H), 6.75-6.82 (m, 3H), 7.07 (d, 1H).

Example 98

6-(2-Amino-4,5-dimethoxyphenyl)-5,6,7,8-tetrahydronaphthalen-2-ol

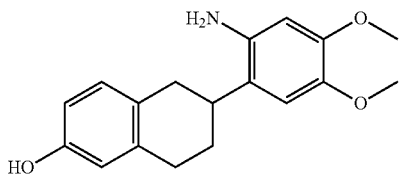 [SMILES: COc1cc(N)c(C2CCc3cc(O)ccc3C2)cc1OC]

Synthesized from 1-bromo-3,4-dimethoxybenzene according to an analogous synthetic method to Preparation Example 108, 1-bromo-4,5-dimethoxy-2-nitrobenzene (7.5 and 7-benzyloxy-3-bromo-1,2-dihydronaphthalene (4.5 g) were used according to an analogous synthetic method to Preparation Example 107 to provide 7-benzyloxy-3-(4,5-dimethoxy-2-nitrophenyl)-1,2-dihydronaphthalene (1.3 g). The total amount of this compound was used according to an analogous synthetic method to Example 30 to provide the title compound (822 mg).

$^1$H-NMR (400 MHz, DMSO-$d_6$); δ (ppm): 1.72 (ddd, 1H), 1.82-1.89 (m, 1H), 2.56 (dd, 1H), 2.64-2.92 (m, 4H), 3.58 (s, 3H), 3.64 (s, 3H), 4.49 (brs, 2H), 6.32 (s, 1H), 6.47 (s, 1H), 6.48 (d, 1H), 6.60 (s, 1H), 6.84 (d, 1H), 8.96 (s, 1H).

Example 99

6-(2-Ethylamino-4,5-dimethoxyphenyl)-5,6,7,8-tetrahydronaphthalen-2-ol

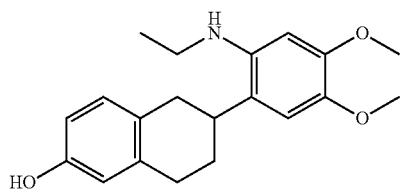 [SMILES: CCNc1cc(OC)c(OC)cc1C1CCc2cc(O)ccc2C1]

Synthesized from 6-(2-amino-4,5-dimethoxyphenyl)-5,6,7,8-tetrahydronaphthalen-2-ol (445 mg) according to an analogous synthetic method to Example 36, the title compound (352 mg) was obtained.

$^1$H-NMR (400 MHz, DMSO-$d_6$); δ (ppm): 1.15 (t, 3H), 1.77 (ddd, 1H), 1.78-1.88 (m, 1H), 2.54 (dd, 1H), 2.67-2.90 (m, 3H), 2.93-3.08 (m, 3H), 3.60 (s, 3H), 3.71 (s, 3H), 4.57 (t, 1H), 6.22 (s, 1H), 6.48 (s, 1H), 6.49 (d, 1H), 6.68 (s, 1H), 6.84 (d, 1H), 8.96 (s, 1H).

Example 100

Pivalic Acid 6-(2-ethylamino-4,5-dimethoxyphenyl)-5,6,7,8-tetrahydronaphthalen-2-yl Ester

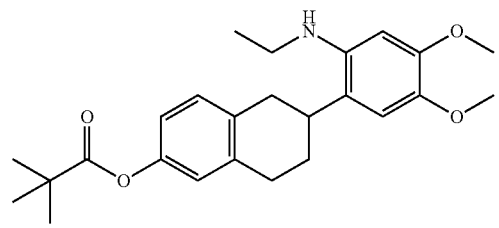 [SMILES: CCNc1cc(OC)c(OC)cc1C1CCc2cc(OC(=O)C(C)(C)C)ccc2C1]

Synthesized from 6-(2-ethylamino-4,5-dimethoxyphenyl)-5,6,7,8-tetrahydronaphthalen-2-ol (278 mg) according to an analogous synthetic method to Example 85, the title compound (307 mg) was obtained.

$^1$H-NMR (400 MHz, CDCl$_3$); δ (ppm): 1.28 (t, 3H), 1.36 (s, 9H), 1.89-2.00 (m, 1H), 2.05-2.12 (m, 1H), 2.77 (dd, 1H), 2.86-3.06 (m, 4H), 3.18 (dq, 2H), 3.30 (brs, 1H), 3.79 (s, 3H), 3.88 (s, 3H), 6.34 (s, 1H), 6.73 (s, 1H), 6.79 (dd, 1H), 6.81 (d, 1H), 7.08 (d, 1H).

Example 101

Pivalic Acid (S)- and (R)-6-(2-ethylamino-4,5-dimethoxyphenyl)-5,6,7,8-tetrahydronaphthalen-2-yl ester

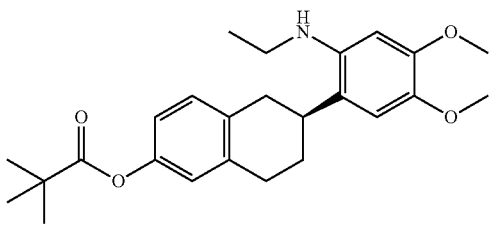

(S)

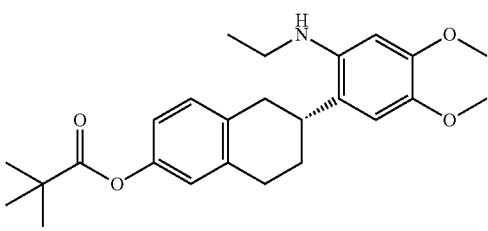

(R)

Optical resolution was carried out according to Example 188 described below to provide pivalic acid (S)-6-(2-ethylamino-4,5-dimethoxyphenyl)-5,6,7,8-tetrahydronaphthalen-2-yl ester exhibiting a short retention time and pivalic acid (R)-6-(2-ethylamino-4,5-dimethoxyphenyl)-5,6,7,8-tetrahydronaphthalen-2-yl ester exhibiting a long retention time.

Pivalic acid (S)-6-(2-ethylamino-4,5-dimethoxyphenyl)-5,6,7,8-tetrahydronaphthalen-2-yl ester:
retention time: 10.6 minutes Pivalic acid (R)-6-(2-ethylamino-4,5-dimethoxyphenyl)-5,6,7,8-tetrahydronaphthalen-2-yl ester:
retention time: 14.9 minutes Preparation Example 109

5-(6-Benzyloxy-3,4-dihydronaphthalen-2-yl)-6-nitrobenzo[1,3]dioxole

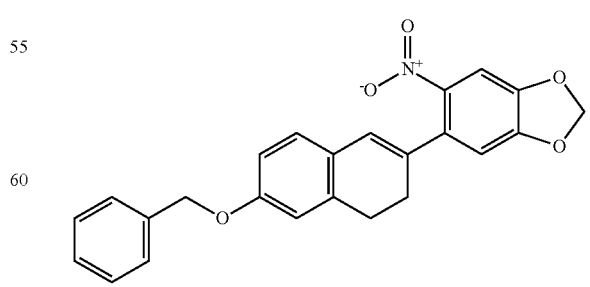

Synthesized from 4-bromo-1,2-(methylenedioxy)benzene according to an analogous synthetic method to Preparation Example 108, 5-bromo-6-nitrobenzo[1,3]dioxole (9.4 g) and 7-benzyloxy-3-bromo-1,2-dihydronaphthalene (6.0 g) were used according to an analogous synthetic method to Preparation Example 107 to provide the title compound (834 mg).

$^1$H-NMR (400 MHz, CDCl$_3$); δ (ppm): 2.45 (t, 2H), 2.95 (t, 2H), 5.07 (s, 2H), 6.10 (s, 2H), 6.38 (s, 1H), 6.76 (dd, 1H), 6.76 (s, 1H), 6.79 (s, 1H), 6.99 (d, 1H), 7.29-7.44 (m, 5H), 7.49 (s, 1H).

Example 102

6-(6-Aminobenzo[1,3]dioxole-5-yl)-5,6,7,8-tetrahydronaphthalen-2-ol

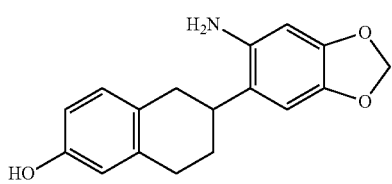 [SMILES: Nc1cc2c(cc1C1CCc3cc(O)ccc3C1)OCO2]

To a solution of 5-(6-benzyloxy-3,4-dihydronaphthalen-2-yl)-6-nitrobenzo[1,3]dioxole (832 mg) in acetic acid (10 ml) was added 20% palladium hydroxide-activated charcoal (200 mg), and the solution was stirred for 13 hours at room temperature under a hydrogen atmosphere at 4 atmospheric pressures. After filtration through celite pad, the solution was concentrated, neutralized with aqueous ammonia, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (240 mg).

$^1$H-NMR (400 MHz, DMSO-d$_6$); δ (ppm): 1.71 (ddd, 1H), 1.79-1.87 (m, 1H), 2.52 (dd, 1H), 2.66-2.93 (m, 4H), 4.59 (brs, 2H), 5.76 (s, 2H), 6.30 (s, 1H), 6.47-6.50 (m, 2H), 6.58 (s, 1H), 6.83 (d, 1H), 8.96 (s, 1H).

Example 103

Pivalic Acid 6-(6-ethylaminobenzo[1,3]dioxole-5-yl)-5,6,7,8-tetrahydronaphthalen-2-yl Ester

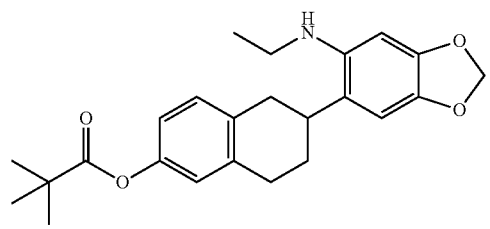 [SMILES: CCNc1cc2c(cc1C1CCc3cc(OC(=O)C(C)(C)C)ccc3C1)OCO2]

Synthesized from 6-(6-aminobenzo[1,3]dioxole-5-yl)-5,6,7,8-tetrahydronaphthalen-2-ol according to an analogous synthetic method to Example 36, 6-(6-ethylaminobenzo[1,3]dioxole-5-yl)-5,6,7,8-tetrahydronaphthalen-2-ol (222 mg) was used according to an analogous synthetic method to Example 85 to provide the title compound (252 mg).

$^1$H-NMR (400 MHz, CDCl$_3$); δ (ppm): 1.26 (t, 3H), 1.35 (s, 9H), 1.86-1.96 (m, 1H), 2.02-2.09 (m, 1H), 2.72 (dd, 1H), 2.83-2.91 (m, 1H), 2.92-3.04 (m, 3H), 3.12 (dq, 2H), 3.31 (brs, 1H), 5.84 (dd, 2H), 6.35 (s, 1H), 6.68 (s, 1H), 6.79 (dd, 1H), 6.81 (s, 1H), 7.07 (d, 1H).

Example 104

2-(6-Methoxy-1,2,3,4-tetrahydronaphthalen-2-yl)-3-methylphenylamine

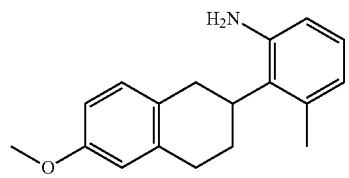 [SMILES: COc1ccc2c(c1)CCC(c1c(C)cccc1N)C2]

Synthesized from 6-methoxy-1-tetralone according to an analogous synthetic method to Preparation Example 106, 3-bromo-7-methoxy-1,2-dihydronaphthalene (2.7 g) and 2-bromo-3-nitrotoluene (4.8 g) were used according to an analogous synthetic method to Preparation Example 107 to provide 7-methoxy-3-(2-methyl-6-nitrophenyl)-1,2-dihydronaphthalene (925 mg). This compound (920 mg) was used according to an analogous synthetic method to Example 30 to provide the title compound (740 mg).

$^1$H-NMR (400 MHz, CDCl$_3$); δ (ppm): 2.00-2.07 (m, 1H), 2.17-2.30 (m, 1H), 2.34 (s, 3H), 2.82-2.94 (m, 3H), 3.20-3.56 (m, 2H), 3.64 (brs, 2H), 3.80 (s, 3H), 6.55 (d, 1H), 6.63 (d, 1H), 6.70 (d, 1H), 6.73 (dd, 1H), 6.93 (t, 1H), 7.04 (d, 1H).

Preparation Example 110

4-Methoxy-1-[2-(4-methoxyphenyl)vinyl]-2-nitrobenzene

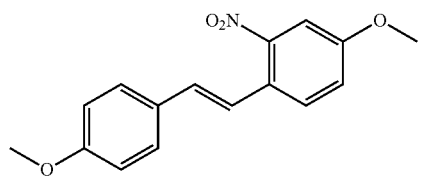

To a solution of 1-bromo-4-methoxy-2-nitrobenzene (2.3 g) in acetonitrile (20 ml) was sequentially added 4-methoxystyrene (1.5 g), N,N-diisopropylethylamine (3.9 g), 2-(di-tert-butylphosphino)biphenyl (145 mg) and palladium(II) acetate (112 mg), and the solution was stirred for 15 hours at 80° C. The solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (1.4 g).

$^1$H-NMR (400 MHz, CDCl$_3$); δ (ppm): 3.84 (s, 3H), 3.88 (s, 3H), 6.88-6.93 (m, 2H), 6.95 (d, 1H), 7.14 (dd, 1H), 7.41 (d, 1H), 7.42-7.48 (m, 4H), 7.66 (d, 1H).

Example 105

5-Methoxy-2-[2-(4-methoxyphenyl)ethyl]phenylamine

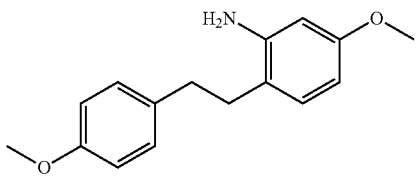

Synthesized from 4-methoxy-1-[2-(4-methoxyphenyl)vinyl]-2-nitrobenzene (1.4 g) according to an analogous synthetic method to Example 22, the title compound (1.0 g) was obtained.

$^1$H-NMR (400 MHz, CDCl$_3$); δ (ppm): 2.54-2.60 (m, 2H), 2.64-2.71 (m, 2H), 3.61 (s, 3H), 3.69 (s, 3H), 4.84 (s, 2H), 6.01-6.06 (m, 1H), 6.18-6.22 (m, 1H), 6.75 (d, 1H), 6.78-6.84 (m, 2H), 7.12-7.18 (m, 2H).

Preparation Example 111

4-Methoxy-1-[2-(4-methoxyphenyl)vinyl]-2-nitrobenzene

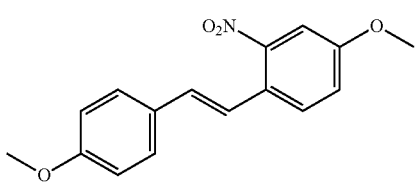

By referring to the synthetic method of *J. Org. Chem.*, 1997, 62, 199, to a solution of lithium acetate (280 mg) in water (3 ml) was added acetonitrile (90 ml), the solution was stirred at room temperature, then 4-methoxycinnamic acid (7.5 g), N-iodosuccinimide (10 g) were sequentially added thereto, the solution was stirred for 2 hours at room temperature, and then neutralized with a saturated aqueous solution of sodium bicarbonate. The solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide 1-(2-iodovinyl)-4-methoxybenzene (8.0 g). By referring to the synthetic method of *J. Am. Chem. Soc.*, 1996, 118, 2748, to a solution of 1-(2-iodovinyl)-4-methoxybenzene (7.1 g) and tributyl(4-methoxy-2-nitrophenyl)tin (10 g) in 1-methyl-2-pyrrolidone (100 ml) was added copper(I) thiophene-2-carboxylate (6.6 g) on an ice bath under a nitrogen atmosphere, and the solution was stirred for 25 minutes at room temperature. Tetrahydrofuran was added thereto, the solution was stirred, then filtered through alumina, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (4.7 g).

$^1$H-NMR (400 MHz, CDCl$_3$); δ (ppm): 3.84 (s, 3H), 3.89 (s, 3H), 6.91 (d, 2H), 6.96 (d, 1H), 7.15 (dd, 1H), 7.42 (d, 1H), 7.45 (d, 1H), 7.46 (d, 2H), 7.67 (d, 1H).

Example 106

5-Methoxy-2-[2-(4-methoxyphenyl)vinyl]phenylamine

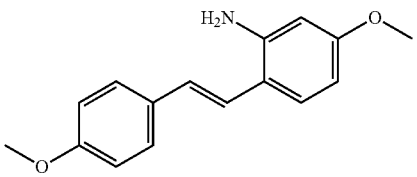

Synthesized from 4-methoxy-1-[2-(4-methoxyphenyl)vinyl]-2-nitrobenzene (1.5 g) according to an analogous synthetic method to Example 57, the title compound (1.2 g) was obtained.

$^1$H-NMR (400 MHz, CDCl$_3$); δ (ppm): 3.78 (s, 3H), 3.83 (s, 5H), 6.26 (d, 1H), 6.38 (dd, 1H), 6.83 (d, 1H), 6.89 (d, 2H), 6.95 (d, 1H), 7.30 (d, 1H), 7.42 (d, 2H).

Example 107

Acetic Acid 4-[2-(2-aminophenyl)vinyl]phenyl Ester

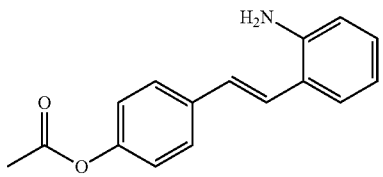 [SMILES: CC(=O)Oc1ccc(/C=C/c2ccccc2N)cc1]

To a solution of 1-bromo-2-nitrobenzene (2.0 g), palladium(II) acetate (112 mg) and 2-(di-tert-butylphosphino)biphenyl (150 mg) in acetonitrile (20 ml) were sequentially added 4-acetoxystyrene (1.7 ml) and N,N-diisopropylethylamine (5 ml) under a nitrogen atmosphere, and the solution was stirred for 3 hours at 80° C. The solution was extracted with ethyl acetate, then sequentially washed with water and brine, dried over anhydrous magnesium sulfate, and then the solvent was evaporated in vacuo. Obtained by purifying the residue by silica gel column chromatography (hexane-ethyl acetate system), acetic acid 4-[2-(2-nitrophenyl)vinyl]phenyl ester (840 mg) was used according to an analogous synthetic method to Example 57 to provide the title compound (330 mg).

$^1$H-NMR (400 MHz, CDCl$_3$); δ (ppm): 2.31 (s, 3H), 3.83 (brs, 2H), 6.73 (dd, 1H), 6.81 (t, 1H), 6.97 (d, 1H), 7.06-7.14 (m, 4H), 7.39 (dd, 1H), 7.51 (d, 2H).

Example 108

Acetic acid 4-[2-(2-amino-4-methoxyphenyl)vinyl]phenyl ester

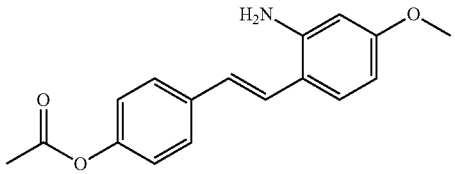 [SMILES: COc1ccc(/C=C/c2ccc(OC(C)=O)cc2)c(N)c1]

Synthesized from 4-bromo-3-nitroanisole (2.3 g) and 4-acetoxystyrene (1.7 ml) according to an analogous synthetic method to Example 107, the title compound (1.2 g) was obtained.

¹H-NMR (400 MHz, CDCl₃); δ (ppm): 2.31 (s, 3H), 3.79 (s, 3H), 3.84 (brs, 2H), 6.27 (d, 1H), 6.39 (dd, 1H), 6.86 (d, 1H), 7.04 (d, 1H), 7.07 (d, 2H), 7.32 (d, 1H), 7.48 (d, 2H).

Example 109

Acetic Acid 4-[2-(4-acetoxy-2-aminophenyl)vinyl]phenyl Ester

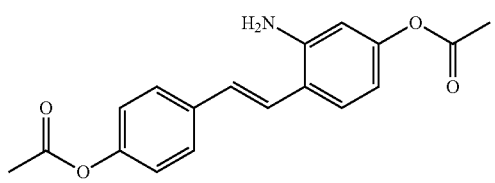 [SMILES: CC(=O)Oc1ccc(/C=C/c2ccc(OC(C)=O)cc2N)cc1]

Synthesized from 4-bromo-3-nitroanisole according to an analogous synthetic method to Example 364 described below, to a solution of 4-bromo-3-nitrophenol (2.0 g) was added pyridine (20 ml) and acetic anhydride (20 ml), and the solution was stirred overnight at room temperature. The reaction mixture was poured into ice water, extracted with ethyl acetate, then sequentially washed with 1N hydrochloric acid, water and brine, dried over anhydrous magnesium sulfate, and then the solvent was evaporated in vacuo. Obtained by purifying the residue by silica gel column chromatography (hexane-ethyl acetate system), acetic acid 4-bromo-3-nitrophenyl ester (1.8 g) and 4-acetoxystyrene (1.2 ml) were used according to an analogous synthetic method to Example 107 to provide the title compound (302 mg).

¹H-NMR (400 MHz, CDCl₃); δ (ppm): 2.29 (s, 3H), 2.31 (s, 3H), 6.46 (d, 1H), 6.53 (dd, 1H), 6.91 (d, 1H), 7.03 (d, 1H), 7.08 (d, 2H), 7.36 (d, 1H), 7.49 (d, 2H).

Example 110

[5-Methoxy-2-(6-methoxynaphthalen-2-yl)phenyl] [4-(2-piperidin-1-ylethoxy)benzyl]amine

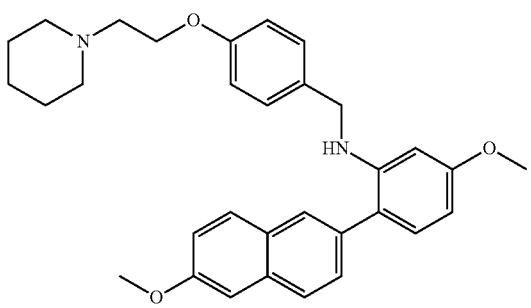 [SMILES: COc1ccc(-c2ccc3cc(OC)ccc3c2)c(NCc2ccc(OCCN3CCCCC3)cc2)c1]

To a solution of 5-methoxy-2-(6-methoxynaphthalen-2-yl) phenylamine (275 mg) in tetrahydrofuran (8 ml) were sequentially added triethylamine (1.3 ml), N,N-diisopropylethylamine (1 ml) and 4-(2-piperidine-1-ylethoxy)benzoyl chloride hydrochloride (1.1 g), and the solution was stirred for 2 days at 60° C. A saturated aqueous solution of ammonium chloride was added thereto, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide N-[5-methoxy-2-(6-methoxynaphthalen-2-yl)phenyl]-4-(2-piperidin-1-ylethoxy)benz amide (234 mg). To a suspension of lithium aluminum hydride (50 mg) in tetrahydrofuran (4 ml) was added aluminum chloride (176 mg) on an ice bath under a nitrogen atmosphere, the solution was stirred for 20 minutes at room temperature, N-[5-methoxy-2-(6-methoxynaphthalen-2-yl)phenyl]-4-(2-piperidin-1-ylethoxy)benzamide (226 mg) was added thereto followed by stirring overnight at room temperature. Obtained by sequentially adding tetrahydrofuran and aqueous ammonia, the suspension was filtered through celite pad, and the filtrate was concentrated in vacuo. The residue was purified by NH silica gel column chromatography (hexane-ethyl acetate system) to provide the title compound (213 mg).

¹H-NMR (400 MHz, CDCl₃); δ (ppm): 1.40-1.47 (m, 2H), 1.57-1.65 (m, 4H), 2.45-2.55 (m, 4H), 2.75 (t, 2H), 3.79 (s, 3H), 3.94 (s, 3H), 4.07 (t, 2H), 4.24 (s, 2H), 4.39 (brs, 1H), 6.28 (d, 1H), 6.36 (dd, 1H), 6.83 (d, 2H), 7.11 (d, 1H), 7.15-7.18 (m, 2H), 7.21 (d, 2H), 7.51 (dd, 1H), 7.71-7.80 (m, 3H).

Example 111

6-{4-Hydroxy-2-[4-(2-piperidin-1-ylethoxy)benzylamino]phenyl}naphthalen-2-ol

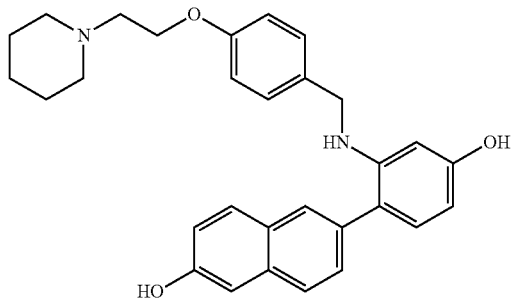 [SMILES: Oc1ccc(-c2ccc3cc(O)ccc3c2)c(NCc2ccc(OCCN3CCCCC3)cc2)c1]

To a solution of [5-methoxy-2-(6-methoxynaphthalen-2-yl)phenyl][4-(2-piperidin-1-ylethoxy)benzyl]amine (198 mg) in dichloromethane (4 ml) were sequentially added aluminum chloride (320 mg) and ethanethiol (0.15 ml), and the solution was stirred for 25 minutes under nitrogen atmosphere at room temperature. Obtained by sequentially adding tetrahydrofuran and aqueous ammonia, the suspension was filtered through celite pad, and the solvent was evaporated in vacuo. The residue was purified by NH silica gel column chromatography (hexane-ethyl acetate-methanol system) to provide the title compound (164 mg).

¹H-NMR (400 MHz, DMSO-d₆); δ (ppm): 1.30-1.38 (m, 2H), 1.41-1.50 (m, 4H), 2.33-2.43 (m, 4H), 2.60 (t, 2H), 3.99 (t, 2H), 4.14 (s, 2H), 5.14 (brs, 1H), 5.97 (s, 1H), 6.07 (d, 1H), 6.79-6.87 (m, 3H), 7.06 (d, 1H), 7.11 (s, 1H), 7.21 (d, 2H), 7.39 (d, 1H), 7.68-7.76 (m, 3H), 9.03 (s, 1H), 9.70 (s, 1H).

ESI-Mass; 469 [M⁺+H]

Example 112

[5-Methoxy-2-(6-methoxynaphthalen-2-yl)phenyl]methyl[4-(2-piperidin-1-ylethoxy)benzyl]amine

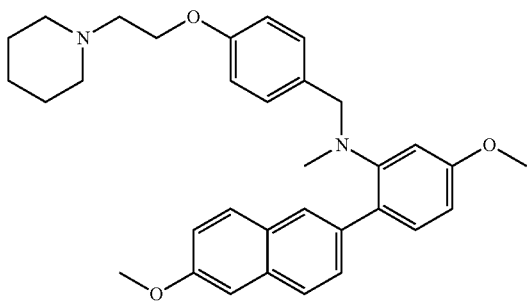 [SMILES: COc1ccc(-c2ccc3cc(OC)ccc3c2)c(N(C)Cc2ccc(OCCN3CCCCC3)cc2)c1]

Synthesized from [5-methoxy-2-(6-methoxynaphthalen-2-yl)phenyl][4-(2-piperidin-1-ylethoxy)benzyl]amine (147 mg) according to an analogous synthetic method to Preparation Example 18, the title compound (93 mg) was obtained.

$^1$H-NMR (400 MHz, CDCl$_3$); δ (ppm): 1.40-1.47 (m, 2H), 1.56-1.63 (m, 4H), 2.44 (s, 3H), 2.44-2.52 (m, 4H), 2.73 (t, 2H), 3.84 (s, 5H), 3.94 (s, 3H), 4.03 (t, 2H), 6.62-6.66 (m, 2H), 6.72 (d, 2H), 6.92 (d, 2H), 7.12-7.16 (m, 2H), 7.24-7.29 (m, 1H), 7.72-7.76 (m, 3H), 7.89 (s, 1H).

Example 113

6-{4-Hydroxy-2-{methyl[4-(2-piperidin-1-ylethoxy)benzyl]amino}phenyl}naphthalen-2-ol

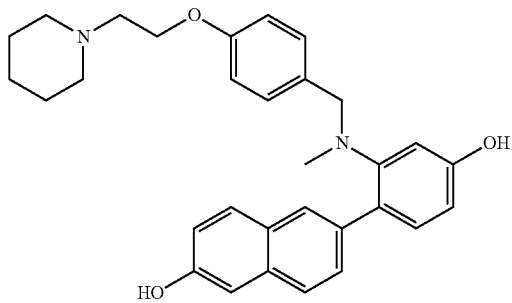 [SMILES: CN(Cc1ccc(OCCN2CCCCC2)cc1)c1cc(O)ccc1-c1ccc2cc(O)ccc2c1]

Synthesized from [5-methoxy-2-(6-methoxynaphthalen-2-yl)phenyl]methyl[4-(2-piperidin-1-ylethoxy)benzyl]amine (93 mg) according to an analogous synthetic method to Example 111, the title compound (64 mg) was obtained.

$^1$H-NMR (400 MHz, DMSO-d$_6$); δ (ppm): 1.30-1.37 (m, 2H), 1.42-1.49 (m, 4H), 2.33 (s, 3H), 2.33-2.41 (m, 4H), 2.57 (t, 2H), 3.73 (s, 2H), 3.95 (t, 2H), 6.43-6.49 (m, 2H), 6.74 (d, 2H), 6.92 (d, 2H), 7.01-7.11 (m, 3H), 7.63 (dd, 2H), 7.73 (d, 1H), 7.81 (s, 1H), 9.32 (s, 1H), 9.66 (s, 1H).

ESI-Mass; 483 [M$^+$+H]

Example 114

[3-Fluoro-4-(2-piperidin-1-ylethoxy)benzyl][5-methoxy-2-(6-methoxynaphthalen-2-yl)phenyl]amine

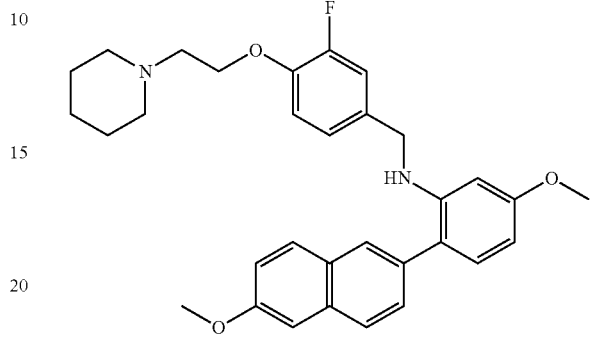

To a solution of 3-fluoro-4-(2-piperidin-1-ylethoxy)benzoic acid hydrochloride (2.5 g) in thionyl chloride (25 ml) was added toluene (25 ml), the solution was stirred for 1.5 hours at 110° C., and then the reaction solution was concentrated in vacuo to provide 3-fluoro-4-(2-piperidin-1-ylethoxy)benzoyl chloride hydrochloride (2.2 g). To a solution of 5-methoxy-2-(6-methoxynaphthalen-2-yl)phenylamine (280 mg) in pyridine (3 ml) was added 3-fluoro-4-(2-piperidin-1-ylethoxy)benzoyl chloride hydrochloride (420 mg), and the solution was stirred overnight at room temperature. A saturated aqueous solution of sodium bicarbonate was added thereto, the solution was stirred, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate-methanol system) to provide 3-fluoro-N-[5-methoxy-2-(6-methoxynaphthalen-2-yl)phenyl]-4-(3-piperidin-1-ylethoxy)benzamide (448 mg). To a suspension of lithium aluminum hydride (130 mg) in tetrahydrofuran (3 ml) was added aluminum chloride (455 mg) on an ice bath under a nitrogen atmosphere, the solution was stirred for 30 minutes at room temperature, then 3-fluoro-N-[5-methoxy-2-(6-methoxynaphthalen-2-yl)phenyl]-4-(2-piperidin-1-ylethoxy)benzamide (446 mg) was added thereto followed by stirring overnight at room temperature. Obtained by sequentially adding tetrahydrofuran and aqueous ammonia, the suspension was filtered through celite pad, and then the filtrate was concentrated in vacuo to provide the title compound (396 mg).

$^1$H-NMR (400 MHz, CDCl$_3$); δ (ppm): 1.40-1.50 (m, 2H), 1.56-1.67 (m, 4H), 2.45-2.56 (m, 4H), 2.78 (t, 2H), 3.78 (s, 3H), 3.94 (s, 3H), 4.13 (t, 2H), 4.23 (d, 2H), 4.43 (t, 1H), 6.21 (d, 1H), 6.37 (dd, 1H), 6.89 (t, 1H), 6.96-7.01 (m, 1H), 7.03 (dd, 1H), 7.11 (d, 1H), 7.16-7.19 (m, 2H), 7.51 (dd, 1H), 7.74 (d, 1H), 7.77-7.81 (m, 2H).

Example 115

6-{2-{Ethyl[3-fluoro-4-(2-piperidin-1-ylethoxy)benzyl]amino}-4-hydroxyphenyl}naphthalen-2-ol

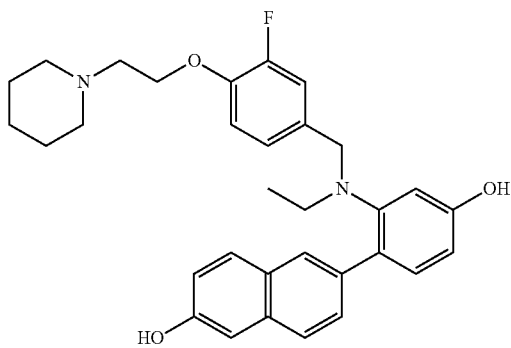 [SMILES: CCN(Cc1ccc(OCCN2CCCCC2)c(F)c1)c1cc(O)ccc1-c1ccc2cc(O)ccc2c1]

Synthesized from [3-fluoro-4-(2-piperidin-1-ylethoxy)benzyl][5-methoxy-2-(6-methoxynaphthalen-2-yl)phenyl]amine according to an analogous synthetic method to Example 36, ethyl[3-fluoro-4-(2-piperidin-1-ylethoxy)benzyl][5-methoxy-2-(6-methoxynaphthalen-2-yl)phenyl]amine (297 mg) was used according to an analogous synthetic method to Example 111 to provide the title compound (227 mg).

$^1$H-NMR (400 MHz, DMSO-$d_6$); δ (ppm): 0.80 (t, 3H), 1.31-1.39 (m, 2H), 1.41-1.49 (m, 4H), 2.34-2.43 (m, 4H), 2.60 (t, 2H), 2.66 (q, 2H), 3.83 (s, 2H), 4.04 (t, 2H), 6.46-6.52 (m, 2H), 6.83-6.89 (m, 2H), 6.98-7.10 (m, 4H), 7.59 (dd, 1H), 7.65 (d, 1H), 7.72 (d, 1H), 7.77 (s, 1H), 9.32 (s, 1H), 9.65 (s, 1H).

ESI-Mass; 515 [M$^+$+H]

Example 116

[5-Methoxy-2-(6-methoxynaphthalen-2-yl)phenyl][4-(2-piperidin-1-ylethoxy)phenyl]amine

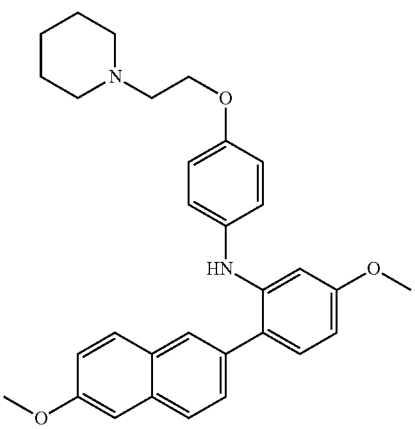

A suspension of 5-methoxy-2-(6-methoxynaphthalen-2-yl)phenylamine (250 mg), 1-[2-(4-bromophenoxy)ethyl]piperidine (250 mg), tris(dibenzylideneacetone)dipalladium(0) (46 mg), tri-tert-butylphosphine (14 mg) and sodium tert-butoxide (130 mg) in toluene (2 ml) was stirred for 2.5 hours under nitrogen atmosphere at 100° C. A saturated aqueous solution of ammonium chloride was added thereto, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (415 mg).

$^1$H-NMR (400 MHz, CDCl$_3$); δ (ppm): 1.40-1.50 (m, 2H), 1.57-1.65 (m, 4H), 2.45-2.55 (m, 4H), 2.76 (t, 2H), 3.77 (s, 3H), 3.94 (s, 3H), 4.08 (t, 2H), 5.60 (s, 1H), 6.48 (dd, 1H), 6.68-6.72 (m, 1H), 6.85 (d, 2H), 7.05 (d, 2H), 7.15-7.22 (m, 3H), 7.54 (dd, 1H), 7.55 (d, 1H), 7.79 (d, 1H), 7.83 (s, 1H).

Example 117

6-{4-Hydroxy-2-[4-(2-piperidin-1-ylethoxy)phenylamino]phenyl}naphthalen-2-ol

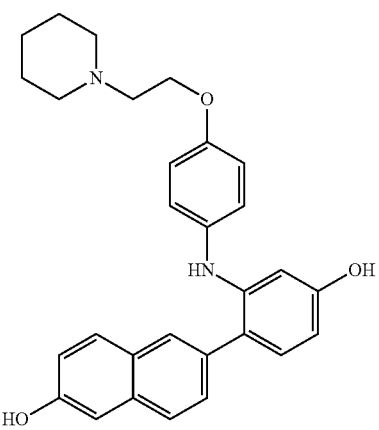 [SMILES: Oc1ccc(-c2ccc3cc(O)ccc3c2)c(Nc2ccc(OCCN3CCCCC3)cc2)c1]

Synthesized from [5-methoxy-2-(6-methoxynaphthalen-2-yl)phenyl][4-(2-piperidin-1-ylethoxy)phenyl]amine (181 mg) according to an analogous synthetic method to Example 111, the title compound (144 mg) was obtained.

$^1$H-NMR (400 MHz, CDCl$_3$); δ (ppm): 1.40-1.50 (m, 2H), 1.60-1.68 (m, 4H), 2.50-2.60 (m, 4H), 2.79 (t, 2H), 4.06 (t, 2H), 5.57 (s, 1H), 6.38 (dd, 1H), 6.54-6.58 (m, 1H), 6.77 (d, 2H), 6.99 (d, 2H), 7.09-7.16 (m, 3H), 7.50 (dd, 1H), 7.68 (d, 1H), 7.73 (d, 1H), 7.81 (s, 1H).

ESI-Mass; 455 [M$^+$+H]

Example 118

6-{2-[3-Fluoro-4-(2-piperidin-1-ylethoxy)phenylamino]-4-hydroxyphenyl}naphthalen-2-ol

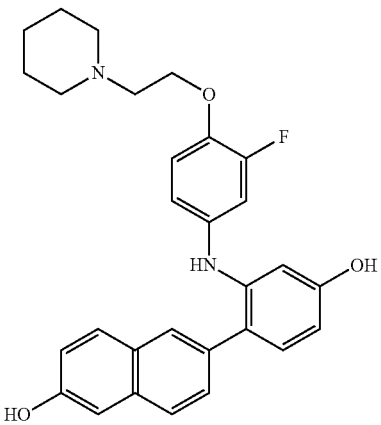 [SMILES: Oc1ccc(-c2ccc3cc(O)ccc3c2)c(Nc2ccc(OCCN3CCCCC3)c(F)c2)c1]

Synthesized from 5-methoxy-2-(6-methoxynaphthalen-2-yl)phenylamine and 1-[2-(4-bromo-2-fluorophenoxy)ethyl]

piperidine according to an analogous synthetic method to Example 116, [3-fluoro-4-(2-piperidin-1-ylethoxy)phenyl][5-methoxy-2-(6-methoxynaphthalen-2-yl)phenyl]amine (425 mg) was used according to an analogous synthetic method to Example 111 to provide the title compound (288 mg).

$^1$H-NMR (400 MHz, DMSO-d$_6$); δ (ppm): 1.31-1.39 (m, 2H), 1.42-1.50 (m, 4H), 2.34-2.43 (m, 4H), 2.58 (t, 2H), 3.99 (t, 2H), 6.45 (dd, 1H), 6.65 (d, 1H), 6.68 (ddd, 1H), 6.75 (dd, 1H), 6.96 (t, 1H), 7.01-7.07 (m, 3H), 7.10 (d, 1H), 7.38 (dd, 1H), 7.60 (d, 1H), 7.70 (d, 1H), 7.71 (s, 1H), 9.34 (s, 1H), 9.66 (s, 1H).

ESI-Mass; 473 [M$^+$+H]

Example 119

[5-Methoxy-2-(6-methoxynaphthalen-2-yl)phenyl]methylamine

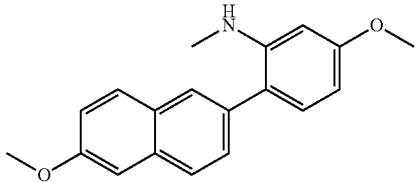

To a solution of 5-methoxy-2-(6-methoxynaphthalen-2-yl)phenylamine (280 mg) in tetrahydrofuran (5 ml) were sequentially added sodium hydroxide (160 mg), potassium carbonate (140 mg), tetrabutylammonium chloride (in catalytic amounts) and dimethyl sulfate (140 mg), and the solution was stirred overnight at 70° C. The solution was filtered through silica gel, the solvent was evaporated in vacuo, and the resulting residue was purified by silica gel column chromatography (hexane-ethyl acetate system) to provide the title compound (89 mg).

$^1$H-NMR (400 MHz, CDCl$_3$); δ (ppm): 2.79 (s, 3H), 3.86 (s, 3H), 3.95 (s, 3H), 4.06 (brs, 1H), 6.28 (d, 1H), 6.36 (dd, 1H), 7.09 (d, 1H), 7.15-7.19 (m, 2H), 7.47 (dd, 1H), 7.72-7.80 (m, 3H).

Example 120

[5-Methoxy-2-(6-methoxynaphthalen-2-yl)phenyl]methyl[4-(2-piperidin-1-ylethoxy)phenyl]amine

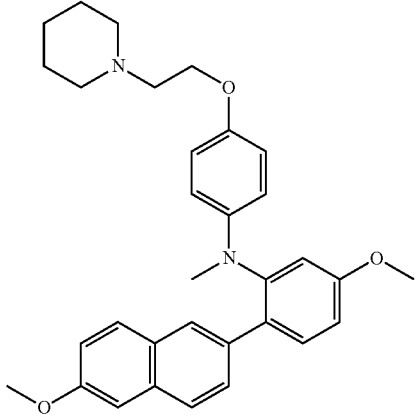

Synthesized from [5-methoxy-2-(6-methoxynaphthalen-2-yl)phenyl]methylamine (85 mg) and 1-[2-(4-bromophenoxy)ethyl]piperidine (87 mg) according to an analogous synthetic method to Example 116, the title compound (124 mg) was obtained.

$^1$H-NMR (400 MHz, CDCl$_3$); δ (ppm): 1.41-1.51 (m, 2H), 1.53-1.67 (m, 4H), 2.47-2.58 (m, 4H), 2.72-2.82 (m, 5H), 3.79 (s, 3H), 3.92 (s, 3H), 4.06 (t, 2H), 6.71-6.87 (m, 6H), 7.09-7.13 (m, 2H), 7.42-7.50 (m, 2H), 7.60-7.73 (m, 3H).

Example 121

6-{4-Hydroxy-2-{methyl[4-(2-piperidin-1-ylethoxy)phenyl]amino}phenyl}naphthalen-2-ol

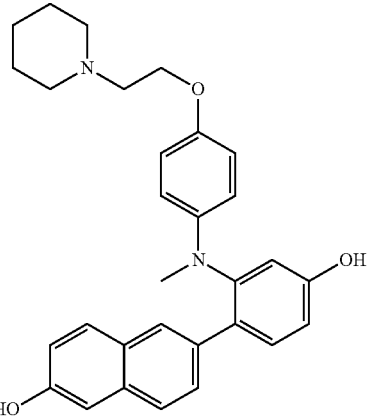

Synthesized from [5-methoxy-2-(6-methoxynaphthalen-2-yl)phenyl]methyl[4-(2-piperidin-1-ylethoxy)phenyl]amine (118 mg) according to an analogous synthetic method to Example 111, the title compound (99 mg) was obtained.

$^1$H-NMR (400 MHz, DMSO-d$_6$); δ (ppm): 1.29-1.39 (m, 2H), 1.42-1.50 (m, 4H), 2.33-2.42 (m, 4H), 2.55 (t, 2H), 2.74 (s, 3H), 3.90 (t, 2H), 6.51-6.61 (m, 3H), 6.68-6.77 (m, 3H), 6.98-7.03 (m, 2H), 7.29 (d, 1H), 7.33 (d, 1H), 7.51 (d, 1H), 7.62-7.68 (m, 2H), 9.52 (s, 1H), 9.67 (s, 1H).

ESI-Mass; 469 [M$^+$+H]

Example 122

6-{2-[3-Fluoro-4-(2-piperidin-1-ylethoxy)phenylamino]phenyl}naphthalen-2-ol

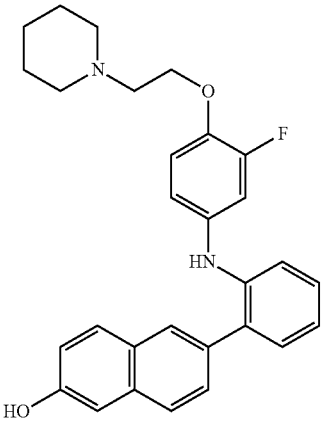 [SMILES: Oc1ccc2cc(-c3ccccc3Nc3ccc(OCCN4CCCCC4)c(F)c3)ccc2c1]

Synthesized from 2-(6-methoxynaphthalen-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][2-(6-methoxynaphthalen-2-yl)phenyl]amine (408 mg) was used according to an analogous synthetic method to Example 111 to provide the title compound (365 mg).

$^1$H-NMR (400 MHz, DMSO-d$_6$); δ (ppm): 1.30-1.38 (m, 2H), 1.41-1.50 (m, 4H), 2.32-2.43 (m, 4H), 2.57 (t, 2H), 3.97

(t, 2H), 6.64 (d, 1H), 6.70 (dd, 1H), 6.94 (t, 1H), 7.02-7.10 (m, 3H), 7.17 (s, 1H), 7.21-7.28 (m, 2H), 7.32 (d, 1H), 7.41 (dd, 1H), 7.64 (d, 1H), 7.73 (d, 1H), 7.79 (s, 1H), 9.73 (s, 1H).
ESI-Mass; 457 [M++H]

Example 123

6-{4-Fluoro-2-[3-fluoro-4-(2-piperidin-1-ylethoxy)phenylamino]phenyl}naphthalen-2-ol

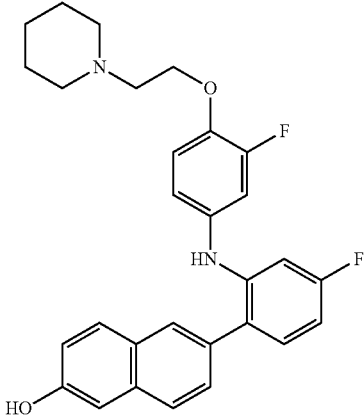 [SMILES: Oc1ccc2cc(-c3ccc(F)cc3Nc3ccc(OCCN4CCCCC4)c(F)c3)ccc2c1]

Synthesized from 5-fluoro-2-(6-methoxynaphthalen-2-yl)phenylamine and 1-[2-(4-bromo-2-fluorophenoxy)ethyl]piperidine according to an analogous synthetic method to Example 116, [5-fluoro-2-(6-methoxynaphthalen-2-yl)phenyl][3-fluoro-4-(2-piperidin-1-ylethoxy)phenyl]amine (406 mg) was used according to an analogous synthetic method to Example 111 to provide the title compound (381 mg).
$^1$H-NMR (400 MHz, DMSO-$d_6$); δ (ppm): 1.31-1.38 (m, 2H), 1.42-1.49 (m, 4H), 2.33-2.43 (m, 4H), 2.59 (t, 2H), 4.01 (t, 2H), 6.74-6.81 (m, 2H), 6.85 (dd, 1H), 6.90 (dd, 1H), 7.01 (t, 1H), 7.06 (dd, 1H), 7.10 (d, 1H), 7.26 (d, 1H), 7.29 (d, 1H), 7.40 (dd, 1H), 7.66 (d, 1H), 7.75 (d, 1H), 7.78 (s, 1H), 9.73 (s, 1H).
ESI-Mass; 475 [M++H]

Example 124

6-{5-Fluoro-2-[3-fluoro-4-(2-piperidin-1-ylethoxy)phenylamino]phenyl}naphthalen-2-ol

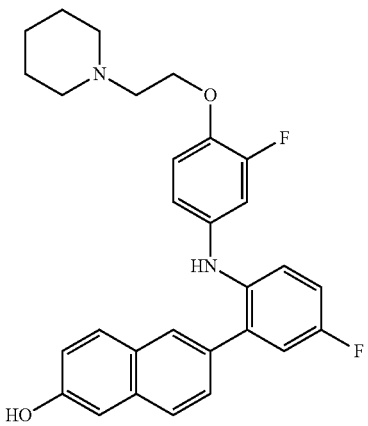 [SMILES: Oc1ccc2cc(-c3cc(F)ccc3Nc3ccc(OCCN4CCCCC4)c(F)c3)ccc2c1]

Synthesized from 4-fluoro-2-(6-methoxynaphthalen-2-yl)phenylamine and 1-[2-(4-bromo-2-fluorophenoxy)ethyl]piperidine according to an analogous synthetic method to Example 116, [4-fluoro-2-(6-methoxynaphthalen-2-yl)phenyl][3-fluoro-4-(2-piperidin-1-ylethoxy)phenyl]amine (404 mg) was used according to an analogous synthetic method to Example 111 to provide the title compound (324 mg).

$^1$H-NMR (400 MHz, DMSO-$d_6$); δ (ppm): 1.29-1.38 (m, 2H), 1.41-1.49 (m, 4H), 2.32-2.42 (m, 4H), 2.55 (t, 2H), 3.95 (t, 2H), 6.52 (d, 1H), 6.59 (dd, 1H), 6.91 (t, 1H), 7.04-7.15 (m, 3H), 7.18-7.27 (m, 3H), 7.42 (dd, 1H), 7.63 (d, 1H), 7.72 (d, 1H), 7.82 (s, 1H), 9.76 (s, 1H).
ESI-Mass; 475 [M++H]

Example 125

3-[3-Fluoro-4-(2-piperidin-1-ylethoxy)phenylamino]-4-naphthalen-2-ylphenol

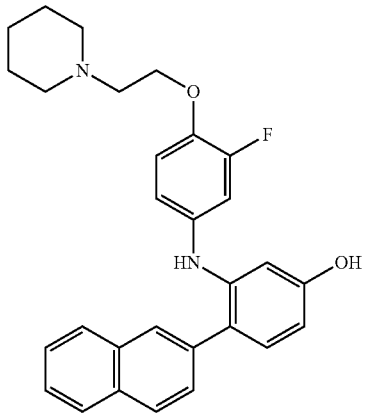 [SMILES: Oc1ccc(-c2ccc3ccccc3c2)c(Nc2ccc(OCCN3CCCCC3)c(F)c2)c1]

Synthesized from 5-methoxy-2-naphthalen-2-ylamine and 1-[2-(4-bromo-2-fluorophenoxy)ethyl]piperidine according to an analogous synthetic method to Example 116, [3-fluoro-4-(2-piperidin-1-ylethoxy)phenyl](5-methoxy-2-naphthalen-2-ylphenyl)amine (350 mg) was used according to an analogous synthetic method to Example 111 to provide the title compound (293 mg).
$^1$H-NMR (400 MHz, DMSO-$d_6$); δ (ppm): 1.31-1.38 (m, 2H), 1.42-1.49 (m, 4H), 2.33-2.42 (m, 4H), 2.57 (t, 2H), 3.98 (t, 2H), 6.48 (dd, 1H), 6.65-6.71 (m, 2H), 6.75 (dd, 1H), 6.96 (t, 1H), 7.13-7.17 (m, 2H), 7.41-7.48 (m, 2H), 7.51 (dd, 1H), 7.81-7.88 (m, 4H), 9.41 (s, 1H).
ESI-Mass; 457 [M++H]

Example 126

6-{3-[3-Fluoro-4-(2-piperidin-1-ylethoxy)phenylamino]pyridin-4-yl}naphthalen-2-ol

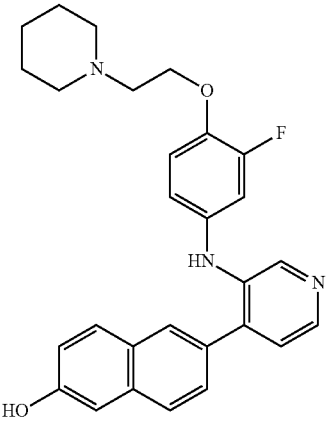 [SMILES: Oc1ccc2cc(-c3ccncc3Nc3ccc(OCCN4CCCCC4)c(F)c3)ccc2c1]

Synthesized from 4-(6-methoxynaphthalen-2-yl)pyridin-3-ylamine and 1-[2-(4-bromo-2-fluorophenoxy)ethyl]piperidine according to an analogous synthetic method to Example 116, [3-fluoro-4-(2-piperidin-1-ylethoxy)phenyl][4-(6-methoxynaphthalen-2-yl)pyridin-3-yl]amine (343 mg) was used according to an analogous synthetic method to Example 111 to provide the title compound (248 mg).

$^1$H-NMR (400 MHz, DMSO-d$_6$); δ (ppm): 1.29-1.37 (m, 2H), 1.41-1.49 (m, 4H), 2.32-2.42 (m, 4H), 2.55 (t, 2H), 3.96 (t, 2H), 6.60 (d, 1H), 6.66 (dd, 1H), 6.93 (t, 1H), 7.05-7.11 (m, 2H), 7.35 (d, 1H), 7.48 (dd, 1H), 7.53 (s, 1H), 7.67 (d, 1H), 7.76 (d, 1H), 7.91 (s, 1H), 8.24 (d, 1H), 8.44 (s, 1H), 9.83 (s, 1H).

ESI-Mass; 458 [M$^+$+H]

Example 127

6-{2-{Ethyl[3-fluoro-4-(2-piperidin-1-ylethoxy)benzyl]amino}phenyl}naphthalen-2-ol

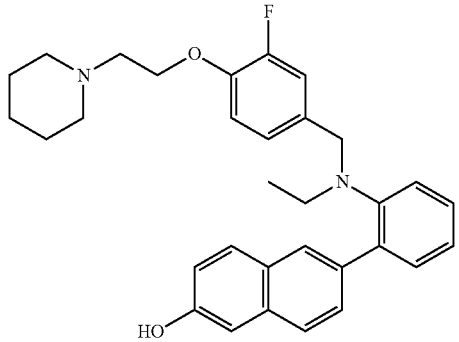 [SMILES: CCN(Cc1ccc(OCCN2CCCCC2)c(F)c1)c1ccccc1-c1ccc2cc(O)ccc2c1]

Synthesized from 2-(6-methoxynaphthalen-2-yl)phenylamine and 3-fluoro-4-(2-piperidin-1-ylethoxy)benzoic acid hydrochloride according to an analogous synthetic method to Example 114, [3-fluoro-4-(2-piperidin-1-ylethoxy)benzyl][2-(6-methoxynaphthalen-2-yl)phenyl]amine (362 mg) was used according to an analogous synthetic method to Example 36 to provide ethyl[3-fluoro-4-(2-piperidin-1-ylethoxy)benzyl][2-(6-methoxynaphthalen-2-yl)phenyl]amine (310 mg). This compound (308 mg) was used according to an analogous synthetic method to Example 111 to provide the title compound (205 mg).

$^1$H-NMR (400 MHz, DMSO-d$_6$); δ (ppm): 0.79 (t, 3H), 1.31-1.39 (m, 2H), 1.42-1.50 (m, 4H), 2.33-2.43 (m, 4H), 2.59 (t, 2H), 2.69 (q, 2H), 3.87 (s, 2H), 4.03 (t, 2H), 6.82-6.88 (m, 2H), 6.99 (t, 1H), 7.04-7.09 (m, 2H), 7.11-7.15 (m, 2H), 7.22-7.28 (m, 2H), 7.62 (dd, 1H), 7.70 (d, 1H), 7.76 (d, 1H), 7.84 (s, 1H), 9.73 (s, 1H).

ESI-Mass; 499 [M$^+$+H]

Example 128

3-{Ethyl[3-fluoro-4-(2-piperidin-1-ylethoxy)benzyl]amino}-4-naphthalen-2-ylphenol

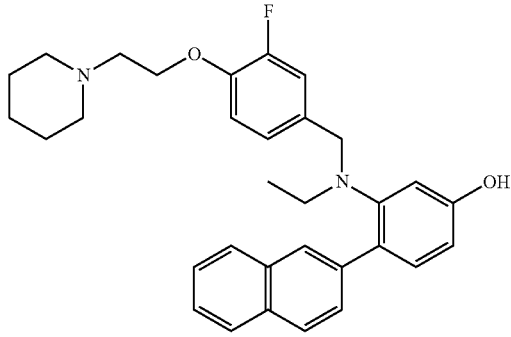 [SMILES: CCN(Cc1ccc(OCCN2CCCCC2)c(F)c1)c1cc(O)ccc1-c1ccc2ccccc2c1]

Synthesized from 5-methoxy-2-naphthalen-2-ylamine and 3-fluoro-4-(2-piperidin-1-ylethoxy)benzoic acid hydrochloride according to an analogous synthetic method to Example 114, [3-fluoro-4-(2-piperidin-1-ylethoxy)benzyl](5-methoxy-2-naphthalen-2-ylphenyl)amine (290 mg) was used according to an analogous synthetic method to Example 36 to provide ethyl[3-fluoro-4-(2-piperidin-1-ylethoxy)benzyl](5-methoxy-2-naphthalen-2-ylphenyl)amine (252 mg). This compound (250 mg) was used according to an analogous synthetic method to Example 111 to provide the title compound (222 mg).

$^1$H-NMR (400 MHz, DMSO-d$_6$); δ (ppm): 0.83 (t, 3H), 1.32-1.40 (m, 2H), 1.44-1.52 (m, 4H), 2.35-2.44 (m, 4H), 2.62 (t, 2H), 2.68 (q, 2H), 3.86 (s, 2H), 4.05 (t, 2H), 6.53 (dd, 1H), 6.57 (d, 1H), 6.85-6.91 (m, 2H), 7.02 (t, 1H), 7.12 (d, 1H), 7.45-7.52 (m, 2H), 7.74 (dd, 1H), 7.88-7.95 (m, 4H), 9.42 (s, 1H).

ESI-Mass; 499 [M$^+$+H]

Example 129

[5-Methoxy-2-(6-methoxy-3,4-dihydronaphthalen-2-yl)phenyl][4-(2-piperidin-1-ylethoxy)benzyl]amine

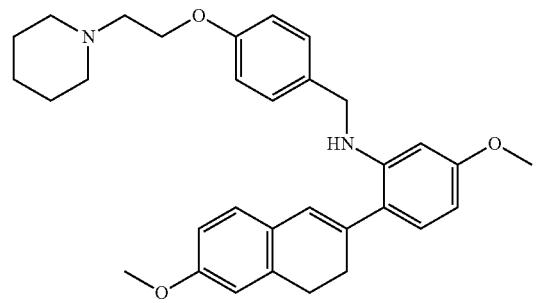 [SMILES: COc1ccc2c(c1)CCC(c1ccc(OC)cc1NCc1ccc(OCCN3CCCCC3)cc1)=C2]

Synthesized from 5-methoxy-2-(6-methoxy-3,4-dihydronaphthalen-2-yl)phenylamine (341 mg) and 4-(2-piperidin-1-ylethoxy)benzoyl chloride hydrochloride (990 mg) according to an analogous synthetic method to Example 110, the title compound (113 mg) was obtained.

$^1$H-NMR (400 MHz, CDCl$_3$); δ (ppm): 1.40-1.48 (m, 2H), 1.56-1.63 (m, 4H), 2.47-2.53 (m, 4H), 2.56 (t, 2H), 2.76 (t, 2H), 2.88 (t, 2H), 3.76 (s, 3H), 3.80 (s, 3H), 4.09 (t, 2H), 4.25 (s, 2H), 4.46 (brs, 1H), 6.23 (d, 1H), 6.27 (dd, 1H), 6.55 (s, 1H), 6.68-6.72 (m, 2H), 6.86 (d, 2H), 6.97 (d, 1H), 7.01 (d, 1H), 7.25 (d, 2H).

Example 130

6-{4-Hydroxy-2-[4-(2-piperidin-1-ylethoxy)benzylamino]phenyl}-7,8-dihydronaphthalen-2-ol

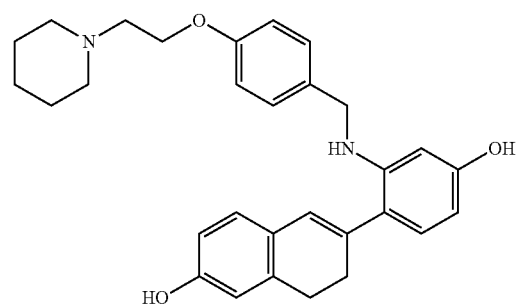 [SMILES: Oc1ccc2c(c1)CCC(c1ccc(O)cc1NCc1ccc(OCCN3CCCCC3)cc1)=C2]

Synthesized from [5-methoxy-2-(6-methoxy-3,4-dihydronaphthalen-2-yl)phenyl][4-(2-piperidin-1-ylethoxy)benzyl]amine (106 mg) according to an analogous synthetic method to Example 111, the title compound (89 mg) was obtained.

$^1$H-NMR (400 MHz, DMSO-d$_6$); δ (ppm): 1.30-1.38 (m, 2H), 1.42-1.50 (m, 4H), 2.36-2.42 (m, 4H), 2.43 (t, 2H), 2.60 (t, 2H), 2.78 (t, 2H), 3.99 (t, 2H), 4.17 (s, 2H), 5.23 (t, 1H), 5.88 (d, 1H), 5.97 (dd, 1H), 6.39 (s, 1H), 6.52 (dd, 1H), 6.56 (s, 1H), 6.75 (d, 1H), 6.82-6.90 (m, 3H), 7.21 (d, 2H), 8.94 (s, 1H), 9.28 (s, 1H).
ESI-Mass; 471 [M$^+$+H]

Example 131

[5-Methoxy-2-(6-methoxy-3,4-dihydronaphthalen-2-yl)phenyl]methyl[4-(2-piperidin-1-ylethoxy)benzyl]amine

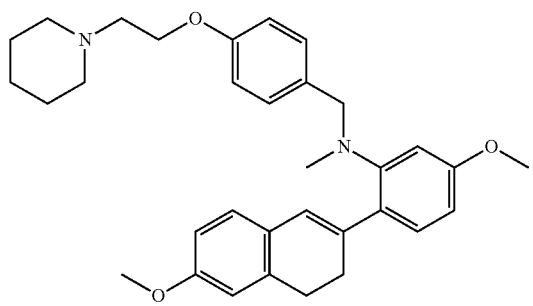 [SMILES: COc1ccc2c(c1)CCC(c1ccc(OC)cc1N(C)Cc1ccc(OCCN3CCCCC3)cc1)=C2]

Synthesized from [5-methoxy-2-(6-methoxy-3,4-dihydronaphthalen-2-yl)phenyl][4-(2-piperidin-1-ylethoxy)benzyl]amine (290 mg) according to an analogous synthetic method to Preparation Example 18, the title compound (176 mg) was obtained.

$^1$H-NMR (400 MHz, CDCl$_3$); δ (ppm): 1.41-1.50 (m, 2H), 1.57-1.65 (m, 4H), 2.47-2.55 (m, 4H), 2.60 (s, 3H), 2.72-2.80 (m, 4H), 2.91 (t, 2H), 3.81 (s, 3H), 3.83 (s, 3H), 4.09 (t, 2H), 4.17 (s, 2H), 6.51-6.58 (m, 3H), 6.70-6.76 (m, 2H), 6.81 (d, 2H), 7.03 (d, 1H), 7.09 (d, 2H), 7.21 (d, 1H).

Example 132

6-{4-Hydroxy-2-{methyl[4-(2-piperidin-1-ylethoxy)benzyl]amino}phenyl}-7,8-dihydronaphthalen-2-ol

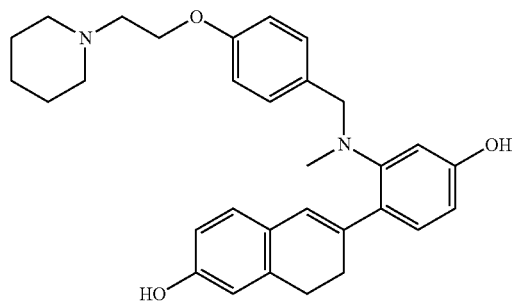 [SMILES: CN(Cc1ccc(OCCN2CCCCC2)cc1)c1cc(O)ccc1C1=Cc2ccc(O)cc2CC1]

Synthesized from [5-methoxy-2-(6-methoxy-3,4-dihydronaphthalen-2-yl)phenyl]methyl[4-(2-piperidin-1-ylethoxy)benzyl]amine (173 mg) according to an analogous synthetic method to Example 111, the title compound (157 mg) was obtained.

$^1$H-NMR (400 MHz, DMSO-d$_6$); δ (ppm): 1.62-1.78 (m, 6H), 2.47 (s, 3H), 2.56-2.63 (m, 2H), 2.70-2.76 (m, 2H), 2.90-3.02 (m, 2H), 3.40-3.50 (m, 2H), 3.58 (t, 3H), 4.10 (s, 2H), 4.28-4.34 (m, 2H), 6.29-6.37 (m, 2H), 6.45 (s, 1H), 6.50-6.58 (m, 2H), 6.82-6.91 (m, 3H), 6.97 (d, 1H), 7.09 (d, 2H), 9.25 (s, 1H), 9.96 (s, 1H).
ESI-Mass; 485 [M$^+$+H]

Example 133

[5-Methoxy-2-(6-methoxy-3,4-dihydronaphthalen-2-yl)phenyl][4-(2-piperidin-1-ylethoxy)phenyl]amine

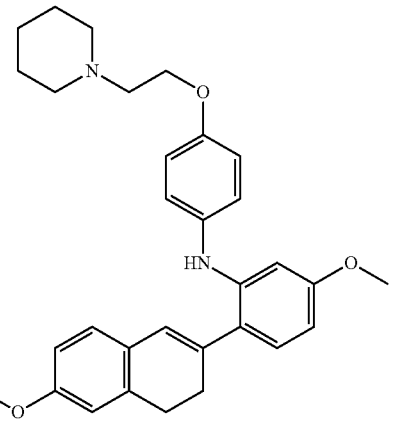

Synthesized from 5-methoxy-2-(6-methoxy-3,4-dihydronaphthalen-2-yl)phenylamine (150 mg) and 1-[2-(4-bromophenoxy)ethyl]piperidine (155 mg) according to an analogous synthetic method to Example 116, the title compound (220 mg) was obtained.

$^1$H-NMR (400 MHz, CDCl$_3$); δ (ppm): 1.41-1.49 (m, 2H), 1.55-1.65 (m, 4H), 2.47-2.55 (m, 4H), 2.59 (t, 2H), 2.77 (t, 2H), 2.91 (t, 2H), 3.73 (s, 3H), 3.82 (s, 3H), 4.09 (t, 2H), 5.73 (s, 1H), 6.41 (dd, 1H), 6.56-6.75 (m, 4H), 6.86 (d, 2H), 6.98-7.12 (m, 4H).

Example 134

6-{4-Hydroxy-2-[4-(2-piperidin-1-ylethoxy)phenylamino]phenyl}-7,8-dihydronaphthalen-2-ol

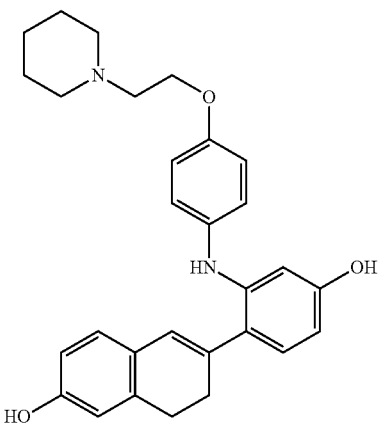 [SMILES: Oc1ccc2c(c1)CCC(c1ccc(O)cc1Nc1ccc(OCCN3CCCCC3)cc1)=C2]

Synthesized from [5-methoxy-2-(6-methoxy-3,4-dihydronaphthalen-2-yl)phenyl][4-(2-piperidin-1-ylethoxy)phenyl]amine (217 mg) according to an analogous synthetic method to Example 111, the title compound (118 mg) was obtained.

¹H-NMR (400 MHz, DMSO-d₆); δ (ppm): 1.30-1.60 (m, 6H), 2.30-2.50 (m, 8H), 2.63 (t, 2H), 3.90-4.05 (m, 2H), 6.28 (d, 1H), 6.39 (s, 1H), 6.46-6.54 (m, 3H), 6.75-7.00 (m, 7H), 9.17 (s, 1H), 9.24 (s, 1H).
ESI-Mass; 457 [M⁺+H]

Example 135

[5-Methoxy-2-(6-methoxy-3,4-dihydronaphthalen-2-yl)phenyl]methylamine

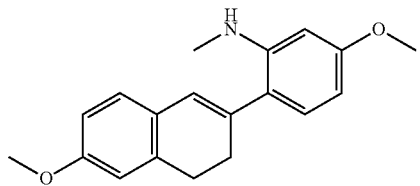

To a solution of 5-methoxy-2-(6-methoxy-3,4-dihydronaphthalen-2-yl)phenylamine (400 mg) in tetrahydrofuran (10 ml) and N,N-diisopropylethylamine (0.5 ml) was added ethyl chlorocarbonate (0.2 ml) on an ice bath, and the solution was stirred overnight at room temperature. A saturated aqueous solution of ammonium chloride was added thereto, the solution was extracted with ethyl acetate, then sequentially washed with water and brine, and the solvent was evaporated in vacuo. The residue was purified by silica gel column chromatography (hexane-ethyl acetate system) to provide ethyl[5-methoxy-2-(6-methoxy-3,4-dihydronaphthalen-2-yl)phenyl]carbamate (445 mg). This compound (438 mg) was used according to an analogous synthetic method to Example 337 described below to provide the title compound (286 mg).
¹H-NMR (400 MHz, CDCl₃); δ (ppm): 2.55 (t, 2H), 2.83 (s, 3H), 2.91 (t, 2H), 3.82 (s, 3H), 4.26 (brs, 1H), 6.22 (d, 1H), 6.27 (dd, 1H), 6.53 (s, 1H), 6.70-6.75 (m, 2H), 6.99 (d, 1H), 7.00 (d, 1H).

Example 136

[5-Methoxy-2-(6-methoxy-3,4-dihydronaphthalen-2-yl)phenyl]methyl[4-(2-piperidin-1-ylethoxy)phenyl]amine

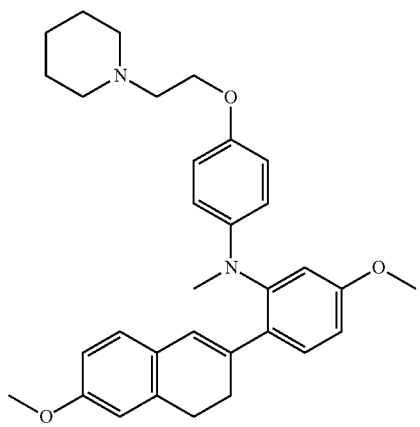

Synthesized from [5-methoxy-2-(6-methoxy-3,4-dihydronaphthalen-2-yl)phenyl]methylamine (285 mg) and 1-[2-(4-bromophenoxy)ethyl]piperidine (285 mg) according to an analogous synthetic method to Example 116, the title compound (228 mg) was obtained.
¹H-NMR (400 MHz, CDCl₃); δ (ppm): 1.38-1.49 (m, 2H), 1.51-1.64 (m, 4H), 2.41-2.53 (m, 6H), 2.55-2.76 (m, 4H), 3.10 (s, 3H), 3.75 (s, 3H), 3.80 (s, 3H), 4.04 (t, 2H), 6.46 (s, 1H), 6.64-6.80 (m, 7H), 6.68 (d, 1H), 7.20-7.32 (m, 2H).

Example 137

6-{4-Hydroxy-2-{methyl[4-(2-piperidin-1-ylethoxy)phenyl]amino}phenyl}-7,8-dihydronaphthalen-2-ol

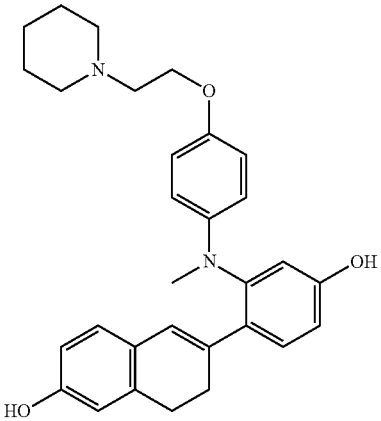 [SMILES: CN(c1ccc(OCCN2CCCCC2)cc1)c1cc(O)ccc1C1=Cc2ccc(O)cc2CC1]

Synthesized from [5-methoxy-2-(6-methoxy-3,4-dihydronaphthalen-2-yl)phenyl]methyl[4-(2-piperidin-1-ylethoxy)phenyl]amine (225 mg) according to an analogous synthetic method to Example 111, the title compound (176 mg) was obtained.
¹H-NMR (400 MHz, DMSO-d₆); δ (ppm): 1.30-1.38 (m, 2H), 1.42-1.49 (m, 4H), 2.31 (t, 2H), 2.31-2.39 (m, 4H), 2.49-2.57 (m, 4H), 3.00 (s, 3H), 3.91 (t, 2H), 6.33 (s, 1H), 6.40-6.60 (m, 6H), 6.73 (d, 2H), 6.83 (d, 1H), 7.15 (d, 1H), 9.26 (s, 1H), 9.41 (s, 1H).
ESI-Mass; 471 [M⁺+H]

Example 138

[5-Methoxy-2-(6-methoxy-1,2,3,4-tetrahydronaphthalen-2-yl)phenyl][4-(2-piperidin-1-ylethoxy)phenyl]amine

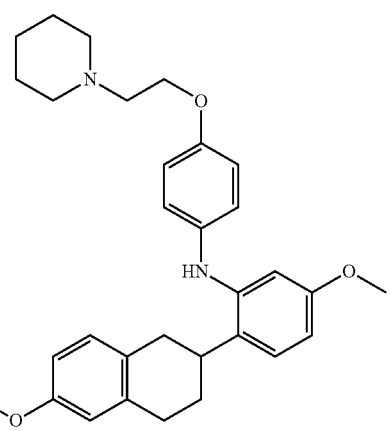

Synthesized from 5-methoxy-2-(6-methoxy-1,2,3,4-tetrahydronaphthalen-2-yl)phenylamine (150 mg) and 1-[2-(4-bromophenoxy)ethyl]piperidine (150 mg) according to an analogous synthetic method to Example 116, the title compound (186 mg) was obtained.

¹H-NMR (400 MHz, CDCl₃); δ (ppm): 1.41-1.49 (m, 2H), 1.56-1.65 (m, 4H), 1.90-2.03 (m, 1H), 2.07-2.15 (m, 1H), 2.46-2.55 (m, 4H), 2.77 (t, 2H), 2.78-3.07 (m, 5H), 3.72 (s, 3H), 3.79 (s, 3H), 4.08 (t, 2H), 5.36 (s, 1H), 6.48 (dd, 1H), 6.62-6.73 (m, 3H), 6.85 (d, 2H), 6.95-7.05 (m, 3H), 7.14 (d, 1H).

Example 139

6-{4-Hydroxy-2-[4-(2-piperidin-1-ylethoxy)phenylamino]phenyl}-5,6,7,8-tetrahydronaphthalen-2-ol

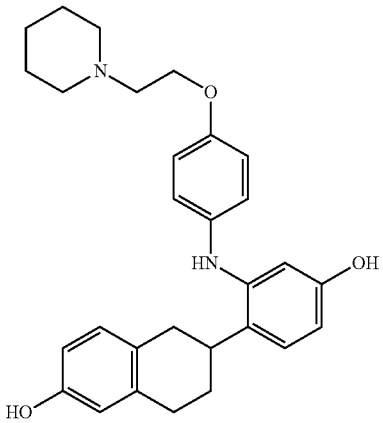 [SMILES: Oc1ccc2c(c1)CCC(c1ccc(O)cc1Nc1ccc(OCCN3CCCCC3)cc1)C2]

Synthesized from [5-methoxy-2-(6-methoxy-1,2,3,4-tetrahydronaphthalen-2-yl)phenyl][4-(2-piperidin-1-ylethoxy)phenyl]amine (183 mg) according to an analogous synthetic method to Example 111, the title compound (99 mg) was obtained.

¹H-NMR (400 MHz, DMSO-d₆); δ (ppm): 1.30-1.60 (m, 6H), 1.69-1.88 (m, 2H), 2.30-2.82 (m, 10H), 3.03-3.13 (m, 1H), 3.91-4.03 (m, 2H), 6.28 (dd, 1H), 6.41-6.49 (m, 3H), 6.77-6.88 (m, 5H), 6.95-7.02 (m, 2H), 8.92 (s, 1H), 8.96 (s, 1H).
ESI-Mass; 459 [M⁺+H]

Example 140

6-{2-[4-(2-Azepan-1-ylethoxy)phenylamino]-4-hydroxyphenyl}-5,6,7,8-tetrahydronaphthalen-2-ol

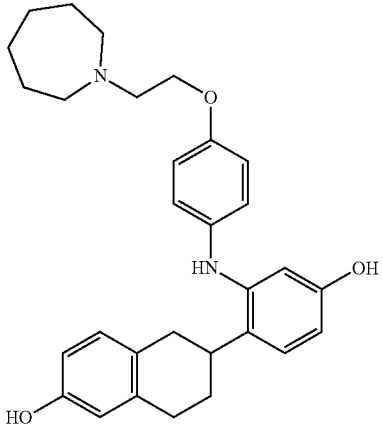 [SMILES: Oc1ccc2c(c1)CCC(c1ccc(O)cc1Nc1ccc(OCCN3CCCCCC3)cc1)C2]

Synthesized from 5-methoxy-2-(6-methoxy-1,2,3,4-tetrahydronaphthalen-2-yl)phenylamine and 1-[2-(4-bromophenoxy)ethyl]azepane according to an analogous synthetic method to Example 116, [4-(2-azepan-1-ylethoxy)phenyl][5-methoxy-2-(6-methoxy-1,2,3,4-tetrahydronaphthalen-2-yl)phenyl]amine (86 mg) was used according to an analogous synthetic method to Example 111 to provide the title compound (28 mg).

¹H-NMR (400 MHz, DMSO-d₆); δ (ppm): 1.46-1.59 (m, 8H), 1.66-1.88 (m, 2H), 2.49-2.77 (m, 8H), 2.79 (t, 2H), 3.04-3.12 (m, 1H), 3.93 (t, 2H), 6.26 (dd, 1H), 6.37-6.52 (m, 3H), 6.76-7.00 (m, 7H), 8.91 (s, 1H), 8.96 (s, 1H).
ESI-Mass; 473 [M⁺+H]

Example 141

6-{2-[3-Fluoro-4-(2-piperidin-1-ylethoxy)phenylamino]-4-hydroxyphenyl}-5,6,7,8-tetrahydronaphthalen-2-ol

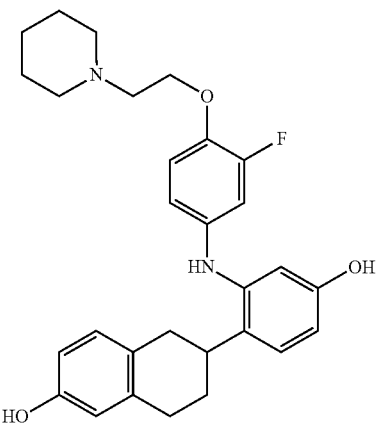 [SMILES: Oc1ccc2c(c1)CCC(c1ccc(O)cc1Nc1ccc(OCCN3CCCCC3)c(F)c1)C2]

Synthesized from 5-methoxy-2-(6-methoxy-1,2,3,4-tetrahydronaphthalen-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(6-methoxy-1,2,3,4-tetrahydronaphthalen-2-yl)phenyl]amine (84 mg) was used according to an analogous synthetic method to Example 111 to provide the title compound (42 mg).

¹H-NMR (400 MHz, DMSO-d₆); δ (ppm): 1.30-1.38 (m, 2H), 1.42-1.50 (m, 4H), 1.67-1.84 (m, 2H), 2.34-2.43 (m, 4H), 2.50-2.58 (m, 1H), 2.59 (t, 2H), 2.67-2.76 (m, 3H), 3.00-3.10 (m, 1H), 4.00 (t, 2H), 6.38 (d, 1H), 6.44-6.48 (m, 2H), 6.52 (d, 1H), 6.59 (d, 1H), 6.66 (dd, 1H), 6.79 (d, 1H), 6.98 (t, 1H), 7.03 (d, 1H), 7.24 (s, 1H), 8.97 (s, 1H), 9.06 (s, 1H).
ESI-Mass; 477 [M⁺+H]

Example 142

6-{2-[4-(2-Azepan-1-ylethoxy)-3-fluorophenylamino]-4-hydroxyphenyl}-5,6,7,8-tetrahydronaphthalen-2-ol

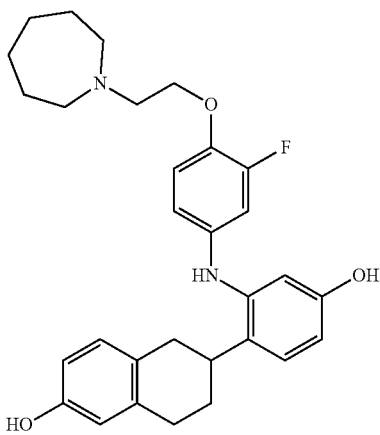 [SMILES: Oc1ccc2c(c1)CCC(c1ccc(O)cc1Nc1ccc(OCCN3CCCCCC3)c(F)c1)C2]

Synthesized from 5-methoxy-2-(6-methoxy-1,2,3,4-tetrahydronaphthalen-2-yl)phenylamine and 1-[2-(4-bromo-2-fluorophenoxy)ethyl]azepane according to an analogous synthetic method to Example 116, [4-(2-azepan-1-ylethoxy)-3-fluorophenyl][5-methoxy-2-(6-methoxy-1,2,3,4-tetrahydronaphthalen-2-yl)phenyl]amine (146 mg) was used according to an analogous synthetic method to Example 111 to provide the title compound (66 mg).

¹H-NMR (400 MHz, DMSO-d₆); δ (ppm): 1.46-1.58 (m, 8H), 1.68-1.85 (m, 2H), 2.48-2.59 (m, 1H), 2.61-2.67 (m, 4H), 2.68-2.77 (m, 3H), 2.78 (t, 2H), 3.00-3.10 (m, 1H), 3.97 (t, 2H), 6.38 (dd, 1H), 6.43-6.48 (m, 2H), 6.52 (d, 1H), 6.59 (d, 1H), 6.66 (dd, 1H), 6.79 (d, 1H), 6.98 (t, 1H), 7.03 (d, 1H), 7.24 (s, 1H), 8.97 (s, 1H), 9.06 (s, 1H).

ESI-Mass; 491 [M⁺+H]

Example 143

6-{2-[4-(2-Diisopropylaminoethoxy)-3-fluorophenylamino]-4-hydroxyphenyl}-5,6,7,8-tetrahydronaphthalen-2-ol

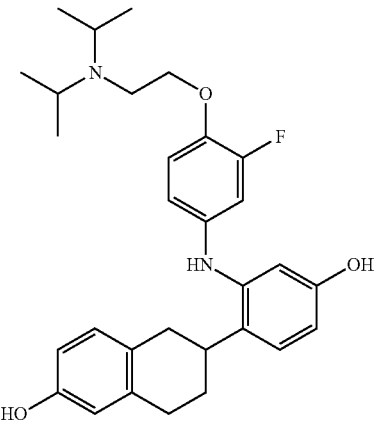 [SMILES: CC(C)N(CCOc1ccc(Nc2cc(O)ccc2C2CCc3cc(O)ccc3C2)cc1F)C(C)C]

Synthesized from 5-methoxy-2-(6-methoxy-1,2,3,4-tetrahydronaphthalen-2-yl)phenylamine and [2-(4-bromo-2-fluorophenoxy)ethyl]diisopropylamine according to an analogous synthetic method to Example 116, [4-(2-diisopropylaminoethoxy)-3-fluorophenyl][5-methoxy-2-(6-methoxy-1,2,3,4-tetrahydronaphthalen-2-yl)phenyl]amine (133 mg) was used according to an analogous synthetic method to Example 111 to provide the title compound (28 mg).

¹H-NMR (400 MHz, DMSO-d₆); δ (ppm): 0.95 (d, 12H), 1.68-1.84 (m, 2H), 2.50-2.59 (m, 1H), 2.66-2.77 (m, 5H), 2.92-3.09 (m, 3H), 3.81 (t, 2H), 6.38 (dd, 1H), 6.44-6.48 (m, 2H), 6.52 (d, 1H), 6.59 (d, 1H), 6.66 (dd, 1H), 6.79 (d, 1H), 6.96 (t, 1H), 7.03 (d, 1H), 7.23 (d, 1H), 8.97 (s, 1H), 9.05 (s, 1H).

ESI-Mass; 493 [M⁺+H]

Example 144

6-{2-[3-Fluoro-4-(3-piperidin-1-ylpropyl)phenylamino]-4-hydroxyphenyl}-5,6,7,8-tetrahydronaphthalen-2-ol

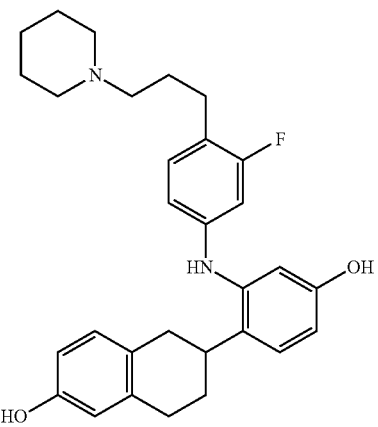

Synthesized from 5-methoxy-2-(6-methoxy-1,2,3,4-tetrahydronaphthalen-2-yl)phenylamine and 1-[3-(4-bromo-2-fluorophenyl)prop-2-ynyl]piperidine according to an analogous synthetic method to Example 116, [3-fluoro-4-(3-piperidin-1-ylprop-1-ynyl)phenyl][5-methoxy-2-(6-methoxy-1,2,3,4-tetrahydronaphthalen-2-yl)phenyl]amine (281 mg) was used according to an analogous synthetic method to Example 22 to provide [3-fluoro-4-(3-piperidin-1-ylpropyl)phenyl][5-methoxy-2-(6-methoxy-1,2,3,4-tetrahydronaphthalen-2-yl)phenyl]amine (235 mg). This compound (233 mg) was used according to an analogous synthetic method to Example 111 to provide the title compound (122 mg).

¹H-NMR (400 MHz, DMSO-d₆); δ (ppm): 1.29-1.38 (m, 2H), 1.41-1.49 (m, 4H), 1.60 (pent, 2H), 1.68-1.84 (m, 2H), 2.19 (t, 2H), 2.19-2.30 (m, 4H), 2.43 (t, 2H), 2.50-2.60 (m, 1H), 2.65-2.74 (m, 3H), 2.99-3.09 (m, 1H), 6.43-6.51 (m, 4H), 6.55 (dd, 1H), 6.58 (d, 1H), 6.78 (d, 1H), 6.99 (t, 1H), 7.07 (d, 1H), 7.45 (s, 1H), 8.97 (s, 1H), 9.12 (s, 1H).

ESI-Mass; 475 [M⁺+H]

Example 145

6-{2-[6-(2-Azepan-1-ylethoxy)pyridin-3-ylamino]-4-hydroxyphenyl}-5,6,7,8-tetrahydronaphthalen-2-ol

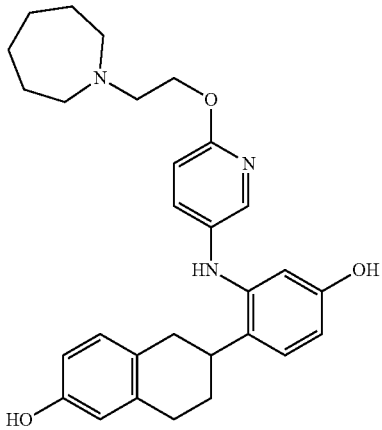

Synthesized from 5-methoxy-2-(6-methoxy-1,2,3,4-tetrahydronaphthalen-2-yl)phenylamine and 1-[2-(5-bromopyridin-2-yloxy)ethyl]azepane according to an analogous synthetic method to Example 116, [6-(2-azepan-1-ylethoxy)pyridin-3-yl][5-methoxy-2-(6-methoxy-1,2,3,4-tetrahydronaphthalen-2-yl)phenyl]amine (308 mg) was used according to an analogous synthetic method to Example 111 to provide the title compound (94 mg).

¹H-NMR (400 MHz, DMSO-d₆); δ (ppm): 1.46-1.59 (m, 8H), 1.68-1.89 (m, 2H), 2.51-2.59 (m, 1H), 2.64 (t, 4H), 2.69-2.84 (m, 5H), 3.03-3.13 (m, 1H), 4.22 (t, 2H), 6.28 (dd, 1H), 6.35 (d, 1H), 6.44-6.50 (m, 2H), 6.68 (d, 1H), 6.82 (d, 1H), 6.99 (d, 1H), 7.11 (s, 1H), 7.33 (dd, 1H), 7.78 (d, 1H), 8.97 (s, 2H).

ESI-Mass; 474 [M⁺+H]

Example 146

[5-Methoxy-2-(6-methoxy-1,2,3,4-tetrahydronaphthalen-2-yl)phenyl]methyl[4-(2-piperidin-1-ylethoxy)phenyl]amine

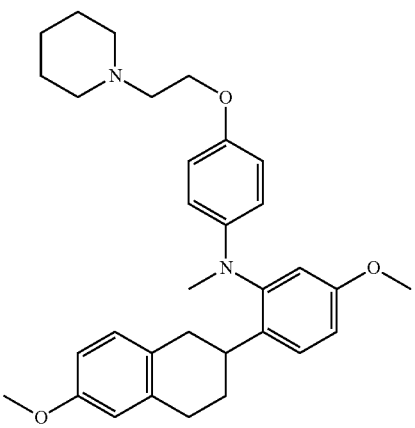

Synthesized from [5-methoxy-2-(6-methoxy-1,2,3,4-tetrahydronaphthalen-2-yl)phenyl]methylamine (96 mg) and 1-[2-(4-bromophenoxy)ethyl]piperidine (96 mg) according to an analogous synthetic method to Example 116, the title compound (108 mg) was obtained.

$^1$H-NMR (400 MHz, CDCl$_3$); δ (ppm): 1.40-1.48 (m, 2H), 1.55-1.63 (m, 4H), 1.78-1.92 (m, 2H), 2.44-2.53 (m, 4H), 2.70-2.84 (m, 6H), 3.09-3.16 (m, 1H), 3.16 (s, 3H), 3.76 (s, 6H), 4.03 (t, 2H), 6.50 (d, 2H), 6.60-6.68 (m, 3H), 6.75 (d, 2H), 6.84 (d, 1H), 6.93 (d, 1H), 7.27 (d, 1H).

Example 147

6-{4-Hydroxy-2-{methyl[4-(2-piperidin-1-ylethoxy)phenyl]amino}phenyl}-5,6,7,8-tetrahydronaphthalen-2-ol

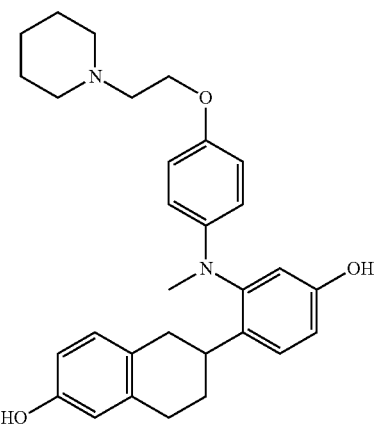

Synthesized from [5-methoxy-2-(6-methoxy-1,2,3,4-tetrahydronaphthalen-2-yl)phenyl]methyl[4-(2-piperidin-1-ylethoxy)phenyl]amine (107 mg) according to an analogous synthetic method to Example 111, the title compound (96 mg) was obtained.

$^1$H-NMR (400 MHz, DMSO-d$_6$); δ (ppm): 1.31-1.37 (m, 2H), 1.42-1.49 (m, 4H), 1.68-1.76 (m, 2H), 2.33-2.41 (m, 4H), 2.55 (t, 2H), 2.55-2.70 (m, 4H), 2.84-2.94 (m, 1H), 3.03 (s, 3H), 3.90 (t, 2H), 6.39-6.47 (m, 5H), 6.67 (dd, 1H), 6.69-6.77 (m, 3H), 7.18 (d, 1H), 8.97 (s, 1H), 9.28 (s, 1H).
ESI-Mass; 474 [M$^+$+H]

Example 148

Ethyl[3-fluoro-4-(2-piperidin-1-ylethoxy)phenyl][5-methoxy-2-(6-methoxy-1,2,3,4-tetrahydronaphthalen-2-yl)phenyl]amine

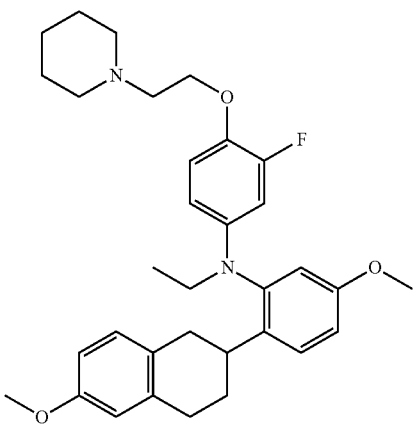

Synthesized from ethyl[5-methoxy-2-(6-methoxy-1,2,3,4-tetrahydronaphthalen-2-yl)phenyl]amine (200 mg) and 1-[2-(4-bromo-2-fluorophenoxy)ethyl]piperidine (238 mg) according to an analogous synthetic method to Example 116, the title compound (81 mg) was obtained.

$^1$H-NMR (400 MHz, CDCl$_3$); δ (ppm): 1.20 (t, 3H), 1.38-1.47 (m, 2H), 1.55-1.59 (m, 4H), 1.77-1.85 (m, 2H), 2.44-2.54 (m, 4H), 2.69-2.84 (m, 6H), 2.98-3.09 (m, 1H), 3.53-3.59 (m, 2H), 3.76 (s, 3H), 3.78 (s, 3H), 4.06 (t, 2H), 6.14-6.18 (m, 1H), 6.25 (dd, 1H), 6.61 (d, 1H), 6.66 (dd, 2H), 6.79 (t, 1H), 6.87-6.94 (m, 2H), 7.29 (d, 1H).

Example 149

6-{2-{Ethyl[3-fluoro-4-(2-piperidin-1-ylethoxy)phenyl]amino}-4-hydroxyphenyl}-5,6,7,8-tetrahydronaphthalen-2-ol

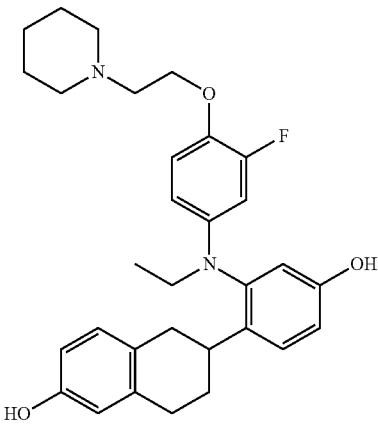 [SMILES: CCN(c1ccc(OCCN2CCCCC2)c(F)c1)c1cc(O)ccc1C1CCc2cc(O)ccc2C1]

Synthesized from ethyl[3-fluoro-4-(2-piperidin-1-ylethoxy)phenyl][5-methoxy-2-(6-methoxy-1,2,3,4-tetrahydronaphthalen-2-yl)phenyl]amine (150 mg) according to an analogous synthetic method to Example 111, the title compound (106 mg) was obtained.

$^1$H-NMR (400 MHz, DMSO-d$_6$); δ (ppm): 1.07 (t, 3H), 1.29-1.38 (m, 2H), 1.41-1.48 (m, 4H), 1.62-1.75 (m, 2H), 2.33-2.41 (m, 4H), 2.50-2.57 (m, 4H), 2.60-2.70 (m, 2H), 2.75-2.84 (m, 1H), 3.44-3.52 (m, 2H), 3.95 (t, 2H), 6.11-6.16 (m, 1H), 6.25 (dd, 1H), 6.38-6.47 (m, 3H), 6.74 (dd, 2H), 6.92 (t, 1H), 7.24 (d, 1H), 8.98 (brs, 1H), 9.38 (brs, 1H).

ESI-Mass; 505 [M$^+$+H]

Example 150

[5-Methoxy-2-(6-methoxy-1,2,3,4-tetrahydronaphthalen-2-yl)phenyl][4-(2-piperidin-1-ylethoxy)benzyl]amine

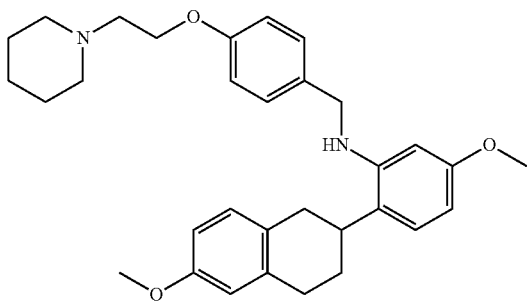 [SMILES: COc1ccc2c(c1)CCC(c1ccc(OC)cc1NCc1ccc(OCCN3CCCCC3)cc1)C2]

Synthesized from 5-methoxy-2-(6-methoxy-1,2,3,4-tetrahydronaphthalen-2-yl)phenylamine (312 mg) and 4-(2-piperidin-1-ylethoxy)benzoyl chloride hydrochloride (1.0 g) according to an analogous synthetic method to Example 110, the title compound (360 mg) was obtained.

$^1$H-NMR (400 MHz, CDCl$_3$); δ (ppm): 1.41-1.48 (m, 2H), 1.57-1.63 (m, 4H), 1.88-1.98 (m, 1H), 2.05-2.12 (m, 1H), 2.45-2.55 (m, 4H), 2.71-3.02 (m, 7H), 3.76 (s, 3H), 3.78 (s, 3H), 4.01 (brs, 1H), 4.09 (t, 2H), 4.26 (s, 2H), 6.27 (d, 1H), 6.30 (dd, 1H), 6.65 (d, 1H), 6.70 (dd, 1H), 6.87 (d, 2H), 7.00 (d, 1H), 7.05 (d, 1H), 7.27 (d, 2H).

Example 151

6-{4-Hydroxy-2-[4-(2-piperidin-1-ylethoxy)benzylamino]phenyl}-5,6,7,8-tetrahydronaphthalen-2-ol

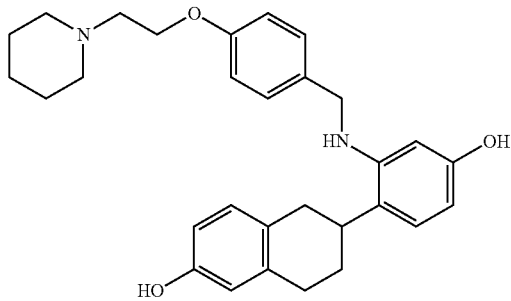 [SMILES: Oc1ccc2c(c1)CCC(c1ccc(O)cc1NCc1ccc(OCCN3CCCCC3)cc1)C2]

Synthesized from [5-methoxy-2-(6-methoxy-1,2,3,4-tetrahydronaphthalen-2-yl)phenyl][4-(2-piperidin-1-ylethoxy) benzyl]amine (350 mg) according to an analogous synthetic method to Example 111, the title compound (248 mg) was obtained.

$^1$H-NMR (400 MHz, DMSO-d$_6$); δ (ppm): 1.30-1.40 (m, 2H), 1.40-1.50 (m, 4H), 1.65-1.80 (m, 1H), 1.80-1.95 (m, 1H), 2.30-2.45 (m, 4H), 2.50-3.00 (m, 7H), 4.00 (t, 2H), 4.17 (s, 2H), 5.71 (brs, 1H), 5.82 (s, 1H), 5.93 (d, 1H), 6.42-6.52 (m, 2H), 6.70-6.88 (m, 4H), 7.21 (d, 2H), 8.67 (s, 1H), 8.98 (s, 1H).

ESI-Mass; 473 [M$^+$+H]

Example 152

[4-(2-Azepan-1-ylethoxy)benzyl][5-methoxy-2-(6-methoxy-1,2,3,4-tetrahydronaphthalen-2-yl)phenyl]amine

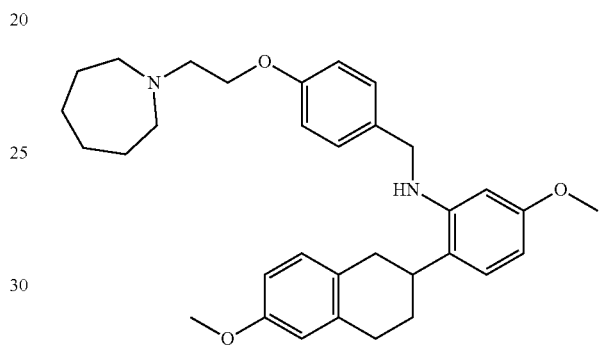

To a suspension of 4-(2-azepan-1-ylethoxy)benzoic acid hydrochloride (300 mg) in 1,2-dichloroethane (15 ml) was added thionyl chloride (0.3 ml), the solution was refluxed for 40 minutes, then the reaction solution was concentrated in vacuo. To a suspension of the resulting 4-(2-azepan-1-ylethoxy)benzoyl chloride hydrochloride in 1,4-dioxane (4 ml) were added 5-methoxy-2-(6-methoxy-1,2,3,4-tetrahydronaphthalen-2-yl)phenylamine (150 mg) and N,N-diisopropylethylamine (1 ml), and the solution was stirred for 1.5 hours at 90° C. Water was added thereto followed by stirring, and the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate-methanol system) to provide 4-(2-azepan-1-ylethoxy)-N-[5-methoxy-2-(6-methoxy-1,2,3,4-tetrahydronaphthalen-2-yl)phenyl] benzamide (156 mg). To a suspension of lithium aluminum hydride (33 mg) in tetrahydrofuran (1.5 ml) was added aluminum chloride (116 mg) on an ice bath under a nitrogen atmosphere, the solution was stirred for 10 minutes at room temperature, 4-(2-azepan-1-ylethoxy)-N-[5-methoxy-2-(6-methoxy-1,2,3,4-tetrahydronaphthalen-2-yl)phenyl]benzamide (153 mg) was then added thereto, followed by stirring for 2 hours at room temperature. Tetrahydrofuran and aqueous ammonia were sequentially added thereto, the solution was filtered through celite pad, and then the solvent was evaporated in vacuo. The residue was purified by NH silica gel column chromatography (hexane-ethyl acetate-methanol system) to provide the title compound (116 mg).

$^1$H-NMR (400 MHz, CDCl$_3$); δ (ppm): 1.55-1.70 (m, 8H), 1.88-2.00 (m, 1H), 2.06-2.13 (m, 1H), 2.70-3.04 (m, 11H), 3.76 (s, 3H), 3.78 (s, 3H), 3.97-4.03 (brs, 1H), 4.05 (t, 2H), 4.26 (s, 2H), 6.26-6.32 (m, 2H), 6.66 (d, 1H), 6.70 (dd, 1H), 6.88 (d, 2H), 7.00 (d, 1H), 7.05 (d, 1H), 7.24-7.28 (m, 2H).

Example 153

3-[4-(2-Azepan-1-ylethoxy)benzylamino]-4-(6-methoxy-1,2,3,4-tetrahydronaphthalen-2-yl)phenol

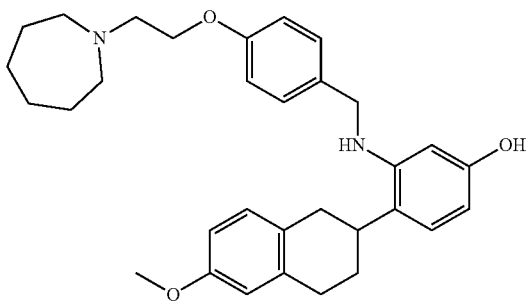 [SMILES: COc1ccc2c(c1)CCC(c1ccc(O)cc1NCc1ccc(OCCN3CCCCCC3)cc1)C2]

Synthesized from [4-(2-azepan-1-ylethoxy)benzyl][5-methoxy-2-(6-methoxy-1,2,3,4-tetrahydronaphthalen-2-yl) phenyl]amine (43 mg) according to an analogous synthetic method to Example 111, the title compound (18 mg) was obtained.

$^1$H-NMR (400 MHz, DMSO-d$_6$); δ (ppm): 1.48-1.58 (m, 8H), 1.70-1.76 (m, 1H), 1.86-1.95 (m, 1H), 2.50-2.60 (m, 1H), 2.61-2.68 (m, 4H), 2.80 (t, 2H), 2.81-3.01 (m, 4H), 3.69 (s, 3H), 3.97 (t, 2H), 4.17 (d, 2H), 5.72 (t, 1H), 5.83 (d, 1H), 5.91-5.94 (m, 1H), 6.63-6.68 (m, 2H), 6.77 (d, 1H), 6.84-6.87 (m, 2H), 6.98 (d, 1H), 7.21 (d, 2H), 8.67 (s, 1H).

ESI-Mass; 501 [M$^+$+H]

Example 154

[4-(2-Diisopropylaminoethoxy)benzyl][5-methoxy-2-(6-methoxy-1,2,3,4-tetrahydronaphthalen-2-yl) phenyl]amine

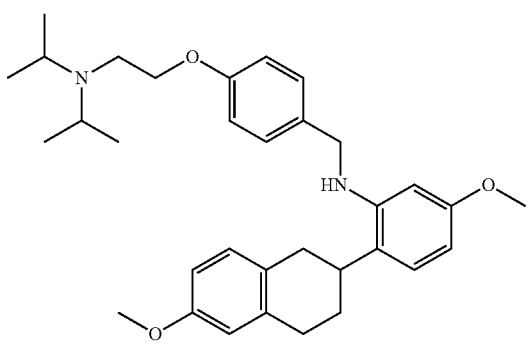 [SMILES: COc1ccc2c(c1)CCC(c1ccc(OC)cc1NCc1ccc(OCCN(C(C)C)C(C)C)cc1)C2]

Synthesized from 4-(2-diisopropylaminoethoxy)benzoic acid hydrochloride (240 mg) and 5-methoxy-2-(6-methoxy-1,2,3,4-tetrahydronaphthalen-2-yl)phenylamine (150 mg) according to an analogous synthetic method to Example 152, the title compound (264 mg) was obtained.

$^1$H-NMR (400 MHz, CDCl$_3$); δ (ppm): 1.04 (d, 12H), 1.88-1.98 (m, 1H), 2.06-2.13 (m, 1H), 2.71-3.08 (m, 9H), 3.76 (s, 3H), 3.78 (s, 3H), 3.86 (t, 2H), 3.96-4.04 (m, 1H), 4.26 (s, 2H), 6.26-6.32 (m, 2H), 6.65 (d, 1H), 6.69 (dd, 1H), 6.86 (d, 2H), 7.00 (d, 1H), 7.05 (d, 1H), 7.23-7.28 (m, 2H).

Example 155

3-[4-(2-Diisopropylaminoethoxy)benzylamino]-4-(6-methoxy-1,2,3,4-tetrahydronaphthalen-2-yl)phenol and 6-{2-[4-(2-diisopropylaminoethoxy)benzylamino]-4-hydroxyphenyl}-5,6,7,8-tetrahydronaphthalen-2-ol

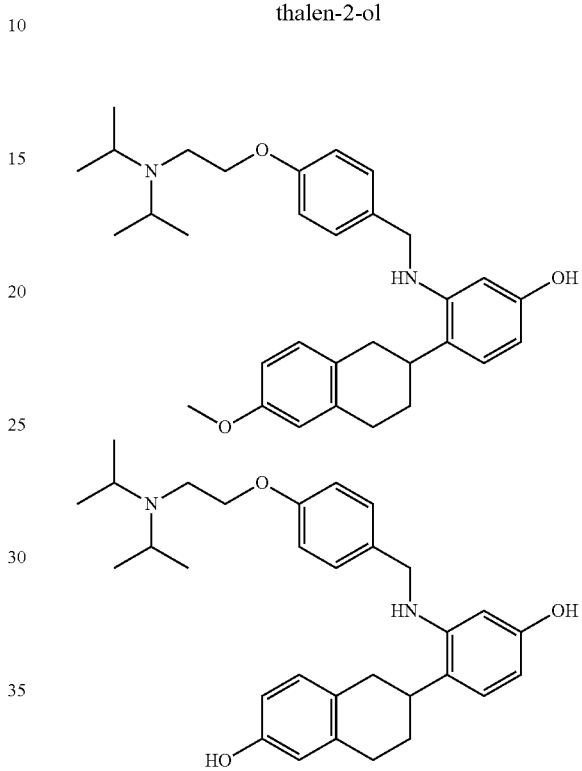

Synthesized from [4-(2-diisopropylaminoethoxy)benzyl][5-methoxy-2-(6-methoxy-1,2,3,4-tetrahydronaphthalen-2-yl)phenyl]amine (70 mg) according to an analogous synthetic method to Example 111, 3-[4-(2-diisopropylaminoethoxy)benzylamino]-4-(6-methoxy-1,2,3,4-tetrahydronaphthalen-2-yl)phenol (25 mg) and 6-{2-[4-(2-diisopropylaminoethoxy)benzylamino]-4-hydroxyphenyl}-5,6,7,8-tetrahydronaphthalen-2-ol (29 mg) were obtained. 3-[4-(2-Diisopropylaminoethoxy)benzylamino]-4-(6-methoxy-1,2,3,4-tetrahydronaphthalen-2-yl)phenol:

$^1$H-NMR (400 MHz, DMSO-d$_6$); δ (ppm): 0.95 (d, 12H), 1.68-1.80 (m, 1H), 1.87-1.94 (m, 1H), 2.51-2.59 (m, 1H), 2.71 (t, 2H), 2.74-3.02 (m, 6H), 3.69 (s, 3H), 3.81 (t, 2H), 4.17 (t, 2H), 5.72 (t, 1H), 5.82 (d, 1H), 5.93 (dd, 1H), 6.64-6.69 (m, 2H), 6.77 (d, 1H), 6.83 (d, 2H), 6.98 (d, 1H), 7.21 (d, 2H), 8.67 (s, 1H).

ESI-Mass; 503 [M$^+$+H]

6-{2-[4-(2-Diisopropylaminoethoxy)benzylamino]-4-hydroxyphenyl}-5,6,7,8-tetrahydronaphthalen-2-ol $^1$H-NMR (400 MHz, DMSO-d$_6$); δ (ppm): 0.95 (d, 12H), 1.65-1.78 (m, 1H), 1.83-1.93 (m, 1H), 2.45-2.55 (m, 1H), 2.71 (t, 2H), 2.73-3.02 (m, 6H), 3.81 (t, 2H), 4.17 (d, 2H), 5.71 (t, 1H), 5.82 (d, 1H), 5.92 (dd, 1H), 6.47-6.51 (m, 2H), 6.77 (d, 1H), 6.80-6.87 (m, 3H), 7.21 (d, 2H), 8.66 (s, 1H), 8.97 (s, 1H).

ESI-Mass; 489 [M$^+$+H]

Example 156

[3-Fluoro-4-(2-piperidin-1-ylethoxy)benzyl][5-methoxy-2-(6-methoxy-1,2,3,4-tetrahydronaphthalen-2-yl)phenyl]amine

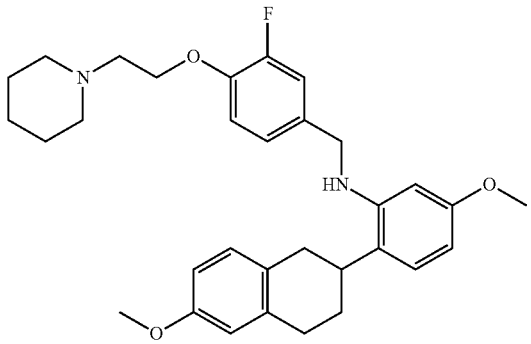 [SMILES: COc1ccc2c(c1)CCC(c1ccc(OC)cc1NCc1ccc(OCCN3CCCCC3)c(F)c1)C2]

Synthesized from 3-fluoro-4-(2-piperidin-1-ylethoxy) benzoic acid hydrochloride (1.2 g) and 5-methoxy-2-(6-methoxy-1,2,3,4-tetrahydronaphthalen-2-yl)phenylamine (600 mg) according to an analogous synthetic method to Example 152, the title compound (770 mg) was obtained.

$^1$H-NMR (400 MHz, CDCl$_3$); δ (ppm): 1.30-1.39 (m, 2H), 1.56-1.64 (m, 4H), 1.90-2.02 (m, 1H), 2.06-2.16 (m, 1H), 2.46-2.56 (m, 4H), 2.74-3.04 (m, 7H), 3.74 (s, 3H), 3.79 (s, 3H), 4.09 (brs, 1H), 4.15 (t, 2H), 4.27 (s, 2H), 6.20 (d, 1H), 6.31 (dd, 1H), 6.67 (d, 1H), 6.71 (dd, 1H), 6.93 (t, 1H), 7.00-7.11 (m, 4H).

Example 157

6-{2-[3-Fluoro-4-(2-piperidin-1-ylethoxy)benzylamino]-4-hydroxyphenyl}-5,6,7,8-tetrahydronaphthalen-2-ol

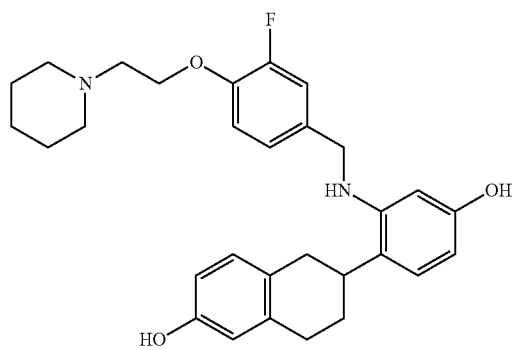

Synthesized from [3-fluoro-4-(2-piperidin-1-ylethoxy)benzyl][5-methoxy-2-(6-methoxy-1,2,3,4-tetrahydronaphthalen-2-yl)phenyl]amine (110 mg) according to an analogous synthetic method to Example 111, the title compound (69 mg) was obtained.

$^1$H-NMR (400 MHz, DMSO-d$_6$); δ (ppm): 1.30-1.39 (m, 2H), 1.42-1.50 (m, 4H), 1.67-1.80 (m, 1H), 1.84-1.93 (m, 1H), 2.34-2.45 (m, 4H), 2.49-2.57 (m, 1H), 2.62 (t, 2H), 2.69-3.01 (m, 4H), 4.07 (t, 2H), 4.17 (d, 2H), 5.77-5.84 (m, 2H), 5.94 (d, 1H), 6.46-6.53 (m, 2H), 6.78 (d, 1H), 6.85 (d, 1H), 7.03-7.14 (m, 3H), 8.68 (s, 1H), 8.97 (s, 1H).

ESI-Mass; 491 [M$^+$+H]

Example 158

[4-(2-Azepan-1-ylethoxy)benzyl][5-methoxy-2-(6-methoxy-1,2,3,4-tetrahydronaphthalen-2-yl)phenyl]amine

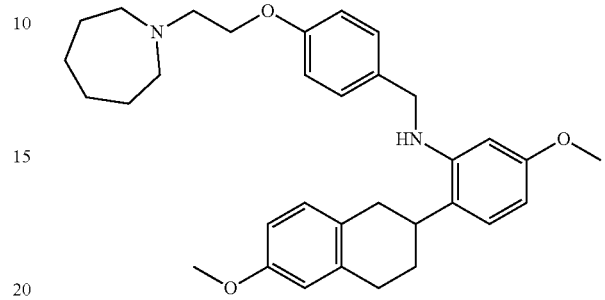

Synthesized from 5-methoxy-2-(6-methoxy-1,2,3,4-tetrahydronaphthalen-2-yl)phenylamine (700 mg) and 4-(2-azepan-1-ylethoxy)benzoic acid hydrochloride (960 mg) according to an analogous synthetic method to Example 152, the title compound (1.2 g) was obtained.

$^1$H-NMR (400 MHz, CDCl$_3$); δ (ppm): 1.54-1.70 (m, 8H), 1.88-2.00 (m, 1H), 2.04-2.14 (m, 1H), 2.71-2.84 (m, 7H), 2.87-3.04 (m, 4H), 3.76 (s, 3H), 3.79 (s, 3H), 3.99-4.02 (m, 1H), 4.06 (t, 2H), 4.26 (s, 2H), 6.27-6.33 (m, 2H), 6.64-6.72 (m, 2H), 6.87 (d, 2H), 7.00 (d, 1H) 7.05 (d, 1H), 7.24-7.30 (m, 2H).

Example 159

6-{2-[4-(2-Azepan-1-ylethoxy)benzylamino]-4-hydroxyphenyl}-5,6,7,8-tetrahydronaphthalen-2-ol

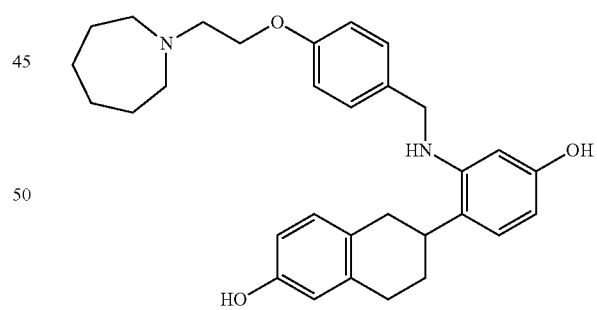

Synthesized from [4-(2-azepan-1-yl-ethoxy)benzyl][5-methoxy-2-(6-methoxy-1,2,3,4-tetrahydronaphthalen-2-yl)phenyl]amine (1.0 g) according to an analogous synthetic method to Example 111, the title compound (960 mg) was obtained.

$^1$H-NMR (400 MHz, DMSO-d$_6$); δ (ppm): 1.49-1.61 (m, 8H), 1.68-1.80 (m, 1H), 1.86-1.95 (m, 1H), 2.46-2.58 (m, 1H), 2.66 (t, 4H), 2.70-3.00 (m, 4H), 2.82 (t, 2H), 3.99 (t, 2H), 4.19 (s, 1H), 5.73 (s, 1H), 5.84 (s, 1H), 5.94 (d, 1H), 6.47-6.52 (m, 2H), 6.78 (d, 1H), 6.85-6.90 (m, 3H), 7.22 (d, 2H), 8.69 (brs, 1H), 9.00 (brs, 1H).

Example 160

6-{2-{Ethyl[4-(2-piperidin-1-ylethoxy)benzyl]amino}-4-hydroxyphenyl}-5,6,7,8-tetrahydronaphthalen-2-ol

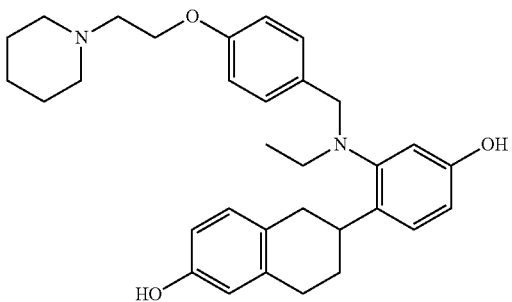 [SMILES: CCN(Cc1ccc(OCCN2CCCCC2)cc1)c1cc(O)ccc1C1CCc2cc(O)ccc2C1]

To a solution of 4-(2-piperidin-1-ylethoxy)benzoic acid hydrochloride (1.0 g) in dichloromethane solution (20 ml) were sequentially added oxalyl chloride (0.4 ml) and N,N-dimethylformamide (0.05 ml), the solution was stirred for 2 hours at room temperature, and then the solvent was evaporated in vacuo. To the residue were sequentially added tetrahydrofuran (20 ml), N,N-diisopropylethylamine (5 ml) and 6-(2-amino-4-methoxyphenyl)-2-methoxy-5,6,7,8-tetrahydronaphthalene (800 mg), and the solution was stirred for 30 minutes at room temperature. To the reaction solution was added a saturated aqueous solution of sodium bicarbonate, the solution was extracted with ethyl acetate, then washed with brine, dried over anhydrous magnesium sulfate, and then the solvent was evaporated in vacuo. Obtained by purifying the residue by NH silica gel column chromatography (hexane-ethyl acetate system), to a solution of the resulting N-[5-methoxy-2-(6-methoxy-1,2,3,4-tetrahydronaphthalen-2-yl)phenyl]-4-(2-piperidin-1-ylethoxy)benzamide (1.1 g) in tetrahydrofuran (30 ml) was added lithium aluminum hydride (0.4 g), and the solution was refluxed for 20 minutes. The solution was cooled on an ice, then ammonia solution (1 ml) and anhydrous magnesium sulfate was added, the solution was filtered, then the solvent was evaporated in vacuo. To a solution of the total amount of the resulting [5-methoxy-2-(6-methoxy-1,2,3,4-tetrahydronaphthalen-2-yl)phenyl][4-(2-piperidin-1-ylethoxy)benzyl]amine (crude product) in dichloromethane (15 ml) were added pyridine (0.5 ml) and acetic anhydride (0.4 ml), and the solution was stirred for 1 hour at room temperature. To the reaction solution was added a saturated aqueous solution of sodium bicarbonate, the solution was extracted with ethyl acetate, then washed with brine, dried over anhydrous magnesium sulfate, then the solvent was evaporated in vacuo. To a solution of the resulting N-[5-methoxy-2-(6-methoxy-1,2,3,4-tetrahydronaphthalen-2-yl)phenyl]-N-[4-(2-piperidin-1-ylethoxy)benzyl]acetamide (1.3 g) in tetrahydrofuran (30 ml) was added lithium aluminum hydride (0.4 g), and the solution was refluxed for 20 minutes. The solution was cooled on an ice, then ammonia solution (1 ml) and anhydrous magnesium sulfate were added thereto, the solution was filtered, and then the solvent was evaporated in vacuo. Obtained by purifying the residue by NH silica gel column chromatography (hexane-ethyl acetate system), ethyl[5-methoxy-2-(6-methoxy-1,2,3,4-tetrahydronaphthalen-2-yl)phenyl][4-(2-piperidin-1-ylethoxy)benzyl]amine (570 mg) was used according to an analogous synthetic method to Example 111 to provide the title compound (480 mg).

$^1$H-NMR (400 MHz, CDCl$_3$); δ (ppm): 0.93 (t, 3H), 1.44-1.47 (m, 2H), 1.62-1.75 (m, 6H), 2.21-2.63 (m, 6H), 2.77-2.80 (m, 4H), 2.86-2.92 (m, 2H), 3.56-3.59 (m, 1H), 3.89 (s, 2H), 4.07 (t, 2H), 6.57-6.61 (m, 3H), 6.66 (d, 1H), 6.69 (d, 2H), 6.86 (d, 2H), 7.05 (d, 2H), 7.08 (d, 2H).

Example 161

[5-Methoxy-2-(6-methoxy-1,2,3,4-tetrahydronaphthalen-2-yl)phenyl]methyl[4-(2-piperidin-1-ylethoxy)benzyl]amine

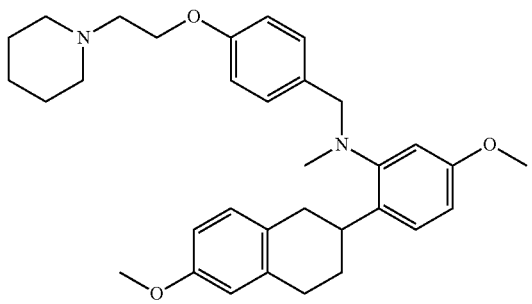 [SMILES: COc1ccc2c(c1)CCC(c1ccc(OC)cc1N(C)Cc1ccc(OCCN3CCCCC3)cc1)C2]

Synthesized from [5-methoxy-2-(6-methoxy-1,2,3,4-tetrahydronaphthalen-2-yl)phenyl][4-(2-piperidin-1-ylethoxy)benzyl]amine (295 mg) according to an analogous synthetic method to Preparation Example 18, the title compound (236 mg) was obtained.

$^1$H-NMR (400 MHz, CDCl$_3$); δ (ppm): 1.41-1.48 (m, 2H), 1.57-1.64 (m, 4H), 1.79-1.97 (m, 2H), 2.46-2.54 (m, 4H), 2.54 (s, 3H), 2.76 (t, 2H), 2.77-2.98 (m, 4H), 3.58-3.68 (m, 1H), 3.80 (s, 3H), 3.81 (s, 3H), 3.93 (s, 2H), 4.09 (t, 2H), 6.66-6.77 (m, 4H), 6.80 (d, 2H), 6.99 (d, 1H), 7.16-7.21 (m, 3H).

Example 162

6-{4-Hydroxy-2-{methyl[4-(2-piperidin-1-ylethoxy)benzyl]amino}phenyl}-5,6,7,8-tetrahydronaphthalen-2-ol

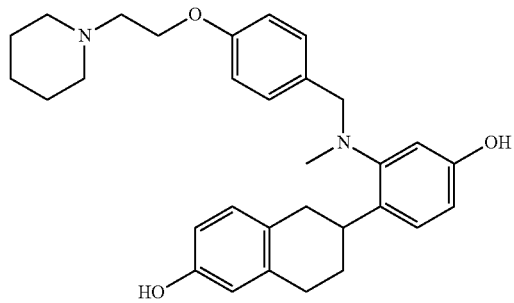 [SMILES: CN(Cc1ccc(OCCN2CCCCC2)cc1)c1cc(O)ccc1C1CCc2cc(O)ccc2C1]

Synthesized from [5-methoxy-2-(6-methoxy-1,2,3,4-tetrahydronaphthalen-2-yl)phenyl]methyl[4-(2-piperidin-1-ylethoxy)benzyl]amine (233 mg) according to an analogous synthetic method to Example 111, the title compound (125 mg) was obtained.

$^1$H-NMR (400 MHz, DMSO-d$_6$); δ (ppm): 1.30-1.40 (m, 1H), 1.61-1.80 (m, 7H), 2.44 (s, 3H), 2.60-2.70 (m, 2H), 2.71-2.80 (m, 2H), 2.90-3.01 (m, 2H), 3.38-3.50 (m, 5H), 3.86 (s, 2H), 4.29-4.32 (m, 2H), 6.45-6.51 (m, 3H), 6.58 (d, 1H), 6.82 (d, 1H), 6.88 (d, 2H), 7.03 (d, 1H), 7.19 (d, 2H), 9.02 (s, 1H), 9.12 (s, 1H).
ESI-Mass; 487 [M+ +H]

Example 163

6-{2-{[4-(2-Azepan-1-ylethoxy)benzyl]methylamino}-4-hydroxyphenyl}-5,6,7,8-tetrahydronaphthalen-2-ol

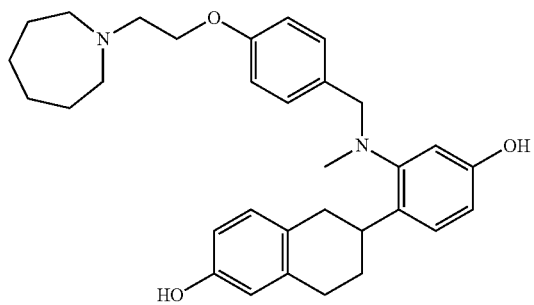 [SMILES: CN(Cc1ccc(OCCN2CCCCCC2)cc1)c1cc(O)ccc1C1CCc2cc(O)ccc2C1]

Synthesized from [4-(2-azepan-1-ylethoxy)benzyl][5-methoxy-2-(6-methoxy-1,2,3,4-tetrahydronaphthalen-2-yl)phenyl]amine (74 mg) according to an analogous synthetic method to Preparation Example 18, [4-(2-azepan-1-ylethoxy)benzyl][5-methoxy-2-(6-methoxy-1,2,3,4-tetrahydronaphthalen-2-yl)phenyl]methylamine (49 mg) was obtained. This compound (48 mg) was used according to an analogous synthetic method to Example 111 to provide the title compound (40 mg).
$^1$H-NMR (400 MHz, DMSO-$d_6$); δ (ppm): 1.46-1.58 (m, 8H), 1.66-1.76 (m, 2H), 2.43 (s, 3H), 2.55-2.77 (m, 8H), 2.79 (t, 2H), 3.36-3.46 (m, 1H), 3.83 (s, 2H), 3.95 (t, 2H), 6.44-6.51 (m, 3H), 6.57 (d, 1H), 6.78-6.84 (m, 3H), 7.02 (d, 1H), 7.12 (d, 2H), 8.99 (s, 1H), 9.08 (s, 1H).
ESI-Mass; 501 [M+ +H]

Example 164

6-{2-{[4-(2-Diisopropylaminoethoxy)benzyl]methylamino}-4-hydroxyphenyl}-5,6,7,8-tetrahydronaphthalen-2-ol

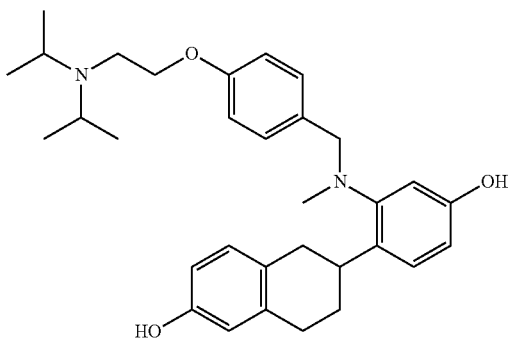 [SMILES: CC(C)N(CCOc1ccc(CN(C)c2cc(O)ccc2C2CCc3cc(O)ccc3C2)cc1)C(C)C]

Synthesized from [4-(2-diisopropylaminoethoxy)benzyl][5-methoxy-2-(6-methoxy-1,2,3,4-tetrahydronaphthalen-2-yl)phenyl]amine (101 mg) according to an analogous synthetic method to Preparation Example 18, [4-(2-diisopropylaminoethoxy)benzyl][5-methoxy-2-(6-methoxy-1,2,3,4-tetrahydronaphthalen-2-yl)phenyl]methylamine (92 mg) was obtained. This compound (91 mg) was used according to an analogous synthetic method to Example 111 to provide the title compound (71 mg).

$^1$H-NMR (400 MHz, DMSO-$d_6$); δ (ppm): 0.95 (d, 12H), 1.68-1.76 (m, 2H), 2.43 (s, 3H), 2.58-2.79 (m, 6H), 2.91-3.02 (m, 2H), 3.35-3.46 (m, 1H), 3.79 (t, 2H), 3.83 (s, 2H), 6.44-6.50 (m, 3H), 6.57 (d, 1H), 6.78 (d, 2H), 6.81 (d, 2H), 7.02 (d, 1H), 7.12 (d, 2H), 8.98 (s, 1H), 9.08 (s, 1H).
ESI-Mass; 503 [M+ +H]

Example 165

6-{2-{[3-Fluoro-4-(2-piperidin-1-ylethoxy)benzyl]methylamino}-4-hydroxyphenyl}-5,6,7,8-tetrahydronaphthalen-2-ol

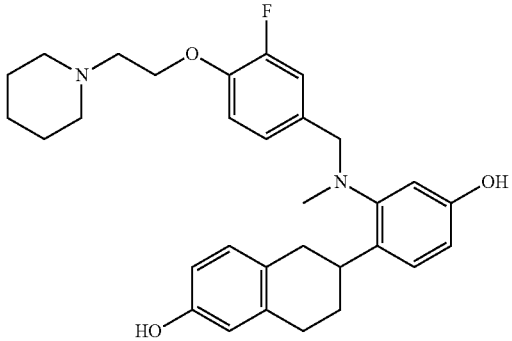

Synthesized from [3-fluoro-4-(2-piperidin-1-ylethoxy)benzyl][5-methoxy-2-(6-methoxy-1,2,3,4-tetrahydronaphthalen-2-yl)phenyl]amine according to an analogous synthetic method to Preparation Example 18, [3-fluoro-4-(2-piperidin-1-ylethoxy)benzyl][5-methoxy-2-(6-methoxy-1,2,3,4-tetrahydronaphthalen-2-yl)phenyl]methylamine (385 mg) was used according to an analogous synthetic method to Example 111 to provide the title compound (224 mg).
$^1$H-NMR (400 MHz, DMSO-$d_6$); δ (ppm): 1.29-1.38 (m, 2H), 1.41-1.49 (m, 4H), 1.64-1.76 (m, 2H), 2.34-2.43 (m, 4H), 2.45 (s, 3H), 2.58-2.68 (m, 4H), 2.72-2.81 (m, 2H), 3.34-3.44 (m, 1H), 3.86 (s, 2H), 4.05 (t, 2H), 6.44-6.51 (m, 3H), 6.57 (d, 1H), 6.81 (d, 1H), 6.84-7.08 (m, 4H), 8.99 (s, 1H), 9.11 (s, 1H).
ESI-Mass; 505 [M+ +H]

Example 166

N-[3-fluoro-4-(2-piperidin-1-ylethoxy)benzyl]-N-[5-hydroxy-2-(6-hydroxy-1,2,3,4-tetrahydronaphthalen-2-yl)phenyl]acetamide

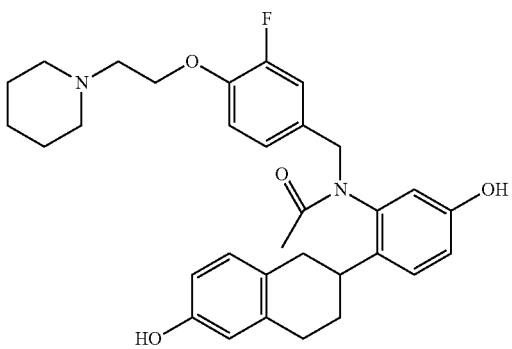 [SMILES: CC(=O)N(Cc1ccc(OCCN2CCCCC2)c(F)c1)c1cc(O)ccc1C1CCc2cc(O)ccc2C1]

To a solution of [3-fluoro-4-(2-piperidin-1-ylethoxy)benzyl][5-methoxy-2-(6-methoxy-1,2,3,4-tetrahydronaphthalen-2-yl)phenyl]amine (386 mg) in dichloromethane (7 ml) was added acetyl chloride (0.1 ml), the solution was stirred for 20 minutes at room temperature, then neutralized with a saturated aqueous solution of sodium bicarbonate. The solution was extracted with ethyl acetate, then sequentially washed with water and brine, dried over anhydrous magnesium sulfate, and then the solvent was evaporated in vacuo. Obtained by purifying the residue by NH silica gel column chromatography (hexane-ethyl acetate system), N-[3-fluoro-4-(2-piperidin-1-ylethoxy)benzyl]-N-[5-methoxy-2-(6-methoxy-1,2,3,4-tetrahydronaphthalen-2-yl)phenyl]acetamide (243 mg) was used according to an analogous synthetic method to Example 111 to provide the title compound (186 mg).

$^1$H-NMR (400 MHz, DMSO-d$_6$); δ (ppm): 1.30-1.40 (m, 2H), 1.43-1.51 (m, 4H), 1.55-1.70 (m, 0.5H), 1.72 (s, 1.5H), 1.73 (s, 1.5H), 1.74-1.85 (m, 0.5H), 1.99-2.06 (m, 0.5H), 2.36-2.46 (m, 4H), 2.46-2.75 (m, 7.5H), 4.00-4.11 (m, 2H), 4.41 (d, 0.5H), 4.43 (d, 0.5H), 4.77 (d, 0.5H), 4.80 (d, 0.5H), 6.34 (d, 1H), 6.40-6.50 (m, 2H), 6.63 (d, 0.5H), 6.76 (dt, 1H), 6.80 (d, 0.5H), 6.89 (t, 1H), 6.93-7.03 (m, 1.5H), 7.08 (t, 0.5H), 7.20 (d, 0.5H), 7.21 (d, 0.5H), 8.99 (s, 0.5H), 9.01 (s, 0.5H), 9.49 (s, 1H).

ESI-Mass; 533 [M$^+$+H]

Example 167

6-{2-{[3-Fluoro-4-(3-piperidin-1-ylpropyl)benzyl]methylamino}-4-hydroxyphenyl}-5,6,7,8-tetrahydronaphthalen-2-ol

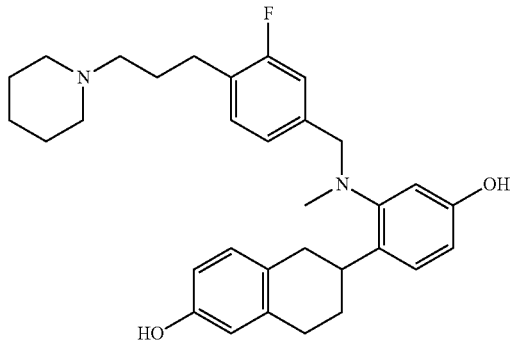

Synthesized from 3-fluoro-4-(3-piperidin-1-ylpropyl)benzoic acid hydrochloride and 5-methoxy-2-(6-methoxy-1,2,3,4-tetrahydronaphthalen-2-yl)phenylamine according to an analogous synthetic method to Example 337 described below, [3-fluoro-4-(3-piperidin-1-ylpropyl)benzyl][5-methoxy-2-(6-methoxy-1,2,3,4-tetrahydronaphthalen-2-yl)phenyl]amine (311 mg) was used according to an analogous synthetic method to Preparation Example 18 to provide [3-fluoro-4-(3-piperidin-1-ylpropyl)benzyl][5-methoxy-2-(6-methoxy-1,2,3,4-tetrahydronaphthalen-2-yl)phenyl]methylamine (272 mg). This compound (270 mg) was used according to an analogous synthetic method to Example 111 to provide the title compound (147 mg).

$^1$H-NMR (400 MHz, DMSO-d$_6$); δ (ppm): 1.28-1.36 (m, 2H), 1.40-1.48 (m, 4H), 1.62 (pent, 2H), 1.66-1.75 (m, 2H), 2.18 (t, 2H), 2.20-2.28 (m, 4H), 2.47 (s, 3H), 2.51 (t, 2H), 2.56-2.69 (m, 2H), 2.70-2.78 (m, 2H), 3.34-3.44 (m, 1H), 3.91 (s, 2H), 6.46-6.51 (m, 3H), 6.59 (d, 1H), 6.81 (d, 1H), 6.94-6.99 (m, 2H), 7.03 (d, 1H), 7.15 (t, 1H), 8.99 (s, 1H), 9.11 (s, 1H).

ESI-Mass; 503 [M$^+$+H]

Example 168

6-{2-{[6-(2-Azepan-1-ylethoxy)pyridin-3-ylmethyl]methylamino}-4-hydroxyphenyl}-5,6,7,8-tetrahydronaphthalen-2-ol

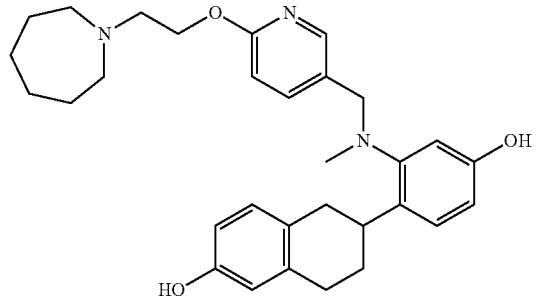 [SMILES: CN(Cc1ccc(OCCN2CCCCCC2)nc1)c1cc(O)ccc1C1CCc2cc(O)ccc2C1]

Synthesized from 6-(2-azepan-1-ylethoxy)nicotinic acid hydrochloride and 5-methoxy-2-(6-methoxy-1,2,3,4-tetrahydronaphthalen-2-yl)phenylamine according to an analogous synthetic method to Example 337 described below, [6-(2-azepan-1-ylethoxy)pyridin-3-ylmethyl][5-methoxy-2-(6-methoxy-1,2,3,4-tetrahydronaphthalen-2-yl)phenyl]amine (274 mg) was used according to an analogous synthetic method to Preparation Example 18 to provide [6-(2-azepan-1-ylethoxy)pyridin-3-ylmethyl][5-methoxy-2-(6-methoxy-1,2,3,4-tetrahydronaphthalen-2-yl)phenyl]methylamine (264 mg). This compound (262 mg) was used according to an analogous synthetic method to Example 111 to provide the title compound (122 mg).

$^1$H-NMR (400 MHz, DMSO-d$_6$); δ (ppm): 1.44-1.57 (m, 8H), 1.62-1.76 (m, 2H), 2.46 (s, 3H), 2.54-2.66 (m, 6H), 2.70-2.81 (m, 4H), 3.31-3.41 (m, 1H), 3.86 (dd, 2H), 4.24 (t, 2H), 6.45-6.51 (m, 3H), 6.58 (d, 1H), 6.67 (d, 1H), 6.80 (d, 1H), 7.02 (d, 1H), 7.46 (dd, 1H), 7.93 (d, 1H), 8.99 (s, 1H), 9.12 (s, 1H).

ESI-Mass; 502 [M$^+$+H]

Example 169

6-{2-{[4-(2-Diisopropylaminoethoxy)-3-fluorobenzyl]ethylamino}-4-hydroxyphenyl}-5,6,7,8-tetrahydronaphthalen-2-ol

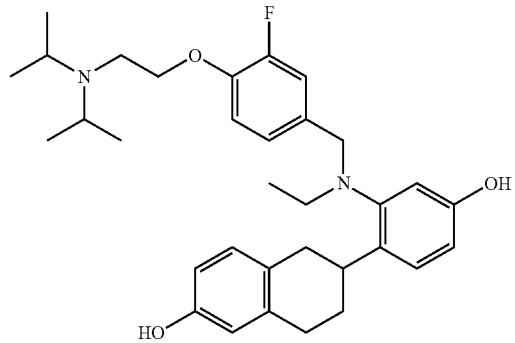 [SMILES: CCN(Cc1ccc(OCCN(C(C)C)C(C)C)c(F)c1)c1cc(O)ccc1C1CCc2cc(O)ccc2C1]

Synthesized from 5-methoxy-2-(6-methoxy-1,2,3,4-tetrahydronaphthalen-2-yl)phenylamine and 4-(2-diisopropylaminoethoxy)-3-fluorobenzoic acid hydrochloride according to an analogous synthetic method to Example 152, [4-(2-diisopropylaminoethoxy)-3-fluorobenzyl][5-methoxy-2-(6-methoxy-1,2,3,4-tetrahydronaphthalen-2-yl)phenyl]amine (459 mg) was used according to an analogous synthetic method to Example 36 to provide [4-(2-diisopropylaminoethoxy)-3-fluorobenzyl]ethyl[5-methoxy-2-(6-methoxy-1,2, 3,4-tetrahydronaphthalen-2-yl)phenyl]amine (429 mg). This compound (427 mg) was used according to an analogous synthetic method to Example 111 to provide the title compound (303 mg).

$^1$H-NMR (400 MHz, DMSO-$d_6$); δ (ppm): 0.86 (t, 3H), 0.94 (d, 12H), 1.50-1.57 (m, 1H), 1.58-1.71 (m, 1H), 2.44-2.59 (m, 2H), 2.68-2.76 (m, 4H), 2.82 (q, 2H), 2.97 (hept, 2H), 3.39-3.48 (m, 1H), 3.86 (t, 2H), 3.89 (dd, 2H), 6.45-6.52 (m, 3H), 6.61 (d, 1H), 6.78 (d, 1H), 6.88-7.02 (m, 4H), 8.98 (s, 1H), 9.07 (s, 1H).

ESI-Mass; 535 [M$^+$+H]

Example 170

7-{2-{Ethyl[3-fluoro-4-(2-piperidin-1-ylethoxy) benzyl]amino}-4-hydroxyphenyl}-5,6,7,8-tetrahydronaphthalen-2-ol

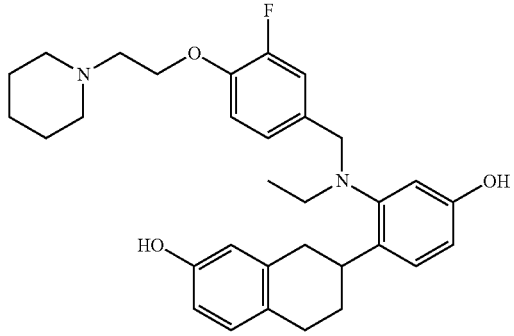 [SMILES: CCN(Cc1ccc(OCCN2CCCCC2)c(F)c1)c1cc(O)ccc1C1CCc2ccc(O)cc2C1]

Synthesized from 5-methoxy-2-(7-methoxy-1,2,3,4-tetrahydronaphthalen-2-yl)phenylamine (420 mg) and 3-fluoro-4-(2-piperidin-1-ylethoxy)benzoic acid hydrochloride (610 mg) according to an analogous synthetic method to Example 169, the title compound (130 mg) was obtained.

$^1$H-NMR (400 MHz, DMSO-$d_6$); δ (ppm): 0.87 (t, 3H), 1.30-1.39 (m, 2H), 1.41-1.50 (m, 4H), 1.51-1.72 (m, 2H), 2.34-2.43 (m, 4H), 2.44-2.56 (m, 2H), 2.61 (t, 2H), 2.63-2.75 (m, 2H), 2.82 (q, 2H), 3.40-3.50 (m, 1H), 3.89 (s, 2H), 4.05 (t, 2H), 6.40 (s, 1H), 6.46-6.52 (m, 2H), 6.61 (s, 1H), 6.86 (d, 1H), 6.90-7.03 (m, 4H), 9.00 (brs, 1H), 9.09 (brs, 1H).

ESI-Mass; 519 [M$^+$+H]

Example 171

{5-(tert-Butyldimethylsilyloxy)-2-[6-(tert-butyldimethylsilyloxy)-1,2,3,4-tetrahydronaphthalen-2-yl] phenyl}[3-fluoro-4-(2-piperidin-1-yl-ethoxy)benzyl] amine

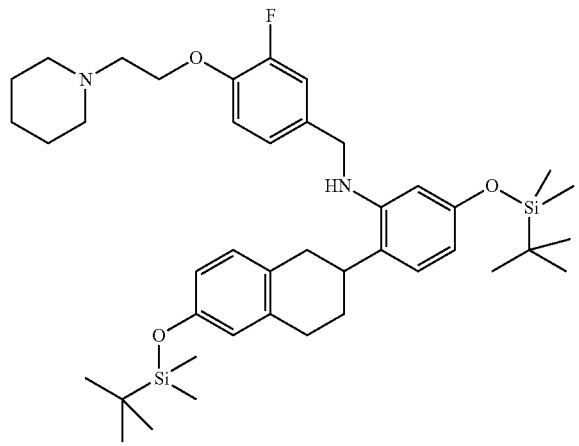 [SMILES: CC(C)(C)[Si](C)(C)Oc1ccc2c(c1)CCC(c1ccc(O[Si](C)(C)C(C)(C)C)cc1NCc1ccc(OCCN3CCCCC3)c(F)c1)C2]

Synthesized from 6-{2-[3-fluoro-4-(2-piperidin-1-ylethoxy)benzylamino]-4-hydroxyphenyl}-5,6,7,8-tetrahydronaphthalen-2-ol (240 mg) and tert-butyldimethylsilyl chloride (220 mg) according to an analogous synthetic method to Example 201 described below, the title compound (300 mg) was obtained.

$^1$H-NMR (400 MHz, CDCl$_3$); δ (ppm): 0.10 (s, 6H), 0.20 (s, 6H), 0.92 (s, 9H), 0.99 (s, 9H), 1.39-1.48 (m, 2H), 1.50-1.64 (m, 4H), 1.88-1.99 (m, 1H), 2.05-2.12 (m, 1H), 2.47-2.55 (m, 4H), 2.70-3.01 (m, 6H), 4.06-4.10 (m, 1H), 4.16 (t, 2H), 4.25 (d, 2H), 6.08 (s, 1H), 6.23 (d, 1H), 6.59-6.63 (m, 2H), 6.91-6.98 (m, 3H) 7.01-7.10 (m, 2H).

Example 172

{5-(tert-Butyldimethylsilyloxy)-2-[6-(tert-butyldimethylsilyloxy)-1,2,3,4-tetrahydronaphthalen-2-yl] phenyl}(2-fluoroethyl)[3-fluoro-4-(2-piperidin-1-ylethoxy)benzyl]amine

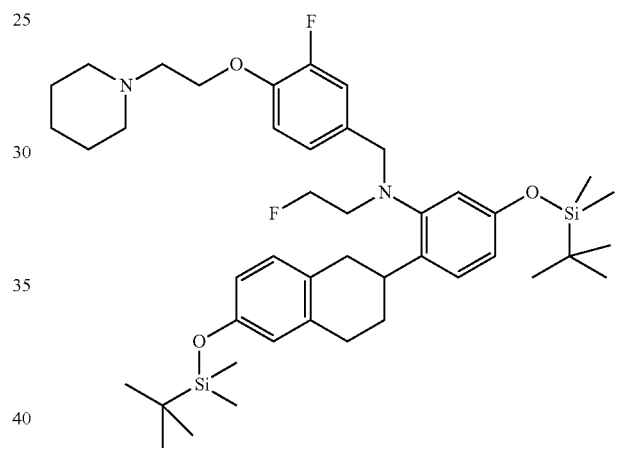

To a solution of sodium fluoroacetate (420 mg) in dichloromethane (20 ml) were added dropwise N,N-dimethylformamide (1 drop) and oxalyl chloride (0.48 ml) on an ice bath, the solution was stirred for 20 minutes at room temperature, an aqueous solution of 1N sodium hydroxide was added thereto, the solution was stirred for 1 minute at room temperature, then a solution of {5-(tert-butyldimethylsilyloxy)-2-[6-(tert-butyldimethylsilyloxy)-1,2,3,4-tetrahydronaphthalen-2-yl]phenyl}[3-fluoro-4-(2-piperidin-1-yl-ethoxy) benzyl]amine (300 mg) in dichloromethane (5 ml) was added thereto followed by stirring at room temperature for 3 hours. The solution extracted with dichloromethane, then washed with brine, dried over anhydrous magnesium sulfate, then the solvent was evaporated in vacuo. Synthesized from the resulting residue according to an analogous synthetic method to Example 337 described below, the title compound (200 mg) was obtained.

$^1$H-NMR (400 MHz, CDCl$_3$); δ (ppm): 0.18 (s, 6H), 0.21 (s, 6H), 0.98 (s, 9H), 1.00 (s, 9H), 1.40-1.50 (m, 2H), 1.56-1.80 (m, 6H), 2.45-2.55 (m, 4H), 2.66-2.93 (m, 6H), 3.16 (t, 1H), 3.23 (t, 1H), 3.56-3.66 (m, 1H), 4.04 (s, 2H), 4.12 (t, 2H), 4.32 (t, 1H), 4.44 (t, 1H), 6.58-6.65 (m, 3H), 6.68 (s, 1H), 6.81 (t, 1H), 6.86-6.96 (m, 3H) 7.06 (d, 1H).

Example 173

6-{2-{(2-Fluoroethyl)[3-fluoro-4-(2-piperidin-1-ylethoxy)benzyl]amino}-4-hydroxyphenyl}-5,6,7,8-tetrahydronaphthalen-2-ol

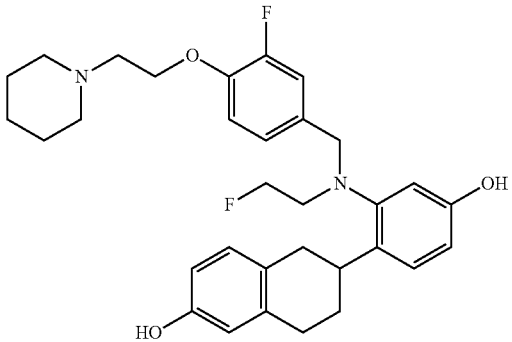

To a solution of {5-(tert-butyldimethylsilyloxy)-2-[6-(tert-butyldimethylsilyloxy)-1,2,3,4-tetrahydronaphthalen-2-yl]phenyl}(2-fluoroethyl)[3-fluoro-4-(2-piperidin-1-ylethoxy)benzyl]amine (200 mg) in tetrahydrofuran (10 ml) were sequentially added tetrabutylammonium fluoride (1.0 M solution in tetrahydrofuran) (1 ml) and hydrochloric acid-methanol solution (1 ml) on an ice bath, and the solution was stirred for 8 hours at 50° C. The reaction solution was alkalinized by adding aqueous ammonia, the solution was extracted with ethyl acetate, then washed with brine, dried over anhydrous magnesium sulfate, and then the solvent was evaporated in vacuo. The residue was purified by NH silica gel column chromatography (hexane-ethyl acetate-methanol system) to provide the title compound (140 mg).

$^1$H-NMR (400 MHz, DMSO-$d_6$); δ (ppm): 1.30-1.39 (m, 2H), 1.40-1.69 (m, 6H), 2.33-2.41 (m, 4H), 2.45-2.64 (m, 4H), 2.67-2.75 (m, 2H), 3.07 (t, 1H), 3.14 (t, 1H), 3.40-3.50 (m, 1H), 3.98 (s, 2H), 4.05 (t, 2H), 4.28 (t, 1H), 4.40 (t, 1H), 6.45-6.54 (m, 3H), 6.67 (s, 1H), 6.76 (d, 1H), 6.89 (d, 1H), 6.93-7.05 (m, 3H), 8.98 (brs, 1H), 9.14 (brs, 1H).

ESI-Mass; 537 [M$^+$+H]

Example 174

[4-(2-Azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}amine

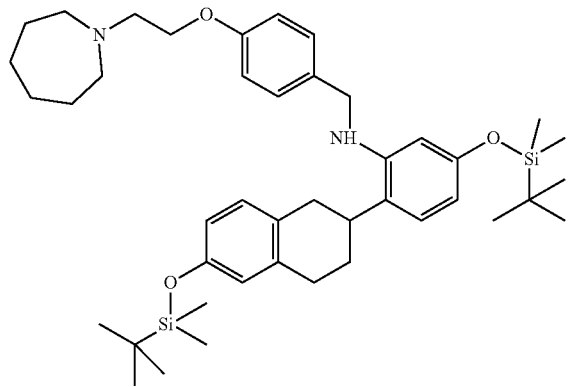 [SMILES: CC(C)(C)[Si](C)(C)Oc1ccc2c(c1)CCC(c1ccc(O[Si](C)(C)C(C)(C)C)cc1NCc1ccc(OCCN3CCCCCC3)cc1)C2]

Synthesized from 6-{2-[4-(2-azepan-1-ylethoxy)benzylamino]-4-hydroxyphenyl}-5,6,7,8-tetrahydronaphthalen-2-ol (960 mg) according to an analogous synthetic method to Example 201 described below, the title compound (1.2 g) was obtained.

$^1$H-NMR (400 MHz, CDCl$_3$); δ (ppm): 0.12 (s, 6H), 0.18 (s, 6H), 0.94 (s, 9H), 0.98 (s, 9H), 1.51-1.70 (m, 8H), 1.85-1.96 (m, 1H), 2.04-2.11 (m, 1H), 2.68-3.01 (m, 11H), 3.98 (t, 1H), 4.06 (t, 2H), 4.24 (s, 2H), 6.17 (s, 1H), 6.22 (d, 1H), 6.57-6.62 (m, 2H), 6.85-6.97 (m, 4H), 7.24-7.28 (m, 2H).

Example 175

[4-(2-Azepan-1-ylethoxy)benzyl](2-benzyloxyethyl){5-(tert-butyldimethylsilyloxy)-2-[6-(tert-butyldimethylsilyloxy)-1,2,3,4-tetrahydronaphthalen-2-yl]phenyl}amine

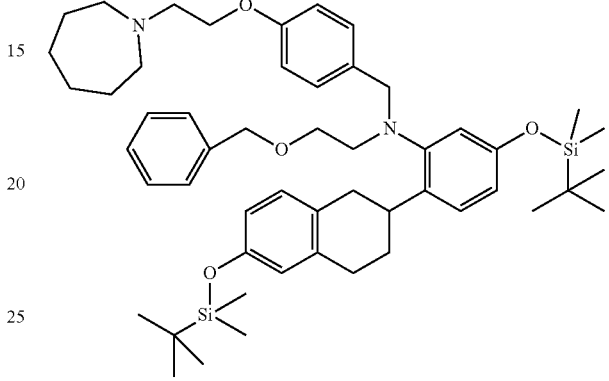

Synthesized from [4-(2-azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}amine (400 mg) and benzyloxyacetyl chloride (520 mg) according to an analogous synthetic method to Example 152, the title compound (450 mg) was obtained.

$^1$H-NMR (400 MHz, CDCl$_3$); δ (ppm): 0.16 (s, 6H), 0.21 (s, 6H), 0.96 (s, 9H), 0.99 (s, 9H), 1.51-1.76 (m, 10H), 2.62-2.85 (m, 8H), 2.93 (t, 2H), 3.13 (t, 2H), 3.45 (t, 2H), 3.60-3.69 (m, 1H), 3.99 (s, 2H), 4.01 (t, 2H), 4.39 (s, 2H), 6.57-6.63 (m, 3H), 6.68 (s, 1H), 6.73 (d, 2H), 6.84 (d, 1H), 7.02-7.09 (m, 4H), 7.20-7.30 (m, 4H).

Example 176

2-{[4-(2-Azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}amino}ethanol

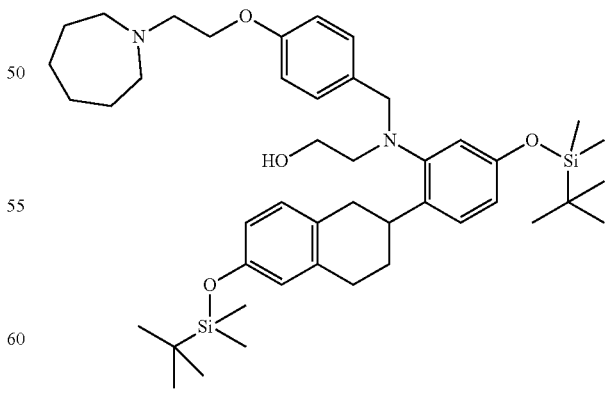

To a solution of [4-(2-azepan-1-ylethoxy)benzyl](2-benzyloxyethyl){5-(tert-butyldimethylsilyloxy)-2-[6-(tert-butyldimethylsilyloxy)-1,2,3,4-tetrahydronaphthalen-2-yl]phenyl}amine (450 mg) in dichloromethane (23 ml) was added dropwise boron trichloride (1.0 M solution in dichloromethane) (4.2 ml) at −78° C., and the solution was stirred for 30 minutes. At −78° C., to the reaction solution was added methanol (2 ml), and the reaction mixture was diluted with a saturated aqueous solution of sodium bicarbonate. The solution was extracted with chloroform, then washed with brine, dried over anhydrous magnesium sulfate, and then the solvent was evaporated in vacuo. The residue was purified by NH silica gel column chromatography (hexane-ethyl acetate system) to provide the title compound (240 mg).

$^1$H-NMR (400 MHz, CDCl$_3$); δ (ppm): 0.16 (s, 6H), 0.21 (s, 6H), 0.96 (s, 9H), 0.99 (s, 9H), 1.45-1.78 (m, 9H), 2.02-2.10 (m, 1H), 2.53-2.99 (m, 11H), 3.04-3.20 (m, 2H), 3.46-3.56 (m, 2H), 3.84-3.92 (m, 1H), 3.94 (s, 2H), 4.02 (t, 2H), 6.56-6.72 (m, 4H), 6.74 (d, 2H), 6.86 (d, 1H), 6.98 (d, 2H), 7.06 (d, 1H).

Example 177

6-{2-{[4-(2-Azepan-1-ylethoxy)benzyl](2-hydroxyethyl)amino}-4-hydroxyphenyl}-5,6,7,8-tetrahydronaphthalen-2-ol

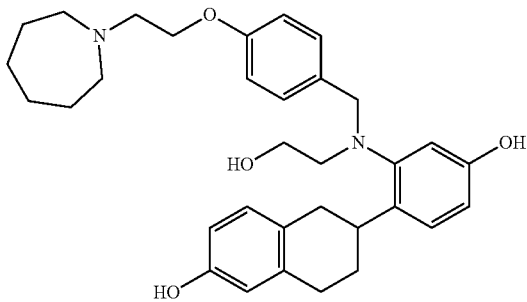 [SMILES: OCCN(Cc1ccc(OCCN2CCCCCC2)cc1)c1cc(O)ccc1C1CCc2cc(O)ccc2C1]

Synthesized from 2-{[4-(2-azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}amino}ethanol (240 mg) according to an analogous synthetic method to Example 173, the title compound (105 mg) was obtained.

$^1$H-NMR (400 MHz, DMSO-d$_6$); δ (ppm): 1.50-1.68 (m, 10H), 2.44-2.57 (m, 2H), 2.64-2.78 (m, 6H), 2.81 (t, 2H), 2.88 (t, 2H), 3.25-3.52 (m, 3H), 3.93 (s, 2H), 3.97 (t, 2H), 4.40 (t, 1H), 6.46-6.53 (m, 3H), 6.68 (s, 1H), 6.76-6.80 (m, 3H), 7.00 (d, 1H), 7.08 (d, 2H).

ESI-Mass; 531 [M$^+$+H]

Example 178

[4-(2-Azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}(2,2,2-trifluoroethyl)amine

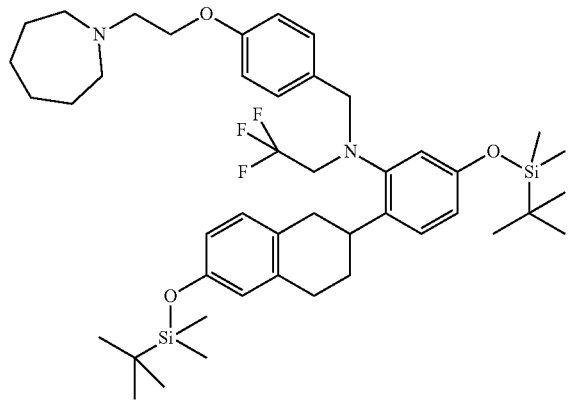 [SMILES: CC(C)(C)[Si](C)(C)Oc1ccc2c(c1)CCC(c1ccc(O[Si](C)(C)C(C)(C)C)cc1N(Cc1ccc(OCCN3CCCCCC3)cc1)CC(F)(F)F)C2]

A mixture of [4-(2-azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}amine (350 mg), trifluoroacetic anhydride (1 ml) and pyridine (1 ml) was stirred for 1 hour at room temperature. The reaction solution was concentrated in vacuo, and a saturated aqueous solution of sodium bicarbonate was added thereto. The solution was extracted with ethyl acetate, then washed with brine, dried over anhydrous magnesium sulfate, and then the solvent was evaporated in vacuo. To a solution of the resulting residue in tetrahydrofuran (10 ml) was added borane-methyl sulfide complex (0.25 ml), the solution was refluxed for 5 hours, then ice water, diethyl ether and concentrated hydrochloric acid (0.5 ml) were added thereto followed by stirring overnight at room temperature. The reaction solution was alkalinized by adding a saturated aqueous solution of sodium bicarbonate, the solution was extracted with ethyl acetate, then washed with brine, dried over anhydrous magnesium sulfate, and then the solvent was evaporated in vacuo. The residue was purified by silica gel column chromatography (hexane-ethyl acetate system) to provide the title compound (130 mg).

$^1$H-NMR (400 MHz, CDCl$_3$); δ (ppm): 0.18 (s, 6H), 0.21 (s, 6H), 0.98 (s, 9H), 1.00 (s, 9H), 1.55-1.78 (m, 10H), 1.83-1.92 (m, 2H), 2.50-2.71 (m, 2H), 2.76-2.80 (m, 2H), 2.97-3.05 (m, 2H), 3.11-3.20 (m, 4H), 3.45-3.55 (m, 3H), 4.11 (s, 2H), 4.42 (t, 2H), 6.59-6.63 (m, 3H), 6.66 (d, 1H), 6.76 (d, 2H), 6.86 (d, 1H), 7.04-7.10 (m, 3H).

Example 179

6-{2-{[4-(2-Azepan-1-ylethoxy)benzyl](2,2,2-trifluoroethyl)amino}-4-hydroxyphenyl}-5,6,7,8-tetrahydronaphthalen-2-ol

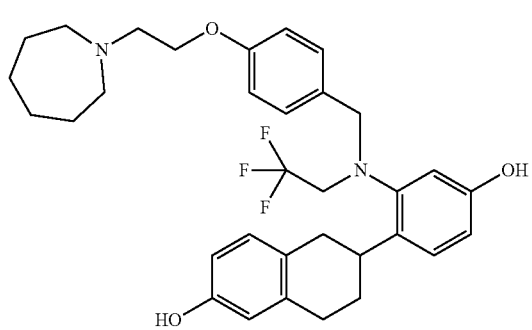 [SMILES: Oc1ccc2c(c1)CCC(c1ccc(O)cc1N(Cc1ccc(OCCN3CCCCCC3)cc1)CC(F)(F)F)C2]

Synthesized from [4-(2-azepan-1-ylethoxy)benzyl]{5-(tert-butyldimethylsilyloxy)-2-[6-(tert-butyldimethylsilyloxy)-1,2,3,4-tetrahydronaphthalen-2-yl]phenyl}(2,2,2-trifluoroethyl)amine (130 mg) according to an analogous synthetic method to Example 173, the title compound (63 mg) was obtained.

$^1$H-NMR (400 MHz, DMSO-d$_6$); δ (ppm): 1.49-1.71 (m, 12H), 2.31-2.90 (m, 8H), 3.11-3.20 (m, 1H), 3.61-3.73 (m, 2H), 3.94-4.10 (m, 4H), 6.46-6.52 (m, 2H), 6.57 (d, 1H), 6.69-6.84 (m, 4H), 7.00-7.08 (m, 3H), 8.99 (brs, 1H), 9.20 (brs, 1H).

ESI-Mass; 569 [M$^+$+H]

Example 180

Cyclopropylmethyl[3-fluoro-4-(2-piperidin-1-ylethoxy)benzyl][5-methoxy-2-(6-methoxy-1,2,3,4-tetrahydronaphthalen-2-yl)phenyl]amine

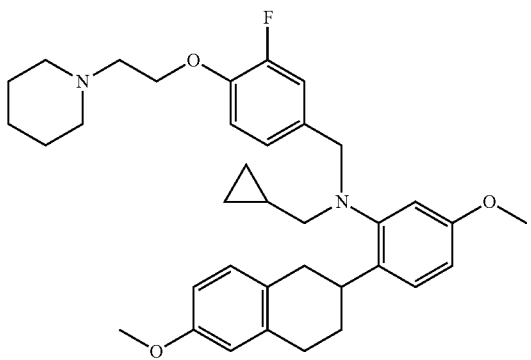 [SMILES: COc1ccc2c(c1)CCC(c1ccc(OC)cc1N(Cc1ccc(OCCN3CCCCC3)c(F)c1)CC1CC1)C2]

Synthesized from [3-fluoro-4-(2-piperidin-1-ylethoxy)benzyl][5-methoxy-2-(6-methoxy-1,2,3,4-tetrahydronaphthalen-2-yl)phenyl]amine (450 mg) and cyclopropanecarbonyl chloride (0.47 ml) according to an analogous synthetic method to Example 152, the title compound (430 mg) was obtained.

$^1$H-NMR (400 MHz, CDCl$_3$); δ (ppm): −0.06-0.02 (m, 2H), 0.34-0.39 (m, 2H), 0.78-0.85 (m, 1H), 1.40-1.48 (m, 2H), 1.52-1.65 (m, 4H), 1.76-1.83 (m, 2H), 2.47-2.55 (m, 4H), 2.68-2.81 (m, 6H), 2.85-3.01 (m, 2H), 3.69-3.78 (m, 1H), 3.79 (s, 3H), 3.81 (s, 3H), 4.05 (s, 2H), 4.12 (t, 2H), 6.67-6.73 (m, 3H), 6.79-6.84 (m, 2H), 6.92 (d, 1H), 6.96-7.02 (m, 2H), 7.14 (d, 1H).

Example 181

6-{2-{Cyclopropylmethyl[3-fluoro-4-(2-piperidin-1-ylethoxy)benzyl]amino}-4-hydroxyphenyl}-5,6,7,8-tetrahydronaphthalen-2-ol

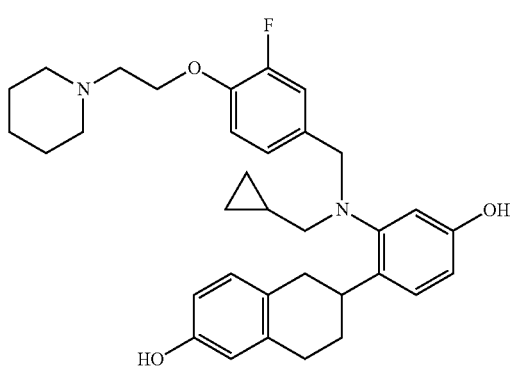 [SMILES: Oc1ccc2c(c1)CCC(c1ccc(O)cc1N(Cc1ccc(OCCN3CCCCC3)c(F)c1)CC1CC1)C2]

Synthesized from cyclopropylmethyl[3-fluoro-4-(2-piperidin-1-yl-ethoxy)benzyl][5-methoxy-2-(6-methoxy-1,2,3,4-tetrahydronaphthalen-2-yl)phenyl]amine (230 mg) according to an analogous synthetic method to Example 111, the title compound (180 mg) was obtained.

$^1$H-NMR (400 MHz, DMSO-d$_6$); δ (ppm): 0.01 (d, 2H), 0.40 (d, 2H), 0.77-0.89 (m, 1H), 1.36-1.46 (m, 2H), 1.50-1.58 (m, 4H), 1.60-1.81 (m, 2H), 2.41-2.52 (m, 4H), 2.55-2.75 (m, 6H), 2.81-2.89 (m, 2H), 3.56-3.67 (m, 1H), 4.07 (s, 2H), 4.13 (t, 2H), 6.55-6.60 (m, 3H), 6.76 (s, 1H), 6.86 (d, 1H), 6.98-7.12 (m, 4H), 9.07 (brs, 1H), 9.15 (brs, 1H).

Example 182

[3-Fluoro-4-(2-piperidin-1-ylethoxy)benzyl](2-methoxyethyl)[5-methoxy-2-(6-methoxy-1,2,3,4-tetrahydronaphthalen-2-yl)phenyl]amine

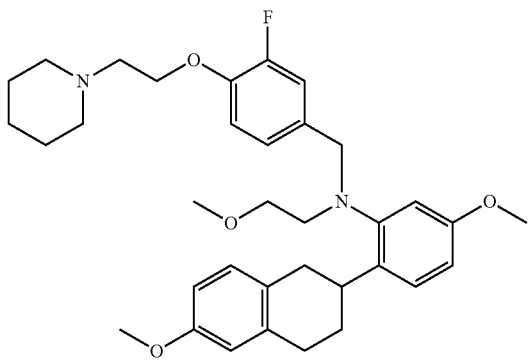 [SMILES: COCCN(Cc1ccc(OCCN2CCCCC2)c(F)c1)c1cc(OC)ccc1C1CCc2cc(OC)ccc2C1]

Synthesized from [3-fluoro-4-(2-piperidin-1-ylethoxy)benzyl][5-methoxy-2-(6-methoxy-1,2,3,4-tetrahydronaphthalen-2-yl)phenyl]amine (450 mg) and methoxyacetyl chloride (0.48 ml) according to an analogous synthetic method to Example 152, the title compound (400 mg) was obtained.

$^1$H-NMR (400 MHz, CDCl$_3$); δ (ppm): 1.41-1.48 (m, 2H), 1.54-1.64 (m, 4H), 1.71-1.84 (m, 2H), 2.46-2.54 (m, 4H), 2.69-2.75 (m, 2H), 2.78 (t, 2H), 2.84-3.00 (m, 2H), 3.09 (t, 2H), 3.24 (s, 2H), 3.35 (t, 2H), 3.60-3.68 (m, 1H), 3.79 (s, 3H), 3.80 (s, 3H), 4.03 (s, 2H), 4.12 (t, 2H), 6.68-6.72 (m, 3H), 6.77 (s, 1H), 6.81 (t, 1H), 6.90 (d, 1H), 6.94-6.99 (m, 2H), 7.14 (d, 1H).

Example 183

6-{2-{[3-Fluoro-4-(2-piperidin-1-ylethoxy)benzyl](2-methoxyethyl)amino}-4-hydroxyphenyl}-5,6,7,8-tetrahydronaphthalen-2-ol

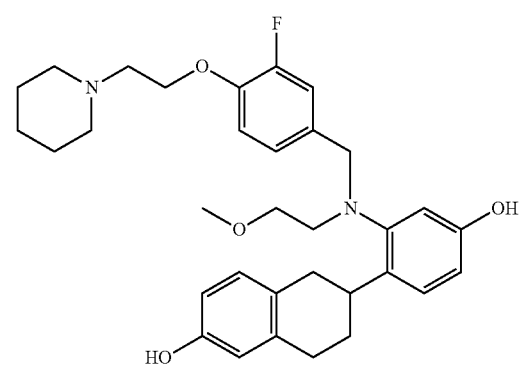 [SMILES: COCCN(Cc1ccc(OCCN2CCCCC2)c(F)c1)c1cc(O)ccc1C1CCc2cc(O)ccc2C1]

Synthesized from [3-fluoro-4-(2-piperidin-1-ylethoxy)benzyl](2-methoxyethyl)[5-methoxy-2-(6-methoxy-1,2,3,4-tetrahydronaphthalen-2-yl)phenyl]amine (200 mg) accord-

Example 184

6-{2-[[3-Fluoro-4-(2-piperidin-1-ylethoxy)benzyl](2-hydroxyethyl)amino]-4-hydroxyphenyl}-5,6,7,8-tetrahydronaphthalen-2-ol

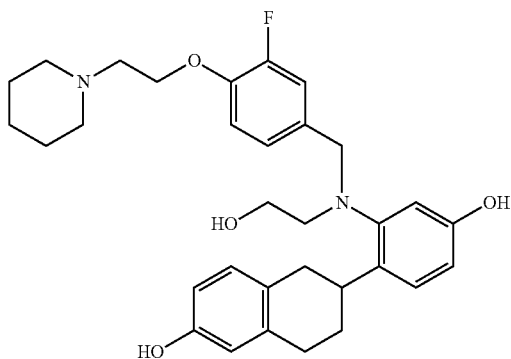 [SMILES: OCCN(Cc1ccc(OCCN2CCCCC2)c(F)c1)c1cc(O)ccc1C1CCc2cc(O)ccc2C1]

Synthesized from [3-fluoro-4-(2-piperidin-1-ylethoxy)benzyl](2-methoxyethyl)[5-methoxy-2-(6-methoxy-1,2,3,4-tetrahydronaphthalen-2-yl)phenyl]amine (250 mg) according to an analogous synthetic method to Example 364 described below, the title compound (78 mg) was obtained.

$^1$H-NMR (400 MHz, DMSO-$d_6$); δ (ppm): 1.30-1.38 (m, 2H), 1.41-1.50 (m, 4H), 1.52-1.70 (m, 2H), 2.33-2.56 (m, 6H), 2.60 (t, 2H), 2.69-2.76 (m, 2H), 2.88 (t, 2H), 3.40-3.50 (m, 1H), 3.95 (s, 2H), 4.00-4.12 (m, 4H), 4.42 (t, 1H), 6.45-6.51 (m, 3H), 6.65 (s, 1H), 6.77 (d, 1H), 6.89 (d, 1H), 6.95-7.04 (m, 3H), 8.99 (brs, 1H), 9.10 (brs, 1H).

ESI-Mass; 535 [M$^+$+H]

Example 185

[3-Fluoro-4-(2-piperidin-1-ylethoxy)benzyl][5-methoxy-2-(6-methoxy-1,2,3,4-tetrahydronaphthalen-2-yl)phenyl]propylamine

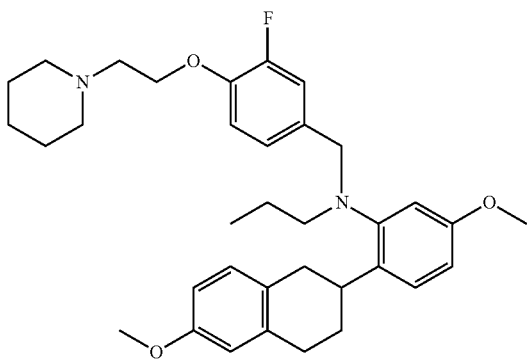 [SMILES: CCCN(Cc1ccc(OCCN2CCCCC2)c(F)c1)c1cc(OC)ccc1C1CCc2cc(OC)ccc2C1]

Synthesized from [3-fluoro-4-(2-piperidin-1-ylethoxy)benzyl][5-methoxy-2-(6-methoxy-1,2,3,4-tetrahydronaphthalen-2-yl)phenyl]amine (450 mg) and propionic anhydride (0.67 ml) according to an analogous synthetic method to Example 36, the title compound (370 mg) was obtained.

$^1$H-NMR (400 MHz, CDCl$_3$); δ (ppm): 0.79 (t, 3H), 1.34-1.48 (m, 4H), 1.56-1.64 (m, 4H), 1.72-1.85 (m, 2H), 2.46-2.55 (m, 4H), 2.70-2.81 (m, 6H), 2.82-3.00 (m, 2H), 3.60-3.71 (m, 1H), 3.78 (s, 3H), 3.80 (s, 3H), 3.93 (s, 2H), 4.12 (t, 2H), 6.67-6.72 (m, 3H), 6.74 (s, 1H), 6.81 (t, 1H), 6.88 (d, 1H), 6.92-6.99 (m, 2H), 7.14 (d, 1H).

Example 186

6-{2-{[3-Fluoro-4-(2-piperidin-1-ylethoxy)benzyl]propylamino}-4-hydroxyphenyl}-5,6,7,8-tetrahydronaphthalen-2-ol

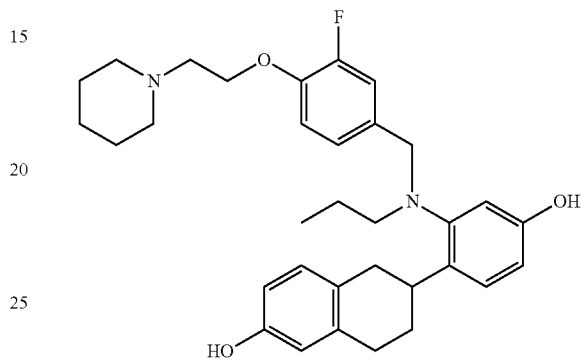

Synthesized from [3-fluoro-4-(2-piperidin-1-ylethoxy)benzyl][5-methoxy-2-(6-methoxy-1,2,3,4-tetrahydronaphthalen-2-yl)phenyl]propylamine (370 mg) according to an analogous synthetic method to Example 111, the title compound (230 mg) was obtained.

$^1$H-NMR (400 MHz, DMSO-$d_6$); δ (ppm): 0.74 (t, 3H), 1.25-1.71 (m, 10H), 2.30-2.64 (m, 8H), 2.72 (t, 4H), 3.40-3.51 (m, 1H), 3.87 (s, 2H), 4.06 (t, 2H), 6.45-6.50 (m, 3H), 6.60 (s, 1H), 6.77 (d, 1H), 6.86-7.04 (m, 4H), 8.99 (brs, 1H), 9.08 (brs, 1H).

Example 187

6-{2-{Ethyl[3-fluoro-4-(2-piperidin-1-ylethoxy)benzyl]amino}-4-hydroxyphenyl}-5,6,7,8-tetrahydronaphthalen-2-ol

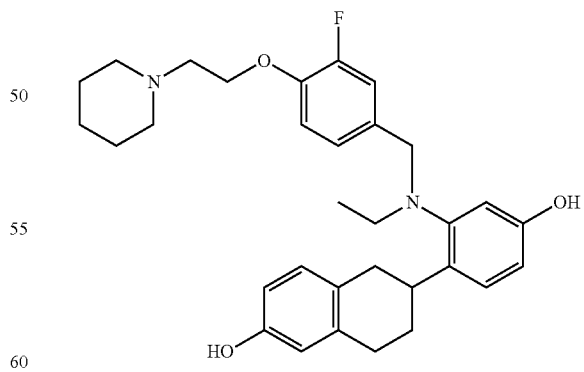

Synthesized from ethyl[5-methoxy-2-(6-methoxy-1,2,3,4-tetrahydronaphthalen-2-yl)phenyl]amine and 3-fluoro-4-(2-piperidin-1-ylethoxy)benzoic acid hydrochloride according to an analogous synthetic method to Example 152, ethyl[3-fluoro-4-(2-piperidin-1-ylethoxy)benzyl][5-methoxy-2-(6-methoxy-1,2,3,4-tetrahydronaphthalen-2-yl)phenyl]amine (276 mg) was used according to an analogous synthetic method to Example 111 to provide the title compound (242 mg).

$^1$H-NMR (400 MHz, DMSO-$d_6$); δ (ppm): 0.86 (t, 3H), 1.29-1.37 (m, 2H), 1.41-1.49 (m, 4H), 1.50-1.59 (m, 1H), 1.60-1.72 (m, 1H), 2.32-2.43 (m, 4H), 2.46-2.57 (m, 2H), 2.60 (t, 2H), 2.70-2.76 (m, 2H), 2.82 (q, 2H), 3.38-3.49 (m, 1H), 3.88 (dd, 2H), 4.05 (t, 2H), 6.46-6.51 (m, 3H), 6.61 (d, 1H), 6.78 (d, 1H), 6.89-7.03 (m, 4H), 8.99 (s, 1H), 9.08 (s, 1H).

ESI-Mass; 519 [M$^+$+H]

Example 188

(S)-6-{2-{Ethyl-[3-fluoro-4-(2-piperidin-1-ylethoxy)benzyl]amino}-4-hydroxyphenyl}-5,6,7,8-tetrahydronaphthalen-2-ol and (R)-6-{2-{ethyl-[3-fluoro-4-(2-piperidin-1-ylethoxy)benzyl]amino}-4-hydroxyphenyl}-5,6,7,8-tetrahydronaphthalen-2-ol

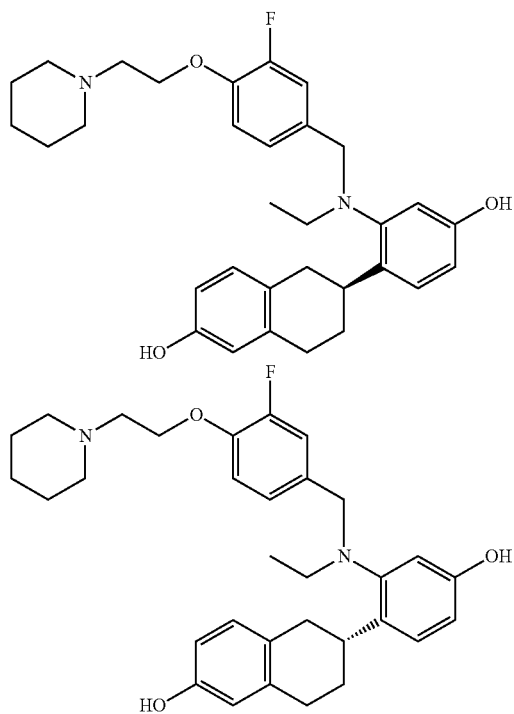

Optical resolution of racemic 6-{2-{ethyl[3-fluoro-4-(2-piperidin-1-ylethoxy)benzyl]amino}-4-hydroxyphenyl}-5,6,7,8-tetrahydronaphthalen-2-ol (1.0 g) was carried out by high performance liquid chromatography using a chiral column (Daicel Chemical) to provide (S)-6-{2-{ethyl[3-fluoro-4-(2-piperidin-1-ylethoxy)benzyl]amino}-4-hydroxyphenyl}-5,6,7,8-tetrahydronaphthalen-2-ol (350 mg) exhibiting a short retention time and (R)-6-{2-{ethyl[3-fluoro-4-(2-piperidin-1-ylethoxy)benzyl]amino}-4-hydroxyphenyl}-5,6,7,8-tetrahydronaphthalen-2-ol (350 mg) exhibiting a long retention time.

(S)-6-{2-{Ethyl[3-fluoro-4-(2-piperidin-1-ylethoxy)benzyl]amino}-4-hydroxyphenyl}-5,6,7,8-tetrahydronaphthalen-2-ol:
retention time: 15.7 minutes
(R)-6-{2-{Ethyl[3-fluoro-4-(2-piperidin-1-ylethoxy)benzyl]amino}-4-hydroxyphenyl}-5,6,7,8-tetrahydronaphthalen-2-ol
retention time: 18.0 minutes

Example 189

6-{2-{[4-(2-Azepan-1-ylethoxy)benzyl]ethylamino}-4-hydroxyphenyl}-5,6,7,8-tetrahydronaphthalen-2-ol

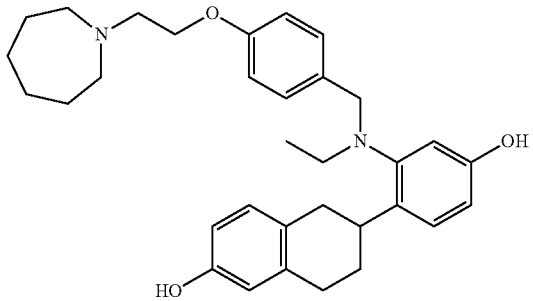

Synthesized from ethyl[5-methoxy-2-(6-methoxy-1,2,3,4-tetrahydronaphthalen-2-yl)phenyl]amine (400 mg) and 4-(2-azepan-1-ylethoxy)benzoyl chloride hydrochloride (530 mg) according to an analogous synthetic method to Example 187, the title compound (390 mg) was obtained.

$^1$H-NMR (400 MHz, DMSO-$d_6$); δ (ppm): 0.85 (t, 3H), 1.45-1.70 (m, 10H), 2.41-2.58 (m, 2H), 2.60-2.85 (m, 10H), 3.40-3.50 (m, 1H), 3.86 (s, 2H), 3.95 (t, 2H), 6.45-6.50 (m, 3H), 6.62 (s, 1H), 6.74-6.80 (m, 3H), 6.99 (d, 1H), 7.06 (d, 2H), 8.99 (brs, 1H), 9.06 (brs, 1H).

ESI-Mass; 515 [M$^+$-1-11]

Example 190

(S)-6-{2-{[4-(2-Azepan-1-ylethoxy)benzyl]ethylamino}-4-hydroxyphenyl}-5,6,7,8-tetrahydronaphthalen-2-ol and (R)-6-{2-{[4-(2-azepan-1-ylethoxy)benzyl]ethylamino}-4-hydroxyphenyl}-5,6,7,8-tetrahydronaphthalen-2-ol

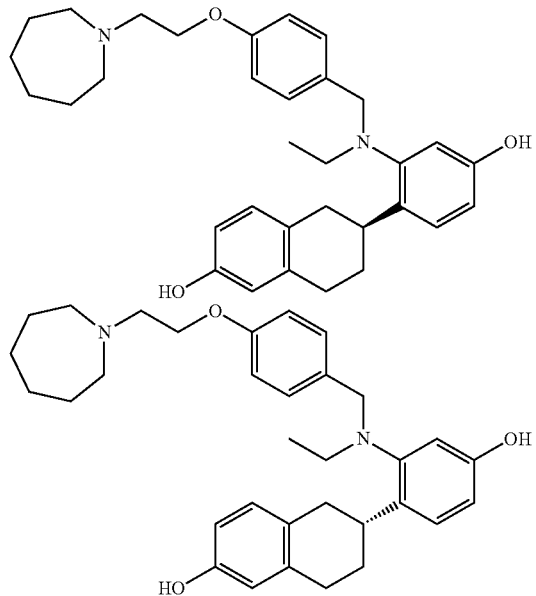

According to an analogous synthetic method to Example 88, from racemic 6-{2-{[4-(2-azepan-1-ylethoxy)benzyl]ethylamino}-4-hydroxyphenyl}-5,6,7,8-tetrahydronaphthalen-2-ol (2.0 g), obtained were (S)-6-{2-{[4-(2-azepan-1-ylethoxy)benzyl]ethylamino}-4-hydroxyphenyl}-5,6,7,8- tetrahydronaphthalen-2-ol (600 mg) exhibiting a short retention time and (R)-6-{2-{[4-(2-azepan-1-ylethoxy)benzyl]ethylamino}-4-hydroxyphenyl}-5,6,7,8-tetrahydronaphthalen-2-ol (750 mg) exhibiting a long retention time.

(S)-6-{2-{[4-(2-Azepan-1-ylethoxy)benzyl]ethylamino}-4-hydroxyphenyl}-5,6,7,8-tetrahydronaphthalen-2-ol:
retention time: 13.9 minutes
[α]$_D$ −27.0° (c=1.01, methanol)

(R)-6-{2-{[4-(2-Azepan-1-ylethoxy)benzyl]ethylamino}-4-hydroxyphenyl}-5,6,7,8-tetrahydronaphthalen-2-ol:
retention time: 15.7 minutes
[α]$_D$ +26.3° (c=1.01, methanol)

Example 191

6-{2-{[4-(2-Azepan-1-ylethoxy)-3-fluorobenzyl]ethylamino}-4-hydroxyphenyl}-5,6,7,8-tetrahydronaphthalen-2-ol

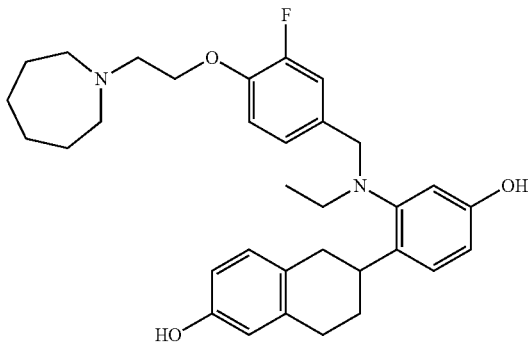 [SMILES: CCN(Cc1ccc(OCCN2CCCCCC2)c(F)c1)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine (400 mg) and 4-(2-azepan-1-ylethoxy)-3-fluorobenzoyl chloride hydrochloride (560 mg) according to an analogous synthetic method to Example 187, the title compound (340 mg) was obtained.

$^1$H-NMR (400 MHz, DMSO-d$_6$); δ (ppm): 0.86 (t, 3H), 1.45-1.71 (m, 10H), 2.45-2.60 (m, 2H), 2.64 (t, 4H), 2.70-2.75 (m, 2H), 2.81 (t, 4H), 3.39-3.50 (m, 1H), 3.89 (s, 2H), 4.02 (t, 2H), 6.45-6.50 (m, 3H), 6.61 (s, 1H), 6.78 (d, 1H), 6.88-7.04 (m, 4H), 8.99 (brs, 1H), 9.09 (brs, 1H).
ESI-Mass; 533 [M$^+$+H]

Example 192

6-{2-{Ethyl[3-fluoro-4-(3-piperidin-1-ylpropyl)benzyl]amino}-4-hydroxyphenyl}-5,6,7,8-tetrahydronaphthalen-2-ol

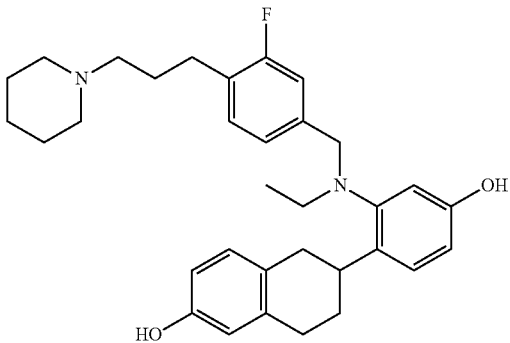 [SMILES: CCN(Cc1ccc(CCCN2CCCCC2)c(F)c1)c1cc(O)ccc1C1CCc2cc(O)ccc2C1]

Synthesized from ethyl[5-methoxy-2-(6-methoxy-1,2,3,4-tetrahydronaphthalen-2-yl)phenyl]amine and 3-fluoro-4-(3-piperidin-1-ylpropyl)benzoic acid hydrochloride according to an analogous synthetic method to Example 152, ethyl[3-fluoro-4-(3-piperidin-1-ylpropyl)benzyl][5-methoxy-2-(6-methoxy-1,2,3,4-tetrahydronaphthalen-2-yl)phenyl]amine (377 mg) was used according to an analogous synthetic method to Example 111 to provide the title compound (320 mg).

$^1$H-NMR (400 MHz, DMSO-d$_6$); δ (ppm): 0.87 (t, 3H), 1.29-1.38 (m, 2H), 1.41-1.49 (m, 4H), 1.50-1.56 (m, 1H), 1.58-1.71 (m, 3H), 2.18 (t, 2H), 2.18-2.30 (m, 4H), 2.50-2.61 (m, 4H), 2.68-2.74 (m, 2H), 2.83 (q, 2H), 3.40-3.49 (m, 1H), 3.93 (dd, 2H), 6.46-6.51 (m, 3H), 6.63 (d, 1H), 6.78 (d, 1H), 6.90 (d, 1H), 6.91-6.94 (m, 1H), 7.00 (d, 1H), 7.11 (t, 1H), 8.99 (s, 1H), 9.09 (s, 1H).
ESI-Mass; 517 [M$^+$+H]

Example 193

6-{2-{[6-(2-Azepan-1-ylethoxy)pyridin-3-ylmethyl]ethylamino}-4-hydroxyphenyl}-5,6,7,8-tetrahydronaphthalen-2-ol

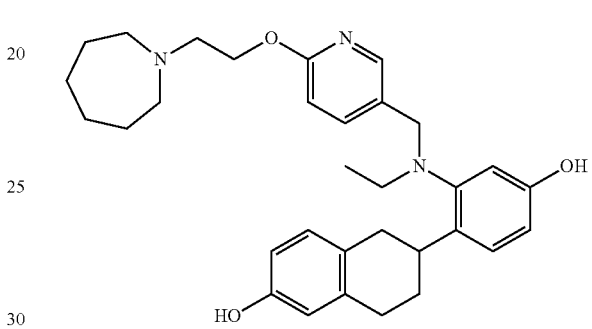

Synthesized from ethyl[5-methoxy-2-(6-methoxy-1,2,3,4-tetrahydronaphthalen-2-yl)phenyl]amine and 6-(2-azepan-1-ylethoxy)nicotinic acid hydrochloride according to an analogous synthetic method to Example 152, [6-(2-azepan-1-ylethoxy)pyridin-3-ylmethyl]ethyl[5-methoxy-2-(6-methoxy-1,2,3,4-tetrahydronaphthalen-2-yl)phenyl]amine (287 mg) was used according to an analogous synthetic method to Example 111 to provide the title compound (230 mg).

$^1$H-NMR (400 MHz, DMSO-d$_6$); δ (ppm): 0.86 (t, 3H), 1.39-1.68 (m, 10H), 2.35-2.53 (m, 2H), 2.63 (t, 4H), 2.65-2.73 (m, 2H), 2.77 (t, 2H), 2.83 (q, 2H), 3.33-3.43 (m, 1H), 3.88 (dd, 2H), 4.23 (t, 2H), 6.45-6.52 (m, 3H), 6.61-6.65 (m, 2H), 6.76 (d, 1H), 6.98 (d, 1H), 7.40 (dd, 1H), 7.85 (d, 1H), 8.99 (s, 1H), 9.11 (s, 1H).
ESI-Mass; 516 [M$^+$+H]

Example 194

6-{2-{[3-Fluoro-4-(2-piperidin-1-ylethoxy)benzyl]isopropylamino}-4-hydroxyphenyl}-5,6,7,8-tetrahydronaphthalen-2-ol

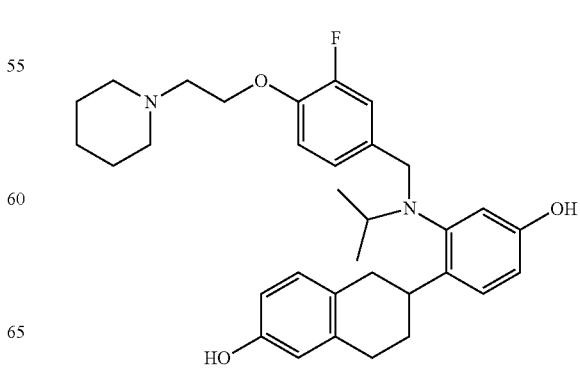

Synthesized from isopropyl[5-methoxy-2-(6-methoxy-1,2,3,4-tetrahydronaphthalen-2-yl)phenyl]amine and 3-fluoro-4-(2-piperidin-1-ylethoxy)benzoic acid hydrochloride according to an analogous synthetic method to Example 152, [3-fluoro-4-(2-piperidin-1-ylethoxy)benzyl]isopropyl[5-methoxy-2-(6-methoxy-1,2,3,4-tetrahydronaphthalen-2-yl)phenyl]amine (402 mg) was used according to an analogous synthetic method to Example 111 to provide the title compound (262 mg).

$^1$H-NMR (400 MHz, DMSO-d$_6$); δ (ppm): 1.03 (d, 3H), 1.09 (d, 3H), 1.29-1.37 (m, 2H), 1.40-1.50 (m, 5H), 1.54-1.70 (m, 1H), 2.32-2.55 (m, 6H), 2.59 (t, 2H), 2.70-2.79 (m, 2H), 3.07 (hept, 1H), 3.33-3.44 (m, 1H), 3.93-4.05 (m, 4H), 6.41 (dd, 1H), 6.46-6.52 (m, 2H), 6.64 (d, 1H), 6.77 (d, 1H), 6.87 (d, 1H), 6.91-6.98 (m, 3H), 9.00 (s, 2H).

ESI-Mass; 533 [M$^+$+H]

Example 195

Cyclopropylmethyl[5-methoxy-2-(6-methoxy-1,2,3,4-tetrahydronaphthalen-2-yl)phenyl][4-(2-pyrrolidin-1-ylethoxy)benzyl]amine

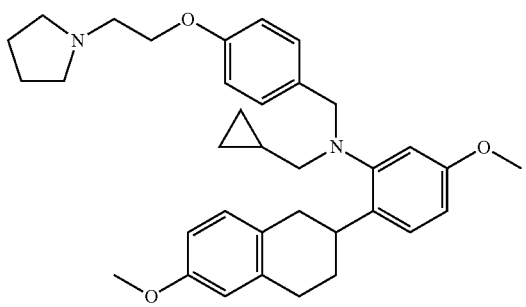 [SMILES: COc1ccc2c(c1)CCC(c1ccc(OC)cc1N(Cc1ccc(OCCN3CCCC3)cc1)CC1CC1)C2]

To a suspension of 4-(2-pyrrolidin-1-ylethoxy)benzoic acid hydrochloride (815 mg) in toluene (5 ml) was added thionyl chloride (5 ml), and the solution was stirred for 40 minutes at 85° C. The reaction solution was concentrated in vacuo. To a solution of the resulting residue in tetrahydrofuran (15 ml) were sequentially added 5-methoxy-2-(6-methoxy-1,2,3,4-tetrahydronaphthalen-2-yl)phenylamine (567 mg) and N,N-diisopropylethylamine (2.1 g), and the solution was stirred for 30 minutes at 70° C. The solution was extracted with ethyl acetate, then sequentially washed with an aqueous solution of 2N sodium hydroxide and brine, dried over anhydrous magnesium sulfate, and then the solvent was evaporated in vacuo. To a suspension of lithium aluminum hydride (380 mg) in tetrahydrofuran (50 ml) was added aluminum chloride (1.33 g) on an ice bath. To the resulting suspension was added dropwise a solution of the above residue in tetrahydrofuran (10 ml). The reaction solution was diluted with tetrahydrofuran, and ammonia solution was added to give the suspension, which was filtered, the filtrate was dried over anhydrous magnesium sulfate, then filtered. To the filtrate was added N,N-diisopropylethylamine (1.0 g), cyclopropanecarbonyl chloride (627 mg) was added dropwise thereto on an ice bath followed by stirring for 2 hours at room temperature. The reaction solution was concentrated in vacuo, extracted with ethyl acetate, then sequentially washed with an aqueous solution of 2N sodium hydroxide and brine, dried over anhydrous magnesium sulfate, then the solvent was evaporated in vacuo. Synthesized from the total amount of the resulting cyclopropanecarboxylic acid [5-methoxy-2-(6-methoxy-1,2,3,4-tetrahydronaphthalen-2-yl)phenyl]-[4-(2-pyrrolidin-1-ylethoxy)benzyl]amide crude product according to an analogous synthetic method to Example 337 described below, the title compound (877 mg) was obtained.

$^1$H-NMR (400 MHz, CDCl$_3$); δ (ppm): −0.04-0.04 (m, 2H), 0.35-0.43 (m, 2H), 0.80-0.90 (m, 1H), 1.75-1.94 (m, 6H), 2.53-2.90 (m, 10H), 2.95-3.04 (m, 2H), 3.66-3.76 (m, 1H), 4.02 (s, 2H), 4.08-4.14 (m, 2H), 6.60-6.68 (m, 3H), 6.72-6.77 (m, 2H), 6.79 (d, 1H), 6.90-6.94 (m, 2H), 7.08 (d, 1H), 7.13-7.18 (m, 2H).

Example 196

6-{2-{Cyclopropylmethyl[4-(2-pyrrolidin-1-ylethoxy)benzyl]amino}-4-hydroxyphenyl}-5,6,7,8-tetrahydronaphthalen-2-ol

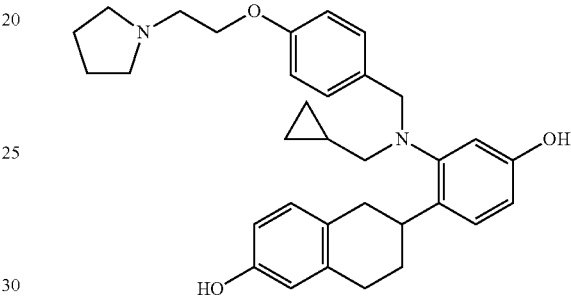

Synthesized from cyclopropylmethyl[5-methoxy-2-(6-methoxy-1,2,3,4-tetrahydronaphthalen-2-yl)phenyl][4-(2-pyrrolidin-1-ylethoxy)benzyl]amine (877 mg) according to an analogous synthetic method to Example 111, the title compound (568 mg) was obtained.

$^1$H-NMR (400 MHz, CDCl$_3$); δ (ppm): −0.04-0.04 (m, 2H), 0.36-0.42 (m, 2H), 0.80-0.90 (m, 1H), 1.80-1.90 (m, 6H), 2.63-2.80 (m, 8H), 2.94-2.98 (m, 4H), 3.84 (s, 3H), 3.86 (s, 3H), 4.08-4.14 (m, 4H), 6.72-6.90 (m, 6H), 7.02 (d, 1H), 7.18-7.22 (m, 3H).

ESI-Mass; 513 [M$^+$+H]

Example 197

Cyclopropylmethyl[5-methoxy-2-(6-methoxy-1,2,3,4-tetrahydronaphthalen-2-yl)phenyl][4-(2-piperidin-1-ylethoxy)benzyl]amine

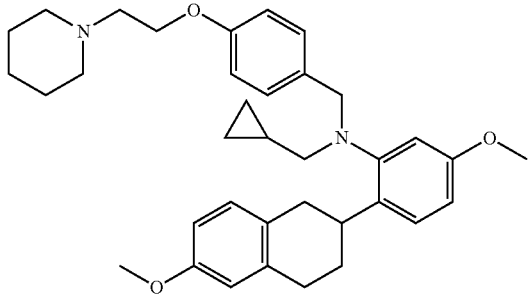 [SMILES: COc1ccc2c(c1)CCC(c1ccc(OC)cc1N(Cc1ccc(OCCN3CCCCC3)cc1)CC1CC1)C2]

Synthesized from 5-methoxy-2-(6-methoxy-1,2,3,4-tetrahydronaphthalen-2-yl)phenylamine (567 mg) and 4-(2-piperidin-1-ylethoxy)benzoic acid hydrochloride (857 mg)

according to an analogous synthetic method to Example 195, the title compound (888 mg) was obtained.

$^1$H-NMR (400 MHz, CDCl$_3$); δ (ppm): −0.04-0.04 (m, 2H), 0.38-0.44 (m, 2H), 0.82-0.90 (m, 1H), 1.48-1.56 (m, 2H), 1.62-1.72 (m, 4H), 1.82-1.92 (m, 2H), 2.58 (s, 4H), 2.70-2.84 (m, 6H), 2.88-3.06 (m, 3H), 3.84 (s, 3H), 3.86 (s, 3H), 4.08-4.18 (m, 4H), 6.72-6.86 (m, 5H), 6.90 (s, 1H), 7.03 (d, 1H), 7.18-7.24 (m, 3H).

Example 198

6-{2-{Cyclopropylmethyl[4-(2-piperidin-1-ylethoxy)benzyl]amino}-4-hydroxyphenyl}-5,6,7,8-tetrahydronaphthalen-2-ol

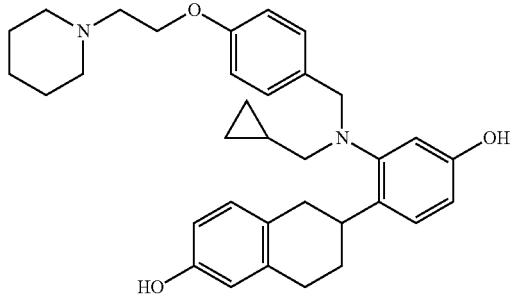 [SMILES: Oc1ccc2c(c1)CCC(c1ccc(O)cc1N(Cc1ccc(OCCN3CCCCC3)cc1)CC1CC1)C2]

Synthesized from cyclopropylmethyl[5-methoxy-2-(6-methoxy-1,2,3,4-tetrahydronaphthalen-2-yl)phenyl][4-(2-piperidin-1-ylethoxy)benzyl]amine (888 mg) according to an analogous synthetic method to Example 111, the title compound (707 mg) was obtained.

$^1$H-NMR (400 MHz, CDCl$_3$); δ (ppm): −0.04-0.06 (m, 2H), 0.36-0.42 (m, 2H), 0.82-0.92 (m, 1H), 1.48-1.58 (m, 2H), 1.68-1.84 (m, 6H), 2.60-2.78 (m, 8H), 2.82-2.96 (m, 4H), 3.70-3.80 (m, 1H), 4.02 (s, 2H), 4.10-4.16 (m, 2H), 6.62-6.70 (m, 3H), 6.72-6.78 (m, 2H), 6.80 (s, 1H), 6.94 (d, 1H), 7.08 (d, 1H), 7.14-7.20 (m, 2H).

ESI-Mass; 527 [M$^+$+H]

Example 199

[4-(2-Azepan-1-ylethoxy)benzyl]cyclopropylmethyl[5-methoxy-2-(6-methoxy-1,2,3,4-tetrahydronaphthalen-2-yl)phenyl]amine

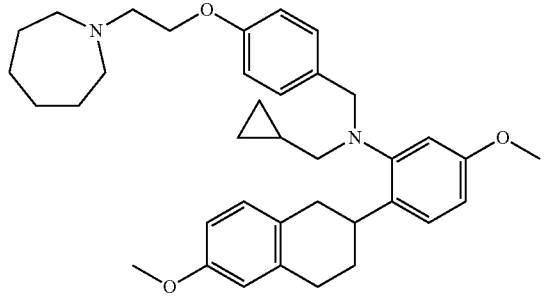 [SMILES: COc1ccc2c(c1)CCC(c1ccc(OC)cc1N(Cc1ccc(OCCN3CCCCCC3)cc1)CC1CC1)C2]

Synthesized from 5-methoxy-2-(6-methoxy-1,2,3,4-tetrahydronaphthalen-2-yl)phenylamine (567 mg) and 4-(2-azepan-1-ylethoxy)benzoic acid hydrochloride (899 mg) according to an analogous synthetic method to Example 195, the title compound (863 mg) was obtained.

$^1$H-NMR (400 MHz, CDCl$_3$); δ (ppm): −0.04-0.04 (m, 2H), 0.36-0.42 (m, 2H), 0.82-0.88 (m, 1H), 1.60-1.76 (m, 10H), 1.80-1.88 (m, 2H), 2.74-2.86 (m, 6H), 2.94-3.02 (m, 4H), 3.78-3.86 (m, 1H), 3.85 (s, 3H), 3.87 (s, 3H), 4.04-4.14 (m, 4H), 6.72-6.86 (m, 5H), 6.90 (s, 1H), 7.02 (d, 1H), 7.14-7.22 (m, 3H).

Example 200

6-{2-{[4-(2-Azepan-1-ylethoxy)benzyl]cyclopropylmethylamino}-4-hydroxyphenyl}-5,6,7,8-tetrahydronaphthalen-2-ol

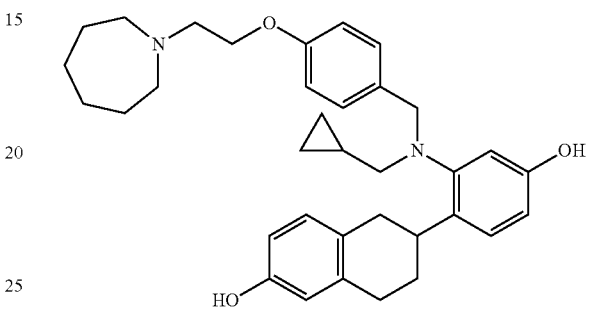

Synthesized from [4-(2-azepan-1-ylethoxy)benzyl]cyclopropylmethyl[5-methoxy-2-(6-methoxy-1,2,3,4-tetrahydronaphthalen-2-yl)phenyl]amine (863 mg) according to an analogous synthetic method to Example 111, the title compound (472 mg) was obtained.

$^1$H-NMR (400 MHz, CDCl$_3$); δ (ppm): −0.06-0.00 (m, 2H), 0.31-0.38 (m, 2H), 0.74-0.84 (m, 1H), 1.54-1.80 (m, 10H), 2.52-3.00 (m, 12H), 3.63-3.73 (m, 1H), 4.00-4.10 (m, 4H), 6.56-6.63 (m, 3H), 6.70-6.77 (m, 3H), 6.89 (d, 1H), 7.06 (d, 1H), 7.10-7.14 (m, 2H).

ESI-Mass; 541 [M$^+$+H]

Example 201

2-[6-(tert-Butyldimethylsilyloxy)-1,2,3,4-tetrahydronaphthalen-2-yl]-5-methoxyphenylamine

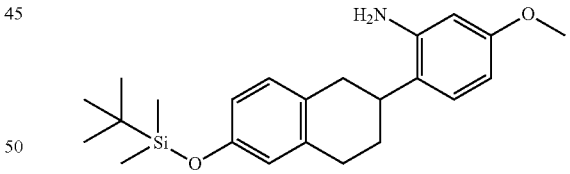

To a solution of 6-(2-amino-4-methoxyphenyl)-5,6,7,8-tetrahydronaphthalen-2-ol (850 mg) in N,N-dimethylformamide (10 ml) were sequentially added imidazole (500 mg) and tert-butyldimethylsilyl chloride (480 mg), and the solution was stirred for 1 hour at room temperature. The solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (805 mg).

$^1$H-NMR (400 MHz, CDCl$_3$); δ (ppm): 0.19 (s, 6H), 0.99 (s, 9H), 1.83-1.97 (m, 1H), 2.04-2.12 (m, 1H), 2.73 (dd, 1H), 2.82-2.93 (m, 3H), 2.95-3.02 (m, 1H), 3.71 (brs, 2H), 3.76 (s, 3H), 6.29 (d, 1H), 6.36 (dd, 1H), 6.59-6.63 (m, 2H), 6.93 (d, 1H), 7.03 (d, 1H).

Example 202

6-{2-{Ethyl[3-fluoro-4-(2-piperidin-1-ylethoxy)benzyl]amino}-4-methoxyphenyl}-5,6,7,8-tetrahydronaphthalen-2-ol

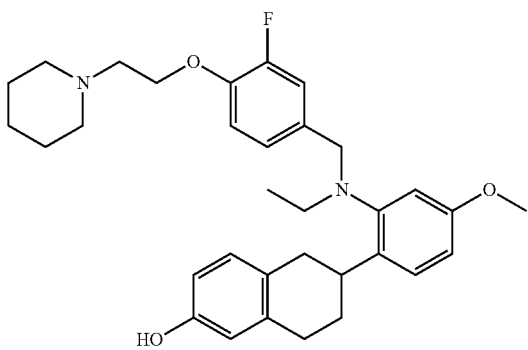 [SMILES: CCN(Cc1ccc(OCCN2CCCCC2)c(F)c1)c1cc(OC)ccc1C1CCc2cc(O)ccc2C1]

Synthesized from 2-[6-(tert-butyldimethylsilyloxy)-1,2,3,4-tetrahydronaphthalen-2-yl]-5-methoxyphenylamine and 3-fluoro-4-(2-piperidin-1-ylethoxy)benzoyl chloride hydrochloride according to an analogous synthetic method to Example 152, {2-[6-(tert-butyldimethylsilyloxy)-1,2,3,4-tetrahydronaphthalen-2-yl]-5-methoxyphenyl}[3-fluoro-4-(2-piperidin-1-ylethoxy)benzyl]amine (480 mg) was used according to an analogous synthetic method to Example 36 to provide {2-[6-(tert-butyldimethylsilyloxy)-1,2,3,4-tetrahydronaphthalen-2-yl]-5-methoxyphenyl}ethyl[3-fluoro-4-(2-piperidin-1-ylethoxy)benzyl]amine (405 mg). This compound (403 mg) was used according to an analogous synthetic method to Example 325 described below to provide the title compound (293 mg).

$^1$H-NMR (400 MHz, DMSO-d$_6$); δ (ppm): 0.87 (t, 3H), 1.30-1.38 (m, 2H), 1.40-1.50 (m, 4H), 1.50-1.58 (m, 1H), 1.62-1.74 (m, 1H), 2.34-2.43 (m, 4H), 2.50-2.62 (m, 4H), 2.69-2.77 (m, 2H), 2.86 (q, 2H), 3.42-3.52 (m, 1H), 3.69 (s, 3H), 3.94 (dd, 2H), 4.04 (t, 2H), 6.46-6.51 (m, 2H), 6.65 (dd, 1H), 6.75-6.80 (m, 2H), 6.91 (d, 1H), 6.97 (dd, 1H), 7.01 (t, 1H), 7.13 (d, 1H), 9.01 (s, 1H).

ESI-Mass; 533 [M$^+$+H]

Example 203

6-{2-{[4-(2-Azepan-1-ylethoxy)benzyl]ethylamino}-4-methoxyphenyl}-5,6,7,8-tetrahydronaphthalen-2-ol

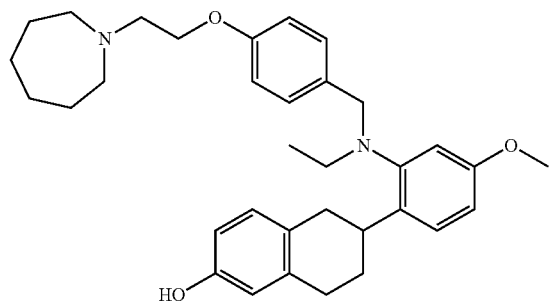 [SMILES: CCN(Cc1ccc(OCCN2CCCCCC2)cc1)c1cc(OC)ccc1C1CCc2cc(O)ccc2C1]

Synthesized from 2-[6-(tert-butyldimethylsilyloxy)-1,2,3,4-tetrahydronaphthalen-2-yl]-5-methoxyphenylamine and 4-(2-azepan-1-ylethoxy)benzoyl chloride hydrochloride according to an analogous synthetic method to Example 152, [4-(2-azepan-1-ylethoxy)benzyl]{2-[6-(tert-butyldimethylsilyloxy)-1,2,3,4-tetrahydronaphthalen-2-yl]-5-methoxyphenyl}amine (448 mg) was used according to an analogous synthetic method to Example 36 to provide [4-(2-azepan-1-ylethoxy)benzyl]{2-[6-(tert-butyldimethylsilyloxy)-1,2,3,4-tetrahydronaphthalen-2-yl]-5-methoxyphenyl}ethylamine (392 mg). This compound (390 mg) was used according to an analogous synthetic method to Example 325 described below to provide the title compound (254 mg).

$^1$H-NMR (400 MHz, DMSO-d$_6$); δ (ppm): 0.85 (t, 3H), 1.46-1.59 (m, 9H), 1.60-1.72 (m, 1H), 2.44-2.60 (m, 2H), 2.61-2.66 (m, 4H), 2.66-2.78 (m, 2H), 2.78 (t, 2H), 2.85 (q, 2H), 3.44-3.54 (m, 1H), 3.69 (s, 3H), 3.92 (dd, 2H), 3.94 (t, 2H), 6.46-6.51 (m, 2H), 6.65 (dd, 1H), 6.74-6.81 (m, 4H), 7.07 (d, 2H), 7.12 (d, 1H), 9.00 (s, 1H).

ESI-Mass; 529 [M$^+$+H]

Example 204

{2-[6-(tert-Butyldimethylsilyloxy)-1,2,3,4-tetrahydronaphthalen-2-yl]-5-methoxyphenyl}ethylamine

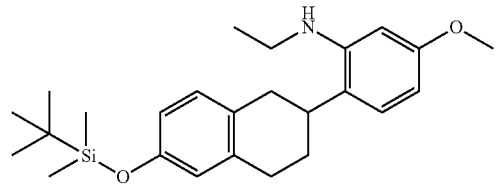 [SMILES: CCNc1cc(OC)ccc1C1CCc2cc(O[Si](C)(C)C(C)(C)C)ccc2C1]

Synthesized from 2-[6-(tert-butyldimethylsilyloxy)-1,2,3,4-tetrahydronaphthalen-2-yl]-5-methoxyphenylamine (663 mg) according to an analogous synthetic method to Example 36, the title compound (490 mg) was obtained.

$^1$H-NMR (400 MHz, CDCl$_3$); δ (ppm): 0.19 (s, 6H), 0.99 (s, 9H), 1.27 (t, 3H), 1.87-1.98 (m, 1H), 2.02-2.10 (m, 1H), 2.67-3.00 (m, 5H), 3.17 (q, 2H), 3.63 (brs, 1H), 3.78 (s, 3H), 6.24 (d, 1H), 6.27 (dd, 1H), 6.59-6.62 (m, 2H), 6.92 (d, 1H), 7.02 (d, 1H).

Example 205

6-{2-[(4-Azepan-1-ylmethylbenzyl)ethylamino]-4-methoxyphenyl}-5,6,7,8-tetrahydronaphthalen-2-ol

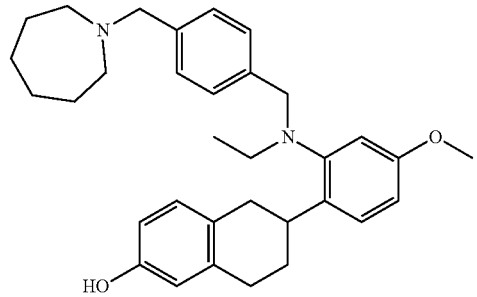 [SMILES: CCN(Cc1ccc(CN2CCCCCC2)cc1)c1cc(OC)ccc1C1CCc2cc(O)ccc2C1]

Synthesized from {2-[6-(tert-butyldimethylsilyloxy)-1,2,3,4-tetrahydronaphthalen-2-yl]-5-methoxyphenyl}ethylamine and 4-azepan-1-ylmethylbenzoic acid hydrochloride according to an analogous synthetic method to Example 152, (4-azepan-1-ylmethylbenzyl){2-[6-(tert-butyldimethylsilyloxy)-1,2,3,4-tetrahydronaphthalen-2-yl]-5-methoxyphenyl}ethylamine (67 mg) was used according to an analogous synthetic method to Example 325 described below to provide the title compound (48 mg).

¹H-NMR (400 MHz, DMSO-d₆); δ (ppm): 0.88 (t, 3H), 1.48-1.55 (m, 9H), 1.58-1.71 (m, 1H), 2.45-2.57 (m, 6H), 2.69-2.74 (m, 2H), 2.87 (q, 2H), 3.46-3.54 (m, 3H), 3.70 (s, 3H), 3.97 (dd, 2H), 6.46-6.50 (m, 2H), 6.65 (dd, 1H), 6.76-6.80 (m, 2H), 7.09-7.15 (m, 5H), 8.98 (s, 1H).

ESI-Mass; 499 [M⁺+H]

Example 206

6-{2-{[4-(2-Azepan-1-ylethyl)benzyl]ethylamino}-4-methoxyphenyl}-5,6,7,8-tetrahydronaphthalen-2-ol

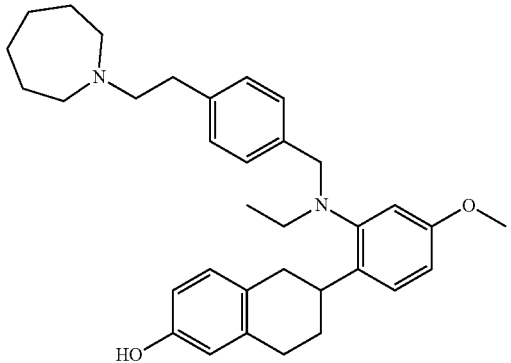 [SMILES: CCN(Cc1ccc(CCN2CCCCCC2)cc1)c1cc(OC)ccc1C1CCc2cc(O)ccc2C1]

Synthesized from {2-[6-(tert-butyldimethylsilyloxy)-1,2,3,4-tetrahydronaphthalen-2-yl]-5-methoxyphenyl}ethylamine and 4-(2-azepan-1-ylethyl)benzoic acid hydrochloride according to an analogous synthetic method to Example 152, 4-(2-azepan-1-ylethyl)benzyl]{2-[6-(tert-butyldimethylsilyloxy)-1,2,3,4-tetrahydronaphthalen-2-yl]-5-methoxyphenyl}ethylamine (59 mg) was used according to an analogous synthetic method to Example 325 described below to provide the title compound (38 mg).

¹H-NMR (400 MHz, DMSO-d₆); δ (ppm): 0.87 (t, 3H), 1.46-1.58 (m, 9H), 1.61-1.72 (m, 1H), 2.52-2.62 (m, 10H), 2.68-2.76 (m, 2H), 2.86 (q, 2H), 3.44-3.54 (m, 1H), 3.69 (s, 3H), 3.95 (dd, 2H), 6.46-6.50 (m, 2H), 6.64 (dd, 1H), 6.76-6.80 (m, 2H), 7.04 (d, 2H), 7.08 (d, 2H), 7.12 (d, 1H), 8.98 (s, 1H).

ESI-Mass; 513 [M⁺+H]

Example 207

6-{2-{[4-(3-Azepan-1-ylpropyl)benzyl]ethylamino}-4-methoxyphenyl}-5,6,7,8-tetrahydronaphthalen-2-ol

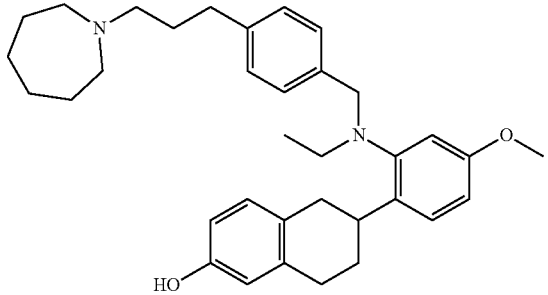 [SMILES: CCN(Cc1ccc(CCCN2CCCCCC2)cc1)c1cc(OC)ccc1C1CCc2cc(O)ccc2C1]

Synthesized from {2-[6-(tert-butyldimethylsilyloxy)-1,2,3,4-tetrahydronaphthalen-2-yl]-5-methoxyphenyl}ethylamine and 4-(3-azepan-1-ylpropyl)benzoic acid hydrochloride according to an analogous synthetic method to Example 152, [4-(3-azepan-1-ylpropyl)benzyl]{2-[6-(tert-butyldimethylsilyloxy)-1,2,3,4-tetrahydronaphthalen-2-yl]-5-methoxyphenyl}ethylamine (60 mg) was used according to an analogous synthetic method to Example 325 described below to provide the title compound (37 mg).

¹H-NMR (400 MHz, DMSO-d₆); δ (ppm): 0.87 (t, 3H), 1.46-1.72 (m, 12H), 2.31-2.39 (m, 2H), 2.40-2.61 (m, 8H), 2.67-2.76 (m, 2H), 2.87 (q, 2H), 3.45-3.54 (m, 1H), 3.70 (s, 3H), 3.95 (dd, 2H), 6.46-6.51 (m, 2H), 6.64 (dd, 1H), 6.76-6.81 (m, 2H), 7.02 (d, 2H), 7.07 (d, 2H), 7.11 (d, 1H), 8.98 (s, 1H).

ESI-Mass; 527 [M⁺+H]

Example 208

6-{2-{Ethyl[4-(1-methylpiperidin-4-yl)benzyl]amino}-4-methoxyphenyl}-5,6,7,8-tetrahydronaphthalen-2-ol

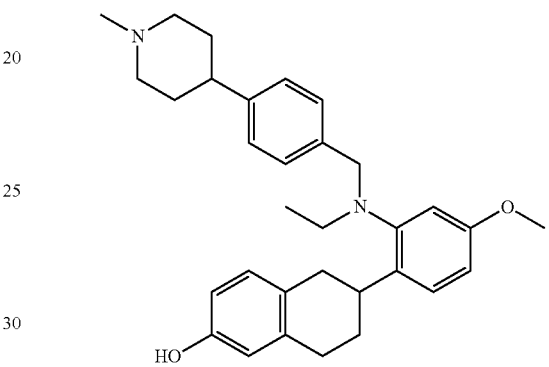

Synthesized from pivalic acid 6-(2-ethylamino-4-methoxyphenyl)-5,6,7,8-tetrahydronaphthalen-2-yl ester (100 mg) and 4-(4-carboxyphenyl)piperidine-1-carboxylic acid tert-butyl ester (120 mg) according to an analogous synthetic method to Example 337 described below, the title compound (37 mg) was obtained.

¹H-NMR (400 MHz, DMSO-d₆); δ (ppm): 0.86 (t, 3H), 1.45-1.70 (m, 6H), 1.84-1.95 (m, 2H), 2.16 (s, 3H), 2.30-2.40 (m, 1H), 2.52-2.59 (m, 2H), 2.66-2.76 (m, 2H), 2.80-2.89 (m, 4H), 3.45-3.54 (m, 1H), 3.70 (s, 3H), 3.95 (dd, 2H), 6.46-6.51 (m, 2H), 6.65 (dd, 1H), 6.76-6.81 (m, 2H), 7.05-7.13 (m, 5H), 8.98 (s, 1H).

ESI-Mass; 485 [M⁺+H]

Example 209

6-{2-[Ethyl(4-piperidin-4-ylbenzyl)amino]-4-methoxyphenyl}-5,6,7,8-tetrahydronaphthalen-2-ol

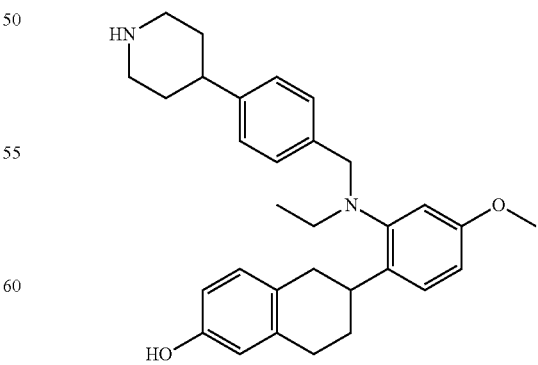

To a solution of 4-(4-carboxyphenyl)piperidine-1-carboxylic acid tert-butyl ester (120 mg) in tetrahydrofuran (3 ml) were sequentially added N,N-dimethylformamide (in catalytic amounts) and oxalyl chloride (0.04 ml), the solution was stirred for 3 hours at room temperature, then the solvent was evaporated in vacuo. To a solution of the resulting 4-(4-chlorocarbonylphenyl)piperidine-1-carboxylic acid tert-butyl ester (120 mg) in 1,4-dioxane (3 ml) were sequentially added pivalic acid 6-(2-ethylamino-4-methoxyphenyl)-5,6,7,8-tetrahydronaphthalen-2-yl ester (100 mg) and N,N-diisopropylethylamine (0.15 ml), and the solution was stirred for 10 minutes at 80° C. Water was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide 4-{4-{{2-[6-(2,2-dimethylpropionyloxy)-1,2,3,4-tetrahydronaphthalen-2-yl]-5-methoxyphenyl}ethylcarbamoyl}phenyl}piperidine-1-carboxylic acid tert-butyl ester (172 mg). To a solution of this compound (90 mg) in dichloromethane (1 ml) was added trifluoroacetic acid (0.1 ml), and the solution was stirred for 2 hours at room temperature. Tetrahydrofuran and aqueous ammonia were sequentially added thereto, the solution was extracted with ethyl acetate, then sequentially washed with water and brine, dried over anhydrous magnesium sulfate, then the solvent was evaporated in vacuo. Synthesized from the resulting pivalic acid 6-{2-[ethyl-(4-piperidin-4-ylbenzoyl)amino]-4-methoxyphenyl}-5,6,7,8-tetrahydronaphthalen-2-yl ester (77 mg) according to an analogous synthetic method to Example 337 described below, the title compound (35 mg) was obtained.

¹H-NMR (400 MHz, DMSO-d₆); δ (ppm): 0.87 (t, 3H), 1.38-1.53 (m, 3H), 1.56-1.72 (m, 3H), 2.42-2.58 (m, 5H), 2.68-2.75 (m, 2H), 2.86 (q, 2H), 2.92-2.98 (m, 2H), 3.45-3.54 (m, 1H), 3.70 (s, 3H), 3.95 (dd, 2H), 6.46-6.51 (m, 2H), 6.65 (dd, 1H), 6.76-6.81 (m, 2H), 7.04-7.13 (m, 5H), 8.99 (s, 1H).

ESI-Mass; 471 [M⁺+H]

Example 210

6-{2-{Ethyl[3-(1-methylpiperidin-4-yl)benzyl]amino}-4-methoxyphenyl}-5,6,7,8-tetrahydronaphthalen-2-ol

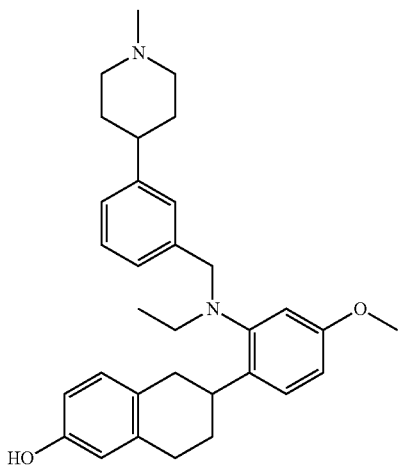 [SMILES: CCN(Cc1cccc(C2CCN(C)CC2)c1)c1cc(OC)ccc1C1CCc2cc(O)ccc2C1]

Synthesized from pivalic acid 6-(2-ethylamino-4-methoxyphenyl)-5,6,7,8-tetrahydronaphthalen-2-yl ester (80 mg) and 4-(3-carboxyphenyl)piperidine-1-carboxylic acid tert-butyl ester (100 mg) according to an analogous synthetic method to Example 337 described below, the title compound (39 mg) was obtained.

¹H-NMR (400 MHz, DMSO-d₆); δ (ppm): 0.89 (t, 3H), 1.22-1.58 (m, 4H), 1.60-1.78 (m, 2H), 1.81-1.89 (m, 2H), 2.16 (s, 3H), 2.21-2.29 (m, 1H), 2.56-2.61 (m, 2H), 2.70-2.80 (m, 4H), 2.87 (q, 2H), 3.48-3.58 (m, 1H), 3.69 (s, 3H), 3.97 (s, 2H), 6.45-6.50 (m, 2H), 6.65 (dd, 1H), 6.76 (d, 1H), 6.79 (d, 1H), 7.00-7.16 (m, 5H), 8.97 (s, 1H).

ESI-Mass; 485 [M⁺+H]

Example 211

6-{2-[Ethyl(3-piperidin-4-ylbenzyl)amino]-4-methoxyphenyl}-5,6,7,8-tetrahydronaphthalen-2-ol

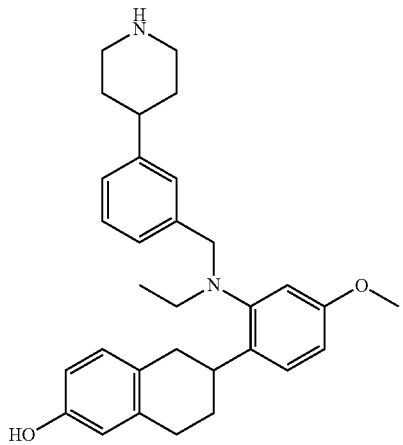 [SMILES: CCN(Cc1cccc(C2CCNCC2)c1)c1cc(OC)ccc1C1CCc2cc(O)ccc2C1]

Synthesized from pivalic acid 6-(2-ethylamino-4-methoxyphenyl)-5,6,7,8-tetrahydronaphthalen-2-yl ester (80 mg) and 4-(3-carboxyphenyl)piperidine-1-carboxylic acid tert-butyl ester (100 mg) according to an analogous synthetic method to Example 209, the title compound (25 mg) was obtained.

¹H-NMR (400 MHz, DMSO-d₆); δ (ppm): 0.89 (t, 3H), 1.22-1.36 (m, 2H), 1.45-1.55 (m, 2H), 1.61-1.78 (m, 2H), 2.31-2.48 (m, 3H), 2.55-2.61 (m, 2H), 2.71-2.79 (m, 2H), 2.82-2.94 (m, 4H), 3.51-3.59 (m, 1H), 3.70 (s, 3H), 3.97 (s, 2H), 6.46-6.50 (m, 2H), 6.65 (dd, 1H), 6.76 (d, 1H), 6.79 (d, 1H), 6.98-7.16 (m, 5H), 8.99 (brs, 1H).

ESI-Mass; 471 [M⁺+H]

Example 212

Pivalic Acid 6-{2-{ethyl[4-(8-methyl-8-azabicyclo[3.2.1]oct-3-yloxy)benzyl]amino}-4-methoxyphenyl}-5,6,7,8-tetrahydronaphthalen-2-yl Ester

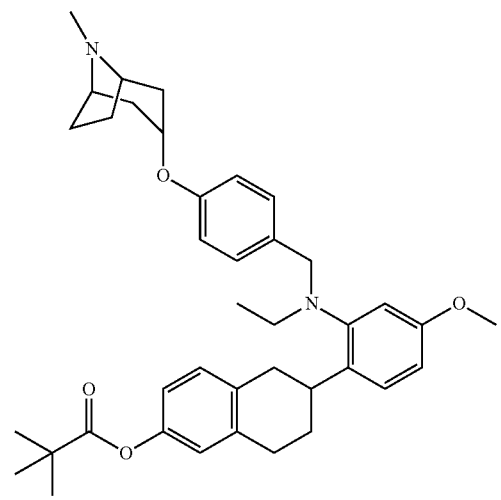 [SMILES: CCN(Cc1ccc(OC2CC3CCC(C2)N3C)cc1)c1cc(OC)ccc1C1CCc2cc(OC(=O)C(C)(C)C)ccc2C1]

To a solution of pivalic acid 6-(2-ethylamino-4-methoxyphenyl)-5,6,7,8-tetrahydronaphthalen-2-yl ester (65 mg) and 4-(8-methyl-8-azabicyclo[3.2.1]oct-3-yloxy)benzaldehyde (65 mg) in 1,2-dichloroethane (2 ml) were sequentially added acetic acid (0.07 ml) and sodium triacetoxyborohydride (120 mg) under a nitrogen atmosphere, and the solution was stirred overnight at room temperature. Tetrahydrofuran and aqueous ammonia were sequentially added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (58 mg).

$^1$H-NMR (400 MHz, CDCl$_3$); δ (ppm): 0.92 (t, 3H), 1.36 (s, 9H), 1.64-1.82 (m, 2H), 1.89-2.12 (m, 8H), 2.29 (s, 3H), 2.71-2.76 (m, 2H), 2.81-2.96 (m, 4H), 3.07-3.12 (m, 2H), 3.64-3.73 (m, 1H), 3.79 (s, 3H), 3.92 (s, 2H), 4.46 (t, 1H), 6.68 (d, 2H), 6.69 (dd, 1H), 6.75-6.81 (m, 3H), 7.01 (d, 1H), 7.09 (d, 2H), 7.12 (d, 1H).

ESI-Mass; 611 [M$^+$+H]

Example 213

6-{2-{Ethyl[4-(8-methyl-8-azabicyclo[3.2.1]oct-3-yloxy)benzyl]amino}-4-methoxyphenyl}-5,6,7,8-tetrahydronaphthalen-2-ol

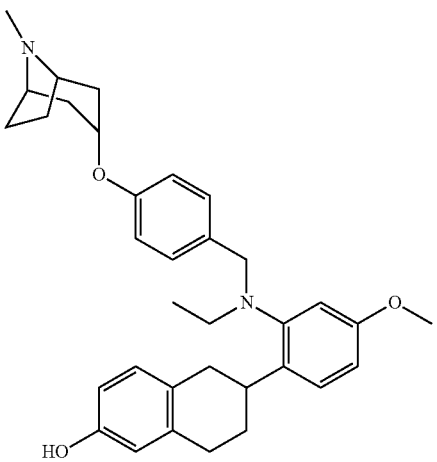 [SMILES: CCN(Cc1ccc(OC2CC3CCC(C2)N3C)cc1)c1cc(OC)ccc1C1CCc2cc(O)ccc2C1]

To a solution of pivalic acid 6-{2-{ethyl[4-(8-methyl-8-azabicyclo[3.2.1]oct-3-yloxy)benzyl]amino}-4-methoxyphenyl}-5,6,7,8-tetrahydronaphthalen-2-yl ester (19 mg) in ethanol (1 ml) was added an aqueous solution of 1N sodium hydroxide (0.2 ml), and the solution was stirred for 1.5 hours at 60° C. The solution was neutralized with 1N hydrochloric acid, extracted with ethyl acetate, then sequentially washed with water and brine, dried over anhydrous magnesium sulfate, and then the solvent was evaporated in vacuo. The residue was purified by NH silica gel column chromatography (ethyl acetate-methanol system) to provide the title compound (12 mg).

As another method, synthesized from pivalic acid 6-{2-{ethyl[4-(8-methyl-8-azabicyclo[3.2.1]oct-3-yloxy)benzyl]amino}-4-methoxyphenyl}-5,6,7,8-tetrahydronaphthalen-2-yl ester (56 mg) according to an analogous synthetic method to Example 337 described below, the title compound (43 mg) was obtained.

$^1$H-NMR (400 MHz, DMSO-d$_6$); δ (ppm): 0.86 (t, 3H), 1.47-1.55 (m, 1H), 1.60-1.72 (m, 3H), 1.84-1.98 (m, 6H), 2.14 (s, 3H), 2.46-2.60 (m, 2H), 2.67-2.74 (m, 2H), 2.87 (q, 2H), 2.94-3.01 (m, 2H), 3.43-3.52 (m, 1H), 3.70 (s, 3H), 3.90 (dd, 2H), 4.46 (t, 1H), 6.46-6.51 (m, 2H), 6.65 (dd, 1H), 6.68 (d, 2H), 6.75-6.80 (m, 2H), 7.05 (d, 2H), 7.12 (d, 1H), 8.98 (s, 1H).

ESI-Mass; 527 [M$^+$+H]

Example 214

Pivalic Acid 6-{2-{[4-(2-tert-butoxycarbonylamino-2-methylpropoxy)benzyl]ethylamino}-4-methoxyphenyl}-5,6,7,8-tetrahydronaphthalen-2-yl ester

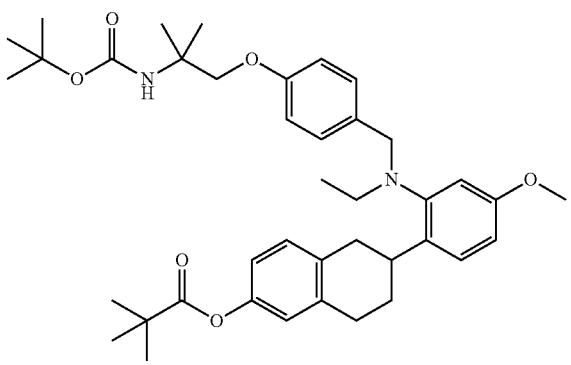 [SMILES: CCN(Cc1ccc(OCC(C)(C)NC(=O)OC(C)(C)C)cc1)c1cc(OC)ccc1C1CCc2cc(OC(=O)C(C)(C)C)ccc2C1]

Synthesized from pivalic acid 6-(2-ethylamino-4-methoxyphenyl)-5,6,7,8-tetrahydronaphthalen-2-yl ester (58 mg) and tert-butyl[2-(4-formylphenoxy)-1,1-dimethylethyl]carbamate (222 mg) according to an analogous synthetic method to Example 212, the title compound (92 mg) was obtained.

$^1$H-NMR (400 MHz, CDCl$_3$); δ (ppm): 0.92 (t, 3H), 1.36 (s, 9H), 1.39 (s, 6H), 1.41 (s, 9H), 1.73-1.79 (m, 2H), 2.70-2.75 (m, 2H), 2.85-2.95 (m, 4H), 3.64-3.73 (m, 1H), 3.79 (s, 3H), 3.87 (s, 2H), 3.94 (s, 2H), 4.75 (s, 1H), 6.68 (dd, 1H), 6.75-6.82 (m, 5H), 7.01 (d, 1H), 7.11 (d, 2H), 7.12 (d, 1H).

Example 215

Pivalic Acid 6-{2-{[4-(2-amino-2-methylpropoxy)benzyl]ethylamino}-4-methoxyphenyl}-5,6,7,8-tetrahydronaphthalen-2-yl Ester

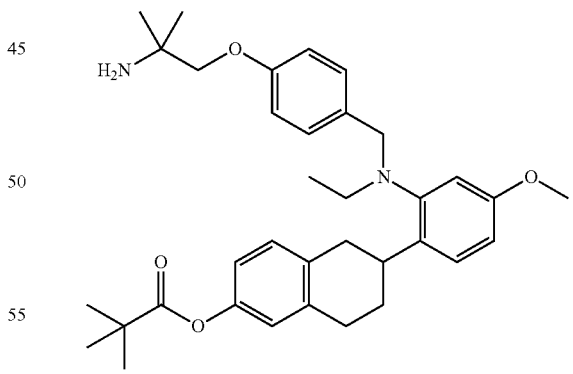

To a solution of pivalic acid 6-{2-{[4-(2-tert-butoxycarbonylamino-2-methylpropoxy)benzyl]ethylamino}-4-methoxyphenyl}-5,6,7,8-tetrahydronaphthalen-2-yl ester (90 mg) in dichloromethane (1.5 ml) was added trifluoroacetic acid (0.2 ml), and the solution was stirred for 1.5 hours at room temperature. The solution was neutralized by sequentially adding tetrahydrofuran and aqueous ammonia, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (72 mg).

$^1$H-NMR (400 MHz, CDCl$_3$); δ (ppm): 0.93 (t, 3H), 1.21 (s, 6H), 1.36 (s, 9H), 1.74-1.82 (m, 2H), 2.75-2.78 (m, 2H), 2.84-2.98 (m, 4H), 3.64 (s, 2H), 3.64-3.73 (m, 1H), 3.79 (s, 3H), 3.94 (s, 2H), 6.68 (dd, 1H), 6.74-6.82 (m, 5H), 7.01 (d, 1H), 7.12 (d, 2H), 7.12 (d, 1H).

Example 216

6-{2-{[4-(2-Amino-2-methylpropoxy)benzyl]ethylamino}-4-methoxyphenyl}-5,6,7,8-tetrahydronaphthalen-2-ol

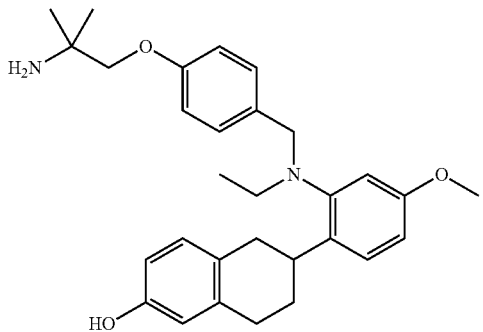

Synthesized from pivalic acid 6-{2-{[4-(2-amino-2-methylpropoxy)benzyl]ethylamino}-4-methoxyphenyl}-5,6,7,8-tetrahydronaphthalen-2-yl ester (35 mg) according to an analogous synthetic method to Example 213, the title compound (22 mg) was obtained.

$^1$H-NMR (400 MHz, DMSO-d$_6$); δ (ppm): 0.87 (t, 3H), 1.06 (s, 6H), 1.54-1.74 (m, 2H), 2.48-2.62 (m, 2H), 2.71-2.78 (m, 2H), 2.86 (q, 2H), 3.45-3.56 (m, 1H), 3.56 (s, 2H), 3.70 (s, 3H), 3.93 (s, 2H), 6.46-6.51 (m, 2H), 6.64 (dd, 1H), 6.75-6.81 (m, 4H), 7.08 (d, 2H), 7.13 (d, 1H), 8.99 (s, 1H).

ESI-Mass; 475 [M$^+$+H]

Example 217

6-{2-{[4-(2-Dimethylamino-2-methylpropoxy)benzyl]ethylamino}-4-methoxyphenyl}-5,6,7,8-tetrahydronaphthalen-2-ol

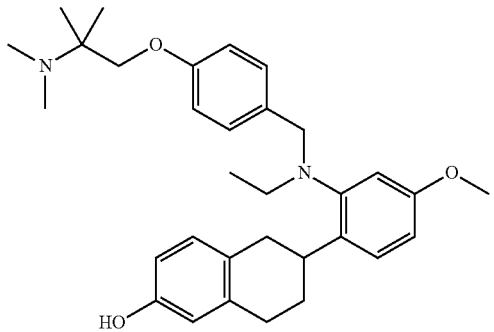

Synthesized from pivalic acid 6-(2-ethylamino-4-methoxyphenyl)-5,6,7,8-tetrahydronaphthalen-2-yl ester and 4-(2-dimethylamino-2-methylpropoxy)benzaldehyde according to an analogous synthetic method to Example 212, to a solution of the resulting pivalic acid 6-{2-{[4-(2-dimethylamino-2-methylpropoxy)benzyl]ethylamino}-4-methoxyphenyl}-5,6,7,8-tetrahydronaphthalen-2-yl ester (73 mg) in tetrahydrofuran (1.5 ml) was added lithium aluminum hydride (20 mg), and the solution was stirred for 1.5 hours at room temperature. Tetrahydrofuran and aqueous ammonia were sequentially added thereto followed by stirring. The solution was then filtered through celite pad, the resulting residue was purified by NH silica gel column chromatography (ethyl acetate-methanol system) to provide the title compound (45 mg).

$^1$H-NMR (400 MHz, DMSO-d$_6$); δ (ppm): 0.87 (t, 3H), 1.05 (s, 6H), 1.53-1.61 (m, 1H), 1.62-1.74 (m, 1H), 2.20 (s, 6H), 2.45-2.61 (m, 2H), 2.71-2.78 (m, 2H), 2.87 (q, 2H), 3.44-3.55 (m, 1H), 3.70 (s, 3H), 3.73 (s, 2H), 3.92 (s, 2H), 6.46-6.51 (m, 2H), 6.64 (dd, 1H), 6.74-6.81 (m, 4H), 7.07 (d, 2H), 7.12 (d, 1H), 8.98 (s, 1H).

ESI-Mass; 503 [M$^+$+H]

Example 218

6-{2-{Ethyl[4-(1-methylpiperidin-4-yloxy)benzyl]amino}-4-methoxyphenyl}-5,6,7,8-tetrahydronaphthalen-2-ol

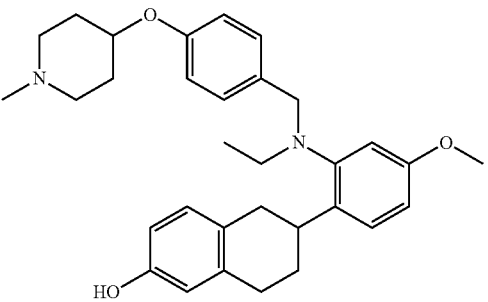

Synthesized from pivalic acid 6-(2-ethylamino-4-methoxyphenyl)-5,6,7,8-tetrahydronaphthalen-2-yl ester and 4-(1-methylpiperidin-4-yloxy)benzaldehyde according to an analogous synthetic method to Example 212, pivalic acid 6-{2-{ethyl[4-(1-methylpiperidin-4-yloxy)benzyl]amino}-4-methoxyphenyl}-5,6,7,8-tetrahydronaphthalen-2-yl ester (70 mg) was used according to an analogous synthetic method to Example 217 to provide the title compound (37 mg).

$^1$H-NMR (400 MHz, DMSO-d$_6$); δ (ppm): 0.86 (t, 3H), 1.50-1.72 (m, 4H), 1.82-1.90 (m, 2H), 2.07-2.16 (m, 5H), 2.46-2.61 (m, 4H), 2.68-2.75 (m, 2H), 2.86 (q, 2H), 3.43-3.53 (m, 1H), 3.70 (s, 3H), 3.91 (dd, 2H), 4.22-4.31 (m, 1H), 6.46-6.50 (m, 2H), 6.65 (dd, 1H), 6.74-6.80 (m, 4H), 7.05 (d, 2H), 7.12 (d, 1H), 8.98 (s, 1H).

ESI-Mass; 502 [M$^+$+H]

Example 219

6-{2-{[4-(1-Azabicyclo[2.2.2]oct-4-ylmethoxy)benzyl]ethylamino}-4-methoxyphenyl}-5,6,7,8-tetrahydronaphthalen-2-ol

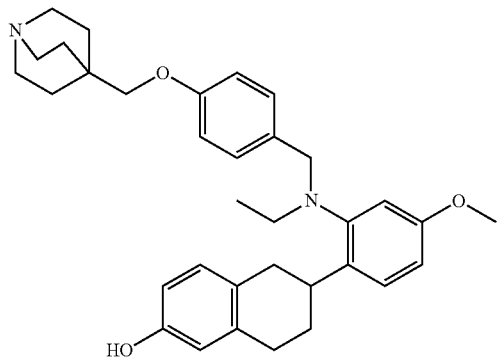 [SMILES: CCN(Cc1ccc(OCC23CCN(CC2)CC3)cc1)c1cc(OC)ccc1C1CCc2cc(O)ccc2C1]

Synthesized from pivalic acid 6-(2-ethylamino-4-methoxyphenyl)-5,6,7,8-tetrahydronaphthalen-2-yl ester and 4-(1-azabicyclo[2.2.2]oct-4-ylmethoxy)benzaldehyde according to an analogous synthetic method to Example 212, pivalic acid 6-{2-{[4-(1-azabicyclo[2.2.2]oct-4-ylmethoxy)benzyl]

ethylamino}-4-methoxyphenyl}-5,6,7,8-tetrahydronaphthalen-2-yl ester (30 mg) was used according to an analogous synthetic method to Example 217 to provide the title compound (18 mg).

$^1$H-NMR (400 MHz, DMSO-d$_6$); δ (ppm): 0.87 (t, 3H), 1.40 (t, 6H), 1.57-1.74 (m, 2H), 2.44-2.60 (m, 2H), 2.70-2.78 (m, 8H), 2.85 (q, 2H), 3.44-3.54 (m, 1H), 3.52 (s, 2H), 3.69 (s, 3H), 3.92 (s, 2H), 6.46-6.50 (m, 2H), 6.64 (dd, 1H), 6.72-6.80 (m, 4H), 7.06 (d, 2H), 7.12 (d, 1H), 8.98 (s, 1H).

ESI-Mass; 527 [M$^+$+H]

Example 220

6-{2-{[5-(2-Azepan-1-ylethyl)pyridin-2-ylmethyl]ethylamino}-4-methoxyphenyl}-5,6,7,8-tetrahydronaphthalen-2-ol

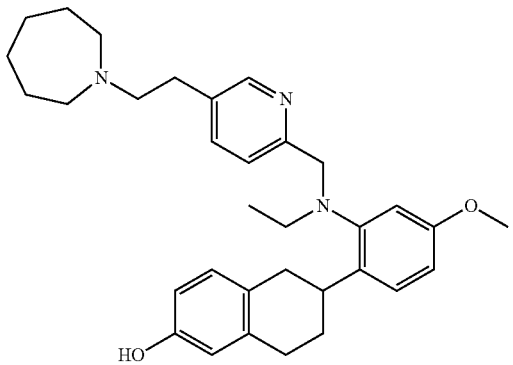

Synthesized from 1-[2-(6-bromopyridin-3-yl)ethyl]azepane (400 mg) according to an analogous synthetic method to Preparation Example 51, to the total amount of lithium 5-(2-azepan-1-ylethyl)pyridine-2-carboxylate crude product was added thionyl chloride (8 ml), the solution was stirred for 30 minutes at 90° C., then the reaction solution was concentrated in vacuo to provide 5-(2-azepan-1-ylethyl)pyridine-2-carbonyl chloride hydrochloride (640 mg). Synthesized from this compound (320 mg) and pivalic acid 6-(2-ethylamino-4-methoxyphenyl)-5,6,7,8-tetrahydronaphthalen-2-yl ester (40 mg) according to an analogous synthetic method to Example 152, the title compound (7 mg) was obtained.

$^1$H-NMR (400 MHz, DMSO-d$_6$); δ (ppm): 0.90 (t, 3H), 1.45-1.76 (m, 10H), 2.55-2.78 (m, 12H), 2.92 (q, 2H), 3.46-3.55 (m, 1H), 3.69 (s, 3H), 4.09 (dd, 2H), 6.46-6.51 (m, 2H), 6.65 (dd, 1H), 6.77 (d, 1H), 6.80 (d, 1H), 7.15 (d, 2H), 7.50 (dd, 1H), 8.28 (d, 1H), 8.99 (s, 1H).

ESI-Mass; 514 [M$^+$+H]

Example 221

6-{2-{[5-(2-Azepan-1-ylethoxy)pyridin-2-ylmethyl]ethylamino}-4-methoxyphenyl}-5,6,7,8-tetrahydronaphthalen-2-ol

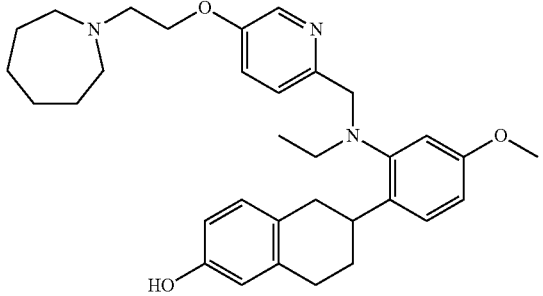 [SMILES: CCN(Cc1ccc(OCCN2CCCCCC2)cn1)c1cc(OC)ccc1C1CCc2cc(O)ccc2C1]

Synthesized from pivalic acid 6-(2-ethylamino-4-methoxyphenyl)-5,6,7,8-tetrahydronaphthalen-2-yl ester (40 mg) and sodium 5-(2-azepan-1-ylethoxy)pyridine-2-carboxylate (120 mg) according to an analogous synthetic method to Example 152, the title compound (28 mg) was obtained.

$^1$H-NMR (400 MHz, DMSO-d$_6$); δ (ppm): 0.90 (t, 3H), 1.48-1.77 (m, 10H), 2.48-2.68 (m, 6H), 2.69-2.79 (m, 2H), 2.81 (t, 2H), 2.92 (q, 2H), 3.44-3.54 (m, 1H), 3.70 (s, 3H), 4.04 (t, 2H), 4.06 (s, 2H), 6.46-6.52 (m, 2H), 6.65 (dd, 1H), 6.76 (d, 1H), 6.80 (d, 1H), 7.13 (d, 1H), 7.15 (d, 1H), 7.26 (d, 1H), 8.11 (d, 1H), 8.99 (s, 1H).

ESI-Mass; 530 [M$^+$+H]

Example 222

6-{2-{[6-(2-Azepan-1-ylethoxy)pyridin-3-ylmethyl]ethylamino}-4-methoxyphenyl}-5,6,7,8-tetrahydronaphthalen-2-ol

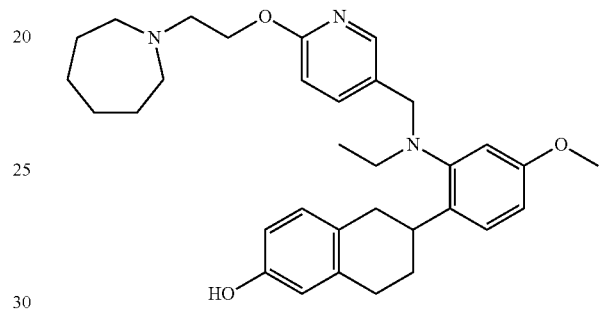

Synthesized from pivalic acid 6-(2-ethylamino-4-methoxyphenyl)-5,6,7,8-tetrahydronaphthalen-2-yl ester (40 mg) and 6-(2-azepan-1-ylethoxy)nicotinic acid hydrochloride (120 mg) according to an analogous synthetic method to Example 337 described below, the title compound (23 mg) was obtained.

$^1$H-NMR (400 MHz, DMSO-d$_6$); δ (ppm): 0.89 (t, 3H), 1.42-1.58 (m, 9H), 1.60-1.72 (m, 1H), 2.39-2.47 (m, 1H), 2.50-2.61 (m, 1H), 2.62-2.68 (m, 4H), 2.69-2.77 (m, 2H), 2.78 (t, 2H), 2.90 (q, 2H), 3.39-3.49 (m, 1H), 3.72 (s, 3H), 3.96 (dd, 2H), 4.25 (t, 2H), 6.47-6.52 (m, 2H), 6.65 (d, 1H), 6.68 (dd, 1H), 6.79 (d, 1H), 6.82 (d, 1H), 7.13 (d, 1H), 7.43 (dd, 1H), 7.88 (d, 1H), 9.00 (s, 1H).

ESI-Mass; 530 [M$^+$+H]

Example 223

6-{2-{[5-(2-Azepan-1-ylethyl)thiophen-2-ylmethyl]ethylamino}-4-methoxyphenyl}-5,6,7,8-tetrahydronaphthalen-2-ol

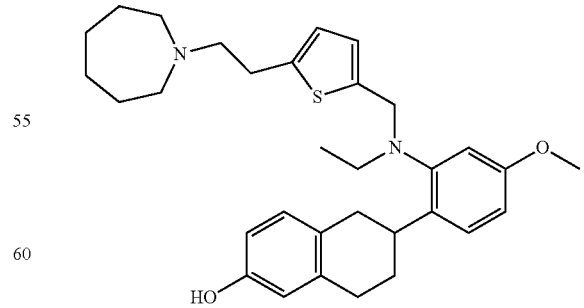

Synthesized from pivalic acid 6-(2-ethylamino-4-methoxyphenyl)-5,6,7,8-tetrahydronaphthalen-2-yl ester (40 mg) and lithium 5-(2-azepan-1-ylethyl)thiophene-2-carboxylate (110 mg) according to an analogous synthetic method to Example 152, the title compound (47 mg) was obtained.

¹H-NMR (400 MHz, DMSO-d₆); δ (ppm): 0.86 (t, 3H), 1.46-1.57 (m, 8H), 1.65-1.79 (m, 2H), 2.52-2.64 (m, 8H), 2.70-2.85 (m, 4H), 2.90 (q, 2H), 3.51-3.60 (m, 1H), 3.71 (s, 3H), 4.09 (dd, 2H), 6.46-6.50 (m, 2H), 6.58 (d, 1H), 6.63 (d, 1H), 6.68 (dd, 1H), 6.77 (d, 1H), 6.80 (d, 1H), 7.17 (d, 1H), 8.98 (s, 1H).

ESI-Mass; 519 [M⁺+H]

Example 224

6-{2-{Ethyl[3-(2-piperidin-1-ylethoxy)benzyl]amino}-4-methoxyphenyl}-5,6,7,8-tetrahydronaphthalen-2-ol

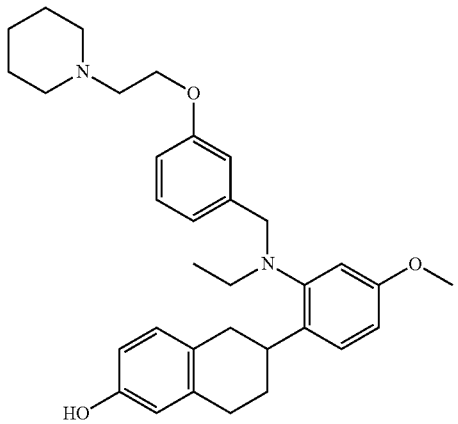 [SMILES: CCN(Cc1cccc(OCCN2CCCCC2)c1)c1cc(OC)ccc1C1CCc2cc(O)ccc2C1]

Synthesized from pivalic acid 6-(2-ethylamino-4-methoxyphenyl)-5,6,7,8-tetrahydronaphthalen-2-yl ester (60 mg) and 3-(2-piperidin-1-ylethoxy)benzoic acid hydrochloride (85 mg) according to an analogous synthetic method to Example 152, the title compound (70 mg) was obtained.

¹H-NMR (400 MHz, DMSO-d₆); δ (ppm): 0.89 (t, 3H), 1.32-1.40 (m, 2H), 1.44-1.51 (m, 4H), 1.59-1.78 (m, 2H), 2.32-2.42 (m, 4H), 2.53 (t, 2H), 2.55-2.62 (m, 2H), 2.72-2.80 (m, 2H), 2.87 (q, 2H), 3.51-3.60 (m, 1H), 3.71 (s, 3H), 3.79-3.88 (m, 2H), 3.98 (s, 2H), 6.46-6.51 (m, 2H), 6.66 (dd, 1H), 6.72 (dd, 1H), 6.76-6.82 (m, 4H), 7.11 (t, 1H), 7.15 (d, 1H), 9.00 (s, 1H).

ESI-Mass; 515 [M⁺+H]

Example 225

6-{2-{Ethyl[4-(4-methylpiperazin-1-yl)benzyl]amino}-4-methoxyphenyl}-5,6,7,8-tetrahydronaphthalen-2-ol

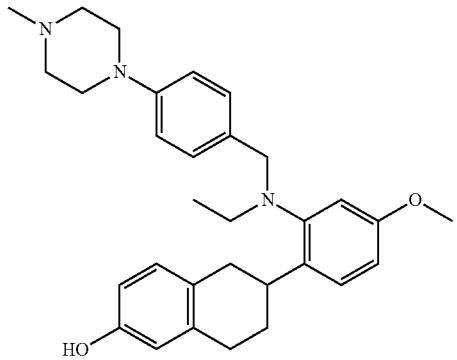

Synthesized from 6-(2-ethylamino-4-methoxyphenyl)-5,6,7,8-tetrahydronaphthalen-2-yl ester and 4-(4-methylpiperazin-1-yl)benzaldehyde according to an analogous synthetic method to Example 212, pivalic acid 6-{2-{ethyl[4-(4-methylpiperazin-1-yl)benzyl]amino}-4-methoxyphenyl}-5,6,7,8-tetrahydronaphthalen-2-yl ester (71 mg) was used according to an analogous synthetic method to Example 213 to provide the title compound (50 mg).

¹H-NMR (400 MHz, DMSO-d₆); δ (ppm): 0.86 (t, 3H), 1.54-1.74 (m, 2H), 2.19 (s, 3H), 2.41 (t, 4H), 2.50-2.62 (m, 2H), 2.71-2.78 (m, 2H), 2.85 (q, 2H), 3.05 (t, 4H), 3.46-3.56 (m, 1H), 3.70 (s, 3H), 3.89 (dd, 2H), 6.47-6.52 (m, 2H), 6.65 (dd, 1H), 6.76-6.82 (m, 4H), 7.02 (d, 2H), 7.13 (d, 1H), 9.01 (s, 1H).

ESI-Mass; 486 [M⁺+H]

Example 226

6-{2-{Ethyl[4-(2-piperidin-1-ylethoxy)naphthalen-1-ylmethyl]amino}-4-methoxyphenyl}-5,6,7,8-tetrahydronaphthalen-2-ol

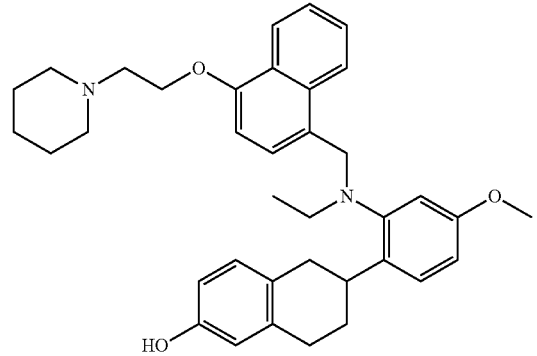 [SMILES: CCN(Cc1ccc(OCCN2CCCCC2)c2ccccc12)c1cc(OC)ccc1C1CCc2cc(O)ccc2C1]

Synthesized from pivalic acid 6-(2-ethylamino-4-methoxyphenyl)-5,6,7,8-tetrahydronaphthalen-2-yl ester (60 mg) and 4-(2-piperidin-1-ylethoxy)naphthalene-1-carboxylic acid hydrochloride (100 mg) according to an analogous synthetic method to Example 152, the title compound (78 mg) was obtained.

¹H-NMR (400 MHz, DMSO-d₆); δ (ppm): 0.93 (t, 3H), 1.32-1.55 (m, 8H), 2.18-2.34 (m, 2H), 2.40-2.58 (m, 6H), 2.78 (t, 2H), 2.94 (q, 2H), 3.22-3.32 (m, 1H), 3.75 (s, 3H), 4.17 (t, 2H), 4.34 (d, 1H), 4.46 (d, 1H), 6.36 (d, 1H), 6.44 (dd, 1H), 6.64 (dd, 1H), 6.66 (d, 1H), 6.78 (d, 1H), 6.96 (d, 1H), 7.05 (d, 1H), 7.18 (d, 1H), 7.34 (t, 1H), 7.40 (t, 1H), 8.11 (d, 1H), 8.15 (d, 1H), 8.93 (s, 1H).

ESI-Mass; 565 [M⁺+H]

Example 227

(R)-6-{2-{[5-(2-Azepan-1-ylethyl)thiophen-2-ylmethyl]ethylamino}-4-methoxyphenyl}-5,6,7,8-tetrahydronaphthalen-2-ol

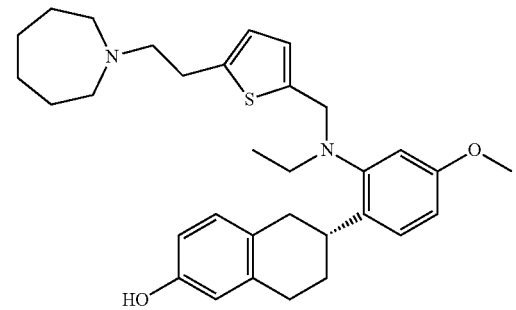 [SMILES: CCN(Cc1ccc(CCN2CCCCCC2)s1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (30 mg) and lithium 5-(2-azepan-1-ylethyl)thiophene-2-carboxylate (60 mg) according to an analogous synthetic method to Example 152 and purified by LC-MS, the title compound (29 mg) was obtained.

ESI-Mass; 519 [M⁺+H]

Example 228

(R)-6-{2-{[6-(2-Azepan-1-ylethoxy)pyridin-3-ylmethyl]ethylamino}-4-methoxyphenyl}-5,6,7,8-tetrahydronaphthalen-2-ol

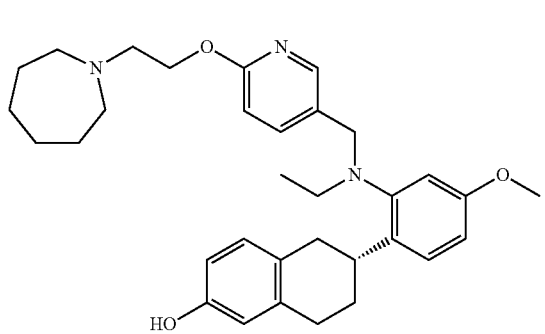 [SMILES: CCN(Cc1ccc(OCCN2CCCCCC2)nc1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (30 mg) and 6-(2-azepan-1-ylethoxy)nicotinic acid hydrochloride (60 mg) according to an analogous synthetic method to Example 337 described below and purified by LC-MS, the title compound (34 mg) was obtained.

ESI-Mass; 530 [M$^+$+H]

Example 229

(R)-6-{2-{Ethyl[4-(1-methylpiperidin-4-yl)benzyl]amino}-4-methoxyphenyl}-5,6,7,8-tetrahydronaphthalen-2-ol

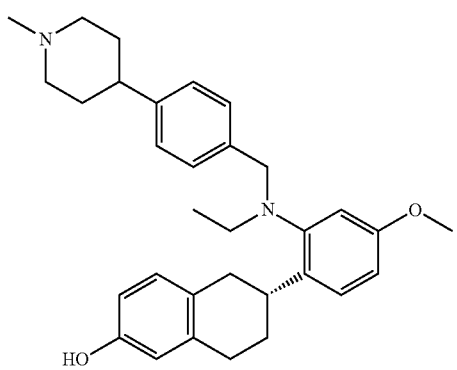

Synthesized from pivalic acid (R)-6-(2-ethylamino-4-methoxyphenyl)-5,6,7,8-tetrahydronaphthalen-2-yl ester (100 mg) and 4-(4-carboxyphenyl)piperidine-1-carboxylic acid tert-butyl ester (250 mg) according to an analogous synthetic method to Example 337 described below and purified by LC-MS, the title compound (32 mg) was obtained.

ESI-Mass; 485 [M$^+$+H]

Example 230

(R)-6-{2-[Ethyl(4-piperidin-4-ylbenzyl)amino]-4-methoxyphenyl}-5,6,7,8-tetrahydronaphthalen-2-ol

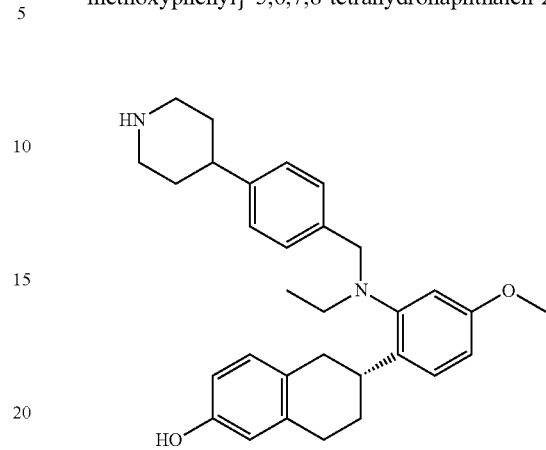

Synthesized from (R)-4-{4-{{2-[6-(2,2-dimethylpropionyloxy)-1,2,3,4-tetrahydronaphthalen-2-yl]-5-methoxyphenyl}ethylcarbamoyl}phenyl}piperidine-1-carboxylic acid tert-butyl ester (112 mg) according to an analogous synthetic method to Example 215, pivalic acid (R)-6-{2-[ethyl-(4-piperidin-4-ylbenzoyl)amino]-4-methoxyphenyl}-5,6,7,8-tetrahydronaphthalen-2-yl ester (70 mg) was obtained. Synthesized using this compound (35 mg) according to an analogous synthetic method to Example 337 described below and purified by LC-MS, the title compound (36 mg) was obtained.

ESI-Mass; 471 [M$^+$+H]

Example 231

(R)-6-{2-{Ethyl[4-(1-ethylpiperidin-4-yl)benzyl]amino}-4-methoxyphenyl}-5,6,7,8-tetrahydronaphthalen-2-ol

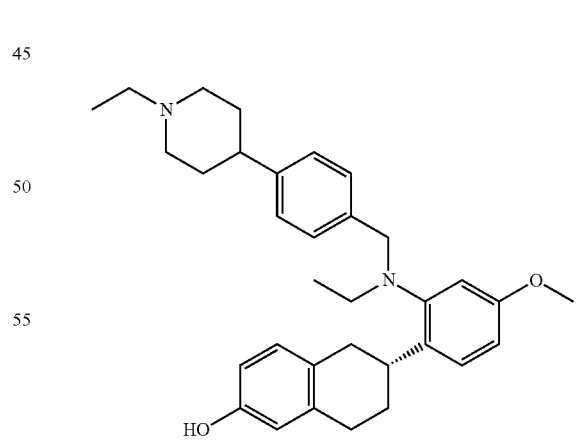

Synthesized from pivalic acid (R)-6-{2-[ethyl(4-piperidin-4-ylbenzoyl)amino]-4-methoxyphenyl}-5,6,7,8-tetrahydronaphthalen-2-yl ester (35 mg) according to an analogous synthetic method to Example 36 and purified by LC-MS, the title compound (36 mg) was obtained.

ESI-Mass; 499 [M$^+$+H]

Example 232

(R)-6-{2-{Ethyl[3-fluoro-4-(1-methylpiperidin-4-yloxy)benzyl]amino}-4-methoxyphenyl}-5,6,7,8-tetrahydronaphthalen-2-ol

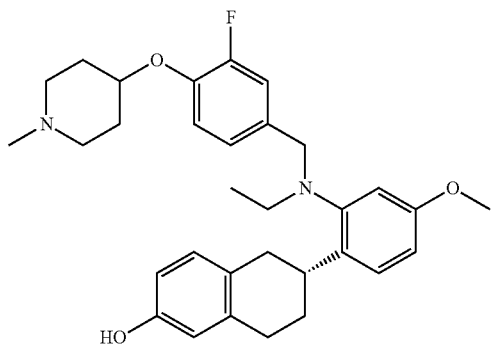

Synthesized from pivalic acid (R)-6-(2-ethylamino-4-methoxyphenyl)-5,6,7,8-tetrahydronaphthalen-2-yl ester (20 mg) and 3-fluoro-4-(1-methylpiperidin-4-yloxy)benzaldehyde (55 mg) according to an analogous synthetic method to Example 264 described below and purified by LC-MS, the title compound (7.7 mg) was obtained.

ESI-Mass; 519 [$M^+$+H]

Example 233

(R)-6-{2-{Ethyl[4-(1-methylpiperidin-4-yloxy)benzyl]amino}-4-methoxyphenyl}-5,6,7,8-tetrahydronaphthalen-2-ol

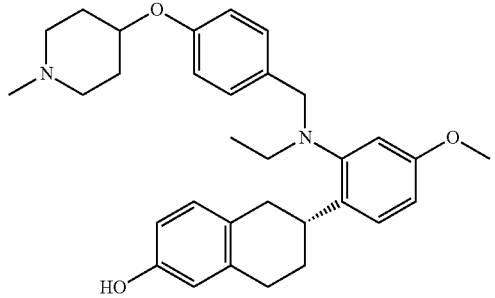

Synthesized from pivalic acid (R)-6-(2-ethylamino-4-methoxyphenyl)-5,6,7,8-tetrahydronaphthalen-2-yl ester (33 mg) and 4-(1-methylpiperidin-4-yloxy)benzaldehyde (94 mg) according to an analogous synthetic method to Example 264 described below and purified by LC-MS, the title compound (31 mg) was obtained.

ESI-Mass; 501 [$M^+$+H]

Example 234

(S)-6-{2-{[4-(2-Dimethylamino-2-methylpropoxy)benzyl]ethylamino}-4-methoxyphenyl}-5,6,7,8-tetrahydronaphthalen-2-ol

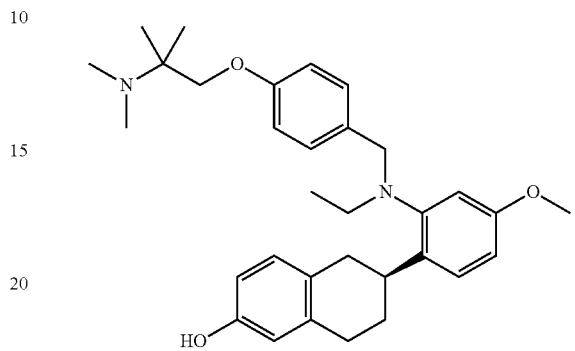

Synthesized from pivalic acid (S)-6-(2-ethylamino-4-methoxyphenyl)-5,6,7,8-tetrahydronaphthalen-2-yl ester (34 mg) and 4-(2-dimethylamino-2-methylpropoxy)benzaldehyde (100 mg) according to an analogous synthetic method to Example 264 described below and purified by LC-MS, the title compound (50 mg) was obtained.

ESI-Mass; 503 [$M^+$+H]

Example 235

(R)-6-{2-{[4-(2-Dimethylamino-2-methylpropoxy)benzyl]ethylamino}-4-methoxyphenyl}-5,6,7,8-tetrahydronaphthalen-2-ol

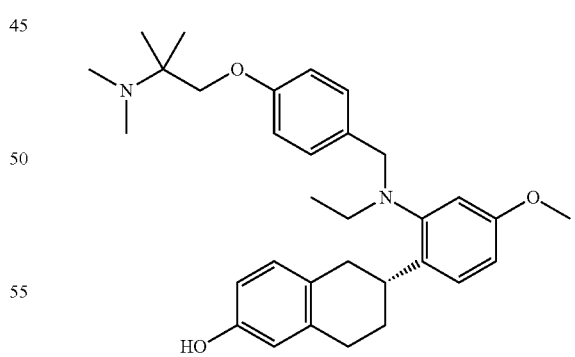

Synthesized from pivalic acid (R)-6-(2-ethylamino-4-methoxyphenyl)-5,6,7,8-tetrahydronaphthalen-2-yl ester (34 mg) and 4-(2-dimethylamino-2-methylpropoxy)benzaldehyde (100 mg) according to an analogous synthetic method to Example 264 described below and purified by LC-MS, the title compound (33 mg) was obtained.

ESI-Mass; 503 [$M^+$+H]

Example 236

(R)-6-{2-{[4-(2-Dimethylamino-2-methylpropoxy)-3-fluorobenzyl]ethylamino}-4-methoxyphenyl}-5,6,7,8-tetrahydronaphthalen-2-ol

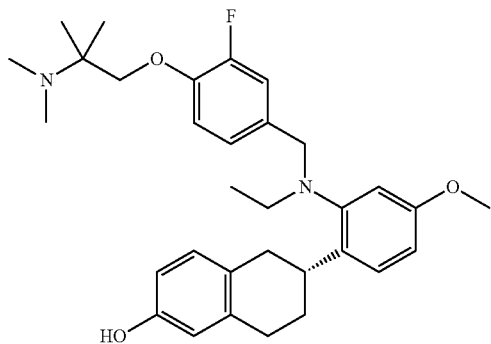

Synthesized from pivalic acid (R)-6-(2-ethylamino-4-methoxyphenyl)-5,6,7,8-tetrahydronaphthalen-2-yl ester (20 mg) and 4-(2-dimethylamino-2-methylpropoxy)-3-fluorobenzaldehyde (55 mg) according to an analogous synthetic method to Example 264 described below and purified by LC-MS, the title compound (6.6 mg) was obtained.

ESI-Mass; 521 [M$^+$+H]

Example 237

(R)-6-{2-{[4-(1-Dimethylaminocyclopentyl-methoxy)benzyl]ethylamino}-4-methoxyphenyl}-5,6,7,8-tetrahydronaphthalen-2-ol

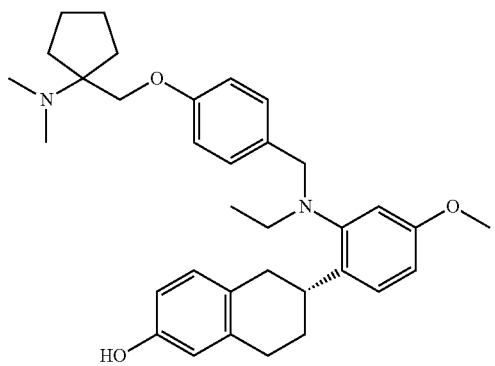

Synthesized from pivalic acid (R)-6-(2-ethylamino-4-methoxyphenyl)-5,6,7,8-tetrahydronaphthalen-2-yl ester (20 mg) and 4-(2-dimethylamino-2-methylpropoxy)-3-fluorobenzaldehyde (57 mg) according to an analogous synthetic method to Example 264 described below and purified by LC-MS, the title compound (14 mg) was obtained.

ESI-Mass; 529 [M$^+$+H]

Example 238

(R)-6-{2-{Ethyl[4-(piperidin-4-yloxy)benzyl]amino}-4-methoxyphenyl}-5,6,7,8-tetrahydronaphthalen-2-ol

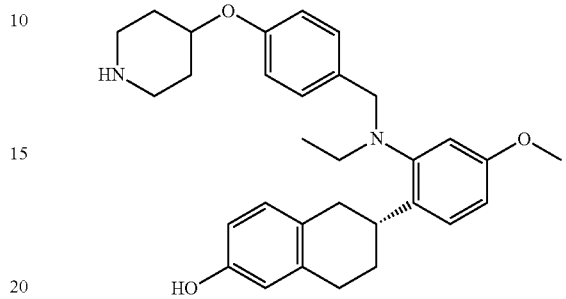

Synthesized from (R)-6-(2-ethylamino-4-methoxyphenyl)-5,6,7,8-tetrahydronaphthalen-2-yl ester (20 mg) and 4-(4-formylphenoxy)piperidine-1-carboxylic acid tert-butyl ester (72 mg) according to an analogous synthetic method to Example 212, to a solution of the resulting (R)-4-{4-{{{2-[6-(2,2-dimethylpropionyloxy)-1,2,3,4-tetrahydronaphthalen-2-yl]-5-methoxyphenyl}ethylamino}methyl}phenoxy}piperidine-1-carboxylic acid tert-butyl ester crude product in dichloromethane (0.5 ml) was added trifluoroacetic acid (0.5 ml), the solution was let to stand for 30 minutes at room temperature, then neutralized with ammonia solution, extracted with chloroform, then concentrated under a nitrogen stream to give pivalic acid (R)-6-{2-{ethyl[4-(piperidin-4-yloxy)benzyl]amino}-4-methoxyphenyl}-5,6,7,8-tetrahydronaphthalen-2-yl ester. Synthesized from the total amount of the resulting crude product according to an analogous synthetic method to Example 213 and purified by LC-MS, the title compound (5.0 mg) was obtained.

ESI-Mass; 487 [M$^+$+H]

Example 239

(R)-6-{2-{Ethyl[3-fluoro-4-(piperidin-4-yloxy)benzyl]amino}-4-methoxyphenyl}-5,6,7,8-tetrahydronaphthalen-2-ol

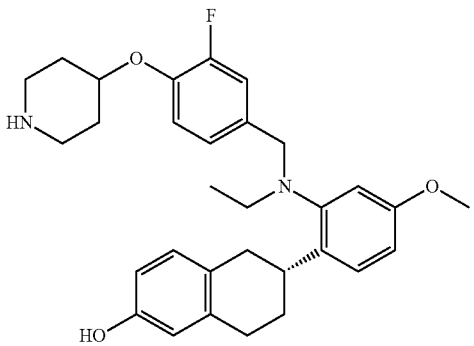 [SMILES: CCN(Cc1ccc(OC2CCNCC2)c(F)c1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (20 mg) and 4-(2-fluoro-4-formylphenoxy)piperidine-1-carboxylic acid tert-butyl ester (75 mg) according to an analogous synthetic method to Example 238 and purified by LC-MS, the title compound (5.1 mg) was obtained.

ESI-Mass; 505 [M$^+$+H]

Example 240

(R)-6-{2-{Ethyl[4-(1-ethylpiperidin-4-yloxy)benzyl]amino}-4-methoxyphenyl}-5,6,7,8-tetrahydronaphthalen-2-ol

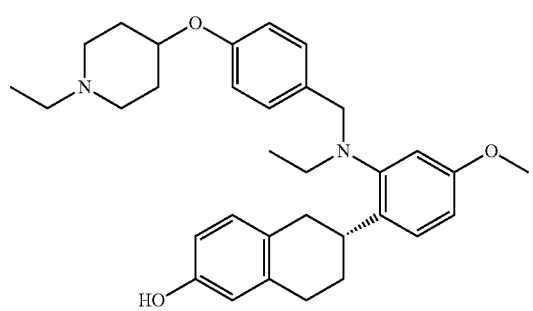 [SMILES: CCN1CCC(Oc2ccc(CN(CC)c3cc(OC)ccc3[C@@H]3CCc4cc(O)ccc4C3)cc2)CC1]

Synthesized from pivalic acid (R)-6-(2-ethylamino-4-methoxyphenyl)-5,6,7,8-tetrahydronaphthalen-2-yl ester (20 mg) and 4-(1-acetylpiperidin-4-yloxy)benzaldehyde (57 mg) according to an analogous synthetic method to Example 264 described below and purified by LC-MS, the title compound (9.2 mg) was obtained.

ESI-Mass; 515 [M$^+$+H]

Example 241

(R)-6-{2-{Ethyl[4-(1-ethylpiperidin-4-yloxy)-3-fluorobenzyl]amino}-4-methoxyphenyl}-5,6,7,8-tetrahydronaphthalen-2-ol

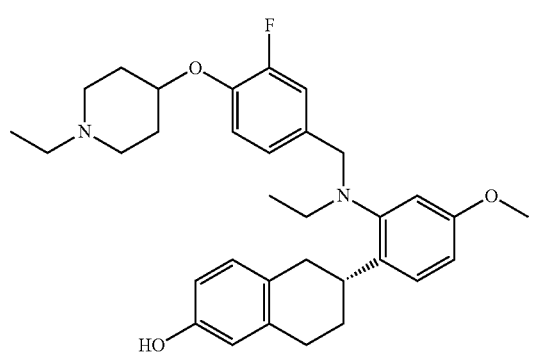 [SMILES: CCN1CCC(Oc2ccc(CN(CC)c3cc(OC)ccc3[C@@H]3CCc4cc(O)ccc4C3)cc2F)CC1]

Synthesized from pivalic acid (R)-6-(2-ethylamino-4-methoxyphenyl)-5,6,7,8-tetrahydronaphthalen-2-yl ester (20 mg) and 4-(1-acetylpiperidin-4-yloxy)benzaldehyde (61 mg) according to an analogous synthetic method to Example 264 described below and purified by LC-MS, the title compound (8.2 mg) was obtained.

ESI-Mass; 533 [M$^+$+H]

Example 242

(R)-6-{2-{[4-(2-Amino-2-methylpropoxy)-3-fluorobenzyl]ethylamino}-4-methoxyphenyl}-5,6,7,8-tetrahydronaphthalen-2-ol

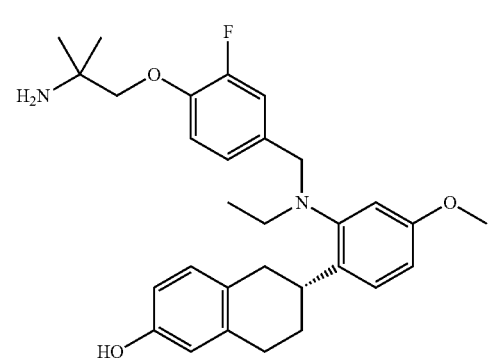 [SMILES: CCN(Cc1ccc(OCC(C)(C)N)c(F)c1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (20 mg) and tert-butyl[2-(2-fluoro-4-formylphenoxy)-1,1-dimethylethyl]carbamate (72 mg) according to an analogous synthetic method to Example 238 and purified by LC-MS, the title compound (19 mg) was obtained.

ESI-Mass; 493 [M$^+$+H]

Example 243

(R)-6-{2-{[4-(2-Amino-2-methylpropoxy)benzyl]ethylamino}-4-methoxyphenyl}-5,6,7,8-tetrahydronaphthalen-2-ol

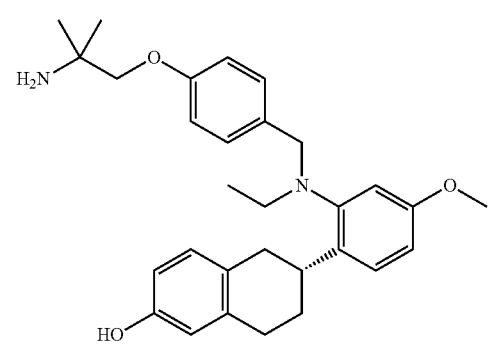 [SMILES: CCN(Cc1ccc(OCC(C)(C)N)cc1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (33 mg) and tert-butyl[2-(4-formylphenoxy)-1,1-dimethylethyl]carbamate (125 mg) according to an analogous synthetic method to Example 238 and purified by LC-MS, the title compound (15 mg) was obtained.

ESI-Mass; 475 [M$^+$+H]

Example 244

(R)-6-{2-{[4-(1-Aminocyclopentylmethoxy)benzyl]ethylamino}-4-methoxyphenyl}-5,6,7,8-tetrahydronaphthalen-2-ol

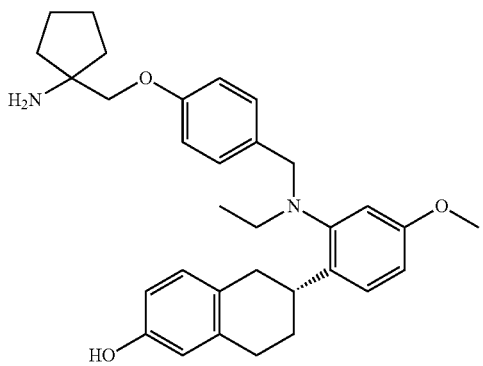 [SMILES: CCN(Cc1ccc(OCC2(N)CCCC2)cc1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (20 mg) and tert-butyl[1-(4-formylphenoxymethyl)cyclopentyl]carbamate (74 mg) according to an analogous synthetic method to Example 238 and purified by LC-MS, the title compound (16 mg) was obtained.

ESI-Mass; 501 [M$^+$+H]

Example 245

(R)-6-{2-{[4-(2-Dimethylamino-2-methylpropoxy)-3-fluorobenzyl]isopropylamino}-4-methoxyphenyl}-5,6,7,8-tetrahydronaphthalen-2-ol

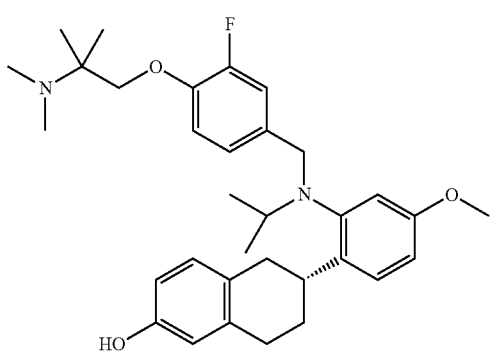

Synthesized from tert-butyl[2-(2-fluoro-4-formylphenoxy)-1,1-dimethylethyl]carbamate according to an analogous synthetic method to Preparation Example 53, to a solution of the resulting 4-(2-tert-butoxycarbonylamino-2-methylpropoxy)-3-fluorobenzoic acid (80 mg) in tetrahydrofuran (2 ml) were sequentially added N,N-dimethylformamide (in catalytic amounts) and oxalyl chloride (0.026 ml), and the solution was stirred for 30 minutes at room temperature. The reaction solution was concentrated in vacuo. To a solution of the resulting residue in 1,4-dioxane (1.5 ml) were sequentially added pivalic acid (R)-6-(2-isopropylamino-4-methoxyphenyl)-5,6,7,8-tetrahydronaphthalen-2-yl ester (70 mg) and N,N-diisopropylethylamine (0.2 ml), and the solution was stirred for 2 hours at 90° C. The solution was extracted with ethyl acetate, then sequentially washed with water and brine, dried over anhydrous magnesium sulfate, and then the solvent was evaporated in vacuo. Obtained by purifying the residue by NH silica gel column chromatography (hexane-ethyl acetate system), pivalic acid (R)-6-{2-{[4-(2-tert-butoxycarbonylamino-2-methylpropoxy)-3-fluorobenzoyl]isopropylamino}-4-methoxyphenyl}-5,6,7,8-tetrahydronaphthalen-2-yl ester (72 mg) was used according to an analogous synthetic method to Example 215 to provide pivalic acid (R)-6-{2-{[4-(2-amino-2-methylpropoxy)-3-fluorobenzoyl]isopropylamino}-4-methoxyphenyl}-5,6,7,8-tetrahydronaphthalen-2-yl ester (56 mg). The total amount of this compound was used according to an analogous synthetic method to Preparation Example 18 to provide pivalic acid (R)-6-{2-{[4-(2-dimethylamino-2-methylpropoxy)-3-fluorobenzoyl]isopropylamino}-4-methoxyphenyl}-5,6,7,8-tetrahydronaphthalen-2-yl ester. This compound (21 mg) was used according to analogous synthetic method to Example 337 described below and purified by LC-MS, the title compound (10 mg) was obtained.

ESI-Mass; 535 [M$^+$+H]

Example 246

6-{2-{[4-(2-Azepan-1-ylethoxy)benzyl]ethylamino}-5-methoxyphenyl}-5,6,7,8-tetrahydronaphthalen-2-ol

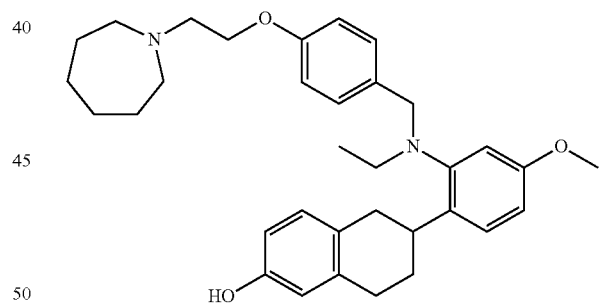

Synthesized from 6-(2-ethylamino-5-methoxyphenyl)-5,6,7,8-tetrahydronaphthalen-2-ol according to an analogous synthetic method to Example 36, 642-ethylamino-5-methoxyphenyl)-5,6,7,8-tetrahydronaphthalen-2-ol (40 mg) and 4-(2-azepan-1-ylethoxy)benzaldehyde (202 mg) were used according to an analogous synthetic method to Example 38 to provide the title compound (32 mg).

$^1$H-NMR (400 MHz, DMSO-d$^6$); δ (ppm): 0.82 (t, 3H), 1.42-1.72 (m, 10H), 2.37-2.61 (m, 2H), 2.62-2.76 (m, 6H), 2.79 (t, 2H), 2.83 (q, 2H), 3.55-3.64 (m, 1H), 3.68 (s, 3H), 3.86 (dd, 2H), 3.95 (t, 2H), 6.46-6.51 (m, 2H), 6.70-6.79 (m, 5H), 7.01 (d, 2H), 7.21 (d, 1H), 8.99 (s, 1H).

ESI-Mass; 529 [M$^+$+H]

Example 247

6-{2-{[4-(2-Azepan-1-ylethyl)benzyl]ethylamino}-5-methoxyphenyl}-5,6,7,8-tetrahydronaphthalen-2-ol

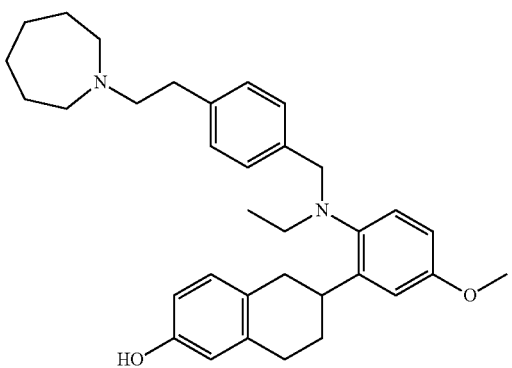 [SMILES: CCN(Cc1ccc(CCN2CCCCCC2)cc1)c1ccc(OC)cc1C1CCc2cc(O)ccc2C1]

Synthesized from pivalic acid 6-(2-ethylamino-5-methoxyphenyl)-5,6,7,8-tetrahydronaphthalen-2-yl ester (50 mg) and 4-(2-azepan-1-ylethyl)benzoic acid hydrochloride (100 mg) according to an analogous synthetic method to Example 152, the title compound (40 mg) was obtained.

$^1$H-NMR (400 MHz, DMSO-d$_6$); δ (ppm): 0.83 (t, 3H), 1.39-1.58 (m, 9H), 1.60-132 (m, 1H), 2.42-2.48 (m, 1H), 2.52-2.64 (m, 9H), 2.68-2.77 (m, 2H), 2.83 (q, 2H), 3.56-3.65 (m, 1H), 3.68 (s, 3H), 3.89 (dd, 2H), 6.46-6.52 (m, 2H), 6.70-6.80 (m, 3H), 7.00-7.06 (m, 4H), 7.02 (d, 1H), 8.99 (s, 1H).

ESI-Mass; 513 [M$^+$+H]

Example 248

6-{2-{Ethyl[4-(1-methylpiperidin-4-yl)benzyl]amino}-5-methoxyphenyl}-5,6,7,8-tetrahydronaphthalen-2-ol

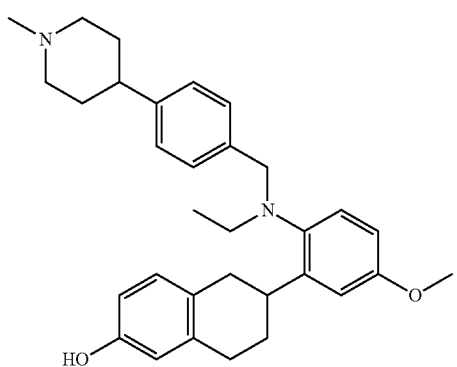

Synthesized from pivalic acid 6-(2-ethylamino-5-methoxyphenyl)-5,6,7,8-tetrahydronaphthalen-2-yl ester (50 mg) and 4-(4-carboxyphenyl)piperidine-1-carboxylic acid tert-butyl ester (100 mg) according to an analogous synthetic method to Example 337 described below, the title compound (50 mg) was obtained.

$^1$H-NMR (400 MHz, DMSO-d$_6$); δ (ppm): 0.82 (t, 3H), 1.33-1.44 (m, 1H), 1.52-1.70 (m, 5H), 1.86-1.95 (m, 2H), 2.16 (s, 3H), 2.31-2.41 (m, 1H), 2.42-2.62 (m, 2H), 2.65-2.73 (m, 2H), 2.78-2.87 (m, 4H), 3.55-3.65 (m, 1H), 3.68 (s, 3H), 3.88 (dd, 2H), 6.46-6.51 (m, 2H), 6.70-6.79 (m, 3H), 7.03-7.07 (m, 4H), 7.24 (d, 1H), 8.99 (s, 1H).

ESI-Mass; 485 [M$^+$+H]

Example 249

6-{2-{[4-(2-Azepan-1-ylethoxy)benzyl]ethylamino}-4,5-dimethoxyphenyl}-5,6,7,8-tetrahydronaphthalen-2-ol

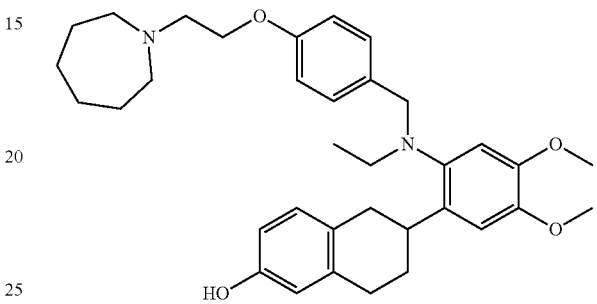

Synthesized from 6-(2-amino-4,5-dimethoxyphenyl)-5,6,7,8-tetrahydronaphthalen-2-ol according to an analogous synthetic method to Example 36, 6-(2-ethylamino-4,5-dimethoxyphenyl)-5,6,7,8-tetrahydronaphthalen-2-ol (55 mg) and 4-(2-azepan-1-ylethoxy)benzaldehyde (192 mg) were used according to an analogous synthetic method to Example 38 to provide the title compound (63 mg).

$^1$H-NMR (400 MHz, DMSO-d$_6$); δ (ppm): 0.83 (s, 3H), 1.38-1.47 (m, 1H), 1.48-1.60 (m, 8H), 1.60-1.74 (m, 1H), 2.36-2.42 (m, 1H), 2.56-2.88 (m, 11H), 3.53-3.62 (m, 1H), 3.67 (s, 3H), 3.72 (s, 3H), 3.88 (dd, 2H), 3.96 (t, 2H), 6.46-6.51 (m, 2H), 6.71-6.79 (m, 3H), 6.85 (s, 1H), 7.04 (d, 2H), 8.97 (s, 1H).

ESI-Mass; 559 [M$^+$+H]

Example 250

6-{2-[(4-Azepan-1-ylmethylbenzyl)ethylamino]-4,5-dimethoxyphenyl}-5,6,7,8-tetrahydronaphthalen-2-ol

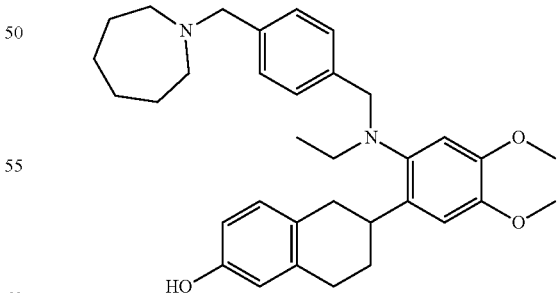

Synthesized from pivalic acid 6-(2-ethylamino-4,5-dimethoxyphenyl)-5,6,7,8-tetrahydronaphthalen-2-yl ester (50 mg) and 4-azepan-1-ylmethylbenzoic acid hydrochloride (100 mg) according to an analogous synthetic method to Example 337 described below, the title compound (52 mg) was obtained.

¹H-NMR (400 MHz, DMSO-d₆); δ (ppm): 0.85 (t, 3H), 1.33-1.41 (m, 1H), 1.50-1.56 (m, 8H), 1.60-1.72 (m, 1H), 2.40-2.72 (m, 8H), 2.86 (q, 2H), 3.50 (s, 2H), 3.55-3.65 (m, 1H), 3.67 (s, 3H), 3.71 (s, 3H), 3.92 (dd, 2H), 6.46-6.50 (m, 2H), 6.71 (s, 1H), 6.77 (d, 1H), 6.86 (s, 1H), 7.08 (d, 2H), 7.13 (d, 2H), 8.97 (s, 1H).

ESI-Mass; 529 [M⁺+H]

Example 251

6-{2-{[4-(2-Azepan-1-ylethyl)benzyl]ethylamino}-4,5-dimethoxyphenyl}-5,6,7,8-tetrahydronaphthalen-2-ol

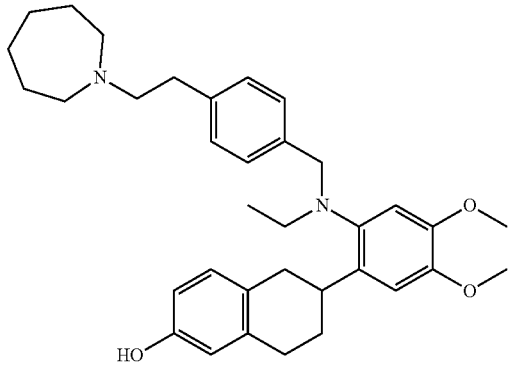 [SMILES: CCN(Cc1ccc(CCN2CCCCCC2)cc1)c1cc(OC)c(OC)cc1C1CCc2cc(O)ccc2C1]

Synthesized from pivalic acid 6-(2-ethylamino-4,5-dimethoxyphenyl)-5,6,7,8-tetrahydronaphthalen-2-yl ester (50 mg) and 4-(2-azepan-1-ylethyl)benzoic acid hydrochloride (100 mg) according to an analogous synthetic method to Example 337 described below, the title compound (32 mg) was obtained.

¹H-NMR (400 MHz, DMSO-d₆); δ (ppm): 0.84 (t, 3H), 1.35-1.44 (m, 1H), 1.47-1.59 (m, 8H), 1.62-1.72 (m, 1H), 2.38-2.47 (m, 1H), 2.57-2.65 (m, 9H), 2.66-2.74 (m, 2H), 2.84 (q, 2H), 3.55-3.64 (m, 1H), 3.67 (s, 3H), 3.71 (s, 3H), 3.90 (dd, 2H), 6.46-6.50 (m, 2H), 6.71 (s, 1H), 6.77 (d, 1H), 6.85 (s, 1H), 7.02-7.07 (m, 4H), 8.97 (s, 1H).

ESI-Mass; 543 [M⁺+H]

Example 252

6-{2-{[4-(3-Azepan-1-ylpropyl)benzyl]ethylamino}-4,5-dimethoxyphenyl}-5,6,7,8-tetrahydronaphthalen-2-ol

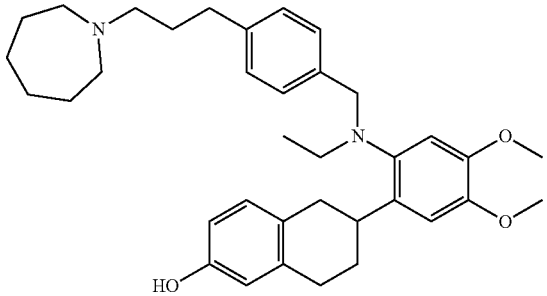 [SMILES: CCN(Cc1ccc(CCCN2CCCCCC2)cc1)c1cc(OC)c(OC)cc1C1CCc2cc(O)ccc2C1]

Synthesized from pivalic acid 6-(2-ethylamino-4,5-dimethoxyphenyl)-5,6,7,8-tetrahydronaphthalen-2-yl ester (50 mg) and 4-(3-azepan-1-ylpropyl)benzoic acid hydrochloride (100 mg) according to an analogous synthetic method to Example 337 described below, the title compound (30 mg) was obtained.

¹H-NMR (400 MHz, DMSO-d₆); δ (ppm): 0.84 (t, 3H), 1.33-1.42 (m, 1H), 1.48-1.57 (m, 8H), 1.58-1.70 (m, 3H), 2.36 (t, 2H), 2.40-2.63 (m, 8H), 2.66-2.73 (m, 2H), 2.85 (q, 2H), 3.54-3.63 (m, 1H), 3.67 (s, 3H), 3.72 (s, 3H), 3.91 (dd, 2H), 6.46-6.51 (m, 2H), 6.70 (s, 1H), 6.77 (d, 1H), 6.86 (s, 1H), 7.01 (d, 2H), 7.04 (d, 2H), 8.97 (s, 1H).

ESI-Mass; 557 [M⁺+H]

Example 253

6-{2-{Ethyl[4-(1-methylpiperidin-4-yl)benzyl]amino}-4,5-dimethoxyphenyl}-5,6,7,8-tetrahydronaphthalen-2-ol

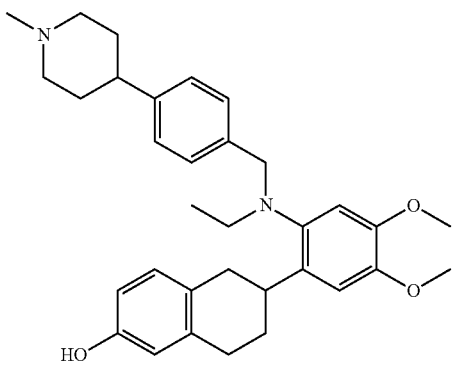

Synthesized from pivalic acid 6-(2-ethylamino-4,5-dimethoxyphenyl)-5,6,7,8-tetrahydronaphthalen-2-yl ester (50 mg) and 4-(4-carboxyphenyl)piperidine-1-carboxylic acid tert-butyl ester (100 mg) according to an analogous synthetic method to Example 337 described below, the title compound (44 mg) was obtained.

¹H-NMR (400 MHz, DMSO-d₆); δ (ppm): 0.83 (t, 3H), 1.30-1.39 (m, 1H), 1.53-1.70 (m, 5H), 1.87-1.95 (m, 2H), 2.16 (s, 3H), 2.32-2.40 (m, 1H), 2.41-2.49 (m, 1H), 2.57-2.72 (m, 3H), 2.79-2.87 (m, 4H), 3.54-3.63 (m, 1H), 3.67 (s, 3H), 3.71 (s, 3H), 3.90 (dd, 2H), 6.46-6.50 (m, 2H), 6.71 (s, 1H), 6.77 (d, 1H), 6.85 (s, 1H), 7.04-7.09 (m, 4H), 8.97 (s, 1H).

ESI-Mass; 515 [M⁺+H]

Example 254

6-{2-[Ethyl(4-piperidin-4-ylbenzyl)amino]-4,5-dimethoxyphenyl}-5,6,7,8-tetrahydronaphthalen-2-ol

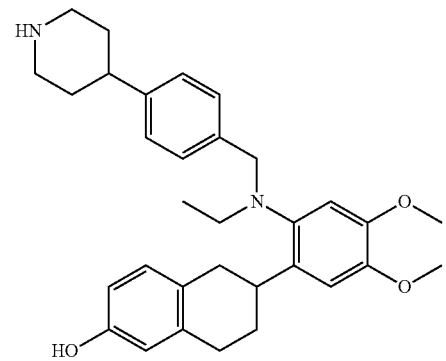 [SMILES: CCN(Cc1ccc(C2CCNCC2)cc1)c1cc(OC)c(OC)cc1C1CCc2cc(O)ccc2C1]

Synthesized from pivalic acid 6-(2-ethylamino-4,5-dimethoxyphenyl)-5,6,7,8-tetrahydronaphthalen-2-yl ester (50 mg) and 4-(4-carboxyphenyl)piperidine-1-carboxylic acid tert-butyl ester (100 mg) according to an analogous synthetic method to Example 209, the title compound (22 mg) was obtained.

¹H-NMR (400 MHz, DMSO-d₆); δ (ppm): 0.83 (t, 3H), 1.30-1.49 (m, 3H), 1.56-1.71 (m, 3H), 2.40-2.62 (m, 5H), 2.63-2.72 (m, 2H), 2.85 (q, 2H), 2.94-3.01 (m, 2H), 3.53-3.64 (m, 1H), 3.67 (s, 3H), 3.71 (s, 3H), 3.90 (dd, 2H), 6.46-6.51 (m, 2H), 6.71 (s, 1H), 6.77 (d, 1H), 6.86 (s, 1H), 7.04 (d, 2H), 7.07 (d, 2H), 8.98 (s, 1H).

ESI-Mass; 501 [M⁺+H]

Example 255

6-{2-{[5-(2-Azepan-1-ylethyl)pyridin-2-ylmethyl]ethylamino}-4,5-dimethoxyphenyl}-5,6,7,8-tetrahydronaphthalen-2-ol

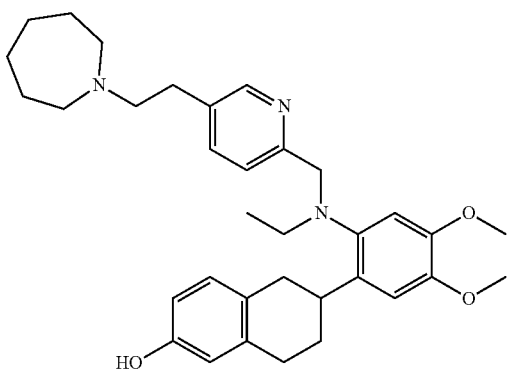 [SMILES: CCN(Cc1ccc(CCN2CCCCCC2)cn1)c1cc(OC)c(OC)cc1C1CCc2cc(O)ccc2C1]

Synthesized from pivalic acid 6-(2-ethylamino-4,5-dimethoxyphenyl)-5,6,7,8-tetrahydronaphthalen-2-yl ester (40 mg) and 5-(2-azepan-1-ylethyl)pyridine-2-carbonyl chloride hydrochloride (320 mg) according to an analogous synthetic method to Example 152, the title compound (10 mg) was obtained.

$^1$H-NMR (400 MHz, DMSO-d$_6$); δ (ppm): 0.87 (t, 3H), 1.43-1.58 (m, 9H), 1.65-1.78 (m, 1H), 2.43-2.50 (m, 1H), 2.56-2.76 (m, 11H), 2.90 (q, 2H), 3.56-3.65 (m, 1H), 3.68 (s, 3H), 3.71 (s, 3H), 4.05 (dd, 2H), 6.46-6.51 (m, 2H), 6.75 (s, 1H), 6.79 (d, 1H), 6.86 (s, 1H), 7.12 (d, 1H), 7.49 (dd, 1H), 8.27 (d, 1H), 8.98 (s, 1H).

ESI-Mass; 544 [M$^+$+H]

Example 256

6-{2-{[5-(2-Azepan-1-ylethoxy)pyridin-2-ylmethyl]ethylamino}-4,5-dimethoxyphenyl}-5,6,7,8-tetrahydronaphthalen-2-ol

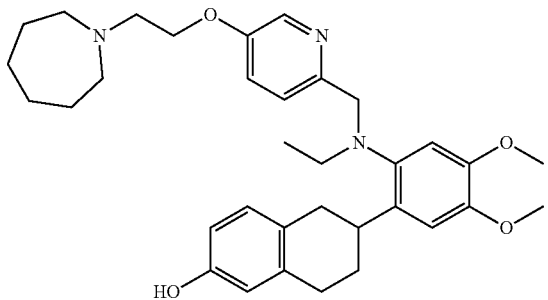 [SMILES: CCN(Cc1ccc(OCCN2CCCCCC2)cn1)c1cc(OC)c(OC)cc1C1CCc2cc(O)ccc2C1]

Synthesized from pivalic acid 6-(2-ethylamino-4,5-dimethoxyphenyl)-5,6,7,8-tetrahydronaphthalen-2-yl ester (25 mg) and sodium 5-(2-azepan-1-ylethoxy)pyridine-2-carboxylate (60 mg) according to an analogous synthetic method to Example 152, the title compound (16 mg) was obtained.

$^1$H-NMR (400 MHz, DMSO-d$_6$); δ (ppm): 0.86 (t, 3H), 1.45-1.60 (m, 9H), 1.66-1.79 (m, 1H), 2.36-2.46 (m, 1H), 2.57-2.69 (m, 5H), 2.70-2.77 (m, 2H), 2.82 (t, 2H), 2.90 (q, 2H), 3.53-3.64 (m, 1H), 3.68 (s, 3H), 3.71 (s, 3H), 4.02 (dd, 2H), 4.04 (t, 2H), 6.46-6.51 (m, 2H), 6.74 (s, 1H), 6.78 (d, 1H), 6.85 (s, 1H), 7.10 (d, 1H), 7.25 (dd, 1H), 8.10 (d, 1H), 8.98 (s, 1H).

ESI-Mass; 560 [M$^+$+H]

Example 257

6-{2-{[6-(2-Azepan-1-ylethoxy)pyridin-3-ylmethyl]ethylamino}-4,5-dimethoxyphenyl}-5,6,7,8-tetrahydronaphthalen-2-ol

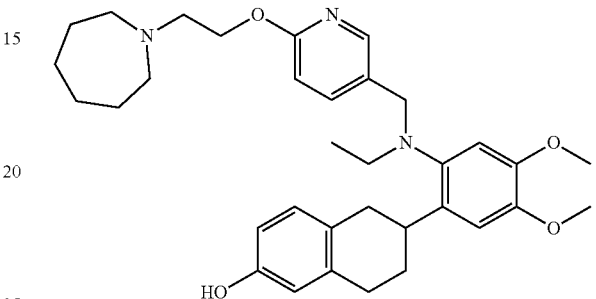

Synthesized from pivalic acid 6-(2-ethylamino-4,5-dimethoxyphenyl)-5,6,7,8-tetrahydronaphthalen-2-yl ester (25 mg) and 6-(2-azepan-1-ylethoxy)nicotinic acid hydrochloride (80 mg) according to an analogous synthetic method to Example 337 described below, the title compound (22 mg) was obtained.

$^1$H-NMR (400 MHz, DMSO-d$_6$); δ (ppm): 0.86 (t, 3H), 1.48-1.59 (m, 9H), 1.60-1.73 (m, 1H), 2.27-2.37 (m, 1H), 2.54-2.61 (m, 1H), 2.61-2.74 (m, 6H), 2.79 (t, 2H), 2.89 (q, 2H), 3.46-3.55 (m, 1H), 3.69 (s, 3H), 3.75 (s, 3H), 3.92 (dd, 2H), 4.25 (t, 2H), 6.47-6.51 (m, 2H), 6.63 (d, 1H), 6.71 (s, 1H), 6.77 (d, 1H), 6.89 (s, 1H), 7.40 (dd, 1H), 7.84 (d, 1H), 8.99 (s, 1H).

ESI-Mass; 560 [M$^+$+H]

Example 258

6-{2-{[5-(2-Azepan-1-ylethyl)thiophen-2-ylmethyl]ethylamino}-4,5-dimethoxyphenyl}-5,6,7,8-tetrahydronaphthalen-2-ol

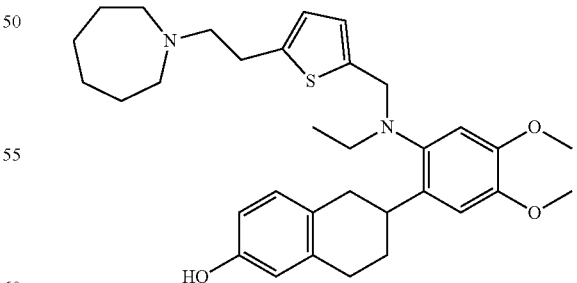

Synthesized from pivalic acid 6-(2-ethylamino-4,5-dimethoxyphenyl)-5,6,7,8-tetrahydronaphthalen-2-yl ester (40 mg) and lithium 5-(2-azepan-1-ylethyl)thiophene-2-carboxylate (100 mg) according to an analogous synthetic method to Example 152, the title compound (40 mg) was obtained.

$^1$H-NMR (400 MHz, DMSO-d$_6$); δ (ppm): 0.83 (t, 3H), 1.46-1.65 (m, 9H), 1.71-1.82 (m, 1H), 2.51-2.82 (m, 12H), 2.87 (q, 2H), 3.62-3.72 (m, 1H), 3.70 (s, 3H), 3.72 (s, 3H), 4.05 (dd, 2H), 6.46-6.51 (m, 2H), 6.57 (d, 1H), 6.60 (d, 1H), 6.77-6.84 (m, 3H), 8.97 (s, 1H).

ESI-Mass; 549 [M$^+$+H]

Example 259

(R)-6-{2-{[5-(2-Azepan-1-ylethyl)thiophen-2-ylmethyl]ethylamino}-4,5-dimethoxyphenyl}-5,6,7,8-tetrahydronaphthalen-2-ol

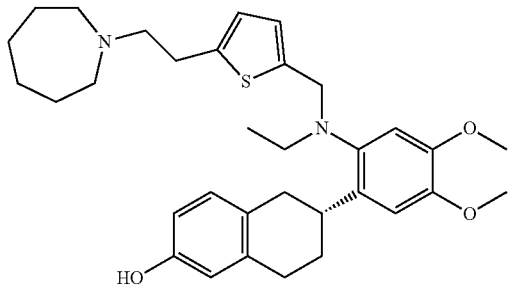 [SMILES: CCN(Cc1ccc(CCN2CCCCCC2)s1)c1cc(OC)c(OC)cc1[C@@H]1CCc2cc(O)ccc2C1]

Synthesized from pivalic acid (R)-6-(2-ethylamino-4,5-dimethoxyphenyl)-5,6,7,8-tetrahydronaphthalen-2-yl ester (30 mg) and lithium 5-(2-azepan-1-ylethyl)thiophene-2-carboxylate (60 mg) according to an analogous synthetic method to Example 152 and purified by LC-MS, the title compound (39 mg) was obtained.

ESI-Mass; 549 [M$^+$+H]

Example 260

(R)-6-{2-{[6-(2-Azepan-1-ylethoxy)pyridin-3-ylmethyl]ethylamino}-4,5-dimethoxyphenyl}-5,6,7,8-tetrahydronaphthalen-2-ol

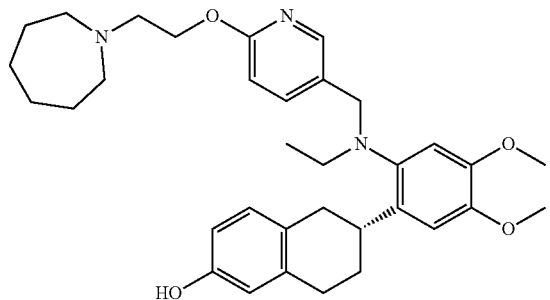 [SMILES: CCN(Cc1ccc(OCCN2CCCCCC2)nc1)c1cc(OC)c(OC)cc1[C@@H]1CCc2cc(O)ccc2C1]

Synthesized from pivalic acid (R)-6-(2-ethylamino-4,5-dimethoxyphenyl)-5,6,7,8-tetrahydronaphthalen-2-yl ester (30 mg) and 6-(2-azepan-1-ylethoxy)nicotinic acid hydrochloride (60 mg) according to an analogous synthetic method to Example 337 described below and purified by LC-MS, the title compound (26 mg) was obtained.

ESI-Mass; 560 [M$^+$+H]

Example 261

(R)-6-{2-{Ethyl[4-(1-methylpiperidin-4-yl)benzyl]amino}-4,5-dimethoxyphenyl}-5,6,7,8-tetrahydronaphthalen-2-ol

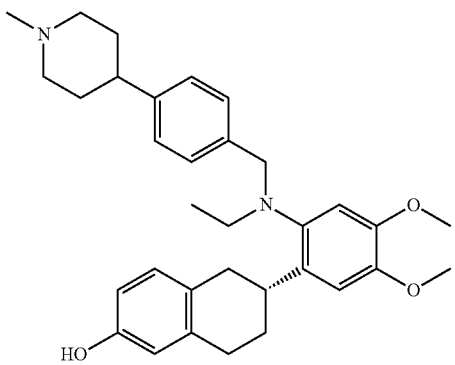

To a solution of pivalic acid (R)-6-(2-ethylamino-4,5-dimethoxyphenyl)-5,6,7,8-tetrahydronaphthalen-2-yl ester (100 mg) and 4-(4-chlorocarbonylphenyl)piperidine-1-carboxylic acid tert-butyl ester (125 mg) in 1,4-dioxane (2 ml) was added N,N-diisopropylethylamine (0.45 ml), and the solution was stirred for 4 hours at 90° C. Water was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide (R)-4-{4-{{2-[6-(2,2-dimethylpropionyloxy)-1,2,3,4-tetrahydronaphthalen-2-yl]-4,5-dimethoxyphenyl}ethylcarbamoyl}phenyl}piperidine-1-carboxylic acid tert-butyl ester (189 mg). Synthesized from this compound (60 mg) according to an analogous synthetic method to Example 337 described below and purified by LC-MS, the title compound (29 mg) was obtained.

ESI-Mass; 515 [M$^+$+H]

Example 262

(R)-6-{2-[Ethyl(4-piperidin-4-ylbenzyl)amino]-4,5-dimethoxyphenyl}-5,6,7,8-tetrahydronaphthalen-2-ol

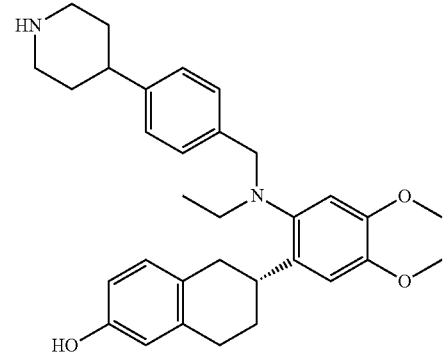 [SMILES: CCN(Cc1ccc(C2CCNCC2)cc1)c1cc(OC)c(OC)cc1[C@@H]1CCc2cc(O)ccc2C1]

Synthesized from (R)-4-{4-{{2-[6-(2,2-dimethylpropionyloxy)-1,2,3,4-tetrahydronaphthalen-2-yl]-4,5-dimethoxyphenyl}ethylcarbamoyl}phenyl}piperidine-1-carboxylic acid tert-butyl ester (129 mg) according to an analogous synthetic method to Example 215, pivalic acid (R)-6-{2-[ethyl(4-piperidin-4-ylbenzoyl)amino]-4,5-dimethoxyphenyl}-5,6,7,8-tetrahydronaphthalen-2-yl ester (100 mg) was obtained. Synthesized from this compound (50 mg) according to an analogous synthetic method to Example 337 described below and purified by LC-MS, the title compound (28 mg) was obtained.

ESI-Mass; 501 [M$^+$+H]

Example 263

(R)-6-{2-{Ethyl[4-(1-ethylpiperidin-4-yl)benzyl]amino}-4,5-dimethoxyphenyl}-5,6,7,8-tetrahydronaphthalen-2-ol

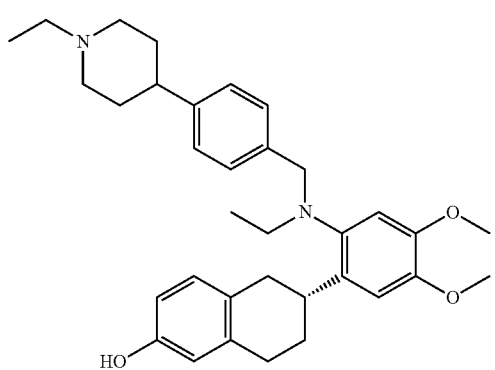 [SMILES: CCN1CCC(c2ccc(CN(CC)c3cc(OC)c(OC)cc3[C@@H]3CCc4cc(O)ccc4C3)cc2)CC1]

Synthesized from pivalic acid (R)-6-{2-[ethyl(4-piperidin-4-ylbenzoyl)amino]-4,5-dimethoxyphenyl}-5,6,7,8-tetrahydronaphthalen-2-yl ester (50 mg) according to an analogous synthetic method to Example 36 and purified by LC-MS, the title compound (23 mg) was obtained.

ESI-Mass; 529 [M$^+$+H]

Example 264

(R)-6-{2-{[4-(2-Dimethylamino-2-methylpropoxy)benzyl]ethylamino}-4,5-dimethoxyphenyl}-5,6,7,8-tetrahydronaphthalen-2-ol

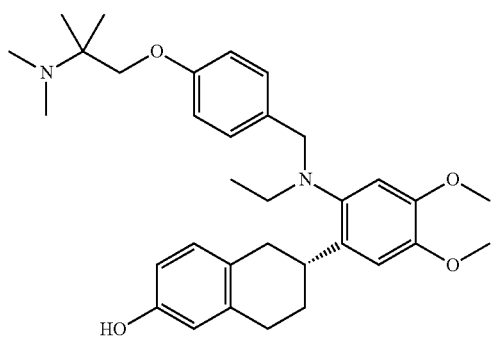

From (R)-6-(2-ethylamino-4,5-dimethoxyphenyl)-5,6,7,8-tetrahydronaphthalen-2-yl ester (20 mg) and 4-(2-dimethylamino-2-methylpropoxy)benzaldehyde (50 mg), synthesis was carried out according to an analogous synthetic method to Example 212. Synthesized from the total amount of the resulting pivalic acid (R)-6-{2-{[4-(2-dimethylamino-2-methylpropoxy)benzyl]ethylamino}-4,5-dimethoxyphenyl}-5,6,7,8-tetrahydronaphthalen-2-yl ester crude product according to an analogous synthetic method to Example 337 described below and purified by LC-MS, the title compound (21 mg) was obtained.

ESI-Mass; 533 [M$^+$+H]

Example 265

(R)-6-{2-{Ethyl[4-(1-methylpiperidin-4-yloxy)benzyl]amino}-4,5-dimethoxyphenyl}-5,6,7,8-tetrahydronaphthalen-2-ol

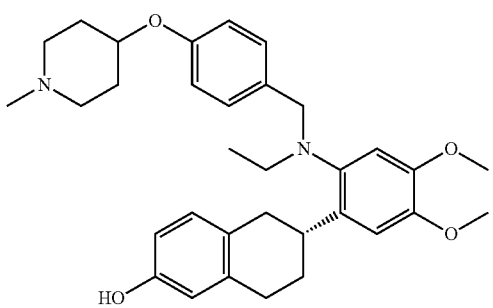

Synthesized from pivalic acid (R)-6-(2-ethylamino-4,5-dimethoxyphenyl)-5,6,7,8-tetrahydronaphthalen-2-yl ester (35 mg) and 4-(1-methylpiperidin-4-yloxy)benzaldehyde (94 mg) according to an analogous synthetic method to Example 264 and purified by LC-MS, the title compound (37 mg) was obtained.

ESI-Mass; 531 [M$^+$+H]

Example 266

(R)-6-{2-{Ethyl[3-fluoro-4-(1-methylpiperidin-4-yloxy)benzyl]amino}-4,5-dimethoxyphenyl}-5,6,7,8-tetrahydronaphthalen-2-ol

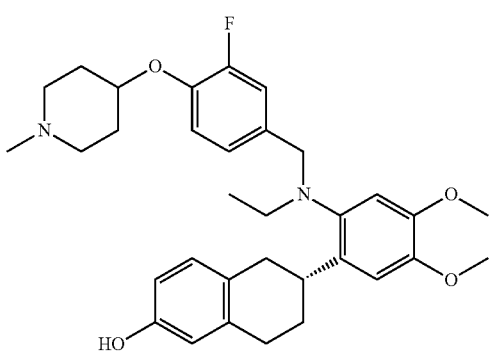

Synthesized from pivalic acid (R)-6-(2-ethylamino-4,5-dimethoxyphenyl)-5,6,7,8-tetrahydronaphthalen-2-yl ester (20 mg) and 3-fluoro-4-(1-methylpiperidin-4-yloxy)benzaldehyde (55 mg) according to an analogous synthetic method to Example 264 and purified by LC-MS, the title compound (9.2 mg) was obtained.

ESI-Mass; 549 [M$^+$+H]

Example 267

(R)-6-{2-{[4-(2-Dimethylamino-2-methylpropoxy)-3-fluorobenzyl]ethylamino}-4,5-dimethoxyphenyl}-5,6,7,8-tetrahydronaphthalen-2-ol

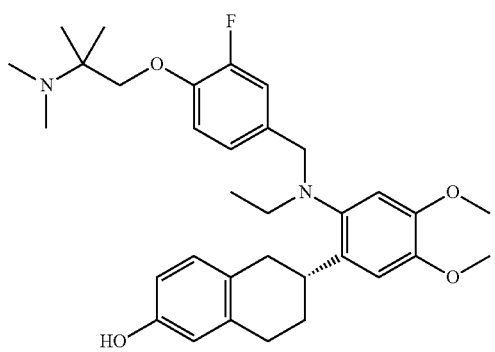

Synthesized from pivalic acid (R)-6-(2-ethylamino-4,5-dimethoxyphenyl)-5,6,7,8-tetrahydronaphthalen-2-yl ester (20 mg) and 4-(2-dimethylamino-2-methylpropoxy)-3-fluorobenzaldehyde (55 mg) according to an analogous synthetic method to Example 264 and purified by LC-MS, the title compound (10 mg) was obtained.

ESI-Mass; 551 [M$^+$+H]

Example 268

(R)-6-{2-{[4-(1-Dimethylaminocyclopentylmethoxy)benzyl]ethylamino}-4,5-dimethoxyphenyl}-5,6,7,8-tetrahydronaphthalen-2-ol

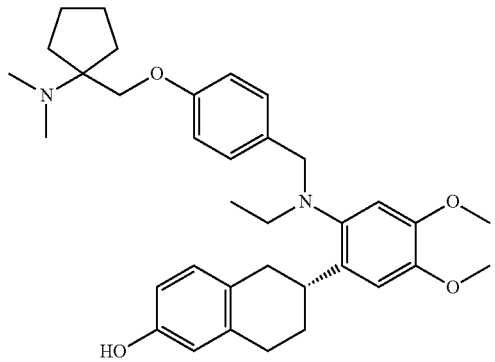

Synthesized from pivalic acid (R)-6-(2-ethylamino-4,5-dimethoxyphenyl)-5,6,7,8-tetrahydronaphthalen-2-yl ester (20 mg) and 4-(2-dimethylamino-2-methylpropoxy)-3-fluorobenzaldehyde (57 mg) according to an analogous synthetic method to Example 264 and purified by LC-MS, the title compound (11 mg) was obtained.

ESI-Mass; 559 [M$^+$+H]

Example 269

(R)-6-{2-{Ethyl[4-(piperidin-4-yloxy)benzyl]amino}-4,5-dimethoxyphenyl}-5,6,7,8-tetrahydronaphthalen-2-ol

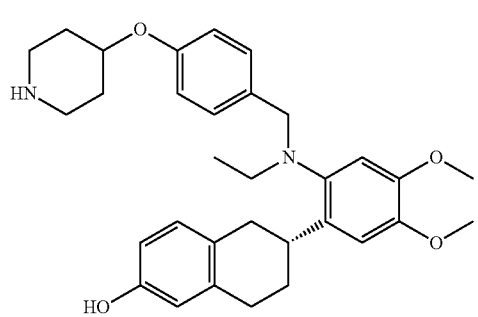 [SMILES: CCN(Cc1ccc(OC2CCNCC2)cc1)c1cc(OC)c(OC)cc1[C@@H]1CCc2cc(O)ccc2C1]

Synthesized from pivalic acid (R)-6-(2-ethylamino-4,5-dimethoxyphenyl)-5,6,7,8-tetrahydronaphthalen-2-yl ester (20 mg) and 4-(2-dimethylamino-2-methylpropoxy)-3-fluorobenzaldehyde (72 mg) according to an analogous synthetic method to Example 238 and purified by LC-MS, the title compound (6.1 mg) was obtained.

ESI-Mass; 517 [M$^+$+H]

Example 270

(R)-6-{2-{Ethyl[3-fluoro-4-(piperidin-4-yloxy)benzyl]amino}-4,5-dimethoxyphenyl}-5,6,7,8-tetrahydronaphthalen-2-ol

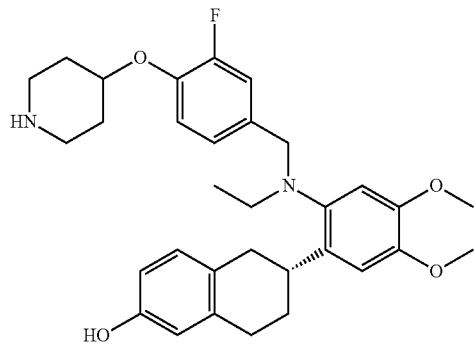 [SMILES: CCN(Cc1ccc(OC2CCNCC2)c(F)c1)c1cc(OC)c(OC)cc1[C@@H]1CCc2cc(O)ccc2C1]

Synthesized from pivalic acid (R)-6-(2-ethylamino-4,5-dimethoxyphenyl)-5,6,7,8-tetrahydronaphthalen-2-yl ester (20 mg) and 4-(2-fluoro-4-formylphenoxy)piperidine-1-carboxylic acid tert-butyl ester (75 mg) according to an analogous synthetic method to Example 238 and purified by LC-MS, the title compound (7.7 mg) was obtained.

ESI-Mass; 535 [M$^+$+H]

Example 271

(R)-6-{2-{Ethyl[4-(1-ethylpiperidin-4-yloxy)benzyl]amino}-4,5-dimethoxyphenyl}-5,6,7,8-tetrahydronaphthalen-2-ol

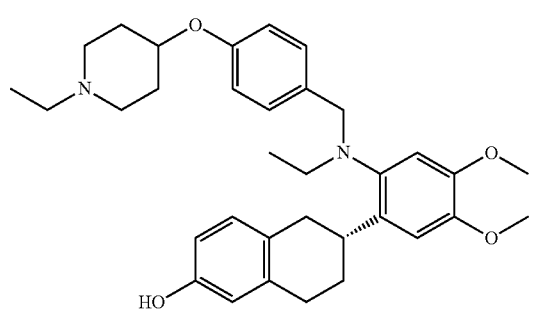 [SMILES: CCN1CCC(Oc2ccc(CN(CC)c3cc(OC)c(OC)cc3[C@@H]3CCc4cc(O)ccc4C3)cc2)CC1]

Synthesized from pivalic acid (R)-6-(2-ethylamino-4,5-dimethoxyphenyl)-5,6,7,8-tetrahydronaphthalen-2-yl ester (20 mg) and 4-(1-acetylpiperidin-4-yloxy)benzaldehyde (57 mg) according to an analogous synthetic method to Example 264 and purified by LC-MS, the title compound (13 mg) was obtained.

ESI-Mass; 545 [M$^+$+H]

Example 272

(R)-6-{2-{Ethyl[4-(1-ethylpiperidin-4-yloxy)-3-fluorobenzyl]amino}-4,5-dimethoxyphenyl}-5,6,7,8-tetrahydronaphthalen-2-ol

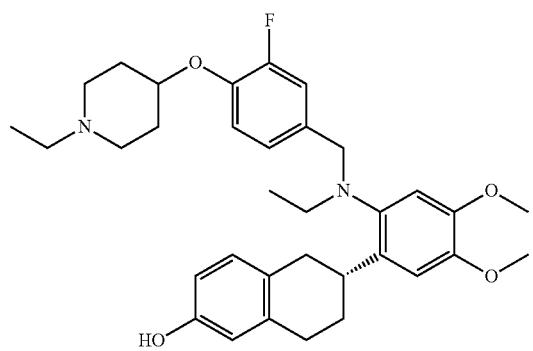 [SMILES: CCN1CCC(Oc2ccc(CN(CC)c3cc(OC)c(OC)cc3[C@@H]3CCc4cc(O)ccc4C3)cc2F)CC1]

Synthesized from pivalic acid (R)-6-(2-ethylamino-4,5-dimethoxyphenyl)-5,6,7,8-tetrahydronaphthalen-2-yl ester (20 mg) and 4-(1-acetylpiperidin-4-yloxy)benzaldehyde (61 mg) according to an analogous synthetic method to Example 264 and purified by LC-MS, the title compound (16 mg) was obtained.

ESI-Mass; 563 [M$^+$+H]

Example 273

(R)-6-{2-{[4-(2-Amino-2-methylpropoxy)-3-fluorobenzyl]ethylamino}-4,5-dimethoxyphenyl}-5,6,7,8-tetrahydronaphthalen-2-ol

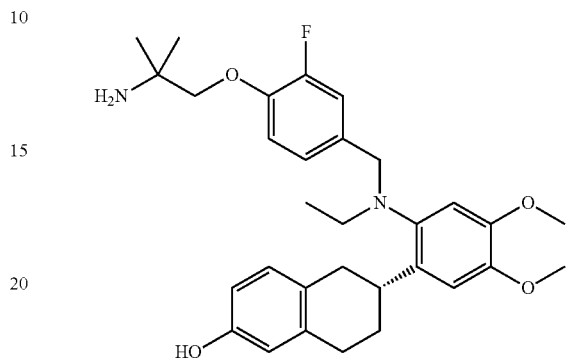

Synthesized from pivalic acid (R)-6-(2-ethylamino-4,5-dimethoxyphenyl)-5,6,7,8-tetrahydronaphthalen-2-yl ester (20 mg) and tert-butyl[2-(2-fluoro-4-formylphenoxy)-1,1-dimethylethyl]carbamate (72 mg) according to an analogous synthetic method to Example 238 and purified by LC-MS, the title compound (13 mg) was obtained.

ESI-Mass; 523 [M$^+$+H]

Example 274

(R)-6-{2-{[4-(2-Amino-2-methylpropoxy)benzyl]ethylamino}-4,5-dimethoxyphenyl}-5,6,7,8-tetrahydronaphthalen-2-ol

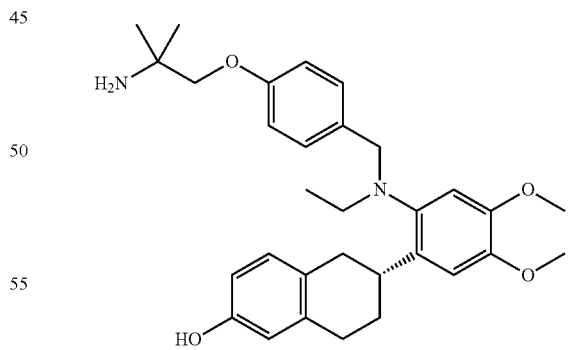

Synthesized from pivalic acid (R)-6-(2-ethylamino-4,5-dimethoxyphenyl)-5,6,7,8-tetrahydronaphthalen-2-yl ester (35 mg) and tert-butyl[2-(4-formylphenoxy)-1,1-dimethylethyl]carbamate (125 mg) according to an analogous synthetic method to Example 238 and purified by LC-MS, the title compound (32 mg) was obtained.

ESI-Mass; 505 [M$^+$+H]

Example 275

(R)-6-{2-{[4-(1-Aminocyclopentylmethoxy)benzyl]ethylamino}-4,5-dimethoxyphenyl}-5,6,7,8-tetrahydronaphthalen-2-ol

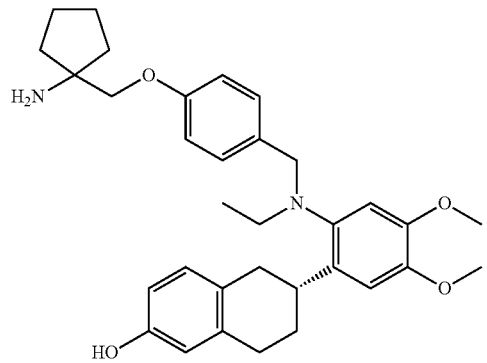 [SMILES: CCN(Cc1ccc(OCC2(N)CCCC2)cc1)c1cc(OC)c(OC)cc1[C@@H]1CCc2cc(O)ccc2C1]

Synthesized from pivalic acid (R)-6-(2-ethylamino-4,5-dimethoxyphenyl)-5,6,7,8-tetrahydronaphthalen-2-yl ester (20 mg) and tert-butyl[1-(4-formylphenoxymethyl)cyclopentyl]carbamate (74 mg) according to an analogous synthetic method to Example 238 and purified by LC-MS, the title compound (24 mg) was obtained.

ESI-Mass; 531 [M$^+$+H]

Example 276

6-{6-{[4-(2-Azepan-1-ylethoxy)benzyl]ethylamino}benzo[1,3]dioxol-5-yl}-5,6,7,8-tetrahydronaphthalen-2-ol

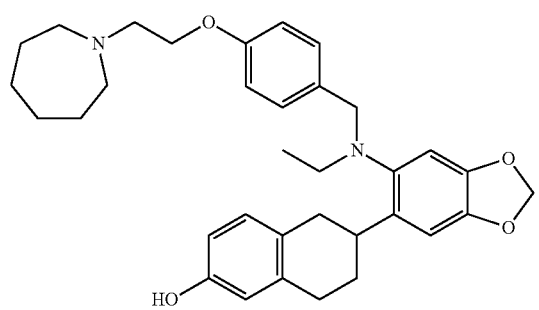 [SMILES: CCN(Cc1ccc(OCCN2CCCCCC2)cc1)c1cc2c(cc1C1CCc3cc(O)ccc3C1)OCO2]

Synthesized from pivalic acid 6-(6-ethylaminobenzo[1,3]dioxol-5-yl)-5,6,7,8-tetrahydronaphthalen-2-yl ester (40 mg) and 4-(2-azepan-1-ylethoxy)benzoic acid hydrochloride (80 mg) according to an analogous synthetic method to Example 337 described below, the title compound (42 mg) was obtained.

$^1$H-NMR (400 MHz, DMSO-d$_6$); δ (ppm): 0.83 (t, 3H), 1.32-1.43 (m, 1H), 1.48-1.69 (m, 9H), 2.26-2.40 (m, 1H), 2.58-2.74 (m, 7H), 2.75-2.86 (m, 4H), 3.54-3.63 (m, 1H), 3.84 (dd, 2H), 3.93-4.01 (m, 2H), 5.94 (s, 2H), 6.46-6.51 (m, 2H), 6.71-6.79 (m, 4H), 6.94 (s, 1H), 7.02 (d, 2H), 8.98 (s, 1H).

ESI-Mass; 543 [M$^+$+H]

Example 277

6-{6-[(4-Azepan-1-ylmethylbenzyl)ethylamino]benzo[1,3]dioxol-5-yl}-5,6,7,8-tetrahydronaphthalen-2-ol Synthesized from pivalic acid 6-(6-ethylaminobenzo[1,3]dioxol-5-yl)-5,6,7,8-tetrahydronaphthalen-2-yl ester (40 mg) and 4-azepan-1-ylmethylbenzoic acid hydrochloride (80 mg) according to an analogous synthetic method to Example 337 described below, the title compound (14 mg) was obtained.

$^1$H-NMR (400 MHz, DMSO-d$_6$); δ (ppm): 0.84 (t, 3H), 1.50-1.64 (m, 10H), 2.34-2.56 (m, 6H), 2.64-2.72 (m, 2H), 2.83 (q, 2H), 3.51 (s, 2H), 3.56-3.64 (m, 1H), 3.89 (dd, 2H), 5.94 (s, 2H), 6.46-6.51 (m, 2H), 6.71-6.79 (m, 2H), 6.97 (s, 1H), 7.06 (d, 2H), 7.13 (d, 2H), 8.98 (s, 1H).

ESI-Mass; 513 [M$^+$+H]

Example 278

6-{6-{[4-(2-Azepan-1-ylethyl)benzyl]ethylamino}benzo[1,3]dioxol-5-yl}-5,6,7,8-tetrahydronaphthalen-2-ol Synthesized from pivalic acid 6-(6-ethylaminobenzo[1,3]dioxol-5-yl)-5,6,7,8-tetrahydronaphthalen-2-yl ester (40 mg) and 4-(2-azepan-1-ylethyl)benzoic acid hydrochloride (80 mg) according to an analogous synthetic method to Example 337 described below, the title compound (34 mg) was obtained.

$^1$H-NMR (400 MHz, DMSO-d$_6$); δ (ppm): 0.84 (t, 3H), 1.30-1.39 (m, 1H), 1.49-1.68 (m, 9H), 2.36-2.44 (m, 1H), 2.56-2.76 (m, 11H), 2.82 (q, 2H), 3.56-3.65 (m, 1H), 3.88 (dd, 2H), 5.94 (s, 2H), 6.47-6.51 (m, 2H), 6.76-6.79 (m, 2H), 6.96 (s, 1H), 7.02-7.08 (m, 4H), 8.99 (s, 1H).
ESI-Mass; 527 [M⁺+H]

Example 279

6-{6-{[4-(3-Azepan-1-ylpropyl)benzyl]ethylamino}benzo[1,3]dioxol-5-yl}-5,6,7,8-tetrahydronaphthalen-2-ol

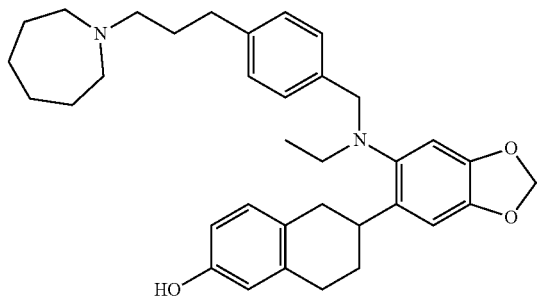 [SMILES: CCN(Cc1ccc(CCCN2CCCCCC2)cc1)c1cc2c(cc1C1CCc3cc(O)ccc3C1)OCO2]

Synthesized from pivalic acid 6-(6-ethylaminobenzo[1,3]dioxol-5-yl)-5,6,7,8-tetrahydronaphthalen-2-yl ester (40 mg) and 4-(3-azepan-1-ylpropyl)benzoic acid hydrochloride (80 mg) according to an analogous synthetic method to Example 337 described below, the title compound (32 mg) was obtained.
¹H-NMR (400 MHz, DMSO-d₆); δ (ppm): 0.84 (t, 3H), 1.28-1.38 (m, 1H), 1.49-1.70 (m, 11H), 2.32-2.62 (m, 10H), 2.64-2.73 (m, 2H), 2.83 (q, 2H), 3.56-3.65 (m, 1H), 3.88 (dd, 2H), 5.95 (s, 2H), 6.47-6.52 (m, 2H), 6.73-6.78 (m, 2H), 6.97 (s, 1H), 7.01-7.07 (m, 4H), 8.99 (s, 1H).
ESI-Mass; 541 [M⁺+H]

Example 280

6-{6-{Ethyl[4-(1-methylpiperidin-4-yl)benzyl]amino}benzo[1,3]dioxol-5-yl}-5,6,7,8-tetrahydronaphthalen-2-ol

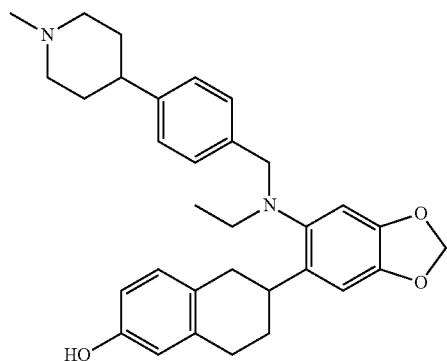 [SMILES: CCN(Cc1ccc(C2CCN(C)CC2)cc1)c1cc2c(cc1C1CCc3cc(O)ccc3C1)OCO2]

Synthesized from pivalic acid 6-(6-ethylaminobenzo[1,3]dioxol-5-yl)-5,6,7,8-tetrahydronaphthalen-2-yl ester (40 mg) and 4-(4-carboxyphenyl)piperidine-1-carboxylic acid text-butyl ester (60 mg) according to an analogous synthetic method to Example 337 described below, the title compound (35 mg) was obtained.

¹H-NMR (400 MHz, DMSO-d₆); δ (ppm): 0.83 (t, 3H), 1.24-1.32 (m, 1H), 1.56-1.70 (m, 5H), 1.88-1.97 (m, 2H), 2.18 (s, 3H), 2.33-2.56 (m, 3H), 2.62-2.72 (m, 2H), 2.78-2.87 (m, 4H), 3.54-3.64 (m, 1H), 3.87 (dd, 2H), 5.95 (s, 2H), 6.46-6.51 (m, 2H), 6.74-6.79 (m, 2H), 6.98 (s, 1H), 7.04-7.11 (m, 4H), 8.99 (s, 1H).
ESI-Mass; 499 [M⁺+H]

Example 281

6-{6-[Ethyl(4-piperidin-4-ylbenzyl)amino]benzo[1,3]dioxol-5-yl}-5,6,7,8-tetrahydronaphthalen-2-ol

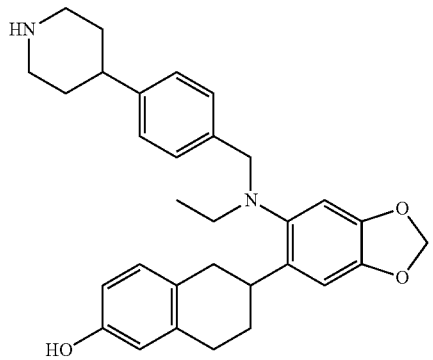 [SMILES: CCN(Cc1ccc(C2CCNCC2)cc1)c1cc2c(cc1C1CCc3cc(O)ccc3C1)OCO2]

Synthesized from pivalic acid 6-(6-ethylaminobenzo[1,3]dioxol-5-yl)-5,6,7,8-tetrahydronaphthalen-2-yl ester (40 mg) and 4-(4-carboxyphenyl)piperidine-1-carboxylic acid tert-butyl ester (60 mg) according to an analogous synthetic method to Example 209, the title compound (20 mg) was obtained.
¹H-NMR (400 MHz, DMSO-d₆); δ (ppm): 0.84 (t, 3H), 1.38-1.51 (m, 3H), 1.56-1.65 (m, 3H), 2.36-2.58 (m, 5H), 2.65-2.71 (m, 2H), 2.83 (q, 2H), 2.86-3.02 (m, 2H), 3.55-3.64 (m, 1H), 3.87 (dd, 2H), 5.95 (s, 2H), 6.46-6.52 (m, 2H), 6.74-6.79 (m, 2H), 6.98 (s, 1H), 7.04-7.08 (m, 4H), 9.00 (s, 1H).
ESI-Mass; 485 [M⁺+H]

Example 282

[3-Fluoro-4-(2-piperidin-1-ylethoxy)benzyl][2-(6-methoxy-1,2,3,4-tetrahydronaphthalen-2-yl)phenyl]amine

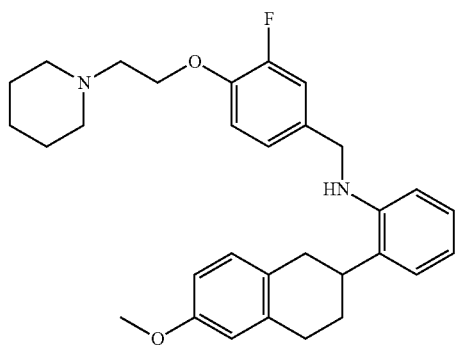 [SMILES: COc1ccc2c(c1)CCC(c1ccccc1NCc1ccc(OCCN3CCCCC3)c(F)c1)C2]

To a solution of 3-fluoro-4-(2-piperidin-1-ylethoxy)benzoic acid hydrochloride (2.0 g) in thionyl chloride (20 ml) was added toluene (20 ml), the solution was stirred for 30 minutes at 100° C., then the reaction solution was concentrated in vacuo to provide 3-fluoro-4-(2-piperidin-1-ylethoxy)benzoyl chloride hydrochloride (2.0 g). To a solution of 2-(6-methoxy-1,2,3,4-tetrahydronaphthalen-2-yl)phenylamine (253 mg) in dichloromethane (8 ml) were sequentially added an aqueous solution of 1N sodium hydroxide (4 ml) and 3-fluoro-4-(2-piperidin-1-ylethoxy)benzoyl chloride hydrochloride (400 mg), and the solution was stirred overnight at room temperature. The solution was extracted with ethyl acetate, then sequentially washed with water and brine, dried over anhydrous magnesium sulfate, then the solvent was evaporated in vacuo. Synthesized from the resulting 3-fluoro-N-[2-(6-methoxy-1,2,3,4-tetrahydronaphthalen-2-yl)phenyl]-4-(2-piperidin-1-ylethoxy)benzamide (423 mg) according to an analogous synthetic method to Example 337 described below, the title compound (418 mg) was obtained.

$^1$H-NMR (400 MHz, CDCl$_3$); δ (ppm): 1.41-1.50 (m, 2H), 1.55-1.65 (m, 4H), 1.94-2.05 (m, 1H), 2.10-2.18 (m, 1H), 2.46-2.55 (m, 4H), 2.75-2.82 (m, 3H), 2.87-2.98 (m, 3H), 3.00-3.07 (m, 1H), 3.79 (s, 3H), 4.07 (brs, 1H), 4.16 (t, 2H), 4.29 (s, 2H), 6.63 (dd, 1H), 6.68 (d, 1H), 6.71 (dd, 1H), 6.77 (dt, 1H), 6.93 (t, 1H), 7.00-7.14 (m, 4H), 7.17 (dd, 1H).

Example 283

6-{2-{Ethyl[3-fluoro-4-(2-piperidin-1-ylethoxy)benzyl]amino}phenyl}-5,6,7,8-tetrahydronaphthalen-2-ol

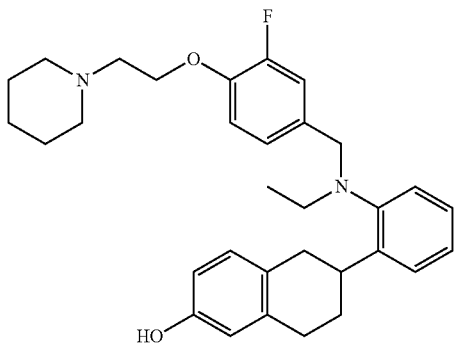 [SMILES: CCN(Cc1ccc(OCCN2CCCCC2)c(F)c1)c1ccccc1C1CCc2cc(O)ccc2C1]

Synthesized from [3-fluoro-4-(2-piperidin-1-ylethoxy)benzyl][2-(6-methoxy-1,2,3,4-tetrahydronaphthalen-2-yl)phenyl]amine according to an analogous synthetic method to Example 36, ethyl[3-fluoro-4-(2-piperidin-1-ylethoxy)benzyl][2-(6-methoxy-1,2,3,4-tetrahydronaphthalen-2-yl)phenyl]amine (332 mg) was used according to an analogous synthetic method to Example 111 to provide the title compound (280 mg).

$^1$H-NMR (400 MHz, DMSO-d$_6$); δ (ppm): 0.86 (t, 3H), 1.30-1.39 (m, 2H), 1.42-1.49 (m, 4H), 1.52-1.60 (m, 1H), 1.66-1.78 (m, 1H), 2.34-2.43 (m, 4H), 2.51-2.64 (m, 4H), 2.71-2.79 (m, 2H), 2.88 (q, 2H), 3.55-3.64 (m, 1H), 3.95 (dd, 2H), 4.04 (t, 2H), 6.47-6.51 (m, 2H), 6.80 (d, 1H), 6.89 (d, 1H), 6.95 (dd, 1H), 7.00 (t, 1H), 7.06 (dt, 1H), 7.15 (dt, 1H), 7.22-7.26 (m, 2H), 9.02 (s, 1H).

ESI-Mass; 503 [M$^+$+H]

Example 284

Ethyl[2-(6-methoxy-1,2,3,4-tetrahydronaphthalen-2-yl)phenyl]amine

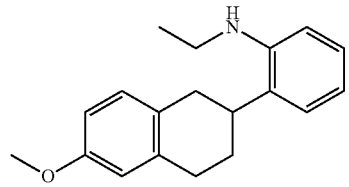 [SMILES: CCNc1ccccc1C1CCc2cc(OC)ccc2C1]

Synthesized from 2-(6-methoxy-1,2,3,4-tetrahydronaphthalen-2-yl)phenylamine (1.0 g) according to an analogous synthetic method to Example 36, the title compound (998 mg) was obtained.

$^1$H-NMR (400 MHz, CDCl$_3$); δ (ppm): 1.28 (t, 3H), 1.84-2.06 (m, 1H), 2.08-2.15 (m, 1H), 2.75 (dd, 1H), 2.85-3.06 (m, 4H), 3.20 (q, 2H), 3.59 (brs, 1H), 3.80 (s, 3H), 6.66-6.77 (m, 4H), 7.02 (d, 1H), 7.14 (d, 1H), 7.16 (dd, 1H).

Example 285

6-{2-{Ethyl[4-(2-pyrrolidin-1-ylethoxy)benzyl]amino}phenyl}-5,6,7,8-tetrahydronaphthalen-2-ol

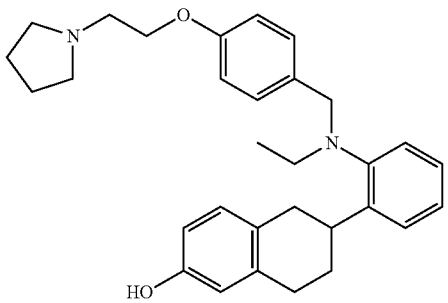 [SMILES: CCN(Cc1ccc(OCCN2CCCC2)cc1)c1ccccc1C1CCc2cc(O)ccc2C1]

Synthesized from ethyl[2-(6-methoxy-1,2,3,4-tetrahydronaphthalen-2-yl)phenyl]amine and 4-(2-pyrrolidin-1-ylethoxy)benzoic acid hydrochloride according to an analogous synthetic method to Example 152, ethyl[2-(6-methoxy-1,2,3,4-tetrahydronaphthalen-2-yl)phenyl][4-(2-pyrrolidin-1-ylethoxy)benzyl]amine (446 mg) was used according to an analogous synthetic method to Example 111 to provide the title compound (303 mg).

$^1$H-NMR (400 MHz, DMSO-d$_6$); δ (ppm): 0.84 (t, 3H), 1.51-1.59 (m, 1H), 1.60-1.85 (m, 5H), 2.41-2.62 (m, 6H), 2.66-2.77 (m, 4H), 2.87 (q, 2H), 3.56-3.65 (m, 1H), 3.92 (dd, 2H), 3.97 (t, 2H), 6.46-6.51 (m, 2H), 6.73-6.81 (m, 3H), 7.02-7.08 (m, 3H), 7.15 (dt, 1H), 7.22 (dd, 1H), 7.24 (dd, 1H), 9.00 (s, 1H).

ESI-Mass; 471 [M$^+$+H]

Example 286

6-{2-{Ethyl[4-(2-piperidin-1-ylethoxy)benzyl]amino}phenyl}-5,6,7,8-tetrahydronaphthalen-2-ol

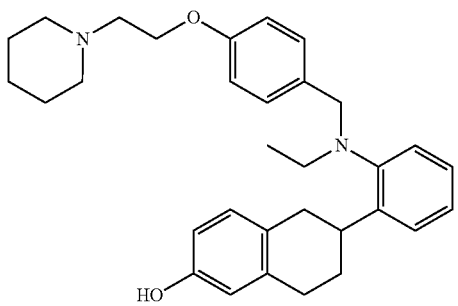

Synthesized from ethyl[2-(6-methoxy-1,2,3,4-tetrahydronaphthalen-2-yl)phenyl]amine and 4-(2-piperidin-1-ylethoxy)benzoic acid hydrochloride according to an analogous synthetic method to Example 152, ethyl[2-(6-methoxy-1,2,3,4-tetrahydronaphthalen-2-yl)phenyl][4-(2-piperidin-1-ylethoxy)benzyl]amine (507 mg) was used according to an analogous synthetic method to Example 111 to provide the title compound (394 mg).

$^1$H-NMR (400 MHz, DMSO-$d_6$); δ (ppm): 0.84 (t, 3H), 1.30-1.38 (m, 2H), 1.41-1.50 (m, 4H), 1.50-1.59 (m, 1H), 1.64-1.75 (m, 1H), 2.33-2.42 (m, 4H), 2.45-2.62 (m, 4H), 2.67-2.77 (m, 2H), 2.87 (q, 2H), 3.56-3.65 (m, 1H), 3.92 (dd, 2H), 3.96 (t, 2H), 6.46-6.51 (m, 2H), 6.73-6.81 (m, 3H), 7.02-7.08 (m, 3H), 7.15 (dt, 1H), 7.22 (dd, 1H), 7.24 (dd, 1H), 9.01 (s, 1H).

ESI-Mass; 485 [M$^+$+H]

Example 287

6-{2-{[4-(2-Azepan-1-ylethoxy)benzyl]ethylamino}phenyl}-5,6,7,8-tetrahydronaphthalen-2-ol

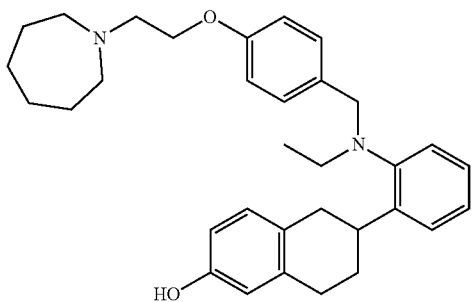 [SMILES: CCN(Cc1ccc(OCCN2CCCCCC2)cc1)c1ccccc1C1CCc2cc(O)ccc2C1]

Synthesized from ethyl[2-(6-methoxy-1,2,3,4-tetrahydronaphthalen-2-yl)phenyl]amine and 4-(2-azepan-1-ylethoxy)benzoic acid hydrochloride according to an analogous synthetic method to Example 152, [4-(2-azepan-1-ylethoxy)benzyl]ethyl[2-(6-methoxy-1,2,3,4-tetrahydronaphthalen-2-yl)phenyl]amine (504 mg) was used according to an analogous synthetic method to Example 111 to provide the title compound (394 mg).

$^1$H-NMR (400 MHz, DMSO-$d_6$); δ (ppm): 0.84 (t, 3H), 1.47-1.59 (m, 9H), 1.64-1.75 (m, 1H), 2.45-2.67 (m, 6H), 2.69-2.78 (m, 2H), 2.78 (t, 2H), 2.87 (q, 2H), 3.56-3.65 (m, 1H), 3.92 (dd, 2H), 3.94 (t, 2H), 6.45-6.51 (m, 2H), 6.73-6.81 (m, 3H), 7.02-7.08 (m, 3H), 7.15 (dt, 1H), 7.22 (dd, 1H), 7.24 (dd, 1H), 9.01 (s, 1H).

ESI-Mass; 499 [M$^+$+H]

Example 288

6-{2-{Ethyl{2-[3-fluoro-4-(2-piperidin-1-ylethoxy)phenyl]ethyl}amino}phenyl}-5,6,7,8-tetrahydronaphthalen-2-ol

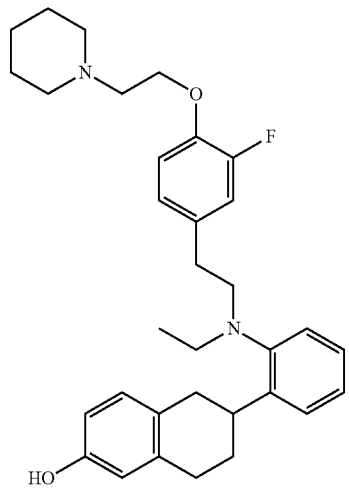 [SMILES: CCN(CCc1ccc(OCCN2CCCCC2)c(F)c1)c1ccccc1C1CCc2cc(O)ccc2C1]

Synthesized from ethyl[2-(6-methoxy-1,2,3,4-tetrahydronaphthalen-2-yl)phenyl]amine and [3-fluoro-4-(2-piperidin-1-ylethoxy)phenyl]acetic acid hydrochloride according to an analogous synthetic method to Example 337 described below, ethyl {2-[3-fluoro-4-(2-piperidin-1-ylethoxy)phenyl]ethyl}[2-(6-methoxy-1,2,3,4-tetrahydronaphthalen-2-yl)phenyl]amine (302 mg) was used according to an analogous synthetic method to Example 111 to provide the title compound (233 mg).

$^1$H-NMR (400 MHz, DMSO-$d_6$); δ (ppm): 0.86 (t, 3H), 1.30-1.39 (m, 2H), 1.41-1.50 (m, 4H), 1.59-1.80 (m, 2H), 2.33-2.43 (m, 4H), 2.47-2.73 (m, 8H), 2.92 (q, 2H), 3.09 (t, 2H), 3.35-3.45 (m, 1H), 3.99 (t, 2H), 6.44-6.51 (d, 2H), 6.79 (t, 2H), 6.89-6.96 (m, 2H), 7.08 (dt, 1H), 7.17 (dt, 1H), 7.23 (dd, 1H), 7.27 (dd, 1H), 9.00 (s, 1H).

ESI-Mass; 517 [M$^+$+H]

Example 289

(R)-6-{2-{Ethyl[4-(1-methylpiperidin-4-yloxy)benzyl]amino}phenyl}-5,6,7,8-tetrahydronaphthalen-2-ol

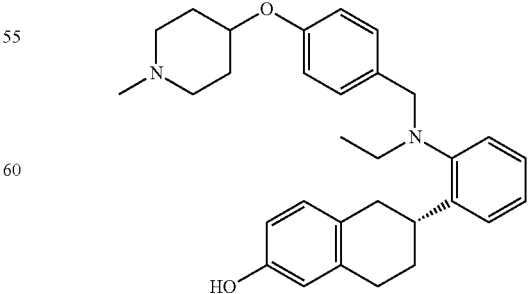

Synthesized from pivalic acid (R)-6-(2-ethylaminophenyl)-5,6,7,8-tetrahydronaphthalen-2-yl ester (30 mg) and 4-(1-methylpiperidin-4-yloxy)benzaldehyde (94 mg) according to an analogous synthetic method to Example 264 and purified by LC-MS, the title compound (24 mg) was obtained.

ESI-Mass; 471 [M++H]

Example 290

(R)-6-{2-{[4-(2-Amino-2-methylpropoxy)benzyl]ethylamino}phenyl}-5,6,7,8-tetrahydronaphthalen-2-ol

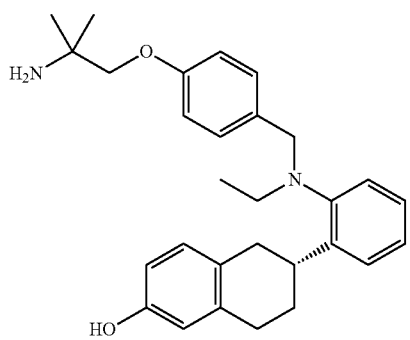 [SMILES: CCN(Cc1ccc(OCC(C)(C)N)cc1)c1ccccc1[C@@H]1CCc2cc(O)ccc2C1]

Synthesized from pivalic acid (R)-6-(2-ethylaminophenyl)-5,6,7,8-tetrahydronaphthalen-2-yl ester (30 mg) and tert-butyl[2-(4-formylphenoxy)-1,1-dimethylethyl]carbamate (125 mg) according to an analogous synthetic method to Example 238 and purified by LC-MS, the title compound (11 mg) was obtained.

ESI-Mass; 445 [M++H]

Example 291

(S)-6-{2-{[4-(2-Amino-2-methylpropoxy)benzyl]ethylamino}phenyl}-5,6,7,8-tetrahydronaphthalen-2-ol

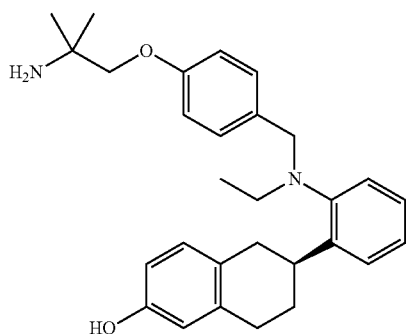 [SMILES: CCN(Cc1ccc(OCC(C)(C)N)cc1)c1ccccc1[C@H]1CCc2cc(O)ccc2C1]

Synthesized from pivalic acid (S)-6-(2-ethylaminophenyl)-5,6,7,8-tetrahydronaphthalen-2-yl ester (30 mg) and tert-butyl[2-(4-formylphenoxy)-1,1-dimethylethyl]carbamate (125 mg) according to an analogous synthetic method to Example 238 and purified by LC-MS, the title compound (20 mg) was obtained.

ESI-Mass; 445 [M++H]

Example 292

6-{2-{Ethyl[3-fluoro-4-(2-piperidin-1-ylethoxy)benzyl]amino}-6-methylphenyl}-5,6,7,8-tetrahydronaphthalen-2-ol

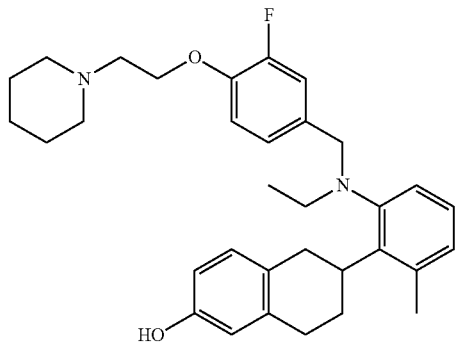 [SMILES: CCN(Cc1ccc(OCCN2CCCCC2)c(F)c1)c1cccc(C)c1C1CCc2cc(O)ccc2C1]

Synthesized from 2-(6-methoxy-1,2,3,4-tetrahydronaphthalen-2-yl)-3-methylphenylamine and 3-fluoro-4-(2-piperidin-1-ylethoxy)benzoyl chloride hydrochloride according to an analogous synthetic method to Example 152, [3-fluoro-4-(2-piperidin-1-ylethoxy)benzyl][2-(6-methoxy-1,2,3,4-tetrahydronaphthalen-2-yl)-3-methylphenyl]amine (578 mg) was used according to an analogous synthetic method to Example 36 to provide ethyl[3-fluoro-4-(2-piperidin-1-ylethoxy)benzyl][2-(6-methoxy-1,2,3,4-tetrahydronaphthalen-2-yl)-3-methylphenyl]amine (449 mg). This compound (447 mg) was used according to an analogous synthetic method to Example 111 to provide the title compound (317 mg).

$^1$H-NMR (400 MHz, DMSO-$d_6$); δ (ppm): 0.84 (t, 3H), 1.29-1.37 (m, 2H), 1.40-1.49 (m, 4H), 2.00-2.25 (m, 2H), 2.32 (s, 3H), 2.33-2.45 (m, 4H), 2.60 (t, 2H), 2.60-2.81 (m, 3H), 2.82 (q, 2H), 2.85-3.10 (m, 1H), 3.91 (s, 2H), 4.04 (t, 2H), 4.12-4.34 (m, 1H), 6.47-6.52 (m, 2H), 6.76-7.02 (m, 5H), 7.05 (t, 1H), 7.12 (d, 1H), 9.00 (s, 1H).

ESI-Mass; 517 [M++H]

Example 293

6-{2-{[4-(2-Azepan-1-ylethoxy)benzyl]ethylamino}-6-methylphenyl}-5,6,7,8-tetrahydronaphthalen-2-ol

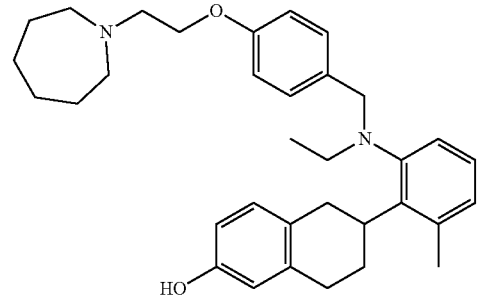 [SMILES: CCN(Cc1ccc(OCCN2CCCCCC2)cc1)c1cccc(C)c1C1CCc2cc(O)ccc2C1]

Synthesized from 2-(6-methoxy-1,2,3,4-tetrahydronaphthalen-2-yl)-3-methylphenylamine and 4-(2-azepan-1- ylethoxy)benzoyl chloride hydrochloride according to an analogous synthetic method to Example 152, [4-(2-azepan-1-ylethoxy)benzyl][2-(6-methoxy-1,2,3,4-tetrahydronaphthalen-2-yl)-3-methylphenyl]amine (565 mg) was used according to an analogous synthetic method to Example 36 to provide [4-(2-azepan-1-ylethoxy)benzyl]ethyl[2-(6-methoxy-1,2,3,4-tetrahydronaphthalen-2-yl)-3-methylphenyl]amine (437 mg). This compound (435 mg) was used according to an analogous synthetic method to Example 111 to provide the title compound (253 mg).

$^1$H-NMR (400 MHz, DMSO-d$_6$); δ (ppm): 0.82 (t, 3H), 1.45-1.59 (m, 8H), 2.00-2.25 (m, 2H), 2.32 (s, 3H), 2.58-3.05 (m, 12H), 3.87 (s, 2H), 3.94 (t, 2H), 4.15-4.35 (m, 1H), 6.47-6.52 (m, 2H), 6.64-6.88 (m, 4H), 7.01 (d, 2H), 7.06 (t, 1H), 7.12 (d, 1H), 9.00 (s, 1H).

ESI-Mass; 513 [M$^+$+H]

Example 294

6-{2-{Ethyl[3-fluoro-4-(2-piperidin-1-ylethoxy)benzyl]amino}-4-fluorophenyl}-5,6,7,8-tetrahydronaphthalen-2-ol

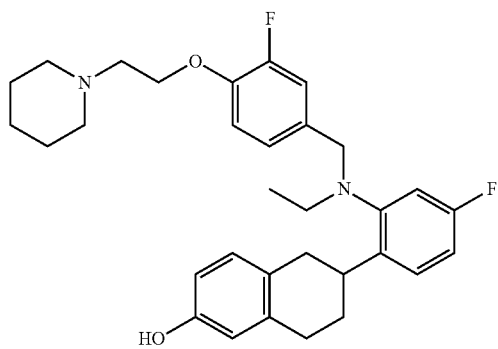 [SMILES: CCN(Cc1ccc(OCCN2CCCCC2)c(F)c1)c1cc(F)ccc1C1CCc2cc(O)ccc2C1]

Synthesized from 5-fluoro-2-(6-methoxy-1,2,3,4-tetrahydronaphthalen-2-yl)phenylamine and 3-fluoro-4-(2-piperidin-1-ylethoxy)benzoic acid hydrochloride according to an analogous synthetic method to Example 282, [5-fluoro-2-(6-methoxy-1,2,3,4-tetrahydronaphthalen-2-yl)phenyl][3-fluoro-4-(2-piperidin-1-ylethoxy)benzyl]amine (376 mg) was used according to an analogous synthetic method to Example 36 to provide ethyl[5-fluoro-2-(6-methoxy-1,2,3,4-tetrahydronaphthalen-2-yl)phenyl][3-fluoro-4-(2-piperidin-1-ylethoxy)benzyl]amine (317 mg). This compound (315 mg) was used according to an analogous synthetic method to Example 111 to provide the title compound (265 mg).

$^1$H-NMR (400 MHz, DMSO-d$_6$); δ (ppm): 0.88 (t, 3H), 1.30-1.39 (m, 2H), 1.41-1.50 (m, 4H), 1.51-1.60 (m, 1H), 1.66-1.78 (m, 1H), 2.33-2.42 (m, 4H), 2.50-2.64 (m, 4H), 2.70-2.79 (m, 2H), 2.88 (q, 2H), 3.45-3.55 (m, 1H), 3.97 (dd, 2H), 4.04 (t, 2H), 6.46-6.51 (m, 2H), 6.79 (d, 1H), 6.84-6.92 (m, 2H), 6.96 (dd, 1H), 7.01 (t, 1H), 7.07 (dd, 1H), 7.25 (dd, 1H), 9.02 (s, 1H).

ESI-Mass; 521 [M$^+$+H]

Example 295

6-{2-{Ethyl[3-fluoro-4-(2-piperidin-1-ylethoxy)benzyl]amino}-5-fluorophenyl}-5,6,7,8-tetrahydronaphthalen-2-ol

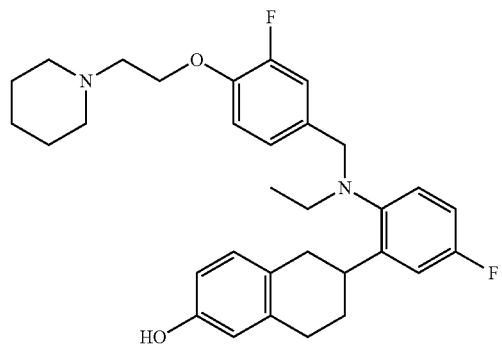 [SMILES: CCN(Cc1ccc(OCCN2CCCCC2)c(F)c1)c1ccc(F)cc1C1CCc2cc(O)ccc2C1]

Synthesized from 4-fluoro-2-(6-methoxy-1,2,3,4-tetrahydronaphthalen-2-yl)phenylamine and 3-fluoro-4-(2-piperidin-1-ylethoxy)benzoic acid hydrochloride according to an analogous synthetic method to Example 152, [4-fluoro-2-(6-methoxy-1,2,3,4-tetrahydronaphthalen-2-yl)phenyl][3-fluoro-4-(2-piperidin-1-ylethoxy)benzyl]amine (448 mg) was used according to an analogous synthetic method to Example 36 to provide ethyl[4-fluoro-2-(6-methoxy-1,2,3,4-tetrahydronaphthalen-2-yl)phenyl][3-fluoro-4-(2-piperidin-1-ylethoxy)benzyl]amine (395 mg). This compound (393 mg) was used according to an analogous synthetic method to Example 111 to provide the title compound (300 mg).

$^1$H-NMR (400 MHz, DMSO-d$_6$); δ (ppm): 0.85 (t, 3H), 1.30-1.39 (m, 2H), 1.41-1.52 (m, 5H), 1.64-1.75 (m, 1H), 2.34-2.50 (m, 5H), 2.52-2.63 (m, 3H), 2.67-2.77 (m, 2H), 2.86 (q, 2H), 3.52-3.63 (m, 1H), 3.92 (dd, 2H), 4.04 (t, 2H), 6.46-6.52 (m, 2H), 6.78 (d, 1H), 6.85 (d, 1H), 6.90-7.06 (m, 4H), 7.31 (dd, 1H), 9.03 (s, 1H).

ESI-Mass; 521 [M$^+$+H]

Example 296

6-{3-{Ethyl[3-fluoro-4-(2-piperidin-1-ylethoxy)benzyl]amino}-6-methoxypyridin-2-yl}-5,6,7,8-tetrahydronaphthalen-2-ol and 5-{ethyl[3-fluoro-4-(2-piperidin-1-ylethoxy)benzyl]amino}-6-(6-hydroxy-1,2,3,4-tetrahydronaphthalen-2-yl)pyridin-2-ol

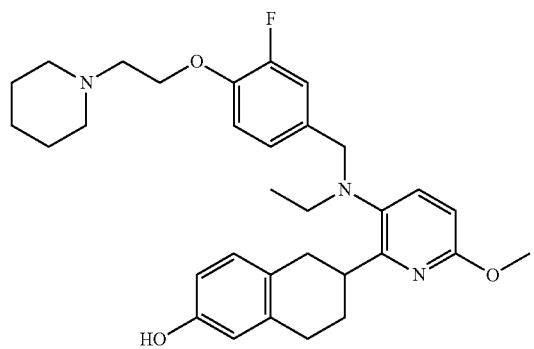

-continued

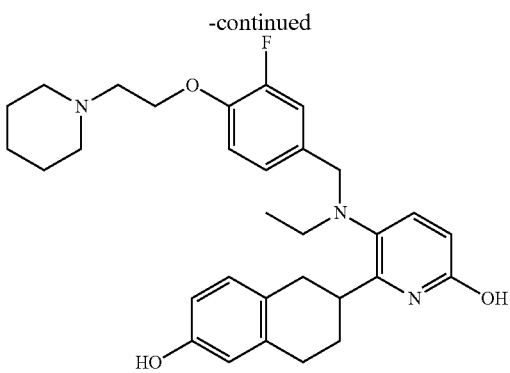

Synthesized from 6-methoxy-2-(6-methoxy-1,2,3,4-tetrahydronaphthalen-2-yl)pyridin-3-ylamine and 3-fluoro-4-(2-piperidin-1-ylethoxy)benzoic acid hydrochloride according to an analogous synthetic method to Example 282, [3-fluoro-4-(2-piperidin-1-ylethoxy)benzyl][6-methoxy-2-(6-methoxy-1,2,3,4-tetrahydronaphthalen-2-yl)pyridin-3-yl]amine (548 mg) was used according to an analogous synthetic method to Example 36 to provide ethyl[3-fluoro-4-(2-piperidin-1-ylethoxy)benzyl][6-methoxy-2-(6-methoxy-1,2,3,4-tetrahydronaphthalen-2-yl)pyridin-3-yl]amine (454 mg). This compound (452 mg) was used according to an analogous synthetic method to Example 111 to provide 6-{3-{ethyl[3-fluoro-4-(2-piperidin-1-ylethoxy)benzyl]amino}-6-methoxypyridin-2-yl}-5,6,7,8-tetrahydronaphthalen-2-ol (140 mg) and 5-{ethyl[3-fluoro-4-(2-piperidin-1-ylethoxy)benzyl]amino}-6-(6-hydroxy-1,2,3,4-tetrahydronaphthalen-2-yl)pyridin-2-ol (60 mg). 6-{3-{Ethyl[3-fluoro-4-(2-piperidin-1-ylethoxy)benzyl]amino}-6-methoxypyridin-2-yl}-5,6,7,8-tetrahydronaphthalen-2-ol $^{1}$H-NMR (400 MHz, DMSO-d$_{6}$); δ (ppm): 0.85 (t, 3H), 1.30-1.50 (m, 7H), 1.71-1.82 (m, 1H), 2.30-2.43 (m, 5H), 2.62 (t, 2H), 2.67-2.75 (m, 2H), 2.80-2.90 (m, 3H), 3.59-3.68 (m, 1H), 3.74 (s, 3H), 3.91 (dd, 2H), 4.05 (t, 2H), 6.46-6.51 (m, 2H), 6.60 (d, 1H), 6.78 (d, 1H), 6.86 (d, 1H), 6.96 (dd, 1H), 7.01 (t, 1H), 7.67 (d, 1H), 8.99 (s, 1H).

ESI-Mass; 534 [M$^{+}$+H]

5-{Ethyl[3-fluoro-4-(2-piperidin-1-ylethoxy)benzyl]amino}-6-(6-hydroxy-1,2,3,4-tetrahydronaphthalen-2-yl)pyridin-2-ol $^{1}$H-NMR (400 MHz, DMSO-d$_{6}$); δ (ppm): 0.83 (t, 3H), 1.30-1.39 (m, 2H), 1.40-1.51 (m, 5H), 1.76-1.93 (m, 1H), 2.34-2.44 (m, 5H), 2.50-2.70 (m, 4H), 2.70-2.90 (m, 3H), 3.41-3.52 (m, 1H), 3.69-3.85 (m, 2H), 4.07 (t, 2H), 6.21 (d, 1H), 6.42-6.48 (m, 2H), 6.65-6.76 (m, 1H), 6.77 (d, 1H), 6.90 (d, 1H), 7.01 (t, 1H), 7.60 (d, 1H), 9.03 (s, 1H), 11.03 (brs, 1H).

ESI-Mass; 520 [M$^{+}$+H]

Example 297

6-{2-{Ethyl[3-fluoro-4-(2-piperidin-1-ylethoxy)benzyl]amino}-4-trifluoromethylphenyl}-5,6,7,8-tetrahydronaphthalen-2-ol

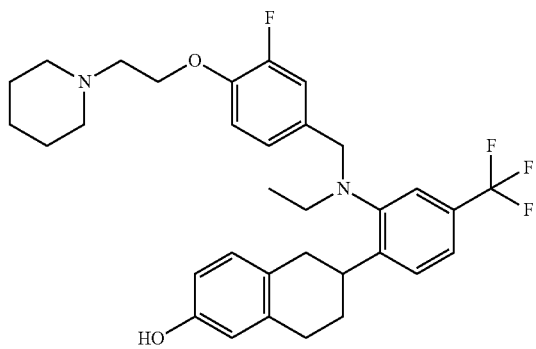 [SMILES: CCN(Cc1ccc(OCCN2CCCCC2)c(F)c1)c1cc(C(F)(F)F)ccc1C1CCc2cc(O)ccc2C1]

Synthesized from 2-(6-methoxy-1,2,3,4-tetrahydronaphthalen-2-yl)-5-trifluoromethylphenylamine and 3-fluoro-4-(2-piperidin-1-ylethoxy)benzoic acid hydrochloride according to an analogous synthetic method to Example 282, [3-fluoro-4-(2-piperidin-1-ylethoxy)benzyl][2-(6-methoxy-1,2,3,4-tetrahydronaphthalen-2-yl)-5-trifluoromethylphenyl]amine (407 mg) was used according to an analogous synthetic method to Example 36 to provide ethyl[3-fluoro-4-(2-piperidin-1-ylethoxy)benzyl][2-(6-methoxy-1,2,3,4-tetrahydronaphthalen-2-yl)-5-trifluoromethylphenyl]amine (343 mg). This compound (341 mg) was used according to an analogous synthetic method to Example 111 to provide the title compound (29 mg).

$^{1}$H-NMR (400 MHz, DMSO-d$_{6}$); δ (ppm): 0.88 (t, 3H), 1.29-1.38 (m, 2H), 1.40-1.49 (m, 4H), 1.55-1.64 (m, 1H), 1.70-1.82 (m, 1H), 2.32-2.43 (m, 4H), 2.50-2.69 (m, 4H), 2.72-2.80 (m, 2H), 2.93 (q, 2H), 3.55-3.65 (m, 1H), 3.99-4.07 (m, 4H), 6.47-6.52 (m, 2H), 6.81 (d, 1H), 6.88 (d, 1H), 6.96 (dd, 1H), 7.02 (t, 1H), 7.38-7.52 (m, 3H), 9.04 (s, 1H).

ESI-Mass; 571 [M$^{+}$+H]

Example 298

6-{2-{[4-(2-Azepan-1-ylethoxy)benzyl]ethylamino}-4-hydroxyphenyl}-6,7,8,9-tetrahydro-5H-benzocyclohepten-2-ol

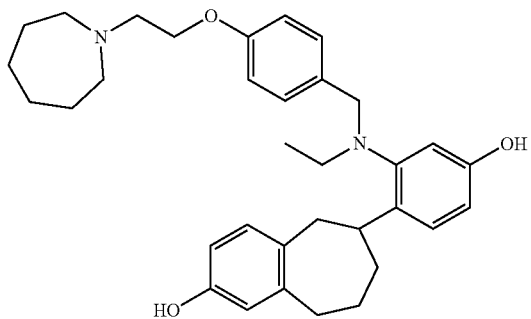 [SMILES: CCN(Cc1ccc(OCCN2CCCCCC2)cc1)c1cc(O)ccc1C1CCCc2cc(O)ccc2C1]

Synthesized from 5-methoxy-2-(2-methoxy-6,7,8,9-tetrahydro-5H-benzocyclohepten-6-yl)phenylamine and 4-(2-azepan-1-ylethoxy)benzoic acid hydrochloride according to an analogous synthetic method to Example 152, [4-(2-azepan-1-ylethoxy)benzyl][5-methoxy-2-(2-methoxy-6,7,8,9-tetrahydro-5H-benzocyclohepten-6-yl)phenyl]amine (485 mg) was used according to an analogous synthetic method to Example 36 to provide [4-(2-azepan-1-ylethoxy)benzyl]ethyl[5-methoxy-2-(2-methoxy-6,7,8,9-tetrahydro-5H-benzocyclohepten-6-yl)phenyl]amine (459 mg). This compound (457 mg) was used according to an analogous synthetic method to Example 111 to provide the title compound (394 mg).

$^{1}$H-NMR (400 MHz, DMSO-d$_{6}$); δ (ppm): 0.83 (t, 3H), 1.22-1.35 (m, 1H), 1.46-1.78 (m, 10H), 1.89-1.98 (m, 1H), 2.32-2.41 (m, 1H), 2.56-2.69 (m, 5H), 2.71-2.85 (m, 5H), 2.98-3.10 (m, 1H), 3.20 (t, 1H), 3.85 (dd, 2H), 3.96 (t, 2H), 6.45 (dd, 1H), 6.49 (dd, 1H), 6.55 (d, 1H), 6.56 (d, 1H), 6.75 (d, 2H), 6.79 (d, 1H), 7.05 (d, 2H), 7.06 (d, 1H), 9.03 (s, 1H), 9.05 (s, 1H).

ESI-Mass; 529 [M$^{+}$+H]

Example 299

6-{2-{[4-(2-Azepan-1-ylethoxy)benzyl]ethylamino}-4-hydroxyphenyl}-8,9-dihydro-7H-benzocyclohepten-2-ol

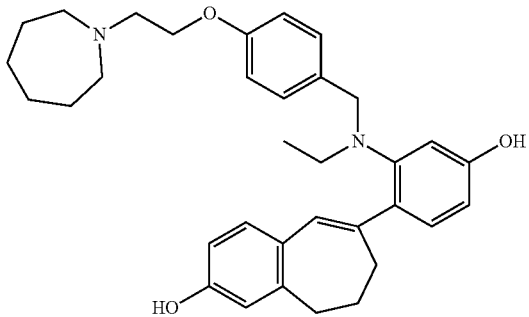 [SMILES: CCN(Cc1ccc(OCCN2CCCCCC2)cc1)c1cc(O)ccc1C1=Cc2ccc(O)cc2CCC1]

Synthesized from 5-methoxy-2-(2-methoxy-8,9-dihydro-7H-benzocyclohepten-6-yl)phenylamine and 4-(2-azepan-1-ylethoxy)benzoic acid hydrochloride according to an analogous synthetic method to Example 152, [4-(2-azepan-1-ylethoxy)benzyl][5-methoxy-2-(2-methoxy-8,9-dihydro-7H-benzocyclohepten-6-yl)phenyl]amine (458 mg) was used according to an analogous synthetic method to Example 36 to provide [4-(2-azepan-1-ylethoxy)benzyl]ethyl[5-methoxy-2-(2-methoxy-8,9-dihydro-7H-benzocyclohepten-6-yl)phenyl]amine (324 mg). This compound (322 mg) was used according to an analogous synthetic method to Example 111 to provide the title compound (280 mg).

$^1$H-NMR (400 MHz, DMSO-$d_6$); δ (ppm): 0.90 (t, 3H), 1.48-1.60 (m, 8H), 1.96-2.03 (m, 2H), 2.61-2.75 (m, 8H), 2.80 (t, 2H), 2.95 (q, 2H), 3.96 (t, 2H), 4.07 (s, 2H), 6.34 (s, 1H), 6.36 (dd, 1H), 6.39 (d, 1H), 6.54 (dd, 1H), 6.56 (d, 1H), 6.80 (d, 2H), 6.95 (d, 1H), 6.96 (d, 1H), 7.10 (d, 2H), 9.15 (s, 1H), 9.30 (s, 1H).

ESI-Mass; 527 [M$^+$+H]

Example 300

6-{2-{[4-(2-Azepan-1-ylethoxy)benzyl]ethylamino}phenyl}-6,7,8,9-tetrahydro-5H-benzocyclohepten-2-ol

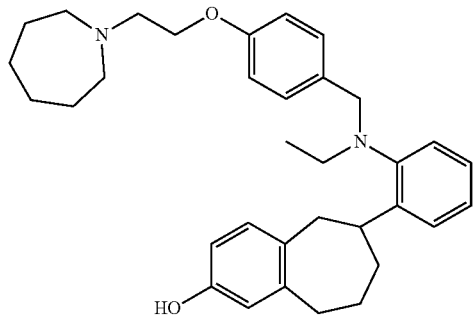 [SMILES: CCN(Cc1ccc(OCCN2CCCCCC2)cc1)c1ccccc1C1CCCc2cc(O)ccc2C1]

Synthesized from 2-(2-methoxy-6,7,8,9-tetrahydro-5H-benzocyclohepten-6-yl)phenylamine and 4-(2-azepan-1-ylethoxy)benzoic acid hydrochloride according to an analogous synthetic method to Example 152, [4-(2-azepan-1-ylethoxy)benzyl][2-(2-methoxy-6,7,8,9-tetrahydro-5H-benzocyclohepten-6-yl)phenyl]amine (477 mg) was used according to an analogous synthetic method to Example 36 to provide [4-(2-azepan-1-ylethoxy)benzyl]ethyl[2-(2-methoxy-6,7,8,9-tetrahydro-5H-benzocyclohepten-6-yl)phenyl]amine (431 mg). This compound (429 mg) was used according to an analogous synthetic method to Example 111 to provide the title compound (371 mg).

$^1$H-NMR (400 MHz, DMSO-$d_6$); δ (ppm): 0.83 (t, 3H), 1.27-1.37 (m, 1H), 1.48-1.82 (m, 10H), 1.91-2.00 (m, 1H), 2.34-2.41 (m, 1H), 2.59-2.70 (m, 5H), 2.76-2.89 (m, 5H), 3.07-3.14 (m, 1H), 3.29-3.40 (m, 1H), 3.91 (dd, 2H), 3.95 (t, 2H), 6.46 (dd, 1H), 6.57 (d, 1H), 6.74 (d, 2H), 6.80 (d, 1H), 7.04 (d, 2H), 7.07 (dt, 1H), 7.12 (dt, 1H), 7.19 (dd, 1H), 7.29 (dd, 1H), 9.07 (s, 1H).

ESI-Mass; 513 [M$^+$+H]

Example 301

6-{2-{[4-(2-Azepan-1-ylethoxy)benzyl]ethylamino}phenyl}-8,9-dihydro-7H-benzocyclohepten-2-ol

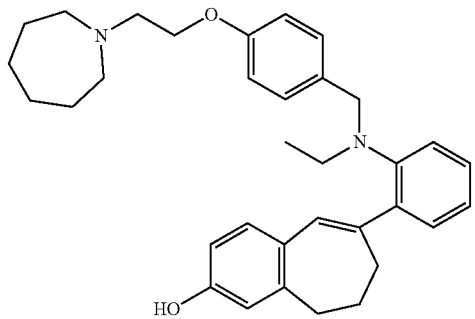 [SMILES: CCN(Cc1ccc(OCCN2CCCCCC2)cc1)c1ccccc1C1=Cc2ccc(O)cc2CCC1]

Synthesized from 2-(2-methoxy-8,9-dihydro-7H-benzocyclohepten-6-yl)phenylamine and 4-(2-azepan-1-ylethoxy)benzoic acid hydrochloride according to an analogous synthetic method to Example 152, [4-(2-azepan-1-ylethoxy)benzyl][2-(2-methoxy-8,9-dihydro-7H-benzocyclohepten-6-yl)phenyl]amine (454 mg) was used according to an analogous synthetic method to Example 36 to provide [4-(2-azepan-1-ylethoxy)benzyl]ethyl[2-(2-methoxy-8,9-dihydro-7H-benzocyclohepten-6-yl)phenyl]amine (345 mg). This compound (343 mg) was used according to an analogous synthetic method to Example 111 to provide the title compound (309 mg).

$^1$H-NMR (400 MHz, DMSO-$d_6$); δ (ppm): 0.90 (t, 3H), 1.46-1.60 (m, 8H), 1.97-2.06 (m, 2H), 2.61-2.71 (m, 6H), 2.73-2.81 (m, 4H), 3.00 (q, 2H), 3.96 (t, 2H), 4.10 (s, 2H), 6.38 (s, 1H), 6.55 (dd, 1H), 6.58 (d, 1H), 6.79 (d, 2H), 6.93-7.01 (m, 3H), 7.10 (d, 2H), 7.13-7.18 (m, 2H), 9.38 (s, 1H).

ESI-Mass; 511 [M$^+$+H]

Example 302

6-{2-{Ethyl[4-(2-pyrrolidin-1-ylethoxy)benzyl]amino}-4-methoxyphenyl}-6,7,8,9-tetrahydro-5H-benzocyclohepten-2-ol

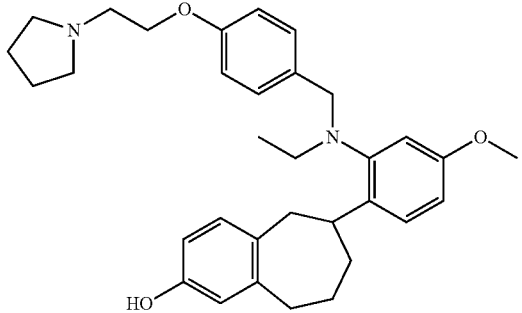 [SMILES: CCN(Cc1ccc(OCCN2CCCC2)cc1)c1cc(OC)ccc1C1CCCc2cc(O)ccc2C1]

Synthesized from {2-[2-(tert-butyldimethylsilyloxy)-6,7,8,9-tetrahydro-5H-benzocyclohepten-6-yl]-5-methoxyphenyl}ethylamine and 4-(2-pyrrolidin-1-ylethoxy)benzoic acid hydrochloride according to an analogous synthetic method to Example 152, {2-[2-(tert-butyldimethylsilyloxy)-6,7,8,9-tetrahydro-5H-benzocyclohepten-6-yl]-5-methoxyphenyl}ethyl[4-(2-pyrrolidin-1-ylethoxy)benzyl]amine (484 mg) was used according to an analogous synthetic method to Example 325 described below to provide the title compound (345 mg).

$^1$H-NMR (400 MHz, DMSO-d$_6$); δ (ppm): 0.83 (t, 3H), 1.24-1.35 (m, 1H), 1.60-1.79 (m, 6H), 1.89-1.97 (m, 1H), 2.35 (d, 1H), 2.42-2.51 (m, 4H), 2.60 (dd, 1H), 2.72 (t, 2H), 2.75-2.85 (m, 3H), 3.05 (dd, 1H), 3.19-3.25 (m, 1H), 3.68 (s, 3H), 3.89 (dd, 2H), 3.97 (t, 2H), 6.44 (dd, 1H), 6.54 (d, 1H), 6.64 (dd, 1H), 6.68 (d, 1H), 6.73 (d, 2H), 6.78 (d, 1H), 7.03 (d, 2H), 7.16 (d, 1H), 9.03 (s, 1H).

ESI-Mass; 515 [M$^+$+H]

Example 303

6-{2-{Ethyl[4-(2-piperidin-1-ylethoxy)benzyl]amino}-4-methoxyphenyl}-6,7,8,9-tetrahydro-5H-benzocyclohepten-2-ol

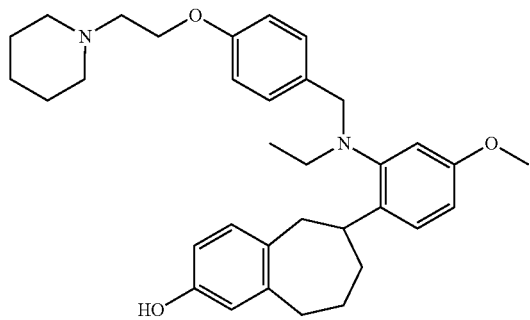 [SMILES: CCN(Cc1ccc(OCCN2CCCCC2)cc1)c1cc(OC)ccc1C1CCCc2cc(O)ccc2C1]

Synthesized from {2-[2-(tert-butyldimethylsilyloxy)-6,7,8,9-tetrahydro-5H-benzocyclohepten-6-yl]-5-methoxyphenyl}ethylamine and 4-(2-piperidin-1-ylethoxy)benzoic acid hydrochloride according to an analogous synthetic method to Example 152, {2-[2-(tert-butyldimethylsilyloxy)-6,7,8,9-tetrahydro-5H-benzocyclohepten-6-yl]-5-methoxyphenyl}ethyl[4-(2-piperidin-1-ylethoxy)benzyl]amine (481 mg) was used according to an analogous synthetic method to Example 325 described below to provide the title compound (357 mg).

$^1$H-NMR (400 MHz, DMSO-d$_6$); δ (ppm): 0.83 (t, 3H), 1.25-1.39 (m, 3H), 1.43-1.49 (m, 4H), 1.59-1.79 (m, 2H), 1.89-1.98 (m, 1H), 2.33-2.40 (m, 5H), 2.58 (t, 2H), 2.58-2.66 (m, 1H), 2.74-2.85 (m, 3H), 3.05 (dd, 1H), 3.19-3.25 (m, 1H), 3.68 (s, 3H), 3.89 (dd, 2H), 3.96 (t, 2H), 6.45 (dd, 1H), 6.54 (d, 1H), 6.64 (dd, 1H), 6.68 (d, 1H), 6.73 (d, 2H), 6.78 (d, 1H), 7.03 (d, 2H), 7.16 (d, 1H), 9.03 (s, 1H).

ESI-Mass; 529 [M$^+$+H]

Example 304

6-{2-{[4-(2-Azepan-1-ylethoxy)benzyl]ethylamino}-4-methoxyphenyl}-6,7,8,9-tetrahydro-5H-benzocyclohepten-2-ol

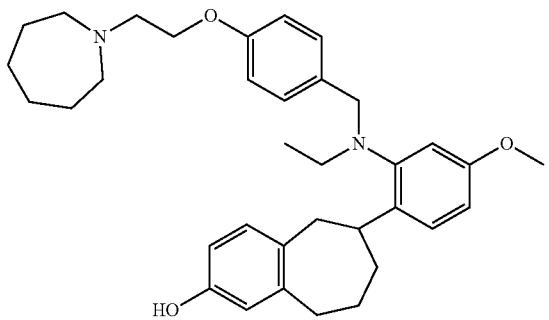 [SMILES: CCN(Cc1ccc(OCCN2CCCCCC2)cc1)c1cc(OC)ccc1C1CCCc2cc(O)ccc2C1]

Synthesized from {2-[2-(tert-butyldimethylsilyloxy)-6,7,8,9-tetrahydro-5H-benzocyclohepten-6-yl]-5-methoxyphenyl}ethylamine and 4-(2-azepan-1-ylethoxy)benzoic acid hydrochloride according to an analogous synthetic method to Example 152, [4-(2-azepan-1-ylethoxy)benzyl]{2-[2-(tert-butyldimethyl silyloxy)-6,7,8,9-tetrahydro-5H-benzocyclohepten-6-yl]-5-methoxyphenyl}ethylamine (584 mg) was used according to an analogous synthetic method to Example 325 described below to provide the title compound (426 mg).

$^1$H-NMR (400 MHz, DMSO-d$_6$); δ (ppm): 0.83 (t, 3H), 1.29 (dd, 1H), 1.48-1.79 (m, 10H), 1.89-1.97 (m, 1H), 2.35 (d, 1H), 2.57-2.66 (m, 5H), 2.74-2.85 (m, 5H), 3.05 (dd, 1H), 3.22 (t, 1H), 3.68 (s, 3H), 3.89 (dd, 2H), 3.94 (t, 2H), 6.44 (dd, 1H), 6.54 (d, 1H), 6.64 (dd, 1H), 6.68 (d, 1H), 6.73 (d, 2H), 6.78 (d, 1H), 7.03 (d, 2H), 7.16 (d, 1H), 9.03 (s, 1H).

ESI-Mass; 543 [M$^+$+H]

Example 305

6-{2-[3-Fluoro-4-(2-piperidin-1-ylethoxy)phenylamino]-4-hydroxyphenyl}-5,5-dimethyl-5,6,7,8-tetrahydronaphthalen-2-ol

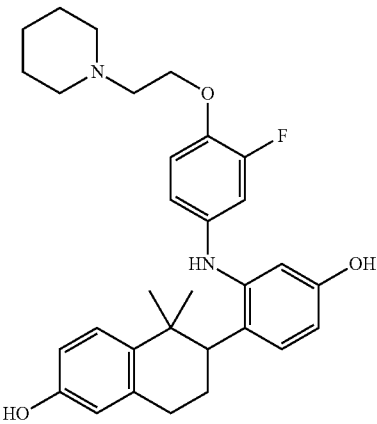 [SMILES: CC1(C)c2ccc(O)cc2CCC1c1ccc(O)cc1Nc1ccc(OCCN2CCCCC2)c(F)c1]

Synthesized from 5-methoxy-2-(6-methoxy-1,1-dimethyl-1,2,3,4-tetrahydronaphthalen-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(6-methoxy-1,1-dimethyl-1,2,3,4-tetrahydronaphthalen-2-yl)phenyl]amine (348 mg) was used according to an analogous synthetic method to Example 111 to provide the title compound (279 mg).

$^1$H-NMR (400 MHz, DMSO-$d_6$); δ (ppm): 0.97 (s, 3H), 1.02 (s, 3H), 1.30-1.38 (m, 2H), 1.41-1.50 (m, 4H), 1.56-1.66 (m, 1H), 2.03-2.17 (m, 1H), 2.33-2.43 (m, 4H), 2.58 (t, 2H), 2.63-2.79 (m, 2H), 3.12-3.17 (m, 1H), 3.98 (t, 2H), 6.36-6.40 (m, 2H), 6.48-6.56 (m, 3H), 6.59 (dd, 1H), 6.91-6.98 (m, 2H), 7.08 (d, 1H), 7.26 (s, 1H), 8.98 (s, 1H), 9.09 (s, 1H).

ESI-Mass; 505 [M$^+$+H]

Example 306

6-{2-{Ethyl[3-fluoro-4-(2-piperidin-1-ylethoxy)benzyl]amino}-4-hydroxyphenyl}-5,5-dimethyl-5,6,7,8-tetrahydronaphthalen-2-ol

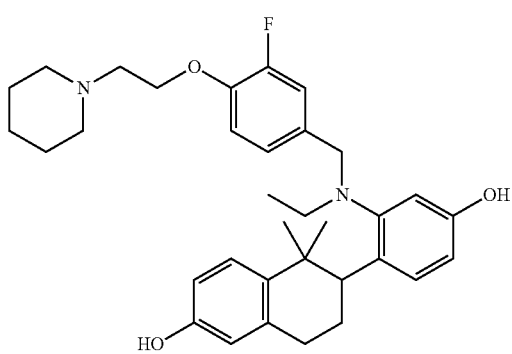 [SMILES: CCN(Cc1ccc(OCCN2CCCCC2)c(F)c1)c1cc(O)ccc1C1CCc2cc(O)ccc2C1(C)C]

Synthesized from 5-methoxy-2-(6-methoxy-1,1-dimethyl-1,2,3,4-tetrahydronaphthalen-2-yl)phenylamine and 3-fluoro-4-(2-piperidin-1-ylethoxy)benzoic acid hydrochloride according to an analogous synthetic method to Example 114, [3-fluoro-4-(2-piperidin-1-ylethoxy)benzyl][5-methoxy-2-(6-methoxy-1,1-dimethyl-1,2,3,4-tetrahydronaphthalen-2-yl)phenyl]amine (306 mg) was used according to an analogous synthetic method to Example 36 to provide ethyl [3-fluoro-4-(2-piperidin-1-ylethoxy)benzyl][5-methoxy-2-(6-methoxy-1,1-dimethyl-1,2,3,4-tetrahydronaphthalen-2-yl)phenyl]amine (253 mg). This compound (251 mg) was used according to an analogous synthetic method to Example 111 to provide the title compound (228 mg).

$^1$H-NMR (400 MHz, DMSO-$d_6$); δ (ppm): 0.88 (t, 3H), 0.98 (s, 3H), 1.11 (s, 3H), 1.30-1.39 (m, 2H), 1.41-1.49 (m, 4H), 1.50-1.58 (m, 1H), 1.85-1.96 (m, 1H), 2.35-2.44 (m, 4H), 2.60-2.68 (m, 4H), 2.74 (q, 2H), 3.56 (dd, 1H), 3.81 (dd, 2H), 4.06 (t, 2H), 6.39 (d, 1H), 6.44 (dd, 1H), 6.53 (dd, 1H), 6.60 (d, 1H), 6.85 (d, 1H), 6.91-6.99 (m, 2H), 7.06 (t, 1H), 7.11 (d, 1H), 9.00 (s, 1H), 9.11 (s, 1H).

ESI-Mass; 547 [M$^+$+H]

Example 307

6-{2-[3-Fluoro-4-(2-piperidin-1-ylethoxy)phenylamino]-4-hydroxyphenyl}-5,8-dihydronaphthalen-2-ol

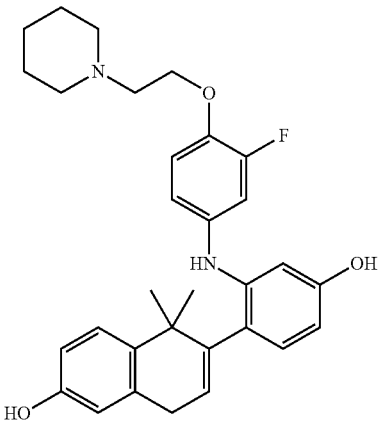 [SMILES: CC1(C)C(c2ccc(O)cc2Nc2ccc(OCCN3CCCCC3)c(F)c2)=CCc2cc(O)ccc21]

Synthesized from 5-methoxy-2-(6-methoxy-1,1-dimethyl-1,4-dihydronaphthalen-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(6-methoxy-1,1-dimethyl-1,4-dihydronaphthalen-2-yl)phenyl]amine (439 mg) was used according to an analogous synthetic method to Example 111 to provide the title compound (303 mg).

$^1$H-NMR (400 MHz, DMSO-$d_6$); δ (ppm): 1.12 (s, 3H), 1.22 (s, 3H), 1.29-1.38 (m, 2H), 1.42-1.49 (m, 4H), 2.33-2.42 (m, 4H), 2.59 (t, 2H), 3.38 (d, 2H), 3.98-4.04 (m, 2H), 5.63 (t, 1H), 6.25 (dd, 1H), 6.47-6.51 (m, 2H), 6.54 (d, 1H), 6.57 (dd, 1H), 6.75-6.81 (m, 2H), 6.87 (dd, 1H), 7.00 (t, 1H), 7.16 (d, 1H), 9.07 (s, 1H), 9.13 (s, 1H).

ESI-Mass; 503 [M$^+$+H]

Example 308

6-{2-{Ethyl[3-fluoro-4-(2-piperidin-1-ylethoxy)benzyl]amino}-4-hydroxyphenyl}-5,5-dimethyl-5,8-dihydronaphthalen-2-ol

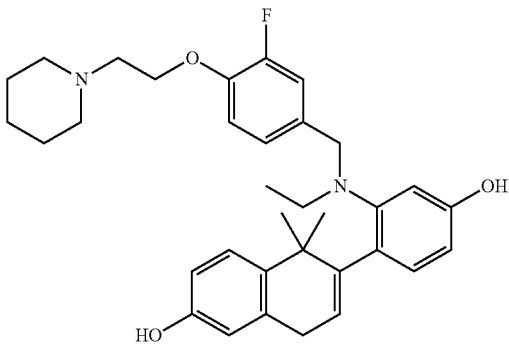 [SMILES: CCN(Cc1ccc(OCCN2CCCCC2)c(F)c1)c1cc(O)ccc1C1=CCc2cc(O)ccc2C1(C)C]

Synthesized from 5-methoxy-2-(6-methoxy-1,1-dimethyl-1,4-dihydronaphthalen-2-yl)phenylamine and 3-fluoro-4-(2-piperidin-1-ylethoxy)benzoic acid hydrochloride according to an analogous synthetic method to Example 114, [3-fluoro-4-(2-piperidin-1-ylethoxy)benzyl][5-methoxy-2-(6-methoxy-1,1-dimethyl-1,4-dihydronaphthalen-2-yl)phenyl]amine (316 mg) was used according to an analogous synthetic method to Example 36 to provide ethyl[3-fluoro-4-(2-piperidin-1-ylethoxy)benzyl][5-methoxy-2-(6-methoxy-1,1-dimethyl-1,4-dihydronaphthalen-2-yl)phenyl]amine (82 mg). The total amount of this compound was used according to an analogous synthetic method to Example 111 to provide the title compound (62 mg).

$^1$H-NMR (400 MHz, DMSO-$d_6$); δ (ppm): 0.83 (t, 3H), 1.10-1.50 (m, 12H), 2.35-2.43 (m, 4H), 2.60 (t, 2H), 3.27 (brs, 2H), 4.02 (t, 2H), 5.71 (t, 1H), 6.38-6.42 (m, 2H), 6.52 (d, 1H), 6.61 (dd, 1H), 6.71-6.79 (m, 3H), 6.85 (t, 1H), 7.17 (d, 1H), 9.05 (s, 1H), 9.18 (s, 1H).

ESI-Mass; 545 [M$^+$+H]

Example 309

6-{2-{2-[4-(2-Azepan-1-ylethoxy)phenyl]ethyl}methylamino}-4-hydroxyphenyl}-5,5-dimethyl-5,6,7,8-tetrahydronaphthalen-2-ol

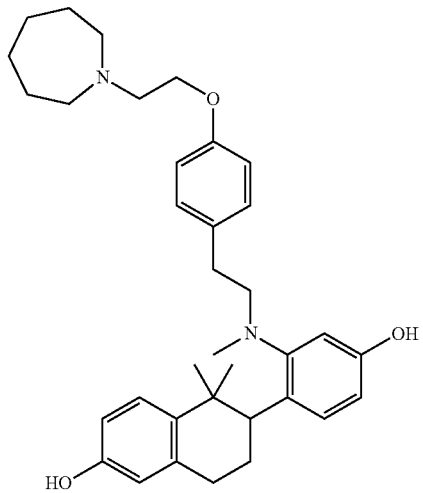 [SMILES: CN(CCc1ccc(OCCN2CCCCCC2)cc1)c1cc(O)ccc1C1CCc2cc(O)ccc2C1(C)C]

Synthesized from 5-methoxy-2-(6-methoxy-1,1-dimethyl-1,2,3,4-tetrahydronaphthalen-2-yl)phenylamine and 4-benzyloxyphenylacetyl chloride according to an analogous synthetic method to Example 152, [2-(4-benzyloxyphenyl)ethyl][5-methoxy-2-(6-methoxy-1,1-dimethyl-1,2,3,4-tetrahydronaphthalen-2-yl)phenyl]amine (89 mg) was used according to an analogous synthetic method to Preparation Example 18 to provide [2-(4-benzyloxyphenyl)ethyl][5-methoxy-2-(6-methoxy-1,1-dimethyl-1,2,3,4-tetrahydronaphthalen-2-yl)phenyl]methylamine (61 mg). This compound (60 mg) was used according to an analogous synthetic method to Example 22 to provide 4-{2-{[5-methoxy-2-(6-methoxy-1,1-dimethyl-1,2,3,4-tetrahydronaphthalen-2-yl)phenyl]methylamino}ethyl}phenol (50 mg). Synthesized from 4-{2-{[5-methoxy-2-(6-methoxy-1,1-dimethyl-1,2,3,4-tetrahydronaphthalen-2-yl)phenyl]methylamino}ethyl}phenol and 1-(2-chloroethyl)azepane according to an analogous synthetic method to Example 383 described below, {2-[4-(2-azepan-1-ylethoxy)phenyl]ethyl}[5-methoxy-2-(6-methoxy-1,1-dimethyl-1,2,3,4-tetrahydro-naphthalen-2-yl)phenyl]methylamine (42 mg) was used according to an analogous synthetic method to Example 111 to provide the title compound (27 mg).

$^1$H-NMR (400 MHz, DMSO-$d_6$); δ (ppm): 0.94 (s, 3H), 1.00 (s, 3H), 1.48-1.58 (m, 8H), 1.58-1.66 (m, 1H), 1.89-2.02 (m, 1H), 2.55 (s, 3H), 2.56-2.72 (m, 9H), 2.79 (t, 2H), 2.80-2.89 (m, 1H), 3.41 (dd, 1H), 3.90 (t, 2H), 6.40 (d, 1H), 6.42 (dd, 1H), 6.60 (d, 1H), 6.74 (d, 2H), 6.85 (d, 1H), 7.03 (d, 2H), 7.08 (d, 1H), 8.99 (s, 1H), 9.09 (s, 1H).

ESI-Mass; 543 [M$^+$+H]

Example 310

6-{2-{[4-(2-Azepan-1-ylethoxy)benzyl]ethylamino}-4-hydroxyphenyl}-7,7-dimethyl-5,6,7,8-tetrahydronaphthalen-2-ol

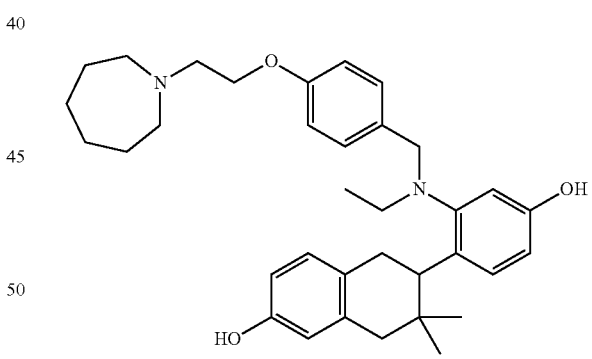

Synthesized from 5-methoxy-2-(6-methoxy-3,3-dimethyl-1,2,3,4-tetrahydronaphthalen-2-yl)phenylamine and 4-(2-azepan-1-ylethoxy)benzoic acid hydrochloride according to an analogous synthetic method to Example 152, [4-(2-azepan-1-ylethoxy)benzyl][5-methoxy-2-(6-methoxy-3,3-dimethyl-1,2,3,4-tetrahydronaphthalen-2-yl)phenyl]amine (522 mg) was used according to an analogous synthetic method to Example 36 to provide [4-(2-azepan-1-ylethoxy)benzyl]ethyl[5-methoxy-2-(6-methoxy-3,3-dimethyl-1,2,3,4-tetrahydronaphthalen-2-yl)phenyl]amine (521 mg). This compound (519 mg) was used according to an analogous synthetic method to Example 111 to provide the title compound (365 mg).

$^1$H-NMR (400 MHz, DMSO-d$_6$); δ (ppm): 0.77 (s, 3H), 0.80-0.88 (m, 6H), 1.48-1.60 (m, 8H), 2.43-2.53 (m, 2H), 2.64-2.86 (m, 10H), 3.68-3.76 (m, 2H), 3.86 (d, 1H), 3.97 (t, 2H), 6.45-6.52 (m, 3H), 6.61 (s, 1H), 6.80-6.85 (m, 3H), 7.03 (d, 1H), 7.13-7.22 (m, 2H), 8.98 (s, 1H), 9.11 (s, 1H).

ESI-Mass; 543 [M$^+$+H]

Example 311

6-{2-{[4-(2-Azepan-1-ylethoxy)benzyl]ethylamino}-4-hydroxyphenyl}-7,7-dimethyl-7,8-dihydronaphthalen-2-ol

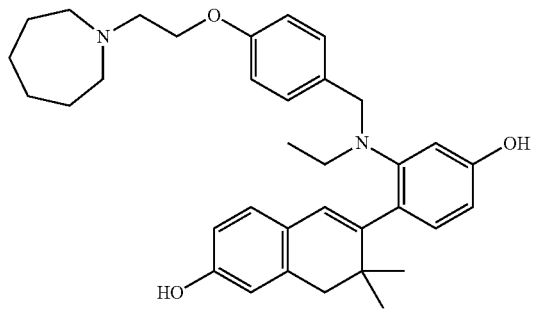 [SMILES: CCN(Cc1ccc(OCCN2CCCCCC2)cc1)c1cc(O)ccc1C1=Cc2ccc(O)cc2CC1(C)C]

Synthesized from 5-methoxy-2-(6-methoxy-3,3-dimethyl-3,4-dihydronaphthalen-2-yl)phenylamine and 4-(2-azepan-1-ylethoxy)benzoic acid hydrochloride according to an analogous synthetic method to Example 152, [4-(2-azepan-1-ylethoxy)benzyl][5-methoxy-2-(6-methoxy-3,3-dimethyl-3,4-dihydronaphthalen-2-yl)phenyl]amine (454 mg) was used according to an analogous synthetic method to Example 36 to provide [4-(2-azepan-1-ylethoxy)benzyl]ethyl[5-methoxy-2-(6-methoxy-3,3-dimethyl-3,4-dihydronaphthalen-2-yl)phenyl]amine (387 mg). This compound (385 mg) was used according to an analogous synthetic method to Example 111 to provide the title compound (345 mg).

$^1$H-NMR (400 MHz, DMSO-d$_6$); δ (ppm): 0.92 (t, 3H), 1.00 (brs, 6H), 1.48-1.60 (m, 8H), 2.61-2.70 (m, 6H), 2.79 (t, 2H), 2.88 (brs, 2H), 3.95 (t, 2H), 4.05 (brs, 2H), 6.18 (s, 1H), 6.34-6.39 (m, 2H), 6.51 (dd, 1H), 6.57 (d, 1H), 6.75-6.80 (m, 3H), 6.87 (d, 1H), 7.03 (d, 2H), 9.13 (s, 1H), 9.26 (s, 1H).

ESI-Mass; 541 [M$^+$+H]

Example 312

6-{2-{[4-(2-Azepan-1-ylethoxy)benzyl]ethylamino}phenyl}-7,7-dimethyl-5,6,7,8-tetrahydronaphthalen-2-ol

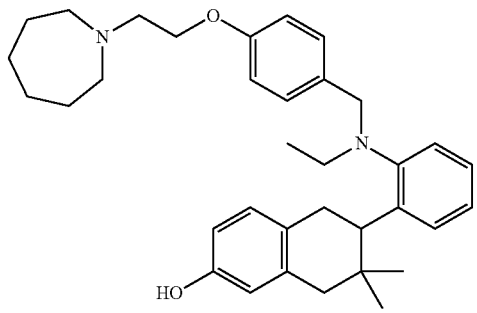

Synthesized from 2-(6-methoxy-3,3-dimethyl-1,2,3,4-tetrahydronaphthalen-2-yl)phenylamine and 4-(2-azepan-1-ylethoxy)benzoic acid hydrochloride according to an analogous synthetic method to Example 152, [4-(2-azepan-1-ylethoxy)benzyl][2-(6-methoxy-3,3-dimethyl-1,2,3,4-tetrahydronaphthalen-2-yl)phenyl]amine (434 mg) was used according to an analogous synthetic method to Example 36 to provide [4-(2-azepan-1-ylethoxy)benzyl]ethyl[2-(6-methoxy-3,3-dimethyl-1,2,3,4-tetrahydronaphthalen-2-yl)phenyl]amine (440 mg). This compound (438 mg) was used according to an analogous synthetic method to Example 111 to provide the title compound (370 mg).

$^1$H-NMR (400 MHz, DMSO-d$_6$); δ (ppm): 0.78 (s, 3H), 0.81-0.88 (m, 6H), 1.49-1.60 (m, 8H), 2.45-2.56 (m, 2H), 2.64-2.90 (m, 1H), 3.78 (d, 1H), 3.85-3.92 (m, 2H), 3.97 (t, 2H), 6.46-6.52 (m, 2H), 6.80-6.86 (m, 3H), 7.08 (dt, 1H), 7.12-7.26 (m, 5H), 9.00 (s, 1H).

ESI-Mass; 527 [M$^+$+H]

Example 313

6-{2-{[4-(2-Azepan-1-ylethoxy)benzyl]ethylamino}phenyl}-7,7-dimethyl-7,8-dihydronaphthalen-2-ol

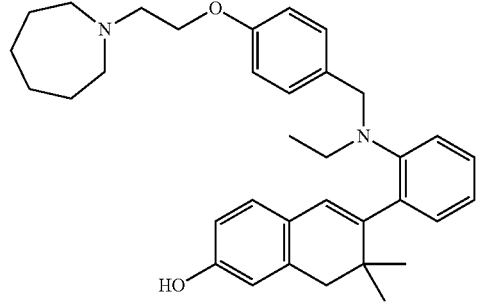 [SMILES: CCN(Cc1ccc(OCCN2CCCCCC2)cc1)c1ccccc1C1=Cc2ccc(O)cc2CC1(C)C]

Synthesized from 2-(6-methoxy-3,3-dimethyl-3,4-dihydronaphthalen-2-yl)phenylamine and 4-(2-azepan-1-ylethoxy)benzoic acid hydrochloride according to an analogous synthetic method to Example 152, [4-(2-azepan-1-ylethoxy)benzyl][2-(6-methoxy-3,3-dimethyl-3,4-dihydronaphthalen-2-yl)phenyl]amine (451 mg) was used according to an analogous synthetic method to Example 36 to provide [4-(2-azepan-1-ylethoxy)benzyl]ethyl[2-(6-methoxy-3,3-dimethyl-3,4-dihydronaphthalen-2-yl)phenyl]amine (423 mg). This compound (421 mg) was used according to an analogous synthetic method to Example 111 to provide the title compound (355 mg).

$^1$H-NMR (400 MHz, DMSO-d$_6$); δ (ppm): 0.91 (t, 3H), 1.01 (brs, 6H), 1.49-1.59 (m, 8H), 2.62-2.68 (m, 6H), 2.79 (t, 2H), 2.93 (brs, 2H), 3.95 (t, 2H), 4.08 (s, 2H), 6.23 (s, 1H), 6.53 (dd, 1H), 6.59 (d, 1H), 6.76 (d, 2H), 6.89-7.04 (m, 6H), 7.18 (ddd, 1H), 9.31 (s, 1H).

ESI-Mass; 525 [M$^+$+H]

Example 314

3-{2-{[4-(2-Azepan-1-ylethoxy)benzyl]ethylamino}-4-hydroxyphenyl}-2,2-dimethylchroman-7-ol

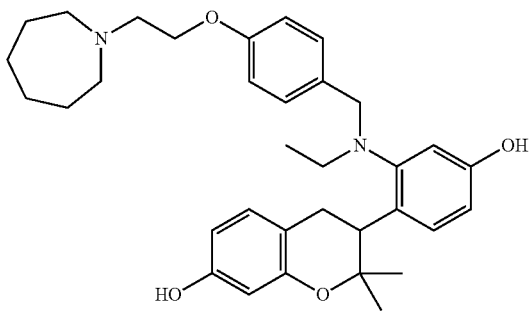 [SMILES: CCN(Cc1ccc(OCCN2CCCCCC2)cc1)c1cc(O)ccc1C1Cc2ccc(O)cc2OC1(C)C]

Synthesized from 5-methoxy-2-(7-methoxy-2,2-dimethylchroman-3-yl)phenylamine and 4-(2-azepan-1-ylethoxy)benzoic acid hydrochloride according to an analogous synthetic method to Example 152, [4-(2-azepan-1-ylethoxy)benzyl][5-methoxy-2-(7-methoxy-2,2-dimethylchroman-3-yl)phenyl]amine (493 mg) was used according to an analogous synthetic method to Example 36 to provide [4-(2-azepan-1-ylethoxy)benzyl]ethyl[5-methoxy-2-(7-methoxy-2,2-dimethylchroman-3-yl)phenyl]amine (504 mg). This compound (502 mg) was used according to an analogous synthetic method to Example 111 to provide the title compound (380 mg).

$^1$H-NMR (400 MHz, DMSO-$d_6$); δ (ppm): 0.89 (t, 3H), 1.08 (s, 3H), 1.17 (s, 3H), 1.49-1.60 (m, 8H), 2.52-2.69 (m, 6H), 2.75 (q, 2H), 2.82 (t, 2H), 3.76-3.87 (m, 3H), 3.98 (t, 2H), 6.16 (d, 1H), 6.24 (dd, 1H), 6.46 (dd, 1H), 6.62 (d, 1H), 6.76 (d, 1H), 6.82 (d, 2H), 6.95 (d, 1H), 7.11 (d, 2H), 9.09 (s, 1H), 9.17 (s, 1H).
ESI-Mass; 545 [M$^+$+H]

Example 315

3-{2-{[4-(2-Azepan-1-ylethoxy)benzyl]ethylamino}phenyl}-2,2-dimethylchroman-7-ol

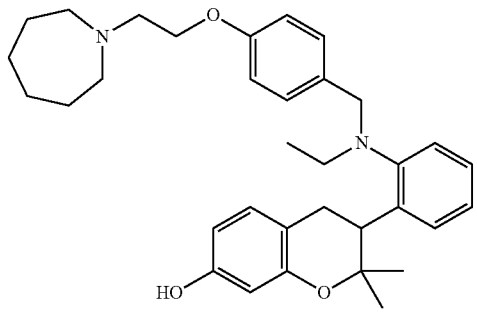 [SMILES: CCN(Cc1ccc(OCCN2CCCCCC2)cc1)c1ccccc1C1Cc2ccc(O)cc2OC1(C)C]

Synthesized from 2-(7-methoxy-2,2-dimethylchroman-3-yl)phenylamine and 4-(2-azepan-1-ylethoxy)benzoic acid hydrochloride according to an analogous synthetic method to Example 152, [4-(2-azepan-1-ylethoxy)benzyl][2-(7-methoxy-2,2-dimethylchroman-3-yl)phenyl]amine (473 mg) was used according to an analogous synthetic method to Example 36 to provide [4-(2-azepan-1-ylethoxy)benzyl]ethyl[2-(7-methoxy-2,2-dimethylchroman-3-yl)phenyl]amine (472 mg). This compound (470 mg) was used according to an analogous synthetic method to Example 111 to provide the title compound (200 mg).

$^1$H-NMR (400 MHz, DMSO-$d_6$); δ (ppm): 0.90 (t, 3H), 1.09 (s, 3H), 1.19 (s, 3H), 1.50-1.61 (m, 8H), 2.56-2.69 (m, 6H), 2.76-2.87 (m, 4H), 3.81-3.97 (m, 3H), 3.98 (t, 2H), 6.18 (d, 1H), 6.25 (dd, 1H), 6.77 (d, 1H), 6.82 (d, 2H), 7.03 (dt, 1H), 7.10 (d, 2H), 7.15 (dd, 1H), 7.20 (dt, 1H), 7.25 (d, 1H), 9.12 (s, 1H).
ESI-Mass; 529 [M$^+$+H]

Example 316

2-{2-[3-Fluoro-4-(2-piperidin-1-ylethoxy)benzylamino]-4-hydroxyphenyl}-1-methyl-1H-indol-6-ol

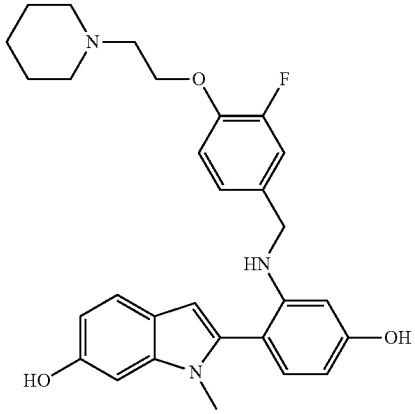 [SMILES: Cn1c(-c2ccc(O)cc2NCc2ccc(OCCN3CCCCC3)c(F)c2)cc2ccc(O)cc21]

Synthesized from 5-methoxy-2-(6-methoxy-1-methyl-1H-indol-2-yl)phenylamine (500 mg) and 3-fluoro-4-(2-piperidin-1-ylethoxy)benzoic acid hydrochloride (920 mg) according to an analogous synthetic method to Example 114, [3-fluoro-4-(2-piperidin-1-ylethoxy)benzyl][5-methoxy-2-(6-methoxy-1-methyl-1H-indol-2-yl)phenyl]amine (210 mg) was used according to an analogous synthetic method to Example 364 described below to provide the title compound (40 mg).

$^1$H-NMR (400 MHz, DMSO-$d_6$); δ (ppm): 1.33-1.40 (m, 2H), 1.44-1.52 (m, 4H), 2.36-2.45 (m, 4H), 2.64 (t, 2H), 3.41 (s, 3H), 4.09 (t, 2H), 4.16 (d, 2H), 5.30 (t, 1H), 5.95 (s, 1H), 6.07 (d, 1H), 6.25 (s, 1H), 6.57 (d, 1H), 6.74 (s, 1H), 6.83 (d, 1H), 7.03-7.14 (m, 3H), 7.31 (d, 1H), 8.99 (s, 1H), 9.20 (s, 1H).
ESI-Mass; 490 [M$^+$+H]

Example 317

2-{2-[3-Fluoro-4-(2-piperidin-1-ylethoxy)phenylamino]-4-hydroxyphenyl}-1-methyl-1H-indol-6-ol

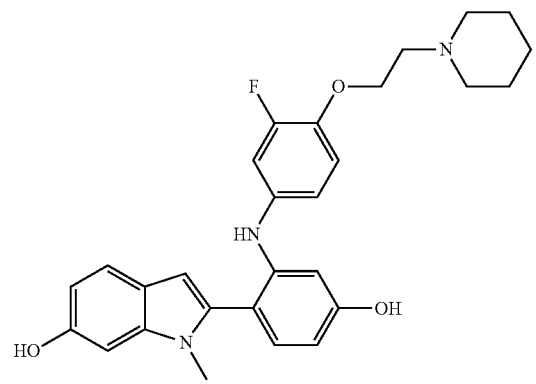 [SMILES: Cn1c(-c2ccc(O)cc2Nc2ccc(OCCN3CCCCC3)c(F)c2)cc2ccc(O)cc21]

Synthesized from 5-methoxy-2-(6-methoxy-1-methyl-1H-indol-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(6-methoxy-1-methyl-1H-indol-2-yl)phenyl]amine (60 mg) was used according to an analogous synthetic method to Example 364 described below to provide the title compound (25 mg).

$^1$H-NMR (400 MHz, DMSO-d$_6$); δ (ppm): 1.31-1.40 (m, 2H), 1.41-1.49 (m, 4H), 2.36-2.43 (m, 4H), 2.61 (t, 2H), 3.38 (s, 3H), 4.01 (t, 2H), 6.25 (s, 1H), 6.36 (d, 1H), 6.55 (d, 1H), 6.63 (s, 1H), 6.69 (s, 1H), 6.83 (d, 1H), 6.89-6.94 (m, 2H), 7.00-7.06 (m, 2H), 7.28 (d, 1H).

ESI-Mass; 476 [M$^+$+H]

Example 318

[5-Methoxy-2-(6-methoxybenzothiazol-2-yl)phenyl][4-(2-piperidin-1-ylethoxy)benzyl]amine

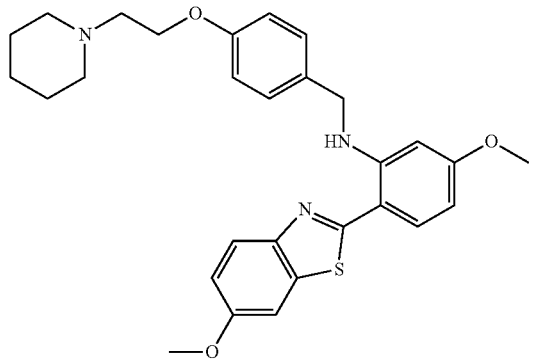 [SMILES: COc1ccc(-c2nc3ccc(OC)cc3s2)c(NCc2ccc(OCCN3CCCCC3)cc2)c1]

To a suspension of 5-methoxy-2-(6-methoxybenzothiazol-2-yl)phenylamine (473 mg) and 4-(2-piperidin-1-ylethoxy)benzaldehyde (484 mg) in tetrahydrofuran (6 ml), dichloromethane (4 ml) and acetic acid (4 ml) was added borane-methyl sulfide complex (0.18 ml), and the solution was stirred for 6 hours at room temperature. The solution was neutralized with ammonia solution on an ice bath, extracted with ethyl acetate, then sequentially washed with water and brine, and the solvent was evaporated in vacuo. The residue was purified by NH silica gel column chromatography (hexane-ethyl acetate system) to provide the title compound (132 mg).

$^1$H-NMR (400 MHz, CDCl$_3$); δ (ppm): 1.41-1.49 (m, 2H), 1.57-1.65 (m, 4H), 2.47-2.54 (m, 4H), 2.78 (t, 2H), 3.78 (s, 1H), 3.89 (s, 3H), 4.12 (t, 2H), 4.49 (s, 2H), 6.20 (s, 1H), 6.28 (d, 1H), 6.91 (d, 2H), 7.00 (d, 1H), 7.31-7.37 (m, 3H), 7.61 (d, 1H), 7.70 (d, 1H), 9.40 (brs, 1H).

Example 319

2-{4-Hydroxy-2-[4-(2-piperidin-1-ylethoxy)benzylamino]phenyl}benzothiazol-6-ol

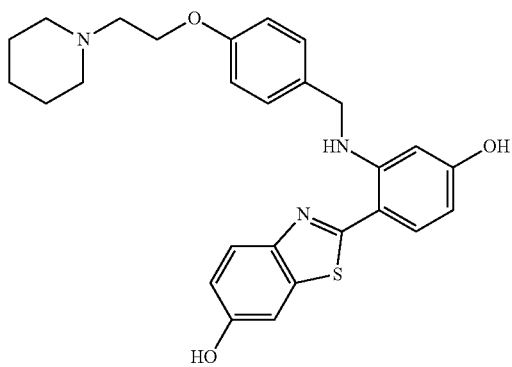 [SMILES: Oc1ccc(-c2nc3ccc(O)cc3s2)c(NCc2ccc(OCCN3CCCCC3)cc2)c1]

Synthesized from [5-methoxy-2-(6-methoxybenzothiazol-2-yl)phenyl][4-(2-piperidin-1-ylethoxy)benzyl]amine (132 mg) according to an analogous synthetic method to Example 364 described below, the title compound (14 mg) was obtained.

$^1$H-NMR (400 MHz, DMSO-d$_6$); δ (ppm): 1.30-1.40 (m, 2H), 1.41-1.50 (m, 4H), 2.33-2.43 (m, 4H), 2.61 (t, 2H), 4.02 (t, 2H), 4.40 (d, 2H), 6.08 (s, 1H), 6.14 (dd, 1H), 6.88 (dd, 1H), 6.92 (d, 2H), 7.28 (d, 2H), 7.30 (d, 1H), 7.43 (d, 1H), 7.60 (d, 1H), 9.22 (brs, 1H).

ESI-Mass; 476 [M$^+$+H]

Example 320

2-{2-[3-Fluoro-4-(2-piperidin-1-ylethoxy)phenylamino]-4-hydroxyphenyl}benzo[b]thiophen-6-ol

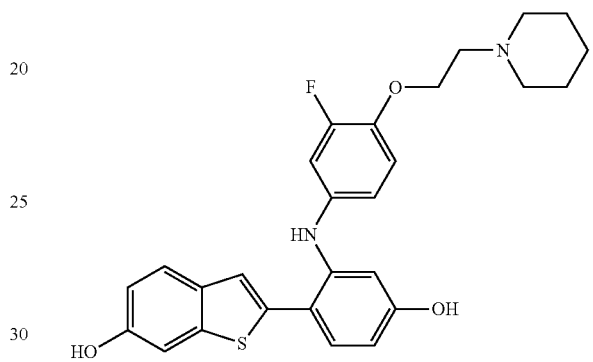

Synthesized from 5-methoxy-2-(6-methoxybenzo[b]thiophen-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(6-methoxybenzo[b]thiophen-2-yl)phenyl]amine (322 mg) was used according to an analogous synthetic method to Example 111 to provide the title compound (141 mg).

$^1$H-NMR (400 MHz, DMSO-d$_6$); δ (ppm): 1.30-1.39 (m, 2H), 1.42-1.50 (m, 4H), 2.34-2.42 (m, 4H), 2.59 (t, 2H), 4.01 (t, 2H), 6.47 (dd, 1H), 6.62 (d, 1H), 6.67 (d, 1H), 6.75 (dd, 1H), 6.79 (dd, 1H), 7.00 (t, 1H), 7.16 (d, 1H), 7.32-7.36 (m, 2H), 7.42 (s, 1H), 7.53 (d, 1H), 9.49 (s, 1H), 9.55 (s, 1H).

ESI-Mass; 479 [M$^+$+H]

Example 321

2-{2-[3-Fluoro-4-(2-piperidin-1-ylethoxy)phenylamino]-4-hydroxyphenyl}benzo[b]thiophen-5-ol


Synthesized from 5-methoxy-2-(5-methoxybenzo[b]thiophen-2-yl)phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(5-methoxybenzo[b]thiophen-2-yl)phenyl]amine (300 mg) was used according to an analogous synthetic method to Example 111 to provide the title compound (216 mg).

$^1$H-NMR (400 MHz, DMSO-$d_6$); δ (ppm): 1.30-1.38 (m, 2H), 1.42-1.50 (m, 4H), 2.34-2.44 (m, 4H), 2.59 (t, 2H), 4.01 (t, 2H), 6.47 (dd, 1H), 6.62 (d, 1H), 6.67 (d, 1H), 6.73-6.78 (m, 2H), 7.00 (t, 1H), 7.07 (d, 1H), 7.35-7.45 (m, 3H), 7.60 (d, 1H), 9.31 (s, 1H), 9.60 (s, 1H).

ESI-Mass; 479 [M$^+$+H]

Example 322

2-{2-{Ethyl[3-fluoro-4-(2-piperidin-1-ylethoxy)benzyl]amino}-4-hydroxyphenyl}benzo[b]thiophen-6-ol

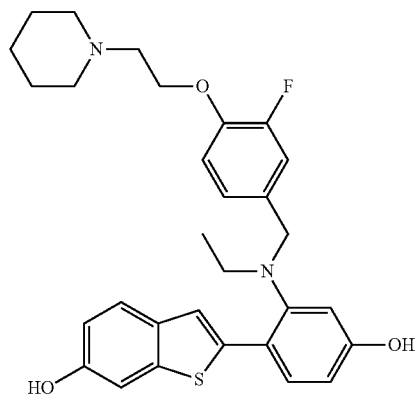 [SMILES: CCN(Cc1ccc(OCCN2CCCCC2)c(F)c1)c1cc(O)ccc1-c1cc2ccc(O)cc2s1]

Synthesized from 5-methoxy-2-(6-methoxybenzo[b]thiophen-2-yl)phenylamine and 3-fluoro-4-(2-piperidin-1-ylethoxy)benzoic acid hydrochloride according to an analogous synthetic method to Example 114, [3-fluoro-4-(2-piperidin-1-ylethoxy)benzyl][5-methoxy-2-(6-methoxybenzo[b]thiophen-2-yl)phenyl]amine (231 mg) was used according to an analogous synthetic method to Example 36 to provide ethyl[3-fluoro-4-(2-piperidin-1-ylethoxy)benzyl][5-methoxy-2-(6-methoxybenzo[b]thiophen-2-yl)phenyl]amine (195 mg). The total amount of this compound was used according to an analogous synthetic method to Example 111 to provide the title compound (170 mg).

$^1$H-NMR (400 MHz, DMSO-$d_6$); δ (ppm): 0.91 (t, 3H), 1.31-1.39 (m, 2H), 1.42-1.50 (m, 4H), 2.35-2.43 (m, 4H), 2.61 (t, 2H), 2.86 (q, 2H), 4.01 (s, 2H), 4.05 (t, 2H), 6.43 (d, 1H), 6.48 (dd, 1H), 6.79 (dd, 1H), 6.99 (dd, 1H), 7.03-7.08 (m, 2H), 7.17 (d, 1H), 7.38 (d, 1H), 7.43 (s, 1H), 7.54 (d, 1H), 9.49 (s, 2H).

ESI-Mass; 521 [M$^+$+H]

Example 323

2-{2-{Ethyl[3-fluoro-4-(2-piperidin-1-ylethoxy)benzyl]amino}-4-hydroxyphenyl}benzo[b]thiophen-5-ol

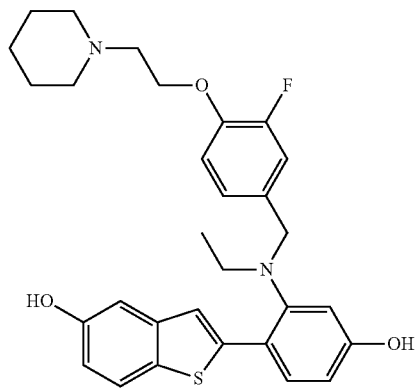 [SMILES: CCN(Cc1ccc(OCCN2CCCCC2)c(F)c1)c1cc(O)ccc1-c1cc2cc(O)ccc2s1]

Synthesized from 5-methoxy-2-(5-methoxybenzo[b]thiophen-2-yl)phenylamine and 3-fluoro-4-(2-piperidin-1-ylethoxy)benzoic acid hydrochloride according to an analogous synthetic method to Example 114, [3-fluoro-4-(2-piperidin-1-ylethoxy)benzyl][5-methoxy-2-(5-methoxybenzo[b]thiophen-2-yl)phenyl]amine (236 mg) was used according to an analogous synthetic method to Example 36 to provide ethyl[3-fluoro-4-(2-piperidin-1-ylethoxy)benzyl][5-methoxy-2-(5-methoxybenzo[b]thiophen-2-yl)phenyl]amine (202 mg). The total amount of this compound was used according to an analogous synthetic method to Example 111 to provide the title compound (136 mg).

$^1$H-NMR (400 MHz, DMSO-$d_6$); δ (ppm): 0.91 (t, 3H), 1.30-1.39 (m, 2H), 1.42-1.49 (m, 4H), 2.34-2.43 (m, 4H), 2.61 (t, 2H), 2.86 (q, 2H), 4.02 (s, 2H), 4.05 (t, 2H), 6.45 (d, 1H), 6.49 (dd, 1H), 6.77 (dd, 1H), 6.98-7.09 (m, 4H), 7.41 (d, 1H), 7.45 (s, 1H), 7.62 (d, 1H), 9.30 (s, 1H), 9.54 (s, 1H).

ESI-Mass; 521 [M$^+$+H]

Example 324

{5-(tert-Butyldimethylsilyloxy)-2-[1-(tert-butyldimethylsilyloxy)indan-5-yl]phenyl}[4-(2-piperidin-1-ylethoxy)phenyl]amine

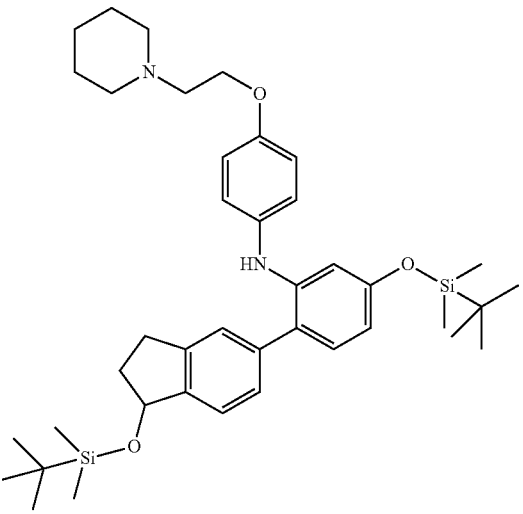 [SMILES: CC(C)(C)[Si](C)(C)Oc1ccc(-c2ccc3c(c2)CCC3O[Si](C)(C)C(C)(C)C)c(Nc2ccc(OCCN3CCCCC3)cc2)c1]

Synthesized from 5-(tert-butyldimethylsilyloxy)-2-[1-(tert-butyldimethylsilyloxy)indan-5-yl]phenylamine (635 mg) and 1-[2-(4-bromophenoxy)ethyl]piperidine (385 mg) according to an analogous synthetic method to Example 116, the title compound (593 mg) was obtained.

$^1$H-NMR (400 MHz, CDCl$_3$); δ (ppm): 0.16-0.21 (m, 12H), 0.94-0.99 (m, 18H), 1.41-1.50 (m, 2H), 1.54-1.65 (m, 4H), 1.90-2.02 (m, 1H), 2.42-2.57 (m, 5H), 2.77 (t, 2H), 2.77-2.84 (m, 1H), 2.96-3.04 (m, 1H), 4.09 (t, 2H), 5.31 (t, 1H), 5.50 (s, 1H), 6.37 (dd, 1H), 6.60 (d, 1H), 6.86 (d, 2H), 6.98-7.05 (m, 3H), 7.23-7.37 (m, 3H).

Example 325

5-{4-Hydroxy-2-[4-(2-piperidin-1-ylethoxy)phenylamino]phenyl}indan-1-ol

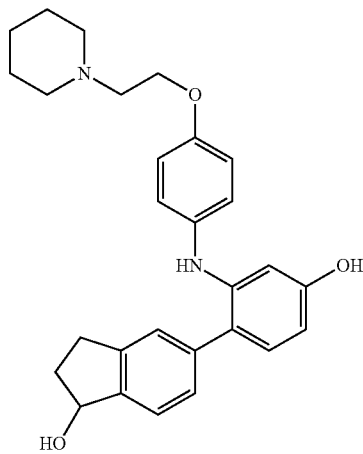 [SMILES: Oc1ccc(-c2ccc3c(c2)CCC3O)c(Nc2ccc(OCCN3CCCCC3)cc2)c1]

To a solution of {5-(tert-butyldimethylsilyloxy)-2-[1-(tert-butyldimethylsilyloxy)indan-5-yl]phenyl}[4-(2-piperidin-1-ylethoxy)phenyl]amine (590 mg) in tetrahydrofuran (8 ml) was added tetrabutylammonium fluoride (1.0 M solution in tetrahydrofuran) (3 ml), and the solution was stirred for 3 hours at room temperature. A saturated aqueous solution of ammonium chloride was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (ethyl acetate-methanol system) to provide the title compound (308 mg).

$^1$H-NMR (400 MHz, DMSO-d$_6$); δ (ppm): 1.28-1.52 (m, 6H), 1.70-1.82 (m, 1H), 2.22-2.50 (m, 5H), 2.60 (t, 2H), 2.51-2.63 (m, 1H), 2.81-2.94 (m, 1H), 3.97 (t, 2H), 5.03 (t, 1H), 5.19 (brs, 1H), 6.25-7.32 (m, 11H), 9.20 (s, 1H).

ESI-Mass; 445 [M$^+$+H]

Example 326

5-{4-Hydroxy-2-[4-(2-piperidin-1-ylethoxy)phenylamino]phenyl}indan-1-one

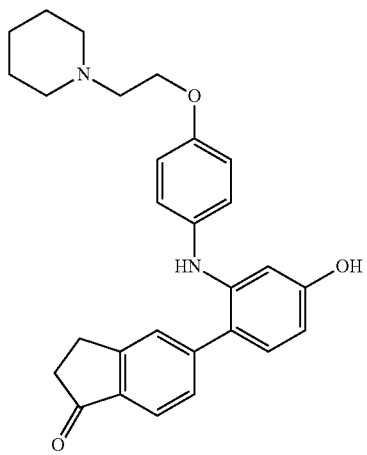 [SMILES: O=C1CCc2cc(-c3ccc(O)cc3Nc3ccc(OCCN4CCCCC4)cc3)ccc21]

To dichloromethane (2 ml) was added oxalyl chloride (0.22 ml) under a nitrogen atmosphere, the solution was cooled at −78° C., a solution of dimethylsulfoxide (245 mg) in dichloromethane (2 ml) was added dropwise thereto over 10 minutes, and then solution was stirred for 45 minutes. A solution of 5-{4-methoxy-2-[4-(2-piperidin-1-ylethoxy)phenylamino]phenyl}indan-1-ol (552 mg) in dichloromethane (4 ml) was added dropwise thereto over 25 minutes, the solution was stirred for 40 minutes, then triethylamine (0.85 ml) was added dropwise thereto followed by stirring for 20 minutes while warming from −78° C. to room temperature. Water was added thereto followed by stirring, the solution was extracted with ethyl acetate, then sequentially washed with water and brine, and the solvent was evaporated in vacuo. Obtained by purifying the residue by NH silica gel column chromatography (hexane-ethyl acetate system), to a solution of the resulting 5-{4-methoxy-2-[4-(2-piperidin-1-ylethoxy)phenylamino]phenyl}indan-1-one (118 mg) in methanesulfonic acid (3 ml) was added DL-methionine (110 mg), the solution was stirred for 5 hours at 80° C., then water was added thereto, the solution was stirred, and neutralized with aqueous ammonia. The solution was extracted with ethyl acetate, then sequentially washed with water and brine, and the solvent was evaporated in vacuo. The residue was purified by NH silica gel column chromatography (ethyl acetate-methanol system) to provide the title compound (42 mg).

$^1$H-NMR (400 MHz, DMSO-d$_6$); δ (ppm): 1.31-1.39 (m, 2H), 1.42-1.50 (m, 4H), 2.32-2.43 (m, 4H), 2.54-2.64 (m, 4H), 3.04-3.09 (m, 2H), 3.96 (t, 2H), 6.35 (dd, 1H), 6.51-6.54 (m, 1H), 6.76-6.81 (m, 3H), 6.90-6.94 (m, 3H), 7.03 (d, 1H), 7.44 (d, 1H), 7.57 (s, 1H).

ESI-Mass; 443 [M$^+$+H]

Example 327

5-{4-Hydroxy-2-[4-(2-piperidin-1-ylethoxy)phenylamino]phenyl}indan-1-one oxime

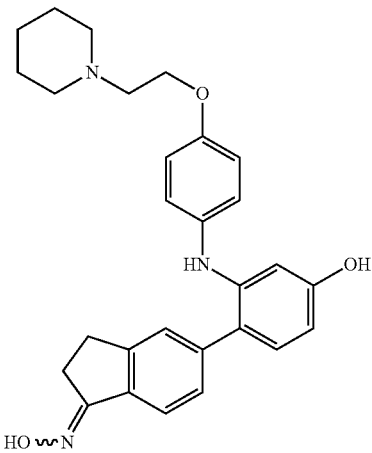 [SMILES: ON=C1CCc2cc(-c3ccc(O)cc3Nc3ccc(OCCN4CCCCC4)cc3)ccc21]

To a solution of 5-{4-hydroxy-2-[4-(2-piperidin-1-ylethoxy)phenylamino]phenyl}indan-1-one (28 mg) in ethanol (1 ml) and tetrahydrofuran (0.2 ml) were sequentially added hydroxylammonium chloride (43 mg) and pyridine (0.2 ml), and the solution was stirred overnight at 60° C. Water was added thereto followed by stirring, the solution was extracted with ethyl acetate, then sequentially washed with water and brine, and the solvent was evaporated in vacuo. The residue was purified by NH silica gel column chromatography (ethyl acetate-methanol system) to provide the title compound (6 mg).

$^1$H-NMR (400 MHz, DMSO-d$_6$); δ (ppm): 1.31-1.39 (m, 2H), 1.42-1.50 (m, 4H), 2.34-2.43 (m, 4H), 2.59 (t, 2H), 2.73-2.79 (m, 2H), 2.93-2.99 (m, 2H), 3.96 (t, 2H), 6.31 (dd, 1H), 6.49 (d, 1H), 6.72 (s, 1H), 6.78 (d, 2H), 6.92 (d, 2H), 6.97 (d, 1H), 7.27 (d, 1H), 7.35 (d, 1H), 7.50 (d, 1H), 9.28 (s, 1H), 10.78 (s, 1H).
ESI-Mass; 458 [M$^+$+H]

Example 328

5-{4-Methoxy-2-[4-(2-piperidin-1-ylethoxy)phenylamino]phenyl}indan-1-ol

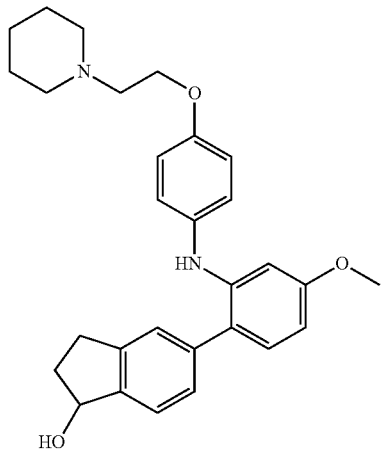 [SMILES: COc1ccc(-c2ccc3c(c2)CCC3O)c(Nc2ccc(OCCN3CCCCC3)cc2)c1]

Synthesized from 2-[1-(tert-butyldimethylsilyloxy)indan-5-yl]-5-methoxyphenylamine and 1-[2-(4-bromophenoxy)ethyl]piperidine according to an analogous synthetic method to Example 116, {2-[1-(tert-butyldimethylsilyloxy)indan-5-yl]-5-methoxyphenyl}[4-(2-piperidin-1-ylethoxy)phenyl]amine (1.1 g) was used according to an analogous synthetic method to Example 325 to provide the title compound (608 mg).

$^1$H-NMR (400 MHz, CDCl$_3$); δ (ppm): 1.42-1.49 (m, 2H), 1.55-1.66 (m, 4H), 1.97-2.05 (m, 1H), 2.47-2.59 (m, 5H), 2.78 (t, 2H), 2.81-2.91 (m, 1H), 3.05-3.15 (m, 1H), 3.76 (s, 3H), 4.10 (t, 2H), 5.31 (t, 1H), 5.55 (s, 1H), 6.45 (dd, 1H), 6.65 (d, 1H), 6.86 (d, 2H), 7.06 (d, 2H), 7.10 (d, 1H), 7.31-7.36 (m, 2H), 7.48 (d, 1H).
ESI-Mass; 459 [M$^+$+H]

Example 329

3-{[4-(2-Azepan-1-ylethoxy)benzyl]ethylamino}-4-[1-(3-hydroxyphenyl)pyrrolidin-3-yl]phenol

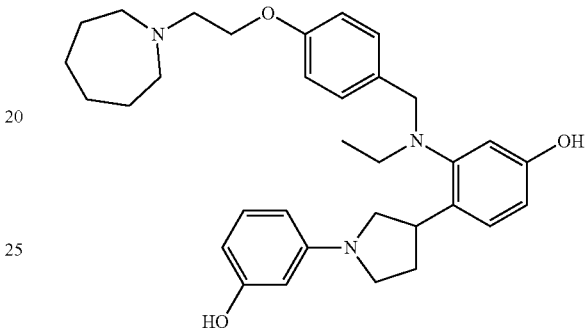

Synthesized from 5-methoxy-2-[1-(3-methoxyphenyl)pyrrolidin-3-yl]phenylamine and 4-(2-azepan-1-ylethoxy)benzoic acid hydrochloride according to an analogous synthetic method to Example 152, [4-(2-azepan-1-ylethoxy)benzyl]{5-methoxy-2-[1-(3-methoxyphenyl)pyrrolidin-3-yl]phenyl}amine (202 mg) was used according to an analogous synthetic method to Example 36 to provide [4-(2-azepan-1-ylethoxy)benzyl]ethyl {5-methoxy-2-[1-(3-methoxyphenyl)pyrrolidin-3-yl]phenyl}amine (188 mg). The total amount of this compound was used according to an analogous synthetic method to Example 111 to provide the title compound (153 mg).

$^1$H-NMR (400 MHz, DMSO-d$_6$); δ (ppm): 0.89 (t, 3H), 1.48-1.59 (m, 8H), 1.84-1.94 (m, 1H), 2.04-2.12 (m, 1H), 2.62-2.67 (m, 4H), 2.80 (t, 2H), 2.85 (q, 2H), 2.93 (t, 1H), 3.24 (dd, 1H), 3.30-3.38 (m, 2H), 3.90 (s, 2H), 3.96 (t, 2H), 3.98-4.07 (m, 1H), 5.90 (d, 1H), 5.94 (d, 1H), 6.01 (dd, 1H), 6.49 (dd, 1H), 6.63 (s, 1H), 6.81 (d, 2H), 6.90 (t, 1H), 7.05 (d, 1H), 7.12 (d, 2H), 8.95 (s, 1H), 9.14 (s, 1H).
ESI-Mass; 530 [M$^+$+H]

Example 330

3-{3-{2-{[4-(2-Azepan-1-ylethoxy)benzyl]ethylamino}phenyl}pyrrolidin-1-yl}phenol

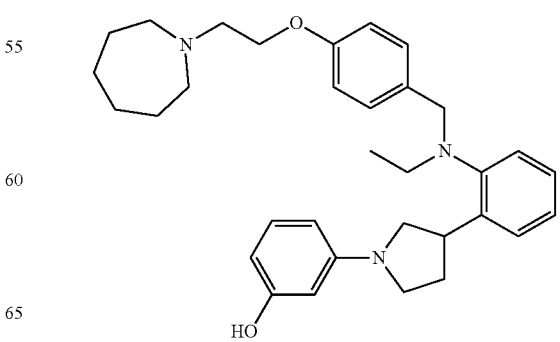

Synthesized from 2-[1-(3-methoxyphenyl)pyrrolidin-3-yl]phenylamine and 4-(2-azepan-1-ylethoxy)benzoic acid hydrochloride according to an analogous method to Example 152, synthetic [4-(2-azepan-1-ylethoxy)benzyl]{2-[1-(3-methoxyphenyl)pyrrolidin-3-yl]phenyl}amine (180 mg) was used according to an analogous synthetic method to Example 36 to provide [4-(2-azepan-1-ylethoxy)benzyl]ethyl {2-[1-(3-methoxyphenyl)pyrrolidin-3-yl]phenyl}amine (153 mg). The total amount of this compound was used according to an analogous synthetic method to Example 111 to provide the title compound (140 mg).

$^{1}$H-NMR (400 MHz, DMSO-$d_{6}$); δ (ppm): 0.89 (t, 3H), 1.48-1.58 (m, 8H), 1.88-1.99 (m, 1H), 2.08-2.17 (m, 1H), 2.62-2.67 (m, 4H), 2.79 (t, 2H), 2.91 (q, 2H), 2.99 (t, 1H), 3.23-3.30 (m, 1H), 3.36-3.42 (m, 2H), 3.96 (s, 2H), 4.13-4.22 (m, 1H), 5.92 (s, 1H), 5.95 (dd, 1H), 6.02 (dd, 1H), 6.80 (d, 2H), 6.91 (t, 1H), 7.06 (dt, 1H), 7.11 (d, 2H), 7.17 (dt, 1H), 7.24-7.28 (m, 2H), 8.96 (s, 1H).

ESI-Mass; 514 [M$^{+}$+H]

Example 331

{2-[3-Fluoro-4-(2-piperidin-1-ylethoxy)phenyl]ethyl}[5-methoxy-2-(6-methoxy-1,2,3,4-tetrahydronaphthalen-2-yl)phenyl]amine

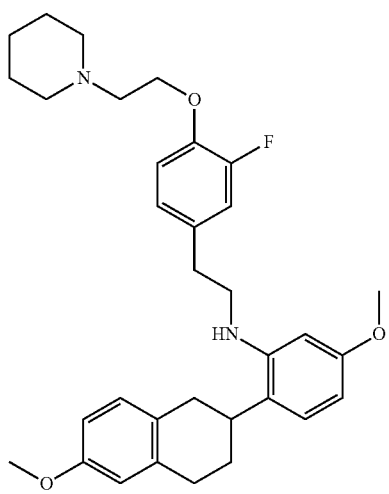 [SMILES: COc1ccc2c(c1)CCC(c1ccc(OC)cc1NCCc1ccc(OCCN3CCCCC3)c(F)c1)C2]

To a suspension of [3-fluoro-4-(2-piperidin-1-ylethoxy)phenyl]acetic acid hydrochloride (300 mg) in tetrahydrofuran (5 ml) were sequentially added oxalyl chloride (0.2 ml) and N,N-dimethylformamide (in catalytic amounts), the solution was stirred for 45 minutes at room temperature, then the reaction solution was concentrated in vacuo. To a suspension of the total amount of the resulting [3-fluoro-4-(2-piperidin-1-ylethoxy)phenyl]acetyl chloride hydrochloride (crude product) in 1,4-dioxane (8 ml) were sequentially added 5-methoxy-2-(6-methoxy-1,2,3,4-tetrahydronaphthalen-2-yl)phenylamine (250 mg) and N,N-diisopropylethylamine (1 ml), and the solution was stirred for 20 minutes at 100° C. A saturated aqueous solution of ammonium chloride was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate-methanol system) to provide 2-[3-fluoro-4-(2-piperidin-1-ylethoxy)phenyl]-N-[5-methoxy-2-(6-methoxy-1,2,3,4-tetrahydronaphthalen-2-yl)phenyl]acetamide (227 mg). To a suspension of lithium aluminum hydride (50 mg) in tetrahydrofuran (1.5 ml) was added aluminum chloride (175 mg) on an ice bath under a nitrogen atmosphere, the solution was stirred for 15 minutes at room temperature, then 2-[3-fluoro-4-(2-piperidin-1-ylethoxy)phenyl]-N-[5-methoxy-2-(6-methoxy-1,2,3,4-tetrahydronaphthalen-2-yl)phenyl]acetamide (225 mg) was added, and the solution was stirred overnight at room temperature. Obtained by sequentially adding tetrahydrofuran and aqueous ammonia, the suspension was filtered through celite pad, and the filtrate was concentrated in vacuo. The residue was purified by NH silica gel column chromatography (hexane-ethyl acetate system) to provide the title compound (224 mg).

$^{1}$H-NMR (400 MHz, CDCl$_{3}$); δ (ppm): 1.42-1.49 (m, 2H), 1.56-1.66 (m, 4H), 1.79-1.91 (m, 1H), 1.94-2.02 (m, 1H), 2.45-2.57 (m, 4H), 2.59-2.72 (m, 2H), 2.79 (t, 2H), 2.81-2.89 (m, 5H), 3.38 (t, 2H), 3.73 (brs, 1H), 3.80 (s, 6H), 4.11 (t, 2H), 6.27-6.31 (m, 2H), 6.66 (d, 1H), 6.70 (dd, 1H), 6.81-7.03 (m, 5H).

Example 332

6-{2-{[2-(3-Fluoro-4-hydroxyphenyl)ethyl]methylamino}-4-hydroxyphenyl}-5,6,7,8-tetrahydronaphthalen-2-ol

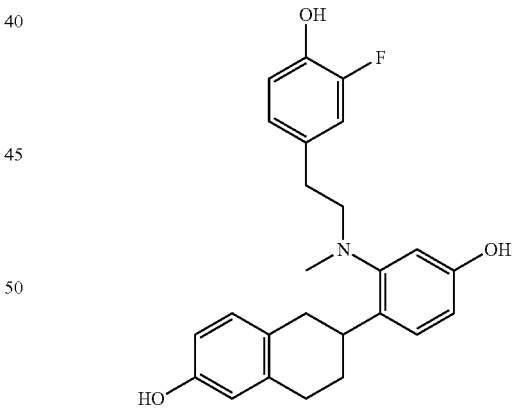

Synthesized from {2-[3-fluoro-4-(2-piperidin-1-ylethoxy)phenyl]ethyl}[5-methoxy-2-(6-methoxy-1,2,3,4-tetrahydronaphthalen-2-yl)phenyl]amine (370 mg) according to an analogous synthetic method to Example 48, the title compound (160 mg) was obtained.

$^{1}$H-NMR (400 MHz, DMSO-$d_{6}$); δ (ppm): 1.60-1.75 (m, 2H), 2.52-2.62 (m, 4H), 2.56 (s, 3H), 2.66-2.72 (m, 2H), 2.91-2.99 (m, 2H), 3.14-3.24 (m, 1H), 6.43-6.50 (m, 3H), 6.56 (s, 1H), 6.65-6.80 (m, 3H), 6.86 (d, 1H), 7.02 (d, 1H), 8.98 (brs, 1H), 9.10 (brs, 1H), 9.40 (brs, 1H).

Example 333

6-{2-{{2-[3-Fluoro-4-(2-piperidin-1-ylethoxy)phenyl]ethyl}methylamino}-4-hydroxyphenyl}-5,6,7,8-tetrahydronaphthalen-2-ol

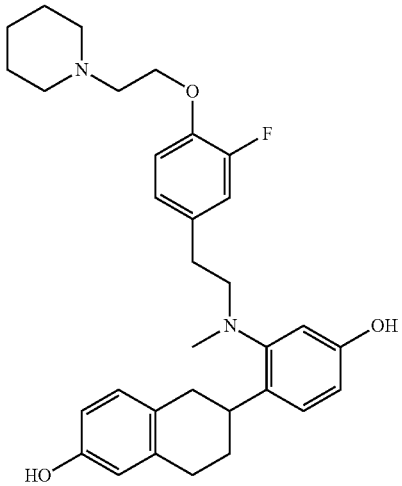

Synthesized from {2-[3-fluoro-4-(2-piperidin-1-ylethoxy)phenyl]ethyl}[5-methoxy-2-(6-methoxy-1,2,3,4-tetrahydronaphthalen-2-yl)phenyl]amine according to an analogous synthetic method to Preparation Example 18, {2-[3-fluoro-4-(2-piperidin-1-ylethoxy)phenyl]ethyl}[5-methoxy-2-(6-methoxy-1,2,3,4-tetrahydronaphthalen-2-yl)phenyl]methylamine (180 mg) was used according to an analogous synthetic method to Example 111 to provide the title compound (110 mg).

$^1$H-NMR (400 MHz, DMSO-$d_6$); δ (ppm): 1.31-1.39 (m, 2H), 1.42-1.51 (m, 4H), 1.56-1.73 (m, 2H), 2.36-2.44 (m, 4H), 2.52-2.68 (m, 11H), 2.91-3.03 (m, 2H), 3.07-3.17 (m, 1H), 3.99 (t, 2H), 6.42-6.50 (m, 3H), 6.56 (d, 1H), 6.77 (d, 1H), 6.82 (dd, 1H), 6.89 (t, 1H), 6.95 (dd, 1H), 7.00 (d, 1H), 8.97 (s, 1H), 9.09 (s, 1H).
ESI-Mass; 519 [M$^+$+H]

Example 334

6-{2-{Ethyl[2-(3-fluoro-4-hydroxyphenyl)ethyl]amino}-4-hydroxyphenyl}-5,6,7,8-tetrahydronaphthalen-2-ol and 6-{2-{ethyl{2-[3-fluoro-4-(2-piperidin-1-yl-ethoxy)phenyl]ethyl}amino}-4-hydroxyphenyl}-5,6,7,8-tetrahydronaphthalen-2-ol

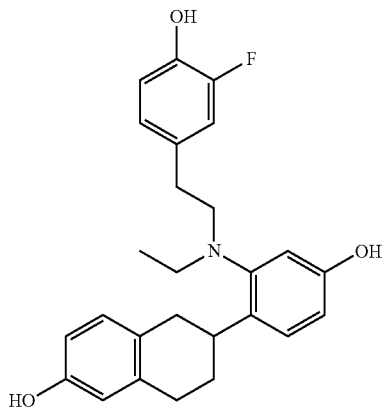 [SMILES: CN(CCc1ccc(O)c(F)c1)c1cc(O)ccc1C1CCc2cc(O)ccc2C1]

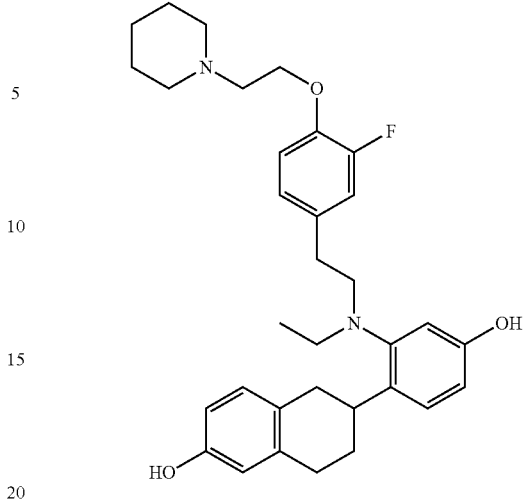

Synthesized from {2-[3-fluoro-4-(2-piperidin-1-yl-ethoxy)phenyl]ethyl}[5-methoxy-2-(6-methoxy-1,2,3,4-tetrahydronaphthalen-2-yl)phenyl]amine (500 mg) was used according to an analogous synthetic method to Example 49 to provide 6-{2-{ethyl[2-(3-fluoro-4-hydroxyphenyl)ethyl]amino}-4-hydroxyphenyl}-5,6,7,8-tetrahydronaphthalen-2-ol (18 mg) and 6-{2-{ethyl{2-[3-fluoro-4-(2-piperidin-1-yl-ethoxy)phenyl]ethyl}amino}-4-hydroxyphenyl}-5,6,7,8-tetrahydronaphthalen-2-ol (210 mg).

6-{2-{Ethyl[2-(3-fluoro-4-hydroxyphenyl)ethyl]amino}-4-hydroxyphenyl}-5,6,7,8-tetrahydronaphthalen-2-ol $^1$H-NMR (400 MHz, DMSO-$d_6$); δ (ppm): 0.86 (t, 3H), 1.56-1.73 (m, 2H), 2.31-2.72 (m, 6H), 2.86 (q, 2H), 3.00 (t, 2H), 3.19-3.30 (m, 1H), 6.46-6.52 (m, 3H), 6.60 (s, 1H), 6.67-6.89 (m, 4H), 7.04 (d, 1H), 8.97 (s, 1H), 9.09 (s, 1H), 9.50 (s, 2H).

6-{2-{Ethyl{2-[3-fluoro-4-(2-piperidin-1-yl-ethoxy)phenyl]ethyl}amino}-4-hydroxyphenyl}-5,6,7,8-tetrahydronaphthalen-2-ol $^1$H-NMR (400 MHz, DMSO-$d_6$); δ (ppm): 0.87 (t, 3H), 1.31-1.39 (m, 2H), 1.41-1.50 (m, 4H), 1.55-1.68 (m, 2H), 2.35-2.42 (m, 4H), 2.50-2.55 (m, 4H), 2.61 (t, 2H), 2.62-2.68 (m, 2H), 2.87 (q, 2H), 3.03 (t, 2H), 3.20-3.31 (m, 1H), 4.00 (t, 2H), 6.44-6.52 (m, 3H), 6.61 (s, 1H), 6.76-6.83 (m, 2H), 6.90-6.97 (m, 2H), 7.03 (d, 1H), 8.97 (brs, 1H), 9.10 (brs, 1H).
ESI-Mass; 533 [M$^+$+H]

Example 335

{2-[4-(2-Azepan-1-ylethoxy)phenyl]ethyl}[5-methoxy-2-(6-methoxy-1,2,3,4-tetrahydronaphthalen-2-yl)phenyl]amine

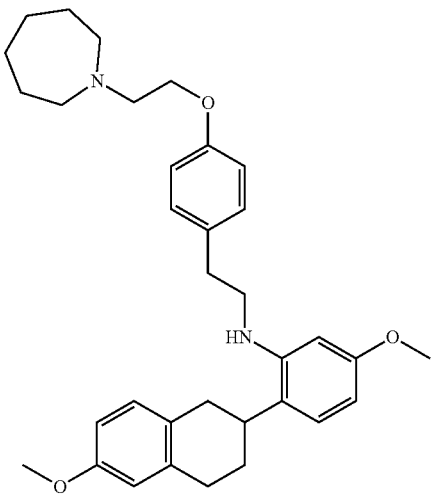 [SMILES: COc1ccc2c(c1)CCC(c1ccc(OC)cc1NCCc1ccc(OCCN3CCCCCC3)cc1)C2]

Synthesized from 5-methoxy-2-(6-methoxy-1,2,3,4-tetrahydronaphthalen-2-yl)phenylamine (425 mg) and [4-(2-azepan-1-ylethoxy)phenyl]acetic acid hydrochloride (700 mg) was used according to an analogous synthetic method to Example 337 to provide the title compound (140 mg).

$^1$H-NMR (400 MHz, CDCl$_3$); δ (ppm): 1.56-1.71 (m, 8H), 1.77-1.88 (m, 1H), 1.91-1.99 (m, 1H), 2.60-2.70 (m, 2H), 2.76-2.92 (m, 9H), 2.94 (t, 2H), 3.37 (t, 2H), 3.72-3.77 (m, 1H), 3.79 (s, 6H), 4.01 (t, 2H), 6.26-6.30 (m, 2H), 6.66 (d, 1H), 6.70 (dd, 1H), 6.80 (d, 2H), 6.94 (d, 1H), 7.01 (d, 1H), 7.09 (d, 2H).

Example 336

6-{2-{{2-[4-(2-Azepan-1-ylethoxy)phenyl]ethyl}ethylamino}-4-hydroxyphenyl}-5,6,7,8-tetrahydronaphthalen-2-ol

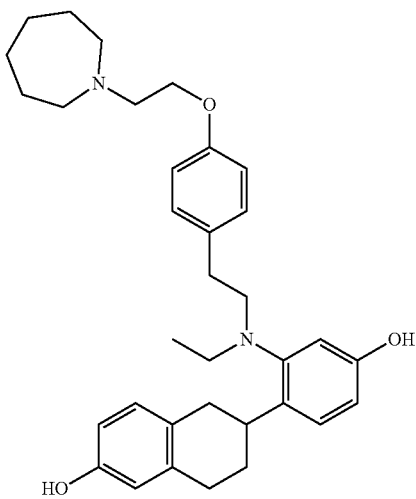 [SMILES: CCN(CCc1ccc(OCCN2CCCCCC2)cc1)c1cc(O)ccc1C1CCc2cc(O)ccc2C1]

Synthesized from {2-[4-(2-azepan-1-ylethoxy)phenyl]ethyl}[5-methoxy-2-(6-methoxy-1,2,3,4-tetrahydronaphthalen-2-yl)phenyl]amine according to an analogous synthetic method to Example 36, {2-[4-(2-azepan-1-ylethoxy)phenyl]ethyl}ethyl[5-methoxy-2-(6-methoxy-1,2,3,4-tetrahydronaphthalen-2-yl)phenyl]amine (130 mg) was used according to an analogous synthetic method to Example 111 to provide the title compound (95 mg).

$^1$H-NMR (400 MHz, DMSO-d$_6$); δ (ppm): 0.86 (t, 3H), 1.47-1.58 (m, 8H), 1.58-1.75 (m, 2H), 2.46-2.76 (m, 11H), 2.79 (t, 2H), 2.88 (q, 2H), 3.00 (t, 2H), 3.91 (t, 2H), 6.43-6.53 (m, 3H), 6.61 (d, 1H), 6.72 (d, 2H), 6.79 (d, 1H), 6.98 (d, 2H), 7.04 (d, 1H), 8.97 (s, 1H), 9.08 (s, 1H).
ESI-Mass; 529 [M$^+$+H]

Preparation Example 112

5-Hydroxy-2-[5-methoxy-2-(6-methoxy-1,2,3,4-tetrahydronaphthalen-2-yl)phenyl]isoindole-1,3-dione

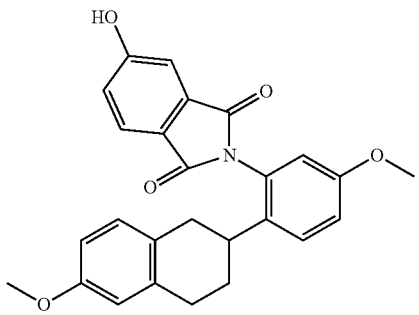

A suspension of 5-methoxy-2-(6-methoxy-1,2,3,4-tetrahydronaphthalen-2-yl)phenylamine (1.0 g) and 4-hydroxyphthalic acid (1.0 g) in acetic acid (10 ml) was stirred for 1 hour at 140° C. Water was added thereto followed by stirring, the solution was extracted with ethyl acetate, then sequentially washed with a saturated aqueous solution of sodium bicarbonate, water and brine, and the solvent was evaporated in vacuo. The residue was purified by silica gel column chromatography (hexane-ethyl acetate system) to provide the title compound (1.5 g).

$^1$H-NMR (400 MHz, DMSO-d$_6$); δ (ppm): 1.74-1.82 (m, 2H), 2.55-2.79 (m, 5H), 3.63 (s, 3H), 3.73 (s, 3H), 6.55-6.62 (m, 2H), 6.88 (dd, 1H), 6.95 (d, 1H), 7.05 (dd, 1H), 7.11-7.19 (m, 2H), 7.41 (d, 1H), 7.74 (dd, 1H), 11.10 (brs, 1H).

Example 337

2-[5-Methoxy-2-(6-methoxy-1,2,3,4-tetrahydronaphthalen-2-yl)phenyl]-2,3-dihydro-1H-isoindol-5-ol

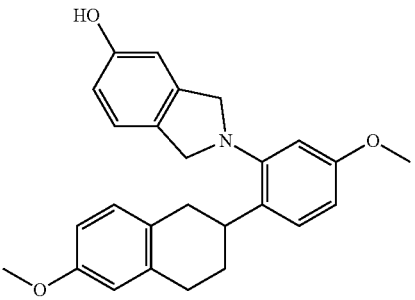

To a suspension of lithium aluminum hydride (330 mg) in tetrahydrofuran (9 ml) was added aluminum chloride (1.2 g) on an ice bath under a nitrogen atmosphere, the solution was stirred for 20 minutes at room temperature, a solution of 5-hydroxy-2-[5-methoxy-2-(6-methoxy-1,2,3,4-tetrahydronaphthalen-2-yl)phenyl]isoindole-1,3-dione (730 mg) in tetrahydrofuran (5 ml) was then added dropwise on an ice bath followed by stirring overnight at room temperature. Obtained by sequentially adding tetrahydrofuran and aqueous ammonia, the suspension was filtered through celite pad, and the filtrate was concentrated in vacuo. The residue was purified by silica gel column chromatography (hexane-ethyl acetate system) to provide the title compound (580 mg).

$^1$H-NMR (400 MHz, DMSO-d$^6$); δ (ppm): 1.80-1.90 (m, 2H), 2.68-2.88 (m, 4H), 3.23-3.30 (m, 1H), 3.67 (s, 3H), 3.70 (s, 3H), 4.27 (d, 2H), 4.34 (d, 2H), 6.58-6.67 (m, 5H), 6.81 (d, 1H), 6.95 (d, 1H), 7.04 (d, 1H), 7.19 (d, 1H), 9.27 (brs, 1H).

Example 338

6-{4-Hydroxy-2-[5-(2-piperidin-1-ylethoxy)-1,3-dihydroisoindol-2-yl]phenyl}-5,6,7,8-tetrahydronaphthalen-2-ol

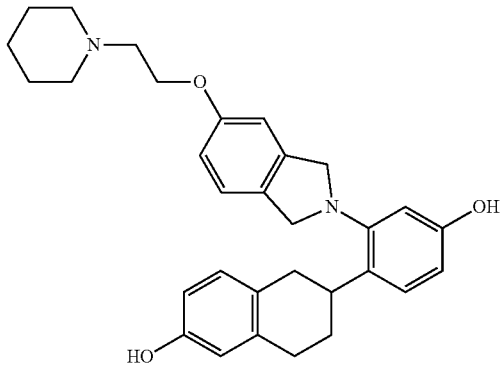 [SMILES: Oc1ccc2c(c1)CCC(c1ccc(O)cc1N1Cc3ccc(OCCN4CCCCC4)cc3C1)C2]

Synthesized from 2-[5-methoxy-2-(6-methoxy-1,2,3,4-tetrahydronaphthalen-2-yl)phenyl]-2,3-dihydro-1H-isoindol-5-ol and 1-(2-chloroethyl)piperidine hydrochloride according to an analogous synthetic method to Preparation Example 40, 2-[5-methoxy-2-(6-methoxy-1,2,3,4-tetrahydronaphthalen-2-yl)phenyl]-5-(2-piperidin-1-ylethoxy)-2,3-dihydro-1H-isoindole (218 mg) was used according to an analogous synthetic method to Example 111 to provide the title compound (123 mg).

$^1$H-NMR (400 MHz, DMSO-d$_6$); δ (ppm): 1.31-1.39 (m, 2H), 1.42-1.50 (m, 4H), 1.75-1.85 (m, 2H), 2.33-2.43 (m, 4H), 2.60 (t, 2H), 2.66-2.84 (m, 4H), 3.17-3.26 (m, 1H), 4.01 (t, 2H), 4.25 (d, 2H), 4.32 (d, 2H), 6.43-6.49 (m, 3H), 6.65 (d, 1H), 6.76 (dd, 1H), 6.82 (d, 1H), 6.89 (d, 1H), 7.06 (d, 1H), 7.15 (d, 1H), 8.98 (s, 1H), 9.12 (s, 1H).

ESI-Mass; 485 [M$^+$+H]

Example 339

6-{2-[5-(2-Azepan-1-ylethoxy)-1,3-dihydroisoindol-2-yl]-4-hydroxyphenyl}-5,6,7,8-tetrahydronaphthalen-2-ol

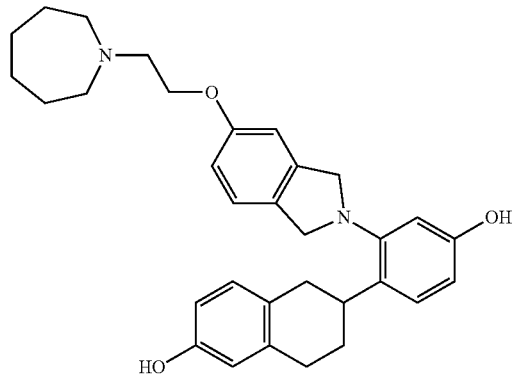 [SMILES: Oc1ccc2c(c1)CCC(c1ccc(O)cc1N1Cc3ccc(OCCN4CCCCCC4)cc3C1)C2]

Synthesized from 2-[5-methoxy-2-(6-methoxy-1,2,3,4-tetrahydronaphthalen-2-yl)phenyl]-2,3-dihydro-1H-isoindol-5-ol and 1-(2-chloroethyl)azepane hydrochloride according to an analogous synthetic method to Preparation Example 40, 5-(2-azepan-1-ylethoxy)-2-[5-methoxy-2-(6-methoxy-1,2,3,4-tetrahydronaphthalen-2-yl)phenyl]-2,3-dihydro-1H-isoindole (223 mg) was used according to an analogous synthetic method to Example 111 to provide the title compound (149 mg).

$^1$H-NMR (400 MHz, DMSO-d$_6$); δ (ppm): 1.47-1.58 (m, 8H), 1.76-1.86 (m, 2H), 2.62-2.82 (m, 10H), 3.17-3.26 (m, 1H), 3.98 (t, 2H), 4.25 (d, 2H), 4.32 (d, 2H), 6.44-6.49 (m, 3H), 6.65 (d, 1H), 6.76 (dd, 1H), 6.82 (d, 1H), 6.89 (d, 1H), 7.06 (d, 1H), 7.15 (d, 1H), 8.98 (s, 1H), 9.12 (s, 1H).

ESI-Mass; 499 [M$^+$+H]

Example 340

6-{2-[5-(2-Diisopropylaminoethoxy)-1,3-dihydroisoindol-2-yl]-4-hydroxyphenyl}-5,6,7,8-tetrahydronaphthalen-2-ol

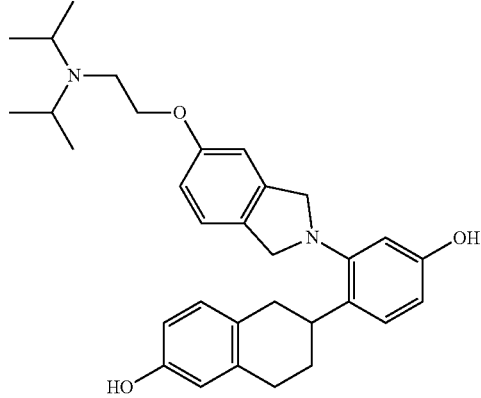 [SMILES: CC(C)N(CCOc1ccc2c(c1)CN(c1cc(O)ccc1C1CCc3cc(O)ccc3C1)C2)C(C)C]

Synthesized from 2-[5-methoxy-2-(6-methoxy-1,2,3,4-tetrahydronaphthalen-2-yl)phenyl]-2,3-dihydro-1H-isoindol-5-ol and (2-chloroethyl)diisopropylamine hydrochloride according to an analogous synthetic method to Preparation Example 40, diisopropyl {2-{2-[5-methoxy-2-(6-methoxy-1,2,3,4-tetrahydronaphthalen-2-yl)phenyl]-2,3-dihydro-1H-isoindol-5-yloxy}ethyl}amine (126 mg) was used according to an analogous synthetic method to Example 111 to provide the title compound (62 mg).

$^1$H-NMR (400 MHz, DMSO-d$_6$); δ (ppm): 0.95 (d, 12H), 1.76-1.85 (m, 2H), 2.63-2.81 (m, 6H), 2.98 (hept, 2H), 3.17-3.26 (m, 1H), 3.82 (t, 2H), 4.25 (d, 2H), 4.32 (d, 2H), 6.44-6.49 (m, 3H), 6.65 (d, 1H), 6.74 (dd, 1H), 6.82 (d, 1H), 6.86 (d, 1H), 7.06 (d, 1H), 7.15 (d, 1H), 8.98 (s, 1H), 9.12 (s, 1H).

ESI-Mass; 501 [M$^+$+H]

Example 341 {5-Methoxy-2-[2-(4-methoxyphenyl)ethyl]phenyl}[4-(2-piperidin-1-ylethoxy)benzyl]amine

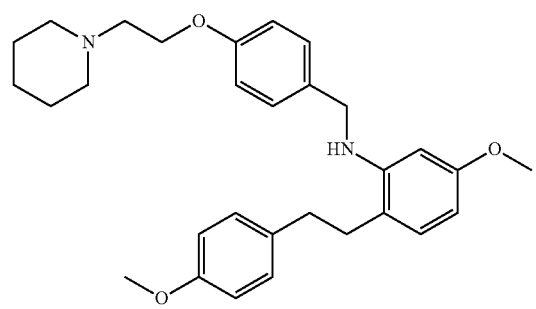 [SMILES: COc1ccc(CCc2ccc(OC)cc2NCc2ccc(OCCN3CCCCC3)cc2)cc1]

Synthesized from 5-methoxy-2-[2-(4-methoxyphenyl)ethyl]phenylamine (643 mg) and 4-(2-piperidin-1-ylethoxy)benzoyl chloride hydrochloride (989 mg) according to an analogous synthetic method to Example 152, the title compound (868 mg) was obtained.

$^1$H-NMR (400 MHz, CDCl$_3$); δ (ppm): 1.40-1.48 (m, 2H), 1.57-1.65 (m, 4H), 2.47-2.55 (m, 4H), 2.63-2.69 (m, 2H), 2.77 (t, 2H), 2.81-2.87 (m, 2H), 3.75 (s, 3H), 3.78 (s, 3H), 4.10 (t, 2H), 4.18 (s, 2H), 6.21-6.27 (m, 2H), 6.77-6.82 (m, 2H), 6.85-6.90 (m, 2H), 6.95 (d, 1H), 7.02-7.08 (m, 2H), 7.20-7.26 (m, 2H).

Example 342

4-[2-(4-Hydroxyphenyl)ethyl]-3-[4-(2-piperidin-1-ylethoxy)benzylamino]phenol

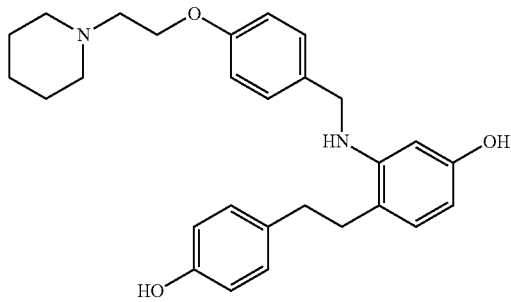 [SMILES: Oc1ccc(CCc2ccc(O)cc2NCc2ccc(OCCN3CCCCC3)cc2)cc1]

Synthesized from {5-methoxy-2-[2-(4-methoxyphenyl)ethyl]phenyl}[4-(2-piperidin-1-ylethoxy)benzyl]amine (356 mg) according to an analogous synthetic method to Example 779 described below, the title compound (10 mg) was obtained.

$^1$H-NMR (400 MHz, CDCl$_3$); δ (ppm): 1.42-1.50 (m, 2H), 1.62-1.70 (m, 4H), 2.57-2.65 (m, 4H), 2.76-2.89 (m, 6H), 3.88 (s, 2H), 4.09 (t, 2H), 6.49 (dd, 1H), 6.59 (d, 1H), 6.61-6.66 (m, 2H), 6.67-6.72 (m, 2H), 6.84-6.89 (m, 2H), 7.04-7.12 (m, 3H).

Example 343

4-[2-(4-Hydroxyphenyl)ethyl]-3-{methyl-[4-(2-piperidin-1-ylethoxy)benzyl]amino}phenol

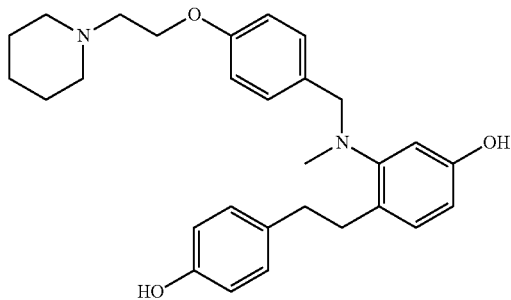 [SMILES: CN(Cc1ccc(OCCN2CCCCC2)cc1)c1cc(O)ccc1CCc1ccc(O)cc1]

Synthesized from {5-methoxy-2-[2-(4-methoxyphenyl)ethyl]phenyl}[4-(2-piperidin-1-ylethoxy)benzyl]amine (780 mg) according to an analogous synthetic method to Preparation Example 18, {5-methoxy-2-[2-(4-methoxyphenyl)ethyl]phenyl}methyl[4-(2-piperidin-1-ylethoxy)benzyl]amine (380 mg) was used according to an analogous synthetic method to Example 111 to provide the title compound (316 mg).

$^1$H-NMR (400 MHz, CDCl$_3$); δ (ppm): 1.42-1.50 (m, 2H), 1.62-1.70 (m, 4H), 2.54 (s, 3H), 2.57-2.65 (m, 4H), 2.76-2.89 (m, 6H), 3.88 (s, 2H), 4.09 (t, 2H), 6.49 (dd, 1H), 6.59 (d, 1H), 6.61-6.66 (m, 2H), 6.67-6.72 (m, 2H), 6.84-6.89 (m, 2H), 7.04-7.12 (m, 3H).

Preparation Example 113

5-Hydroxy-2-{5-methoxy-2-[2-(4-methoxyphenyl)ethyl]phenyl}isoindole-1,3-dione

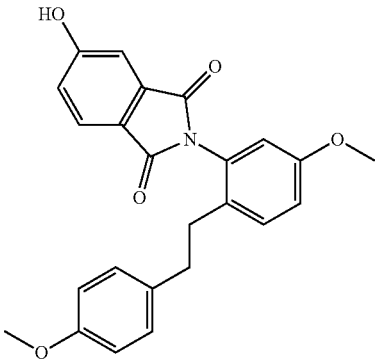

Synthesized from 5-methoxy-2-[2-(4-methoxyphenyl)ethyl]phenylamine (1.5 g) and 4-hydroxyphthalic acid (1.6 g) according to an analogous synthetic method to Preparation Example 112, the title compound (2.6 g) was obtained.

$^1$H-NMR (400 MHz, CDCl$_3$); δ (ppm): 2.65-2.78 (m, 4H), 3.74 (s, 3H), 3.77 (s, 3H), 6.70-6.75 (m, 2H), 6.92 (dd, 1H), 6.93-6.98 (m, 2H), 7.13 (dd, 1H), 7.19 (d, 1H), 7.33 (d, 1H), 7.78 (d, 1H).

Example 344

2-{5-Methoxy-2-[2-(4-methoxyphenyl)ethyl]phenyl}-5-(2-piperidin-1-ylethoxy)-2,3-dihydro-1H-isoindole

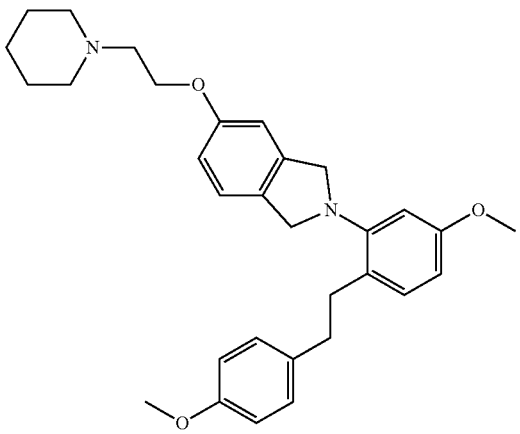 [SMILES: COc1ccc(CCc2ccc(OC)cc2N2Cc3ccc(OCCN4CCCCC4)cc3C2)cc1]

Synthesized from 5-hydroxy-2-{5-methoxy-2-[2-(4-methoxyphenyl)ethyl]phenyl}isoindole-1,3-dione and 1-(2-chloroethyl)piperidine hydrochloride according to an analogous synthetic method to Example 383 described below, 2-{5-methoxy-2-[2-(4-methoxyphenyl)ethyl]phenyl}-5-(2-piperidin-1-ylethoxy)isoindole-1,3-dione (772 mg) was used according to an analogous synthetic method to Example 337 to provide the title compound (630 mg).

¹H-NMR (400 MHz, CDCl₃); δ (ppm): 1.41-1.49 (m, 2H), 1.57-1.66 (m, 4H), 2.48-2.59 (m, 4H), 2.79 (t, 2H), 2.80-3.02 (m, 4H), 3.77 (s, 3H), 3.80 (s, 3H), 4.12 (t, 2H), 4.53 (d, 4H), 6.49-6.53 (m, 1H), 6.69 (s, 1H), 6.79-6.85 (m, 4H), 7.09-7.13 (m, 4H).

Example 345

4-[2-(4-Hydroxyphenyl)ethyl]-3-[5-(2-piperidin-1-ylethoxy)-1,3-dihydroisoindol-2-yl]phenol

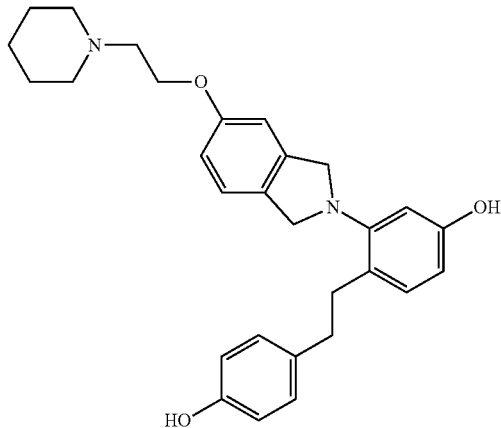 [SMILES: Oc1ccc(CCc2ccc(O)cc2N2Cc3ccc(OCCN4CCCCC4)cc3C2)cc1]

Synthesized from 2-{5-methoxy-2-[2-(4-methoxyphenyl)ethyl]phenyl}-5-(2-piperidin-1-ylethoxy)-2,3-dihydro-1H-isoindole (464 mg) according to an analogous synthetic method to Example 111, the title compound (304 mg) was obtained.

¹H-NMR (400 MHz, CDCl₃); δ (ppm): 1.42-1.53 (m, 2H), 1.62-1.72 (m, 4H), 2.52-2.68 (m, 4H), 2.77-2.93 (m, 6H), 4.11 (t, 2H), 4.36 (d, 4H), 6.41 (dd, 1H), 6.54 (d, 1H), 6.66-6.72 (m, 4H), 6.96-7.08 (m, 4H).

Example 346

3-[3-Fluoro-4-(2-piperidin-1-ylethoxy)phenylamino]-4-(4-hydroxyphenylethynyl)phenol

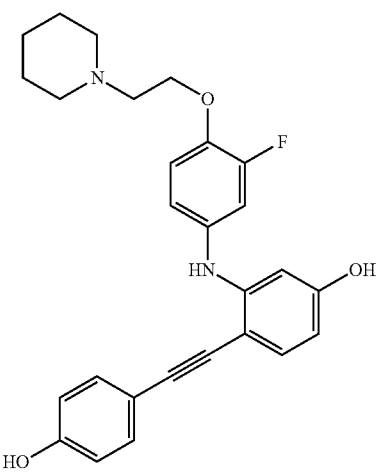 [SMILES: Oc1ccc(C#Cc2ccc(O)cc2Nc2ccc(OCCN3CCCCC3)c(F)c2)cc1]

Synthesized from 5-methoxy-2-[2-(4-methoxyphenyl)vinyl]phenylamine and 1-[2-(4-bromo-2-fluorophenoxy)ethyl]piperidine according to an analogous synthetic method to Example 116, [3-fluoro-4-(2-piperidin-1-ylethoxy)phenyl][5-methoxy-2-(4-methoxyphenylethynyl)phenyl]amine (124 mg) was used according to an analogous synthetic method to Example 111 to provide the title compound (66 mg).

¹H-NMR (400 MHz, DMSO-d₆); δ (ppm): 1.32-1.40 (m, 2H), 1.44-1.52 (m, 4H), 2.37-2.46 (m, 4H), 2.67 (t, 2H), 4.16 (t, 2H), 6.48 (d, 1H), 6.52 (s, 1H), 6.59 (dd, 1H), 6.65 (d, 2H), 6.94 (d, 1H), 7.02 (d, 2H), 7.17 (dd, 1H), 7.24 (t, 1H), 7.34 (d, 1H), 9.02 (s, 1H), 9.51 (s, 1H).

ESI-Mass; 447 [M⁺+H]

Example 347

4-{2-{2-[3-Fluoro-4-(2-piperidin-1-ylethoxy)benzylamino]phenyl}vinyl}phenol

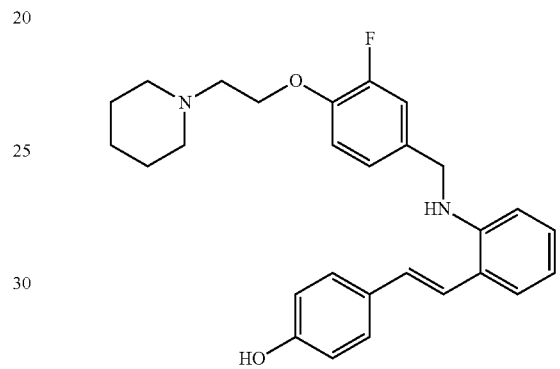

Synthesized from acetic acid 4-[2-(2-aminophenyl)vinyl]phenyl ester (328 mg) and 3-fluoro-4-(2-piperidin-1-ylethoxy)benzoyl chloride hydrochloride (500 mg) according to an analogous synthetic method to Example 152, the title compound (365 mg) was obtained.

¹H-NMR (400 MHz, DMSO-d₆); δ (ppm): 1.30-1.38 (m, 2H), 1.41-1.49 (m, 4H), 2.39-2.44 (m, 4H), 2.61 (t, 2H), 4.06 (t, 2H), 4.28 (d, 2H), 6.26 (t, 1H), 6.39 (d, 1H), 6.53 (t, 1H), 6.75 (d, 2H), 6.89 (d, 1H), 6.92 (ddd, 1H), 7.07-7.17 (m, 3H), 7.25 (d, 1H), 7.37 (dd, 1H), 7.45 (d, 2H), 9.51 (s, 1H).

ESI-Mass; 447 [M⁺+H]

Example 348

4-{2-{2-[3-Fluoro-4-(2-piperidin-1-ylethoxy)benzylamino]-4-methoxyphenyl}vinyl}phenol

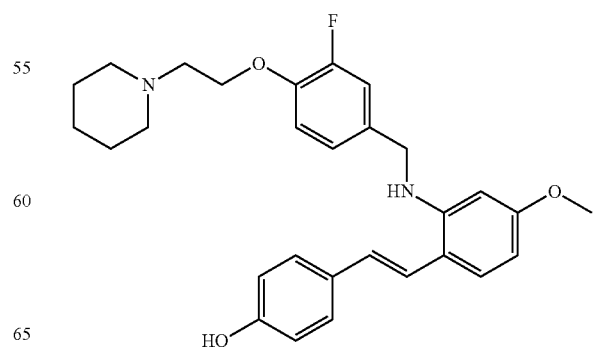

Synthesized from acetic acid 4-[2-(2-amino-4-methoxyphenyl)vinyl]phenyl ester (240 mg) and 3-fluoro-4-(2-piperidin-1-ylethoxy)benzoyl chloride hydrochloride (660 mg) according to an analogous synthetic method to Example 152, the title compound (273 mg) was obtained.

$^1$H-NMR (400 MHz, DMSO-d$_6$); δ (ppm): 1.31-1.38 (m, 2H), 1.42-1.49 (m, 4H), 2.34-2.42 (m, 4H), 2.61 (t, 2H), 3.58 (s, 3H), 4.07 (t, 2H), 4.26 (d, 2H), 5.92 (d, 1H), 6.14 (dd, 1H), 6.33 (t, 1H), 6.73 (d, 2H), 6.76 (d, 1H), 7.07-7.18 (m, 3H), 7.17 (d, 1H), 7.29 (d, 1H), 7.41 (d, 2H), 9.44 (s, 1H).

ESI-Mass; 477 [M$^+$+H]

Example 349

3-[3-Fluoro-4-(2-piperidin-1-ylethoxy)benzylamino]-4-[2-(4-hydroxyphenyl)vinyl]phenol

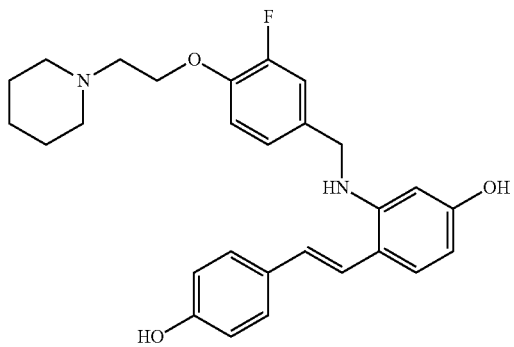 [SMILES: Oc1ccc(/C=C/c2ccc(O)cc2NCc2ccc(OCCN3CCCCC3)c(F)c2)cc1]

Synthesized from acetic acid 4-[2-(4-acetoxy-2-aminophenyl)vinyl]phenyl ester (300 mg) and 3-fluoro-4-(2-piperidin-1-ylethoxy)benzoyl chloride hydrochloride (370 mg) according to an analogous synthetic method to Example 152, the title compound (89 mg) was obtained.

$^1$H-NMR (400 MHz, DMSO-d$_6$); δ (ppm): 1.30-1.38 (m, 2H), 1.42-1.49 (m, 4H), 2.34-2.44 (m, 4H), 2.62 (t, 2H), 4.07 (t, 2H), 4.22 (d, 2H), 5.81 (d, 1H), 5.98 (dd, 1H), 6.21 (t, 1H), 6.68 (d, 1H), 6.72 (d, 2H), 7.04-7.20 (m, 5H), 7.39 (d, 2H), 9.01 (s, 1H), 9.40 (s, 1H).

ESI-Mass; 463 [M$^+$+H]

Example 350

4-{2-{2-{Ethyl[3-fluoro-4-(2-piperidin-1-ylethoxy)benzyl]amino}phenyl}vinyl}phenol

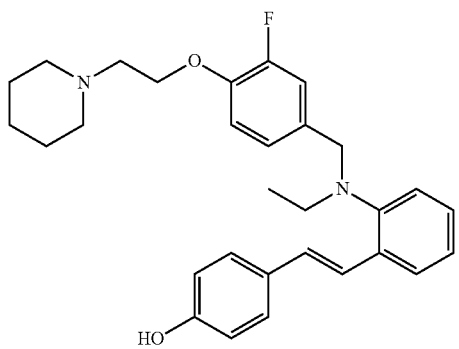 [SMILES: CCN(Cc1ccc(OCCN2CCCCC2)c(F)c1)c1ccccc1/C=C/c1ccc(O)cc1]

Synthesized from 4-{2-{2-[3-fluoro-4-(2-piperidin-1-ylethoxy)benzylamino]phenyl}vinyl}phenol (285 mg) according to an analogous synthetic method to Example 36, the title compound (258 mg) was obtained.

$^1$H-NMR (400 MHz, DMSO-d$_6$); δ (ppm): 0.95 (t, 3H), 1.29-1.38 (m, 2H), 1.41-1.49 (m, 4H), 2.33-2.42 (m, 4H), 2.60 (t, 2H), 2.97 (q, 2H), 4.05 (t, 2H), 4.08 (s, 2H), 6.75 (d, 2H), 6.97-7.15 (m, 7H), 7.34 (d, 2H), 7.35 (d, 1H), 7.58 (dd, 1H), 9.55 (s, 1H).

ESI-Mass; 475 [M$^+$+H]

Example 351

4-{2-{2-{Ethyl[3-fluoro-4-(2-piperidin-1-ylethoxy)benzyl]amino}-4-methoxyphenyl}vinyl}phenol

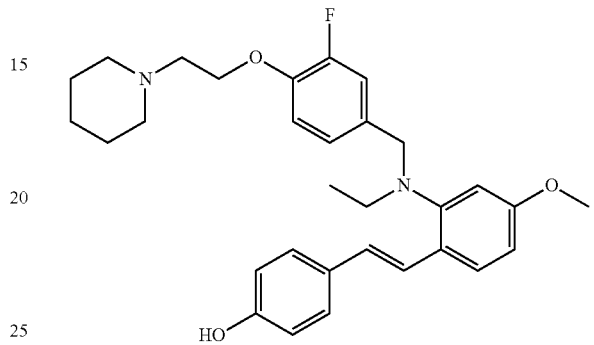

Synthesized from 4-{2-{2-[3-fluoro-4-(2-piperidin-1-ylethoxy)benzylamino]-4-methoxyphenyl}vinyl}phenol (200 mg) according to an analogous synthetic method to Example 36, the title compound (179 mg) was obtained.

$^1$H-NMR (400 MHz, DMSO-d$_6$); δ (ppm): 0.96 (t, 3H), 1.30-1.39 (m, 2H), 1.40-1.49 (m, 4H), 2.33-2.43 (m, 4H), 2.61 (t, 2H), 2.97 (q, 2H), 3.69 (s, 3H), 4.04 (t, 2H), 4.09 (s, 2H), 6.57-6.62 (m, 2H), 6.73 (d, 2H), 6.89 (d, 1H), 7.03-7.13 (m, 3H), 7.24 (d, 1H), 7.30 (d, 2H), 7.50 (d, 1H), 9.50 (s, 1H).

ESI-Mass; 505 [M$^+$+H]

Example 352

3-{Ethyl[3-fluoro-4-(2-piperidin-1-ylethoxy)benzyl]amino}-4-[2-(4-hydroxyphenyl)vinyl]phenol

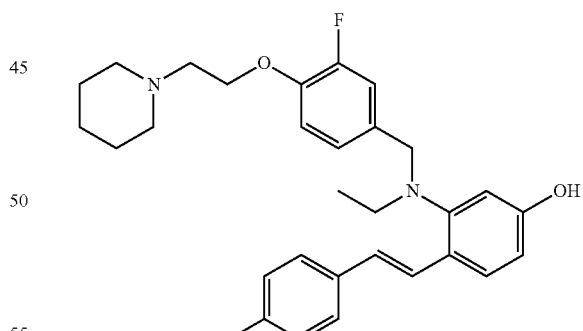

Synthesized from 3-[3-fluoro-4-(2-piperidin-1-ylethoxy)benzylamino]-4-[2-(4-hydroxyphenyl)vinyl]phenol (77 mg) according to an analogous synthetic method to Example 36, the title compound (59 mg) was obtained.

$^1$H-NMR (400 MHz, DMSO-d$_6$); δ (ppm): 0.95 (t, 3H), 1.30-1.38 (m, 2H), 1.42-1.50 (m, 4H), 2.34-2.42 (m, 4H), 2.61 (t, 2H), 2.92 (q, 2H), 4.03 (s, 2H), 4.06 (t, 2H), 6.43 (dd, 1H), 6.46 (d, 1H), 6.71 (d, 2H), 6.82 (d, 1H), 7.01-7.11 (m, 3H), 7.22 (d, 1H), 7.27 (d, 2H), 7.39 (d, 1H), 9.33 (brs, 1H), 9.45 (brs, 1H).

ESI-Mass; 491 [M$^+$+H]

Preparation Example 114

2-(3'-Benzyloxy-5-methoxybiphenyl-2-yl)-6-methoxynaphthalene

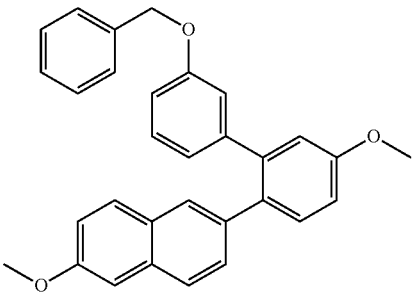

The title compound was synthesized by referring to *Tetrahedron Lett.*, 1996, 37, 3857. To a solution of 5-methoxy-2-(6-methoxynaphthalen-2-yl)phenyl amine (340 mg) in tetrahydrofuran (8 ml) was added tetrafluoroboric acid (42% aqueous solution) (0.22 ml) under a nitrogen atmosphere, the solution was cooled at −40° C., isoamyl nitrite (2.4 ml) was then added dropwise thereto followed by stirring for 2 hours at −40° C. Diethyl ether (20 ml) was added thereto and the solid that was precipitated was filtered. A suspension of the resulting 5-methoxy-2-(6-methoxynaphthalen-2-yl)benzenediazonium tetrafluoroborate (320 mg), 3-benzyloxyphenylboronic acid (235 mg) and palladium(II) acetate (10 mg) in 1,4-dioxane (4 ml) was stirred overnight at room temperature under a nitrogen atmosphere. Water was added thereto followed by stirring, the solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (181 mg).

$^1$H-NMR (400 MHz, CDCl$_3$); δ (ppm): 3.89 (s, 3H), 3.91 (s, 3H), 4.73 (s, 2H), 6.76-7.65 (m, 18H).

Example 353

1-{2-[5'-Methoxy-2'-(6-methoxymphthalen-2-yl)biphenyl-3-yloxy]ethyl}piperidine

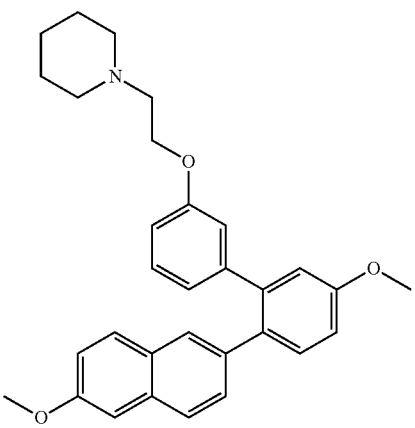

Synthesized from 2-(3'-benzyloxy-5-methoxybiphenyl-2-yl)-6-methoxynaphthalene (205 mg) according to an analogous synthetic method to Example 22, 5'-methoxy-2'-(6-methoxynaphthalen-2-yl)biphenyl-3-ol (176 mg) was obtained. To a solution of 5'-methoxy-2'-(6-methoxynaphthalen-2-yl)biphenyl-3-ol (276 mg) in N,N-dimethylformamide (7 ml) were sequentially added potassium carbonate (220 mg) and 1-(2-chloroethyl)piperidine (280 mg), and the solution was stirred for 2 hours at 60° C. Water was added thereto followed by stirring, the solution was extracted with ethyl acetate, then sequentially washed with water and brine, and the solvent was evaporated in vacuo. The residue was purified by NH silica gel column chromatography (hexane-ethyl acetate system) to provide the title compound (319 mg).

$^1$H-NMR (400 MHz, CDCl$_3$); δ (ppm): 1.35-1.43 (m, 2H), 1.49-1.57 (m, 4H), 2.26-2.33 (m, 4H), 2.54 (t, 2H), 3.78 (t, 2H), 3.89 (s, 6H), 6.69-6.81 (m, 4H), 6.98-7.11 (m, 5H), 7.42 (dd, 1H), 7.48 (d, 1H), 7.63-7.66 (m, 2H).

Example 354

6-[5-Hydroxy-3'-(2-piperidin-1-ylethoxy)biphenyl-2-yl]naphthalen-2-ol

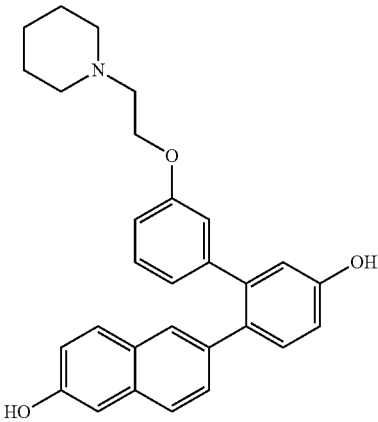 [SMILES: Oc1ccc(-c2ccc3cc(O)ccc3c2)c(-c2cccc(OCCN3CCCCC3)c2)c1]

Synthesized from 1-{2-[5'-methoxy-2'-(6-methoxynaphthalen-2-yl)biphenyl-3-yloxy]ethyl}piperidine (317 mg) according to an analogous synthetic method to Example 111, the title compound (208 mg) was obtained.

$^1$H-NMR (400 MHz, DMSO-d$_6$); δ (ppm): 1.35-1.42 (m, 6H), 2.08-2.18 (m, 4H), 2.34 (t, 2H), 3.66 (t, 2H), 6.54 (s, 1H), 6.67-6.75 (m, 2H), 6.79-6.89 (m, 3H), 6.98-7.03 (m, 2H), 7.11 (t, 1H), 7.27 (d, 1H), 7.39 (d, 1H), 7.57 (s, 1H), 7.62 (d, 1H), 9.64 (brs, 2H).

ESI-Mass; 440 [M$^+$+H]

Preparation Example 115

2-(2-Iodo-4-methoxyphenyl)-6-methoxy-1,2,3,4-tetrahydronaphthalene

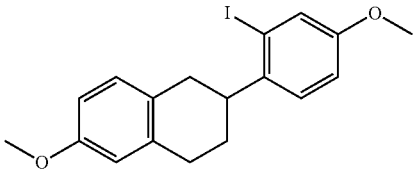

The title compound was synthesized by referring to *J. Org. Chem.*, 1984, 49, 296. To 5-methoxy-2-(6-methoxy-1,2,3,4-tetrahydronaphthalen-2-yl)phenylamine (5.0 g) was added dropwise acetic acid (50 ml) and concentrated sulfuric acid (2 ml) over 30 minutes on an ice bath, a solution of sodium nitrite (1.3 g) in water (20 ml) was then added thereto followed by stirring for 30 minutes. A solution of potassium iodide (3.5 g) and iodide (2.7 g) in water (30 ml) was added dropwise thereto over 30 minutes followed by stirring for 3 hours at room temperature. The reaction solution was neutralized with ammonia solution and a saturated aqueous solution of sodium carbonate on an ice bath, extracted with ethyl acetate, then sequentially washed with an aqueous solution of sodium thiosulfate, water and brine, dried over anhydrous magnesium sulfate, and then the solvent was evaporated in vacuo. The residue was purified by NH silica gel column chromatography (hexane-ethyl acetate system) to provide the title compound (3.1 g).

$^1$H-NMR (400 MHz, CDCl$_3$); δ (ppm): 1.90 (ddd, 1H), 2.02-2.10 (m, 1H), 2.69 (dd, 1H), 2.86-2.92 (m, 1H), 2.95-3.05 (m, 2H), 3.19 (dddd, 1H), 3.78 (s, 3H), 3.79 (s, 3H), 6.68 (d, 1H), 6.72 (dd, 1H), 6.90 (dd, 1H), 7.02 (d, 1H), 7.12 (d, 1H), 7.41 (d, 1H).

Preparation Example 116

4-{2-[5-Methoxy-2-(6-methoxy-1,2,3,4-tetrahydronaphthalen-2-yl)phenyl]ethyl}phenol

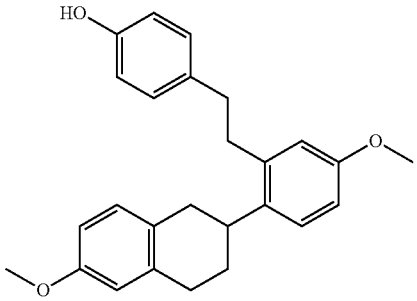

Synthesized from 4-bromophenol according to an analogous synthetic method to Preparation Example 117 described below, 1-benzyloxy-4-ethynylbenzene (470 mg) and 2-(2-iodo-4-methoxyphenyl)-6-methoxy-1,2,3,4-tetrahydronaphthalene (690 mg) were used according to an analogous synthetic method to Preparation Example 45 to provide 2-[2-(4-benzyloxyphenylethynyl)-4-methoxyphenyl]-6-methoxy-1,2,3,4-tetrahydronaphthalene (559 mg). This compound (557 mg) was used according to an analogous synthetic method to Example 22 to provide the title compound (482 mg).

$^1$H-NMR (400 MHz, DMSO-d$_6$); δ (ppm): 1.72-1.86 (m, 2H), 2.59-2.74 (m, 4H), 2.76-2.85 (m, 4H), 2.90-2.99 (m, 1H), 3.69 (s, 6H), 6.60 (d, 2H), 6.62-6.68 (m, 2H), 6.70-6.75 (m, 2H), 6.89-6.96 (m, 3H), 7.16 (d, 1H), 9.11 (s, 1H).

Example 355

6-{4-Hydroxy-2-{2-[4-(2-piperidin-1-ylethoxy)phenyl]ethyl}phenyl}-5,6,7,8-tetrahydronaphthalen-2-ol

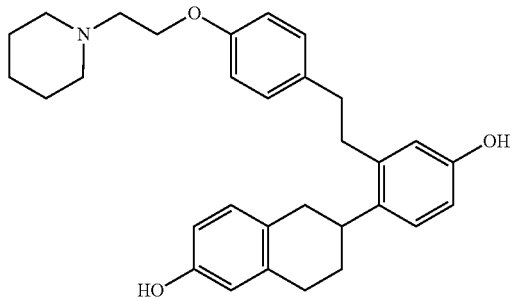 [SMILES: Oc1ccc2c(c1)CCC(c1ccc(O)cc1CCc1ccc(OCCN3CCCCC3)cc1)C2]

Synthesized from 4-{2-[5-methoxy-2-(6-methoxy-1,2,3,4-tetrahydronaphthalen-2-yl)phenyl]ethyl}phenol and 1-(2-chloroethyl)piperidine hydrochloride according to an analogous synthetic method to Preparation Example 40, 1-{2-{4-{2-[5-methoxy-2-(6-methoxy-1,2,3,4-tetrahydronaphthalen-2-yl)phenyl]ethyl}phenoxy}ethyl}piperidine (167 mg) was used according to an analogous synthetic method to Example 111 to provide the title compound (116 mg).

$^1$H-NMR (400 MHz, DMSO-d$_6$); δ (ppm): 1.30-1.38 (m, 2H), 1.42-1.49 (m, 4H), 1.64-1.80 (m, 2H), 2.32-2.43 (m, 4H), 2.53-2.62 (m, 4H), 2.63-2.78 (m, 6H), 2.81-2.90 (m, 1H), 3.97 (t, 2H), 6.44-6.49 (m, 2H), 6.4-6.59 (m, 2H), 6.75-6.82 (m, 3H), 6.98-7.04 (m, 3H), 8.99 (s, 1H), 9.03 (s, 1H).
ESI-Mass; 472 [M$^+$+H]

Example 356

6-{2-{2-[4-(2-Azepan-1-ylethoxy)phenyl]ethyl}-4-hydroxyphenyl}-5,6,7,8-tetrahydronaphthalen-2-ol

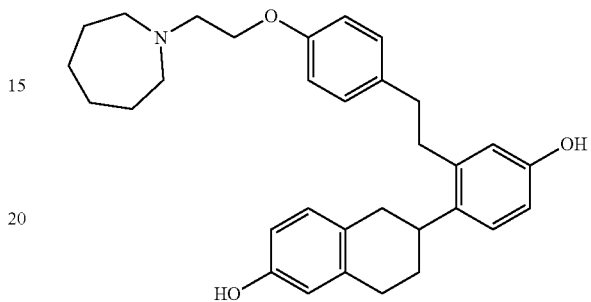

Synthesized from 4-{2-[5-methoxy-2-(6-methoxy-1,2,3,4-tetrahydronaphthalen-2-yl)phenyl]ethyl}phenol and 1-(2-chloroethyl)azepane hydrochloride according to an analogous synthetic method to Preparation Example 40, 1-{2-{4-{2-[5-methoxy-2-(6-methoxy-1,2,3,4-tetrahydronaphthalen-2-yl)phenyl]ethyl}phenoxy}ethyl}azepane (174 mg) was used according to an analogous synthetic method to Example 111 to provide the title compound (112 mg).

$^1$H-NMR (400 MHz, DMSO-d$_6$); δ (ppm): 1.47-1.58 (m, 8H), 1.63-1.81 (m, 2H), 2.53-2.90 (m, 15H), 3.96 (t, 2H), 6.44-6.49 (m, 2H), 6.53-6.59 (m, 2H), 6.74-6.81 (m, 3H), 6.98-7.04 (m, 3H), 8.99 (s, 1H), 9.03 (s, 1H).
ESI-Mass; 486 [M$^+$+H]

Example 357

6-{2-{2-[4-(2-Diisopropylaminoethoxy)phenyl]ethyl}-4-hydroxyphenyl}-5,6,7,8-tetrahydronaphthalen-2-ol

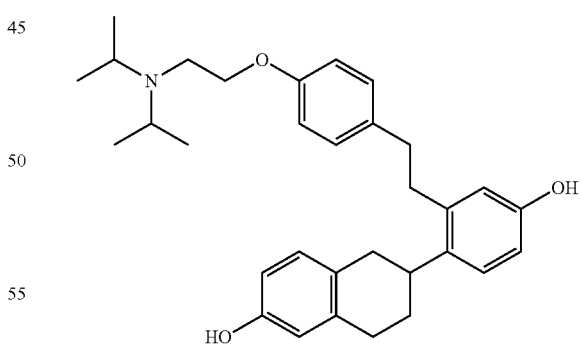

Synthesized from 4-{2-[5-methoxy-2-(6-methoxy-1,2,3,4-tetrahydronaphthalen-2-yl)phenyl]ethyl}phenol and (2-chloroethyl)diisopropylamine hydrochloride according to an analogous synthetic method to Preparation Example 40, diisopropyl {2-{4-{2-[5-methoxy-2-(6-methoxy-1,2,3,4-tetrahydronaphthalen-2-yl)phenyl]ethyl}phenoxy}ethyl}amine (183 mg) was used according to an analogous synthetic method to Example 111 to provide the title compound (62 mg).

$^1$H-NMR (400 MHz, DMSO-d$_6$); δ (ppm): 0.95 (d, 12H), 1.63-1.81 (m, 2H), 2.53-2.60 (m, 2H), 2.64-2.78 (m, 8H), 2.80-2.89 (m, 1H), 2.98 (hept, 2H), 3.79 (t, 2H), 6.44-6.49 (m, 2H), 6.54-6.59 (m, 2H), 6.75 (d, 2H), 6.79 (d, 1H), 6.98-7.04 (m, 3H), 8.99 (s, 1H), 9.03 (s, 1H).
ESI-Mass; 488 [M$^+$+H]

Preparation Example 117

1-Benzyloxy-4-ethynyl-2-fluorobenzene

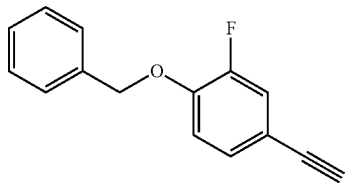 [SMILES: C#Cc1ccc(OCc2ccccc2)c(F)c1]

To a solution of 4-bromo-2-fluorophenol (2.0 g) in acetone (40 ml) were sequentially added potassium carbonate (2.0 g) and benzyl bromide (1.5 ml), and the solution was stirred for 2 hours at 50° C. Water was added thereto followed by stirring, the solution was extracted with ethyl acetate, then sequentially washed with water and brine, dried over anhydrous magnesium sulfate, then the solvent was evaporated in vacuo. A suspension of the resulting 1-benzyloxy-4-bromo-2-fluorobenzene (3.3 g), (trimethylsilyl)acetylene (1.5 g), dichlorobis(triphenylphosphine)palladium(II) (370 mg) and copper(I) iodide (50 mg) in triethylamine (30 ml) and pyridine (15 ml) was stirred for 1.5 hours at 80° C. under a nitrogen atmosphere. The insoluble material was removed by filtration, then the filtrate was neutralized with 5N hydrochloric acid. The solution was extracted with ethyl acetate, then sequentially washed with water and brine, dried over anhydrous magnesium sulfate, then the solvent was evaporated in vacuo. To the resulting residue were sequentially added methanol (40 ml) and an aqueous solution of 2N sodium hydroxide (5 ml), the solution was stirred for 45 minutes at 80° C., and then neutralized with 1N hydrochloric acid. The solution was extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (2.2 g).
$^1$H-NMR (400 MHz, CDCl$_3$); δ (ppm): 3.01 (s, 1H), 5.15 (s, 2H), 6.92 (t, 1H), 7.18 (ddd, 1H), 7.22 (dd, 1H), 7.31-7.44 (m, 5H).

Preparation Example 118

2-Fluoro-4-{2-[5-methoxy-2-(6-methoxy-1,2,3,4-tetrahydronaphthalen-2-yl)phenyl]ethyl}phenol

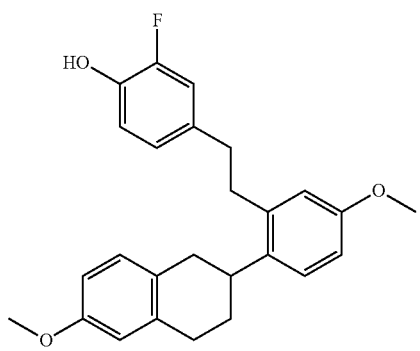

Synthesized from 1-benzyloxy-4-ethynyl-2-fluorobenzene and 2-(2-iodo-4-methoxyphenyl)-6-methoxy-1,2,3,4-tetrahydronaphthalene according to an analogous synthetic method to Preparation Example 45, 2-[2-(4-benzyloxy-3-fluorophenylethynyl)-4-methoxyphenyl]-6-methoxy-1,2,3,4-tetrahydronaphthalene (776 mg) was used according to an analogous synthetic method to Example 22 to provide the title compound (546 mg).
$^1$H-NMR (400 MHz, DMSO-d$_6$); δ (ppm): 1.68-1.86 (m, 2H), 2.59-2.86 (m, 8H), 2.89-2.98 (m, 1H), 3.69 (s, 6H), 6.63-6.67 (m, 2H), 6.70-6.80 (m, 4H), 6.88-6.95 (m, 2H), 7.15 (d, 1H), 9.53 (s, 1H).

Example 358

6-{2-{2-[3-Fluoro-4-(2-piperidin-1-ylethoxy)phenyl]ethyl}-4-hydroxyphenyl}-5,6,7,8-tetrahydronaphthalen-2-ol

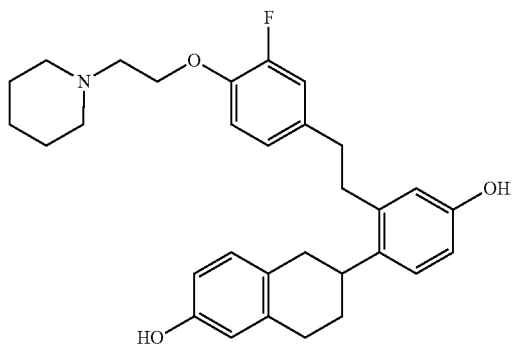 [SMILES: Oc1ccc2c(c1)CCC(c1ccc(O)cc1CCc1ccc(OCCN3CCCCC3)c(F)c1)C2]

Synthesized from 2-fluoro-4-{2-[5-methoxy-2-(6-methoxy-1,2,3,4-tetrahydronaphthalen-2-yl)phenyl]ethyl}phenol and 1-(2-chloroethyl)piperidine hydrochloride according to an analogous synthetic method to Preparation Example 40, 1-{2-{2-fluoro-4-{2-[5-methoxy-2-(6-methoxy-1,2,3,4-tetrahydronaphthalen-2-yl)phenyl]ethyl}phenoxy}ethyl}piperidine (175 mg) was used according to an analogous synthetic method to Example 111 to provide the title compound (123 mg).
$^1$H-NMR (400 MHz, DMSO-d$_6$); δ (ppm): 1.30-1.38 (m, 2H), 1.42-1.50 (m, 4H), 1.60-1.80 (m, 2H), 2.33-2.43 (m, 4H), 2.52-2.63 (m, 4H), 2.64-2.89 (m, 7H), 4.04 (t, 2H), 6.45-6.50 (m, 2H), 6.54-6.58 (m, 2H), 6.79 (d, 1H), 6.83 (d, 1H), 6.96-7.04 (m, 3H), 8.99 (s, 1H), 9.04 (s, 1H).
ESI-Mass; 490 [M$^+$+H]

Example 359

6-{2-{2-[4-(2-Azepan-1-ylethoxy)-3-fluorophenyl]ethyl}-4-hydroxyphenyl}-5,6,7,8-tetrahydronaphthalen-2-ol

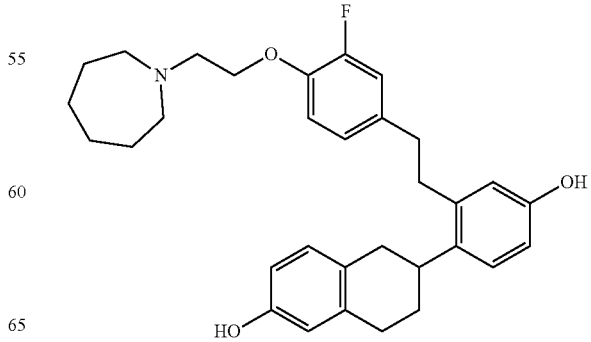

Synthesized from 2-fluoro-4-{2-[5-methoxy-2-(6-methoxy-1,2,3,4-tetrahydronaphthalen-2-yl)phenyl]ethyl}phenol and 1-(2-chloroethyl)azepane hydrochloride according to an analogous synthetic method to Preparation Example 40, 1-{2-{2-fluoro-4-{2-[5-methoxy-2-(6-methoxy-1,2,3,4-tetrahydronaphthalen-2-yl)phenyl]ethyl}phenoxy}ethyl}azepane (203 mg) was used according to an analogous synthetic method to Example 111 to provide the title compound (119 mg).

$^1$H-NMR (400 MHz, DMSO-d$_6$); δ (ppm): 1.46-1.58 (m, 8H), 1.62-1.80 (m, 2H), 2.52-2.89 (m, 15H), 4.01 (t, 2H), 6.44-6.49 (m, 2H), 6.53-6.59 (m, 2H), 6.79 (d, 1H), 6.83 (d, 1H), 6.93-7.04 (m, 3H), 8.99 (s, 1H), 9.04 (s, 1H).

ESI-Mass; 504 [M$^+$+H]

Example 360

6-{2-{2-[4-(2-Diisopropylaminoethoxy)-3-fluorophenyl]ethyl}-4-hydroxyphenyl}-5,6,7,8-tetrahydronaphthalen-2-ol

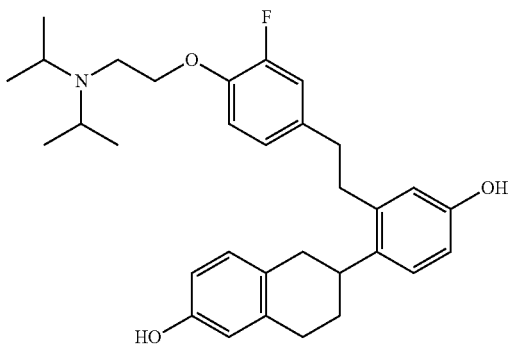 [SMILES: CC(C)N(CCOc1ccc(CCc2cc(O)ccc2C2CCc3cc(O)ccc3C2)cc1F)C(C)C]

Synthesized from 2-fluoro-4-{2-[5-methoxy-2-(6-methoxy-1,2,3,4-tetrahydronaphthalen-2-yl)phenyl]ethyl}phenol and (2-chloroethyl)diisopropylamine hydrochloride according to an analogous synthetic method to Preparation Example 40, {2-{2-fluoro-4-{2-[5-methoxy-2-(6-methoxy-1,2,3,4-tetrahydronaphthalen-2-yl)phenyl]ethyl}phenoxy}ethyl}diisopropylamine (199 mg) was used according to an analogous synthetic method to Example 111 to provide the title compound (104 mg).

$^1$H-NMR (400 MHz, DMSO-d$_6$); δ (ppm): 0.95 (d, 12H), 1.62-1.79 (m, 2H), 2.50-2.62 (m, 2H), 2.64-2.88 (m, 9H), 2.98 (hept, 2H), 3.85 (t, 2H), 6.44-6.49 (m, 2H), 6.52-6.58 (m, 2H), 6.79 (d, 1H), 6.83 (d, 1H), 6.92-7.03 (m, 3H), 8.99 (s, 1H), 9.04 (s, 1H).

ESI-Mass; 506 [M$^+$+H]

Preparation Example 119

2-Chloro-N-ethylacetamide

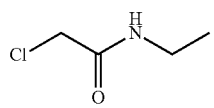

To a solution of ethylamine hydrochloride (5.0 g) in an aqueous solution of 5N sodium hydroxide (35 ml) was added dichloromethane (50 ml), chloroacetyl chloride (6 ml) was added dropwise thereto on an ice bath, and the solution was stirred for 1.5 hours at room temperature. The solution was extracted with diethyl ether, then washed with brine, dried over anhydrous magnesium sulfate, and then the solvent was evaporated in vacuo to provide the title compound (6.0 g).

$^1$H-NMR (400 MHz, CDCl$_3$); δ (ppm): 1.20 (t, 3H), 3.36 (dt, 2H), 4.04 (s, 2H), 6.55 (brs, 1H).

Preparation Example 120

2-Chloro-N-isopropylacetamide

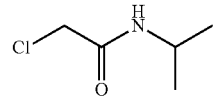

Synthesized from isopropylamine (3.0 g) according to an analogous synthetic method to Preparation Example 119, the title compound (4.2 g) was obtained.

$^1$H-NMR (400 MHz, CDCl$_3$); δ (ppm): 1.20 (d, 6H), 4.02 (s, 2H), 4.05-4.14 (m, 1H), 6.36 (brs, 1H).

Preparation Example 121

2-Chloro-N-cyclopropylacetamide

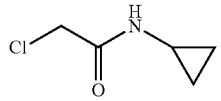

Synthesized from cyclopropylamine (5.0 g) according to an analogous synthetic method to Preparation Example 119, the title compound (8.5 g) was obtained.

$^1$H-NMR (400 MHz, CDCl$_3$); δ (ppm): 0.56-0.60 (m, 2H), 0.81-0.86 (m, 2H), 2.72-2.78 (m, 1H), 4.02 (s, 2H), 6.62 (brs, 1H).

Preparation Example 122

2-Chloro-N-cyclohexylacetamide

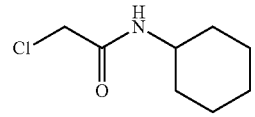 [SMILES: O=C(CCl)NC1CCCCC1]

Synthesized from cyclohexylamine (5.0 g) according to an analogous synthetic method to Preparation Example 119, the title compound (7.0 g) was obtained.

$^1$H-NMR (400 MHz, CDCl$_3$); δ (ppm): 1.14-1.25 (m, 3H), 1.33-1.44 (m, 2H), 1.59-1.67 (m, 1H), 1.69-1.76 (m, 2H), 1.89-1.96 (m, 2H), 3.74-3.84 (m, 1H), 4.02 (s, 2H), 6.42 (brs, 1H).

Preparation Example 123

2-Chloro-N-(2-methoxyethyl)acetamide

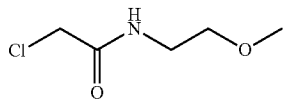

Synthesized from 2-methoxyethylamine (5.0 g) according to an analogous synthetic method to Preparation Example 119, the title compound (7.0 g) was obtained.

$^1$H-NMR (400 MHz, DMSO-$d_6$); δ (ppm): 3.23 (s, 3H), 3.21-3.36 (m, 4H), 4.04 (s, 2H), 8.25 (s, 1H).

Preparation Example 124

2-Chloro-N-(2-methylthioethyl)acetamide

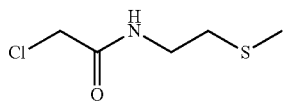

Synthesized from 2-(methylthio)ethylamine (3.0 g) according to an analogous synthetic method to Preparation Example 119, the title compound (3.5 g) was obtained.

$^1$H-NMR (400 MHz, CDCl$_3$); δ (ppm): 2.13 (s, 3H), 2.68 (t, 2H), 3.53 (dt, 2H), 4.07 (s, 2H), 6.98 (brs, 1H).

Preparation Example 125

2-Chloro-N-(2-fluoroethyl)acetamide

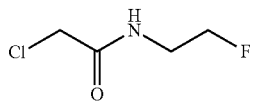

Synthesized from 2-fluoroethylamine hydrochloride (2.2 g) according to an analogous synthetic method to Preparation Example 119, the title compound (2.3 g) was obtained.

$^1$H-NMR (400 MHz, CDCl$_3$); δ (ppm): 3.60 (dt, 1H), 3.67 (dt, 1H), 4.08 (s, 2H), 4.47 (t, 1H), 4.59 (t, 1H), 6.96 (brs, 1H).

Preparation Example 126

2-Chloro-N-phenylacetamide

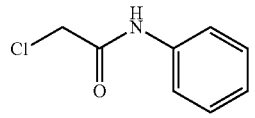 [SMILES: O=C(CCl)Nc1ccccc1]

Synthesized from aniline (5.0 g) according to an analogous synthetic method to Preparation Example 119, the title compound (8.2 g) was obtained.

$^1$H-NMR (400 MHz, CDCl$_3$); δ (ppm): 4.18 (s, 2H), 7.16 (t, 1H), 7.35 (t, 2H), 7.53 (d, 2H), 8.22 (brs, 1H).

Preparation Example 127

2-Chloro-N-(1,2,2,6,6-pentamethylpiperidin-4-yl)acetamide

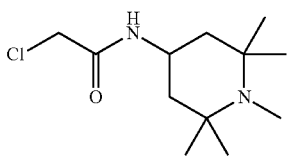 [SMILES: CN1C(C)(C)CC(NC(=O)CCl)CC1(C)C]

Synthesized from 4-amino-1,2,2,6,6-pentamethylpiperidine (3.0 g) according to an analogous synthetic method to Preparation Example 119, the title compound (2.5 g) was obtained.

$^1$H-NMR (400 MHz, CDCl$_3$); δ (ppm): 1.08 (s, 6H), 1.16 (s, 6H), 1.32 (dd, 2H), 1.79-1.83 (m, 2H), 2.25 (s, 3H), 4.02 (s, 2H), 4.10-4.21 (m, 1H), 6.29 (brs, 1H).

Preparation Example 128

2-Chloro-1-(1,4-dioxa-8-azaspiro[4.5]dec-8-yl)ethanone

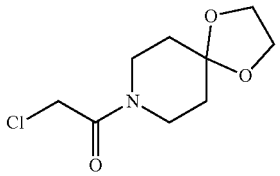 [SMILES: O=C(CCl)N1CCC2(CC1)OCCO2]

Synthesized from 1,4-dioxa-8-azaspiro[4.5]decane (3.3 ml) according to an analogous synthetic method to Preparation Example 119, the title compound (3.8 g) was obtained.

$^1$H-NMR (400 MHz, CDCl$_3$); δ (ppm): 1.72 (t, 2H), 1.79 (t, 2H), 3.59 (t, 2H), 3.72 (t, 2H), 4.00 (s, 4H), 4.09 (s, 2H).

Preparation Example 129

2-Chloro-N-(2-methoxyethyl)-N-methylacetamide

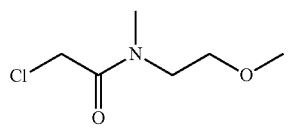

Synthesized from N-(2-methoxyethyl)methylamine (410 mg) according to an analogous synthetic method to Preparation Example 119, the title compound (585 mg) was obtained.

$^1$H-NMR (400 MHz, CDCl$_3$); δ (ppm): 2.99 (s, 1.5H), 3.16 (s, 1.5H), 3.35 (s, 3H), 3.49-3.60 (m, 4H), 4.10 (s, 1H), 4.19 (s, 1H).

Preparation Example 130

4-(2-Chloroacetyl)-[1,4]diazepane-1-carboxylic acid tert-butyl Ester

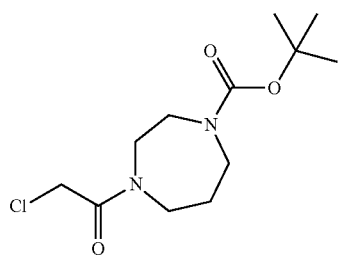 [SMILES: CC(C)(C)OC(=O)N1CCCN(C(=O)CCl)CC1]

Synthesized from [1,4]diazepane-1-carboxylic acid tert-butyl ester (4.9 ml) according to an analogous synthetic method to Preparation Example 119, the title compound (6.5 g) was obtained.
$^1$H-NMR (400 MHz, CDCl$_3$); δ (ppm): 1.45 (s, 4.5H), 1.46 (s, 4.5H), 1.81-1.97 (m, 2H), 3.35-3.69 (m, 8H), 4.09 (s, 1H), 4.10 (s, 1H).

Preparation Example 131

1-Azepan-1-yl-2-chloroethanone

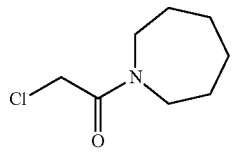 [SMILES: O=C(CCl)N1CCCCCC1]

To a solution of hexamethyleneimine (2.9 ml) in tetrahydrofuran (25 ml) was added triethylamine (3.5 ml). Chloroacetyl chloride (2.0 ml) was added thereto on an ice bath followed by stirring for 1.5 hours while warming to room temperature. An aqueous solution of 10% citric acid was added thereto, the solution was extracted with ethyl acetate, then sequentially washed with a saturated aqueous solution of sodium bicarbonate and brine, dried over anhydrous magnesium sulfate, then the solvent was evaporated in vacuo, and the residue was purified by silica gel column chromatography (hexane-ethyl acetate system) to provide the title compound (3.5 g).
$^1$H-NMR (400 MHz, CDCl$_3$); δ (ppm): 1.55-1.65 (m, 4H), 1.70-1.82 (m, 4H), 3.48-3.58 (m, 4H), 4.09 (s, 2H).

Preparation Example 132

1-Azocan-1-yl-2-chloroethanone

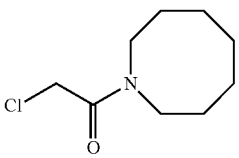 [SMILES: O=C(CCl)N1CCCCCCC1]

Synthesized from heptamethylene imine (3.2 ml) according to an analogous synthetic method to Preparation Example 131, the title compound (4.4 g) was obtained.
$^1$H-NMR (400 MHz, CDCl$_3$); δ (ppm): 1.50-1.57 (m, 4H), 1.60-1.68 (m, 2H), 1.72-1.82 (m, 4H), 3.43-3.51 (m, 4H), 4.09 (s, 2H).

Preparation Example 133

2-Chloro-1-(4-methylpiperidin-1-yl)ethanone

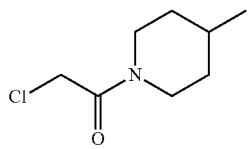

Synthesized from 4-methylpiperidine (3.0 ml) according to an analogous synthetic method to Preparation Example 131, the title compound (3.7 g) was obtained.
$^1$H-NMR (400 MHz, CDCl$_3$); δ (ppm): 0.97 (d, 3H), 1.07-1.28 (m, 2H), 1.61-1.77 (m, 3H), 2.63 (ddd, 1H), 3.09 (ddd, 1H), 3.82 (ddd, 1H), 4.07 (dd, 2H), 4.52 (ddd, 1H).

Preparation Example 134

2-Chloro-N-cyclohexyl-N-methylacetamide

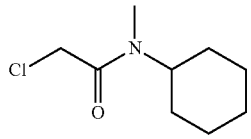

Synthesized from N-methylcyclohexylamine (3.3 ml) according to an analogous synthetic method to Preparation Example 131, the title compound (3.7 g) was obtained.
$^1$H-NMR (400 MHz, CDCl$_3$); δ (ppm): 1.02-1.18 (m, 1H), 1.30-1.47 (m, 3H), 1.49-1.58 (m, 1H), 1.64-1.92 (m, 5H), 2.84 (s, 1.5H), 2.92 (s, 1.5H), 3.51-3.60 (m, 0.5H), 4.07 (s, 1H), 4.10 (s, 1H), 4.33-4.43 (m, 0.5H).

Preparation Example 135

2-Chloro-N,N-bis(2-methoxyethyl)acetamide

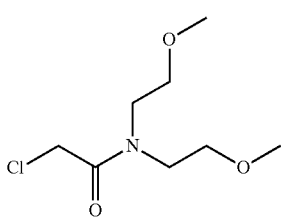

Synthesized from bis(2-methoxyethyl)amine (3.8 ml) according to an analogous synthetic method to Preparation Example 131, the title compound (3.8 g) was obtained.

¹H-NMR (400 MHz, CDCl₃); δ (ppm): 3.33 (s, 6H), 3.51 (t, 2H), 3.56 (s, 4H), 3.62 (t, 2H), 4.24 (s, 2H).

Preparation Example 136

1-Azetidin-1-yl-2-chloroethanone

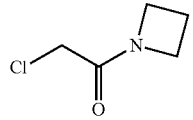

Synthesized from azetidine hydrochloride (2.4 g) according to an analogous synthetic method to Preparation Example 131, the title compound (822 mg) was obtained.

¹H-NMR (400 MHz, CDCl₃); δ (ppm): 2.29-2.39 (m, 2H), 3.88 (s, 2H), 4.10 (t, 2H), 4.30 (t, 2H).

Preparation Example 137

1-(3-Azabicyclo[3.2.2]non-3-yl)-2-chloroethanone

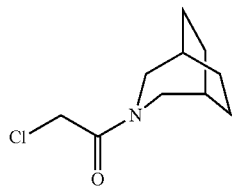 [SMILES: O=C(CCl)N1CC2CCC(CC2)C1]

Synthesized from 3-azabicyclo[3.2.2]nonane (1.2 g) according to an analogous synthetic method to Preparation Example 131, the title compound (1.6 g) was obtained.

¹H-NMR (400 MHz, CDCl₃); δ (ppm): 1.59-1.77 (m, 8H), 2.06-2.14 (m, 2H), 3.60 (d, 2H), 3.73 (d, 2H), 4.14 (s, 2H).

Preparation Example 138

2-Bromo-1-(3,3-dimethylpiperidin-1-yl)ethanone

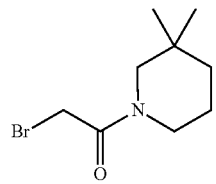

To a solution of 3,3-dimethylpiperidine (250 mg) in dichloromethane (3 ml) was added an aqueous solution of 5N sodium hydroxide (1.1 ml), bromoacetyl chloride (0.2 ml) was added dropwise thereto on an ice bath, and the solution was stirred for 1 hour at room temperature. The solution was extracted with diethyl ether, then sequentially washed with an aqueous solution of 10% citric acid and brine, dried over anhydrous magnesium sulfate, and then the solvent was evaporated in vacuo to provide the title compound (420 mg).

¹H-NMR (400 MHz, CDCl₃); δ (ppm): 0.94 (s, 3H), 0.97 (s, 3H), 1.40-1.45 (m, 2H), 1.56-1.62 (m, 1H), 1.68-1.76 (m, 1H), 3.11 (s, 1H), 3.26 (s, 1H), 3.39 (t, 1H), 3.53 (t, 1H), 3.87 (d, 2H).

Preparation Example 139

1-(7-Azabicyclo[2.2.1]hept-7-yl)-2-bromoethanone

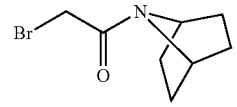 [SMILES: O=C(CBr)N1C2CCC1CC2]

Synthesized from 7-azabicyclo[2.2.1]heptane hydrochloride (250 mg) according to an analogous synthetic method to Preparation Example 138, the title compound (320 mg) was obtained.

¹H-NMR (400 MHz, CDCl₃); δ (ppm): 1.45-1.58 (m, 4H), 1.79-1.96 (m, 4H), 3.78 (s, 2H), 4.24 (t, 1H), 4.64 (t, 1H).

Preparation Example 140

2-Bromo-1-(2,2,6,6-tetramethylpiperidin-1-yl)ethanone

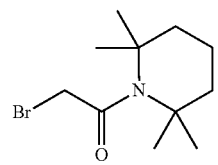

Synthesized from 2,2,6,6-tetramethylpiperidine (4.1 ml) according to an analogous synthetic method to Preparation Example 138, the title compound (4.8 g) was obtained.

¹H-NMR (400 MHz, CDCl₃); δ (ppm): 1.48 (s, 12H), 1.78 (s, 6H), 3.99 (s, 2H).

Preparation Example 141 tert-Butyl (2-ethoxyethyl)methylcarbamate

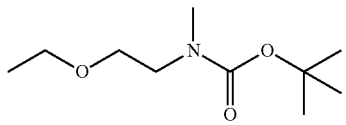

To a solution of 2-ethoxyethylamine (502 mg) in water (4 ml) was added 1,4-dioxane (10 ml), and an aqueous solution of 1N sodium hydroxide (6 ml) and di-tert-butyl dicarbonate (1.4 g) were sequentially added thereto on an ice bath. The solution was stirred overnight while warming to room temperature. Water was added thereto, the solution was extracted with diethyl ether, then washed with brine, dried over anhydrous magnesium sulfate, then the solvent was evaporated in vacuo to provide tert-butyl (2-ethoxyethyl)carbamate (1.1 g). To a suspension of 60% sodium hydride (253 mg) in tetrahydrofuran (2 ml) was added dropwise a solution of tert-butyl (2-ethoxyethyl)carbamate (1.1 g) in tetrahydrofuran (8 ml) on an ice bath. The solution was stirred for 30 minutes while warming to room temperature, then methyl iodide (0.7 ml) was added thereto on an ice bath, and the solution was stirred overnight while warming to room temperature. Water was added thereto, the solution was extracted with ethyl acetate, then washed with brine, dried over anhydrous magnesium sulfate, and then the solvent was evaporated in vacuo to provide the title compound (1.2 g).

$^1$H-NMR (400 MHz, CDCl$_3$); δ (ppm): 1.19 (t, 3H), 1.46 (s, 9H), 2.91 (s, 3H), 3.32-3.42 (m, 2H), 3.45-3.57 (m, 4H).

Preparation Example 142

2-Chloro-N-(2-ethoxyethyl)-N-methylacetamide

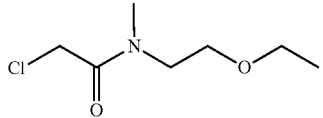

To a solution of tert-butyl (2-ethoxyethyl)methylcarbamate (1.2 g) in dichloromethane (6 ml) was added trifluoroacetic acid (6 ml) on an ice bath. The solution was stirred for 30 minutes while warming to room temperature, then the solvent was evaporated in vacuo. Synthesized from the resulting (2-ethoxyethyl)methylamine trifluoroacetate (crude product) (2.3 g) according to an analogous synthetic method to Preparation Example 119, the title compound (799 mg) was obtained.

$^1$H-NMR (400 MHz, CDCl$_3$); δ (ppm): 1.14-1.21 (m, 3H), 2.99 (s, 1.5H), 3.16 (s, 1.5H), 3.43-3.61 (m, 6H), 4.09 (s, 1H), 4.21 (s, 1H).

Preparation Example 143

2-Chloro-N-cyclobutyl-N-methylacetamide

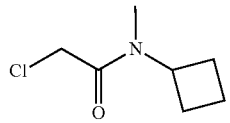

Synthesized from cyclobutylamine according to an analogous synthetic method to Preparation Example 141, tert-butyl cyclobutylmethylcarbamate (1.0 g) was used according to an analogous synthetic method to Preparation Example 142 to provide the title compound (801 mg).

$^1$H-NMR (400 MHz, CDCl$_3$); δ (ppm): 1.62-1.80 (m, 2H), 2.05-2.35 (m, 4H), 2.96 (s, 1.5H), 3.02 (s, 1.5H), 4.07 (s, 1H), 4.10 (s, 1H), 4.28-4.43 (m, 0.5H), 4.84-4.94 (m, 0.5H).

Preparation Example 144

2-Chloro-N-(3-methoxypropyl)-N-methylacetamide

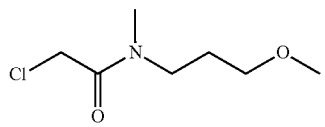

Synthesized from 3-methoxypropylamine according to an analogous synthetic method to Preparation Example 141, tert-butyl (3-methoxypropyl)methylcarbamate (1.2 g) was used according to an analogous synthetic method to Preparation Example 142 to provide the title compound (581 mg).

$^1$H-NMR (400 MHz, CDCl$_3$); δ (ppm): 1.79-1.89 (m, 2H), 2.94 (s, 1.5H), 3.09 (s, 1.5H), 3.32 (s, 1.5H), 3.33 (s, 1.5H), 3.35-3.48 (m, 4H), 4.06 (s, 1H), 4.15 (s, 1H).

Preparation Example 145

2-Chloro-N-methyl-N—[(S)-tetrahydrofuran-2-ylmethyl]acetamide

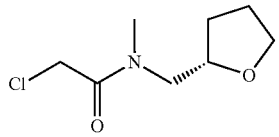

Synthesized from (S)-tetrahydrofurfurylamine according to an analogous synthetic method to Preparation Example 141, tert-butylmethyl[(S)-tetrahydrofuran-2-ylmethyl]carbamate (1.3 g) was used according to an analogous synthetic method to Preparation Example 142 to provide the title compound (859 mg).

$^1$H-NMR (400 MHz, CDCl$_3$); δ (ppm): 1.46-1.58 (m, 1H), 1.81-2.08 (m, 3H), 3.02 (s, 1H), 3.14-3.22 (m, 2.5H), 3.35 (dd, 0.5H), 3.50 (dd, 0.5H), 3.71-3.80 (m, 1.5H), 3.82-3.89 (m, 1H), 4.00-4.14 (m, 2.5H), 4.27 (d, 0.5H).

Preparation Example 146

2-Chloro-N-methyl-N—[(R)-tetrahydrofuran-2-ylmethyl]acetamide

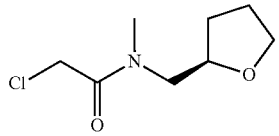

Synthesized from (R)-tetrahydrofurfurylamine according to an analogous synthetic method to Preparation Example 141, tert-butylmethyl[(R)-tetrahydrofuran-2-ylmethyl]carbamate (1.3 g) was used according to an analogous synthetic method to Preparation Example 142 to provide the title compound (909 mg).

$^1$H-NMR (400 MHz, CDCl$_3$); δ (ppm): 1.46-1.58 (m, 1H), 1.81-2.08 (m, 3H), 3.02 (s, 1H), 3.14-3.22 (m, 2.5H), 3.35 (dd, 0.5H), 3.50 (dd, 0.5H), 3.71-3.80 (m, 1.5H), 3.82-3.89 (m, 1H), 4.00-4.14 (m, 2.5H), 4.27 (d, 0.5H).

Preparation Example 147

2-Chloro-N-methyl-N-(tetrahydropyran-4-yl)acetamide

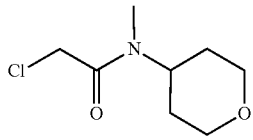

Synthesized from 4-tetrahydropyranylamine according to an analogous synthetic method to Preparation Example 141, tert-butyl methyl(tetrahydropyran-4-yl)carbamate (376 mg) was used according to an analogous synthetic method to Preparation Example 142 to provide the title compound (198 mg).
$^1$H-NMR (400 MHz, CDCl$_3$); δ (ppm): 1.51-1.82 (m, 4H), 1.88-1.97 (m, 1H), 2.86 (s, 1H), 2.95 (s, 2H), 3.45-3.54 (m, 2H), 3.97-4.12 (m, 3.5H), 4.60-4.70 (m, 0.5H).

Preparation Example 148

2-Chloro-N-methyl-N-(tetrahydropyran-4-ylmethyl)acetamide

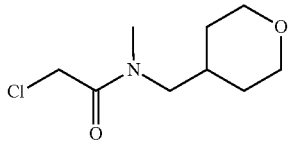

Synthesized from 4-aminomethyltetrahydropyran according to an analogous synthetic method to Preparation Example 141, tert-butyl methyl(tetrahydropyran-4-ylmethyl)carbamate (249 mg) was used according to an analogous synthetic method to Preparation Example 142 to provide the title compound (100 mg).
$^1$H-NMR (400 MHz, CDCl$_3$); δ (ppm): 1.27-1.43 (m, 2H), 1.52-1.62 (m, 2H), 1.74-2.02 (m, 1H), 2.97 (s, 1H), 3.11 (s, 2H), 3.19-3.42 (m, 4H), 3.93-4.03 (m, 2H), 4.05-4.11 (m, 2H).

Example 361

N-Ethyl-N-[5-methoxy-2-(6-methoxy-1,2,3,4-tetrahydronaphthalen-2-yl)phenyl]-4-(2-piperidin-1-ylethylamino)benzamide

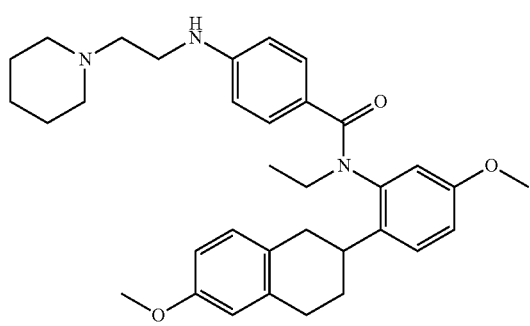 [SMILES: CCN(C(=O)c1ccc(NCCN2CCCCC2)cc1)c1cc(OC)ccc1C1CCc2cc(OC)ccc2C1]

Synthesized from ethyl[5-methoxy-2-(6-methoxy-1,2,3,4-tetrahydronaphthalen-2-yl)phenyl]amine and 4-bromobenzoyl chloride according to an analogous synthetic method to Preparation Example 86, to a suspension of the resulting 4-bromo-N-ethyl-N-[5-methoxy-2-(6-methoxy-1,2,3,4-tetrahydronaphthalen-2-yl)phenyl]benzamide (299 mg) in 1,4-dioxane (10 ml) were sequentially added 1-(2-aminoethyl) piperidine (0.13 ml), sodium tert-butoxide (88 mg), (±)-2,2'-bis(diphenylphosphino)-1,1'-binaphthyl (23 mg) and tris (dibenzylideneacetone)dipalladium(0) chloroform adduct (13 mg), and the solution was stirred overnight at 100° C. The solution was let to cool, then the insoluble material was filtered through celite pad, and the solvent was evaporated in vacuo. The residue was purified by NH silica gel column chromatography (hexane-ethyl acetate-tetrahydrofuran system) to provide the title compound (253 mg).
$^1$H-NMR (400 MHz, CDCl$_3$); δ (ppm): 1.21 (t, 3H), 1.40-1.47 (m, 2H), 1.52-1.57 (m, 4H), 1.71-1.89 (m, 1H), 2.32-2.42 (m, 4H), 2.49-2.56 (m, 2H), 2.64-2.90 (m, 4H), 3.07-3.15 (m, 2H), 3.75-4.00 (m, 8H), 4.54 (brs, 1H), 6.30-6.37 (m, 2H), 6.59-6.71 (m, 3H), 6.77-6.94 (m, 3H), 7.07-7.22 (m, 4H).

Example 362

Ethyl[5-methoxy-2-(6-methoxy-1,2,3,4-tetrahydronaphthalen-2-yl)phenyl][4-(2-piperidin-1-ylethylamino)benzyl]amine

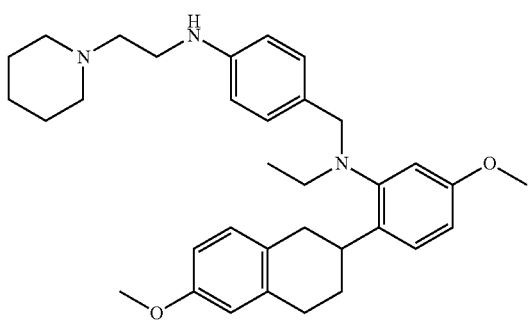 [SMILES: CCN(Cc1ccc(NCCN2CCCCC2)cc1)c1cc(OC)ccc1C1CCc2cc(OC)ccc2C1]

Synthesized from N-ethyl-N-[5-methoxy-2-(6-methoxy-1,2,3,4-tetrahydronaphthalen-2-yl)phenyl]-4-(2-piperidin-1-ylethylamino)benzamide (237 mg) according to an analogous synthetic method to Example 337, the title compound (225 mg) was obtained.
$^1$H-NMR (400 MHz, CDCl$_3$); δ (ppm): 0.91 (t, 3H), 1.40-1.47 (m, 2H), 1.53-1.58 (m, 4H), 1.75-1.82 (m, 2H), 2.34-2.43 (m, 4H), 2.55 (t, 2H), 2.66-2.80 (m, 2H), 2.83-3.00 (m, 4H), 3.11 (t, 2H), 3.68-3.77 (m, 1H), 3.79 (s, 3H), 3.80 (s, 3H), 3.89 (s, 2H), 6.51 (dd, 2H), 6.67-6.72 (m, 3H), 6.77 (d, 1H), 6.97 (d, 1H), 7.03 (d, 2H), 7.14 (d, 1H).

Example 363

Ethyl[5-methoxy-2-(6-methoxy-1,2,3,4-tetrahydronaphthalen-2-yl)phenyl]{4-[methyl(2-piperidin-1-ylethyl)amino]benzyl}amine

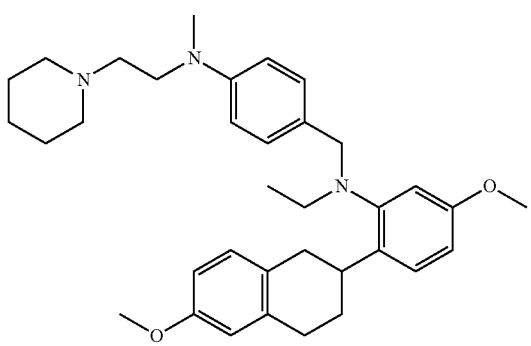 [SMILES: CCN(Cc1ccc(N(C)CCN2CCCCC2)cc1)c1cc(OC)ccc1C1CCc2cc(OC)ccc2C1]

Synthesized from ethyl[5-methoxy-2-(6-methoxy-1,2,3,4-tetrahydronaphthalen-2-yl)phenyl][4-(2-piperidin-1-ylethylamino)benzyl]amine (123 mg) according to an analogous synthetic method to Preparation Example 18, the title compound (118 mg) was obtained.

¹H-NMR (400 MHz, CDCl₃); δ (ppm): 0.91 (t, 3H), 1.40-1.47 (m, 2H), 1.58-1.64 (m, 4H), 1.74-1.82 (m, 2H), 2.38-2.50 (m, 6H), 2.68-2.80 (m, 2H), 2.82-2.99 (m, 7H), 3.45 (t, 2H), 3.69-3.78 (m, 1H), 3.80 (s, 3H), 3.81 (s, 3H), 3.90 (s, 2H), 6.58 (d, 2H), 6.67-6.73 (m, 3H), 6.78 (d, 1H), 6.97 (d, 1H), 7.07 (d, 2H), 7.15 (d, 1H).

Example 364

6-{2-{Ethyl{4-[methyl(2-piperidin-1-ylethyl)amino]benzyl}amino}-4-hydroxyphenyl}-5,6,7,8-tetrahydronaphthalen-2-ol

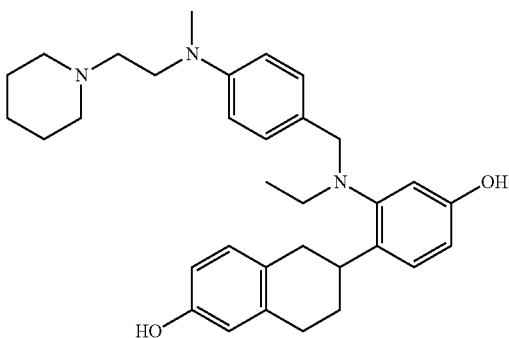 [SMILES: CCN(Cc1ccc(N(C)CCN2CCCCC2)cc1)c1cc(O)ccc1C1CCc2cc(O)ccc2C1]

To a solution of ethyl[5-methoxy-2-(6-methoxy-1,2,3,4-tetrahydronaphthalen-2-yl)phenyl]{4-[methyl(2-piperidin-1-ylethyl)amino]benzyl}amine (108 mg) in dichloromethane (5 ml) was added boron tribromide (1.0 M solution in dichloromethane) (1.0 ml) on an ice bath. The solution was stirred for 30 minutes while warming to room temperature, then methanol (2 ml) was added thereto on an ice bath. A saturated aqueous solution of sodium bicarbonate was added thereto, the solution was extracted with ethyl acetate, then washed with brine, dried over anhydrous magnesium sulfate, and then the solvent was evaporated in vacuo. The resulting residue was purified by NH silica gel column chromatography (chloroform-methanol system) to provide the title compound (58 mg).

¹H-NMR (400 MHz, DMSO-d₆); δ (ppm): 0.83 (t, 3H), 1.30-1.37 (m, 2H), 1.40-1.48 (m, 4H), 1.50-1.70 (m, 2H), 2.26-2.35 (m, 6H), 2.49-2.56 (m, 2H), 2.65-2.84 (m, 9H), 3.43-3.52 (m, 1H), 3.78 (s, 2H), 6.44-6.53 (m, 5H), 6.62 (d, 1H), 6.78 (d, 1H), 6.95 (d, 2H), 6.99 (d, 1H), 9.00 (brs, 1H), 9.06 (brs, 1H).

ESI-Mass; 514 [M⁺+H]

Example 365

6-{2-{Ethyl[4-(2-piperidin-1-ylethylamino)benzyl]amino}-4-hydroxyphenyl}-5,6,7,8-tetrahydronaphthalen-2-ol

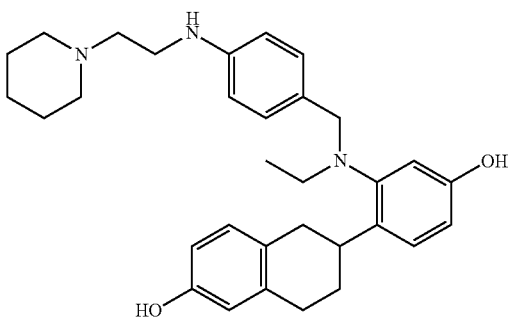 [SMILES: CCN(Cc1ccc(NCCN2CCCCC2)cc1)c1cc(O)ccc1C1CCc2cc(O)ccc2C1]

Synthesized from ethyl[5-methoxy-2-(6-methoxy-1,2,3,4-tetrahydronaphthalen-2-yl)phenyl][4-(2-piperidin-1-ylethylamino)benzyl]amine (213 mg) according to an analogous synthetic method to Example 364, the title compound (142 mg) was obtained.

¹H-NMR (400 MHz, DMSO-d₆); δ (ppm): 0.83 (t, 3H), 1.31-1.39 (m, 2H), 1.43-1.51 (m, 4H), 1.54-1.70 (m, 2H), 2.28-2.37 (m, 4H), 2.40 (t, 2H), 2.49-2.55 (m, 2H), 2.70-2.83 (m, 4H), 3.02 (q, 2H), 3.42-3.53 (m, 1H), 3.75 (s, 2H), 5.17 (t, 1H), 6.41 (d, 2H), 6.45-6.50 (m, 3H), 6.59 (d, 1H), 6.78 (d, 1H), 6.87 (d, 2H), 6.99 (d, 1H), 9.00 (brs, 1H), 9.04 (brs, 1H).

ESI-Mass; 500 [M⁺+H]

Example 366

N-Ethyl-3-fluoro-N-[5-methoxy-2-(6-methoxy-1,2,3,4-tetrahydronaphthalen-2-yl)phenyl]-4-(8-methyl-8-azabicyclo[3.2.1]oct-3-yloxy)benzamide

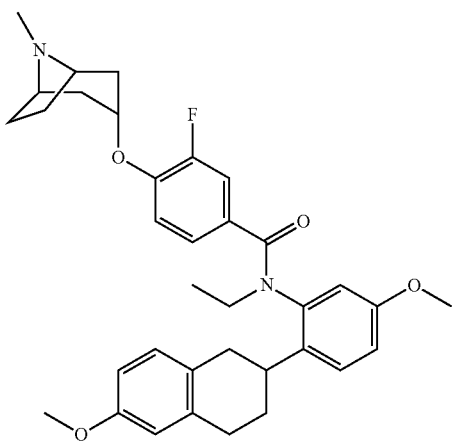 [SMILES: CCN(C(=O)c1ccc(OC2CC3CCC(C2)N3C)c(F)c1)c1cc(OC)ccc1C1CCc2cc(OC)ccc2C1]

To a suspension of 60% sodium hydride (187 mg) in N,N-dimethylformamide (2 ml) was added tropine (599 mg) on an ice bath. The solution was stirred for 30 minutes while warming to room temperature. Synthesized from ethyl[5-methoxy-2-(6-methoxy-1,2,3,4-tetrahydronaphthalen-2-yl)phenyl]amine and 3,4-difluorobenzoyl chloride according to an analogous synthetic method to Preparation Example 87, a solution of N-ethyl-3,4-difluoro-N-[5-methoxy-2-(6-methoxy-1,2,3,4-tetrahydronaphthalen-2-yl)phenyl]benzamide (383 mg) in N,N-dimethylformamide (5 ml) was added the above solution followed by stirring overnight at 80° C. The reaction mixture was let to cool, then a saturated aqueous solution of sodium bicarbonate was added thereto, the solution was extracted with ethyl acetate, then sequentially washed with water and brine, dried over anhydrous potassium carbonate, and then the solvent was evaporated in vacuo. The residue was purified by NH silica gel column chromatography (chloroform-methanol system) to provide the title compound (143 mg).

¹H-NMR (400 MHz, CDCl₃); δ (ppm): 0.66-0.74 (m, 0.5H), 1.23 (t, 3H), 1.83-2.16 (m, 9H), 2.28 (s, 3H), 2.45-2.57 (m, 0.5H), 2.66-2.91 (m, 4H), 3.08-3.14 (m, 2H), 3.77-3.83 (m, 6H), 3.85-3.96 (m, 2H), 4.48-4.55 (m, 1H), 6.57-7.15 (m, 10H).

Example 367

6-{2-{Ethyl[3-fluoro-4-(8-methyl-8-azabicyclo[3.2.1]oct-3-yloxy)benzyl]amino}-4-hydroxyphenyl}-5,6,7,8-tetrahydronaphthalen-2-ol

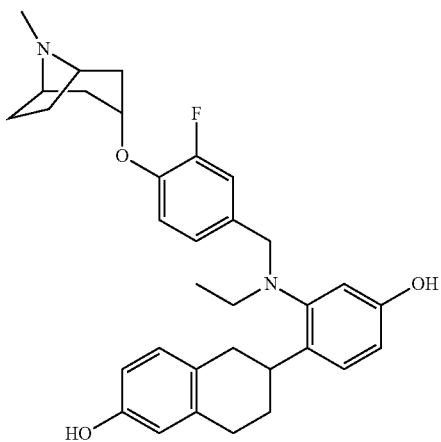 [SMILES: CCN(Cc1ccc(OC2CC3CCC(C2)N3C)c(F)c1)c1cc(O)ccc1C1CCc2cc(O)ccc2C1]

Synthesized from N-ethyl-3-fluoro-N-[5-methoxy-2-(6-methoxy-1,2,3,4-tetrahydronaphthalen-2-yl)phenyl]-4-(8-methyl-8-azabicyclo[3.2.1]oct-3-yloxy)benzamide according to an analogous synthetic method to Example 337, ethyl [3-fluoro-4-(8-methyl-8-azabicyclo[3.2.1]oct-3-yloxy)benzyl][5-methoxy-2-(6-methoxy-1,2,3,4-tetrahydronaphthalen-2-yl)phenyl]amine (123 mg) was used according to an analogous synthetic method to Example 111 to provide the title compound (108 mg).

$^1$H-NMR (400 MHz, DMSO-$d_6$); δ (ppm): 0.86 (t, 3H), 1.44-1.53 (m, 1H), 1.58-1.74 (m, 3H), 1.83-2.00 (m, 6H), 2.14 (s, 3H), 2.49-2.59 (m, 2H), 2.66-2.73 (m, 2H), 2.82 (q, 2H), 2.93-2.99 (m, 2H), 3.37-3.48 (m, 1H), 3.87 (dd, 2H), 4.51 (t, 1H), 6.44-6.52 (m, 3H), 6.62 (d, 1H), 6.77 (d, 1H), 6.84-6.89 (m, 2H), 6.98 (dd, 2H), 8.98 (brs, 1H), 9.09 (brs, 1H).

ESI-Mass; 531 [M$^+$+H]

Example 368

6-{2-{Ethyl[4-(2-pyrrolidin-1-ylethoxy)benzyl]amino}-4-hydroxyphenyl}-5,6,7,8-tetrahydronaphthalen-2-ol

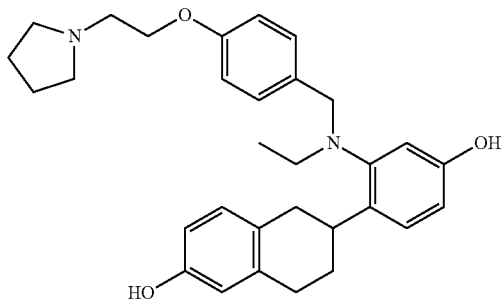 [SMILES: CCN(Cc1ccc(OCCN2CCCC2)cc1)c1cc(O)ccc1C1CCc2cc(O)ccc2C1]

To a solution of 4-benzyloxybenzoic acid (1.2 g) in dichloromethane (20 ml) were added oxalyl chloride (0.7 ml) and N,N-dimethylformamide (0.05 ml), the solution was stirred overnight at room temperature, and then the solvent was evaporated in vacuo. To the total amount of the resulting 4-benzyloxybenzoyl chloride in tetrahydrofuran (30 ml) were sequentially added N,N-diisopropylethylamine (5 ml) and 5-methoxy-2-(6-methoxy-1,2,3,4-tetrahydronaphthalen-2-yl)phenylamine (1.0 g), and the solution was stirred for 15 minutes at room temperature. To the reaction solution was added 1N hydrochloric acid, the solution was extracted with ethyl acetate, then sequentially washed with a saturated aqueous solution of sodium bicarbonate and brine, dried over anhydrous magnesium sulfate, and then the solvent was evaporated in vacuo. Obtained by purifying the residue by silica gel column chromatography (hexane-ethyl acetate system), to a solution of the resulting 4-benzyloxy-N-[5-methoxy-2-(6-methoxy-1,2,3,4-tetrahydronaphthalen-2-yl)phenyl]benzamide (2.0 g) in methanol (40 ml) and tetrahydrofuran (20 ml) was added 10% palladium-activated charcoal (0.3 g), the solution was stirred under a hydrogen atmosphere at ambient pressure, then the reaction solution was filtered, and the solvent was evaporated in vacuo. To a solution of the total amount of the resulting 4-hydroxy-N-[5-methoxy-2-(6-methoxy-1,2,3,4-tetrahydronaphthalen-2-yl)phenyl]benzamide in N,N-dimethylformamide (30 ml) were sequentially added cesium carbonate (3.4 g), 1-(2-chloroethyl)pyrrolidine hydrochloride (773 mg), and the solution was stirred overnight at 80° C. To the reaction solution was added a saturated aqueous solution of sodium bicarbonate, the solution was extracted with ethyl acetate, then washed with brine, dried over anhydrous magnesium sulfate, and then the solvent was evaporated in vacuo. Obtained by purifying the residue by NH silica gel column chromatography (hexane-ethyl acetate system), N-[5-methoxy-2-(6-methoxy-1,2,3,4-tetrahydronaphthalen-2-yl)phenyl]-4-(2-pyrrolidin-1-ylethoxy)benzamide (1.3 g) was used according to an analogous synthetic method to Example 160 to provide the title compound (243 mg).

$^1$H-NMR (400 MHz, CDCl$_3$); δ (ppm): 0.92 (t, 3H), 1.28-1.75 (m, 2H), 1.83-1.88 (m, 4H), 2.62-2.77 (m, 8H), 2.86-2.97 (m, 4H), 3.52-3.59 (m, 1H), 3.88 (s, 2H), 4.06 (t, 2H), 6.54-6.59 (m, 3H), 6.65 (d, 1H), 6.69 (d, 2H), 6.85 (d, 2H), 7.03 (d, 2H), 7.07 (d, 2H).

ESI-Mass; 487 [M$^+$+H]

Example 369

6-{2-{Ethyl[3-fluoro-4-(2-pyrrolidin-1-ylethoxy)benzyl]amino}-4-hydroxyphenyl}-5,6,7,8-tetrahydronaphthalen-2-ol

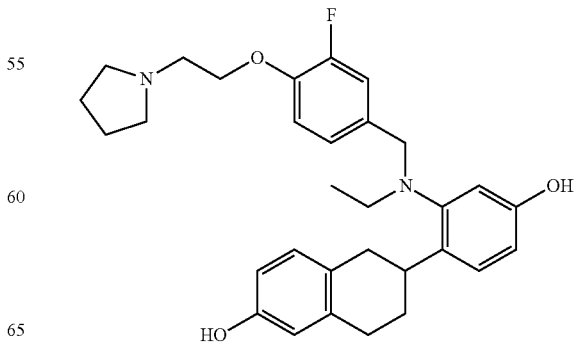

Synthesized from 5-methoxy-2-(6-methoxy-1,2,3,4-tetrahydronaphthalen-2-yl)phenylamine (1.3 g) and 4-benzyloxy-3-fluorobenzoic acid (1.0 g) according to an analogous synthetic method to Example 368, the title compound (460 mg) was obtained.

$^1$H-NMR (400 MHz, CDCl$_3$); δ (ppm): 0.94 (t, 3H), 1.68-1.77 (m, 2H), 1.83-1.86 (m, 4H), 2.64 (d, 2H), 2.75-2.83 (m, 6H), 2.93-3.04 (m, 4H), 3.69-3.71 (m, 1H), 3.92 (s, 2H), 4.14 (t, 2H), 6.55-6.61 (m, 3H), 6.65 (d, 1H), 6.70 (t, 1H), 6.84 (d, 1H), 6.91-6.94 (m, 1H), 6.98 (s, 1H), 7.06 (d, 1H).

ESI-Mass; 505 [M$^+$+H]

Preparation Example 149

N-Ethyl-4-hydroxy-N-[5-methoxy-2-(6-methoxy-1,2,3,4-tetrahydronaphthalen-2-yl)phenyl]benzamide

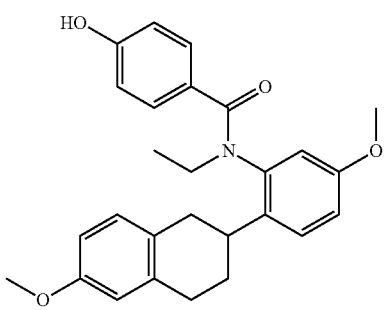

To a solution of 5-methoxy-2-(6-methoxy-1,2,3,4-tetrahydronaphthalen-2-yl)phenylamine (9.3 g) in tetrahydrofuran (100 ml) were sequentially added pyridine (8.0 ml) and acetic anhydride (6.2 ml), and the solution was stirred overnight at room temperature. To the reaction solution was added 1N hydrochloric acid, the solution was extracted with ethyl acetate, then sequentially washed with a saturated aqueous solution of sodium bicarbonate and brine, dried over anhydrous magnesium sulfate, and then the solvent was evaporated in vacuo. To a solution of the resulting N-[5-methoxy-2-(6-methoxy-1,2,3,4-tetrahydronaphthalen-2-yl)phenyl]acetamide (9.1 g) in tetrahydrofuran (100 ml) was added lithium aluminum hydride (2.7 g), and the solution was refluxed for 2 hours. Ammonia solution (1 ml) and anhydrous magnesium sulfate were added on an ice bath, the solution was filtered, and then the solvent was evaporated in vacuo to provide ethyl[5-methoxy-2-(6-methoxy-1,2,3,4-tetrahydronaphthalen-2-yl)phenyl]amine (8.8 g). To a solution of 4-benzyloxybenzoic acid (9.1 g) in dichloromethane (80 ml) were sequentially added oxalyl chloride (5.1 ml) and N,N-dimethylformamide (0.05 ml), the solution was stirred overnight at room temperature, then the solvent was evaporated in vacuo. To the total amount of the resulting 4-benzyloxybenzoyl chloride were sequentially added 1,4-dioxane (100 ml), N,N-diisopropylethylamine (15 ml) and ethyl[5-methoxy-2-(6-methoxy-1,2,3,4-tetrahydronaphthalen-2-yl)phenyl]amine (8.3 g), and the solution was refluxed for 30 minutes. To the reaction solution was added 1N hydrochloric acid, the solution was extracted with ethyl acetate, then sequentially washed with a saturated aqueous solution of sodium bicarbonate and brine, dried over anhydrous magnesium sulfate, then the solvent was evaporated in vacuo. Synthesized from the total amount of the resulting 4-benzyloxy-N-ethyl-N-[5-methoxy-2-(6-methoxy-1,2,3,4-tetrahydronaphthalen-2-yl) phenyl]benzamide (crude product) according to an analogous synthetic method to Example 22, the title compound (13 g) was obtained.

$^1$H-NMR (400 MHz, CDCl$_3$); δ (ppm): 1.21-1.28 (m, 3H), 1.57-1.70 (m, 2H), 2.40-2.50 (m, 1H), 2.60-2.90 (m, 6H), 3.76-4.00 (m, 6H), 6.56 (d, 2H), 6.60-6.74 (m, 3H), 6.79 (dd, 1H), 6.85 (d, 1H), 6.91 (d, 1H), 7.05-7.10 (m, 1H), 7.16 (d, 1H), 7.20 (d, 1H).

Example 370

6-{2-{Ethyl[4-(2-morpholin-4-ylethoxy)benzyl]amino}-4-hydroxyphenyl}-5,6,7,8-tetrahydronaphthalen-2-ol

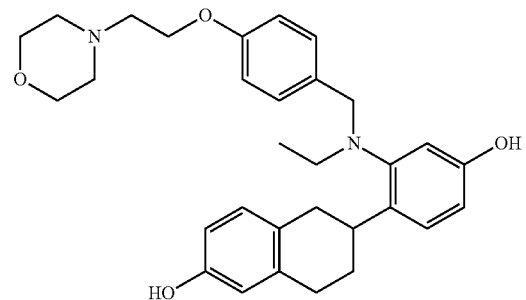 [SMILES: CCN(Cc1ccc(OCCN2CCOCC2)cc1)c1cc(O)ccc1C1CCc2cc(O)ccc2C1]

Synthesized from N-ethyl-4-hydroxy-N-[5-methoxy-2-(6-methoxy-1,2,3,4-tetrahydronaphthalen-2-yl)phenyl]benzamide (250 mg) and 4-(2-chloroethyl)morpholine hydrochloride (140 mg) according to an analogous synthetic method to Example 368, the title compound (225 mg) was obtained.

$^1$H-NMR (400 MHz, CDCl$_3$); δ (ppm): 0.93 (t, 3H), 1.71-1.77 (m, 2H), 2.59-2.68 (m, 6H), 2.79-2.91 (m, 6H), 3.58-3.65 (m, 1H), 3.74-3.76 (m, 4H), 3.93 (s, 2H), 4.07 (t, 2H), 6.57-6.62 (m, 3H), 6.68 (d, 1H), 6.74 (d, 2H), 6.89 (d, 1H), 7.06 (d, 1H), 7.11 (d, 2H).

Example 371

6-{2-{Ethyl[4-(3-piperidin-1-ylpropoxy)benzyl]amino}-4-hydroxyphenyl}-5,6,7,8-tetrahydronaphthalen-2-ol

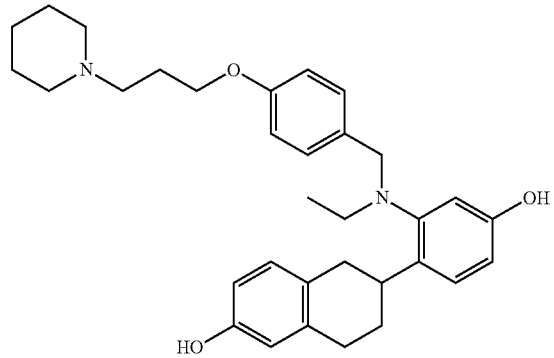 [SMILES: CCN(Cc1ccc(OCCCN2CCCCC2)cc1)c1cc(O)ccc1C1CCc2cc(O)ccc2C1]

Synthesized from N-ethyl-4-hydroxy-N-[5-methoxy-2-(6-methoxy-1,2,3,4-tetrahydronaphthalen-2-yl)phenyl]benzamide (500 mg) and 1-(3-chloropropyl)piperidine hydrochloride (298 mg) according to an analogous synthetic method to Example 368, the title compound (410 mg) was obtained.

$^1$H-NMR (400 MHz, CDCl$_3$); δ (ppm): 0.96 (t, 3H), 1.63-1.67 (m, 6H), 1.73-1.76 (m, 2H), 1.91-1.96 (m, 2H), 2.45-2.65 (m, 8H), 2.72-2.78 (m, 2H), 2.89-2.98 (m, 2H), 3.50-3.58 (m, 1H), 3.93-3.97 (m, 4H), 6.53 (s, 1H), 6.55-6.59 (m, 2H), 6.61 (s, 1H), 6.68 (d, 2H), 6.84 (d, 1H), 7.06-7.08 (m, 3H).

Example 372

6-{2-{Ethyl[4-(2-piperazin-1-ylethoxy)benzyl]amino}-4-hydroxyphenyl}-5,6,7,8-tetrahydronaphthalen-2-ol

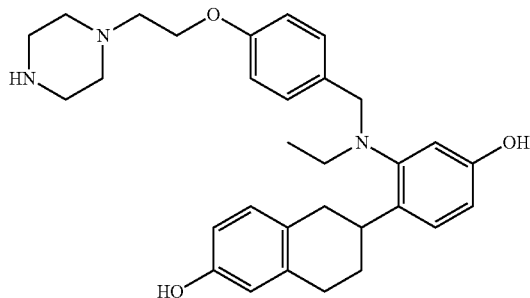 [SMILES: CCN(Cc1ccc(OCCN2CCNCC2)cc1)c1cc(O)ccc1C1CCc2cc(O)ccc2C1]

To a solution of N-ethyl-4-hydroxy-N-[5-methoxy-2-(6-methoxy-1,2,3,4-tetrahydronaphthalen-2-yl)phenyl]benzamide (1.0 g) and 4-(2-chloroacetyl)piperazine-1-carboxylic acid benzyl ester (830 mg) in N,N-dimethylformamide (20 ml) was added cesium carbonate (1.0 g), and the solution was stirred for 1 hour at 60° C. To the reaction solution was added brine, the solution was extracted with ethyl acetate, then dried over anhydrous magnesium sulfate, and the solvent was evaporated in vacuo. The residue was purified by NH silica gel column chromatography (hexane-ethyl acetate-methanol system) to provide 4-{2-{4-{ethyl[5-methoxy-2-(6-methoxy-1,2,3,4-tetrahydronaphthalen-2-yl)phenyl]carbamoyl}phenoxy}acetyl}piperazine-1-carboxylic acid benzyl ester (2.2 g). Synthesized from the total amount of this compound according to an analogous synthetic method to Example 22, N-ethyl-N-[5-methoxy-2-(6-methoxy-1,2,3,4-tetrahydronaphthalen-2-yl)phenyl]-4-(2-oxo-2-piperazin-1-ylethoxy)benzamide (1.5 g) was used according to an analogous synthetic method to Example 160 to provide the title compound (300 mg).

$^1$H-NMR (400 MHz, CDCl$_3$); δ (ppm): 0.95 (t, 3H), 1.69-1.79 (m, 1H), 1.82-1.90 (m, 2H), 2.55-2.60 (m, 4H), 2.66-2.68 (m, 2H), 2.76-2.82 (m, 4H), 2.86-2.96 (m, 6H), 3.57-3.72 (m, 1H), 3.93 (s, 2H), 4.08 (t, 2H), 6.57-6.61 (m, 3H), 6.65 (d, 1H), 6.74 (d, 2H), 6.87 (d, 1H), 7.06 (d, 1H), 7.11 (d, 2H).

ESI-Mass; 502 [M$^+$+H]

Example 373

6-{2-{Ethyl{4-[2-(4-ethylpiperazin-1-yl)ethoxy]benzyl}amino}-4-hydroxyphenyl}-5,6,7,8-tetrahydronaphthalen-2-ol

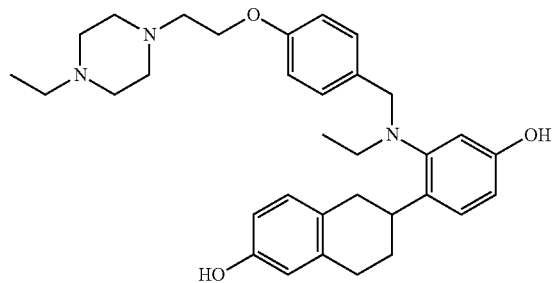 [SMILES: CCN1CCN(CCOc2ccc(CN(CC)c3cc(O)ccc3C3CCc4cc(O)ccc4C3)cc2)CC1]

Synthesized from 6-{2-{ethyl[4-(2-piperazin-1-ylethoxy)benzyl]amino}-4-hydroxyphenyl}-5,6,7,8-tetrahydronaphthalen-2-ol (200 mg) according to an analogous synthetic method to Example 786 described below, the title compound (102 mg) was obtained.

$^1$H-NMR (400 MHz, CDCl$_3$); δ (ppm): 0.94 (t, 3H), 1.11 (t, 3H), 1.67-1.77 (m, 2H), 2.49 (q, 2H), 2.60-2.70 (m, 8H), 2.77-2.81 (m, 4H), 2.88-2.97 (m, 4H), 3.51-3.57 (m, 1H), 3.91 (s, 2H), 4.07 (t, 2H), 6.56-6.59 (m, 3H), 6.65 (d, 1H), 6.71 (d, 2H), 6.86 (d, 1H), 7.06 (d, 1H), 7.10 (d, 2H).

Example 374

6-{2-{Ethyl{4-[2-(4-methylpiperazin-1-yl)ethoxy]benzyl}amino}-4-hydroxyphenyl}-5,6,7,8-tetrahydronaphthalen-2-ol

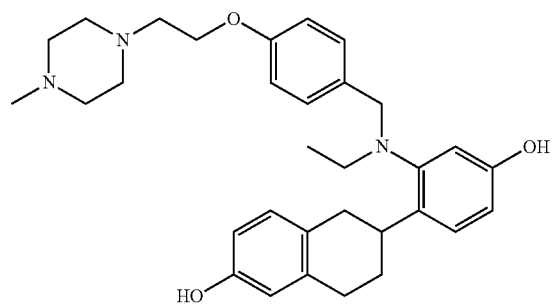 [SMILES: CCN(Cc1ccc(OCCN2CCN(C)CC2)cc1)c1cc(O)ccc1C1CCc2cc(O)ccc2C1]

Synthesized from N-ethyl-N-[5-methoxy-2-(6-methoxy-1,2,3,4-tetrahydronaphthalen-2-yl)phenyl]-4-(2-oxo-2-piperazin-1-ylethoxy)benzamide according to an analogous synthetic method to Example 337, ethyl[5-methoxy-2-(6-methoxy-1,2,3,4-tetrahydronaphthalen-2-yl)phenyl][4-(2-piperazin-1-ylethoxy)benzyl]amine (650 mg) was used according to an analogous synthetic method to Preparation Example 18 to provide ethyl[5-methoxy-2-(6-methoxy-1,2,3,4-tetrahydronaphthalen-2-yl)phenyl]{4-[2-(4-methylpiperazin-1-yl)ethoxy]benzyl}amine (490 mg). The total amount of this compound was used according to an analogous synthetic method to Example 111 to provide the title compound (70 mg).

$^1$H-NMR (400 MHz, CDCl$_3$); δ (ppm): 0.97 (t, 3H), 1.71-1.77 (m, 2H), 2.32 (s, 3H), 2.50-2.68 (m, 11H), 2.76-2.82 (m, 4H), 2.91-2.96 (m, 2H), 3.93 (s, 2H), 4.07 (t, 2H), 6.54-6.60 (m, 3H), 6.67 (d, 1H), 6.72 (d, 2H), 6.86 (d, 1H), 7.07 (d, 1H), 7.11 (d, 2H).

Example 375

6-{2-{Ethyl{4-[2-(4-isobutylpiperazin-1-yl)ethoxy]benzyl}amino}-4-hydroxyphenyl}-5,6,7,8-tetrahydronaphthalen-2-ol

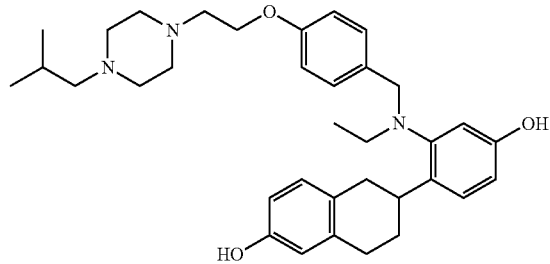 [SMILES: CCN(Cc1ccc(OCCN2CCN(CC(C)C)CC2)cc1)c1cc(O)ccc1C1CCc2cc(O)ccc2C1]

To a solution of N-ethyl-N-[5-methoxy-2-(6-methoxy-1,2,3,4-tetrahydronaphthalen-2-yl)phenyl]-4-(2-oxo-2-piperazin-1-ylethoxy)benzamide (650 mg) in tetrahydrofuran (20 ml) were sequentially added acetic acid (in catalytic amounts), sodium triacetoxyborohydride (760 mg) and isobutylaldehyde (260 mg), and the solution was stirred overnight at room temperature. To the reaction solution was added a saturated aqueous solution of sodium bicarbonate, the solution was extracted with ethyl acetate, then washed with brine, dried over anhydrous magnesium sulfate, and then the solvent was evaporated in vacuo. Synthesized from the resulting N-ethyl-4-[2-(4-isobutylpiperazin-1-yl)-2-oxoethoxy]-N-[5-methoxy-2-(6-methoxy-1,2,3,4-tetrahydronaphthalen-2-yl)phenyl]benzamide (560 mg) according to an analogous synthetic method to Example 160, the title compound (120 mg) was obtained.

$^1$H-NMR (400 MHz, CDCl$_3$); δ (ppm): 0.89 (s, 3H), 0.90 (s, 3H), 0.94 (t, 3H), 1.70-1.78 (m, 1H), 1.84-1.87 (m, 2H), 2.11 (d, 2H), 2.47-2.50 (m, 4H), 2.64-2.69 (m, 4H), 2.77-2.81 (m, 4H), 2.90 (q, 2H), 3.54-3.60 (m, 1H), 3.74-3.77 (m, 2H), 3.91 (s, 2H), 4.06 (t, 2H), 6.56-6.60 (m, 3H), 6.66 (d, 1H), 6.70 (d, 2H), 6.87 (d, 1H), 7.05 (d, 1H), 7.09 (d, 2H).

Example 376

4-(2-Diethylaminoethoxy)-N-ethyl-N-[5-methoxy-2-(6-methoxy-1,2,3,4-tetrahydronaphthalen-2-yl)phenyl]benzamide

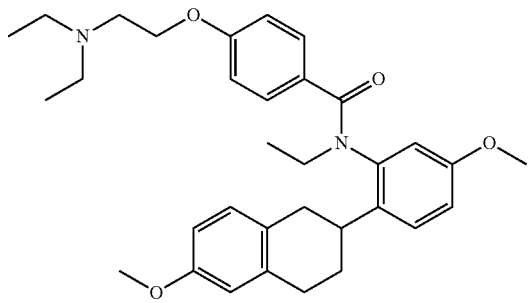 [SMILES: CCN(CC)CCOc1ccc(C(=O)N(CC)c2cc(OC)ccc2C2CCc3cc(OC)ccc3C2)cc1]

Synthesized from N-ethyl-4-hydroxy-N-[5-methoxy-2-(6-methoxy-1,2,3,4-tetrahydronaphthalen-2-yl)phenyl]benzamide (250 mg) and 2-diethylaminoethyl chloride hydrochloride (130 mg) according to an analogous synthetic method to Preparation Example 40, the title compound (223 mg) was obtained.

$^1$H-NMR (400 MHz, CDCl$_3$); δ (ppm): 0.56-0.65 (m, 0.5H), 1.02-1.08 (m, 6H), 1.23 (t, 3H), 1.42-1.52 (m, 0.5H), 1.65-1.89 (m, 1.5H), 2.37-2.47 (m, 0.5H), 2.56-2.90 (m, 10H), 3.77-3.83 (m, 6H), 3.84-4.08 (m, 4H), 6.59-6.97 (m, 7H), 7.05-7.10 (m, 1H), 7.20-7.31 (m, 2H).

Example 377

6-{2-{[4-(2-Diethylaminoethoxy)benzyl]ethylamino}-4-hydroxyphenyl}-5,6,7,8-tetrahydronaphthalen-2-ol

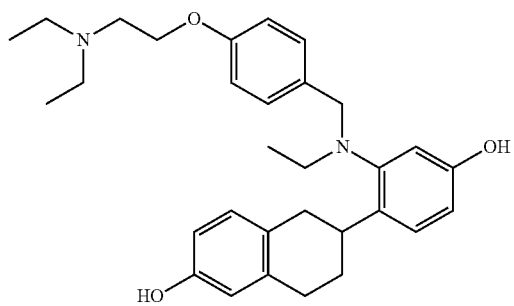 [SMILES: CCN(CC)CCOc1ccc(CN(CC)c2cc(O)ccc2C2CCc3cc(O)ccc3C2)cc1]

Synthesized from 4-(2-diethylaminoethoxy)-N-ethyl-N-[5-methoxy-2-(6-methoxy-1,2,3,4-tetrahydronaphthalen-2-yl)phenyl]benzamide according to an analogous synthetic method to Example 337, [4-(2-diethylaminoethoxy)benzyl]ethyl[5-methoxy-2-(6-methoxy-1,2,3,4-tetrahydronaphthalen-2-yl)phenyl]amine (149 mg) was used according to an analogous synthetic method to Example 111 to provide the title compound (159 mg).

$^1$H-NMR (400 MHz, DMSO-d$_6$); δ (ppm): 0.85 (t, 3H), 0.94 (t, 6H), 1.50-1.70 (m, 2H), 2.49-2.55 (m, 6H), 2.68-2.76 (m, 4H), 2.80 (q, 2H), 3.39-3.50 (m, 1H), 3.86 (s, 2H), 3.92 (t, 2H), 6.45-6.50 (m, 3H), 6.61 (d, 1H), 6.73-6.80 (m, 3H), 7.00 (d, 1H), 7.06 (d, 2H), 9.00 (brs, 1H), 9.07 (brs, 1H).

ESI-Mass; 489 [M$^+$+H]

Preparation Example 150

{4-{Ethyl[5-methoxy-2-(6-methoxy-1,2,3,4-tetrahydronaphthalen-2-yl)phenyl]carbamoyl}phenoxy}acetic acid

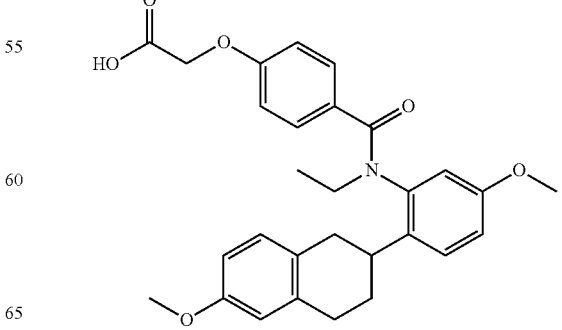

Synthesized from N-ethyl-4-hydroxy-N-[5-methoxy-2-(6-methoxy-1,2,3,4-tetrahydronaphthalen-2-yl)phenyl]benzamide and ethyl chloroacetate according to an analogous synthetic method to Preparation Example 40, to a solution of the resulting {4-{ethyl[5-methoxy-2-(6-methoxy-1,2,3,4-tetrahydronaphthalen-2-yl)phenyl]carbamoyl}phenoxy} acetic acid ethyl ester (275 mg) in tetrahydrofuran (5 ml) was added an aqueous solution of 1N sodium hydroxide (5 ml) on an ice bath. The solution was stirred for 1.5 hours while warming to room temperature, then the reaction solution was acidified with 2N hydrochloric acid on the ice bath. Water was added thereto, the solution was extracted with ethyl acetate, then sequentially washed with water and brine, dried over anhydrous magnesium sulfate, then the solvent was evaporated in vacuo to provide the title compound (246 mg).

$^1$H-NMR (400 MHz, CDCl$_3$); δ (ppm): 0.48-0.57 (m, 0.5H), 1.23 (t, 3H), 1.42-1.88 (m, 2H), 2.38-2.46 (m, 0.5H), 2.60-2.89 (m, 4H), 3.75-3.82 (m, 6H), 3.84-4.00 (m, 2H), 4.53-4.64 (m, 2H), 6.58-6.93 (m, 7H), 7.07 (t, 1H), 7.22-7.35 (m, 2H).

Example 378

N-Ethyl-4-ethylcarbamoylmethoxy-N-[5-methoxy-2-(6-methoxy-1,2,3,4-tetrahydronaphthalen-2-yl)phenyl]benzamide

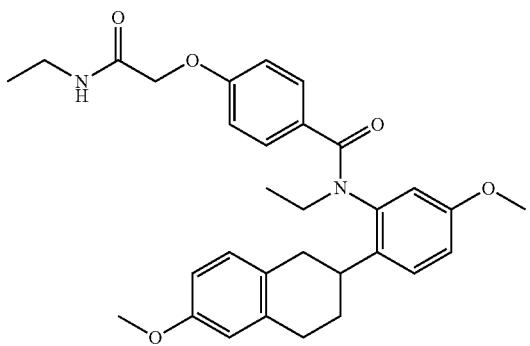 [SMILES: CCNC(=O)COc1ccc(C(=O)N(CC)c2cc(OC)ccc2C2CCc3cc(OC)ccc3C2)cc1]

To a solution of {4-{ethyl[5-methoxy-2-(6-methoxy-1,2,3,4-tetrahydronaphthalen-2-yl)phenyl]carbamoyl}phenoxy}acetic acid (244 mg) in tetrahydrofuran (8 ml) was added N,N-dimethylformamide (1 drop), and oxalyl chloride (0.06 ml) was added dropwise thereto followed by stirring for 20 minutes at room temperature. Then the solvent was evaporated in vacuo, the resulting {4-{ethyl[5-methoxy-2-(6-methoxy-1,2,3,4-tetrahydronaphthalen-2-yl)phenyl]carbamoyl}phenoxy}acetyl chloride (310 mg) was added to ethylamine (2.0 M solution in tetrahydrofuran) (3.1 ml) on an ice bath, and the solution was stirred for 2 hours while warming to room temperature. To the solution was added 0.1 N hydrochloric acid, the solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate-tetrahydrofuran system) to provide the title compound (269 mg).

$^1$H-NMR (400 MHz, CDCl$_3$); δ (ppm): 0.55-0.64 (m, 0.5H), 1.13-1.29 (m, 6H), 1.47-1.90 (m, 2H), 2.42-2.52 (m, 0.5H), 2.65-2.92 (m, 4H), 3.32-3.42 (m, 2H), 3.76-3.83 (m, 6H), 3.88-3.96 (m, 2H), 4.39-4.46 (m, 2H), 6.39-6.50 (m, 1H), 6.59-6.95 (m, 7H), 7.06-7.11 (m, 1H), 7.22-7.35 (m, 2H).

Example 379

6-{2-{Ethyl[4-(2-ethylaminoethoxy)benzyl]amino}-4-hydroxyphenyl}-5,6,7,8-tetrahydronaphthalen-2-ol

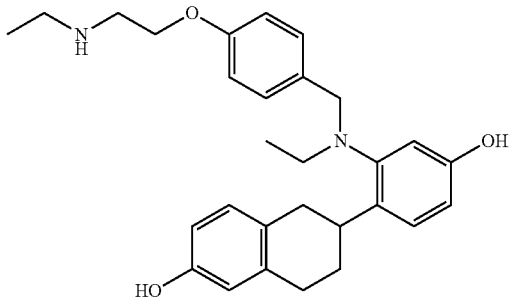 [SMILES: CCNCCOc1ccc(CN(CC)c2cc(O)ccc2C2CCc3cc(O)ccc3C2)cc1]

Synthesized from N-ethyl-4-ethylcarbamoylmethoxy-N-[5-methoxy-2-(6-methoxy-1,2,3,4-tetrahydronaphthalen-2-yl)phenyl]benzamide according to an analogous synthetic method to Example 337, ethyl[4-(2-ethylaminoethoxy)benzyl][5-methoxy-2-(6-methoxy-1,2,3,4-tetrahydronaphthalen-2-yl)phenyl]amine (143 mg) was used according to an analogous synthetic method to Example 111 to provide the title compound (138 mg).

$^1$H-NMR (400 MHz, DMSO-d$_6$); δ (ppm): 0.85 (t, 3H), 0.99 (t, 3H), 1.51-1.69 (m, 2H), 2.50-2.58 (m, 5H), 2.66-2.83 (m, 6H), 3.41-3.50 (m, 1H), 3.86 (s, 2H), 3.92 (t, 2H), 6.44-6.50 (m, 3H), 6.61 (d, 1H), 6.74-6.80 (m, 3H), 7.00 (d, 1H), 7.07 (d, 2H), 9.00 (brs, 1H), 9.07 (brs, 1H).

ESI-Mass; 461 [M$^+$+H]

Example 380

6-{2-{[4-(2-Azocan-1-ylethoxy)benzyl]ethylamino}-4-hydroxyphenyl}-5,6,7,8-tetrahydronaphthalen-2-ol

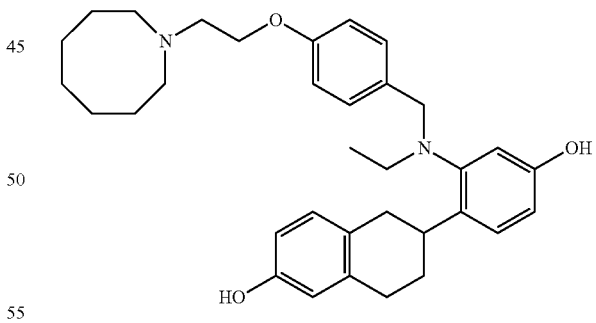

Synthesized from {4-{ethyl[5-methoxy-2-(6-methoxy-1,2,3,4-tetrahydronaphthalen-2-yl)phenyl]carbamoyl}phenoxy}acetic acid and heptamethyleneimine according to an analogous synthetic method to Example 378, 4-(2-azocan-1-yl-2-oxoethoxy)-N-ethyl-N-[5-methoxy-2-(6-methoxy-1,2,3,4-tetrahydronaphthalen-2-yl)phenyl]benzamide (262 mg) was used according to an analogous synthetic method to Example 337 to provide [4-(2-azocan-1-ylethoxy)benzyl]ethyl[5-methoxy-2-(6-methoxy-1,2,3,4-tetrahydronaphthalen-2-yl)phenyl]amine (226 mg). Synthesized from this compound (218 mg) according to an analogous synthetic method to Example 111, the title compound (168 mg) was obtained.

¹H-NMR (400 MHz, DMSO-d₆); δ (ppm): 0.84 (t, 3H), 1.42-1.68 (m, 12H), 2.43-2.63 (m, 6H), 2.68-2.85 (m, 6H), 3.40-3.50 (m, 1H), 3.86 (dd, 2H), 3.93 (t, 2H), 6.44-6.51 (m, 3H), 6.62 (d, 1H), 6.73-6.79 (m, 3H), 6.99 (d, 1H), 7.06 (d, 2H), 8.99 (brs, 1H), 9.07 (brs, 1H).
ESI-Mass; 529 [M⁺+H]

Example 381

[2-(4-Benzyloxyphenyl)ethyl][5-methoxy-2-(6-methoxy-1,2,3,4-tetrahydronaphthalen-2-yl)phenyl]amine

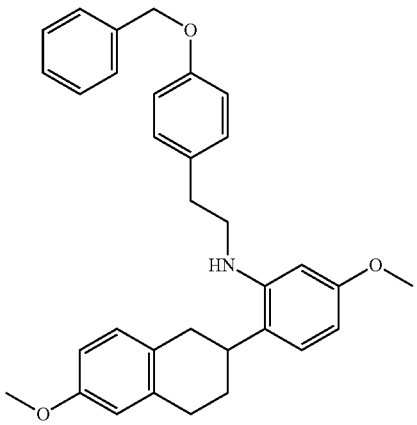

Synthesized from 5-methoxy-2-(6-methoxy-1,2,3,4-tetrahydronaphthalen-2-yl)phenylamine (400 mg) and 4-benzyloxyphenylacetyl chloride (700 mg) according to an analogous synthetic method to Example 152, the title compound (591 mg) was obtained.
¹H-NMR (400 MHz, CDCl₃); δ (ppm): 1.76-1.88 (m, 1H), 1.91-1.98 (m, 1H), 2.55-2.69 (m, 2H), 2.76-2.87 (m, 3H), 2.90 (t, 2H), 3.33-3.42 (m, 2H), 3.74 (brs, 1H), 3.77 (s, 3H), 3.79 (s, 3H), 5.00 (s, 2H), 6.26-6.31 (m, 2H), 6.65 (d, 1H), 6.69 (dd, 1H), 6.86 (d, 2H), 6.94 (d, 1H), 7.01 (d, 1H), 7.11 (d, 2H), 7.30-7.46 (m, 5H).

Example 382

4-{2-{[5-Methoxy-2-(6-methoxy-1,2,3,4-tetrahydronaphthalen-2-yl)phenyl]methylamino}ethyl}phenol

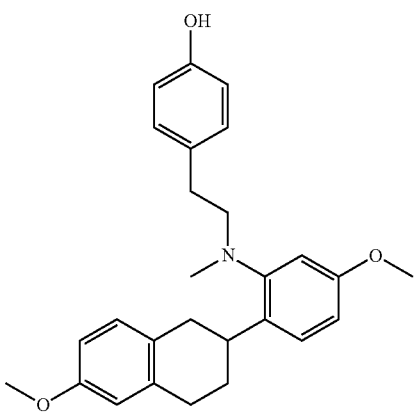

Synthesized from [2-(4-benzyloxyphenyl)ethyl][5-methoxy-2-(6-methoxy-1,2,3,4-tetrahydronaphthalen-2-yl)phenyl]amine according to an analogous synthetic method to Preparation Example 18, [2-(4-benzyloxyphenyl)ethyl][5-methoxy-2-(6-methoxy-1,2,3,4-tetrahydronaphthalen-2-yl)phenyl]methylamine (367 mg) was used according to an analogous synthetic method to Example 22 to provide the title compound (320 mg).
¹H-NMR (400 MHz, DMSO-d₆); δ (ppm): 1.66-1.83 (d, 2H), 2.52-2.59 (m, 2H), 2.61 (s, 3H), 2.63-2.70 (m, 2H), 2.74-2.82 (m, 2H), 2.90-3.01 (m, 2H), 3.24-3.30 (m, 1H), 3.70 (s, 3H), 3.71 (s, 3H), 6.55 (d, 2H), 6.62-6.70 (m, 4H), 6.87 (d, 2H), 6.93 (d, 1H), 7.16 (d, 1H), 9.08 (s, 1H).

Example 383

{2-[4-(2-Azepan-1-ylethoxy)phenyl]ethyl}[5-methoxy-2-(6-methoxy-1,2,3,4-tetrahydronaphthalen-2-yl)phenyl]methylamine

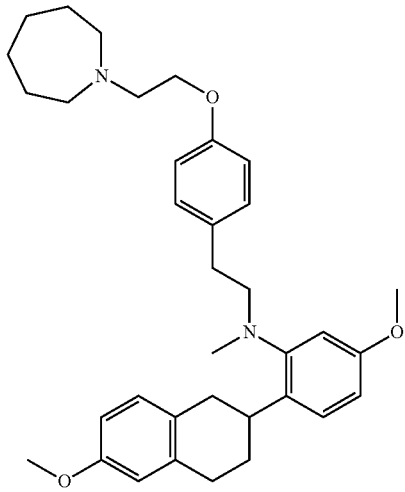 [SMILES: COc1ccc2c(c1)CCC(c1ccc(OC)cc1N(C)CCc1ccc(OCCN3CCCCCC3)cc1)C2]

To a solution of 4-{2-{[5-methoxy-2-(6-methoxy-1,2,3,4-tetrahydronaphthalen-2-yl)phenyl]methylamino}ethyl}phenol (160 mg) in N,N-dimethylformamide (3 ml) were sequentially added potassium carbonate (100 mg) and 1-(2-chloroethyl)azepane (110 mg), and the solution was stirred for 2 hours at 60° C. Water was added thereto followed by stirring, the solution was extracted with ethyl acetate, then sequentially washed with water and brine, and the solvent was evaporated in vacuo. The residue was purified by NH silica gel column chromatography (hexane-ethyl acetate system) to provide the title compound (157 mg).
¹H-NMR (400 MHz, CDCl₃); δ (ppm): 1.57-1.70 (m, 8H), 1.75-1.90 (m, 2H), 2.76-2.89 (m, 13H), 2.93 (t, 2H), 3.02-3.09 (m, 2H), 3.37-3.47 (m, 1H), 3.80 (s, 6H), 3.99 (t, 2H), 6.64-6.76 (m, 6H), 6.97 (d, 1H), 7.02 (d, 2H), 7.16 (d, 1H).

Example 384

6-{2-{{2-[4-(2-Azepan-1-ylethoxy)phenyl]ethyl}methylamino}-4-hydroxyphenyl}-5,6,7,8-tetrahydronaphthalen-2-ol

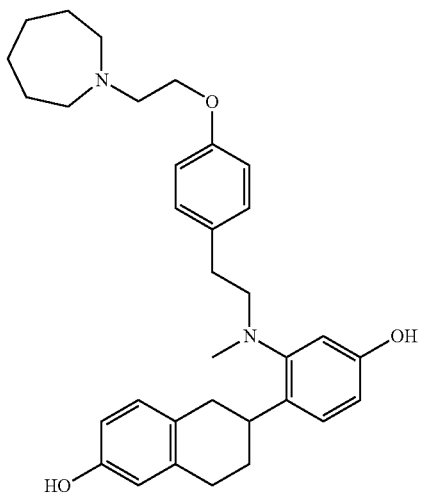 [SMILES: CN(CCc1ccc(OCCN2CCCCCC2)cc1)c1cc(O)ccc1C1CCc2cc(O)ccc2C1]

Synthesized from {2-[4-(2-azepan-1-ylethoxy)phenyl]ethyl}[5-methoxy-2-(6-methoxy-1,2,3,4-tetrahydronaphthalen-2-yl)phenyl]methylamine (154 mg) according to an analogous synthetic method to Example 111, the title compound (108 mg) was obtained.

$^1$H-NMR (400 MHz, DMSO-$d_6$); δ (ppm): 1.47-1.58 (m, 8H), 1.60-1.78 (m, 2H), 2.52-2.73 (m, 13H), 2.79 (t, 2H), 2.86-3.00 (m, 2H), 3.11-3.21 (m, 1H), 3.91 (t, 2H), 6.43-6.51 (m, 3H), 6.56 (d, 1H), 6.69 (d, 2H), 6.79 (d, 1H), 6.96-7.03 (m, 3H), 8.97 (s, 1H), 9.08 (s, 1H).

ESI-Mass; 515 [M$^+$+H]

Example 385

6-{2-{{2-[4-(2-Diisopropylaminoethoxy)phenyl]ethyl}methylamino}-4-hydroxyphenyl}-5,6,7,8-tetrahydronaphthalen-2-ol

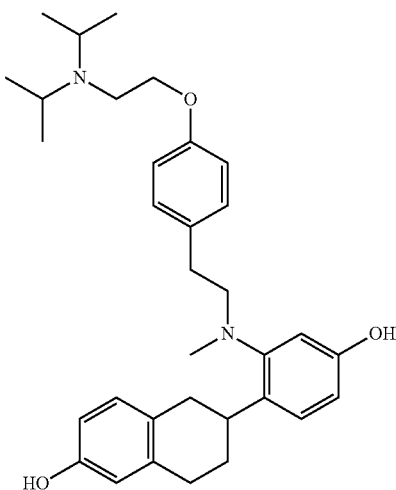 [SMILES: CC(C)N(CCOc1ccc(CCN(C)c2cc(O)ccc2C2CCc3cc(O)ccc3C2)cc1)C(C)C]

Synthesized from 4-{2-{[5-methoxy-2-(6-methoxy-1,2,3,4-tetrahydronaphthalen-2-yl)phenyl]methylamino}ethyl}phenol and (2-chloroethyl)diisopropylamine according to an analogous synthetic method to Example 383, {2-[4-(2-diisopropylaminoethoxy)phenyl]ethyl}[5-methoxy-2-(6-methoxy-1,2,3,4-tetrahydronaphthalen-2-yl)phenyl]methylamine (177 mg) was used according to an analogous synthetic method to Example 111 to provide the title compound (130 mg).

$^1$H-NMR (400 MHz, DMSO-$d_6$); δ (ppm): 0.96 (d, 12H), 1.58-1.76 (m, 2H), 2.53-2.69 (m, 9H), 2.71 (t, 2H), 2.89-3.03 (m, 4H), 3.12-3.22 (m, 1H), 3.76 (t, 2H), 6.43-6.50 (m, 3H), 6.56 (d, 1H), 6.68 (d, 2H), 6.79 (d, 1H), 6.96-7.02 (m, 3H), 8.97 (s, 1H), 9.08 (s, 1H).

ESI-Mass; 517 [M$^+$+H]

Preparation Example 151

2-(4-Benzyloxyphenyl)-N-[5-methoxy-2-(6-methoxy-1,2,3,4-tetrahydronaphthalen-2-yl)phenyl]acetamide

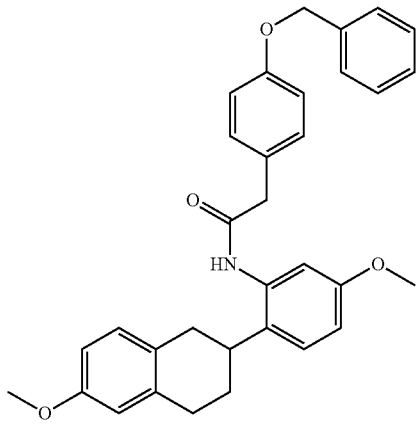

Synthesized from 5-methoxy-2-(6-methoxy-1,2,3,4-tetrahydronaphthalen-2-yl)phenylamine (1.1 g) and 4-benzyloxyphenylacetyl chloride (1.3 g) according to an analogous synthetic method to Preparation Example 87, the title compound (1.6 g) was obtained.

$^1$H-NMR (400 MHz, CDCl$_3$); δ (ppm): 1.68-1.84 (m, 2H), 2.25-2.35 (m, 1H), 2.51-2.70 (m, 3H), 2.76-2.84 (m, 1H), 3.68 (s, 3H), 3.70 (s, 2H), 3.80 (s, 3H), 4.79 (s, 2H), 6.62 (d, 1H), 6.65-6.74 (m, 4H), 6.93 (d, 1H), 7.06 (d, 1H), 7.14-7.20 (m, 3H), 7.30-7.42 (m, 3H), 7.65 (d, 1H).

Example 386

4-{2-{Ethyl[5-methoxy-2-(6-methoxy-1,2,3,4-tetrahydronaphthalen-2-yl)phenyl]amino}ethyl}phenol

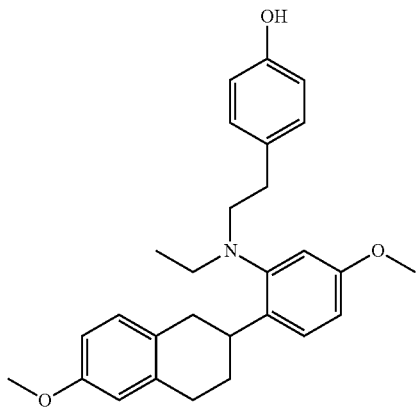

Synthesized from 2-(4-benzyloxyphenyl)-N-[5-methoxy-2-(6-methoxy-1,2,3,4-tetrahydronaphthalen-2-yl)phenyl]acetamide according to an analogous synthetic method to Example 337, [2-(4-benzyloxyphenyl)ethyl][5-methoxy-2-(6-methoxy-1,2,3,4-tetrahydronaphthalen-2-yl)phenyl]amine (1.3 g) was used according to an analogous synthetic method to Example 36 to provide [2-(4-benzyloxyphenyl)ethyl]ethyl[5-methoxy-2-(6-methoxy-1,2,3,4-tetrahydronaphthalen-2-yl)phenyl]amine (1.2 g). The total amount of this compound was used according to an analogous synthetic method to Example 22 to provide the title compound (920 mg).
$^1$H-NMR (400 MHz, CDCl$_3$); δ (ppm): 0.97 (t, 3H), 1.76-1.86 (m, 2H), 2.58-2.64 (m, 2H), 2.65-2.79 (m, 2H), 2.82-2.90 (m, 2H), 2.92-3.03 (m, 2H), 3.04-3.14 (m, 2H), 3.46-3.56 (m, 1H), 3.80 (s, 3H), 3.81 (s, 3H), 4.64 (s, 1H), 6.61-6.73 (m, 5H), 6.78 (d, 1H), 6.94-7.00 (m, 3H), 7.17 (d, 1H).

Example 387

Ethyl[5-methoxy-2-(6-methoxy-1,2,3,4-tetrahydronaphthalen-2-yl)phenyl]{2-[4-(2-pyrrolidin-1-ylethoxy)phenyl]ethyl}amine

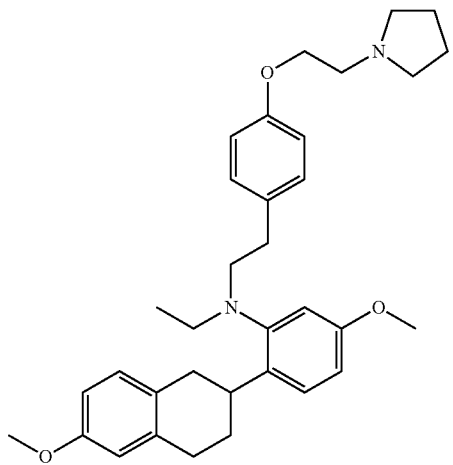 [SMILES: CCN(CCc1ccc(OCCN2CCCC2)cc1)c1cc(OC)ccc1C1CCc2cc(OC)ccc2C1]

Synthesized from 4-{2-{ethyl[5-methoxy-2-(6-methoxy-1,2,3,4-tetrahydronaphthalen-2-yl)phenyl]amino}ethyl}phenol (302 mg) and 1-(2-chloroethyl)pyrrolidine hydrochloride (155 mg) according to an analogous synthetic method to Preparation Example 40, the title compound (314 mg) was obtained.
$^1$H-NMR (400 MHz, CDCl$_3$); δ (ppm): 0.97 (t, 3H), 1.75-1.87 (m, 6H), 2.58-2.66 (m, 6H), 2.67-3.02 (m, 8H), 3.06-3.14 (m, 2H), 3.54-3.63 (m, 1H), 3.79 (s, 3H), 3.81 (s, 3H), 4.04 (t, 2H), 6.66-6.72 (m, 3H), 6.74-6.80 (m, 3H), 6.95-7.04 (m, 3H), 7.18 (d, 1H).

Example 388

6-{2-{Ethyl{2-[4-(2-pyrrolidin-1-ylethoxy)phenyl]ethyl}amino}-4-hydroxyphenyl}-5,6,7,8-tetrahydronaphthalen-2-ol

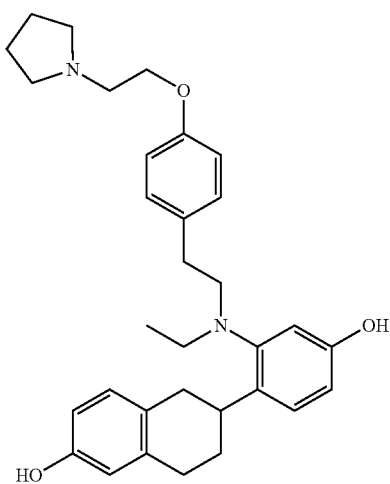 [SMILES: CCN(CCc1ccc(OCCN2CCCC2)cc1)c1cc(O)ccc1C1CCc2cc(O)ccc2C1]

Synthesized from ethyl[5-methoxy-2-(6-methoxy-1,2,3,4-tetrahydronaphthalen-2-yl)phenyl]{2-[4-(2-pyrrolidin-1-ylethoxy)phenyl]ethyl}amine (314 mg) according to an analogous synthetic method to Example 111, the title compound (235 mg) was obtained.
$^1$H-NMR (400 MHz, CDCl$_3$); δ (ppm): 0.95 (t, 3H), 1.48-1.62 (m, 4H), 1.86-1.98 (m, 5H), 2.44-3.12 (m, 14H), 3.74-3.84 (m, 2H), 6.34 (d, 1H), 6.36-6.41 (m, 2H), 6.58-6.63 (m, 2H), 6.74 (d, 1H), 6.81 (d, 1H), 6.95-7.01 (m, 2H), 7.04 (d, 1H).
ESI-Mass; 501 [M$^+$+H]

Example 389

Ethyl[5-methoxy-2-(6-methoxy-1,2,3,4-tetrahydronaphthalen-2-yl)phenyl]{2-[4-(2-piperidin-1-ylethoxy)phenyl]ethyl}amine

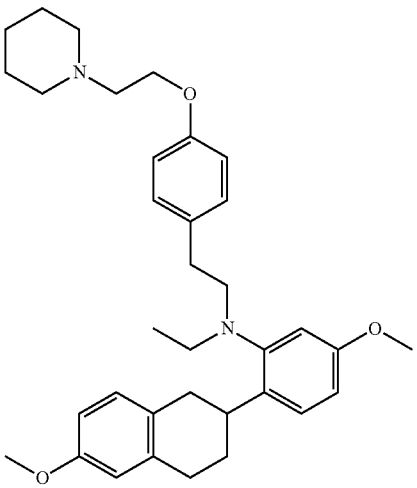

Synthesized from 4-{2-{ethyl[5-methoxy-2-(6-methoxy-1,2,3,4-tetrahydronaphthalen-2-yl)phenyl]amino}ethyl}phenol (302 mg) and 1-(2-chloroethyl)piperidine hydrochloride (168 mg) according to an analogous synthetic method to Preparation Example 40, the title compound (364 mg) was obtained.
$^1$H-NMR (400 MHz, CDCl$_3$); δ (ppm): 0.97 (t, 3H), 1.38-1.47 (m, 2H), 1.55-1.63 (m, 4H), 1.80-1.90 (m, 2H), 2.40-3.03 (m, 14H), 3.06-3.14 (m, 2H), 3.53-3.62 (m, 1H), 3.80 (s, 3H), 3.81 (s, 3H), 4.01-4.05 (m, 2H), 6.66-6.79 (m, 6H), 6.97 (d, 1H), 6.99-7.04 (m, 2H), 7.18 (d, 1H).

Example 390

6-{2-{Ethyl{2-[4-(2-piperidin-1-ylethoxy)phenyl]ethyl}amino}-4-hydroxyphenyl}-5,6,7,8-tetrahydronaphthalen-2-ol

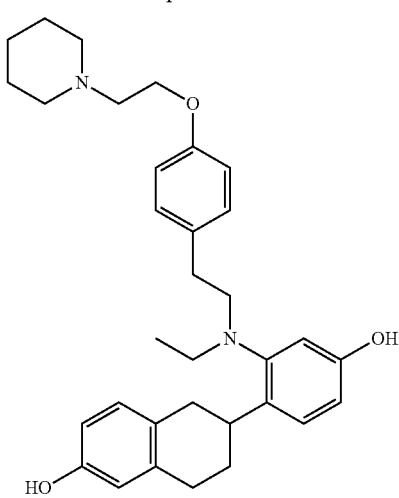

Synthesized from ethyl[5-methoxy-2-(6-methoxy-1,2,3,4-tetrahydronaphthalen-2-yl)phenyl]{2-[4-(2-piperidin-1-ylethoxy)phenyl]ethyl}amine (364 mg) according to an analogous synthetic method to Example 111, the title compound (265 mg) was obtained.

$^1$H-NMR (400 MHz, DMSO-$d_6$); δ (ppm): 0.95 (t, 3H), 1.30-1.38 (m, 2H), 1.42-1.50 (m, 4H), 1.58-1.70 (m, 2H), 2.30-2.72 (m, 14H), 2.84-2.90 (m, 2H), 2.96-3.02 (m, 2H), 3.90-3.96 (m, 2H), 6.43-6.62 (m, 3H), 6.68-6.80 (m, 3H), 6.95-7.05 (m, 3H), 9.00 (s, 1H), 9.10 (s, 1H).

ESI-Mass; 515 [M$^+$+H]

Example 391

6-{2-{{2-[4-(2-Diethylaminoethoxy)phenyl]ethyl}ethylamino}-4-hydroxyphenyl}-5,6,7,8-tetrahydronaphthalen-2-ol

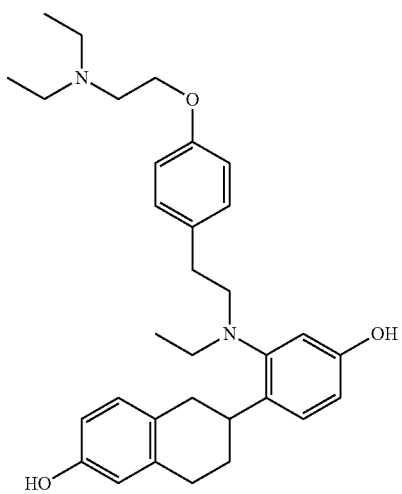 [SMILES: CCN(CC)CCOc1ccc(CCN(CC)c2cc(O)ccc2C2CCc3cc(O)ccc3C2)cc1]

Synthesized from 4-{2-{ethyl[5-methoxy-2-(6-methoxy-1,2,3,4-tetrahydronaphthalen-2-yl)phenyl]amino}ethyl}phenol (324 mg) and (2-chloroethyl)diethylamine hydrochloride (168 mg) according to an analogous synthetic method to Preparation Example 40, the total amount of {2-[4-(2-diethylaminoethoxy)phenyl]ethyl}ethyl[5-methoxy-2-(6-methoxy-1,2,3,4-tetrahydronaphthalen-2-yl)phenyl]amine was used according to an analogous synthetic method to Example 111 to provide the title compound (212 mg).

$^1$H-NMR (400 MHz, CDCl$_3$); δ (ppm): 0.95 (t, 3H), 1.16 (t, 3H), 1.25 (t, 3H), 1.43-1.52 (m, 4H), 2.54-3.16 (m, 15H), 3.78-3.82 (m, 2H), 6.40-6.46 (m, 3H), 6.58-6.63 (m, 2H), 6.64 (s, 1H), 6.81-6.84 (m, 1H), 6.86-7.00 (m, 2H), 7.05-7.08 (m, 1H).

ESI-Mass; 503 [M$^+$+H]

Example 392

4-{2-[5-Methoxy-2-(6-methoxy-1,2,3,4-tetrahydronaphthalen-2-yl)phenylamino]ethyl}phenol

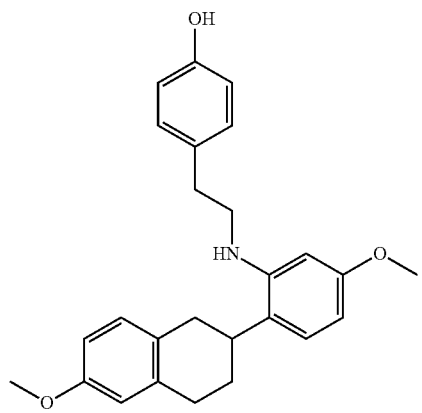

Synthesized from 2-(4-benzyloxyphenyl)-N-[5-methoxy-2-(6-methoxy-1,2,3,4-tetrahydronaphthalen-2-yl)phenyl]acetamide according to an analogous synthetic method to Example 337, [2-(4-benzyloxyphenyl)ethyl][5-methoxy-2-(6-methoxy-1,2,3,4-tetrahydronaphthalen-2-yl)phenyl]amine (2.3 g) was used according to an analogous synthetic method to Example 22 to provide the title compound (1.9 g).

$^1$H-NMR (400 MHz, CDCl$_3$); δ (ppm): 1.75-1.89 (m, 1H), 1.92-2.00 (m, 1H), 2.56-2.68 (m, 2H), 2.73-2.93 (m, 5H), 3.28-3.42 (m, 2H), 3.79 (s, 3H), 3.80 (s, 3H), 6.26-6.31 (m, 2H), 6.65-6.74 (m, 4H), 6.94 (d, 1H), 6.97-7.08 (m, 3H).

Preparation Example 152

Cyclopropanecarboxylic Acid {2-[4-(tert-butyldimethylsilyloxy)phenyl]ethyl}[5-methoxy-2-(6-methoxy-1,2,3,4-tetrahydronaphthalen-2-yl)phenyl]amide

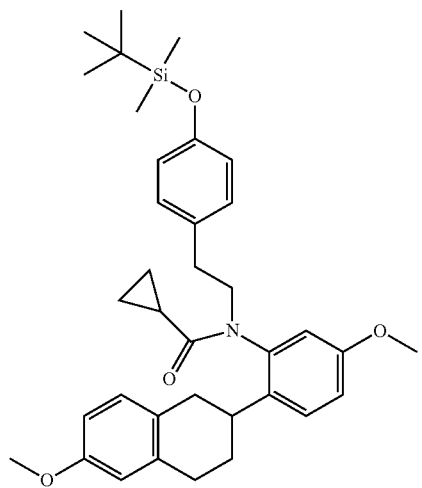

Synthesized from 4-{2-[5-methoxy-2-(6-methoxy-1,2,3,4-tetrahydronaphthalen-2-yl)phenylamino]ethyl}phenol according to an analogous synthetic method to Example 201, to a solution of the resulting {2-[4-(tert-butyldimethylsilyloxy)phenyl]ethyl}[5-methoxy-2-(6-methoxy-1,2,3,4-tetrahydronaphthalen-2-yl)phenyl]amine (2.3 g) in tetrahydrofuran (50 ml) was added triethylamine (895 mg), cyclopropanecarbonyl chloride (693 mg) was added dropwise thereto on an ice bath followed by stirring for 30 minutes at room temperature. The solution was extracted with ethyl acetate, then sequentially washed with a saturated aqueous solution of sodium bicarbonate and brine, dried over anhydrous magnesium sulfate, and then the solvent was evaporated in vacuo. The residue was purified by silica gel column chromatography (hexane-ethyl acetate system) to provide the title compound (2.3 g).

$^1$H-NMR (400 MHz, CDCl$_3$); δ (ppm): 0.10 (s, 3H), 0.17 (s, 3H), 0.55-0.68 (m, 2H), 0.92 (s, 9H), 1.84-1.98 (m, 2H), 2.72-2.95 (m, 6H), 2.97-3.08 (m, 1H), 3.23-3.33 (m, 1H), 3.78 (s, 6H), 4.18-4.27 (m, 1H), 6.59 (dd, 1H), 6.64 (d, 1H), 6.66-6.71 (m, 1H), 6.71-6.76 (m, 1H), 6.91-6.97 (m, 2H), 7.01-7.07 (m, 1H), 7.29 (dd, 1H).

Example 393

4-{2-{Cyclopropylmethyl[5-methoxy-2-(6-methoxy-1,2,3,4-tetrahydronaphthalen-2-yl)phenyl]amino}ethyl}phenol

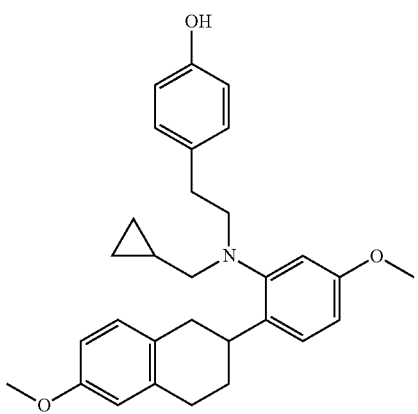

Synthesized from cyclopropanecarboxylic acid {2-[4-(tert-butyldimethylsilyloxy)phenyl]ethyl}[5-methoxy-2-(6-methoxy-1,2,3,4-tetrahydronaphthalen-2-yl)phenyl]amide (2.3 g) according to an analogous synthetic method to Example 337, to a filtrate of the resulting {2-[4-(tert-butyldimethylsilyloxy)phenyl]ethyl}cyclopropylmethyl[5-methoxy-2-(6-methoxy-1,2,3,4-tetrahydronaphthalen-2-yl)phenyl]amine was added tetrabutylammonium fluoride (1M solution in tetrahydrofuran) (4 ml), and the solution was stirred for 20 minutes at room temperature. The reaction solution was concentrated in vacuo, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (1.7 g).

$^1$H-NMR (400 MHz, CDCl$_3$); δ (ppm): 0.02-0.14 (m, 2H), 0.37-0.44 (m, 2H), 0.78-0.86 (m, 1H), 1.75-1.88 (m, 2H), 2.56-2.90 (m, 8H), 3.14-3.25 (m, 2H), 3.53-3.63 (m, 1H), 3.80 (s, 6H), 6.61-6.73 (m, 5H), 6.82 (d, 1H), 6.95-7.00 (m, 3H), 7.17 (d, 1H).

Example 394

6-{2-{Cyclopropylmethyl {2-[4-(2-piperidin-1-ylethoxy)phenyl]ethyl}amino}-4-hydroxyphenyl}-5,6,7,8-tetrahydronaphthalen-2-ol

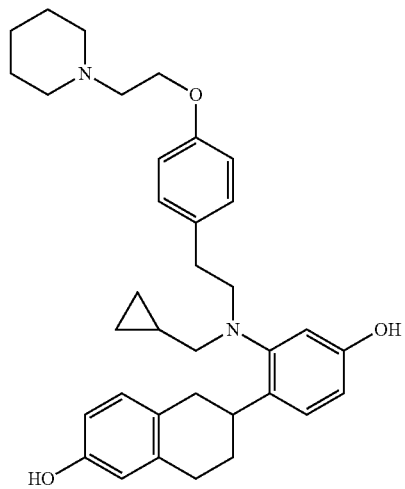 [SMILES: Oc1ccc2c(c1)CCC(c1ccc(O)cc1N(CCc1ccc(OCCN3CCCCC3)cc1)CC1CC1)C2]

Synthesized from 4-{2-{cyclopropylmethyl[5-methoxy-2-(6-methoxy-1,2,3,4-tetrahydronaphthalen-2-yl)phenyl]amino}ethyl}phenol and 1-(2-chloroethyl)piperidine hydrochloride according to an analogous synthetic method to Preparation Example 40, cyclopropylmethyl[5-methoxy-2-(6-methoxy-1,2,3,4-tetrahydronaphthalen-2-yl)phenyl]{2-[4-(2-piperidin-1-ylethoxy)phenyl]ethyl}amine (351 mg) was used according to an analogous synthetic method to Example 111 to provide the title compound (159 mg).

$^1$H-NMR (400 MHz, CDCl$_3$); δ (ppm): 0.04-0.16 (m, 2H), 0.32-0.44 (m, 2H), 0.72-0.80 (m, 1H), 1.48-1.82 (m, 10H), 2.54-2.92 (m, 12H), 2.96-3.16 (m, 3H), 3.76-3.88 (m, 2H), 6.36-6.42 (m, 3H), 6.58-6.64 (m, 2H), 6.78-6.82 (m, 2H), 6.94-7.00 (m, 2H), 7.16 (d, 1H).
ESI-Mass; 541 [M$^+$+H]

Example 395

6-{2-{{2-[4-(2-Azepan-1-ylethoxy)phenyl]ethyl}cyclopropylmethylamino}-4-hydroxyphenyl}-5,6,7,8-tetrahydronaphthalen-2-ol

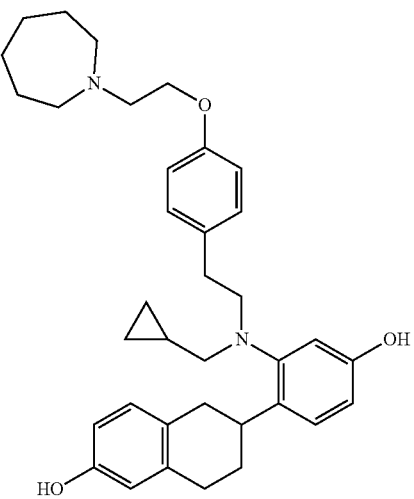 [SMILES: Oc1ccc2c(c1)CCC(c1ccc(O)cc1N(CCc1ccc(OCCN3CCCCCC3)cc1)CC1CC1)C2]

Synthesized from 4-{2-{cyclopropylmethyl[5-methoxy-2-(6-methoxy-1,2,3,4-tetrahydronaphthalen-2-yl)phenyl]amino}ethyl}phenol and 1-(2-chloroethyl)azepane hydrochloride according to an analogous synthetic method to Preparation Example 40, {2-[4-(2-azepan-1-ylethoxy)phenyl]ethyl}cyclopropylmethyl[5-methoxy-2-(6-methoxy-1,2,3,4-tetrahydronaphthalen-2-yl)phenyl]amine (392 mg) was used according to an analogous synthetic method to Example 111 to provide the title compound (188 mg).

$^1$H-NMR (400 MHz, CDCl$_3$); δ (ppm): 0.02-0.06 (m, 2H), 0.37-0.42 (m, 2H), 0.82-0.88 (m, 1H), 1.58-1.82 (m, 12H), 2.57-2.68 (m, 4H), 2.76-2.94 (m, 8H), 3.02-3.12 (m, 2H), 3.16-3.24 (m, 1H), 3.78-3.86 (m, 2H), 6.42-6.46 (m, 3H), 6.58-6.63 (m, 2H), 6.78 (s, 1H), 6.82 (d, 1H), 6.96-6.98 (m, 2H), 7.06 (d, 1H).

ESI-Mass; 555 [M$^+$+H]

Example 396

6-{2-{Cyclopropylmethyl {2-[4-(2-pyrrolidin-1-ylethoxy)phenyl]ethyl}amino}-4-hydroxyphenyl}-5,6,7,8-tetrahydronaphthalen-2-ol

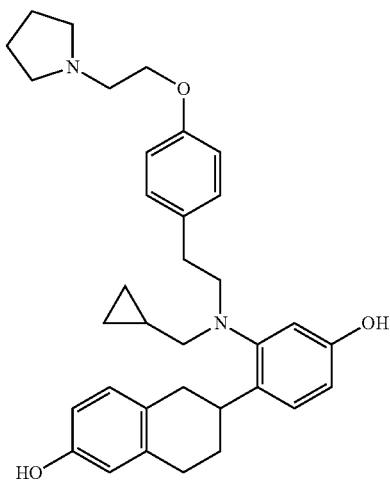 [SMILES: Oc1ccc2c(c1)CCC(c1ccc(O)cc1N(CCc1ccc(OCCN3CCCC3)cc1)CC1CC1)C2]

Synthesized from 4-{2-{cyclopropylmethyl[5-methoxy-2-(6-methoxy-1,2,3,4-tetrahydronaphthalen-2-yl)phenyl]amino}ethyl}phenol and 1-(2-chloroethyl)pyrrolidine hydrochloride according to an analogous synthetic method to Preparation Example 40, cyclopropylmethyl[5-methoxy-2-(6-methoxy-1,2,3,4-tetrahydronaphthalen-2-yl)phenyl]{2-[4-(2-pyrrolidin-1-ylethoxy)phenyl]ethyl}amine (284 mg) was used according to an analogous synthetic method to Example 111 to provide the title compound (241 mg).

$^1$H-NMR (400 MHz, CDCl$_3$); δ (ppm): 0.02-0.06 (m, 2H), 0.37-0.42 (m, 2H), 0.78-0.88 (m, 1H), 1.50-1.62 (m, 6H), 2.52-2.90 (m, 14H), 2.96-3.06 (m, 3H), 3.74-3.84 (m, 2H), 6.36-6.40 (m, 3H), 6.68-6.62 (m, 2H), 6.78-6.82 (m, 2H), 6.96-7.00 (m, 2H), 7.08 (d, 1H).

ESI-Mass; 527 [M$^+$+H]

Example 397

[2-(4-Benzyloxyphenyl)ethyl][2-(6-methoxy-1,2,3,4-tetrahydronaphthalen-2-yl)phenyl]amine

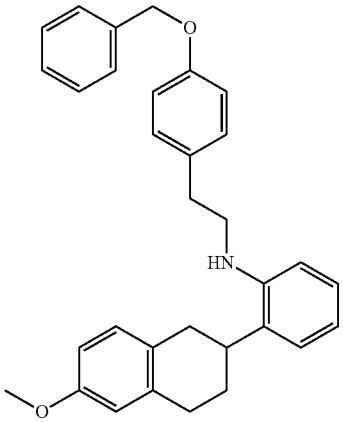 [SMILES: COc1ccc2c(c1)CCC(c1ccccc1NCCc1ccc(OCc3ccccc3)cc1)C2]

Synthesized from 4-benzyloxyphenylacetyl chloride (2.3 g) and 2-(6-methoxy-1,2,3,4-tetrahydronaphthalen-2-yl)phenylamine (1.5 g) according to an analogous synthetic method to Example 152, the title compound (1.0 g) was obtained.

$^1$H-NMR (400 MHz, CDCl$_3$); δ (ppm): 1.81-1.92 (m, 1H), 1.93-2.01 (m, 1H), 2.63-2.73 (m, 2H), 2.78-2.89 (m, 3H), 2.90 (t, 2H), 3.36-3.44 (m, 2H), 3.72 (brs, 1H), 3.77 (s, 3H), 5.00 (s, 2H), 6.66 (d, 1H), 6.69 (dd, 1H), 6.71-6.78 (m, 2H), 6.86 (d, 2H), 6.95 (d, 1H), 7.09-7.13 (m, 3H), 7.16 (dt, 1H), 7.30-7.45 (m, 5H).

Example 398

4-{2-{Ethyl[2-(6-methoxy-1,2,3,4-tetrahydronaphthalen-2-yl)phenyl]amino}ethyl}phenol

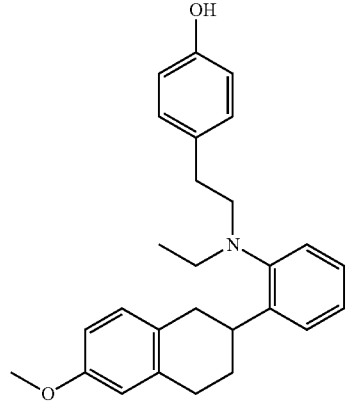 [SMILES: CCN(CCc1ccc(O)cc1)c1ccccc1C1CCc2cc(OC)ccc2C1]

Synthesized from [2-(4-benzyloxyphenyl)ethyl][2-(6-methoxy-1,2,3,4-tetrahydronaphthalen-2-yl)phenyl]amine according to an analogous synthetic method to Example 36, [2-(4-benzyloxyphenyl)ethyl][2-(6-methoxy-1,2,3,4-tetrahydronaphthalen-2-yl)phenyl]amine (976 mg) was used according to an analogous synthetic method to Example 22 to provide the title compound (835 mg).

$^1$H-NMR (400 MHz, DMSO-d$_6$); δ (ppm): 0.87 (t, 3H), 1.69-1.86 (m, 2H), 2.42-2.50 (m, 2H), 2.64-2.88 (m, 4H), 2.93 (q, 2H), 3.03 (t, 2H), 3.50-3.58 (m, 1H), 3.69 (s, 3H), 6.57 (d, 2H), 6.63-6.68 (m, 2H), 6.87 (d, 2H), 6.94 (d, 1H), 7.09 (dt, 1H), 7.19 (dt, 1H), 7.24 (dd, 1H), 7.29 (dd, 1H), 9.10 (s, 1H).

Example 399

6-{2-{Ethyl{2-[4-(2-pyrrolidin-1-ylethoxy)phenyl]ethyl}amino}phenyl}-5,6,7,8-tetrahydronaphthalen-2-ol

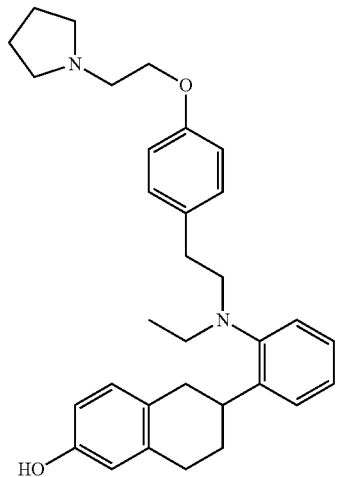 [SMILES: CCN(CCc1ccc(OCCN2CCCC2)cc1)c1ccccc1C1CCc2cc(O)ccc2C1]

Synthesized from 4-{2-{ethyl[2-(6-methoxy-1,2,3,4-tetrahydronaphthalen-2-yl)phenyl]amino}ethyl}phenol and 1-(2-chloroethyl)pyrrolidine hydrochloride according to an analogous synthetic method to Preparation Example 40, ethyl [2-(6-methoxy-1,2,3,4-tetrahydronaphthalen-2-yl)phenyl]{2-[4-(2-pyrrolidin-1-ylethoxy)phenyl]ethyl}amine (230 mg) was used according to an analogous synthetic method to Example 111 to provide the title compound (116 mg).

$^1$H-NMR (400 MHz, DMSO-d$_6$); δ (ppm): 0.86 (t, 3H), 1.60-1.82 (m, 6H), 2.43-2.75 (m, 12H), 2.93 (q, 2H), 3.06 (t, 2H), 3.41-3.50 (m, 1H), 3.93 (t, 2H), 6.45-6.51 (m, 2H), 6.71 (d, 2H), 6.80 (d, 1H), 6.98 (d, 2H), 7.08 (dt, 1H), 7.18 (dt, 1H), 7.23 (dd, 1H), 7.27 (dd, 1H), 9.01 (s, 1H).

ESI-Mass; 485 [M$^+$+H]

Example 400

6-{2-{Ethyl{2-[4-(2-piperidin-1-ylethoxy)phenyl]ethyl}amino}phenyl}-5,6,7,8-tetrahydronaphthalen-2-ol

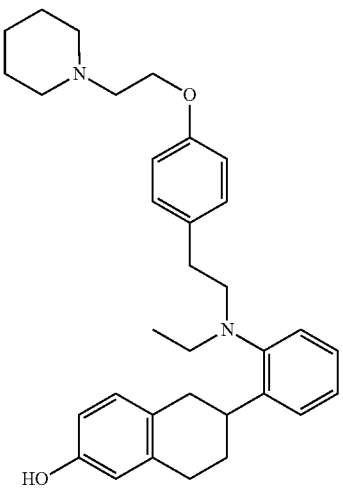 [SMILES: CCN(CCc1ccc(OCCN2CCCCC2)cc1)c1ccccc1C1CCc2cc(O)ccc2C1]

Synthesized from 4-{2-{ethyl[2-(6-methoxy-1,2,3,4-tetrahydronaphthalen-2-yl)phenyl]amino}ethyl}phenol and 1-(2-chloroethyl)piperidine hydrochloride according to an analogous synthetic method to Preparation Example 40, ethyl [2-(6-methoxy-1,2,3,4-tetrahydronaphthalen-2-yl)phenyl]{2-[4-(2-piperidin-1-ylethoxy)phenyl]ethyl}amine (308 mg) was used according to an analogous synthetic method to Example 111 to provide the title compound (260 mg).

$^1$H-NMR (400 MHz, DMSO-d$_6$); δ (ppm): 0.86 (t, 3H), 1.31-1.39 (m, 2H), 1.42-1.50 (m, 4H), 1.62-1.82 (m, 2H), 2.33-2.44 (m, 4H), 2.48-2.76 (m, 8H), 2.93 (q, 2H), 3.06 (t, 2H), 3.41-3.50 (m, 1H), 3.93 (t, 2H), 6.45-6.51 (m, 2H), 6.72 (d, 2H), 6.80 (d, 1H), 6.98 (d, 2H), 7.08 (dt, 1H), 7.18 (dt, 1H), 7.23 (dd, 1H), 7.28 (dd, 1H), 9.01 (s, 1H).

ESI-Mass; 499 [M$^+$+H]

Example 401

6-{2-{{2-[4-(2-Azepan-1-ylethoxy)phenyl]ethyl}ethylamino}phenyl}-5,6,7,8-tetrahydronaphthalen-2-ol

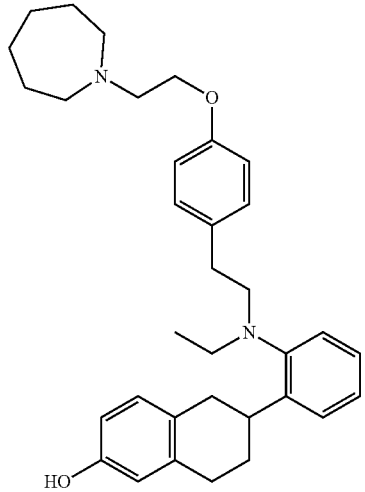 [SMILES: CCN(CCc1ccc(OCCN2CCCCCC2)cc1)c1ccccc1C1CCc2cc(O)ccc2C1]

Synthesized from 4-{2-{ethyl[2-(6-methoxy-1,2,3,4-tetrahydronaphthalen-2-yl)phenyl]amino}ethyl}phenol and 1-(2-chloroethyl)azepane hydrochloride according to an analogous synthetic method to Preparation Example 40, {2-[4-(2-azepan-1-ylethoxy)phenyl]ethyl}ethyl[2-(6-methoxy-1,2,3,4-tetrahydronaphthalen-2-yl)phenyl]amine (298 mg) was used according to an analogous synthetic method to Example 111 to provide the title compound (255 mg).

$^1$H-NMR (400 MHz, DMSO-d$_6$); δ (ppm): 0.86 (t, 3H), 1.47-1.59 (m, 8H), 1.62-1.82 (m, 2H), 2.46-2.53 (m, 2H), 2.54-2.72 (m, 8H), 2.78 (t, 2H), 2.93 (q, 2H), 3.06 (t, 2H), 3.41-3.51 (m, 1H), 3.90 (t, 2H), 6.45-6.51 (m, 2H), 6.72 (d, 2H), 6.80 (d, 1H), 6.97 (d, 2H), 7.08 (dt, 1H), 7.18 (dt, 1H), 7.23 (dd, 1H), 7.28 (dd, 1H), 9.00 (s, 1H).

ESI-Mass; 513 [M$^+$+H]

Preparation Example 153

Pivalic acid 6-{2-[ethyl(5-hydroxypyridine-2-carbonyl)amino]-4-methoxyphenyl}-5,6,7,8-tetrahydronaphthalen-2-yl ester

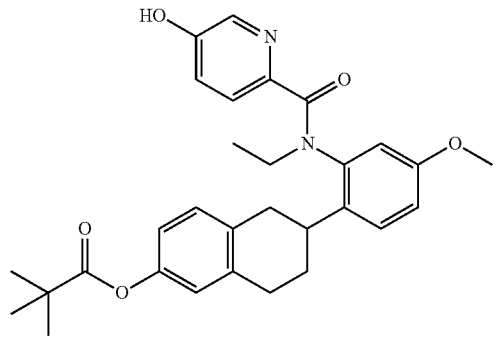

Synthesized from 6-(2-ethylamino-4-methoxyphenyl)-5,6,7,8-tetrahydronaphthalen-2-yl ester and 5-benzyloxypyridine-2-carboxylic acid according to an analogous synthetic method to Example 152, pivalic acid 6-{2-[(5-benzyloxypyridine-2-carbonyl)ethylamino]-4-methoxyphenyl}-5,6,7,8-tetrahydronaphthalen-2-yl ester (163 mg) was used according to an analogous synthetic method to Example 22 to provide the title compound (124 mg).

$^1$H-NMR (400 MHz, DMSO-$d_6$); δ (ppm): 1.06-1.15 (m, 3H), 1.29 (s, 9H), 1.56-1.86 (m, 2H), 2.58-3.02 (m, 5H), 3.44-3.62 (m, 1H), 3.66 (s, 1.5H), 3.70 (s, 1.5H), 3.86-4.00 (m, 1H), 6.62 (d, 0.5H), 6.71 (d, 0.5H), 6.76-6.82 (m, 3H), 6.92 (d, 0.5H), 7.01-7.07 (m, 1.5H), 7.17 (d, 0.5H), 7.21 (d, 0.5H), 7.32 (d, 0.5H), 7.41 (d, 0.5H), 7.73 (d, 0.5H), 7.76 (d, 0.5H), 10.28 (brs, 1H).

Example 402

6-{2-{[5-(2-Dimethylaminoethoxy)pyridin-2-ylmethyl]ethylamino}-4-methoxyphenyl}-5,6,7,8-tetrahydronaphthalen-2-ol

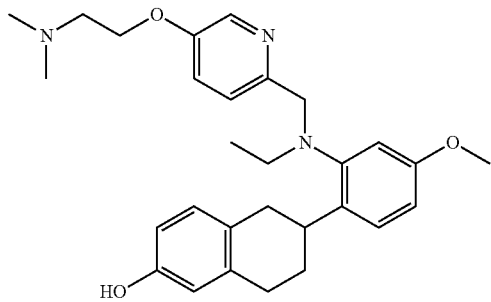

Synthesized from pivalic acid 6-{2-[ethyl(5-hydroxypyridine-2-carbonyl)amino]-4-methoxyphenyl}-5,6,7,8-tetrahydronaphthalen-2-yl ester (25 mg) and 2-chloro-N,N-dimethylacetamide (12 mg) following the synthetic method of Example 404 described below and purified by LC-MS, the title compound (24 mg) was obtained.

ESI-Mass; 476 [M$^+$+H]

Example 403

6-{2-{Ethyl[5-(2-piperidin-1-ylethoxy)pyridin-2-ylmethyl]amino}-4-methoxyphenyl}-5,6,7,8-tetrahydronaphthalen-2-ol

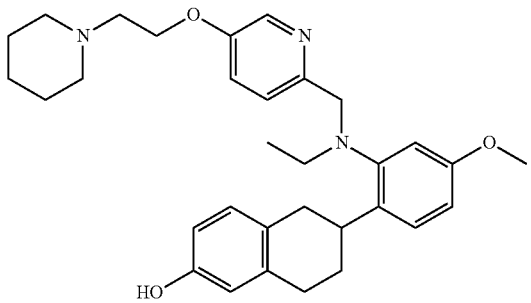 [SMILES: CCN(Cc1ccc(OCCN2CCCCC2)cn1)c1cc(OC)ccc1C1CCc2cc(O)ccc2C1]

Synthesized from pivalic acid 6-{2-[ethyl(5-hydroxypyridine-2-carbonyl)amino]-4-methoxyphenyl}-5,6,7,8-tetrahydronaphthalen-2-yl ester (25 mg) and 2-chloro-1-piperidin-1-ylethanone (16 mg) according to an analogous synthetic method to Example 404 described below and purified by LC-MS, the title compound (12 mg) was obtained.

ESI-Mass; 516 [M$^+$+H]

Preparation Example 154

Pivalic Acid 6-{2-[(4-acetoxy-3-fluorobenzoyl)isopropylamino]-4-methoxyphenyl}-5,6,7,8-tetrahydronaphthalen-2-yl ester

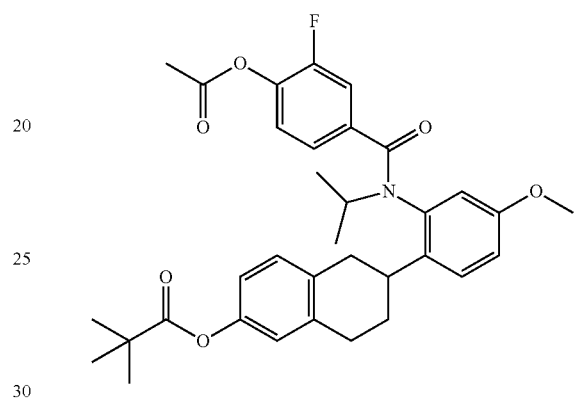

To a solution of 4-acetoxy-3-fluorobenzoic acid (451 mg) in tetrahydrofuran (8 ml) was added N,N-dimethylformamide (3 drops), and oxalyl chloride (0.24 ml) was added dropwise thereto. The solution was stirred for 1 hour at room temperature, then the solvent was evaporated in vacuo. Synthesized from the resulting 4-acetoxy-3-fluorobenzoyl chloride (583 mg) and pivalic acid 6-(2-isopropylamino-4-methoxyphenyl)-5,6,7,8-tetrahydronaphthalen-2-yl ester (600 mg) according to an analogous synthetic method to Preparation Example 86, the title compound (1.1 g) was obtained.

$^1$H-NMR (400 MHz, CDCl$_3$); δ (ppm): 0.81-0.91 (m, 0.5H), 1.04-1.14 (m, 3H), 1.35 (s, 9H), 1.36-1.52 (m, 4.5H), 1.70-1.89 (m, 1H), 2.26-2.40 (m, 0.5H), 2.63-2.91 (m, 4H), 3.71 (s, 3H), 3.85 (s, 3H), 4.82-4.96 (m, 0.5H), 6.74-7.37 (m, 8H), 7.91-7.99 (m, 1H).

Preparation Example 155

Pivalic Acid 6-{2-[(3-fluoro-4-hydroxybenzoyl)isopropylamino]-4-methoxyphenyl}-5,6,7,8-tetrahydronaphthalen-2-yl ester

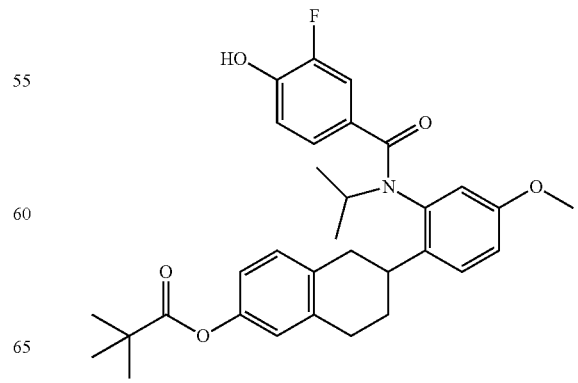

To a solution of pivalic acid 6-{2-[(4-acetoxy-3-fluorobenzoyl)isopropylamino]-4-methoxyphenyl}-5,6,7,8-tetrahydronaphthalen-2-yl ester (1.1 g) in methanol (18 ml) were sequentially added water (2 ml) and potassium carbonate (321 mg), and the solution was stirred for 1 hour at room temperature. Water was added thereto, the solution was extracted with ethyl acetate, then washed with brine, dried over anhydrous magnesium sulfate, and then the solvent was evaporated in vacuo. The residue was purified by silica gel column chromatography (hexane-ethyl acetate system) to provide the title compound (637 mg).

$^1$H-NMR (400 MHz, CDCl$_3$); δ (ppm): 0.34-0.48 (m, 0.5H), 1.09 (t, 3H), 1.35 (s, 9H), 1.36-1.55 (m, 4.5H), 1.71-1.91 (m, 1H), 2.31-2.44 (m, 0.5H), 2.56-2.94 (m, 4H), 3.83-3.88 (m, 3H), 4.79-4.94 (m, 1H), 5.52-5.60 (m, 0.5H), 6.68-7.16 (m, 9H).

Preparation Example 156

Pivalic Acid (R)-6-{2-[(3-fluoro-4-hydroxybenzoyl)isopropylamino]-4-methoxyphenyl}-5,6,7,8-tetrahydronaphthalen-2-yl ester

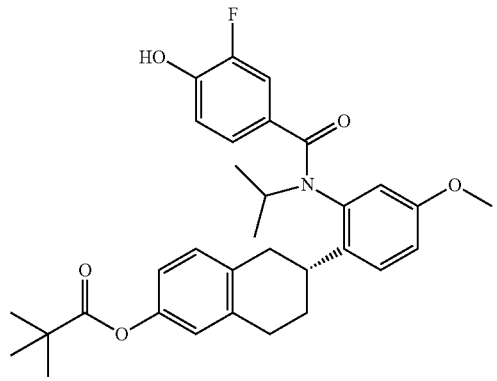 [SMILES: COc1ccc([C@@H]2CCc3cc(OC(=O)C(C)(C)C)ccc3C2)c(N(C(=O)c2ccc(O)c(F)c2)C(C)C)c1]

Synthesized from pivalic acid (R)-6-(2-isopropylamino-4-methoxyphenyl)-5,6,7,8-tetrahydronaphthalen-2-yl ester (152 mg) according to an analogous synthetic methods to the above-mentioned Preparation Example 154 and the above-mentioned Preparation Example 155, the title compound (184 mg) was obtained.

Preparation Example 157

Pivalic acid 6-{2-[(4-hydroxybenzoyl)isopropylamino]-4-methoxyphenyl}-5,6,7,8-tetrahydronaphthalen-2-yl ester

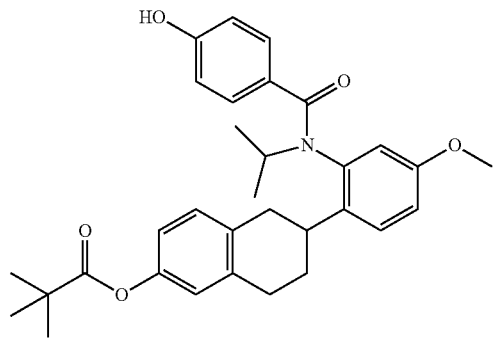 [SMILES: COc1ccc(C2CCc3cc(OC(=O)C(C)(C)C)ccc3C2)c(N(C(=O)c2ccc(O)cc2)C(C)C)c1]

Synthesized from pivalic acid 6-(2-isopropylamino-4-methoxyphenyl)-5,6,7,8-tetrahydronaphthalen-2-yl ester (270 mg) according to an analogous synthetic methods to the above-mentioned Preparation Example 154 and the above-mentioned Preparation Example 155, the title compound (266 mg) was obtained.

$^1$H-NMR (400 MHz, CDCl$_3$); δ (ppm): 1.01-1.10 (m, 3H), 1.36 (s, 9H), 1.41-1.48 (m, 4H), 1.80-1.91 (m, 1H), 2.21-2.30 (m, 1H), 2.58-2.89 (m, 5H), 3.82 (s, 3H), 5.84-5.90 (m, 1H), 6.50-6.60 (m, 2H), 6.70-6.80 (m, 2H), 6.82-6.90 (m, 2H), 6.98-7.00 (m, 1H), 7.01-7.10 (m, 1H), 7.12 (d, 1H), 7.13-7.21 (m, 1H).

Preparation Example 158

Pivalic Acid 6-{2-[ethyl(4-hydroxybenzoyl)amino]-4-methoxyphenyl}-5,6,7,8-tetrahydronaphthalen-2-yl Ester

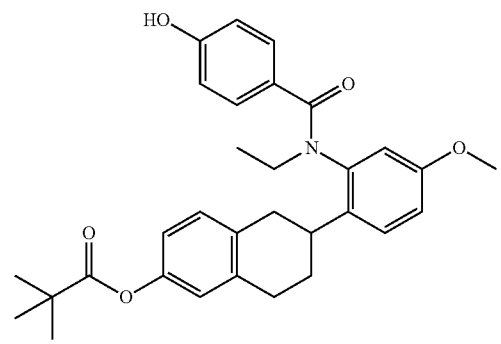 [SMILES: CCN(C(=O)c1ccc(O)cc1)c1cc(OC)ccc1C1CCc2cc(OC(=O)C(C)(C)C)ccc2C1]

Synthesized from pivalic acid 6-(2-ethylamino-4-methoxyphenyl)-5,6,7,8-tetrahydronaphthalen-2-yl ester and 4-acetoxybenzoic acid according to an analogous synthetic method to Preparation Example 154, pivalic acid 6-{2-[(4-acetoxybenzoyl)ethylamino]-4-methoxyphenyl}-5,6,7,8-tetrahydronaphthalen-2-yl ester (3.2 g) was used according to an analogous synthetic method to Preparation Example 155 to provide the title compound (2.1 g).

$^1$H-NMR (400 MHz, CDCl$_3$); δ (ppm): 0.57-0.66 (m, 0.5H), 1.16-1.27 (m, 3H), 1.35 (s, 9H), 1.39-1.90 (m, 2H), 2.38-2.48 (m, 0.5H), 2.57-2.90 (m, 4H), 3.76-4.03 (m, 5H), 5.97-6.05 (m, 1H), 6.54 (d, 2H), 6.71-7.22 (m, 8H).

Preparation Example 159

Pivalic Acid (R)- and (S)-6-{2-[ethyl(4-hydroxybenzoyl)amino]-4-methoxyphenyl}-5,6,7,8-tetrahydronaphthalen-2-yl Ester

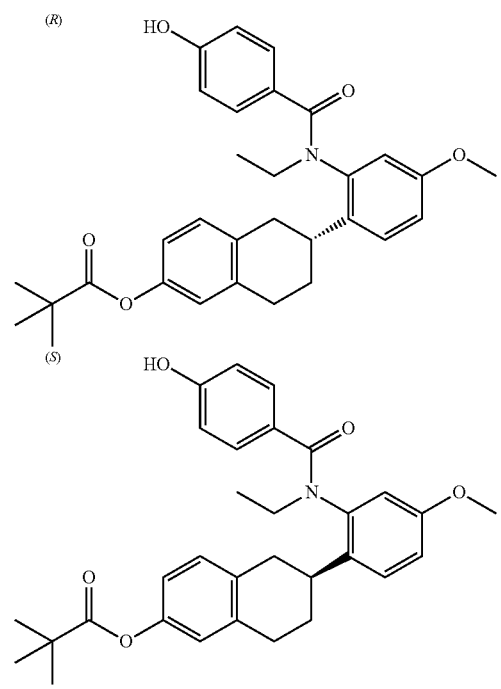

Optical resolution was carried out according to Example 188 described above to provide pivalic acid (R)-6-{2-[ethyl(4-hydroxybenzoyl)amino]-4-methoxyphenyl}-5,6,7,8-tetrahydronaphthalen-2-yl ester exhibiting a short retention time and pivalic acid (S)-6-[2-{ethyl(4-hydroxybenzoyl)amino]-4-methoxyphenyl}-5,6,7,8-tetrahydronaphthalen-2-yl ester exhibiting a long retention time.

Pivalic acid (R)-6-{2-[ethyl(4-hydroxybenzoyl)amino]-4-methoxyphenyl}-5,6,7,8-tetrahydronaphthalen-2-yl ester:
retention time: 8.5 minutes Pivalic acid (S)-6-{2-[ethyl(4-hydroxybenzoyl)amino]-4-methoxyphenyl}-5,6,7,8-tetrahydronaphthalen-2-yl ester
retention time: 14.6 minutes Preparation Example 160

Pivalic Acid 6-{2-[ethyl(3-fluoro-4-hydroxybenzoyl)amino]-4-methoxyphenyl}-5,6,7,8-tetrahydronaphthalen-2-yl ester

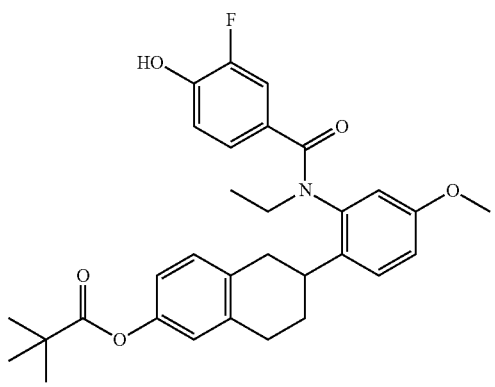

Synthesized from pivalic acid 6-(2-ethylamino-4-methoxyphenyl)-5,6,7,8-tetrahydronaphthalen-2-yl ester and 4-acetoxy-3-fluorobenzoic acid according to Preparation Example 154 mentioned above, pivalic acid 6-{2-[(4-acetoxy-3-fluorobenzoyl)ethylamino]-4-methoxyphenyl}-5,6,7,8-tetrahydronaphthalen-2-yl ester (3.8 g) was used according to an analogous synthetic method to Preparation Example 155 to provide the title compound (2.3 g).

$^1$H-NMR (400 MHz, CDCl$_3$); δ (ppm): 0.70-0.79 (m, 0.5H), 1.18-1.27 (m, 3H), 1.35 (s, 9H), 1.50-1.91 (m, 2H), 2.48-2.58 (m, 0.5H), 2.62-2.91 (m, 4H), 3.78-3.95 (m, 5H), 5.44-5.51 (m, 1H), 6.71-7.14 (m, 9H).

Preparation Example 161

Pivalic Acid (R)- and (S)-6-{2-[ethyl(3-fluoro-4-hydroxybenzoyl)amino]-4-methoxyphenyl}-5,6,7,8-tetrahydronaphthalen-2-yl Ester (R)

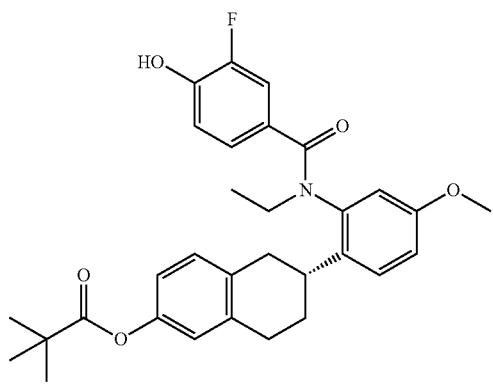 [SMILES: CCN(C(=O)c1ccc(O)c(F)c1)c1cc(OC)ccc1C1CCc2cc(OC(=O)C(C)(C)C)ccc2C1]

(S)

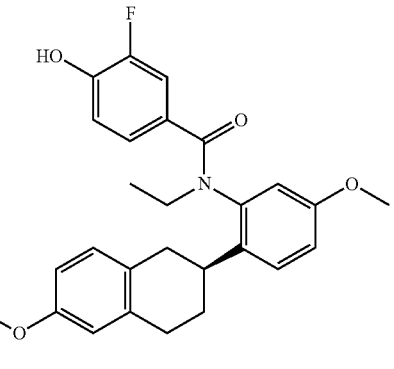

Optical resolution was carried out according to Example 188 described above to provide pivalic acid (R)-6-{2-[ethyl(3-fluoro-4-hydroxybenzoyl)amino]-4-methoxyphenyl}-5,6,7,8-tetrahydronaphthalen-2-yl ester exhibiting a short retention time and pivalic acid (S)-6-{2-[ethyl(3-fluoro-4-hydroxybenzoyl)amino]-4-methoxyphenyl}-5,6,7,8-tetrahydronaphthalen-2-yl ester exhibiting a long retention time.

Pivalic acid (R)-6-{2-[ethyl(3-fluoro-4-hydroxybenzoyl)amino]-4-methoxyphenyl}-5,6,7,8-tetrahydronaphthalen-2-yl ester:
retention time: 8.8 minutes Pivalic acid (S)-6-{2-[ethyl(3-fluoro-4-hydroxybenzoyl)amino]-4-methoxyphenyl}-5,6,7,8-tetrahydronaphthalen-2-yl ester:
retention time: 13.5 minutes Preparation Example 162

Pivalic Acid 6-{2-[(4-hydroxybenzoyl)methylamino]-4-methoxyphenyl}-5,6,7,8-tetrahydronaphthalen-2-yl Ester

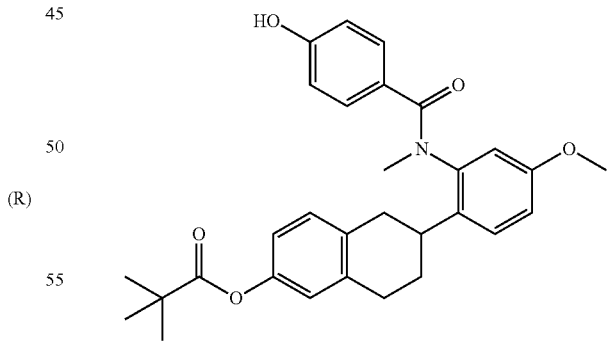

Synthesized from pivalic acid 6-(4-methoxy-2-methylaminophenyl)-5,6,7,8-tetrahydronaphthalen-2-yl ester (400 mg) according to an analogous synthetic methods to the above-mentioned Preparation Example 154 and the above-mentioned Preparation Example 155, the title compound (510 mg) was obtained.

$^1$H-NMR (400 MHz, CDCl$_3$); δ (ppm): 1.35 (s, 9H), 1.52-2.01 (m, 2H), 2.50-2.95 (m, 5H), 3.38 (s, 1.5H), 3.41 (s, 1.5H), 3.76 (s, 1.5H), 3.79 (s, 1.5H), 6.48-6.54 (m, 2H), 6.71-6.86 (m, 5H), 6.94-7.18 (m, 3H).

Preparation Example 163

Pivalic Acid 6-{2-[(3-fluoro-4-hydroxybenzoyl)methylamino]-4-methoxyphenyl}-5,6,7,8-tetrahydronaphthalen-2-yl Ester

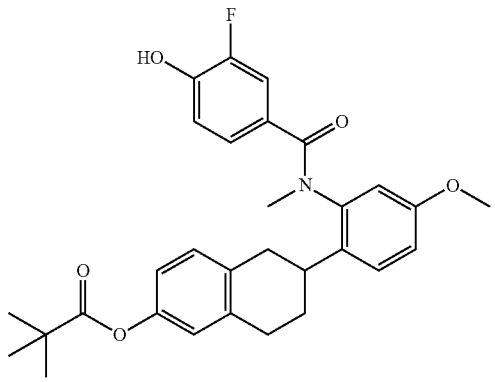

Synthesized from pivalic acid 6-(4-methoxy-2-methylaminophenyl)-5,6,7,8-tetrahydronaphthalen-2-yl ester (400 mg) according to an analogous synthetic methods to the above-mentioned Preparation Example 154 and the above-mentioned Preparation Example 155, the title compound (610 mg) was obtained.

$^1$H-NMR (400 MHz, CDCl$_3$); δ (ppm): 1.35 (s, 9H), 1.50-2.16 (m, 2H), 2.58-2.90 (m, 5H), 3.37 (s, 1.5H), 3.40 (s, 1.5H), 3.77 (s, 1.5H), 3.80 (s, 1.5H), 5.61 (brs, 1H), 6.68-6.80 (m, 2H), 6.81-6.88 (m, 2H), 6.95-7.02 (m, 2H), 7.04-7.12 (m, 2H).

Preparation Example 164

Pivalic Acid (R)- and (S)-6-{2-[(3-fluoro-4-hydroxybenzoyl)methylamino]-4-methoxyphenyl}-5,6,7,8-tetrahydronaphthalen-2-yl Ester

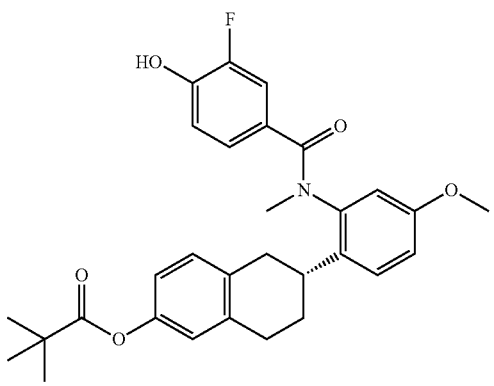 [SMILES: COc1ccc(C2CCc3cc(OC(=O)C(C)(C)C)ccc3C2)c(N(C)C(=O)c2ccc(O)c(F)c2)c1]
(R)

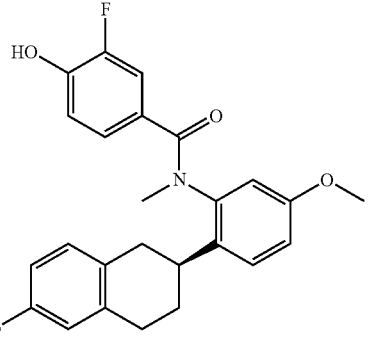
(S)

Optical resolution was carried out according to Example 188 described above to provide pivalic acid (R)-6-{2-[(3-fluoro-4-hydroxybenzoyl)methylamino]-4-methoxyphenyl}-5,6,7,8-tetrahydronaphthalen-2-yl ester exhibiting a short retention time and pivalic acid (S)-6-{2-[(3-fluoro-4-hydroxybenzoyl)methylamino]-4-methoxyphenyl}-5,6,7,8-tetrahydronaphthalen-2-yl ester exhibiting a long retention time.

Pivalic acid (R)-6-{2-[(3-fluoro-4-hydroxybenzoyl)methylamino]-4-methoxyphenyl}-5,6,7,8-tetrahydronaphthalen-2-yl ester:
retention time: 9.0 minutes Pivalic acid (S)-6-{2-[(3-fluoro-4-hydroxybenzoyl)methylamino]-4-methoxyphenyl}-5,6,7,8-tetrahydronaphthalen-2-yl ester:
retention time: 11.7 minutes

Preparation Example 165

Pivalic Acid 6-{2-[(4-hydroxybenzoyl)propylamino]-4-methoxyphenyl}-5,6,7,8-tetrahydronaphthalen-2-yl ester

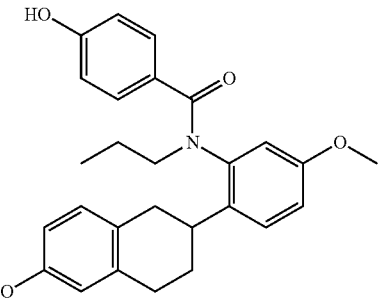

Synthesized from pivalic acid 6-(4-methoxy-2-propylaminophenyl)-5,6,7,8-tetrahydronaphthalen-2-yl ester (120 mg) according to an analogous synthetic methods to the above-mentioned Preparation Example 154 and the above-mentioned Preparation Example 155, the title compound (157 mg) was obtained.

$^1$H-NMR (400 MHz, CDCl$_3$); δ (ppm): 0.84-0.99 (m, 3H), 1.36 (s, 9H), 1.48-1.90 (m, 4H), 2.60-2.91 (m, 5H), 3.69-3.80 (m, 2H), 3.81 (s, 3H), 6.50-6.58 (m, 2H), 6.71-6.89 (m, 4H), 6.95-7.18 (m, 4H).

Preparation Example 166

Pivalic Acid 6-{2-[ethyl(4-hydroxybenzoyl)amino]phenyl}-5,6,7,8-tetrahydronaphthalen-2-yl Ester

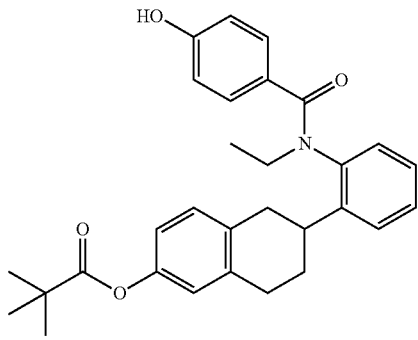 [SMILES: CCN(C(=O)c1ccc(O)cc1)c1ccccc1C1CCc2cc(OC(=O)C(C)(C)C)ccc2C1]

Synthesized from pivalic acid 6-(2-ethylaminophenyl)-5,6,7,8-tetrahydronaphthalen-2-yl ester (1.0 g) according to an analogous synthetic method to the above-mentioned Preparation Example 154 and the above-mentioned Preparation Example 155, the title compound (1.4 g) was obtained.

$^1$H-NMR (400 MHz, CDCl$_3$); δ (ppm): 1.03-1.30 (m, 3H), 1.36 (s, 9H), 1.52-1.90 (m, 2H), 2.04-2.96 (m, 5H), 3.82-3.99 (m, 2H), 6.48-6.54 (m, 2H), 6.62-6.65 (m, 0.5H), 6.71-6.84 (m, 3H), 6.96-7.01 (m, 0.5H), 7.06-7.32 (m, 5H).

Preparation Example 167

Pivalic Acid (R)- and (S)-6-{2-[ethyl(4-hydroxybenzoyl)amino]phenyl}-5,6,7,8-tetrahydronaphthalen-2-yl Ester

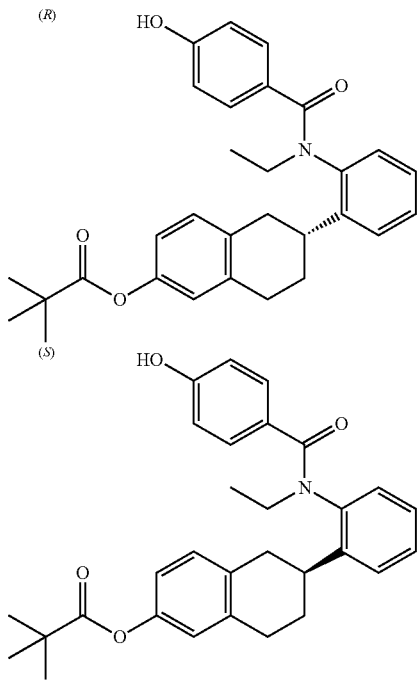

Optical resolution was carried out according to Example 188 described above to provide pivalic acid (R)-6-{2-[ethyl(4-hydroxybenzoyl)amino]phenyl}-5,6,7,8-tetrahydronaphthalen-2-yl ester exhibiting a short retention time and pivalic acid (S)-6-{2-[ethyl(4-hydroxybenzoyl)amino]phenyl}-5,6,7,8-tetrahydronaphthalen-2-yl ester exhibiting a long retention time.

Pivalic acid (R)-6-{2-[ethyl(4-hydroxybenzoyl)amino]phenyl}-5,6,7,8-tetrahydronaphthalen-2-yl ester:
retention time: 8.1 minutes
Pivalic acid (S)-6-{2-[ethyl(4-hydroxybenzoyl)amino]phenyl}-5,6,7,8-tetrahydronaphthalen-2-yl ester:
retention time: 9.5 minutes

Preparation Example 168

Pivalic Acid (R)-6-{2-[ethyl(4-hydroxybenzoyl)amino]-4,5-dimethoxyphenyl}-5,6,7,8-tetrahydronaphthalen-2-yl Ester

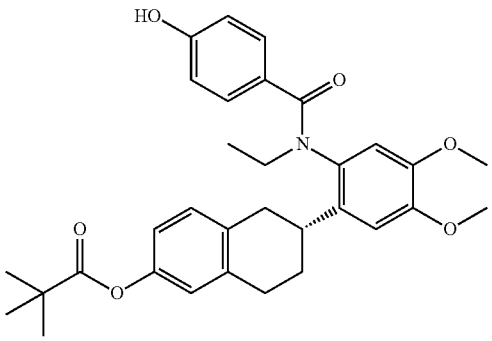 [SMILES: CCN(C(=O)c1ccc(O)cc1)c1cc(OC)c(OC)cc1[C@@H]1CCc2cc(OC(=O)C(C)(C)C)ccc2C1]

Synthesized from pivalic acid (R)-6-(2-ethylamino-4,5-dimethoxyphenyl)-5,6,7,8-tetrahydronaphthalen-2-yl ester and 4-acetoxybenzoic acid according to an analogous synthetic method to Preparation Example 154, pivalic acid (R)-6-{2-[(4-acetoxybenzoyl)ethylamino]-4,5-dimethoxyphenyl}-5,6,7,8-tetrahydronaphthalen-2-yl ester (471 mg) was used according to an analogous synthetic method to Preparation Example 155 to provide the title compound (311 mg).

$^1$H-NMR (400 MHz, CDCl$_3$); δ (ppm): 0.55-0.64 (m, 0.5H), 1.17-1.23 (m, 3H), 1.35 (s, 9H), 1.39-1.91 (m, 2H), 2.35-2.46 (m, 0.5H), 2.60-2.90 (m, 4H), 3.71-3.89 (m, 7H), 3.93-4.07 (m, 1H), 5.96-6.03 (m, 1H), 6.51-6.59 (m, 3H), 6.71-6.78 (m, 3.5H), 6.96-7.00 (m, 0.5H), 7.10-7.19 (m, 2H).

Preparation Example 169

Pivalic Acid (R)-6-{2-[ethyl(3-fluoro-4-hydroxybenzoyl)amino]-4,5-dimethoxyphenyl}-5,6,7,8-tetrahydronaphthalen-2-yl Ester

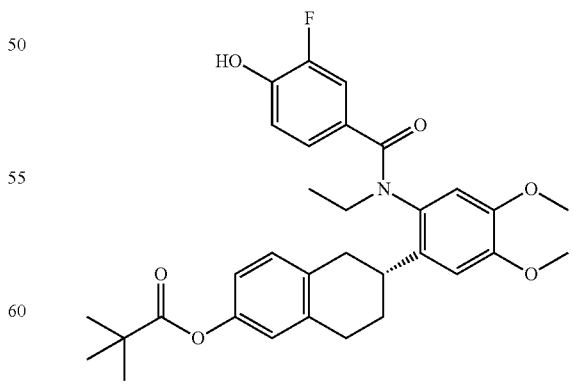

Synthesized from pivalic acid (R)-6-(2-ethylamino-4,5-dimethoxyphenyl)-5,6,7,8-tetrahydronaphthalen-2-yl ester and 4-acetoxy-3-fluorobenzoic acid according to an analogous synthetic method to Preparation Example 154, pivalic acid (R)-6-{2-[(4-acetoxy-3-fluorobenzoyl)ethylamino]-4,5-dimethoxyphenyl}-5,6,7,8-tetrahydronaphthalen-2-yl ester (537 mg) was used according to an analogous synthetic method to Preparation Example 155 to provide the title compound (298 mg).

$^1$H-NMR (400 MHz, CDCl$_3$); δ (ppm): 0.68-0.76 (m, 0.5H), 1.16-1.24 (m, 3H), 1.35 (s, 9H), 1.49-1.93 (m, 2H), 2.45-2.55 (m, 0.5H), 2.61-2.92 (m, 4H), 3.76-3.96 (m, 8H), 5.49-5.57 (m, 1H), 6.59 (s, 1H), 6.65-6.82 (m, 4.5H), 6.93-7.13 (m, 2.5H).

Example 404

6-{2-{[4-(2-Dimethylaminoethoxy)-3-fluorobenzyl]isopropylamino}-4-methoxyphenyl}-5,6,7,8-tetrahydronaphthalen-2-ol

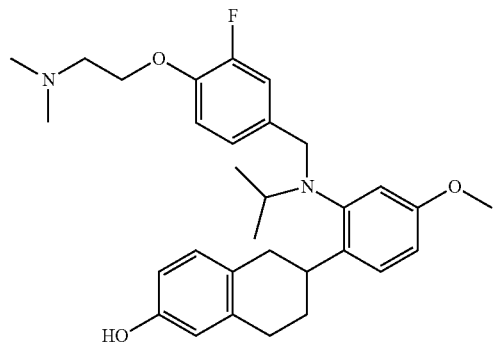

To cesium carbonate (36 mg) and potassium iodide (5.0 mg) were sequentially added a solution of pivalic acid 6-{2-[(3-fluoro-4-hydroxybenzoyl)isopropylamino]-4-methoxyphenyl}-5,6,7,8-tetrahydronaphthalen-2-yl ester (25 mg) in tetrahydrofuran (0.8 ml) and a solution of 2-chloro-N,N-dimethylacetamide (11 mg) in tetrahydrofuran (0.2 ml), and the solution was stirred for 1.5 hours at 60° C. The reaction solution was let to cool, then lithium aluminum hydride-aluminum chloride (1.0 M solution in tetrahydrofuran) (0.57 ml) was added dropwise thereto followed by stirring for 1 hour at room temperature. Tetrahydrofuran and ammonia solution were sequentially added thereto, the solution was filtered through celite pad and concentrated under a nitrogen stream; purified from a solution of the resulting residue in N,N-dimethylformamide by LC-MS, the title compound (9.1 mg) was obtained.

ESI-Mass; 507 [M$^+$+H]

Example 405

6-{2-{[4-(2-Diethylaminoethoxy)-3-fluorobenzyl]isopropylamino}-4-methoxyphenyl}-5,6,7,8-tetrahydronaphthalen-2-ol

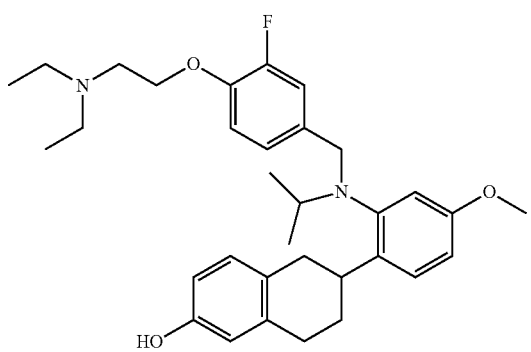 [SMILES: CCN(CC)CCOc1ccc(CN(c2cc(OC)ccc2C2CCc3cc(O)ccc3C2)C(C)C)cc1F]

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-N,N-diethylacetamide (14 mg) according to an analogous synthetic method to Example 404 and purified by LC-MS, the title compound (7.9 mg) was obtained.

ESI-Mass; 535 [M$^+$+H]

Example 406

6-{2-{[4-(2-Azetidin-1-ylethoxy)-3-fluorobenzyl]isopropylamino}-4-methoxyphenyl}-5,6,7,8-tetrahydronaphthalen-2-ol

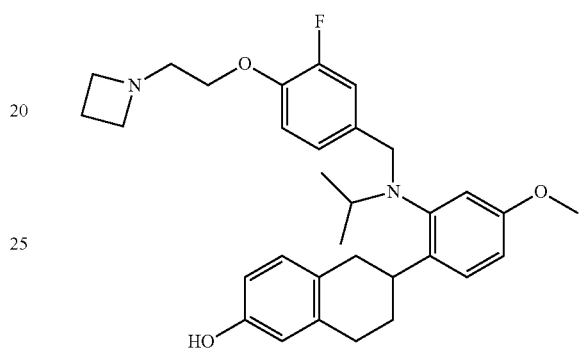

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 1-azetidin-1-yl-2-chloroethanone (13 mg) according to an analogous synthetic method to Example 404 and purified by LC-MS, the title compound (11 mg) was obtained.

ESI-Mass; 519 [M$^+$+H]

Example 407

6-{2-{[3-Fluoro-4-(2-pyrrolidin-1-ylethoxy)benzyl]isopropylamino}-4-methoxyphenyl}-5,6,7,8-tetrahydronaphthalen-2-ol

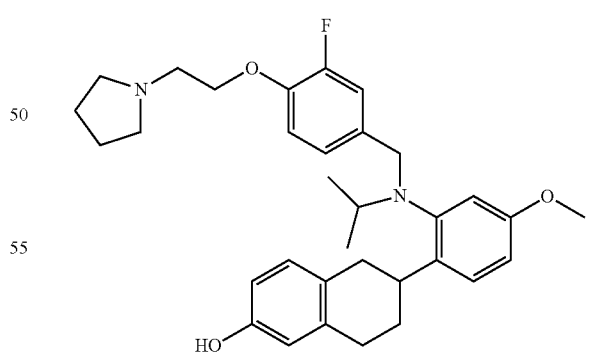

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-1-pyrrolidin-1-ylethanone (14 mg) according to an analogous synthetic method to Example 404 and purified by LC-MS, the title compound (19 mg) was obtained.

ESI-Mass; 533 [M$^+$+H]

Example 408

6-{2-{{3-Fluoro-4-[2-(4-methylpiperidin-1-yl)ethoxy]benzyl}isopropylamino}-4-methoxyphenyl}-5,6,7,8-tetrahydronaphthalen-2-ol

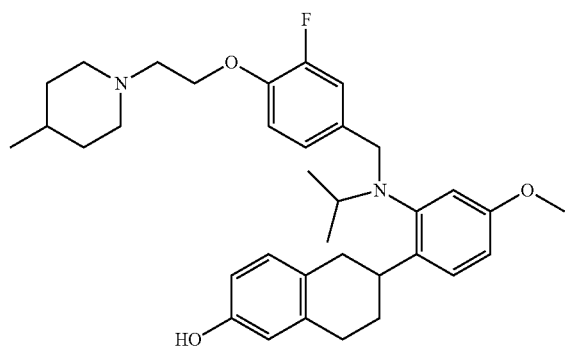

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-1-(4-methylpiperidin-1-yl)ethanone (17 mg) according to an analogous synthetic method to Example 404 and purified by LC-MS, the title compound (4.2 mg) was obtained.

ESI-Mass; 561 [M$^+$+H]

Example 409

6-{2-{[4-(2-Azepan-1-ylethoxy)-3-fluorobenzyl]isopropylamino}-4-methoxyphenyl}-5,6,7,8-tetrahydronaphthalen-2-ol

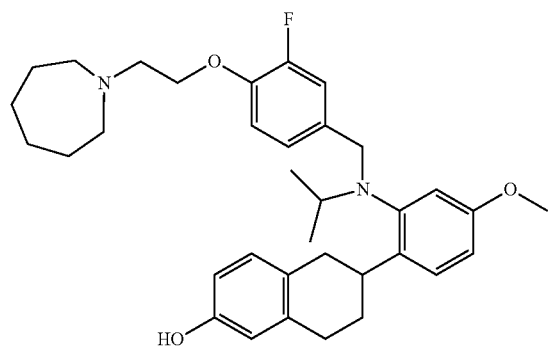 [SMILES: COc1ccc(C2CCc3cc(O)ccc3C2)c(N(Cc2ccc(OCCN3CCCCCC3)c(F)c2)C(C)C)c1]

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 1-azepan-1-yl-2-chloroethanone (17 mg) according to an analogous synthetic method to Example 404 and purified by LC-MS, the title compound (4.2 mg) was obtained.

ESI-Mass; 561 [M$^+$+H]

Example 410

6-{2-{[4-(2-Azocan-1-ylethoxy)-3-fluorobenzyl]isopropylamino}-4-methoxyphenyl}-5,6,7,8-tetrahydronaphthalen-2-ol

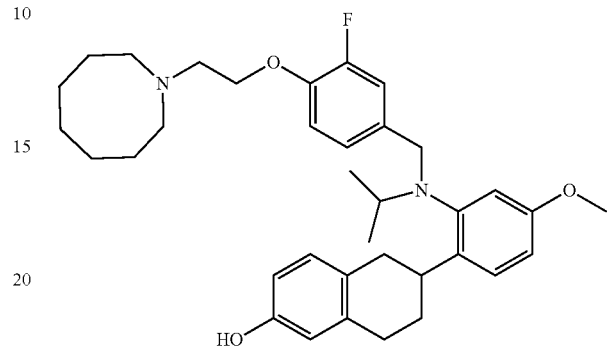

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 1-azocan-1-yl-2-chloroethanone (18 mg) according to an analogous synthetic method to Example 404 and purified by LC-MS, the title compound (9.5 mg) was obtained.

ESI-Mass; 575 [M$^+$+H]

Example 411

6-{2-{[3-Fluoro-4-(2-piperidin-1-ylethoxy)benzyl]isopropylamino}-4-methoxyphenyl}-5,6,7,8-tetrahydronaphthalen-2-ol

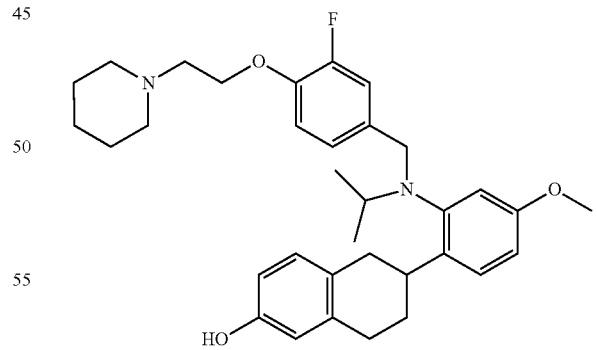

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-1-piperidin-1-ylethanone (15 mg) according to an analogous synthetic method to Example 404 and purified by LC-MS, the title compound (2.9 mg) was obtained.

ESI-Mass; 547 [M$^+$+H]

Example 412

6-{2-{{4-[2-(3-Azabicyclo[3.2.2]non-3-yl)ethoxy]-3-fluorobenzyl}isopropylamino}-4-methoxyphenyl}-5,6,7,8-tetrahydronaphthalen-2-ol

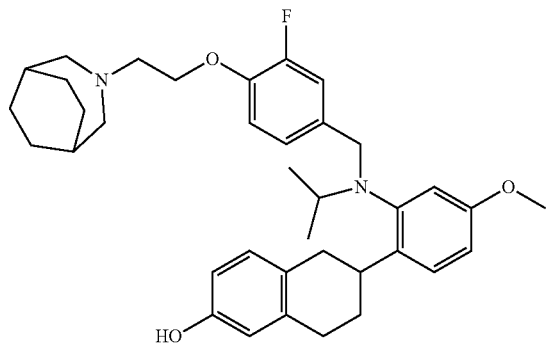 [SMILES: COc1ccc(C2CCc3cc(O)ccc3C2)c(N(Cc2ccc(OCCN3CC4CCC(CC4)C3)c(F)c2)C(C)C)c1]

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 1-(3-azabicyclo[3.2.2]non-3-yl)-2-chloroethanone (19 mg) according to an analogous synthetic method to Example 404 and purified by LC-MS, the title compound (3.3 mg) was obtained.

ESI-Mass; 587 [M$^+$+H]

Example 413

6-{2-{{4-[2-(1,4-Dioxa-8-azaspiro[4.5]dec-8-yl)ethoxy]-3-fluorobenzyl}isopropylamino}-4-methoxyphenyl}-5,6,7,8-tetrahydronaphthalen-2-ol

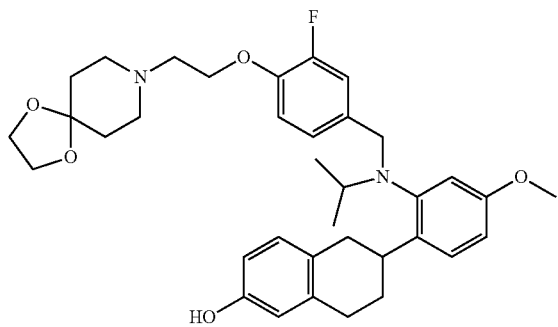 [SMILES: COc1ccc(C2CCc3cc(O)ccc3C2)c(N(Cc2ccc(OCCN3CCC4(CC3)OCCO4)c(F)c2)C(C)C)c1]

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-1-(1,4-dioxa-8-azaspiro[4.5]dec-8-yl)ethanone (21 mg) according to an analogous synthetic method to Example 404 and purified by LC-MS, the title compound (6.2 mg) was obtained.

ESI-Mass; 605 [M$^+$+H]

Example 414

6-{2-{[3-Fluoro-4-(2-morpholin-4-ylethoxy)benzyl]isopropylamino}-4-methoxyphenyl}-5,6,7,8-tetrahydronaphthalen-2-ol

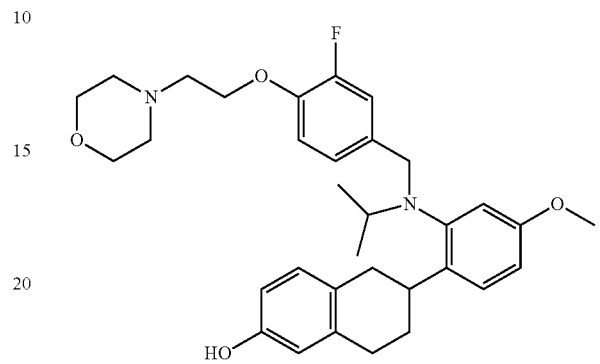

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-1-morpholin-4-ylethanone (15 mg) according to an analogous synthetic method to Example 404 and purified by LC-MS, the title compound (12 mg) was obtained.

ESI-Mass; 549 [M$^+$+H]

Example 415

6-{2-{{4-{2-[Bis(2-methoxyethyl)amino]ethoxy}-3-fluorobenzyl}isopropylamino}-4-methoxyphenyl}-5,6,7,8-tetrahydronaphthalen-2-ol

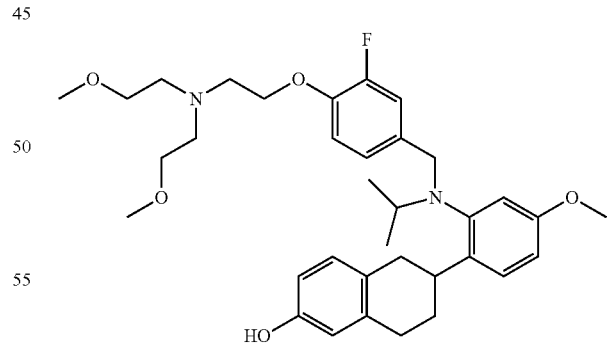

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-N,N-bis(2-methoxyethyl)acetamide (20 mg) according to an analogous synthetic method to Example 404 and purified by LC-MS, the title compound (3.8 mg) was obtained.

ESI-Mass; 595 [M$^+$+H]

Example 416

6-{2-{{3-Fluoro-4-{2-[(2-methoxyethyl)methy-lamino]ethoxy}benzyl}isopropylamino}-4-methoxyphenyl}-5,6,7,8-tetrahydronaphthalen-2-ol

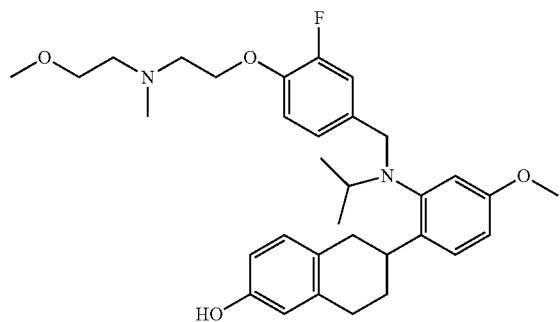

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-N-(2-methoxyethyl)-N-methylacetamide (16 mg) according to an analogous synthetic method to Example 404 and purified by LC-MS, the title compound (1.4 mg) was obtained.

ESI-Mass; 551 [M$^+$+H]

Example 417

6-{2-{{4-[2-(Cyclohexylmethylamino)ethoxy]-3-fluorobenzyl}isopropylamino}-4-methoxyphenyl}-5,6,7,8-tetrahydronaphthalen-2-ol

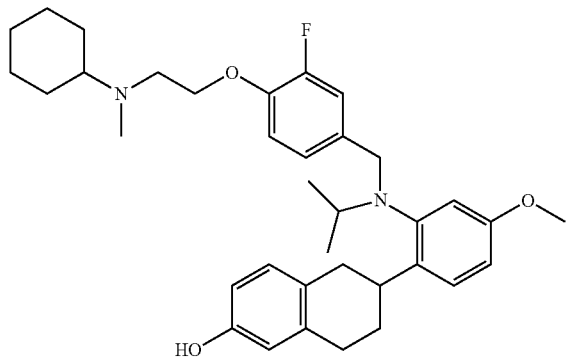 [SMILES: COc1ccc(C2CCc3cc(O)ccc3C2)c(N(Cc2ccc(OCCN(C)C3CCCCC3)c(F)c2)C(C)C)c1]

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 2-chloro-N-cyclohexyl-N-methylacetamide (18 mg) according to an analogous synthetic method to Example 404 and purified by LC-MS, the title compound (7.4 mg) was obtained.

ESI-Mass; 575 [M$^+$+H]

Example 418

6-{2-{{3-Fluoro-4-[2-(4-methyl-[1,4]diazepan-1-yl)ethoxy]benzyl}isopropylamino}-4-methoxyphenyl}-5,6,7,8-tetrahydronaphthalen-2-ol

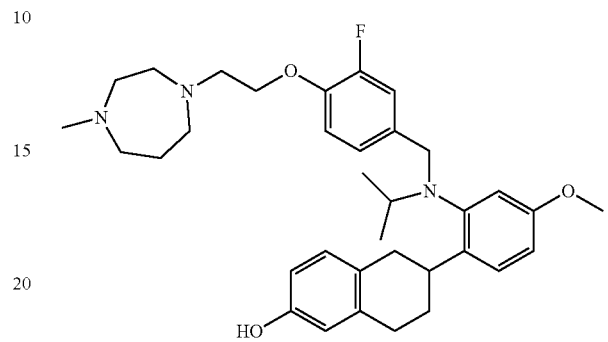

Synthesized from pivalic acid 6-{2-[(3-fluoro-4-hydroxybenzoyl)isopropylamino]-4-methoxyphenyl}-5,6,7,8-tetrahydronaphthalen-2-yl ester (25 mg) and 4-(2-chloroacetyl)-[1,4]diazepane-1-carboxylic acid tert-butyl ester (26 mg) according to an analogous synthetic method to Example 404 and purified by LC-MS, the title compound (16 mg) was obtained.

ESI-Mass; 576 [M$^+$+H]

Example 419

6-{2-{[4-(2-Dimethylaminoethoxy)benzyl]isopropylamino}-4-methoxyphenyl}-5,6,7,8-tetrahydronaphthalen-2-ol

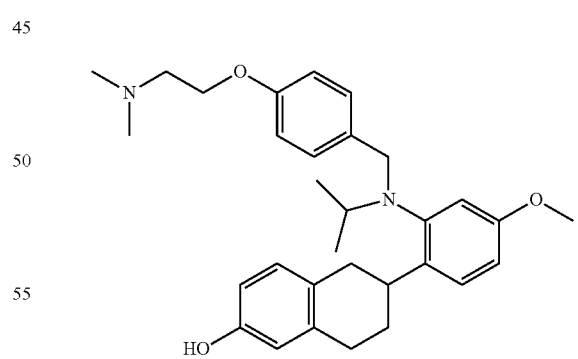

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-N,N-dimethylacetamide (14 mg) according to an analogous synthetic method to Example 404 and purified by LC-MS, the title compound (13 mg) was obtained.

ESI-Mass; 489 [M$^+$+H]

Example 420

6-{2-{[4-(2-Diethylaminoethoxy)benzyl]isopropylamino}-4-methoxyphenyl}-5,6,7,8-tetrahydronaphthalen-2-ol

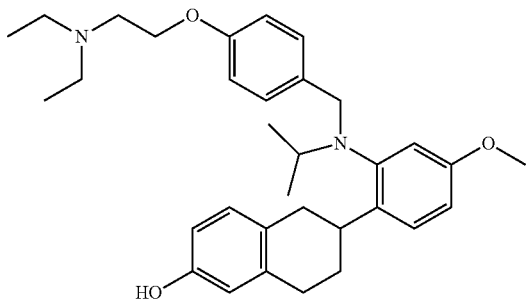 [SMILES: CCN(CC)CCOc1ccc(CN(c2cc(OC)ccc2C2CCc3cc(O)ccc3C2)C(C)C)cc1]

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-N,N-diethyl acetamide (18 mg) according to an analogous synthetic method to Example 404 and purified by LC-MS, the title compound (22 mg) was obtained.

ESI-Mass; 517 [M$^+$+H]

Example 421

6-{2-{[4-(2-Azetidin-1-ylethoxy)benzyl]isopropylamino}-4-methoxyphenyl}-5,6,7,8-tetrahydronaphthalen-2-ol

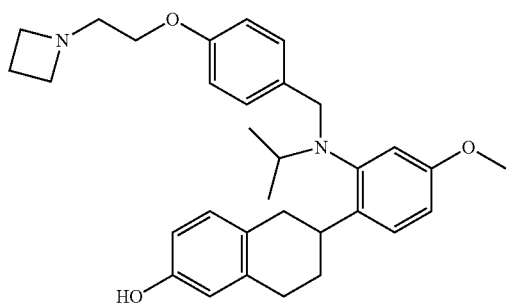 [SMILES: COc1ccc(C2CCc3cc(O)ccc3C2)c(N(Cc2ccc(OCCN3CCC3)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (27 mg) and 1-azetidin-1-yl-2-chloro-ethanone (15 mg) according to an analogous synthetic method to Example 404 and purified by LC-MS, the title compound (5.3 mg) was obtained.

ESI-Mass; 501 [M$^+$+H]

Example 422

6-{2-{Isopropyl[4-(2-pyrrolidin-1-ylethoxy)benzyl]amino}-4-methoxyphenyl}-5,6,7,8-tetrahydronaphthalen-2-ol

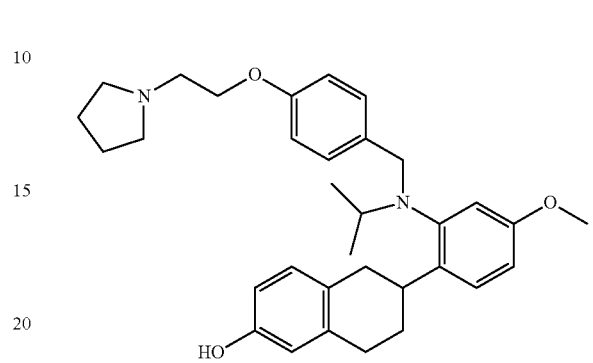

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-1-pyrrolidin-1-ylethanone (17 mg) according to an analogous synthetic method to Example 404 and purified by LC-MS, the title compound (24 mg) was obtained.

ESI-Mass; 515 [M$^+$+H]

Example 423

6-{2-{Isopropyl[4-(2-piperidin-1-ylethoxy)benzyl]amino}-4-methoxyphenyl}-5,6,7,8-tetrahydronaphthalen-2-ol

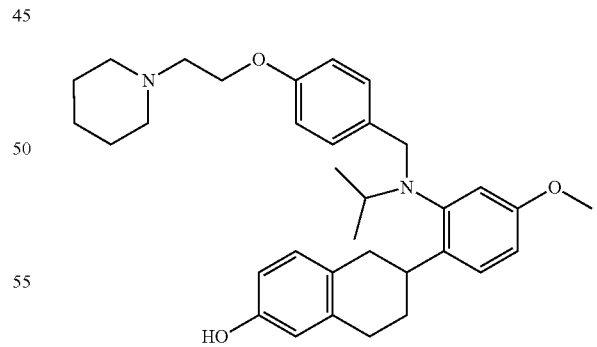

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-1-piperidin-1-ylethanone (19 mg) according to an analogous synthetic method to Example 404 and purified by LC-MS, the title compound (24 mg) was obtained.

ESI-Mass; 529 [M$^+$+H]

Example 424

6-{2-{Isopropyl{4-[2-(4-methylpiperidin-1-yl)ethoxy]benzyl]amino}-4-methoxyphenyl}-5,6,7,8-tetrahydronaphthalen-2-ol

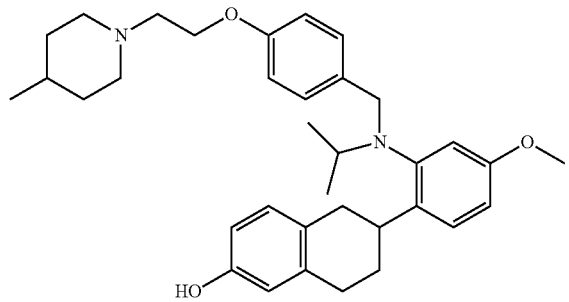

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-1-(4-methylpiperidin-1-yl)ethanone (21 mg) according to an analogous synthetic method to Example 404 and purified by LC-MS, the title compound (21 mg) was obtained.

ESI-Mass; 543 [M$^+$+H]

Example 425

6-{2-{[4-(2-Azepan-1-yl-ethoxy)benzyl]isopropylamino}-4-methoxyphenyl}-5,6,7,8-tetrahydronaphthalen-2-ol

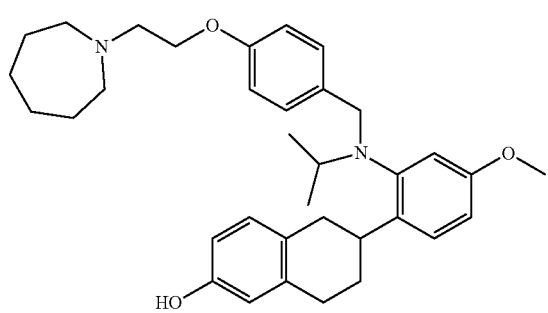 [SMILES: COc1ccc(C2CCc3cc(O)ccc3C2)c(N(Cc2ccc(OCCN3CCCCCC3)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (30 mg) and 1-(2-chloroethyl)azepane (23 mg) according to an analogous synthetic method to Example 404 and purified by NH silica gel column chromatography (hexane-ethyl acetate system), the title compound (6.0 mg) was obtained.

$^1$H-NMR (400 MHz, CDCl$_3$); δ (ppm): 1.09 (d, 3H), 1.15 (d, 3H), 1.50-1.71 (m, 12H), 2.42-2.61 (m, 2H), 2.71-2.80 (m, 6H), 2.92 (t, 2H), 3.15-3.24 (m, 1H), 3.50-3.62 (m, 1H), 3.80 (s, 3H), 4.00 (t, 2H), 4.04 (d, 2H), 6.59-6.64 (m, 3H), 6.67-6.73 (m, 2H), 6.82 (d, 1H), 6.87 (d, 1H), 7.03-7.08 (m, 3H).

ESI-Mass; 543 [M$^+$+H]

Example 426

6-{2-{[4-(2-Azocan-1-ylethoxy)benzyl]isopropylamino}-4-methoxyphenyl}-5,6,7,8-tetrahydronaphthalen-2-ol

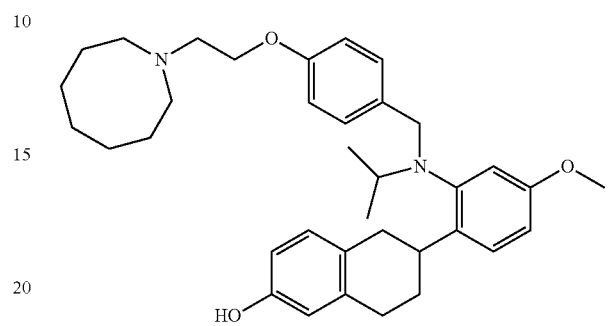

Synthesized from pivalic acid 6-{2-[(4-hydroxybenzoyl)isopropylamino]-4-methoxyphenyl}-5,6,7,8-tetrahydronaphthalen-2-yl ester (30 mg) and 1-azocan-1-yl-2-chloroethanone (22 mg) according to an analogous synthetic method to Example 404 and purified by LC-MS, the title compound (20 mg) was obtained.

ESI-Mass; 557 [M$^+$+H]

Example 427

6-{2-{Isopropyl[4-(1-methyl-2-piperidin-1-ylethoxy)benzyl]amino}-4-methoxyphenyl}-5,6,7,8-tetrahydronaphthalen-2-ol

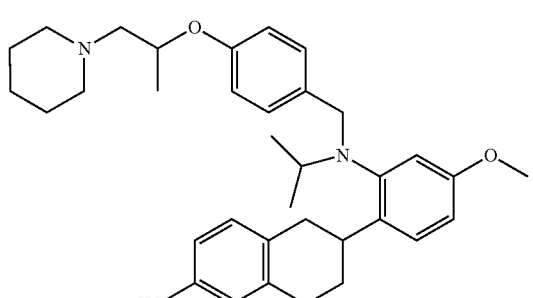

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-1-piperidin-1-yl propan-1-one (20 mg) according to an analogous synthetic method to Example 404 and purified by LC-MS, the title compound (19 mg) was obtained.

ESI-Mass; 543 [M$^+$+H]

Example 428

6-{2-{Isopropyl[4-(2-morpholin-4-ylethoxy)benzyl]amino}-4-methoxyphenyl}-5,6,7,8-tetrahydronaphthalen-2-ol

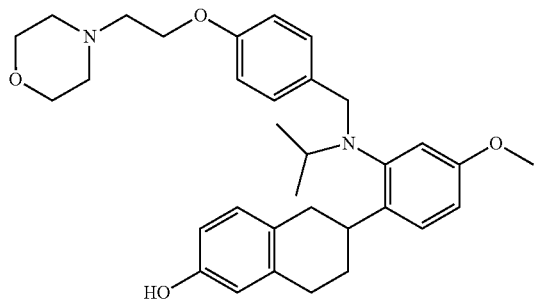 [SMILES: COc1ccc(C2CCc3cc(O)ccc3C2)c(N(Cc2ccc(OCCN3CCOCC3)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (30 mg) and 2-chloro-1-morpholin-4-ylethanone (19 mg) according to an analogous synthetic method to Example 404 and purified by LC-MS, the title compound (22 mg) was obtained.

ESI-Mass; 531 [M$^+$+H]

Example 430

6-{2-{{4-[2-(4-Ethylpiperazin-1-yl)ethoxy]benzyl}isopropylamino}-4-methoxyphenyl}-5,6,7,8-tetrahydronaphthalen-2-ol

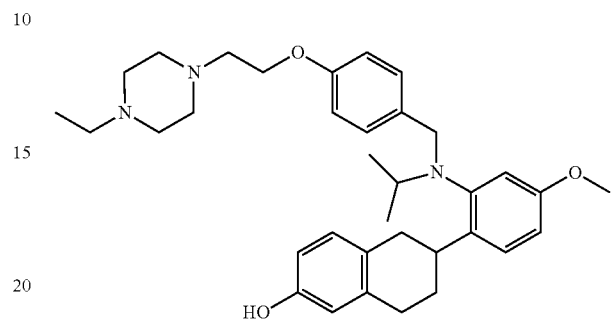

Synthesized from pivalic acid 6-{2-[(4-hydroxybenzoyl)isopropylamino]-4-methoxyphenyl}-5,6,7,8-tetrahydronaphthalen-2-yl ester (21 mg) and 2-chloro-1-(4-ethylpiperazin-1-yl)ethanone (16 mg) according to an analogous synthetic method to Example 404 and purified by LC-MS, the title compound (12 mg) was obtained.

ESI-Mass; 558 [M$^+$+H]

Example 429

6-{2-{{4-[2-(3-Azabicyclo[3.2.2]non-3-yl)ethoxy]benzyl}isopropylamino}-4-methoxyphenyl}-5,6,7,8-tetrahydronaphthalen-2-ol

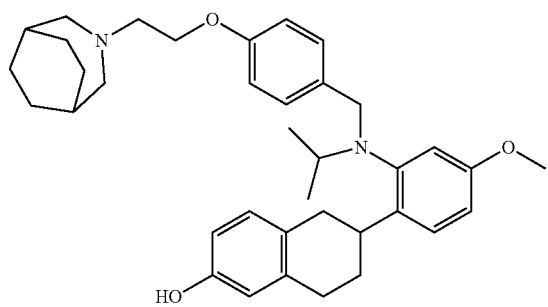 [SMILES: COc1ccc(C2CCc3cc(O)ccc3C2)c(N(Cc2ccc(OCCN3CC4CCC(CC4)C3)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (21 mg) and 1-(3-azabicyclo[3.2.2]non-3-yl)-2-chloroethanone (17 mg) according to an analogous synthetic method to Example 404 and purified by LC-MS, the title compound (8.0 mg) was obtained.

ESI-Mass; 569 [M$^+$+H]

Example 431

6-{2-{{4-[2-(1,4-Dioxa-8-azaspiro[4.5]dec-8-yl)ethoxy]benzyl}isopropylamino}-4-methoxyphenyl}-5,6,7,8-tetrahydronaphthalen-2-ol

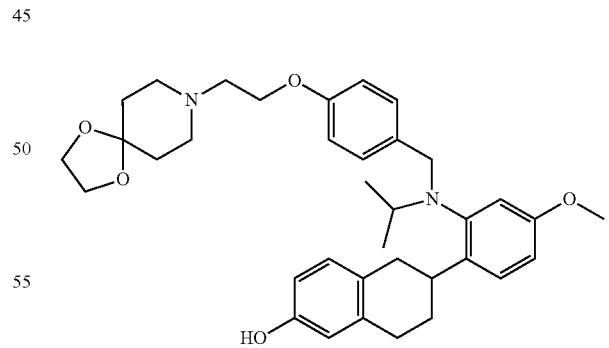

Synthesized from pivalic acid 6-{2-[(4-hydroxybenzoyl)isopropylamino]-4-methoxyphenyl}-5,6,7,8-tetrahydronaphthalen-2-yl ester (21 mg) and 2-chloro-1-(1,4-dioxa-8-azaspiro[4.5]dec-8-yl)ethanone (18 mg) according to an analogous synthetic method to Example 404 and purified by LC-MS, the title compound (4.2 mg) was obtained.

ESI-Mass; 587 [M$^+$+H]

Example 432

6-{2-{{4-{2-[Bis(2-methoxyethyl)amino]ethoxy}benzyl}isopropylamino}-4-methoxyphenyl}-5,6,7,8-tetrahydronaphthalen-2-ol

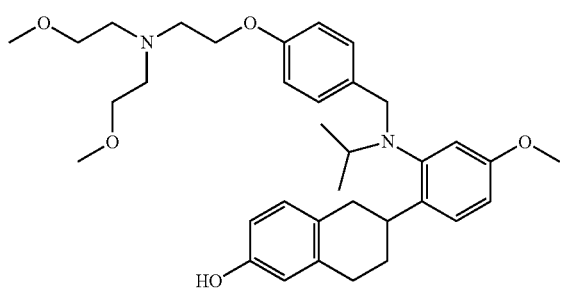

Synthesized from pivalic acid 6-{2-[(4-hydroxybenzoyl)isopropylamino]-4-methoxyphenyl}-5,6,7,8-tetrahydronaphthalen-2-yl ester (21 mg) and 2-chloro-N,N-bis(2-methoxyethyl)acetamide (17 mg) according to an analogous synthetic method to Example 404 and purified by LC-MS, the title compound (4.9 mg) was obtained.

ESI-Mass; 577 [M$^+$+H]

Example 433

6-{2-{{4-[2-(Cyclohexylmethylamino)ethoxy]benzyl}isopropylamino}-4-methoxyphenyl}-5,6,7,8-tetrahydronaphthalen-2-ol

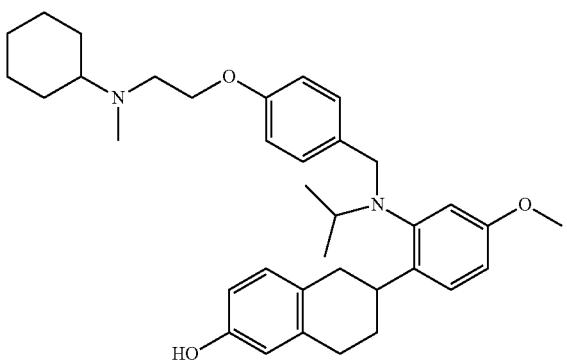 [SMILES: COc1ccc(C2CCc3cc(O)ccc3C2)c(N(Cc2ccc(OCCN(C)C3CCCCC3)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (21 mg) and 2-chloro-N-cyclohexyl-N-methylacetamide (16 mg) according to an analogous synthetic method to Example 404 and purified by LC-MS, the title compound (6.1 mg) was obtained.

ESI-Mass; 557 [M$^+$+H]

Example 434

6-{2-{Isopropyl{4-{2-[(2-methoxyethyl)methylamino]ethoxy}benzyl}amino}-4-methoxyphenyl}-5,6,7,8-tetrahydronaphthalen-2-ol

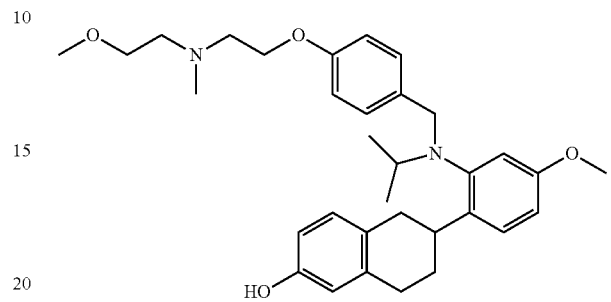

Synthesized from pivalic acid 6-{2-[(4-hydroxybenzoyl)isopropylamino]-4-methoxyphenyl}-5,6,7,8-tetrahydronaphthalen-2-yl ester (22 mg) and 2-chloro-N-(2-methoxyethyl)-N-methylacetamide (14 mg) according to an analogous synthetic method to Example 404 and purified by LC-MS, the title compound (12 mg) was obtained.

ESI-Mass; 533 [M$^+$+H]

Example 435

6-{2-{[4-(2-Diethylaminoethoxy)benzyl]ethylamino}-4-methoxyphenyl}-5,6,7,8-tetrahydronaphthalen-2-ol

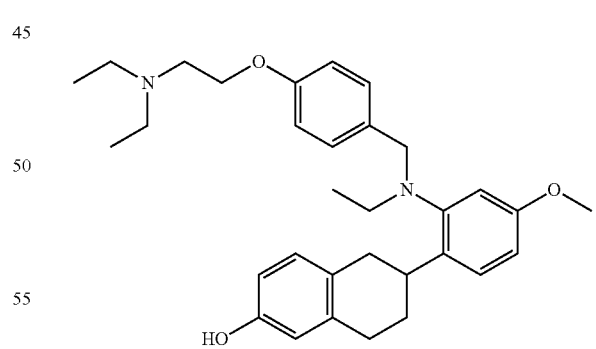

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-N,N-diethylacetamide (18 mg) according to an analogous synthetic method to Example 404 and purified by LC-MS, the title compound (27 mg) was obtained.

ESI-Mass; 503 [M$^+$+H]

Example 436

6-{2-{[4-(2-Azetidin-1-ylethoxy)benzyl]ethy-lamino}-4-methoxyphenyl}-5,6,7,8-tetrahydronaphthalen-2-ol

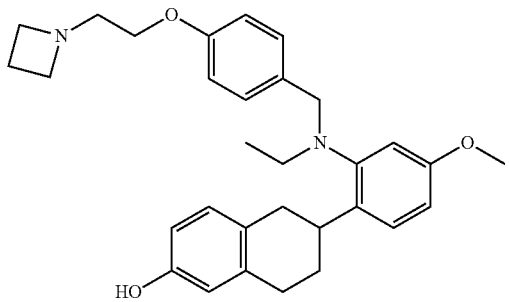 [SMILES: CCN(Cc1ccc(OCCN2CCC2)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphthalen-2-yl ester (26 mg) and 1-azetidin-1-yl-2-chloroethanone (15 mg) according to an analogous synthetic method to Example 404 and purified by LC-MS, the title compound (4.7 mg) was obtained.

ESI-Mass; 487 [M$^+$+H]

Example 437

6-{2-{Ethyl[4-(2-pyrrolidin-1-yl-ethoxy)benzyl]amino}-4-methoxyphenyl}-5,6,7,8-tetrahydronaphthalen-2-ol

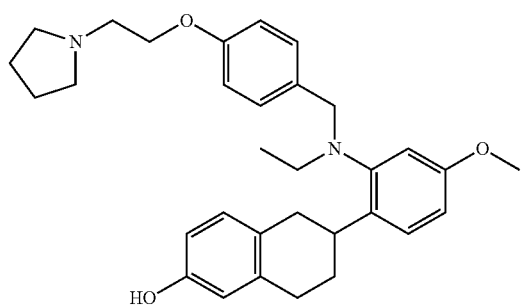 [SMILES: CCN(Cc1ccc(OCCN2CCCC2)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-1-pyrrolidin-1-ylethanone (17 mg) according to an analogous synthetic method to Example 404 and purified by LC-MS, the title compound (28 mg) was obtained.

ESI-Mass; 501 [M$^+$+H]

Example 438

6-{2-{Ethyl[4-(2-piperidin-1-ylethoxy)benzyl]amino}-4-methoxyphenyl}-5,6,7,8-tetrahydronaphthalen-2-ol

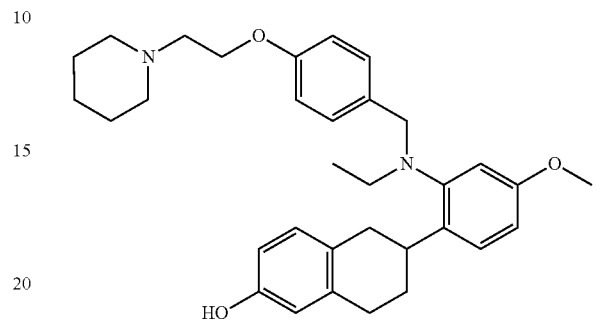

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-1-piperidin-1-ylethanone (19 mg) according to an analogous synthetic method to Example 404 and purified by LC-MS, the title compound (25 mg) was obtained.

ESI-Mass; 515 [M$^+$+H]

Example 439

6-{2-{Ethyl[4-(2-morpholin-4-ylethoxy)benzyl]amino}-4-methoxyphenyl}-5,6,7,8-tetrahydronaphthalen-2-ol

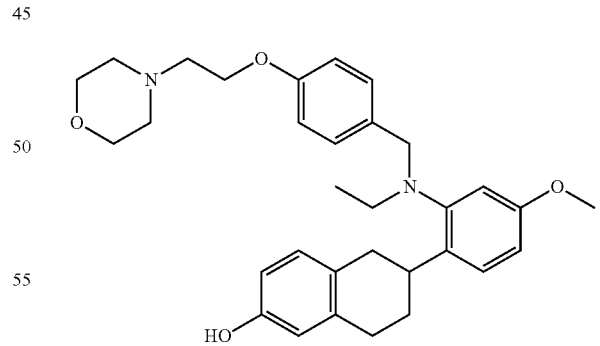

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-1-morpholin-4-ylethanone (19 mg) according to an analogous synthetic method to Example 404 and purified by LC-MS, the title compound (28 mg) was obtained.

ESI-Mass; 517 [M$^+$+H]

Example 440

6-{2-{[4-(2-Dimethylaminoethoxy)benzyl]ethylamino}-4-methoxyphenyl}-5,6,7,8-tetrahydronaphthalen-2-ol

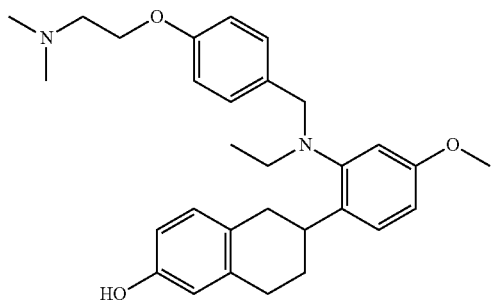

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-N,N-dimethylacetamide (14 mg) according to an analogous synthetic method to Example 404 and purified by LC-MS, the title compound (17 mg) was obtained.

ESI-Mass; 475 [M$^+$+H]

Example 441

6-{2-{Ethyl{4-[2-(4-methylpiperidin-1-yl)ethoxy]benzyl}amino}-4-methoxyphenyl}-5,6,7,8-tetrahydronaphthalen-2-ol

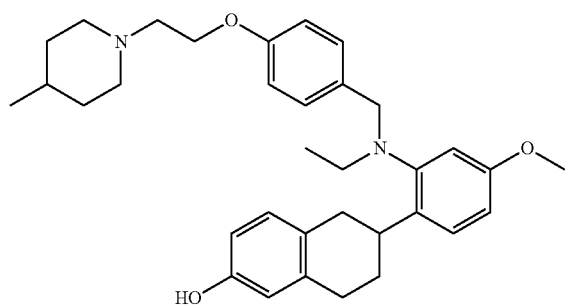

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-1-(4-methylpiperidin-1-yl)ethanone (21 mg) according to an analogous synthetic method to Example 404 and purified by LC-MS, the title compound (17 mg) was obtained.

ESI-Mass; 529 [M$^+$+H]

Example 442

6-{2-{[4-(2-Azocan-1-ylethoxy)benzyl]ethylamino}-4-methoxyphenyl}-5,6,7,8-tetrahydronaphthalen-2-ol

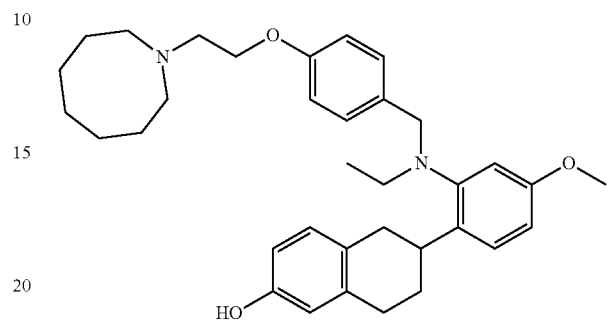

Synthesized from pivalic acid 6-{2-[ethyl(4-hydroxybenzoyl)amino]-4-methoxyphenyl}-5,6,7,8-tetrahydronaphthalen-2-yl ester (29 mg) and 1-azocan-1-yl-2-chloroethanone (22 mg) according to an analogous synthetic method to Example 404 and purified by LC-MS, the title compound (20 mg) was obtained.

ESI-Mass; 543 [M$^+$+H]

Example 443

6-{2-{Ethyl[4-(1-methyl-2-piperidin-1-ylethoxy)benzyl]amino}-4-methoxyphenyl}-5,6,7,8-tetrahydronaphthalen-2-ol

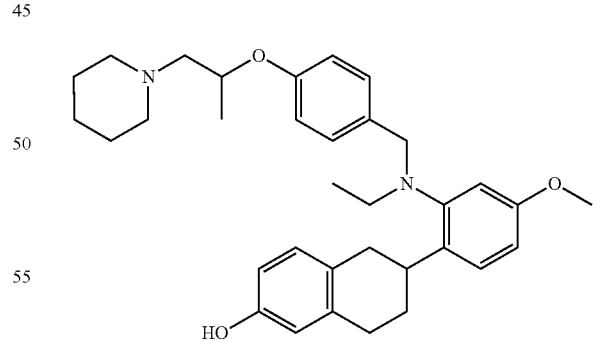

Synthesized from pivalic acid 6-{2-[ethyl(4-hydroxybenzoyl)amino]-4-methoxyphenyl}-5,6,7,8-tetrahydronaphthalen-2-yl ester (29 mg) and 2-chloro-1-piperidin-1-ylpropan-1-one (20 mg) according to an analogous synthetic method to Example 404 and purified by LC-MS, the title compound (13 mg) was obtained.

ESI-Mass; 529 [M$^+$+H]

Example 444

6-{2-{Ethyl{4-[2-(2,2,6,6-tetramethylpiperidin-1-yl)ethoxy]benzyl}amino}-4-methoxyphenyl}-5,6,7,8-tetrahydronaphthalen-2-ol

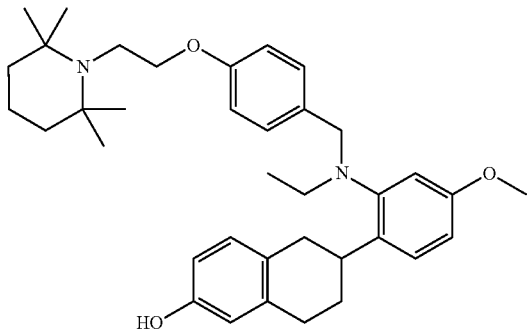 [SMILES: CCN(Cc1ccc(OCCN2C(C)(C)CCCC2(C)C)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-bromo-1-(2,2,6,6-tetramethylpiperidin-1-yl)ethanone (26 mg) according to an analogous synthetic method to Example 404 and purified by LC-MS, the title compound (8.6 mg) was obtained.

ESI-Mass; 571 [M$^+$+H]

Example 445

6-{2-{{4-[2-(3,3-Dimethylpiperidin-1-yl)ethoxy]benzyl}ethylamino}-4-methoxyphenyl}-5,6,7,8-tetrahydronaphthalen-2-ol

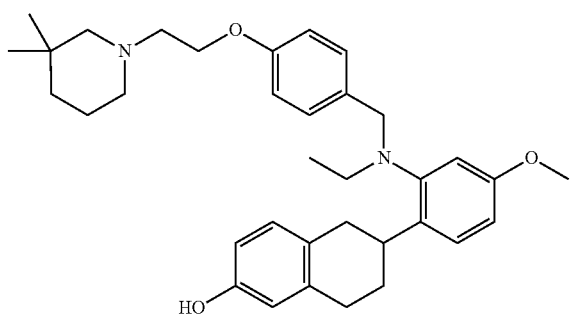

Synthesized from pivalic acid 6-{2-[ethyl(4-hydroxybenzoyl)amino]-4-methoxyphenyl}-5,6,7,8-tetrahydronaphthalen-2-yl ester (20 mg) and 2-bromo-1-(3,3-dimethylpiperidin-1-yl)ethanone (19 mg) according to an analogous synthetic method to Example 404 and purified by LC-MS, the title compound (17 mg) was obtained.

ESI-Mass; 543 [M$^+$+H]

Example 446

6-{2-{{4-[2-(7-Azabicyclo[2.2.1]hept-7-yl)ethoxy]benzyl}ethylamino}-4-methoxyphenyl}-5,6,7,8-tetrahydronaphthalen-2-ol

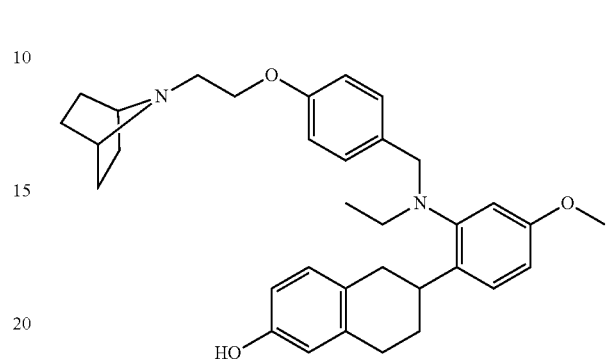

Synthesized from pivalic acid 6-{2-[ethyl(4-hydroxybenzoyl)amino]-4-methoxyphenyl}-5,6,7,8-tetrahydronaphthalen-2-yl ester (20 mg) and 1-(7-azabicyclo[2.2.1]hept-7-yl)-2-bromoethanone (18 mg) according to an analogous synthetic method to Example 404 and purified by LC-MS, the title compound (14 mg) was obtained.

ESI-Mass; 527 [M$^+$+H]

Example 447

6-{2-{{4-[2-(3-Azabicyclo[3.2.2]non-3-yl)ethoxy]benzyl}ethylamino}-4-methoxyphenyl}-5,6,7,8-tetrahydronaphthalen-2-ol

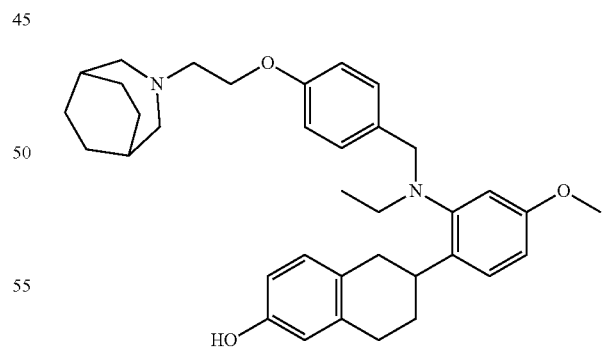

Synthesized from pivalic acid 6-{2-[ethyl(4-hydroxybenzoyl)amino]-4-methoxyphenyl}-5,6,7,8-tetrahydronaphthalen-2-yl ester (26 mg) and 1-(3-azabicyclo[3.2.2]non-3-yl)-2-chloroethanone (21 mg) according to an analogous synthetic method to Example 404 and purified by LC-MS, the title compound (1.7 mg) was obtained.

ESI-Mass; 555 [M$^+$+H]

Example 448

6-{2-{Ethyl{4-[2-(4-ethylpiperazin-1-yl)ethoxy]benzyl}amino}-4-methoxyphenyl}-5,6,7,8-tetrahydronaphthalen-2-ol

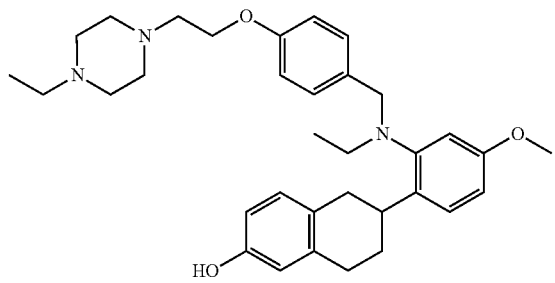 [SMILES: CCN1CCN(CCOc2ccc(CN(CC)c3cc(OC)ccc3C3CCc4cc(O)ccc4C3)cc2)CC1]

Synthesized from pivalic acid 6-{2-[ethyl(4-hydroxybenzoyl)amino]-4-methoxyphenyl}-5,6,7,8-tetrahydronaphthalen-2-yl ester (26 mg) and 2-chloro-1-(4-ethylpiperazin-1-yl)ethanone (20 mg) according to an analogous synthetic method to Example 404 and purified by LC-MS, the title compound (5.2 mg) was obtained.

ESI-Mass; 544 [M$^+$+H]

Example 449

6-{2-{{4-[2-(1,4-Dioxa-8-azaspiro[4.5]dec-8-yl)ethoxy]benzyl}ethylamino}-4-methoxyphenyl}-5,6,7,8-tetrahydronaphthalen-2-ol

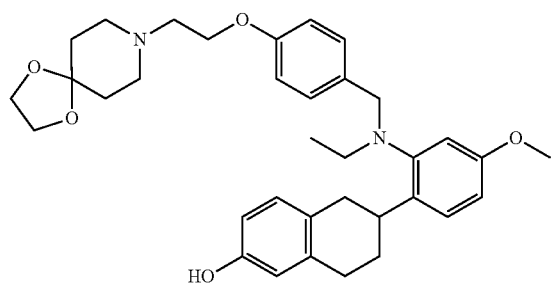 [SMILES: CCN(Cc1ccc(OCCN2CCC3(CC2)OCCO3)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphthalen-2-yl ester (26 mg) and 2-chloro-1-(1,4-dioxa-8-azaspiro[4.5]dec-8-yl)ethanone (23 mg) according to an analogous synthetic method to Example 404 and purified by LC-MS, the title compound (5.6 mg) was obtained.

ESI-Mass; 573 [M$^+$+H]

Example 450

6-{2-{Ethyl{4-[2-(ethylmethylamino)ethoxy]benzyl}amino}-4-methoxyphenyl}-5,6,7,8-tetrahydronaphthalen-2-ol

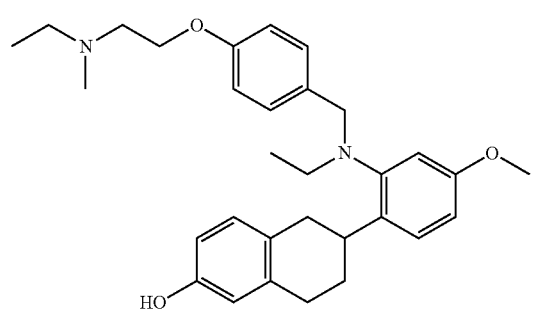 [SMILES: CCN(C)CCOc1ccc(CN(CC)c2cc(OC)ccc2C2CCc3cc(O)ccc3C2)cc1]

Synthesized from pivalic acid 6-{2-[ethyl(4-hydroxybenzoyl)amino]-4-methoxyphenyl}-5,6,7,8-tetrahydronaphthalen-2-yl ester (20 mg) and 2-chloro-N-ethyl-N-methylacetamide (11 mg) according to an analogous synthetic method to Example 404 and purified by LC-MS, the title compound (8.6 mg) was obtained.

ESI-Mass; 489 [M$^+$+H]

Example 451

6-{2-{{4-[2-(Butylmethylamino)ethoxy]benzyl}ethylamino}-4-methoxyphenyl}-5,6,7,8-tetrahydronaphthalen-2-ol

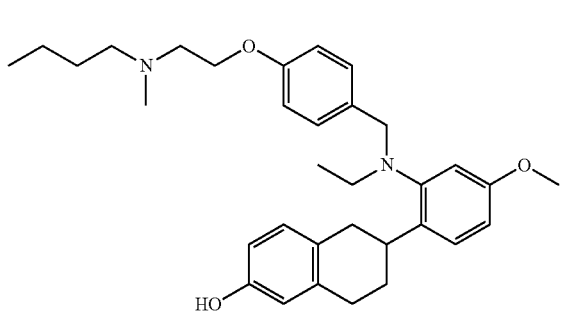 [SMILES: CCCCN(C)CCOc1ccc(CN(CC)c2cc(OC)ccc2C2CCc3cc(O)ccc3C2)cc1]

Synthesized from pivalic acid 6-{2-[ethyl(4-hydroxybenzoyl)amino]-4-methoxyphenyl}-5,6,7,8-tetrahydronaphthalen-2-yl ester (20 mg) and N-butyl-2-chloro-N-methylacetamide (13 mg) according to an analogous synthetic method to Example 404 and purified by LC-MS, the title compound (4.8 mg) was obtained.

ESI-Mass; 517 [M$^+$+H]

Example 452

6-{2-{Ethyl{4-[2-(isobutylmethylamino)ethoxy]benzyl}amino}-4-methoxyphenyl}-5,6,7,8-tetrahydronaphthalen-2-ol

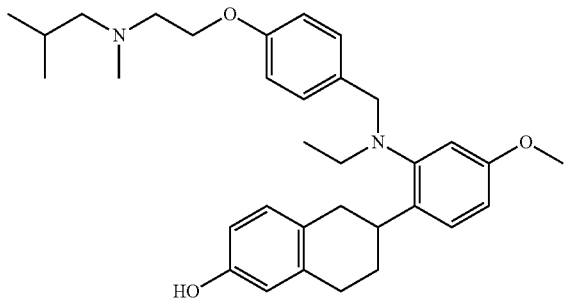 [SMILES: CCN(Cc1ccc(OCCN(C)CC(C)C)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphtalen-2-yl ester (20 mg) and 2-chloro-N-isobutyl-N-methylacetamide (13 mg) according to an analogous synthetic method to Example 404 and purified by LC-MS, the title compound (8.0 mg) was obtained.

ESI-Mass; 517 [M$^+$+H]

Example 453

6-{2-{{4-[2-(tert-Butylmethylamino)ethoxy]benzyl}ethylamino}-4-methoxyphenyl}-5,6,7,8-tetrahydronaphthalen-2-ol

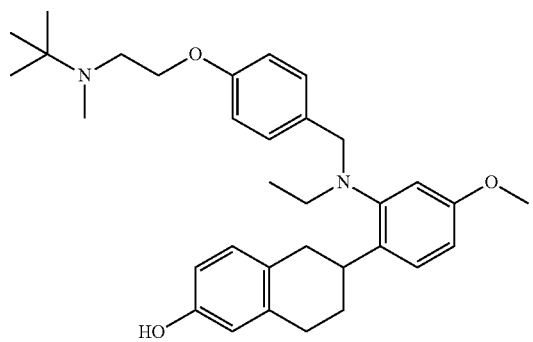 [SMILES: CCN(Cc1ccc(OCCN(C)C(C)(C)C)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphtalen-2-yl ester (20 mg) and N-tert-butyl-2-chloro-N-methylacetamide (13 mg) according to an analogous synthetic method to Example 404 and purified by LC-MS, the title compound (15 mg) was obtained.

ESI-Mass; 517 [M$^+$+H]

Example 454

6-{2-{{4-[2-(Cyclopropylmethylamino)ethoxy]benzyl}ethylamino}-4-methoxyphenyl}-5,6,7,8-tetrahydronaphthalen-2-ol

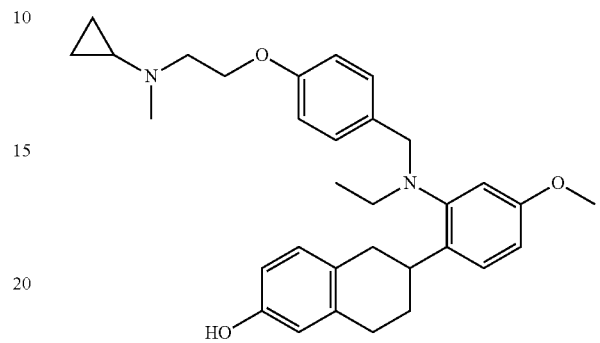

Synthesized from pivalic acid 6-{2-[ethyl(4-hydroxybenzoyl)amino]-4-methoxyphenyl}-5,6,7,8-tetrahydronaphtalen-2-yl ester (20 mg) and 2-chloro-N-cyclopropyl-N-methylacetamide (12 mg) according to an analogous synthetic method to Example 404 and purified by LC-MS, the title compound (13 mg) was obtained.

ESI-Mass; 501 [M$^+$+H]

Example 455

6-{2-{Ethyl{4-[2-(4-methyl-[1,4]diazepan-1-yl)ethoxy]benzyl}amino}-4-methoxyphenyl}-5,6,7,8-tetrahydronaphthalen-2-ol

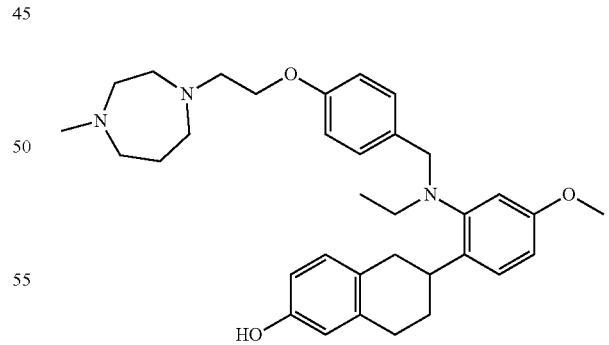

Synthesized from pivalic acid 6-{2-[ethyl(4-hydroxybenzoyl)amino]-4-methoxyphenyl}-5,6,7,8-tetrahydronaphtalen-2-yl ester (20 mg) and 4-(2-chloroacetyl)-[1,4]diazepane-1-carboxylic acid tert-butyl ester (22 mg) according to an analogous synthetic method to Example 404 and purified by LC-MS, the title compound (9.6 mg) was obtained.

ESI-Mass; 544 [M$^+$+H]

Example 456

6-{2-{{4-{2-[Bis(2-methoxyethyl)amino]ethoxy}benzyl}ethylamino}-4-methoxyphenyl}-5,6,7,8-tetrahydronaphthalen-2-ol

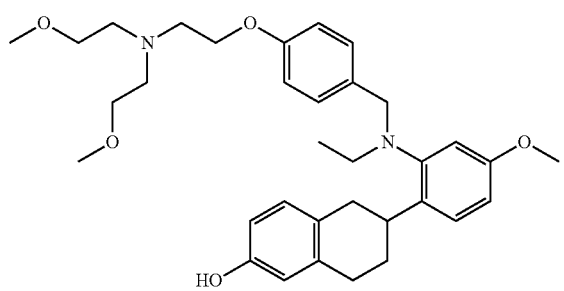

Synthesized from pivalic acid 6-{2-[ethyl(4-hydroxybenzoyl)amino]-4-methoxyphenyl}-5,6,7,8-tetrahydronaphthalen-2-yl ester (26 mg) and 2-chloro-N,N-bis(2-methoxyethyl)acetamide (22 mg) according to an analogous synthetic method to Example 404 and purified by LC-MS, the title compound (2.7 mg) was obtained.

ESI-Mass; 563 [$M^+$+H]

Example 457

6-{2-{Ethyl{4-[2-(methylpropylamino)ethoxy]benzyl}amino}-4-methoxyphenyl}-5,6,7,8-tetrahydronaphthalen-2-ol

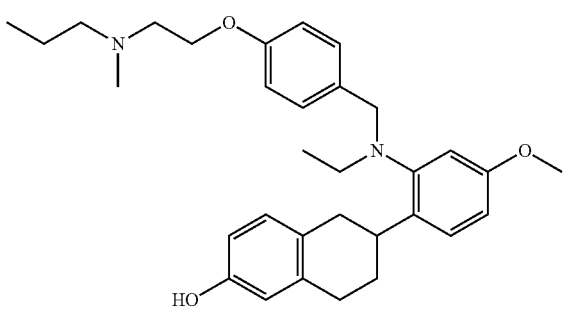 [SMILES: CCCN(C)CCOc1ccc(CN(CC)c2cc(OC)ccc2C2CCc3cc(O)ccc3C2)cc1]

Synthesized from pivalic acid 6-{2-[ethyl(4-hydroxybenzoyl)amino]-4-methoxyphenyl}-5,6,7,8-tetrahydronaphthalen-2-yl ester (20 mg) and 2-chloro-N-methyl-N-propylacetamide (12 mg) according to an analogous synthetic method to Example 404 and purified by LC-MS, the title compound (7.5 mg) was obtained.

ESI-Mass; 503 [$M^+$+H]

Example 458

6-{2-{Ethyl{4-[2-(isopropylmethylamino)ethoxy]benzyl}amino}-4-methoxyphenyl}-5,6,7,8-tetrahydronaphthalen-2-ol

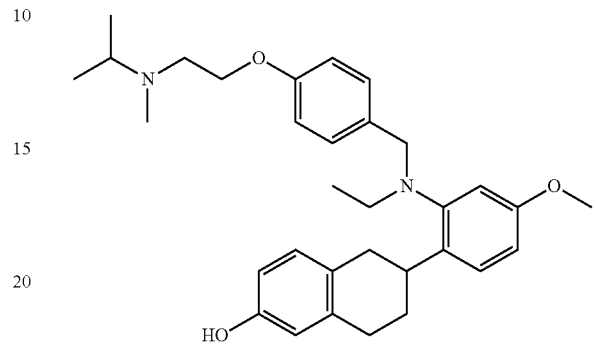

Synthesized from pivalic acid 6-{2-[ethyl(4-hydroxybenzoyl)amino]-4-methoxyphenyl}-5,6,7,8-tetrahydronaphthalen-2-yl ester (20 mg) and 2-chloro-N-isopropyl-N-methylacetamide (12 mg) according to an analogous synthetic method to Example 404 and purified by LC-MS, the title compound (11 mg) was obtained.

ESI-Mass; 503 [$M^+$+H]

Example 459

6-{2-{{4-[2-(Allylmethylamino)ethoxy]benzyl}ethylamino}-4-methoxyphenyl}-5,6,7,8-tetrahydronaphthalen-2-ol

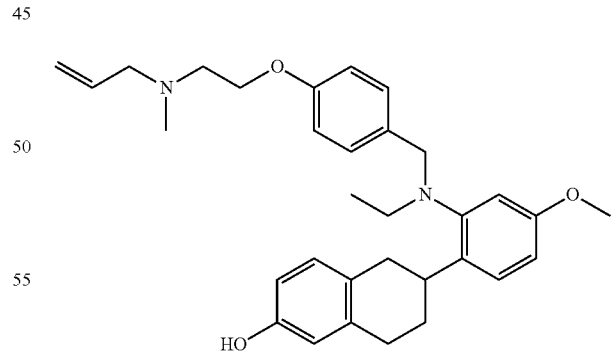

Synthesized from pivalic acid 6-{2-[ethyl(4-hydroxybenzoyl)amino]-4-methoxyphenyl}-5,6,7,8-tetrahydronaphthalen-2-yl ester (20 mg) and N-allyl-2-chloro-N-methylacetamide (12 mg) according to an analogous synthetic method to Example 404 and purified by LC-MS, the title compound (13 mg) was obtained.

ESI-Mass; 501 [$M^+$+H]

Example 460

6-{2-{Ethyl{4-{2-[(2-methoxyethyl)methylamino]ethoxy}benzyl}amino}-4-methoxyphenyl}-5,6,7,8-tetrahydronaphthalen-2-ol

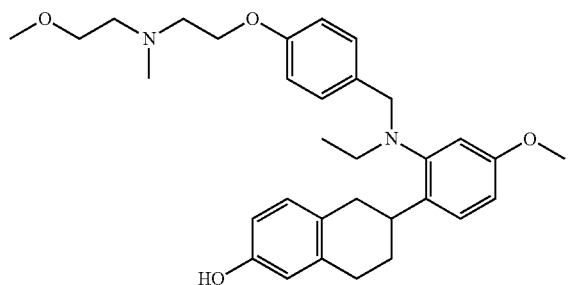

Synthesized from pivalic acid 6-{2-[ethyl(4-hydroxybenzoyl)amino]-4-methoxyphenyl}-5,6,7,8-tetrahydronaphthalen-2-yl ester (22 mg) and 2-chloro-N-(2-methoxyethyl)-N-methylacetamide (14 mg) according to an analogous synthetic method to Example 404 and purified by LC-MS, the title compound (14 mg) was obtained.

ESI-Mass; 519 [M$^+$+H]

Example 461

6-{2-{{4-[2-(Cyclohexylmethylamino)ethoxy]benzyl}ethylamino}-4-methoxyphenyl}-5,6,7,8-tetrahydronaphthalen-2-ol

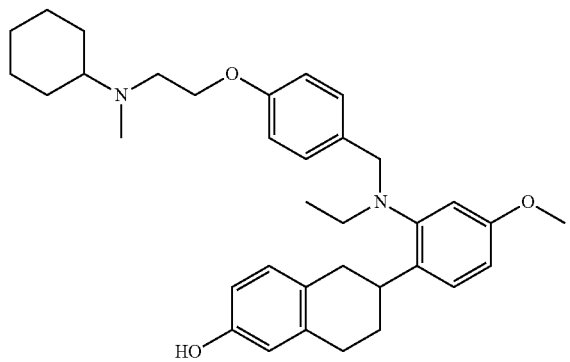 [SMILES: CCN(Cc1ccc(OCCN(C)C2CCCCC2)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphthalen-2-yl ester (26 mg) and 2-chloro-N-cyclohexyl-N-methylacetamide (20 mg) according to an analogous synthetic method to Example 404 and purified by LC-MS, the title compound (3.6 mg) was obtained.

ESI-Mass; 543 [M$^+$+H]

Example 462

6-{2-{[4-(2-Diethylaminoethoxy)-3-fluorobenzyl]ethylamino}-4-methoxyphenyl}-5,6,7,8-tetrahydronaphthalen-2-ol

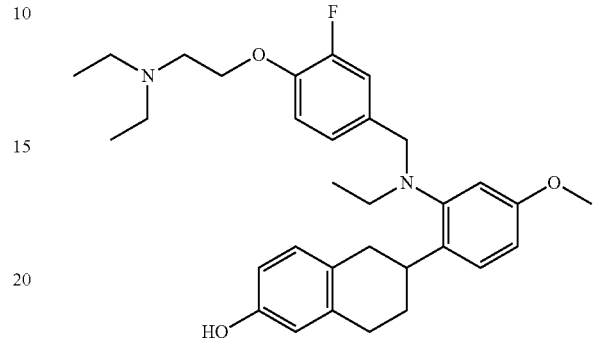

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-N,N-diethylacetamide (14 mg) according to an analogous synthetic method to Example 404 and purified by LC-MS, the title compound (16 mg) was obtained.

ESI-Mass; 521 [M$^+$+H]

Example 463

6-{2-{[4-(2-Azetidin-1-ylethoxy)-3-fluorobenzyl]ethylamino}-4-methoxyphenyl}-5,6,7,8-tetrahydronaphthalen-2-ol

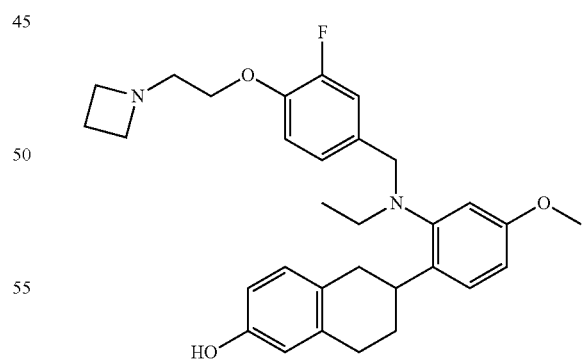

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 1-azetidin-1-yl-2-chloroethanone (13 mg) according to an analogous synthetic method to Example 404 and purified by LC-MS, the title compound (21 mg) was obtained.

ESI-Mass; 505 [M$^+$+H]

Example 464

6-{2-{Ethyl[3-fluoro-4-(2-pyrrolidin-1-ylethoxy)benzyl]amino}-4-methoxyphenyl}-5,6,7,8-tetrahydronaphthalen-2-ol

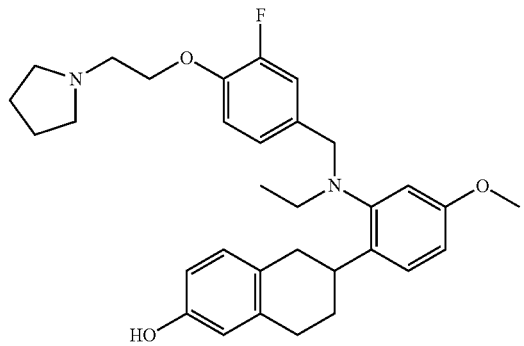 [SMILES: CCN(Cc1ccc(OCCN2CCCC2)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-1-pyrrolidin-1-ylethanone (14 mg) according to an analogous synthetic method to Example 404 and purified by LC-MS, the title compound (23 mg) was obtained.

ESI-Mass; 519 [M$^+$+H]

Example 465

6-{2-{[4-(2-Azepan-1-ylethoxy)-3-fluorobenzyl]ethylamino}-4-methoxyphenyl}-5,6,7,8-tetrahydronaphthalen-2-ol

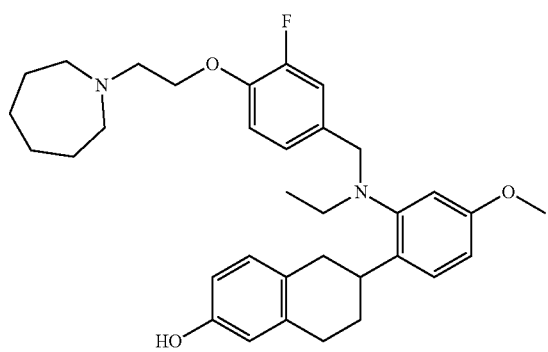 [SMILES: CCN(Cc1ccc(OCCN2CCCCCC2)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 1-azepan-1-yl-2-chloroethanone (17 mg) according to an analogous synthetic method to Example 404 and purified by LC-MS, the title compound (13 mg) was obtained.

ESI-Mass; 547 [M$^+$+H]

Example 466

6-{2-{{4-[2-(3-Azabicyclo[3.2.2]non-3-yl)ethoxy]-3-fluorobenzyl}ethylamino}-4-methoxyphenyl}-5,6,7,8-tetrahydronaphthalen-2-ol

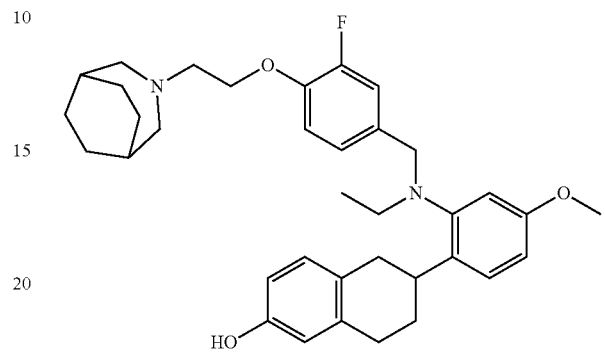

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 1-(3-azabicyclo[3.2.2]non-3-yl)-2-chloroethanone (19 mg) according to an analogous synthetic method to Example 404 and purified by LC-MS, the title compound (24 mg) was obtained.

ESI-Mass; 573 [M$^+$+H]

Example 467

6-{2-{Ethyl{4-[2-(4-ethylpiperidin-1-yl)ethoxy]-3-fluorobenzyl}amino}-4-methoxyphenyl}-5,6,7,8-tetrahydronaphthalen-2-ol

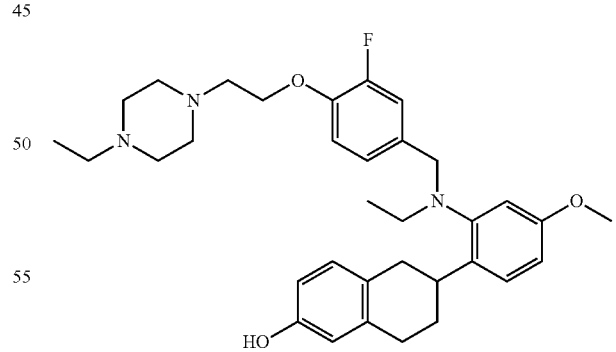

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-1-(4-ethylpiperazin-1-yl)ethanone (18 mg) according to an analogous synthetic method to Example 404 and purified by LC-MS, the title compound (22 mg) was obtained.

ESI-Mass; 562 [M$^+$+H]

Example 468

6-{2-{{4-[2-(1,4-Dioxa-8-azaspiro[4.5]dec-8-yl)ethoxy]-3-fluorobenzyl}ethylamino}-4-methoxyphenyl}-5,6,7,8-tetrahydronaphthalen-2-ol

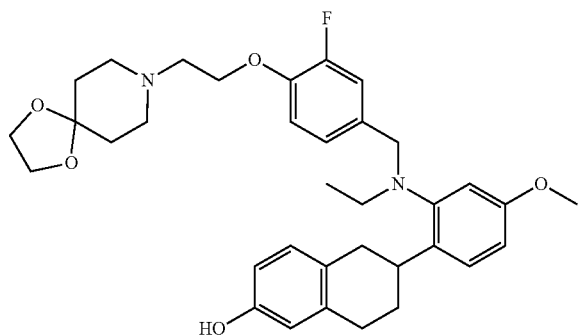 [SMILES: CCN(Cc1ccc(OCCN2CCC3(CC2)OCCO3)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-1-(1,4-dioxa-8-azaspiro[4.5]dec-8-yl)ethanone (21 mg) according to an analogous synthetic method to Example 404 and purified by LC-MS, the title compound (23 mg) was obtained.

ESI-Mass; 591 [M$^+$+H]

Example 469

6-{2-{{4-{2-[Bis(2-methoxyethyl)amino]ethoxy}-3-fluorobenzyl}ethylamino}-4-methoxyphenyl}-5,6,7,8-tetrahydronaphthalen-2-ol

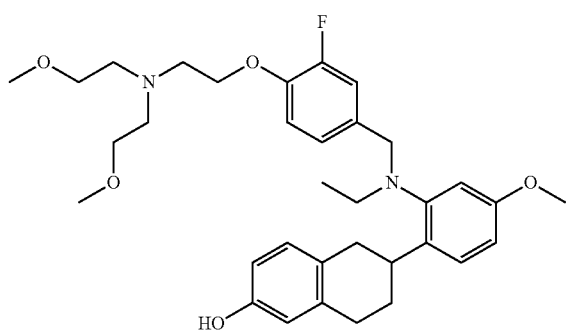

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-N,N-bis(2-methoxyethyl)acetamide (20 mg) according to an analogous synthetic method to Example 404 and purified by LC-MS, the title compound (16 mg) was obtained.

ESI-Mass; 581 [M$^+$+H]

Example 470

6-{2-{Ethyl{3-fluoro-4-{2-[(2-methoxyethyl)methylamino]ethoxy}benzyl}amino}-4-methoxyphenyl}-5,6,7,8-tetrahydronaphthalen-2-ol

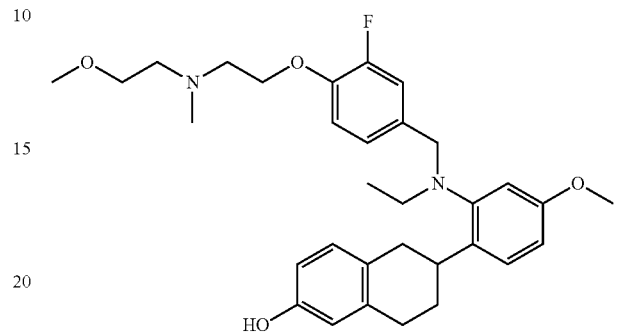

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 2-chloro-N-(2-methoxyethyl)-N-methylacetamide (14 mg) according to an analogous synthetic method to Example 404 and purified by LC-MS, the title compound (6.0 mg) was obtained.

ESI-Mass; 537 [M$^+$+H]

Example 471

6-{2-{[4-(2-Dimethylaminoethoxy)-3-fluorobenzyl]ethylamino}-4-methoxyphenyl}-5,6,7,8-tetrahydronaphthalen-2-ol

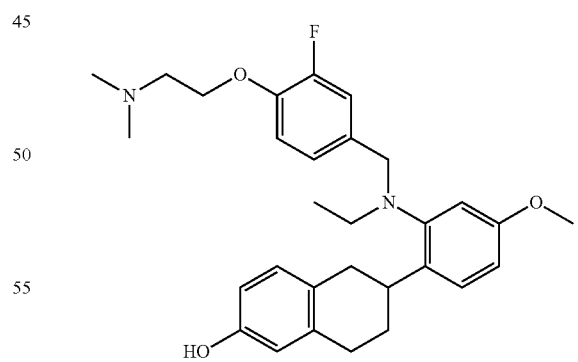

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 2-chloro-N,N-dimethylacetamide (11 mg) according to an analogous synthetic method to Example 404 and purified by LC-MS, the title compound (9.5 mg) was obtained.

ESI-Mass; 493 [M$^+$+H]

Example 472

6-{2-{Ethyl{3-fluoro-4-[2-(4-methylpiperidin-1-yl)ethoxy]benzyl}amino}-4-methoxyphenyl}-5,6,7,8-tetrahydronaphthalen-2-ol

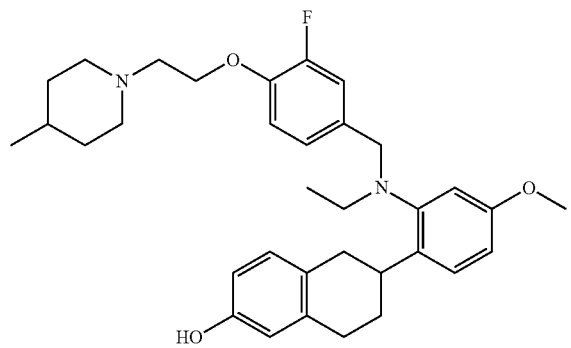

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 2-chloro-1-(4-methylpiperidin-1-yl)ethanone (16 mg) according to an analogous synthetic method to Example 404 and purified by LC-MS, the title compound (15 mg) was obtained.

ESI-Mass; 547 [M$^+$+H]

Example 473

6-{2-{[4-(2-Azocan-1-ylethoxy)-3-fluorobenzyl]ethylamino}-4-methoxyphenyl}-5,6,7,8-tetrahydronaphthalen-2-ol

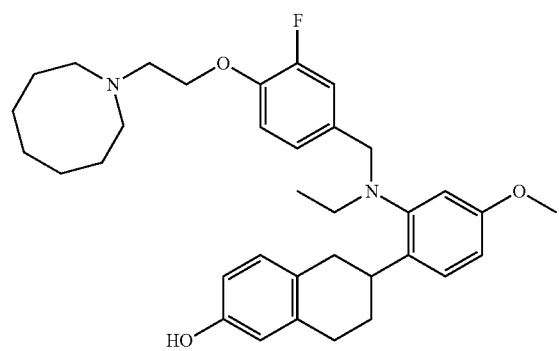 [SMILES: CCN(Cc1ccc(OCCN2CCCCCCC2)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 1-azocan-1-yl-2-chloroethanone (17 mg) according to an analogous synthetic method to Example 404 and purified by LC-MS, the title compound (15 mg) was obtained.

ESI-Mass; 561 [M$^+$+H]

Example 474

6-{2-{Ethyl[3-fluoro-4-(1-methyl-2-piperidin-1-ylethoxy)benzyl]amino}-4-methoxyphenyl}-5,6,7,8-tetrahydronaphthalen-2-ol

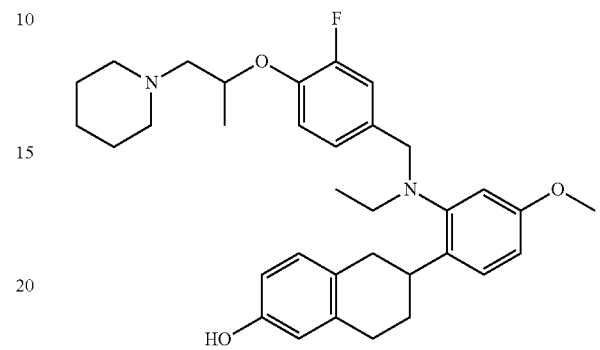

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 2-chloro-1-piperidin-1-ylpropan-1-one (16 mg) according to an analogous synthetic method to Example 404 and purified by LC-MS, the title compound (14 mg) was obtained.

ESI-Mass; 547 [M$^+$+H]

Example 475

6-{2-{Ethyl[3-fluoro-4-(2-morpholin-4-ylethoxy)benzyl]amino}-4-methoxyphenyl}-5,6,7,8-tetrahydronaphthalen-2-ol

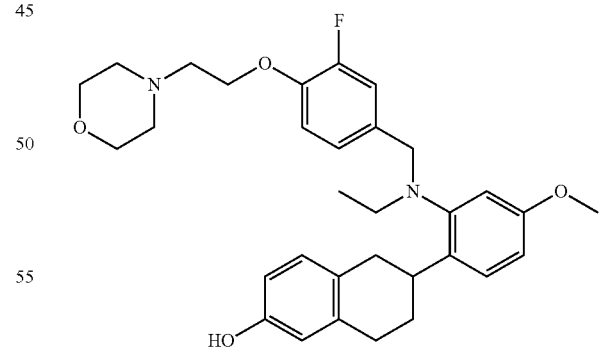

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 2-chloro-1-morpholin-4-ylethanone (15 mg) according to an analogous synthetic method to Example 404 and purified by LC-MS, the title compound (7.4 mg) was obtained.

ESI-Mass; 535 [M$^+$+H]

Example 476

6-{2-{{4-[2-(Cyclohexylmethylamino)ethoxy]-3-fluorobenzyl}ethylamino}-4-methoxyphenyl}-5,6,7,8-tetrahydronaphthalen-2-ol

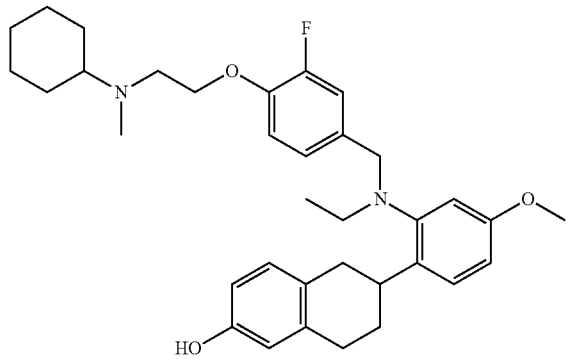 [SMILES: CCN(Cc1ccc(OCCN(C)C2CCCCC2)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (21 mg) and 2-chloro-N-cyclohexyl-N-methylacetamide (17 mg) according to an analogous synthetic method to Example 404 and purified by LC-MS, the title compound (4.7 mg) was obtained.

ESI-Mass; 561 [M$^+$+H]

Example 477

6-{2-{Ethyl{3-fluoro-4-[2-(4-methyl-[1,4]diazepan-1-yl)ethoxy]benzyl}amino}-4-methoxyphenyl}-5,6,7,8-tetrahydronaphthalen-2-ol

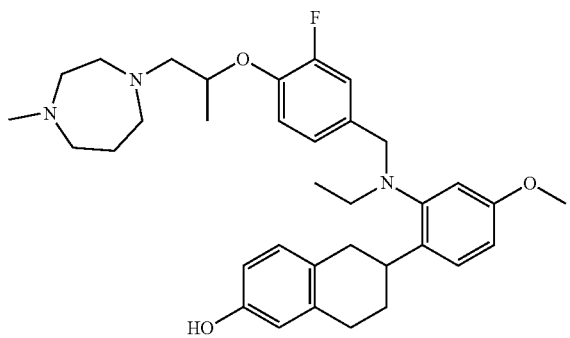

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 4-(2-chloroacetyl)-[1,4]diazepane-1-carboxylic acid tert-butyl ester (21 mg) according to an analogous synthetic method to Example 404 and purified by LC-MS, the title compound (9.4 mg) was obtained.

ESI-Mass; 562 [M$^+$+H]

Example 478

6-{2-{{4-[2-(3,3-Dimethylpiperidin-1-yl)ethoxy]-3-fluorobenzyl}ethylamino}-4-methoxyphenyl}-5,6,7,8-tetrahydronaphthalen-2-ol

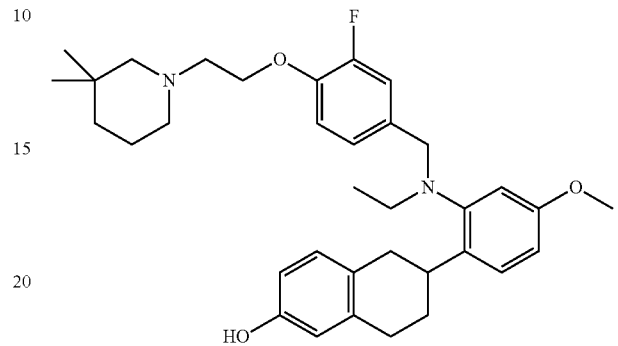

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-bromo-1-(3,3-dimethylpiperidin-1-yl)ethanone (18 mg) according to an analogous synthetic method to Example 404 and purified by LC-MS, the title compound (8.1 mg) was obtained.

ESI-Mass; 561 [M$^+$+H]

Example 479

6-{2-{Ethyl{3-fluoro-4-[2-(2,2,6,6-tetramethylpiperidin-1-yl)ethoxy]benzyl}amino}-4-methoxyphenyl}-5,6,7,8-tetrahydronaphthalen-2-ol

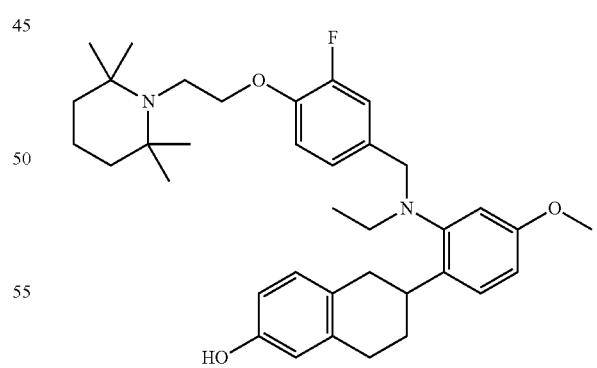

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-bromo-1-(2,2,6,6-tetramethylpiperidin-1-yl)ethanone (20 mg) according to an analogous synthetic method to Example 404 and purified by LC-MS, the title compound (6.5 mg) was obtained.

ESI-Mass; 589 [M$^+$+H]

Example 480

6-{2-{{4-[2-(7-Azabicyclo[2.2.1]hept-7-yl)ethoxy]-3-fluorobenzyl}ethylamino}-4-methoxyphenyl}-5,6,7,8-tetrahydronaphthalen-2-ol

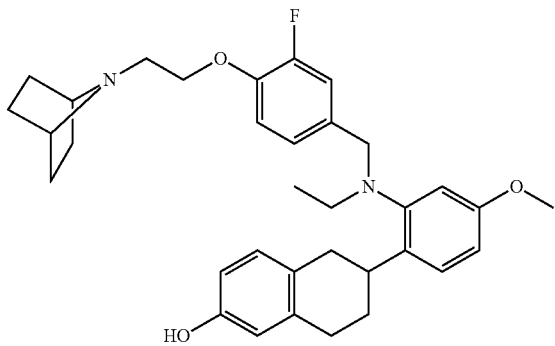 [SMILES: CCN(Cc1ccc(OCCN2C3CCC2CC3)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 1-(7-azabicyclo[2.2.1]hept-7-yl)-2-bromoethanone (17 mg) according to an analogous synthetic method to Example 404 and purified by LC-MS, the title compound (7.6 mg) was obtained.

ESI-Mass; 545 [M$^+$+H]

Example 481

6-{2-{Ethyl{4-[2-(ethylmethylamino)ethoxy]-3-fluorobenzyl}amino}-4-methoxyphenyl}-5,6,7,8-tetrahydronaphthalen-2-ol

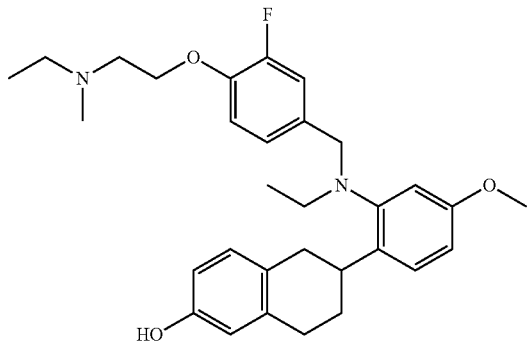 [SMILES: CCN(C)CCOc1ccc(CN(CC)c2cc(OC)ccc2C2CCc3cc(O)ccc3C2)cc1F]

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-chloro-N-ethyl-N-methylacetamide (10 mg) according to an analogous synthetic method to Example 404 and purified by LC-MS, the title compound (13 mg) was obtained.

ESI-Mass; 507 [M$^+$+H]

Example 482

6-{2-{{4-[2-(Butylmethylamino)ethoxy]-3-fluorobenzyl}ethylamino}-4-methoxyphenyl}-5,6,7,8-tetrahydronaphthalen-2-ol

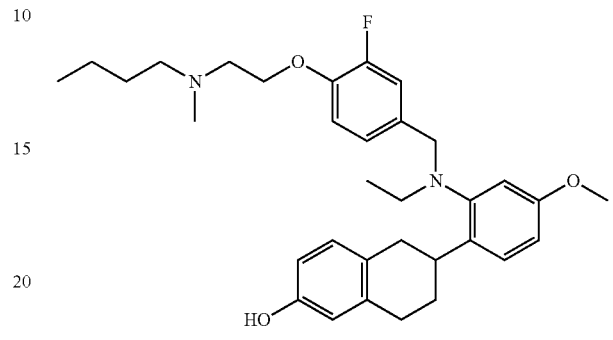

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and N-butyl-2-chloro-N-methylacetamide (13 mg) according to an analogous synthetic method to Example 404 and purified by LC-MS, the title compound (8.1 mg) was obtained.

ESI-Mass; 535 [M$^+$+H]

Example 483

6-{2-{Ethyl{3-fluoro-4-[2-(isobutylmethylamino)ethoxy]benzyl}amino}-4-methoxyphenyl}-5,6,7,8-tetrahydronaphthalen-2-ol

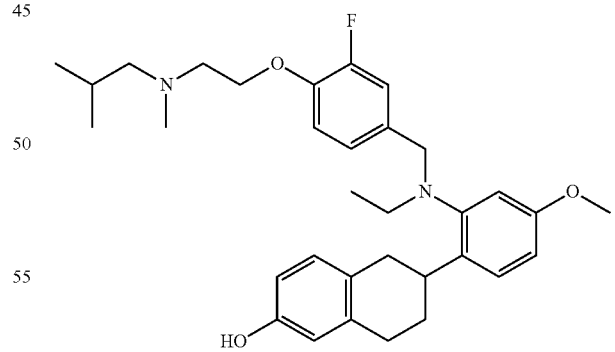

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-chloro-N-isobutyl-N-methylacetamide (13 mg) according to an analogous synthetic method to Example 404 and purified by LC-MS, the title compound (8.5 mg) was obtained.

ESI-Mass; 535 [M$^+$+H]

Example 484

6-{2-{{4-[2-(tert-Butylmethylamino)ethoxy]-3-fluorobenzyl}ethylamino}-4-methoxyphenyl}-5,6,7,8-tetrahydronaphthalen-2-ol

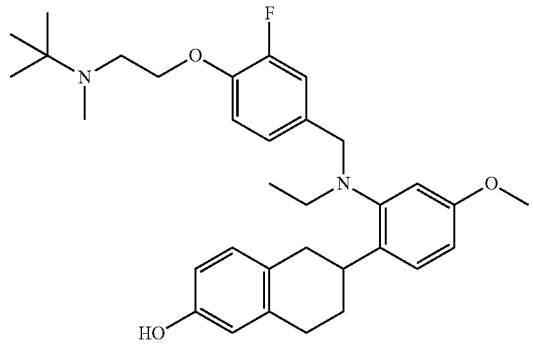

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and N-tert-butyl-2-chloro-N-methylacetamide (13 mg) according to an analogous synthetic method to Example 404 and purified by LC-MS, the title compound (9.9 mg) was obtained.

ESI-Mass; 535 [M$^+$+H]

Example 485

6-{2-{{4-[2-(Cyclopropylmethylamino)ethoxy]-3-fluorobenzyl}ethylamino}-4-methoxyphenyl}-5,6,7,8-tetrahydronaphthalen-2-ol

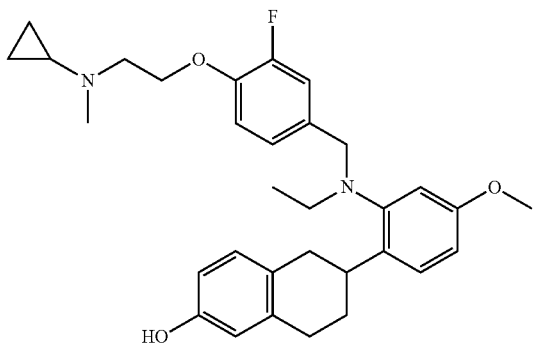 [SMILES: CCN(Cc1ccc(OCCN(C)C2CC2)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-chloro-N-cyclopropyl-N-methylacetamide (11 mg) according to an analogous synthetic method to Example 404 and purified by LC-MS, the title compound (4.8 mg) was obtained.

ESI-Mass; 519 [M$^+$+H]

Example 486

6-{2-{Ethyl{3-fluoro-4-[2-(methylpropylamino)ethoxy]benzyl}amino}-4-methoxyphenyl}-5,6,7,8-tetrahydronaphthalen-2-ol

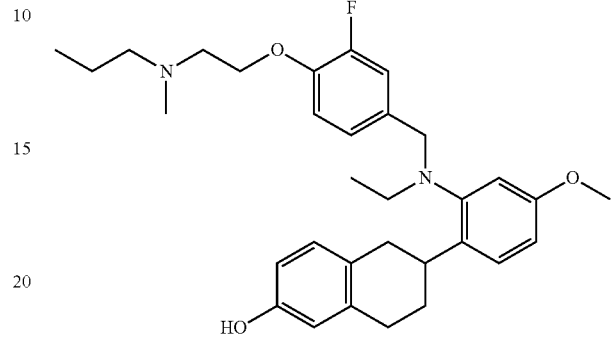

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-chloro-N-methyl-N-propyl acetamide (12 mg) according to an analogous synthetic method to Example 404 and purified by LC-MS, the title compound (6.1 mg) was obtained.

ESI-Mass; 521 [M$^+$+H]

Example 487

6-{2-{Ethyl{3-fluoro-4-[2-(isopropylmethylamino)ethoxy]benzyl}amino}-4-methoxyphenyl}-5,6,7,8-tetrahydronaphthalen-2-ol

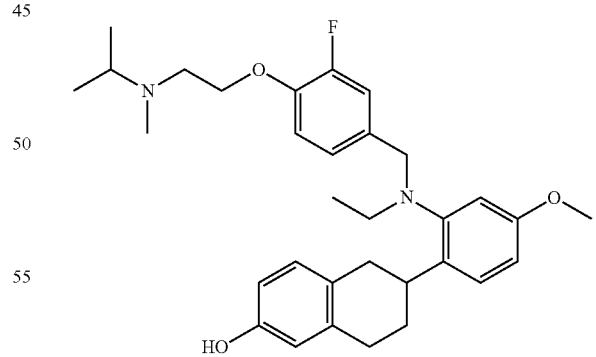

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and 2-chloro-N-isopropyl-N-methylacetamide (12 mg) according to an analogous synthetic method to Example 404 and purified by LC-MS, the title compound (3.8 mg) was obtained.

ESI-Mass; 521 [M$^+$+H]

Example 488

6-{2-{{4-[2-(Allylmethylamino)ethoxy]-3-fluorobenzyl}ethylamino}-4-methoxyphenyl}-5,6,7,8-tetrahydronaphthalen-2-ol

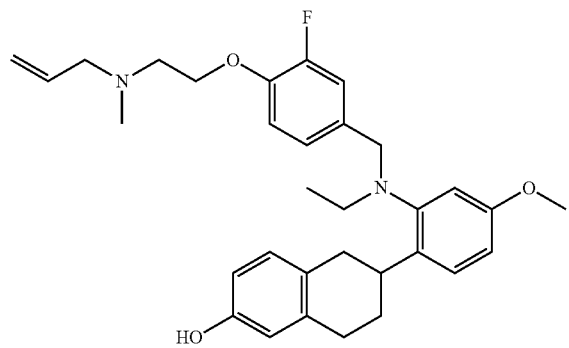 [SMILES: C=CCN(C)CCOc1ccc(CN(CC)c2cc(OC)ccc2C2CCc3cc(O)ccc3C2)cc1F]

Synthesized from pivalic acid 6-{2-[ethyl(3-fluoro-4-hydroxybenzoyl)amino]-4-methoxyphenyl}-5,6,7,8-tetrahydronaphthalen-2-yl ester (20 mg) and N-allyl-2-chloro-N-methylacetamide (11 mg) according to an analogous synthetic method to Example 404 and purified by LC-MS, the title compound (3.1 mg) was obtained.

ESI-Mass; 519 [M$^+$+H]

Example 489

6-{2-{[4-(2-Dimethylaminoethoxy)benzyl]methylamino}-4-methoxyphenyl}-5,6,7,8-tetrahydronaphthalen-2-ol

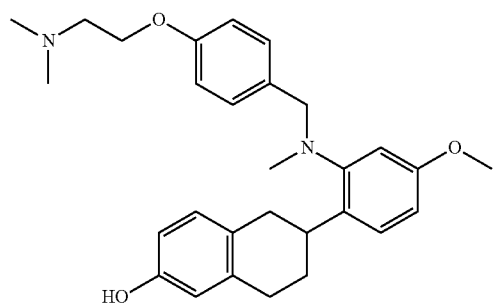

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-N,N-dimethylacetamide (13 mg) according to an analogous synthetic method to Example 404 and purified by LC-MS, the title compound (5.4 mg) was obtained.

ESI-Mass; 461 [M$^+$+H]

Example 490

6-{2-{[4-(2-Diethylaminoethoxy)benzyl]methylamino}-4-methoxyphenyl}-5,6,7,8-tetrahydronaphthalen-2-ol

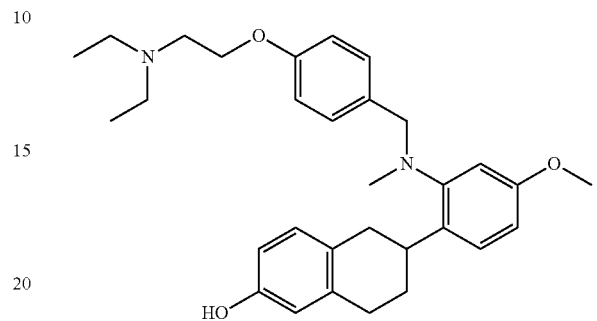

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-N,N-diethylacetamide (15 mg) according to an analogous synthetic method to Example 404 and purified by LC-MS, the title compound (7.1 mg) was obtained.

ESI-Mass; 489 [M$^+$+H]

Example 491

6-{2-{[4-(2-Azetidin-1-ylethoxy)benzyl]methylamino}-4-methoxyphenyl}-5,6,7,8-tetrahydronaphthalen-2-ol

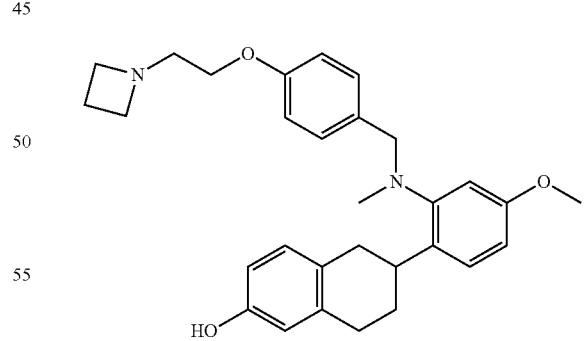

Synthesized from pivalic acid 6-{2-[(4-hydroxybenzoyl)methylamino]-4-methoxyphenyl}-5,6,7,8-tetrahydronaphthalen-2-yl ester (25 mg) and 1-azetidin-1-yl-2-chloroethanone (14 mg) according to an analogous synthetic method to Example 404 and purified by LC-MS, the title compound (4.8 mg) was obtained.

ESI-Mass; 473 [M$^+$+H]

Example 492

6-{4-Methoxy-2-{methyl[4-(2-pyrrolidin-1-ylethoxy)benzyl]amino}phenyl}-5,6,7,8-tetrahydronaphthalen-2-ol

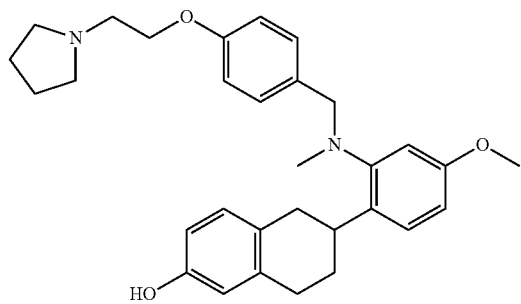 [SMILES: COc1ccc(C2CCc3cc(O)ccc3C2)c(N(C)Cc2ccc(OCCN3CCCC3)cc2)c1]

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-1-pyrrolidin-1-ylethanone (15 mg) according to an analogous synthetic method to Example 404 and purified by LC-MS, the title compound (6.1 mg) was obtained.

ESI-Mass; 487 [M$^+$+H]

Example 493

6-{4-Methoxy-2-{methyl[4-(2-piperidin-1-ylethoxy)benzyl]amino}phenyl}-5,6,7,8-tetrahydronaphthalen-2-ol

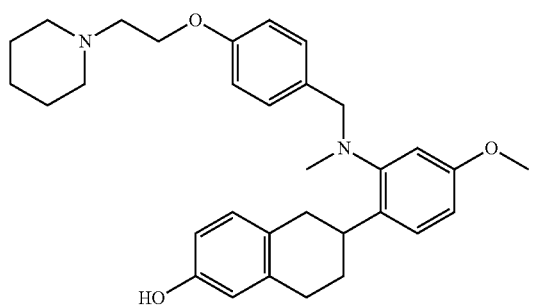 [SMILES: COc1ccc(C2CCc3cc(O)ccc3C2)c(N(C)Cc2ccc(OCCN3CCCCC3)cc2)c1]

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-1-piperidin-1-ylethanone (17 mg) according to an analogous synthetic method to Example 404 and purified by LC-MS, the title compound (3.1 mg) was obtained.

ESI-Mass; 501 [M$^+$+H]

Example 494

6-{4-Methoxy-2-{methyl{4-[2-(4-methylpiperidin-1-yl)ethoxy]benzyl}amino}phenyl}-5,6,7,8-tetrahydronaphthalen-2-ol

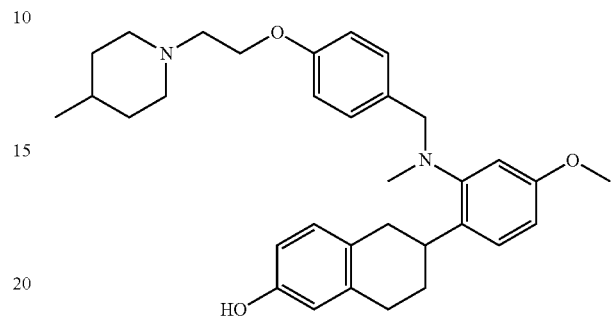

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-1-(4-methylpiperidin-1-yl)ethanone (18 mg) according to an analogous synthetic method to Example 404 and purified by LC-MS, the title compound (2.4 mg) was obtained.

ESI-Mass; 515 [M$^+$+H]

Example 495

6-{2-{[4-(2-Azepan-1-ylethoxy)benzyl]methylamino}-4-methoxyphenyl}-5,6,7,8-tetrahydronaphthalen-2-ol

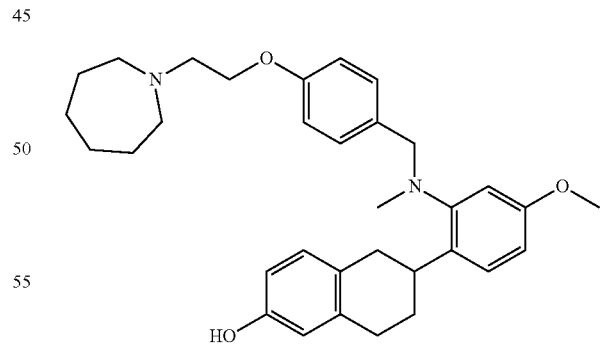

Synthesized from pivalic acid 6-{2-[(4-hydroxybenzoyl)methylamino]-4-methoxyphenyl}-5,6,7,8-tetrahydronaphthalen-2-yl ester (25 mg) and 1-azepan-1-yl-2-chloroethanone (18 mg) according to an analogous synthetic method to Example 404 and purified by LC-MS, the title compound (2.1 mg) was obtained.

ESI-Mass; 515 [M$^+$+H]

Example 496

6-{2-{[4-(2-Azocan-1-ylethoxy)benzyl]methylamino}-4-methoxyphenyl}-5,6,7,8-tetrahydronaphthalen-2-ol

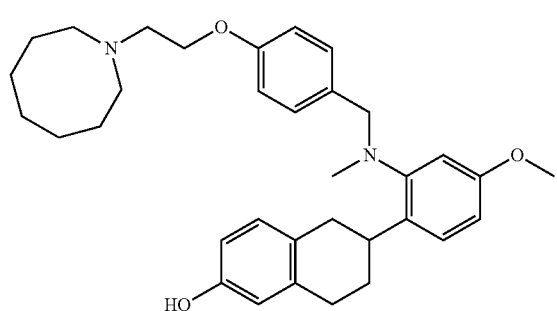 [SMILES: COc1ccc(C2CCc3cc(O)ccc3C2)c(N(C)Cc2ccc(OCCN3CCCCCCC3)cc2)c1]

Synthesized from pivalic acid 6-{2-[(4-hydroxybenzoyl)methylamino]-4-methoxyphenyl}-5,6,7,8-tetrahydronaphthalen-2-yl ester (25 mg) and 1-azocan-1-yl-2-chloroethanone (19 mg) according to an analogous synthetic method to Example 404 and purified by LC-MS, the title compound (3.5 mg) was obtained.

ESI-Mass; 529 [M$^+$+H]

Example 497

6-{2-{{4-[2-(1,4-Dioxa-8-azaspiro[4.5]dec-8-yl)ethoxy]benzyl}methylamino}-4-methoxyphenyl}-5,6,7,8-tetrahydronaphthalen-2-ol

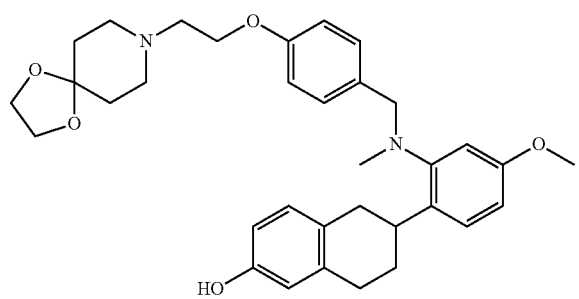 [SMILES: COc1ccc(C2CCc3cc(O)ccc3C2)c(N(C)Cc2ccc(OCCN3CCC4(CC3)OCCO4)cc2)c1]

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-1-(1,4-dioxa-8-azaspiro[4.5]dec-8-yl)ethanone (22 mg) according to an analogous synthetic method to Example 404 and purified by LC-MS, the title compound (13 mg) was obtained.

ESI-Mass; 559 [M$^+$+H]

Example 498

6-{4-Methoxy-2-{methyl[4-(2-morpholin-4-ylethoxy)benzyl]amino}phenyl}-5,6,7,8-tetrahydronaphthalen-2-ol

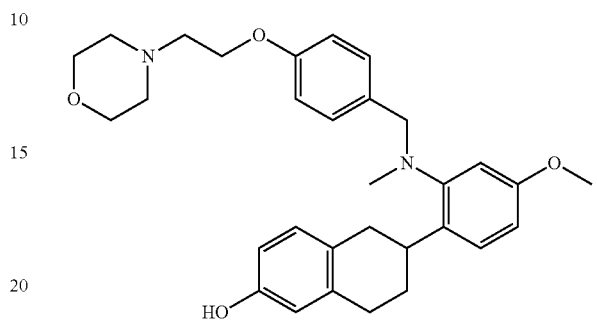

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-1-morpholin-4-ylethanone (16 mg) according to an analogous synthetic method to Example 404 and purified by LC-MS, the title compound (20 mg) was obtained.

ESI-Mass; 503 [M$^+$+H]

Example 499

6-{2-{{4-{2-[Bis(2-methoxyethyl)amino]ethoxy}benzyl}methylamino}-4-methoxyphenyl}-5,6,7,8-tetrahydronaphthalen-2-ol

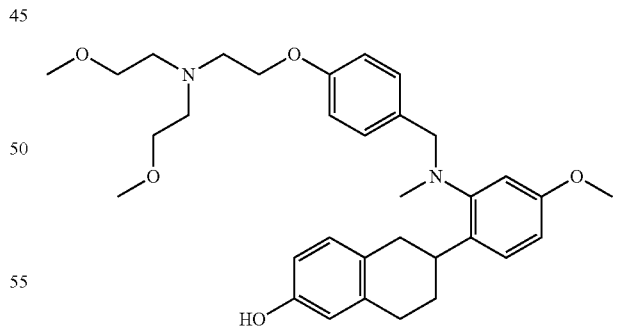

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-N,N-bis(2-methoxyethyl)acetamide (21 mg) according to an analogous synthetic method to Example 404 and purified by LC-MS, the title compound (13 mg) was obtained.

ESI-Mass; 549 [M$^+$+H]

Example 500

6-{4-Methoxy-2-{{4-{2-[(2-methoxyethyl)methylamino]ethoxy}benzyl}methylamino}phenyl}-5,6,7,8-tetrahydronaphthalen-2-ol

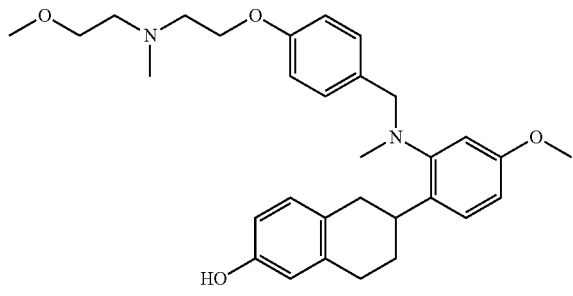

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-N-(2-methoxyethyl)-N-methylacetamide (16 mg) according to an analogous synthetic method to Example 404 and purified by LC-MS, the title compound (13 mg) was obtained.

ESI-Mass; 505 [M$^+$+H]

Example 501

6-{2-{{4-[2-(Cyclohexylmethylamino)ethoxy]benzyl}methylamino}-4-methoxyphenyl}-5,6,7,8-tetrahydronaphthalen-2-ol

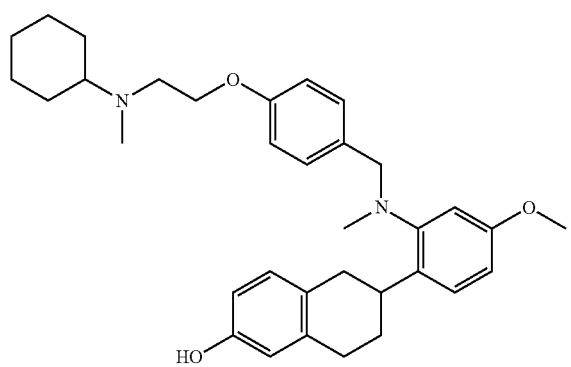 [SMILES: COc1ccc(C2CCc3cc(O)ccc3C2)c(N(C)Cc2ccc(OCCN(C)C3CCCCC3)cc2)c1]

Synthesized from pivalic acid 6-{2-[(4-hydroxybenzoyl)methylamino]-4-methoxyphenyl}-5,6,7,8-tetrahydronaphthalen-2-yl ester (25 mg) and 2-chloro-N-cyclohexyl-N-methylacetamide (19 mg) according to an analogous synthetic method to Example 404 and purified by LC-MS, the title compound (3.3 mg) was obtained.

ESI-Mass; 529 [M$^+$+H]

Example 502

6-{2-{{4-[2-(3,3-Dimethylpiperidin-1-yl)ethoxy]benzyl}methylamino}-4-methoxyphenyl}-5,6,7,8-tetrahydronaphthalen-2-ol

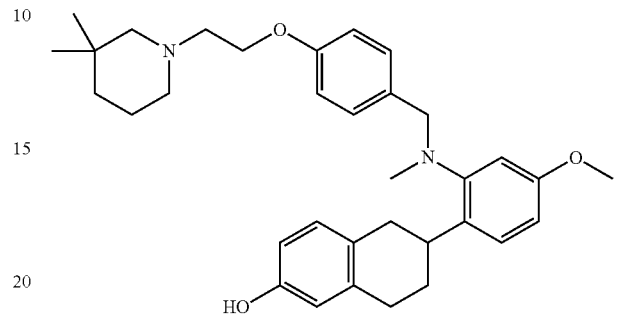

Synthesized from pivalic acid 6-{2-[(4-hydroxybenzoyl)methylamino]-4-methoxyphenyl}-5,6,7,8-tetrahydronaphthalen-2-yl ester (25 mg) and 2-bromo-1-(3,3-dimethylpiperidin-1-yl)ethanone (23 mg) according to an analogous synthetic method to Example 404 and purified by LC-MS, the title compound (16 mg) was obtained.

ESI-Mass; 529 [M$^+$+H]

Example 503

6-{4-Methoxy-2-{methyl {4-[2-(2,2,6,6-tetramethylpiperidin-1-yl)ethoxy]benzyl}amino}phenyl}-5,6,7,8-tetrahydronaphthalen-2-ol

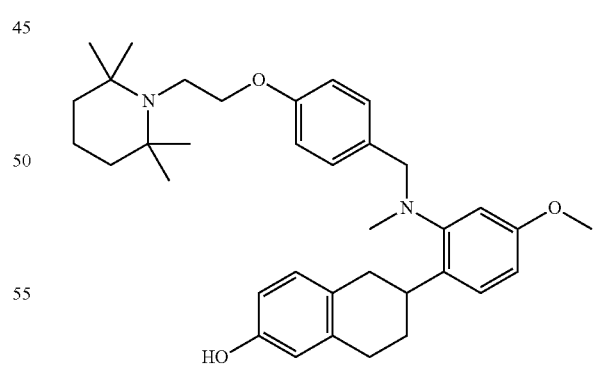

Synthesized from pivalic acid 6-{2-[(4-hydroxybenzoyl)methylamino]-4-methoxyphenyl}-5,6,7,8-tetrahydronaphthalen-2-yl ester (25 mg) and 2-bromo-1-(2,2,6,6-tetramethylpiperidin-1-yl)ethanone (26 mg) according to an analogous synthetic method to Example 404 and purified by LC-MS, the title compound (13 mg) was obtained.

ESI-Mass; 557 [M$^+$+H]

Example 504

6-{2-{{4-[2-(7-Azabicyclo[2.2.1]hept-7-yl)ethoxy]benzyl}methylamino}-4-methoxyphenyl}-5,6,7,8-tetrahydronaphthalen-2-ol

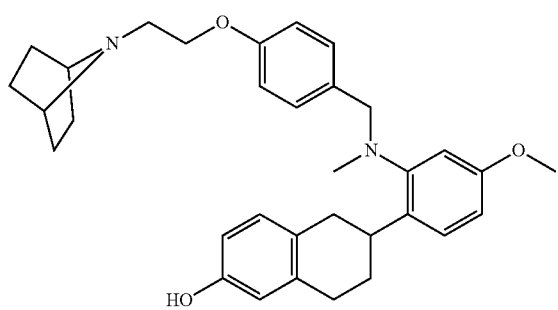 [SMILES: COc1ccc(C2CCc3cc(O)ccc3C2)c(N(C)Cc2ccc(OCCN3C4CCC3CC4)cc2)c1]

Synthesized from pivalic acid 6-{2-[(4-hydroxybenzoyl)methylamino]-4-methoxyphenyl}-5,6,7,8-tetrahydronaphthalen-2-yl ester (25 mg) and 1-(7-azabicyclo[2.2.1]hept-7-yl)-2-bromoethanone (22 mg) according to an analogous synthetic method to Example 404 and purified by LC-MS, the title compound (15 mg) was obtained.

ESI-Mass; 513 [M$^+$+H]

Example 505

6-{2-{[4-(2-Dimethylaminoethoxy)-3-fluorobenzyl]methylamino}-4-methoxyphenyl}-5,6,7,8-tetrahydronaphthalen-2-ol

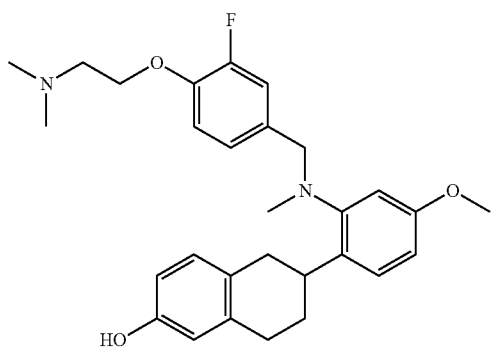

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-N,N-dimethylacetamide (9.6 mg) according to an analogous synthetic method to Example 404 and purified by LC-MS, the title compound (2.1 mg) was obtained.

ESI-Mass; 479 [M$^+$+H]

Example 506

6-{2-{[4-(2-Diethylaminoethoxy)-3-fluorobenzyl]methylamino}-4-methoxyphenyl}-5,6,7,8-tetrahydronaphthalen-2-ol

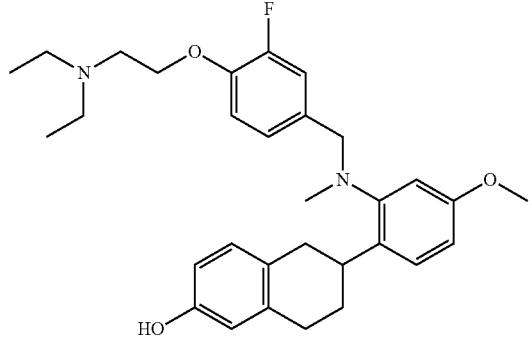 [SMILES: CCN(CC)CCOc1ccc(CN(C)c2cc(OC)ccc2C2CCc3cc(O)ccc3C2)cc1F]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-N,N-diethylacetamide (12 mg) according to an analogous synthetic method to Example 404 and purified by LC-MS, the title compound (6.7 mg) was obtained.

ESI-Mass; 507 [M$^+$+H]

Example 507

6-{2-{[4-(2-Azetidin-1-ylethoxy)-3-fluorobenzyl]methylamino}-4-methoxyphenyl}-5,6,7,8-tetrahydronaphthalen-2-ol

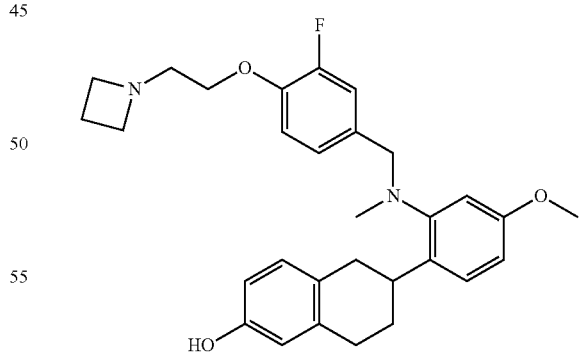

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 1-azetidin-1-yl-2-chloroethanone (11 mg) according to an analogous synthetic method to Example 404 and purified by LC-MS, the title compound (7.7 mg) was obtained.

ESI-Mass; 491 [M$^+$+H]

Example 508

6-{2-{[3-Fluoro-4-(2-pyrrolidin-1-ylethoxy)benzyl]methylamino}-4-methoxyphenyl}-5,6,7,8-tetrahydronaphthalen-2-ol

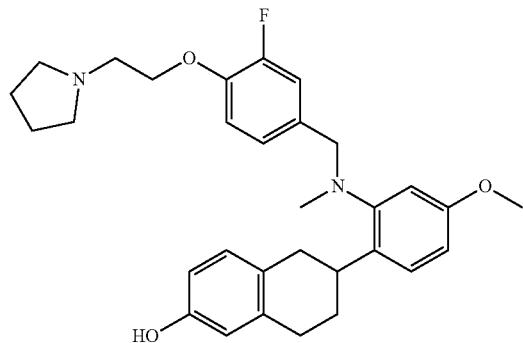 [SMILES: COc1ccc(C2CCc3cc(O)ccc3C2)c(N(C)Cc2ccc(OCCN3CCCC3)c(F)c2)c1]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-1-pyrrolidin-1-ylethanone (12 mg) according to an analogous synthetic method to Example 404 and purified by LC-MS, the title compound (7.7 mg) was obtained.

ESI-Mass; 505 [$M^+$+H]

Example 509

6-{2-{[3-Fluoro-4-(2-piperidin-1-ylethoxy)benzyl]methylamino}-4-methoxyphenyl}-5,6,7,8-tetrahydronaphthalen-2-ol

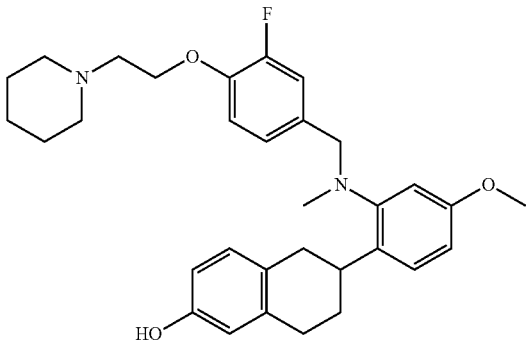 [SMILES: COc1ccc(C2CCc3cc(O)ccc3C2)c(N(C)Cc2ccc(OCCN3CCCCC3)c(F)c2)c1]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-1-piperidin-1-ylethanone (13 mg) according to an analogous synthetic method to Example 404 and purified by LC-MS, the title compound (2.2 mg) was obtained.

ESI-Mass; 519 [$M^+$+H]

Example 510

6-{2-{{3-Fluoro-4-[2-(4-methylpiperidin-1-yl)ethoxy]benzyl}methylamino}-4-methoxyphenyl}-5,6,7,8-tetrahydronaphthalen-2-ol

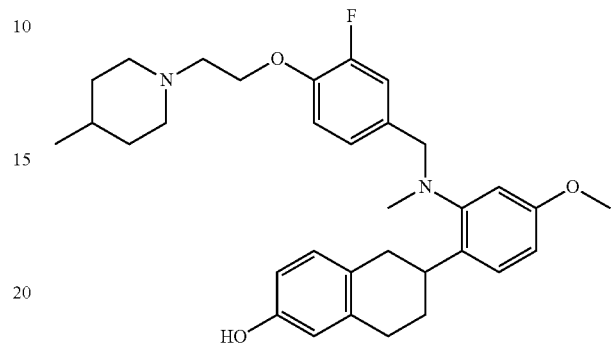

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-1-(4-methylpiperidin-1-yl)ethanone (14 mg) according to an analogous synthetic method to Example 404 and purified by LC-MS, the title compound (3.7 mg) was obtained.

ESI-Mass; 533 [$M^+$+H]

Example 511

6-{2-{[4-(2-Azepan-1-ylethoxy)-3-fluorobenzyl]methylamino}-4-methoxyphenyl}-5,6,7,8-tetrahydronaphthalen-2-ol

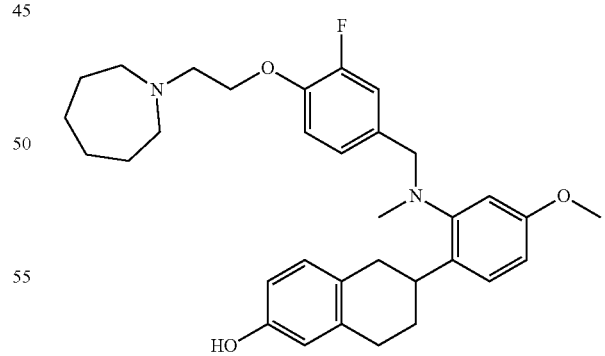

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 1-azepan-1-yl-2-chloroethanone (14 mg) according to an analogous synthetic method to Example 404 and purified by LC-MS, the title compound (7.5 mg) was obtained.

ESI-Mass; 533 [$M^+$+H]

Example 512

6-{2-{[4-(2-Azocan-1-ylethoxy)-3-fluorobenzyl]methylamino}-4-methoxyphenyl}-5,6,7,8-tetrahydronaphthalen-2-ol

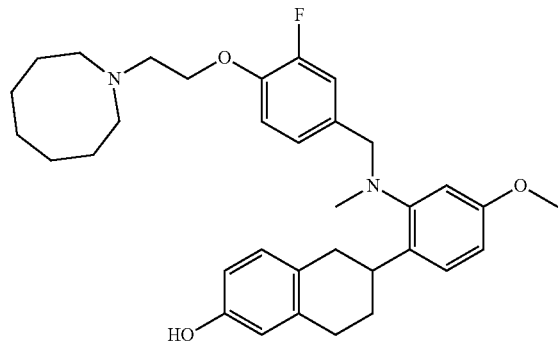 [SMILES: COc1ccc(C2CCc3cc(O)ccc3C2)c(N(C)Cc2ccc(OCCN3CCCCCCC3)c(F)c2)c1]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 1-azocan-1-yl-2-chloroethanone (15 mg) according to an analogous synthetic method to Example 404 and purified by LC-MS, the title compound (6.9 mg) was obtained.

ESI-Mass; 547 [M$^+$+H]

Example 513

6-{2-{{4-[2-(1,4-Dioxa-8-azaspiro[4.5]dec-8-yl)ethoxy]-3-fluorobenzyl}methylamino}-4-methoxyphenyl}-5,6,7,8-tetrahydronaphthalen-2-ol

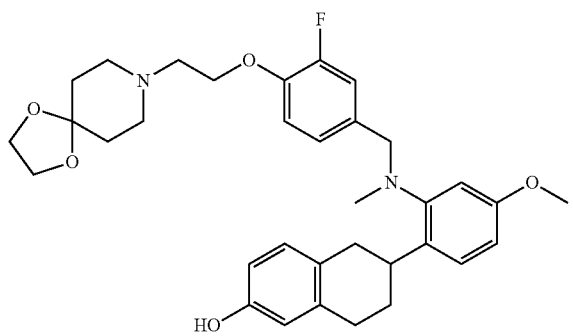 [SMILES: COc1ccc(C2CCc3cc(O)ccc3C2)c(N(C)Cc2ccc(OCCN3CCC4(CC3)OCCO4)c(F)c2)c1]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-1-(1,4-dioxa-8-azaspiro[4.5]dec-8-yl)ethanone (17 mg) according to an analogous synthetic method to Example 404 and purified by LC-MS, the title compound (8.4 mg) was obtained.

ESI-Mass; 577 [M$^+$+H]

Example 514

6-{2-{[3-Fluoro-4-(2-morpholin-4-ylethoxy)benzyl]methylamino}-4-methoxyphenyl}-5,6,7,8-tetrahydronaphthalen-2-ol

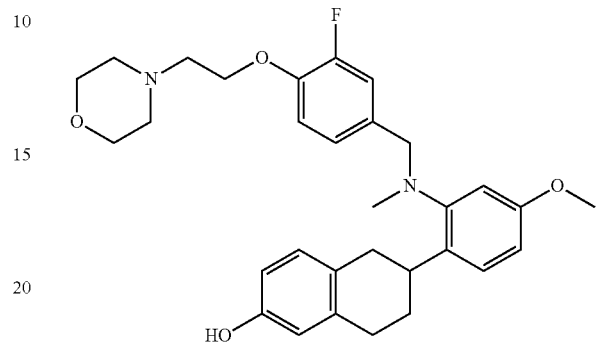

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-1-morpholin-4-ylethanone (13 mg) according to an analogous synthetic method to Example 404 and purified by LC-MS, the title compound (8.2 mg) was obtained.

ESI-Mass; 521 [M$^+$+H]

Example 515

6-{2-{{4-{2-[Bis(2-methoxyethyl)amino]ethoxy}-3-fluorobenzyl}methylamino}-4-methoxyphenyl}-5,6,7,8-tetrahydronaphthalen-2-ol

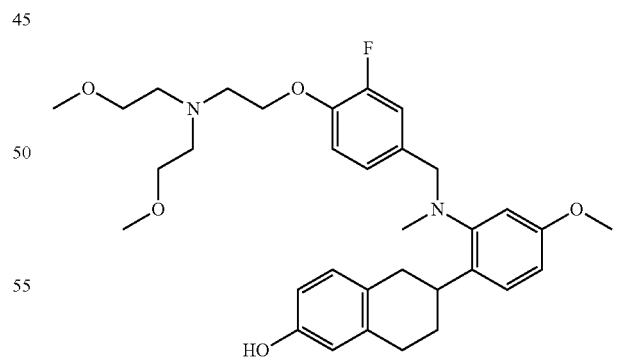

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-N,N-bis(2-methoxyethyl)acetamide (17 mg) according to an analogous synthetic method to Example 404 and purified by LC-MS, the title compound (5.1 mg) was obtained.

ESI-Mass; 567 [M$^+$+H]

Example 516

6-{2-{{3-Fluoro-4-{2-[(2-methoxyethyl)methylamino]ethoxy}benzyl}methylamino}-4-methoxyphenyl}-5,6,7,8-tetrahydronaphthalen-2-ol

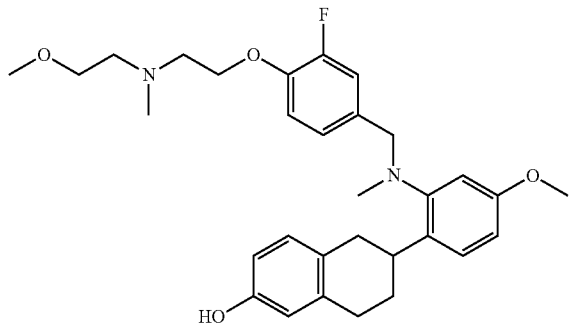

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-N-(2-methoxyethyl)-N-methylacetamide (13 mg) according to an analogous synthetic method to Example 404 and purified by LC-MS, the title compound (7.3 mg) was obtained.

ESI-Mass; 523 [M$^+$+H]

Example 517

6-{2-{{4-[2-(Cyclohexylmethylamino)ethoxy]-3-fluorobenzyl}methylamino}-4-methoxyphenyl}-5,6,7,8-tetrahydronaphthalen-2-ol

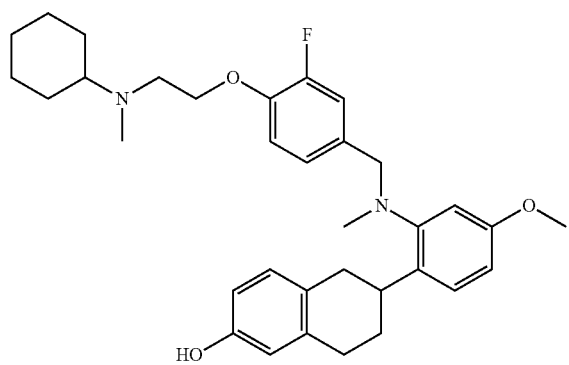 [SMILES: COc1ccc(C2CCc3cc(O)ccc3C2)c(N(C)Cc2ccc(OCCN(C)C3CCCCC3)c(F)c2)c1]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-chloro-N-cyclohexyl-N-methylacetamide (15 mg) according to an analogous synthetic method to Example 404 and purified by LC-MS, the title compound (3.1 mg) was obtained.

ESI-Mass; 547 [M$^+$+H]

Example 518

6-{2-{{4-[2-(3,3-Dimethylpiperidin-1-yl)ethoxy]-3-fluorobenzyl}methylamino}-4-methoxyphenyl}-5,6,7,8-tetrahydronaphthalen-2-ol

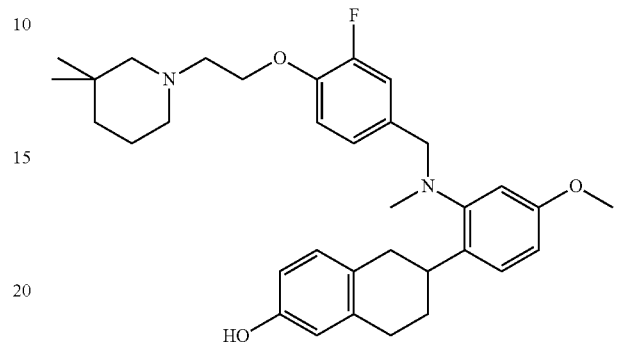

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-bromo-1-(3,3-dimethylpiperidin-1-yl)ethanone (19 mg) according to an analogous synthetic method to Example 404 and purified by LC-MS, the title compound (11 mg) was obtained.

ESI-Mass; 547 [M$^+$+H]

Example 519

6-{2-{{3-Fluoro-4-[2-(2,2,6,6-tetramethylpiperidin-1-yl)ethoxy]benzyl}methylamino}-4-methoxyphenyl}-5,6,7,8-tetrahydronaphthalen-2-ol

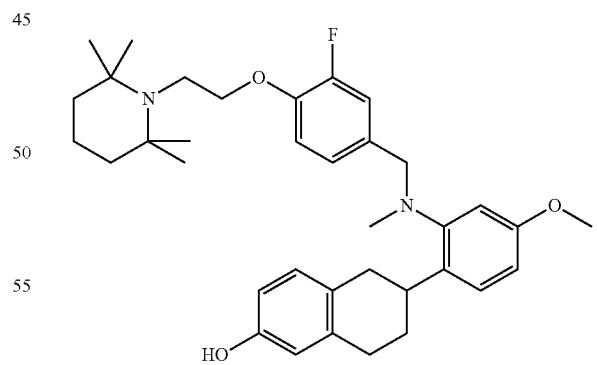

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 2-bromo-1-(2,2,6,6-tetramethylpiperidin-1-yl)ethanone (21 mg) according to an analogous synthetic method to Example 404 and purified by LC-MS, the title compound (7.7 mg) was obtained.

ESI-Mass; 575 [M$^+$+H]

Example 520

6-{2-{{4-[2-(7-Azabicyclo[2.2.1]hept-7-yl)ethoxy]-3-fluorobenzyl}methylamino}-4-methoxyphenyl}-5,6,7,8-tetrahydronaphthalen-2-ol

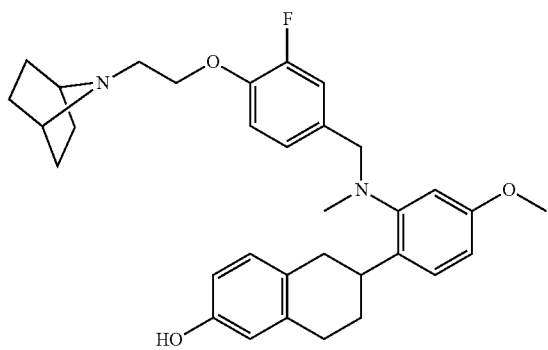 [SMILES: COc1ccc(C2CCc3cc(O)ccc3C2)c(N(C)Cc2ccc(OCCN3C4CCC3CC4)c(F)c2)c1]

Synthesized from pivalic acid 6-{2-[(3-fluoro-4-hydroxybenzoyl)methylamino]-4-methoxyphenyl}-5,6,7,8-tetrahydronaphthalen-2-yl ester (20 mg) and 1-(7-azabicyclo[2.2.1]hept-7-yl)-2-bromoethanone (17 mg) according to an analogous synthetic method to Example 404 and purified by LC-MS, the title compound (11 mg) was obtained.

ESI-Mass; 531 [M$^+$+H]

Example 521

6-{2-{[4-(2-Diethylaminoethoxy)benzyl]propylamino}-4-methoxyphenyl}-5,6,7,8-tetrahydronaphthalen-2-ol

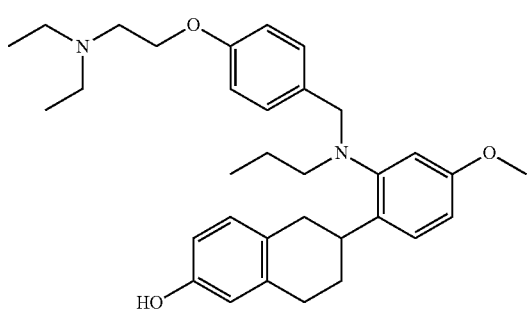 [SMILES: CCCN(Cc1ccc(OCCN(CC)CC)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (30 mg) and 2-chloro-N,N-diethylacetamide (18 mg) according to an analogous synthetic method to Example 404 and purified by LC-MS, the title compound (23 mg) was obtained.

ESI-Mass; 517 [M$^+$+H]

Example 522

6-{4-Methoxy-2-{propyl[4-(2-pyrrolidin-1-ylethoxy)benzyl]amino}phenyl}-5,6,7,8-tetrahydronaphthalen-2-ol

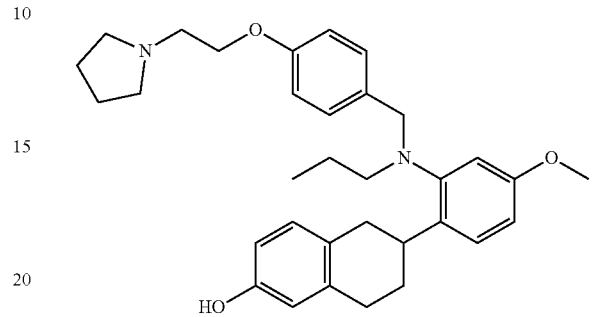

Synthesized from pivalic acid 6-{2-[(4-hydroxybenzoyl)propylamino]-4-methoxyphenyl}-5,6,7,8-tetrahydronaphthalen-2-yl ester (30 mg) and 2-chloro-1-pyrrolidin-1-ylethanone (17 mg) according to an analogous synthetic method to Example 404 and purified by LC-MS, the title compound (24 mg) was obtained.

ESI-Mass; 515 [M$^+$+H]

Example 523

6-{4-Methoxy-2-{[4-(2-piperidin-1-ylethoxy)benzyl]propylamino}phenyl}-5,6,7,8-tetrahydronaphthalen-2-ol

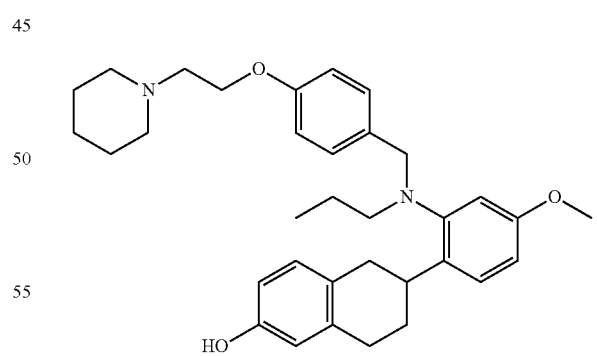

Synthesized from pivalic acid 6-{2-[(4-hydroxybenzoyl)propylamino]-4-methoxyphenyl}-5,6,7,8-tetrahydronaphthalen-2-yl ester (30 mg) and 2-chloro-1-piperidin-1-ylethanone (19 mg) according to an analogous synthetic method to Example 404 and purified by LC-MS, the title compound (24 mg) was obtained.

ESI-Mass; 529 [M$^+$+H]

Example 524

6-{4-Methoxy-2-{[4-(2-morpholin-4-ylethoxy)benzyl]propylamino}phenyl}-5,6,7,8-tetrahydronaphthalen-2-ol

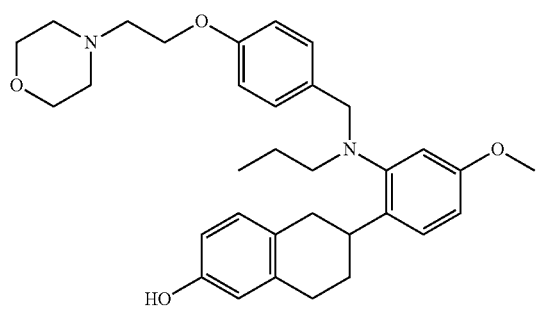 [SMILES: CCCN(Cc1ccc(OCCN2CCOCC2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (30 mg) and 2-chloro-1-morpholin-4-ylethanone (19 mg) according to an analogous synthetic method to Example 404 and purified by LC-MS, the title compound (27 mg) was obtained.

ESI-Mass; 531 [M$^+$+H]

Example 525

6-{4-Methoxy-2-{[4-(1-methyl-2-piperidin-1-ylethoxy)benzyl]propylamino}phenyl}-5,6,7,8-tetrahydronaphthalen-2-ol

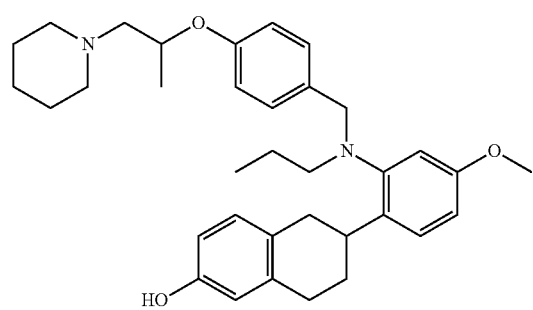 [SMILES: CCCN(Cc1ccc(OC(C)CN2CCCCC2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (30 mg) and 2-chloro-1-piperidin-1-ylpropan-1-one (21 mg) according to an analogous synthetic method to Example 404 and purified by LC-MS, the title compound (9.4 mg) was obtained.

ESI-Mass; 543 [M$^+$+H]

Example 526

6-{2-{[4-(2-Dimethylaminoethoxy)benzyl]propylamino}-4-methoxyphenyl}-5,6,7,8-tetrahydronaphthalen-2-ol

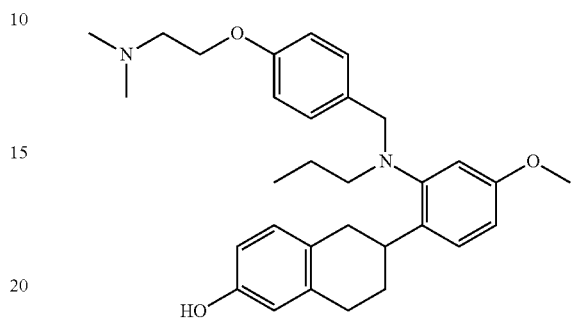

Synthesized from pivalic acid 6-{2-[4-hydroxybenzoyl)propylamino]-4-methoxyphenyl}-5,6,7,8-tetrahydronaphthalen-2-yl ester (30 mg) and 2-chloro-N,N-dimethylacetamide (14 mg) according to an analogous synthetic method to Example 404 and purified by LC-MS, the title compound (16 mg) was obtained.

ESI-Mass; 489 [M$^+$+H]

Example 527

6-{4-Methoxy-2-{{4-[2-(4-methylpiperidin-1-yl)ethoxy]benzyl}propylamino}phenyl}-5,6,7,8-tetrahydronaphthalen-2-ol

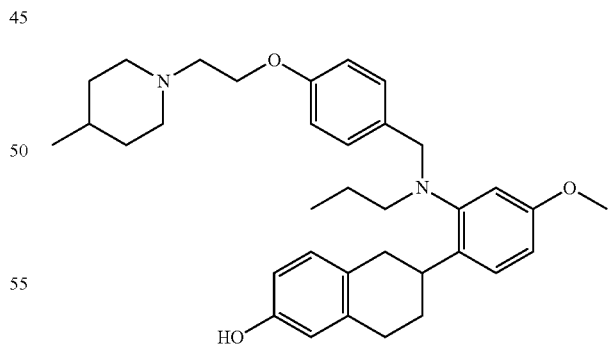

Synthesized from pivalic acid 6-{2-[(4-hydroxybenzoyl)propylamino]-4-methoxyphenyl}-5,6,7,8-tetrahydronaphthalen-2-yl ester (30 mg) and 2-chloro-1-(4-methylpiperidin-1-yl)ethanone (21 mg) according to an analogous synthetic method to Example 404 and purified by LC-MS, the title compound (19 mg) was obtained.

ESI-Mass; 543 [M$^+$+H]

Example 528

6-{2-{[4-(2-Azepan-1-yl-ethoxy)benzyl]propylamino}-4-methoxyphenyl}-5,6,7,8-tetrahydronaphthalen-2-ol

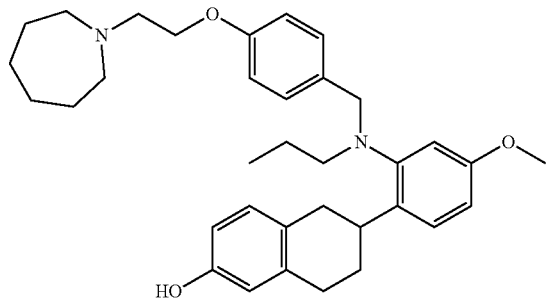 [SMILES: CCCN(Cc1ccc(OCCN2CCCCCC2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (30 mg) and 1-(2-chloroethyl)azepane (23 mg) according to an analogous synthetic method to Example 404 and purified by NH silica gel column chromatography (hexane-ethyl acetate system), the title compound (9 mg) was obtained.

$^1$H-NMR (400 MHz, CDCl$_3$); δ (ppm): 0.79 (t, 3H), 1.35-1.43 (m, 2H), 1.55-1.80 (m, 12H), 2.66 (d, 2H), 2.74-2.85 (m, 6H), 2.94 (t, 2H), 3.60-3.70 (m, 1H), 3.78 (s, 3H), 3.93 (s, 2H), 4.03 (t, 2H), 6.58-6.62 (m, 2H), 6.68 (d, 1H), 6.73-6.77 (m, 3H), 6.88 (d, 1H), 7.08-7.15 (m, 3H).

ESI-Mass; 543 [M$^+$+H]

Example 529

6-{2-{[4-(2-Azocan-1-ylethoxy)benzyl]propylamino}-4-methoxyphenyl}-5,6,7,8-tetrahydronaphthalen-2-ol

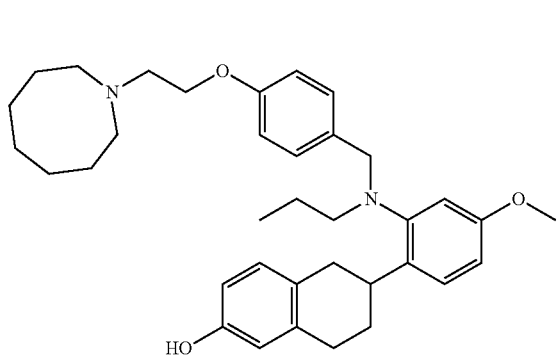 [SMILES: CCCN(Cc1ccc(OCCN2CCCCCCC2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (30 mg) and 1-azocan-1-yl-2-chloroethanone (22 mg) according to an analogous synthetic method to Example 404 and purified by LC-MS, the title compound (21 mg) was obtained.

ESI-Mass; 557 [M$^+$+H]

Example 530

6-{2-{[4-(2-Azetidin-1-ylethoxy)benzyl]propylamino}-4-methoxyphenyl}-5,6,7,8-tetrahydronaphthalen-2-ol

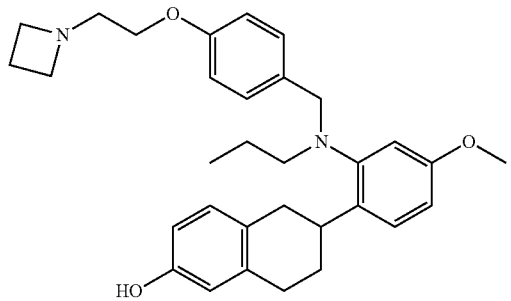 [SMILES: CCCN(Cc1ccc(OCCN2CCC2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (27 mg) and 1-azetidin-1-yl-2-chloroethanone (15 mg) according to an analogous synthetic method to Example 404 and purified by LC-MS, the title compound (2.3 mg) was obtained.

ESI-Mass; 501 [M$^+$+H]

Example 531

6-{2-{{4-[2-(3-Azabicyclo[3.2.2]non-3-yl)ethoxy]benzyl}propylamino}-4-methoxyphenyl}-5,6,7,8-tetrahydronaphthalen-2-ol

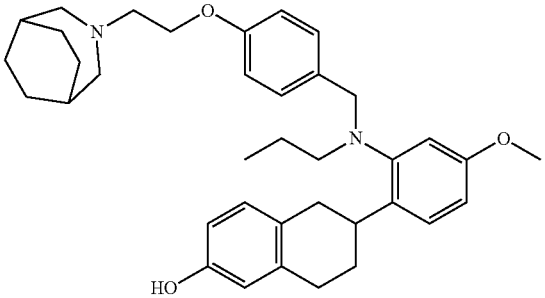 [SMILES: CCCN(Cc1ccc(OCCN2CC3CCC(CC3)C2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (21 mg) and 1-(3-azabicyclo[3.2.2]non-3-yl)-2-chloroethanone (17 mg) according to an analogous synthetic method to Example 404 and purified by LC-MS, the title compound (9.7 mg) was obtained.

ESI-Mass; 569 [M$^+$+H]

Example 532

6-{2-{{4-[2-(4-Ethylpiperazin-1-yl)ethoxy]benzyl}propylamino}-4-methoxyphenyl}-5,6,7,8-tetrahydronaphthalen-2-ol

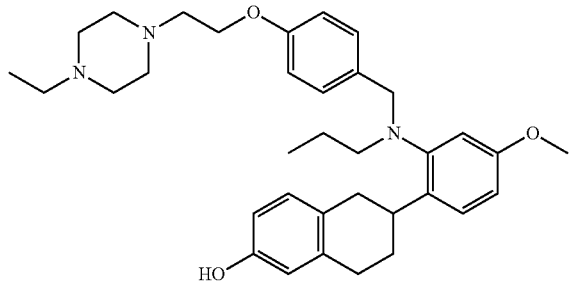 [SMILES: CCCN(Cc1ccc(OCCN2CCN(CC)CC2)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (21 mg) and 2-chloro-1-(4-ethylpiperazin-1-yl)ethanone (16 mg) according to an analogous synthetic method to Example 404 and purified by LC-MS, the title compound (12 mg) was obtained.

ESI-Mass; 558 [M$^+$+H]

Example 533

6-{2-{{4-[2-(1,4-Dioxa-8-azaspiro[4.5]dec-8-yl)ethoxy]benzyl}propylamino}-4-methoxyphenyl}-5,6,7,8-tetrahydronaphthalen-2-ol

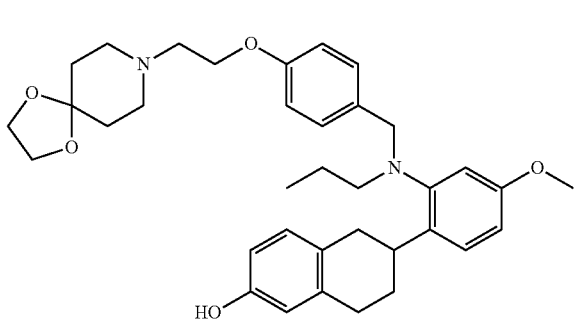 [SMILES: CCCN(Cc1ccc(OCCN2CCC3(CC2)OCCO3)cc1)c1cc(OC)ccc1C1CCc2cc(O)ccc2C1]

Synthesized from pivalic acid 6-{2-[(4-hydroxybenzoyl)propylamino]-4-methoxyphenyl}-5,6,7,8-tetrahydronaphthalen-2-yl ester (21 mg) and 2-chloro-1-(1,4-dioxa-8-azaspiro[4.5]dec-8-yl)ethanone (18 mg) according to an analogous synthetic method to Example 404 and purified by LC-MS, the title compound (9.1 mg) was obtained.

ESI-Mass; 587 [M$^+$+H]

Example 534

6-{2-{{4-{2-[Bis(2-methoxyethyl)amino]ethoxy}benzyl}propylamino}-4-methoxyphenyl}-5,6,7,8-tetrahydronaphthalen-2-ol

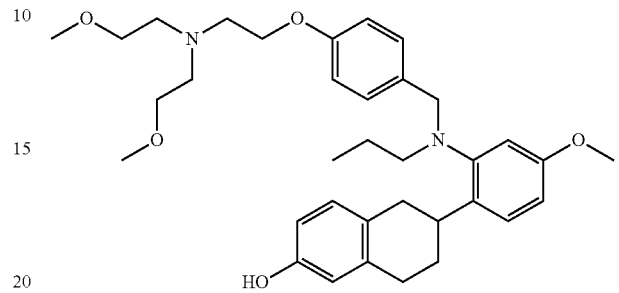

Synthesized from pivalic acid 6-{2-[(4-hydroxybenzoyl)propylamino]-4-methoxyphenyl}-5,6,7,8-tetrahydronaphthalen-2-yl ester (21 mg) and 2-chloro-N,N-bis(2-methoxyethyl)acetamide (17 mg) according to an analogous synthetic method to Example 404 and purified by LC-MS, the title compound (3.7 mg) was obtained.

ESI-Mass; 577 [M$^+$+H]

Example 535

6-{2-{{4-[2-(Cyclohexylmethylamino)ethoxy]benzyl}propylamino}-4-methoxyphenyl}-5,6,7,8-tetrahydronaphthalen-2-ol

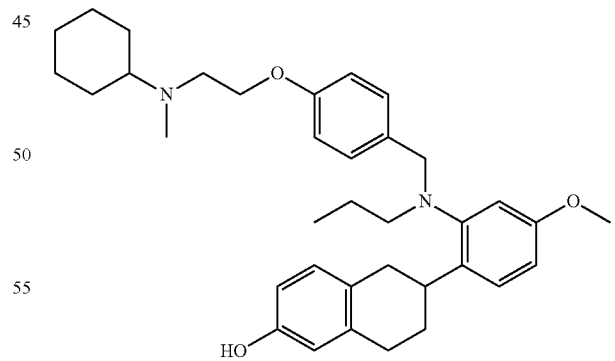

Synthesized from pivalic acid 6-{2-[(4-hydroxybenzoyl)propylamino]-4-methoxyphenyl}-5,6,7,8-tetrahydronaphthalen-2-yl ester (21 mg) and 2-chloro-N-cyclohexyl-N-methylacetamide (16 mg) according to an analogous synthetic method to Example 404 and purified by LC-MS, the title compound (6.0 mg) was obtained.

ESI-Mass; 557 [M$^+$+H]

Example 536

6-{4-Methoxy-2-{{4-{2-[(2-methoxyethyl)methylamino]ethoxy}benzyl}propylamino}phenyl}-5,6,7,8-tetrahydronaphthalen-2-ol

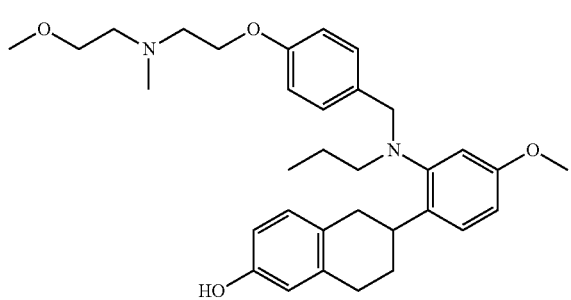

Synthesized from pivalic acid 6-{2-[(4-hydroxybenzoyl)propylamino]-4-methoxyphenyl}-5,6,7,8-tetrahydronaphthalen-2-yl ester (21 mg) and 2-chloro-N-(2-methoxyethyl)-N-methylacetamide (14 mg) according to an analogous synthetic method to Example 404 and purified by LC-MS, the title compound (15 mg) was obtained.

ESI-Mass; 533 [M$^+$+H]

Example 537

6-{2-{[4-(2-Dimethylaminoethoxy)benzyl]ethylamino}-4,5-dimethoxyphenyl}-5,6,7,8-tetrahydronaphthalen-2-ol

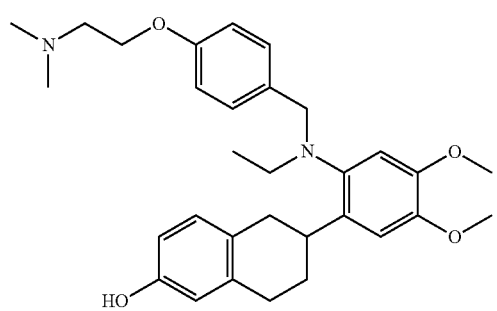

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N,N-dimethylacetamide (8.5 mg) according to an analogous synthetic method to Example 404 and purified by LC-MS, the title compound (2.7 mg) was obtained.

ESI-Mass; 505 [M$^+$+H]

Example 538

6-{2-{Ethyl{4-[2-(ethylmethylamino)ethoxy]benzyl}amino}-4,5-dimethoxyphenyl}-5,6,7,8-tetrahydronaphthalen-2-ol

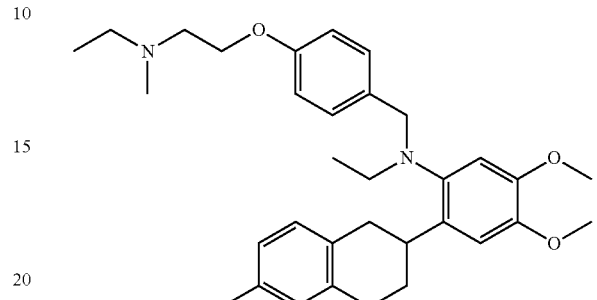

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N-ethyl-N-methylacetamide (9.5 mg) according to an analogous synthetic method to Example 404 and purified by LC-MS, the title compound (1.6 mg) was obtained.

ESI-Mass; 519 [M$^+$+H]

Example 539

6-{2-{Ethyl{4-[2-(methylpropylamino)ethoxy]benzyl}amino}-4,5-dimethoxyphenyl}-5,6,7,8-tetrahydronaphthalen-2-ol

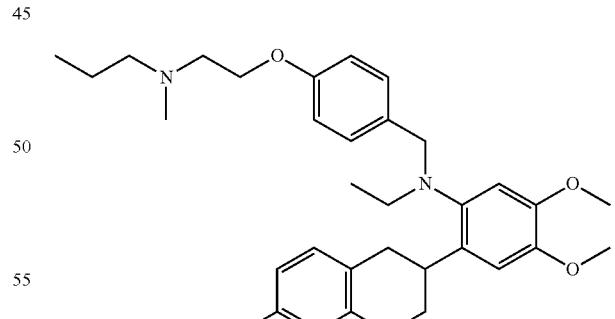

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N-methyl-N-propyl acetamide (11 mg) according to an analogous synthetic method to Example 404 and purified by LC-MS, the title compound (0.9 mg) was obtained.

ESI-Mass; 533 [M$^+$+H]

Example 540

6-{2-{Ethyl{4-[2-(isopropylmethylamino)ethoxy] benzyl}amino}-4,5-dimethoxyphenyl}-5,6,7,8-tetrahydronaphthalen-2-ol

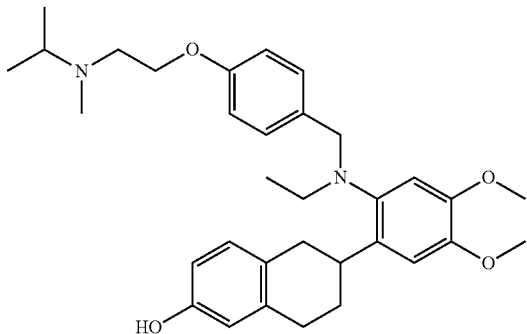 [SMILES: CCN(Cc1ccc(OCCN(C)C(C)C)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N-isopropyl-N-methylacetamide (11 mg) according to an analogous synthetic method to Example 404 and purified by LC-MS, the title compound (2.1 mg) was obtained.

ESI-Mass; 533 [M$^+$+H]

Example 541

6-{2-{{4-[2-(Allylmethylamino)ethoxy] benzyl}ethylamino}-4,5-dimethoxyphenyl}-5,6,7,8-tetrahydronaphthalen-2-ol

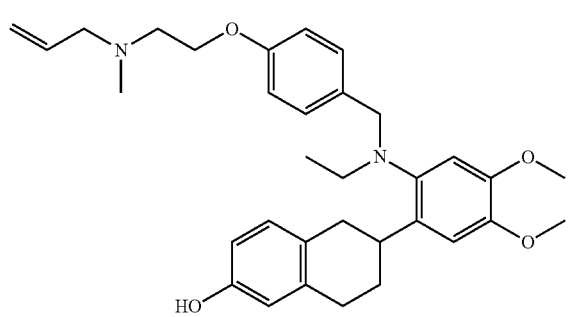 [SMILES: C=CCN(C)CCOc1ccc(CN(CC)c2cc(OC)c(OC)cc2C2CCc3cc(O)ccc3C2)cc1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and N-allyl-2-chloro-N-methylacetamide (11 mg) according to an analogous synthetic method to Example 404 and purified by LC-MS, the title compound (1.7 mg) was obtained.

ESI-Mass; 531 [M$^+$+H]

Example 542

6-{2-{{4-[2-(Butylmethylamino)ethoxy] benzyl}ethylamino}-4,5-dimethoxyphenyl}-5,6,7,8-tetrahydronaphthalen-2-ol

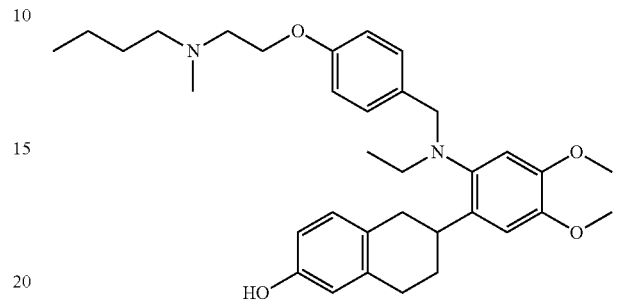

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and N-butyl-2-chloro-N-methylacetamide (12 mg) according to an analogous synthetic method to Example 404 and purified by LC-MS, the title compound (1.6 mg) was obtained.

ESI-Mass; 547 [M$^+$+H]

Example 543

6-{2-{Ethyl{4-[2-(isobutylmethylamino)ethoxy] benzyl}amino}-4,5-dimethoxyphenyl}-5,6,7,8-tetrahydronaphthalen-2-ol

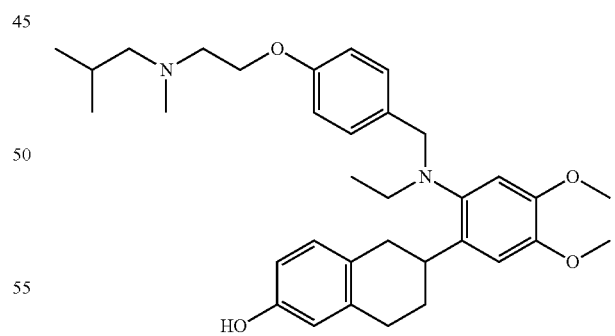

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N-isobutyl-N-methylacetamide (12 mg) according to an analogous synthetic method to Example 404 and purified by LC-MS, the title compound (2.1 mg) was obtained.

ESI-Mass; 547 [M$^+$+H]

Example 544

6-{2-{{4-[2-(tert-Butylmethylamino)ethoxy]benzyl}ethylamino}-4,5-dimethoxyphenyl}-5,6,7,8-tetrahydronaphthalen-2-ol

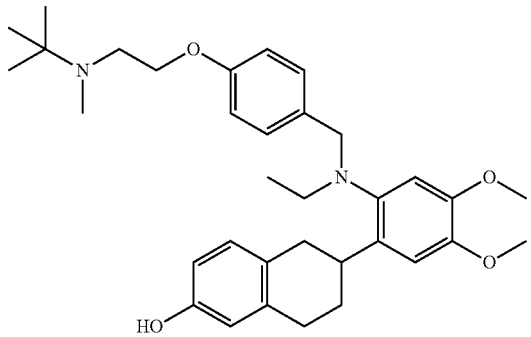 [SMILES: CCN(Cc1ccc(OCCN(C)C(C)(C)C)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and N-tert-butyl-2-chloro-N-methylacetamide (12 mg) according to an analogous synthetic method to Example 404 and purified by LC-MS, the title compound (2.4 mg) was obtained.

ESI-Mass; 547 [M$^+$+H]

Example 545

6-{2-{{4-[2-(Cyclopropylmethylamino)ethoxy]benzyl}ethylamino}-4,5-dimethoxyphenyl}-5,6,7,8-tetrahydronaphthalen-2-ol

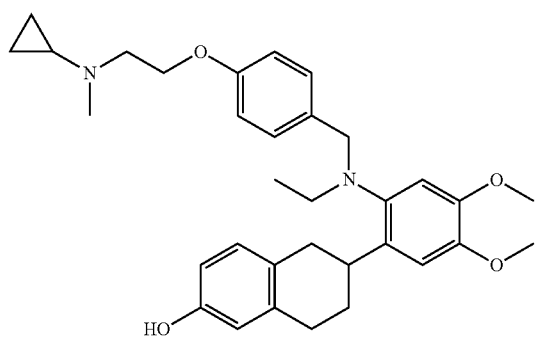 [SMILES: CCN(Cc1ccc(OCCN(C)C2CC2)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N-cyclopropyl-N-methylacetamide (10 mg) according to an analogous synthetic method to Example 404 and purified by LC-MS, the title compound (2.4 mg) was obtained.

ESI-Mass; 531 [M$^+$+H]

Example 546

6-{2-{[4-(2-Diethylaminoethoxy)benzyl]ethylamino}-4,5-dimethoxyphenyl}-5,6,7,8-tetrahydronaphthalen-2-ol

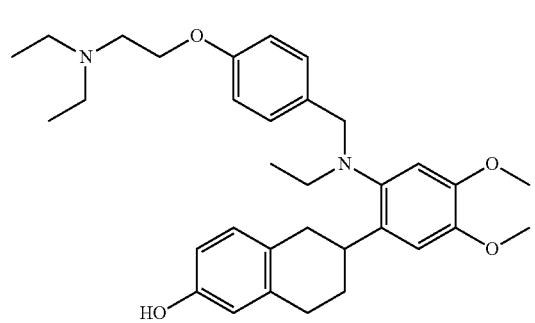

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N,N-diethylacetamide (11 mg) according to an analogous synthetic method to Example 404 and purified by LC-MS, the title compound (1.3 mg) was obtained.

ESI-Mass; 533 [M$^+$+H]

Example 547

6-{2-{[4-(2-Azetidin-1-ylethoxy)benzyl]ethylamino}-4,5-dimethoxyphenyl}-5,6,7,8-tetrahydronaphthalen-2-ol

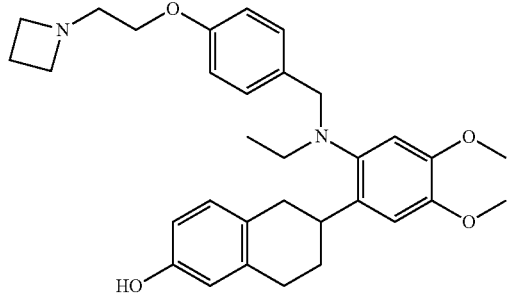 [SMILES: CCN(Cc1ccc(OCCN2CCC2)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 1-azetidin-1-yl-2-chloroethanone (9.4 mg) according to an analogous synthetic method to Example 404 and purified by LC-MS, the title compound (0.9 mg) was obtained.

ESI-Mass; 517 [M$^+$+H]

Example 548

6-{2-{Ethyl[4-(2-pyrrolidin-1-ylethoxy)benzyl]amino}-4,5-dimethoxyphenyl}-5,6,7,8-tetrahydronaphthalen-2-ol

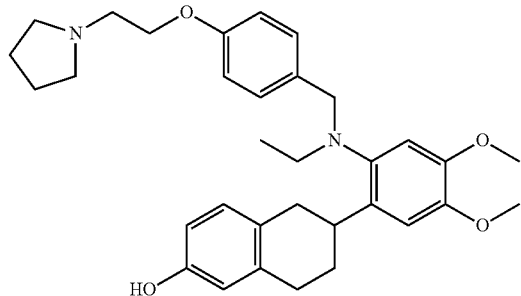

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-1-pyrrolidin-1-ylethanone (10 mg) according to an analogous synthetic method to Example 404 and purified by LC-MS, the title compound (2.2 mg) was obtained.

ESI-Mass; 531 [M$^+$+H]

Example 549

6-{2-{Ethyl[4-(2-piperidin-1-ylethoxy)benzyl]amino}-4,5-dimethoxyphenyl}-5,6,7,8-tetrahydronaphthalen-2-ol

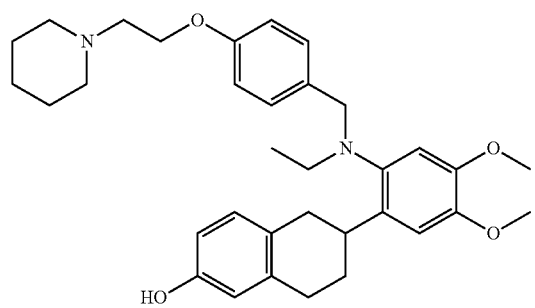 [SMILES: CCN(Cc1ccc(OCCN2CCCCC2)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-1-piperidin-1-ylethanone (11 mg) according to an analogous synthetic method to Example 404 and purified by LC-MS, the title compound (0.7 mg) was obtained.

ESI-Mass; 545 [M$^+$+H]

Example 550

6-{2-{Ethyl{4-[2-(4-methylpiperidin-1-yl)ethoxy]benzyl}amino}-4,5-dimethoxyphenyl}-5,6,7,8-tetrahydronaphthalen-2-ol

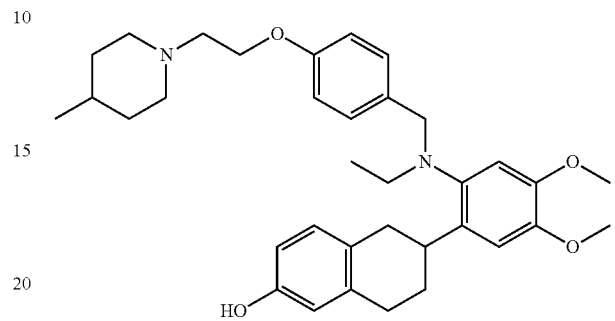

Synthesized from pivalic acid 6-{2-[ethyl(4-hydroxybenzoyl)amino]-4,5-dimethoxyphenyl}-5,6,7,8-tetrahydronaphthalen-2-yl ester (18.6 mg) and 2-chloro-1-(4-methylpiperidin-1-yl)ethanone (12 mg) according to an analogous synthetic method to Example 404 and purified by LC-MS, the title compound (2.2 mg) was obtained.

ESI-Mass; 559 [M$^+$+H]

Example 551

6-{2-{{4-[2-(3,3-Dimethylpiperidin-1-yl)ethoxy]benzyl}ethylamino}-4,5-dimethoxyphenyl}-5,6,7,8-tetrahydronaphthalen-2-ol

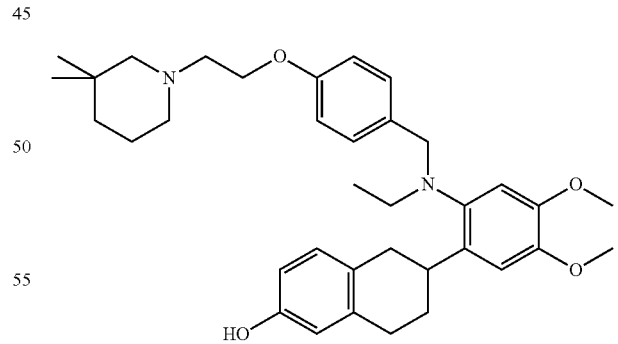

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-bromo-1-(3,3-dimethylpiperidin-1-yl)ethanone (16 mg) according to an analogous synthetic method to Example 404 and purified by LC-MS, the title compound (2.1 mg) was obtained.

ESI-Mass; 573 [M$^+$+H]

Example 552

6-{2-{Ethyl{4-[2-(2,2,6,6-tetramethylpiperidin-1-yl)ethoxy]benzyl}amino}-4,5-dimethoxyphenyl}-5,6,7,8-tetrahydronaphthalen-2-ol

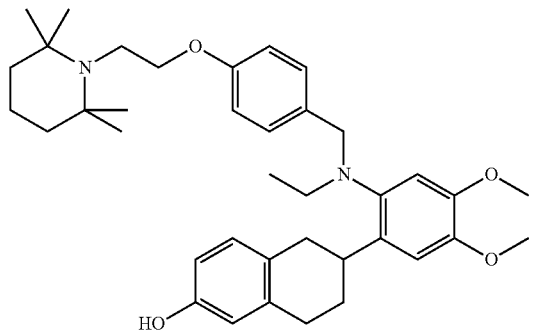 [SMILES: CCN(Cc1ccc(OCCN2C(C)(C)CCCC2(C)C)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-bromo-1-(2,2,6,6-tetramethylpiperidin-1-yl)ethanone (18 mg) according to an analogous synthetic method to Example 404 and purified by LC-MS, the title compound (2.4 mg) was obtained.

ESI-Mass; 601 [M$^+$+H]

Example 553

6-{2-{[4-(2-Azocan-1-ylethoxy)benzyl]ethylamino}-4,5-dimethoxyphenyl}-5,6,7,8-tetrahydronaphthalen-2-ol

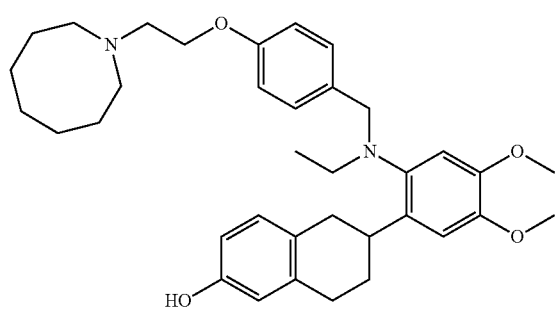 [SMILES: CCN(Cc1ccc(OCCN2CCCCCCC2)cc1)c1cc(OC)c(OC)cc1C1CCc2cc(O)ccc2C1]

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 1-azocan-1-yl-2-chloroethanone (13 mg) according to an analogous synthetic method to Example 404 and purified by LC-MS, the title compound (1.2 mg) was obtained.

ESI-Mass; 573 [M$^+$+H]

Example 554

6-{2-{{4-[2-(7-Azabicyclo[2.2.1]hept-7-yl)ethoxy]benzyl}ethylamino}-4,5-dimethoxyphenyl}-5,6,7,8-tetrahydronaphthalen-2-ol

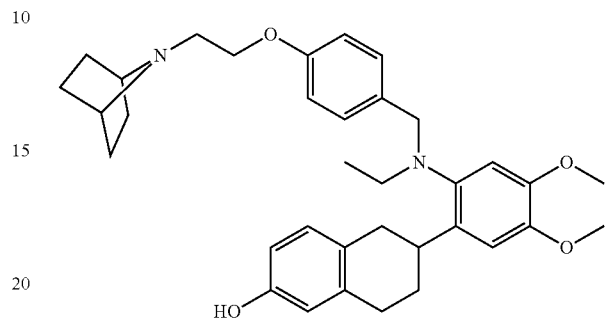

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 1-(7-azabicyclo[2.2.1]hept-7-yl)-2-bromoethanone (15 mg) according to an analogous synthetic method to Example 404 and purified by LC-MS, the title compound (1.7 mg) was obtained.

ESI-Mass; 557 [M$^+$+H]

Example 555

6-{2-{Ethyl{4-{2-[(2-methoxyethyl)methylamino]ethoxy}benzyl}amino}-4,5-dimethoxyphenyl}-5,6,7,8-tetrahydronaphthalen-2-ol

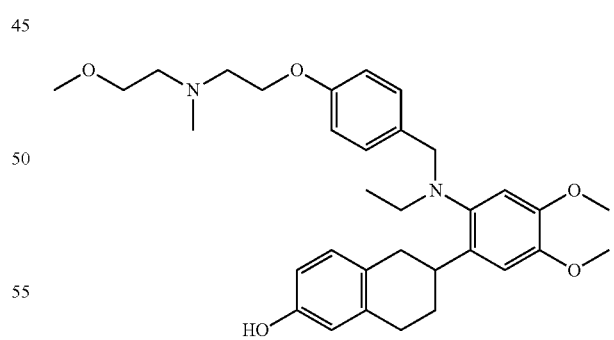

Synthesized from pivalic acid 6-{2-[ethyl(4-hydroxybenzoyl)amino]-4,5-dimethoxyphenyl}-5,6,7,8-tetrahydronaphthalen-2-yl ester (19 mg) and 2-chloro-N-(2-methoxyethyl)-N-methylacetamide (12 mg) according to an analogous synthetic method to Example 404 and purified by LC-MS, the title compound (2.1 mg) was obtained.

ESI-Mass; 549 [M$^+$+H]

Example 556

6-{2-{[4-(2-Dimethylaminoethoxy)-3-fluorobenzyl]ethylamino}-4,5-dimethoxyphenyl}-5,6,7,8-tetrahydronaphthalen-2-ol

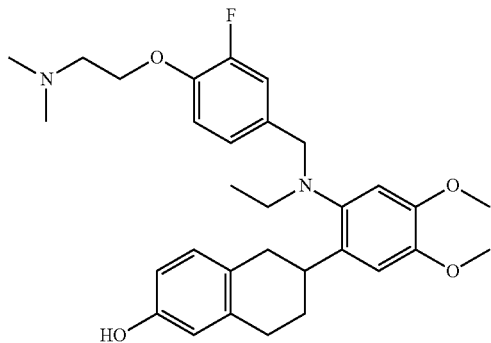

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N,N-dimethylacetamide (8.5 mg) according to an analogous synthetic method to Example 404 and purified by LC-MS, the title compound (1.3 mg) was obtained.

ESI-Mass; 523 [M$^+$+H]

Example 557

6-{2-{Ethyl{4-[2-(ethylmethylamino)ethoxy]-3-fluorobenzyl}amino}-4,5-dimethoxyphenyl}-5,6,7,8-tetrahydronaphthalen-2-ol

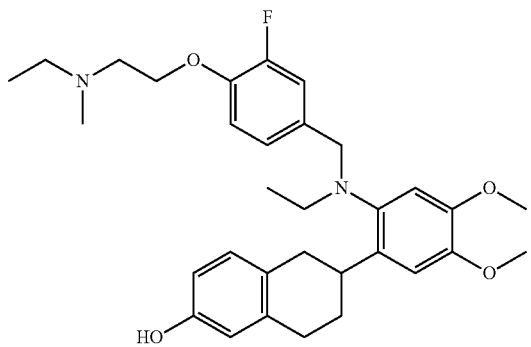 [SMILES: CCN(C)CCOc1ccc(CN(CC)c2cc(OC)c(OC)cc2C2CCc3cc(O)ccc3C2)cc1F]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N-ethyl-N-methylacetamide (9.5 mg) according to an analogous synthetic method to Example 404 and purified by LC-MS, the title compound (2.2 mg) was obtained.

ESI-Mass; 537 [M$^+$+H]

Example 558

6-{2-{Ethyl{3-fluoro-4-[2-(methylpropylamino)ethoxy]benzyl}amino}-4,5-dimethoxyphenyl}-5,6,7,8-tetrahydronaphthalen-2-ol

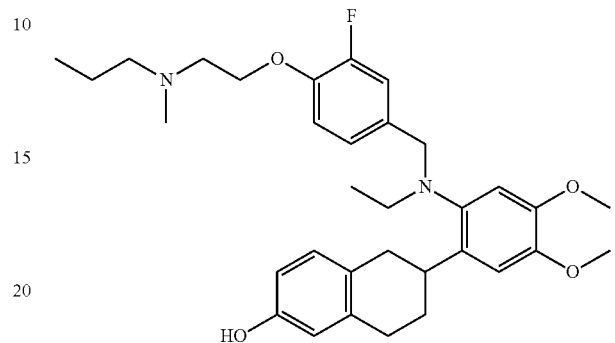

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N-methyl-N-propylacetamide (11 mg) according to an analogous synthetic method to Example 404 and purified by LC-MS, the title compound (2.0 mg) was obtained.

ESI-Mass; 551 [M$^+$+H]

Example 559

6-{2-{Ethyl{3-fluoro-4-[2-(isopropylmethylamino)ethoxy]benzyl}amino}-4,5-dimethoxyphenyl}-5,6,7,8-tetrahydronaphthalen-2-ol

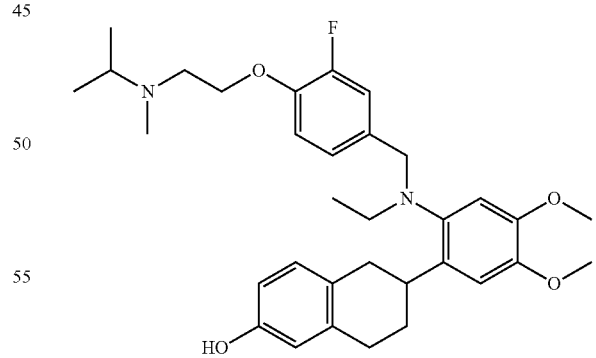

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N-isopropyl-N-methylacetamide (11 mg) according to an analogous synthetic method to Example 404 and purified by LC-MS, the title compound (1.4 mg) was obtained.

ESI-Mass; 551 [M$^+$+H]

Example 560

6-{2-{{4-[2-(Allylmethylamino)ethoxy]-3-fluorobenzyl}ethylamino}-4,5-dimethoxyphenyl}-5,6,7,8-tetrahydronaphthalen-2-ol

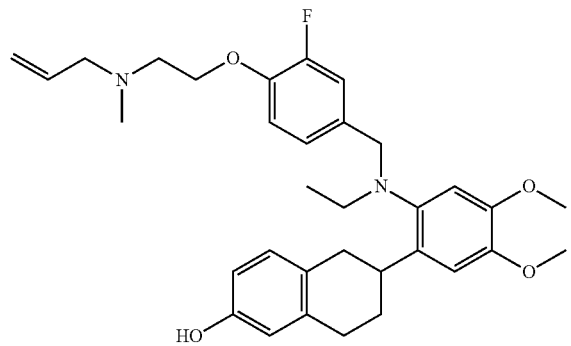 [SMILES: C=CCN(C)CCOc1ccc(CN(CC)c2cc(OC)c(OC)cc2C2CCc3cc(O)ccc3C2)cc1F]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and N-allyl-2-chloro-N-methylacetamide (10 mg) according to an analogous synthetic method to Example 404 and purified by LC-MS, the title compound (1.4 mg) was obtained.

ESI-Mass; 549 [M$^+$+H]

Example 561

6-{2-{{4-[2-(Butylmethylamino)ethoxy]-3-fluorobenzyl}ethylamino}-4,5-dimethoxyphenyl}-5,6,7,8-tetrahydronaphthalen-2-ol

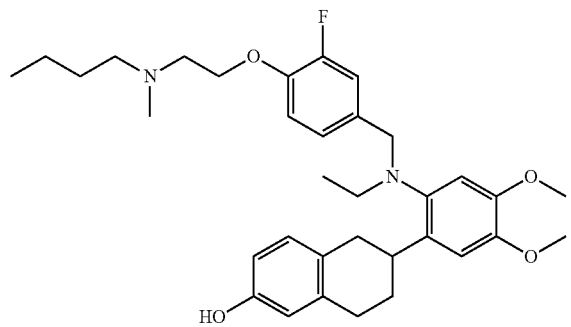 [SMILES: CCCCN(C)CCOc1ccc(CN(CC)c2cc(OC)c(OC)cc2C2CCc3cc(O)ccc3C2)cc1F]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and N-butyl-2-chloro-N-methylacetamide (12 mg) according to an analogous synthetic method to Example 404 and purified by LC-MS, the title compound (1.4 mg) was obtained.

ESI-Mass; 565 [M$^+$+H]

Example 562

6-{2-{Ethyl{3-fluoro-4-[2-(isobutylmethylamino)ethoxy]benzyl}amino}-4,5-dimethoxyphenyl}-5,6,7,8-tetrahydronaphthalen-2-ol

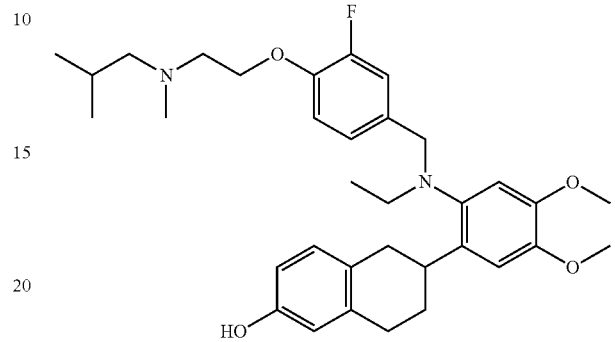

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N-isobutyl-N-methylacetamide (12 mg) according to an analogous synthetic method to Example 404 and purified by LC-MS, the title compound (1.5 mg) was obtained.

ESI-Mass; 565 [M$^+$+H]

Example 563

6-{2-{{4-[2-(tert-Butylmethylamino)ethoxy]-3-fluorobenzyl}ethylamino}-4,5-dimethoxyphenyl}-5,6,7,8-tetrahydronaphthalen-2-ol

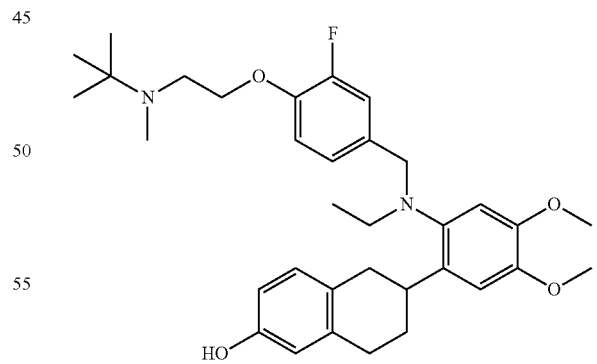

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and N-tert-butyl-2-chloro-N-methylacetamide (12 mg) according to an analogous synthetic method to Example 404 and purified by LC-MS, the title compound (1.4 mg) was obtained.

ESI-Mass; 565 [M$^+$+H]

Example 564

6-{2-{{4-[2-(Cyclopropylmethylamino)ethoxy]-3-fluorobenzyl}ethylamino}-4,5-dimethoxyphenyl}-5,6,7,8-tetrahydronaphthalen-2-ol

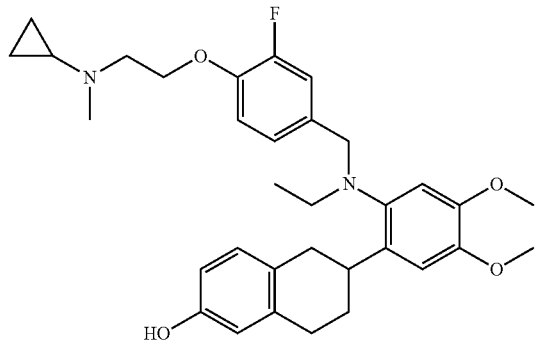 [SMILES: CCN(Cc1ccc(OCCN(C)C2CC2)c(F)c1)c1cc(OC)c(OC)cc1C1CCc2cc(O)ccc2C1]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N-cyclopropyl-N-methylacetamide (10 mg) according to an analogous synthetic method to Example 404 and purified by LC-MS, the title compound (0.9 mg) was obtained.

ESI-Mass; 549 [M$^+$+H]

Example 565

6-{2-{[4-(2-Diethylaminoethoxy)-3-fluorobenzyl]ethylamino}-4,5-dimethoxyphenyl}-5,6,7,8-tetrahydronaphthalen-2-ol

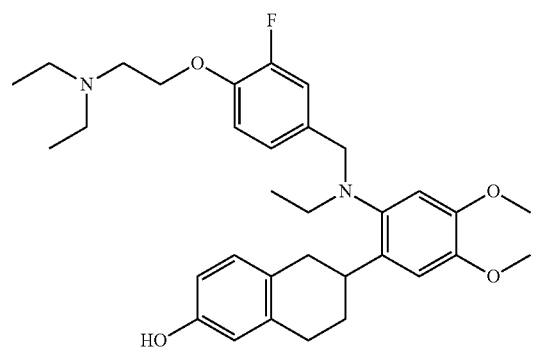

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N,N-diethylacetamide (11 mg) according to an analogous synthetic method to Example 404 and purified by LC-MS, the title compound (2.8 mg) was obtained.

ESI-Mass; 551 [M$^+$+H]

Example 566

6-{2-{[4-(2-Azetidin-1-ylethoxy)-3-fluorobenzyl]ethylamino}-4,5-dimethoxyphenyl}-5,6,7,8-tetrahydronaphthalen-2-ol

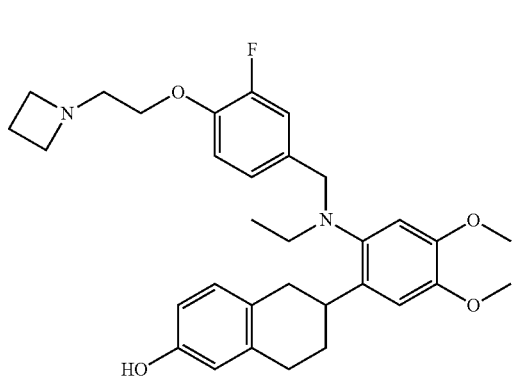 [SMILES: CCN(Cc1ccc(OCCN2CCC2)c(F)c1)c1cc(OC)c(OC)cc1C1CCc2cc(O)ccc2C1]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 1-azetidin-1-yl-2-chloroethanone (9.4 mg) according to an analogous synthetic method to Example 404 and purified by LC-MS, the title compound (0.9 mg) was obtained.

ESI-Mass; 535 [M$^+$+H]

Example 567

6-{2-{Ethyl[3-fluoro-4-(2-pyrrolidin-1-ylethoxy)benzyl]amino}-4,5-dimethoxyphenyl}-5,6,7,8-tetrahydronaphthalen-2-ol

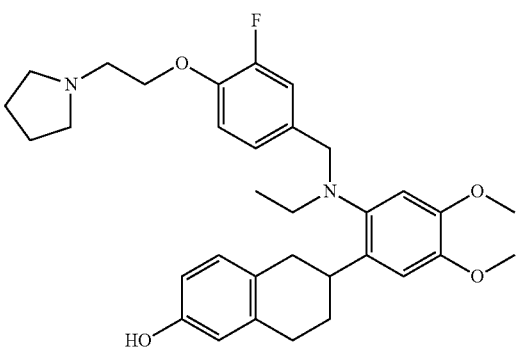

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-1-pyrrolidin-1-ylethanone (10 mg) according to an analogous synthetic method to Example 404 and purified by LC-MS, the title compound (1.6 mg) was obtained.

ESI-Mass; 549 [M$^+$+H]

Example 568

6-{2-{Ethyl[3-fluoro-4-(2-piperidin-1-ylethoxy)benzyl]amino}-4,5-dimethoxyphenyl}-5,6,7,8-tetrahydronaphthalen-2-ol

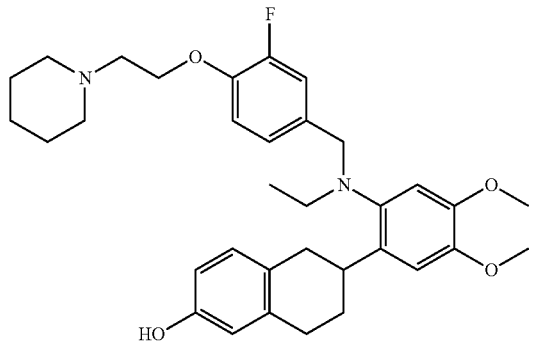 [SMILES: CCN(Cc1ccc(OCCN2CCCCC2)c(F)c1)c1cc(OC)c(OC)cc1C1CCc2cc(O)ccc2C1]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-1-piperidin-1-ylethanone (11 mg) according to an analogous synthetic method to Example 404 and purified by LC-MS, the title compound (1.7 mg) was obtained.

ESI-Mass; 563 [M$^+$+H]

Example 569

6-{2-{Ethyl{3-fluoro-4-[2-(4-methylpiperidin-1-yl)ethoxy]benzyl}amino}-4,5-dimethoxyphenyl}-5,6,7,8-tetrahydronaphthalen-2-ol

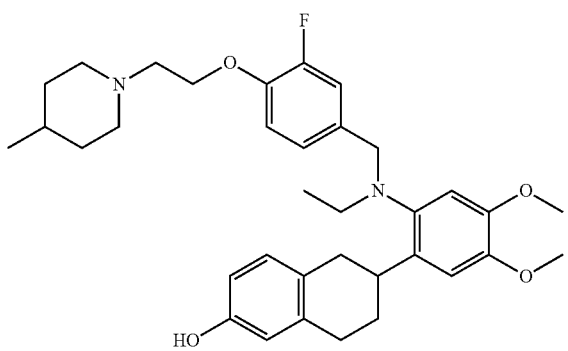

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-1-(4-methylpiperidin-1-yl)ethanone (12 mg) according to an analogous synthetic method to Example 404 and purified by LC-MS, the title compound (0.8 mg) was obtained.

ESI-Mass; 577 [M$^+$+H]

Example 570

6-{2-{{4-[2-(3,3-Dimethylpiperidin-1-yl)ethoxy]-3-fluorobenzyl}ethylamino}-4,5-dimethoxyphenyl}-5,6,7,8-tetrahydronaphthalen-2-ol

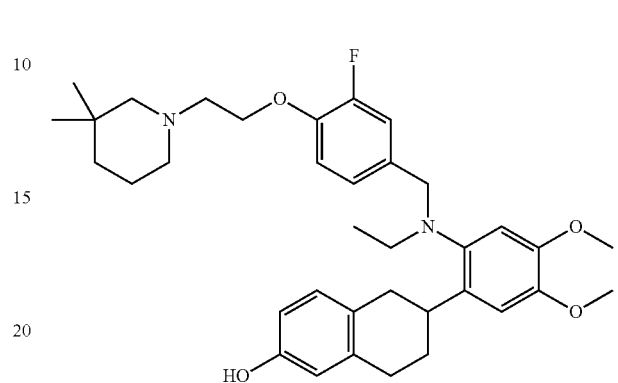

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-bromo-1-(3,3-dimethylpiperidin-1-yl)ethanone (16 mg) according to an analogous synthetic method to Example 404 and purified by LC-MS, the title compound (2.2 mg) was obtained.

ESI-Mass; 591 [M$^+$+H]

Example 571

6-{2-{Ethyl{3-fluoro-4-[2-(2,2,6,6-tetramethylpiperidin-1-yl)ethoxy]benzyl}amino}-4,5-dimethoxyphenyl}-5,6,7,8-tetrahydronaphthalen-2-ol

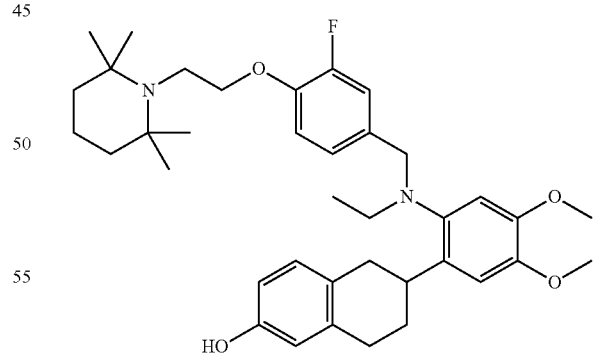

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-bromo-1-(2,2,6,6-tetramethylpiperidin-1-yl)ethanone (18 mg) according to an analogous synthetic method to Example 404 and purified by LC-MS, the title compound (1.4 mg) was obtained.

ESI-Mass; 619 [M$^+$+H]

Example 572

6-{2-{[4-(2-Azepan-1-ylethoxy)-3-fluorobenzyl]ethylamino}-4,5-dimethoxyphenyl}-5,6,7,8-tetrahydronaphthalen-2-ol

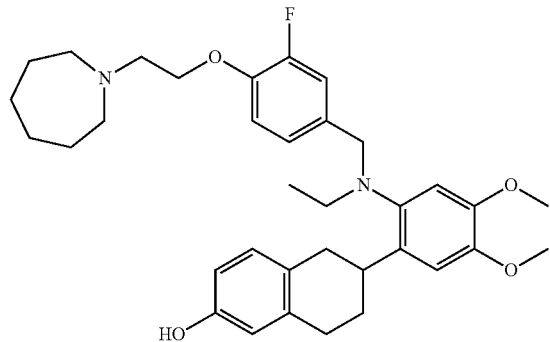 [SMILES: CCN(Cc1ccc(OCCN2CCCCCC2)c(F)c1)c1cc(OC)c(OC)cc1C1CCc2cc(O)ccc2C1]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 1-azepan-1-yl-2-chloroethanone (12 mg) according to an analogous synthetic method to Example 404 and purified by LC-MS, the title compound (1.0 mg) was obtained.

ESI-Mass; 577 [M$^+$+H]

Example 573

6-{2-{[4-(2-Azocan-1-ylethoxy)-3-fluorobenzyl]ethylamino}-4,5-dimethoxyphenyl}-5,6,7,8-tetrahydronaphthalen-2-ol

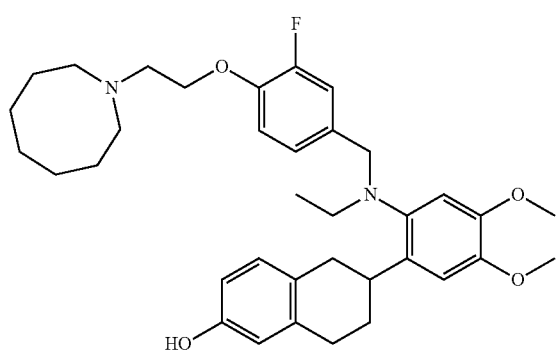 [SMILES: CCN(Cc1ccc(OCCN2CCCCCCC2)c(F)c1)c1cc(OC)c(OC)cc1C1CCc2cc(O)ccc2C1]

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 1-azocan-1-yl-2-chloroethanone (13 mg) according to an analogous synthetic method to Example 404 and purified by LC-MS, the title compound (1.0 mg) was obtained.

ESI-Mass; 591 [M$^+$+H]

Example 574

6-{2-{{4-[2-(7-Azabicyclo[2.2.1]hept-7-yl)ethoxy]-3-fluorobenzyl}ethylamino}-4,5-dimethoxyphenyl}-5,6,7,8-tetrahydronaphthalen-2-ol

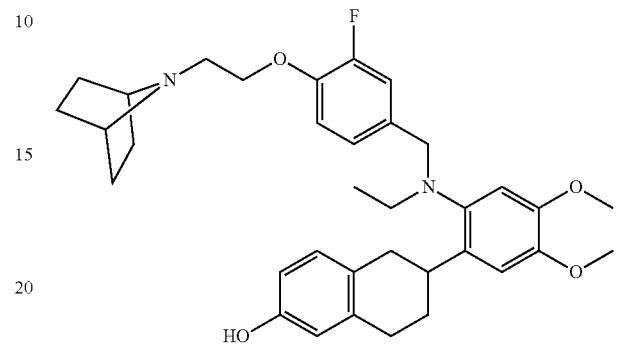

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 1-(7-azabicyclo[2.2.1]hept-7-yl)-2-bromoethanone (15 mg) according to an analogous synthetic method to Example 404 and purified by LC-MS, the title compound (1.1 mg) was obtained.

ESI-Mass; 575 [M$^+$+H]

Example 575

6-{2-{Ethyl{3-fluoro-4-{2-[(2-methoxyethyl)methylamino]ethoxy}benzyl}amino}-4,5-dimethoxyphenyl}-5,6,7,8-tetrahydronaphthalen-2-ol

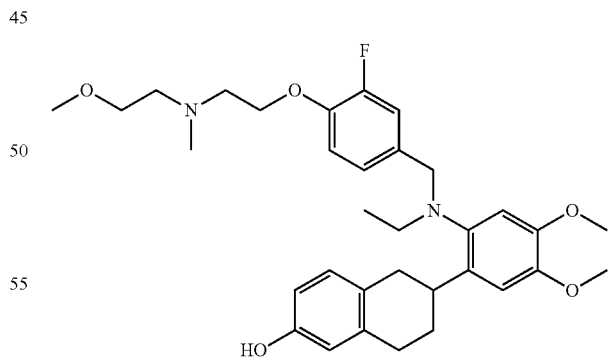

Synthesized from pivalic acid 6-{2-[ethyl(3-fluoro-4-hydroxybenzoyl)amino]-4,5-dimethoxyphenyl}-5,6,7,8-tetrahydronaphthalen-2-yl ester (19 mg) and 2-chloro-N-(2-methoxyethyl)-N-methylacetamide (12 mg) according to an analogous synthetic method to Example 404 and purified by LC-MS, the title compound (1.3 mg) was obtained.

ESI-Mass; 567 [M$^+$+H]

Example 576

6-{2-{[4-(2-Ethylaminoethoxy)benzyl]isopropylamino}-4-methoxyphenyl}-5,6,7,8-tetrahydronaphthalen-2-ol

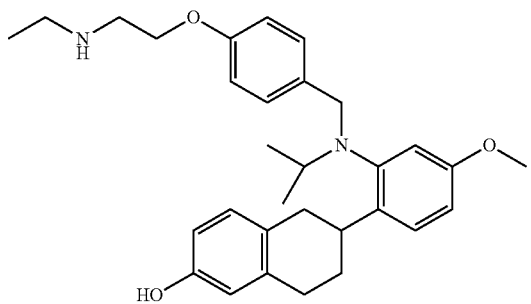 [SMILES: CCNCCOc1ccc(CN(c2cc(OC)ccc2C2CCc3cc(O)ccc3C2)C(C)C)cc1]

Synthesized from pivalic acid 6-{2-[(4-hydroxybenzoyl)isopropylamino]-4-methoxyphenyl}-5,6,7,8-tetrahydronaphthalen-2-yl ester (31 mg) and 2-chloro-N-ethylacetamide (22 mg) according to an analogous synthetic method to Example 404 and purified by LC-MS, the title compound (2.2 mg) was obtained.

ESI-Mass; 489 [M$^+$+H]

Example 577

6-{2-{Isopropyl[4-(2-phenylaminoethoxy)benzyl]amino}-4-methoxyphenyl}-5,6,7,8-tetrahydronaphthalen-2-ol

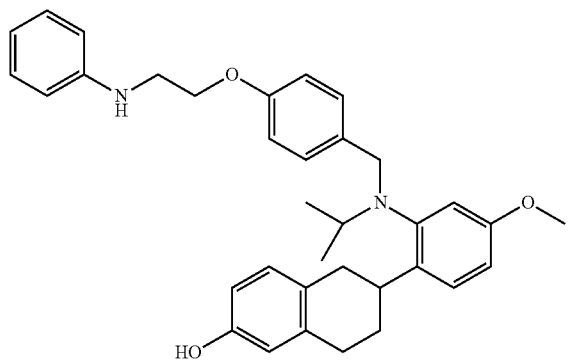 [SMILES: COc1ccc(C2CCc3cc(O)ccc3C2)c(N(Cc2ccc(OCCNc3ccccc3)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (31 mg) and 2-chloro-N-phenylacetamide (28 mg) according to an analogous synthetic method to Example 404 and purified by LC-MS, the title compound (18 mg) was obtained.

ESI-Mass; 537 [M$^+$+H]

Example 578

6-{2-{[4-(2-Cyclopropylaminoethoxy)benzyl]isopropylamino}-4-methoxyphenyl}-5,6,7,8-tetrahydronaphthalen-2-ol

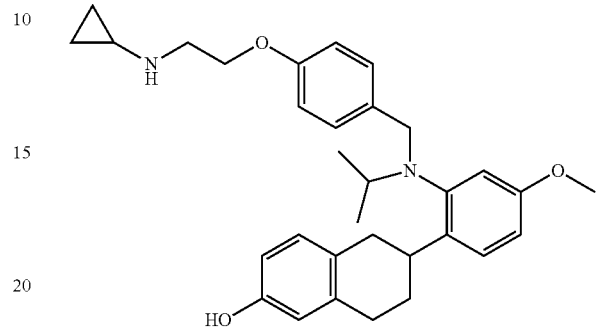

A mixture of pivalic acid 6-{2-[(4-hydroxybenzoyl)isopropylamino]-4-methoxyphenyl}-5,6,7,8-tetrahydronaphthalen-2-yl ester (25 mg), 2-chloro-N-cyclopropylacetamide (13 mg), cesium carbonate (32 mg), potassium iodide (5.0 mg) and tetrahydrofuran (2 ml) was stirred for 5 hours at 60° C. To the reaction solution was added dropwise borane-tetrahydrofuran complex (1.0 M solution in tetrahydrofuran) (0.49 ml), and the solution was stirred at 60° C. for one day and one night. The reaction solution was cooled to room temperature, concentrated hydrochloric acid (0.08 ml) was added thereto, the solution was stirred for 1.5 hours at 60° C., then an aqueous solution of 5N sodium hydroxide (1 ml) was added thereto, and the solution was stirred for 8 hours at 60° C. The reaction solution was diluted with water, then extracted with ethyl acetate. The organic layer was concentrated under a nitrogen stream; purified from a solution of the resulting residue in N,N-dimethylformamide by LC-MS, the title compound (9.0 mg) was obtained.

ESI-Mass; 501 [M$^+$+H]

Example 579

6-{2-{[4-(2-Cyclopropylaminoethoxy)-3-fluorobenzyl]isopropylamino}-4-methoxyphenyl}-5,6,7,8-tetrahydronaphthalen-2-ol

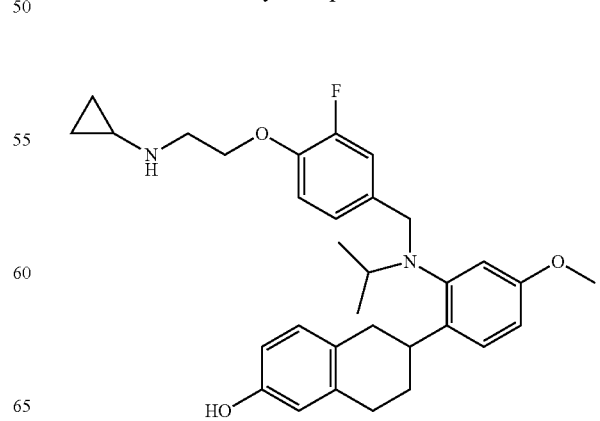

Synthesized from pivalic acid 6-{2-[(3-fluoro-4-hydroxybenzoyl)isopropylamino]-4-methoxyphenyl}-5,6,7,8-tetrahydronaphthalen-2-yl ester (26 mg) and 2-chloro-N-cyclopropylacetamide (13 mg) according to an analogous synthetic method to Example 567 and purified by LC-MS, the title compound (10 mg) was obtained.

ESI-Mass; 519 [M++H]

Example 580

6-{2-{{4-[2-(2-Fluoroethylamino)ethoxy]benzyl}isopropylamino}-4-methoxyphenyl}-5,6,7,8-tetrahydronaphthalen-2-ol

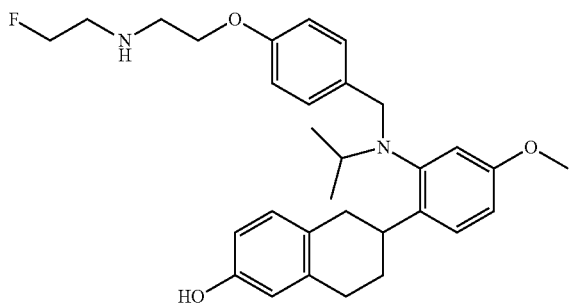 [SMILES: COc1ccc(C2CCc3cc(O)ccc3C2)c(N(Cc2ccc(OCCNCCF)cc2)C(C)C)c1]

Synthesized from pivalic acid 6-{2-[(4-hydroxybenzoyl)isopropylamino]-4-methoxyphenyl}-5,6,7,8-tetrahydronaphthalen-2-yl ester (25 mg) and 2-chloro-N-(2-fluoroethyl)acetamide (14 mg) according to an analogous synthetic method to Example 567 and purified by LC-MS, the title compound (8.9 mg) was obtained.

ESI-Mass; 507 [M++H]

Example 581

6-{2-{{3-Fluoro-4-[2-(2-fluoroethylamino)ethoxy]benzyl}isopropylamino}-4-methoxyphenyl}-5,6,7,8-tetrahydronaphthalen-2-ol

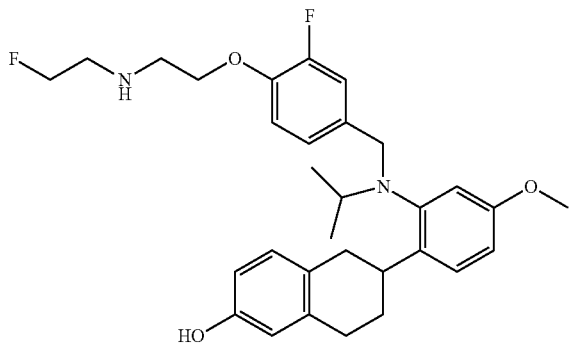 [SMILES: COc1ccc(C2CCc3cc(O)ccc3C2)c(N(Cc2ccc(OCCNCCF)c(F)c2)C(C)C)c1]

Synthesized from pivalic acid 6-{2-[(3-fluoro-4-hydroxybenzoyl)isopropylamino]-4-methoxyphenyl}-5,6,7,8-tetrahydronaphthalen-2-yl ester (26 mg) and 2-chloro-N-(2-fluoroethyl)acetamide (14 mg) according to an analogous synthetic method to Example 567 and purified by LC-MS, the title compound (5.8 mg) was obtained.

ESI-Mass; 525 [M++H]

Example 582

6-{2-{[4-(2-Cyclopropylaminoethoxy)-3-fluorobenzyl]methylamino}-4-methoxyphenyl}-5,6,7,8-tetrahydronaphthalen-2-ol

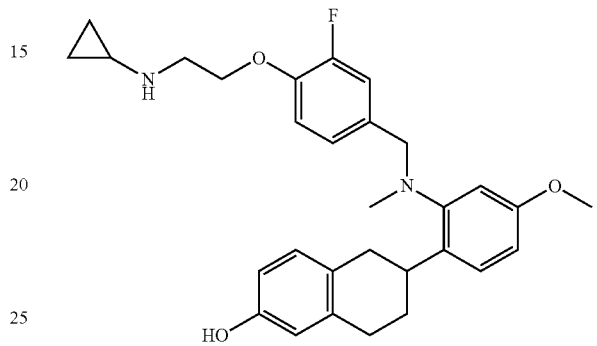

Synthesized from pivalic acid 6-{2-[(3-fluoro-4-hydroxybenzoyl)methylamino]-4-methoxyphenyl}-5,6,7,8-tetrahydronaphthalen-2-yl ester (37 mg) and 2-chloro-N-cyclopropylacetamide (19 mg) according to an analogous synthetic method to Example 567 and purified by LC-MS, the title compound (2.2 mg) was obtained.

ESI-Mass; 491 [M++H]

Example 583

6-{2-{Ethyl{4-[2-(1,2,2,6,6-pentamethylpiperidin-4-ylamino)ethoxy]benzyl}amino}-4-methoxyphenyl}-5,6,7,8-tetrahydronaphthalen-2-ol

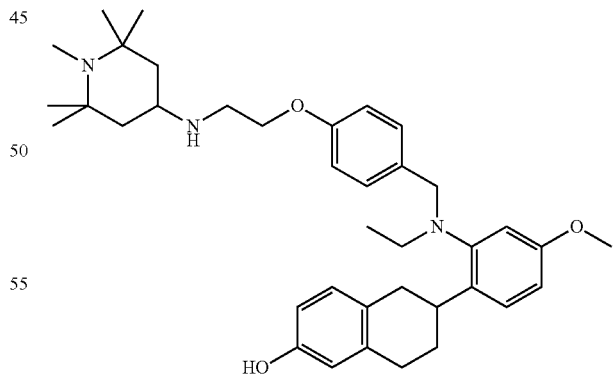

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-(1,2,2,6,6-pentamethylpiperidin-4-yl)acetamide (23 mg) according to an analogous synthetic method to Example 567 and purified by LC-MS, the title compound (4.2 mg) was obtained.

ESI-Mass; 600 [M++H]

Example 584

6-{2-{Ethyl[4-(2-isopropylaminoethoxy)benzyl]amino}-4-methoxyphenyl}-5,6,7,8-tetrahydronaphthalen-2-ol

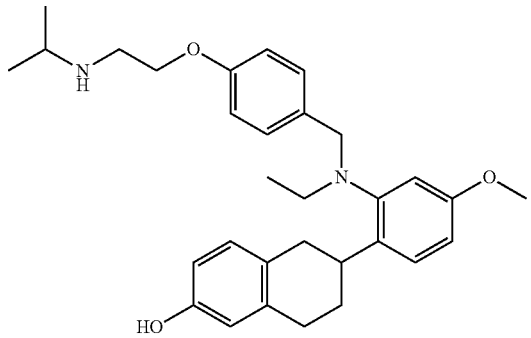 [SMILES: CCN(Cc1ccc(OCCNC(C)C)cc1)c1cc(OC)ccc1C1CCc2cc(O)ccc2C1]

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-isopropylacetamide (13 mg) according to an analogous synthetic method to Example 567 and purified by LC-MS, the title compound (2.7 mg) was obtained.

ESI-Mass; 489 [M$^+$+H]

Example 585

6-{2-{[4-(2-Cyclopropylaminoethoxy)benzyl]ethylamino}-4-methoxyphenyl}-5,6,7,8-tetrahydronaphthalen-2-ol

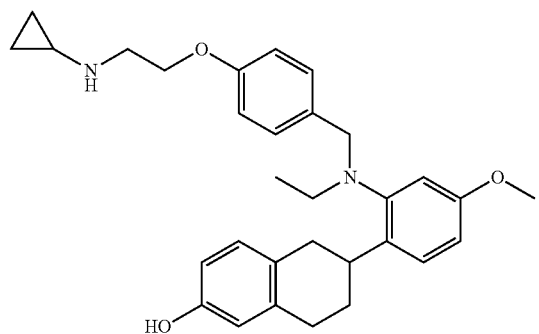

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-cyclopropylacetamide (13 mg) according to an analogous synthetic method to Example 567 and purified by LC-MS, the title compound (3.9 mg) was obtained.

ESI-Mass; 487 [M$^+$+H]

Example 586

6-{2-{[4-(2-Cyclohexylaminoethoxy)benzyl]ethylamino}-4-methoxyphenyl}-5,6,7,8-tetrahydronaphthalen-2-ol

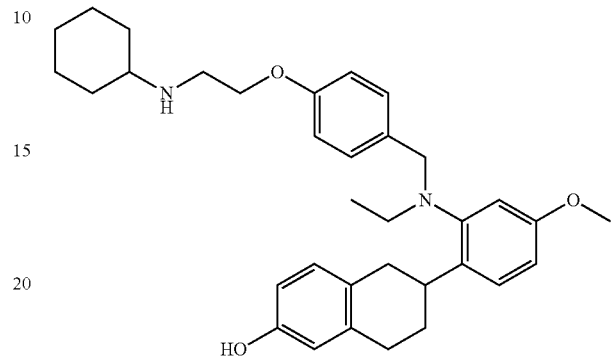

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-cyclohexylacetamide (17 mg) according to an analogous synthetic method to Example 567 and purified by LC-MS, the title compound (0.8 mg) was obtained.

ESI-Mass; 529 [M$^+$+H]

Example 587

6-{2-{Ethyl{4-[2-(2-fluoroethylamino)ethoxy]benzyl}amino}-4-methoxyphenyl}-5,6,7,8-tetrahydronaphthalen-2-ol

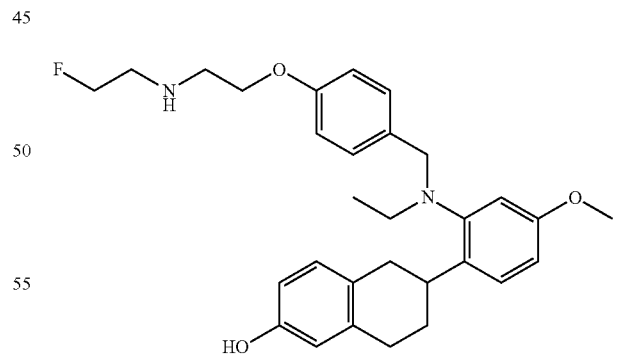

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-(2-fluoroethyl)acetamide (13 mg) according to an analogous synthetic method to Example 567 and purified by LC-MS, the title compound (10 mg) was obtained.

ESI-Mass; 493 [M$^+$+H]

Example 588

6-{2-{Ethyl{4-[2-(2-methoxyethylamino)ethoxy]benzyl}amino}-4-methoxyphenyl}-5,6,7,8-tetrahydronaphthalen-2-ol

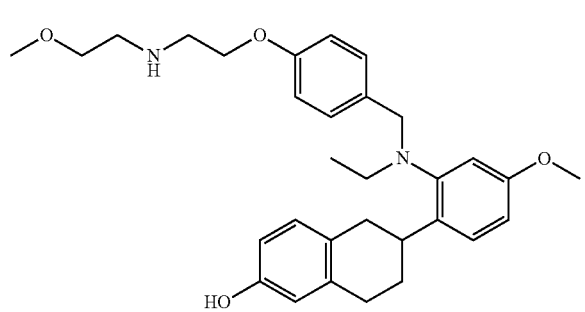

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-(2-methoxyethyl)acetamide (14 mg) according to an analogous synthetic method to Example 567 and purified by LC-MS, the title compound (3.5 mg) was obtained.

ESI-Mass; 505 [M$^+$+H]

Example 589

6-{2-{Ethyl{4-[2-(2-methylsulfanylethylamino)ethoxy]benzyl}amino}-4-methoxyphenyl}-5,6,7,8-tetrahydronaphthalen-2-ol

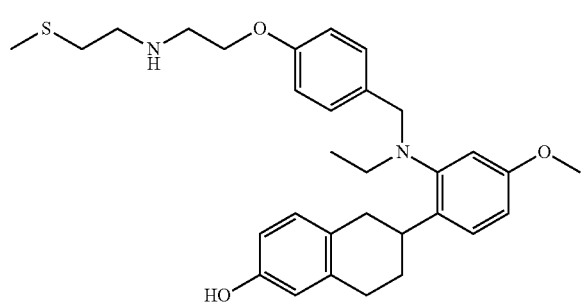

Synthesized from pivalic acid 6-{2-[ethyl(4-hydroxybenzoyl)amino]-4-methoxyphenyl}-5,6,7,8-tetrahydronaphthalen-2-yl ester (25 mg) and 2-chloro-N-(2-methylsulfanylethyl)acetamide (16 mg) according to an analogous synthetic method to Example 567 and purified by LC-MS, the title compound (1.8 mg) was obtained.

ESI-Mass; 521 [M$^+$+H]

Example 590

6-{2-{Ethyl{3-fluoro-4-[2-(1,2,2,6,6-pentamethylpiperidin-4-ylamino)ethoxy]benzyl}amino}-4-methoxyphenyl}-5,6,7,8-tetrahydronaphthalen-2-ol

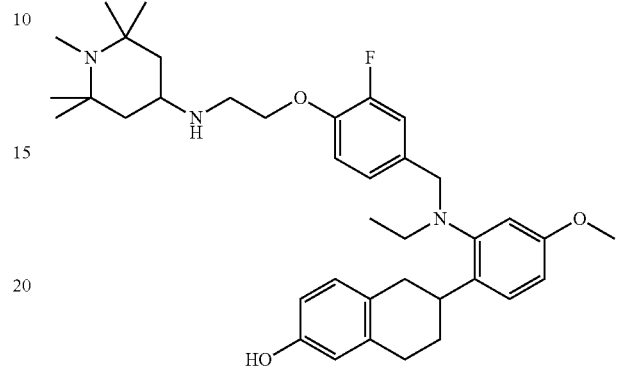

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-N-(1,2,2,6,6-pentamethylpiperidin-4-yl)acetamide (23 mg) according to an analogous synthetic method to Example 567 and purified by LC-MS, the title compound (9.6 mg) was obtained.

ESI-Mass; 618 [M$^+$+H]

Example 591

6-{2-{Ethyl[4-(2-ethylaminoethoxy)-3-fluorobenzyl]amino}-4-methoxyphenyl}-5,6,7,8-tetrahydronaphthalen-2-ol

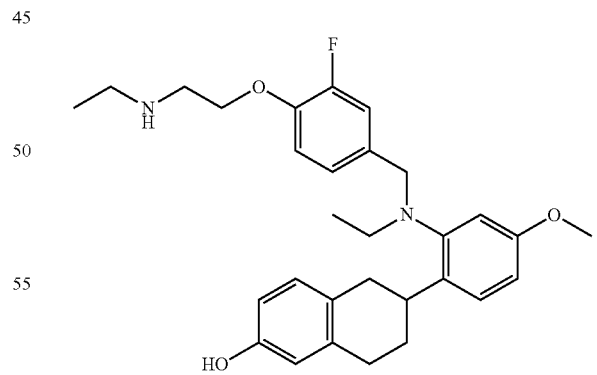

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-N-ethylacetamide (11 mg) according to an analogous synthetic method to Example 567 and purified by LC-MS, the title compound (5.0 mg) was obtained.

ESI-Mass; 493 [M$^+$+H]

Example 592

6-{2-{Ethyl[3-fluoro-4-(2-isopropylaminoethoxy)benzyl]amino}-4-methoxyphenyl}-5,6,7,8-tetrahydronaphthalen-2-ol

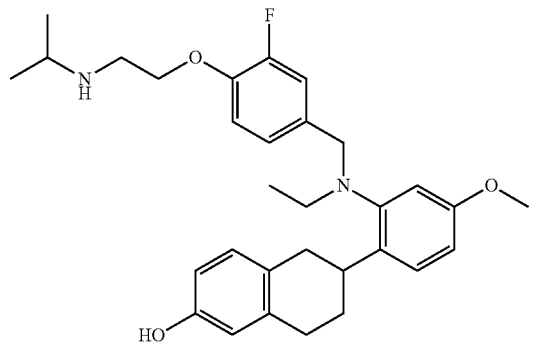 [SMILES: CCN(Cc1ccc(OCCNC(C)C)c(F)c1)c1cc(OC)ccc1C1CCc2cc(O)ccc2C1]

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-N-isopropylacetamide (12 mg) according to an analogous synthetic method to Example 567 and purified by LC-MS, the title compound (3.9 mg) was obtained.

ESI-Mass; 507 [M$^+$+H]

Example 593

6-{2-{[4-(2-Cyclohexylaminoethoxy)-3-fluorobenzyl]ethylamino}-4-methoxyphenyl}-5,6,7,8-tetrahydronaphthalen-2-ol

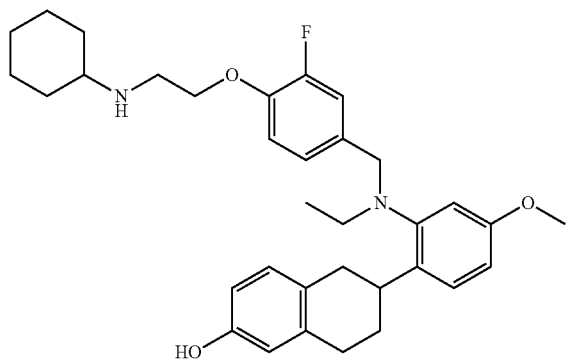

Synthesized from pivalic acid 6-{2-[ethyl(3-fluoro-4-hydroxybenzoyl)amino]-4-methoxyphenyl}-5,6,7,8-tetrahydronaphthalen-2-yl ester (25 mg) and 2-chloro-N-cyclohexylacetamide (16 mg) according to an analogous synthetic method to Example 567 and purified by LC-MS, the title compound (3.9 mg) was obtained.

ESI-Mass; 547 [M$^+$+H]

Example 594

(R)-6-{2-{[4-(2-Dimethylaminoethoxy)benzyl]ethylamino}-4-methoxyphenyl}-5,6,7,8-tetrahydronaphthalen-2-ol

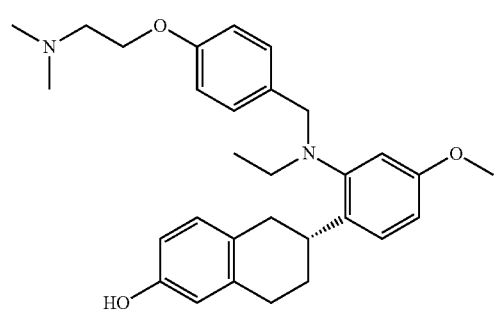

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 2-chloro-N,N-dimethylacetamide (10 mg) according to an analogous synthetic method to Example 404 and purified by LC-MS, the title compound (2.9 mg) was obtained.

ESI-Mass; 475 [M$^+$+H]

Example 595

(R)-6-{2-{[4-(2-diethylaminoethoxy)benzyl]ethylamino}-4-methoxyphenyl}-5,6,7,8-tetrahydronaphthalen-2-ol

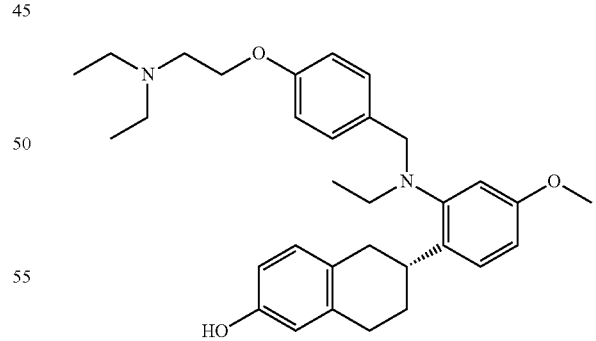

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 2-chloro-N,N-diethylacetamide (12 mg) according to an analogous synthetic method to Example 404 and purified by LC-MS, the title compound (5.6 mg) was obtained.

ESI-Mass; 503 [M$^+$+H]

Example 596

(R)-6-{2-{[4-(2-Azetidin-1-ylethoxy)benzyl]ethylamino}-4-methoxyphenyl}-5,6,7,8-tetrahydronaphthalen-2-ol

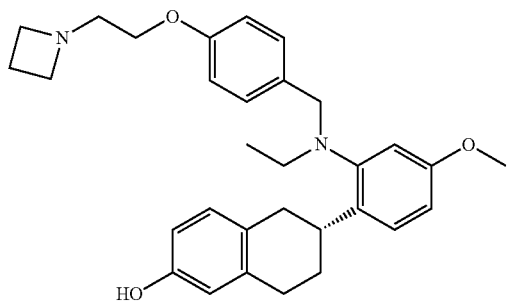 [SMILES: CCN(Cc1ccc(OCCN2CCC2)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 1-azetidin-1-yl-2-chloroethanone (11 mg) according to an analogous synthetic method to Example 404 and purified by LC-MS, the title compound (5.8 mg) was obtained.

ESI-Mass; 487 [M$^+$+H]

Example 597

(R)-6-{2-{Ethyl[4-(2-pyrrolidin-1-ylethoxy)benzyl]amino}-4-methoxyphenyl}-5,6,7,8-tetrahydronaphthalen-2-ol

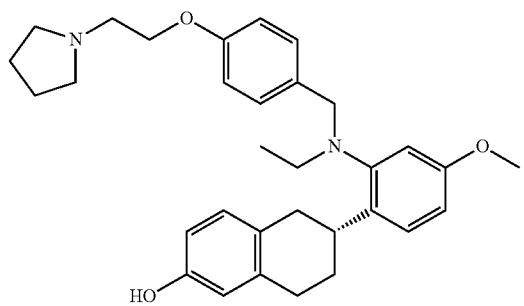

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 2-chloro-1-pyrrolidin-1-ylethanone (12 mg) according to an analogous synthetic method to Example 404 and purified by LC-MS, the title compound (7.9 mg) was obtained.

ESI-Mass; 501 [M$^+$+H]

Example 598

(R)-6-{2-{Ethyl[4-(2-piperidin-1-ylethoxy)benzyl]amino}-4-methoxyphenyl}-5,6,7,8-tetrahydronaphthalen-2-ol

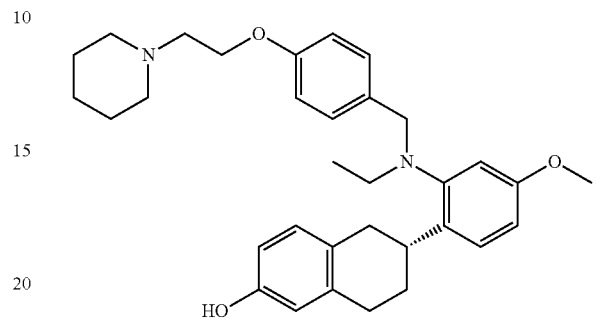

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 2-chloro-1-piperidin-1-ylethanone (13 mg) according to an analogous synthetic method to Example 404 and purified by LC-MS, the title compound (7.7 mg) was obtained.

ESI-Mass; 515 [M$^+$+H]

Example 599

(R)-6-{2-{{4-[2-(3,3-Dimethylpiperidin-1-yl)ethoxy]benzyl}ethylamino}-4-methoxyphenyl}-5,6,7,8-tetrahydronaphthalen-2-ol

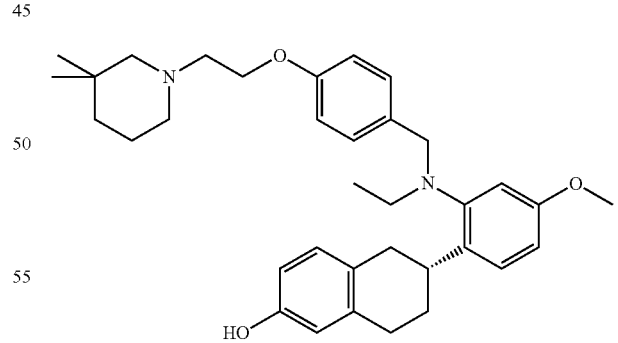

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 2-bromo-1-(3,3-dimethylpiperidin-1-yl)ethanone (19 mg) according to an analogous synthetic method to Example 404 and purified by LC-MS, the title compound (10 mg) was obtained.

ESI-Mass; 543 [M$^+$+H]

Example 600

(R)-6-{2-{[4-(2-Azepan-1-ylethoxy)benzyl]ethylamino}-4-methoxyphenyl}-5,6,7,8-tetrahydronaphthalen-2-ol

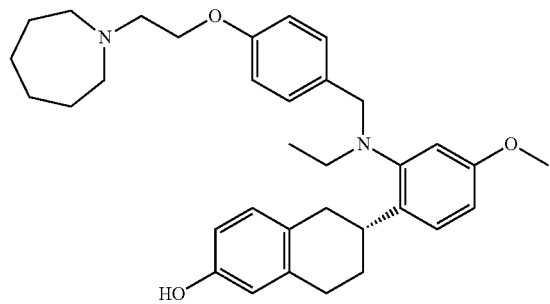 [SMILES: CCN(Cc1ccc(OCCN2CCCCCC2)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 1-azepan-1-yl-2-chloroethanone (14 mg) according to an analogous synthetic method to Example 404 and purified by LC-MS, the title compound (6.9 mg) was obtained.

ESI-Mass; 529 [M$^+$+H]

Example 601

(R)-6-{2-{[4-(2-Azocan-1-ylethoxy)benzyl]ethylamino}-4-methoxyphenyl}-5,6,7,8-tetrahydronaphthalen-2-ol

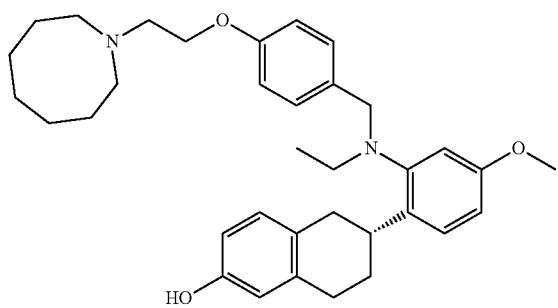 [SMILES: CCN(Cc1ccc(OCCN2CCCCCCC2)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 1-azocan-1-yl-2-chloroethanone (15 mg) according to an analogous synthetic method to Example 404 and purified by LC-MS, the title compound (9.6 mg) was obtained.

ESI-Mass; 543 [M$^+$+H]

Example 602

(R)-6-{2-{Ethyl{4-{2-[(2-methoxyethyl)methylamino]ethoxy}benzyl}amino}-4-methoxyphenyl}-5,6,7,8-tetrahydronaphthalen-2-ol

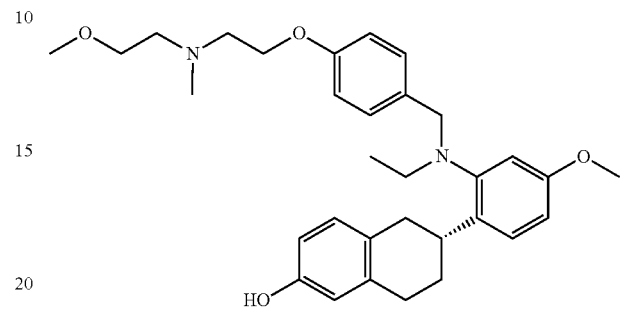

Synthesized from pivalic acid (R)-6-{2-[ethyl(4-hydroxybenzoyl)amino]-4-methoxyphenyl}-5,6,7,8-tetrahydronaphthalen-2-yl ester (20 mg) and 2-chloro-N-(2-methoxyethyl)-N-methylacetamide (13 mg) according to an analogous synthetic method to Example 404 and purified by LC-MS, the title compound (6.9 mg) was obtained.

ESI-Mass; 519 [M$^+$+H]

Example 603

(S)-6-{2-{[4-(2-Dimethylaminoethoxy)benzyl]ethylamino}-4-methoxyphenyl}-5,6,7,8-tetrahydronaphthalen-2-ol

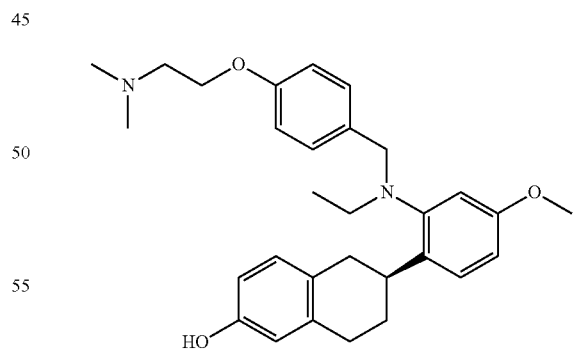

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 2-chloro-N,N-dimethylacetamide (10 mg) according to an analogous synthetic method to Example 404 and purified by LC-MS, the title compound (6.9 mg) was obtained.

ESI-Mass; 475 [M$^+$+H]

Example 604

(S)-6-{2-{[4-(2-Diethylaminoethoxy)benzyl]ethylamino}-4-methoxyphenyl}-5,6,7,8-tetrahydronaphthalen-2-ol

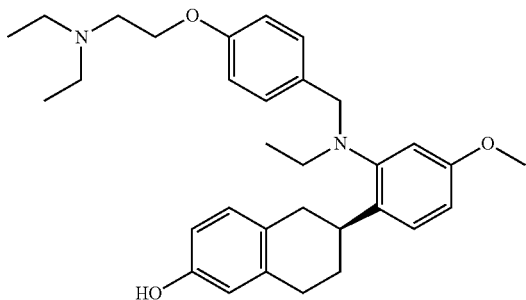 [SMILES: CCN(CC)CCOc1ccc(CN(CC)c2cc(OC)ccc2[C@H]2CCc3cc(O)ccc3C2)cc1]

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 2-chloro-N,N-diethylacetamide (12 mg) according to an analogous synthetic method to Example 404 and purified by LC-MS, the title compound (7.0 mg) was obtained.

ESI-Mass; 503 [M$^+$+H]

Example 605

(S)-6-{2-{[4-(2-Azetidin-1-ylethoxy)benzyl]ethylamino}-4-methoxyphenyl}-5,6,7,8-tetrahydronaphthalen-2-ol

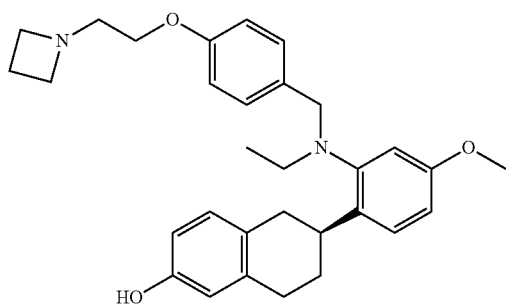 [SMILES: CCN(Cc1ccc(OCCN2CCC2)cc1)c1cc(OC)ccc1[C@H]1CCc2cc(O)ccc2C1]

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 1-azetidin-1-yl-2-chloroethanone (11 mg) according to an analogous synthetic method to Example 404 and purified by LC-MS, the title compound (6.6 mg) was obtained.

ESI-Mass; 487 [M$^+$+H]

Example 606

(S)-6-{2-{Ethyl[4-(2-pyrrolidin-1-ylethoxy)benzyl]amino}-4-methoxyphenyl}-5,6,7,8-tetrahydronaphthalen-2-ol

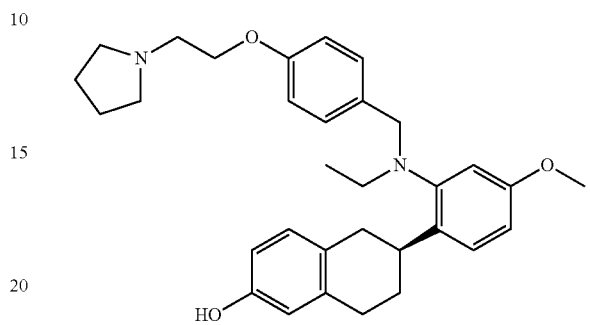

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 2-chloro-1-pyrrolidin-1-ylethanone (12 mg) according to an analogous synthetic method to Example 404 and purified by LC-MS, the title compound (8.5 mg) was obtained.

ESI-Mass; 501 [M$^+$+H]

Example 607

(S)-6-{2-{Ethyl[4-(2-piperidin-1-ylethoxy)benzyl]amino}-4-methoxyphenyl}-5,6,7,8-tetrahydronaphthalen-2-ol

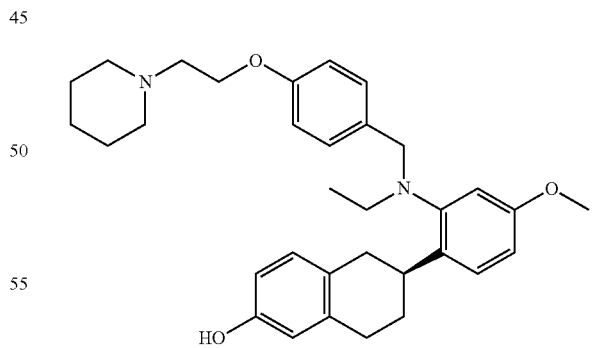

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 2-chloro-1-piperidin-1-ylethanone (13 mg) according to an analogous synthetic method to Example 404 and purified by LC-MS, the title compound (8.4 mg) was obtained.

ESI-Mass; 515 [M$^+$+H]

Example 608

(S)-6-{2-{{4-[2-(3,3-Dimethylpiperidin-1-yl)ethoxy]benzyl}ethylamino}-4-methoxyphenyl}-5,6,7,8-tetrahydronaphthalen-2-ol

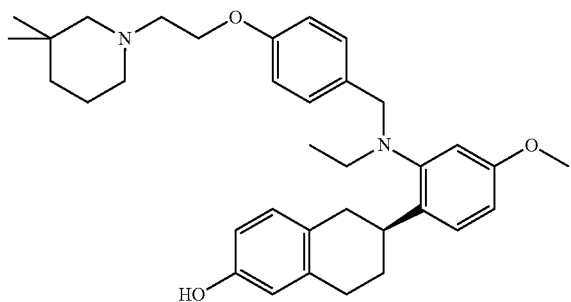

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 2-bromo-1-(3,3-dimethylpiperidin-1-yl)ethanone (19 mg) according to an analogous synthetic method to Example 404 and purified by LC-MS, the title compound (11 mg) was obtained.

ESI-Mass; 543 [M$^+$+H]

Example 609

(S)-6-{2-{[4-(2-Azepan-1-ylethoxy)benzyl]ethylamino}-4-methoxyphenyl}-5,6,7,8-tetrahydronaphthalen-2-ol

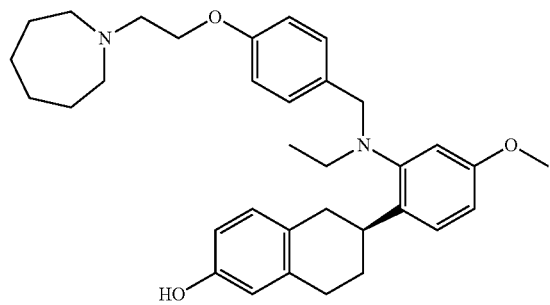 [SMILES: CCN(Cc1ccc(OCCN2CCCCCC2)cc1)c1cc(OC)ccc1[C@H]1CCc2cc(O)ccc2C1]

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 1-azepan-1-yl-2-chloroethanone (14 mg) according to an analogous synthetic method to Example 404 and purified by LC-MS, the title compound (8.2 mg) was obtained.

ESI-Mass; 529 [M$^+$+H]

Example 610

(S)-6-{2-{[4-(2-Azocan-1-ylethoxy)benzyl]ethylamino}-4-methoxyphenyl}-5,6,7,8-tetrahydronaphthalen-2-ol

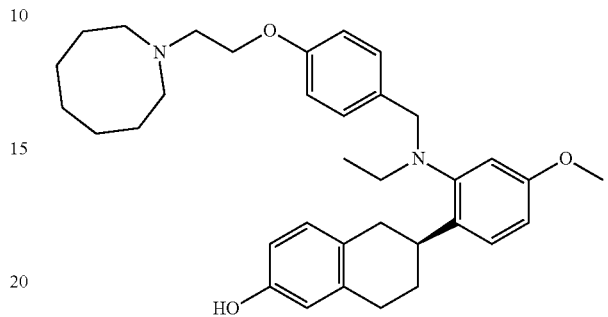

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 1-azocan-1-yl-2-chloroethanone (15 mg) according to an analogous synthetic method to Example 404 and purified by LC-MS, the title compound (9.0 mg) was obtained.

ESI-Mass; 543 [M$^+$+H]

Example 611

(S)-6-{2-{Ethyl{4-{2-[(2-methoxyethyl)methylamino]ethoxy}benzyl}amino}-4-methoxyphenyl}-5,6,7,8-tetrahydronaphthalen-2-ol

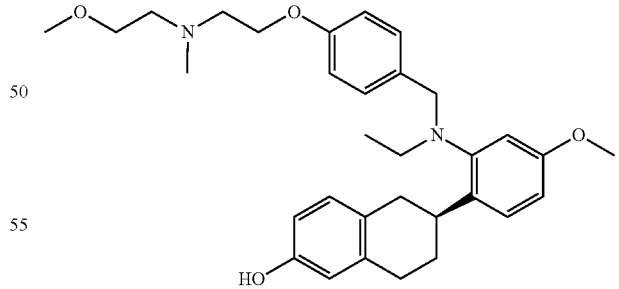

Synthesized from pivalic acid (S)-6-{2-[ethyl(4-hydroxybenzoyl)amino]-4-methoxyphenyl}-5,6,7,8-tetrahydronaphthalen-2-yl ester (20 mg) and 2-chloro-N-(2-methoxyethyl)-N-methylacetamide (13 mg) according to an analogous synthetic method to Example 404 and purified by LC-MS, the title compound (7.5 mg) was obtained.

ESI-Mass; 519 [M$^+$+H]

Example 612

(R)-6-{2-{Ethyl{4-[2-(4-methylpiperidin-1-yl)ethoxy]benzyl}amino}-4-methoxyphenyl}-5,6,7,8-tetrahydronaphthalen-2-ol

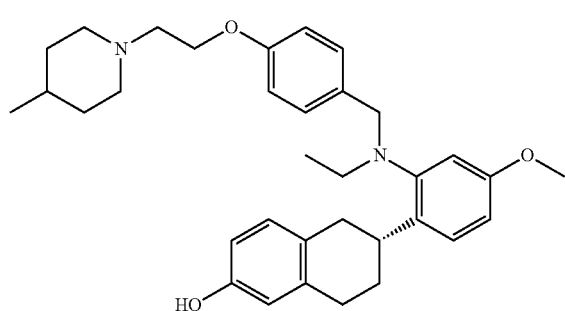

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-1-(4-methylpiperidin-1-yl)ethanone (10 mg) according to an analogous synthetic method to Example 404 and purified by LC-MS, the title compound (5.7 mg) was obtained.

ESI-Mass; 529 [M$^+$+H]

Example 613

(R)-6-{2-{{4-[2-(7-Azabicyclo[2.2.1]hept-7-yl)ethoxy]benzyl}ethylamino}-4-methoxyphenyl}-5,6,7,8-tetrahydronaphthalen-2-ol

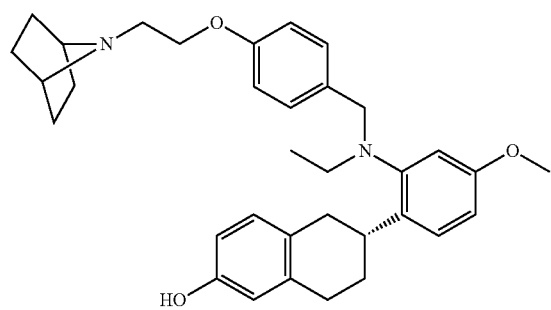 [SMILES: CCN(Cc1ccc(OCCN2C3CCC2CC3)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 1-(7-azabicyclo[2.2.1]hept-7-yl)-2-bromoethanone (13 mg) according to an analogous synthetic method to Example 404 and purified by LC-MS, the title compound (12 mg) was obtained.

ESI-Mass; 527 [M$^+$+H]

Example 614

(R)-6-{2-{Ethyl{4-[2-(ethylmethylamino)ethoxy]benzyl}amino}-4-methoxyphenyl}-5,6,7,8-tetrahydronaphthalen-2-ol

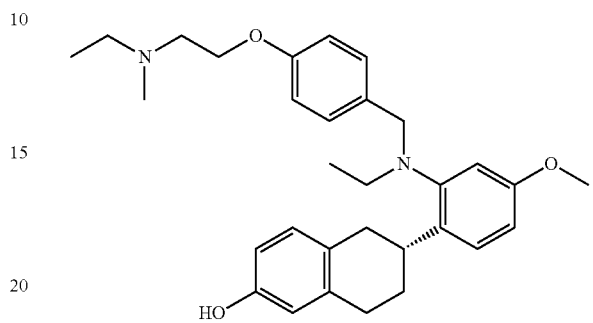

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-ethyl-N-methylacetamide (7.9 mg) according to an analogous synthetic method to Example 404 and purified by LC-MS, the title compound (8.4 mg) was obtained.

ESI-Mass; 489 [M$^+$+H]

Example 615

(R)-6-{2-{{4-[2-(Butylmethylamino)ethoxy]benzyl}ethylamino}-4-methoxyphenyl}-5,6,7,8-tetrahydronaphthalen-2-ol

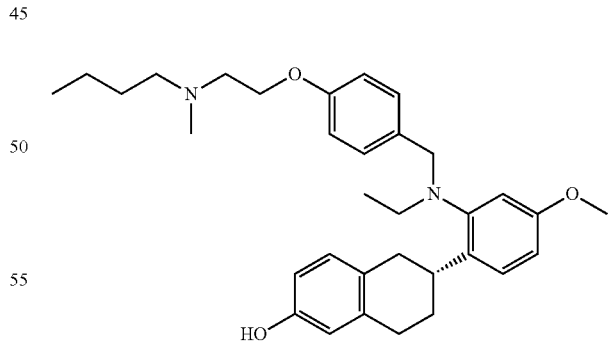

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and N-butyl-2-chloro-N-methylacetamide (9.5 mg) according to an analogous synthetic method to Example 404 and purified by LC-MS, the title compound (4.1 mg) was obtained.

ESI-Mass; 517 [M$^+$+H]

Example 616

(R)-6-{2-{Ethyl{4-[2-(methylpropylamino)ethoxy]benzyl}amino}-4-methoxyphenyl}-5,6,7,8-tetrahydronaphthalen-2-ol

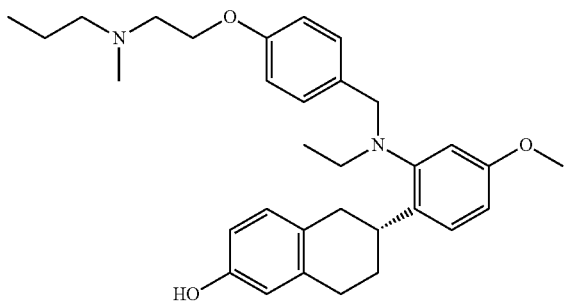 [SMILES: CCCN(C)CCOc1ccc(CN(CC)c2cc(OC)ccc2[C@@H]2CCc3cc(O)ccc3C2)cc1]

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-methyl-N-propyl acetamide (8.7 mg) according to an analogous synthetic method to Example 404 and purified by LC-MS, the title compound (7.4 mg) was obtained.

ESI-Mass; 503 [M$^+$+H]

Example 617

(R)-6-{2-{Ethyl{4-[2-(isopropylmethylamino)ethoxy]benzyl}amino}-4-methoxyphenyl}-5,6,7,8-tetrahydronaphthalen-2-ol

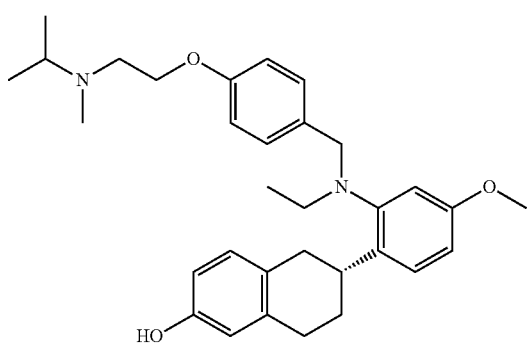 [SMILES: CCN(Cc1ccc(OCCN(C)C(C)C)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-isopropyl-N-methylacetamide (8.7 mg) according to an analogous synthetic method to Example 404 and purified by LC-MS, the title compound (11 mg) was obtained.

ESI-Mass; 503 [M$^+$+H]

Example 618

(R)-6-{2-{{4-{2-[(2-Ethoxyethyl)methylamino]ethoxy}benzyl}ethylamino}-4-methoxyphenyl}-5,6,7,8-tetrahydronaphthalen-2-ol

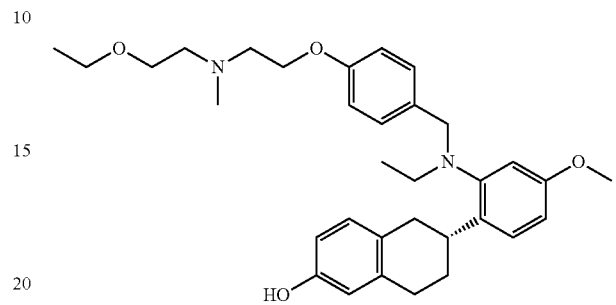

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-(2-ethoxyethyl)-N-methylacetamide (10 mg) according to an analogous synthetic method to Example 404 and purified by LC-MS, the title compound (4.7 mg) was obtained.

ESI-Mass; 533 [M$^+$+H]

Example 619

(R)-6-{2-{Ethyl{4-{2-[(3-methoxypropyl)methylamino]ethoxy}benzyl}amino}-4-methoxyphenyl}-5,6,7,8-tetrahydronaphthalen-2-ol

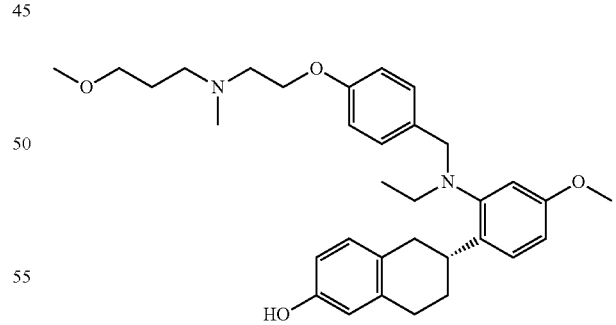

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-(3-methoxypropyl)-N-methylacetamide (10 mg) according to an analogous synthetic method to Example 404 and purified by LC-MS, the title compound (8.8 mg) was obtained.

ESI-Mass; 533 [M$^+$+H]

Example 620

(R)-6-{2-{Ethyl{4-{2-{methyl[(S)-tetrahydrofuran-2-ylmethyl]amino}ethoxy}benzyl}amino}-4-methoxyphenyl}-5,6,7,8-tetrahydronaphthalen-2-ol

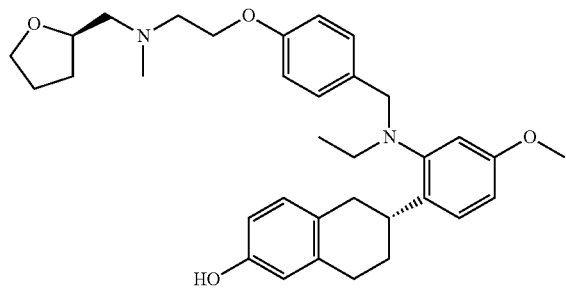 [SMILES: CCN(Cc1ccc(OCCN(C)C[C@H]2CCCO2)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-methyl-N—[(S)-tetrahydrofuran-2-ylmethyl]acetamide (11 mg) according to an analogous synthetic method to Example 404 and purified by LC-MS, the title compound (13 mg) was obtained.

ESI-Mass; 545 [M$^+$+H]

Example 621

(R)-6-{2-{Ethyl{4-{2-{methyl[(R)-tetrahydrofuran-2-ylmethyl]amino}ethoxy}benzyl}amino}-4-methoxyphenyl}-5,6,7,8-tetrahydronaphthalen-2-ol

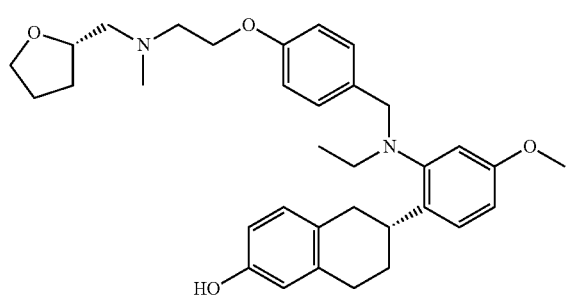 [SMILES: CCN(Cc1ccc(OCCN(C)C[C@@H]2CCCO2)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-methyl-N—[(R)-tetrahydrofuran-2-ylmethyl]acetamide (11 mg) according to an analogous synthetic method to Example 404 and purified by LC-MS, the title compound (12 mg) was obtained.

ESI-Mass; 545 [M$^+$+H]

Example 622

(R)-6-{2-{Ethyl{4-{2-[methyl(tetrahydropyran-4-yl)amino]ethoxy}benzyl}amino}-4-methoxyphenyl}-5,6,7,8-tetrahydronaphthalen-2-ol

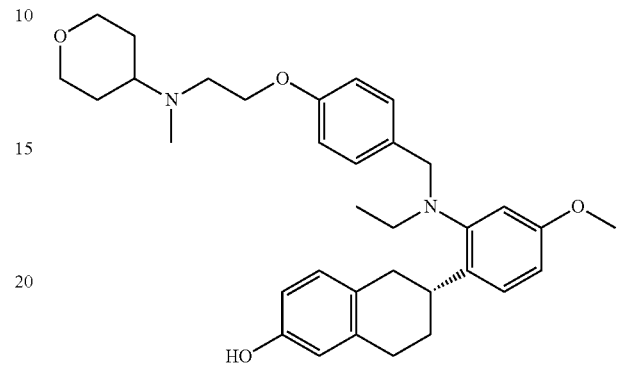

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-methyl-N-(tetrahydropyran-4-yl)acetamide (11 mg) according to an analogous synthetic method to Example 404 and purified by LC-MS, the title compound (5.9 mg) was obtained.

ESI-Mass; 545 [M$^+$+H]

Example 623

(R)-6-{2-{Ethyl{4-{2-[methyl(tetrahydropyran-4-ylmethyl)amino]ethoxy}benzyl}amino}-4-methoxyphenyl}-5,6,7,8-tetrahydronaphthalen-2-ol

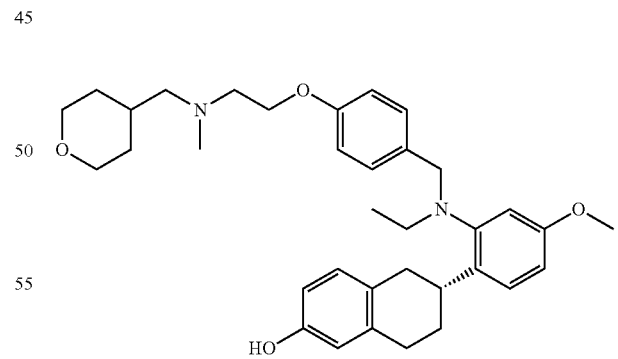

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-methyl-N-(tetrahydropyran-4-ylmethyl)acetamide (12 mg) according to an analogous synthetic method to Example 404 and purified by LC-MS, the title compound (9.9 mg) was obtained.

ESI-Mass; 559 [M$^+$+H]

Example 624

(R)-6-{2-{{4-[2-(Cyclobutylmethylamino)ethoxy]benzyl}ethylamino}-4-methoxyphenyl}-5,6,7,8-tetrahydronaphthalen-2-ol

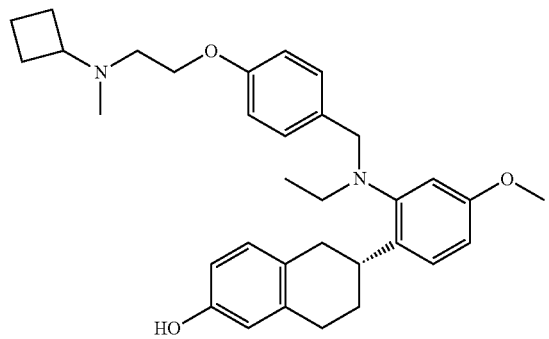 [SMILES: CCN(Cc1ccc(OCCN(C)C2CCC2)cc1)c1cc(OC)ccc1[C@@H]1CCc2cc(O)ccc2C1]

Synthesized from pivalic acid (R)-6-{2-[ethyl(4-hydroxybenzoyl)amino]-4-methoxyphenyl}-5,6,7,8-tetrahydronaphthalen-2-yl ester (15 mg) and 2-chloro-N-cyclobutyl-N-methylacetamide (9.4 mg) according to an analogous synthetic method to Example 404 and purified by LC-MS, the title compound (7.0 mg) was obtained.

ESI-Mass; 515 [M$^+$+H]

Example 625

(R)-6-{2-{[4-(2-Dimethylaminoethoxy)-3-fluorobenzyl]ethylamino}-4-methoxyphenyl}-5,6,7,8-tetrahydronaphthalen-2-ol

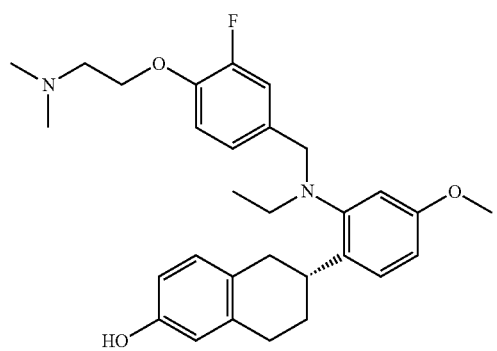

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 2-chloro-N,N-dimethylacetamide (9.4 mg) according to an analogous synthetic method to Example 404 and purified by LC-MS, the title compound (3.5 mg) was obtained.

ESI-Mass; 493 [M$^+$+H]

Example 626

(R)-6-{2-{[4-(2-Diethylaminoethoxy)-3-fluorobenzyl]ethylamino]-4-methoxyphenyl]-5,6,7,8-tetrahydronaphthalen-2-ol

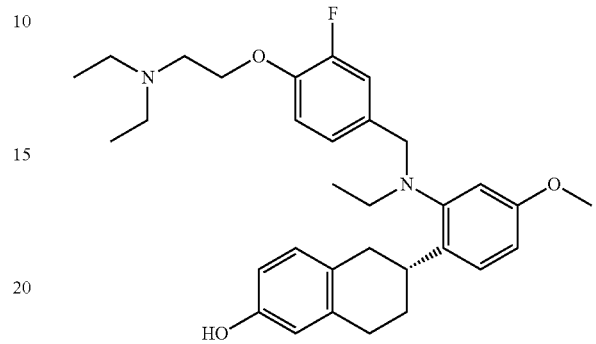

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg), 2-chloro-N,N-diethylacetamide (12 mg) according to an analogous synthetic method to Example 404 and purified by LC-MS, the title compound (2.9 mg) was obtained.

ESI-Mass; 521 [M$^+$+H]

Example 627

(R)-6-{2-{[4-(2-Azetidin-1-ylethoxy)-3-fluorobenzyl]ethylamino}-4-methoxyphenyl}-5,6,7,8-tetrahydronaphthalen-2-ol

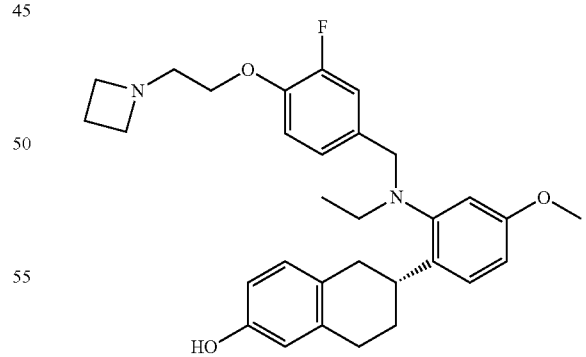

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 1-azetidin-1-yl-2-chloroethanone (10 mg) according to an analogous synthetic method to Example 404 and purified by LC-MS, the title compound (3.1 mg) was obtained.

ESI-Mass; 505 [M$^+$+H]

Example 628

(R)-6-{2-{Ethyl[3-fluoro-4-(2-pyrrolidin-1-ylethoxy)benzyl]amino}-4-methoxyphenyl}-5,6,7,8-tetrahydronaphthalen-2-ol

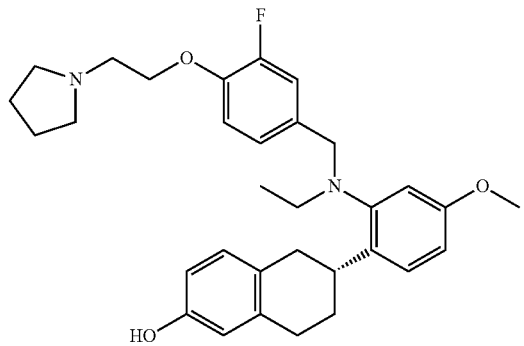 [SMILES: CCN(Cc1ccc(OCCN2CCCC2)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 2-chloro-1-pyrrolidin-1-ylethanone (11 mg) according to an analogous synthetic method to Example 404 and purified by LC-MS, the title compound (2.7 mg) was obtained.

ESI-Mass; 519 [M$^+$+H]

Example 629

(R)-6-{2-{Ethyl[3-fluoro-4-(2-piperidin-1-ylethoxy)benzyl]amino}-4-methoxyphenyl}-5,6,7,8-tetrahydronaphthalen-2-ol

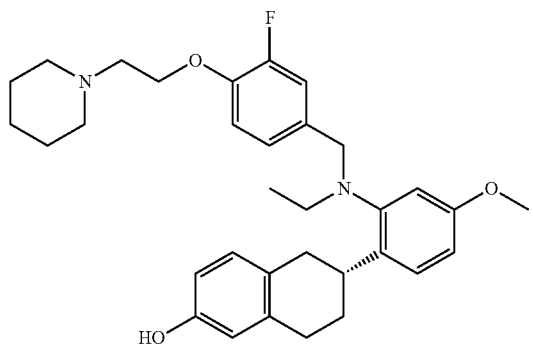

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 2-chloro-1-piperidin-1-ylethanone (13 mg) according to an analogous synthetic method to Example 404 and purified by LC-MS, the title compound (2.0 mg) was obtained.

ESI-Mass; 533 [M$^+$+H]

Example 630

(R)-6-{2-{{4-[2-(3,3-Dimethylpiperidin-1-yl)ethoxy]-3-fluorobenzyl}ethylamino}-4-methoxyphenyl}-5,6,7,8-tetrahydronaphthalen-2-ol

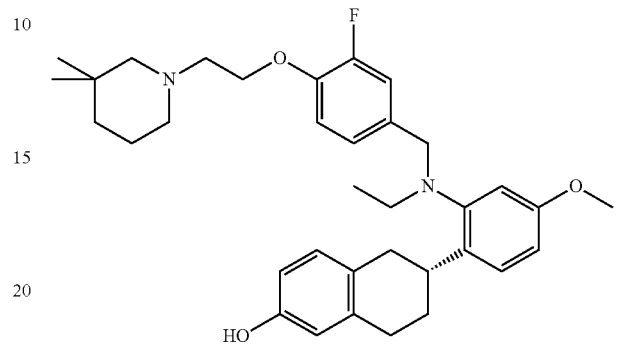

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 2-bromo-1-(3,3-dimethylpiperidin-1-yl)ethanone (18 mg) according to an analogous synthetic method to Example 404 and purified by LC-MS, the title compound (7.0 mg) was obtained.

ESI-Mass; 561 [M$^+$-1-11]

Example 631

(R)-6-{2-{[4-(2-Azepan-1-ylethoxy)-3-fluorobenzyl]ethylamino}-4-methoxyphenyl}-5,6,7,8-tetrahydronaphthalen-2-ol

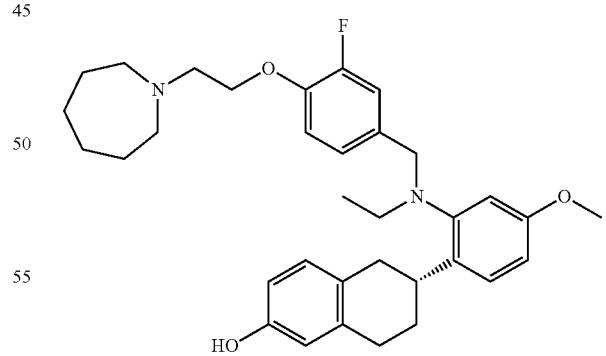

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 1-azepan-1-yl-2-chloroethanone (14 mg) according to an analogous synthetic method to Example 404 and purified by LC-MS, the title compound (2.5 mg) was obtained.

ESI-Mass; 547 [M$^+$+H]

Example 632

(R)-6-{2-{[4-(2-Azocan-1-ylethoxy)-3-fluorobenzyl]ethylamino}-4-methoxyphenyl}-5,6,7,8-tetrahydronaphthalen-2-ol

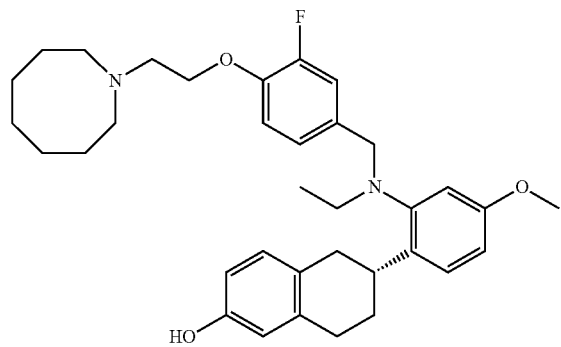 [SMILES: CCN(Cc1ccc(OCCN2CCCCCCC2)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 1-azocan-1-yl-2-chloroethanone (15 mg) according to an analogous synthetic method to Example 404 and purified by LC-MS, the title compound (2.0 mg) was obtained.

ESI-Mass; 561 [M$^+$+H]

Example 633

(R)-6-{2-{Ethyl{3-fluoro-4-{2-[(2-methoxyethyl)methylamino]ethoxy}benzyl]amino}-4-methoxyphenyl]-5,6,7,8-tetrahydronaphthalen-2-ol

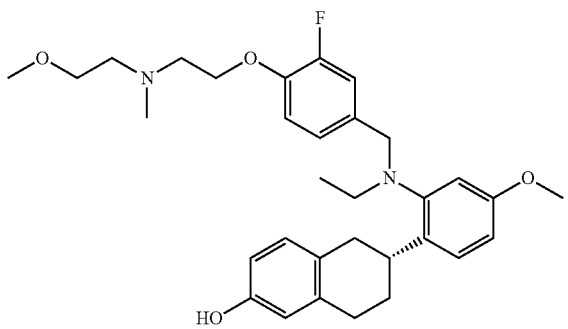

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (20 mg) and 2-chloro-N-(2-methoxyethyl)-N-methylacetamide (13 mg) according to an analogous synthetic method to Example 404 and purified by LC-MS, the title compound (4.9 mg) was obtained.

ESI-Mass; 537 [M$^+$+H]

Example 634

(S)-6-{2-{[4-(2-Dimethylaminoethoxy)-3-fluorobenzyl]ethylamino]-4-methoxyphenyl}-5,6,7,8-tetrahydronaphthalen-2-ol

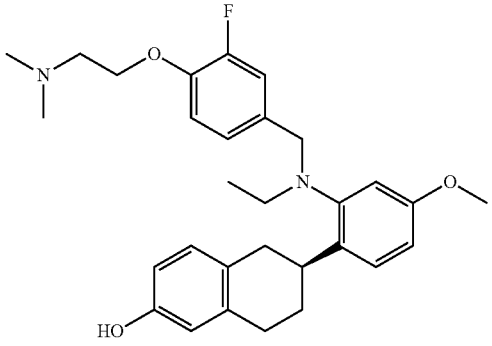

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 2-chloro-N,N-dimethylacetamide (9.4 mg) according to an analogous synthetic method to Example 404 and purified by LC-MS, the title compound (2.7 mg) was obtained.

ESI-Mass; 493 [M$^+$+H]

Example 635

(S)-6-{2-{[4-(2-Diethylaminoethoxy)-3-fluorobenzyl]ethylamino}-4-methoxyphenyl}-5,6,7,8-tetrahydronaphthalen-2-ol

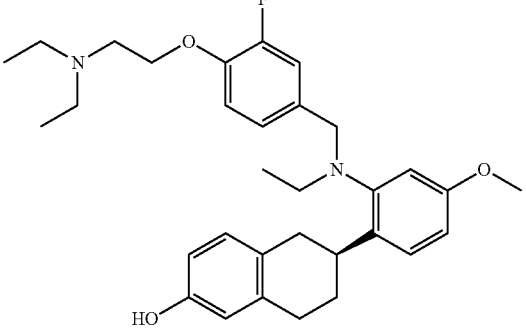

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 2-chloro-N,N-diethylacetamide (12 mg) according to an analogous synthetic method to Example 404 and purified by LC-MS, the title compound (3.1 mg) was obtained.

ESI-Mass; 521 [M$^+$+H]

Example 636

(S)-6-{2-{[4-(2-Azetidin-1-ylethoxy)-3-fluorobenzyl]ethylamino}-4-methoxyphenyl}-5,6,7,8-tetrahydronaphthalen-2-ol

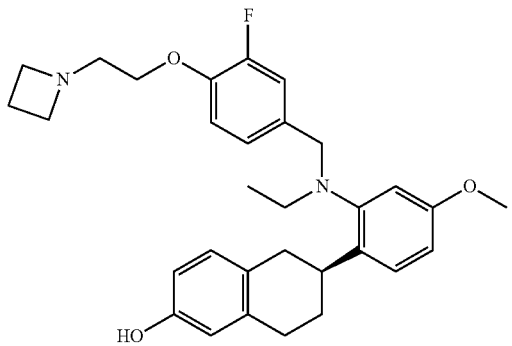 [SMILES: CCN(Cc1ccc(OCCN2CCC2)c(F)c1)c1cc(OC)ccc1[C@H]1CCc2cc(O)ccc2C1]

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 1-azetidin-1-yl-2-chloroethanone (10 mg) according to an analogous synthetic method to Example 404 and purified by LC-MS, the title compound (2.7 mg) was obtained.

ESI-Mass; 505 [M$^+$+H]

Example 637

(S)-6-{2-{Ethyl[3-fluoro-4-(2-pyrrolidin-1-ylethoxy)benzyl]amino}-4-methoxyphenyl}-5,6,7,8-tetrahydronaphthalen-2-ol

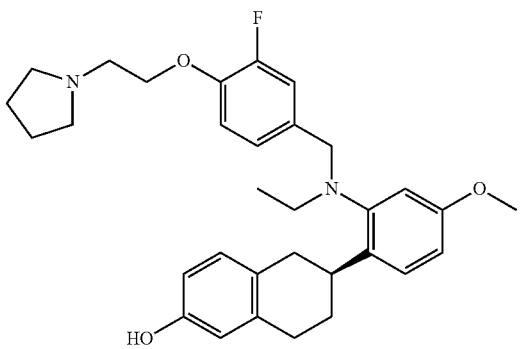 [SMILES: CCN(Cc1ccc(OCCN2CCCC2)c(F)c1)c1cc(OC)ccc1[C@H]1CCc2cc(O)ccc2C1]

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 2-chloro-1-pyrrolidin-1-ylethanone (11 mg) according to an analogous synthetic method to Example 404 and purified by LC-MS, the title compound (2.7 mg) was obtained.

ESI-Mass; 519 [M$^+$+H]

Example 638

(S)-6-{2-{Ethyl[3-fluoro-4-(2-piperidin-1-ylethoxy)benzyl]amino}-4-methoxyphenyl}-5,6,7,8-tetrahydronaphthalen-2-ol

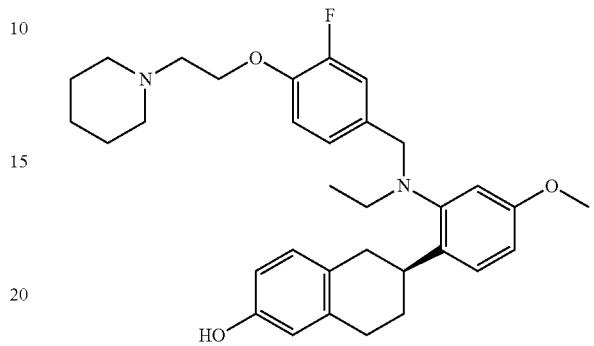

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 2-chloro-1-piperidin-1-ylethanone (13 mg) according to an analogous synthetic method to Example 404 and purified by LC-MS, the title compound (0.8 mg) was obtained.

ESI-Mass; 533 [M$^+$+H]

Example 639

(S)-6-{2-{{4-[2-(3,3-Dimethylpiperidin-1-yl)ethoxy]-3-fluorobenzyl}ethylamino}-4-methoxyphenyl}-5,6,7,8-tetrahydronaphthalen-2-ol

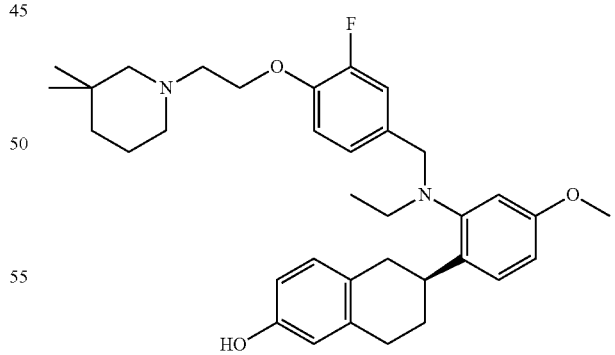

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 2-bromo-1-(3,3-dimethylpiperidin-1-yl)ethanone (18 mg) according to an analogous synthetic method to Example 404 and purified by LC-MS, the title compound (1.6 mg) was obtained.

ESI-Mass; 561 [M$^+$+H]

Example 640

(S)-6-{2-{[4-(2-Azepan-1-ylethoxy)-3-fluorobenzyl]ethylamino}-4-methoxyphenyl}-5,6,7,8-tetrahydronaphthalen-2-ol

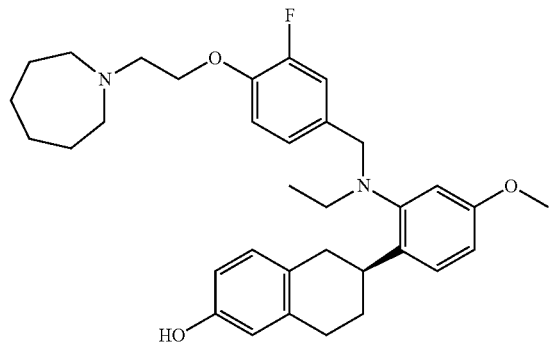 [SMILES: CCN(Cc1ccc(OCCN2CCCCCC2)c(F)c1)c1cc(OC)ccc1[C@H]1CCc2cc(O)ccc2C1]

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 1-azepan-1-yl-2-chloroethanone (14 mg) according to an analogous synthetic method to Example 404 and purified by LC-MS, the title compound (1.3 mg) was obtained.

ESI-Mass; 547 [M$^+$+H]

Example 641

(S)-6-{2-{[4-(2-Azocan-1-ylethoxy)-3-fluorobenzyl]ethylamino}-4-methoxyphenyl}-5,6,7,8-tetrahydronaphthalen-2-ol

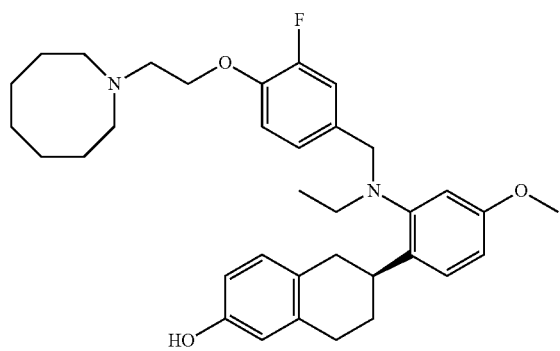 [SMILES: CCN(Cc1ccc(OCCN2CCCCCCC2)c(F)c1)c1cc(OC)ccc1[C@H]1CCc2cc(O)ccc2C1]

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 1-azocan-1-yl-2-chloroethanone (15 mg) according to an analogous synthetic method to Example 404 and purified by LC-MS, the title compound (0.7 mg) was obtained.

ESI-Mass; 561 [M$^+$+H]

Example 642

(S)-6-{2-{Ethyl{3-fluoro-4-{2-[(2-methoxyethyl)methylamino]ethoxy}benzyl}amino}-4-methoxyphenyl}-5,6,7,8-tetrahydronaphthalen-2-ol

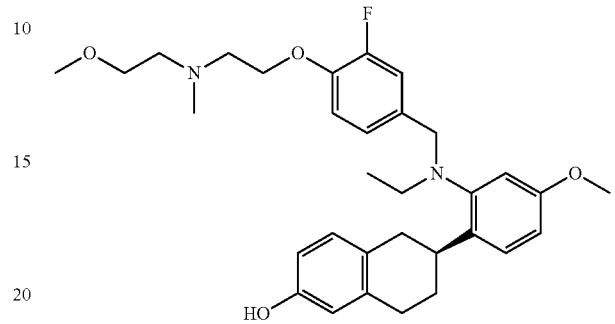

Synthesized from pivalic acid (S)-6-{2-[ethyl(3-fluoro-4-hydroxybenzoyl)amino]-4-methoxyphenyl}-5,6,7,8-tetrahydronaphthalen-2-yl ester (20 mg) and 2-chloro-N-(2-methoxyethyl)-N-methylacetamide (13 mg) according to an analogous synthetic method to Example 404 and purified by LC-MS, the title compound (2.1 mg) was obtained.

ESI-Mass; 537 [M$^+$+H]

Example 643

(R)-6-{2-{Ethyl[3-fluoro-4-(3-piperidin-1-ylpropoxy)benzyl]amino}-4-methoxyphenyl}-5,6,7,8-tetrahydronaphthalen-2-ol

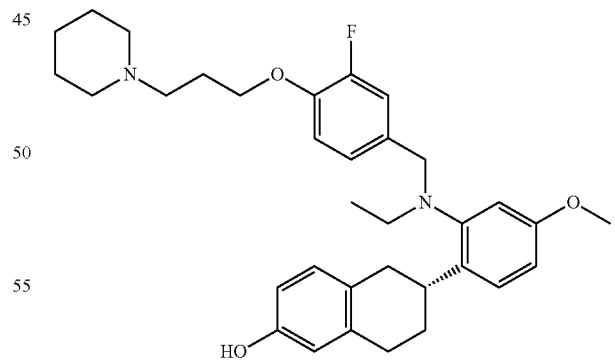

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (25 mg) and 1-(3-chloropropyl)piperidine (19 mg) according to an analogous synthetic method to Example 404 and purified by LC-MS, the title compound (13 mg) was obtained.

ESI-Mass; 547 [M$^+$+H]

Example 644

(R)-6-{2-{{4-[2-(Butylmethylamino)ethoxy]-3-fluorobenzyl}ethylamino}-4-methoxyphenyl}-5,6,7,8-tetrahydronaphthalen-2-ol

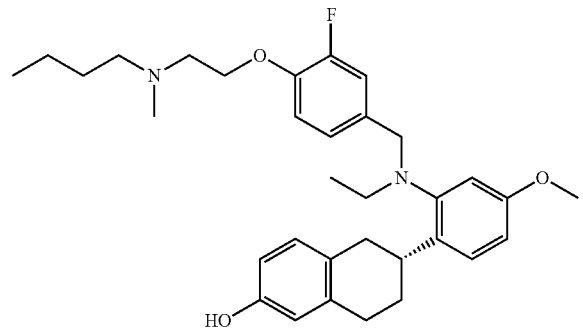

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (21 mg) and N-butyl-2-chloro-N-methylacetamide (13 mg) according to an analogous synthetic method to Example 404 and purified by LC-MS, the title compound (9.0 mg) was obtained.

ESI-Mass; 535 [$M^+ +H$]

Example 645

(R)-6-{2-{{4-[2-(7-Azabicyclo[2.2.1]hept-7-yl)ethoxy]-3-fluorobenzyl}ethylamino}-4-methoxyphenyl}-5,6,7,8-tetrahydronaphthalen-2-ol

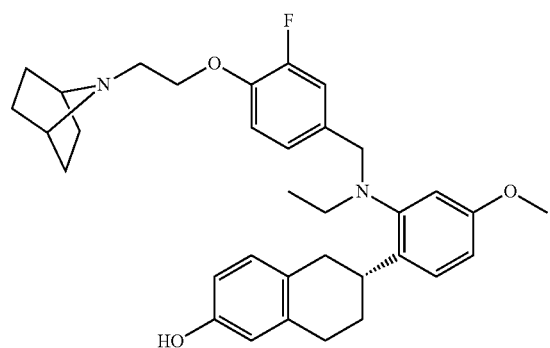 [SMILES: CCN(Cc1ccc(OCCN2C3CCC2CC3)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (21 mg) and 1-(7-azabicyclo[2.2.1]hept-7-yl)-2-bromoethanone (17 mg) according to an analogous synthetic method to Example 404 and purified by LC-MS, the title compound (9.5 mg) was obtained.

ESI-Mass; 545 [$M^+ +H$]

Example 646

(R)-6-{2-{Ethyl{3-fluoro-4-[2-(4-methylpiperidin-1-yl)ethoxy]benzyl}amino}-4-methoxyphenyl}-5,6,7,8-tetrahydronaphthalen-2-ol

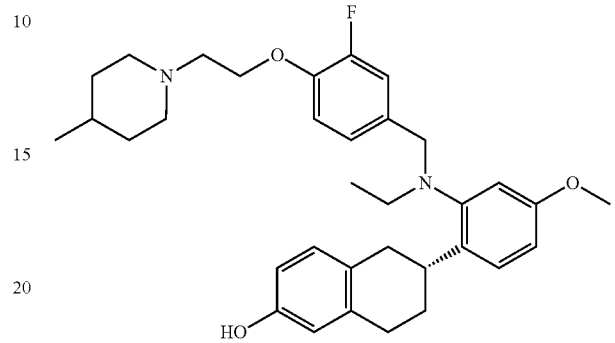

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-1-(4-methylpiperidin-1-yl)ethanone (10 mg) according to an analogous synthetic method to Example 404 and purified by LC-MS, the title compound (6.8 mg) was obtained.

ESI-Mass; 547 [$M^+ +H$]

Example 647

(R)-6-{2-{Ethyl{4-[2-(ethylmethylamino)ethoxy]-3-fluorobenzyl}amino}-4-methoxyphenyl}-5,6,7,8-tetrahydronaphthalen-2-ol Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-ethyl-N-methylacetamide (7.9 mg) according to an analogous synthetic method to Example 404 and purified by LC-MS, the title compound (10 mg) was obtained.

ESI-Mass; 507 [$M^+ +H$]

Example 648

(R)-6-{2-{Ethyl{3-fluoro-4-[2-(methylpropylamino)ethoxy]benzyl}amino}-4-methoxyphenyl}-5,6,7,8-tetrahydronaphthalen-2-ol

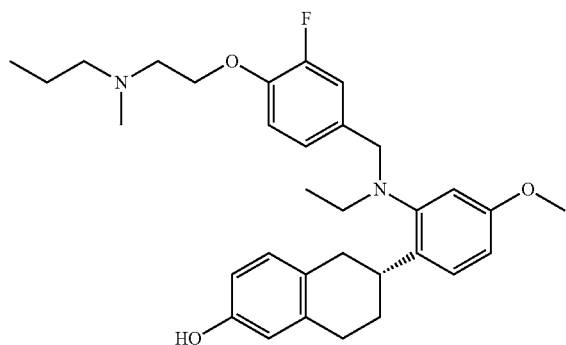

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-methyl-N-propylacetamide (8.7 mg) according to an analogous synthetic method to Example 404 and purified by LC-MS, the title compound (2.5 mg) was obtained.

ESI-Mass; 521 [$M^+$+H]

Example 649

(R)-6-{2-{Ethyl{3-fluoro-4-[2-(isopropylmethylamino)ethoxy]benzyl}amino}-4-methoxyphenyl}-5,6,7,8-tetrahydronaphthalen-2-ol

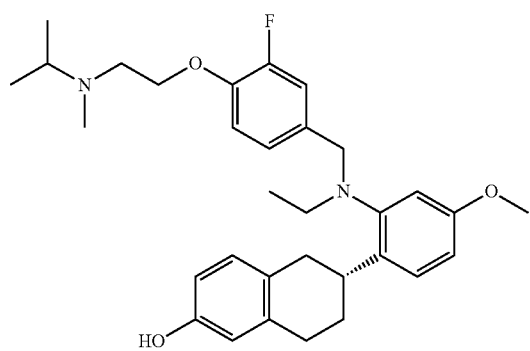 [SMILES: CCN(Cc1ccc(OCCN(C)C(C)C)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-isopropyl-N-methylacetamide (8.7 mg) according to an analogous synthetic method to Example 404 and purified by LC-MS, the title compound (10 mg) was obtained.

ESI-Mass; 521 [$M^+$+H]

Example 650

(R)-6-{2-{{4-{2-[(2-Ethoxyethyl)methylamino]ethoxy}-3-fluorobenzyl}ethylamino}-4-methoxyphenyl}-5,6,7,8-tetrahydronaphthalen-2-ol

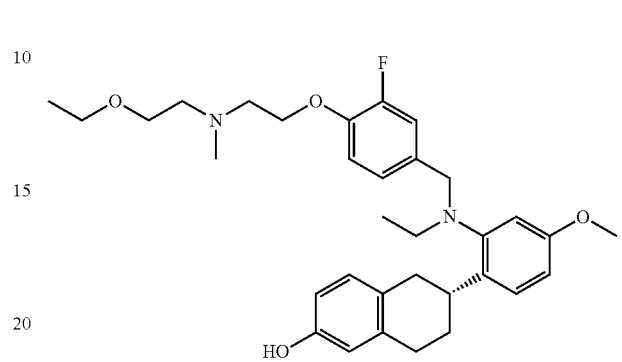

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-(2-ethoxyethyl)-N-methylacetamide (10 mg) according to an analogous synthetic method to Example 404 and purified by LC-MS, the title compound (3.0 mg) was obtained.

ESI-Mass; 551 [$M^+$+H]

Example 651

(R)-6-{2-{Ethyl{3-fluoro-4-{2-[(3-methoxypropyl)methylamino]ethoxy}benzyl}amino}-4-methoxyphenyl}-5,6,7,8-tetrahydronaphthalen-2-ol

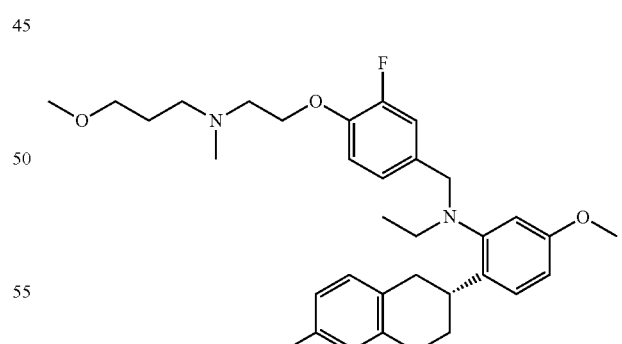

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-(3-methoxypropyl)-N-methylacetamide (10 mg) according to an analogous synthetic method to Example 404 and purified by LC-MS, the title compound (2.8 mg) was obtained.

ESI-Mass; 551 [$M^+$+H]

Example 652

(R)-6-{2-{Ethyl{3-fluoro-4-{2-{methyl[(S)-tetrahydrofuran-2-ylmethyl]amino}ethoxy}benzyl}amino}-4-methoxyphenyl}-5,6,7,8-tetrahydronaphthalen-2-ol

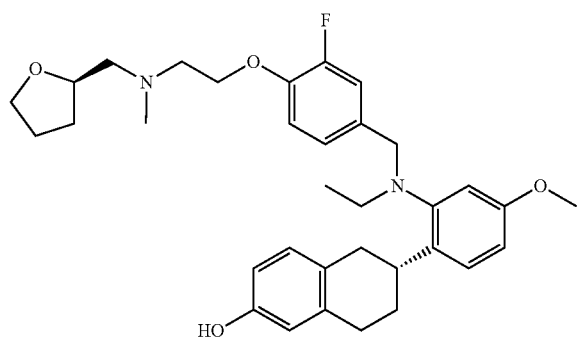 [SMILES: CCN(Cc1ccc(OCCN(C)C[C@H]2CCCO2)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-methyl-N—[(S)-tetrahydrofuran-2-ylmethyl]acetamide (11 mg) according to an analogous synthetic method to Example 404 and purified by LC-MS, the title compound (3.4 mg) was obtained.

ESI-Mass; 563 [M$^+$+H]

Example 653

(R)-6-{2-{Ethyl{3-fluoro-4-{2-{methyl[(R)-tetrahydrofuran-2-ylmethyl]amino}ethoxy}benzyl}amino}-4-methoxyphenyl}-5,6,7,8-tetrahydronaphthalen-2-ol

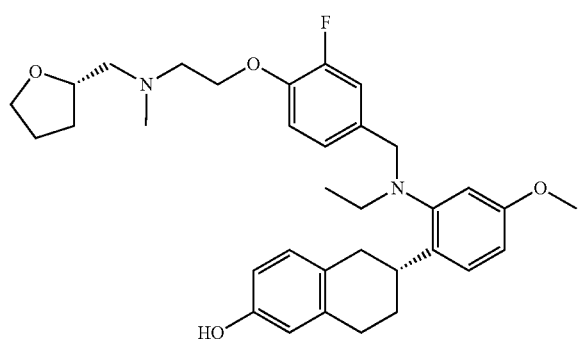 [SMILES: CCN(Cc1ccc(OCCN(C)C[C@@H]2CCCO2)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-methyl-N—[(R)-tetrahydrofuran-2-ylmethyl]acetamide (11 mg) according to an analogous synthetic method to Example 404 and purified by LC-MS, the title compound (3.2 mg) was obtained.

ESI-Mass; 563 [M$^+$+H]

Example 654

(R)-6-{2-{Ethyl{3-fluoro-4-{2-[methyl(tetrahydropyran-4-yl)amino]ethoxy}benzyl}amino}-4-methoxyphenyl}-5,6,7,8-tetrahydronaphthalen-2-ol

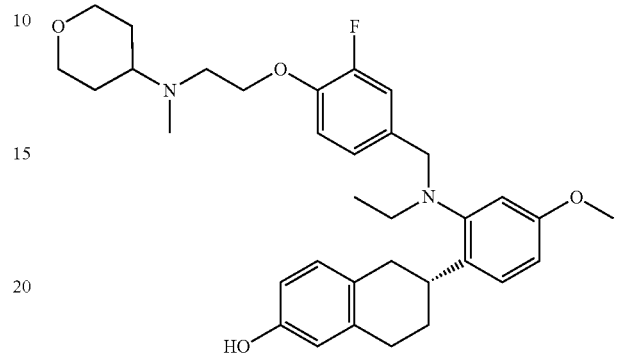

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-methyl-N-(tetrahydropyran-4-yl)acetamide (11 mg) according to an analogous synthetic method to Example 404 and purified by LC-MS, the title compound (3.8 mg) was obtained.

ESI-Mass; 563 [M$^+$+H]

Example 655

(R)-6-{2-{Ethyl{3-fluoro-4-{2-[methyl(tetrahydropyran-4-ylmethyl)amino]ethoxy}benzyl}amino}-4-methoxyphenyl}-5,6,7,8-tetrahydronaphthalen-2-ol

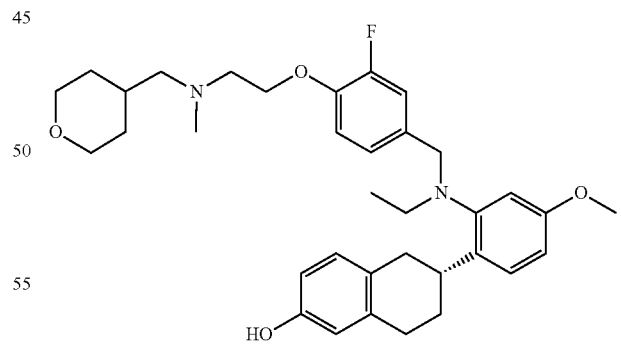

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-methyl-N-(tetrahydropyran-4-ylmethyl)acetamide (12 mg) according to an analogous synthetic method to Example 404 and purified by LC-MS, the title compound (9.5 mg) was obtained.

ESI-Mass; 577 [M$^+$+H]

Example 656

(R)-6-{2-{{4-[2-(cyclobutylmethylamino)ethoxy]-3-fluorobenzyl}ethylamino}-4-methoxyphenyl}-5,6,7,8-tetrahydronaphthalen-2-ol

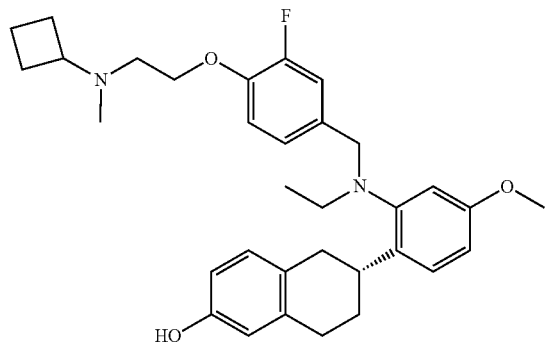 [SMILES: CCN(Cc1ccc(OCCN(C)C2CCC2)c(F)c1)c1cc(OC)ccc1[C@@H]1CCc2cc(O)ccc2C1]

Synthesized from pivalic acid (R)-6-{2-[ethyl(3-fluoro-4-hydroxybenzoyl)amino]-4-methoxyphenyl}-5,6,7,8-tetrahydronaphthalen-2-yl ester (15 mg) and 2-chloro-N-cyclobutyl-N-methylacetamide (9.4 mg) according to an analogous synthetic method to Example 404 and purified by LC-MS, the title compound (7.2 mg) was obtained.

ESI-Mass; 533 [M$^+$+H]

Example 657

(R)-6-{2-{[4-(2-Diethylaminoethoxy)-3-fluorobenzyl]methylamino}-4-methoxyphenyl}-5,6,7,8-tetrahydronaphthalen-2-ol

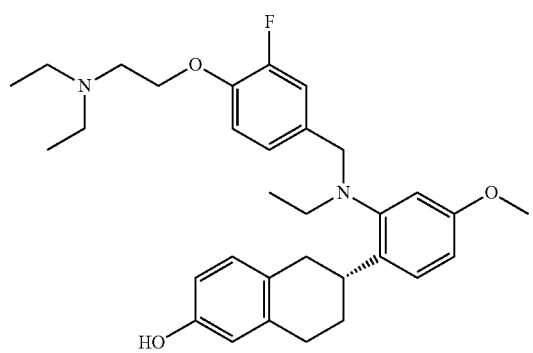

Synthesized from pivalic acid (R)-6-{2-[(3-fluoro-4-hydroxybenzoyl)methylamino]-4-methoxyphenyl}-5,6,7,8-tetrahydronaphthalen-2-yl ester (20 mg) and 2-chloro-N,N-diethylacetamide (12 mg) according to an analogous synthetic method to Example 404 and purified by LC-MS, the title compound (9.5 mg) was obtained.

ESI-Mass; 507 [M$^+$+H]

Example 658

(R)-6-{2-{[3-Fluoro-4-(2-piperidin-1-ylethoxy)benzyl]methylamino}-4-methoxyphenyl}-5,6,7,8-tetrahydronaphthalen-2-ol

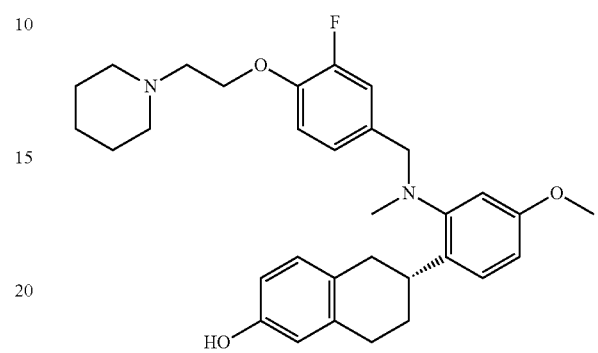

Synthesized from pivalic acid (R)-6-{2-[(3-fluoro-4-hydroxybenzoyl)methylamino]-4-methoxyphenyl}-5,6,7,8-tetrahydronaphthalen-2-yl ester (20 mg) and 2-chloro-1-piperidin-1-ylethanone (13 mg) according to an analogous synthetic method to Example 404 and purified by LC-MS, the title compound (8.8 mg) was obtained.

ESI-Mass; 519 [M$^+$+H]

Example 659

(R)-6-{2-{{3-Fluoro-4-{2-[(2-methoxyethyl)methylamino]ethoxy}benzyl}methylamino}-4-methoxyphenyl}-5,6,7,8-tetrahydronaphthalen-2-ol

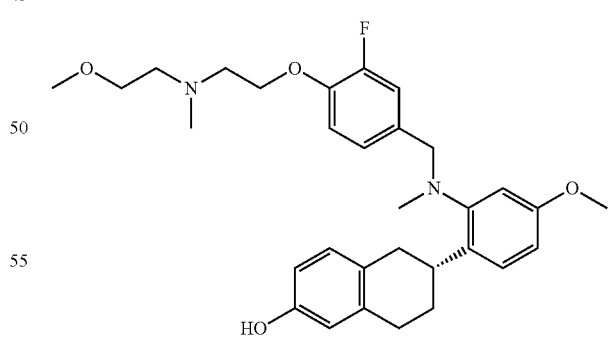

Synthesized from pivalic acid (R)-6-{2-[(3-fluoro-4-hydroxybenzoyl)methylamino]-4-methoxyphenyl}-5,6,7,8-tetrahydronaphthalen-2-yl ester (20 mg) and 2-chloro-N-(2-methoxyethyl)-N-methylacetamide (13 mg) according to an analogous synthetic method to Example 404 and purified by LC-MS, the title compound (9.5 mg) was obtained.

ESI-Mass; 523 [M$^+$+H]

Example 660

(R)-6-{2-{[4-(2-Dimethylaminoethoxy)benzyl]ethylamino}-4,5-dimethoxyphenyl}-5,6,7,8-tetrahydronaphthalen-2-ol

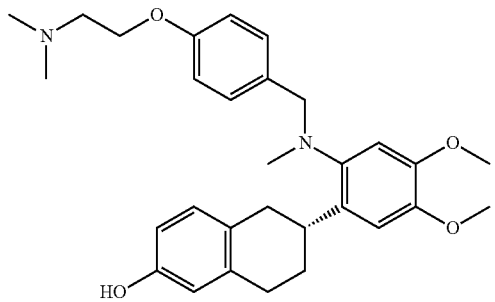

Synthesized from pivalic acid (R)-6-{2-[ethyl(4-hydroxybenzoyl)amino]-4,5-dimethoxyphenyl}tetrahydronaphthalen-2-yl ester (16 mg) and 2-chloro-N,N-dimethylacetamide (6.6 mg) according to an analogous synthetic method to Example 404 and purified by LC-MS, the title compound (5.3 mg) was obtained.

ESI-Mass; 505 [M$^+$+H]

Example 661

(R)-6-{2-{[4-(2-Diethylaminoethoxy)benzyl]ethylamino}-4,5-dimethoxyphenyl}-5,6,7,8-tetrahydronaphthalen-2-ol

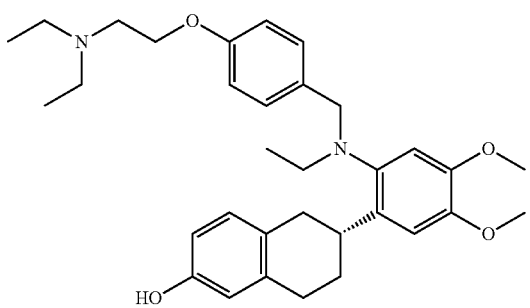

Synthesized from pivalic acid (R)-6-{2-[ethyl(4-hydroxybenzoyl)amino]-4,5-dimethoxyphenyl}tetrahydronaphthalen-2-yl ester (16 mg) and 2-chloro-N,N-diethylacetamide (8.1 mg) according to an analogous synthetic method to Example 404 and purified by LC-MS, the title compound (7.2 mg) was obtained.

ESI-Mass; 533 [M$^+$+H]

Example 662

(R)-6-{2-{Ethyl[4-(2-pyrrolidin-1-ylethoxy)benzyl]amino}-4,5-dimethoxyphenyl}-5,6,7,8-tetrahydronaphthalen-2-ol

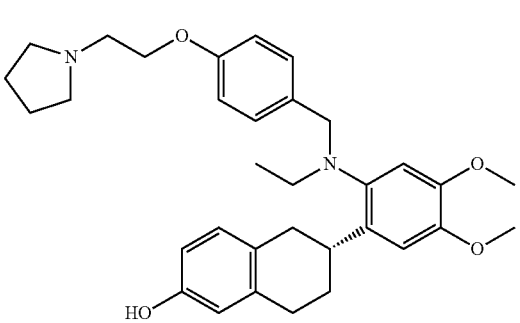 [SMILES: CCN(Cc1ccc(OCCN2CCCC2)cc1)c1cc(OC)c(OC)cc1[C@@H]1CCc2cc(O)ccc2C1]

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-1-pyrrolidin-1-ylethanone (8.0 mg) according to an analogous synthetic method to Example 404 and purified by LC-MS, the title compound (7.8 mg) was obtained.

ESI-Mass; 531 [M$^+$+H]

Example 663

(R)-6-{2-{Ethyl[4-(2-piperidin-1-ylethoxy)benzyl]amino}-4,5-dimethoxyphenyl}-5,6,7,8-tetrahydronaphthalen-2-ol

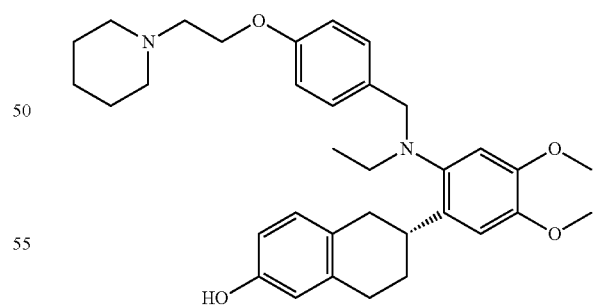

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-1-piperidin-1-ylethanone (8.8 mg) according to an analogous synthetic method to Example 404 and purified by LC-MS, the title compound (6.8 mg) was obtained.

ESI-Mass; 545 [M$^+$+H]

Example 664

(R)-6-{2-{Ethyl{4-[2-(4-methylpiperidin-1-yl)ethoxy]benzyl}amino}-4,5-dimethoxyphenyl}-5,6,7,8-tetrahydronaphthalen-2-ol

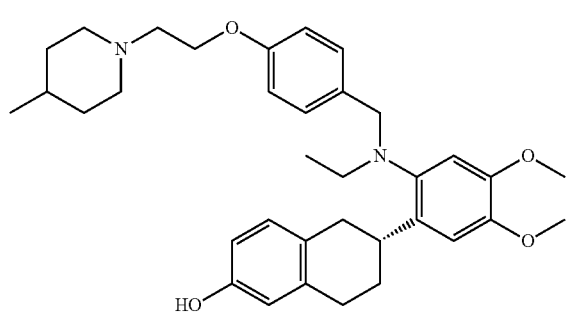

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-1-(4-methylpiperidin-1-yl)ethanone (9.5 mg) according to an analogous synthetic method to Example 404 and purified by LC-MS, the title compound (6.9 mg) was obtained.

ESI-Mass; 559 [M$^+$+H]

Example 665

(R)-6-{2-{[4-(2-Azepan-1-ylethoxy)benzyl]ethylamino}-4,5-dimethoxyphenyl}-5,6,7,8-tetrahydronaphthalen-2-ol

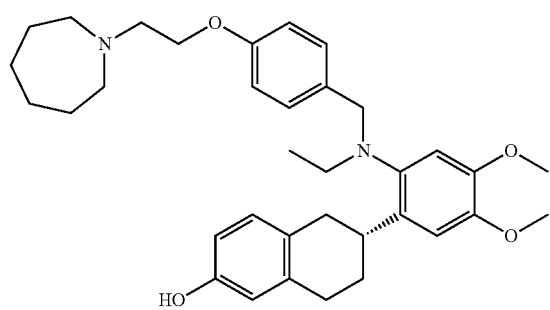 [SMILES: CCN(Cc1ccc(OCCN2CCCCCC2)cc1)c1cc(OC)c(OC)cc1[C@@H]1CCc2cc(O)ccc2C1]

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 1-azepan-1-yl-2-chloroethanone (9.5 mg) according to an analogous synthetic method to Example 404 and purified by LC-MS, the title compound (7.5 mg) was obtained.

ESI-Mass; 559 [M$^+$+H]

Example 666

(R)-6-{2-{Ethyl{4-[2-(2,2,6,6-tetramethylpiperidin-1-yl)ethoxy]benzyl}amino}-4,5-dimethoxyphenyl}-5,6,7,8-tetrahydronaphthalen-2-ol

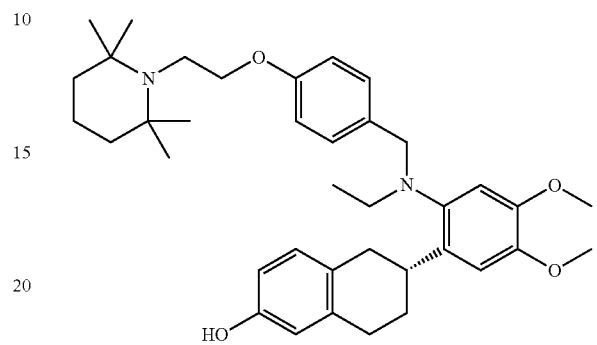

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-bromo-1-(2,2,6,6-tetramethylpiperidin-1-yl)ethanone (14 mg) according to an analogous synthetic method to Example 404 and purified by LC-MS, the title compound (1.0 mg) was obtained.

ESI-Mass; 601 [M$^+$+H]

Example 667

(R)-6-{2-{{4-[2-(7-Azabicyclo[2.2.1]hept-7-yl)ethoxy]benzyl}ethylamino}-4,5-dimethoxyphenyl}-5,6,7,8-tetrahydronaphthalen-2-ol

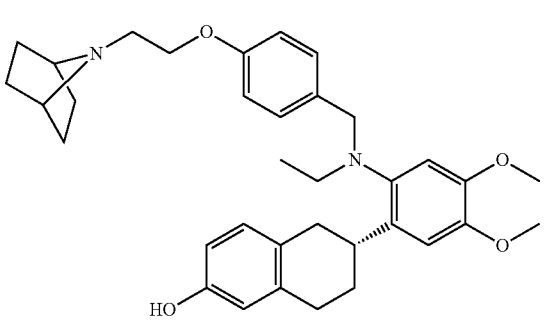 [SMILES: CCN(Cc1ccc(OCCN2C3CCC2CC3)cc1)c1cc(OC)c(OC)cc1[C@@H]1CCc2cc(O)ccc2C1]

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 1-(7-azabicyclo[2.2.1]hept-7-yl)-2-bromoethanone (12 mg) according to an analogous synthetic method to Example 404 and purified by LC-MS, the title compound (8.3 mg) was obtained.

ESI-Mass; 557 [M$^+$+H]

Example 668

(R)-6-{2-{Ethyl{4-[2-(ethylmethylamino)ethoxy]benzyl}amino}-4,5-dimethoxyphenyl}-5,6,7,8-tetrahydronaphthalen-2-ol

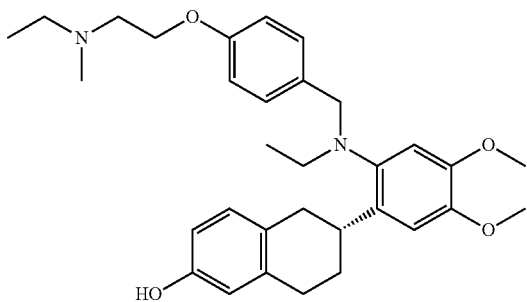

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-ethyl-N-methylacetamide (7.4 mg) according to an analogous synthetic method to Example 404 and purified by LC-MS, the title compound (3.0 mg) was obtained.

ESI-Mass; 519 [M$^+$+H]

Example 669

(R)-6-{2-{{4-[2-(Butylmethylamino)ethoxy]benzyl}ethylamino}-4,5-dimethoxyphenyl}-5,6,7,8-tetrahydronaphthalen-2-ol

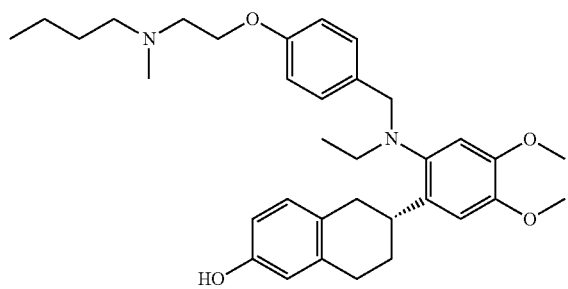

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and N-butyl-2-chloro-N-methylacetamide (8.9 mg) according to an analogous synthetic method to Example 404 and purified by LC-MS, the title compound (6.6 mg) was obtained.

ESI-Mass; 547 [M$^+$+H]

Example 670

(R)-6-{2-{{4-[2-(tert-Butylmethylamino)ethoxy]benzyl}ethylamino}-4,5-dimethoxyphenyl}-5,6,7,8-tetrahydronaphthalen-2-ol

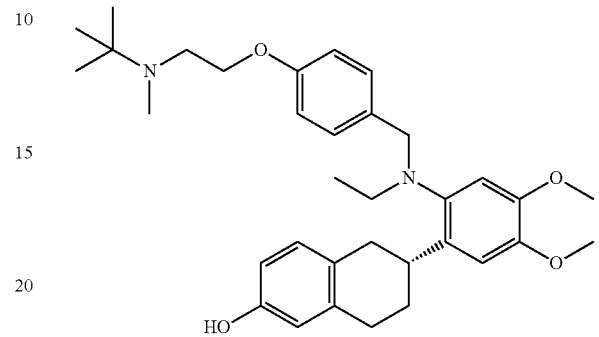

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and N-tert-butyl-2-chloro-N-methylacetamide (8.9 mg) according to an analogous synthetic method to Example 404 and purified by LC-MS, the title compound (8.6 mg) was obtained.

ESI-Mass; 547 [M$^+$+H]

Example 671

(R)-6-{2-{Ethyl{4-[2-(isopropylmethylamino)ethoxy]benzyl}amino}-4,5-dimethoxyphenyl}-5,6,7,8-tetrahydronaphthalen-2-ol

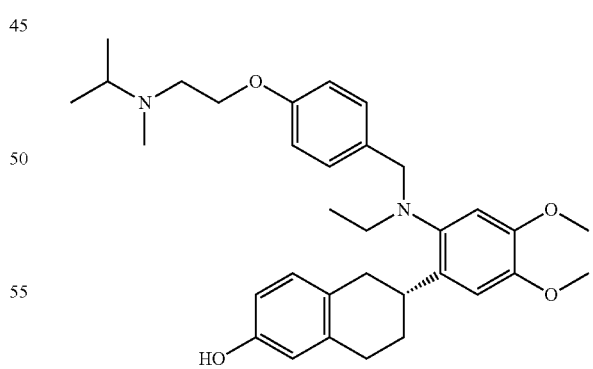

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-isopropyl-N-methylacetamide (8.1 mg) according to an analogous synthetic method to Example 404 and purified by LC-MS, the title compound (5.7 mg) was obtained.

ESI-Mass; 533 [M$^+$+H]

Example 672

(R)-6-{2-{{4-{2-[(2-Ethoxyethyl)methylamino]ethoxy}benzyl}ethylamino}-4,5-dimethoxyphenyl}-5,6,7,8-tetrahydronaphthalen-2-ol

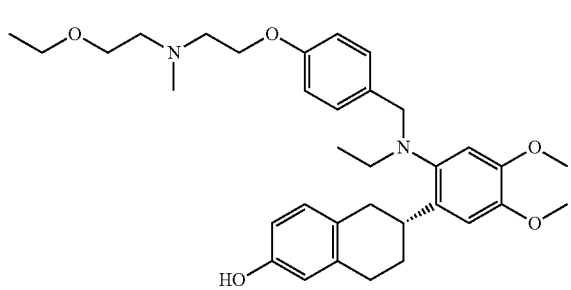

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-(2-ethoxyethyl)-N-methylacetamide (9.8 mg) according to an analogous synthetic method to Example 404 and purified by LC-MS, the title compound (2.3 mg) was obtained.

ESI-Mass; 563 [M$^+$+H]

Example 673

(R)-6-{2-{Ethyl{4-{2-[(3-methoxypropyl)methylamino]ethoxy}benzyl}amino}-4,5-dimethoxyphenyl}-5,6,7,8-tetrahydronaphthalen-2-ol

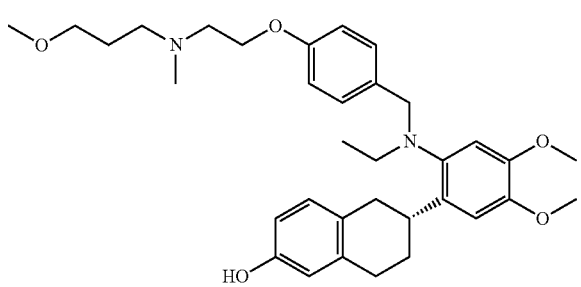 [SMILES: CCOCCN(C)CCOc1ccc(CN(CC)c2cc(OC)c(OC)cc2[C@@H]2CCc3cc(O)ccc3C2)cc1]

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-(3-methoxypropyl)-N-methylacetamide (9.8 mg) according to an analogous synthetic method to Example 404 and purified by LC-MS, the title compound (3.5 mg) was obtained.

ESI-Mass; 563 [M$^+$+H]

Example 674

(R)-6-{2-{Ethyl{4-{2-{methyl[(S)-tetrahydrofuran-2-ylmethyl]amino}ethoxy}benzyl}amino}-4,5-dimethoxyphenyl}-5,6,7,8-tetrahydronaphthalen-2-ol

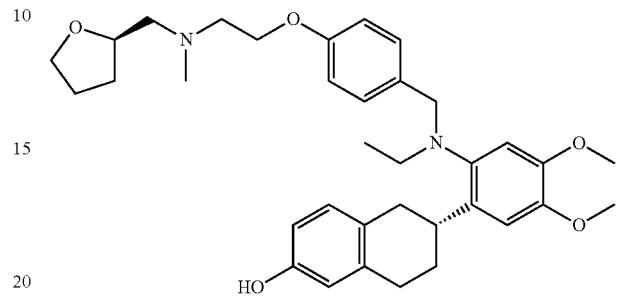

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-methyl-N—[(S)-tetrahydrofuran-2-ylmethyl]acetamide (10 mg) according to an analogous synthetic method to Example 404 and purified by LC-MS, the title compound (4.8 mg) was obtained.

ESI-Mass; 575 [M$^+$+H]

Example 675

(R)-6-{2-{Ethyl{4-{2-{methyl[(R)-tetrahydrofuran-2-ylmethyl]amino}ethoxy}benzyl}amino}-4,5-dimethoxyphenyl}-5,6,7,8-tetrahydronaphthalen-2-ol

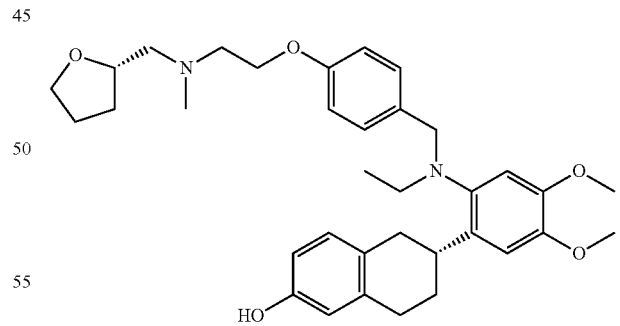

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-methyl-N—[(R)-tetrahydrofuran-2-ylmethyl]acetamide (10 mg) according to an analogous synthetic method to Example 404 and purified by LC-MS, the title compound (3.6 mg) was obtained.

ESI-Mass; 575 [M$^+$+H]

Example 676

(R)-6-{2-{Ethyl{4-{2-[methyl(tetrahydropyran-4-yl)amino]ethoxy}benzyl}amino}-4,5-dimethoxyphenyl}-5,6,7,8-tetrahydronaphthalen-2-ol

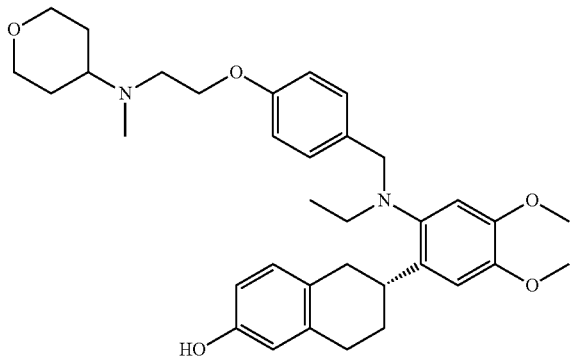 [SMILES: CCN(Cc1ccc(OCCN(C)C2CCOCC2)cc1)c1cc(OC)c(OC)cc1[C@@H]1CCc2cc(O)ccc2C1]

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-methyl-N-(tetrahydropyran-4-yl)acetamide (10 mg) according to an analogous synthetic method to Example 404 and purified by LC-MS, the title compound (4.1 mg) was obtained.

ESI-Mass; 575 [M$^+$+H]

Example 677

(R)-6-{2-{Ethyl{4-{2-[methyl(tetrahydropyran-4-ylmethyl)amino]ethoxy}benzyl}amino}-4,5-dimethoxyphenyl}-5,6,7,8-tetrahydronaphthalen-2-ol

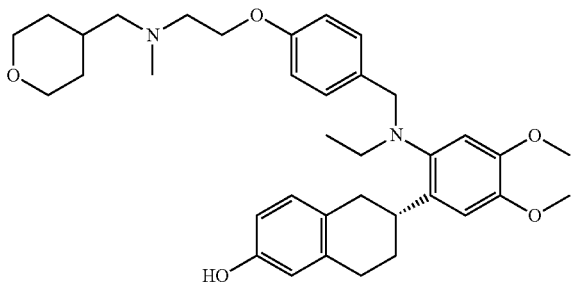 [SMILES: CCN(Cc1ccc(OCCN(C)CC2CCOCC2)cc1)c1cc(OC)c(OC)cc1[C@@H]1CCc2cc(O)ccc2C1]

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-methyl-N-(tetrahydropyran-4-ylmethyl)acetamide (11 mg) according to an analogous synthetic method to Example 404 and purified by LC-MS, the title compound (4.2 mg) was obtained.

ESI-Mass; 589 [M$^+$+H]

Example 678

(R)-6-{2-{{4-[2-(Cyclobutylmethylamino)ethoxy]benzyl}ethylamino}-4,5-dimethoxyphenyl}-5,6,7,8-tetrahydronaphthalen-2-ol

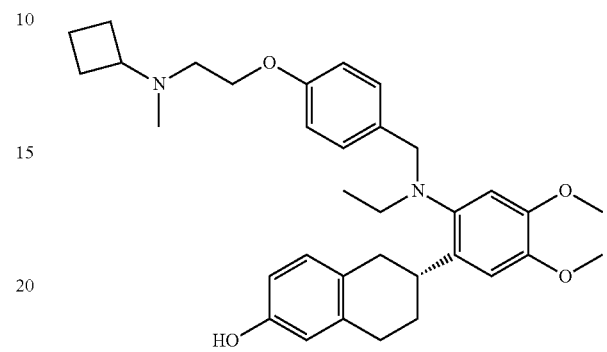

Synthesized from pivalic acid (R)-6-{2-[ethyl(4-hydroxybenzoyl)amino]-4,5-dimethoxyphenyl}-5,6,7,8-tetrahydronaphthalen-2-yl ester (16 mg) and 2-chloro-N-cyclobutyl-N-methylacetamide (8.8 mg) according to an analogous synthetic method to Example 404 and purified by LC-MS, the title compound (3.6 mg) was obtained.

ESI-Mass; 545 [M$^+$+H]

Example 679

(R)-6-{2-{[4-(2-Dimethylaminoethoxy)-3-fluorobenzyl]ethylamino}-4,5-dimethoxyphenyl}-5,6,7,8-tetrahydronaphthalen-2-ol

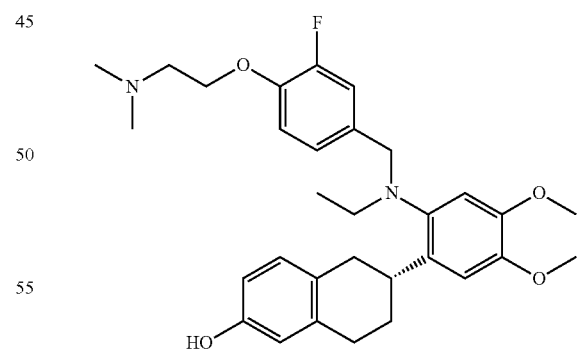

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N,N-dimethylacetamide (6.6 mg) according to an analogous synthetic method to Example 404 and purified by LC-MS, the title compound (3.4 mg) was obtained.

ESI-Mass; 523 [M$^+$+H]

Example 680

(R)-6-{2-{[4-(2-Diethylaminoethoxy)-3-fluorobenzyl]ethylamino}-4,5-dimethoxyphenyl}-5,6,7,8-tetrahydronaphthalen-2-ol

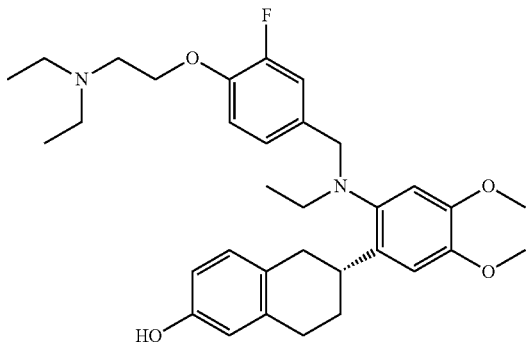

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N,N-diethylacetamide (8.1 mg) according to an analogous synthetic method to Example 404 and purified by LC-MS, the title compound (6.8 mg) was obtained.

ESI-Mass; 551 [M$^+$+H]

Example 681

(R)-6-{2-{Ethyl[3-fluoro-4-(2-pyrrolidin-1-ylethoxy)benzyl]amino}-4,5-dimethoxyphenyl}-5,6,7,8-tetrahydronaphthalen-2-ol

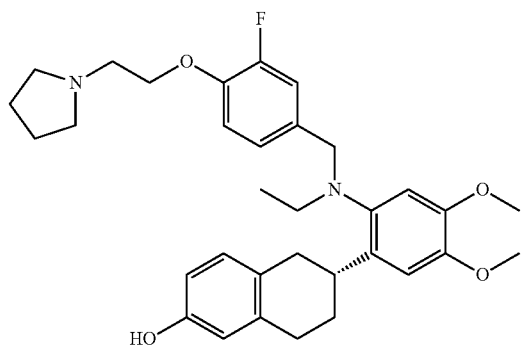 [SMILES: CCN(Cc1ccc(OCCN2CCCC2)c(F)c1)c1cc(OC)c(OC)cc1[C@@H]1CCc2cc(O)ccc2C1]

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-1-pyrrolidin-1-ylethanone (8.0 mg) according to an analogous synthetic method to Example 404 and purified by LC-MS, the title compound (4.2 mg) was obtained.

ESI-Mass; 549 [M$^+$+H]

Example 682

(R)-6-{2-{Ethyl[3-fluoro-4-(2-piperidin-1-ylethoxy)benzyl]amino}-4,5-dimethoxyphenyl}-5,6,7,8-tetrahydronaphthalen-2-ol

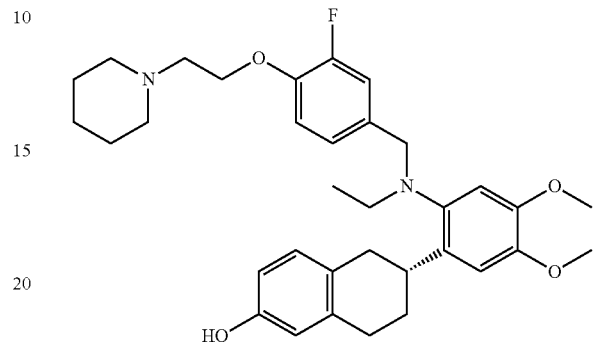

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-1-piperidin-1-ylethanone (8.8 mg) according to an analogous synthetic method to Example 404 and purified by LC-MS, the title compound (3.8 mg) was obtained.

ESI-Mass; 563 [M$^+$+H]

Example 683

(R)-6-{2-{Ethyl{3-fluoro-4-[2-(4-methylpiperidin-1-yl)ethoxy]benzyl}amino}-4,5-dimethoxyphenyl}-5,6,7,8-tetrahydronaphthalen-2-ol

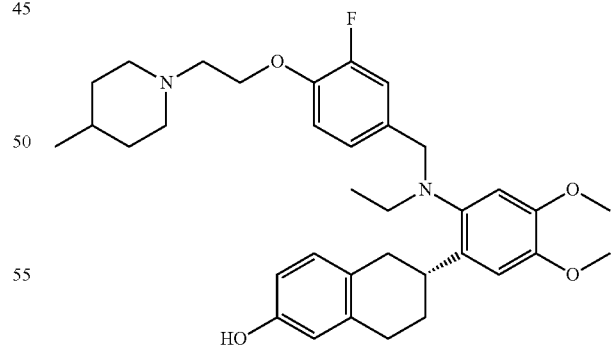

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-1-(4-methylpiperidin-1-yl)ethanone (9.5 mg) according to an analogous synthetic method to Example 404 and purified by LC-MS, the title compound (5.9 mg) was obtained.

ESI-Mass; 577 [M$^+$+H]

Example 684

(R)-6-{2-{[4-(2-Azepan-1-ylethoxy)-3-fluorobenzyl]ethylamino}-4,5-dimethoxyphenyl}-5,6,7,8-tetrahydronaphthalen-2-ol

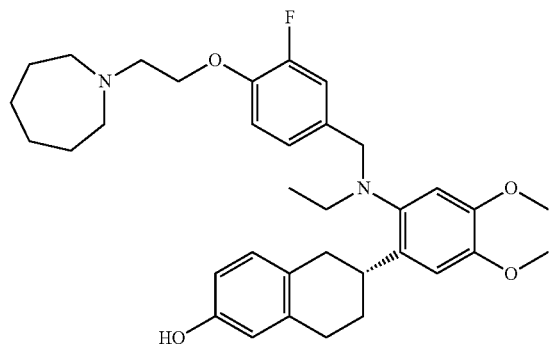

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 1-azepan-1-yl-2-chloroethanone (9.5 mg) according to an analogous synthetic method to Example 404 and purified by LC-MS, the title compound (5.6 mg) was obtained.

ESI-Mass; 577 [M$^+$+H]

Example 685

(R)-6-{2-{Ethyl{3-fluoro-4-[2-(2,2,6,6-tetramethylpiperidin-1-yl)ethoxy]benzyl}amino}-4,5-dimethoxyphenyl}-5,6,7,8-tetrahydronaphthalen-2-ol

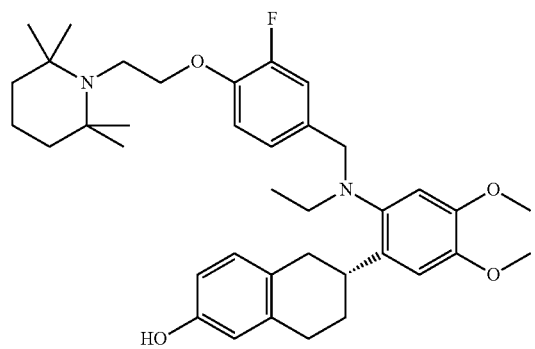 [SMILES: CCN(Cc1ccc(OCCN2C(C)(C)CCCC2(C)C)c(F)c1)c1cc(OC)c(OC)cc1[C@@H]1CCc2cc(O)ccc2C1]

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-bromo-1-(2,2,6,6-tetramethylpiperidin-1-yl)ethanone (14 mg) according to an analogous synthetic method to Example 404 and purified by LC-MS, the title compound (3.9 mg) was obtained.

ESI-Mass; 619 [M$^+$+H]

Example 686

(R)-6-{2-{{4-[2-(7-Azabicyclo[2.2.1]hept-7-yl)ethoxy]-3-fluorobenzyl}ethylamino}-4,5-dimethoxyphenyl}-5,6,7,8-tetrahydronaphthalen-2-ol

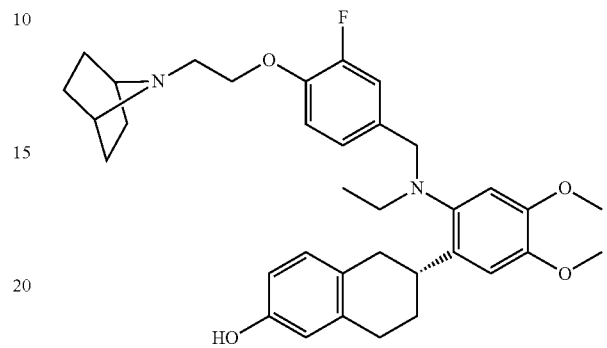

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 1-(7-azabicyclo[2.2.1]hept-7-yl)-2-bromoethanone (12 mg) according to an analogous synthetic method to Example 404 and purified by LC-MS, the title compound (7.1 mg) was obtained.

ESI-Mass; 575 [M$^+$+H]

Example 687

(R)-6-{2-{Ethyl{4-[2-(ethylmethylamino)ethoxy]-3-fluorobenzyl}amino}-4,5-dimethoxyphenyl}-5,6,7,8-tetrahydronaphthalen-2-ol

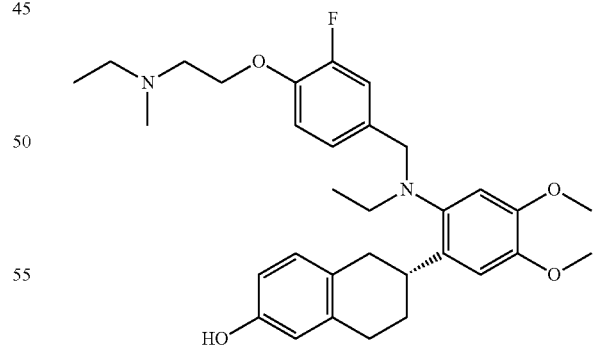

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-ethyl-N-methylacetamide (7.4 mg) according to an analogous synthetic method to Example 404 and purified by LC-MS, the title compound (4.1 mg) was obtained.

ESI-Mass; 537 [M$^+$+H]

Example 688

(R)-6-{2-{{4-[2-(Butylmethylamino)ethoxy]-3-fluorobenzyl}ethylamino}-4,5-dimethoxyphenyl}-5,6,7,8-tetrahydronaphthalen-2-ol

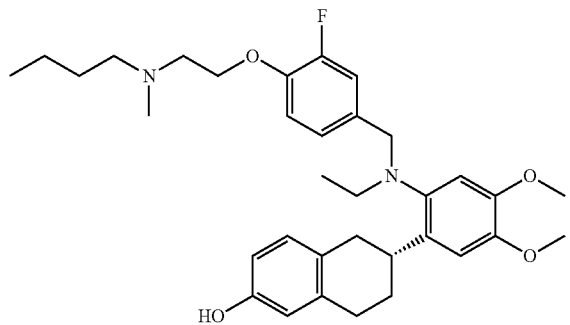 [SMILES: CCCCN(C)CCOc1ccc(CN(CC)c2cc(OC)c(OC)cc2[C@@H]2CCc3cc(O)ccc3C2)cc1F]

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and N-butyl-2-chloro-N-methylacetamide (8.9 mg) according to an analogous synthetic method to Example 404 and purified by LC-MS, the title compound (3.1 mg) was obtained.

ESI-Mass; 565 [M$^+$+H]

Example 689

(R)-6-{2-{{4-[2-(tert-Butylmethylamino)ethoxy]-3-fluorobenzyl}ethylamino}-4,5-dimethoxyphenyl}-5,6,7,8-tetrahydronaphthalen-2-ol

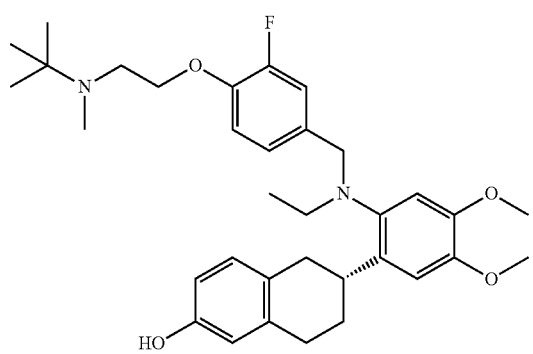

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and N-tert-butyl-2-chloro-N-methylacetamide (8.9 mg) according to an analogous synthetic method to Example 404 and purified by LC-MS, the title compound (6.9 mg) was obtained.

ESI-Mass; 565 [M$^+$+H]

Example 690

(R)-6-{2-{Ethyl{3-fluoro-4-[2-(isopropylmethylamino)ethoxy]benzyl}amino}-4,5-dimethoxyphenyl}-5,6,7,8-tetrahydronaphthalen-2-ol

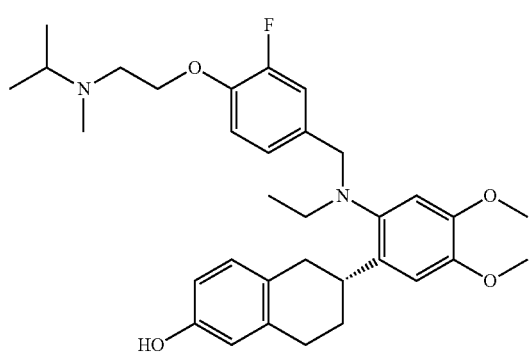

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-isopropyl-N-methylacetamide (8.1 mg) according to an analogous synthetic method to Example 404 and purified by LC-MS, the title compound (7.4 mg) was obtained.

ESI-Mass; 551 [M$^+$+H]

Example 691

(R)-6-{2-{{4-{2-[(2-Ethoxyethyl)methylamino]ethoxy}-3-fluorobenzyl}ethylamino}-4,5-dimethoxyphenyl}-5,6,7,8-tetrahydronaphthalen-2-ol

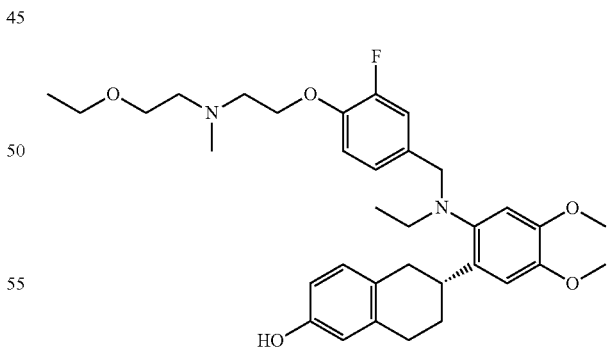

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-(2-ethoxyethyl)-N-methylacetamide (9.8 mg) according to an analogous synthetic method to Example 404 and purified by LC-MS, the title compound (1.9 mg) was obtained.

ESI-Mass; 581 [M$^+$+H]

Example 692

(R)-6-{2-{Ethyl{3-fluoro-4-{2-[(3-methoxypropyl)methylamino]ethoxy}benzyl}amino}-4,5-dimethoxyphenyl}-5,6,7,8-tetrahydronaphthalen-2-ol

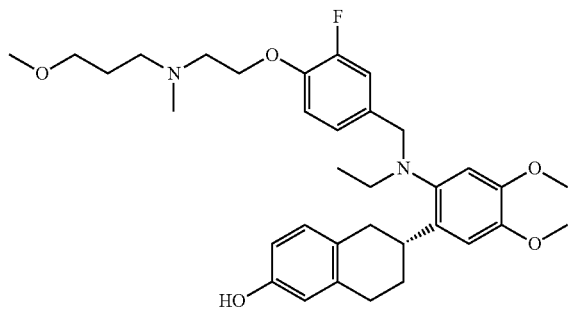

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-(3-methoxypropyl)-N-methylacetamide (9.8 mg) according to an analogous synthetic method to Example 404 and purified by LC-MS, the title compound (3.4 mg) was obtained.

ESI-Mass; 581 [M$^+$+H]

Example 693

(R)-6-{2-{Ethyl{3-fluoro-4-{2-{methyl[(S)-tetrahydrofuran-2-ylmethyl]amino}ethoxy}benzyl}amino}-4,5-dimethoxyphenyl}-5,6,7,8-tetrahydronaphthalen-2-ol

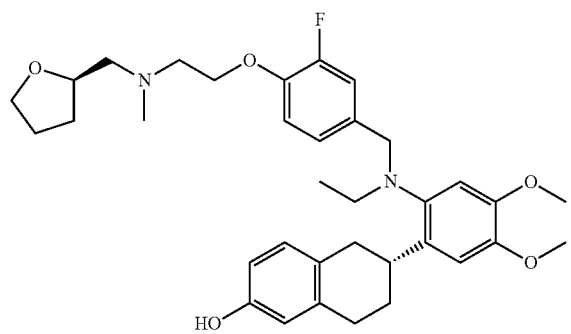 [SMILES: CCN(Cc1ccc(OCCN(C)C[C@H]2CCCO2)c(F)c1)c1cc(OC)c(OC)cc1[C@@H]1CCc2cc(O)ccc2C1]

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-methyl-N—[(S)-tetrahydrofuran-2-ylmethyl]acetamide (10 mg) according to an analogous synthetic method to Example 404 and purified by LC-MS, the title compound (6.9 mg) was obtained.

ESI-Mass; 593 [M$^+$+H]

Example 694

(R)-6-{2-{Ethyl{3-fluoro-4-{2-{methyl[(R)-tetrahydrofuran-2-ylmethyl]amino}ethoxy}benzyl}amino}-4,5-dimethoxyphenyl}-5,6,7,8-tetrahydronaphthalen-2-ol

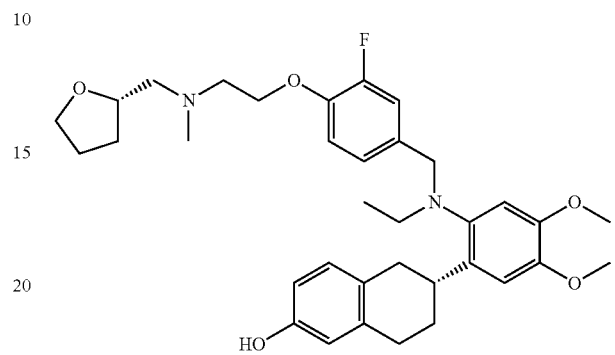

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-methyl-N—[(R)-tetrahydrofuran-2-ylmethyl]acetamide (10 mg) according to an analogous synthetic method to Example 404 and purified by LC-MS, the title compound (6.5 mg) was obtained.

ESI-Mass; 593 [M$^+$+H]

Example 695

(R)-6-{2-{Ethyl{3-fluoro-4-{2-[methyl(tetrahydropyran-4-yl)amino]ethoxy}benzyl}amino}-4,5-dimethoxyphenyl}-5,6,7,8-tetrahydronaphthalen-2-ol

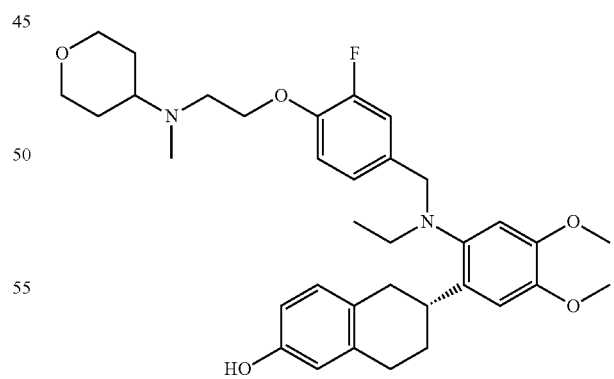

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-methyl-N-(tetrahydropyran-4-yl)acetamide (10 mg) according to an analogous synthetic method to Example 404 and purified by LC-MS, the title compound (6.1 mg) was obtained.

ESI-Mass; 593 [M$^+$+H]

Example 696

(R)-6-{2-{Ethyl{3-fluoro-4-{2-[methyl(tetrahydro-pyran-4-ylmethyl)amino]ethoxy}benzyl}amino}-4,5-dimethoxyphenyl}-5,6,7,8-tetrahydronaphthalen-2-ol

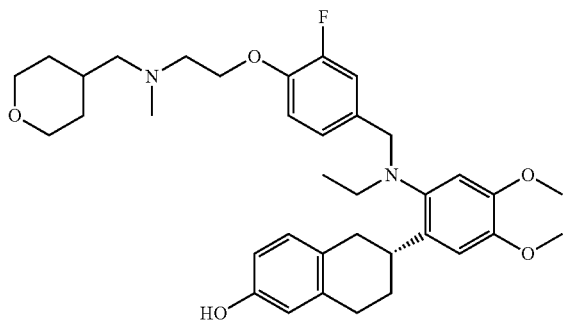 [SMILES: CCN(Cc1ccc(OCCN(C)CC2CCOCC2)c(F)c1)c1cc(OC)c(OC)cc1[C@@H]1CCc2cc(O)ccc2C1]

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-methyl-N-(tetrahydropyran-4-ylmethyl)acetamide (11 mg) according to an analogous synthetic method to Example 404 and purified by LC-MS, the title compound (3.5 mg) was obtained.

ESI-Mass; 607 [M$^+$+H]

Example 697

(R)-6-{2-{{4-[2-(cyclobutylmethylamino)ethoxy]-3-fluorobenzyl}ethylamino}-4,5-dimethoxyphenyl}-5,6,7,8-tetrahydronaphthalen-2-ol

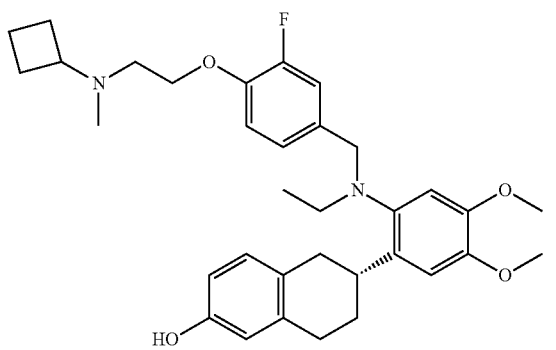 [SMILES: CCN(Cc1ccc(OCCN(C)C2CCC2)c(F)c1)c1cc(OC)c(OC)cc1[C@@H]1CCc2cc(O)ccc2C1]

Synthesized from pivalic acid (R)-6-{2-[ethyl(3-fluoro-4-hydroxybenzoyl)amino]-4,5-dimethoxyphenyl}-5,6,7,8-tetrahydronaphthalen-2-yl ester (15 mg) and 2-chloro-N-cyclobutyl-N-methylacetamide (8.8 mg) according to an analogous synthetic method to Example 404 and purified by LC-MS, the title compound (2.8 mg) was obtained.

ESI-Mass; 563 [M$^+$+H]

Example 698

(R)-6-{2-{[4-(2-Dimethylaminoethoxy)-3-fluorobenzyl]isopropylamino}-4-methoxyphenyl}-5,6,7,8-tetrahydronaphthalen-2-ol

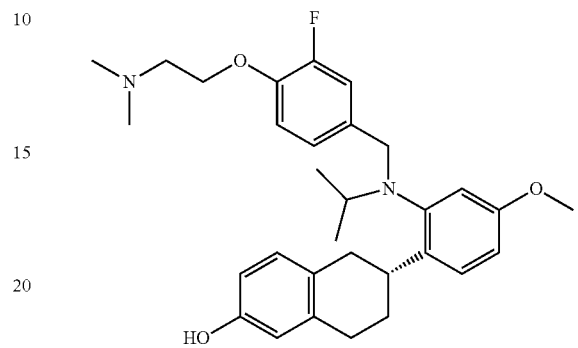

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (21 mg) and 2-chloro-N,N-dimethylacetamide (9.4 mg) according to an analogous synthetic method to Example 404 and purified by LC-MS, the title compound (10 mg) was obtained.

ESI-Mass; 507 [M$^+$+H]

Example 699

(R)-6-{2-{[4-(2-Diethylaminoethoxy)-3-fluorobenzyl]isopropylamino}-4-methoxyphenyl}-5,6,7,8-tetrahydronaphthalen-2-ol

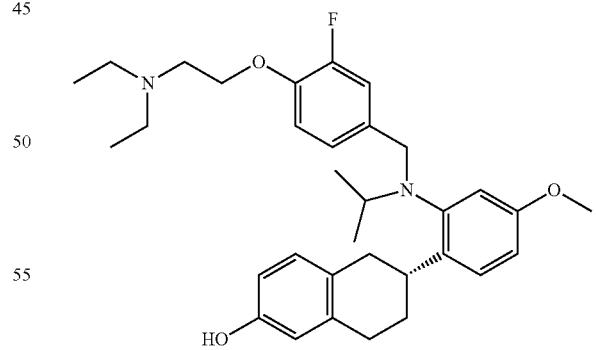

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (21 mg) and 2-chloro-N,N-diethylacetamide (12 mg) according to an analogous synthetic method to Example 404 and purified by LC-MS, the title compound (8.1 mg) was obtained.

ESI-Mass; 535 [M$^+$+H]

Example 700

(R)-6-{2-{{3-Fluoro-4-{2-[(2-methoxyethyl)methylamino]ethoxy}benzyl)isopropylamino}-4-methoxyphenyl}-5,6,7,8-tetrahydronaphthalen-2-ol

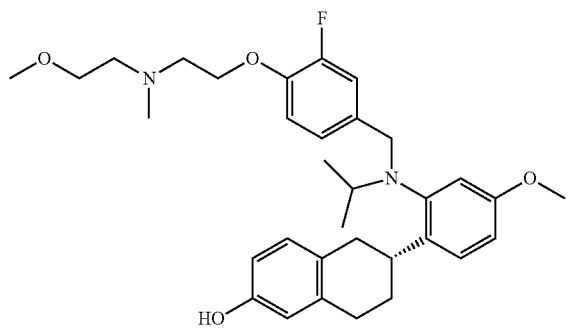

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (21 mg) and 2-chloro-N-(2-methoxyethyl)-N-methylacetamide (13 mg) according to an analogous synthetic method to Example 404 and purified by LC-MS, the title compound (7.2 mg) was obtained.

ESI-Mass; 551 [M$^+$+H]

Example 701

(R)-6-{2-{{4-[2-(Ethylmethylamino)ethoxy]-3-fluorobenzyl}isopropylamino}-4-methoxyphenyl}-5,6,7,8-tetrahydronaphthalen-2-ol

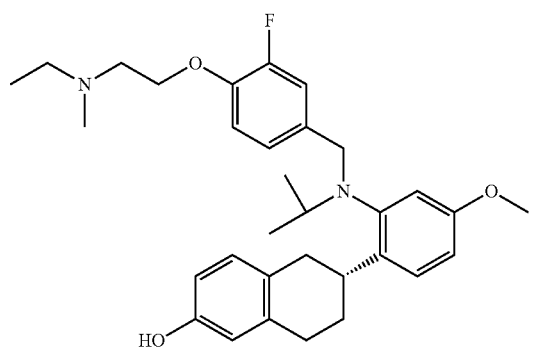 [SMILES: CCN(C)CCOc1ccc(CN(c2cc(OC)ccc2[C@@H]2CCc3cc(O)ccc3C2)C(C)C)cc1F]

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (19 mg) and 2-chloro-N-ethyl-N-methylacetamide (9.5 mg) according to an analogous synthetic method to Example 404 and purified by LC-MS, the title compound (8.5 mg) was obtained.

ESI-Mass; 521 [M$^+$+H]

Example 702

(R)-6-{2-{{3-Fluoro-4-[2-(methylpropylamino)ethoxy]benzyl}isopropylamino}-4-methoxyphenyl}-5,6,7,8-tetrahydronaphthalen-2-ol

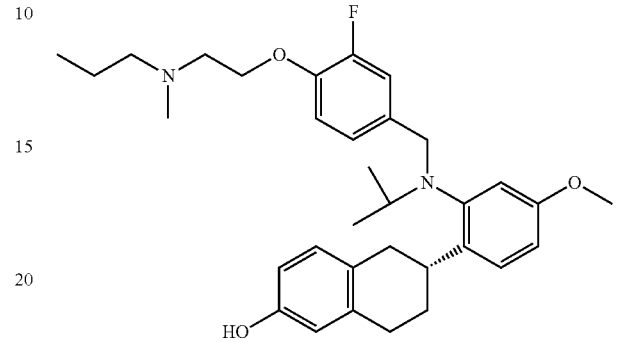

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (19 mg) and 2-chloro-N-methyl-N-propylacetamide (11 mg) according to an analogous synthetic method to Example 404 and purified by LC-MS, the title compound (9.4 mg) was obtained.

ESI-Mass; 535 [M$^+$+H]

Example 703

(R)-6-{2-{[3-Fluoro-4-(2-pyrrolidin-1-ylethoxy)benzyl]isopropylamino}-4-methoxyphenyl}-5,6,7,8-tetrahydronaphthalen-2-ol

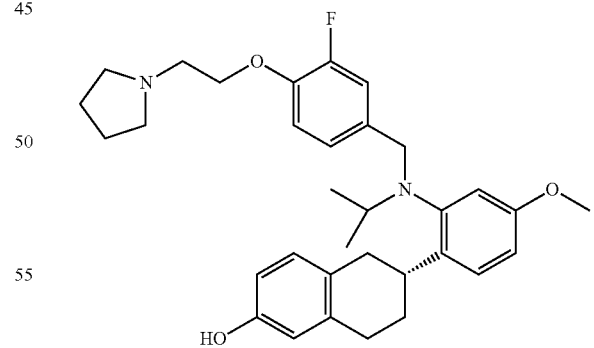

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (19 mg) and 2-chloro-1-pyrrolidin-1-ylethanone (10 mg) according to an analogous synthetic method to Example 404 and purified by LC-MS, the title compound (8.5 mg) was obtained.

ESI-Mass; 533 [M$^+$+H]

Example 704

(R)-6-{2-{[3-Fluoro-4-(2-piperidin-1-ylethoxy)benzyl]isopropylamino}-4-methoxyphenyl}-5,6,7,8-tetrahydronaphthalen-2-ol

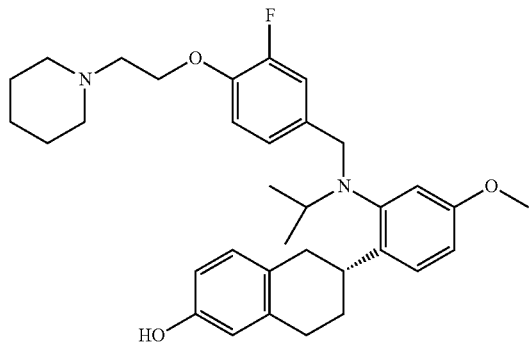 [SMILES: COc1ccc([C@@H]2CCc3cc(O)ccc3C2)c(N(Cc2ccc(OCCN3CCCCC3)c(F)c2)C(C)C)c1]

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (19 mg) and 2-chloro-1-piperidin-1-ylethanone (11 mg) according to an analogous synthetic method to Example 404 and purified by LC-MS, the title compound (7.2 mg) was obtained.

ESI-Mass; 547 [M$^+$+H]

Example 705

(R)-6-{2-{[4-(2-Azepan-1-ylethoxy)-3-fluorobenzyl]isopropylamino}-4-methoxyphenyl}-5,6,7,8-tetrahydronaphthalen-2-ol

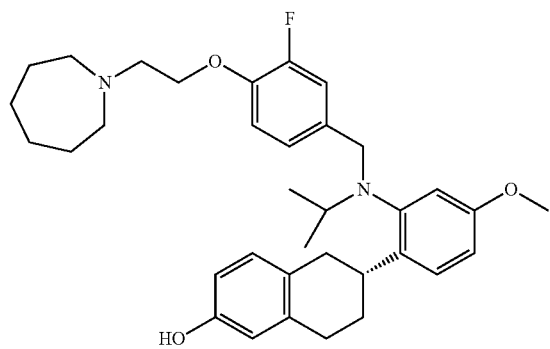 [SMILES: COc1ccc([C@@H]2CCc3cc(O)ccc3C2)c(N(Cc2ccc(OCCN3CCCCCC3)c(F)c2)C(C)C)c1]

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (19 mg) and 1-azepan-1-yl-2-chloroethanone (12 mg) according to an analogous synthetic method to Example 404 and purified by LC-MS, the title compound (5.0 mg) was obtained.

ESI-Mass; 561 [M$^+$+H]

Example 706

(R)-6-{2-{{4-[2-(7-Azabicyclo[2.2.1]hept-7-yl)-ethoxy]-3-fluorobenzyl}isopropylamino}-4-methoxyphenyl}-5,6,7,8-tetrahydronaphthalen-2-ol

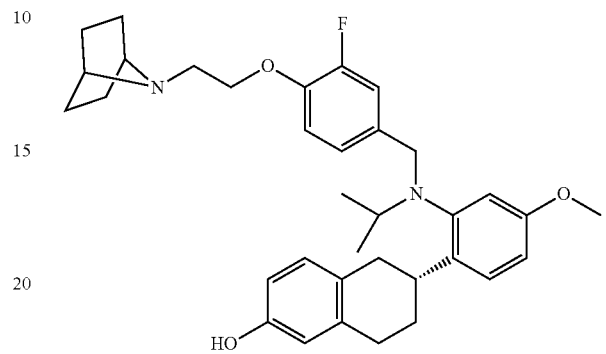

Synthesized from pivalic acid (R)-6-{2-[(3-fluoro-4-hydroxybenzoyl)isopropylamino]-4-methoxyphenyl}-5,6,7,8-tetrahydronaphthalen-2-yl ester (19 mg) and 1-(7-azabicyclo[2.2.1]hept-7-yl)-2-bromoethanone (15 mg) according to an analogous synthetic method to Example 404 and purified by LC-MS, the title compound (13 mg) was obtained.

ESI-Mass; 559 [M$^+$+H]

Example 707

(R)-6-{2-{[4-(2-Dimethylaminoethoxy)benzyl]ethylamino}phenyl}-5,6,7,8-tetrahydronaphthalen-2-ol

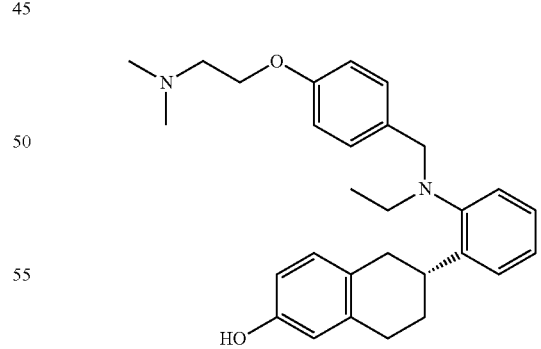

Synthesized from pivalic acid (R)-6-{2-[ethyl(4-hydroxybenzoyl)amino]phenyl}-5,6,7,8-tetrahydronaphthalen-2-yl ester (18 mg) and 2-chloro-N,N-dimethylacetamide (9.4 mg) according to an analogous synthetic method to Example 404 and purified by LC-MS, the title compound (6.0 mg) was obtained.

ESI-Mass; 445 [M$^+$+H]

Example 708

(R)-6-{2-{[4-(2-Diethylaminoethoxy)benzyl]ethylamino}phenyl}-5,6,7,8-tetrahydronaphthalen-2-ol

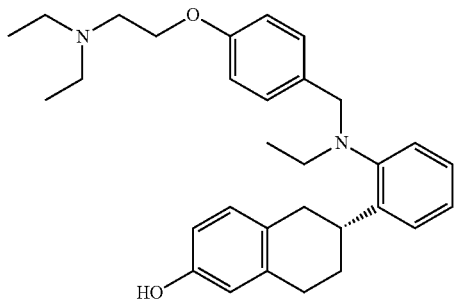 [SMILES: CCN(CC)CCOc1ccc(CN(CC)c2ccccc2[C@@H]2CCc3cc(O)ccc3C2)cc1]

Synthesized from pivalic acid (R)-6-{2-[ethyl(4-hydroxybenzoyl)amino]phenyl}-5,6,7,8-tetrahydronaphthalen-2-yl ester (18 mg) and 2-chloro-N,N-diethylacetamide (12 mg) according to an analogous synthetic method to Example 404 and purified by LC-MS, the title compound (9.8 mg) was obtained.

ESI-Mass; 473 [M$^+$+H]

Example 709

(R)-6-{2-{Ethyl{4-{2-[(2-methoxyethyl)methylamino]ethoxy}benzyl}amino}phenyl}-5,6,7,8-tetrahydronaphthalen-2-ol

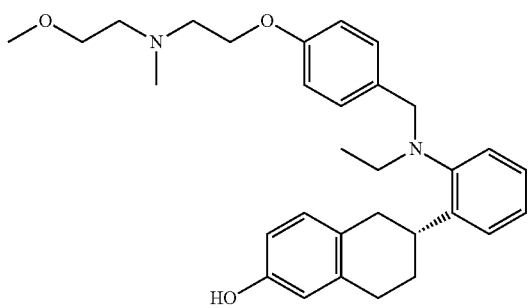 [SMILES: CCN(Cc1ccc(OCCN(C)CCOC)cc1)c1ccccc1[C@@H]1CCc2cc(O)ccc2C1]

Synthesized from pivalic acid (R)-6-{2-[ethyl(4-hydroxybenzoyl)amino]phenyl}-5,6,7,8-tetrahydronaphthalen-2-yl ester (18 mg) and 2-chloro-N-(2-methoxyethyl)-N-methylacetamide (13 mg) according to an analogous synthetic method to Example 404 and purified by LC-MS, the title compound (8.0 mg) was obtained.

ESI-Mass; 489 [M$^+$+H]

Example 710

(R)-6-{2-{[4-(2-Azetidin-1-ylethoxy)benzyl]ethylamino}phenyl}-5,6,7,8-tetrahydronaphthalen-2-ol

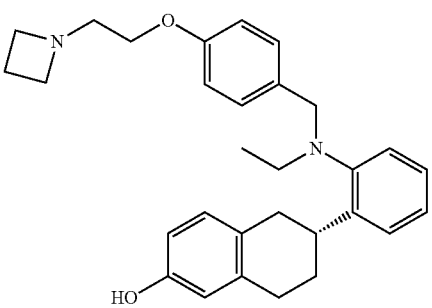 [SMILES: CCN(Cc1ccc(OCCN2CCC2)cc1)c1ccccc1[C@@H]1CCc2cc(O)ccc2C1]

Synthesized from pivalic acid (R)-6-{2-[ethyl(4-hydroxybenzoyl)amino]phenyl}-5,6,7,8-tetrahydronaphthalen-2-yl ester (18 mg) and 1-azetidin-1-yl-2-chloroethanone (10 mg) according to an analogous synthetic method to Example 404 and purified by LC-MS, the title compound (4.1 mg) was obtained.

ESI-Mass; 457 [M$^+$+H]

Example 711

(R)-6-{2-{Ethyl[4-(2-pyrrolidin-1-ylethoxy)benzyl]amino}phenyl}-5,6,7,8-tetrahydronaphthalen-2-ol

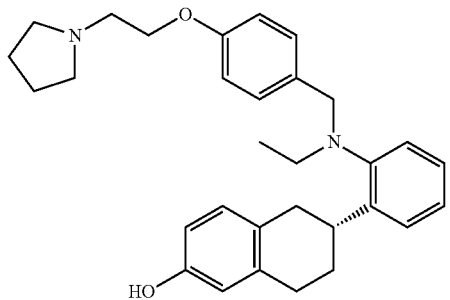 [SMILES: CCN(Cc1ccc(OCCN2CCCC2)cc1)c1ccccc1[C@@H]1CCc2cc(O)ccc2C1]

Synthesized from pivalic acid (R)-6-{2-[ethyl(4-hydroxybenzoyl)amino]phenyl}-5,6,7,8-tetrahydronaphthalen-2-yl ester (18 mg) and 2-chloro-1-pyrrolidin-1-ylethanone (11 mg) according to an analogous synthetic method to Example 404 and purified by LC-MS, the title compound (8.5 mg) was obtained.

ESI-Mass; 471 [M$^+$+H]

Example 712

(R)-6-{2-{Ethyl[4-(2-piperidin-1-ylethoxy)benzyl]amino}phenyl}-5,6,7,8-tetrahydronaphthalen-2-ol

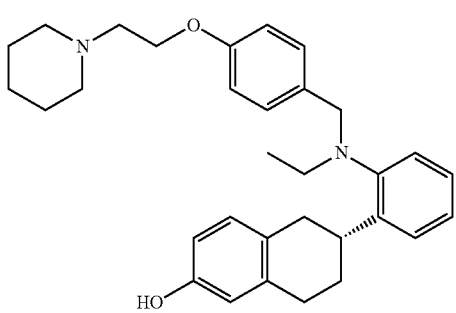 [SMILES: CCN(Cc1ccc(OCCN2CCCCC2)cc1)c1ccccc1[C@@H]1CCc2cc(O)ccc2C1]

Synthesized from pivalic acid (R)-6-{2-[ethyl(4-hydroxybenzoyl)amino]phenyl}-5,6,7,8-tetrahydronaphthalen-2-yl ester (18 mg) and 2-chloro-1-piperidin-1-ylethanone (12 mg) according to an analogous synthetic method to Example 404 and purified by LC-MS, the title compound (7.7 mg) was obtained.

ESI-Mass; 485 [M$^+$+H]

Example 713

(R)-6-{2-{[4-(2-Azepan-1-ylethoxy)benzyl]ethylamino}phenyl}-5,6,7,8-tetrahydronaphthalen-2-ol

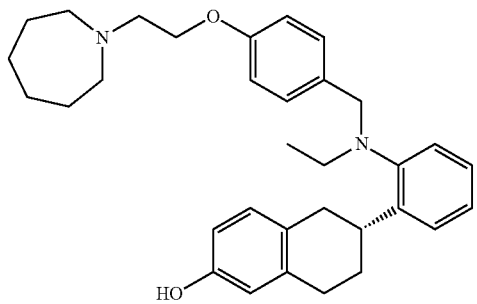 [SMILES: CCN(Cc1ccc(OCCN2CCCCCC2)cc1)c1ccccc1[C@@H]1CCc2cc(O)ccc2C1]

Synthesized from pivalic acid (R)-6-{2-[ethyl(4-hydroxybenzoyl)amino]phenyl}-5,6,7,8-tetrahydronaphthalen-2-yl ester (18 mg) and 1-azepan-1-yl-2-chloroethanone (14 mg) according to an analogous synthetic method to Example 404 and purified by LC-MS, the title compound (6.8 mg) was obtained.

ESI-Mass; 499 [M$^+$+H]

Preparation Example 170

(4-Formylphenyl)acetic Acid

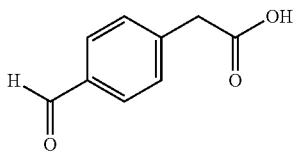

The title compound was synthesized by referring to *Org. Synth.*, 1963, IV, 690. A suspension of (4-bromomethylphenyl)acetic acid (6.0 g) and hexamethylenetetramine (11.1 g) in ethanol (80 ml) was stirred for 2 hours at 100° C., then acetic acid (20 ml) and water (20 ml) were sequentially added thereto followed by stirring for 1.5 hours at 100° C. The solvent was evaporated in vacuo, extracted with ethyl acetate, then sequentially washed with water and brine, dried over anhydrous magnesium sulfate, and then the solvent was evaporated in vacuo. A solution of the residue in tetrahydrofuran was filtered through silica gel, then the solvent was evaporated in vacuo, and the resulting solid was washed with a hexane-diethyl ether system to provide the title compound (2.0 g).

$^1$H-NMR (400 MHz, DMSO-d$_6$); δ (ppm): 3.71 (s, 2H), 7.48 (d, 2H), 7.85 (d, 2H), 9.97 (s, 1H), 12.47 (brs, 1H).

Example 714

Pivalic acid 6-{2-[(4-carboxymethylbenzyl)ethylamino]-4-methoxyphenyl}-5,6,7,8-tetrahydronaphthalen-2-yl ester

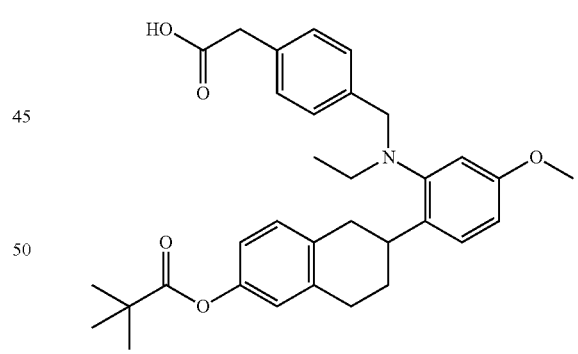

Synthesized from pivalic acid 6-(2-ethylamino-4-methoxyphenyl)-5,6,7,8-tetrahydronaphthalen-2-yl ester (70 mg) and (4-formylphenyl)acetic acid (150 mg) according to an analogous synthetic method to Example 212, the title compound (56 mg) was obtained.

$^1$H-NMR (400 MHz, DMSO-d$_6$); δ (ppm): 0.89 (t, 3H), 1.30 (s, 9H), 1.55-1.64 (m, 1H), 1.65-1.79 (m, 1H), 2.59-2.73 (m, 2H), 2.80-2.92 (m, 4H), 3.48 (s, 2H), 3.52-3.62 (m, 1H), 3.71 (s, 3H), 3.99 (dd, 2H), 6.67 (dd, 1H), 6.78-6.83 (m, 3H), 7.05 (d, 1H), 7.10 (d, 2H), 7.14 (d, 2H), 7.16 (d, 1H), 12.25 (brs, 1H).

Example 715

6-{2-{[4-(2-Dimethylaminoethyl)benzyl]ethylamino}-4-methoxyphenyl}-5,6,7,8-tetrahydronaphthalen-2-ol

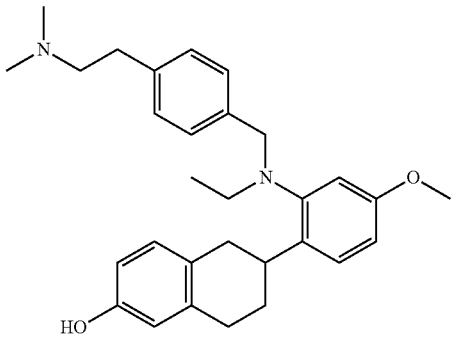

To a solution of pivalic acid 6-{2-[(4-carboxymethylbenzyl)ethylamino]-4-methoxyphenyl}-5,6,7,8-tetrahydronaphthalen-2-yl ester (54 mg) in tetrahydrofuran (1.5 ml) were sequentially added N,N-dimethylformamide (in catalytic amounts) and oxalyl chloride (0.027 ml) under a nitrogen atmosphere, the solution was stirred for 30 minutes at room temperature, then the solvent was evaporated in vacuo to provide pivalic acid 6-{2-[(4-chlorocarbonylmethylbenzyl)ethylamino]-4-methoxyphenyl}-5,6,7,8-tetrahydronaphthalen-2-yl ester (74 mg). A solution of this compound (37 mg) and dimethylamine (2.0 M solution in tetrahydrofuran) (0.08 ml) in tetrahydrofuran (0.7 ml) was stirred for 30 minutes at room temperature. To a suspension of lithium aluminum hydride (76 mg) in tetrahydrofuran (2 ml) was added aluminum chloride (267 mg) on an ice bath under a nitrogen atmosphere, and the solution was stirred for 1 hour at room temperature. Among the resulting suspension, 0.5 ml was added dropwise thereto followed by stirring for 2 hours at room temperature. Tetrahydrofuran and concentrated aqueous ammonia were sequentially added thereto, the solution was filtered through celite pad, and concentrated under a nitrogen stream. A solution of the resulting residue in N,N-dimethylformamide was purified by LC-MS, and the title compound (7.1 mg) was obtained.

ESI-Mass; 459 [M$^+$+H]

Example 716

6-{2-{Ethyl[4-(2-piperidin-1-ylethyl)benzyl]amino}-4-methoxyphenyl}-5,6,7,8-tetrahydronaphthalen-2-ol

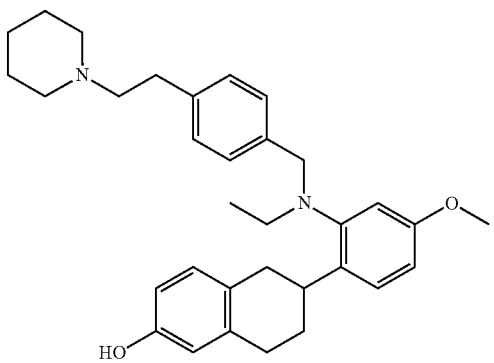 [SMILES: CCN(Cc1ccc(CCN2CCCCC2)cc1)c1cc(OC)ccc1C1CCc2cc(O)ccc2C1]

Synthesized from pivalic acid 6-{2-[(4-carboxymethylbenzyl)ethylamino]-4-methoxyphenyl}-5,6,7,8-tetrahydronaphthalen-2-yl ester (27 mg) and piperidine (14 mg) according to an analogous synthetic method to Example 715 and purified by LC-MS, the title compound (6.6 mg) was obtained.

ESI-Mass; 499 [M$^+$+H]

Example 717

Pivalic acid (R)-6-{2-[(4-carboxymethylbenzyl)ethylamino]-4-methoxyphenyl}-5,6,7,8-tetrahydronaphthalen-2-yl ester

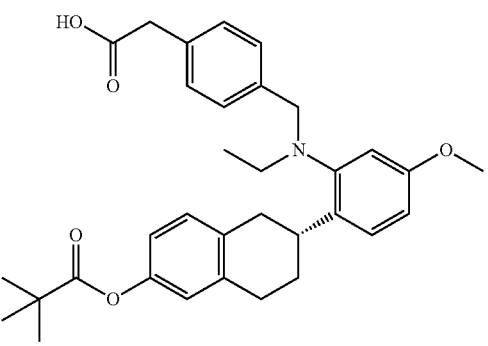 [SMILES: CCN(Cc1ccc(CC(=O)O)cc1)c1cc(OC)ccc1[C@@H]1CCc2cc(OC(=O)C(C)(C)C)ccc2C1]

Synthesized from pivalic acid (R)-6-(2-ethylamino-4-methoxyphenyl)-5,6,7,8-tetrahydronaphthalen-2-yl ester (296 mg) and (4-formylphenyl)acetic acid (630 mg) according to an analogous synthetic method to Example 212, the title compound (379 mg) was obtained.

$^1$H-NMR (400 MHz, DMSO-d$_6$); δ (ppm): 0.89 (t, 3H), 1.30 (s, 9H), 1.55-1.64 (m, 1H), 1.65-1.79 (m, 1H), 2.59-2.73 (m, 2H), 2.80-2.92 (m, 4H), 3.48 (s, 2H), 3.52-3.62 (m, 1H), 3.71 (s, 3H), 3.99 (dd, 2H), 6.67 (dd, 1H), 6.78-6.83 (m, 3H), 7.05 (d, 1H), 7.10 (d, 2H), 7.14 (d, 2H), 7.16 (d, 1H), 12.25 (brs, 1H).

Example 718

(R)-6-{2-{[4-(2-Dimethylaminoethyl)benzyl]ethylamino}-4-methoxyphenyl}-5,6,7,8-tetrahydronaphthalen-2-ol

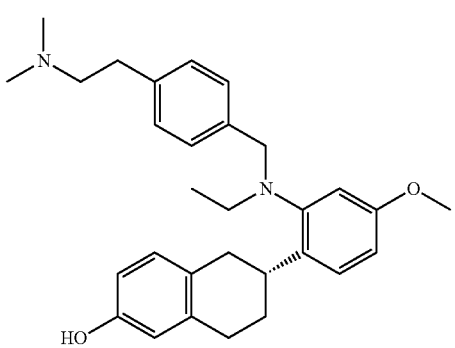

Synthesized from pivalic acid (R)-6-{2-[(4-carboxymethylbenzyl)ethylamino]-4-methoxyphenyl}-5,6,7,8-tetrahydro-naphthalen-2-yl ester (19 mg) and dimethylamine (2.0 M solution in tetrahydrofuran) (0.07 ml) according to an analogous synthetic method to Example 715 and purified by LC-MS, the title compound (3.5 mg) was obtained.

ESI-Mass; 459 [M$^+$+H]

Example 719

(R)-6-{2-{[4-(2-Diethylaminoethyl)benzyl]ethylamino}-4-methoxyphenyl}-5,6,7,8-tetrahydronaphthalen-2-ol

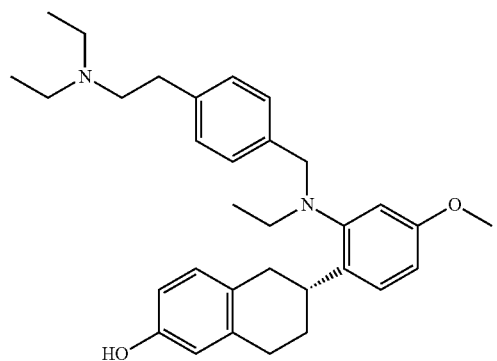 [SMILES: CCN(CC)CCc1ccc(CN(CC)c2cc(OC)ccc2[C@@H]2CCc3cc(O)ccc3C2)cc1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and diethylamine (12 mg) according to an analogous synthetic method to Example 715 and purified by LC-MS, the title compound (2.0 mg) was obtained.

ESI-Mass; 487 [M$^+$+H]

Example 720

(R)-6-{2-{Ethyl{4-[2-(ethylmethylamino)ethyl]benzyl}amino}-4-methoxyphenyl}-5,6,7,8-tetrahydronaphthalen-2-ol

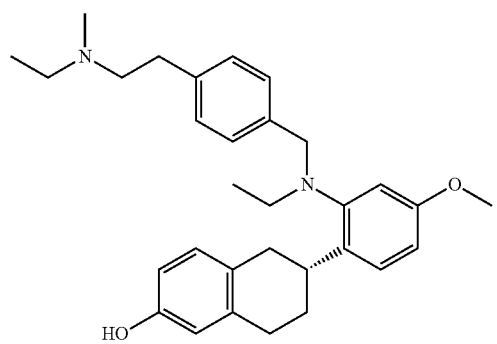 [SMILES: CCN(C)CCc1ccc(CN(CC)c2cc(OC)ccc2[C@@H]2CCc3cc(O)ccc3C2)cc1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and ethylmethylamine (17 mg) according to an analogous synthetic method to Example 715 and purified by LC-MS, the title compound (3.8 mg) was obtained.

ESI-Mass; 473 [M$^+$+H]

Example 721

(R)-6-{2-{Ethyl{4-[2-(isopropylmethylamino)ethyl]benzyl}amino}-4-methoxyphenyl}-5,6,7,8-tetrahydronaphthalen-2-ol

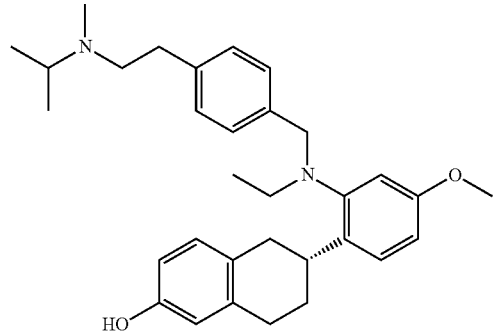 [SMILES: CCN(Cc1ccc(CCN(C)C(C)C)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and isopropylmethylamine (13 mg) according to an analogous synthetic method to Example 715 and purified by LC-MS, the title compound (3.8 mg) was obtained.

ESI-Mass; 487 [M$^+$+H]

Example 722

(R)-6-{2-{{4-[2-(Allylmethylamino)ethyl]benzyl}ethylamino}-4-methoxyphenyl}-5,6,7,8-tetrahydronaphthalen-2-ol

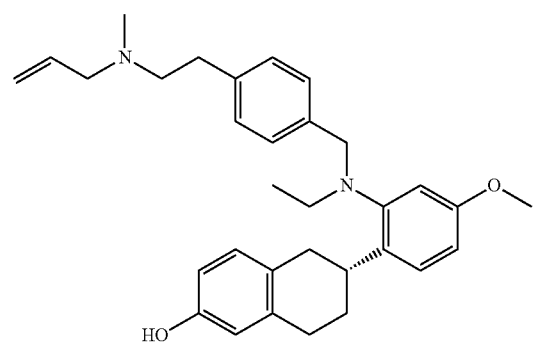 [SMILES: C=CCN(C)CCc1ccc(CN(CC)c2cc(OC)ccc2[C@@H]2CCc3cc(O)ccc3C2)cc1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and allylmethylamine (13 mg) according to an analogous synthetic method to Example 715 and purified by LC-MS, the title compound (2.7 mg) was obtained.

ESI-Mass; 485 [M$^+$+H]

Example 723

(R)-6-{2-{{4-[2-(Butylmethylamino)ethyl]benzyl}ethylamino}-4-methoxyphenyl}-5,6,7,8-tetrahydronaphthalen-2-ol

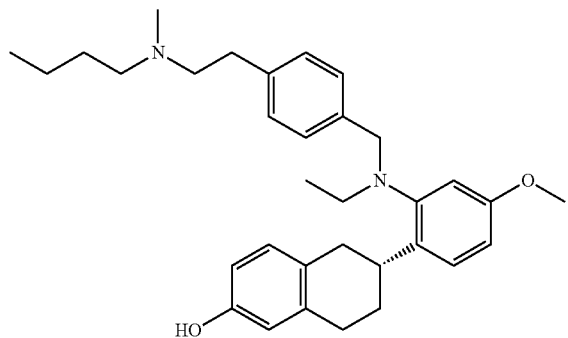 [SMILES: CCCCN(C)CCc1ccc(CN(CC)c2cc(OC)ccc2[C@@H]2CCc3cc(O)ccc3C2)cc1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and butylmethylamine (22 mg) according to an analogous synthetic method to Example 715 and purified by LC-MS, the title compound (3.2 mg) was obtained.

ESI-Mass; 501 [M$^+$+H]

Example 724

(R)-6-{2-{Ethyl{4-[2-(isobutylmethylamino)ethyl]benzyl}amino}-4-methoxyphenyl}-5,6,7,8-tetrahydronaphthalen-2-ol

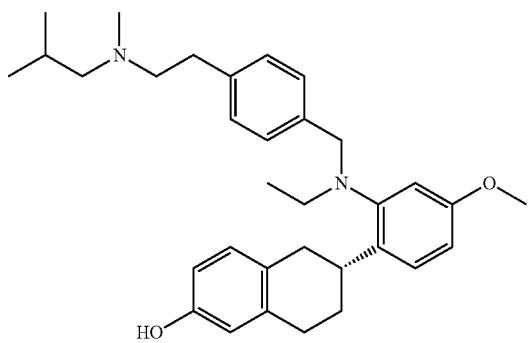 [SMILES: CCN(Cc1ccc(CCN(C)CC(C)C)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and isobutylmethylamine (18 mg) according to an analogous synthetic method to Example 715 and purified by LC-MS, the title compound (2.8 mg) was obtained.

ESI-Mass; 501 [M$^+$+H]

Example 725

(R)-6-{2-{[4-(2-Azetidin-1-ylethyl)benzyl]ethylamino}-4-methoxyphenyl}-5,6,7,8-tetrahydronaphthalen-2-ol

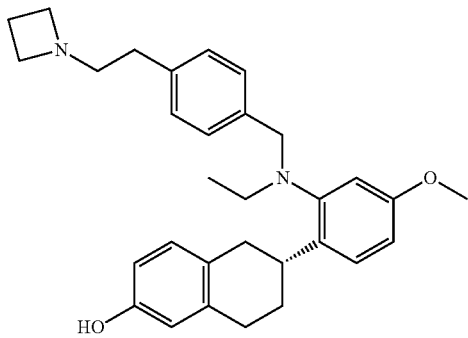 [SMILES: CCN(Cc1ccc(CCN2CCC2)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and azetidine (10 mg) according to an analogous synthetic method to Example 715 and purified by LC-MS, the title compound (3.4 mg) was obtained.

ESI-Mass; 471 [M$^+$+H]

Example 726

(R)-6-{2-{Ethyl[4-(2-pyrrolidin-1-ylethyl)benzyl]amino}-4-methoxyphenyl}-5,6,7,8-tetrahydronaphthalen-2-ol

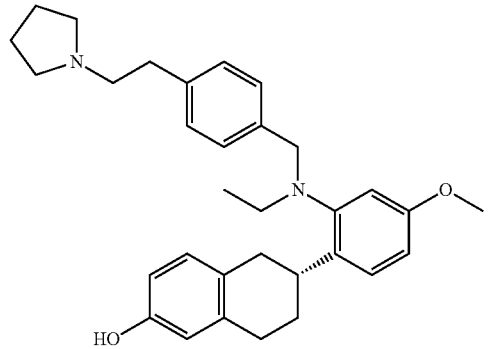 [SMILES: CCN(Cc1ccc(CCN2CCCC2)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and pyrrolidine (12 mg) according to an analogous synthetic method to Example 715 and purified by LC-MS, the title compound (2.0 mg) was obtained.

ESI-Mass; 485 [M$^+$+H]

Example 727

(R)-6-{2-{Ethyl[4-(2-piperidin-1-ylethyl)benzyl]amino}-4-methoxyphenyl}-5,6,7,8-tetrahydronaphthalen-2-ol

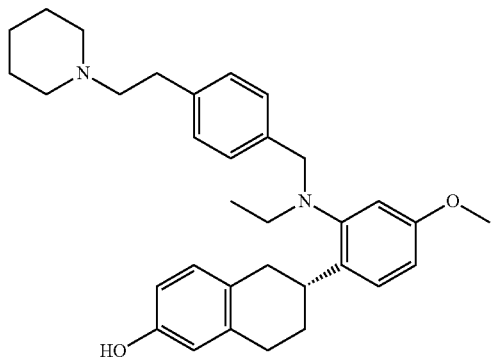 [SMILES: CCN(Cc1ccc(CCN2CCCCC2)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and piperidine (20 mg) according to an analogous synthetic method to Example 715 and purified by LC-MS, the title compound (1.9 mg) was obtained.

ESI-Mass; 499 [M$^+$+H]

Example 728

(R)-6-{2-{Ethyl{4-[2-(4-methylpiperidin-1-yl)ethyl]benzyl}amino}-4-methoxyphenyl}-5,6,7,8-tetrahydronaphthalen-2-ol

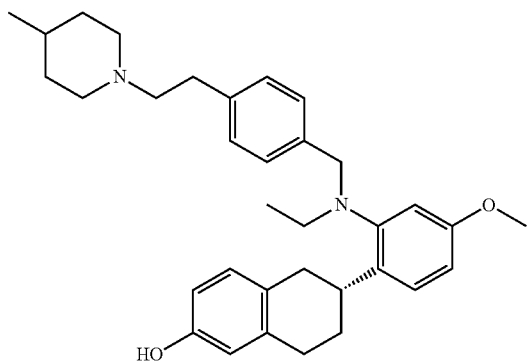

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and 4-methylpiperidine (17 mg) according to an analogous synthetic method to Example 715 and purified by LC-MS, the title compound (3.1 mg) was obtained.

ESI-Mass; 513 [M$^+$+H]

Example 729

(R)-6-{2-{{4-[2-(3,3-Dimethylpiperidin-1-yl)ethyl]benzyl}ethylamino}-4-methoxyphenyl}-5,6,7,8-tetrahydronaphthalen-2-ol

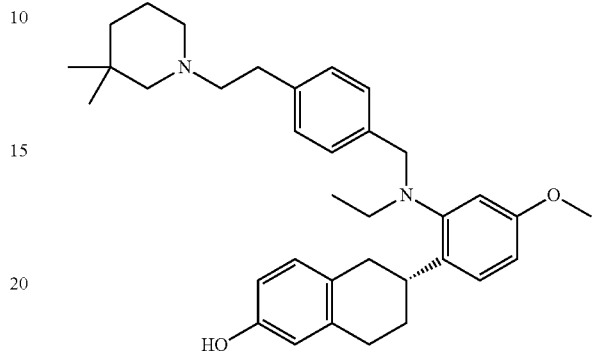

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and 3,3-dimethylpiperidine (20 mg) according to an analogous synthetic method to Example 715 and purified by LC-MS, the title compound (2.4 mg) was obtained.

ESI-Mass; 527 [M$^+$+H]

Example 730

(R)-6-{2-{[4-(2-Azepan-1-ylethyl)benzyl]ethylamino}-4-methoxyphenyl}-5,6,7,8-tetrahydronaphthalen-2-ol

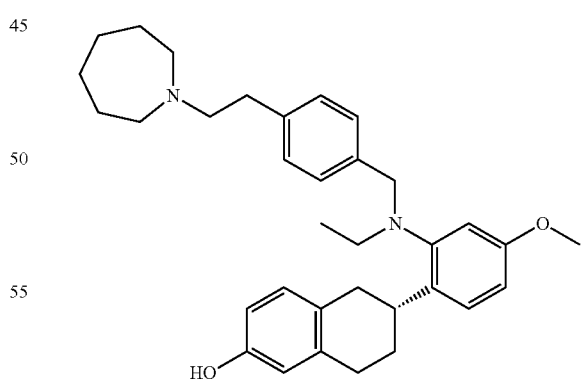

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and hexamethyleneimine (17 mg) according to an analogous synthetic method to Example 715 and purified by LC-MS, the title compound (2.4 mg) was obtained.

ESI-Mass; 513 [M$^+$+H]

Example 731

(R)-6-{2-{[4-(2-Azocan-1-ylethyl)benzyl]ethylamino}-4-methoxyphenyl}-5,6,7,8-tetrahydronaphthalen-2-ol

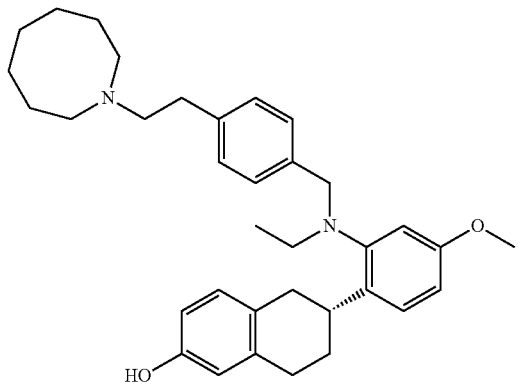 [SMILES: CCN(Cc1ccc(CCN2CCCCCCC2)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and heptamethyleneimine (25 mg) according to an analogous synthetic method to Example 715 and purified by LC-MS, the title compound (1.9 mg) was obtained.

ESI-Mass; 527 [M$^+$+H]

Example 732

(R)-6-{2-{{4-[2-(7-Azabicyclo[2.2.1]hept-7-yl)ethyl]benzyl}ethylamino}-4-methoxyphenyl}-5,6,7,8-tetrahydronaphthalen-2-ol

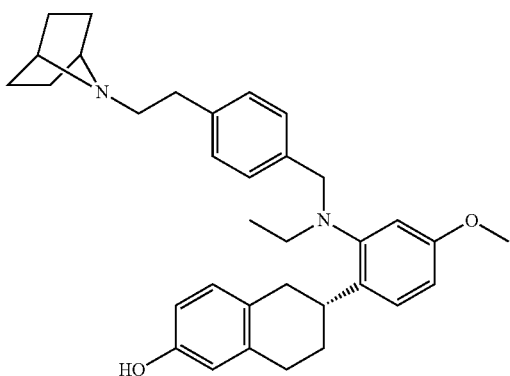 [SMILES: CCN(Cc1ccc(CCN2C3CCC2CC3)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and 7-azabicyclo[2.2.1]heptane hydrochloride (20 mg) according to an analogous synthetic method to Example 715 and purified by LC-MS, the title compound (1.1 mg) was obtained.

ESI-Mass; 511 [M$^+$+H]

Example 733

(R)-6-{2-{Ethyl{4-{2-[(2-methoxyethyl)methylamino]ethyl}benzyl}amino}-4-methoxyphenyl}-5,6,7,8-tetrahydronaphthalen-2-ol

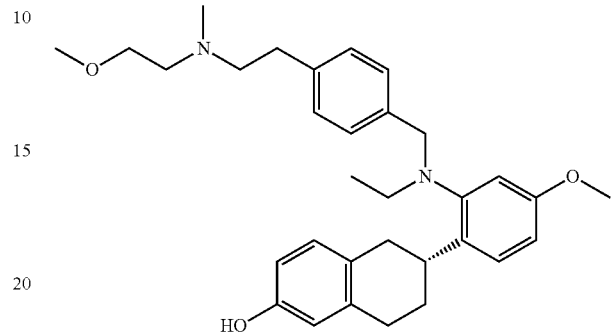

Synthesized from pivalic acid (R)-6-{2-[(4-carboxymethylbenzyl)ethylamino]-4-methoxyphenyl}-5,6,7,8-tetrahydronaphthalen-2-yl ester (19 mg) and (2-methoxymethyl)methylamine (15 mg) according to an analogous synthetic method to Example 715 and purified by LC-MS, the title compound (2.8 mg) was obtained.

ESI-Mass; 503 [M$^+$+H]

Example 734

(R)-6-{2-{Ethyl{4-[2-(methylpropylamino)ethyl]benzyl}amino}-4-methoxyphenyl}-5,6,7,8-tetrahydronaphthalen-2-ol

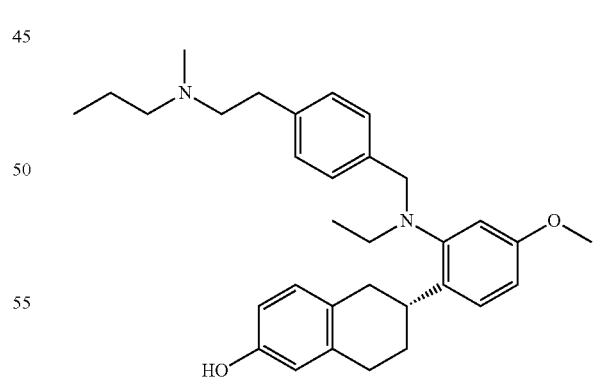

Synthesized from pivalic acid (R)-6-{2-[(4-carboxymethylbenzyl)ethylamino]-4-methoxyphenyl}-5,6,7,8-tetrahydronaphthalen-2-yl ester (16 mg) and methylpropylamine (13 mg) according to an analogous synthetic method to Example 715 and purified by LC-MS, the title compound (0.8 mg) was obtained.

ESI-Mass; 487 [M$^+$+H]

Example 735

(R)-6-{2-{{4-[2-(tert-Butylmethylamino)ethyl]benzyl}ethylamino}-4-methoxyphenyl}-5,6,7,8-tetrahydronaphthalen-2-ol

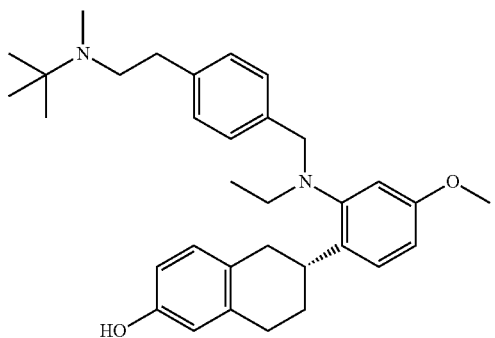 [SMILES: CCN(Cc1ccc(CCN(C)C(C)(C)C)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (16 mg) and tert-butylmethylamine (14 mg) according to an analogous synthetic method to Example 715 and purified by LC-MS, the title compound (4.8 mg) was obtained.

ESI-Mass; 501 [M$^+$+H]

Example 736

(R)-6-{2-{Ethyl[4-(2-ethylaminoethyl)benzyl]amino}-4-methoxyphenyl}-5,6,7,8-tetrahydronaphthalen-2-ol

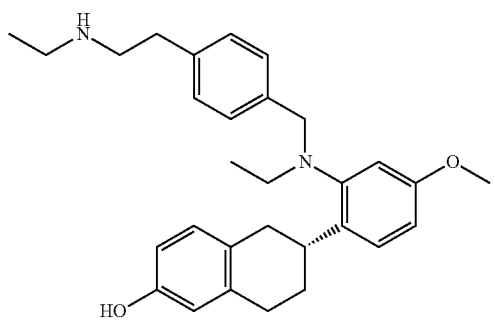 [SMILES: CCNCCc1ccc(CN(CC)c2cc(OC)ccc2[C@@H]2CCc3cc(O)ccc3C2)cc1]

Synthesized from pivalic acid (R)-6-{2-[(4-carboxymethylbenzyl)ethylamino]-4-methoxyphenyl}-5,6,7,8-tetrahydronaphthalen-2-yl ester (16 mg) and ethylamine (2.0 M solution in tetrahydrofuran) (0.06 ml) according to an analogous synthetic method to Example 715 and purified by LC-MS, the title compound (2.4 mg) was obtained.

ESI-Mass; 459 [M$^+$+H]

Example 737

(S)-pivalic acid 6-{2-[(4-carboxymethylbenzyl)ethylamino]-4-methoxyphenyl}-5,6,7,8-tetrahydronaphthalen-2-yl ester

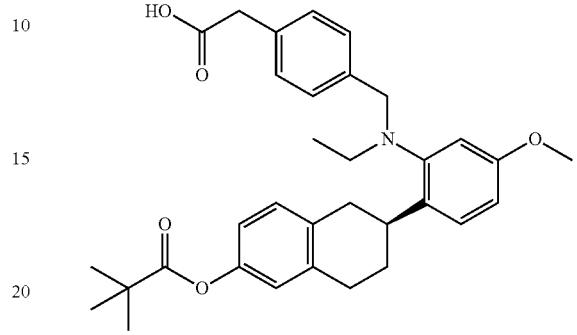

Synthesized from pivalic acid (S)-6-(2-ethylamino-4-methoxyphenyl)-5,6,7,8-tetrahydronaphthalen-2-yl ester (59 mg) and (4-formylphenyl)acetic acid (126 mg) according to an analogous synthetic method to Example 212, the title compound (77 mg) was obtained.

$^1$H-NMR (400 MHz, DMSO-d$_6$); δ (ppm): 0.89 (t, 3H), 1.30 (s, 9H), 1.55-1.64 (m, 1H), 1.65-1.79 (m, 1H), 2.59-2.73 (m, 2H), 2.80-2.92 (m, 4H), 3.48 (s, 2H), 3.52-3.62 (m, 1H), 3.71 (s, 3H), 3.99 (dd, 2H), 6.67 (dd, 1H), 6.78-6.83 (m, 3H), 7.05 (d, 1H), 7.10 (d, 2H), 7.14 (d, 2H), 7.16 (d, 1H), 12.25 (brs, 1H).

Example 738

(S)-6-{2-{[4-(2-Dimethylaminoethyl)benzyl]ethylamino}-4-methoxyphenyl}-5,6,7,8-tetrahydronaphthalen-2-ol

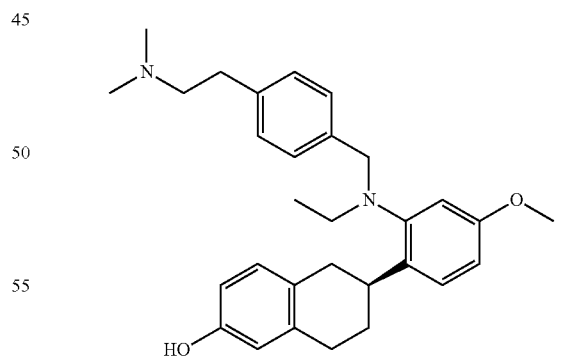

Synthesized from pivalic acid (S)-6-{2-[(4-carboxymethylbenzyl)ethylamino]-4-methoxyphenyl}-5,6,7,8-tetrahydronaphthalen-2-yl ester (38 mg) and dimethylamine (2.0 M solution in tetrahydrofuran) (0.14 ml) according to an analogous synthetic method to Example 715 and purified by LC-MS, the title compound (3.3 mg) was obtained.

ESI-Mass; 459 [M$^+$+H]

Example 739

(S)-6-{2-{[4-(2-Azepan-1-ylethyl)benzyl]ethylamino}-4-methoxyphenyl}-5,6,7,8-tetrahydronaphthalen-2-ol

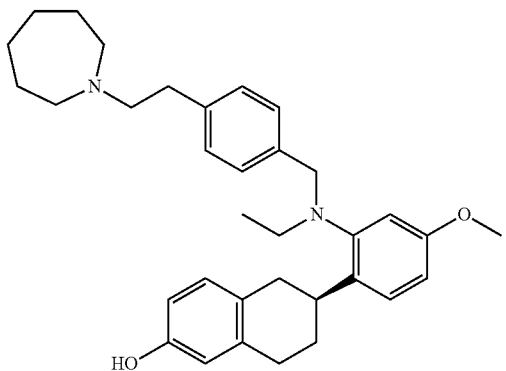 [SMILES: CCN(Cc1ccc(CCN2CCCCCC2)cc1)c1cc(OC)ccc1[C@H]1CCc2cc(O)ccc2C1]

Synthesized from pivalic acid (S)-6-{2-[(4-carboxymethylbenzyl)ethylamino]-4-methoxyphenyl}-5,6,7,8-tetrahydronaphthalen-2-yl ester (38 mg) and hexamethyleneimine (35 mg) according to an analogous synthetic method to Example 715 and purified by LC-MS, the title compound (3.3 mg) was obtained.

ESI-Mass; 513 [M$^+$+H]

Example 740

Pivalic acid (R)-6-{2-[(4-carboxymethylbenzyl)ethylamino]-4,5-dimethoxyphenyl}-5,6,7,8-tetrahydronaphthalen-2-yl ester

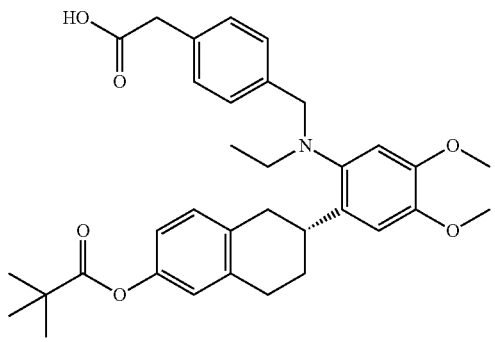 [SMILES: CCN(Cc1ccc(CC(=O)O)cc1)c1cc(OC)c(OC)cc1[C@@H]1CCc2cc(OC(=O)C(C)(C)C)ccc2C1]

Synthesized from pivalic acid (R)-6-(2-ethylamino-4,5-dimethoxyphenyl)-5,6,7,8-tetrahydronaphthalen-2-yl ester (296 mg) and (4-formylphenyl)acetic acid (360 mg) according to an analogous synthetic method to Example 212, the title compound (375 mg) was obtained.

$^1$H-NMR (400 MHz, DMSO-d$_6$); δ (ppm): 0.86 (t, 3H), 1.30 (s, 9H), 1.42-1.52 (m, 1H), 1.68-1.80 (m, 1H), 2.50-2.90 (m, 6H), 3.48 (s, 2H), 3.60-3.70 (m, 1H), 3.69 (s, 3H), 3.73 (s, 3H), 3.94 (dd, 2H), 6.75 (s, 1H), 6.79 (dd, 1H), 6.81 (s, 1H), 6.88 (s, 1H), 7.03 (d, 1H), 7.09 (d, 2H), 7.11 (d, 2H), 12.26 (brs, 1H).

Example 741

(R)-6-{2-{[4-(2-Dimethylaminoethyl)benzyl]ethylamino}-4,5-dimethoxyphenyl}-5,6,7,8-tetrahydronaphthalen-2-ol

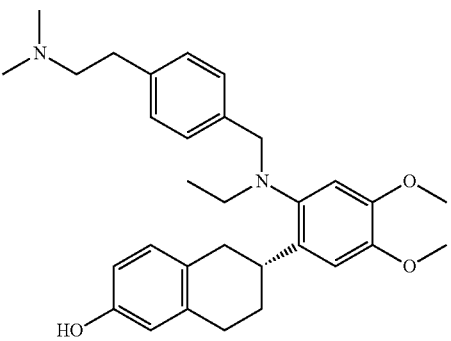

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and dimethylamine (2.0 M solution in tetrahydrofuran) (0.07 ml) according to an analogous synthetic method to Example 715 and purified by LC-MS, the title compound (3.6 mg) was obtained.

ESI-Mass; 489 [M$^+$+H]

Example 742

(R)-6-{2-{[4-(2-Diethylaminoethyl)benzyl]ethylamino}-4,5-dimethoxyphenyl}-5,6,7,8-tetrahydronaphthalen-2-ol

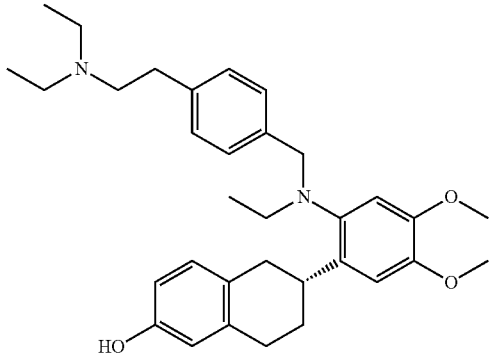 [SMILES: CCN(CC)CCc1ccc(CN(CC)c2cc(OC)c(OC)cc2[C@@H]2CCc3cc(O)ccc3C2)cc1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and diethylamine (12 mg) according to an analogous synthetic method to Example 715 and purified by LC-MS, the title compound (3.4 mg) was obtained.

ESI-Mass; 517 [M$^+$+H]

Example 743

(R)-6-{2-{Ethyl{4-[2-(ethylmethylamino)ethyl]benzyl}amino}-4,5-dimethoxyphenyl}-5,6,7,8-tetrahydronaphthalen-2-ol

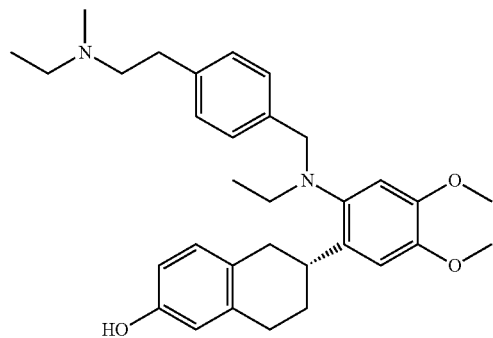 [SMILES: CCN(C)CCc1ccc(CN(CC)c2cc(OC)c(OC)cc2[C@@H]2CCc3cc(O)ccc3C2)cc1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and ethylmethylamine (17 mg) according to an analogous synthetic method to Example 715 and purified by LC-MS, the title compound (1.2 mg) was obtained.

ESI-Mass; 503 [M$^+$+H]

Example 744

(R)-6-{2-{Ethyl{4-[2-(isopropylmethylamino)ethyl]benzyl}amino}-4,5-dimethoxyphenyl}-5,6,7,8-tetrahydronaphthalen-2-ol

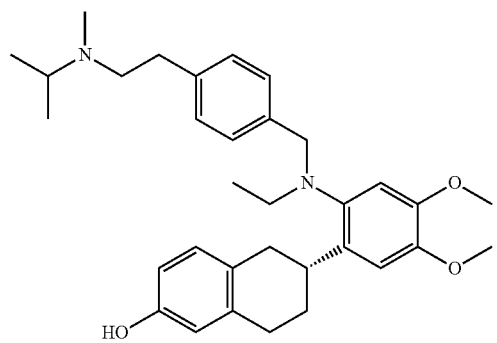 [SMILES: CCN(Cc1ccc(CCN(C)C(C)C)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and isopropylmethylamine (13 mg) according to an analogous synthetic method to Example 715 and purified by LC-MS, the title compound (3.5 mg) was obtained.

ESI-Mass; 517 [M$^+$+H]

Example 745

(R)-6-{2-{{4-[2-(Allylmethylamino)ethyl]benzyl}ethylamino}-4,5-dimethoxyphenyl}-5,6,7,8-tetrahydronaphthalen-2-ol

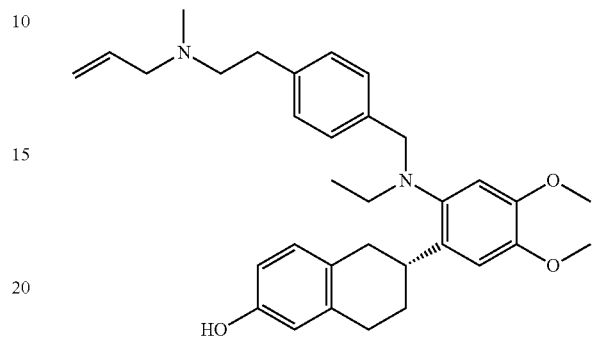

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and allylmethylamine (13 mg) according to an analogous synthetic method to Example 715 and purified by LC-MS, the title compound (3.1 mg) was obtained.

ESI-Mass; 515 [M$^+$+H]

Example 746

(R)-6-{2-{{4-[2-(Butylmethylamino)ethyl]benzyl}ethylamino}-4,5-dimethoxyphenyl}-5,6,7,8-tetrahydronaphthalen-2-ol

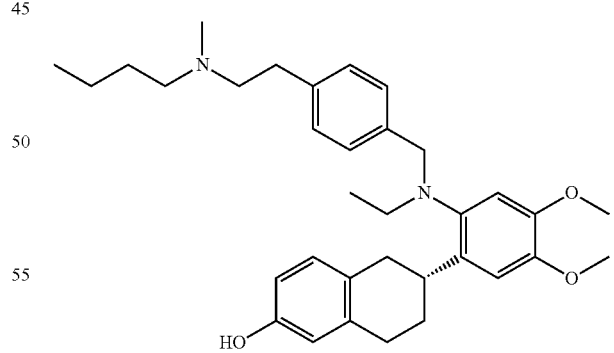

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and butylmethylamine (22 mg) according to an analogous synthetic method to Example 715 and purified by LC-MS, the title compound (3.4 mg) was obtained.

ESI-Mass; 531 [M$^+$+H]

Example 747

(R)-6-{2-{Ethyl{4-[2-(isobutylmethylamino)ethyl]benzyl}amino}-4,5-dimethoxyphenyl}-5,6,7,8-tetrahydronaphthalen-2-ol

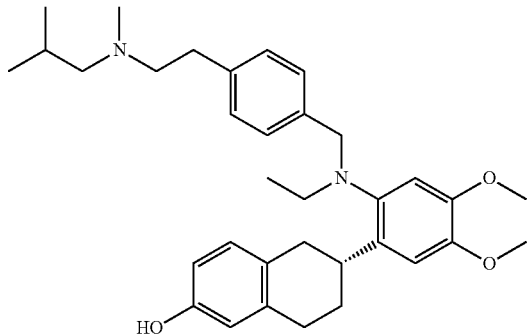

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and isobutylmethylamine (18 mg) according to an analogous synthetic method to Example 715 and purified by LC-MS, the title compound (3.1 mg) was obtained.

ESI-Mass; 531 [M$^+$+H]

Example 748

(R)-6-{2-{[4-(2-Azetidin-1-ylethyl)benzyl]ethylamino}-4,5-dimethoxyphenyl}-5,6,7,8-tetrahydronaphthalen-2-ol

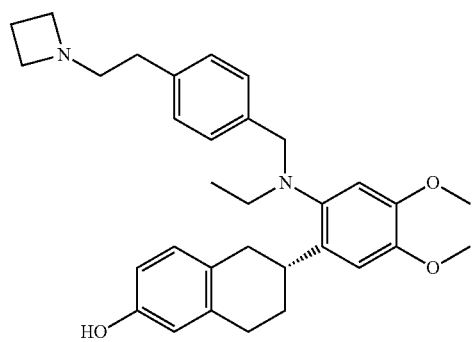 [SMILES: CCN(Cc1ccc(CCN2CCC2)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and azetidine (10 mg) according to an analogous synthetic method to Example 715 and purified by LC-MS, the title compound (3.3 mg) was obtained.

ESI-Mass; 501 [M$^+$+H]

Example 749

(R)-6-{2-{Ethyl[4-(2-pyrrolidin-1-ylethyl)benzyl]amino}-4,5-dimethoxyphenyl}-5,6,7,8-tetrahydronaphthalen-2-ol

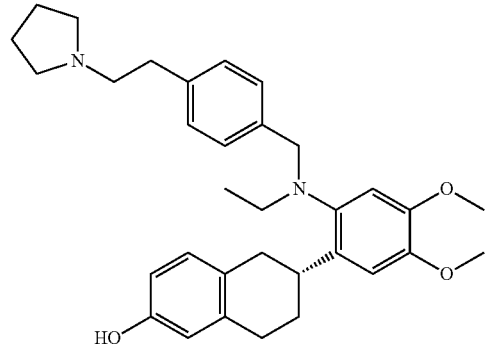 [SMILES: CCN(Cc1ccc(CCN2CCCC2)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and pyrrolidine (12 mg) according to an analogous synthetic method to Example 715 and purified by LC-MS, the title compound (3.8 mg) was obtained.

ESI-Mass; 515 [M$^+$+H]

Example 750

(R)-6-{2-{Ethyl[4-(2-piperidin-1-ylethyl)benzyl]amino}-4,5-dimethoxyphenyl}-5,6,7,8-tetrahydronaphthalen-2-ol

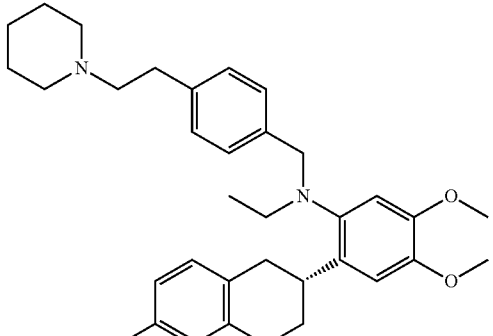

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and piperidine (20 mg) according to an analogous synthetic method to Example 715 and purified by LC-MS, the title compound (3.5 mg) was obtained.

ESI-Mass; 529 [M$^+$+H]

Example 751

(R)-6-{2-{Ethyl{4-[2-(4-methylpiperidin-1-yl)ethyl]benzyl}amino}-4,5-dimethoxyphenyl}-5,6,7,8-tetrahydronaphthalen-2-ol

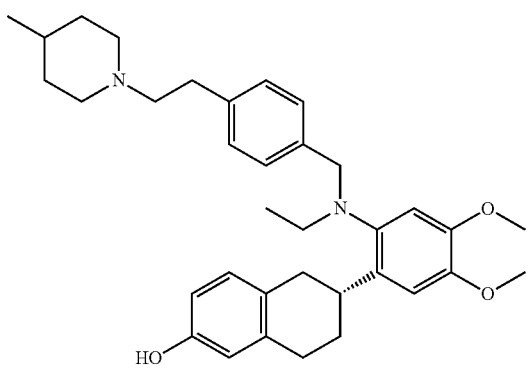

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and 4-methylpiperidine (17 mg) according to an analogous synthetic method to Example 715 and purified by LC-MS, the title compound (3.3 mg) was obtained.

ESI-Mass; 543 [M$^+$+H]

Example 752

(R)-6-{2-{{4-[2-(3,3-Dimethylpiperidin-1-yl)ethyl]benzyl}ethylamino}-4,5-dimethoxyphenyl}-5,6,7,8-tetrahydronaphthalen-2-ol

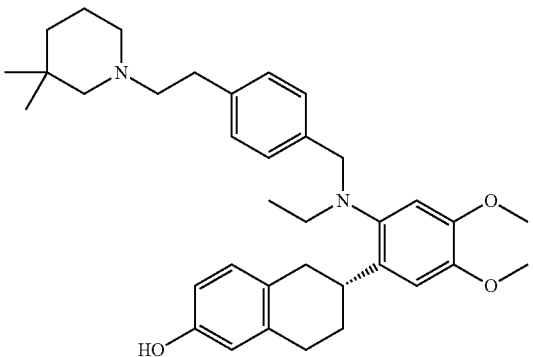

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and 3,3-dimethylpiperidine (20 mg) according to an analogous synthetic method to Example 715 and purified by LC-MS, the title compound (4.3 mg) was obtained.

ESI-Mass; 557 [M$^+$+H]

Example 753

(R)-6-{2-{[4-(2-Azepan-1-ylethyl)benzyl]ethylamino}-4,5-dimethoxyphenyl}-5,6,7,8-tetrahydronaphthalen-2-ol

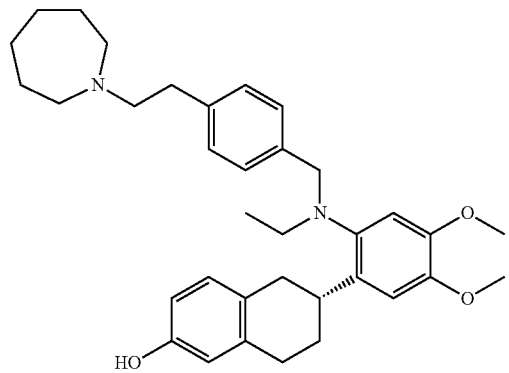 [SMILES: CCN(Cc1ccc(CCN2CCCCCC2)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and hexamethyleneimine (17 mg) according to an analogous synthetic method to Example 715 and purified by LC-MS, the title compound (3.1 mg) was obtained.

ESI-Mass; 543 [M$^+$+H]

Example 754

(R)-6-{2-{[4-(2-Azocan-1-ylethyl)benzyl]ethylamino}-4,5-dimethoxyphenyl}-5,6,7,8-tetrahydronaphthalen-2-ol

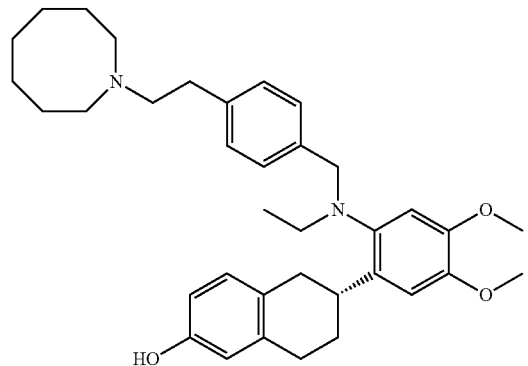 [SMILES: CCN(Cc1ccc(CCN2CCCCCCC2)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and heptamethyleneimine (25 mg) according to an analogous synthetic method to Example 715 and purified by LC-MS, the title compound (1.9 mg) was obtained.

ESI-Mass; 557 [M$^+$+H]

Example 755

(R)-6-{2-{{4-[2-(7-Azabicyclo[2.2.1]hept-7-yl)ethyl]benzyl}ethylamino}-4,5-dimethoxyphenyl}-5,6,7,8-tetrahydronaphthalen-2-ol

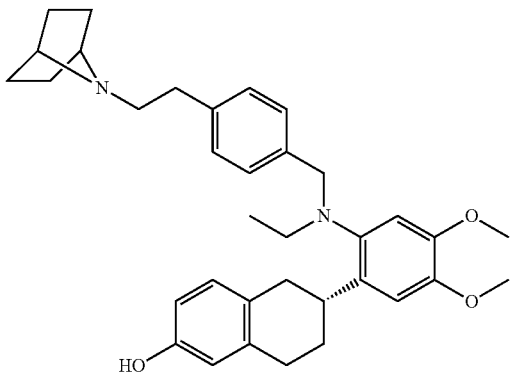 [SMILES: CCN(Cc1ccc(CCN2C3CCC2CC3)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and 7-azabicyclo[2.2.1]heptane hydrochloride (20 mg) according to an analogous synthetic method to Example 715 and purified by LC-MS, the title compound (2.4 mg) was obtained.

ESI-Mass; 541 [M$^+$+H]

Example 756

(R)-6-{2-{Ethyl{4-{2-[(2-methoxyethyl)methylamino]ethyl}benzyl}amino}-4,5-dimethoxyphenyl}-5,6,7,8-tetrahydronaphthalen-2-ol

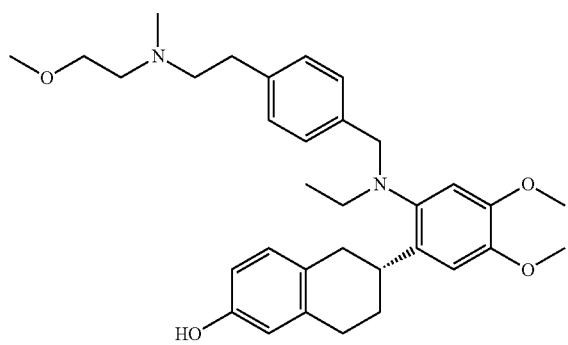

Synthesized from pivalic acid (R)-6-{2-[(4-carboxymethylbenzyl)ethylamino]-4,5-dimethoxyphenyl}-5,6,7,8-tetrahydronaphthalen-2-yl ester (19 mg) and (2-methoxymethyl)methylamine (15 mg) according to an analogous synthetic method to Example 715 and purified by LC-MS, the title compound (3.8 mg) was obtained.

ESI-Mass; 533 [M$^+$+H]

Example 757

(R)-6-{2-{Ethyl{4-[2-(methylpropylamino)ethyl]benzyl}amino}-4,5-dimethoxyphenyl}-5,6,7,8-tetrahydronaphthalen-2-ol

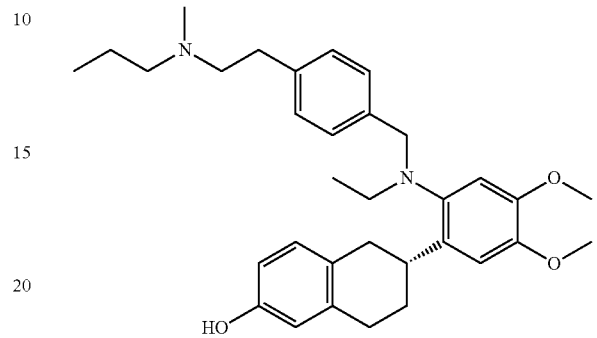

Synthesized from pivalic acid (R)-6-{2-[(4-carboxymethylbenzyl)ethylamino]-4,5-dimethoxyphenyl}-5,6,7,8-tetrahydronaphthalen-2-yl ester (15 mg) and methylpropylamine (13 mg) according to an analogous synthetic method to Example 715 and purified by LC-MS, the title compound (2.5 mg) was obtained.

ESI-Mass; 517 [M$^+$+H]

Example 758

(R)-6-{2-{{4-[2-(tert-Butylmethylamino)ethyl]benzyl}ethylamino}-4,5-dimethoxyphenyl}-5,6,7,8-tetrahydronaphthalen-2-ol

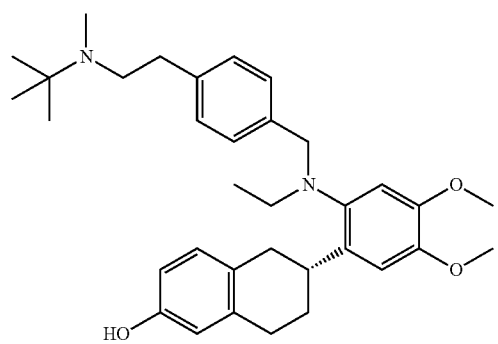 [SMILES: CCN(Cc1ccc(CCN(C)C(C)(C)C)cc1)c1cc(OC)c(OC)cc1[C@@H]1CCc2cc(O)ccc2C1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (15 mg) and tert-butylmethylamine (14 mg) according to an analogous synthetic method to Example 715 and purified by LC-MS, the title compound (4.9 mg) was obtained.

ESI-Mass; 531 [M$^+$+H]

Example 759

(R)-6-{2-{Ethyl[4-(2-ethylaminoethyl)benzyl]amino}-4,5-dimethoxyphenyl}-5,6,7,8-tetrahydronaphthalen-2-ol

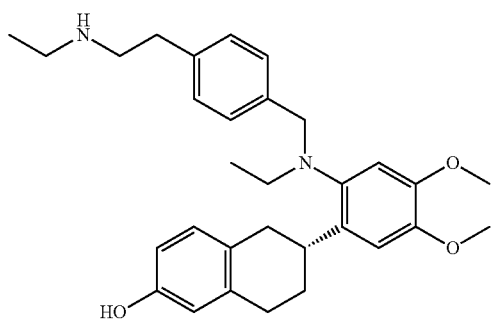 [SMILES: CCNCCc1ccc(CN(CC)c2cc(OC)c(OC)cc2[C@@H]2CCc3cc(O)ccc3C2)cc1]

Synthesized from pivalic acid (R)-6-{2-[(4-carboxymethylbenzyl)ethylamino]-4,5-dimethoxyphenyl}-5,6,7,8-tetrahydronaphthalen-2-yl ester (15 mg) and ethylamine (2.0 M solution in tetrahydrofuran) (0.06 ml) according to an analogous synthetic method to Example 715 and purified by LC-MS, the title compound (1.9 mg) was obtained.

ESI-Mass; 489 [M$^+$+H]

Example 760

Pivalic Acid (S)-6-{2-[(4-carboxymethylbenzyl)ethylamino]-4,5-dimethoxyphenyl}-5,6,7,8-tetrahydronaphthalen-2-yl Ester

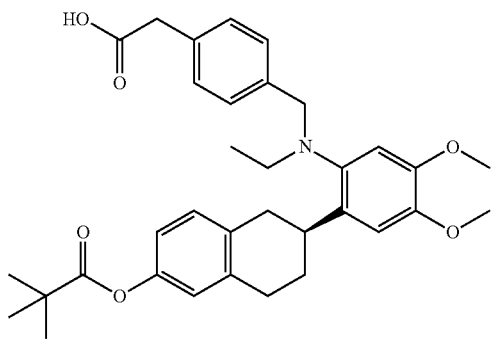 [SMILES: CCN(Cc1ccc(CC(=O)O)cc1)c1cc(OC)c(OC)cc1[C@H]1CCc2cc(OC(=O)C(C)(C)C)ccc2C1]

Synthesized from pivalic acid (S)-6-(2-ethylamino-4,5-dimethoxyphenyl)-5,6,7,8-tetrahydronaphthalen-2-yl ester (59 mg) and (4-formylphenyl)acetic acid (72 mg) according to an analogous synthetic method to Example 212, the title compound (79 mg) was obtained.

$^1$H-NMR (400 MHz, DMSO-d$_6$); δ (ppm): 0.86 (t, 3H), 1.30 (s, 9H), 1.42-1.52 (m, 1H), 1.68-1.80 (m, 1H), 2.50-2.90 (m, 6H), 3.48 (s, 2H), 3.60-3.70 (m, 1H), 3.69 (s, 3H), 3.73 (s, 3H), 3.94 (dd, 2H), 6.75 (s, 1H), 6.79 (dd, 1H), 6.81 (s, 1H), 6.88 (s, 1H), 7.03 (d, 1H), 7.09 (d, 2H), 7.11 (d, 2H), 12.26 (brs, 1H).

Example 761

(S)-6-{2-{[4-(2-Dimethylaminoethyl)benzyl]ethylamino}-4,5-dimethoxyphenyl}-5,6,7,8-tetrahydronaphthalen-2-ol

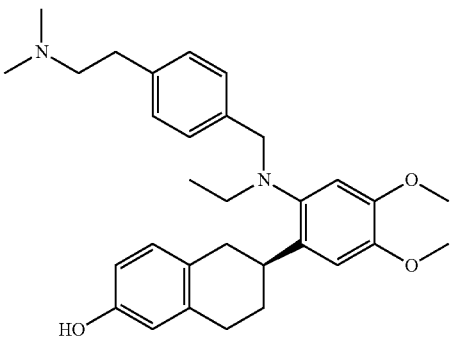

Synthesized from pivalic acid (S)-6-{2-[(4-carboxymethylbenzyl)ethylamino]-4,5-dimethoxyphenyl}-5,6,7,8-tetrahydronaphthalen-2-yl ester (39 mg) and dimethylamine (2.0 M solution in tetrahydrofuran) (0.14 ml) according to an analogous synthetic method to Example 715 and purified by LC-MS, the title compound (5.7 mg) was obtained.

ESI-Mass; 489 [M$^+$+H]

Example 762

(S)-6-{2-{[4-(2-Azepan-1-ylethyl)benzyl]ethylamino}-4,5-dimethoxyphenyl}-5,6,7,8-tetrahydronaphthalen-2-ol

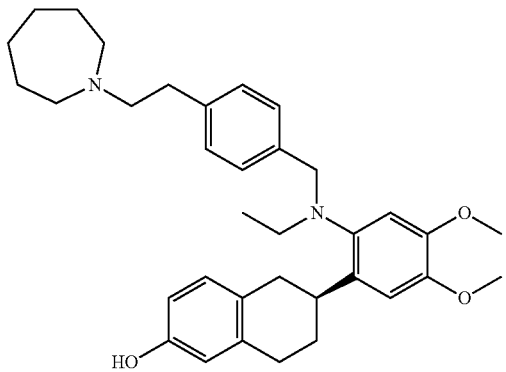 [SMILES: CCN(Cc1ccc(CCN2CCCCCC2)cc1)c1cc(OC)c(OC)cc1[C@H]1CCc2cc(O)ccc2C1]

Synthesized from pivalic acid (S)-6-{2-[(4-carboxymethylbenzyl)ethylamino]-4,5-dimethoxyphenyl}-5,6,7,8-tetrahydronaphthalen-2-yl ester (39 mg) and hexamethyleneimine (35 mg) according to an analogous synthetic method to Example 715 and purified by LC-MS, the title compound (5.6 mg) was obtained.

ESI-Mass; 543 [M$^+$+H]

Example 763

Pivalic Acid (R)-6-{2-[(4-carboxymethylbenzyl)ethylamino]phenyl}-5,6,7,8-tetrahydronaphthalen-2-yl Ester

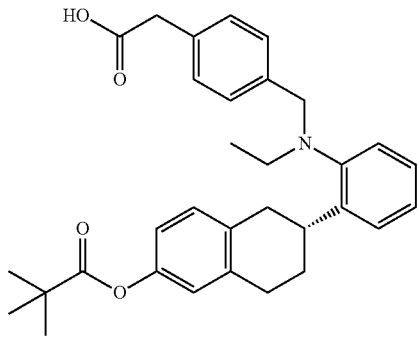 [SMILES: CCN(Cc1ccc(CC(=O)O)cc1)c1ccccc1[C@@H]1CCc2cc(OC(=O)C(C)(C)C)ccc2C1]

Synthesized from pivalic acid (R)-6-(2-ethylaminophenyl)-5,6,7,8-tetrahydronaphthalen-2-yl ester (182 mg) and (4-formylphenyl)acetic acid (420 mg) according to an analogous synthetic method to Example 212, the title compound (227 mg) was obtained.

$^1$H-NMR (400 MHz, CDCl$_3$); δ (ppm): 0.88 (t, 3H), 1.30 (s, 9H), 1.56-1.64 (m, 1H), 1.69-1.81 (m, 1H), 2.59-2.74 (m, 2H), 2.81-2.89 (m, 2H), 2.91 (q, 2H), 3.47 (s, 2H), 3.54-3.63 (m, 1H), 4.00 (dd, 2H), 6.80 (dd, 1H), 6.83 (d, 1H), 7.04-7.13 (m, 6H), 7.18 (dt, 1H), 7.26 (dd, 1H), 7.30 (dd, 1H).

Example 764

(R)-6-{2-{[4-(2-Dimethylaminoethyl)benzyl]ethylamino}phenyl}-5,6,7,8-tetrahydronaphthalen-2-ol

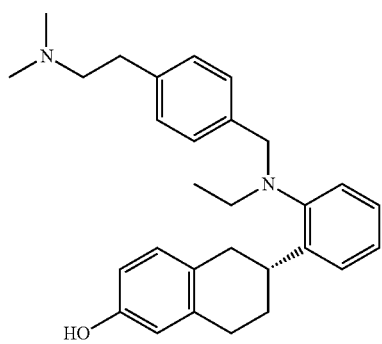 [SMILES: CCN(Cc1ccc(CCN(C)C)cc1)c1ccccc1[C@@H]1CCc2cc(O)ccc2C1]

Synthesized from pivalic acid (R)-6-{2-[(4-carboxymethylbenzyl)ethylamino]phenyl}-5,6,7,8-tetrahydronaphthalen-2-yl ester (28 mg) and dimethylamine (2.0 M solution in tetrahydrofuran) (0.14 ml) according to an analogous synthetic method to Example 715 and purified by LC-MS, the title compound (6.6 mg) was obtained.

ESI-Mass; 429 [M$^+$+H]

Example 765

(R)-6-{2-{[4-(2-Diethylaminoethyl)benzyl]ethylamino}phenyl}-5,6,7,8-tetrahydronaphthalen-2-ol

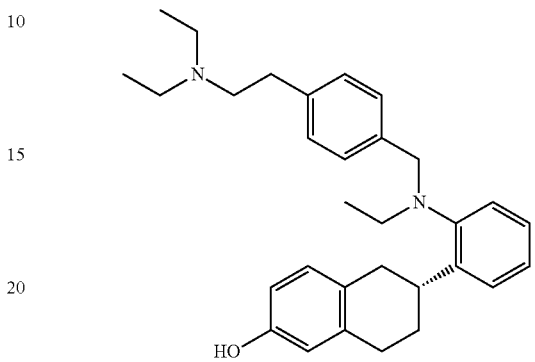

Synthesized from pivalic acid (R)-6-{2-[(4-carboxymethylbenzyl)ethylamino]phenyl}-5,6,7,8-tetrahydronaphthalen-2-yl ester (28 mg) and diethylamine (21 mg) according to an analogous synthetic method to Example 715 and purified by LC-MS, the title compound (6.9 mg) was obtained.

ESI-Mass; 457 [M$^+$+H]

Example 766

(R)-6-{2-{[4-(2-Azetidin-1-yl)benzyl]ethylamino}phenyl}-5,6,7,8-tetrahydronaphthalen-2-ol

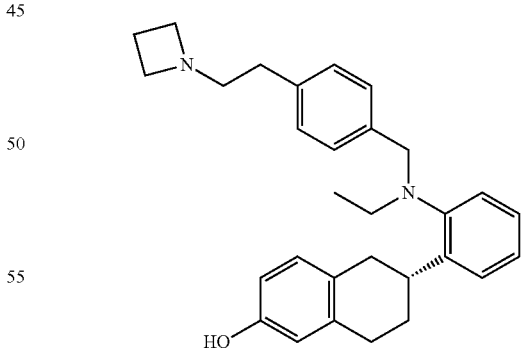

Synthesized from pivalic acid (R)-6-{2-[(4-carboxymethylbenzyl)ethylamino]phenyl}-5,6,7,8-tetrahydronaphthalen-2-yl ester (28 mg) and azetidine hydrochloride (27 mg) according to an analogous synthetic method to Example 715 and purified by LC-MS, the title compound (3.7 mg) was obtained.

ESI-Mass; 441 [M$^+$+H]

Example 767

(R)-6-{2-{Ethyl[4-(2-pyrrolidin-1-ylethyl)benzyl]amino}phenyl}-5,6,7,8-tetrahydronaphthalen-2-ol

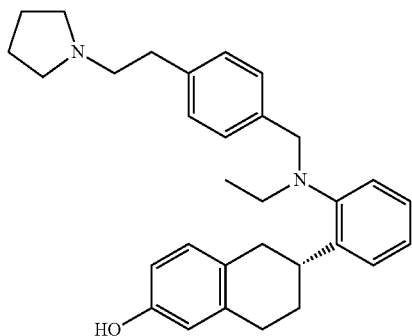 [SMILES: CCN(Cc1ccc(CCN2CCCC2)cc1)c1ccccc1[C@@H]1CCc2cc(O)ccc2C1]

Synthesized from pivalic acid (R)-6-{2-[(4-carboxymethylbenzyl)ethylamino]phenyl}-5,6,7,8-tetrahydronaphthalen-2-yl ester (28 mg) and pyrrolidine (20 mg) according to an analogous synthetic method to Example 715 and purified by LC-MS, the title compound (11 mg) was obtained.

ESI-Mass; 455 [M$^+$+H]

Example 768

(R)-6-{2-{Ethyl[4-(2-piperidin-1-ylethyl)benzyl]amino}phenyl}-5,6,7,8-tetrahydronaphthalen-2-ol

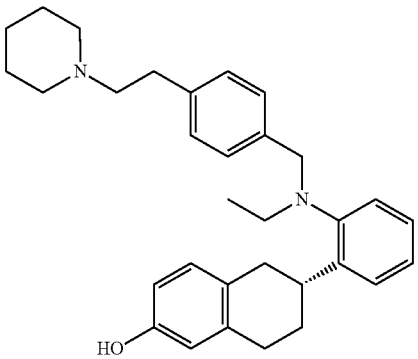 [SMILES: CCN(Cc1ccc(CCN2CCCCC2)cc1)c1ccccc1[C@@H]1CCc2cc(O)ccc2C1]

Synthesized from pivalic acid (R)-6-{2-[(4-carboxymethylbenzyl)ethylamino]phenyl}-5,6,7,8-tetrahydronaphthalen-2-yl ester (28 mg) and piperidine (24 mg) according to an analogous synthetic method to Example 715 and purified by LC-MS, the title compound (7.6 mg) was obtained.

ESI-Mass; 469 [M$^+$+H]

Example 769

(R)-6-{2-{[4-(2-Azepan-1-ylethyl)benzyl]ethylamino}phenyl}-5,6,7,8-tetrahydronaphthalen-2-ol

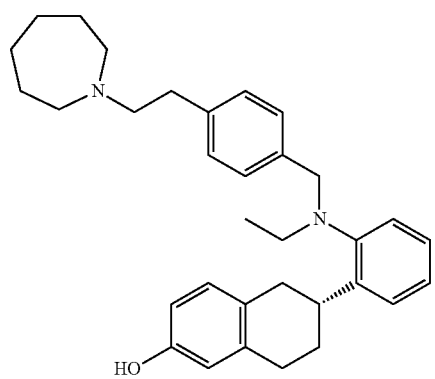 [SMILES: CCN(Cc1ccc(CCN2CCCCCC2)cc1)c1ccccc1[C@@H]1CCc2cc(O)ccc2C1]

Synthesized from pivalic acid (R)-6-{2-[(4-carboxymethylbenzyl)ethylamino]phenyl}-5,6,7,8-tetrahydronaphthalen-2-yl ester (28 mg) and hexamethyleneimine (28 mg) according to an analogous synthetic method to Example 715 and purified by LC-MS, the title compound (6.5 mg) was obtained.

ESI-Mass; 483 [M$^+$+H]

Example 770

(R)-6-{2-{{4-[2-(7-Azabicyclo[2.2.1]hept-7-yl)ethyl]benzyl}ethylamino}phenyl}-5,6,7,8-tetrahydronaphthalen-2-ol

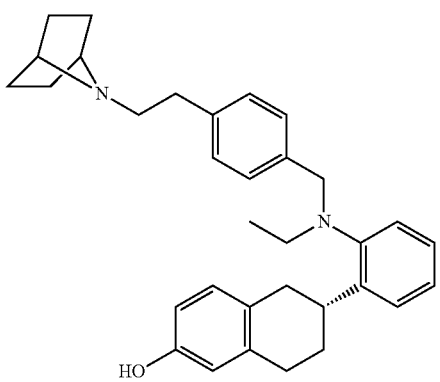 [SMILES: CCN(Cc1ccc(CCN2C3CCC2CC3)cc1)c1ccccc1[C@@H]1CCc2cc(O)ccc2C1]

Synthesized from pivalic acid (R)-6-{2-[(4-carboxymethylbenzyl)ethylamino]phenyl}-5,6,7,8-tetrahydronaphthalen-2-yl ester (28 mg) and 7-azabicyclo[2.2.1]heptane hydrochloride (38 mg) according to an analogous synthetic method to Example 715 and purified by LC-MS, the title compound (6.2 mg) was obtained.

ESI-Mass; 481 [M$^+$+H]

Example 771

(R)-6-{2-{Ethyl{4-{2-[(2-methoxyethyl)methylamino]ethyl}benzyl}amino}phenyl}-5,6,7,8-tetrahydronaphthalen-2-ol

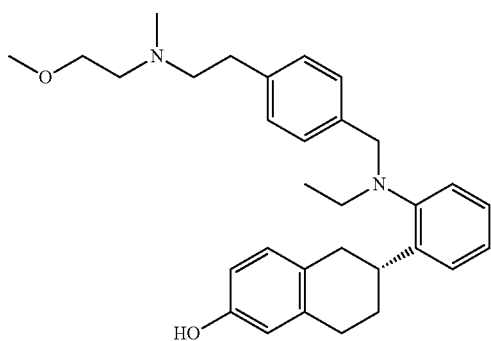 [SMILES: CCN(Cc1ccc(CCN(C)CCOC)cc1)c1ccccc1[C@@H]1CCc2cc(O)ccc2C1]

Synthesized from pivalic acid (R)-6-{2-[(4-carboxymethylbenzyl)ethylamino]phenyl}-5,6,7,8-tetrahydronaphthalen-2-yl ester (28 mg) and (2-methoxymethyl)methylamine (25 mg) according to an analogous synthetic method to Example 715 and purified by LC-MS, the title compound (7.8 mg) was obtained.

ESI-Mass; 473 [M$^+$+H]

Preparation Example 171

3-(3,5-Dimethoxyphenyl)acrylic Acid Ethyl Ester

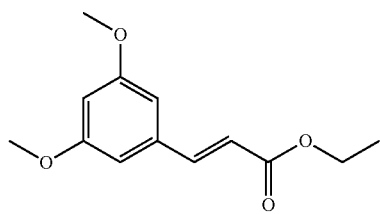 [SMILES: CCOC(=O)/C=C/c1cc(OC)cc(OC)c1]

To a suspension of 60% sodium hydride (6.7 g) in tetrahydrofuran (500 ml) were sequentially added triethyl phosphonoacetate (44.4 g) and 3,5-dimethoxybenzaldehyde (25.3 g) on an ice bath, then the reaction solution was concentrated in vacuo, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (38.4 g).

$^1$H-NMR (400 MHz, CDCl$_3$); δ (ppm): 1.34 (t, 3H), 3.81 (s, 6H), 4.26 (q, 2H), 6.40 (d, 1H), 6.47-6.50 (m, 1H), 6.66 (d, 2H), 7.59 (d, 1H).

Preparation Example 172

3-(3,5-Dimethoxyphenyl)propan-1-ol

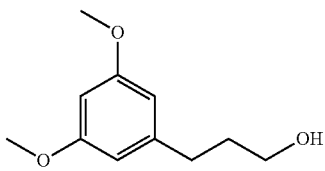

Synthesized from 3-(3,5-dimethoxyphenyl)acrylic acid ethyl ester according to an analogous synthetic method to Example 22, ethyl 3-(3,5-dimethoxyphenyl)propionate (38.4 g) was added dropwise to a solution of lithium aluminum hydride (12.3 g) in tetrahydrofuran (200 ml) on an ice bath, and the solution was stirred for 15 minutes at room temperature. To the reaction solution were sequentially added water (12 ml), an aqueous solution of 5N sodium hydroxide (12 ml) and water (28 ml), the suspension was filtered, and then the solvent was evaporated in vacuo. The residue was purified by silica gel column chromatography (hexane-ethyl acetate system) to provide the title compound (24.3 g).

$^1$H-NMR (400 MHz, CDCl$_3$); δ (ppm): 1.83-1.92 (m, 2H), 2.65 (t, 2H), 3.67 (t, 2H), 3.77 (s, 6H), 6.29-6.32 (m, 1H), 6.36 (d, 2H).

Preparation Example 173

4-(3,5-Dimethoxyphenyl)butyric Acid Ethyl Ester

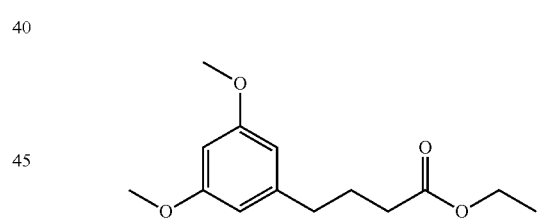

To a solution of 3-(3,5-dimethoxyphenyl)propan-1-ol (24.3 g) in ethyl acetate (500 ml) were sequentially added triethylamine (16.3 g) and methanesulfonyl chloride (16.3 g) on an ice bath, and the solution was stirred for 25 minutes at room temperature. The solution was extracted with ethyl acetate, then sequentially washed with water and brine, dried over anhydrous magnesium sulfate, then the solvent was evaporated in vacuo. To a solution of the total amount of the resulting 3-(3,5-dimethoxyphenyl)propyl methanesulfonate (crude product) in N,N-dimethylformamide (150 ml) was added sodium cyanide (15.2 g), and the solution was stirred for 8.5 hours at 80° C. The solution was extracted with ethyl acetate, then sequentially washed with water and brine, dried over anhydrous magnesium sulfate, then the solvent was evaporated in vacuo. To a solution of the total amount of the resulting 4-(3,5-dimethoxyphenyl)butyronitrile (crude product) in ethylene glycol (100 ml) was added an aqueous solution of 5N sodium hydroxide (75 ml), and the solution was refluxed for 9.5 hours. The reaction solution was acidified with concentrated sulfuric acid, the solution was extracted with ethyl acetate, then sequentially washed with water and brine, dried over anhydrous magnesium sulfate, then the solvent was evaporated in vacuo. To a solution of the resulting residue in ethanol (400 ml) was added concentrated sulfuric acid (4 ml), and the solution was stirred for 1 hour and 20 minutes at 70° C. The reaction solution was concentrated in vacuo, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (25.3 g).

$^1$H-NMR (400 MHz, CDCl$_3$); δ (ppm): 1.25 (t, 3H), 1.85-2.00 (m, 2H), 2.31 (t, 2H), 2.59 (t, 2H), 3.77 (s, 6H), 4.12 (q, 2H), 6.29-6.32 (m, 1H), 6.32-6.35 (m, 2H).

Preparation Example 174

4-(3,5-Dimethoxyphenyl)butyric Acid

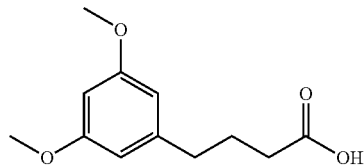 [SMILES: COc1cc(CCCC(=O)O)cc(OC)c1]

Synthesized from 4-(3,5-dimethoxyphenyl) butyric acid ethyl ester (25.3 g) according to an analogous synthetic method to Preparation Example 1, the title compound (20.7 g) was obtained.

$^1$H-NMR (400 MHz, CDCl$_3$); δ (ppm): 1.92-2.00 (m, 2H), 2.39 (t, 2H), 2.42 (t, 2H), 3.78 (s, 6H), 6.29-6.32 (m, 1H), 6.34-6.38 (m, 2H).

Preparation Example 175

6,8-Dimethoxy-3,4-dihydro-2H-naphthalen-1-one

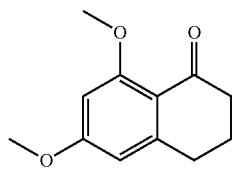

Synthesized from 4-(3,5-dimethoxyphenyl)butyric acid (18.1 g) according to an analogous synthetic method to Preparation Example 66, the title compound (16.0 g) was obtained.

$^1$H-NMR (400 MHz, CDCl$_3$); δ (ppm): 1.98-2.06 (m, 2H), 2.58 (t, 2H), 2.87 (t, 2H), 3.84 (s, 3H), 3.88 (s, 3H), 6.31-6.35 (m, 2H).

Preparation Example 176

6,8-Dimethoxy-2-(4-methoxyphenyl)-3,4-dihydro-2H-naphthalen-1-one

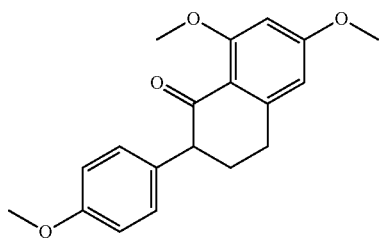

The title compound was synthesized by referring to *J. Am. Chem. Soc.*, 1997, 119 (45), 11108. To a solution of 6,8-dimethoxy-3,4-dihydro-2H-naphthalen-1-one (11.9 g) in tetrahydrofuran (200 ml) were sequentially added 4-bromoanisole (16.2 g), sodium tert-butoxide (11.1 g), (±)-2,2'-bis(diphenylphosphino)-1,1'-binaphthyl (1.3 g) and tris(dibenzylidene)acetone dipalladium(0) (792 mg), and the solution was stirred for 1.5 hours at 75° C. under a nitrogen atmosphere. The solution was extracted with ethyl acetate, then sequentially washed with water and brine, dried over anhydrous magnesium sulfate, then the solvent was evaporated in vacuo; the resulting crude crystal was suspended in diethyl ether and then filtered. The mother liquor was concentrated in vacuo, the resulting residue was purified by silica gel column chromatography (hexane-ethyl acetate system); the resulting crystal was suspended in diethyl ether, then filtered, and combined to provide the title compound (14.2 g).

$^1$H-NMR (400 MHz, CDCl$_3$); δ (ppm): 2.28-2.36 (m, 2H), 2.94-3.00 (m, 2H), 3.68-3.72 (m, 1H), 3.78 (s, 3H), 3.86 (s, 3H), 6.33-6.37 (m, 2H), 6.82-6.84 (m 2H), 7.10-7.13 (m, 2H).

Preparation Example 177

3-Methoxy-7-(4-methoxyphenyl)-5,6-dihydronaphthalen-1-ol

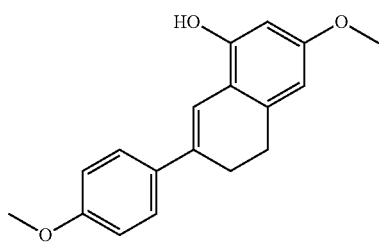

Synthesized from 6,8-dimethoxy-2-(4-methoxyphenyl)-3,4-dihydro-2H-naphthalen-1-one according to an analogous synthetic method to Preparation Example 192 described below, a solution of 8-hydroxy-6-methoxy-2-(4-methoxyphenyl)-3,4-dihydro-2H-naphthalen-1-one (6.2 g) in tetrahydrofuran (130 ml) was added dropwise to a suspension of lithium borohydride (1.1 g) in tetrahydrofuran (60 ml) on an ice bath, and the solution was stirred for 20 minutes at room temperature. To the reaction solution was added 2N hydrochloric acid on the ice bath, the solution was stirred, extracted with ethyl acetate, then washed with brine, dried over anhydrous magnesium sulfate, and then the solvent was evaporated in vacuo. The residue was purified by silica gel column chromatography (hexane-tetrahydrofuran system) to provide the title compound (5.6 g).

$^1$H-NMR (400 MHz, CDCl$_3$); δ (ppm): 2.64-2.72 (m, 2H), 2.83-2.91 (m, 2H), 3.78 (s, 3H), 3.83 (s, 3H), 4.96 (s, 1H), 6.23 (d, 1H), 6.36 (d, 1H), 6.87-6.93 (m, 2H), 6.98 (s, 1H), 7.46-7.52 (m, 2H).

Preparation Example 178

3-Methoxy-7-(4-methoxyphenyl)-5,6,7,8-tetrahydronaphthalen-1-ol

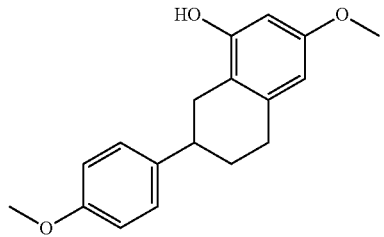

Synthesized from 3-methoxy-7-(4-methoxyphenyl)-5,6-dihydronaphthalen-1-ol (5.6 g) according to an analogous synthetic method to Example 22, the title compound (4.7 g) was obtained.

$^1$H-NMR (400 MHz, CDCl$_3$); δ (ppm): 1.76-1.86 (m, 1H), 1.97-2.03 (m, 1H), 2.19-2.30 (m, 1H), 2.76-2.94 (m, 4H), 3.70 (s, 3H), 3.74 (s, 3H), 4.68 (s, 1H), 6.18-6.26 (m, 2H), 6.78-6.83 (m 2H), 7.14-7.18 (m, 2H).

Preparation Example 179

8-(4-Benzyloxyphenoxy)-6-methoxy-2-(4-methoxyphenyl)-1,2,3,4-tetrahydronaphthalene

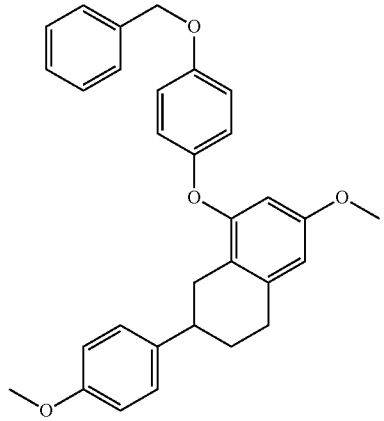

The title compound was synthesized by referring to *Tetrahedron Lett.*, 1998, (19), 2937-2940. To a solution of 3-methoxy-7-(4-methoxyphenyl)-5,6,7,8-tetrahydronaphthalen-1-ol (853 mg) and 4-benzyloxyphenylboronic acid (1.4 g) in dichloromethane (30 ml) were sequentially added copper(II) acetate (545 mg), molecular sieves 4 A and triethylamine (1.5 g), and the solution was stirred for 8 hours and 40 minutes at room temperature. The insoluble material was filtered through celite pad, the filtrate was adsorbed onto silica gel and purified by silica gel column chromatography (hexane-ethyl acetate system) to provide the title compound (1.2 g).

$^1$H-NMR (400 MHz, CDCl$_3$); δ (ppm): 1.82-1.95 (m, 1H), 2.04-2.13 (m, 1H), 2.57 (dd, 1H), 2.83-3.01 (m, 3H), 3.06-3.15 (m, 1H), 3.71 (s, 3H), 3.79 (s, 3H), 5.03 (s, 2H), 6.21 (s, 1H), 6.43 (s, 1H), 6.82-7.01 (m 6H), 7.08-7.46 (m, 7H).

Preparation Example 180

4-[3-Methoxy-7-(4-methoxyphenyl)-5,6,7,8-tetrahydronaphthalen-1-yloxy]phenol

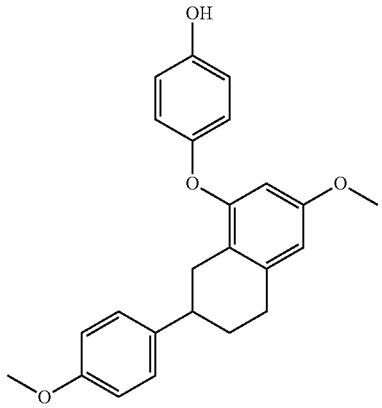

Synthesized from 8-(4-benzyloxy phenoxy)-6-methoxy-2-(4-methoxyphenyl)-1,2,3,4-tetrahydronaphthalene (1.2 g) according to an analogous synthetic method to Example 22, the title compound (782 mg) was obtained.

$^1$H-NMR (400 MHz, CDCl$_3$); δ (ppm): 1.82-1.95 (m, 1H), 2.04-2.14 (m, 1H), 2.57 (dd, 1H), 2.84-3.01 (m, 3H), 3.07-3.16 (m, 1H), 3.71 (s, 3H), 3.79 (s, 3H), 6.20 (d, 1H), 6.43 (d, 1H), 6.74-6.80 (m, 2H), 6.81-6.89 (m, 4H), 7.17-7.22 (m, 2H).

Example 772

4-[4-(2-Azepan-1-ylethoxy)phenoxy]-6-(4-hydroxyphenyl)-5,6,7,8-tetrahydronaphthalen-2-ol

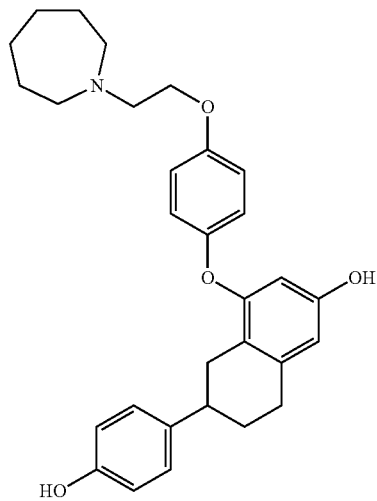 [SMILES: Oc1ccc(C2CCc3cc(O)cc(Oc4ccc(OCCN5CCCCCC5)cc4)c3C2)cc1]

Synthesized from 4-[3-methoxy-7-(4-methoxyphenyl)-5,6,7,8-tetrahydronaphthalen-1-yloxy]phenol and 1-(2-chloroethyl)azepane hydrochloride according to an analogous synthetic method to Preparation Example 40, 1-{2-{4-[3-methoxy-7-(4-methoxyphenyl)-5,6,7,8-tetrahydronaphthalen-1-yloxy]phenoxy}ethyl}azepane (345 mg) was used according to an analogous synthetic method to Example 779 described below to provide the title compound (116 mg).

¹H-NMR (400 MHz, DMSO-d₆); δ (ppm): 1.48-1.94 (m, 9H), 2.28-2.40 (m, 1H), 2.67-2.87 (m, 5H), 3.12-3.28 (m, 3H), 3.42-3.52 (m, 2H), 4.07-4.16 (m, 1H), 4.28-4.38 (m, 2H), 5.99 (s, 1H), 6.31 (s, 1H), 6.66 (d, 2H), 6.87 (d, 2H), 6.96 (d, 2H), 7.03 (d, 2H), 9.19 (s, 1H), 9.23 (s, 1H).
ESI-Mass; 474 [M⁺+H]

Example 773

4-[4-(2-Diisopropylaminoethoxy)phenoxy]-6-(4-hydroxyphenyl)-5,6,7,8-tetrahydronaphthalen-2-ol

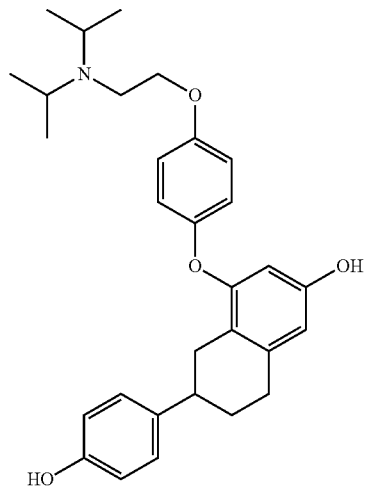 [SMILES: CC(C)N(CCOc1ccc(Oc2cc(O)cc3c2CC(c2ccc(O)cc2)CC3)cc1)C(C)C]

Synthesized from 4-[3-methoxy-7-(4-methoxyphenyl)-5,6,7,8-tetrahydronaphthalen-1-yloxy]phenol and (2-chloroethyl)diisopropylamine hydrochloride according to an analogous synthetic method to Preparation Example 40, diisopropyl{2-{4-[3-methoxy-7-(4-methoxyphenyl)-5,6,7,8-tetrahydronaphthalen-1-yloxy]phenoxy}ethyl}amine (408 mg) was used according to an analogous synthetic method to Example 779 described below to provide the title compound (86 mg).
¹H-NMR (400 MHz, CDCl₃); δ (ppm): 1.03 (d, 6H), 1.05 (d, 6H), 1.78-1.90 (m, 1H), 2.01-2.10 (m, 1H), 2.55 (dd, 1H), 2.78-2.92 (m, 3H), 2.81 (t, 2H), 3.00-3.14 (m, 3H), 3.87 (t, 2H), 6.08 (d, 1H), 6.34 (d, 1H), 6.74-6.89 (m, 6H), 7.19-7.20 (m, 2H).
ESI-Mass; 476 [M⁺+H]

Example 774

6-(4-Hydroxyphenyl)-4-[4-(2-piperidin-1-ylethoxy)phenoxy]-5,6,7,8-tetrahydronaphthalen-1-ol

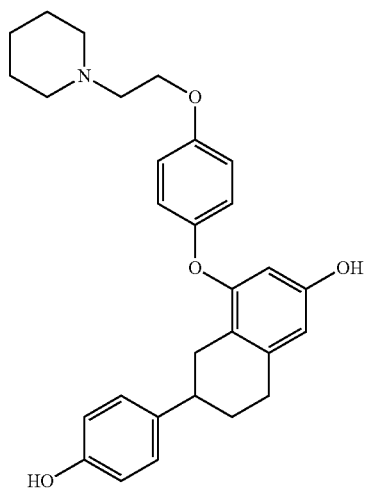 [SMILES: Oc1ccc(C2CCc3cc(O)cc(Oc4ccc(OCCN5CCCCC5)cc4)c3C2)cc1]

Synthesized from 4-[3-methoxy-7-(4-methoxyphenyl)-5,6,7,8-tetrahydronaphthalen-1-yloxy]phenol and 1-(2-chloroethyl)piperidine hydrochloride according to an analogous synthetic method to Preparation Example 40, 1-{2-{4-[3-methoxy-7-(4-methoxyphenyl)-5,6,7,8-tetrahydronaphthalen-1-yloxy]phenoxy}ethyl}piperidine (180 mg) was used according to an analogous synthetic method to Example 779 described below to provide the title compound (104 mg).
¹H-NMR (400 MHz, DMSO-d₆); δ (ppm): 1.60-1.94 (m, 7H), 2.28-2.40 (m, 1H), 2.68-3.10 (m, 7H), 3.12-3.17 (m, 1H), 3.42 (s, 2H), 4.07-4.16 (m, 1H), 4.28-4.38 (m, 2H), 5.99 (s, 1H), 6.30 (s, 1H), 6.66 (d, 2H), 6.87 (d, 2H), 6.96 (d, 2H), 7.03 (d, 2H), 9.18 (s, 1H), 9.22 (s, 1H).
ESI-Mass; 460 [M⁺+H]

Example 775

2-(4-Hydroxyphenyl)-7-[4-(2-piperidin-1-ylethoxy)phenoxy]indan-5-ol

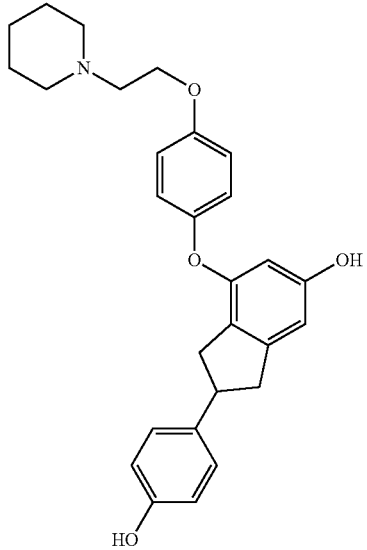 [SMILES: Oc1ccc(C2Cc3cc(O)cc(Oc4ccc(OCCN5CCCCC5)cc4)c3C2)cc1]

Synthesized according to an analogous synthetic method to Example 774 described above, the title compound (84 mg) was obtained.
¹H-NMR (400 MHz, DMSO-d₆); δ (ppm): 1.30-1.38 (m, 2H), 1.42-1.50 (m, 4H), 2.34-2.44 (m, 4H), 2.56 (dd, 1H), 2.60 (t, 2H), 2.82 (dd, 1H), 3.00 (dd, 1H), 3.12 (dd, 1H), 3.40-3.52 (m, 1H), 3.99 (t, 2H), 5.99 (d, 1H), 6.38 (d, 1H), 6.62-6.66 (m, 2H), 6.85-6.93 (m, 4H), 7.01-7.06 (m, 2H), 9.18 (s, 1H), 9.22 (s, 1H).

Preparation Example 181

1-(2,4-Dimethoxyphenyl)-2-(4-methoxyphenyl)-2-methylpropan-1-one

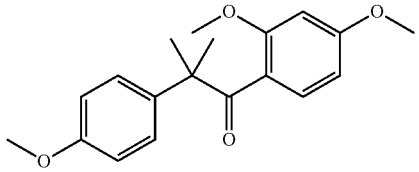

To a solution of potassium tert-butoxide (8.0 g) in tetrahydrofuran (200 ml) was added 18-crown-6 (626 mg), then was added dropwise a solution of 1-(2,4-dimethoxyphenyl)-2-(4-methoxyphenyl)ethanone (6.8 g) and methyl iodide (13.4 g) in tetrahydrofuran (50 ml), and the solution was stirred for 30 minutes at room temperature. The reaction solution was filtered, the filtrate was adsorbed onto silica gel and purified by silica gel column chromatography (hexane-ethyl acetate system). To a solution of the resulting oil in tetrahydrofuran (200 ml) were sequentially added methyl iodide (8.4 g) and a solution of potassium tert-butoxide (6.6 g) in tetrahydrofuran (60 ml), and the solution was stirred for 20 minutes at room temperature. The reaction solution was filtered, the filtrate was adsorbed onto silica gel and purified by silica gel column chromatography (hexane-ethyl acetate system) to provide the title compound (6.2 g).

$^1$H-NMR (400 MHz, CDCl$_3$); δ (ppm): 1.52 (s, 6H), 3.68 (s, 3H), 3.74 (s, 3H), 3.81 (s, 3H), 6.19 (dd, 1H), 6.35 (d, 1H), 6.42 (d, 1H), 6.83-6.89 (m, 2H), 7.22-7.28 (m, 2H).

Preparation Example 182

5-Methoxy-2-[2-(4-methoxyphenyl)-2-methylpropyl]phenol

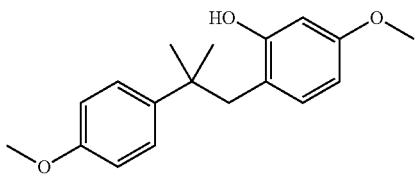

Synthesized from 1-(2,4-dimethoxyphenyl)-2-(4-methoxyphenyl)-2-methylpropan-1-one according to an analogous synthetic method to Preparation Example 192 described below, 1-(2-hydroxy-4-methoxyphenyl)-2-(4-methoxyphenyl)-2-methylpropan-1-one (2.9 g) was used according to an analogous synthetic method to Preparation Example 185 described below to provide the title compound (1.9 g).

$^1$H-NMR (400 MHz, CDCl$_3$); δ (ppm): 1.36 (s, 6H), 2.76 (s, 2H), 3.73 (s, 3H), 3.80 (s, 3H), 4.02 (s, 1H), 6.25 (d, 1H), 6.36 (dd, 1H), 6.74 (d, 1H), 6.83-6.88 (m, 2H), 7.20-7.28 (m, 2H).

Preparation Example 183

4-{5-Methoxy-2-[2-(4-methoxyphenyl)-2-methylpropyl]phenoxy}phenol

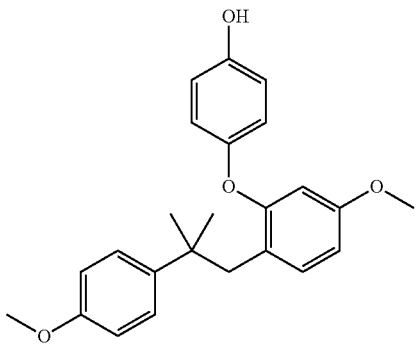

Synthesized from 5-methoxy-2-[2-(4-methoxyphenyl)-2-methylpropyl]phenol and 4-fluorobenzaldehyde according to an analogous synthetic method to Preparation Example 189 described below, 4-{5-methoxy-2-[2-(4-methoxyphenyl)-2-methylpropyl]phenoxy}benzaldehyde (860 mg) was used according to an analogous synthetic method to Preparation Example 190 described below to provide the title compound (201 mg).

$^1$H-NMR (400 MHz, CDCl$_3$); δ (ppm): 1.33 (s, 6H), 2.87 (s, 2H), 3.66 (s, 3H), 3.80 (s, 3H), 6.24 (d, 1H), 6.38 (dd, 1H), 6.61 (d, 1H), 6.78 (s, 2H), 6.79-6.84 (m, 2H), 7.22-7.28 (m, 2H), 7.26 (s, 2H)

Example 776

4-[2-(4-Hydroxyphenyl)-2-methylpropyl]-3-[4-(2-piperidin-1-ylethoxy)phenoxy]phenol

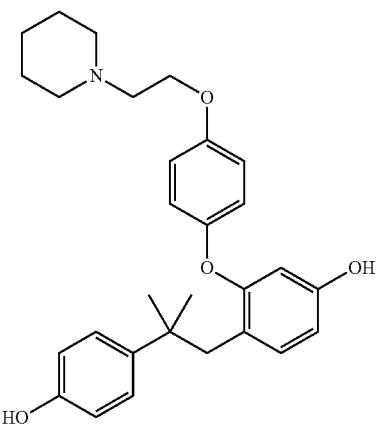 [SMILES: CC(C)(Cc1ccc(O)cc1Oc1ccc(OCCN2CCCCC2)cc1)c1ccc(O)cc1]

Synthesized from 4-{5-methoxy-2-[2-(4-methoxyphenyl)-2-methylpropyl]phenoxy}phenol and 1-(2-chloroethyl)piperidine hydrochloride according to an analogous synthetic method to Preparation Example 40, 1-{2-[4-{5-methoxy-2-[2-(4-methoxyphenyl)-2-methylpropyl]phenoxy]phenoxy}ethyl}piperidine (190 mg) was used according to an analogous synthetic method to Example 779 described below to provide the title compound (118 mg).

$^1$H-NMR (400 MHz, CDCl$_3$); δ (ppm): 1.32 (s, 6H), 1.40-1.47 (m, 2H), 1.57-1.65 (m, 4H), 2.48-2.57 (m, 4H), 2.73 (t, 2H), 2.84 (s, 2H), 4.00 (t, 2H), 6.09 (d, 1H), 6.29 (dd, 1H), 6.61 (d, 1H), 6.62-6.73 (m, 6H), 7.10-7.16 (m, 2H).

Preparation Example 184

(2-Hydroxy-4-methoxyphenyl)(3-methoxyphenyl)methanone

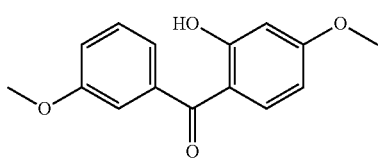

Synthesized from resorcinol and 3-methoxybenzoyl chloride according to an analogous synthetic method to Preparation Example 66, (2,4-dihydroxyphenyl)(3-methoxyphenyl)methanone (14.7 g) and methyl iodide (9.4 g) were used according to an analogous synthetic method to Example 383 to provide the title compound (10.3 g).

$^1$H-NMR (400 MHz, CDCl$_3$); δ (ppm): 3.86 (s, 6H), 6.41 (dd, 1H), 6.52 (d, 1H), 7.09 (dd, 1H), 7.15-7.22 (m, 2H), 7.39 (dd, 1H), 7.53 (d, 1H), 12.66 (s, 1H).

Preparation Example 185

5-Methoxy-2-(3-methoxybenzyl)phenol

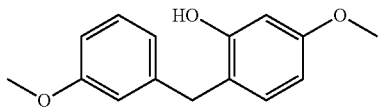

The title compound was synthesized by referring to *Tetrahedron Lett.*, 1995, (30), 5335. To a solution of (2-hydroxy-4-methoxyphenyl)(3-methoxyphenyl)methanone (5.2 g) in tetrahydrofuran (100 ml) were sequentially added triethylamine (3.0 g) and methyl chloroformate (2.2 g) on an ice bath, the solution was stirred for 48 minutes, and then the reaction mixture was filtered. To a solution of sodium borohydride (3.0 g) in water (50 ml) was added dropwise the above-mentioned filtrate on an ice bath, and the solution was stirred for 1 hour and 10 minutes. The reaction solution was concentrated in vacuo, extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (4.8 g).

$^1$H-NMR (400 MHz, CDCl$_3$); δ (ppm): 3.75 (s, 3H), 3.76 (s, 3H), 3.90 (s, 2H), 4.95 (s, 1H), 6.38 (d, 1H), 6.45 (dd, 1H), 6.72-6.82 (m, 3H), 7.01 (d, 1H), 7.18-7.23 (m, 1H).

Preparation Example 186

4-[5-Methoxy-2-(3-methoxybenzyl)phenoxy]phenol

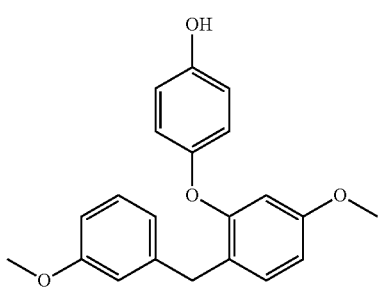

The title compound was synthesized by referring to *J. Am. Chem. Soc.*, 1999, 121 (18), 4369. To a suspension of 60% sodium hydride (600 mg) in toluene (50 ml) was added 5-methoxy-2-(3-methoxybenzyl)phenol (2.4 g), and the solution was stirred at 90° C. until generation of gas was stopped. The reaction solution was cooled to room temperature, then 1-benzyloxy-4-bromobenzene (2.6 g), palladium(II) acetate (112 mg), 2-(di-tert-butylphosphino)biphenyl (149 mg) were sequentially added thereto, and the solution was stirred for 18 hours and 50 minutes at 95° C. To the reaction solution was added water, the solution was extracted with ethyl acetate, then the insoluble material was filtered through celite pad, the filtrate was dried over anhydrous magnesium sulfate, and then the solvent was evaporated in vacuo. Obtained by purifying the residue by silica gel column chromatography (hexane-ethyl acetate system), 2-(4-benzyloxy phenoxy)-4-methoxy-1-(3-methoxybenzyl)benzene (1.4 g) was used according to an analogous synthetic method to Example 22 to provide the title compound (690 mg).

$^1$H-NMR (400 MHz, CDCl$_3$); δ (ppm): 3.68 (s, 3H), 3.74 (s, 3H), 3.92 (s, 2H), 6.33 (d, 1H), 6.55 (dd, 1H), 6.69-6.83 (m, 6H), 7.08 (d, 1H), 7.14-7.19 (m, 1H).

Example 777

4-(3-Hydroxybenzyl)-3-[4-(2-piperidin-1-ylethoxy)phenoxy]phenol

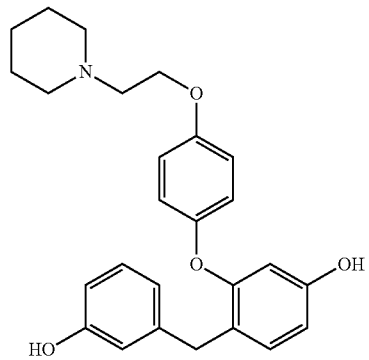 [SMILES: Oc1cccc(Cc2ccc(O)cc2Oc2ccc(OCCN3CCCCC3)cc2)c1]

Synthesized from 4-[5-methoxy-2-(3-methoxybenzyl)phenoxy]phenol and 1-(2-chloroethyl)piperidine hydrochloride according to an analogous synthetic method to Preparation Example 40, 1-{2-{4-[5-methoxy-2-(3-methoxybenzyl)phenoxy]phenoxy}ethyl}piperidine (228 mg) was used according to an analogous synthetic method to Example 364 to provide the title compound (105 mg).

$^1$H-NMR (400 MHz, CDCl$_3$); δ (ppm): 1.40-1.47 (m, 2H), 1.57-1.66 (m, 4H), 2.48-2.56 (m, 4H), 2.71 (t, 2H), 3.85 (s, 2H), 3.95 (t, 2H), 6.18 (d, 1H), 6.45 (dd, 1H), 6.57-6.62 (m, 4H), 6.67-6.71 (m, 2H), 6.73-6.78 (m, 1H), 7.01 (d, 1H), 7.06 (dd, 1H).

Preparation Example 187

(2-Hydroxy-4-methoxyphenyl) (4-methoxyphenyl)methanone

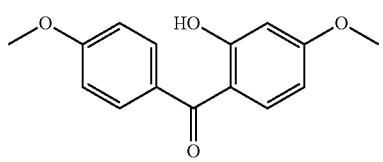

Synthesized from resorcinol and 4-methoxybenzoyl chloride according to an analogous synthetic method to Preparation Example 66, (2,4-dihydroxyphenyl)(4-methoxyphenyl)methanone (9.7 g) and methyl iodide (13.1 g) were used according to an analogous synthetic method to Example 383 to provide the title compound (7.0 g).

¹H-NMR (400 MHz, CDCl₃); δ (ppm): 3.87 (s, 3H), 3.89 (s, 3H), 6.42 (dd, 1H), 6.52 (d, 1H), 6.96-7.01 (m, 2H), 7.55 (d, 1H), 7.64-7.69 (m, 2H), 12.68 (s, 1H).

Preparation Example 188

5-Methoxy-2-(4-methoxybenzyl)phenol

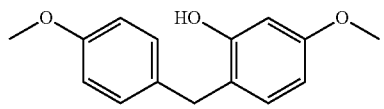

Synthesized from (2-hydroxy-4-methoxyphenyl)(4-methoxyphenyl)methanone (7.0 g) according to an analogous synthetic method to Preparation Example 185, the title compound (5.0 g) was obtained.

¹H-NMR (400 MHz, CDCl₃); δ (ppm): 3.75 (s, 3H), 3.77 (s, 3H), 3.86 (s, 2H), 4.94 (s, 1H), 6.38 (d, 1H), 6.45 (dd, 1H), 6.80-6.86 (m, 2H), 6.99 (d, 1H), 7.10-7.14 (m, 1H).

Preparation Example 189

4-[5-Methoxy-2-(4-methoxybenzyl)phenoxy]benzaldehyde

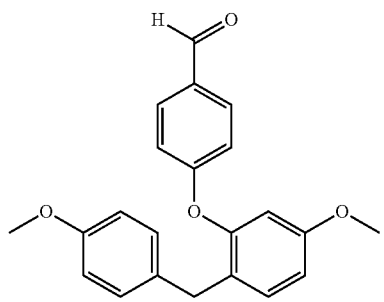

The title compound was synthesized by referring to *Synthesis*, 1991, (1), 63. To a solution of 5-methoxy-2-(4-methoxybenzyl)phenol (1.9 g) in N,N-dimethylacetamide (6 ml) was added 4-fluorobenzaldehyde (960 mg) and potassium carbonate (1.3 g), and the solution was refluxed for 1 hour and 10 minutes. The solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide the title compound (2.0 g).

¹H-NMR (400 MHz, CDCl₃); δ (ppm): 3.74 (s, 3H), 3.75 (s, 3H), 3.76 (s, 2H), 6.55 (d, 1H), 6.72-6.77 (m, 3H), 6.92-6.96 (m, 2H), 6.98-7.04 (m, 2H), 7.15 (d, 1H), 7.77-7.82 (m, 2H), 9.89 (s, 1H).

Preparation Example 190

4-[5-Methoxy-2-(4-methoxybenzyl)phenoxy]phenol

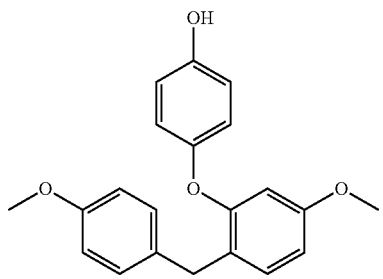

To a solution of 4-[5-methoxy-2-(4-methoxybenzyl)phenoxy]benzaldehyde (2.0 g) in dichloromethane (20 ml) was added 80% m-chloroperbenzoic acid (1.5 g), and the solution was stirred for 15 hours and 20 minutes at room temperature. The reaction solution was concentrated in vacuo, extracted with ethyl acetate, then sequentially washed with a saturated aqueous solution of sodium bicarbonate and brine, dried over anhydrous magnesium sulfate, and then the solvent was evaporated in vacuo. Obtained by purifying the residue by silica gel column chromatography (hexane-ethyl acetate system), to a solution of the resulting formic acid 4-[5-methoxy-2-(4-methoxybenzyl)phenoxy]phenyl ester (1.1 g) in methanol (5 ml) and tetrahydrofuran (5 ml) was added an aqueous solution of 1N sodium hydroxide (4 ml), and the solution was stirred for 40 minutes at room temperature. The reaction solution was concentrated in vacuo, extracted with ethyl acetate, then sequentially washed with 1N hydrochloric acid, water and brine, dried over anhydrous magnesium sulfate, and then the solvent was evaporated in vacuo. The residue was purified by silica gel column chromatography (hexane-ethyl acetate system) to provide the title compound (692 mg).

¹H-NMR (400 MHz, CDCl₃); δ (ppm): 3.69 (s, 3H), 3.77 (s, 3H), 3.89 (s, 2H), 4.97 (s, 1H), 6.33 (d, 1H), 6.55 (dd, 1H), 6.75-6.83 (m, 6H), 7.06 (d, 1H), 7.10-7.15 (m, 2H).

Example 778

4-(4-Hydroxybenzyl)-3-[4-(2-piperidin-1-ylethoxy)phenoxy]phenol

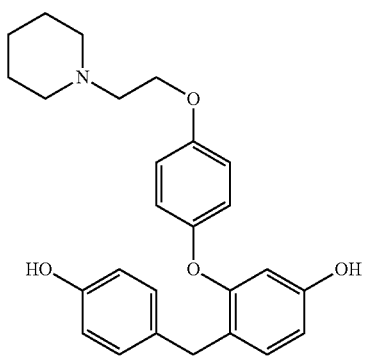 [SMILES: Oc1ccc(Cc2ccc(O)cc2Oc2ccc(OCCN3CCCCC3)cc2)cc1]

Synthesized from 4-[5-methoxy-2-(4-methoxybenzyl)phenoxy]phenol and 1-(2-chloroethyl)piperidine hydrochloride according to an analogous synthetic method to Preparation Example 40, 1-{2-{4-[5-methoxy-2-(4-methoxybenzyl)phenoxy]phenoxy}ethyl}piperidine (223 mg) was used according to an analogous synthetic method to Example 111 to provide the title compound (59 mg).

$^1$H-NMR (400 MHz, DMSO-d$_6$); δ (ppm): 1.32-1.39 (m, 2H), 1.44-1.51 (m, 4H), 2.37-2.43 (m, 4H), 2.61 (t, 2H), 3.69 (s, 2H), 4.00 (t, 2H), 6.09 (d, 1H), 6.39 (dd, 1H), 6.59-6.64 (m, 2H), 6.80-6.84 (m, 2H), 6.88-6.98 (m, 5H).

Preparation Example 191

1-(2,4-Dimethoxyphenyl)-2-(4-methoxyphenyl)ethanone

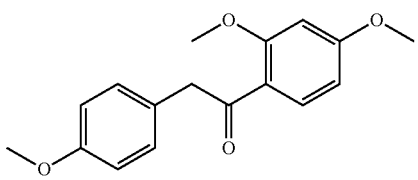

Synthesized from 1,3-dimethoxybenzene (8.2 g) and 4-methoxyphenylacetyl chloride (10.0 g) according to an analogous synthetic method to Preparation Example 66, the title compound (8.0 g) was obtained.

$^1$H-NMR (400 MHz, CDCl$_3$); δ (ppm): 3.78 (s, 3H), 3.84 (s, 3H), 3.89 (s, 3H), 4.21 (s, 2H), 6.44 (d, 1H), 6.51 (dd, 1H), 6.81-6.86 (m, 2H), 7.10-7.15 (m, 2H), 7.78 (d, 1H).

Preparation Example 192

1-(2-Hydroxy-4-methoxyphenyl)-2-(4-methoxyphenyl)ethanone

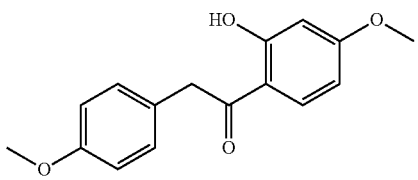

The title compound was synthesized by referring to *Chem. Lett.*, 2000, (7), 738. To a solution of 1-(2,4-dimethoxyphenyl)-2-(4-methoxyphenyl)ethanone (2.8 g) in acetonitrile (150 ml) were sequentially added sodium iodide (3.0 g) and cerium(III) chloride heptahydrate (5.7 g), and the solution was refluxed for 20 hours and 30 minutes. Sodium iodide (760 mg) and cerium(III) chloride heptahydrate (1.9 g) were added thereto, and the solution was further refluxed for 22 hours 30 minutes. To the reaction solution were added ethyl acetate and water, the solution was filtered through celite pad, extracted with ethyl acetate, then washed with brine, dried over anhydrous magnesium sulfate, and then filtered. The filtrate was adsorbed onto silica gel and purified by silica gel column chromatography (hexane-ethyl acetate system) to provide the title compound (2.5 g).

$^1$H-NMR (400 MHz, CDCl$_3$); δ (ppm): 3.79 (s, 3H), 3.83 (s, 3H), 4.16 (s, 2H), 6.40-6.46 (m, 2H), 6.85-6.90 (m, 2H), 7.16-7.21 (m, 2H), 7.75 (d, 1H), 12.73 (s, 1H).

Preparation Example 193

5-Methoxy-2-[2-(4-methoxyphenyl)ethyl]phenol

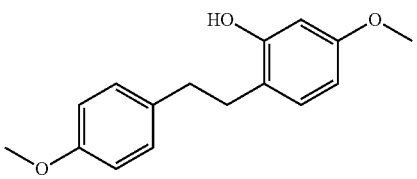

Synthesized from 1-(2-hydroxy-4-methoxyphenyl)-2-(4-methoxyphenyl)ethanone (3.5 g) according to an analogous synthetic method to Example 30, the title compound (2.7 g) was obtained.

$^1$H-NMR (400 MHz, CDCl$_3$); δ (ppm): 2.81 (s, 4H), 3.76 (s, 3H), 3.79 (s, 3H), 4.69 (s, 1H), 6.35 (d, 1H), 6.43 (dd, 1H), 6.80-6.85 (m, 2H), 6.97 (d, 1H), 7.07-7.12 (m, 2H).

Preparation Example 194

4-{5-Methoxy-2-[2-(4-methoxyphenyl)ethyl]phenoxy}phenol

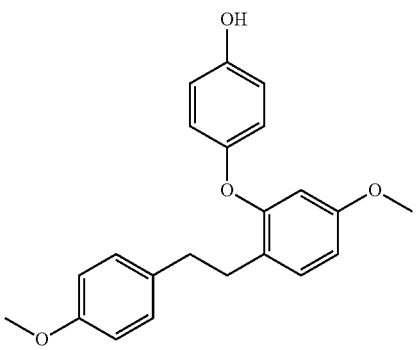

Synthesized from 5-methoxy-2-[2-(4-methoxyphenyl)ethyl]phenol and 4-fluorobenzaldehyde according to an analogous synthetic method to Preparation Example 189, 4-{5-methoxy-2-[2-(4-methoxyphenyl)ethyl]phenoxy}benzaldehyde (1.8 g) was used according to an analogous synthetic method to Preparation Example 190 to provide the title compound (603 mg).

$^1$H-NMR (400 MHz, CDCl$_3$); δ (ppm): 2.79-2.89 (m, 4H), 3.70 (s, 3H), 3.78 (s, 3H), 4.93 (s, 1H), 6.34 (d, 1H), 6.55 (dd, 1H), 6.76-6.86 (m, 6H), 7.03-7.08 (m, 3H).

Example 779

4-[2-(4-Hydroxyphenyl)ethyl]-3-[4-(2-piperidin-1-ylethoxy)phenoxy]phenol

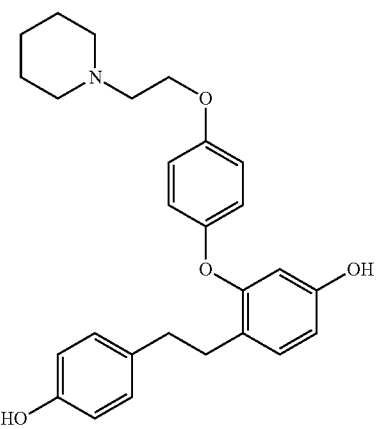 [SMILES: Oc1ccc(CCc2ccc(O)cc2Oc2ccc(OCCN3CCCCC3)cc2)cc1]

Synthesized from 4-{5-methoxy-2-[2-(4-methoxyphenyl)ethyl]phenoxy}phenol and 1-(2-chloroethyl)piperidine hydrochloride according to an analogous synthetic method to Preparation Example 40, to 1-{2-{4-{5-methoxy-2-[2-(4-methoxyphenyl)ethyl]phenoxy}phenoxy}ethyl}piperidine (344 mg) was added pyridine hydrochloride (1.2 g), and the solution was stirred for 3 hours and 10 minutes at 170° C. To the reaction solution were added tetrahydrofuran and an aqueous solution of 1N sodium hydroxide, the solution was extracted with ethyl acetate, then washed with brine, dried over anhydrous magnesium sulfate, and then the solvent was evaporated in vacuo. The residue was purified by NH silica gel column chromatography (ethyl acetate-methanol system) to provide the title compound (111 mg).

$^1$H-NMR (400 MHz, DMSO-d$_6$); δ (ppm): 1.32-1.39 (m, 2H), 1.43-1.52 (m, 4H), 2.37-2.43 (m, 4H), 2.61 (t, 2H), 2.66 (s, 4H), 4.00 (t, 2H), 6.12 (d, 1H), 6.49 (dd, 1H), 6.58-6.63 (m, 2H), 6.82-6.94 (m, 6H), 6.98 (d, 1H).

Preparation Example 195

5-Methoxy-2-(3-methoxybenzyl)phenyl trifluoromethanesulfonate

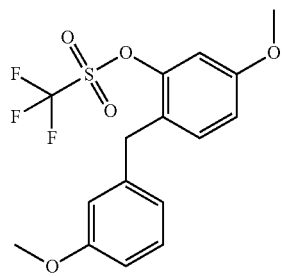

Synthesized from 5-methoxy-2-(3-methoxybenzyl)phenol (3.9 g) according to an analogous synthetic method to Preparation Example 80, the title compound (3.9 g) was obtained.

$^1$H-NMR (400 MHz, CDCl$_3$); δ (ppm): 3.77 (s, 3H), 3.80 (s, 3H), 3.97 (s, 2H), 6.69-6.72 (m, 1H), 6.74-6.79 (m, 2H), 6.81-6.85 (m, 2H), 7.09 (d, 1H), 7.21 (dd, 1H).

Preparation Example 196

4-Benzyloxyphenylboronic acid

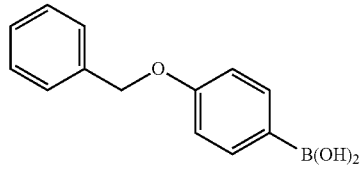 [SMILES: OB(O)c1ccc(OCc2ccccc2)cc1]

Synthesized from 4-bromophenol and benzyl chloride according to an analogous synthetic method to Example 383, 1-benzyloxy-4-bromobenzene (10.0 g) was used according to an analogous synthetic method to Preparation Example 78 to provide the title compound (5.7 g).

$^1$H-NMR (400 MHz, CDCl$_3$); δ (ppm): 5.15 (s, 2H), 7.07-7.12 (m, 2H), 7.30-7.48 (m, 5H), 8.15-8.21 (m, 2H).

Preparation Example 197

5'-Methoxy-2'-(3-methoxybenzyl)biphenyl-4-ol

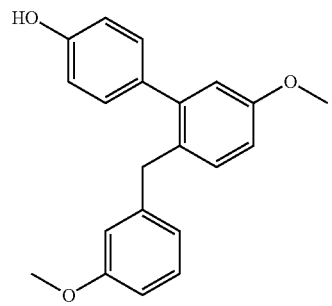

Synthesized from 5-methoxy-2-(3-methoxybenzyl)phenyl trifluoromethanesulfonate and 4-benzyloxyphenylboronic acid according to an analogous synthetic method to Example 24, 4'-benzyloxy-5-methoxy-2-(3-methoxybenzyl)biphenyl (332 mg) was used according to an analogous synthetic method to Example 22 to provide the title compound (167 mg).

$^1$H-NMR (400 MHz, CDCl$_3$); δ (ppm): 3.72 (s, 3H), 3.80 (s, 3H), 3.85 (s, 2H), 5.16 (s, 1H), 6.50-6.53 (m, 1H), 6.58 (d, 1H), 6.68 (dd, 1H), 6.77-6.85 (m, 4H), 7.09-7.15 (m, 4H).

Example 780

6-(3-Hydroxybenzyl)-4'-(2-piperidin-1-ylethoxy)biphenyl-3-ol

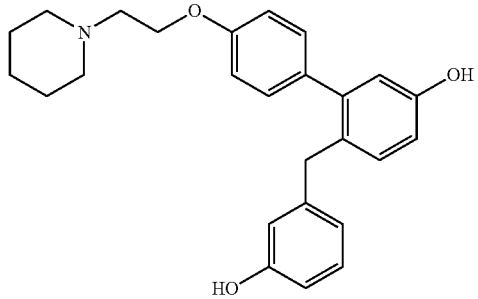 [SMILES: Oc1cccc(Cc2ccc(O)cc2-c2ccc(OCCN3CCCCC3)cc2)c1]

Synthesized from 5'-methoxy-2'-(3-methoxybenzyl)biphenyl-4-ol and 1-(2-chloroethyl)piperidine hydrochloride according to an analogous synthetic method to Preparation Example 40, 1-{2-[5'-methoxy-2'-(3-methoxybenzyl)biphenyl-4-yloxy]ethyl}piperidine (158 mg) was used according to an analogous synthetic method to Example 779 to provide the title compound (70 mg).

$^1$H-NMR (400 MHz, DMSO-d$_6$); δ (ppm): 1.34-1.41 (m, 2H), 1.46-1.53 (m, 4H), 2.38-2.47 (m, 4H), 2.65 (t, 2H), 3.70 (s, 2H), 4.07 (t, 2H), 6.32-6.38 (m, 2H), 6.50 (d, 1H), 6.58 (d, 1H), 6.68 (dd, 1H), 6.90-7.00 (m, 4H), 7.13 (d, 2H), 9.16 (brs, 1H), 9.31 (brs, 1H).

Preparation Example 198

5-Methoxy-2-[2-(4-methoxyphenyl)ethyl]phenyl trifluoromethanesulfonate

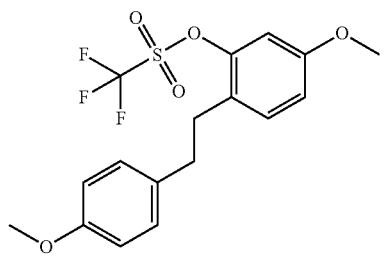

Synthesized from 5-methoxy-2-[2-(4-methoxyphenyl)ethyl]phenol (2.7 g) according to an analogous synthetic method to Preparation Example 80, the title compound (3.3 g) was obtained.

$^1$H-NMR (400 MHz, CDCl$_3$); δ (ppm): 2.79-2.85 (m, 2H), 2.87-2.92 (m, 2H), 3.79 (s, 3H), 3.80 (s, 3H), 6.78-6.85 (m, 4H), 7.06-7.15 (m, 3H).

Preparation Example 199

5'-Methoxy-2'-[2-(4-methoxyphenyl)ethyl]biphenyl-4-ol

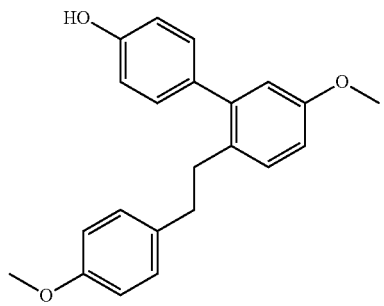

Synthesized from 5-methoxy-2-[2-(4-methoxyphenyl)ethyl]phenyl trifluoromethanesulfonate and 4-benzyloxyphenylboronic acid according to an analogous synthetic method to Example 24, 4'-benzyloxy-5-methoxy-2-[2-(4-methoxyphenyl)ethyl]biphenyl (600 mg) was used according to an analogous synthetic method to Example 22 to provide the title compound (417 mg).

$^1$H-NMR (400 MHz, CDCl$_3$); δ (ppm): 2.62 (dd, 2H), 2.77 (dd, 2H), 3.76 (s, 3H), 3.81 (s, 3H), 5.11 (s, 1H), 6.72-6.78 (m, 2H), 6.81-6.90 (m, 6H), 7.13-7.20 (m, 3H).

Example 781

6-[2-(4-Hydroxyphenyl)ethyl]-4'-(2-piperidin-1-ylethoxy)biphenyl-3-ol

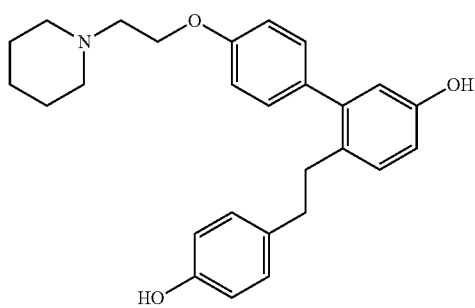 [SMILES: Oc1ccc(CCc2ccc(O)cc2-c2ccc(OCCN3CCCCC3)cc2)cc1]

Synthesized from 5'-methoxy-2'-[2-(4-methoxyphenyl)ethyl]biphenyl-4-ol and 1-(2-chloroethyl)piperidine hydrochloride according to an analogous synthetic method to Preparation Example 40, 1-{2-{5'-methoxy-2'-[2-(4-methoxyphenyl)ethyl]biphenyl-4-yloxy}ethyl}piperidine (250 mg) was used according to an analogous synthetic method to Example 779 to provide the title compound (98 mg).

$^1$H-NMR (400 MHz, CDCl$_3$); δ (ppm): 1.42-1.53 (m, 2H), 1.62-1.73 (m, 4H), 2.54-2.64 (m, 6H), 2.69-2.76 (m, 2H), 2.82 (t, 2H), 4.12 (t, 2H), 6.60-6.65 (m, 3H), 6.73-6.78 (m, 5H), 6.99-7.04 (m, 2H), 7.11 (d, 1H).

Preparation Example 200

3-Benzyloxyphenylboronic Acid

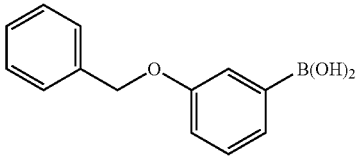 [SMILES: OB(O)c1cccc(OCc2ccccc2)c1]

Synthesized from 3-bromophenol and benzyl chloride according to an analogous synthetic method to Example 383, 1-benzyloxy-3-bromobenzene (15.0 g) was used according to an analogous synthetic method to Preparation Example 78 to provide the title compound (5.6 g).

$^1$H-NMR (400 MHz, DMSO-d$_6$); δ (ppm): 5.07 (s, 2H), 6.98-7.03 (m, 1H), 7.20-7.46 (m, 6H), 8.03-8.07 (m, 2H).

Preparation Example 201

5'-Methoxy-2'-[2-(4-methoxyphenyl)ethyl]biphenyl-3-ol

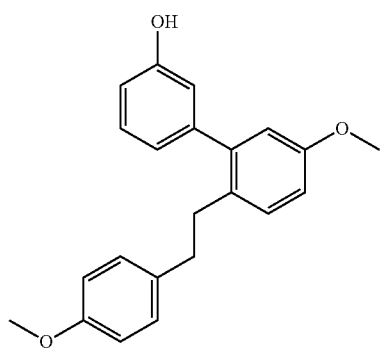

Synthesized from 5-methoxy-2-[2-(4-methoxyphenyl)ethyl]phenyl trifluoromethanesulfonate and 3-benzyloxyphenylboronic acid according to an analogous synthetic method to Example 24, 3'-benzyloxy-5-methoxy-2-[2-(4-methoxyphenyl)ethyl]biphenyl (527 mg) was used according to an analogous synthetic method to Example 22 to provide the title compound (184 mg).

$^1$H-NMR (400 MHz, CDCl$_3$); δ (ppm): 2.61-2.67 (m, 2H), 2.74-2.80 (m, 2H), 3.76 (s, 3H), 3.80 (s, 3H), 5.09 (s, 1H), 6.59-6.62 (m, 1H), 6.72-6.77 (m, 3H), 6.80-6.88 (m, 5H), 7.18 (d, 1H), 7.23-7.28 (m, 1H).

Example 782

6-[2-(4-Hydroxyphenyl)ethyl]-3'-(2-piperidin-1-ylethoxy)biphenyl-3-ol

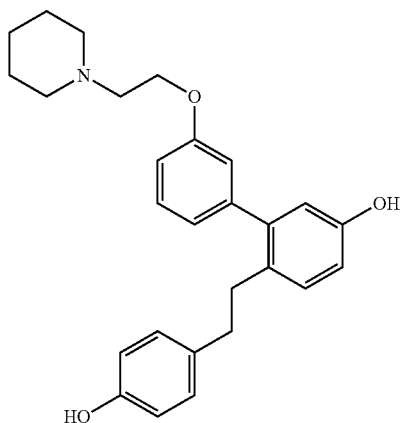 [SMILES: Oc1ccc(CCc2ccc(O)cc2-c2cccc(OCCN3CCCCC3)c2)cc1]

Synthesized from 5'-methoxy-2'-[2-(4-methoxyphenyl)ethyl]biphenyl-3-ol and 1-(2-chloroethyl)piperidine hydrochloride according to an analogous synthetic method to Preparation Example 40, 1-{2-{5'-methoxy-2'-[2-(4-methoxyphenyl)ethyl]biphenyl-3-yloxy}ethyl}piperidine (200 mg) was used according to an analogous synthetic method to Example 779 to provide the title compound (122 mg).

$^1$H-NMR (400 MHz, CDCl$_3$); δ (ppm): 1.42-1.52 (m, 2H), 1.68-1.77 (m, 4H), 2.42-2.57 (m, 6H), 2.58-2.70 (m, 4H), 3.52-3.59 (m, 2H), 2.74-2.82 (m, 4H), 6.28-6.34 (m, 3H), 6.38-6.43 (m, 2H), 6.51-6.55 (m, 1H), 6.73 (d, 1H), 6.87 (dd, 1H), 6.98 (dd, 1H), 7.21 (d, 1H).

Preparation Example 202

6-Methoxy-2-(4-methoxyphenyl)indan-4-yl trifluoromethanesulfonate

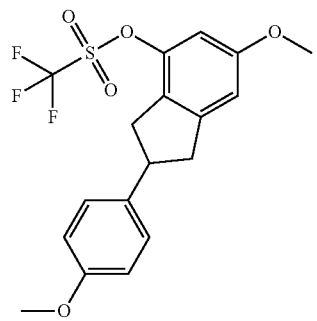 [SMILES: COc1ccc(C2Cc3cc(OC)cc(OS(=O)(=O)C(F)(F)F)c3C2)cc1]

Synthesized from 6-methoxy-2-(4-methoxyphenyl)indan-4-ol (3.5 g) according to an analogous synthetic method to Preparation Example 80, the title compound (5.0 g) was obtained.

$^1$H-NMR (400 MHz, CDCl$_3$); δ (ppm): 2.98-3.12 (m, 2H), 3.30-3.42 (m, 2H), 3.64-3.74 (m, 1H), 3.80 (s, 3H), 3.81 (s, 3H), 6.63 (d, 1H), 6.81-6.83 (m, 1H), 6.84-6.88 (m, 2H), 7.17-7.22 (m, 2H).

Preparation Example 203

4-Benzyloxybenzylamine

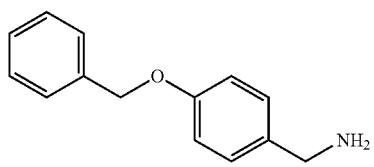 [SMILES: NCc1ccc(OCc2ccccc2)cc1]

To a solution of 4-benzyloxybenzyl alcohol (3.1 g) in toluene (40 ml) were sequentially added diphenylphosphoryl azide (4.8 g) and 1,8-diazabicyclo[5.4.0]undec-7-ene (2.6 g), and the solution was stirred for 25 hours at room temperature. The solution was extracted with ethyl acetate, then sequentially washed with water and brine, dried over anhydrous magnesium sulfate, and then the solvent was evaporated in vacuo. Obtained by purifying the residue by silica gel column chromatography (hexane-ethyl acetate system), to a solution of the resulting 1-azidomethyl-4-benzyloxybenzene (3.0 g) in tetrahydrofuran (40 ml) were sequentially added water (3 ml) and triethylphosphine (2.0 ml), and the solution was stirred for 1 hour and 10 minutes at room temperature. The reaction solution was concentrated in vacuo, extracted with ethyl acetate, then sequentially washed with water and brine, dried over anhydrous magnesium sulfate, and then the solvent was evaporated in vacuo. The residue was purified by NH silica gel column chromatography (hexane-ethyl acetate system) to provide the title compound (2.5 g).

$^1$H-NMR (400 MHz, CDCl$_3$); δ (ppm): 3.80 (S, 2H), 5.06 (s, 2H), 6.92-6.97 (m, 2H), 7.20-7.46 (m, 7H).

Example 783

(4-Benzyloxybenzyl)[6-methoxy-2-(4-methoxyphenyl)indan-4-yl]methylamine

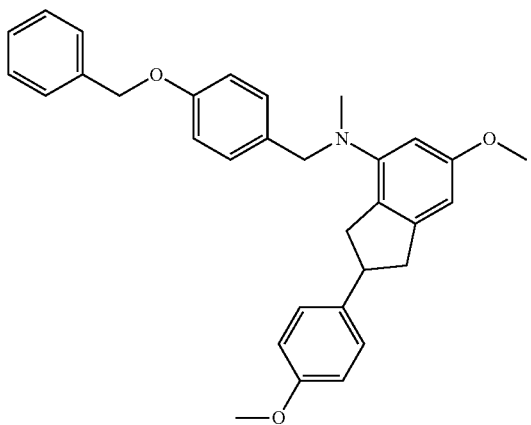 [SMILES: COc1ccc(C2Cc3cc(OC)cc(N(C)Cc4ccc(OCc5ccccc5)cc4)c3C2)cc1]

Synthesized from 6-methoxy-2-(4-methoxyphenyl)indan-4-yl trifluoromethanesulfonate and 4-benzyloxybenzylamine according to an analogous synthetic method to Example 116, (4-benzyloxybenzyl)[6-methoxy-2-(4-methoxyphenyl)indan-4-yl]amine (1.2 g) was used according to an analogous synthetic method to Preparation Example 18 to provide the title compound (1.0 g).

$^1$H-NMR (400 MHz, CDCl$_3$); δ (ppm): 2.65 (s, 3H), 2.96 (dd, 1H), 3.05 (dd, 1H), 3.24 (dd, 1H), 3.34 (dd, 1H), 3.58-3.68 (m, 1H), 3.79 (s, 6H), 4.07-4.20 (m, 2H), 5.05 (s, 2H), 6.35 (d, 1H), 6.46 (d, 1H), 6.83-6.87 (m, 2H), 6.89-6.94 (m, 2H), 7.20-7.26 (m, 4H), 7.30-7.45 (m, 5H).

Example 784

7-{[4-(2-Azepan-1-ylethoxy)benzyl]methylamino}-2-(4-hydroxyphenyl)indan-5-ol

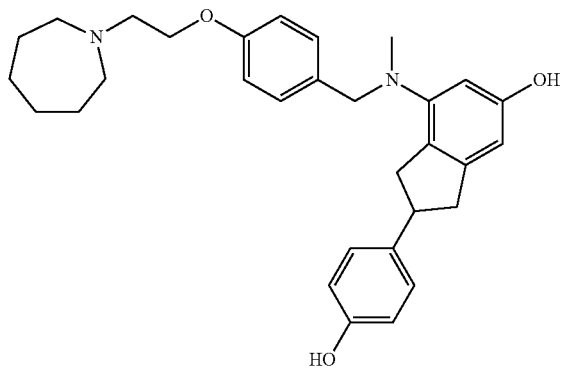 [SMILES: CN(Cc1ccc(OCCN2CCCCCC2)cc1)c1cc(O)cc2c1CC(c1ccc(O)cc1)C2]

Synthesized from (4-benzyloxybenzyl)[6-methoxy-2-(4-methoxyphenyl)indan-4-yl]methylamine according to an analogous synthetic method to Example 22, [6-methoxy-2-(4-methoxyphenyl)indan-4-yl]methylamine (553 mg) and 4-(2-azepan-1-ylethoxy)benzoic acid hydrochloride (795 mg) were used according to an analogous synthetic method to Example 152 to provide [4-(2-azepan-1-ylethoxy)benzyl][6-methoxy-2-(4-methoxyphenyl)indan-4-yl]methyl amine (172 mg). This compound was used according to an analogous synthetic method to Example 111 to provide the title compound (64 mg).

$^1$H-NMR (400 MHz, DMSO-d$_6$); δ (ppm): 1.47-1.58 (m, 8H), 2.51 (s, 3H), 2.60-2.67 (m, 4H), 2.72-2.84 (m, 2H), 2.79 (t, 2H), 3.03 (dd, 1H), 3.12 (dd, 1H), 3.41 (dd, 1H), 3.96 (t, 2H), 3.96-4.08 (m, 2H), 6.10 (s, 1H), 6.22 (s, 1H), 6.54 (d, 2H), 6.84 (d, 2H), 7.07 (d, 2H), 7.14 (d, 2H), 8.92 (s, 1H), 9.14 (s, 1H).

ESI-Mass; 487 [M$^+$+H]

Preparation Example 204

2-(6-Methoxy-1,2,3,4-tetrahydronaphthalen-2-ylmethyl)phenyl trifluoromethanesulfonate

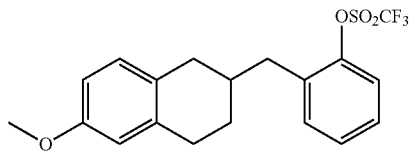

To a solution of 6-methoxy-1-tetralone (30 g) and 2-hydroxybenzaldehyde (25 g) in ethanol (200 ml) was added concentrated hydrochloric acid (10 ml), and the solution was refluxed for one day and one night. To the reaction solution was added brine, the solution was extracted with ethyl acetate, dried over anhydrous magnesium sulfate, and then the solvent was evaporated in vacuo. The residue was purified by silica gel column chromatography (hexane-ethyl acetate system) to provide 2-(2-hydroxybenzylidene)-6-methoxy-3,4-dihydro-2H-naphthalen-1-one (30 g). To a solution of a portion thereof (15 g) in ethanol (200 ml) was added platinum (IV) oxide (0.1 g), and the solution was stirred overnight under a hydrogen atmosphere at ambient pressure. The reaction solution was filtered, and the solvent was evaporated in vacuo. To a solution of a portion of the resulting 2-(2-hydroxybenzyl)-6-methoxy-3,4-dihydro-2H-naphthalen-1-one crude product (1.0 g) in ethylene glycol (15 ml) was added potassium hydroxide (1.2 g) and hydrazine hydrate (2 ml), and the solution was refluxed overnight. To the reaction solution was added 5N hydrochloric acid, the solution was extracted with ethyl acetate, then washed with brine, dried over anhydrous magnesium sulfate, and then the solvent was evaporated in vacuo. Obtained by purifying the residue by silica gel column chromatography (hexane-ethyl acetate system), 2-(6-methoxy-1,2,3,4-tetrahydronaphthalen-2-ylmethyl)phenol (810 mg) was used according to an analogous synthetic method to Preparation Example 80 to provide the title compound (1.1 g).

$^1$H-NMR (400 MHz, CDCl$_3$); δ (ppm): 1.40-1.54 (m, 1H), 1.85-1.95 (m, 1H), 2.05-2.10 (m, 1H), 2.38-2.46 (m, 1H), 2.70-2.82 (m, 5H), 3.76 (s, 3H), 6.62 (s, 1H), 6.64 (d, 1H), 6.86 (d, 1H), 7.28-7.36 (m, 4H).

Example 785

6-{2-[2-(4-Hydroxyphenyl)ethylamino]benzyl}-5,6,7,8-tetrahydronaphthalen-2-ol

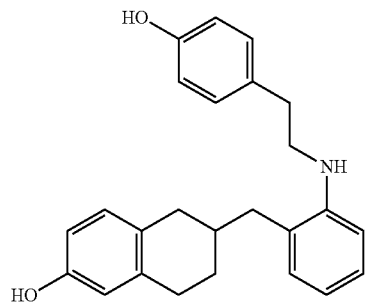 [SMILES: Oc1ccc(CCNc2ccccc2CC2CCc3cc(O)ccc3C2)cc1]

Synthesized from 2-(6-methoxy-1,2,3,4-tetrahydronaphthalen-2-ylmethyl)phenyl trifluoromethanesulfonate (1.6 g) and 2-(4-methoxyphenyl)ethylamine (0.9 g) according to an analogous synthetic method to Example 116, to the total amount of [2-(4-methoxyphenyl)ethyl][2-(6-methoxy-1,2,3,4-tetrahydronaphthalen-2-ylmethyl)phenyl]amine (crude product) was added 48% hydrobromic acid (30 ml), and the solution was refluxed overnight. To the reaction solution was added concentrated aqueous ammonia, the solution was extracted with ethyl acetate, then washed with brine, dried over anhydrous magnesium sulfate, and then the solvent was evaporated in vacuo. The residue was purified by silica gel column chromatography (hexane-ethyl acetate system) to provide the title compound (1.1 g).

$^1$H-NMR (400 MHz, DMSO-$d_6$); δ (ppm): 1.74-1.87 (m, 1H), 2.21-2.28 (m, 1H), 2.41-2.74 (m, 9H), 3.18-3.23 (m, 2H), 4.66 (t, 1H), 6.41-6.46 (m, 2H), 6.50 (t, 1H), 6.57 (d, 1H), 6.63 (d, 2H), 6.74 (d, 1H), 6.90 (d, 1H), 6.99-7.02 (m, 3H), 8.93 (s, 1H), 9.14 (s, 1H).

Example 786

6-{2-{Ethyl[2-(4-hydroxyphenyl)ethyl]amino}benzyl}-5,6,7,8-tetrahydronaphthalen-2-ol

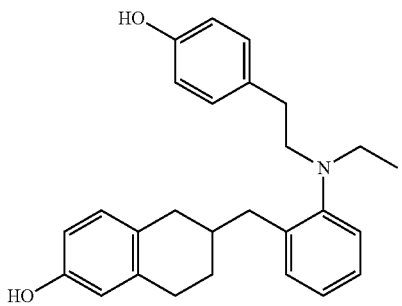 [SMILES: CCN(CCc1ccc(O)cc1)c1ccccc1CC1CCc2cc(O)ccc2C1]

To a solution of 6-{2-[2-(4-hydroxyphenyl)ethylamino]benzyl}-5,6,7,8-tetrahydronaphthalen-2-ol (1.0 g) in tetrahydrofuran (15 ml) were sequentially added acetic acid (in catalytic amounts), sodium triacetoxyborohydride (2.8 g) and acetaldehyde (572 mg), and the solution was stirred overnight at room temperature. To the reaction solution was added a saturated aqueous solution of sodium bicarbonate, the solution was extracted with ethyl acetate, then washed with brine, dried over anhydrous magnesium sulfate, and then the solvent was evaporated in vacuo. The residue was purified by silica gel column chromatography (hexane-ethyl acetate system) to provide the title compound (730 mg).

$^1$H-NMR (400 MHz, CDCl$_3$); δ (ppm): 0.98 (t, 3H), 1.34-1.82 (m, 1H), 2.08-2.13 (m, 1H), 2.24-2.31 (m, 1H), 2.55-2.75 (m, 7H), 2.99-3.06 (m, 4H), 3.31 (brs, 1H), 6.45-6.50 (m, 2H), 6.25 (d, 2H), 6.76 (d, 1H), 6.90 (d, 2H), 7.02 (dt, 1H), 7.14-7.22 (m, 3H).

Example 787

6-{2-[4-(2-Piperidin-1-ylethoxy)benzylamino]benzyl}-5,6,7,8-tetrahydronaphthalen-2-ol

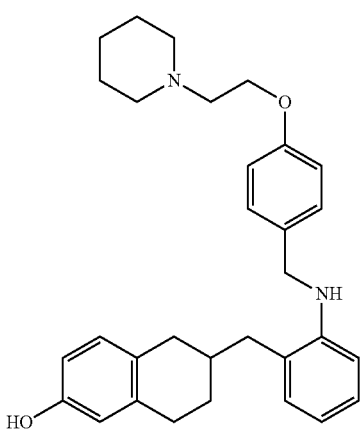 [SMILES: Oc1ccc2c(c1)CCC(Cc1ccccc1NCc1ccc(OCCN3CCCCC3)cc1)C2]

Obtained by reducing 4-(2-piperidin-1-ylethoxy)benzonitrile with lithium aluminum hydride, 4-(2-piperidin-1-ylethoxy)benzylamine (1.3 g) and 2-(6-methoxy-1,2,3,4-tetrahydronaphthalen-2-ylmethyl)phenyl trifluoromethanesulfonate (1.4 g) were used according to an analogous synthetic method to Example 116 to provide [2-(6-methoxy-1,2,3,4-tetrahydronaphthalen-2-ylmethyl)phenyl][4-(2-piperidin-1-ylethoxy)benzyl]amine (1.2 g). A portion thereof (200 mg) was used according to an analogous synthetic method to Example 364 to provide the title compound (100 mg).

$^1$H-NMR (400 MHz, DMSO-$d_6$); δ (ppm): 1.31-1.38 (m, 6H), 1.65-1.76 (m, 2H), 2.32 (t, 2H), 2.52-2.70 (m, 4H), 2.91-2.98 (m, 2H), 3.42-3.54 (m, 6H), 4.28-4.51 (m, 4H), 6.43-6.55 (m, 4H), 6.76 (d, 1H), 6.88-6.94 (m, 4H), 7.25 (d, 2H), 10.09 (s, 1H).

Example 788

6-{2-{Ethyl[4-(2-piperidin-1-ylethoxy)benzyl]amino}benzyl}-5,6,7,8-tetrahydronaphthalen-2-ol

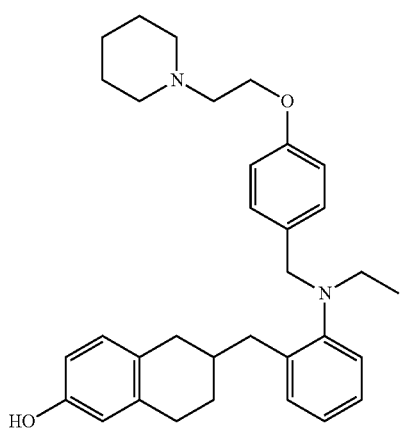 [SMILES: CCN(Cc1ccc(OCCN2CCCCC2)cc1)c1ccccc1CC1CCc2cc(O)ccc2C1]

Synthesized from [2-(6-methoxy-1,2,3,4-tetrahydronaphthalen-2-ylmethyl)phenyl][4-(2-piperidin-1-ylethoxy)benzyl]amine (600 mg) according to an analogous synthetic method to Example 786, ethyl[2-(6-methoxy-1,2,3,4-tetrahydronaphthalen-2-ylmethyl)phenyl][4-(2-piperidin-1-ylethoxy)benzyl]amine (370 mg) was used according to an analogous synthetic method to Example 364 to provide the title compound (170 mg).

$^1$H-NMR (400 MHz CDCl$_3$); δ (ppm): 0.97 (t, 3H), 1.38-1.50 (m, 4H), 1.64-1.70 (m, 4H), 2.34-2.94 (m, 15H), 3.92 (s, 2H), 4.03 (t, 2H), 6.74 (s, 1H), 6.77-6.79 (m, 1H), 6.81 (d, 2H), 6.90 (d, 1H), 7.01-7.04 (m, 3H), 7.09-7.11 (m, 3H).

Example 789

6-(2-Benzylaminobenzyl)-5,6,7,8-tetrahydronaphthalen-2-ol

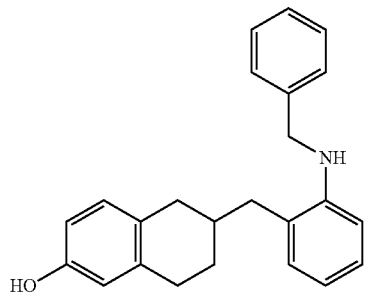 [SMILES: Oc1ccc2c(c1)CCC(Cc1ccccc1NCc1ccccc1)C2]

Synthesized from 2-(6-methoxy-1,2,3,4-tetrahydronaphthalen-2-ylmethyl)phenyl trifluoromethanesulfonate (1.4 g) and benzylamine (650 mg) according to an analogous synthetic method to Example 116, benzyl[2-(6-methoxy-1,2,3,4-tetrahydronaphthalen-2-ylmethyl)phenyl]amine was used according to an analogous synthetic method to Example 785 to provide the title compound (440 mg).

$^1$H-NMR (400 MHz, CD$_3$OD); δ (ppm): 1.30-1.36 (m, 2H), 1.75-1.85 (m, 2H), 1.95-2.05 (m, 2H), 2.29-2.35 (m, 2H), 2.53-2.66 (m, 4H), 6.43-6.47 (m, 3H), 6.56-6.62 (m, 1H), 6.76 (d, 1H), 6.92 (t, 1H), 6.96 (d, 1H), 7.17 (t, 1H), 7.24-7.31 (m, 4H).

Preparation Example 205

5-Methoxy-2-(6-methoxy-1,2,3,4-tetrahydronaphthalen-2-ylmethyl)phenyl trifluoromethanesulfonate

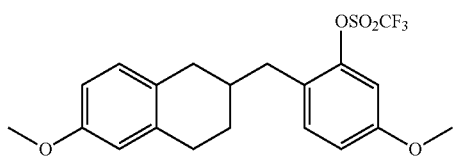

Synthesized from 6-methoxy-1-tetralone (15 g) and 2-hydroxy-4-methoxybenzaldehyde (15 g) according to an analogous synthetic method to Preparation Example 204, the title compound (3.5 g) was obtained.

$^1$H-NMR (400 MHz, CD$_3$OD); δ (ppm): 1.38-1.48 (m, 1H), 1.86-1.91 (m, 1H), 1.91-2.10 (m, 1H), 2.37-2.44 (m, 1H), 2.64-2.83 (m, 5H), 3.76 (s, 3H), 3.82 (s, 3H), 6.61 (d, 1H), 6.66 (d, 1H), 6.82 (d, 1H), 6.88 (d, 1H), 6.93 (d, 1H), 7.21 (d, 1H).

Example 790

6-{4-Hydroxy-2-[4-(2-piperidin-1-ylethoxy)benzylamino]benzyl}-5,6,7,8-tetrahydronaphthalen-2-ol

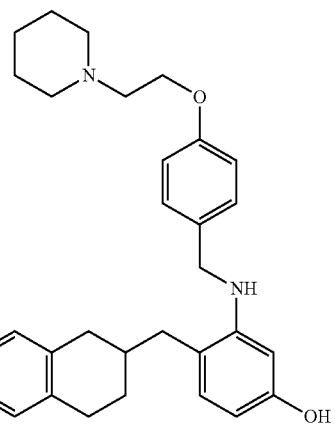

Obtained by reducing 4-(2-piperidin-1-ylethoxy)benzonitrile with lithium aluminum hydride, 4-(2-piperidin-1-ylethoxy)benzylamine (350 mg) and 5-methoxy-2-(6-methoxy-1,2,3,4-tetrahydronaphthalen-2-ylmethyl)phenyl trifluoromethanesulfonate (1.0 g) were used according to an analogous synthetic method to Example 116 to synthesize [5-methoxy-2-(6-methoxy-1,2,3,4-tetrahydronaphthalen-2-ylmethyl)phenyl][4-(2-piperidin-1-ylethoxy)benzyl]amine (400 mg), which was used according to an analogous synthetic method to Example 111 to provide the title compound (260 mg).

$^1$H-NMR (400 MHz, CD$_3$OD); δ (ppm): 1.27-1.48 (m, 8H), 1.82-2.05 (m, 2H), 2.24-2.65 (m, 7H), 3.35-3.39 (m, 4H), 3.97-3.99 (m, 2H), 4.17-4.18 (m, 2H), 5.52 (brs, 1H), 5.79-6.00 (m, 2H), 6.42-6.46 (m, 1H), 6.65 (d, 1H), 6.80 (d, 2H), 7.17 (d, 1H), 8.65 (s, 1H), 8.93 (s, 1H).

Example 791

6-{2-{Ethyl[4-(2-piperidin-1-ylethoxy)benzyl]amino}-4-hydroxybenzyl}-5,6,7,8-tetrahydronaphthalen-2-ol

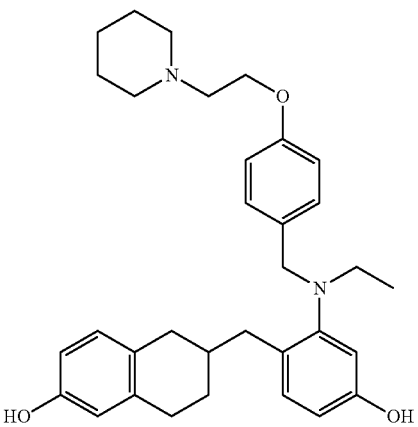 [SMILES: CCN(Cc1ccc(OCCN2CCCCC2)cc1)c1cc(O)ccc1CC1CCc2cc(O)ccc2C1]

Synthesized from 6-{4-hydroxy-2-[4-(2-piperidin-1-ylethoxy)benzylamino]benzyl}-5,6,7,8-tetrahydronaphthalen-2-ol (250 mg) according to an analogous synthetic method to Example 786, the title compound (174 mg) was obtained.

$^1$H-NMR (400 MHz CDCl$_3$); δ (ppm): 0.94 (t, 3H), 1.36-1.52 (m, 4H), 1.66-1.75 (m, 4H), 2.31-2.35 (m, 2H), 2.45-2.56 (m, 13H), 3.85 (s, 2H), 4.03 (t, 2H), 6.49 (s, 1H), 6.52-6.58 (m, 2H), 6.59 (d, 2H), 6.70 (d, 1H), 6.83 (d, 1H), 6.99 (d, 2H), 7.06 (d, 1H).

Example 792

(R)-6-{2-[(4-Azepan-1-ylmethylbenzyl)ethylamino]-4,5-dimethoxyphenyl}-5,6,7,8-tetrahydronaphthalen-2-ol

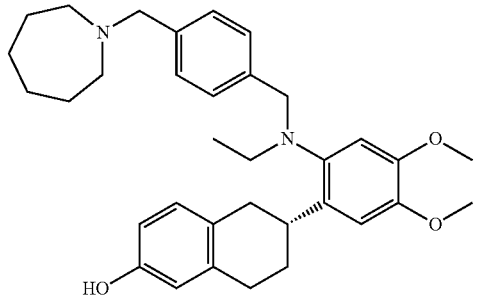 [SMILES: CCN(Cc1ccc(CN2CCCCCC2)cc1)c1cc(OC)c(OC)cc1[C@@H]1CCc2cc(O)ccc2C1]

Synthesized from pivalic acid (R)-6-(2-ethylamino-4,5-dimethoxyphenyl)-5,6,7,8-tetrahydronaphthalen-2-yl ester (416 mg) and 4-azepan-1-ylmethylbenzoic acid hydrochloride (328 mg) according to an analogous synthetic method to the above-mentioned Preparation Example 86 and Example 337, the title compound (386 mg) was obtained.

$^1$H-NMR (400 MHz, DMSO-d$_6$); δ (ppm): 0.85 (t, 3H), 1.33-1.41 (m, 1H), 1.50-1.56 (m, 8H), 1.60-1.72 (m, 1H), 2.40-2.72 (m, 8H), 2.86 (q, 2H), 3.50 (s, 2H), 3.55-3.65 (m, 1H), 3.67 (s, 3H), 3.71 (s, 3H), 3.92 (dd, 2H), 6.46-6.50 (m, 2H), 6.71 (s, 1H), 6.77 (d, 1H), 6.86 (s, 1H), 7.08 (d, 2H), 7.13 (d, 2H), 8.97 (s, 1H).

ESI-Mass; 529 [M$^+$+H]

Example 793

6-[2-(2-Hydroxyethylamino)-4-methoxyphenyl]-5,6,7,8-tetrahydronaphthalen-2-ol

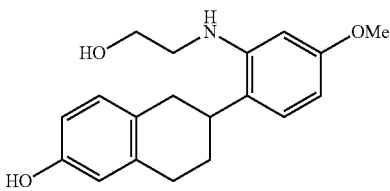 [SMILES: COc1ccc(C2CCc3cc(O)ccc3C2)c(NCCO)c1]

To a solution of 6-(2-amino-4-methoxyphenyl)-5,6,7,8-tetrahydronaphthalen-2-ol (1.6 g) in pyridine (6 ml) was added dropwise 2-chloroethyl chloroformate (1.4 ml) on an ice bath, and the solution was stirred for 6.5 hours. The solution was diluted with ice water, and then extracted with ethyl acetate. The solution was washed with brine, dried over anhydrous magnesium sulfate, and then the solvent was evaporated in vacuo. To the residue were added potassium hydroxide (3.0 g) and ethylene glycol (15 ml), and the solution was heated for 3 hours at 180° C. The solution was diluted with ice water, and then extracted with ethyl acetate. The solution was washed with brine, dried over anhydrous magnesium sulfate, and then the solvent was evaporated in vacuo. The residue was purified by silica gel column chromatography (hexane-ethyl acetate system) to provide the title compound (800 mg).

$^1$H-NMR (400 MHz, CDCl$_3$); δ (ppm): 1.82-2.00 (m, 1H), 2.01-2.18 (m, 1H), 2.69-3.02 (m, 5H), 3.30-3.37 (m, 2H), 3.80 (s, 3H), 3.82-3.89 (m, 2H), 6.28-6.34 (m, 2H), 6.59-6.63 (m, 2H), 6.93 (d, 1H), 7.02 (d, 1H).

ESI-Mass; 314 [M$^+$+H]

Example 794

[2-(tert-Butyldimethylsilyloxy)ethyl]{2-[6-(tert-butyldimethylsilyloxy)-1,2,3,4-tetrahydronaphthalen-2-yl]-5-methoxyphenyl}amine

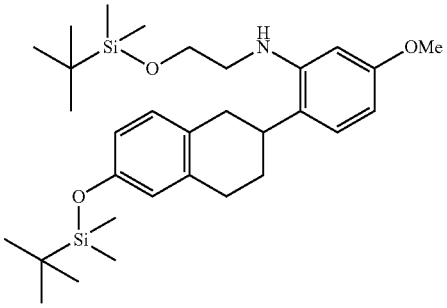 [SMILES: COc1ccc(C2CCc3cc(O[Si](C)(C)C(C)(C)C)ccc3C2)c(NCCO[Si](C)(C)C(C)(C)C)c1]

Synthesized from 6-[2-(2-hydroxyethylamino)-4-methoxyphenyl]-5,6,7,8-tetrahydronaphthalen-2-ol (800 mg) according to an analogous synthetic method to Example 201, the title compound (870 mg) was obtained.

$^1$H-NMR (400 MHz, CDCl$_3$); δ (ppm): 0.01 (s, 6H), 0.18 (s, 6H), 0.81 (s, 9H), 0.98 (s, 9H), 1.90-1.98 (m, 1H), 2.01-2.18 (m, 1H), 2.68-3.00 (m, 5H), 3.19-3.22 (m, 2H), 3.78 (s, 3H), 3.83-3.86 (m, 3H), 6.24 (d, 1H), 6.27-6.30 (m, 1H), 6.57-6.61 (m, 2H), 6.87-6.91 (m, 1H), 7.02 (d, 1H).

Preparation Example 206

N-[2-(tert-Butyldimethylsilyloxy)ethyl]-N-{2-[6-(tert-butyldimethylsilyloxy)-1,2,3,4-tetrahydronaphthalen-2-yl]-5-methoxyphenyl}-4-hydroxybenzamide

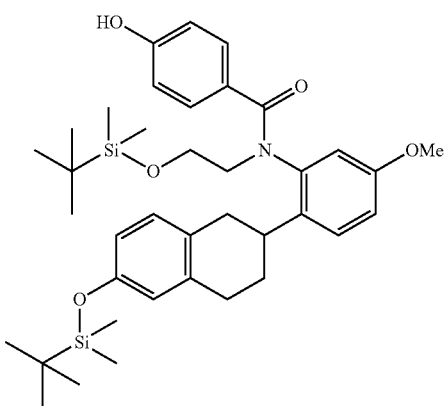 [SMILES: COc1ccc(C2CCc3cc(O[Si](C)(C)C(C)(C)C)ccc3C2)c(N(CCO[Si](C)(C)C(C)(C)C)C(=O)c2ccc(O)cc2)c1]

Synthesized from [2-(tert-butyldimethylsilyloxy)ethyl]{2-[6-(tert-butyldimethylsilyloxy)-1,2,3,4-tetrahydronaphthalen-2-yl]-5-methoxyphenyl}amine (870 mg) according to an analogous synthetic method to the above-mentioned Preparation Example 154 and Preparation Example 155, the title compound (120 mg) was obtained.

¹H-NMR (400 MHz, CDCl₃); δ (ppm): 0.07 (s, 6H), 0.20 (s, 6H), 0.88 (s, 9H), 0.99 (s, 9H), 1.52-1.80 (m, 12H), 2.60-2.81 (m, 4H), 3.45-3.70 (m, 5H), 3.78 (s, 3H), 4.01-4.18 (m, 2H), 4.63 (s, 2H), 6.54-6.59 (m, 2H), 6.65-6.76 (m, 2H), 6.78-6.91 (m, 2H), 6.98-7.06 (m, 2H), 7.22-7.32 (m, 2H).

Example 795

[4-(2-Azepan-1-ylethoxy)benzyl][2-(tert-butyldimethylsilyloxy)ethyl]{2-[6-(tert-butyldimethylsilyloxy)-1,2,3,4-tetrahydronaphthalen-2-yl]-5-methoxyphenyl}amine

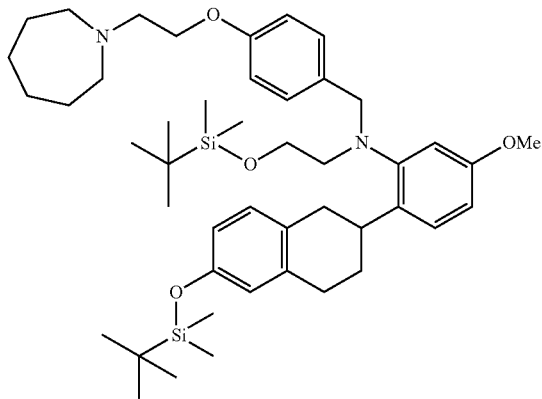 [SMILES: COc1ccc(C2CCc3cc(O[Si](C)(C)C(C)(C)C)ccc3C2)c(N(CCO[Si](C)(C)C(C)(C)C)Cc2ccc(OCCN3CCCCCC3)cc2)c1]

Synthesized from N-[2-(tert-butyldimethylsilyloxy)ethyl]-N-{2-[6-(tert-butyldimethylsilyloxy)-1,2,3,4-tetrahydronaphthalen-2-yl]-5-methoxyphenyl}-4-hydroxybenzamide (120 mg) according to an analogous synthetic method to Preparation Example 404, the title compound (85 mg) was obtained.

¹H-NMR (400 MHz, CDCl₃); δ (ppm): −0.06 (s, 6H), 0.21 (s, 6H), 0.82 (s, 9H), 1.00 (s, 9H), 1.60-1.85 (m, 10H), 2.71-3.19 (m, 12H), 3.61-3.74 (m, 3H), 3.78 (s, 3H), 4.04 (s, 2H), 4.10-4.21 (m, 2H), 6.65-6.68 (m, 2H), 6.74 (dd, 1H), 6.80-6.83 (m, 2H), 6.86 (d, 1H), 6.91-6.96 (m, 1H), 7.16-7.22 (m, 3H).

ESI-Mass; 773 [M⁺+H]

Example 796

6-{2-{[4-(2-Azepan-1-ylethoxy)benzyl](2-hydroxyethyl)amino}-4-methoxyphenyl}-5,6,7,8-tetrahydronaphthalen-2-ol

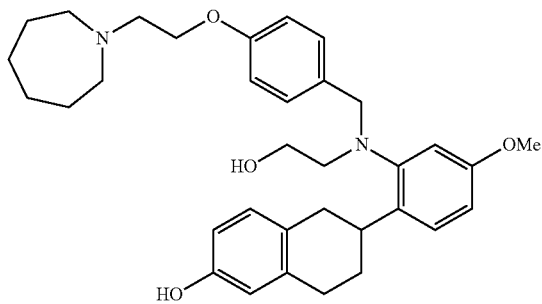 [SMILES: COc1ccc(C2CCc3cc(O)ccc3C2)c(N(CCO)Cc2ccc(OCCN3CCCCCC3)cc2)c1]

Synthesized from [4-(2-azepan-1-ylethoxy)benzyl][2-(tert-butyldimethylsilyloxy)ethyl]{2-[6-(tert-butyldimethylsilyloxy)-1,2,3,4-tetrahydronaphthalen-2-yl]-5-methoxyphenyl}amine (85 mg) according to an analogous synthetic method to Example 325, the title compound (60 mg) was obtained.

¹H-NMR (400 MHz, CDCl₃); δ (ppm): 1.60-1.82 (m, 10H), 2.58-2.70 (m, 2H), 2.79-2.82 (m, 2H), 2.90-3.06 (m, 4H), 3.13-3.16 (m, 4H), 3.47-3.57 (m, 3H), 3.79 (s, 3H), 3.97 (s, 2H), 4.09-4.13 (m, 2H), 6.59-6.62 (m, 2H), 6.71-6.75 (m, 4H), 6.85 (d, 1H), 7.02-7.05 (m, 2H), 7.13-7.16 (m, 1H).

ESI-Mass; 545 [M⁺+H]

Example 797

Pivalic acid 6-[2-(ethoxycarbonylmethylamino)-4-methoxyphenyl]-5,6,7,8-tetrahydronaphthalen-2-yl ester

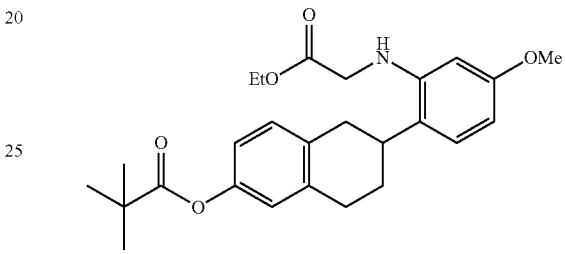

A mixture of pivalic acid 6-(2-amino-4-methoxyphenyl)-5,6,7,8-tetrahydronaphthalen-2-yl ester (110 mg), bromoethyl acetate (400 mg), sodium acetate (200 mg) and ethanol (2 ml) was refluxed overnight. A saturated aqueous solution of sodium bicarbonate was added, and the solution was extracted with ethyl acetate. The solution was washed with brine, dried over magnesium sulfate, and then the solvent was evaporated in vacuo. The residue was purified by silica gel column chromatography (hexane-ethyl acetate system) to provide the title compound (83 mg).

¹H-NMR (400 MHz, CDCl₃); δ (ppm): 1.30 (t, 3H), 1.36 (s, 9H), 1.89-1.99 (m, 1H), 2.09-2.15 (m, 1H), 2.79-3.10 (m, 5H), 3.78 (s, 3H), 3.89-3.93 (m, 2H), 4.24 (q, 2H), 4.42-4.46 (m, 1H), 6.11 (s, 1H), 6.29-6.34 (m, 1H), 6.78-6.83 (m, 2H), 7.01-7.11 (m, 2H).

Example 798

Pivalic Acid (S)-6-[2-(ethoxycarbonylmethylamino)-4-methoxyphenyl]-5,6,7,8-tetrahydronaphthalen-2-yl Ester and Pivalic Acid (R)-6-[2-(ethoxycarbonylmethylamino)-4-methoxyphenyl]-5,6,7,8-tetrahydronaphthalen-2-yl Ester

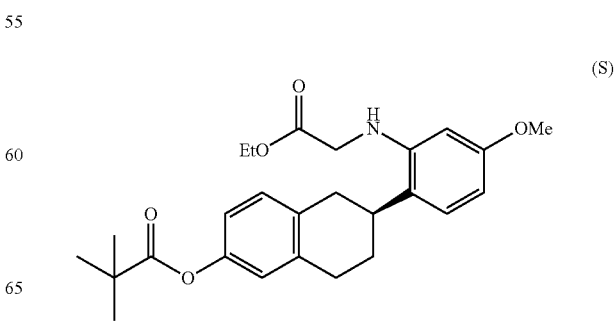

-continued

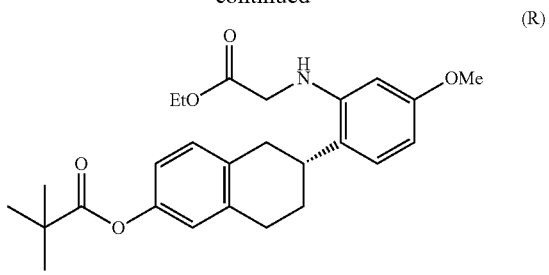

Optical resolution was carried out according to Example 188 described above to provide pivalic acid (S)-6-[2-(ethoxycarbonylmethylamino)-4-methoxyphenyl]-5,6,7,8-tetrahydronaphthalen-2-yl ester exhibiting a retention time of 13.3 minutes and pivalic acid (R)-6-[2-(ethoxycarbonylmethylamino)-4-methoxyphenyl]-5,6,7,8-tetrahydronaphthalen-2-yl ester exhibiting a retention time of 20.2 minutes.

Preparation Example 206

Pivalic Acid 6-{2-[ethoxycarbonylmethyl(4-hydroxybenzoyl)amino]-4-methoxyphenyl}-5,6,7,8-tetrahydronaphthalen-2-yl Ester

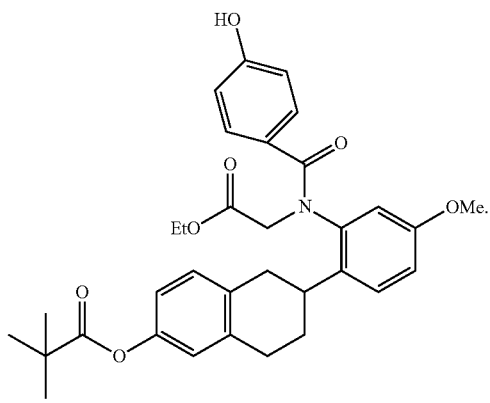 [SMILES: CCOC(=O)CN(C(=O)c1ccc(O)cc1)c1cc(OC)ccc1C1CCc2cc(OC(=O)C(C)(C)C)ccc2C1]

Synthesized from pivalic acid 6-[2-(ethoxycarbonylmethylamino)-4-methoxyphenyl]-5,6,7,8-tetrahydronaphthalen-2-yl ester (38 mg) according to an analogous synthetic method to the above-mentioned Preparation Example 154 and Preparation Example 155, the title compound (28 mg) was obtained.

$^1$H-NMR (400 MHz, CDCl$_3$); δ (ppm): 1.26 (t, 1.5H), 1.27 (t, 1.5H), 1.35 (s, 9H), 1.60-1.99 (m, 2H), 2.50-3.20 (m, 4H), 3.76 (s, 1.5H), 3.78 (s, 1.5H), 3.99-4.26 (m, 3H), 4.76 (d, 1H), 4.83 (d, 1H), 5.93 (brs, 1H), 6.55-6.57 (m, 2H), 6.72-6.87 (m, 3H), 6.96-7.10 (m, 3H), 7.16-7.28 (m, 2H).

Preparation Example 207

Pivalic Acid (R)-6-{2-[ethoxycarbonylmethyl(4-hydroxybenzoyl)amino]-4-methoxyphenyl}-5,6,7,8-tetrahydronaphthalen-2-yl Ester

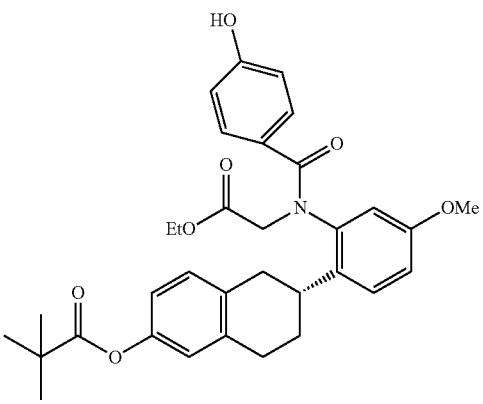 [SMILES: CCOC(=O)CN(C(=O)c1ccc(O)cc1)c1cc(OC)ccc1[C@@H]1CCc2cc(OC(=O)C(C)(C)C)ccc2C1]

Synthesized from pivalic acid (R)-6-[2-(ethoxycarbonylmethylamino)-4-methoxyphenyl]-5,6,7,8-tetrahydronaphthalen-2-yl ester (137 mg) according to an analogous synthetic method to the above-mentioned Preparation Example 154 and Preparation Example 155, the title compound (162 mg) was obtained.

Preparation Example 208

Pivalic Acid (R)-6-{2-[ethoxycarbonylmethyl(3-fluoro-4-hydroxybenzoyl)amino]-4-methoxyphenyl}-5,6,7,8-tetrahydronaphthalen-2-yl Ester

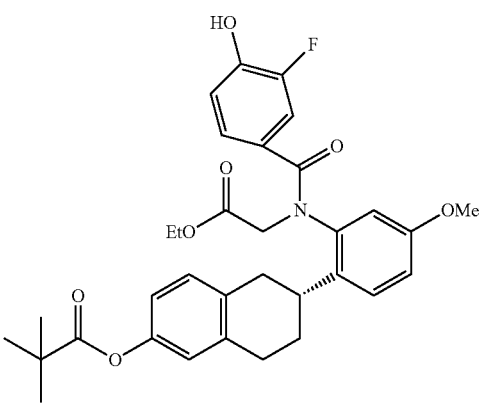 [SMILES: CCOC(=O)CN(C(=O)c1ccc(O)c(F)c1)c1cc(OC)ccc1[C@@H]1CCc2cc(OC(=O)C(C)(C)C)ccc2C1]

Synthesized from pivalic acid (R)-6-[2-(ethoxycarbonylmethylamino)-4-methoxyphenyl]-5,6,7,8-tetrahydronaphthalen-2-yl ester (150 mg) according to an analogous synthetic method to the above-mentioned Preparation Example 154 and Preparation Example 155, the title compound (173 mg) was obtained.

$^1$H-NMR (400 MHz, CDCl$_3$); δ (ppm): 1.24 (t, 1.5H), 1.26 (t, 1.5H), 1.35 (s, 9H), 1.50-2.01 (m, 2H), 2.64-3.01 (m, 4H), 3.76 (s, 1.5H), 3.78 (s, 1.5H), 3.97-4.24 (m, 3H), 4.73-4.85 (m, 2H), 5.86 (brs, 1H), 6.70-6.78 (m, 2H), 6.81-6.90 (m, 1H), 6.94-7.04 (m, 2H), 7.06-7.15 (m, 2H).

Example 799

Pivalic Acid (R)-6-[2-(ethoxycarbonylmethylamino)-4,5-dimethoxyphenyl]-5,6,7,8-tetrahydronaphthalen-2-yl Ester and Pivalic Acid (S)-6-[2-(ethoxycarbonylmethylamino)-4,5-dimethoxyphenyl]-5,6,7,8-tetrahydronaphthalen-2-yl Ester

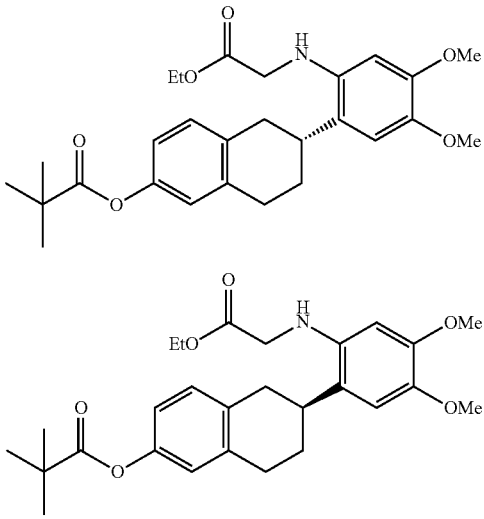

A mixture of pivalic acid 6-(2-amino-4,5-dimethoxyphenyl)-5,6,7,8-tetrahydronaphthalen-2-yl ester (200 mg), bromoethyl acetate (131 mg), sodium acetate (64 mg) and ethanol (2 ml) was refluxed for 2 hours. A saturated aqueous solution of sodium bicarbonate was added, and the solution was extracted with ethyl acetate. The solution was washed with brine, dried over anhydrous magnesium sulfate, and then the solvent was evaporated in vacuo. The residue was purified by silica gel column chromatography (hexane-ethyl acetate system) to provide a racemic mixture of the title compound (170 mg). Optical resolution was carried out according to Example 188 described above to provide pivalic acid (S)-6-[2-(ethoxycarbonylmethylamino)-4,5-methoxyphenyl]-5,6,7,8-tetrahydronaphthalen-2-yl ester exhibiting a retention time of 5.5 minutes and pivalic acid (R)-6-[2-(ethoxycarbonylmethylamino)-4,5-methoxyphenyl]-5,6,7,8-tetrahydronaphthalen-2-yl ester exhibiting a retention time of 10.5 minutes.

$^1$H-NMR (400 MHz, CDCl$_3$); δ (ppm): 1.29 (t, 3H), 1.35 (s, 9H), 1.85-2.00 (m, 1H), 2.05-2.15 (m, 1H), 2.75-3.10 (m, 5H), 3.78 (s, 3H), 3.86 (s, 3H), 3.93 (s, 2H), 4.23 (q, 2H), 6.23 (s, 1H), 6.75 (s, 1H), 6.77-6.81 (m, 2H), 7.07 (d, 1H).

Example 800

6-{2-{[4-(2-Dimethylaminoethoxy)benzyl](2-hydroxyethyl)amino}-4-methoxyphenyl}-5,6,7,8-tetrahydronaphthalen-2-ol

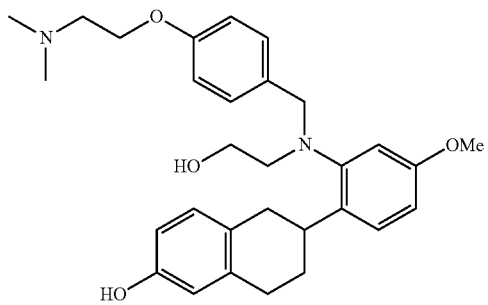 [SMILES: COc1ccc(C2CCc3cc(O)ccc3C2)c(N(CCO)Cc2ccc(OCCN(C)C)cc2)c1]

Synthesized from pivalic acid 6-{2-[ethoxycarbonylmethyl(4-hydroxybenzoyl)amino]-4-methoxyphenyl}-5,6,7,8-tetrahydronaphthalen-2-yl ester (28 mg) according to an analogous synthetic method to Preparation Example 404, the title compound (19 mg) was obtained.

$^1$H-NMR (400 MHz, CDCl$_3$); δ (ppm): 1.62-1.81 (m, 2H), 2.50 (s, 6H), 2.53-2.73 (m, 2H), 2.75-2.84 (m, 2H), 2.89-2.96 (m, 2H), 3.11-3.20 (m, 2H), 3.42-3.69 (m, 3H), 3.78 (s, 3H), 3.96 (s, 2H), 4.05-4.10 (m, 2H), 6.56-6.60 (m, 2H), 6.70-6.74 (m, 4H), 6.83 (d, 1H), 7.02-7.05 (m, 2H), 7.12-7.15 (m, 1H).

ESI-Mass; 491 [M$^+$+H]

Example 801

(S)-6-{2-{{3-Fluoro-4-{2-[(2-methoxyethyl)methylamino]ethoxy}benzyl}isopropylamino}-4-methoxyphenyl}-5,6,7,8-tetrahydronaphthalen-2-ol

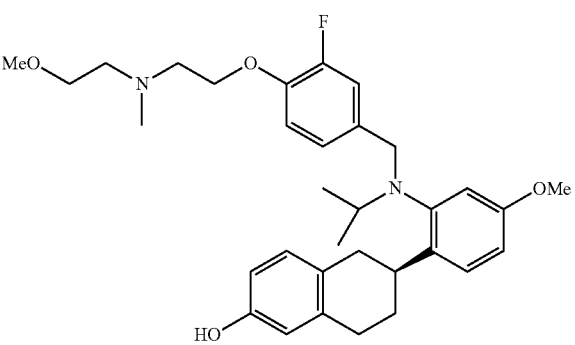 [SMILES: COCCN(C)CCOc1ccc(CN(c2cc(OC)ccc2[C@H]2CCc3cc(O)ccc3C2)C(C)C)cc1F]

Synthesized from pivalic acid (S)-6-{2-[(3-fluoro-4-hydroxybenzoyl)isopropylamino]-4-methoxyphenyl}-5,6,7,8-tetrahydronaphthalen-2-yl ester (154 mg) and 2-chloro-N-(2-methoxyethyl)-N-methylacetamide (96 mg) according to an analogous synthetic method to Example 404, the title compound (150 mg) was obtained.

$^1$H-NMR (400 MHz, CDCl$_3$); δ (ppm): 1.10 (d, 3H), 1.15 (d, 3H), 1.51-1.86 (m, 4H), 2.41 (s, 3H), 2.59-2.74 (m, 4H), 2.81-2.92 (m, 4H), 3.15-3.23 (m, 1H), 3.35 (s, 3H), 3.50-3.60 (m, 3H), 3.76 (s, 3H), 4.00-4.10 (m, 4H), 6.60-6.64 (m, 3H), 6.71-6.78 (m, 2H), 6.83-6.96 (m, 3H), 7.07 (d, 1H).

ESI-Mass; 551 [M$^+$+H]

Example 802

(R)-6-{2-{2-Hydroxyethyl[4-(1-methylpiperidin-4-yl)benzyl]amino}-4-methoxyphenyl}-5,6,7,8-tetrahydronaphthalen-2-ol

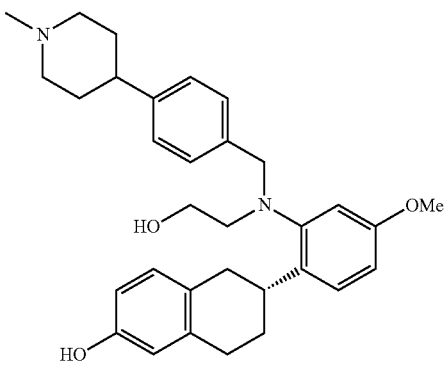 [SMILES: COc1ccc([C@@H]2CCc3cc(O)ccc3C2)c(N(CCO)Cc2ccc(C3CCN(C)CC3)cc2)c1]

Synthesized from pivalic acid (R)-6-[2-(ethoxycarbonylmethylamino)-4-methoxyphenyl]-5,6,7,8-tetrahydronaphthalen-2-yl ester (35 mg) and 4-(4-carboxyphenyl)piperidine-1-carboxylic acid tert-butyl ester (73 mg) according to an analogous synthetic method to the above-mentioned Preparation Example 86 and Example 337, the title compound (18 mg) was obtained.

¹H-NMR (400 MHz, CDCl₃); δ (ppm): 1.53-1.62 (m, 1H), 1.65-1.80 (m, 2H), 1.86-2.11 (m, 5H), 2.52-2.84 (m, 9H), 3.14-3.20 (m, 2H), 3.40-3.58 (m, 3H), 3.59-3.61 (m, 2H), 3.70-3.78 (m, 1H), 3.79 (s, 3H), 4.00 (s, 2H), 6.57-6.64 (m, 2H), 6.71-6.75 (m, 2H), 6.85 (d, 1H), 7.02-7.05 (m, 2H), 7.09-7.16 (m, 3H).

ESI-Mass; 501 [M⁺+H]

Example 803

(S)-6-{2-{2-Hydroxyethyl[4-(1-methylpiperidin-4-yl)benzyl]amino}-4-methoxyphenyl}-5,6,7,8-tetrahydronaphthalen-2-ol

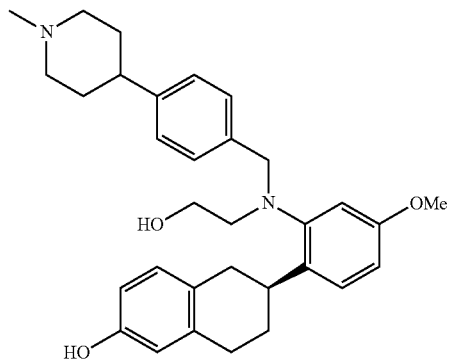 [SMILES: COc1ccc([C@H]2CCc3cc(O)ccc3C2)c(N(CCO)Cc2ccc(C3CCN(C)CC3)cc2)c1]

Synthesized from pivalic acid (S)-6-[2-(ethoxycarbonylmethylamino)-4-methoxyphenyl]-5,6,7,8-tetrahydronaphthalen-2-yl ester (35 mg) and 4-(4-carboxyphenyl)piperidine-1-carboxylic acid tert-butyl ester (73 mg) according to an analogous synthesis method to the above-mentioned Preparation Example 86 and Example 337, the title compound (41 mg) was obtained.

¹H-NMR (400 MHz, CDCl₃); δ (ppm): 1.53-1.62 (m, 1H), 1.65-1.80 (m, 2H), 1.86-2.11 (m, 5H), 2.52-2.84 (m, 9H), 3.14-3.20 (m, 2H), 3.40-3.58 (m, 3H), 3.59-3.61 (m, 2H), 3.70-3.78 (m, 1H), 3.79 (s, 3H), 4.00 (s, 2H), 6.57-6.64 (m, 2H), 6.71-6.75 (m, 2H), 6.85 (d, 1H), 7.02-7.05 (m, 2H), 7.09-7.16 (m, 3H).

ESI-Mass; 501 [M⁺+H]

Example 804

(R)-6-{2-{[4-(2-Dimethylamino-2-methylpropoxy)-3-fluorobenzyl](2-hydroxyethyl)amino}-4-methoxyphenyl}-5,6,7,8-tetrahydronaphthalen-2-ol

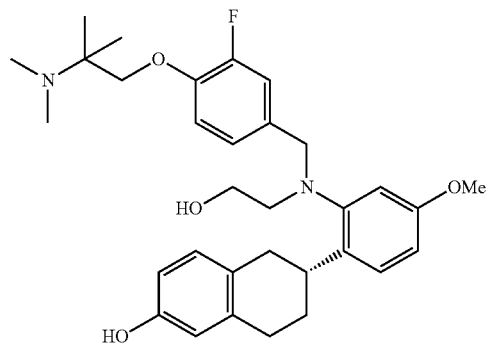 [SMILES: COc1ccc([C@@H]2CCc3cc(O)ccc3C2)c(N(CCO)Cc2ccc(OCC(C)(C)N(C)C)c(F)c2)c1]

Synthesized from pivalic acid (R)-6-[2-(ethoxycarbonylmethylamino)-4-methoxyphenyl]-5,6,7,8-tetrahydronaphthalen-2-yl ester (50 mg) and 4-(2-tert-butoxycarbonylamino-2-methylpropoxy)-3-fluorobenzoic acid (56 mg) according to an analogous synthetic method to Example 245, the title compound (21 mg) was obtained.

¹H-NMR (400 MHz, CDCl₃); δ (ppm): 1.24-1.32 (m, 6H), 1.66-1.82 (m, 2H), 2.45-2.74 (m, 8H), 2.80-2.86 (m, 2H), 3.11-3.18 (m, 2H), 3.42-3.60 (m, 3H), 3.68-3.73 (m, 1H), 3.79 (s, 3H), 3.90 (s, 2H), 3.97 (s, 2H), 6.58-6.62 (m, 2H), 6.71-6.90 (m, 6H), 7.13-7.18 (m, 1H).

ESI-Mass; 537 [M⁺+H]

Preparation Example 209

Pivalic Acid 6-{4-methoxy-2-{2-[4-(2-piperidin-1-ylethoxy)phenyl]acetylamino}phenyl}-5,6,7,8-tetrahydronaphthalen-2-yl Ester

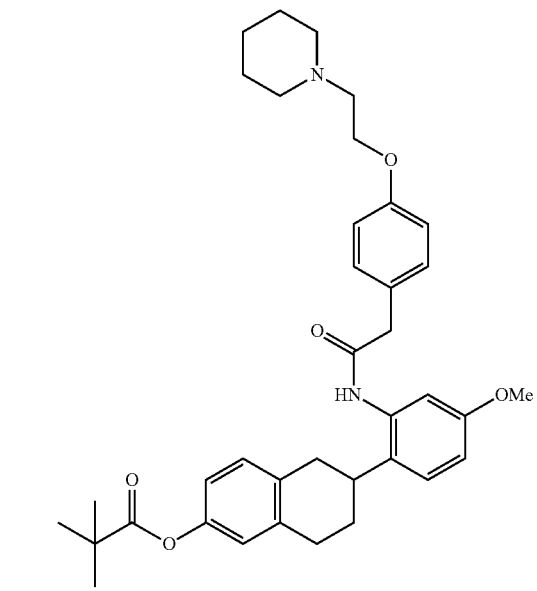 [SMILES: COc1ccc(C2CCc3cc(OC(=O)C(C)(C)C)ccc3C2)c(NC(=O)Cc2ccc(OCCN3CCCCC3)cc2)c1]

Synthesized from pivalic acid 6-(2-amino-4-methoxyphenyl)-5,6,7,8-tetrahydronaphthalen-2-yl ester (100 mg) and [4-(2-piperidin-1-ylethoxy)phenyl]acetic acid hydrochloride (140 mg) according to an analogous synthetic method to Preparation Example 154, the title compound (93 mg) was obtained.

¹H-NMR (400 MHz, CDCl₃); δ (ppm): 1.37 (s, 9H), 1.68-1.85 (m, 8H), 2.28-2.85 (m, 1H), 3.69 (s, 2H), 3.79 (s, 3H), 3.85-3.96 (m, 2H), 6.65-6.69 (m, 3H), 6.76-6.83 (m, 2H), 6.96-7.16 (m, 5H), 7.54-7.57 (m, 1H).

ESI-Mass; 599 [M⁺+H]

Example 805

6-{2-{2-Hydroxyethyl {2-[4-(2-piperidin-1-ylethoxy)phenyl]ethyl}amino}-4-methoxyphenyl}-5,6,7,8-tetrahydronaphthalen-2-ol

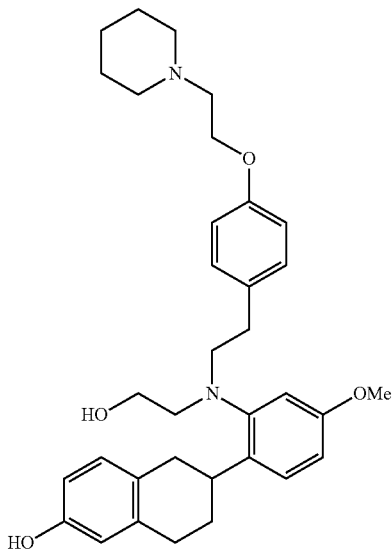 [SMILES: COc1ccc(C2CCc3cc(O)ccc3C2)c(N(CCO)CCc2ccc(OCCN3CCCCC3)cc2)c1]

To a solution of pivalic acid 6-{4-methoxy-2-{2-[4-(2-piperidin-1-ylethoxy)phenyl]acetylamino}phenyl}-5,6,7,8-tetrahydronaphthalen-2-yl ester (30 mg) in tetrahydrofuran (1 ml) was added 60% sodium hydride (2.2 mg), the solution was stirred for 30 minutes at room temperature, then bromoethyl acetate (6.1 µl) was added thereto followed by stirring for 1 hour. To the reaction solution was added a saturated aqueous solution of ammonium chloride, the solution was extracted with chloroform, and concentrated in vacuo. The residue was subjected to the synthetic method of Example 337 described above to provide the title compound (14 mg).

ESI-Mass; 545 [M$^+$+H]

Example 806

(R)-6-{2-{Ethyl[4-(2-methylaminoethyl)benzyl]amino}-4-methoxyphenyl}-5,6,7,8-tetrahydronaphthalen-2-ol

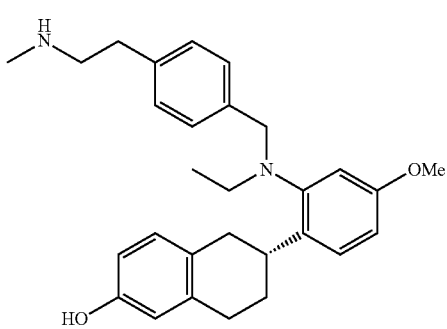 [SMILES: CCN(Cc1ccc(CCNC)cc1)c1cc(OC)ccc1[C@@H]1CCc2cc(O)ccc2C1]

A solution of pivalic acid (R)-6-{2-[(4-carboxymethylbenzyl)ethylamino]-4-methoxyphenyl}-5,6,7,8-tetrahydronaphthalen-2-yl ester (30 mg), methylamine hydrochloride (6 mg), benzotriazol-1-yloxytris(dimethylamino)phosphonium hexafluorophosphate (30 mg), triethylamine (0.03 ml) in dichloromethane (0.8 ml) was stirred for 1 hour at room temperature. The reaction solution was diluted with water, then the solution was extracted with chloroform, and the solvent was concentrated in vacuo, the resulting residue was subjected to the synthetic method of Example 337 to provide the title compound (16 mg).

$^1$H-NMR (400 MHz, CDCl$_3$); δ (ppm): 0.94 (t, 3H), 1.66-1.86 (m, 2H), 2.46 (s, 3H), 2.64-2.90 (m, 8H), 2.92 (q, 2H), 3.60-3.70 (m, 1H), 3.78 (s, 3H), 3.98 (s, 2H), 6.58-6.63 (m, 2H), 6.69 (dd, 1H), 6.79 (d, 1H), 6.90 (d, 1H), 7.07 (d, 2H), 7.14 (d, 1H), 7.18 (d, 2H).

ESI-Mass; 445 [M$^+$+H]

Example 807

(R)-6-{2-{Ethyl{4-[2-(2-methoxyethylamino)ethyl]benzyl}amino}-4-methoxyphenyl}-5,6,7,8-tetrahydronaphthalen-2-ol

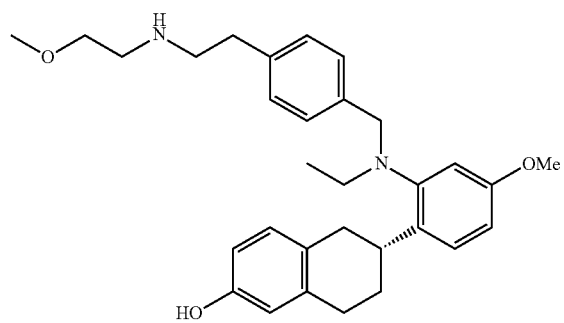

Synthesized from pivalic acid (R)-6-{2-[(4-carboxymethylbenzyl)ethylamino]-4-methoxyphenyl}-5,6,7,8-tetrahydronaphthalen-2-yl ester (30 mg) and (2-methoxymethyl)methylamine (7 mg) according to an analogous synthetic method to Example 806, the title compound (23 mg) was obtained.

$^1$H-NMR (400 MHz, CDCl$_3$); δ (ppm): 0.94 (t, 3H), 1.67-1.84 (m, 2H), 2.63-2.96 (m, 12H), 3.33 (s, 3H), 3.50 (t, 2H), 3.61-3.71 (m, 1H), 3.80 (s, 3H), 3.98 (s, 2H), 6.58-6.64 (m, 2H), 6.69 (dd, 1H), 6.79 (d, 1H), 6.90 (d, 1H), 7.06 (d, 2H), 7.14 (d, 1H), 7.17 (d, 2H).

ESI-Mass; 489 [M$^+$+H]

Example 808

(R)-6-{2-{[4-(2-Dimethylaminoethoxy)benzyl](2-hydroxyethyl)amino}-4-methoxyphenyl}-5,6,7,8-tetrahydronaphthalen-2-ol

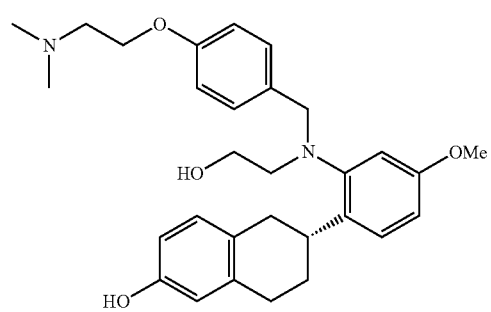

Synthesized from pivalic acid (R)-6-{2-[ethoxycarbonylmethyl(4-hydroxybenzoyl)amino]-4-methoxyphenyl}-5,6,7,8-tetrahydronaphthalen-2-yl ester (25 mg) according to an analogous synthetic method to Preparation Example 404, the title compound (12 mg) was obtained.

ESI-Mass; 491 [M$^+$+H]

Example 809

(R)-6-{2-{[4-(2-Diethylaminoethoxy)benzyl](2-hydroxyethyl)amino}-4-methoxyphenyl}-5,6,7,8-tetrahydronaphthalen-2-ol

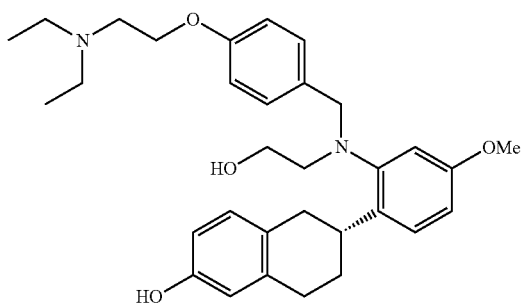 [SMILES: CCN(CC)CCOc1ccc(CN(CCO)c2cc(OC)ccc2[C@@H]2CCc3cc(O)ccc3C2)cc1]

Synthesized from pivalic acid (R)-6-{2-[ethoxycarbonylmethyl(4-hydroxybenzoyl)amino]-4-methoxyphenyl}-5,6,7,8-tetrahydronaphthalen-2-yl ester (25 mg) according to an analogous synthetic method to Preparation Example 404, the title compound (11 mg) was obtained.
ESI-Mass; 519 [M$^+$+H]

Example 810

(R)-6-{2-{(2-Hydroxyethyl)[4-(2-pyrrolidin-1-ylethoxy)benzyl]amino}-4-methoxyphenyl}-5,6,7,8-tetrahydronaphthalen-2-ol

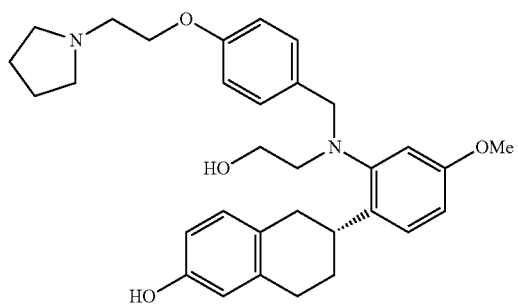 [SMILES: COc1ccc([C@@H]2CCc3cc(O)ccc3C2)c(N(CCO)Cc2ccc(OCCN3CCCC3)cc2)c1]

Synthesized from pivalic acid (R)-6-{2-[ethoxycarbonylmethyl(4-hydroxybenzoyl)amino]-4-methoxyphenyl}-5,6,7,8-tetrahydronaphthalen-2-yl ester (25 mg) according to an analogous synthetic method to Preparation Example 404, the title compound (15 mg) was obtained.
ESI-Mass; 517 [M$^+$+H]

Example 811

(R)-6-{2-{(2-Hydroxyethyl)[4-(2-piperidin-1-ylethoxy)benzyl]amino}-4-methoxyphenyl}-5,6,7,8-tetrahydronaphthalen-2-ol

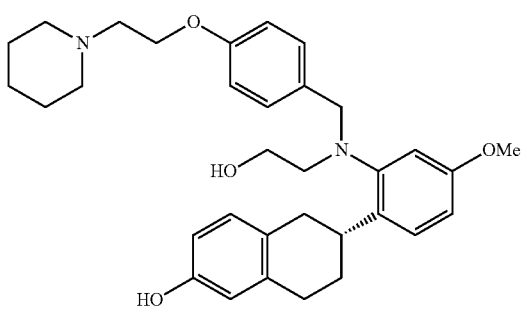 [SMILES: COc1ccc([C@@H]2CCc3cc(O)ccc3C2)c(N(CCO)Cc2ccc(OCCN3CCCCC3)cc2)c1]

Synthesized from pivalic acid (R)-6-{2-[ethoxycarbonylmethyl(4-hydroxybenzoyl)amino]-4-methoxyphenyl}-5,6,7,8-tetrahydronaphthalen-2-yl ester (25 mg) according to an analogous synthetic method to Preparation Example 404, the title compound (14 mg) was obtained.
ESI-Mass; 531 [M$^+$+H]

Example 812

6-{2-{[4-(2-Azepan-1-ylethoxy)benzyl](2-hydroxyethyl)amino}-4-methoxyphenyl}-5,6,7,8-tetrahydronaphthalen-2-ol

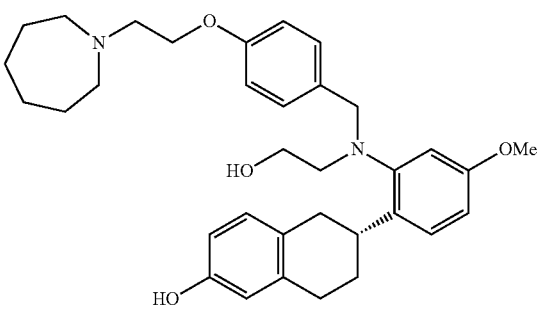

Synthesized from pivalic acid (R)-6-{2-[ethoxycarbonylmethyl(4-hydroxybenzoyl)amino]-4-methoxyphenyl}-5,6,7,8-tetrahydronaphthalen-2-yl ester (25 mg) according to an analogous synthetic method to Preparation Example 404, the title compound (11 mg) was obtained.
ESI-Mass; 545 [M$^+$+H]

Example 813

(R)-6-{2-{(2-Hydroxyethyl){4-{2-[(2-methoxyethyl)methylamino]ethoxy}benzyl}amino}-4-methoxyphenyl}-5,6,7,8-tetrahydronaphthalen-2-ol

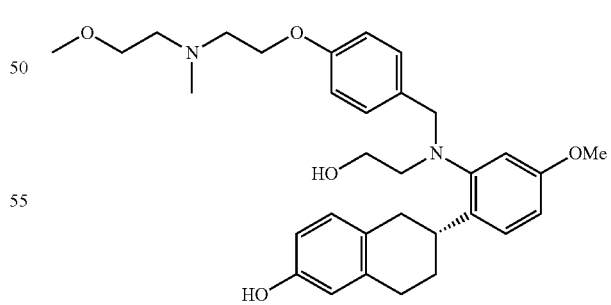

Synthesized from pivalic acid (R)-6-{2-[ethoxycarbonylmethyl(4-hydroxybenzoyl)amino]-4-methoxyphenyl}-5,6,7,8-tetrahydronaphthalen-2-yl ester (25 mg) according to an analogous synthetic method to Preparation Example 404, the title compound (13 mg) was obtained.
ESI-Mass; 535 [M$^+$+H]

Example 814

(R)-6-{2-[[4-(2-Dimethylamino-2-methylpropoxy)benzyl](2-hydroxyethyl)amino]-4-methoxyphenyl}-5,6,7,8-tetrahydronaphthalen-2-ol

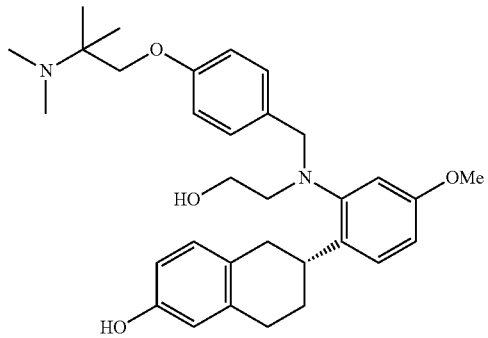 [SMILES: COc1ccc([C@@H]2CCc3cc(O)ccc3C2)c(N(CCO)Cc2ccc(OCC(C)(C)N(C)C)cc2)c1]

Synthesized from pivalic acid (R)-6-[2-(ethoxycarbonylmethylamino)-4-methoxyphenyl]-5,6,7,8-tetrahydronaphthalen-2-yl ester (50 mg) and 4-(2-tert-butoxycarbonylamino-2-methylpropoxy)benzoic acid (53 mg) according to an analogous synthetic method to Example 245, the title compound (24 mg) was obtained.

$^1$H-NMR (400 MHz, CDCl$_3$); δ (ppm): 1.29 (s, 6H), 1.61-1.82 (m, 2H), 2.48 (s, 6H), 2.49-2.70 (m, 2H), 2.80-2.85 (m, 2H), 3.11-3.19 (m, 2H), 3.43-3.60 (m, 3H), 3.79 (s, 3H), 3.82 (s, 2H), 3.99 (s, 2H), 6.58-6.61 (m, 2H), 6.70-6.79 (m, 4H), 6.82-6.85 (m, 1H), 7.02-7.09 (m, 2H), 7.10-7.18 (m, 1H).
ESI-Mass; 519 [M$^+$+H]

Preparation Example 210

Pivalic Acid (R)-6-{2-{[4-(2-tert-butoxycarbonylamino-2-methylpropoxy)benzoyl]ethoxycarbonylmethylamino}-4-methoxyphenyl}-5,6,7,8-tetrahydronaphthalen-2-yl ester

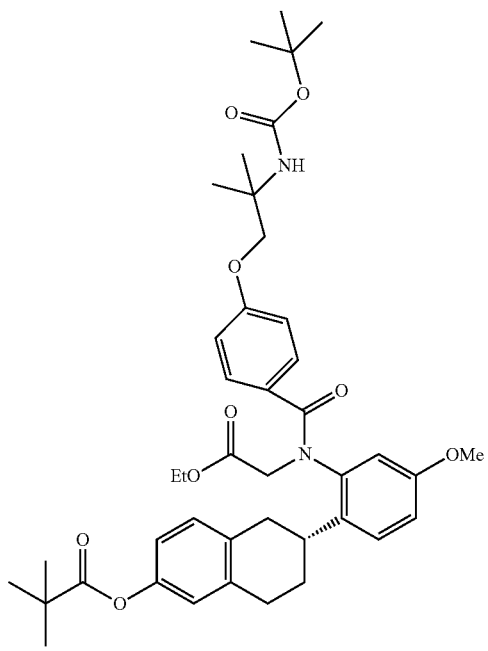 [SMILES: CCOC(=O)CN(C(=O)c1ccc(OCC(C)(C)NC(=O)OC(C)(C)C)cc1)c1cc(OC)ccc1[C@@H]1CCc2cc(OC(=O)C(C)(C)C)ccc2C1]

Synthesized from pivalic acid (R)-6-[2-(ethoxycarbonylmethylamino)-4-methoxyphenyl]-5,6,7,8-tetrahydronaphthalen-2-yl ester (1.2 g) and 4-(2-tert-butoxycarbonylamino-2-methylpropoxy)benzoic acid (1.27 g) according to an analogous synthetic method to Preparation Example 154, the title compound (1.56 g) was obtained.

$^1$H-NMR (400 MHz, CDCl$_3$); δ (ppm): 1.24-1.26 (m, 3H), 1.27-1.40 (m, 27H), 1.79-1.99 (m, 2H), 2.51-2.62 (m, 5H), 3.75-4.25 (m, 8H), 4.65 (brs, 0.5H), 4.66 (brs, 0.5H), 4.75-4.87 (m, 1H), 6.65-6.70 (m, 2H), 6.74-6.87 (m, 4H), 6.95-7.10 (m, 3H), 7.26-7.31 (m, 1H).

Example 815

(R)-6-{2-{[4-(2-Ethylamino-2-methylpropoxy)benzyl](2-hydroxyethyl)amino}-4-methoxyphenyl}-5,6,7,8-tetrahydronaphthalen-2-ol

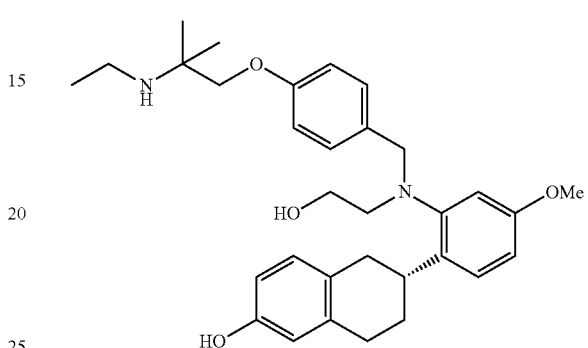

Pivalic acid (R)-6-{2-{[4-(2-tert-butoxycarbonylamino-2-methylpropoxy)benzoyl]ethoxycarbonylmethylamino}-4-methoxyphenyl}-5,6,7,8-tetrahydronaphthalen-2-yl ester (80 mg) was subjected to the synthetic method of Example 215 mentioned above and deprotected followed by carring out an analogous synthetic method to Example 36 to provide the title compound (16 mg).

$^1$H-NMR (400 MHz, CDCl$_3$); δ (ppm): 1.15 (t, 3H), 1.23 (s, 6H), 1.60-1.79 (m, 2H), 2.49-2.82 (m, 6H), 3.10-3.15 (m, 2H), 3.40-3.59 (m, 3H), 3.72 (s, 2H), 3.78 (s, 3H), 3.95 (s, 2H), 6.52-6.58 (m, 2H), 6.71-6.81 (m, 5H), 7.01-7.04 (m, 2H), 7.13 (d, 1H).
ESI-Mass; 519 [M$^+$+H]

Example 816

(R)-6-{2-{[4-(2-Dimethylaminoethoxy)-3-fluorobenzyl](2-hydroxyethyl)amino}-4-methoxyphenyl}-5,6,7,8-tetrahydronaphthalen-2-ol

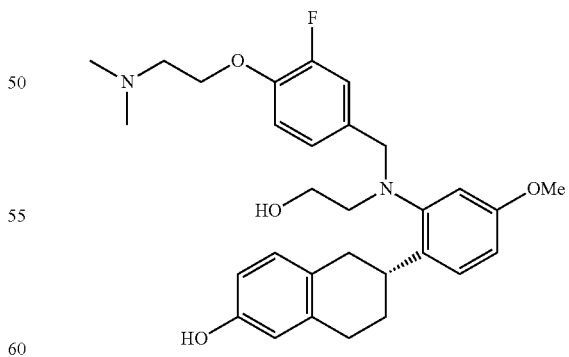

Synthesized from pivalic acid (R)-6-{2-[ethoxycarbonylmethyl(3-fluoro-4-hydroxybenzoyl)amino]-4-methoxyphenyl}-5,6,7,8-tetrahydronaphthalen-2-yl ester (23 mg) according to an analogous synthetic method to Preparation Example 404, the title compound (16 mg) was obtained.
ESI-Mass; 509 [M$^+$+H]

Example 817

(R)-6-{2-{[4-(2-Diethylaminoethoxy)-3-fluorobenzyl](2-hydroxyethyl)amino}-4-methoxyphenyl}-5,6,7,8-tetrahydronaphthalen-2-ol

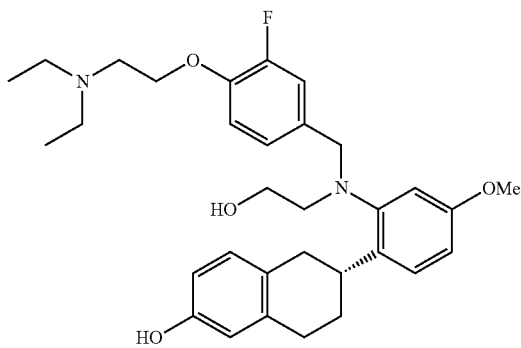 [SMILES: CCN(CC)CCOc1ccc(CN(CCO)c2cc(OC)ccc2[C@@H]2CCc3cc(O)ccc3C2)cc1F]

Synthesized from pivalic acid (R)-6-{2-[ethoxycarbonylmethyl(3-fluoro-4-hydroxybenzoyl)amino]-4-methoxyphenyl}-5,6,7,8-tetrahydronaphthalen-2-yl ester (23 mg) according to an analogous synthetic method to Preparation Example 404, the title compound (16 mg) was obtained.

ESI-Mass; 537 [M$^+$+H]

Example 818

(R)-6-{2-{[3-Fluoro-4-(2-pyrrolidin-1-ylethoxy)benzyl](2-hydroxyethyl)amino}-4-methoxyphenyl}-5,6,7,8-tetrahydronaphthalen-2-ol

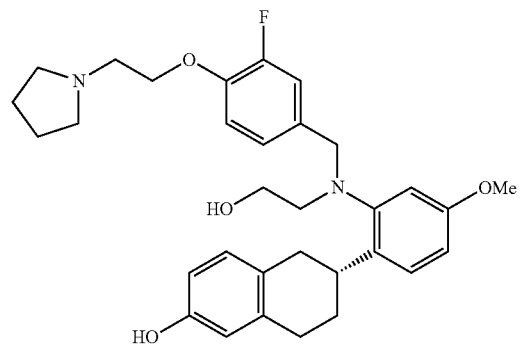 [SMILES: COc1ccc([C@@H]2CCc3cc(O)ccc3C2)c(N(CCO)Cc2ccc(OCCN3CCCC3)c(F)c2)c1]

Synthesized from pivalic acid (R)-6-{2-[ethoxycarbonylmethyl(3-fluoro-4-hydroxybenzoyl)amino]-4-methoxyphenyl}-5,6,7,8-tetrahydronaphthalen-2-yl ester (23 mg) according to an analogous synthetic method to Preparation Example 404, the title compound (16 mg) was obtained.

ESI-Mass; 535 [M$^+$+H]

Example 819

(R)-6-{2-{[3-Fluoro-4-(2-piperidin-1-ylethoxy)benzyl](2-hydroxyethyl)amino}-4-methoxyphenyl}-5,6,7,8-tetrahydronaphthalen-2-ol

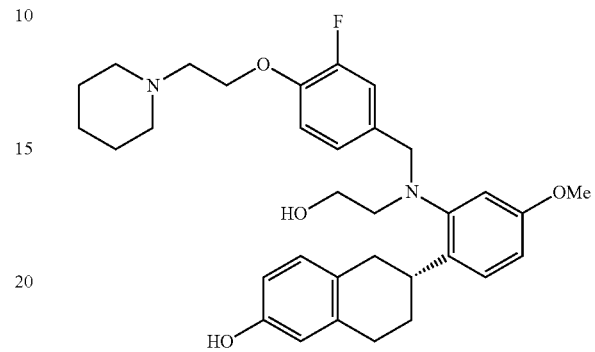

Synthesized from pivalic acid (R)-6-{2-[ethoxycarbonylmethyl(3-fluoro-4-hydroxybenzoyl)amino]-4-methoxyphenyl}-5,6,7,8-tetrahydronaphthalen-2-yl ester (23 mg) according to an analogous synthetic method to Preparation Example 404, the title compound (16 mg) was obtained.

ESI-Mass; 549 [M$^+$+H]

Example 820

(R)-6-{2-{[4-(2-Azepan-1-ylethoxy)-3-fluorobenzyl](2-hydroxyethyl)amino}-4-methoxyphenyl}-5,6,7,8-tetrahydronaphthalen-2-ol

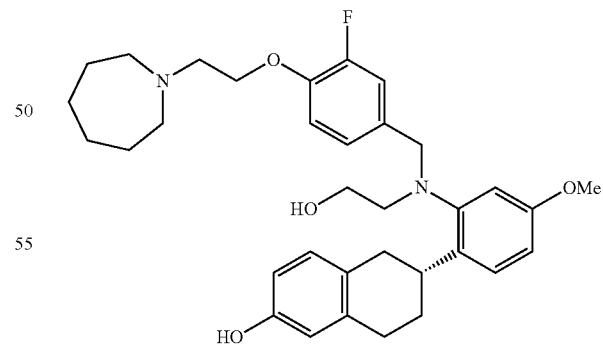

Synthesized from pivalic acid (R)-6-{2-[ethoxycarbonylmethyl(3-fluoro-4-hydroxybenzoyl)amino]-4-methoxyphenyl}-5,6,7,8-tetrahydronaphthalen-2-yl ester (23 mg) according to an analogous synthetic method to Preparation Example 404, the title compound (16 mg) was obtained.

ESI-Mass; 563 [M$^+$+H]

Example 821

(R)-6-{2-{{3-Fluoro-4-{2-[(2-methoxyethyl)methylamino]ethoxy}benzyl}(2-hydroxyethyl)amino}-4-methoxyphenyl}-5,6,7,8-tetrahydronaphthalen-2-ol

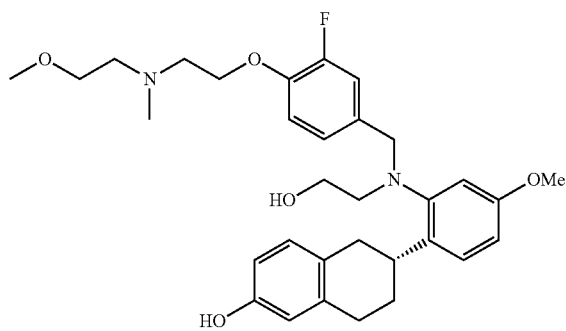 [SMILES: COCCN(C)CCOc1ccc(CN(CCO)c2cc(OC)ccc2[C@@H]2CCc3cc(O)ccc3C2)cc1F]

Synthesized from pivalic acid (R)-6-{2-[ethoxycarbonylmethyl(3-fluoro-4-hydroxybenzoyl)amino]-4-methoxyphenyl}-5,6,7,8-tetrahydronaphthalen-2-yl ester (23 mg) according to an analogous synthetic method to Preparation Example 404, the title compound (16 mg) was obtained.

ESI-Mass; 553 [M$^+$+H]

Preparation Example 211 tert-Butyl[2-(4-iodophenyl)-1,1-dimethylethyl]carbamate

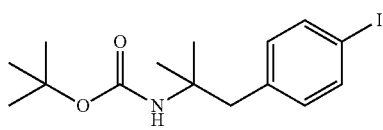 [SMILES: CC(C)(Cc1ccc(I)cc1)NC(=O)OC(C)(C)C]

The title compound was synthesized by referring to *J. Med. Chem.*, 1987, 30 (9), 1563. Concentrated sulfuric acid (30 ml) was cooled to −10° C., 1,1-dimethyl-2-phenylethylamine (10 g) was added dropwise thereto, then 70% nitric acid (6 ml) was added dropwise thereto over 50 minutes followed by stirring on an ice bath for 10 minutes. Concentrated sulfuric acid (10 ml) was added dropwise thereto followed by stirring for 30 minutes at room temperature. The reaction solution was poured into ice water (400 ml), the resulting crude crystal was filtered and sequentially washed with ice water and methanol to provide 1,1-dimethyl-2-(4-nitrophenyl)ethylamine 1/2 sulfate (8.2 g). To a suspension of this compound (6 g) in ethanol (60 ml) were sequentially added an aqueous solution of 5N sodium hydroxide (8 ml) and hydrazine hydrate (1.5 g), Raney nickel (50% suspension in water) (6 ml) was added dropwise thereto on an ice bath followed by stirring for 5 minutes at room temperature. Then hydrazine hydrate (0.7 g) was added dropwise thereto followed by stirring for 30 minutes at room temperature. After filtrating through celite pad and washing with ethanol, the solvent was evaporated in vacuo, and the residue was purified by NH silica gel column chromatography (chloroform-methanol system) to provide 4-(2-amino-2-methylpropyl)phenylamine (4.0 g). To a solution of this compound (1 g) in water (20 ml) was added concentrated sulfuric acid (1.3 ml), a solution of sodium nitrite (480 mg) in water (3 ml) was added dropwise thereto on an ice bath over 10 minutes followed by stirring for 40 minutes. A solution of sodium iodide (4.6 g) in water (4 ml) was added dropwise thereto over 4 minutes, and the solution was stirred for 2.5 hours at room temperature. The reaction solution was neutralized with ammonia solution, extracted with ethyl acetate, then washed with an aqueous solution of sodium thiosulfate, dried over anhydrous magnesium sulfate, and then the solvent was evaporated in vacuo. The residue was purified by NH silica gel column chromatography (chloroform-methanol system); the resulting 2-(4-iodophenyl)-1,1-dimethylethylamine (1.4 g) was used according to an analogous synthetic method to Preparation Example 19 to provide the title compound (1.8 g).

$^1$H-NMR (400 MHz, CDCl$_3$); δ (ppm): 1.24 (s, 6H), 1.46 (s, 9H), 2.93 (s, 2H), 4.22 (brs, 1H), 6.88 (d, 2H), 7.58 (d, 2H).

Preparation Example 212

4-[2-(tert-Butoxycarbonylmethylamino)-2-methylpropyl]benzoic acid

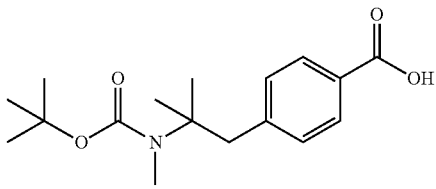 [SMILES: CN(C(=O)OC(C)(C)C)C(C)(C)Cc1ccc(C(=O)O)cc1]

Synthesized from tert-butyl[2-(4-iodophenyl)-1,1-dimethylethyl]carbamate (1.4 g) and methyl iodide (2 ml) according to an analogous synthetic method to Example 71, tert-butyl [2-(4-iodophenyl)-1,1-dimethylethyl]methylcarbamate (1.5 g) was used according to an analogous synthetic method to Preparation Example 51 to provide the title compound (790 mg).

$^1$H-NMR (400 MHz, DMSO-d$_6$); δ (ppm): 1.33 (s, 6H), 1.46 (s, 9H), 2.44 (s, 3H), 3.12 (s, 2H), 7.21 (d, 2H), 7.83 (d, 2H), 12.76 (brs, 1H).

Preparation Example 213

4-[2-(tert-Butoxycarbonylethylamino)-2-methylpropyl]benzoic acid

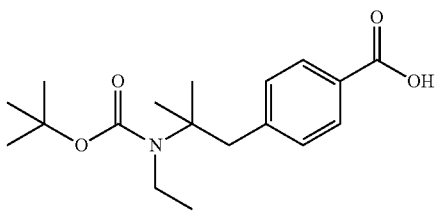 [SMILES: CCN(C(=O)OC(C)(C)C)C(C)(C)Cc1ccc(C(=O)O)cc1]

Synthesized from tert-butyl[2-(4-iodophenyl)-1,1-dimethylethyl]carbamate (2 g) and ethyl iodide (4 ml) according to an analogous synthetic method to Example 71, tert-butyl[2-(4-iodophenyl)-1,1-dimethylethyl]methylcarbamate (2 g) was used according to an analogous synthetic method to Preparation Example 51 to provide the title compound (1.3 g).

¹H-NMR (400 MHz, DMSO-d₆); δ (ppm): 0.65 (t, 3H), 1.35 (s, 6H), 1.46 (s, 9H), 2.85 (q, 2H), 3.15 (s, 2H), 7.20 (d, 2H), 7.82 (d, 2H), 12.77 (brs, 1H).

Example 822

(R)-6-{2-{Ethyl[4-(2-methyl-2-methylaminopropyl)benzyl]amino}-4-methoxyphenyl}-5,6,7,8-tetrahydronaphthalen-2-ol

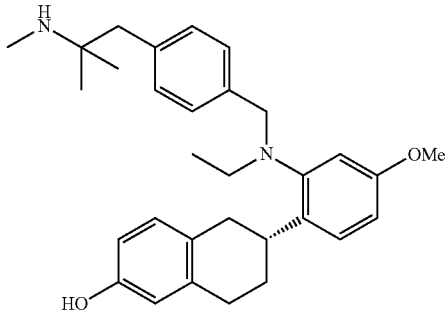 [SMILES: CCN(Cc1ccc(CC(C)(C)NC)cc1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (100 mg) and 4-[2-(tert-butoxycarbonylmethylamino)-2-methylpropyl]benzoic acid (120 mg) according to an analogous synthetic method to Preparation Example 86, pivalic acid 6-{2-{{4-[2-(tert-butoxycarbonylmethylamino)-2-methylpropyl]benzoyl}ethylamino}-4-methoxyphenyl}-5,6,7,8-tetrahydronaphthalen-2-yl ester (97 mg) was used according to analogous synthetic method to the above-mentioned Example 215 and Example 337 to provide the title compound (48 mg).

¹H-NMR (400 MHz, DMSO-d₆); δ (ppm): 0.95 (s, 6H), 0.95 (t, 3H), 1.50-1.77 (m, 2H), 2.22 (s, 3H), 2.52 (s, 2H), 2.56-2.61 (m, 2H), 2.68-2.77 (m, 2H), 2.88 (q, 2H), 3.48-3.58 (m, 1H), 3.71 (s, 3H), 3.95 (d, 1H), 3.99 (d, 1H), 6.45-6.51 (m, 2H), 6.66 (dd, 1H), 6.75-6.82 (m, 2H), 6.99 (d, 2H), 7.09 (d, 2H), 7.13 (d, 1H), 8.98 (s, 1H).

ESI-Mass; 473 [M⁺+H]

Example 823

(R)-6-{2-{Ethyl[4-(2-ethylamino-2-methylpropyl)benzyl]amino}-4-methoxyphenyl}-5,6,7,8-tetrahydronaphthalen-2-ol

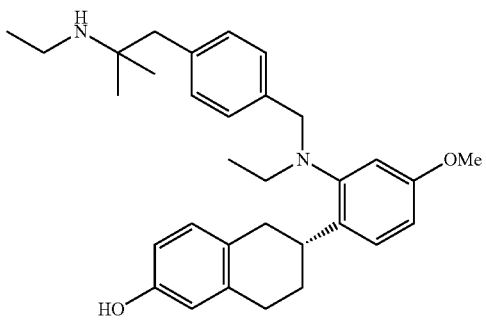 [SMILES: CCNC(C)(C)Cc1ccc(CN(CC)c2cc(OC)ccc2[C@@H]2CCc3cc(O)ccc3C2)cc1]

Synthesized from pivalic acid (R)-6-(2-ethylamino-4-methoxyphenyl)-5,6,7,8-tetrahydronaphthalen-2-yl ester (100 mg) and 4-[2-(tert-butoxycarbonylethylamino)-2-methylpropyl]benzoic acid (125 mg) according to analogous synthetic method to Preparation Example 86, pivalic acid 6-{2-{{4-[2-(tert-butoxycarbonylethylamino)-2-methylpropyl]benzoyl}ethylamino}-4-methoxyphenyl}-5,6,7,8-tetrahydronaphthalen-2-yl ester (94 mg) was used according to an analogous synthetic method to the above-mentioned Example 215 and Example 337 to provide the title compound (55 mg).

¹H-NMR (400 MHz, DMSO-d₆); δ (ppm): 0.89 (t, 3H), 0.90 (s, 6H), 0.98 (t, 3H), 1.49-1.58 (m, 1H), 1.60-1.73 (m, 1H), 2.50-2.61 (m, 6H), 2.68-2.76 (m, 2H), 2.88 (q, 2H), 3.47-3.58 (m, 1H), 3.71 (s, 3H), 3.95 (d, 1H), 4.00 (d, 1H), 6.44-6.51 (m, 2H), 6.65 (dd, 1H), 6.75-6.81 (m, 2H), 6.98 (d, 2H), 7.09 (d, 2H), 7.13 (d, 1H), 8.98 (s, 1H).

ESI-Mass; 487 [M⁺+H]

Example 824

(R)-6-{2-{[4-(2-Dimethylamino-2-methylpropyl)benzyl]ethylamino}-4-methoxyphenyl}-5,6,7,8-tetrahydronaphthalen-2-ol

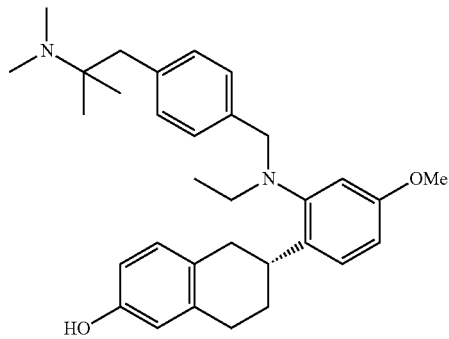 [SMILES: CCN(Cc1ccc(CC(C)(C)N(C)C)cc1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (100 mg) and 4-[2-(tert-butoxycarbonylmethylamino)-2-methylpropyl]benzoic acid (120 mg) according to an analogous synthetic method to Preparation Example 86, pivalic acid 6-{2-{{4-[2-(tert-butoxycarbonylmethylamino)-2-methylpropyl]benzoyl}ethylamino}-4-methoxyphenyl}-5,6,7,8-tetrahydronaphthalen-2-yl ester (67 mg) was used according to an analogous synthetic method to Example 337 to provide the title compound (18 mg).

¹H-NMR (400 MHz, DMSO-d₆); δ (ppm): 0.85 (s, 6H), 0.88 (t, 3H), 1.51-1.60 (m, 1H), 1.61-1.74 (m, 1H), 2.19 (s, 6H), 2.52-2.62 (m, 4H), 2.69-2.78 (m, 2H), 2.87 (q, 2H), 3.47-3.58 (m, 1H), 3.71 (s, 3H), 3.94 (d, 1H), 3.98 (d, 1H), 6.46-6.52 (m, 2H), 6.66 (dd, 1H), 6.75-6.83 (m, 2H), 7.02 (d, 2H), 7.07 (d, 2H), 7.13 (d, 1H), 8.99 (s, 1H).

ESI-Mass; 487 [M⁺+H]

Example 825

(R)-6-{2-{Ethyl{4-[2-(ethylmethylamino)-2-methyl-propyl]benzyl}amino}-4-methoxyphenyl}-5,6,7,8-tetrahydronaphthalen-2-ol

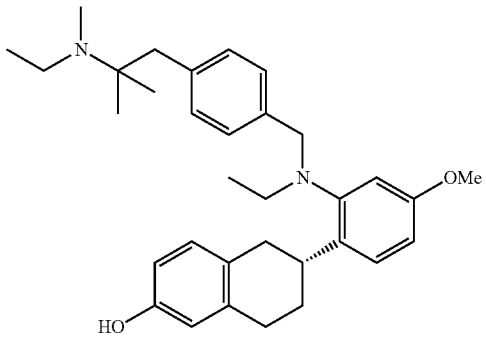 [SMILES: CCN(Cc1ccc(CC(C)(C)N(C)CC)cc1)c1cc(OC)ccc1[C@@H]1CCc2cc(O)ccc2C1]

Synthesized from pivalic acid (R)-6-(2-ethylamino-4-methoxyphenyl)-5,6,7,8-tetrahydronaphthalen-2-yl ester (100 mg) and 4-[2-(tert-butoxycarbonylethylamino)-2-methylpropyl]benzoic acid (125 mg) according to an analogous synthetic method to Preparation Example 86, pivalic acid 6-{2-{{4-[2-(tert-butoxycarbonylethylamino)-2-methylpropyl]benzoyl}ethylamino}-4-methoxyphenyl}-5,6,7,8-tetrahydronaphthalen-2-yl ester (69 mg) was used according to an analogous synthetic method to Example 337 to provide the title compound (19 mg).

$^1$H-NMR (400 MHz, DMSO-d$_6$); δ (ppm): 0.87 (s, 6H), 0.88 (t, 3H), 0.97 (t, 3H), 1.51-1.60 (m, 1H), 1.61-1.74 (m, 1H), 2.15 (s, 3H), 2.46 (q, 2H), 2.52-2.61 (m, 4H), 2.69-2.78 (m, 2H), 2.87 (q, 2H), 3.48-3.58 (m, 1H), 3.70 (s, 3H), 3.94 (d, 1H), 3.98 (d, 1H), 6.46-6.52 (m, 2H), 6.65 (dd, 1H), 6.76-6.82 (m, 2H), 7.03 (d, 2H), 7.07 (d, 2H), 7.13 (d, 1H), 8.98 (s, 1H).

ESI-Mass; 501 [M$^+$+H]

Example 826

(S)-6-{2-{(2-Hydroxyethyl)[4-(1-methylpiperidin-4-yl)benzyl]amino}-4,5-dimethoxyphenyl}-5,6,7,8-tetrahydronaphthalen-2-ol

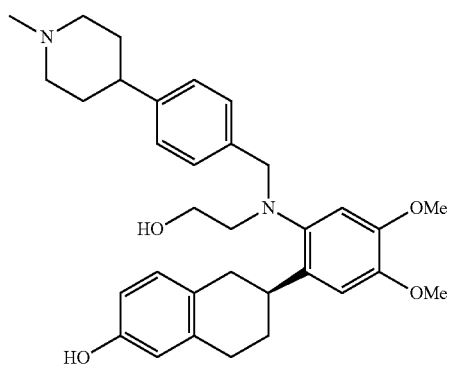 [SMILES: COc1cc([C@H]2CCc3cc(O)ccc3C2)c(N(CCO)Cc2ccc(C3CCN(C)CC3)cc2)cc1OC]

Synthesized from pivalic acid (S)-6-[2-(ethoxycarbonylmethylamino)-4,5-dimethoxyphenyl]-5,6,7,8-tetrahydronaphthalen-2-yl ester (90 mg) and 4-(4-carboxyphenyl)piperidine-1-carboxylic acid tert-butyl ester (88 mg) according to an analogous synthetic method to the above-mentioned Preparation Example 86 and Example 337, the title compound (37 mg) was obtained.

$^1$H-NMR (400 MHz, DMSO-d$_6$); δ (ppm): 1.75-1.89 (m, 4H), 2.10-2.20 (m, 2H), 2.37-2.40 (m, 1H), 2.38 (s, 3H), 2.60-2.83 (m, 4H), 3.00-3.19 (m, 4H), 3.45-3.60 (m, 4H), 3.65-3.70 (m, 1H), 3.82 (s, 3H), 3.83 (s, 3H), 3.93 (d, 1H), 3.97 (d, 1H), 6.57-6.59 (m, 2H), 6.64 (s, 1H), 6.72 (s, 1H), 6.85-6.87 (m, 1H), 6.98-7.08 (m, 4H).

ESI-Mass; 531 [M$^+$+H]

Example 827

(R)-6-{2-{(2-Hydroxyethyl)[4-(1-methylpiperidin-4-yl)benzyl]amino}-4,5-dimethoxyphenyl}-5,6,7,8-tetrahydronaphthalen-2-ol

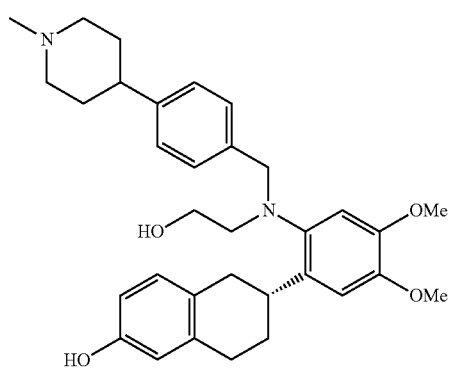 [SMILES: COc1cc([C@@H]2CCc3cc(O)ccc3C2)c(N(CCO)Cc2ccc(C3CCN(C)CC3)cc2)cc1OC]

Synthesized from pivalic acid (R)-6-[2-(ethoxycarbonylmethylamino)-4,5-dimethoxyphenyl]-5,6,7,8-tetrahydronaphthalen-2-yl ester (39 mg) and 4-(4-carboxyphenyl)piperidine-1-carboxylic acid tert-butyl ester (38 mg) according to an analogous synthetic method to the above-mentioned Preparation Example 86 and Example 337, the title compound (25 mg) was obtained.

$^1$H-NMR (400 MHz, DMSO-d$_6$); δ (ppm): 1.75-1.89 (m, 4H), 2.10-2.20 (m, 2H), 2.37-2.40 (m, 1H), 2.38 (s, 3H), 2.60-2.83 (m, 4H), 3.00-3.19 (m, 4H), 3.45-3.60 (m, 4H), 3.65-3.70 (m, 1H), 3.82 (s, 3H), 3.83 (s, 3H), 3.93 (d, 1H), 3.97 (d, 1H), 6.57-6.59 (m, 2H), 6.64 (s, 1H), 6.72 (s, 1H), 6.85-6.87 (m, 1H), 6.98-7.08 (m, 4H).

ESI-Mass; 531 [M$^+$+H]

Example 828

(R)-6-{2-{(2-Hydroxyethyl)[4-(2-methyl-2-methylaminopropyl)benzyl]amino}-4-methoxyphenyl}-5,6,7,8-tetrahydronaphthalen-2-ol

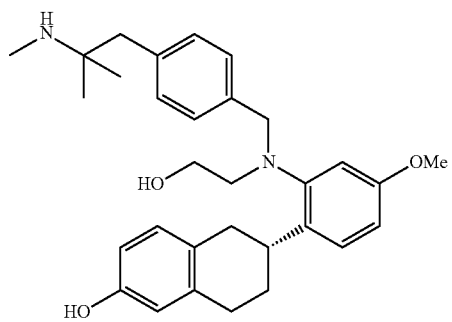 [SMILES: CNC(C)(C)Cc1ccc(CN(CCO)c2cc(OC)ccc2[C@@H]2CCc3cc(O)ccc3C2)cc1]

Synthesized from pivalic acid (R)-6-[2-(ethoxycarbonylmethylamino)-4-methoxyphenyl]-5,6,7,8-tetrahydronaphthalen-2-yl ester (50 mg) and 4-[2-(tert-butoxycarbonylmethylamino)-2-methylpropyl]benzoic acid (53 mg) according to an analogous synthetic method to the above-mentioned Preparation Example 86, pivalic acid (R)-6-{2-{{4-[2-(tert-butoxycarbonylmethylamino)-2-methylpropoxy]benzoyl}ethoxycarbonylmethylamino}-4-methoxyphenyl}-5,6,7,8-tetrahydronaphthalen-2-yl ester (60 mg) was obtained. A portion thereof (36 mg) was subjected to the synthetic method of the above-mentioned Example 215 and Example 337 to provide the title compound (15 mg).
ESI-Mass; 489 [M⁺+H]

Example 829

(R)-6-{2-{[4-(2-Ethylamino-2-methylpropyl)benzyl](2-hydroxyethyl)amino}-4-methoxyphenyl}-5,6,7,8-tetrahydronaphthalen-2-ol

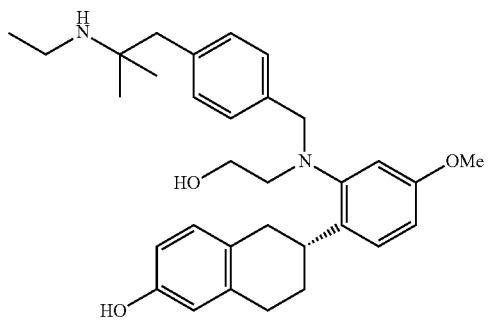 [SMILES: CCNC(C)(C)Cc1ccc(CN(CCO)c2cc(OC)ccc2[C@@H]2CCc3cc(O)ccc3C2)cc1]

Synthesized from pivalic acid (R)-6-[2-(ethoxycarbonylmethylamino)-4-methoxyphenyl]-5,6,7,8-tetrahydronaphthalen-2-yl ester (50 mg) and 4-[2-(tert-butoxycarbonylethylamino)-2-methylpropyl]benzoic acid (55 mg) according to an analogous synthetic method to the above-mentioned Preparation Example 86, pivalic acid (R)-6-{2-{{4-[2-(tert-butoxycarbonylethylamino)-2-methylpropoxy]benzoyl}ethoxycarbonylmethylamino}-4-methoxyphenyl}-5,6,7,8-tetrahydronaphthalen-2-yl ester (45 mg) was obtained. A portion thereof (27 mg) was subjected to the synthesis method of the above-mentioned Example 215 and Example 337 to provide the title compound (5.0 mg).
ESI-Mass; 503 [M⁺+H]

Example 830

(R)-6-{2-{[4-(2-Dimethylamino-2-methylpropyl)benzyl](2-hydroxyethyl)amino}-4-methoxyphenyl}-5,6,7,8-tetrahydronaphthalen-2-ol

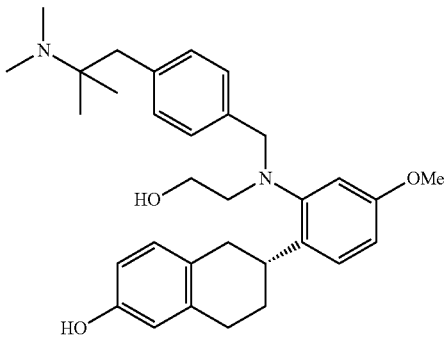 [SMILES: COc1ccc([C@@H]2CCc3cc(O)ccc3C2)c(N(CCO)Cc2ccc(CC(C)(C)N(C)C)cc2)c1]

Synthesized from pivalic acid (R)-6-[2-(ethoxycarbonylmethylamino)-4-methoxyphenyl]-5,6,7,8-tetrahydronaphthalen-2-yl ester (50 mg) and 4-[2-(tert-butoxycarbonylmethylamino)-2-methylpropyl]benzoic acid (53 mg) according to an analogous synthetic method to the above-mentioned Preparation Example 86, pivalic acid (R)-6-{2-{{4-[2-(tert-butoxycarbonylmethylamino)-2-methylpropoxy]benzoyl}ethoxycarbonylmethylamino}-4-methoxyphenyl}-5,6,7,8-tetrahydronaphthalen-2-yl ester (60 mg) was obtained. A portion thereof (24 mg) was subjected to the synthesis method of the above-mentioned Example 337 to provide the title compound (3.8 mg).
ESI-Mass; 503 [M⁺+H]

Preparation Example 214

4-Benzyloxycarbonylmethylbenzoic Acid

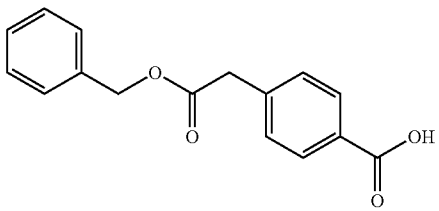 [SMILES: O=C(Cc1ccc(C(=O)O)cc1)OCc1ccccc1]

Synthesized from (4-formylphenyl)acetic acid (1 g) and benzyl alcohol (730 mg) according to an analogous synthetic method to Example 806, benzyl (4-formylphenyl)acetate (1.4 g) was used according to an analogous synthetic method to Preparation Example 53 to provide the title compound (1.2 g).
¹H-NMR (400 MHz, DMSO-d₆); δ (ppm): 3.84 (s, 2H), 5.11 (s, 2H), 7.28-7.39 (m, 5H), 7.39 (d, 2H), 7.88 (d, 2H), 12.90 (brs, 1H).

Preparation Example 215

4-(1-Benzyloxycarbonyl-1-methylethyl)benzoic Acid

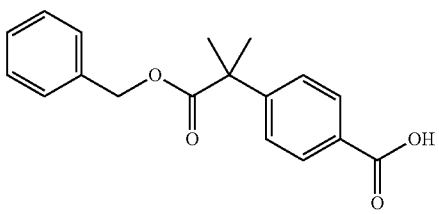 [SMILES: CC(C)(C(=O)OCc1ccccc1)c1ccc(C(=O)O)cc1]

To a solution of 4-benzyloxycarbonylmethylbenzoic acid (1.5 g) in tetrahydrofuran (40 ml) was added N,N-dimethylformamide (1 drop), and oxalyl chloride (0.9 ml) was added dropwise thereto followed by stirring for 1.5 hours at room temperature. The solvent was then evaporated in vacuo. To a solution of the resulting residue in tetrahydrofuran (30 ml) were sequentially added 2-(trimethylsilyl)ethanol (2.5 ml) and pyridine (5 ml), and the solution was stirred for 2 hours at room temperature. The solution was extracted with ethyl acetate, then sequentially washed with water and brine, dried over anhydrous magnesium sulfate, and then the solvent was evaporated in vacuo. The residue was purified by silica gel column chromatography (hexane-ethyl acetate system) to provide 4-benzyloxycarbonylmethylbenzoic acid 2-(trimethylsilyl)ethyl ester (1.9 g). Synthesized from this compound (520 mg) according to an analogous synthetic method to the above-mentioned Preparation Example 181 and Example 325, the title compound (246 mg) was obtained.

Preparation Example 216

(R)-2-{4-{{2-[6-(2,2-Dimethylpropionyloxy)-1,2,3,4-tetrahydronaphthalen-2-yl]-5-methoxyphenyl}ethylcarbamoyl}phenyl}-2-methylpropionic Acid

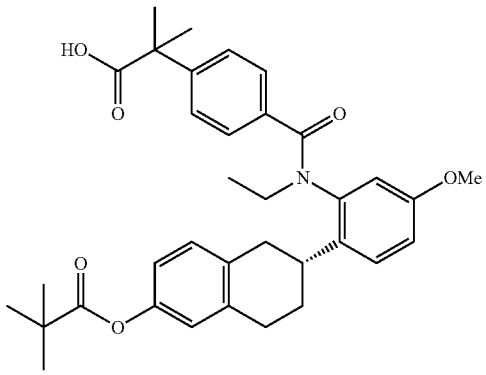 [SMILES: CCN(C(=O)c1ccc(C(C)(C)C(=O)O)cc1)c1cc(OC)ccc1[C@@H]1CCc2cc(OC(=O)C(C)(C)C)ccc2C1]

Synthesized from pivalic acid (R)-6-(2-ethylamino-4-methoxyphenyl)-5,6,7,8-tetrahydronaphthalen-2-yl ester (141 mg) and 4-(1-benzyloxycarbonyl-1-methylethyl)benzoic acid (140 mg) according to an analogous synthetic method to the above-mentioned Preparation Example 86 and Example 22, the title compound (200 mg) was obtained.

$^1$H-NMR (400 MHz, CDCl$_3$); δ (ppm): 1.05-1.78 (m, 6H), 1.35 (s, 9H), 1.49 (s, 1.5H), 1.50 (s, 1.5H), 1.54 (s, 3H), 1.78-1.90 (m, 0.5H), 2.25-2.40 (m, 0.5H), 2.56-292 (m, 4H), 3.75-4.09 (m, 1H), 3.80 (s, 3H), 6.65-6.88 (m, 5H), 6.94-7.06 (m, 2H), 7.11-7.30 (m, 3H).

Example 831

(R)-6-{2-{[4-(1,1-Dimethyl-2-methylaminoethyl)benzyl]ethylamino}-4-methoxyphenyl}-5,6,7,8-tetrahydronaphthalen-2-ol

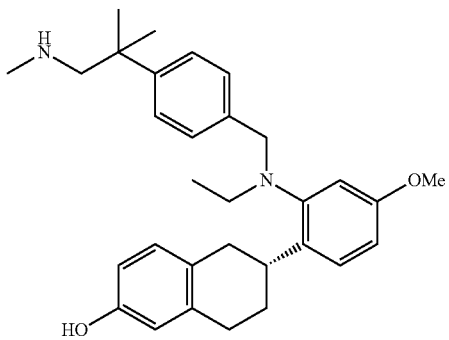 [SMILES: CCN(Cc1ccc(C(C)(C)CNC)cc1)c1cc(OC)ccc1[C@@H]1CCc2cc(O)ccc2C1]

Synthesized from (R)-2-{4-{{2-[6-(2,2-dimethylpropionyloxy)-1,2,3,4-tetrahydronaphthalen-2-yl]-5-methoxyphenyl}ethylcarbamoyl}phenyl}-2-methylpropionic acid (40 mg) and methylamine hydrochloride (10 mg) according to an analogous synthetic method to Example 806, the title compound (13 mg) was obtained.

$^1$H-NMR (400 MHz, CDCl$_3$); δ (ppm): 0.93 (t, 3H), 1.31 (s, 6H), 1.64-1.82 (m, 2H), 2.34 (s, 3H), 2.63-2.87 (m, 6H), 2.91 (q, 2H), 3.61-3.72 (m, 1H), 3.80 (s, 3H), 3.95 (d, 1H), 3.99 (d, 1H), 6.56-6.62 (m, 2H), 6.69 (dd, 1H), 6.79 (d, 1H), 6.89 (d, 1H), 7.13 (d, 1H), 7.16-7.24 (m, 4H).
ESI-Mass; 473 [M$^+$+H]

Example 832

(R)-6-{2-{Ethyl[4-(2-ethylamino-1,1-dimethylethyl)benzyl]amino}-4-methoxyphenyl}-5,6,7,8-tetrahydronaphthalen-2-ol

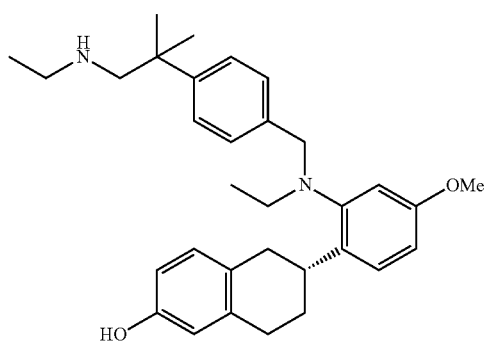 [SMILES: CCNCC(C)(C)c1ccc(CN(CC)c2cc(OC)ccc2[C@@H]2CCc3cc(O)ccc3C2)cc1]

Synthesized from (R)-2-{4-{{2-[6-(2,2-dimethylpropionyloxy)-1,2,3,4-tetrahydronaphthalen-2-yl]-5-methoxyphenyl}ethylcarbamoyl}phenyl}-2-methylpropionic acid (40 mg) and ethylamine hydrochloride (12 mg) according to an analogous synthetic method to Example 806, the title compound (23 mg) was obtained.

$^1$H-NMR (400 MHz, CDCl$_3$); δ (ppm): 0.93 (t, 3H), 1.00 (t, 3H), 1.33 (s, 6H), 1.63-1.81 (m, 2H), 2.57 (q, 2H), 2.63-2.87 (m, 6H), 2.91 (q, 2H), 3.62-3.72 (m, 1H), 3.79 (s, 3H), 3.96 (d, 1H), 4.00 (d, 1H), 6.56-6.60 (m, 2H), 6.68 (dd, 1H), 6.78 (d, 1H), 6.89 (d, 1H), 7.13 (d, 1H), 7.16-7.33 (m, 4H).
ESI-Mass; 487 [M$^+$+H]

Example 833

(R)-6-{2-{[4-(2-Dimethylamino-1,1-dimethylethyl)benzyl]ethylamino}-4-methoxyphenyl}-5,6,7,8-tetrahydronaphthalen-2-ol

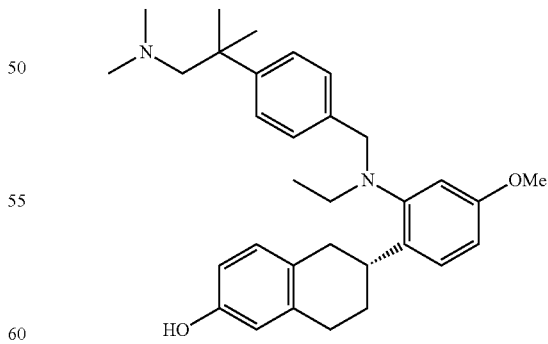

Synthesized from (R)-2-{4-{{2-[6-(2,2-dimethylpropionyloxy)-1,2,3,4-tetrahydronaphthalen-2-yl]-5-methoxyphenyl}ethylcarbamoyl}phenyl}-2-methylpropionic acid (40 mg) and dimethylamine hydrochloride (12 mg) according to an analogous synthetic method to Example 806, the title compound (23 mg) was obtained.

¹H-NMR (400 MHz, CDCl₃); δ (ppm): 0.93 (t, 3H), 1.30 (s, 6H), 1.70-1.82 (m, 2H), 2.05 (s, 6H), 2.44 (s, 2H), 2.65-2.85 (m, 4H), 2.89 (q, 2H), 3.64-3.73 (m, 1H), 3.78 (s, 3H), 3.97 (s, 2H), 6.58-6.62 (m, 2H), 6.67 (dd, 1H), 6.75 (d, 1H), 6.91 (d, 1H), 7.12 (d, 1H), 7.15 (d, 2H), 7.23 (d, 2H).
ESI-Mass; 487 [M⁺+H]

Example 834

(R)-6-{2-{Ethyl[4-(2-ethylmethylamino-1,1-dimethylethyl)benzyl]amino}-4-methoxyphenyl}-5,6,7,8-tetrahydronaphthalen-2-ol

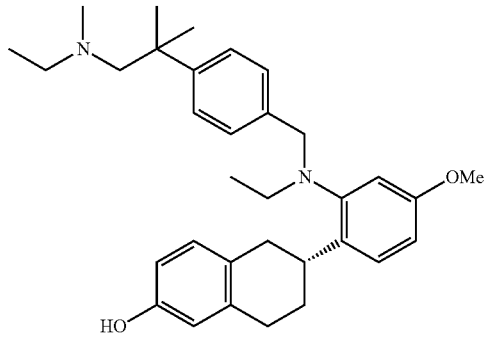 [SMILES: CCN(C)CC(C)(C)c1ccc(CN(CC)c2cc(OC)ccc2[C@@H]2CCc3cc(O)ccc3C2)cc1]

Synthesized from (R)-2-{4-{{2-[6-(2,2-dimethylpropionyloxy)-1,2,3,4-tetrahydronaphthalen-2-yl]-5-methoxyphenyl}ethylcarbamoyl}phenyl}-2-methylpropionic acid (40 mg) and ethylmethylamine (15 mg) according to an analogous synthetic method to Example 806, the title compound (26 mg) was obtained.
¹H-NMR (400 MHz, CDCl₃); δ (ppm): 0.89 (t, 3H), 0.92 (t, 3H), 1.29 (s, 6H), 1.71-1.82 (m, 2H), 1.99 (s, 3H), 2.28 (q, 2H), 2.41 (s, 2H), 2.65-2.85 (m, 4H), 2.89 (q, 2H), 3.63-3.75 (m, 1H), 3.78 (s, 3H), 3.97 (s, 2H), 6.59-6.63 (m, 2H), 6.67 (dd, 1H), 6.76 (d, 1H), 6.91 (d, 1H), 7.13 (d, 1H), 7.15 (d, 2H), 7.23 (d, 2H).
ESI-Mass; 501 [M⁺+H]

Preparation Example 217

Pivalic Acid (R)-6-{2-[(4-carboxymethylbenzoyl)ethoxycarbonylmethylamino]-4-methoxyphenyl}-5,6,7,8-tetrahydronaphthalen-2-yl ester

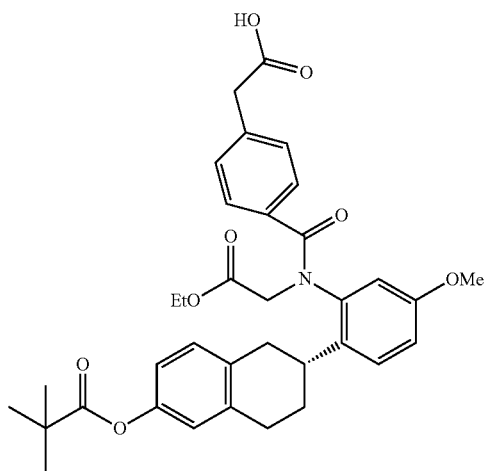 [SMILES: CCOC(=O)CN(C(=O)c1ccc(CC(=O)O)cc1)c1cc(OC)ccc1[C@@H]1CCc2cc(OC(=O)C(C)(C)C)ccc2C1]

From pivalic acid (R)-6-[2-(ethoxycarbonylmethylamino)-4-methoxyphenyl]-5,6,7,8-tetrahydronaphthalen-2-yl ester (150 mg) and 4-benzyloxycarbonylmethylbenzoic acid (138 mg), according to an analogous synthetic method to Preparation Example 154, obtained was pivalic acid (R)-6-{2-[(4-benzyloxycarbonylmethylbenzoyl)ethoxycarbonylmethylamino]-4-methoxyphenyl}-5,6,7,8-tetrahydronaphthalen-2-yl ester (200 mg). A solution thereof in methanol (5 ml) was subjected to a catalytic reduction in the presence of 10% palladium-activated charcoal (40 mg) for 2 hours at room temperature under hydrogen atmosphere at ambient pressure. After filtration through celite pad, the solution was concentrated in vacuo to provide the title compound (170 mg).
¹H-NMR (400 MHz, DMSO-d₆); δ (ppm): 1.14 (t, 1.5H), 1.21 (t, 1.5H), 1.29 (s, 9H), 1.50-1.88 (m, 2H), 2.41-3.07 (m, 5H), 3.52 (s, 1H), 3.56 (s, 1H), 3.71 (s, 1.5H), 3.74 (s, 1.5H), 4.04-4.20 (m, 2H), 4.32 (d, 0.5H), 4.33 (d, 0.5H), 4.55 (d, 0.5H), 4.57 (d, 0.5H), 6.74-6.81 (m, 2H), 6.86-6.89 (m, 2H), 6.95-7.40 (m, 2H), 7.09-7.23 (m, 4H).

Example 835

(R)-6-{2-{(2-Hydroxyethyl)[4-(2-methylaminoethyl)benzyl]amino}-4-methoxyphenyl}-5,6,7,8-tetrahydronaphthalen-2-ol

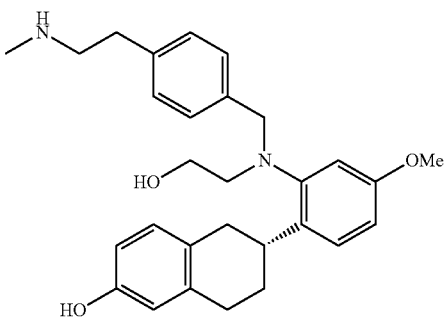 [SMILES: CNCCc1ccc(CN(CCO)c2cc(OC)ccc2[C@@H]2CCc3cc(O)ccc3C2)cc1]

Synthesized from pivalic acid (R)-6-{2-[(4-carboxymethylbenzoyl)ethoxycarbonylmethylamino]-4-methoxyphenyl}-5,6,7,8-tetrahydronaphthalen-2-yl ester (36 mg) and methylamine hydrochloride (14 mg) according to an analogous synthetic method to Example 806, the title compound (11 mg) was obtained.
¹H-NMR (400 MHz, CDCl₃); δ (ppm): 1.59-1.80 (m, 2H), 2.45 (s, 3H), 2.60-2.89 (m, 8H), 3.10-3.14 (m, 2H), 3.51-3.56 (m, 3H), 3.78 (s, 3H), 3.99 (s, 2H), 6.56-6.60 (m, 2H), 6.71-6.78 (m, 2H), 6.85 (d, 1H), 7.04-7.09 (m, 4H), 7.13 (d, 1H).
ESI-Mass; 461 [M⁺+H]

Example 836

(R)-6-{2-{[4-(2-Ethylaminoethyl)benzyl](2-hydroxyethyl)amino}-4-methoxyphenyl}-5,6,7,8-tetrahydronaphthalen-2-ol

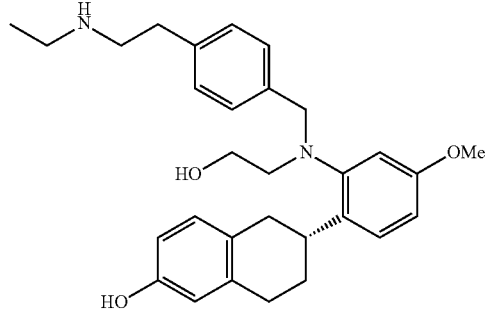 [SMILES: CCNCCc1ccc(CN(CCO)c2cc(OC)ccc2[C@@H]2CCc3cc(O)ccc3C2)cc1]

Synthesized from pivalic acid (R)-6-{2-[(4-carboxymethylbenzoyl)ethoxycarbonylmethylamino]-4-methoxyphenyl}-5,6,7,8-tetrahydronaphthalen-2-yl ester (36 mg) according to an analogous synthetic method to Example 806, the title compound (8.0 mg) was obtained.

$^1$H-NMR (400 MHz, CDCl$_3$); δ (ppm): 1.12 (t, 3H), 1.55-1.85 (m, 4H), 2.59-2.92 (m, 8H), 3.11-3.14 (m, 2H), 3.52-3.55 (m, 3H), 3.78 (s, 3H), 3.99 (s, 2H), 6.56-6.60 (m, 2H), 6.71-6.77 (m, 2H), 6.85 (d, 1H), 7.05-7.07 (m, 4H), 7.13 (d, 1H).

ESI-Mass; 475 [M$^+$+H]

Example 837

(R)-6-{2-{(2-Hydroxyethyl)[4-(2-isopropylaminoethyl)benzyl]amino}-4-methoxyphenyl}-5,6,7,8-tetrahydronaphthalen-2-ol

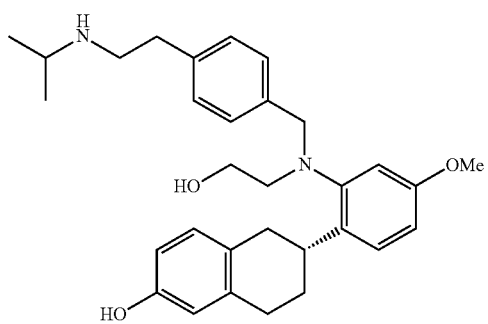 [SMILES: COc1ccc([C@@H]2CCc3cc(O)ccc3C2)c(N(CCO)Cc2ccc(CCNC(C)C)cc2)c1]

Synthesized from pivalic acid (R)-6-{2-[(4-carboxymethylbenzoyl)ethoxycarbonylmethylamino]-4-methoxyphenyl}-5,6,7,8-tetrahydronaphthalen-2-yl ester (36 mg) according to an analogous synthetic method to Example 806, the title compound (9.4 mg) was obtained.

$^1$H-NMR (400 MHz, CDCl$_3$); δ (ppm): 1.11 (d, 6H), 1.60-1.79 (m, 3H), 2.55-2.92 (m, 9H), 3.11-3.19 (m, 2H), 3.51-3.60 (m, 3H), 3.68-3.71 (m, 1H), 3.78 (s, 3H), 3.99 (s, 2H), 6.57-6.61 (m, 2H), 6.71-6.77 (m, 2H), 6.84 (d, 1H), 7.05-7.08 (m, 4H), 7.13 (d, 1H).

ESI-Mass; 489 [M$^+$+H]

Example 838

(R)-6-{2-{(2-Hydroxyethyl){4-[2-(2-methoxyethylamino)ethyl]benzyl}amino}-4-methoxyphenyl}-5,6,7,8-tetrahydronaphthalen-2-ol

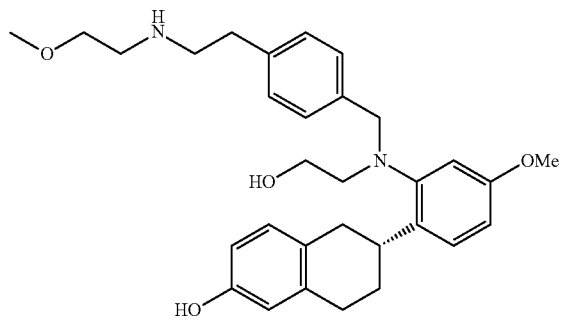 [SMILES: COCCNCCc1ccc(CN(CCO)c2cc(OC)ccc2[C@@H]2CCc3cc(O)ccc3C2)cc1]

Synthesized from pivalic acid (R)-6-{2-[(4-carboxymethylbenzoyl)ethoxycarbonylmethylamino]-4-methoxyphenyl}-5,6,7,8-tetrahydronaphthalen-2-yl ester (36 mg) according to an analogous synthetic method to Example 806, the title compound (10 mg) was obtained.

$^1$H-NMR (400 MHz, CDCl$_3$); δ (ppm): 1.67-1.80 (m, 3H), 2.55-2.90 (m, 11H), 3.12-3.20 (m, 2H), 3.33 (s, 3H), 3.50-3.61 (m, 5H), 3.68-3.71 (m, 1H), 3.78 (s, 3H), 3.99 (s, 2H), 6.56-6.62 (m, 2H), 6.71-6.77 (m, 2H), 6.85 (d, 1H), 7.04-7.11 (m, 4H), 7.13 (d, 1H).

ESI-Mass; 505 [M$^+$+H]

Example 839

(R)-6-{2-{[4-(2-Aminoethyl)benzyl]ethylamino}-4-methoxyphenyl}-5,6,7,8-tetrahydronaphthalen-2-ol

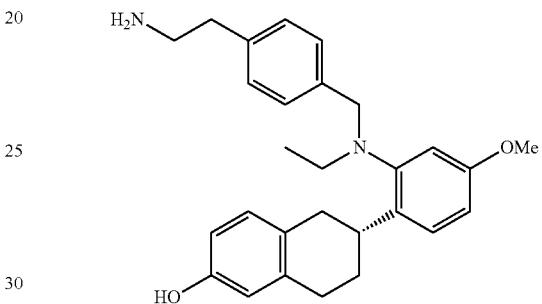

Synthesized from pivalic acid (R)-6-{2-[(4-carboxymethylbenzoyl)ethylamino]-4-methoxyphenyl}-5,6,7,8-tetrahydronaphthalen-2-yl ester (31 mg) and a saturated ammonia solution in chloroform (0.1 ml) according to an analogous synthetic method to Example 806, the title compound (0.7 mg) was obtained.

ESI-Mass; 431 [M$^+$+H]

Example 840

(R)-6-{2-{Ethyl[4-(2-propylaminoethyl)benzyl]amino}-4-methoxyphenyl}-5,6,7,8-tetrahydronaphthalen-2-ol

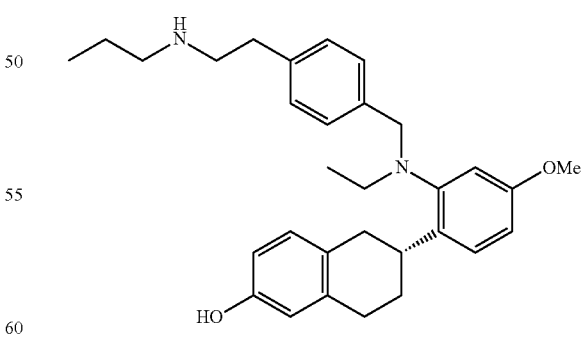

Synthesized from pivalic acid (R)-6-{2-[(4-carboxymethylbenzoyl)ethylamino]-4-methoxyphenyl}-5,6,7,8-tetrahydronaphthalen-2-yl ester (31 mg) and propylamine (5.5 mg) according to an analogous synthetic method to Example 806, the title compound (4.6 mg) was obtained.

ESI-Mass; 473 [M$^+$+H]

Example 841

(R)-6-{2-{[4-(2-Butylaminoethyl)benzyl]ethylamino}-4-methoxyphenyl}-5,6,7,8-tetrahydronaphthalen-2-ol

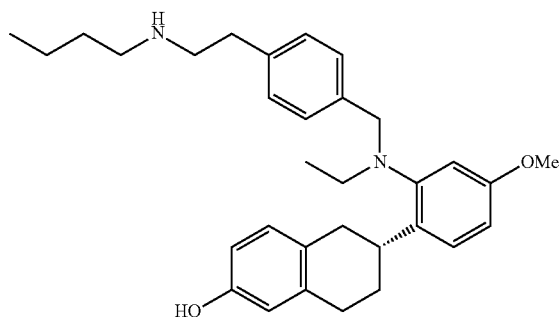 [SMILES: CCCCNCCc1ccc(CN(CC)c2cc(OC)ccc2[C@@H]2CCc3cc(O)ccc3C2)cc1]

Synthesized from pivalic acid (R)-6-{2-[(4-carboxymethylbenzyl)ethylamino]-4-methoxyphenyl}-5,6,7,8-tetrahydronaphthalen-2-yl ester (31 mg) and butylamine (6.8 mg) according to an analogous synthetic method to Example 806, the title compound (4.6 mg) was obtained.

ESI-Mass; 487 [M$^+$+H]

Example 842

(R)-6-{2-{Ethyl[4-(2-isopropylaminoethyl)benzyl]amino}-4-methoxyphenyl}-5,6,7,8-tetrahydronaphthalen-2-ol

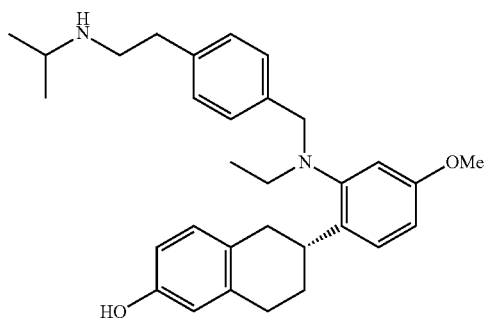 [SMILES: CCN(Cc1ccc(CCNC(C)C)cc1)c1cc(OC)ccc1[C@@H]1CCc2cc(O)ccc2C1]

Synthesized from pivalic acid (R)-6-{2-[(4-carboxymethylbenzyl)ethylamino]-4-methoxyphenyl}-5,6,7,8-tetrahydronaphthalen-2-yl ester (31 mg) and isopropylamine (5.5 mg) according to an analogous synthetic method to Example 806, the title compound (4.6 mg) was obtained.

ESI-Mass; 473 [M$^+$+H]

Example 843

(R)-6-{2-{[4-(2-tert-Butylaminoethyl)benzyl]ethylamino}-4-methoxyphenyl}-5,6,7,8-tetrahydronaphthalen-2-ol

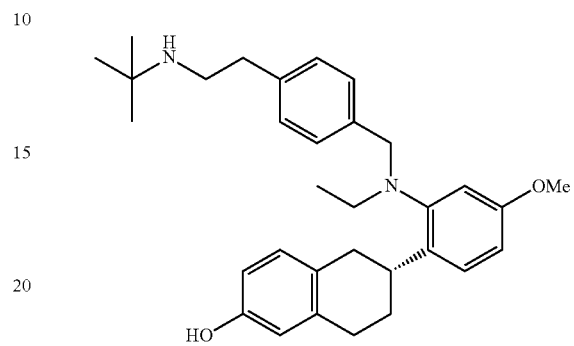

Synthesized from pivalic acid (R)-6-{2-[(4-carboxymethylbenzyl)ethylamino]-4-methoxyphenyl}-5,6,7,8-tetrahydronaphthalen-2-yl ester (31 mg) and tert-butylamine (6.8 mg) according to an analogous synthetic method to Example 806, the title compound (4.6 mg) was obtained.

ESI-Mass; 487 [M$^+$+H]

Example 844

(R)-6-{2-{[4-(2-Cyclohexylaminoethyl)benzyl]ethylamino}-4-methoxyphenyl}-5,6,7,8-tetrahydronaphthalen-2-ol

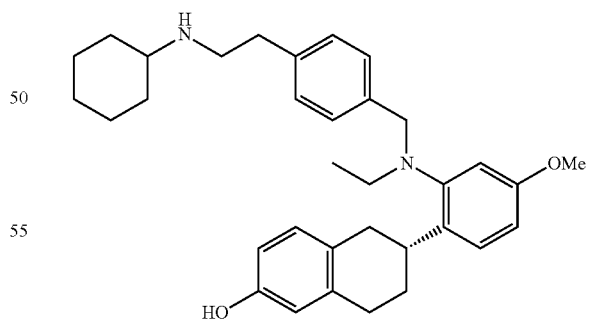

Synthesized from pivalic acid (R)-6-{2-[(4-carboxymethylbenzyl)ethylamino]-4-methoxyphenyl}-5,6,7,8-tetrahydronaphthalen-2-yl ester (31 mg) and cyclohexylamine (9.3 mg) according to an analogous synthetic method to Example 806, the title compound (4.6 mg) was obtained.

ESI-Mass; 513 [M$^+$+H]

Preparation Example 218 tert-Butyl (R)-{2-{4-{(2-hydroxyethyl)-[2-(6-hydroxy-1,2,3,4-tetrahydronaphthalen-2-yl)-5-methoxyphenyl]carbamoyl}phenoxy}-1,1-dimethylethyl}carbamate

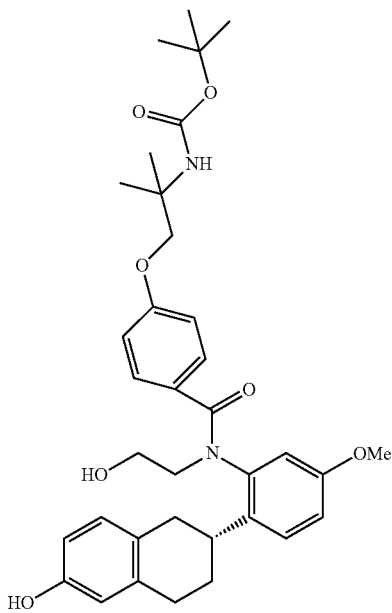 [SMILES: COc1ccc([C@@H]2CCc3cc(O)ccc3C2)c(N(CCO)C(=O)c2ccc(OCC(C)(C)NC(=O)OC(C)(C)C)cc2)c1]

To a solution of pivalic acid (R)-6-{2-{[4-(2-tert-butoxycarbonylamino-2-methylpropoxy)benzoyl]ethoxycarbonylmethylamino}-4-methoxyphenyl}-5,6,7,8-tetrahydronaphthalen-2-yl ester (9.3 mg) in tetrahydrofuran (0.5 ml) was added lithium borohydride (0.85 mg) and the solution was stirred for 2 hours at room temperature. Methanol (10 drops) was added thereto followed by stirring for 30 minutes. An aqueous solution of 5N sodium hydroxide (3 drops) was then added thereto and the solution was extracted with chloroform. After concentration in vacuo, the residue was purified by silica gel column chromatography (hexane-ethyl acetate system) to provide the title compound (4.6 mg).

$^1$H-NMR (400 MHz, CDCl$_3$); δ (ppm): 1.40 (s, 6H), 1.42 (s, 6H), 1.62-1.81 (m, 2H), 2.08 (brs, 1H), 2.50-2.61 (m, 2H), 2.75-2.86 (m, 2H), 3.10-3.19 (m, 2H), 3.45-3.60 (m, 3H), 3.78 (s, 3H), 3.87 (s, 3H), 3.96 (s, 2H), 4.74 (brs, 1H), 4.95 (brs, 1H), 6.57-6.62 (m, 2H), 6.72-6.76 (m, 4H), 6.84 (d, 1H), 6.97-7.01 (m, 2H), 7.13 (d, 1H).

Example 845

(R)-6-{2-{[4-(2-Amino-2-methylpropoxy)benzyl](2-hydroxyethyl)amino}-4-methoxyphenyl}-5,6,7,8-tetrahydronaphthalen-2-ol

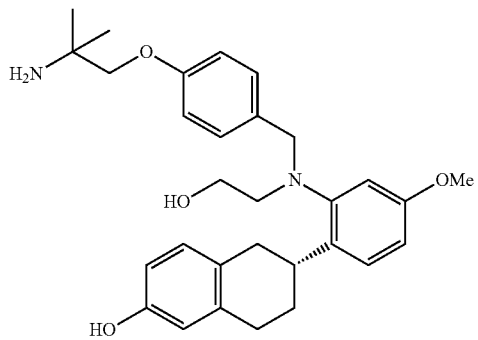 [SMILES: COc1ccc([C@@H]2CCc3cc(O)ccc3C2)c(N(CCO)Cc2ccc(OCC(C)(C)N)cc2)c1]

Synthesized from tert-butyl (R)-{2-{4-{(2-hydroxyethyl)-[2-(6-hydroxy-1,2,3,4-tetrahydronaphthalen-2-yl)-5-methoxyphenyl]carbamoyl}phenoxy}-1,1-dimethylethyl}carbamate (4.6 mg) according to an analogous synthetic method to Example 215 mentioned above, the title compound (3.2 mg) was obtained.

$^1$H-NMR (400 MHz, CDCl$_3$); δ (ppm): 1.25 (s, 6H), 1.65-1.87 (m, 2H), 2.46-2.71 (m, 2H), 2.76-2.86 (m, 2H), 3.10-3.19 (m, 2H), 3.43-3.59 (m, 3H), 3.65 (s, 2H), 3.79 (s, 3H), 3.96 (s, 2H), 6.56-6.60 (m, 2H), 6.72-6.76 (m, 4H), 6.83 (d, 1H), 7.01-7.05 (m, 2H), 7.15 (d, 1H).

ESI-Mass; 491 [M$^+$+H]

PHARMACOLOGICAL TEST EXAMPLE

Test Example 1

In Vitro Estrogen Receptor Binding Assay

The binding affinity of the compound according to the present invention to estrogen receptor was measured using an in vitro estrogen receptor binding assay. The binding affinity measures the ability of the compound according to the present invention to remove [$^3$H]-estradiol from estrogen receptor derived from bovine uterus. The following materials were used in this assay: (1) the assay buffer solution was 20 mM Tris/HCl (pH 7.5) containing 1 mM dithiothreitol (DTT), 1 mM EDTA and 10% glycerol; (2) radioactive ligand was [$^3$H]-estradiol purchased from Amersham Life Science; (3) the cold ligand was diethylstilbestrol purchased from sigma (Sigma); and (4) the estrogen receptor was derived from bovine uterus.

The compound to be tested was prepared as a 10% DMSO solution. [$^3$H]-estradiol was dissolved in the assay buffer solution so as to obtain a final concentration of 1 nM. The estrogen receptor derived from bovine uterus was diluted with the assay buffer solution so that 10 to 20 μg total protein was present in each assay well. Using a small titration plate, in each assay well were added a solution (10 μl) of cold diethylstilbestrol (non-specific binding) or compound, [$^3$H]-estradiol (10 μl) and a solution (80 μl) of estrogen receptor derived from bovine uterus. Each plate contains total binding, non-specific binding and the binding which were not inhibited by various concentrations of the compound. The plate was incubated for 1 hour at room temperature. Then, by adding 2% charcoal dextran (100 μl) to the assay buffer solution, mixing and incubating the solution at room temperature for 10 minutes, the binding reaction was terminated. These mixtures were centrifuged, and the supernatant thereof was evaluated for its radioactivity using a liquid scintillation counter. Specific binding was calculated by subtracting non-specific binding dpm (counts remaining in the supernatant obtained by centrifugal separation of a reaction mixture containing estrogen receptor derived from bovine uterus, radioactive ligand and excess cold ligand) from the total binding dpm (counts remaining in the supernatant obtained by centrifugal separation of a reaction mixture containing estrogen receptor derived from bovine uterus and radioactive ligand only). The effectiveness of the compound was evaluated by Ki. Ki was determined according to the following calculation formula: Ki=IC$_{50}$/(1+(C/Kd)), wherein IC$_{50}$ (concentration of the compound required to inhibit the total specific [$^3$H]-estradiol binding by 50%) is a value obtained by measuring the specific binding in the presence of various concentrations of the compound, then calculating the percentage of binding relative to the total specific binding and producing a plot with the latter as the vertical axis and the compound concentration (log scale) as the horizontal axis. C is the concentration of [$^3$H]-estradiol in the reaction mixture, and Kd is the [$^3$H]-estradiol dissociation constant. The Kd was determined by Scatchard analysis. That is to say, various concentrations of [$^3$H]-estradiol were used to measure the concentration of specifically bound [$^3$H]-estradiol, which served as the horizontal axis, the value which was obtained by dividing the concentration of specifically bound [$^3$H]-estradiol by the concentration [$^3$H]-estradiol not bound to the receptor served as the vertical axis to produce a plot, and the negative value of the inverse of the slope of the resulting straight line was used as Kd.

Results:

Tamoxifen, a well known selective estrogen receptor modulator, was used as a comparative example. Estrogen receptor binding affinity results for the compound according to the present invention are shown in the following (Table 1).

TABLE 1

| Example No. | Estrogen receptor binding affinity: Ki (nM) |
|---|---|
| 8 | 0.64 |
| 15 | 60 |
| 21 | 47 |
| 44 | 21 |
| 45 | 8.4 |
| 48 | 13 |
| 54 | 32 |
| 55 | 84 |
| 113 | 1.6 |
| 130 | 8.2 |
| 177 | 18 |
| 179 | 9 |
| 183 | 18 |
| 188 (R) | 1.2 |
| 190 (R) | 1 |
| 228 | 2.3 |
| 255 | 1.4 |
| 259 | 2.8 |
| 293 | 32 |
| 295 | 17 |
| 298 | 13 |
| 305 | 8.6 |
| 311 | 5.1 |
| 319 | 1.6 |
| 322 | 3.1 |
| 327 | 42 |
| 329 | 94 |
| 338 | 22 |
| 343 | 31 |
| 349 | 16 |
| 357 | 8.2 |
| 379 | 1.1 |
| 367 | 1.8 |
| 373 | 5 |
| 618 | 2.9 |
| 736 | 6.0 |
| 741 | 0.2 |
| 774 | 10 |
| 776 | 6.3 |
| 791 | 9.8 |
| 814 | 8.4 |
| Comparative Example | 140 |

Test Example 2

MCF-7 Growth Analysis

Test Example 2 determines the estrogen agonist and antagonist activities of the compound according to the present invention in reproduction system cells. It shows that the higher the agonist activity, the less it is desirable in the reproduction system. On the other hand, the antagonist activity demonstrates that the compound is effective in the treatment of cancers whose growth is dependent on steroid hormones in particular breast cancers. The present test was carried out according to the following procedures. MCF-7 breast cancer cells were cultured in the preservation medium until the compound evaluation. The preservation medium is the MEM (minimum essential medium, phenol red-free, Gibco, ##51200-038) supplemented with 10% (volume/volume) fetal bovine serum (FBS), 2 mM L-glutamine, 1 mM sodium pyruvate, non-essential amino acids (0.1 mM, Gibco, #15240-062), and antibiotic-antimycotic solution (1/50 of culture medium volume, Gibco). Five days prior to analysis, the preservation medium was exchanged with analytical medium to which 10% charcoal-stripped fetal bovine serum (charcoal-FBS) was added instead of 10% FBS, so as to deprive the MCF-7 cells of endogenous steroids. Twenty-four hours after exchange to the analytical medium, the MCF-7 cells were removed from the preservation flask using cell isolation medium (trypsin-EDTA solution, Gibco). The cells were washed with analytical medium once, and cell suspension at 50,000 cell/ml was prepared using the analytical medium. The prepared cell suspension was added to a 96 well flat-bottomed microculture at 1000 (5,000 cells) per well, the cells were cultured in a 5% CO2 incubator for 24 hours at 37° C., to equilibrate the cells after cell transfer. Serial dilution of dimethylsulfoxide (DMSO) solution of each drug was carried out using analytical medium to serve as a drug or diluent control, drug/DMSO solution was added to the microculture at 10 µl per well, then the analytical medium (10 µl) or 120 pM 17β-estradiol analytical medium solution (10 µl) was added for agonist activity assay or antagonist activity assay respectively so that the final volume of each well was set to 120 µl. The cells were further cultured in the 5% CO2 incubator for 72 hours at 37° C. After culturing, the cell growth was examined by the MTT assay. MTT assay was carried out as the following protocols. MTT solution at 8 mg/ml (MTT dissolved in phosphate saline water buffer) was added to the microculture at 10 µl/well, and the cells were cultured in the 5% CO2 incubator for 30 minutes at 37° C. Thereafter, resulting from the reduction of MTT by the cells, formazan crystals were dissolved by adding a dissolution buffer (400 g/l of an aqueous solution of SDS (50%) and dimethylformamide (50%)) to the microculture at 100 µl/well, and incubated the microculture for more than 4 hours in the dark. For each well of the microculture, the optical density at 590 nm due to the dissolved formazan crystals was measured.

The results of the evaluation of the compound according to the present invention by the above-mentioned test are shown below (Table 2). Identically to Test Example 1, tamoxifen, a well known selective estrogen receptor modulator, was used as the comparative example. The agonist activity is a value converted from the growth rate for 100 nM test compound, by taking the growth rate for the diluent control as 100, and the growth rate for 17β-estradiol (1 nM) as 200. The antagonist activity is a value obtained by measuring the concentration of test compound required to inhibit the growth by 50% (IC$_{50}$) when culturing with 17β-estradiol (10 pM) and the test compound present simultaneously.

TABLE 2

| Example No. | Agonist activity: growth rate (100 nM test compound) | Antagonist activity: IC50 (nM) |
|---|---|---|
| 190 | 124 | 7.95 |
| 228 | 101 | 2.62 |
| 255 | 106 | 1.4 |
| 259 | 103 | 4.12 |
| 618 | 96 | 2.9 |
| 736 | 73 | 0.74 |
| 741 | 98 | 2.06 |
| 814 | 95 | 3.23 |
| Comparative Example | 133 | 86.1 |

Test Example 3

Effect of SERM Compounds on Bone Resorption in Ovariectomized Rats

Experimental Method

Animals:

Ten weeks old Female Fischer rats (F344/N, Japan SLC, Shizuoka, Japan) were used. Rats were grouped to eliminate the effect of body weight between each group and housed with free access to food and water. Animals were anesthetized with Nembutal (Abbott Laboratories, Chicago, Ill.) and the ovaries were removed. In sham-operated group, ovaries were only touched with tweezers. Administration of compounds was started one day after the operation.

Drugs:

Estradiol (Sigma-Aldrich, St. Louis, Mo.) was dissolved in DMSO to 150 mg/mL then diluted with sesame oil to 0.15 mg/mL. The compounds in Examples 736 and 814, and Raloxifene were suspended in sesame oil to 5, 5 and 1.5 mg/mL, respectively. Samples were divided into aliquots for daily administration and preserved at −18° C. until use.

Administration:

The samples were orally administered at 2 mL/kg. Administration was carried out once a day from Monday to Friday for 8 weeks.

The Measurement of Deoxypyridinoline in Urine:

Urine was gathered overnight (17 hours) using the metabolic cage under fasting. The amount of urinary deoxypyridinoline was measured with ELISA kit, Osteorincs-DPD (Sumitomo Seiyaku Biomedical Co., Ltd., Osaka, Japan) and evaluated as total amount produced in 17 hours or as the amount per 1 mg of creatinine.

The Measurement of Bone Density:

After animals were sacrificed by decapitation, left femur and the fifth lumbar vertebrae were removed. The bone density was measured by using QDR-1000/W (Ho logic Inc., Bedford, Mass.).

The Measurement of Uterus Wet Weight:

After animals were sacrificed by decapitation, uterus was removed and adipose tissue and vagina was separated from uterus prior to uterus weight measurement.

Results

The results are summarized in Table 3, the results show the following effects;

The Effects on Excretion of Deoxypyridinoline in Urine:

Excretion of deoxypyridinoline in urinary was increased two-fold after ovariectomy over sham-operated rats. The compounds in Examples 736 and 814 significantly attenuated the excretion of deoxypyridinoline after 5 and 8 weeks administrations.

The Effects on Bone Mineral Density of Femur and Fifth Lumbar Vertebrae:

Eight weeks after ovariectomy, the bone mineral density of total femur, distal femur and fifth lumber vertebrae was decreased about 4, 5 and 10% compared with sham-operated rats, respectively. The compounds in Examples 736 and 814 preserved bone mineral density at the level in sham-operated rats.

The Effects on Uterus Wet Weight:

After eight weeks administrations, the compound in Example 736 did not influence the wet weight of the uterus at all. On the other hand, both Raloxifene and the compound in Example 814 slightly increased uterus wet weight to the same level.

TABLE 3

Summary of the effect of SERM compounds

| | Compound | Dose (mg/kg) | Deoxypyridinoline(nM/mg/dl) | | Bone Mineral Density(g/cm$^2$) | | | Uterus (g) |
| | | | 5 weeks | 8 weeks | Whole femur | Distal femur | Lumber 5 | |
|---|---|---|---|---|---|---|---|---|
| Sham | Vehicle | — | 10.89 ± 1.51 | 10.55 ± 1.52 | 0.241 ± 0.003 | 0.254 ± 0.005 | 0.164 ± 0.003 | 0.285 ± 0.023 |
| OVX | Vehicle | — | 17.49 ± 1.10## | 21.49 ± 1.68### | 0.231 ± 0.001# | 0.241 ± 0.002# | 0.149 ± 0.001## | 0.064 ± 0.003### |
| OVX | Estradiol | 0.3 | 12.06 ± 1.60* | 11.61 ± 2.10** | 0.237 ± 0.001** | 0.250 ± 0.001** | 0.150 ± 0.005 | 0.213 ± 0.013*** |
| OVX | Raloxifene | 3 | 8.83 ± 0.41*** | 10.87 ± 1.16*** | 0.239 ± 0.002** | 0.254 ± 0.002*** | 0.160 ± 0.003** | 0.098 ± 0.005*** |
| OVX | Example 736 | 10 | 10.48 ± 0.52*** | 15.33 ± 0.78** | 0.241 ± 0.002** | 0.256 ± 0.002*** | 0.156 ± 0.003* | 0.071 ± 0.004 |
| OVX | Example 814 | 10 | 11.22 ± 1.12*** | 15.48 ± 0.98* | 0.237 ± 0.002* | 0.248 ± 0.002* | 0.159 ± 0.001*** | 0.107 ± 0.008** |

*, $p < 0.05$;
**, $p < 0.01$;
***, $p < 0.001$ treatment group versus vehicle group in ovariectomized rats.
, $p < 0.05$;
, $p < 0.01$;
, $p < 0.001$ vehicle group in ovariectomized rats versus sham-operated rats
n = 7 for Sham and Vehicle Group,
n = 6 for treatment Group

INDUSTRIAL APPLICABILITY

From the above results, it was confirmed that the compound according to the present invention exhibits an affinity for estrogen receptor, and not has an undesirable effect in cells from the reproduction system. It was also confirmed that the compound according to the present invention is effective in the treatment of hormone-dependent cancers. Accordingly, the present invention provides a novel compound having a strongly selective estrogen receptor modulator activity and the compound according to the present invention is very useful as a preventive and therapeutic agent for the diseases caused by estrogen.

The invention claimed is:

1. A hydrochloric acid salt of the compound of the following structural:

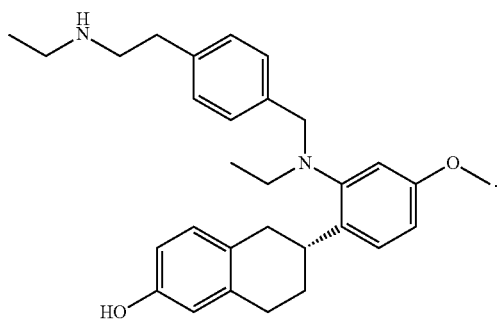 [SMILES: CCNCCc1ccc(CN(CC)c2cc(OC)ccc2[C@@H]2CCc3cc(O)ccc3C2)cc1]

2. A pharmaceutical composition comprising a hydrochloric acid salt of the compound of the following structural formula and a pharmaceutically acceptable carrier:

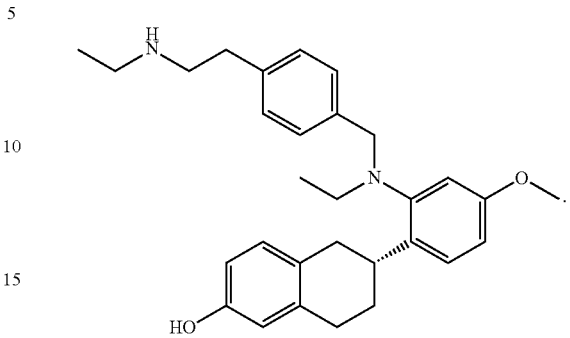

3. A method for treating estrogen-dependent osteoporosis or estrogen-dependent breast cancer in a subject in need thereof, comprising administering to said subject an effective amount of the pharmaceutical composition of claim 1.

* * * * *

UNITED STATES PATENT AND TRADEMARK OFFICE
CERTIFICATE OF CORRECTION

PATENT NO. : 8,399,520 B2
APPLICATION NO. : 13/048391
DATED : March 19, 2013
INVENTOR(S) : Shinichi Hamaoka et al.

It is certified that error appears in the above-identified patent and that said Letters Patent is hereby corrected as shown below:

IN THE CLAIMS:

In claim 3, at column 642, line 22, change "claim 1" to --claim 2--.

Signed and Sealed this
Twenty-first Day of June, 2016

Michelle K. Lee
*Director of the United States Patent and Trademark Office*